United States Patent
Chae et al.

(10) Patent No.: US 10,651,392 B2
(45) Date of Patent: May 12, 2020

(54) ORGANIC LIGHT-EMITTING DEVICE

(71) Applicants: SAMSUNG ELECTRONICS CO., LTD., Suwon-si, Gyeonggi-do (KR); President and Fellows of Harvard College, Cambridge, MA (US)

(72) Inventors: Hyun Sik Chae, Cambridge, MA (US); Soonok Jeon, Seoul (KR); Hosuk Kang, Suwon-si (KR); Hiroshi Miyazaki, Suwon-si (KR); Sooghang Ihn, Hwaseong-si (KR); Seongik Hong, Suwon-si (KR); Masaki Numata, Suwon-si (KR); Sunghan Kim, Seongnam-si (KR); Rafael Gomez-Bombarelli, Cambridge, MA (US); Martin B. Z. Forsythe, Cambridge, MA (US); Jorge Aguilera-Iparraguirre, Cambridge, MA (US); Alan Aspuru-Guzik, Cambridge, MA (US); Timothy D. Hirzel, Cambridge, MA (US)

(73) Assignees: SAMSUNG ELECTRONICS CO., LTD., Gyeonggi-Do (KR); PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 237 days.

(21) Appl. No.: 15/225,117

(22) Filed: Aug. 1, 2016

(65) Prior Publication Data
US 2017/0092872 A1 Mar. 30, 2017

Related U.S. Application Data

(60) Provisional application No. 62/235,498, filed on Sep. 30, 2015.

(51) Int. Cl.
*H01L 51/00* (2006.01)
*C07D 403/10* (2006.01)
(Continued)

(52) U.S. Cl.
CPC ........ *H01L 51/0067* (2013.01); *C07D 403/10* (2013.01); *C07D 403/14* (2013.01);
(Continued)

(58) Field of Classification Search
CPC .. C07D 471/06; C07D 471/10; C07D 471/14; C07D 471/20; C07D 471/22;
(Continued)

(56) References Cited

U.S. PATENT DOCUMENTS 8,911,886 B2  12/2014  Iwakuma et al.
9,048,434 B2  6/2015   Otsu et al.
(Continued)

FOREIGN PATENT DOCUMENTS

EP    2240446 B1    10/2010
EP    2461390 A1    6/2012
(Continued)

OTHER PUBLICATIONS

Nature Materials, vol. 15, pp. 1120-1128 (2016). (Year: 2016).*
(Continued)

*Primary Examiner* — Dawn L Garrett
(74) *Attorney, Agent, or Firm* — Cantor Colburn LLP

(57) ABSTRACT

An organic light-emitting device including a first electrode; a second electrode; and an organic layer disposed between the first electrode and the second electrode, wherein the organic layer comprises an emission layer, and wherein the organic layer comprises a first compound represented by Formula 1 and a second compound having the lowest excited triplet energy level greater than 2.73 electron volts:
(Continued)

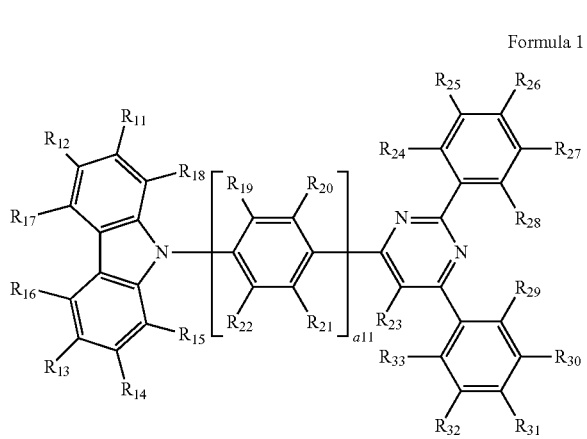

Formula 1 wherein in Formula 1, $R_{11}$ to $R_{33}$ are the same as described in the specification.

19 Claims, 8 Drawing Sheets

(51) Int. Cl.
C07D 403/14 (2006.01)
C09K 11/02 (2006.01)
C09K 11/06 (2006.01)
H01L 51/50 (2006.01)
H01L 51/52 (2006.01)

(52) U.S. Cl.
CPC ............ *C09K 11/025* (2013.01); *C09K 11/06* (2013.01); *H01L 51/005* (2013.01); *H01L 51/0061* (2013.01); *H01L 51/0072* (2013.01); C09K 2211/1007 (2013.01); C09K 2211/1014 (2013.01); C09K 2211/1044 (2013.01); H01L 51/5004 (2013.01); H01L 51/5016 (2013.01); H01L 51/5028 (2013.01); H01L 51/5206 (2013.01); H01L 51/5221 (2013.01); H01L 2251/552 (2013.01)

(58) Field of Classification Search
CPC .. C07D 487/04; C07D 491/04; C07D 493/10; C07D 493/20; C07D 493/22; C07D 495/04; C07D 495/14; C07D 495/20; C07D 495/22; C07D 519/00; C23F 11/10; C23F 11/145; H04L 67/04; H04L 67/18; H04L 67/306; H04L 69/329; H04M 2242/30; H04M 3/42229; H04M 3/493; H04W 4/02; H04W 64/00; C07C 407/00; C07C 409/24; C07C 225/22; C07C 255/09; C07C 255/51; C07F 7/0814; C07F 7/0816; C07F 9/65683; C07F 9/657163; C07F 5/02; C07F 7/10; C11D 3/3945

See application file for complete search history.

(56) References Cited

U.S. PATENT DOCUMENTS

| | | | |
|---|---|---|---|
| 9,059,410 B2 | 6/2015 | Sasada et al. | |
| 9,099,659 B2 | 8/2015 | Oshiyama et al. | |
| 9,130,188 B2 | 9/2015 | Chun et al. | |
| 9,153,788 B2 | 10/2015 | Adachi et al. | |
| 9,184,399 B2 | 11/2015 | Dyatkin et al. | |
| 2012/0138915 A1 | 6/2012 | Nishimura et al. | |
| 2012/0211736 A1 | 8/2012 | Kim et al. | |
| 2012/0298966 A1 | 11/2012 | Zeng et al. | |
| 2013/0056720 A1 | 3/2013 | Kim et al. | |
| 2013/0141011 A1 | 6/2013 | Fushimi | |
| 2013/0292659 A1* | 11/2013 | Kim .................... | C07D 209/82 257/40 |
| 2013/0306963 A1 | 11/2013 | Yamamoto et al. | |
| 2013/0308145 A1* | 11/2013 | Yoshida ................ | B41J 2/2114 358/1.9 |
| 2014/0145173 A1 | 5/2014 | Chin et al. | |
| 2014/0158992 A1 | 6/2014 | Xia et al. | |
| 2014/0159023 A1 | 6/2014 | Matsumoto et al. | |
| 2015/0021555 A1 | 1/2015 | Kwong et al. | |
| 2015/0126736 A1 | 5/2015 | Cho et al. | |
| 2015/0243910 A1 | 8/2015 | De Cola et al. | |
| 2015/0325794 A1 | 11/2015 | Nishimura et al. | |
| 2015/0357582 A1 | 12/2015 | Hirata et al. | |
| 2016/0197286 A1* | 7/2016 | Kawamura ............ | C09K 11/06 257/40 |

FOREIGN PATENT DOCUMENTS

| | | |
|---|---|---|
| EP | 2690681 A1 | 1/2014 |
| EP | 2883880 A1 | 6/2015 |
| EP | 2315753 B1 | 10/2015 |
| JP | 2012-028634 A | 2/2012 |
| JP | 2014-141571 A | 8/2014 |
| KR | 10-2014-0096182 A | 8/2014 |
| WO | 2009-086028 A2 | 7/2009 |
| WO | 2011-139055 A3 | 11/2011 |
| WO | 2012-023947 A1 | 2/2012 |
| WO | 2012-108881 A1 | 8/2012 |
| WO | 2012-157211 A1 | 11/2012 |
| WO | 2013-165192 A1 | 11/2013 |
| WO | 2014-087657 A1 | 6/2014 |
| WO | WO 2014/092083 A1 * | 6/2014 |
| WO | 2014-115743 A1 | 7/2014 |
| WO | 2015-029964 A1 | 3/2015 |
| WO | WO 2015/072470 A1 * | 5/2015 |

OTHER PUBLICATIONS

Kohler A. et al. "Triplet states in organic semiconductors", Materials Science and Engineering, R 66, 2009, 71-109.
Chihaya Adachi et al. "High Performance TADF for OLEDs", OPERA research team Kyushu University, DOE SSL R&R Workshop, 2015, 26 pages.
Heiner Detert et al. "Star-Shaped Conjugated Systems", Materials, 2010, 3, 3218-3330.
Hiroki Uoyama et al. "Highly efficient organic light-emitting diodes from delayed fluorescence", Nature 2012, 492, 234.
Martina Congiu et al. "Preparation and photophysical studies of [Ln(hfac)3DPEPO], Ln=Eu, Tb, Yb, Nd, Gd; Interpretation of total photoluminescence quantum yields", Dalton Trans., 2013, 42, 13537-13545.
Sae Youn Lee et al. "High-efficiency organic light-emitting diodes utilizing thermally activated delayed fluorescence from triazine-based donor-acceptor hybrid molecules", Applied Physics Letter, 2012, 101, 093306.
Shuzo Hirata et al. "Highly efficient blue electroluminescence based on thermally activated delayed fluorescence", Nature Materials, 2014, pp. 1-7.
Sung Hyun Kim et al. "High efficiency phosphorescent organic light emitting diodes using triplet quantum well structure", Applied Physics Letters, 90, 173501, 2007.
Sylvain Achelle et al. "Luminescent materials incorporating pyrazine or quinoxaline moieties", Dyes and Pigments, Elsevier, 2013, 98(3), pp. 575-600.
Takehiro Takahashi et al. "Donor-acceptor-structured 1,4-diazatriphenylene derivatives exhibiting thermally activated delayed fluorescence: design and synthesis, photophysical properties and OLED characteristics", Sci. Technol. Adv. Mater., 15, 2014, 034202 (10pp).

* cited by examiner

ORGANIC LIGHT-EMITTING DEVICE

CROSS-REFERENCE TO RELATED APPLICATION

This application claims priority to U.S. Provisional Application No. 62/235,498, filed on Sep. 30, 2015, in the United States Patent and Trademark Office, and all the benefits accruing therefrom under 35 U.S.C. § 119, the content of which is incorporated herein in its entirety by reference.

BACKGROUND

1. Field

The present disclosure relates to an organic light-emitting device.

2. Description of the Related Art

Organic light-emitting devices (OLEDs) are self-emission devices, which have wide viewing angles, high contrast ratios, short response times, excellent luminance, driving voltage, and response speed characteristics, and produce full-color images.

In an example, an organic light-emitting device includes an anode, a cathode, and an organic layer that is disposed between the anode and the cathode, wherein the organic layer includes an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. Carriers, such as holes and electrons, recombine in the emission layer to produce excitons. These excitons transit from an excited state to a ground state, thereby generating light.

Various types of organic light emitting devices are known. However, there still remains a need in OLEDs having low driving voltage, high efficiency, high brightness, and long lifespan.

SUMMARY

Provided is an organic light-emitting device having high efficiency, a low driving voltage, high color-coordination, and long lifespan.

Additional aspects will be set forth in part in the description which follows and, in part, will be apparent from the description, or may be learned by practice of the presented embodiments.

According to an aspect of an embodiment, an organic light-emitting device includes:

a first electrode;

a second electrode; and an organic layer disposed between the first electrode and the second electrode, wherein the organic layer includes an emission layer, and wherein the organic layer includes a first compound represented by Formula 1 and a second compound having the lowest excited triplet energy level greater than 2.73 electron volts:

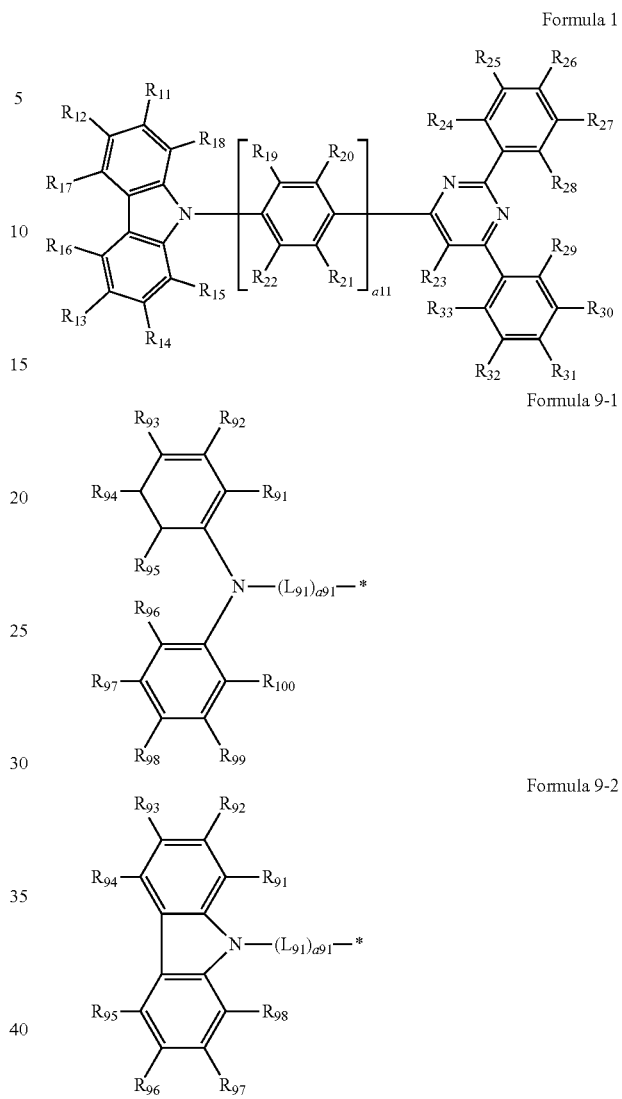

wherein, in Formulae 1, 9-1, and 9-2, $R_{11}$ to $R_{14}$ are each independently selected from hydrogen, deuterium, —F, —Cl, —Br, —I, a cyano group, a nitro group, an amidino group, a hydrazino group, a hydrazono group, a substituted or unsubstituted $C_1$-$C_{60}$ alkyl group, a substituted or unsubstituted $C_1$-$C_{60}$ alkoxy group, a substituted or unsubstituted $C_1$-$C_{60}$ alkylthio group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted $C_6$-$C_{60}$ aryloxy group, a substituted or unsubstituted $C_6$-$C_{60}$ arylthio group, a substituted or unsubstituted monovalent non-aromatic condensed polycyclic group, a substituted or unsubstituted monovalent non-aromatic condensed heteropolycyclic group, —Si(Q$_1$)(Q$_2$)(Q$_3$), —N(Q$_1$)(Q$_2$), —B(Q$_1$)(Q$_2$), —C(=O)(Q$_1$), —S(=O)$_2$(Q$_1$), —P(=O)(Q$_1$)(Q$_2$), groups represented by Formula 9-1, and groups represented by Formula 9-2, provided that at least one selected from $R_{11}$ to $R_{14}$ is selected from groups represented by Formula 9-1 and groups represented by Formula 9-2, $R_{15}$ to $R_{33}$ and $R_{91}$ to $R_{100}$ are each independently selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_1$-$C_{60}$ alkoxy group, a substituted or unsubstituted $C_1$-$C_{60}$ alkylthio group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted $C_6$-$C_{60}$ aryloxy group, a substituted or unsubstituted $C_6$-$C_{60}$ arylthio group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)$_2$($Q_1$), and —P(=O)($Q_1$)($Q_2$), a11 is selected from 1, 2, and 3, $L_{91}$ is selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, a91 is selected from 0, 1, and 2, wherein $Q_1$ to $Q_3$ are each independently selected from hydrogen, deuterium, —F, —Cl, —Br, —I, a hydroxyl group, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group, and

* indicates a binding site to an adjacent atom.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
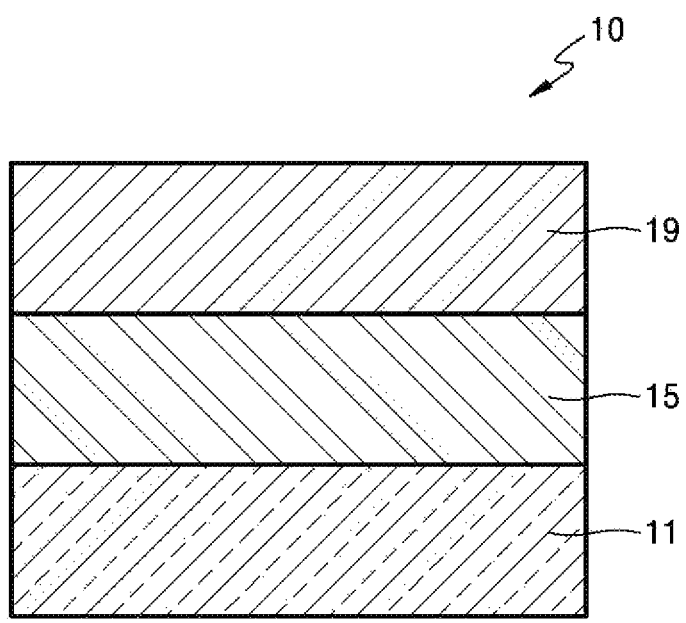
FIG. 1 is a schematic cross-sectional view illustrating an organic light-emitting device according to an embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

An organic light-emitting device may include:
a first electrode;
a second electrode; and
an organic layer that is disposed between the first electrode and the second electrode,
wherein the organic layer includes an emission layer, and
wherein the organic layer may include a first compound represented by Formula 1 and a second compound having the lowest excited triplet energy level greater than 2.73 electron volts (eV):

Formula 1

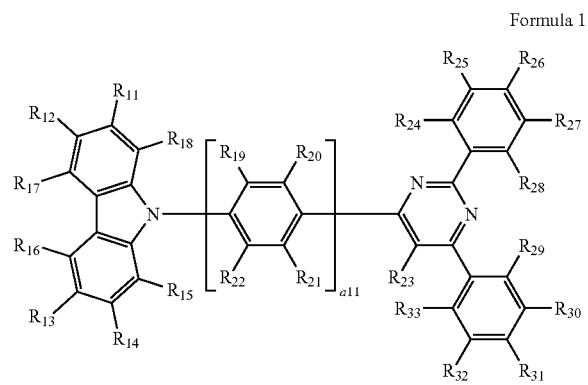

Formula 9-1

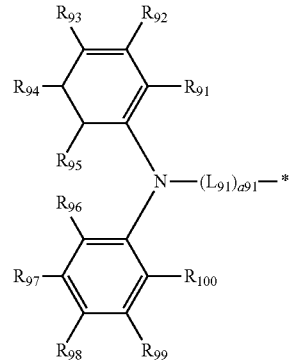

Formula 9-2

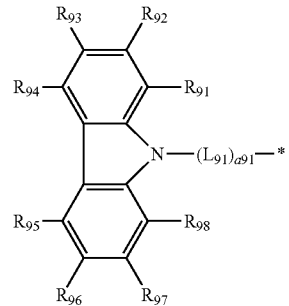

wherein, in Formulae 1, 9-1, and 9-2, $R_{11}$ to $R_{14}$ may be each independently selected from hydrogen, deuterium, —F, —Cl, —Br, —I, a cyano group, a nitro group, an amidino group, a hydrazino group, a hydrazono group, a substituted or unsubstituted $C_1$-$C_{60}$ alkyl group, a substituted or unsubstituted $C_1$-$C_{60}$ alkoxy group, a substituted or unsubstituted $C_1$-$C_{60}$ alkylthio group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted $C_6$-$C_{60}$ aryloxy group, a substituted or unsubstituted $C_6$-$C_{60}$ arylthio group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)$_2$($Q_1$), —P(=O)($Q_1$)($Q_2$), groups represented by Formula 9-1, and groups represented by Formula 9-2, provided that at least one selected from $R_{11}$ to $R_{14}$ may be selected from groups represented by Formula 9-1 and groups represented by Formula 9-2, $R_{15}$ to $R_{33}$ and $R_{91}$ to $R_{100}$ may be each independently selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_1$-$C_{60}$ alkoxy group, a substituted or unsubstituted $C_1$-$C_{60}$ alkylthio group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted $C_6$-$C_{60}$ aryloxy group, a substituted or unsubstituted $C_6$-$C_{60}$ arylthio group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)$_2$($Q_1$), and —P(=O)($Q_1$)($Q_2$), a11 may be selected from 1, 2, and 3, $L_{91}$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, a91 may be selected from 0, 1, and 2, wherein $Q_1$ to $Q_3$ may be each independently selected from hydrogen, deuterium, —F, —Cl, —Br, —I, a hydroxyl group, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group, and \* indicates a binding site to an adjacent atom.

Since the difference ($\Delta E_{ST1}$) between the lowest excited triplet energy level of the first compound and the lowest excited singlet energy level of the first compound is small, the first compound may have thermally activated delayed fluorescence characteristics. Accordingly, when an organic light-emitting device includes the first compound, the organic light-emitting device may have high external quantum efficiency.

As shown in Formula 1' below, since the first compound includes an asymmetric pyrimidine group having a relatively low lowest unoccupied molecular orbital (LUMO) energy level (particularly, the LUMO energy level of the asymmetric pyrimidine group is relatively low, as compared with that of a symmetric pyrimidine group), the first compound may have relatively high electron acceptability. When an organic light-emitting device includes the first compound, the organic light-emitting device may have particularly high external quantum efficiency.

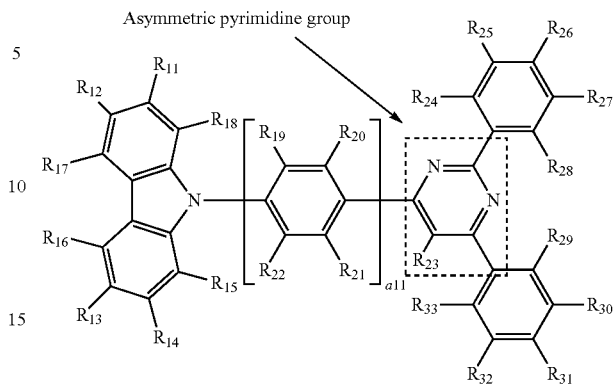

Formula 1'

In some embodiments, a difference between the highest occupied molecular orbital (HOMO) energy level of the first compound and the HOMO of the second compound may be in a range of about 0 eV or greater to about 0.1 eV or less, but embodiments are not limited thereto. While not wishing to be bound by theory, it is understood that when the difference is within this range, the organic light-emitting device may have a low driving voltage.

In some embodiments, the emission layer may include the first compound and the second compound, but embodiments are not limited thereto. In this case, the first compound may be a dopant and the second compound may be a host. That is, the first compound may emit light. The first compound may emit green, blue, or deep blue light.

In some embodiments, the lowest excited triplet energy level of the second compound may be 3.5 eV or less, but embodiments are not limited thereto.

In some embodiments, the lowest excited triplet energy level of the second compound may be in a range of about 2.8 eV or greater or about 3.0 eV or greater, but embodiments are not limited thereto. While not wishing to be bound by theory, it is understood that when the lowest excited triplet energy level of the second compound is within these ranges, for example, the lowest excited triplet energy level of the second compound may be higher than that of the first compound, triplet exciton quenching may be prevented.

In some embodiments, the lowest excited triplet energy level of the second compound may be higher than that of the first compound, but embodiments are not limited thereto. In this case, the first compound may effectively emit light.

In some embodiments, the lowest excited triplet energy level of the first compound may be 2.73 eV or less, but embodiments are not limited thereto. While not wishing to be bound by theory, it is understood that when the lowest excited triplet energy level of the first compound is within this range, triplet excition quenching of the first compound may be prevented, and the efficiency of the organic light-emitting device including the first compound may be improved.

In some embodiments, the HOMO energy level of the first compound may be in a range of about −5.5 eV to about −5.1 eV, but embodiments are not limited thereto.

In some embodiments, the HOMO energy level of the second compound may be in a range of about −6.5 eV to about −5.5 eV, but embodiments are not limited thereto.

Since the HOMO energy level of the second compound is lower than that of the first compound, the second compound may easily trap holes.

For example, a difference ($\Delta E_{ST1}$) between the lowest excited triplet energy level of the first compound and the lowest excited singlet energy level of the first compound may be in a range of about 0 eV or greater to about 0.34 eV or less, but embodiments are not limited thereto. While not wishing to be bound by theory, it is understood that when the difference ($\Delta E_{ST1}$) is within this range, reverse intersystem crossing may occur effectively, and the first compound may effectively emit delayed fluorescence.

In some embodiments, $\Delta E_{ST1}$ may be in a range of about 0 eV or greater to about 0.2 eV or less, but embodiments are not limited thereto.

In some embodiments, $\Delta E_{ST1}$ may be in a range of about 0 eV to about 0.1 eV, but embodiments are not limited thereto.

In some embodiments, a weight ratio of the first compound to the second compound may be in a range of about 1:100 to about 30:100, but embodiments are not limited thereto. For example, a weight ratio of the first compound to the second compound may be in a range of about 10:100 to about 20:100 or about 10:100 to about 15:100, but embodiments are not limited thereto.

In some embodiments, in Formula 1, $R_{11}$ and $R_{14}$ may be each independently selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_1$-$C_{60}$ alkoxy group, a substituted or unsubstituted $C_1$-$C_{60}$ alkylthio group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted $C_6$-$C_{60}$ aryloxy group, a substituted or unsubstituted $C_6$-$C_{60}$ arylthio group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)$_2$($Q_1$), and —P(=O)($Q_1$)($Q_2$), $R_{12}$ and $R_{13}$ may be each independently selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_1$-$C_{60}$ alkoxy group, a substituted or unsubstituted $C_1$-$C_{60}$ alkylthio group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted $C_6$-$C_{60}$ aryloxy group, a substituted or unsubstituted $C_6$-$C_{60}$ arylthio group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)$_2$($Q_1$), —P(=O)($Q_1$)($Q_2$), groups represented by Formula 9-1, and groups represented by Formula 9-2, provided that at least one selected from $R_{12}$ and $R_{13}$ may be selected from groups represented by Formula 9-1 and groups represented by Formula 9-2, and $Q_1$ to $Q_3$ may be the same as those described herein in relation to Formula 1, but embodiments are not limited thereto.

In some embodiments, in Formula 1, $R_{11}$, $R_{12}$, and $R_{14}$ may be each independently selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_1$-$C_{60}$ alkoxy group, a substituted or unsubstituted $C_1$-$C_{60}$ alkylthio group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted $C_6$-$C_{60}$ aryloxy group, a substituted or unsubstituted $C_6$-$C_{60}$ arylthio group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)$_2$ ($Q_1$), and —P(=O)($Q_1$)($Q_2$), $R_{13}$ may be selected from groups represented by Formula 9-1 and groups represented by Formula 9-2, and $Q_1$ to $Q_3$ may be the same as those described herein in relation to Formula 1, but embodiments are not limited thereto.

In some embodiments, $R_{11}$ to $R_{14}$ in Formula 1 may be each independently selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a $C_1$-$C_{20}$ alkylthio group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, and —N($Q_1$)($Q_2$), a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a $C_1$-$C_{20}$ alkylthio group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, and —N($Q_{31}$)($Q_{32}$); and groups represented by Formula 9-1 and groups represented by Formula 9-2, provided that at least one selected from $R_{11}$ to $R_{14}$ may be selected from groups represented by Formula 9-1 and groups represented by Formula 9-2, wherein $Q_1$, $Q_2$, $Q_{31}$, and $Q_{32}$ may be each independently selected from a $C_1$-$C_{20}$ alkyl group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, but embodiments are not limited thereto.

In some embodiments, $R_{11}$ to $R_{14}$ in Formula 1 may be each independently selected from hydrogen, deuterium, —F, —Cl, —Br, —I, a cyano group, a nitro group, a $C_1$-$C_{20}$ alkyl group, a phenyl group, a biphenyl group, a terphenyl group, a naphthyl group, a fluorenyl group, a spiro-bifluorenyl group, a benzofluorenyl group, a dibenzofluorenyl group, a carbazolyl group, a dibenzofuranyl group, a dibenzothiophenyl group, a benzocarbazolyl group, a dibenzocarbazolyl group, and —N($Q_1$)($Q_2$);

a phenyl group, a biphenyl group, a terphenyl group, a naphthyl group, a fluorenyl group, a spiro-bifluorenyl group, a benzofluorenyl group, a dibenzofluorenyl group, a carbazolyl group, a dibenzofuranyl group, a dibenzothiophenyl group, a benzocarbazolyl group, and a dibenzocarbazolyl group, each substituted with at least one selected from deuterium, —F, —Cl, —Br, —I, a hydroxyl group, a cyano group, a nitro group, a $C_1$-$C_{20}$ alkyl group, a phenyl group, a biphenyl group, a terphenyl group, a naphthyl group, a fluorenyl group, a spiro-bifluorenyl group, a benzofluorenyl group, a dibenzofluorenyl group, a carbazolyl group, a dibenzofuranyl group, a dibenzothiophenyl group, a benzocarbazolyl group, a dibenzocarbazolyl group, and —N($Q_{31}$)($Q_{32}$); and groups represented by Formula 9-1 and groups represented by Formula 9-2, provided that at least one selected from $R_{11}$ to $R_{14}$ may be selected from groups represented by Formula 9-1 and groups represented by Formula 9-2, wherein $Q_1$, $Q_2$, $Q_{31}$, and $Q_{32}$ may be each independently selected from a $C_1$-$C_{20}$ alkyl group, a phenyl group, a biphenyl group, a terphenyl group, a naphthyl group, a fluorenyl group, a spiro-bifluorenyl group, a benzofluorenyl group, a dibenzofluorenyl group, a carbazolyl group, a dibenzofuranyl group, a dibenzothiophenyl group, a benzocarbazolyl group, and a dibenzocarbazolyl group, but embodiments are not limited thereto.

In some embodiments, $R_{11}$ to $R_{14}$ in Formula 1 may be each independently selected from hydrogen, a phenyl group, a biphenyl group, a terphenyl group, a naphthyl group, a carbazolyl group, a dibenzofuranyl group, a dibenzothiophenyl group, a benzocarbazolyl group, a dibenzocarbazolyl group, and —N($Q_1$)($Q_2$);

a phenyl group, a biphenyl group, a terphenyl group, a naphthyl group, a fluorenyl group, a spiro-bifluorenyl group, a benzofluorenyl group, a dibenzofluorenyl group, a carbazolyl group, a dibenzofuranyl group, a dibenzothiophenyl group, a benzocarbazolyl group, and a dibenzocarbazolyl group, each substituted with at least one selected from deuterium, —F, —Cl, —Br, —I, a hydroxyl group, a cyano group, a nitro group, a $C_1$-$C_{20}$ alkyl group, a phenyl group, a biphenyl group, a terphenyl group, a naphthyl group, a fluorenyl group, a spiro-bifluorenyl group, a benzofluorenyl group, a dibenzofluorenyl group, a carbazolyl group, a dibenzofuranyl group, a dibenzothiophenyl group, a benzocarbazolyl group, a dibenzocarbazolyl group, and —N($Q_{31}$)($Q_{32}$); and groups represented by Formula 9-1 and groups represented by Formula 9-2, provided that at least one selected from $R_{11}$ to $R_{14}$ may be selected from groups represented by Formula 9-1 and groups represented by Formula 9-2, wherein $Q_1$, $Q_2$, $Q_{31}$, and $Q_{32}$ may be each independently selected from a $C_1$-$C_{20}$ alkyl group, a phenyl group, a biphenyl group, a terphenyl group, a naphthyl group, a fluorenyl group, a spiro-bifluorenyl group, a benzofluorenyl group, a dibenzofluorenyl group, a carbazolyl group, a dibenzofuranyl group, a dibenzothiophenyl group, a benzocarbazolyl group, and a dibenzocarbazolyl group, but embodiments are not limited thereto.

In some embodiments, $R_{15}$ to $R_{33}$ and $R_{91}$ to $R_{100}$ in Formulae 1, 9-1 and 9-2 may be each independently selected from hydrogen, deuterium, —F, —Cl, —Br, —I, a cyano group, a nitro group, an amidino group, a hydrazino group, a hydrazono group, a $C_1$-$C_{20}$ alkyl group, a $C_1$-$C_{20}$ alkoxy group, a $C_1$-$C_{20}$ alkylthio group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, and —N($Q_1$)($Q_2$); and a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a $C_1$-$C_{20}$ alkylthio group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, and —N($Q_{31}$)($Q_{32}$), wherein $Q_1$, $Q_2$, $Q_{31}$, and $Q_{32}$ may be each independently selected from a $C_1$-$C_{20}$ alkyl group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, but embodiments are not limited thereto.

In some embodiments, $R_{15}$ to $R_{33}$ and $R_{91}$ to $R_{100}$ in Formulae 1, 9-1 and 9-2 may be each independently selected from hydrogen, deuterium, —F, —Cl, —Br, —I, a cyano group, a nitro group, a $C_1$-$C_{20}$ alkyl group, a phenyl group, a biphenyl group, a terphenyl group, a naphthyl group, a fluorenyl group, a spiro-bifluorenyl group, a benzofluorenyl group, a dibenzofluorenyl group, a carbazolyl group, a dibenzofuranyl group, a dibenzothiophenyl group, a benzocarbazolyl group, a dibenzocarbazolyl group, and —N($Q_1$)($Q_2$); and a phenyl group, a biphenyl group, a terphenyl group, a naphthyl group, a fluorenyl group, a spiro-bifluorenyl group, a benzofluorenyl group, a dibenzofluorenyl group, a carbazolyl group, a dibenzofuranyl group, a dibenzothiophenyl group, a benzocarbazolyl group, and a dibenzocarbazolyl group, each substituted with at least one selected from deuterium, —F, —Cl, —Br, —I, a hydroxyl group, a cyano group, a nitro group, a $C_1$-$C_{20}$ alkyl group, a phenyl group, a biphenyl group, a terphenyl group, a naphthyl group, a fluorenyl group, a spiro-bifluorenyl group, a benzofluorenyl group, a dibenzofluorenyl group, a carbazolyl group, a dibenzofuranyl group, a dibenzothiophenyl group, a benzocarbazolyl group, a dibenzocarbazolyl group, and —N($Q_{31}$)($Q_{32}$), wherein $Q_1$, $Q_2$, $Q_{31}$, and $Q_{32}$ may be each independently selected from a $C_1$-$C_{20}$ alkyl group, a phenyl group, a biphenyl group, a terphenyl group, a naphthyl group, a fluorenyl group, a spiro-bifluorenyl group, a benzofluorenyl group, a dibenzofluorenyl group, a carbazolyl group, a dibenzofuranyl group, a dibenzothiophenyl group, a benzocarbazolyl group, and a dibenzocarbazolyl group, but embodiments are not limited thereto.

In some embodiments, $R_{15}$ to $R_{33}$ and $R_{91}$ to $R_{100}$ in Formulae 1, 9-1 and 9-2 may be each independently selected from hydrogen, a cyano group, a $C_1$-$C_{20}$ alkyl group, a phenyl group, a biphenyl group, a terphenyl group, a naphthyl group, a carbazolyl group, a dibenzofuranyl group, a dibenzothiophenyl group, a benzocarbazolyl group, a dibenzocarbazolyl group, and —N($Q_1$)($Q_2$); and a phenyl group, a biphenyl group, a terphenyl group, a naphthyl group, a fluorenyl group, a spiro-bifluorenyl group, a benzofluorenyl group, a dibenzofluorenyl group, a carbazolyl group, a dibenzofuranyl group, a dibenzothiophenyl group, a benzocarbazolyl group, and a dibenzocarbazolyl group, each substituted with at least one selected from deuterium, —F, —Cl, —Br, —I, a hydroxyl group, a cyano group, a nitro group, a $C_1$-$C_{20}$ alkyl group, a phenyl group, a biphenyl group, a terphenyl group, a naphthyl group, a fluorenyl group, a spiro-bifluorenyl group, a benzofluorenyl group, a dibenzofluorenyl group, a carbazolyl group, a dibenzofuranyl group, a dibenzothiophenyl group, a benzocarbazolyl group, a dibenzocarbazolyl group, and —N($Q_{31}$)($Q_{32}$), wherein $Q_1$, $Q_2$, $Q_{31}$, and $Q_{32}$ may be each independently selected from a $C_1$-$C_{20}$ alkyl group, a phenyl group, a biphenyl group, a terphenyl group, a naphthyl group, a fluorenyl group, a spiro-bifluorenyl group, a benzofluorenyl group, a dibenzofluorenyl group, a carbazolyl group, a dibenzofuranyl group, a dibenzothiophenyl group, a benzocarbazolyl group, and a dibenzocarbazolyl group, but embodiments are not limited thereto.

In some embodiments, $R_{91}$ to $R_{100}$ in Formulae 9-1 and 9-2 may be each independently selected from hydrogen, a cyano group, a $C_1$-$C_{20}$ alkyl group, a carbazolyl group, and —N($Q_1$)($Q_2$); and a carbazolyl group substituted with at least one selected from deuterium, —F, —Cl, —Br, —I, a hydroxyl group, a cyano group, a nitro group, a $C_1$-$C_{20}$ alkyl group, a phenyl group, a biphenyl group, a terphenyl group, a naphthyl group, a carbazolyl group, and —N($Q_{31}$)($Q_{32}$), wherein $Q_1$, $Q_2$, $Q_{31}$, and $Q_{32}$ may be each independently selected from a phenyl group, a biphenyl group, a terphenyl group, a naphthyl group, and a carbazolyl group, but embodiments are not limited thereto.

In some embodiments, a11 in Formula 1 may be selected from 1 and 2, but embodiments are not limited thereto.

In some embodiments, a11 in Formula 1 may be 1, but embodiments are not limited thereto.

When a11 in Formula 1 is 2 or greater, groups

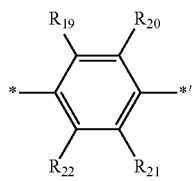

may be identical to or different from each other.

In some embodiments, $L_{91}$ in Formulae 9-1 and 9-2 may be selected from a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, and —N($Q_{31}$)($Q_{32}$), wherein $Q_{31}$ and $Q_{32}$ may be each independently selected from a $C_1$-$C_{20}$ alkyl group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, but embodiments are not limited thereto.

In some embodiments, $L_{91}$ in Formulae 9-1 and 9-2 may be selected from a phenylene group; and a phenylene group substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a $C_1$-$C_{20}$ alkylthio group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, and —N($Q_{31}$)($Q_{32}$), wherein $Q_{31}$ and $Q_{32}$ may be each independently selected from a $C_1$-$C_{20}$ alkyl group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, but embodiments are not limited thereto.

In some embodiments, $L_{91}$ in Formulae 9-1 and 9-2 may be selected from a phenylene group; and a phenylene group substituted with at least one selected from a carbazolyl group and $—N(Q_{31})(Q_{32})$, wherein $Q_{31}$ and $Q_{32}$ may be each independently selected from a $C_1$-$C_{20}$ alkyl group, a phenyl group, a biphenyl group, a terphenyl group, a naphthyl group, a fluorenyl group, a spiro-bifluorenyl group, a benzofluorenyl group, a dibenzofluorenyl group, a carbazolyl group, a dibenzofuranyl group, a dibenzothiophenyl group, a benzocarbazolyl group, and a dibenzocarbazolyl group, but embodiments are not limited thereto.

In some embodiments, a91 in Formulae 9-1 and 9-2 may be selected from 0 and 1, but embodiments are not limited thereto.

When a91 in Formulae 9-1 and 9-2 is 2, groups $L_{91}$ may be identical to or different from each other. When a91 in Formulae 9-1 and 9-2 is 0, $(L_{91})_{a91}$ may be a single bond.

In some embodiments, the first compound may be represented by one of Formulae 1-1 and 1-2, but embodiments are not limited thereto:

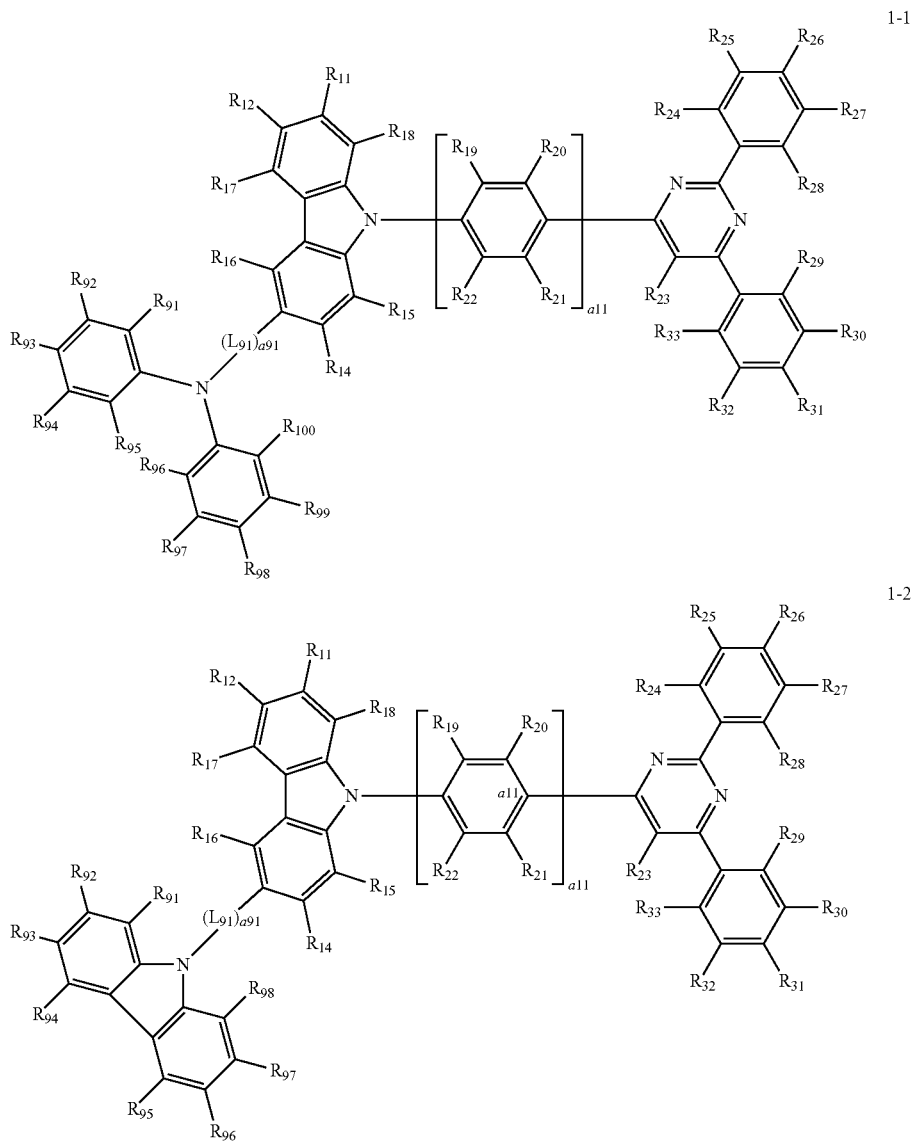

wherein, in Formulae 1-1 and 1-2, $R_{11}$ to $R_{33}$ and a11 may be the same as those described herein in relation to Formula 1, and $R_{91}$ to $R_{100}$, $L_{91}$, and a91 may be the same as those described herein in relation to Formulae 9-1 and 9-2.

In some embodiments, the first compound may be selected from compounds below, but embodiments are not limited thereto:
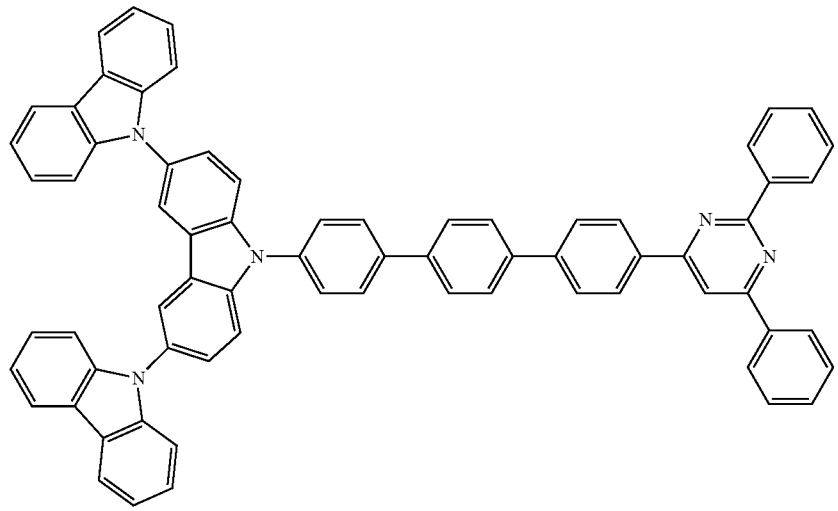
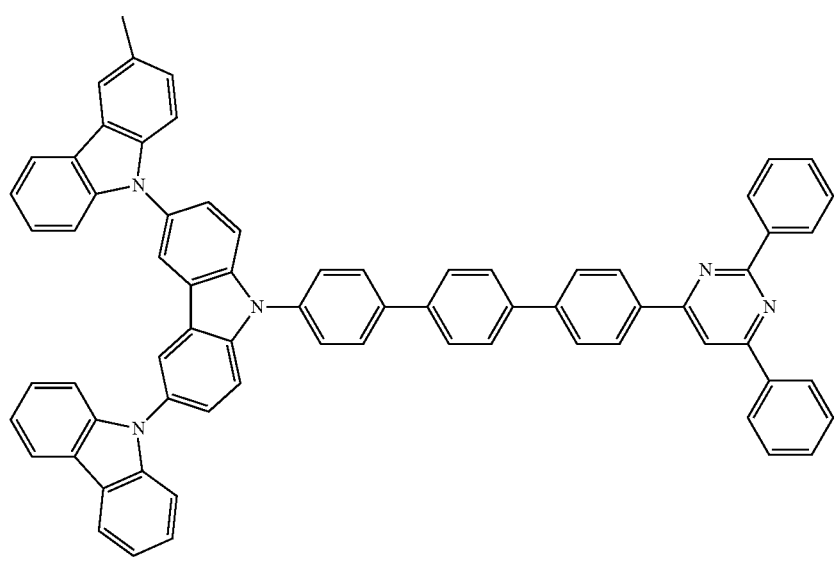
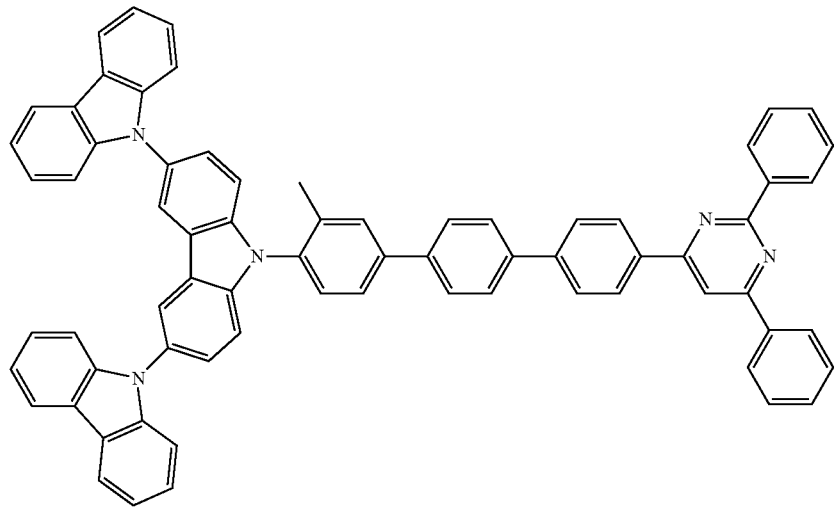

-continued
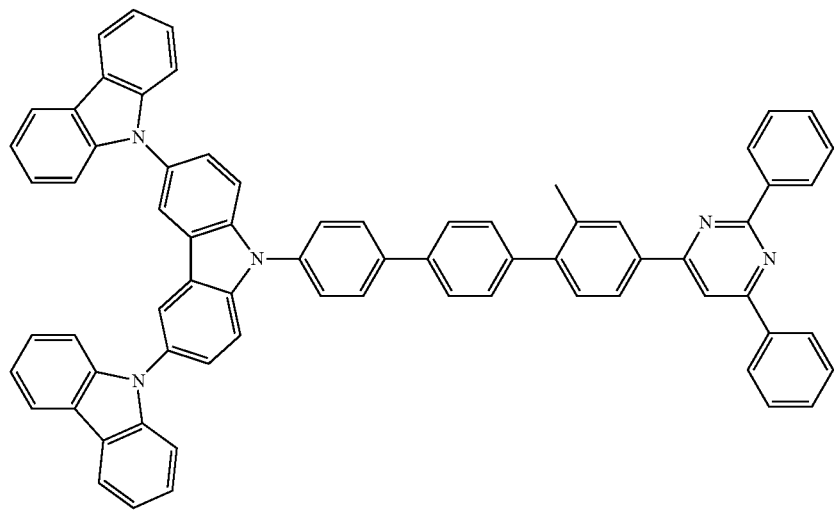
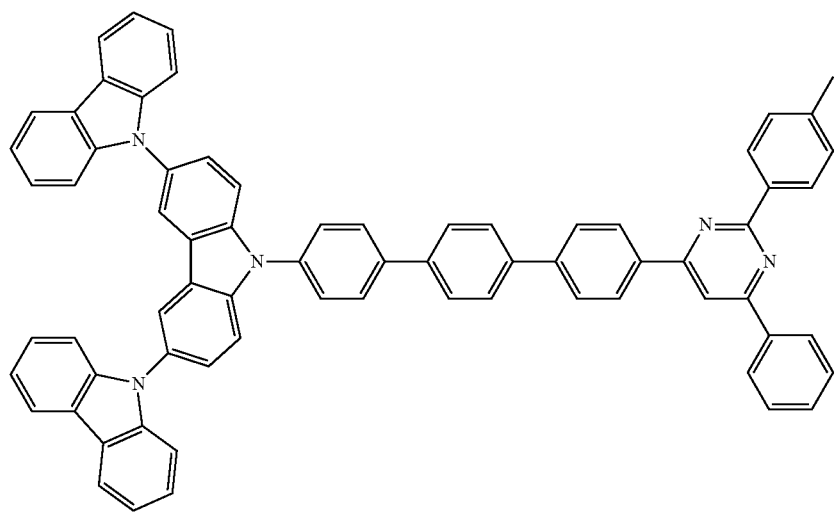
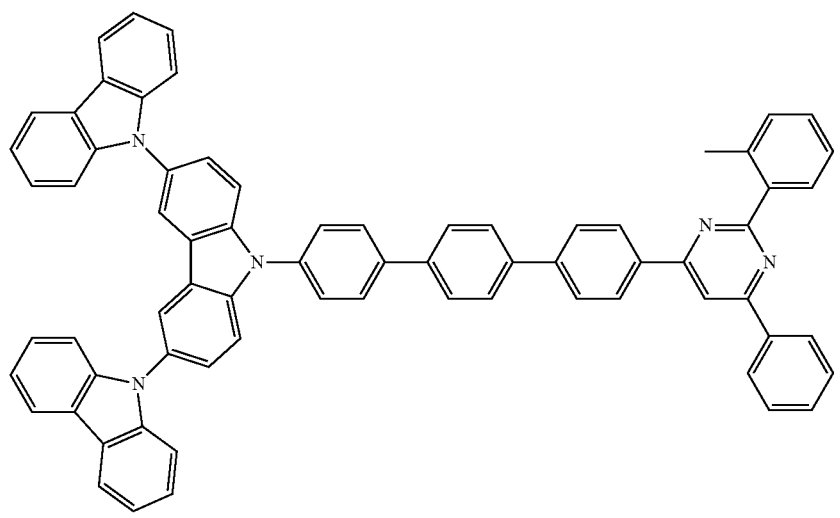

-continued
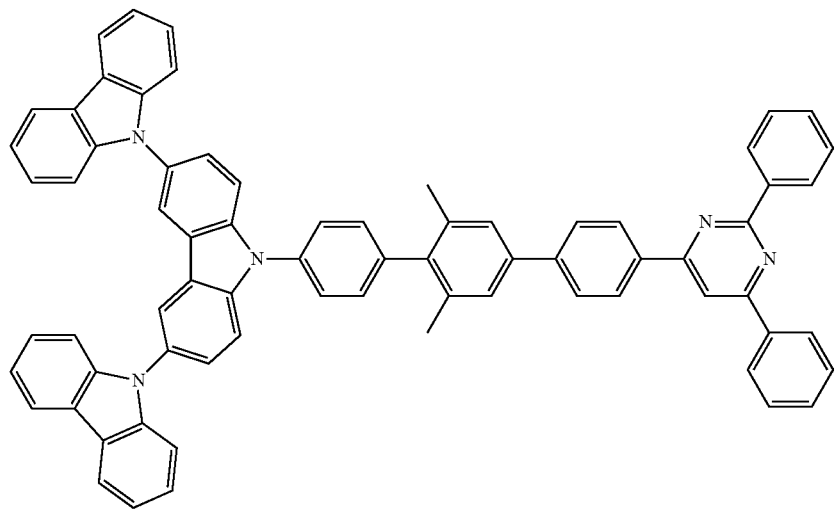
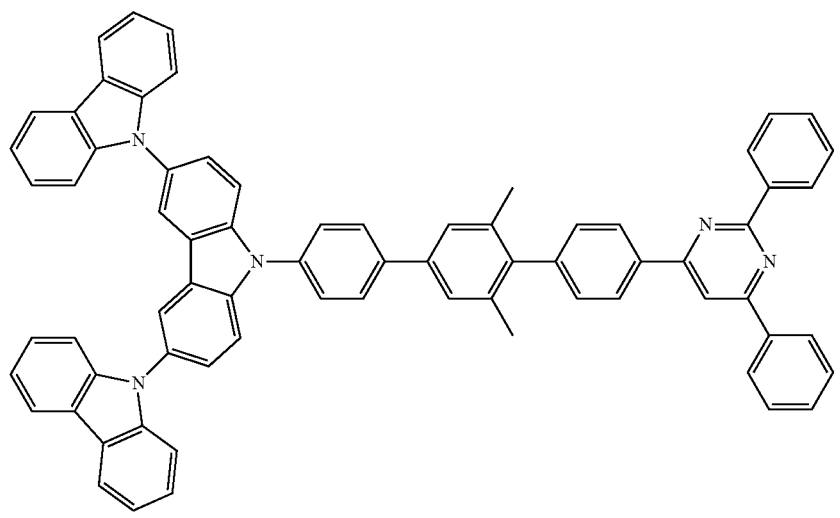
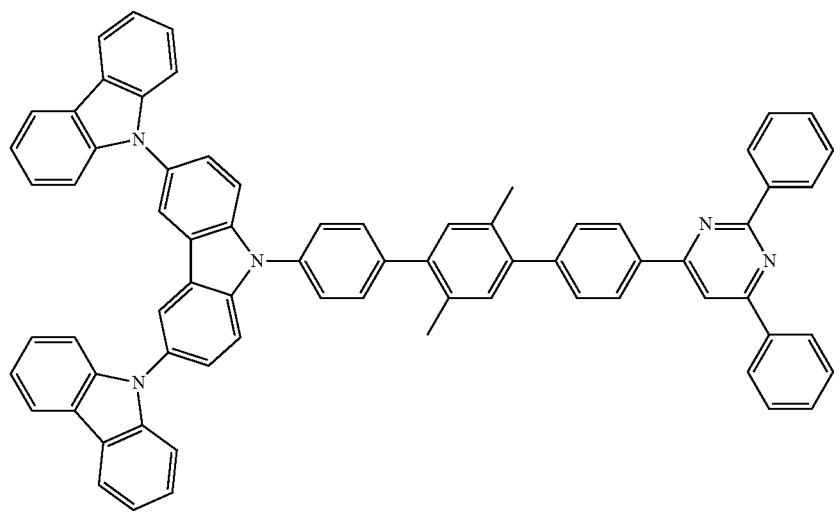

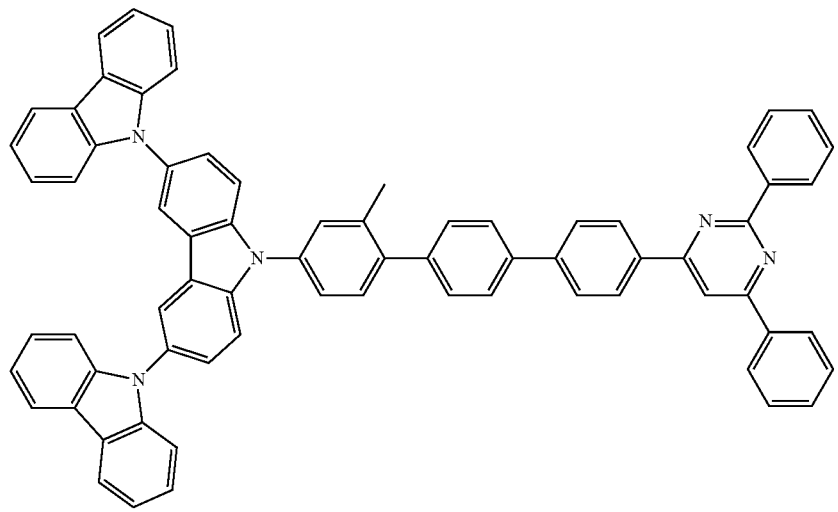
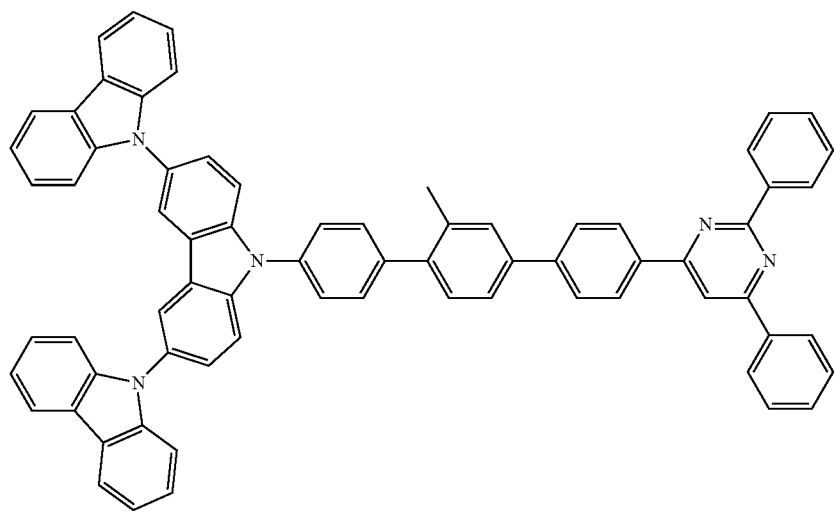
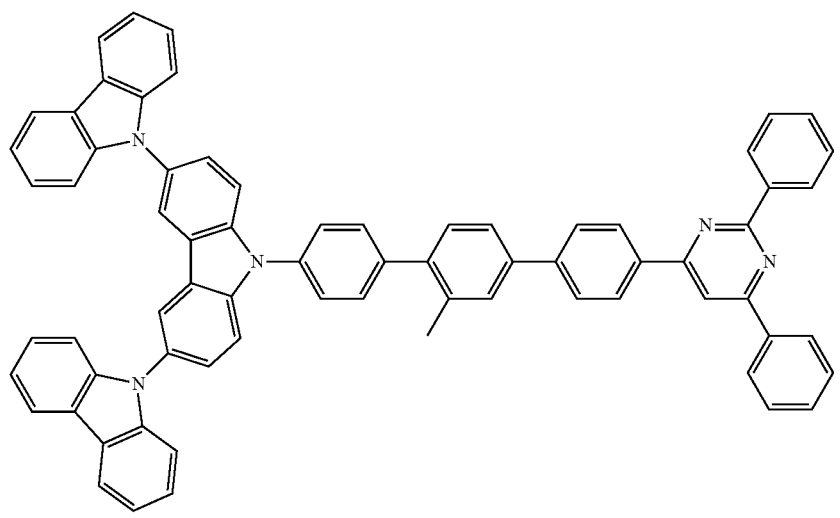

-continued
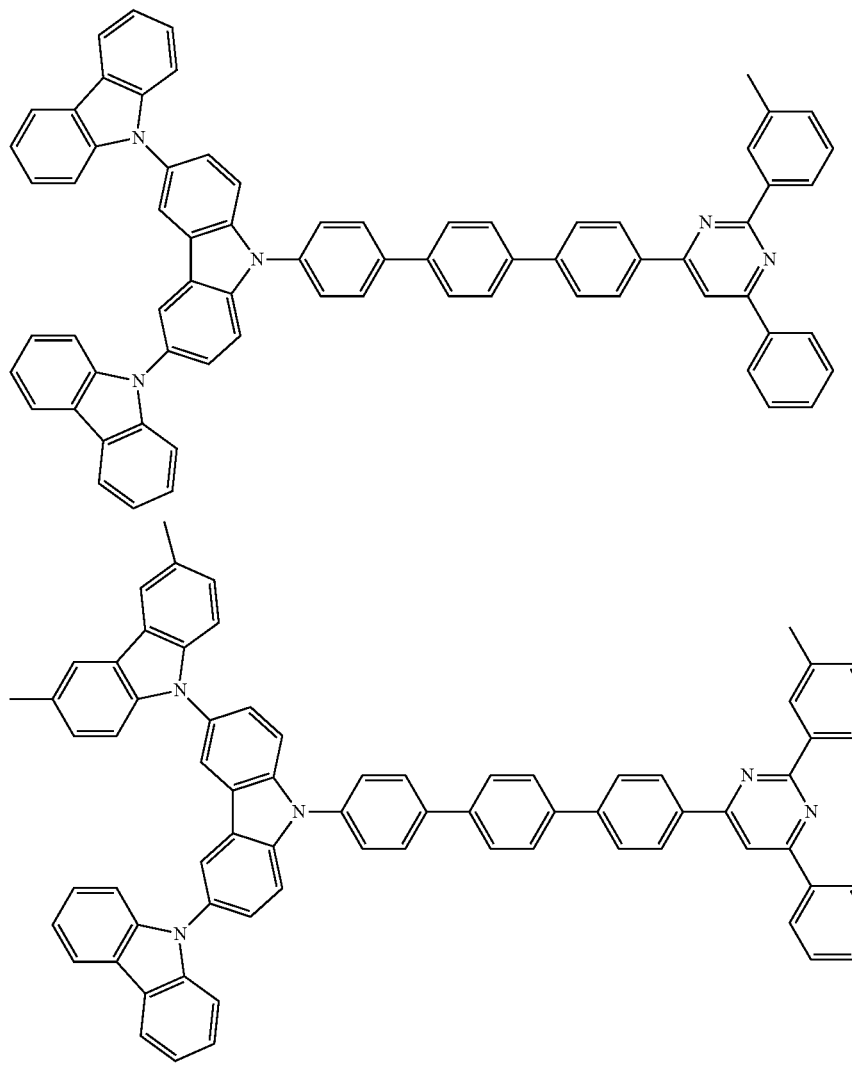
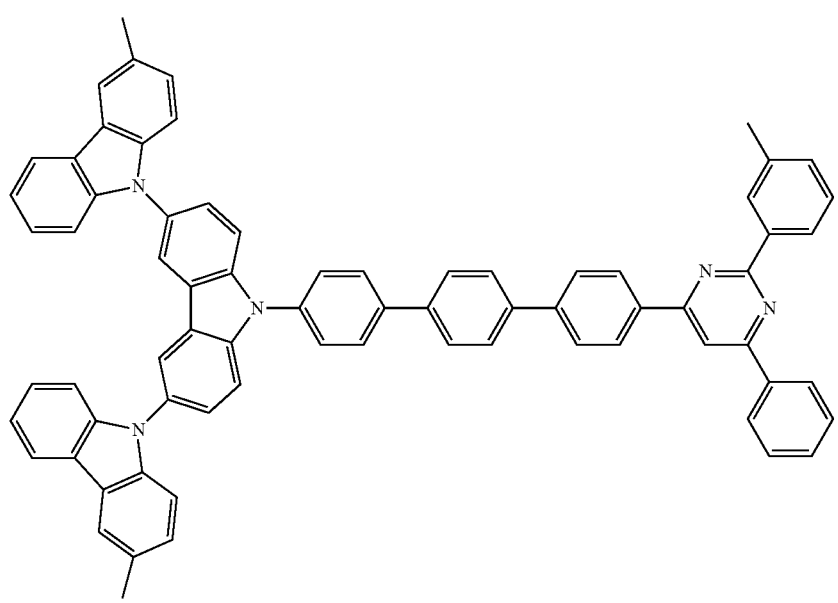

-continued
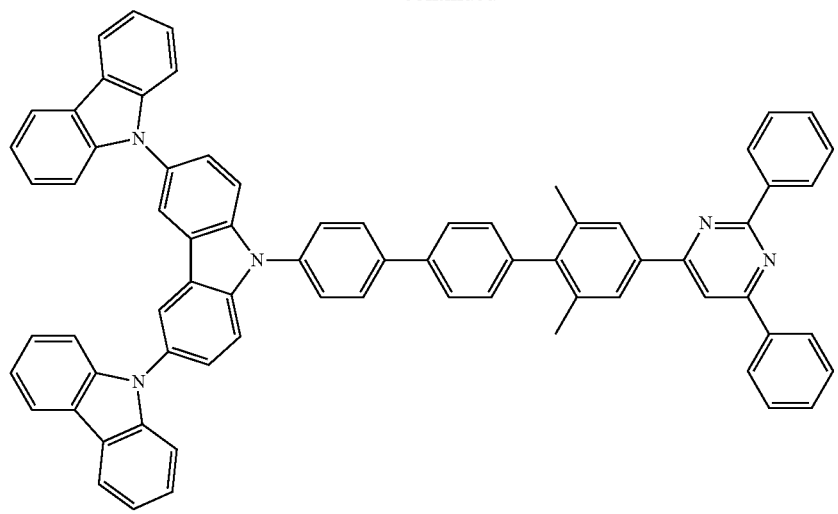
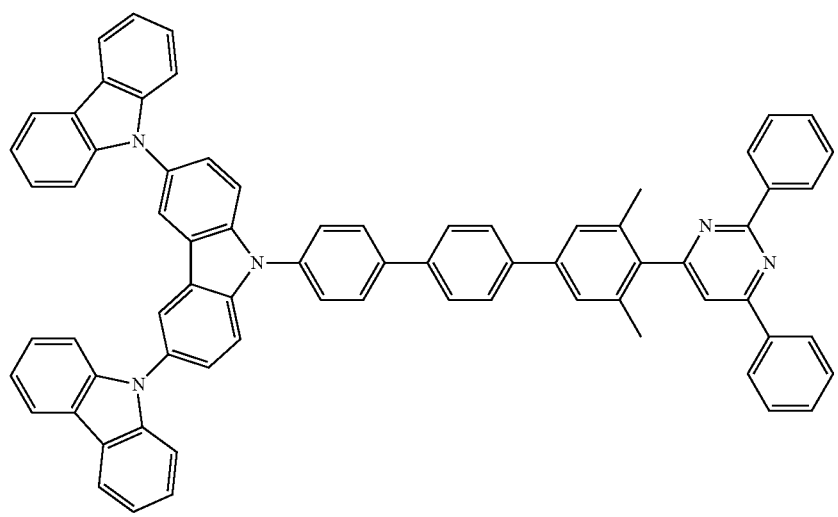
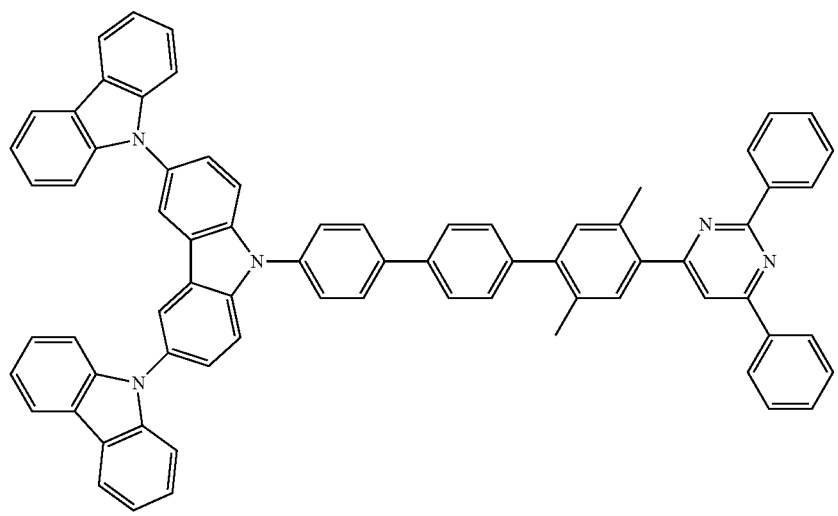

-continued
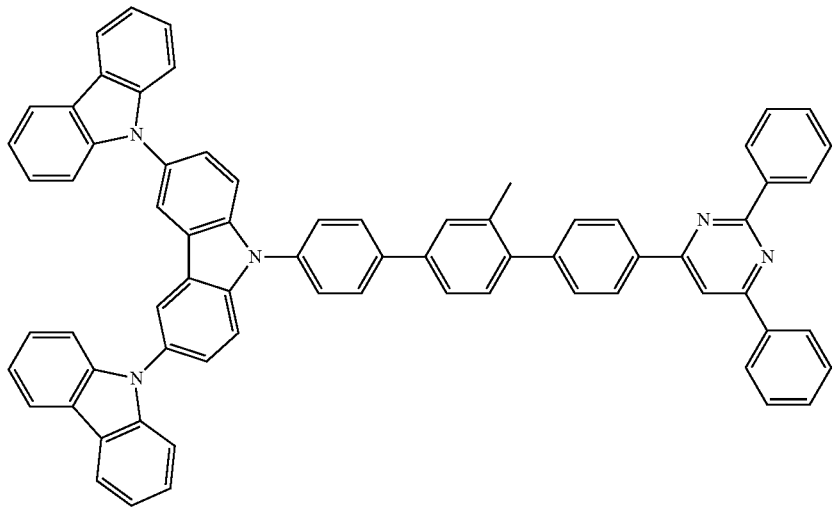
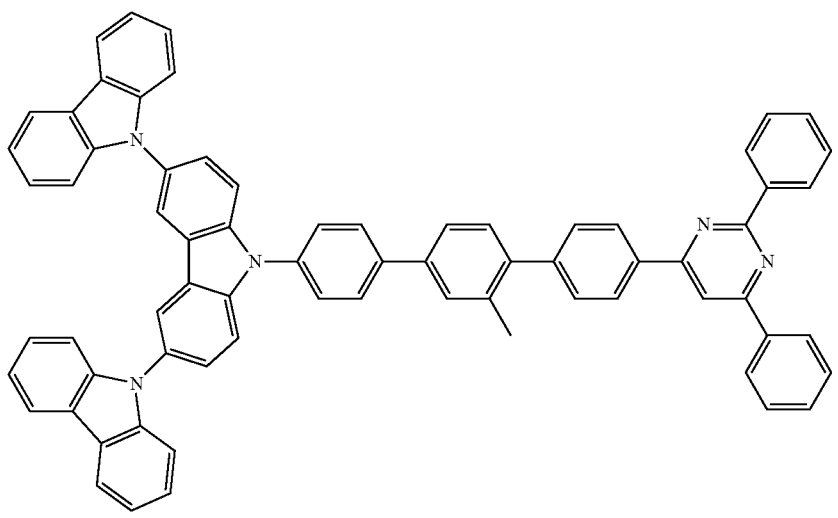
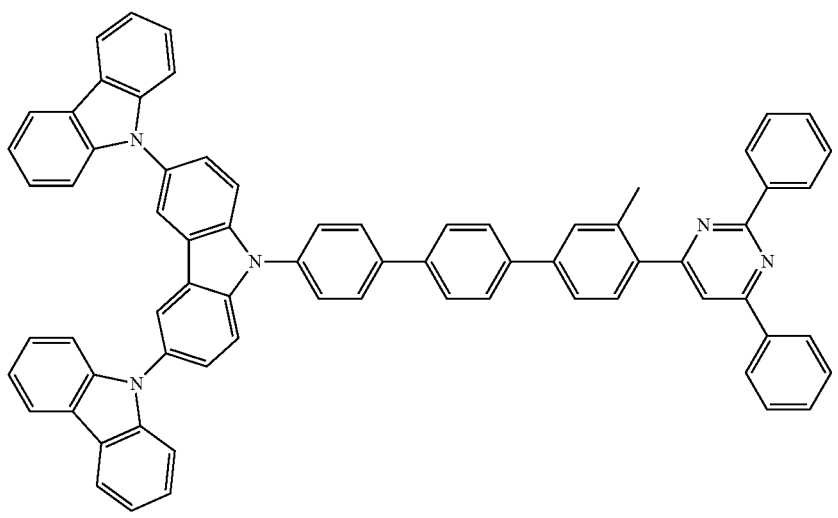

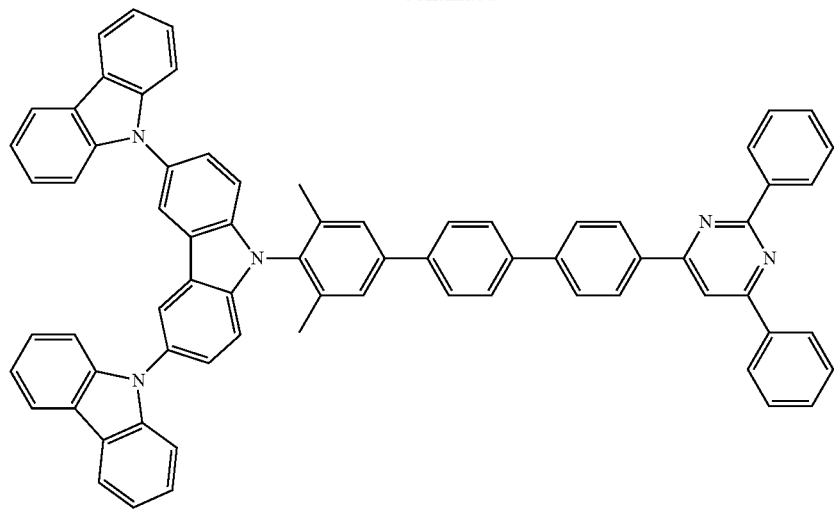
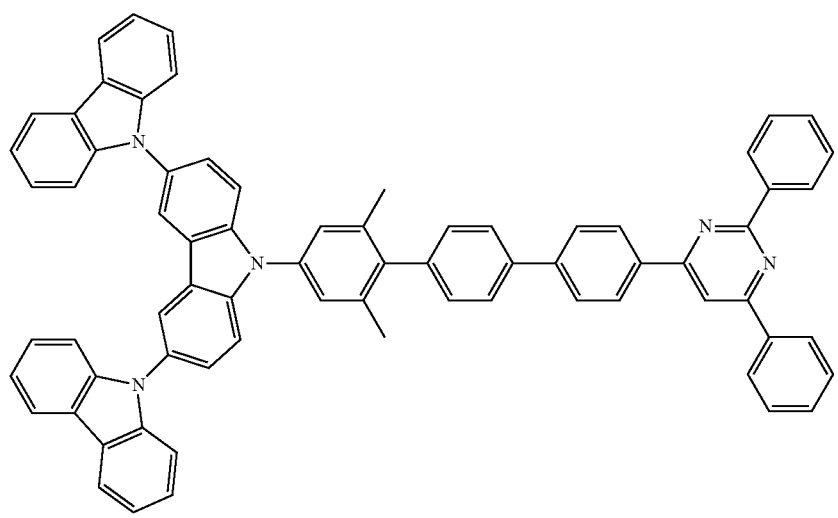
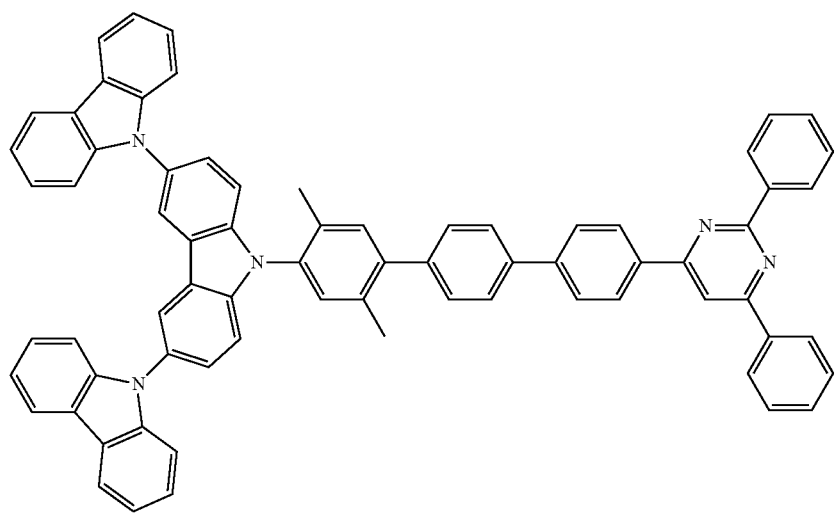

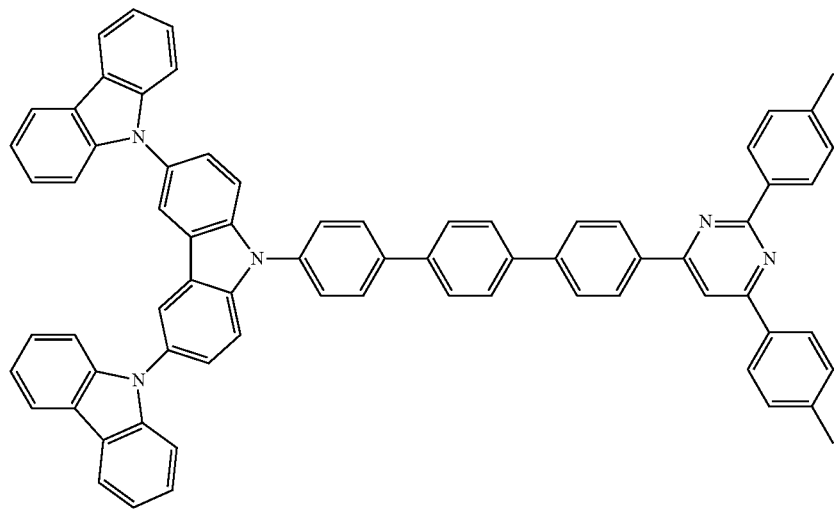
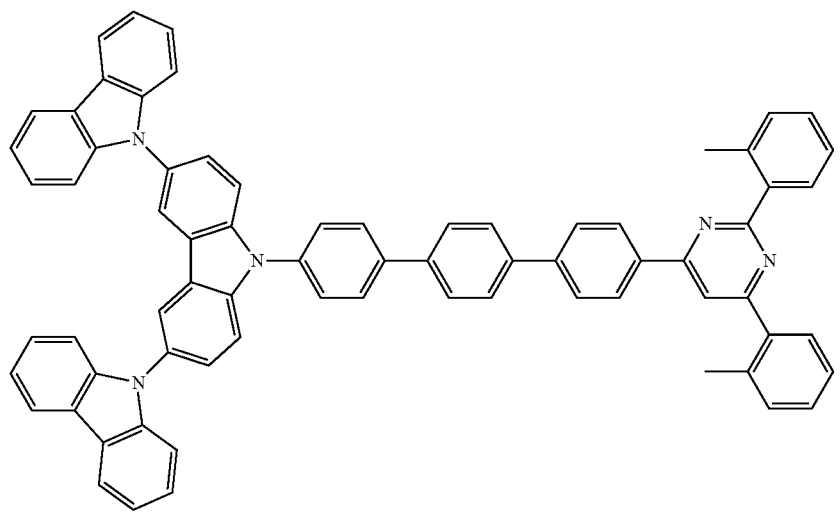

-continued

-continued
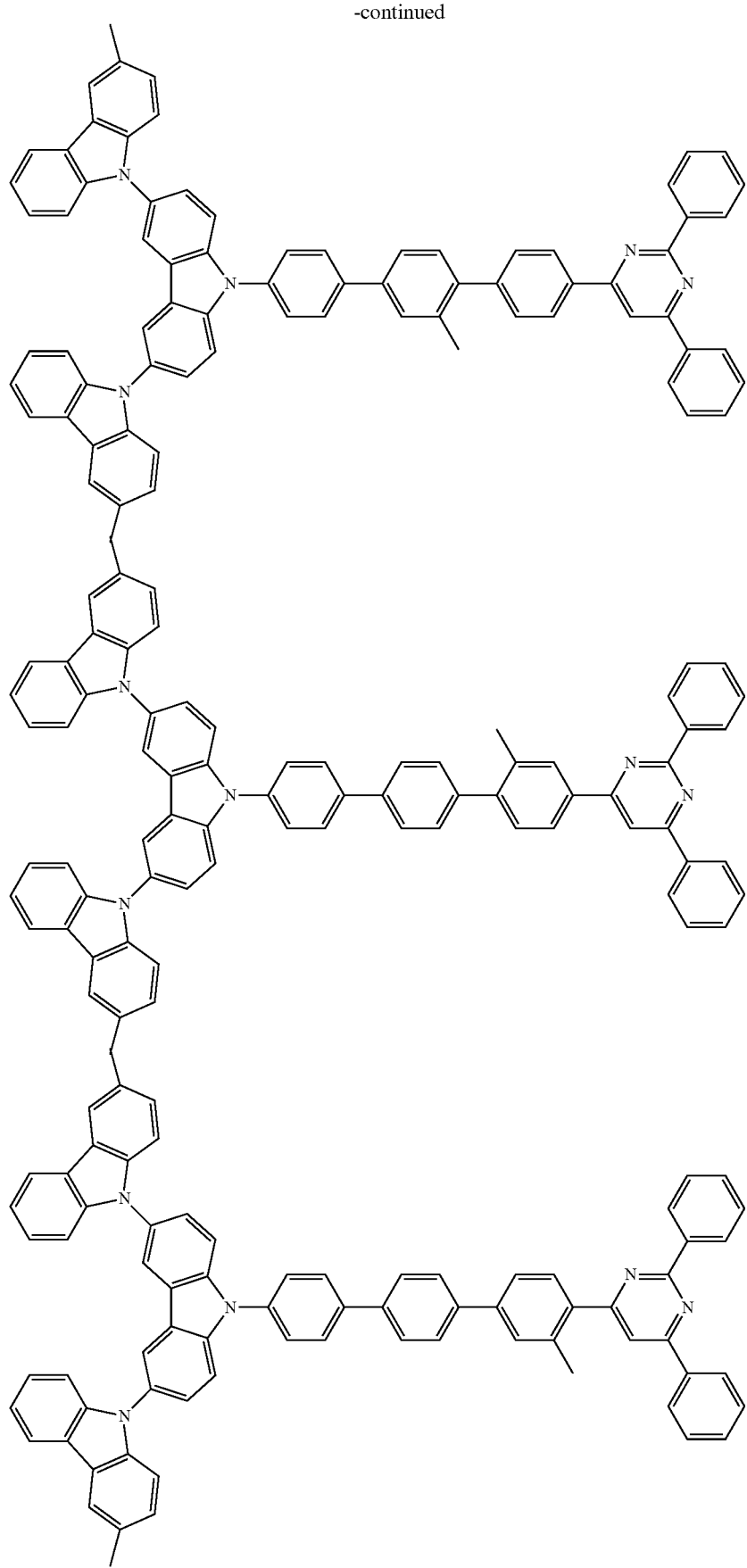

-continued
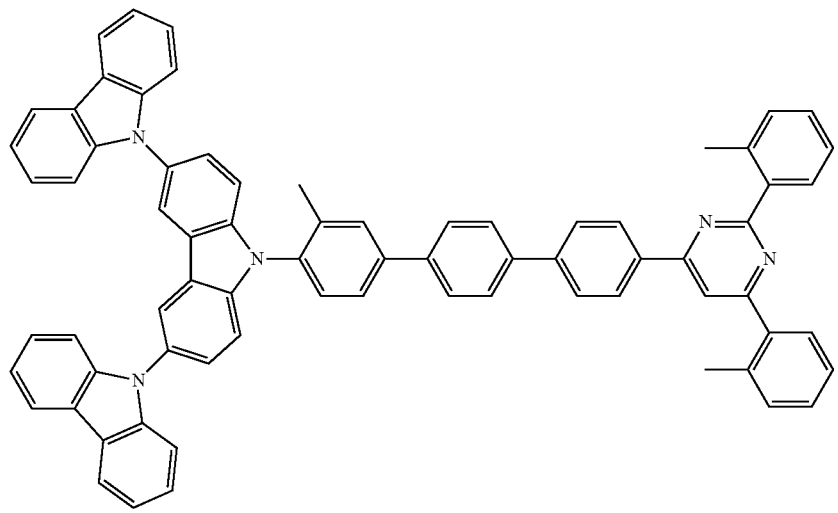
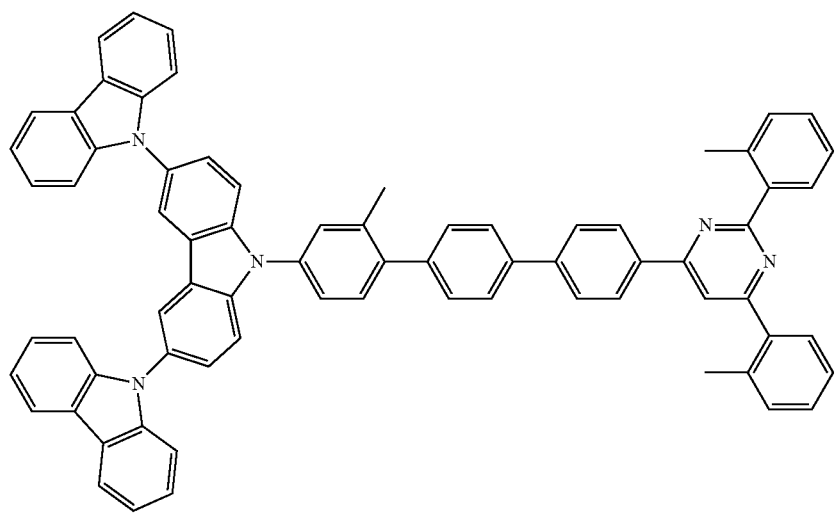
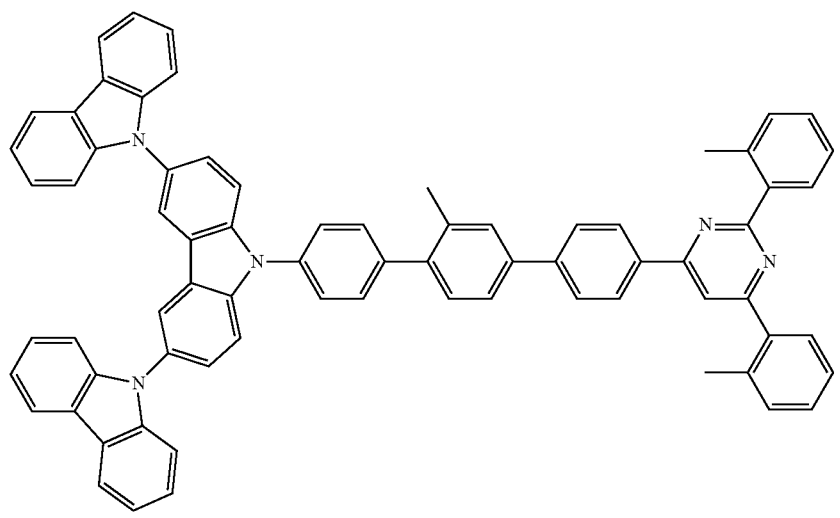

-continued
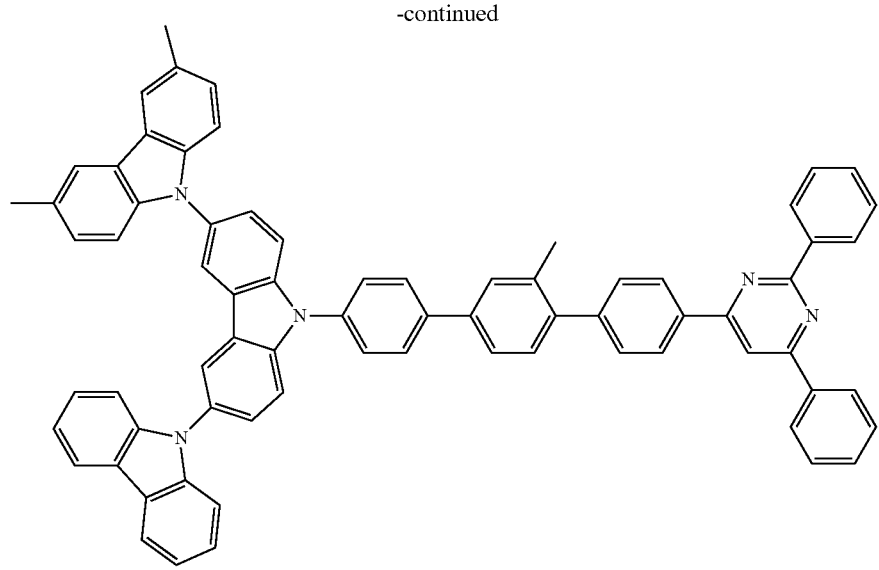
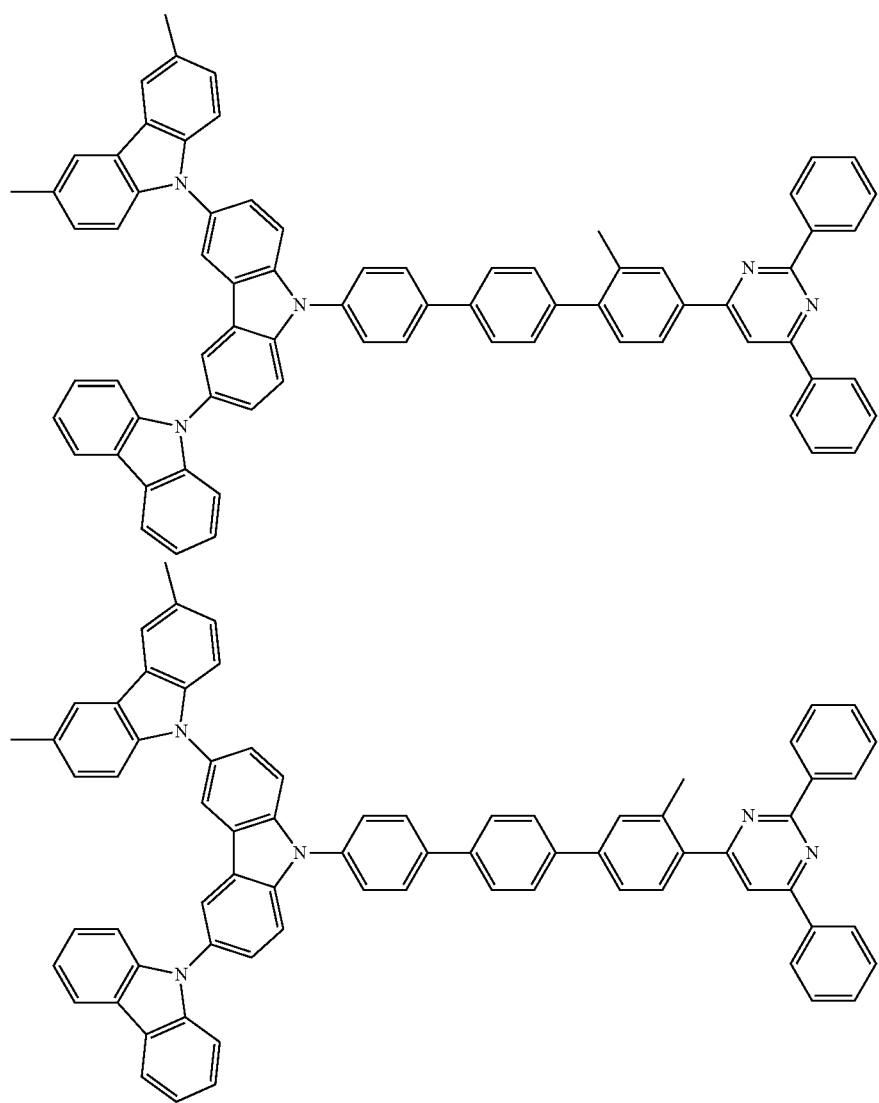

-continued
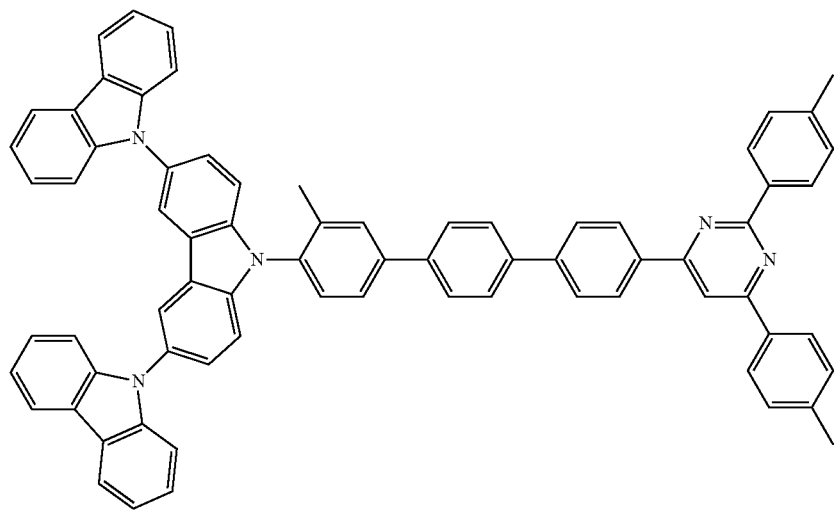
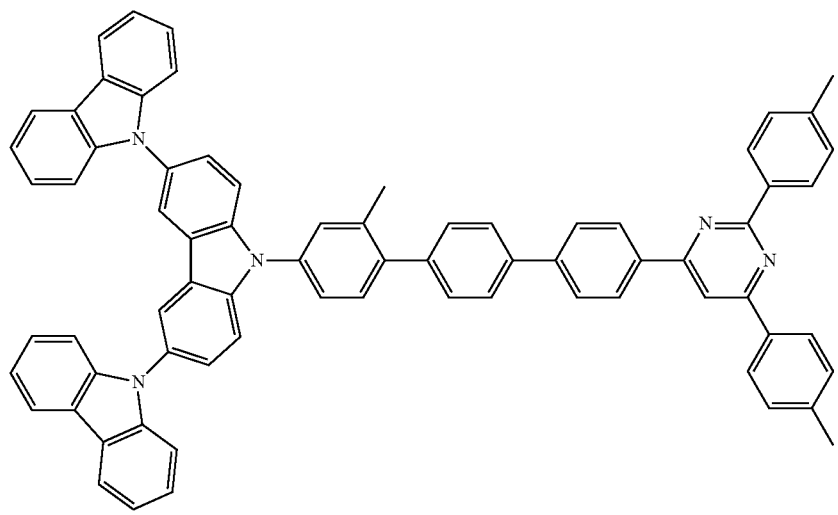
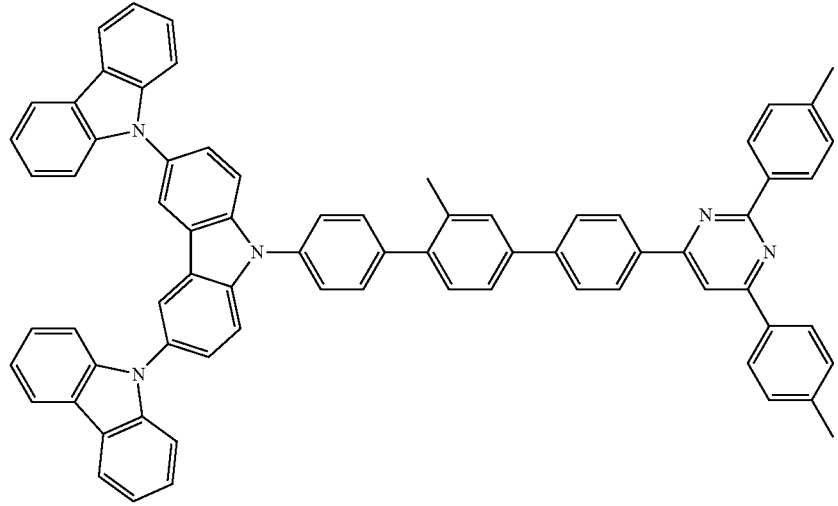

-continued
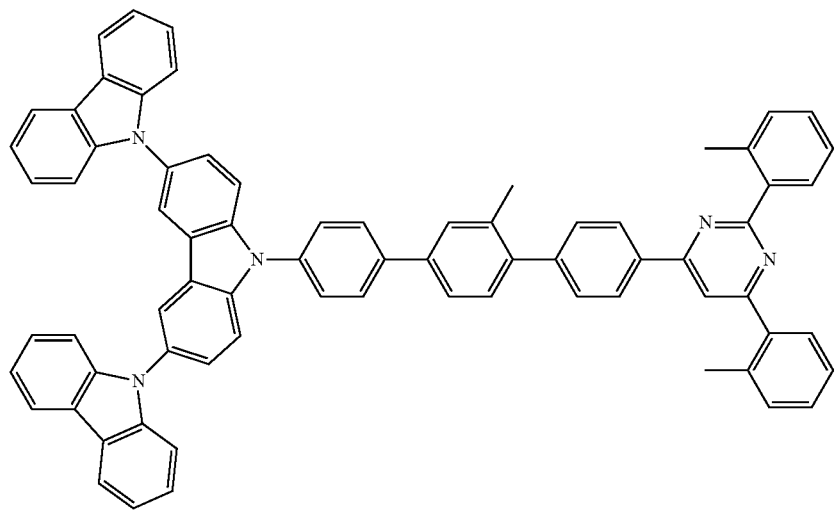
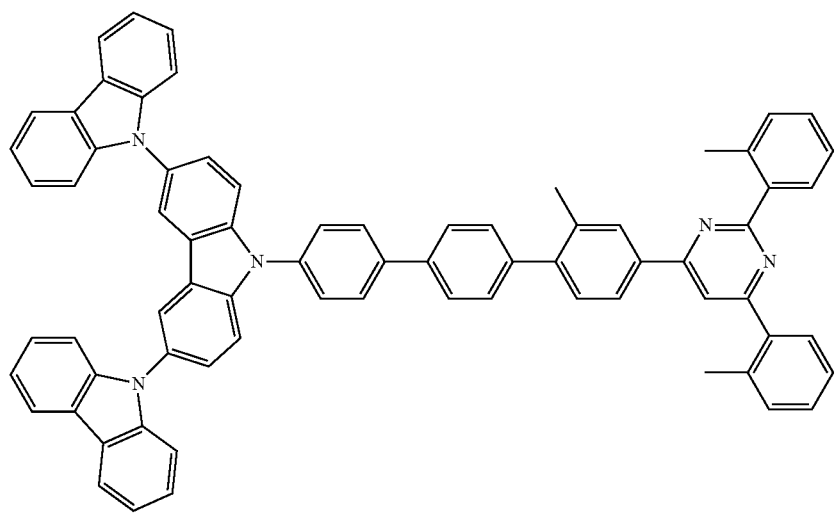
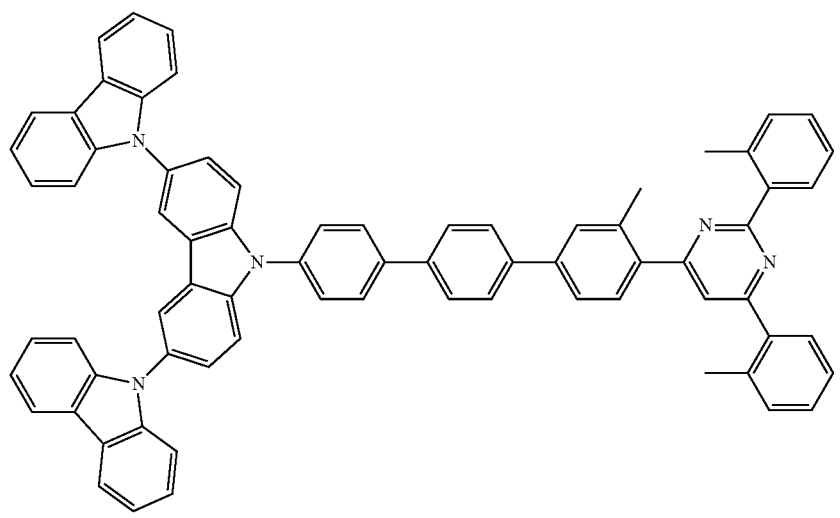

-continued
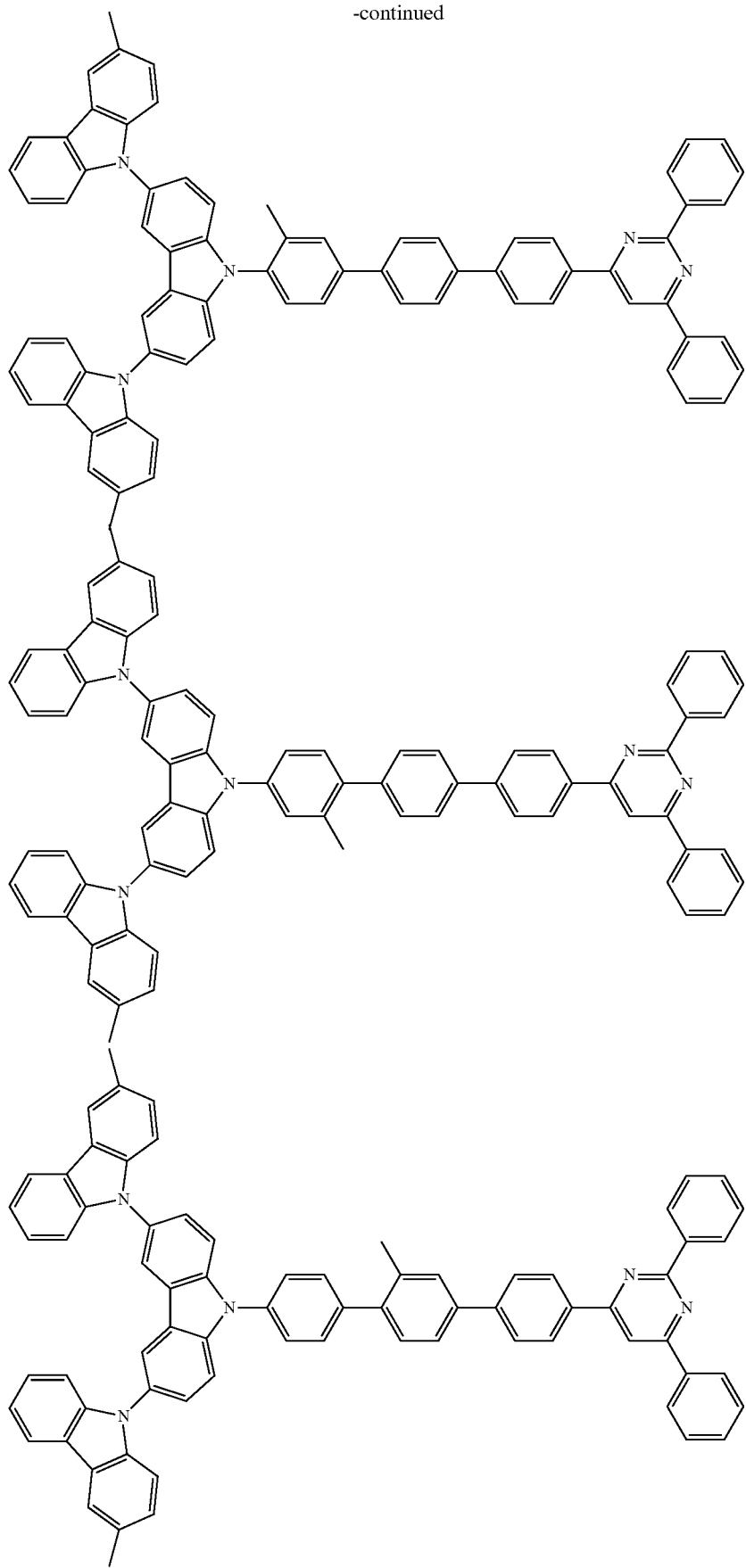

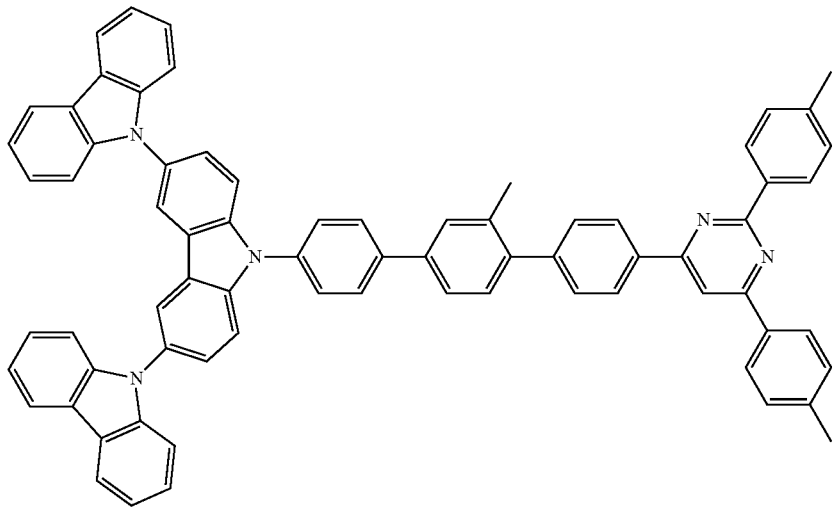
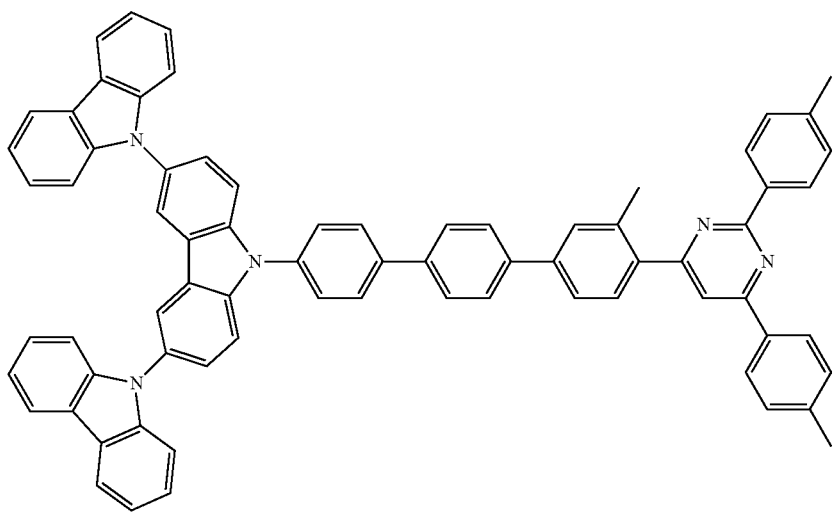

-continued
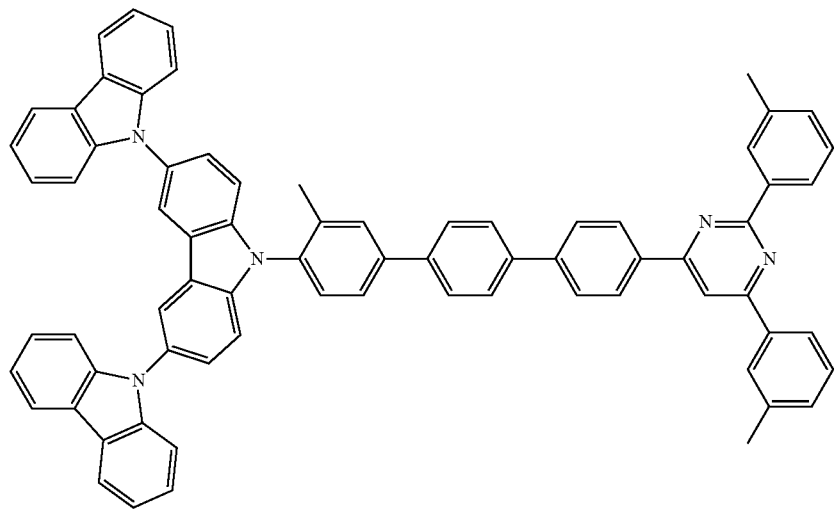
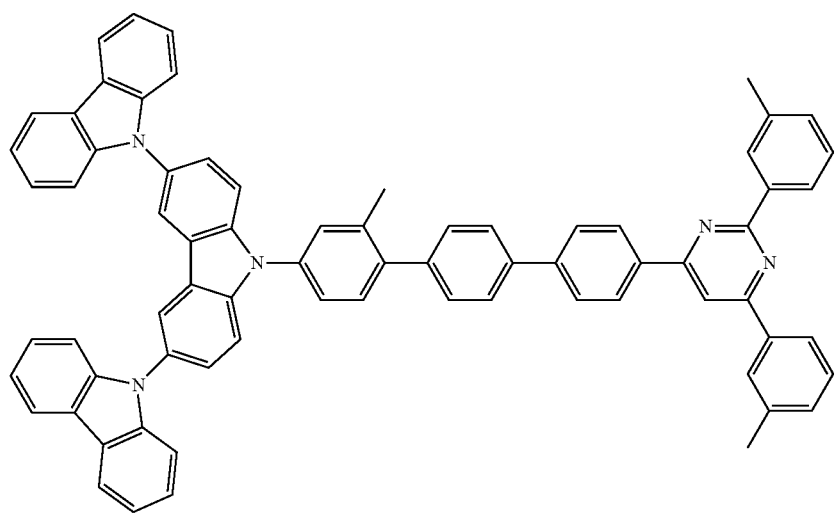
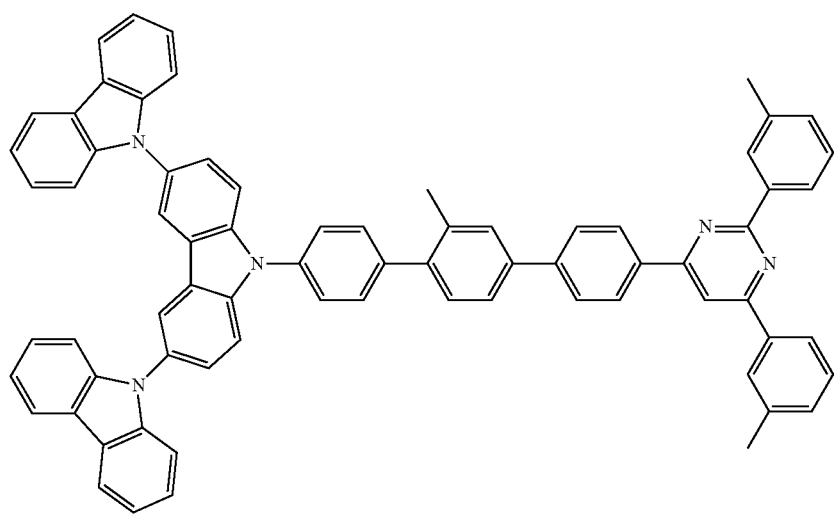

-continued
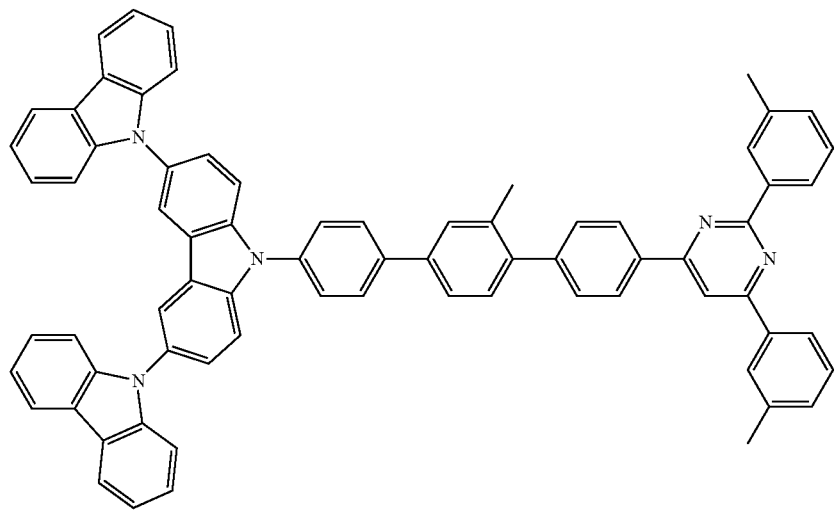
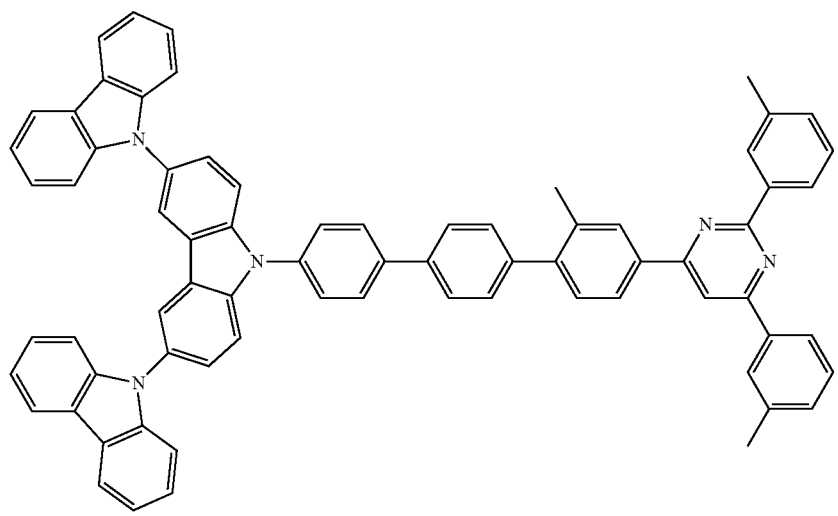
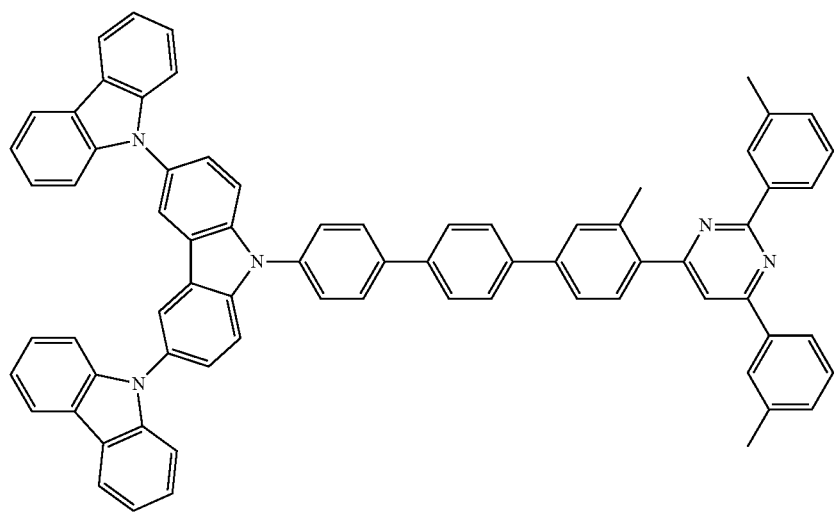

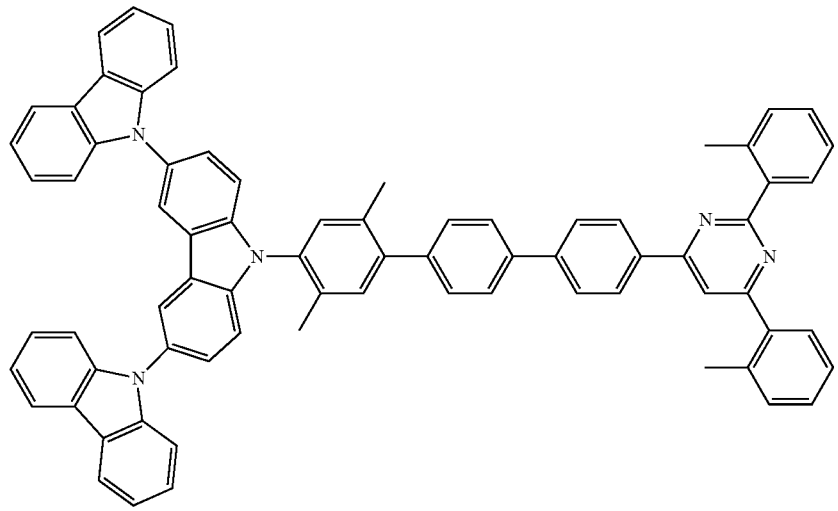
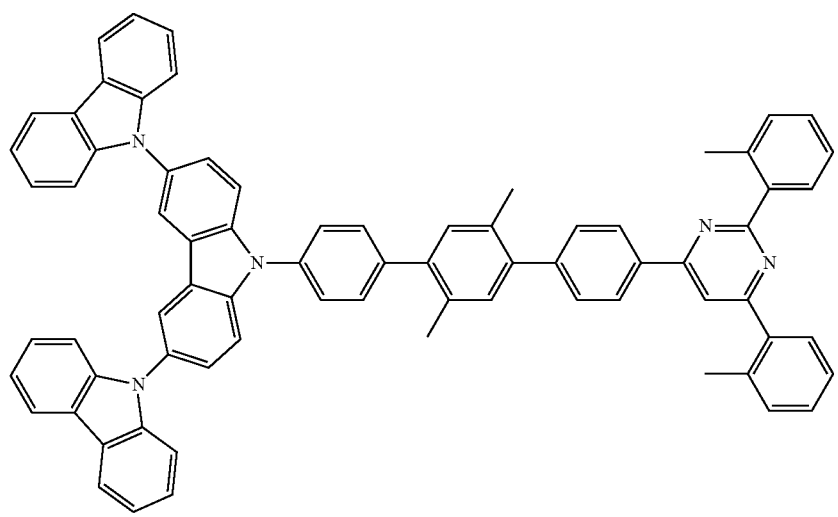
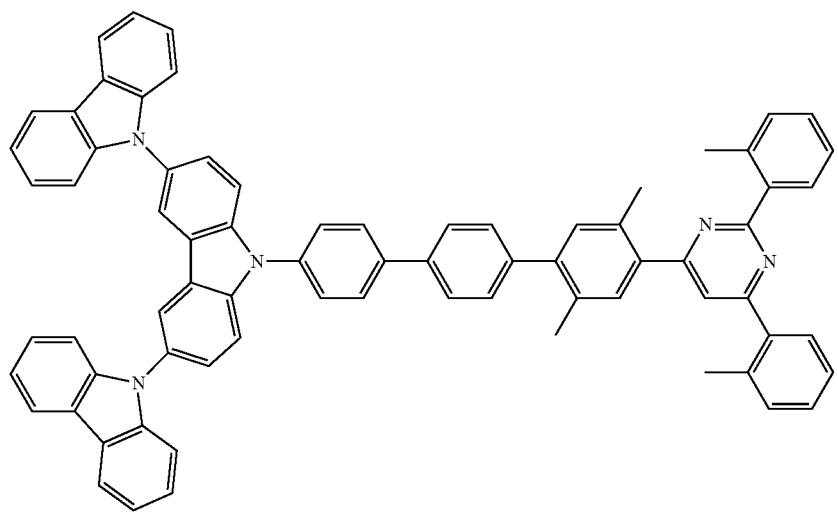

-continued
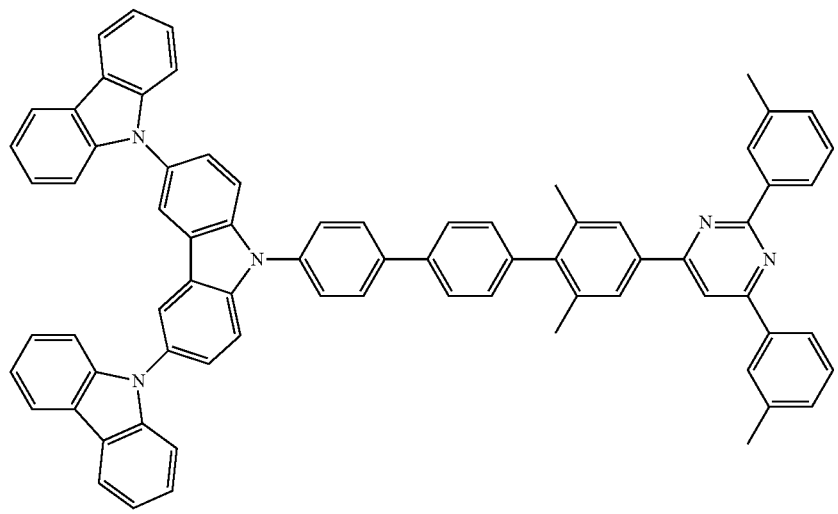
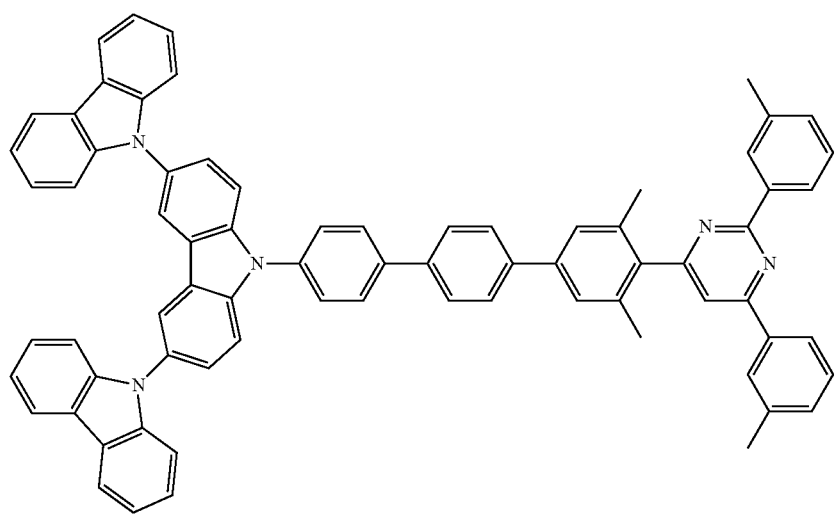
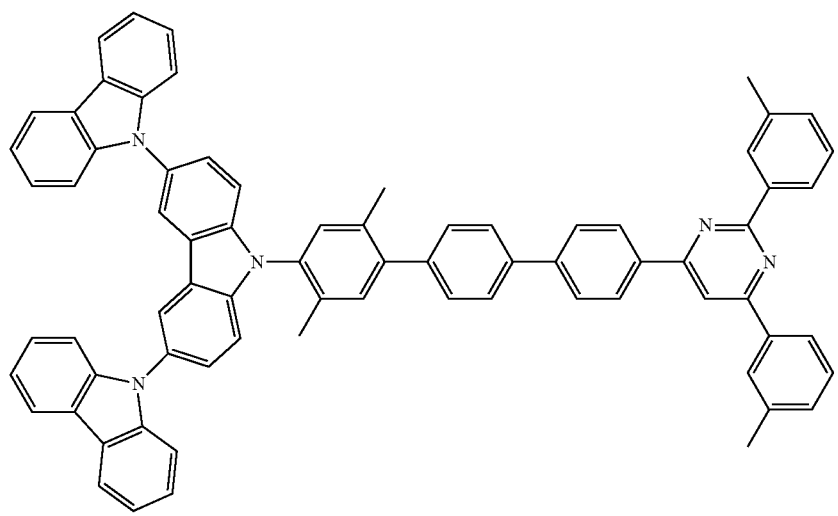

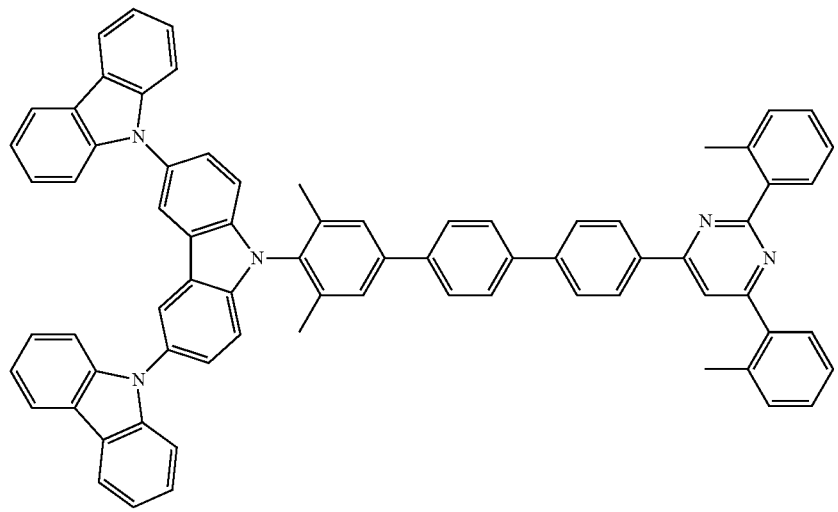
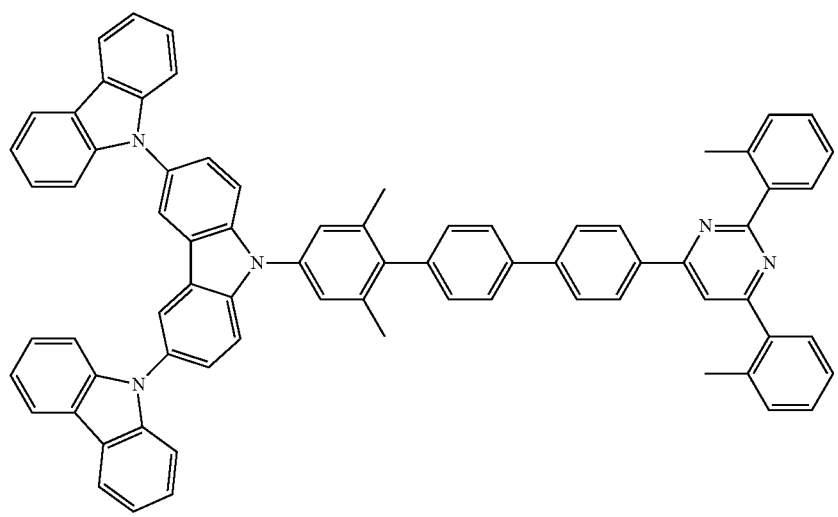
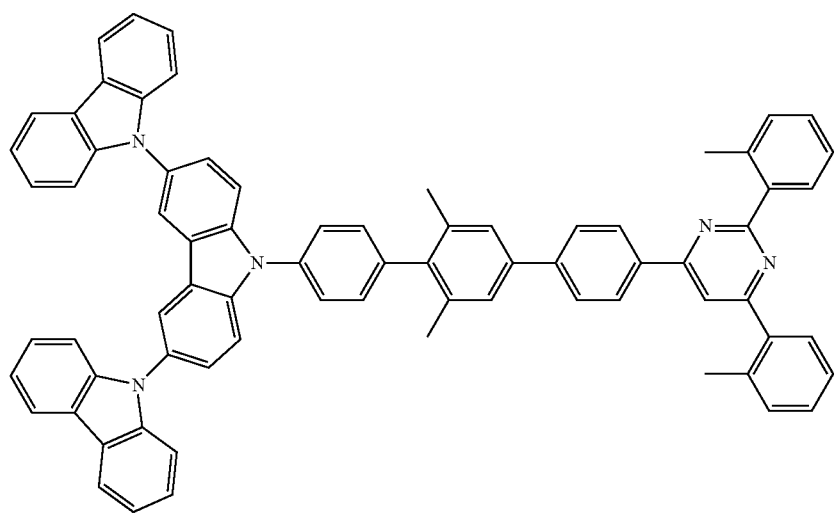

-continued
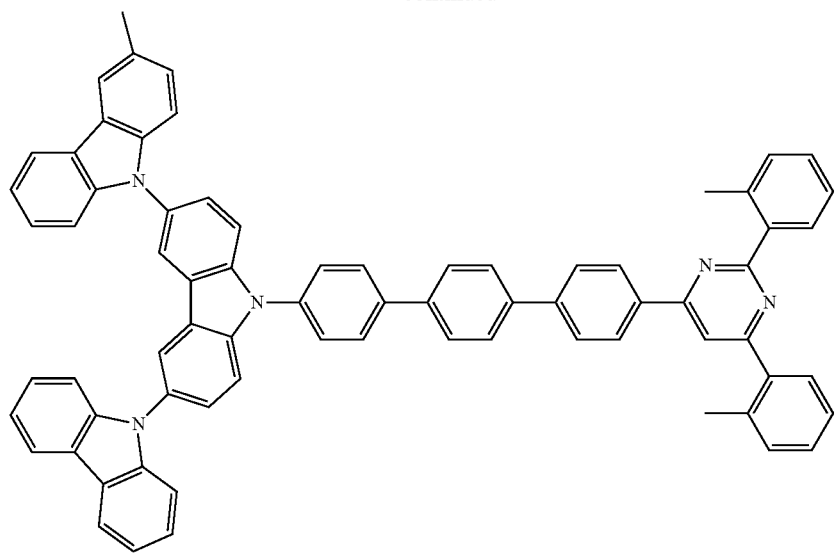
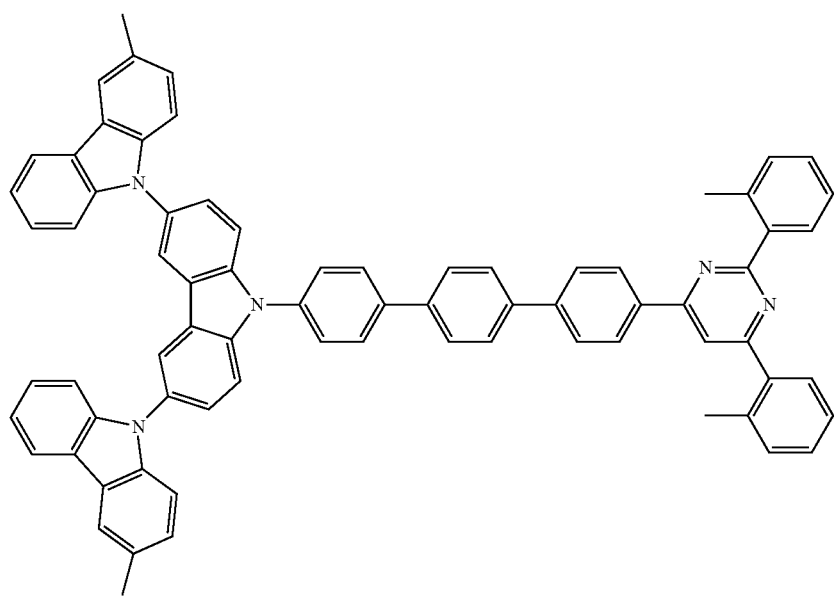
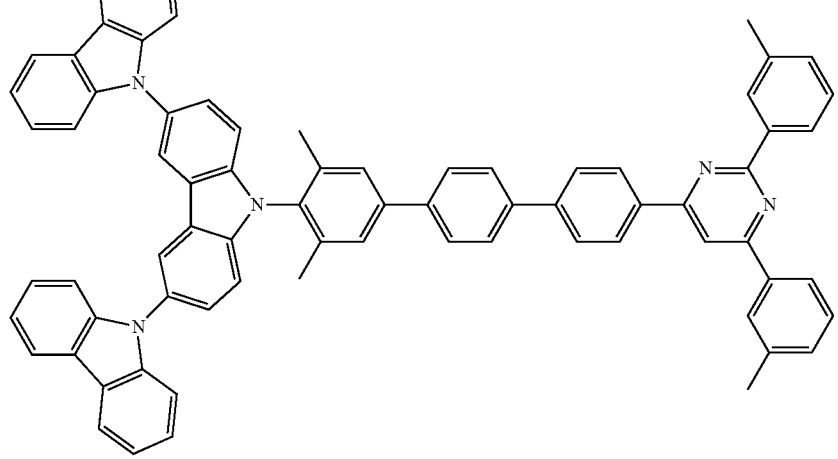

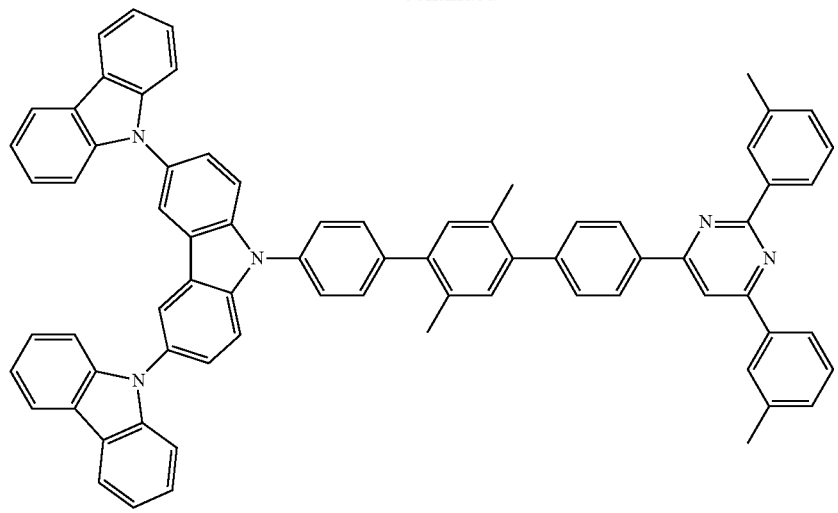
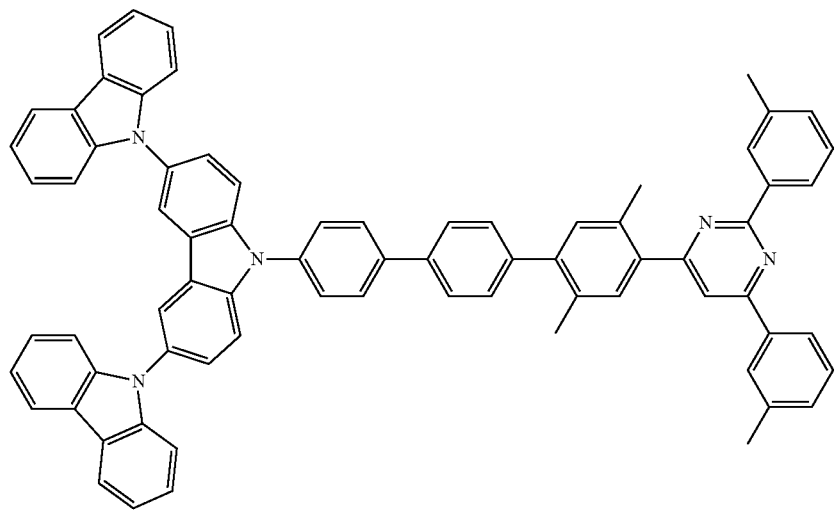
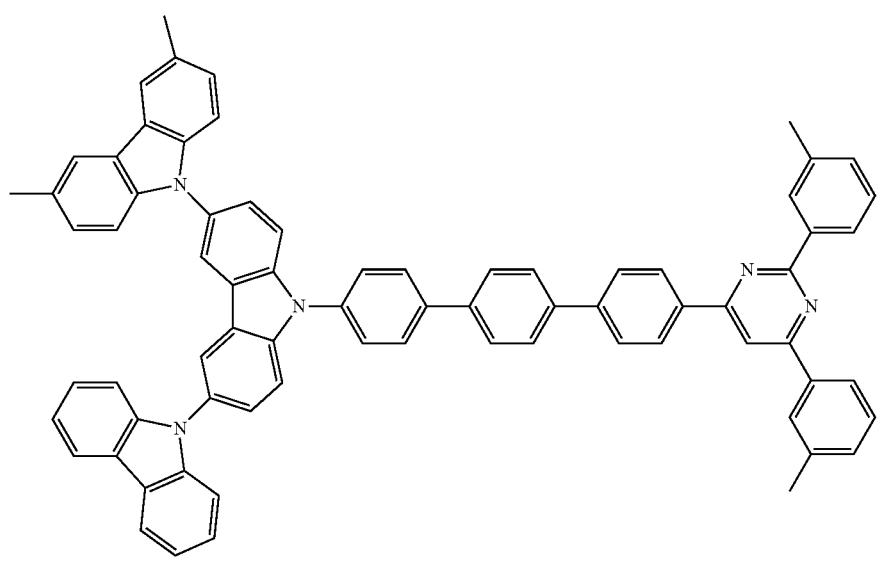

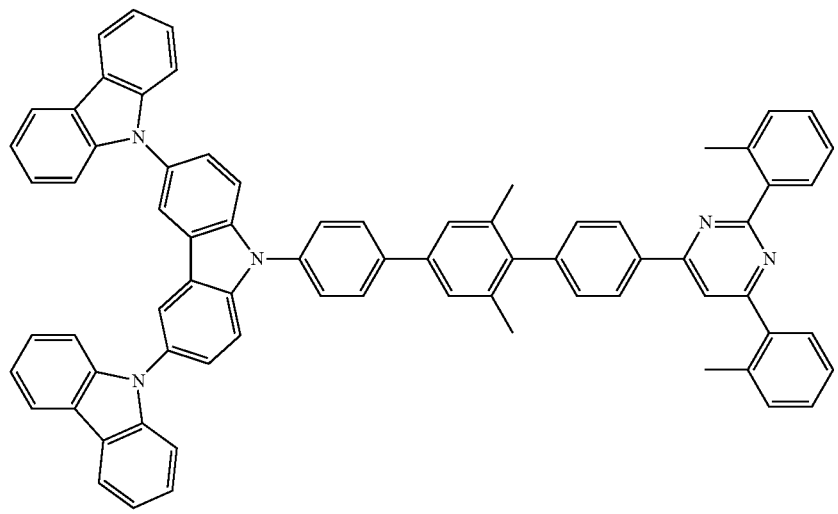
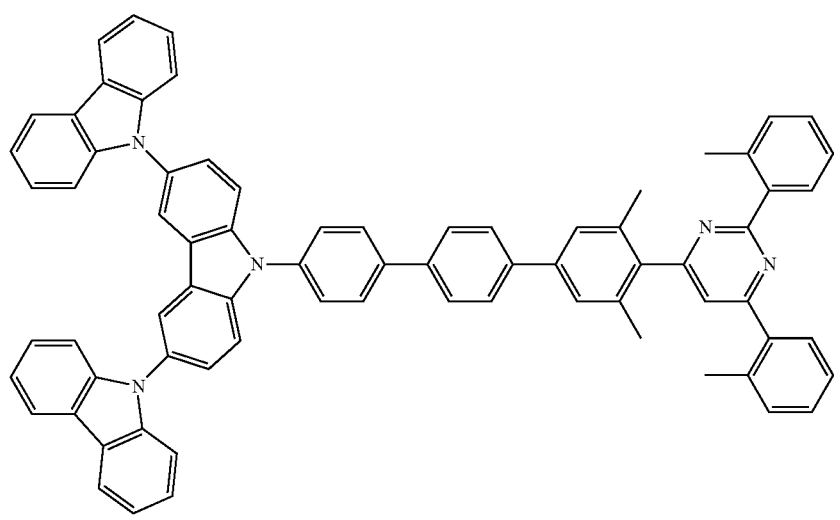

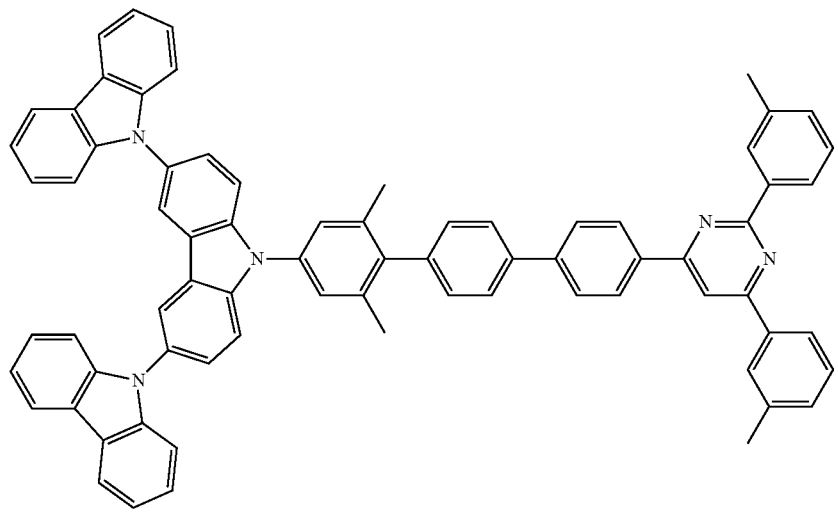
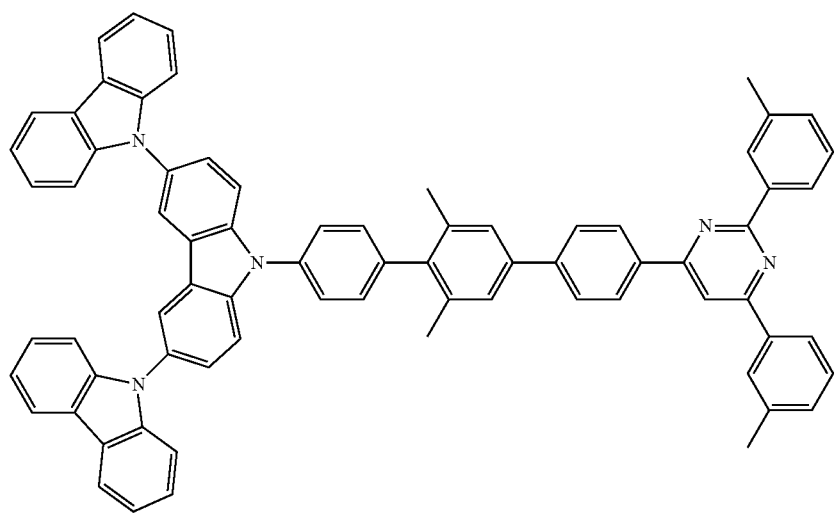
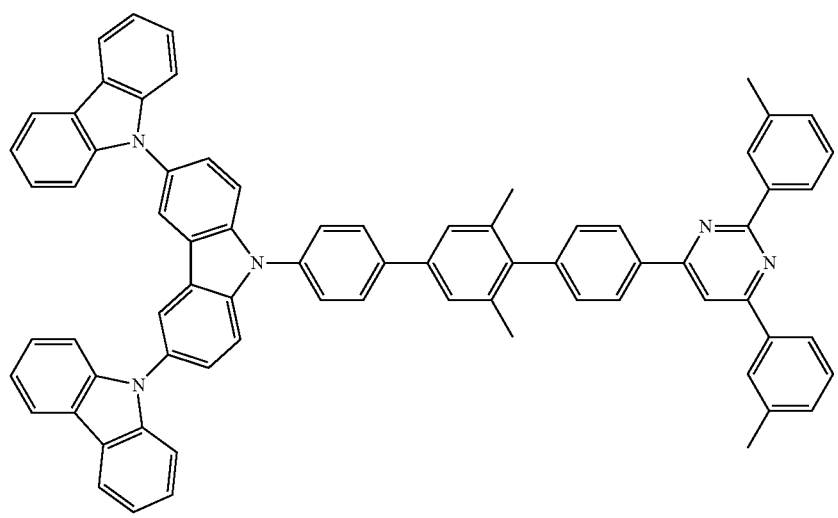

-continued
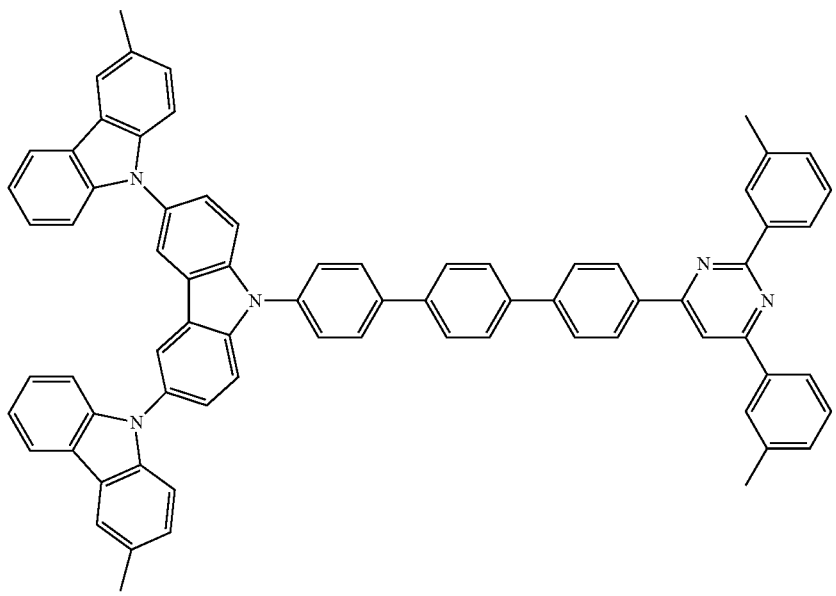
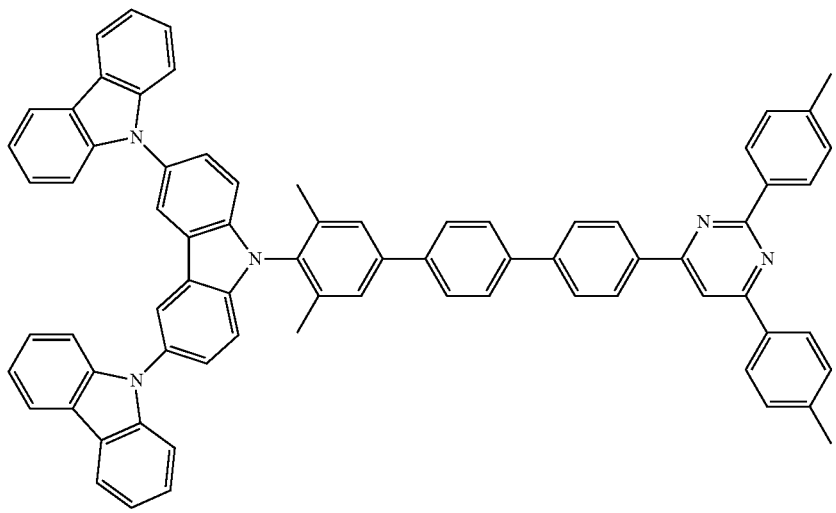
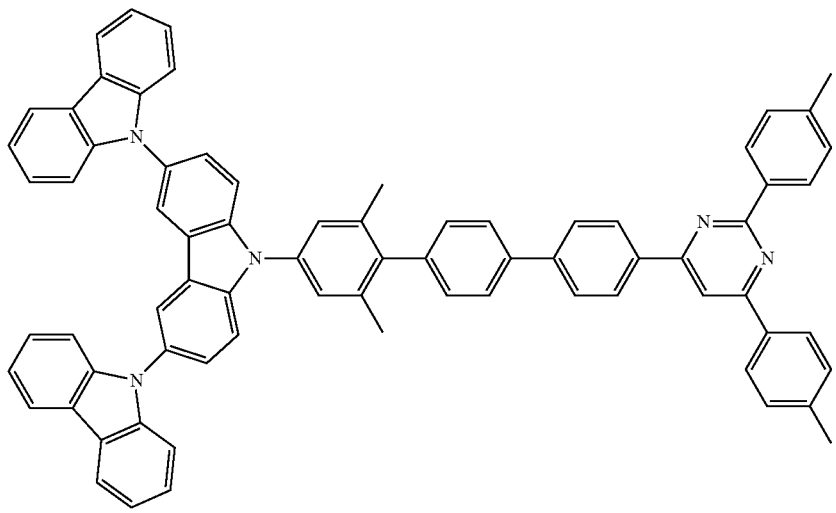

-continued
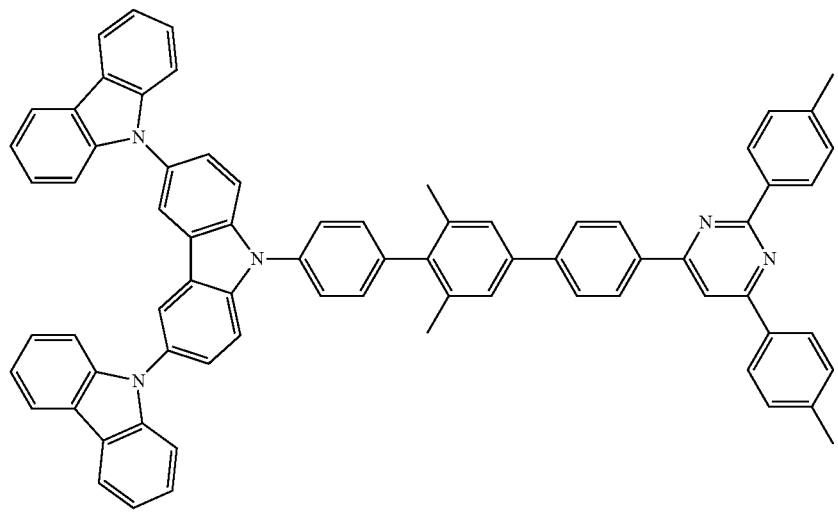
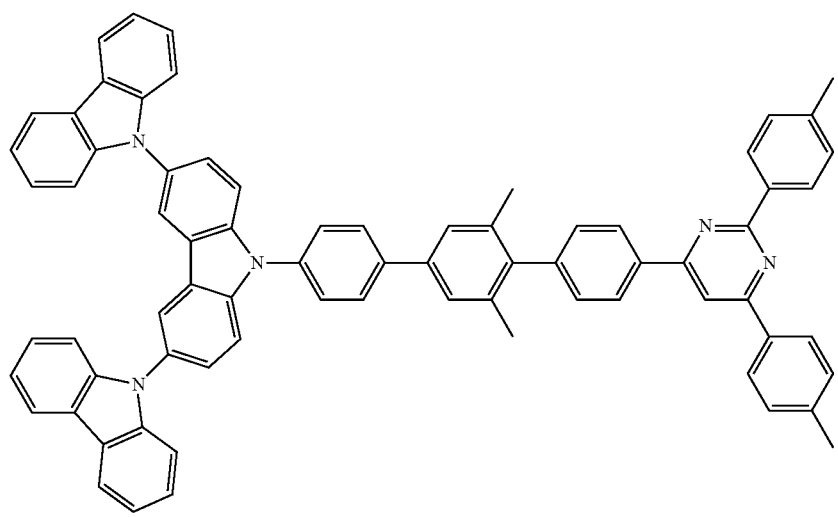
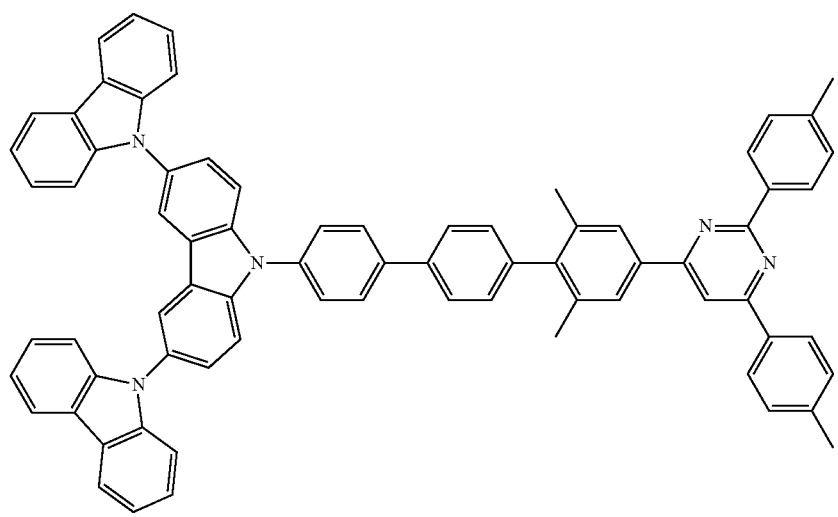

-continued
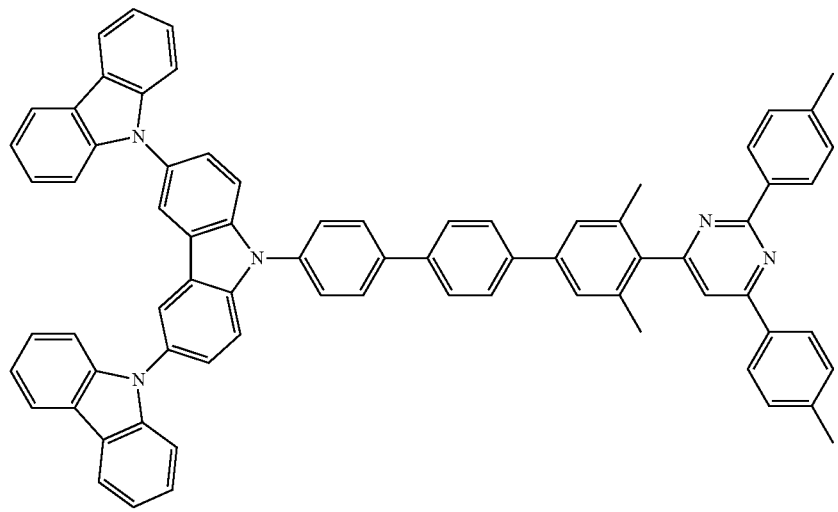
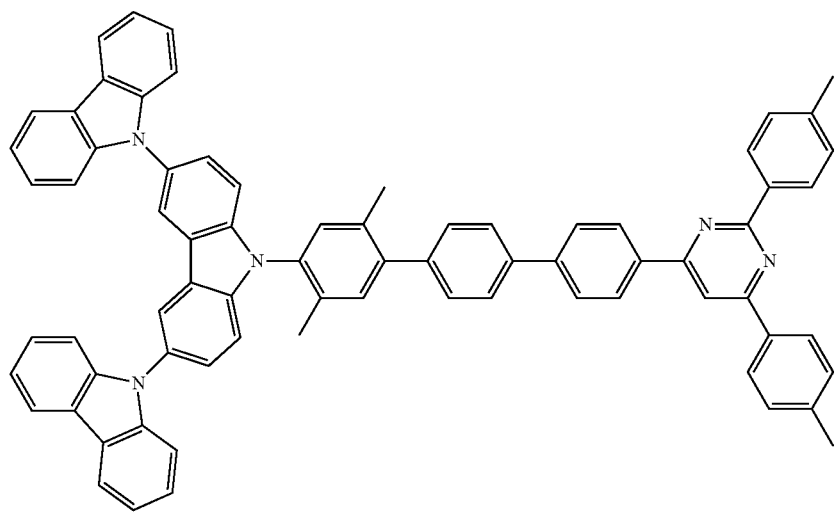
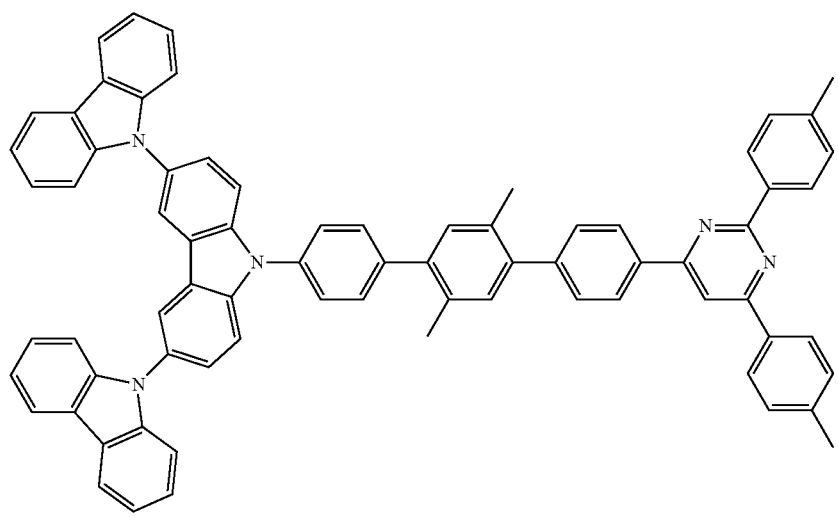

-continued
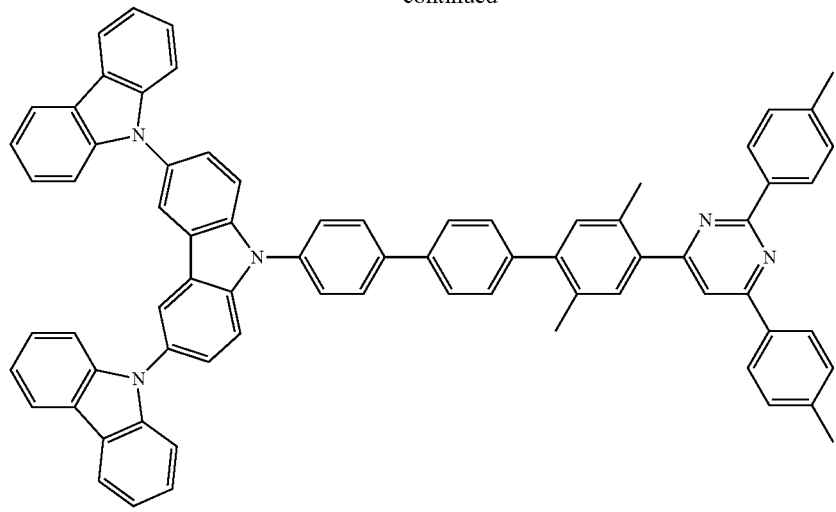
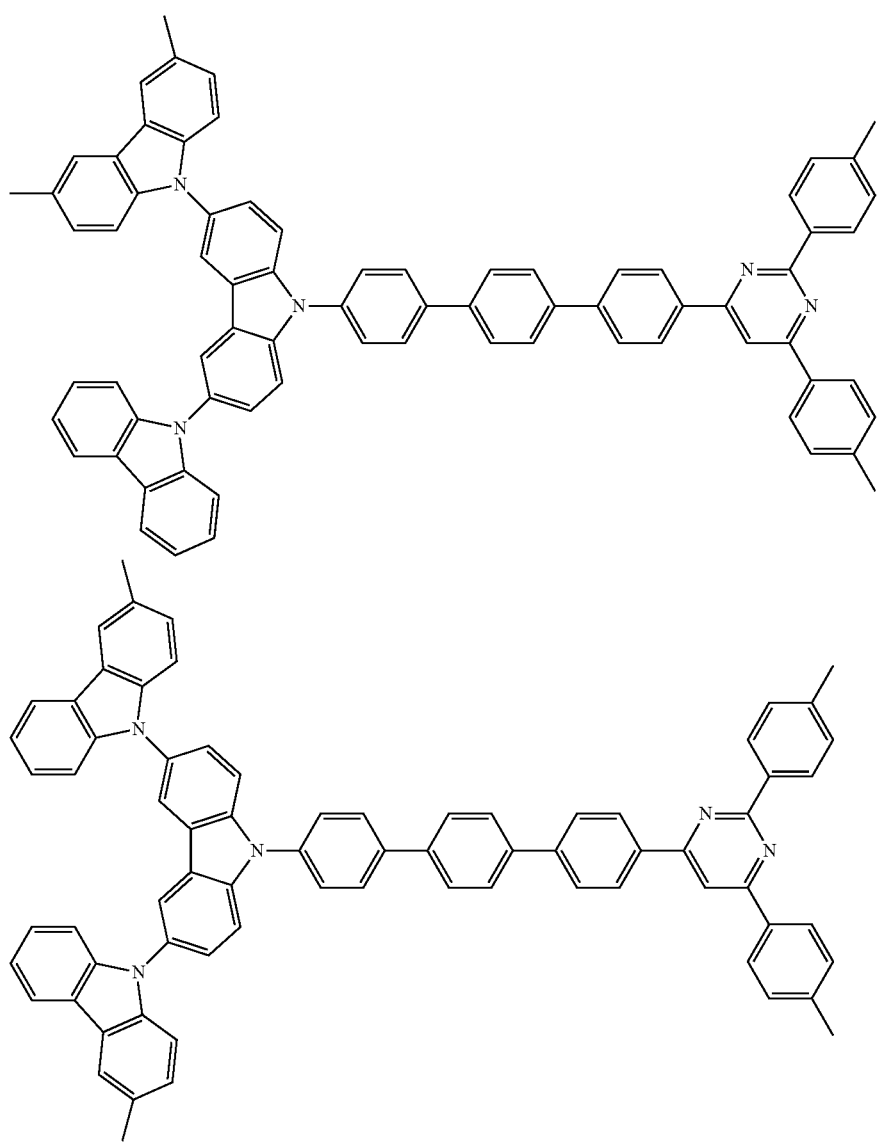

-continued
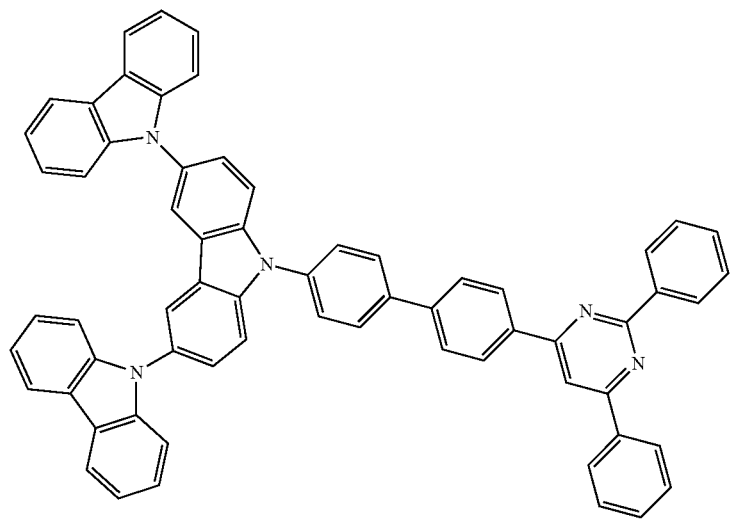
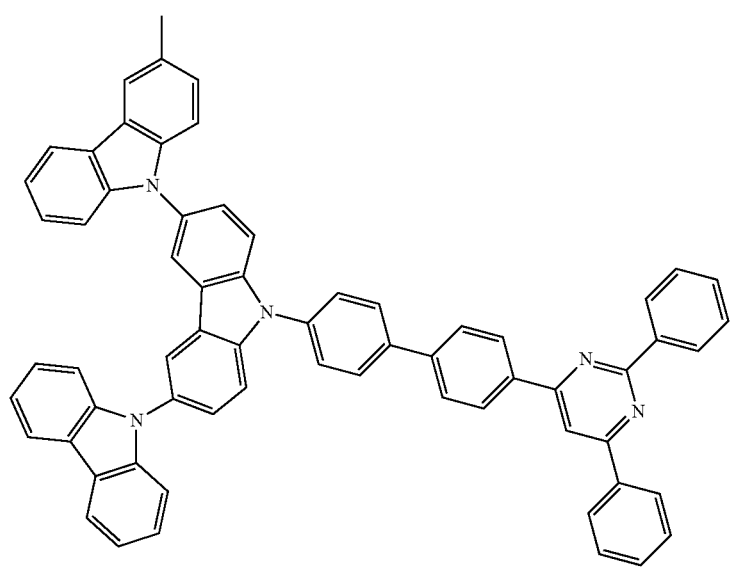
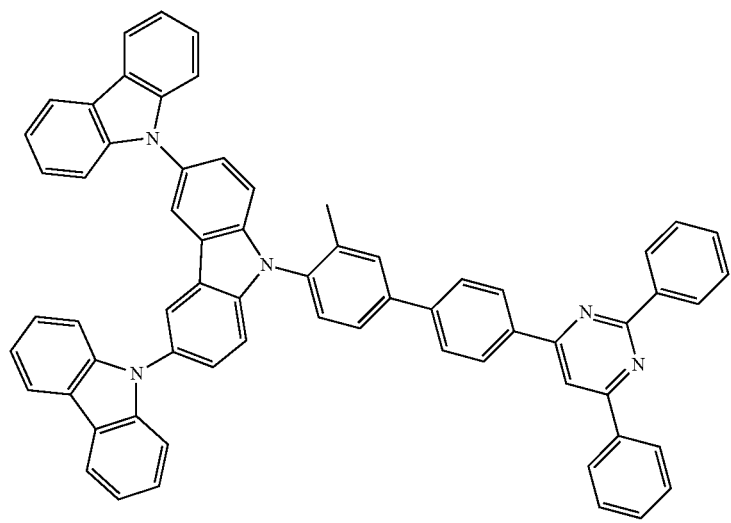

-continued
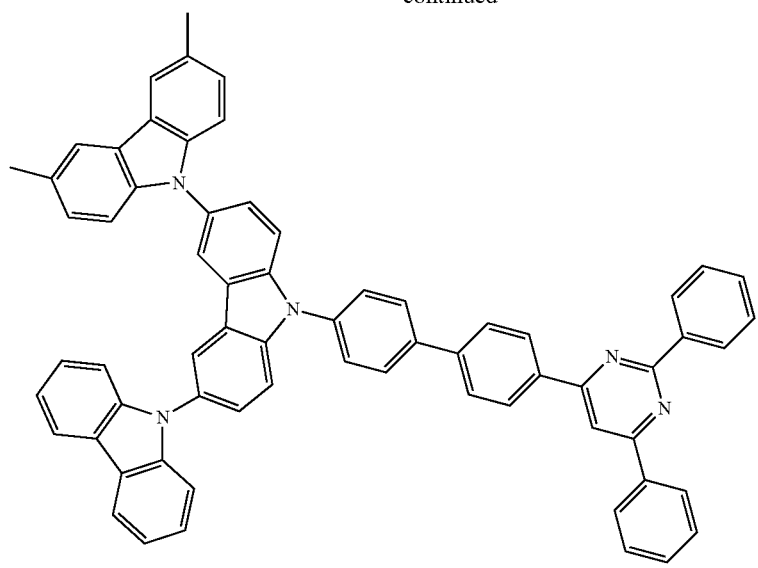
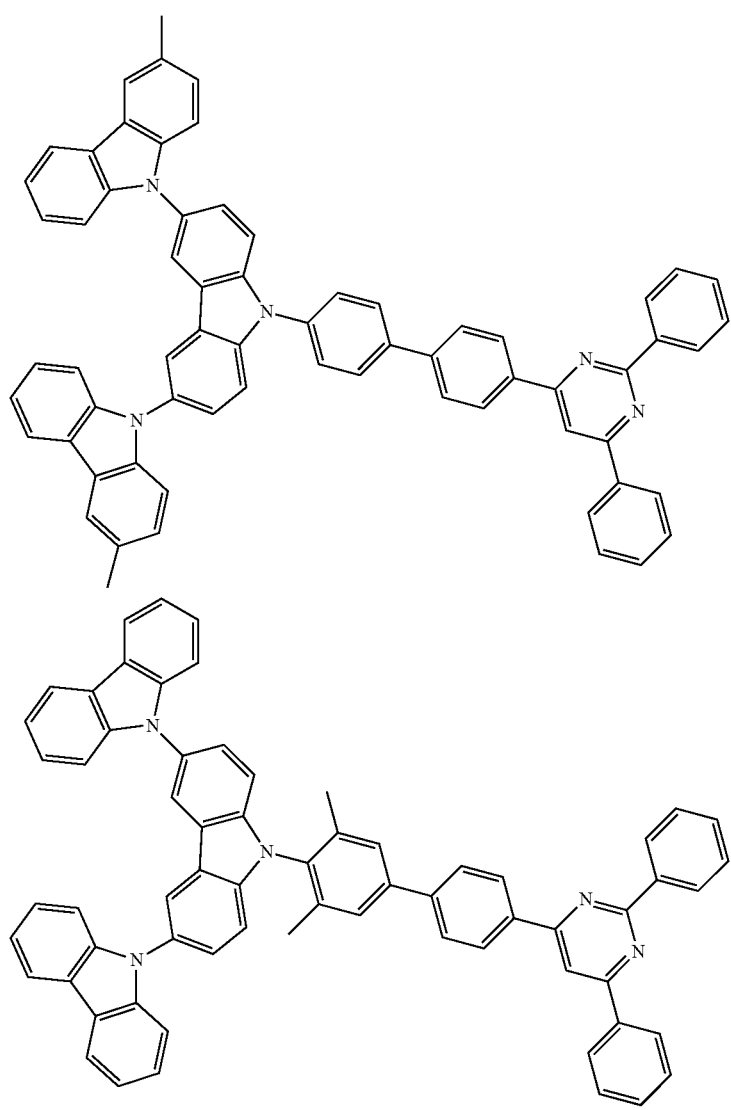

-continued
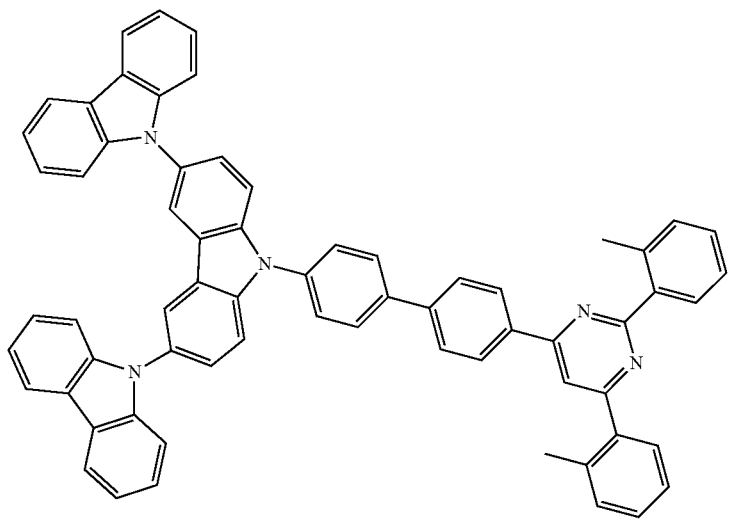
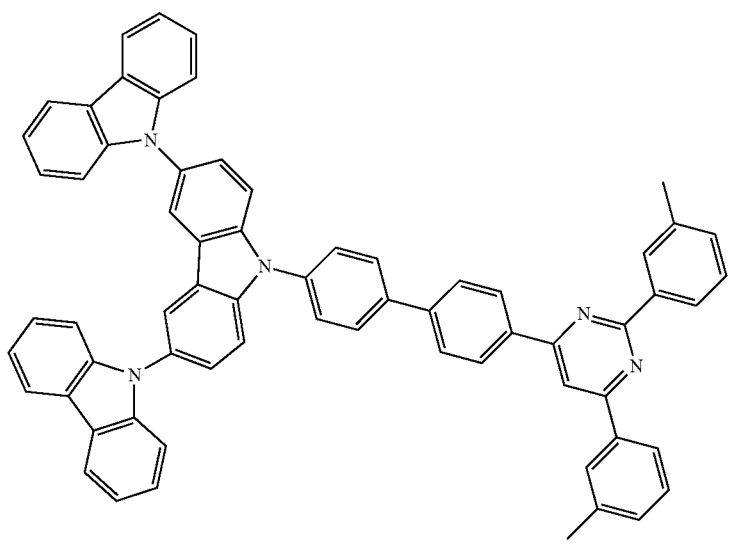
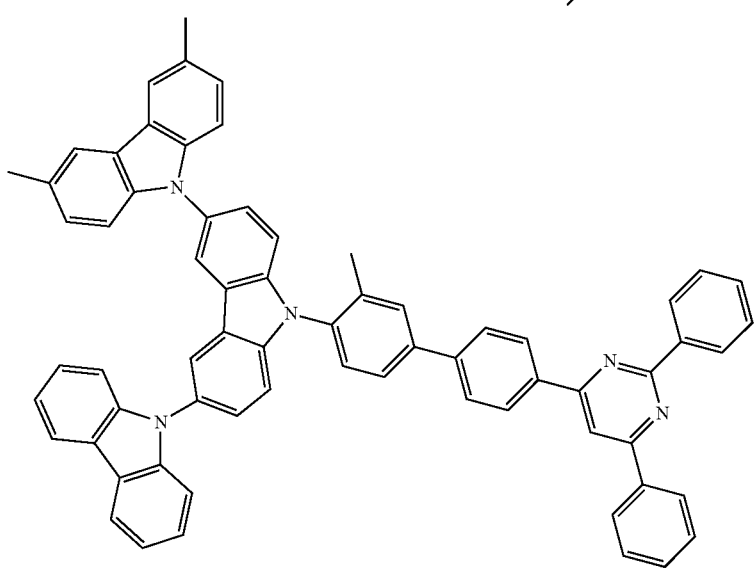

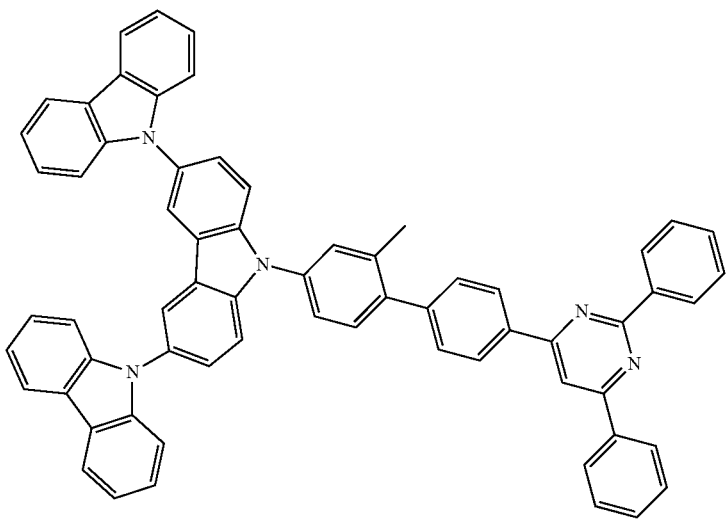

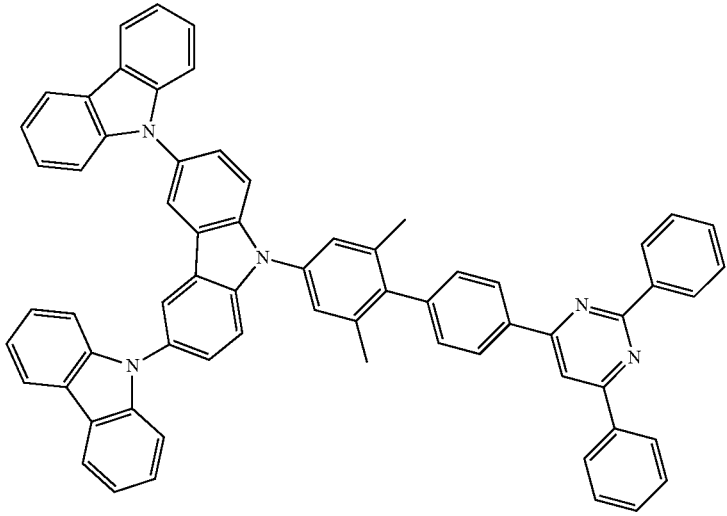
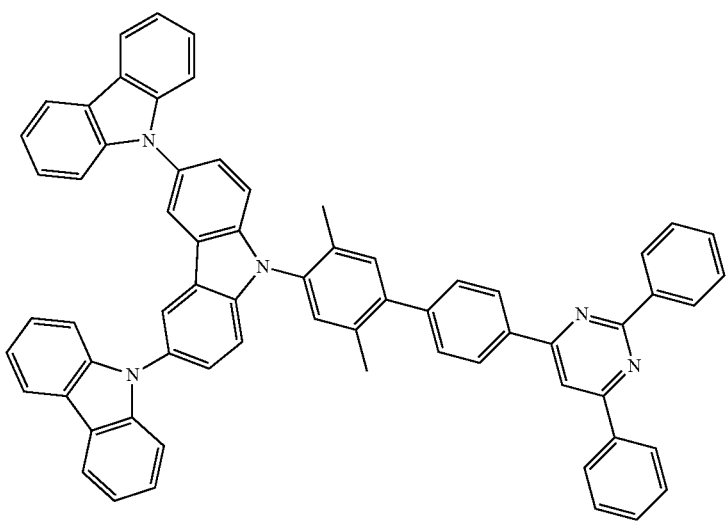
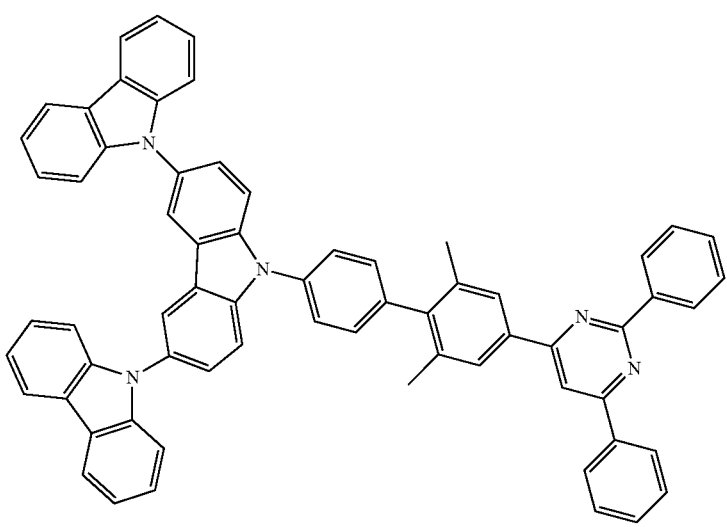

-continued
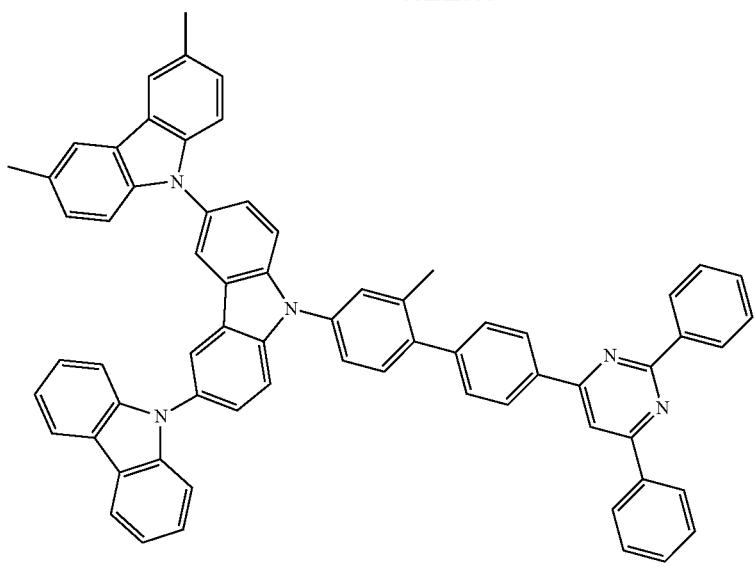
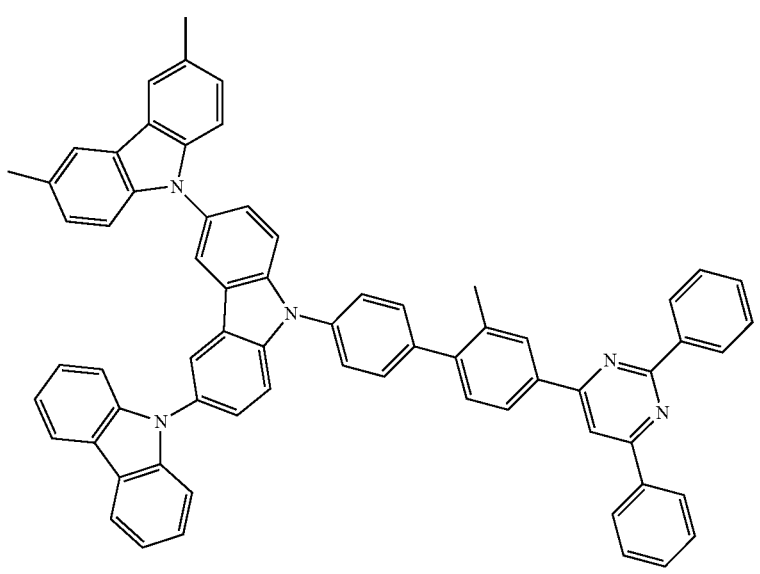
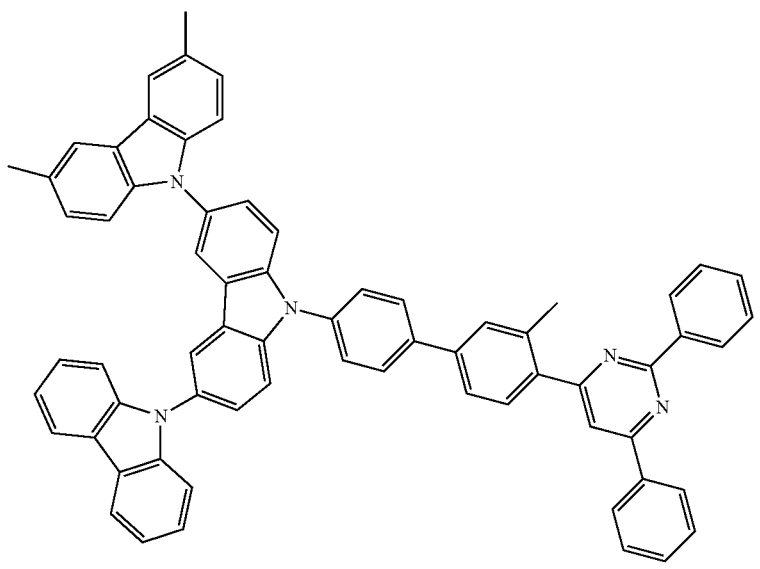

-continued
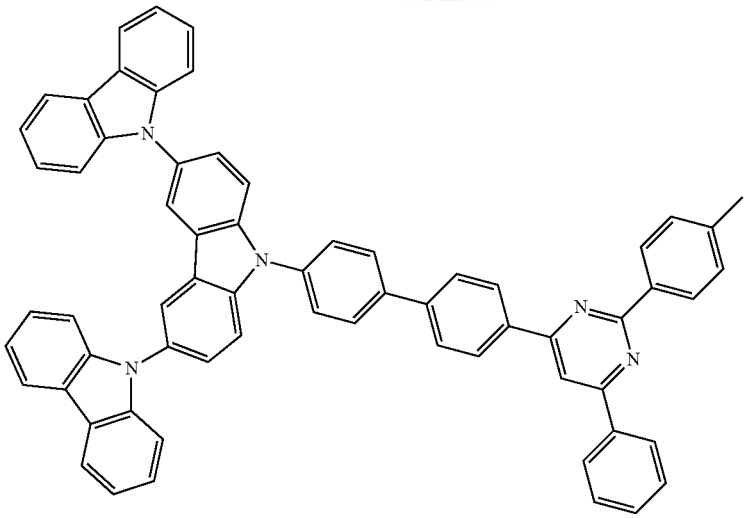
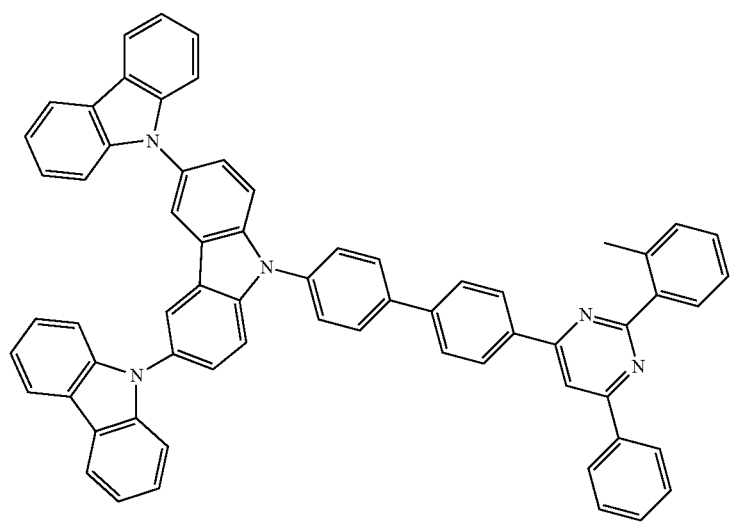
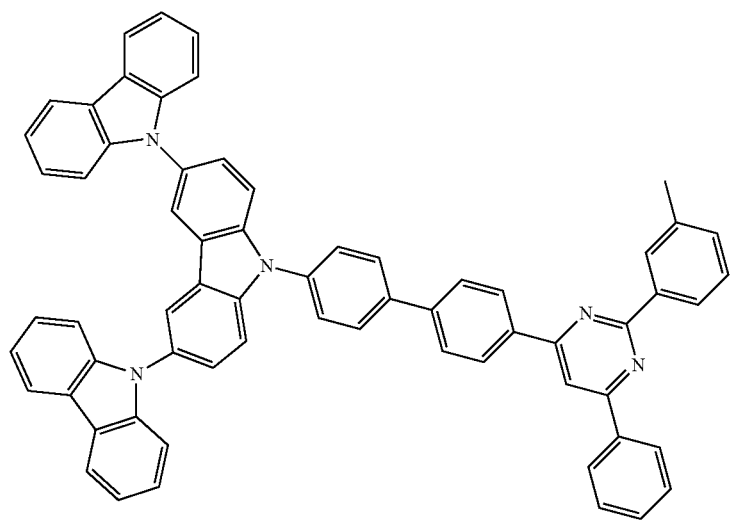

-continued
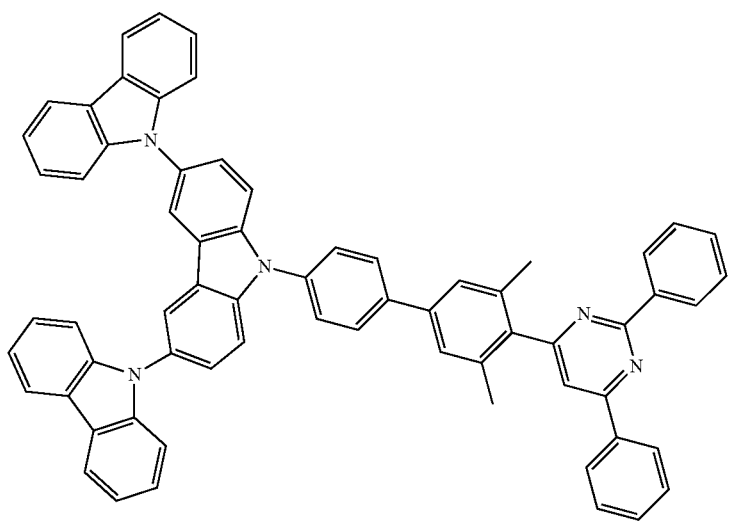
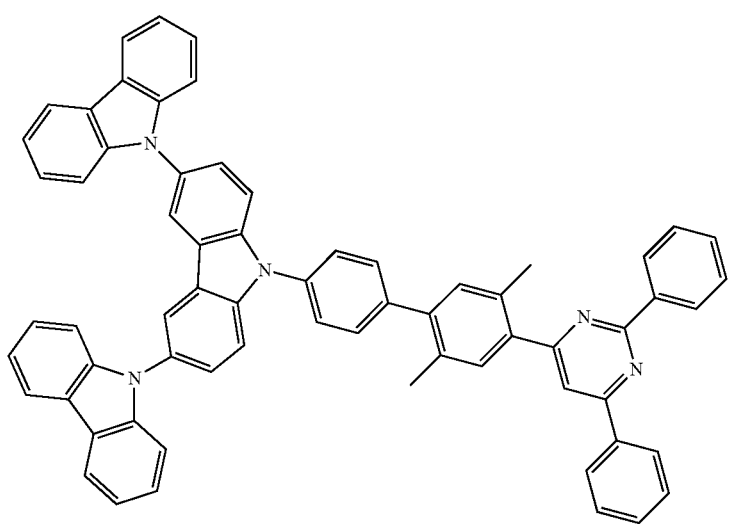
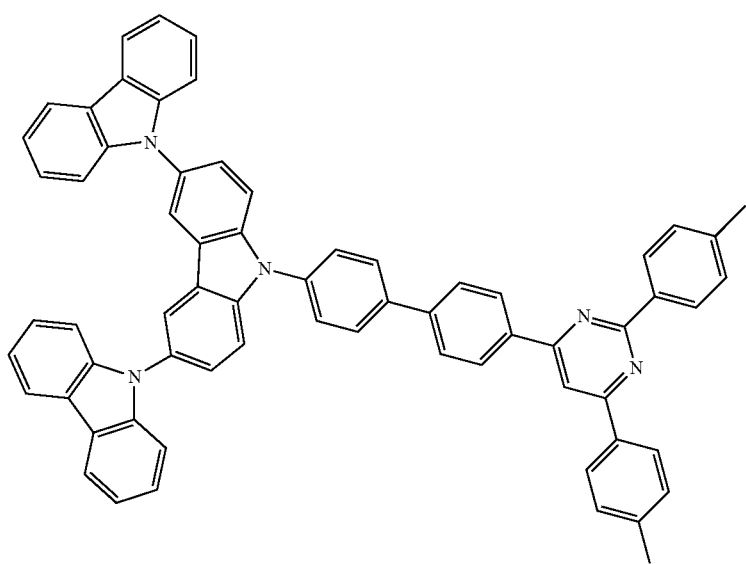

-continued
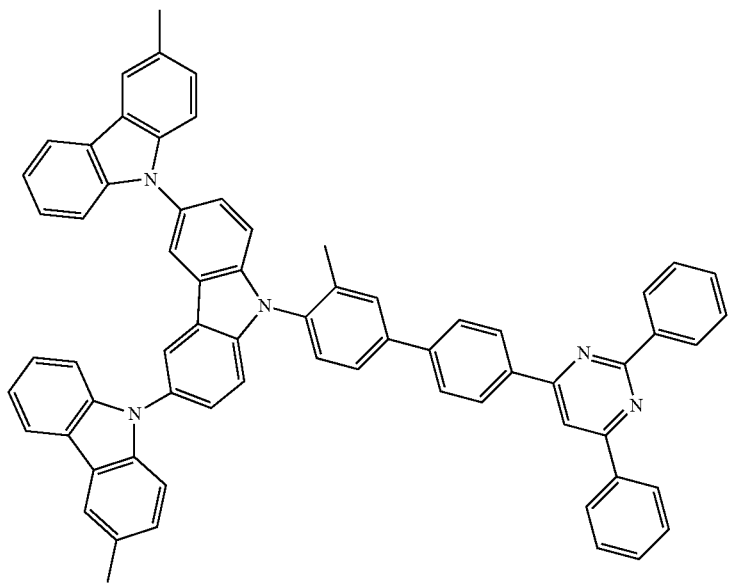
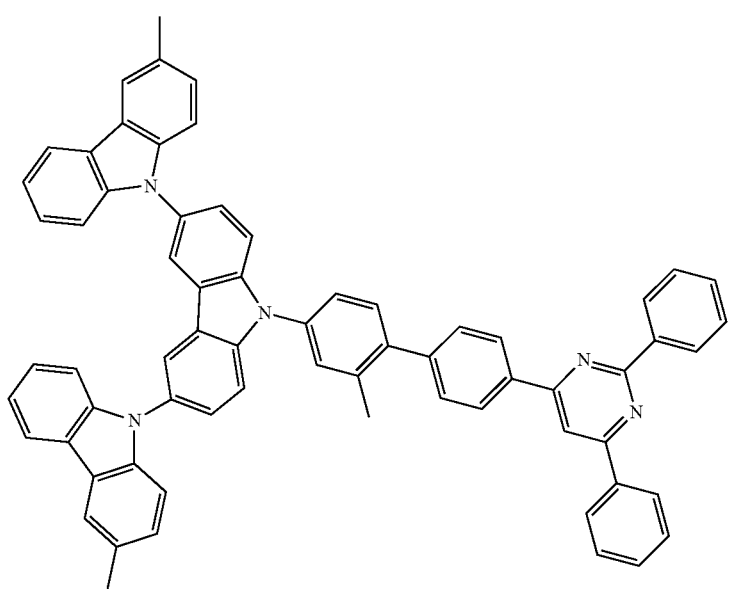

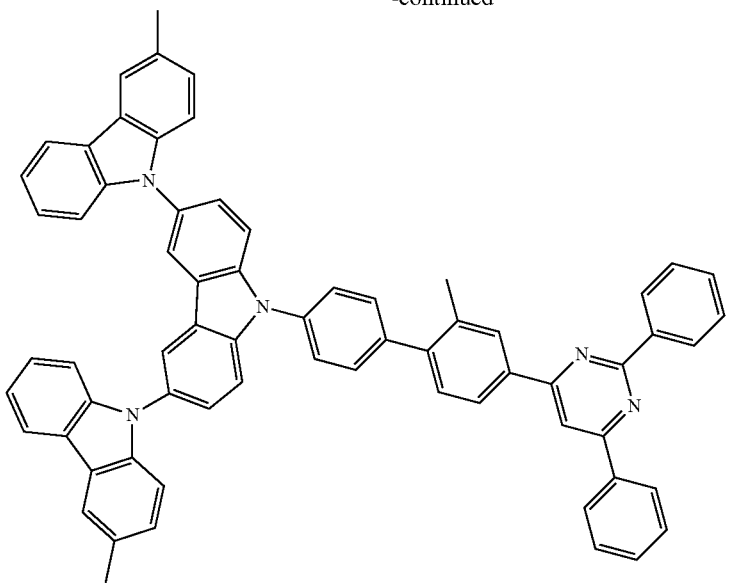
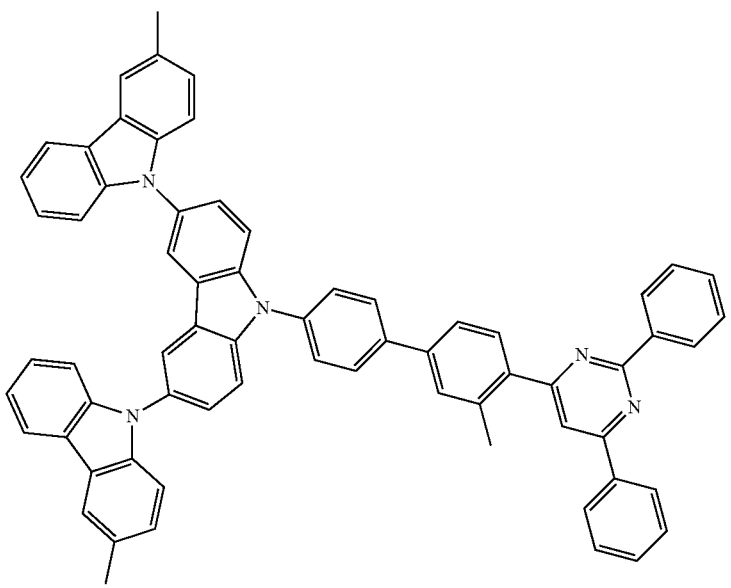
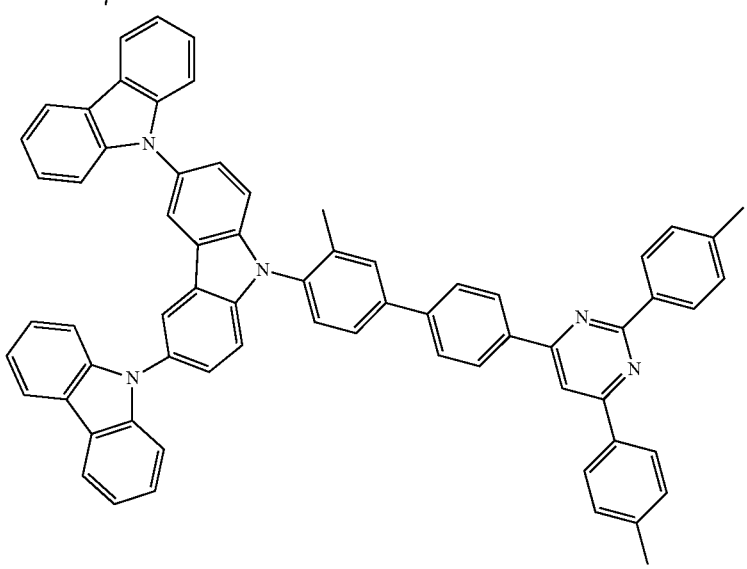

-continued
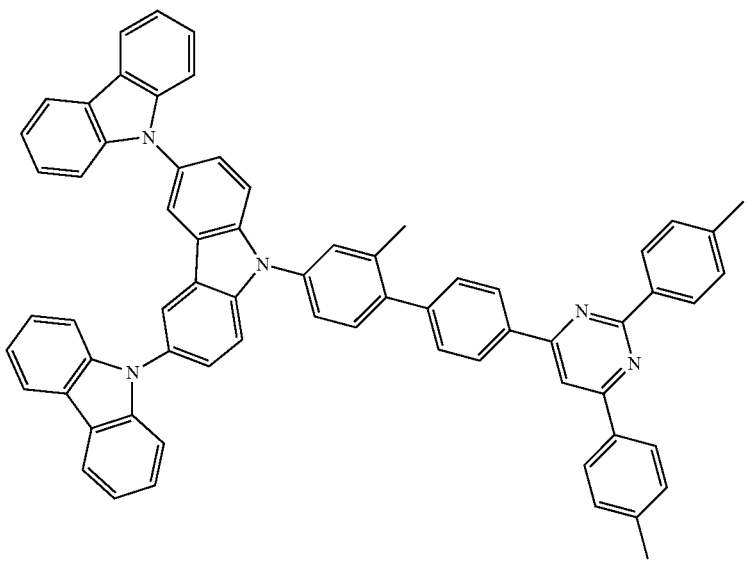
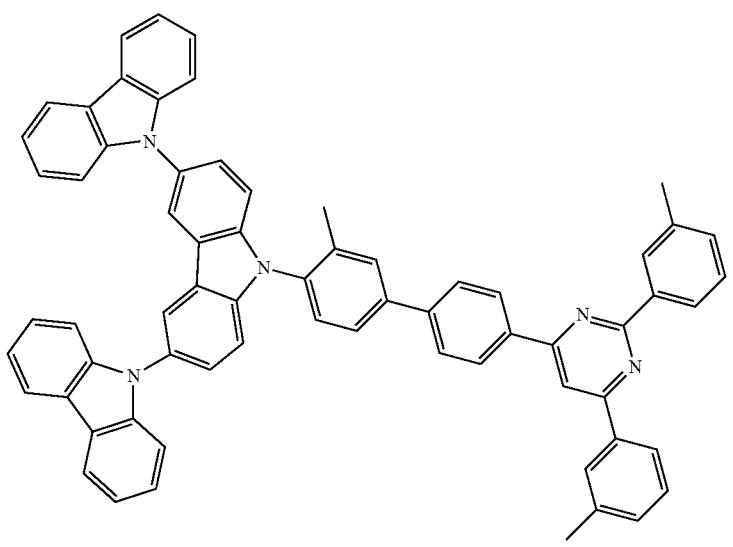
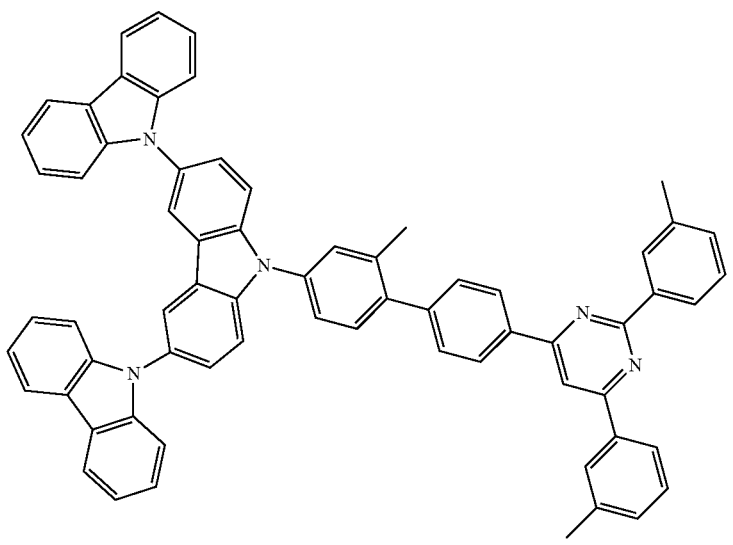

-continued
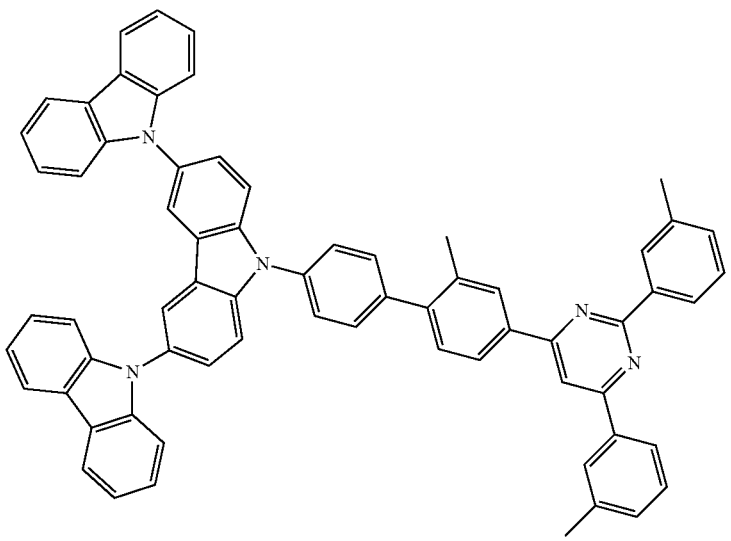
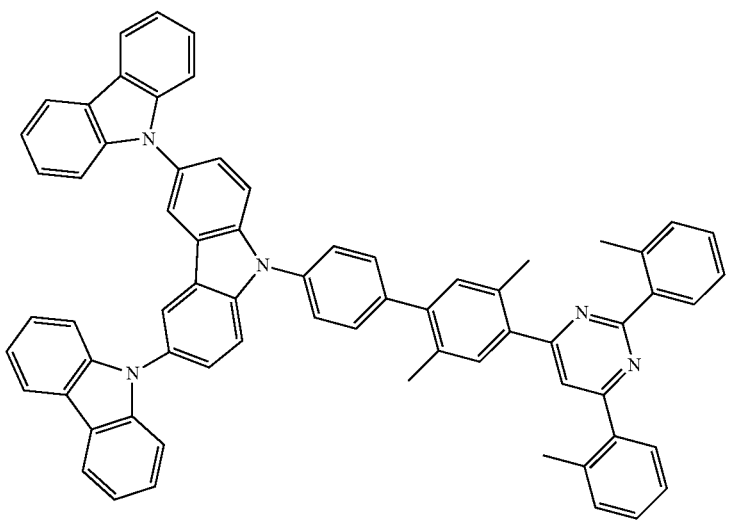
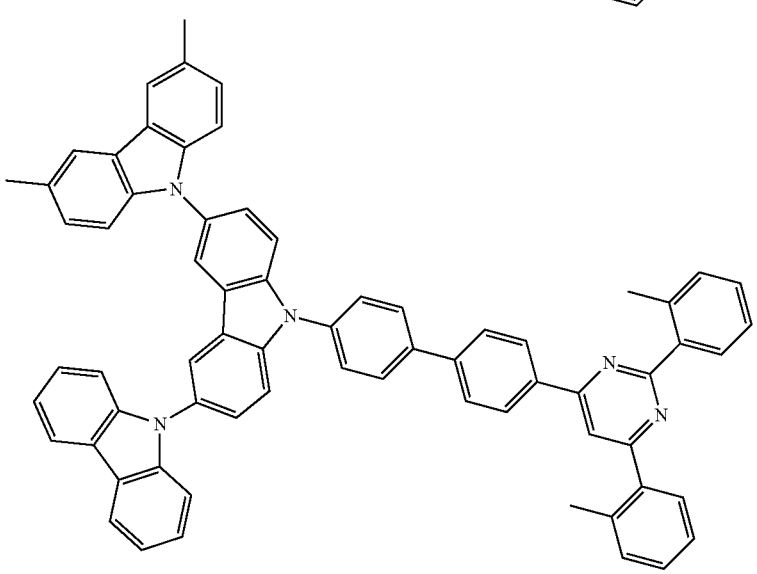

-continued
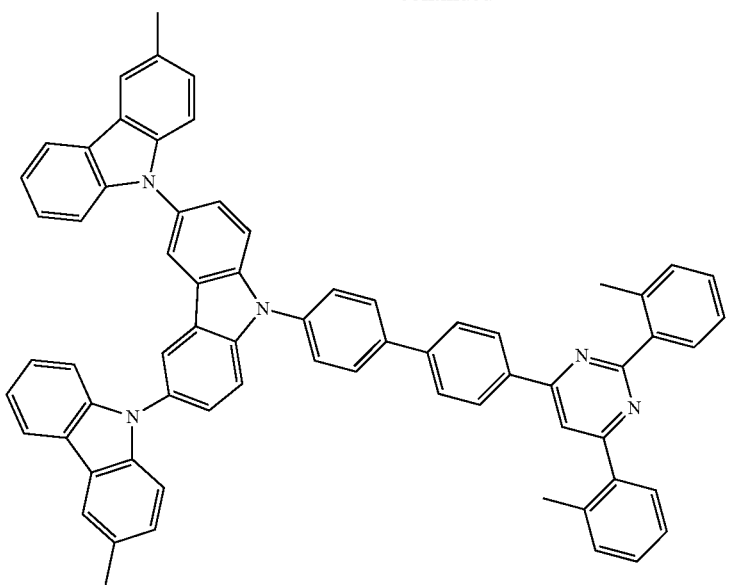
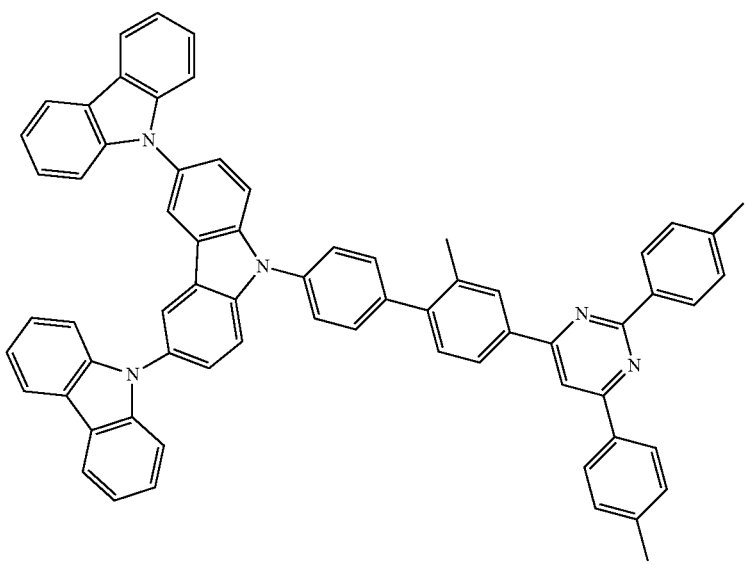
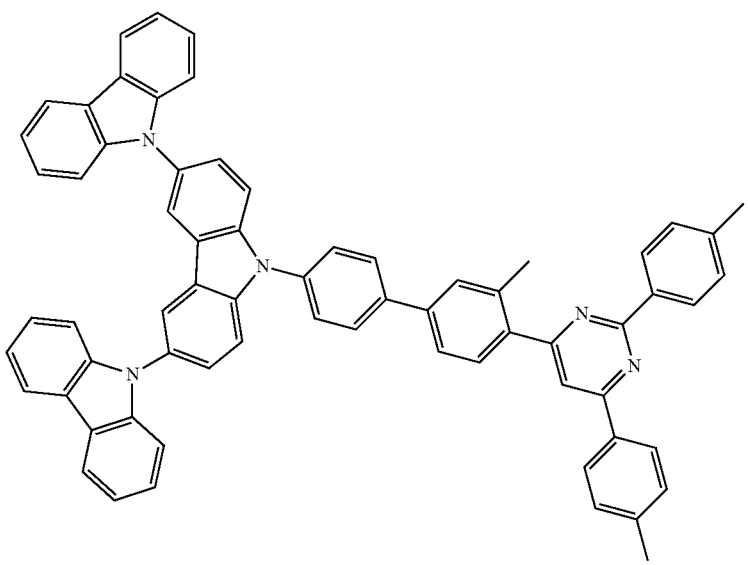

-continued
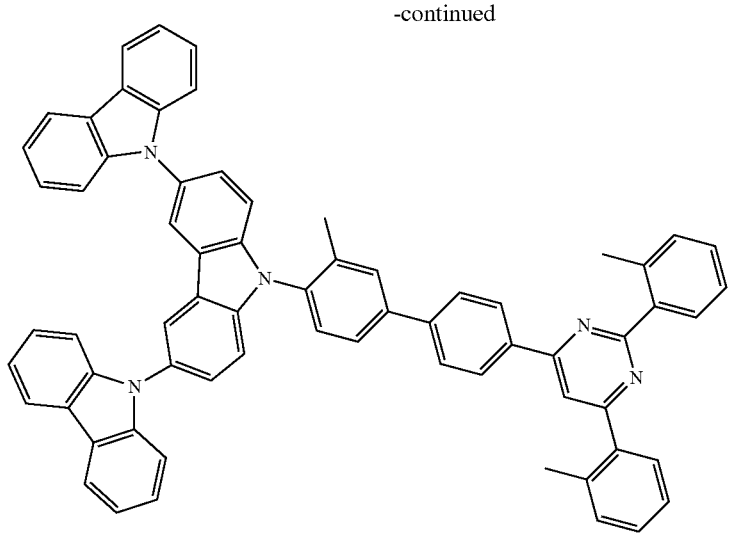
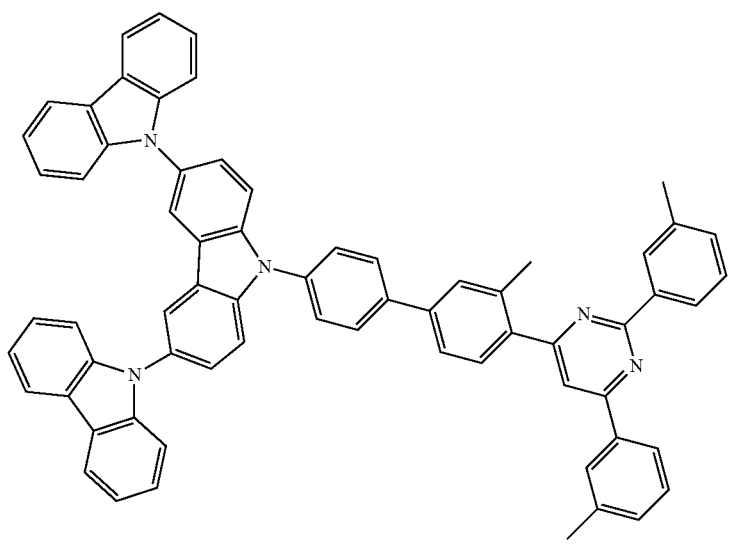
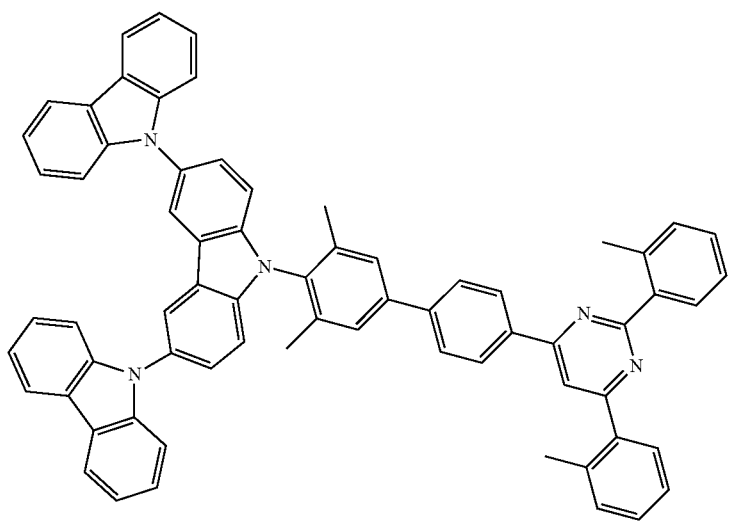

-continued
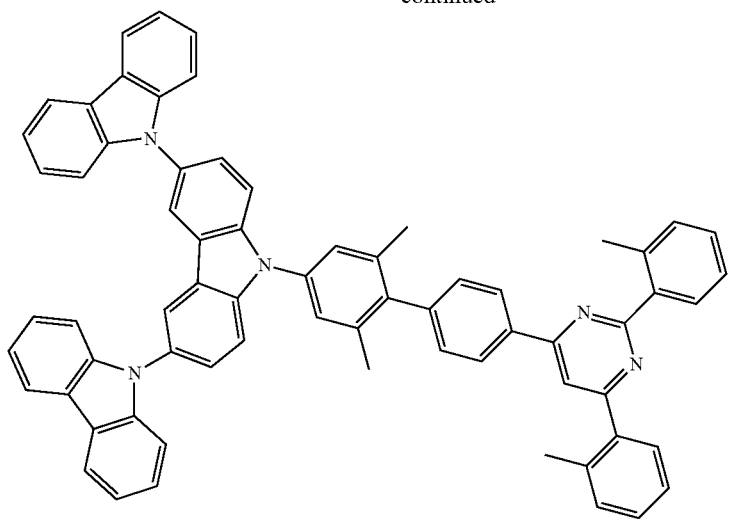
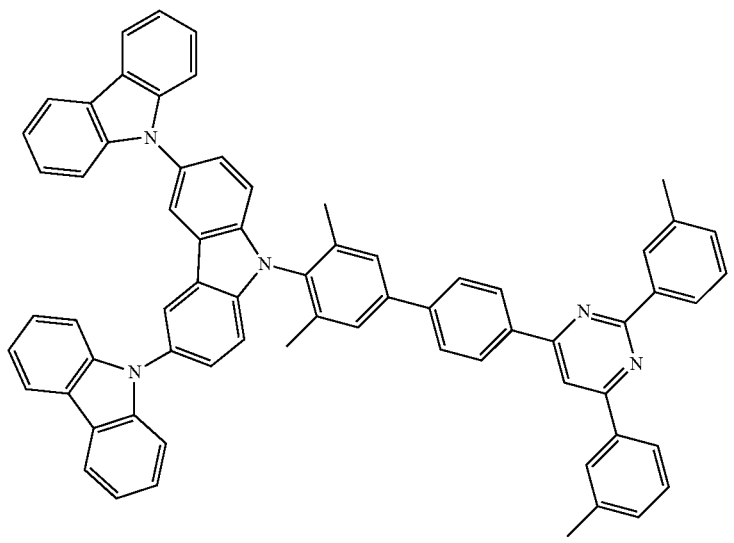

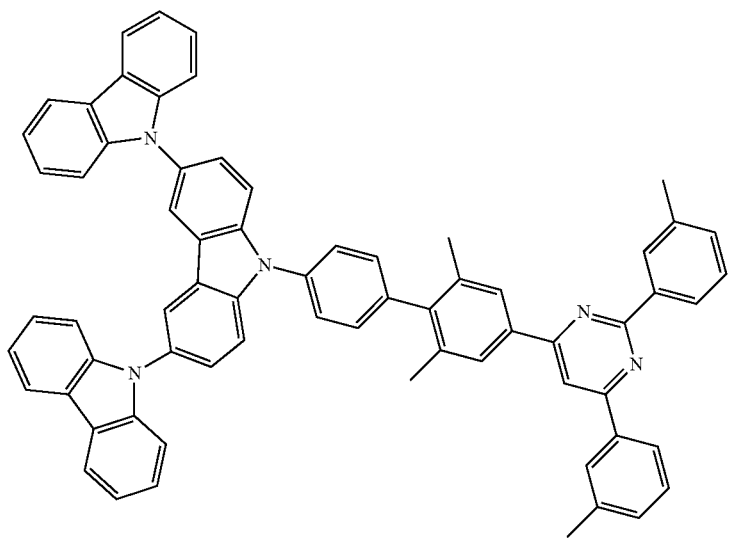
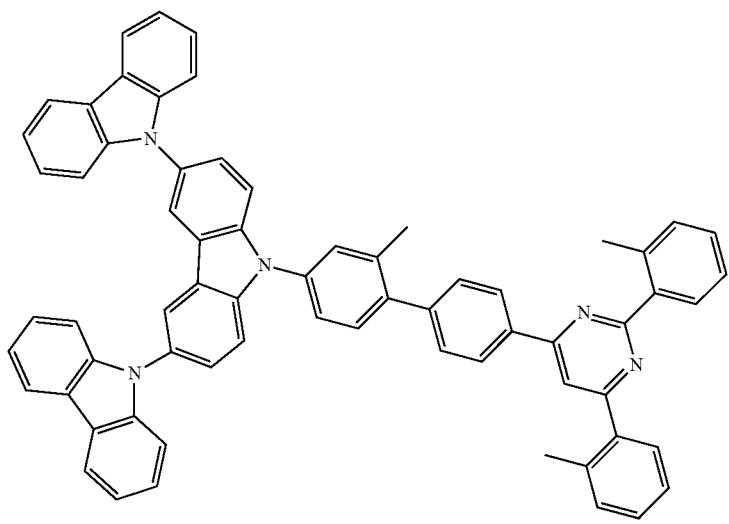
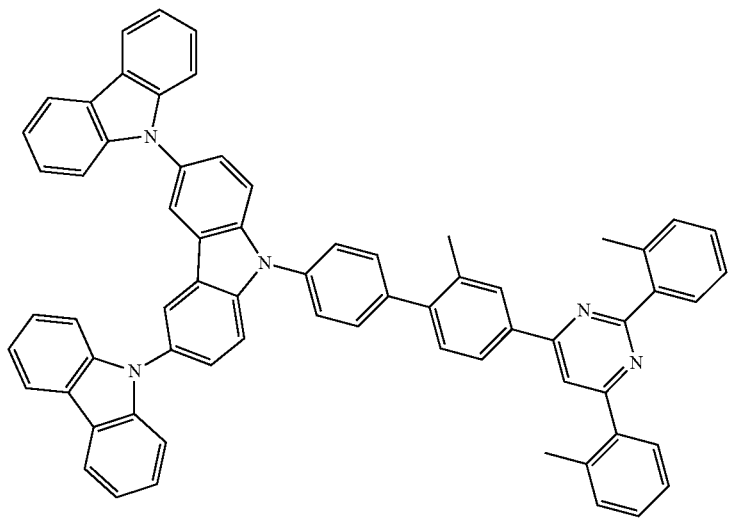

-continued
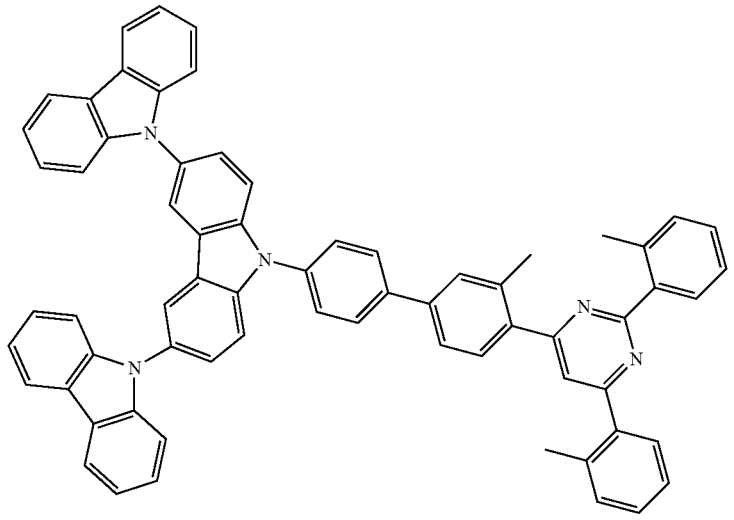
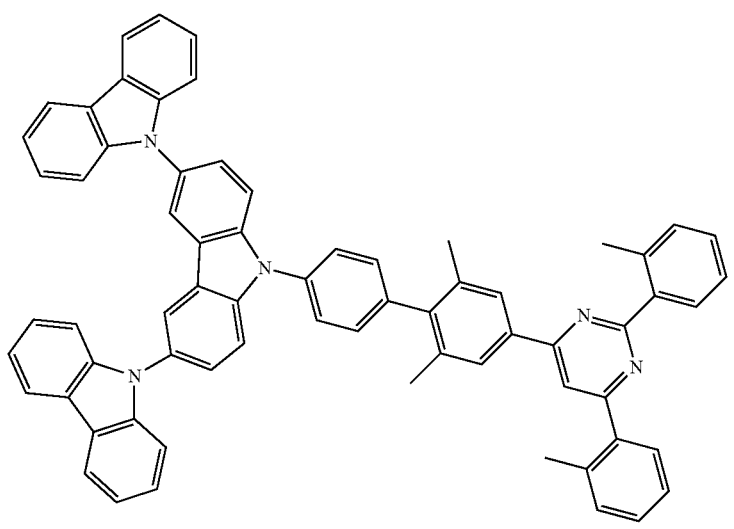
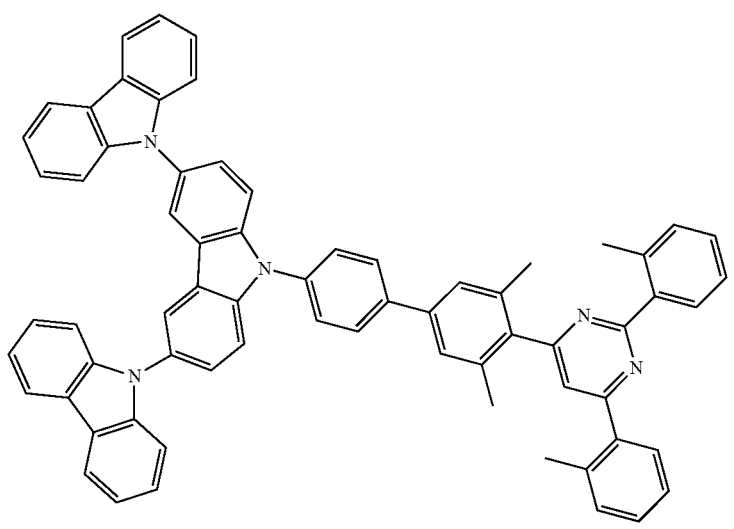

-continued
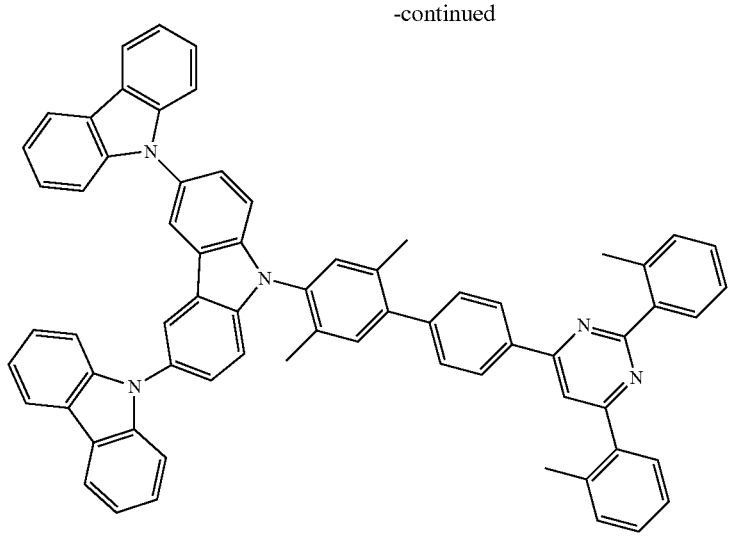
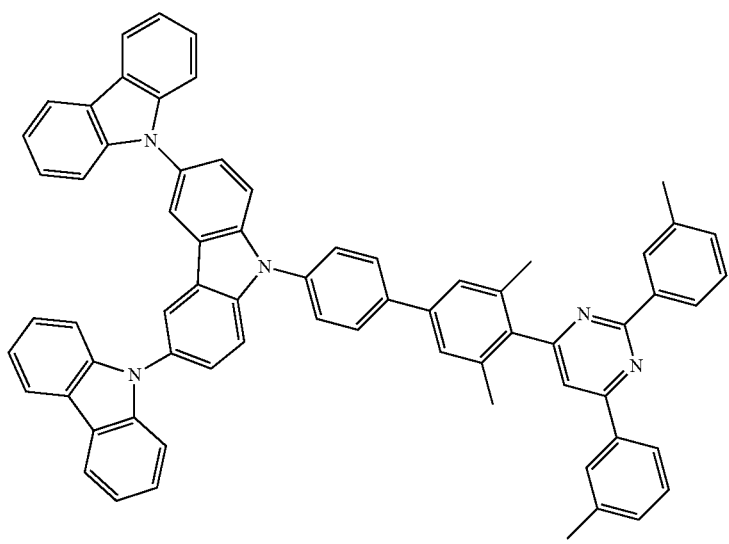
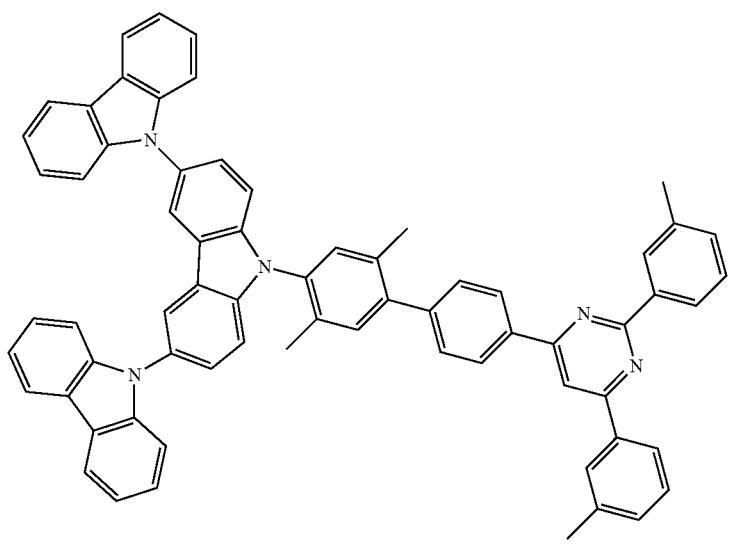

-continued
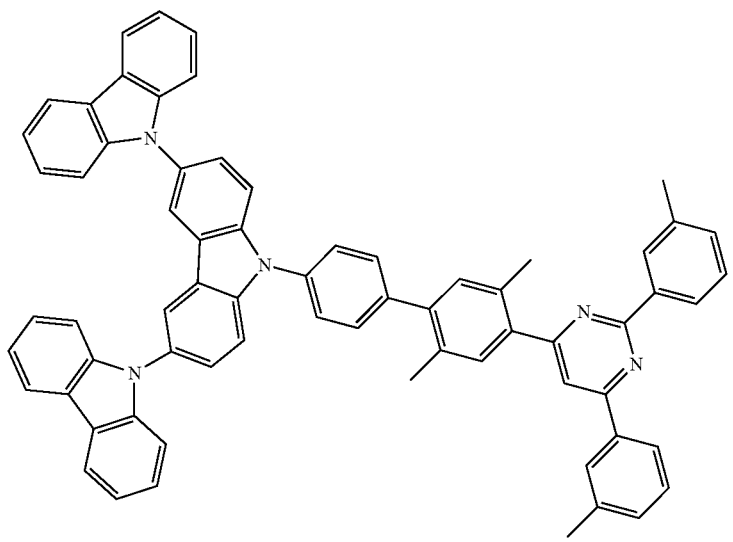
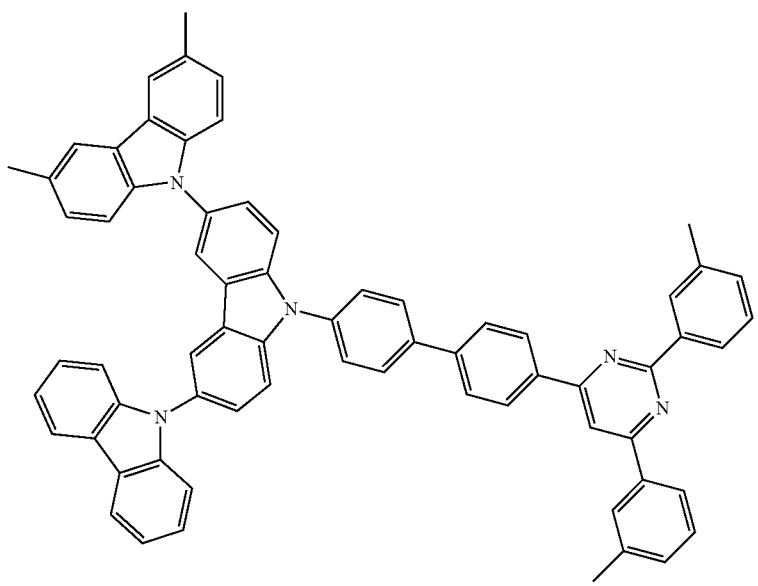
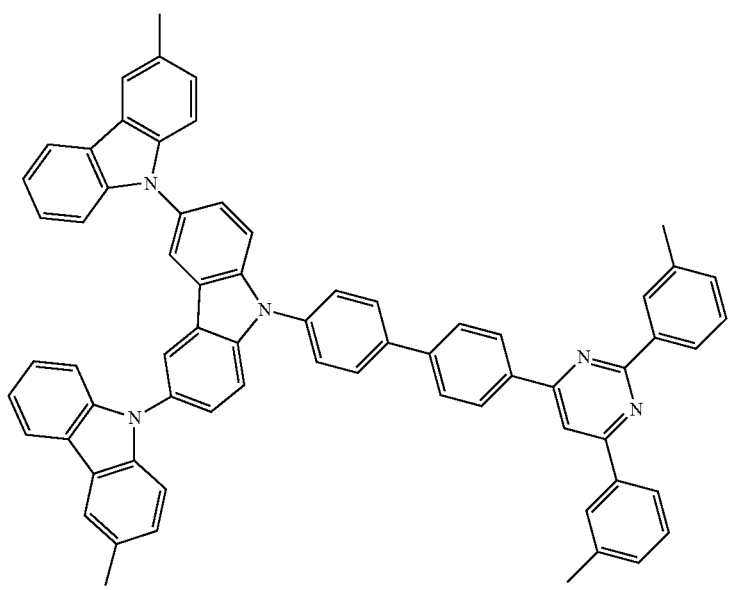

-continued
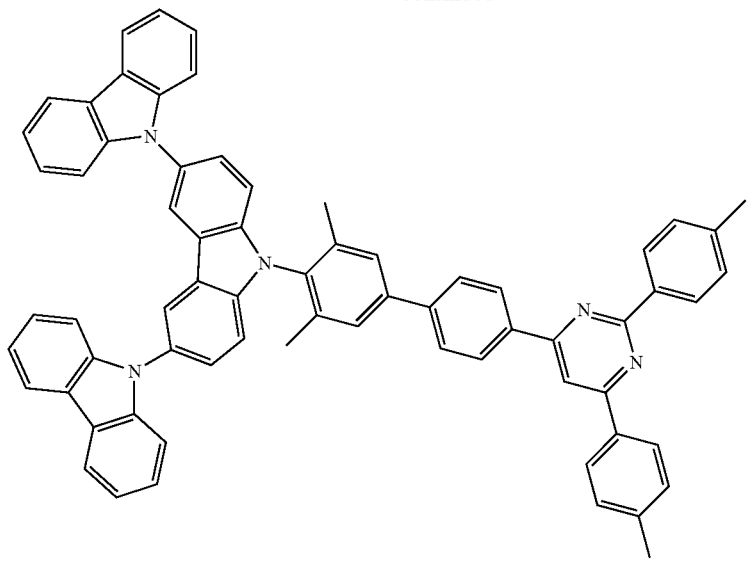
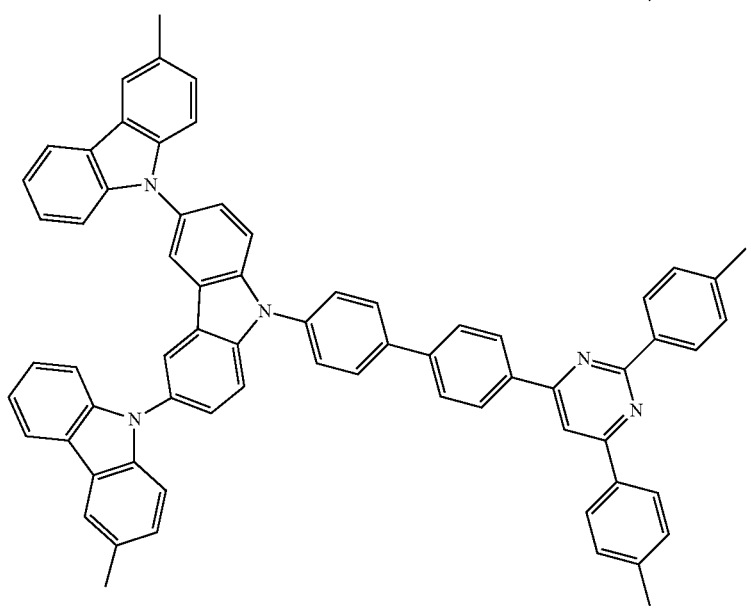
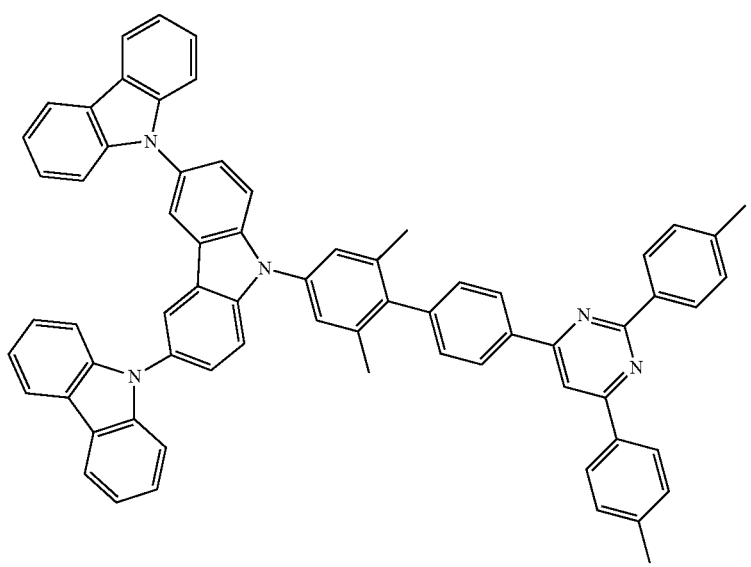

-continued
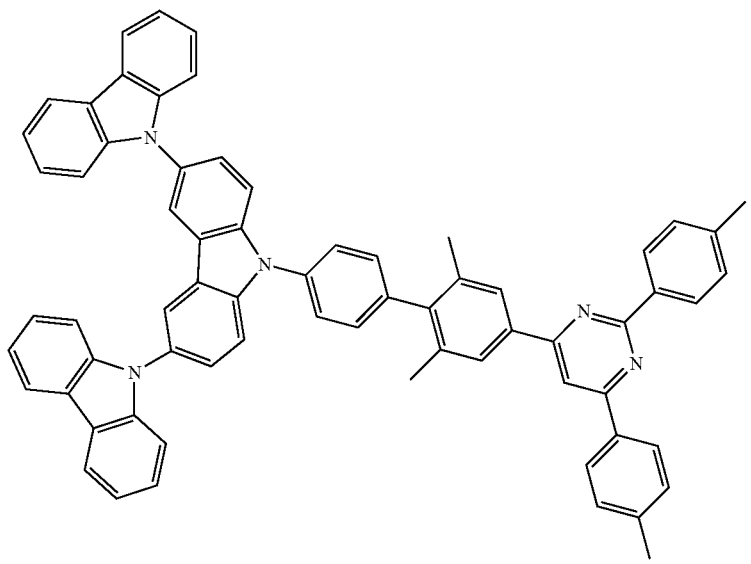
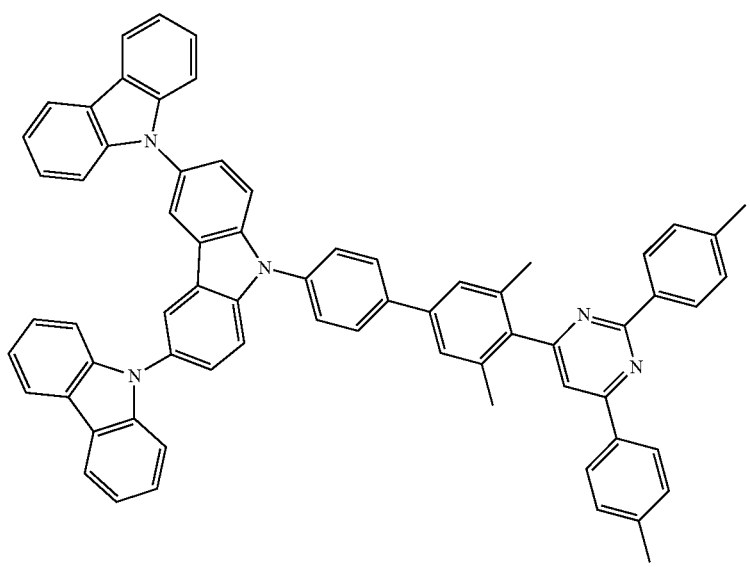
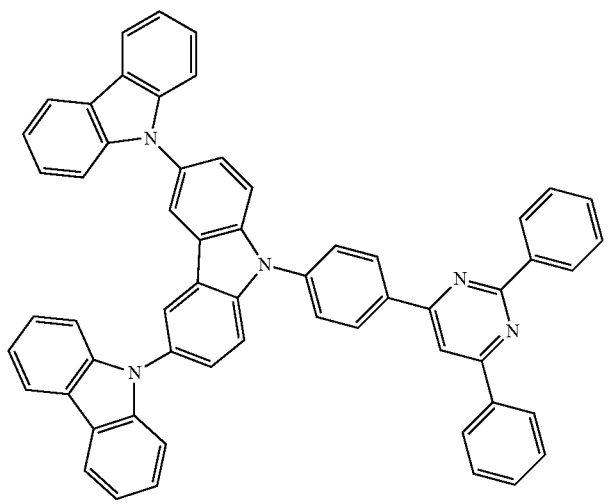

-continued
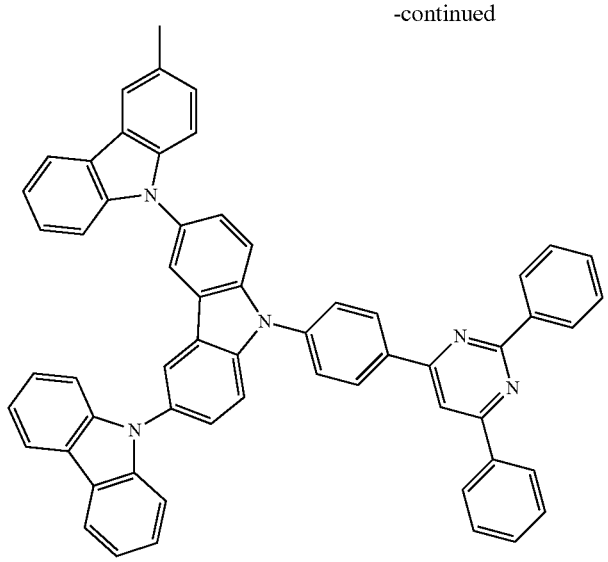
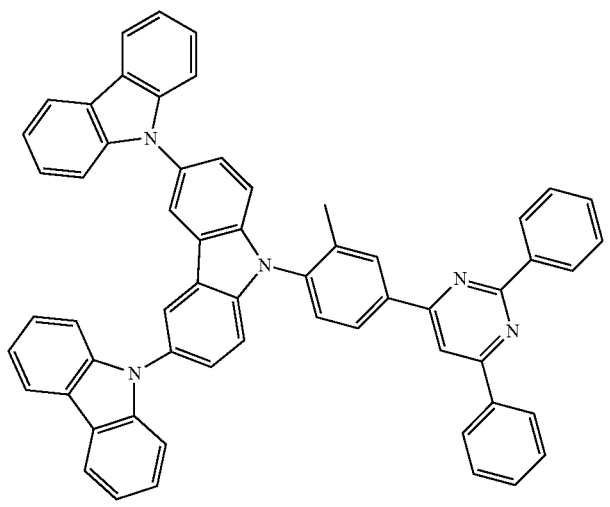
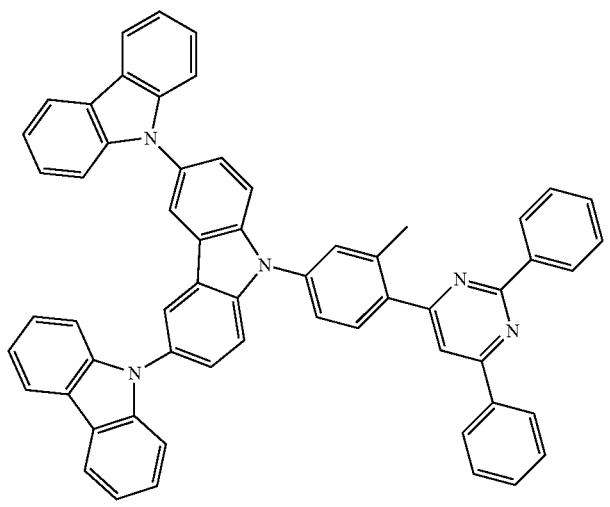

-continued
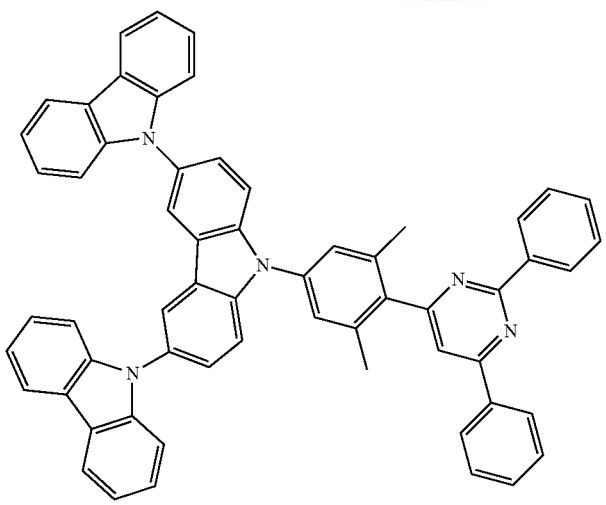
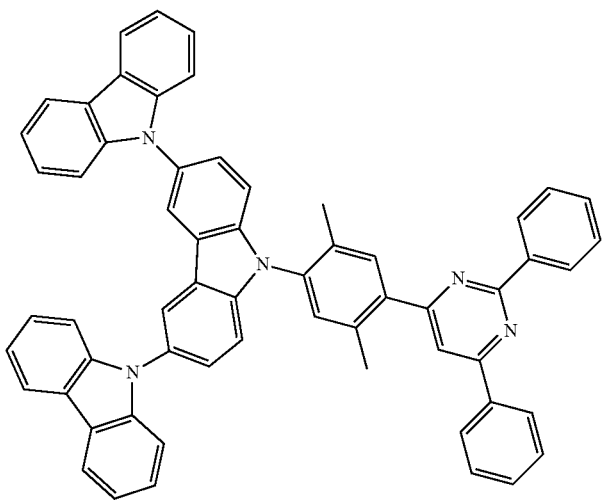
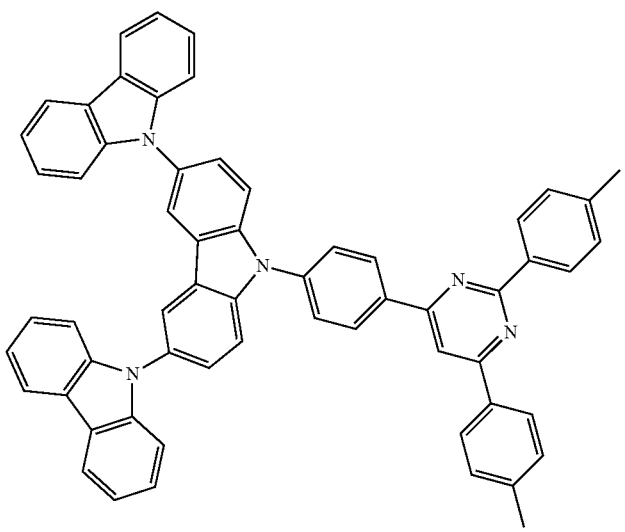

-continued
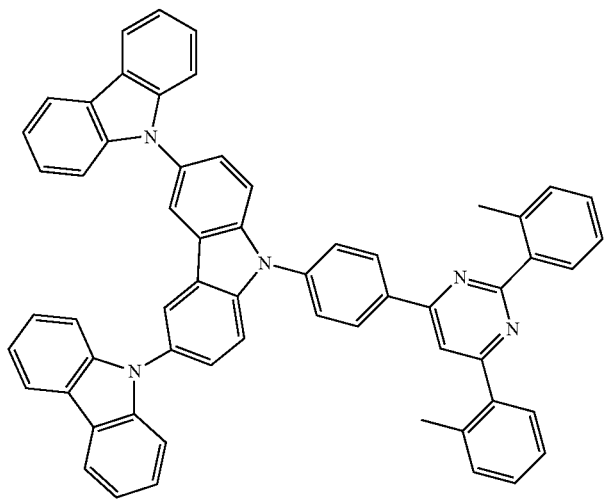
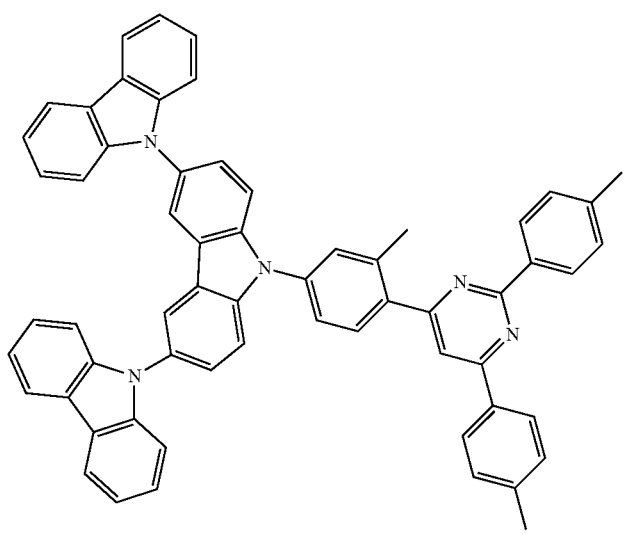
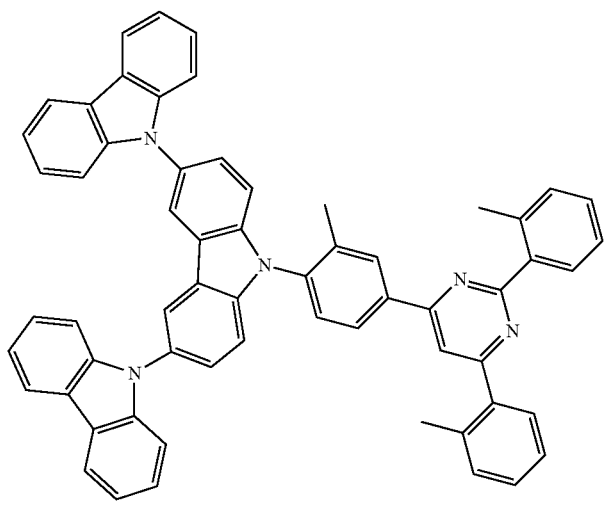

-continued
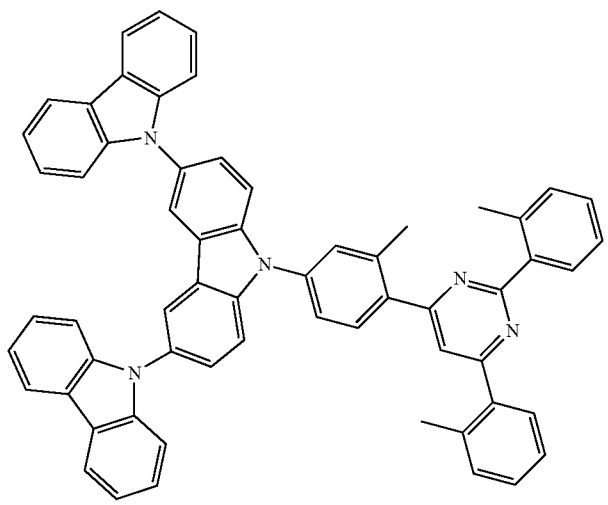
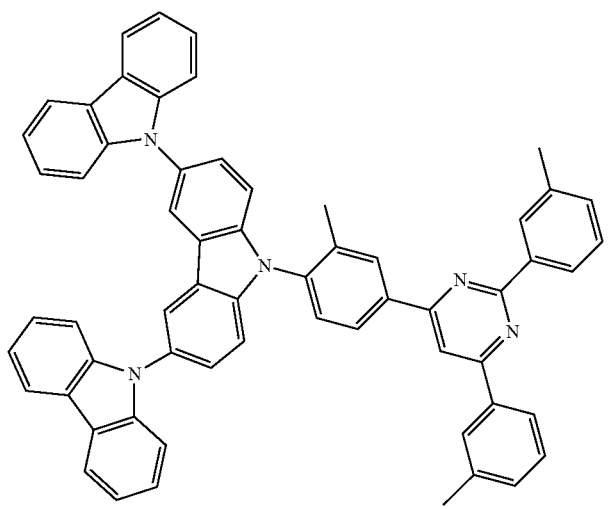
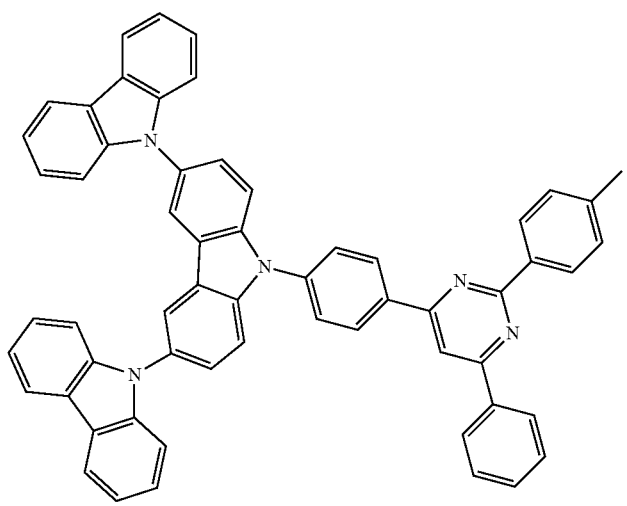

-continued
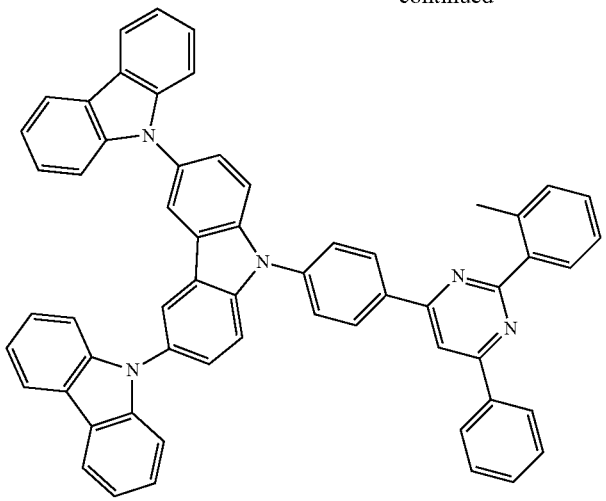
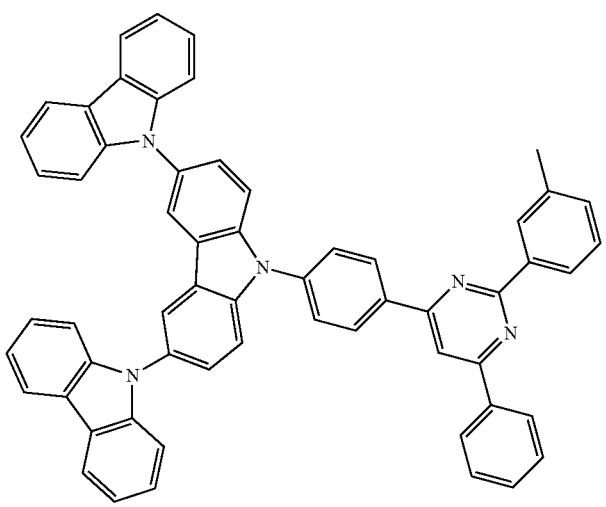
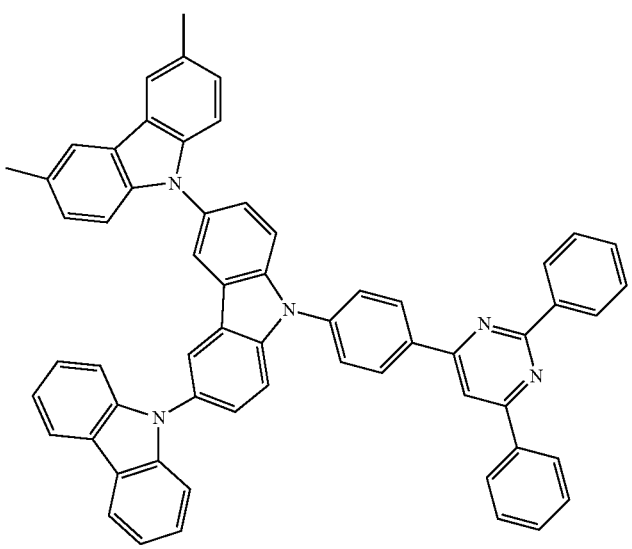

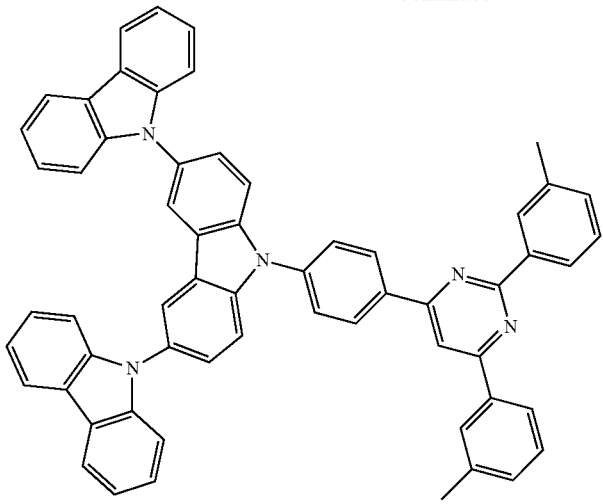
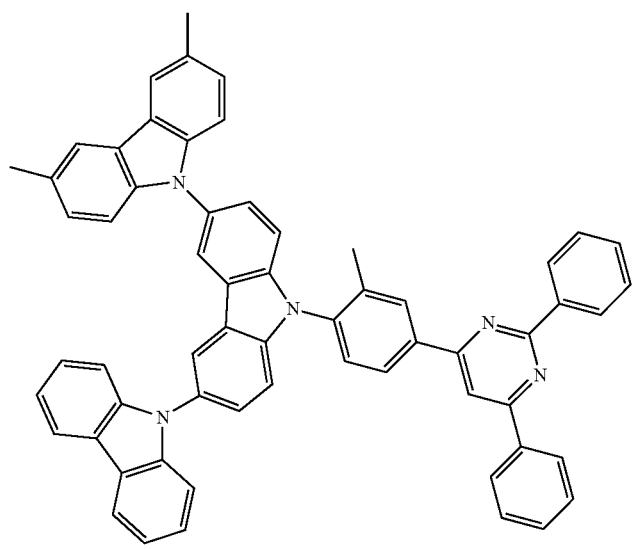
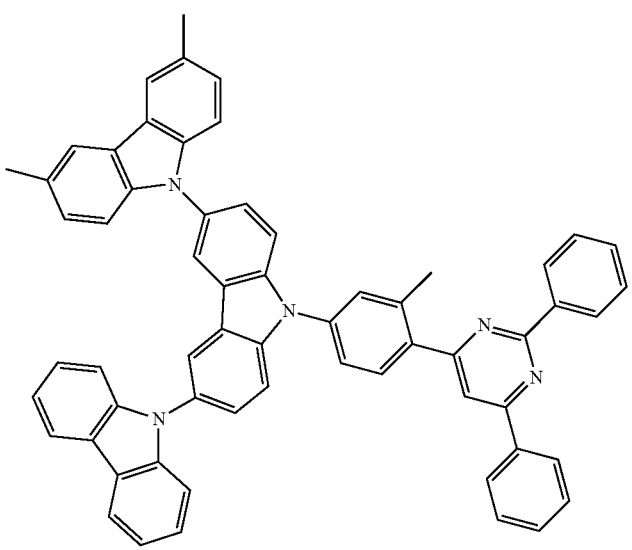

-continued
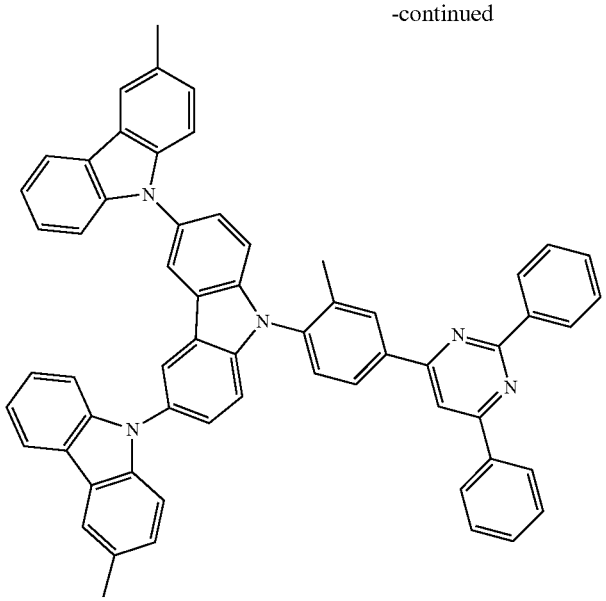
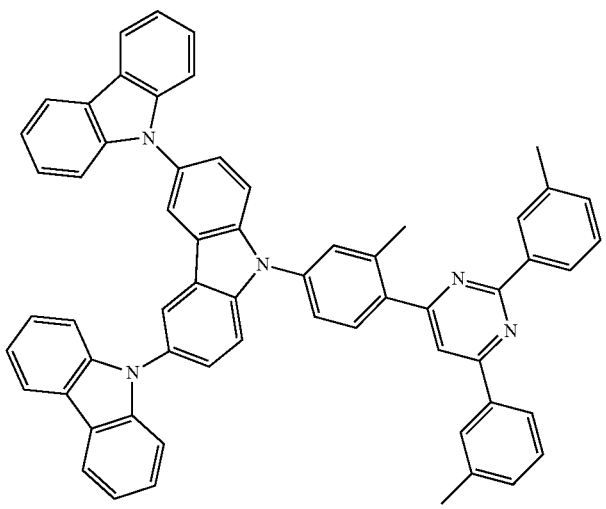
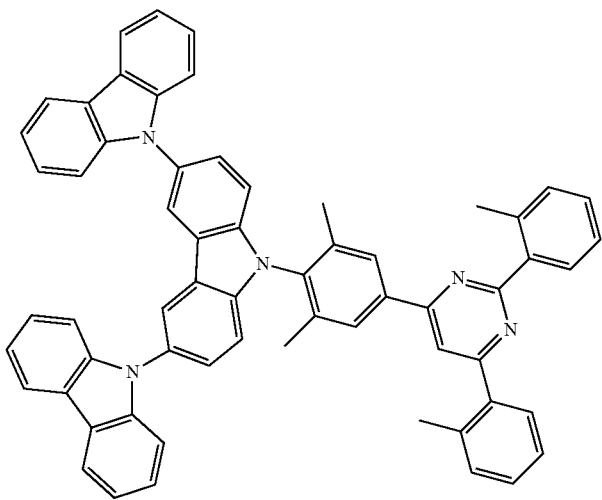

-continued
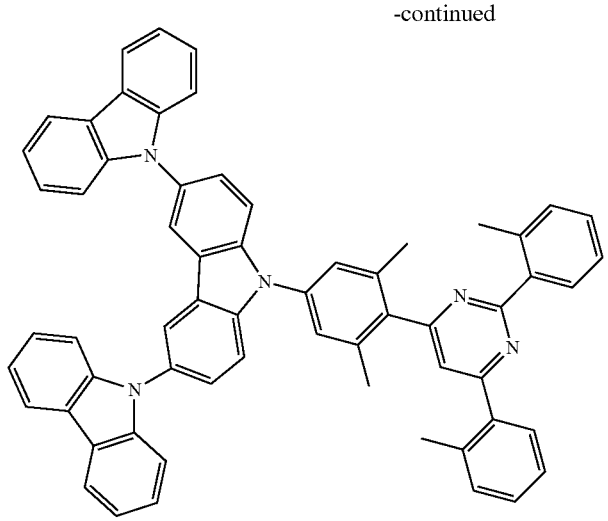
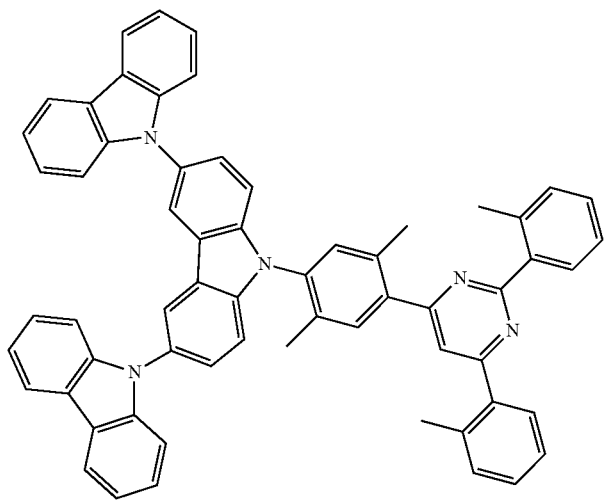
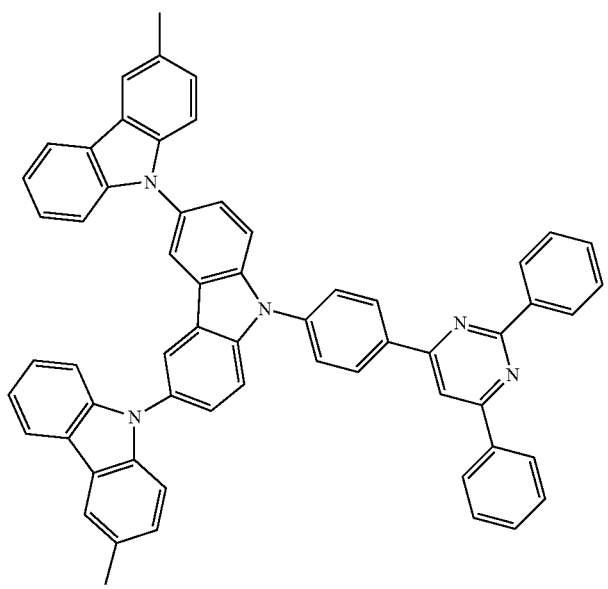

-continued
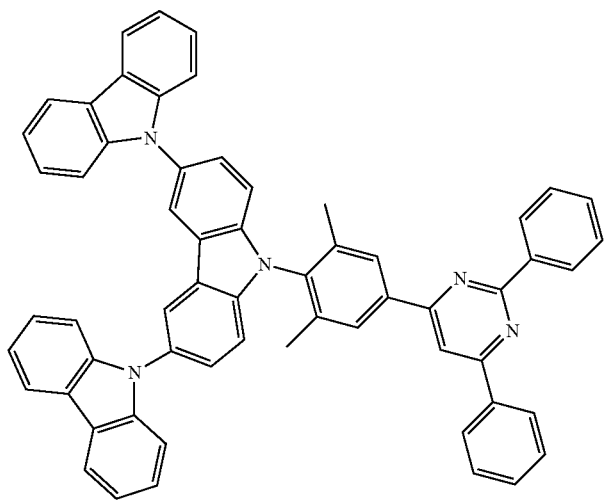
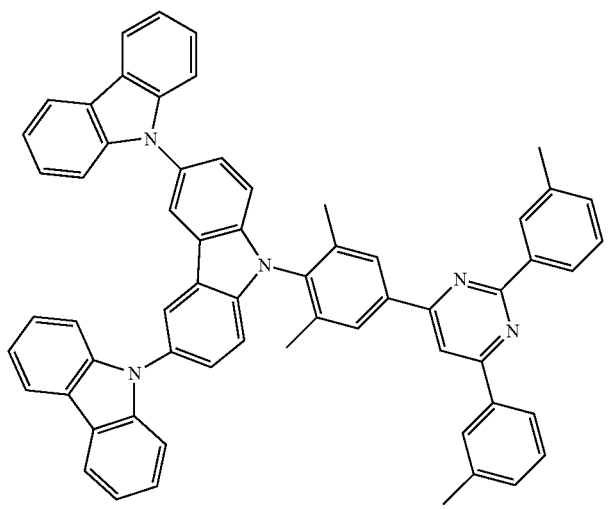
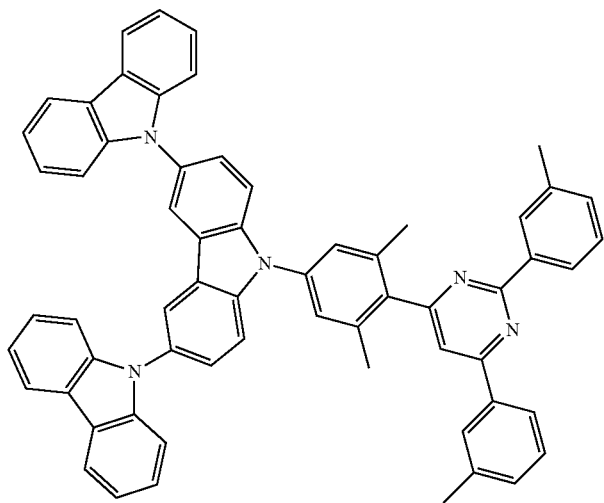

-continued
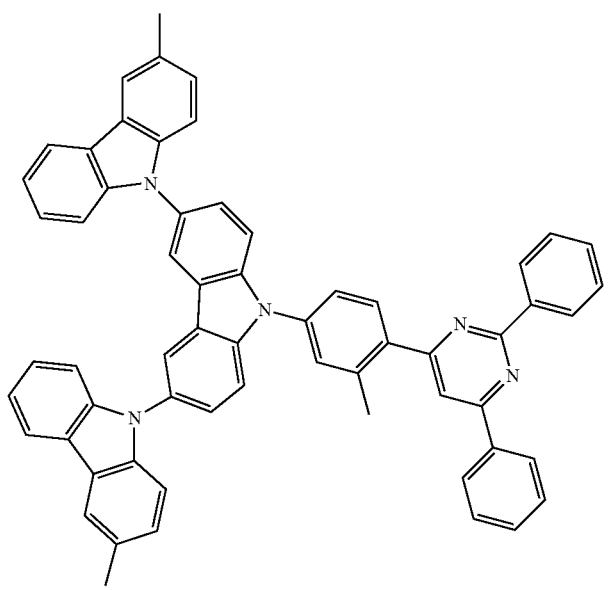
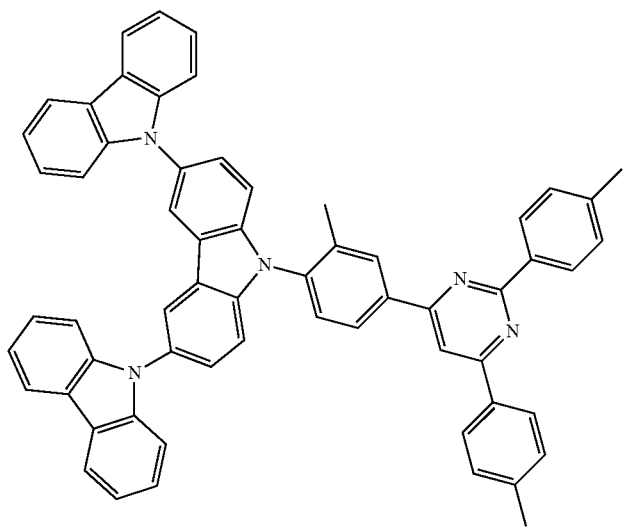
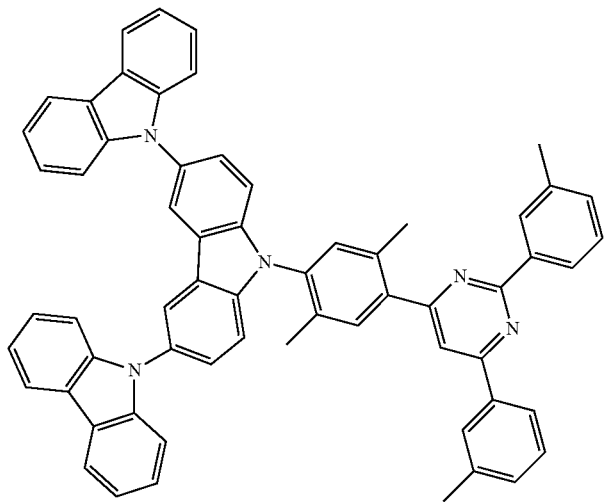

-continued
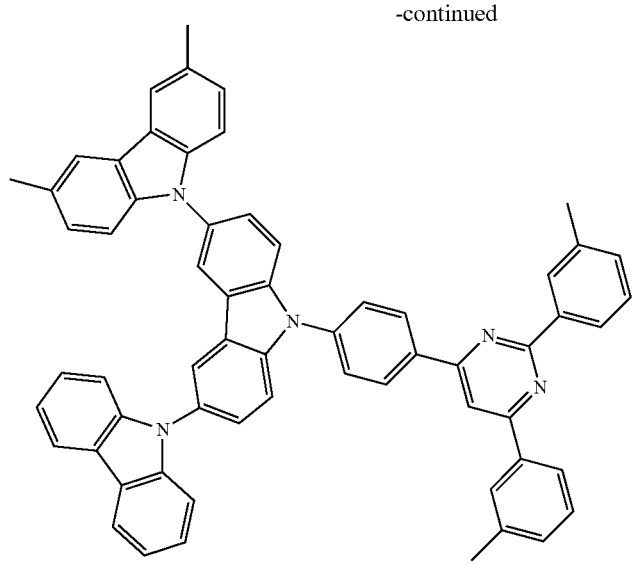
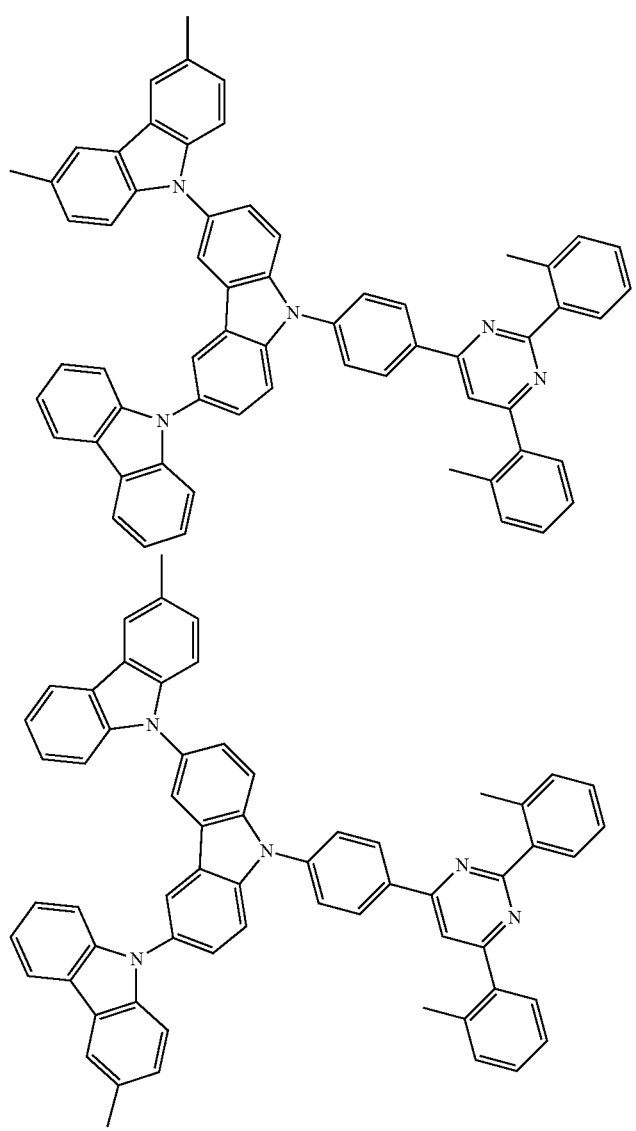

-continued
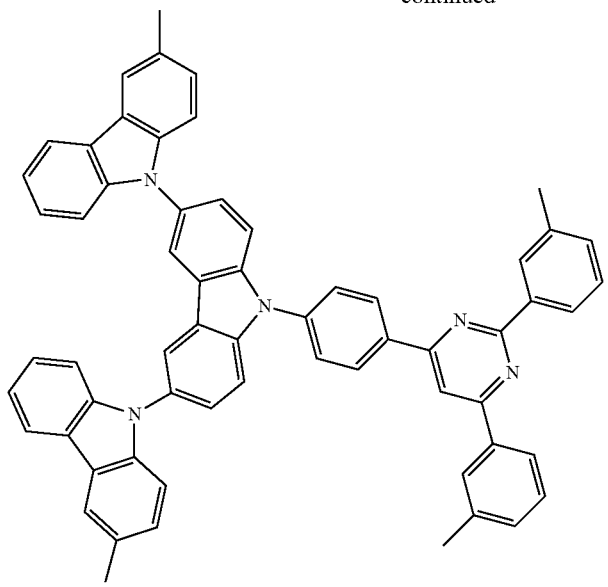
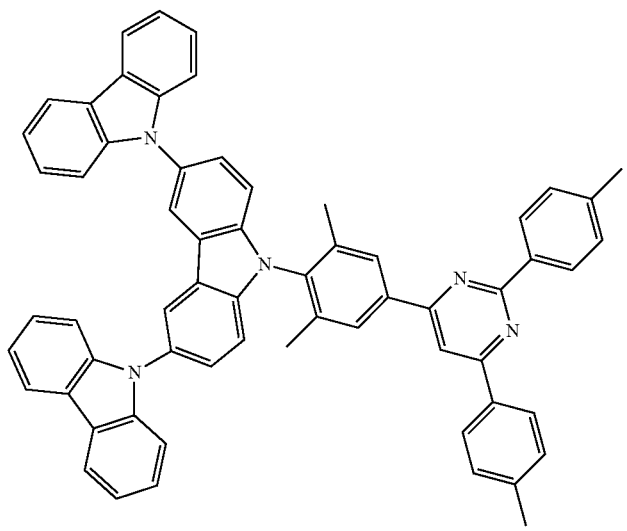
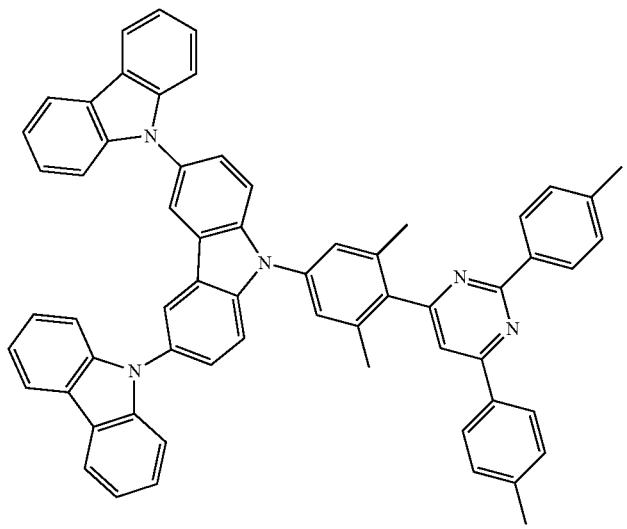

-continued
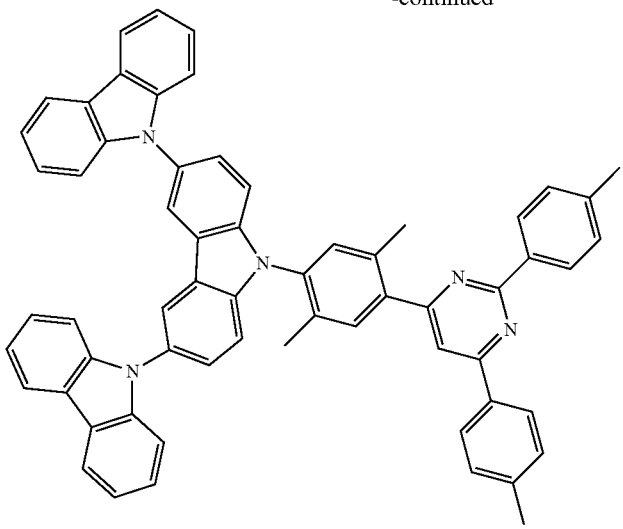
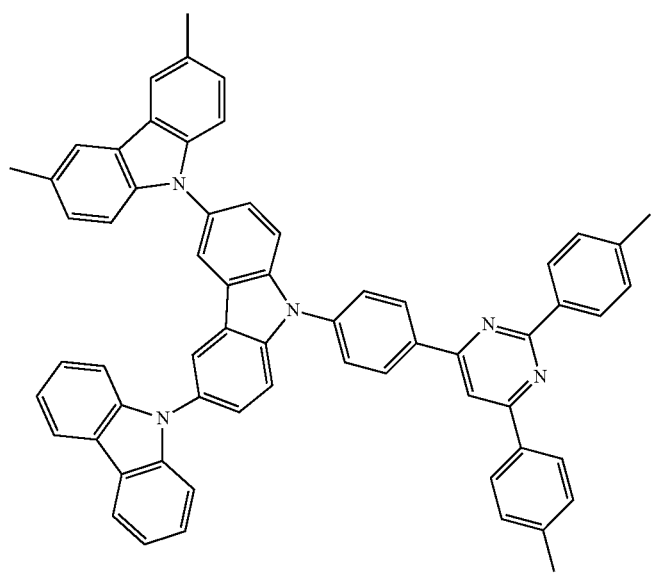
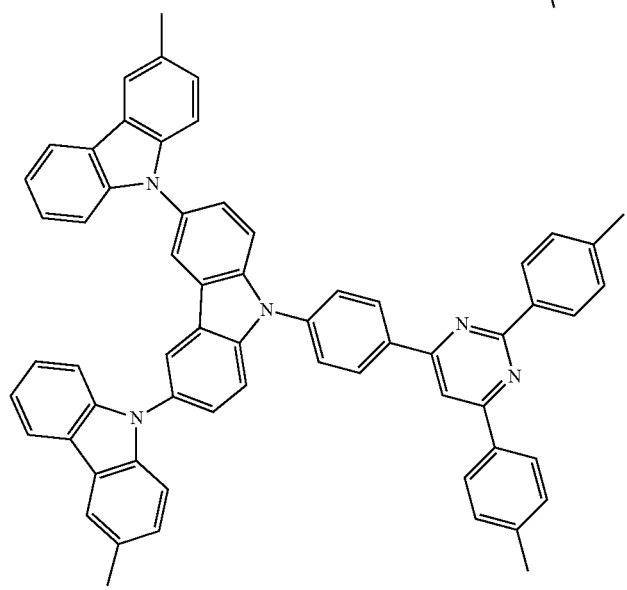

-continued
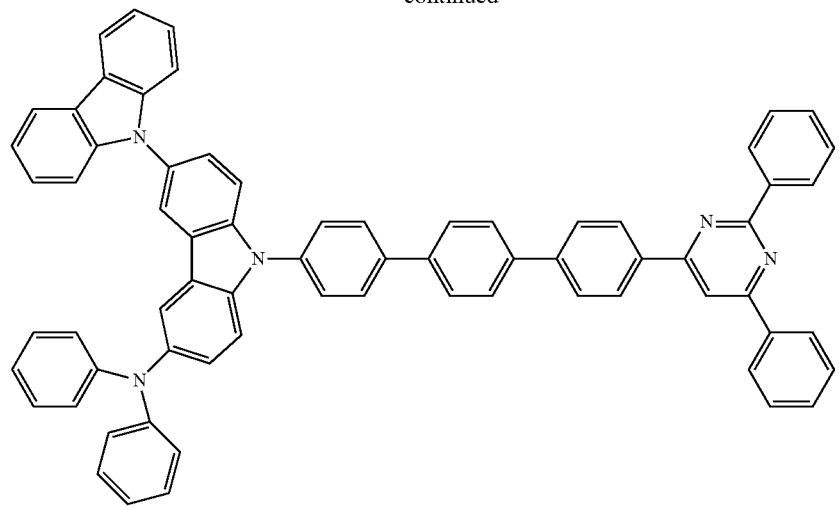
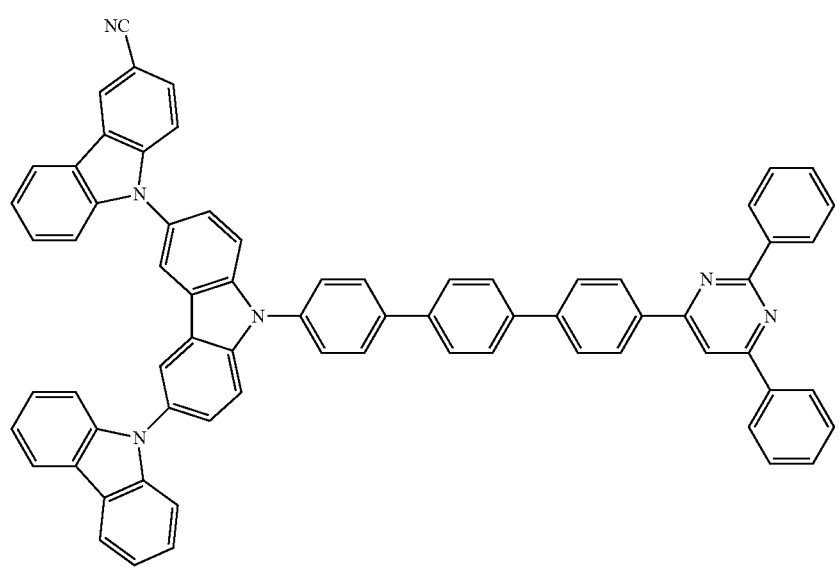
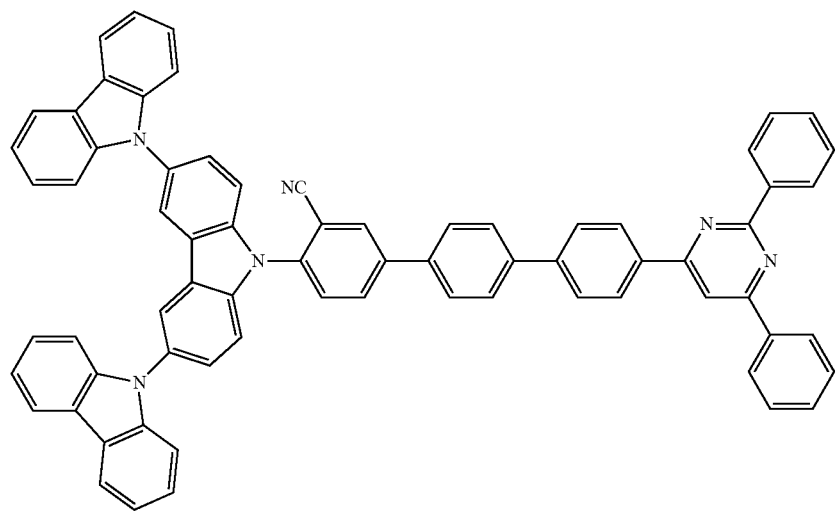

-continued
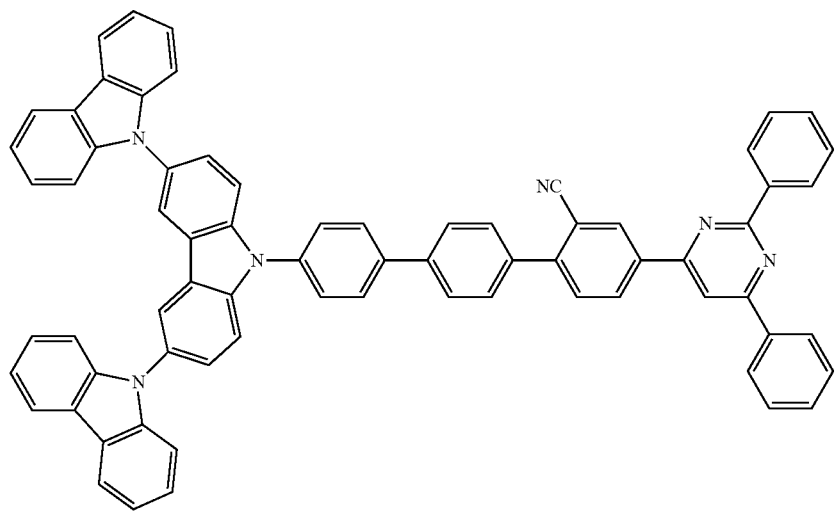
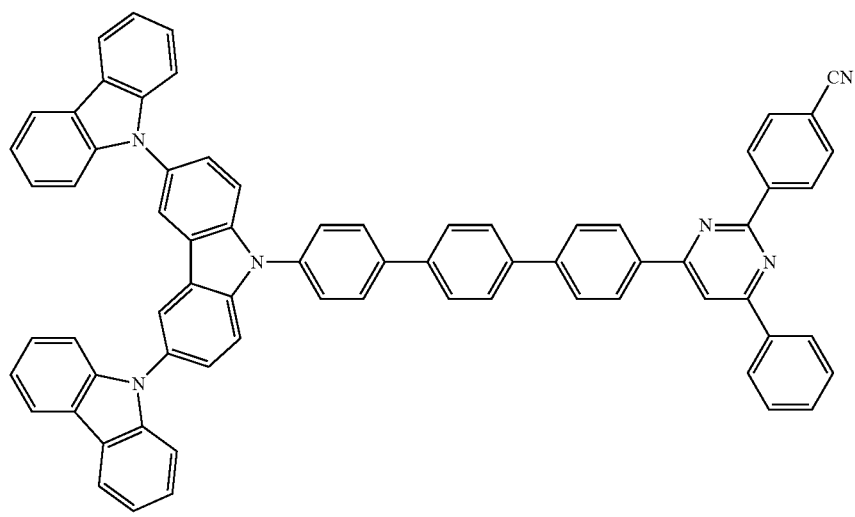
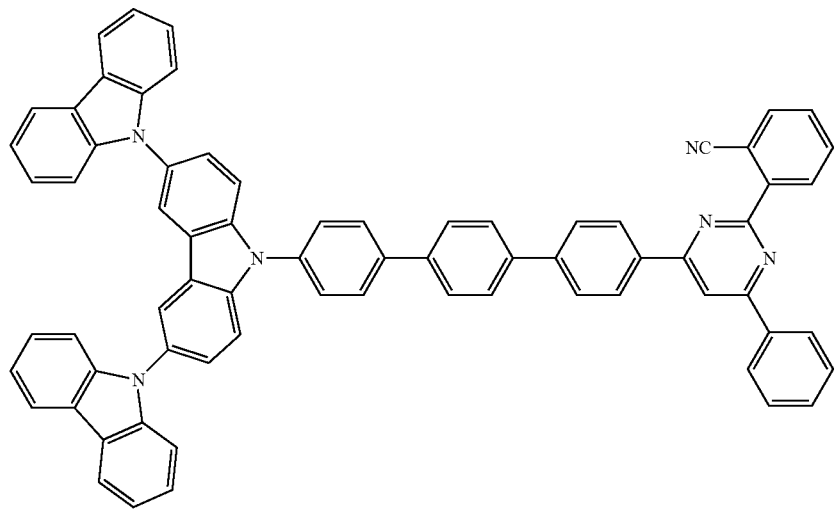

-continued
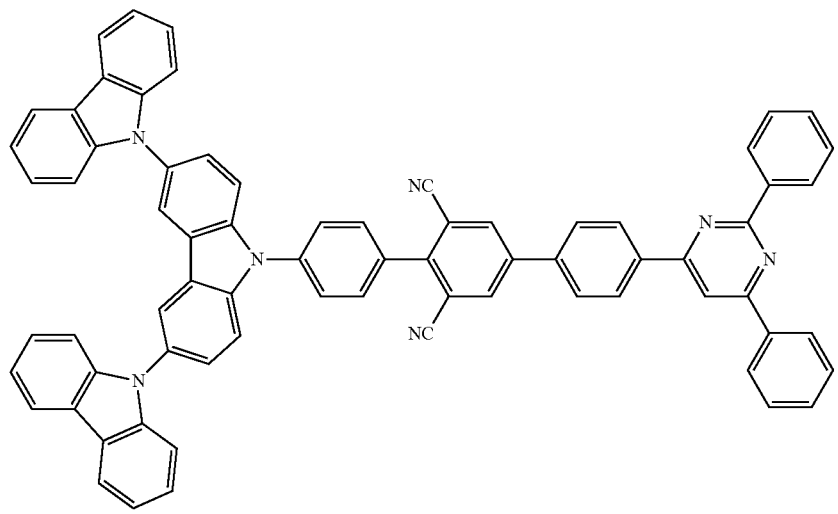
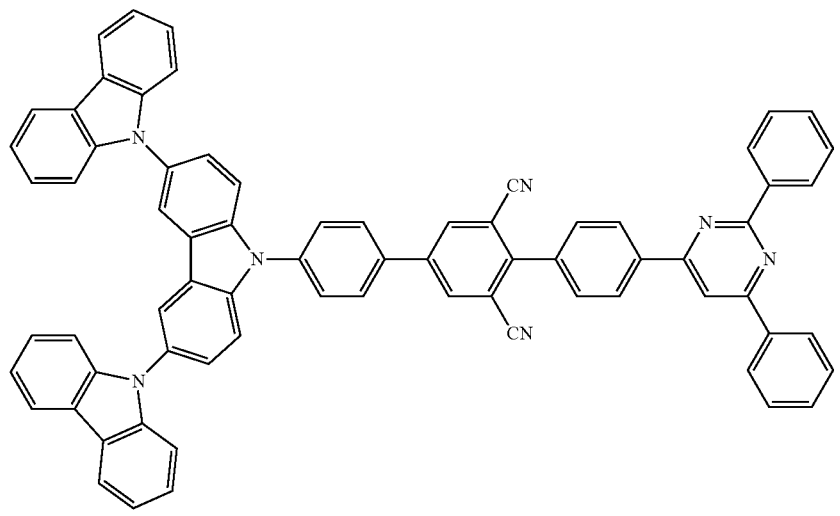
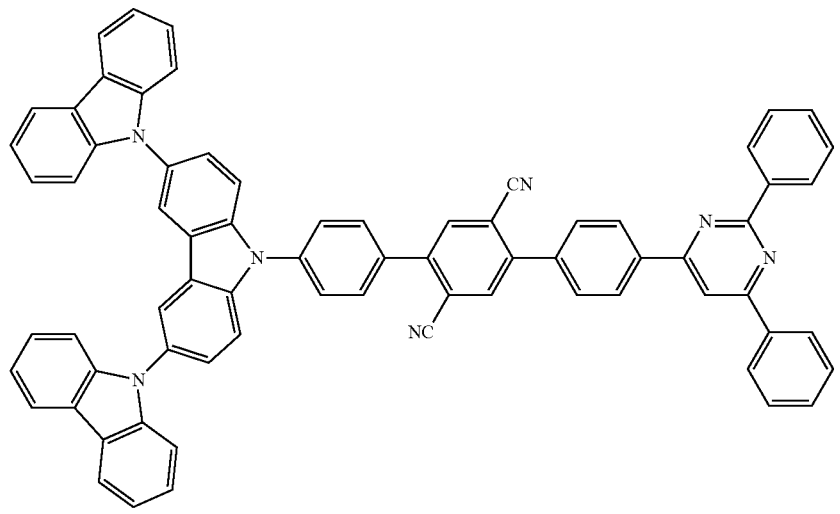

-continued
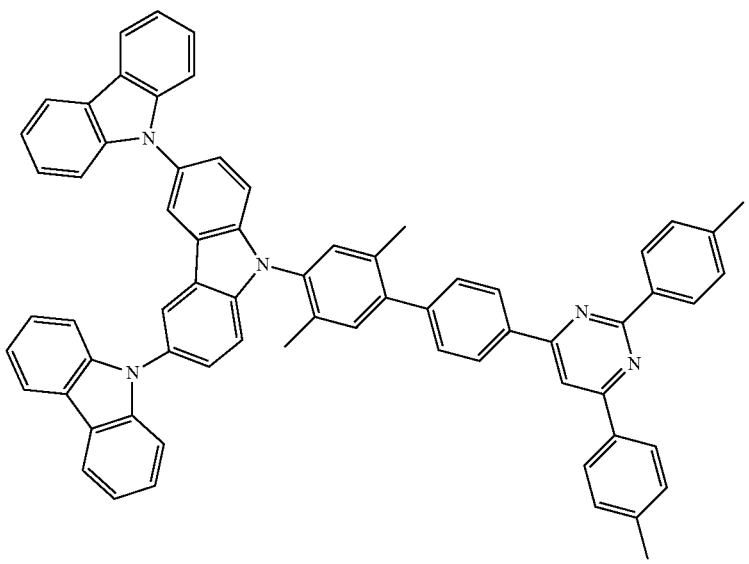
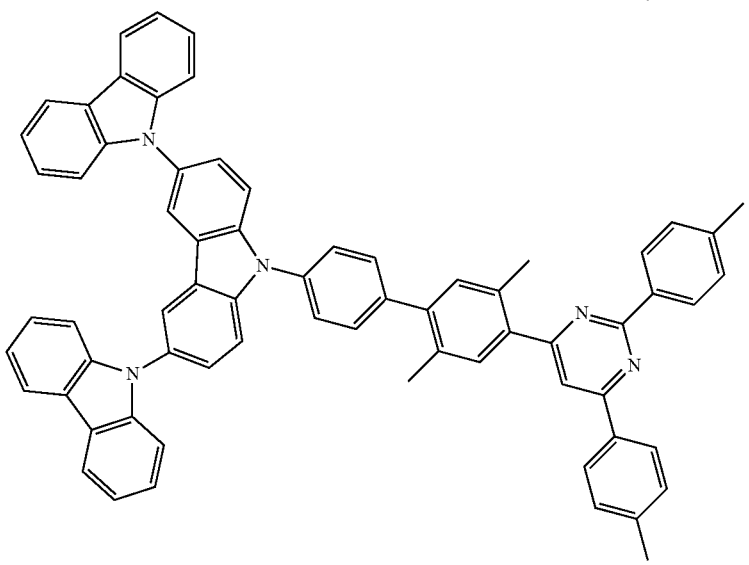
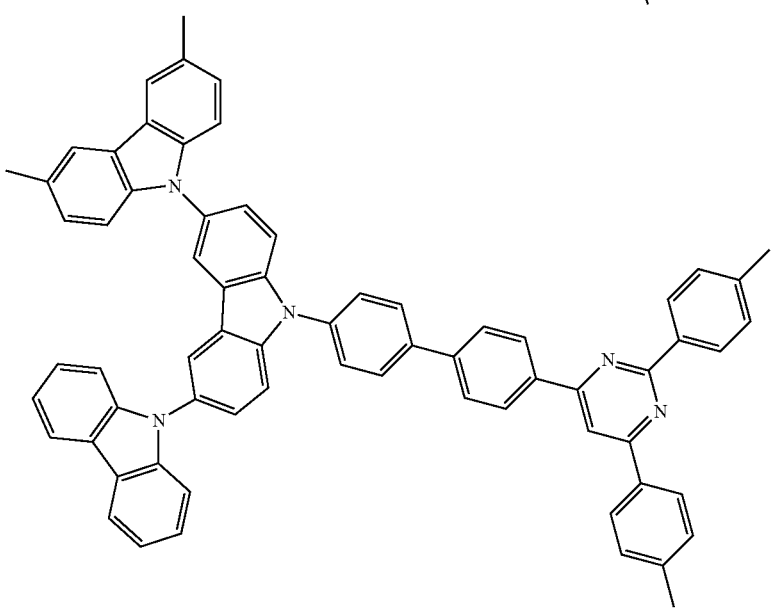

-continued
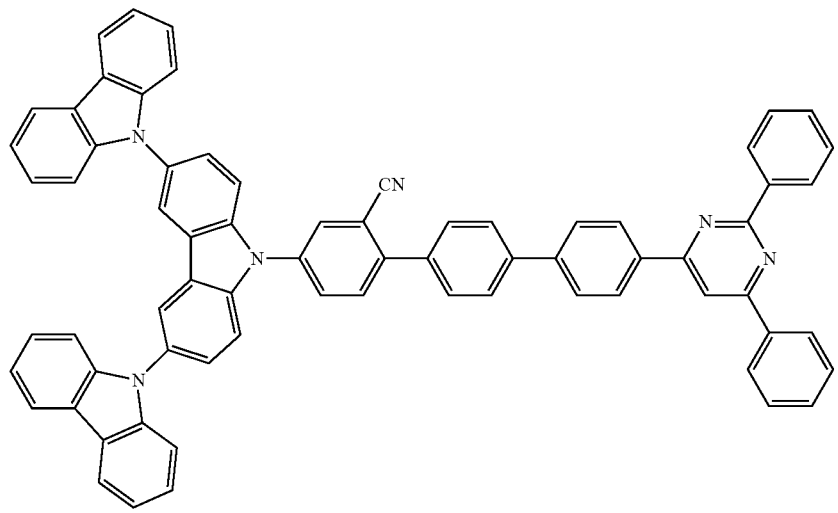

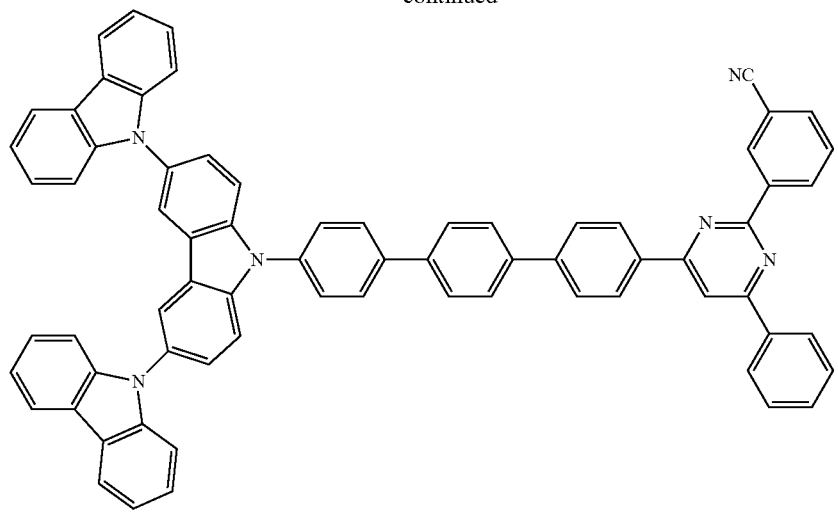
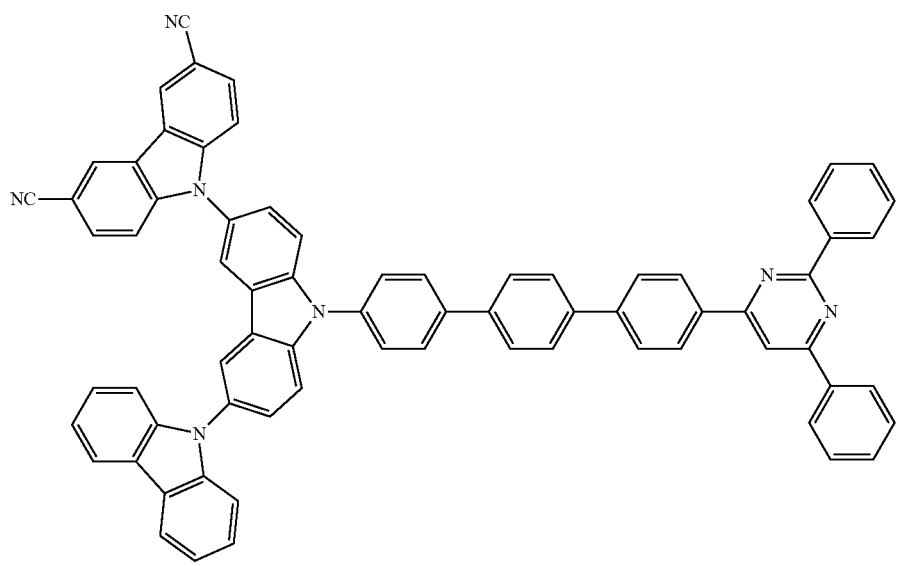
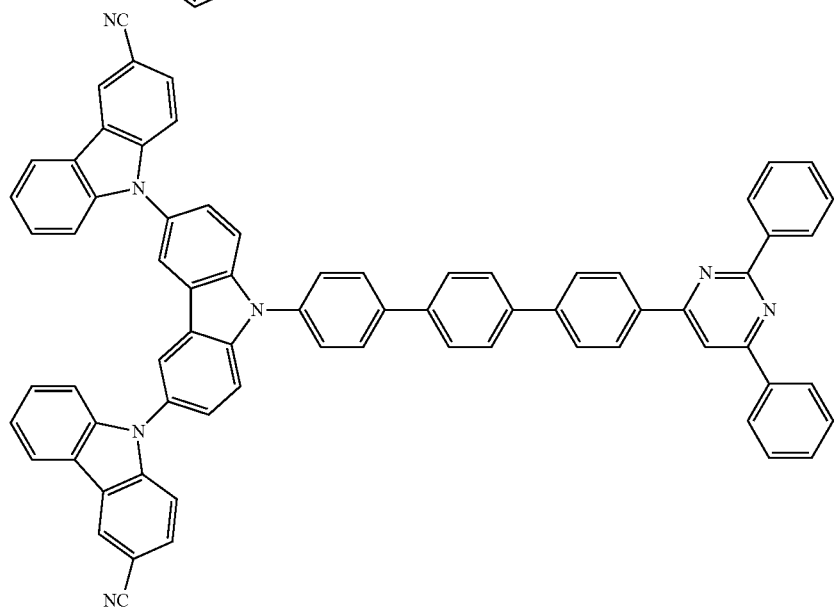

-continued
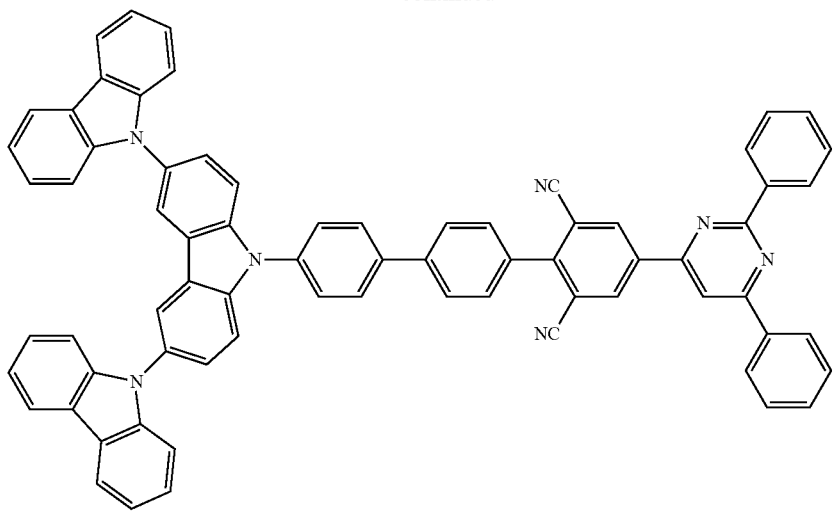

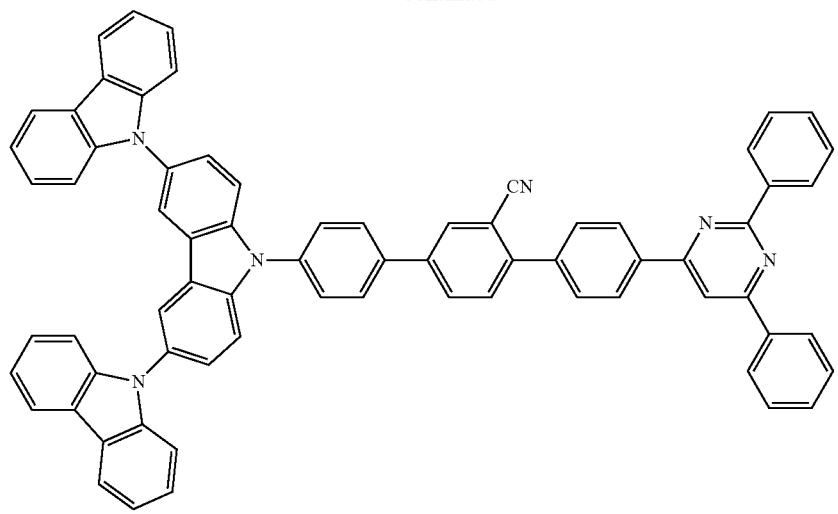
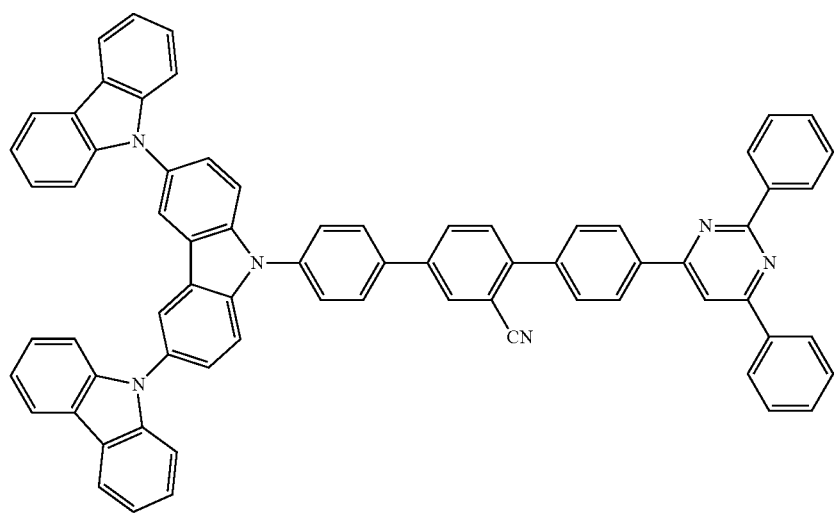
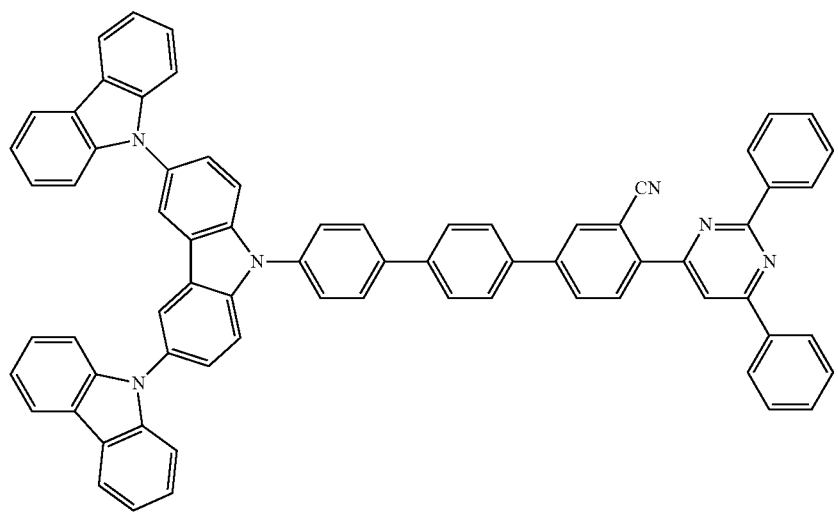

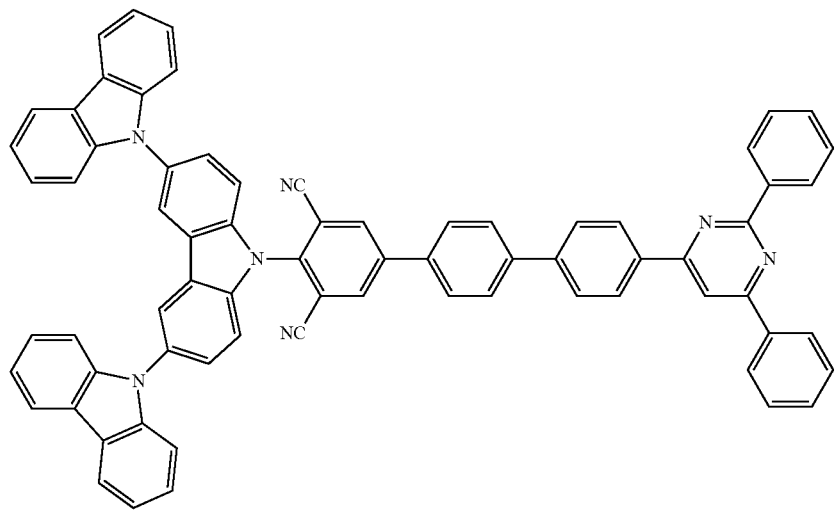
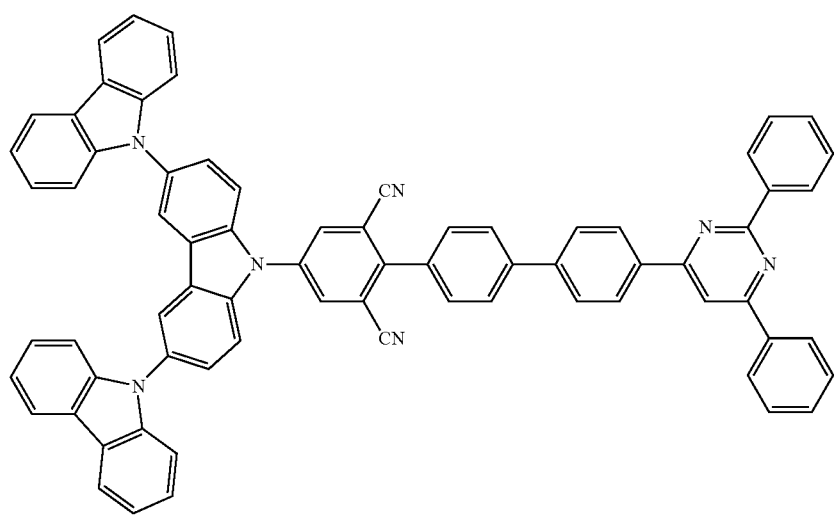
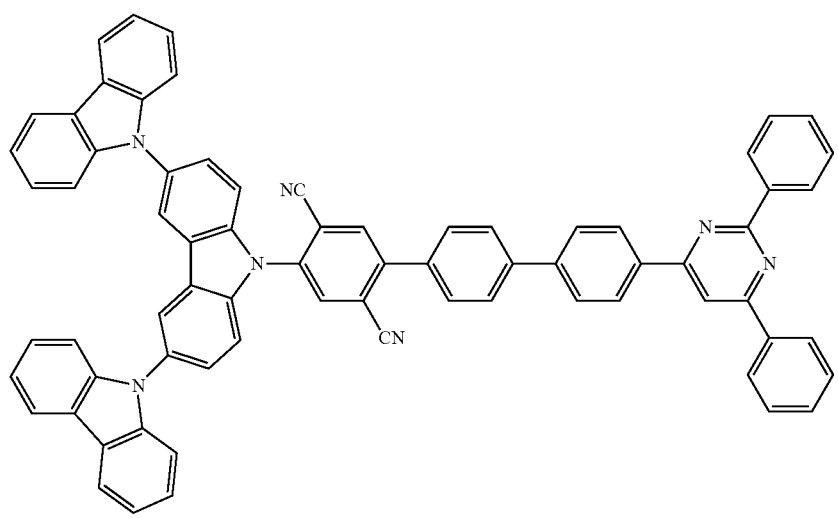

-continued
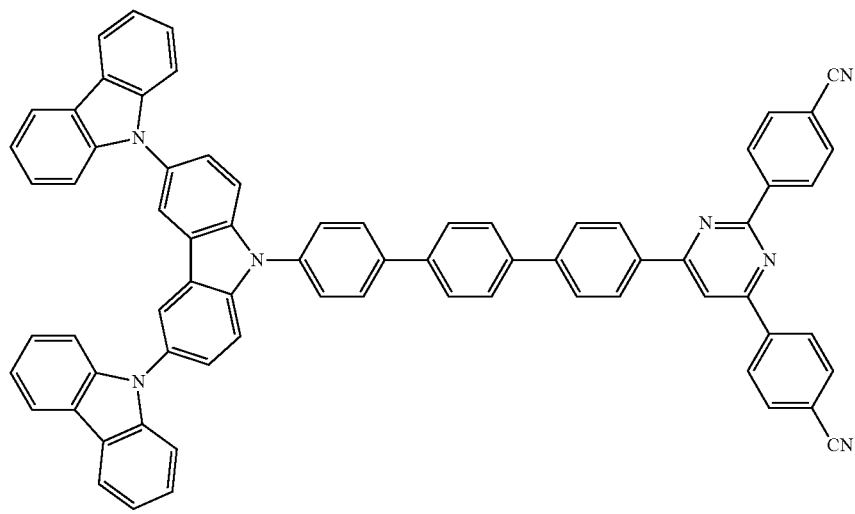
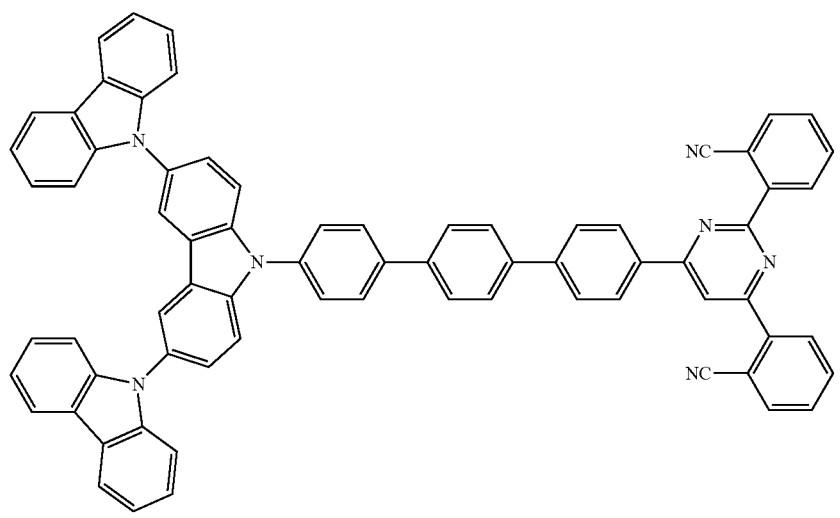
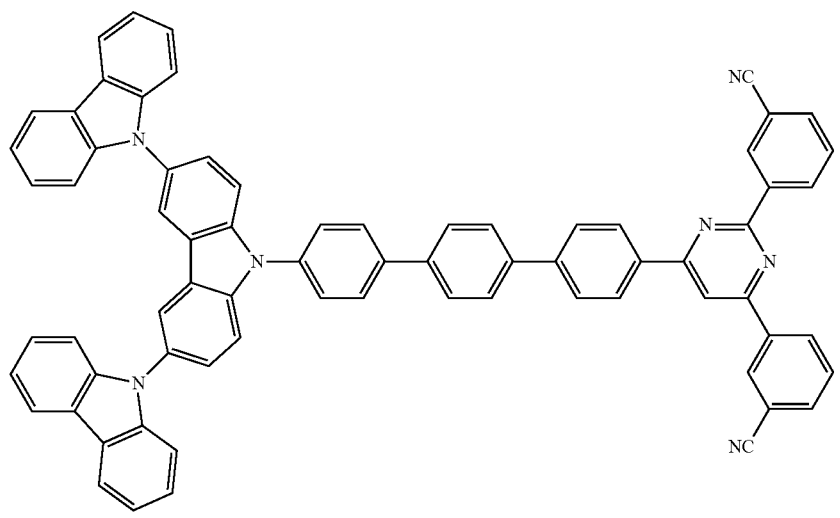

-continued
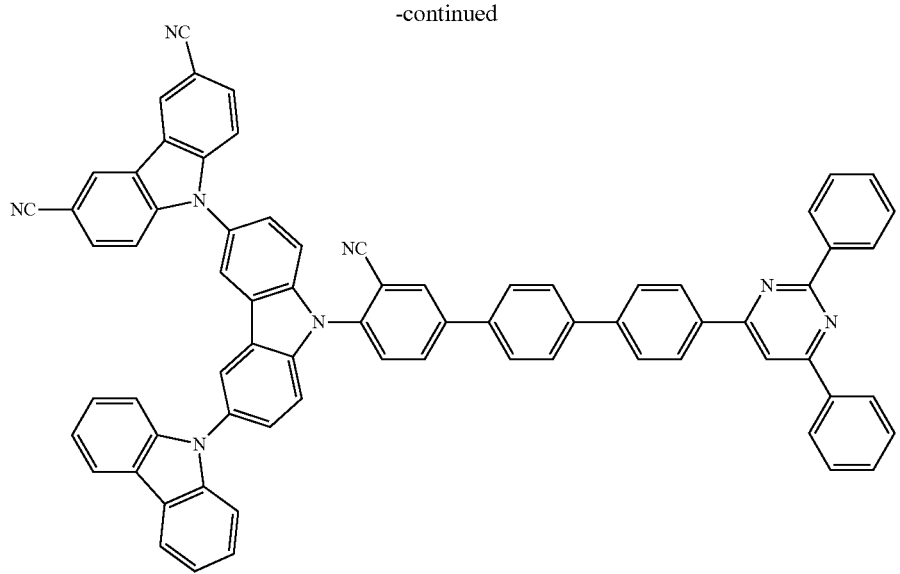
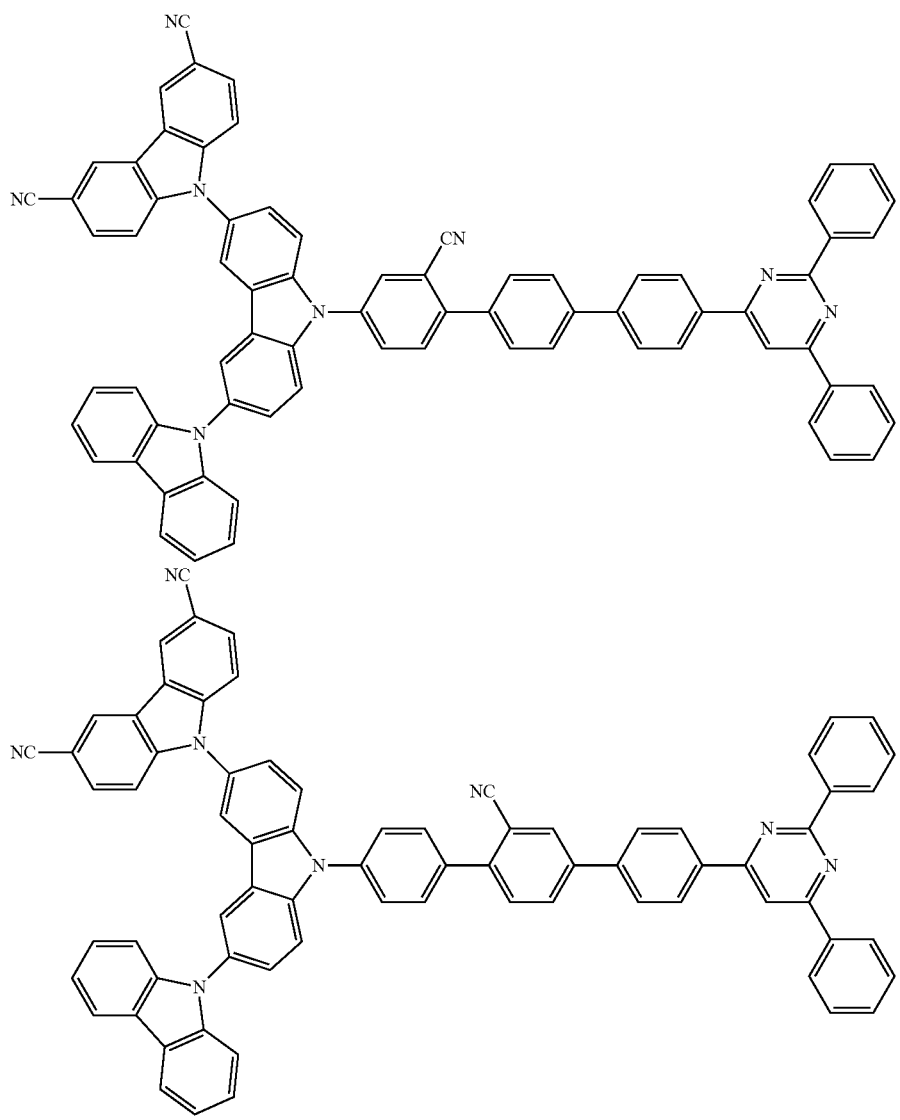

-continued
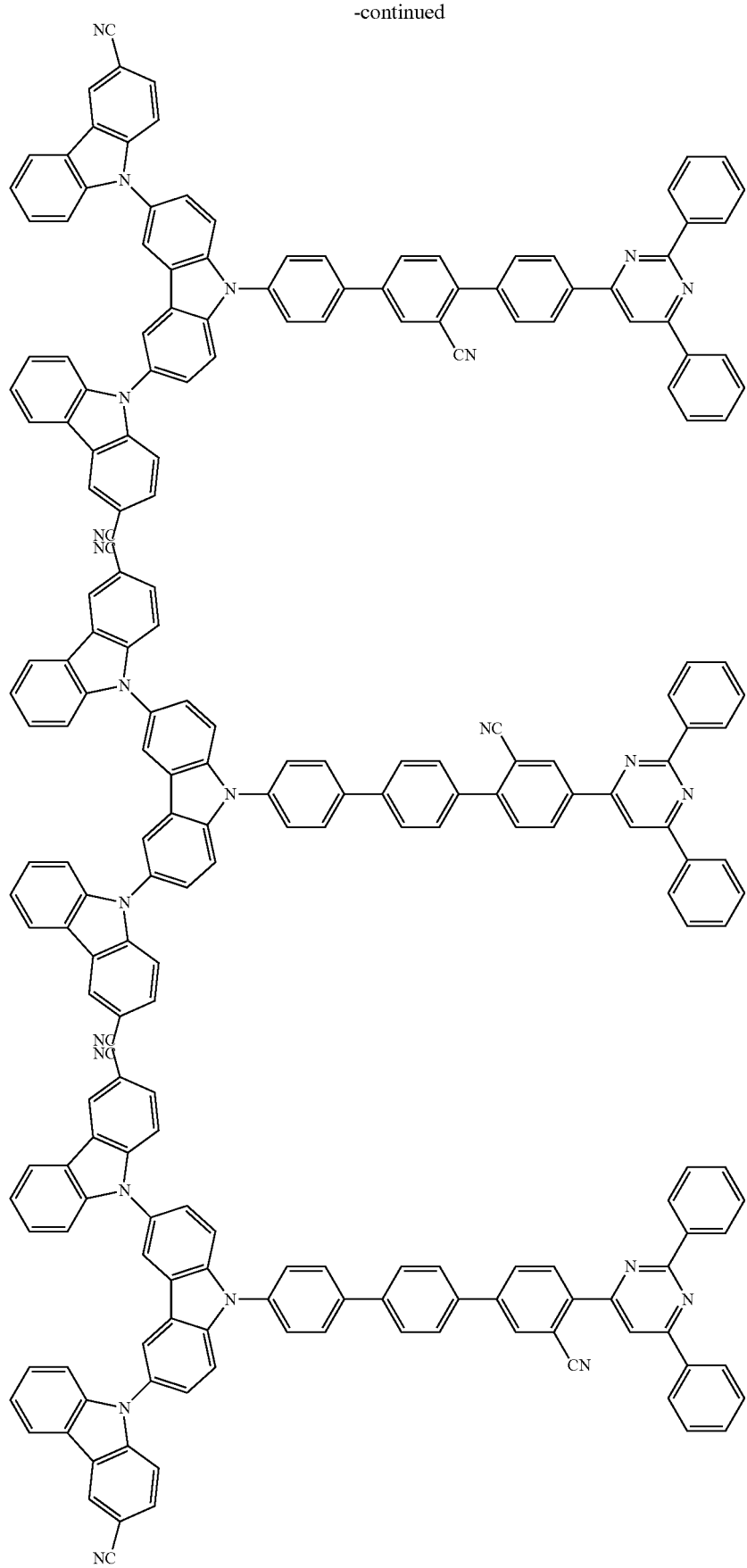

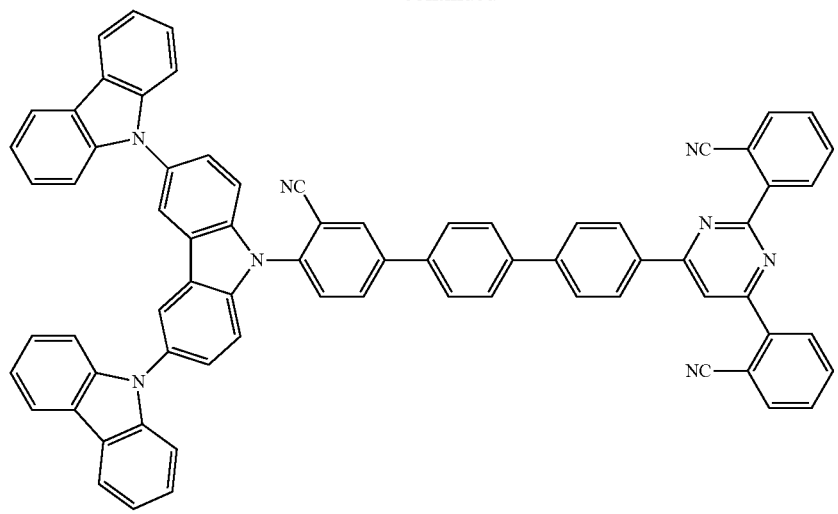
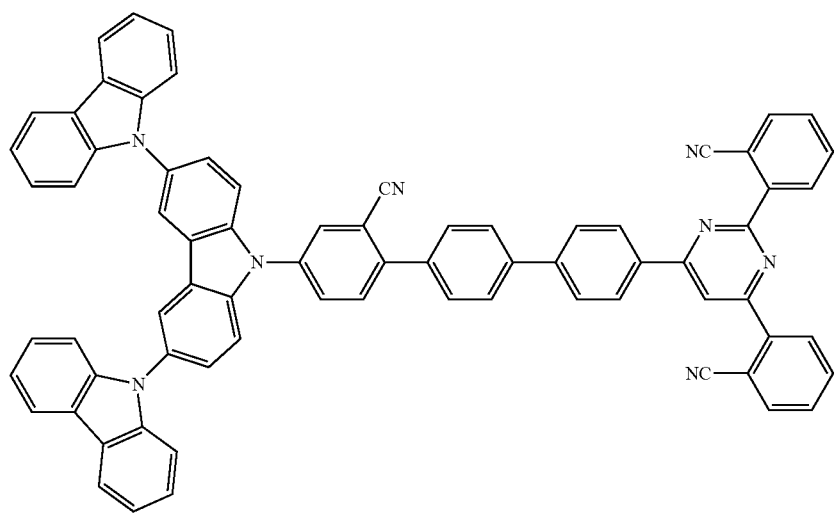
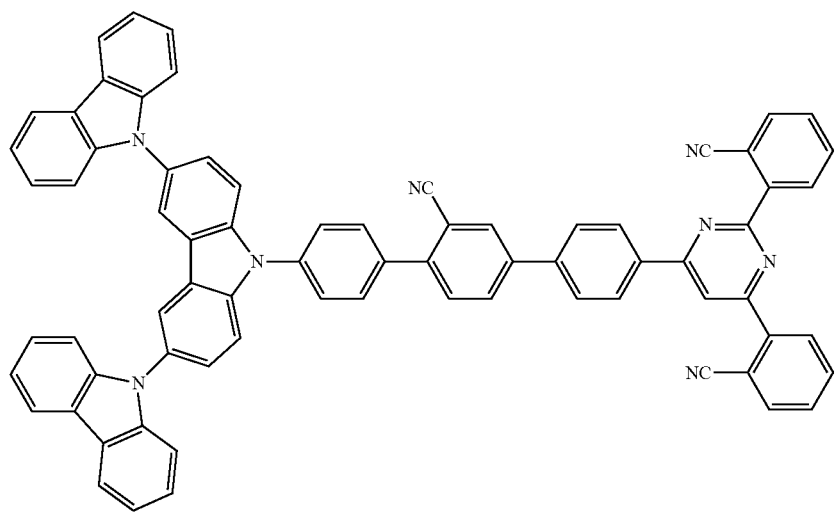

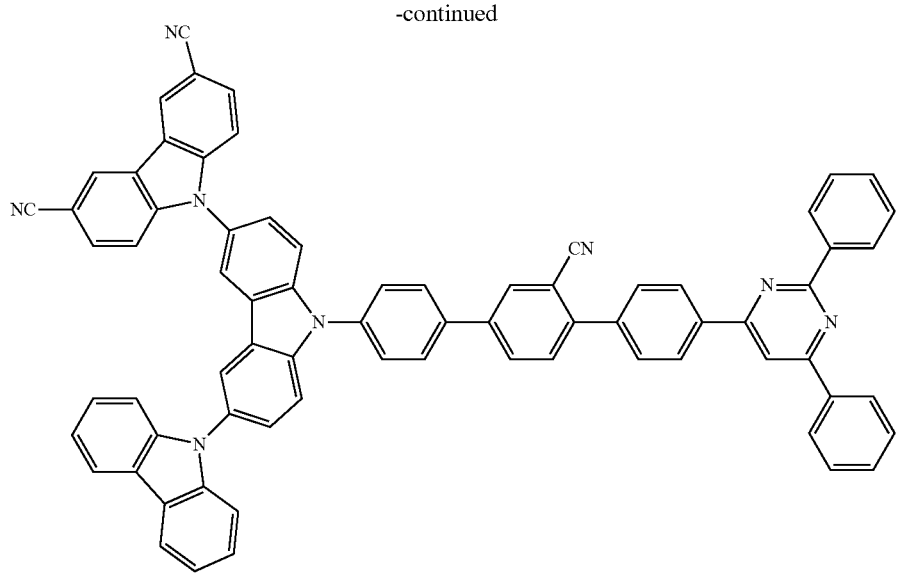
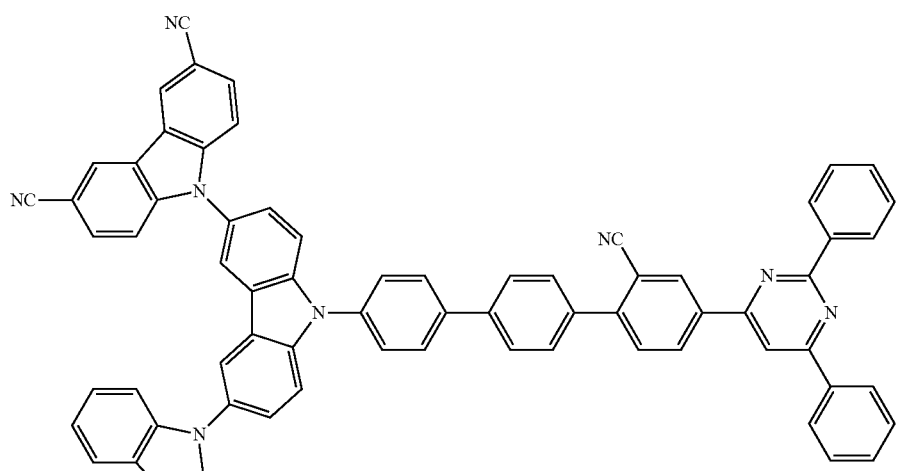
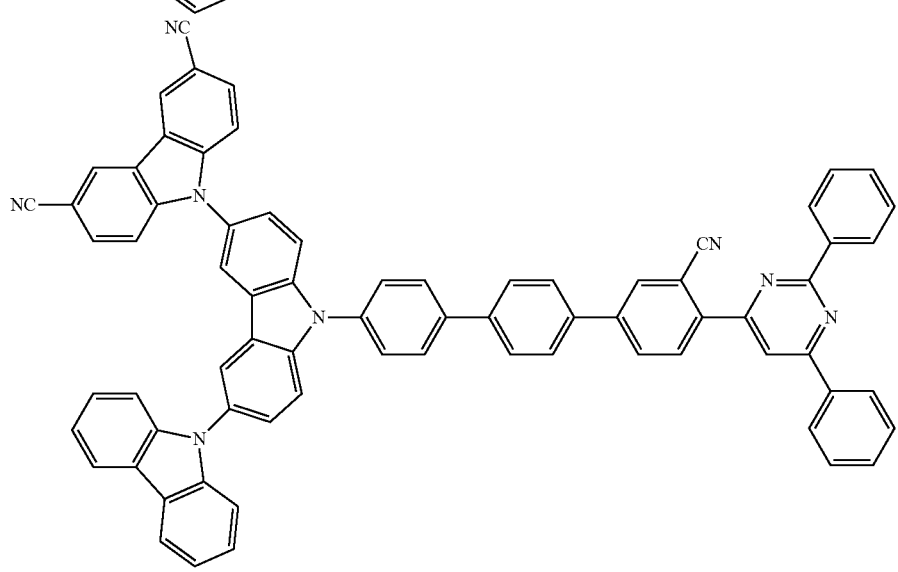

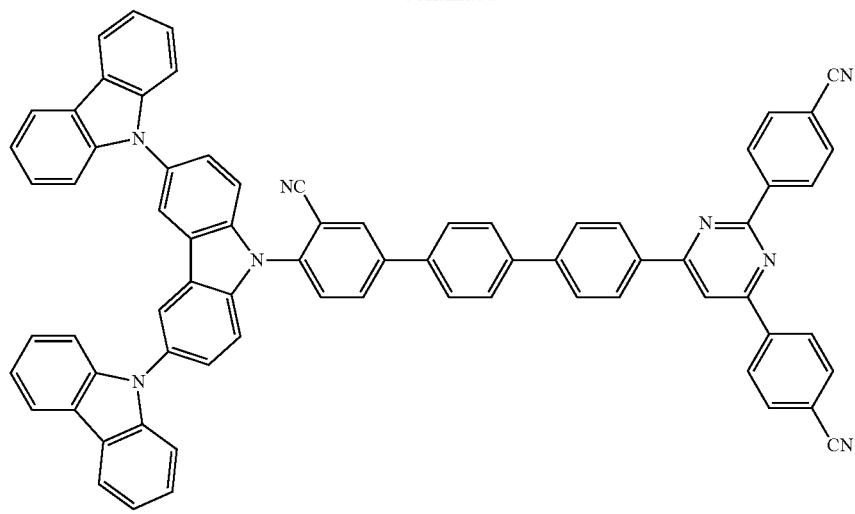
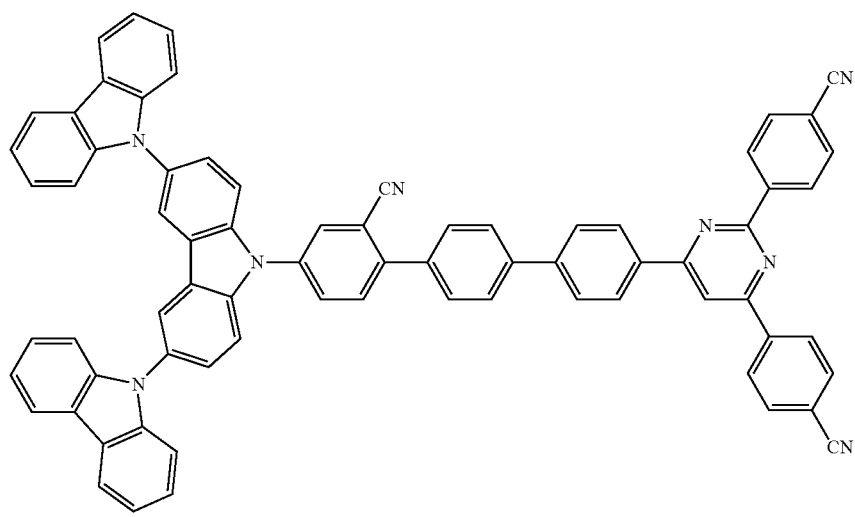
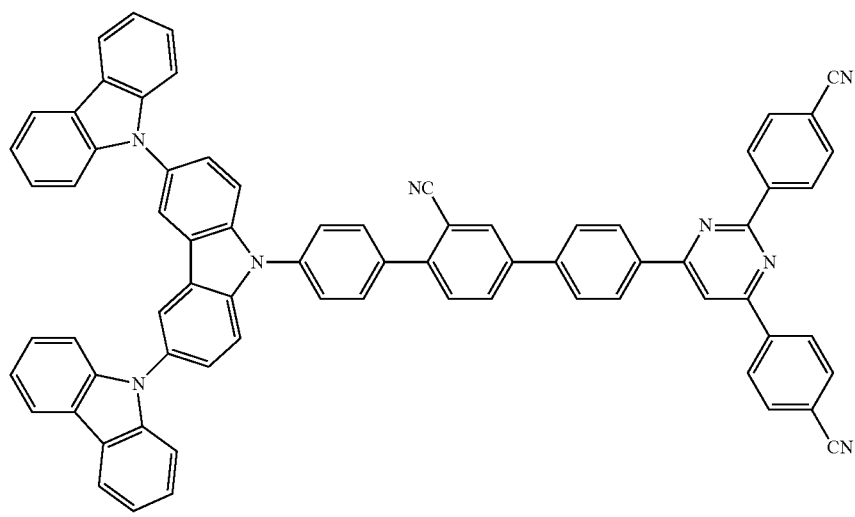

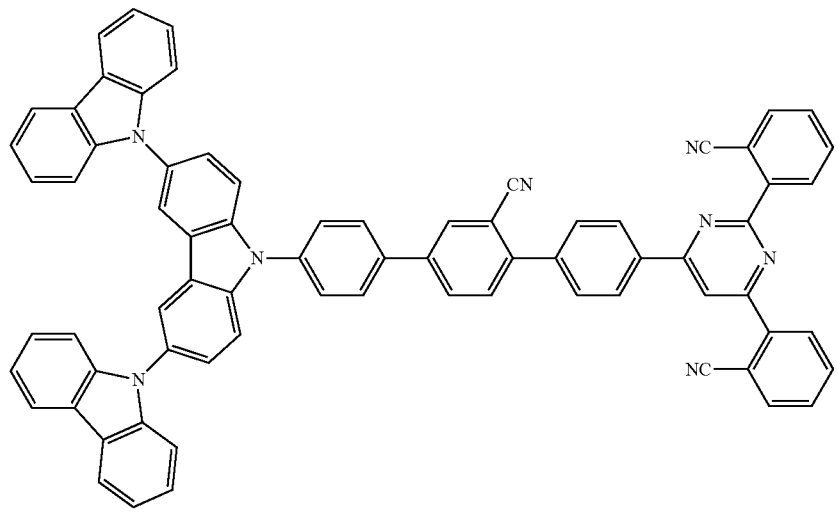
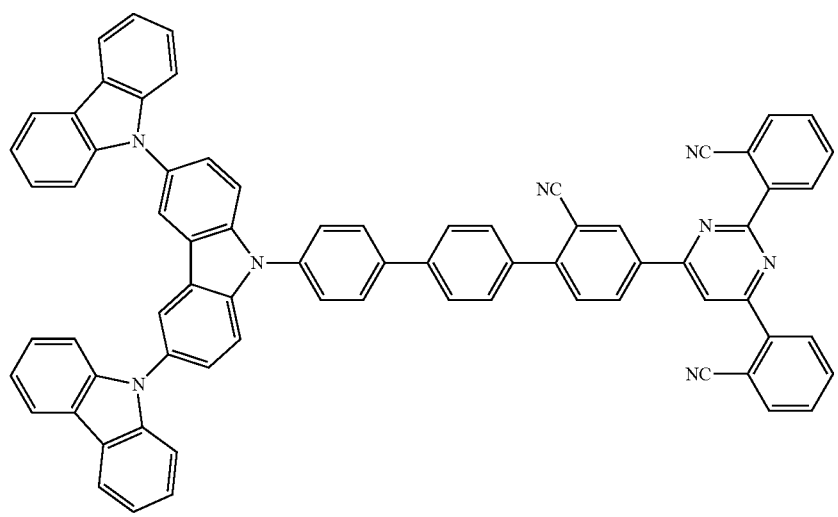
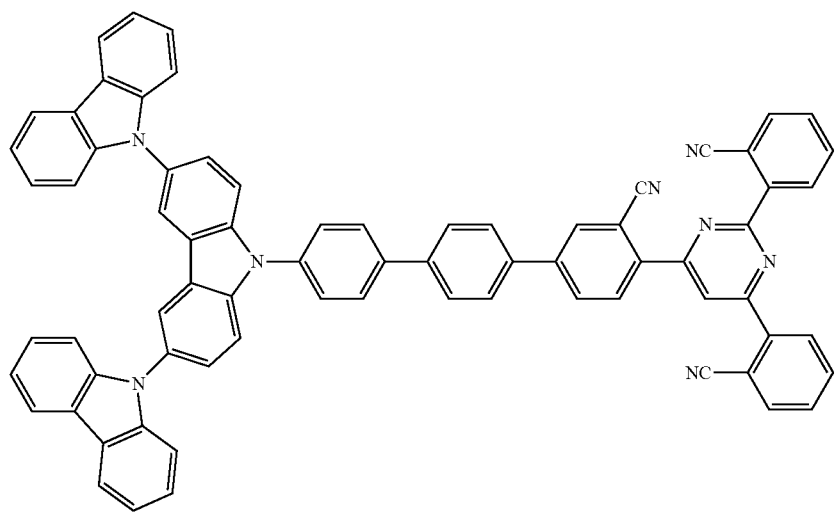

-continued
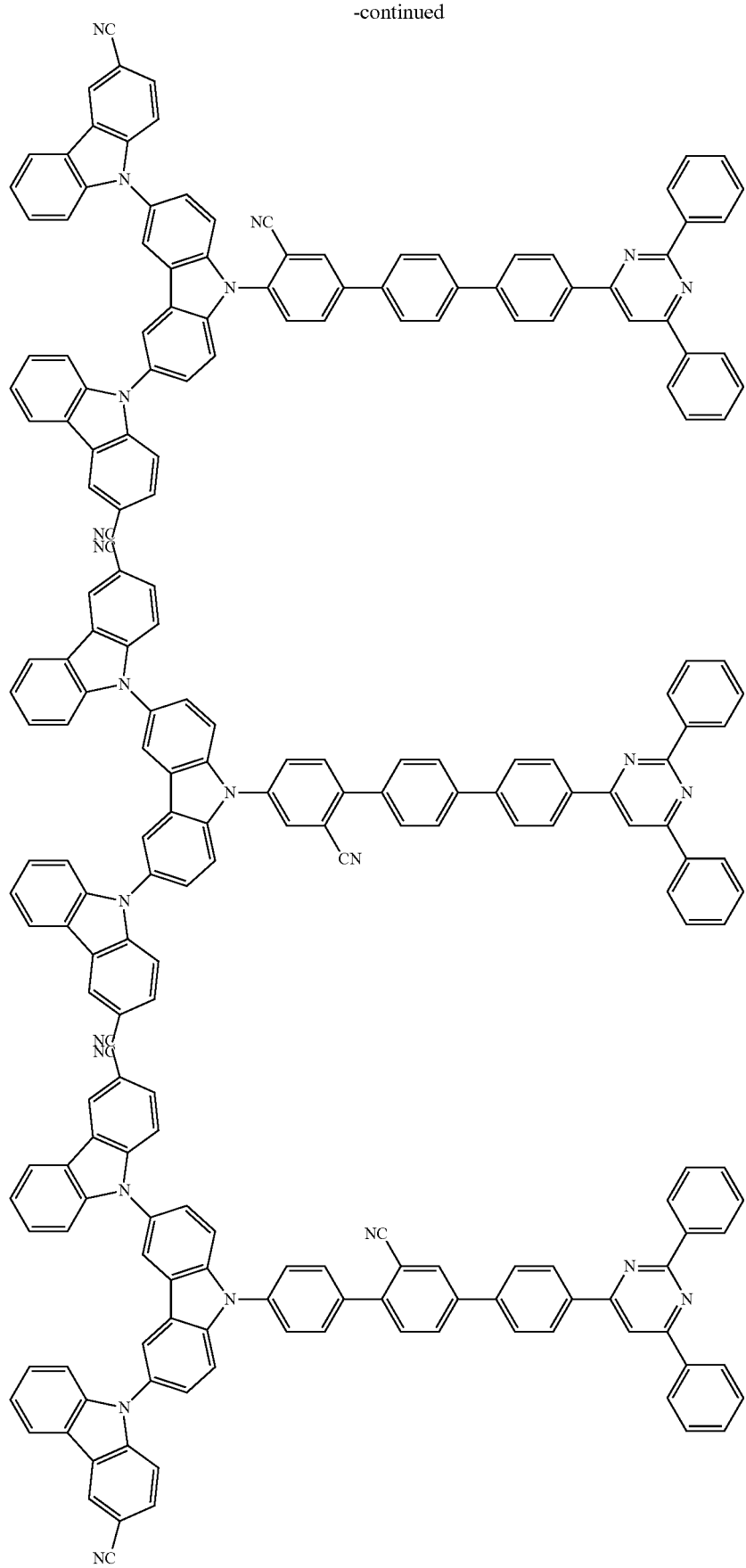

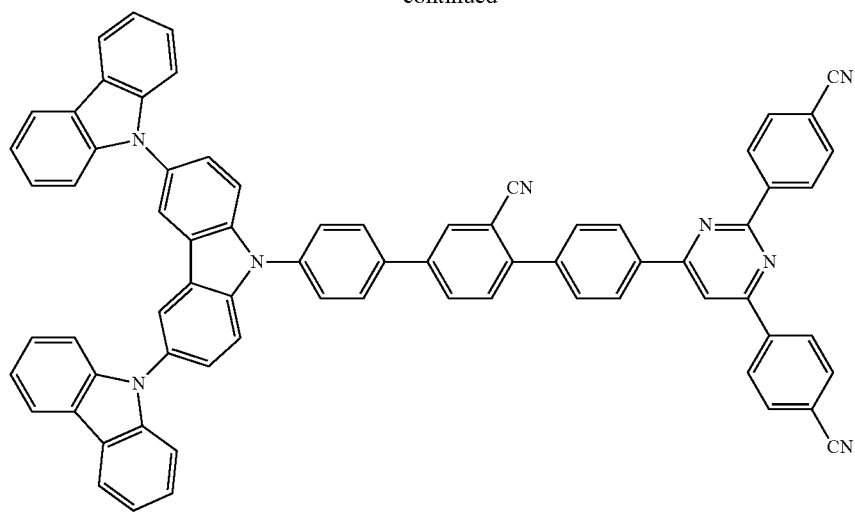
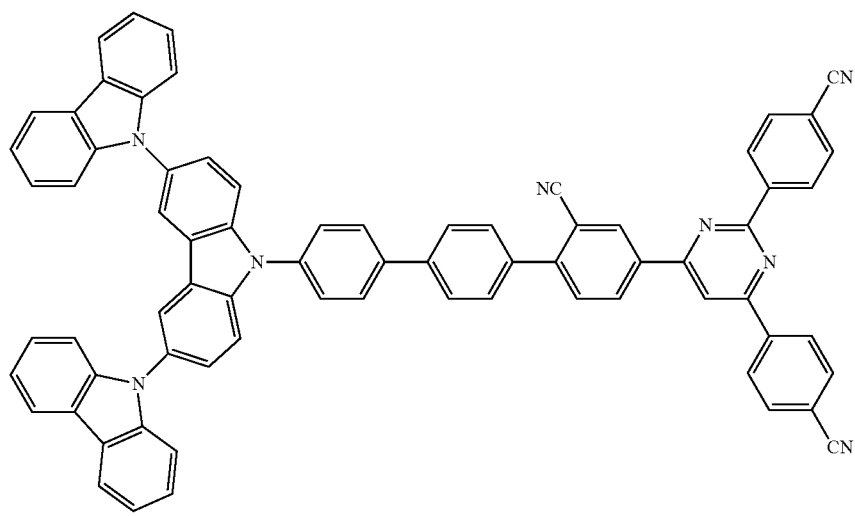
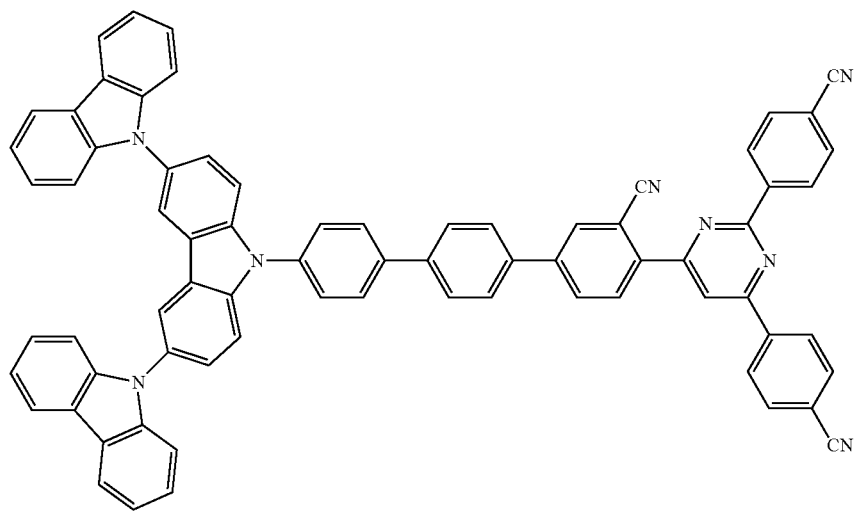

-continued
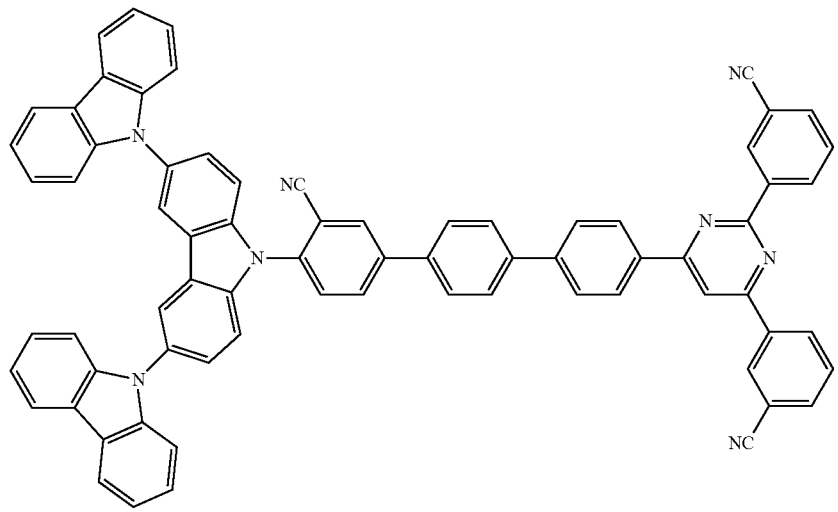
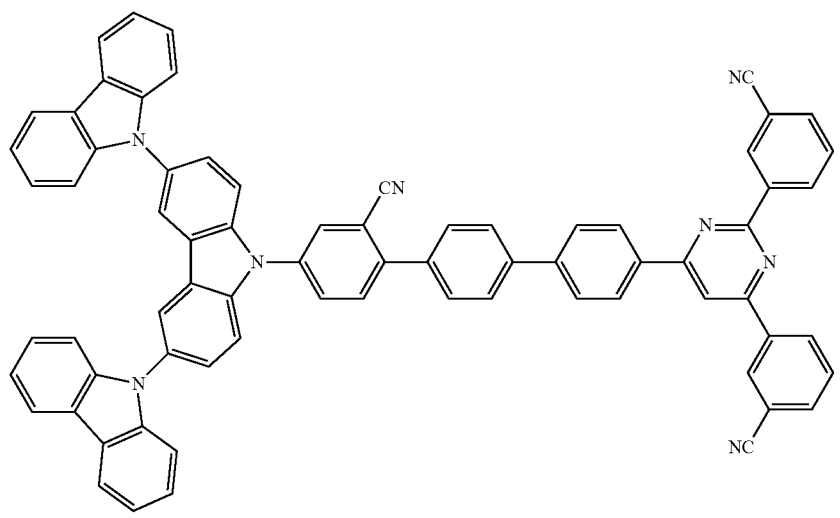
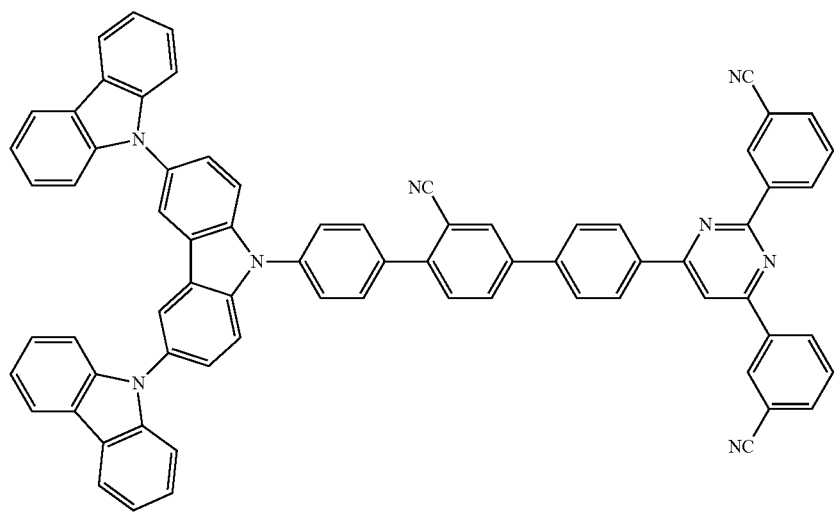

-continued
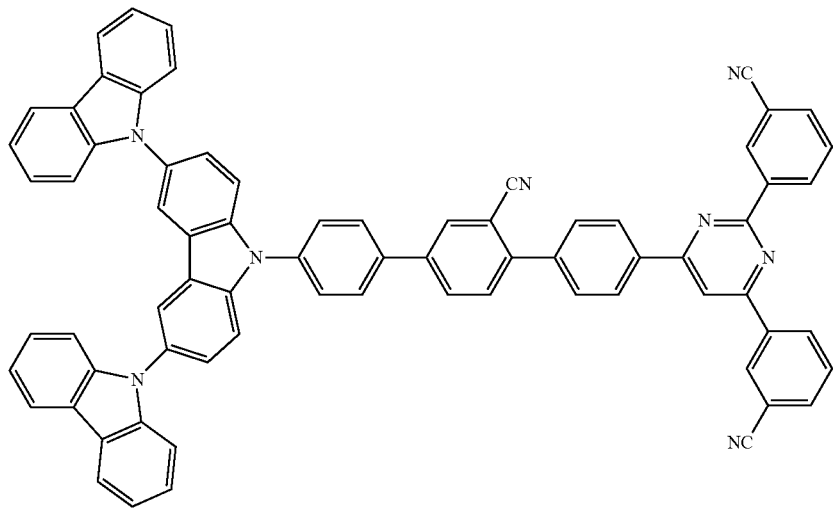
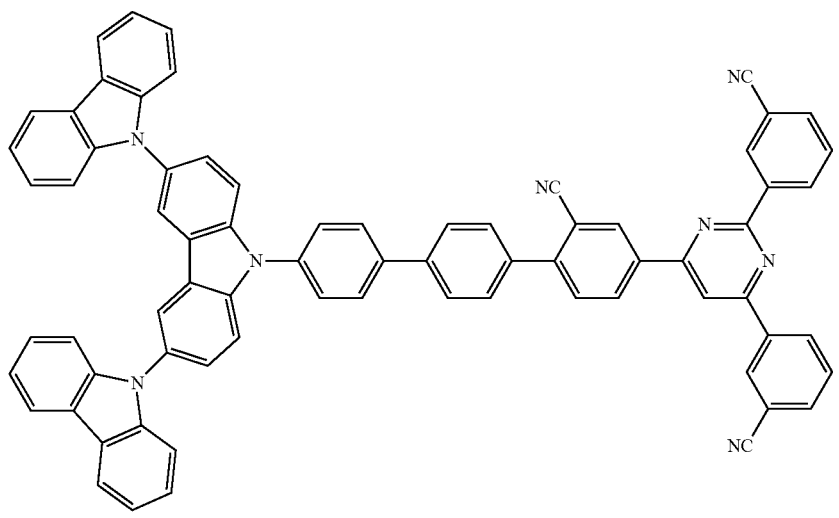
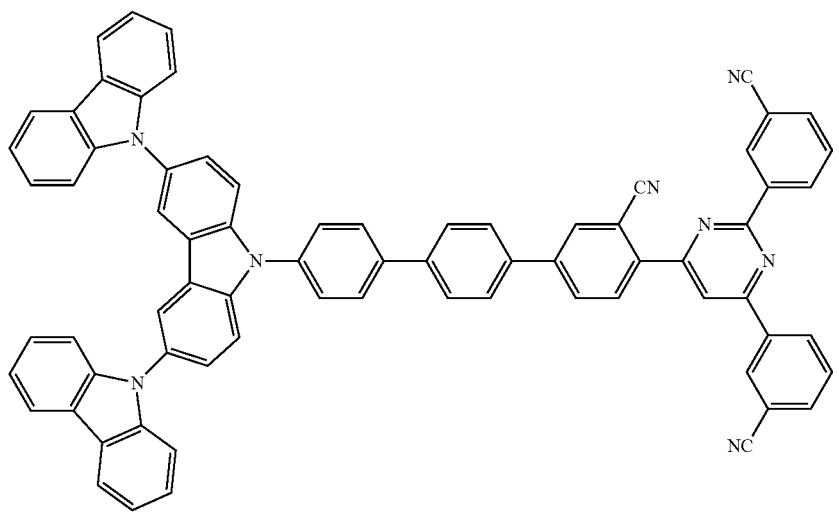

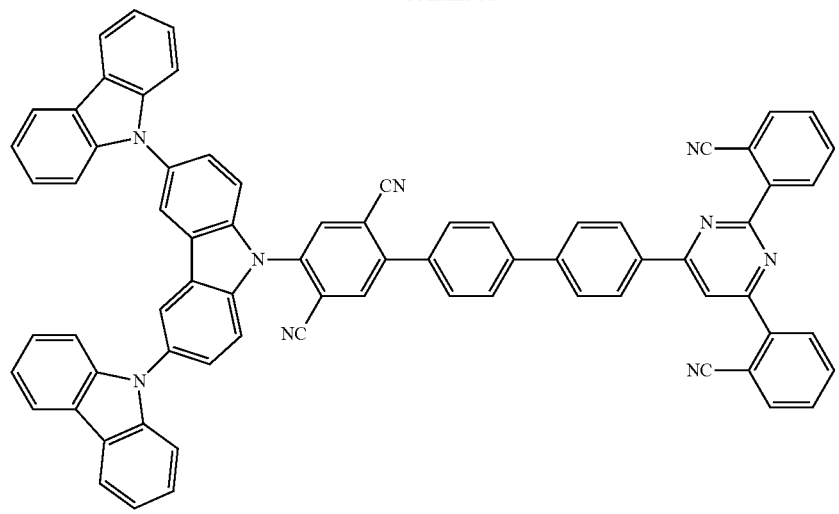
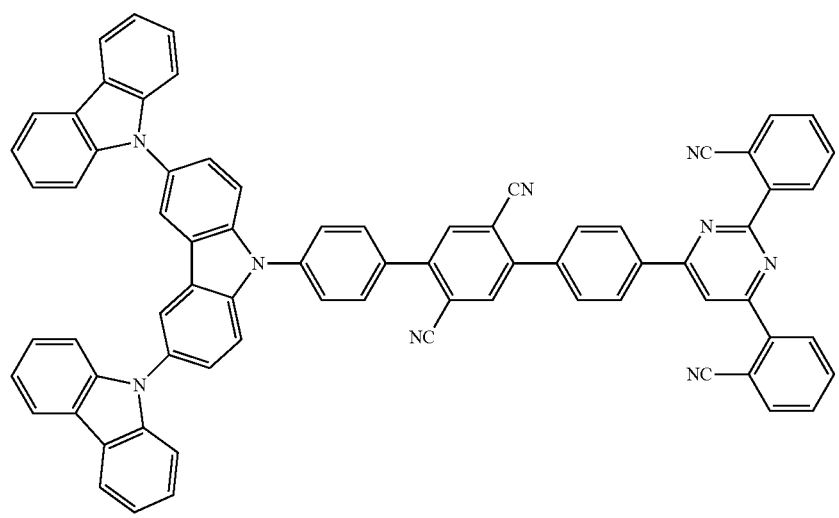
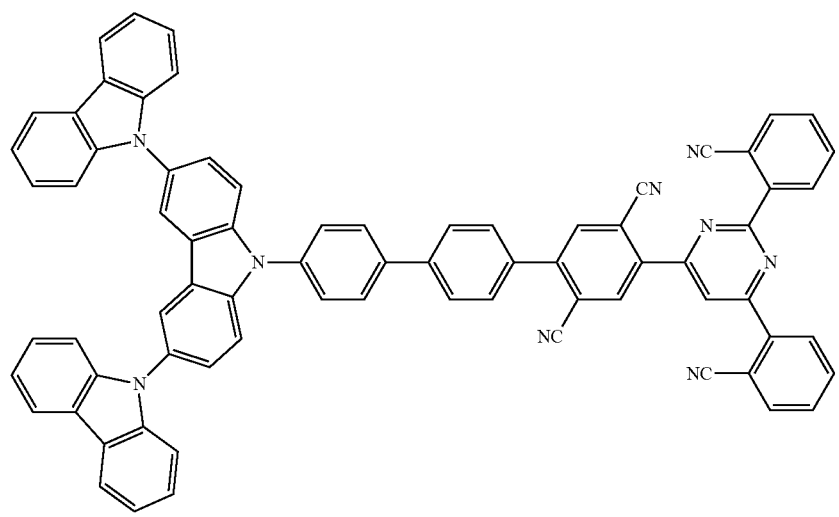

-continued
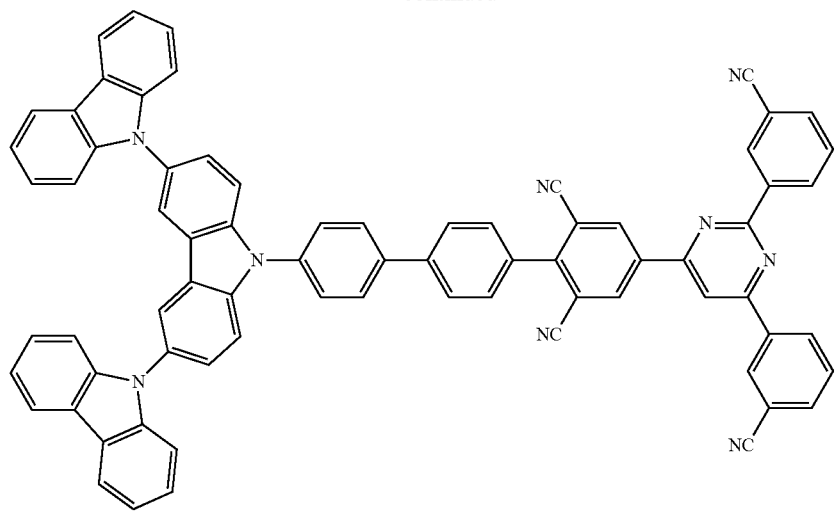
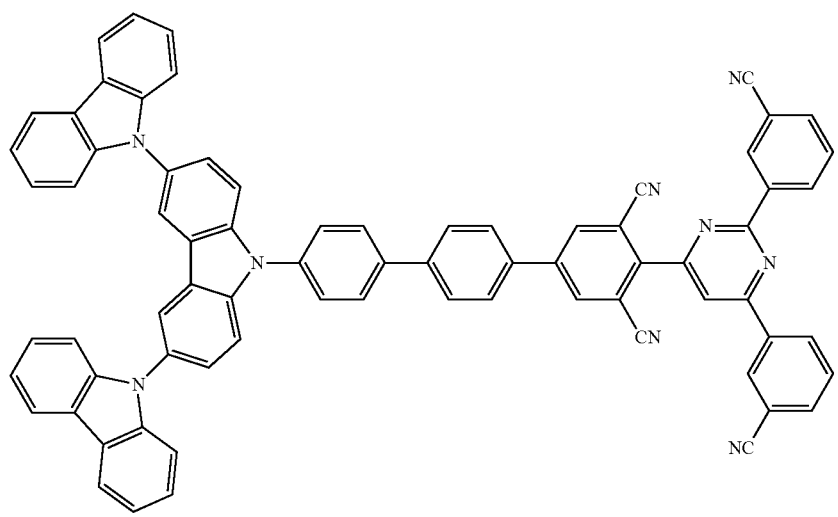
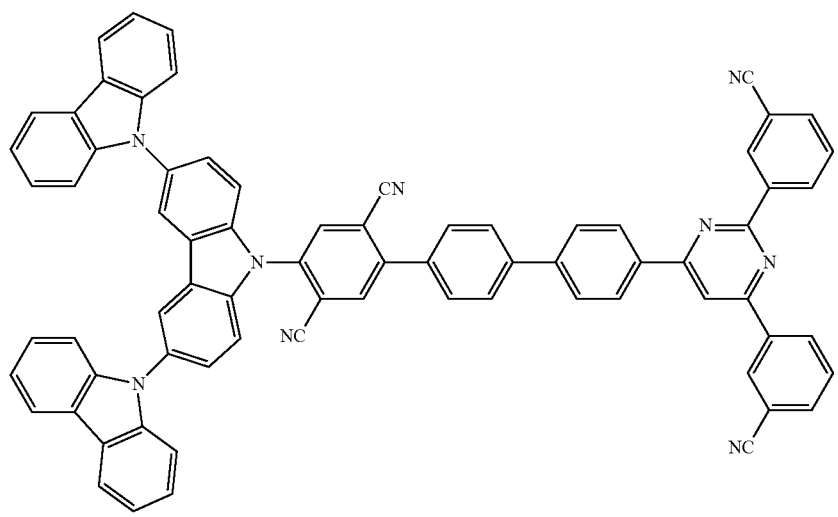

-continued
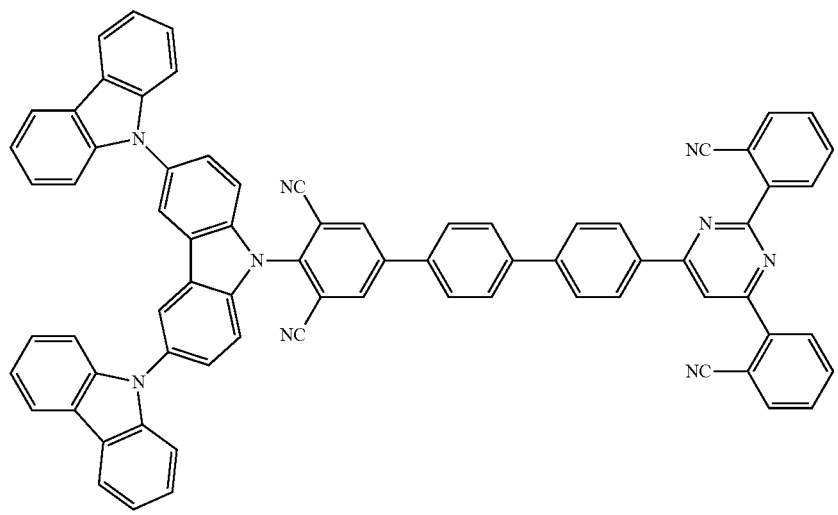
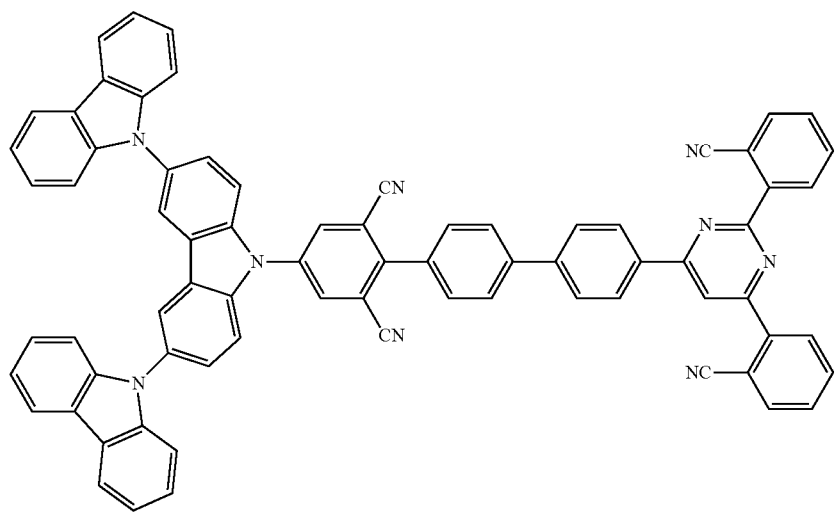
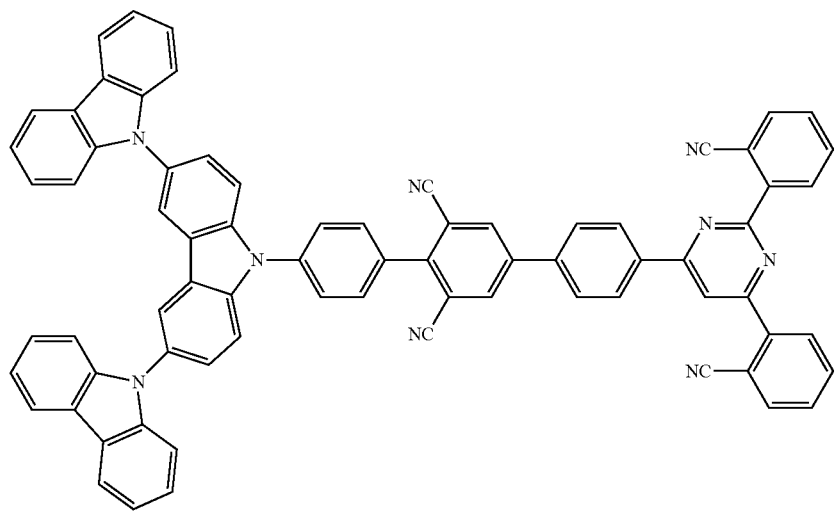

-continued
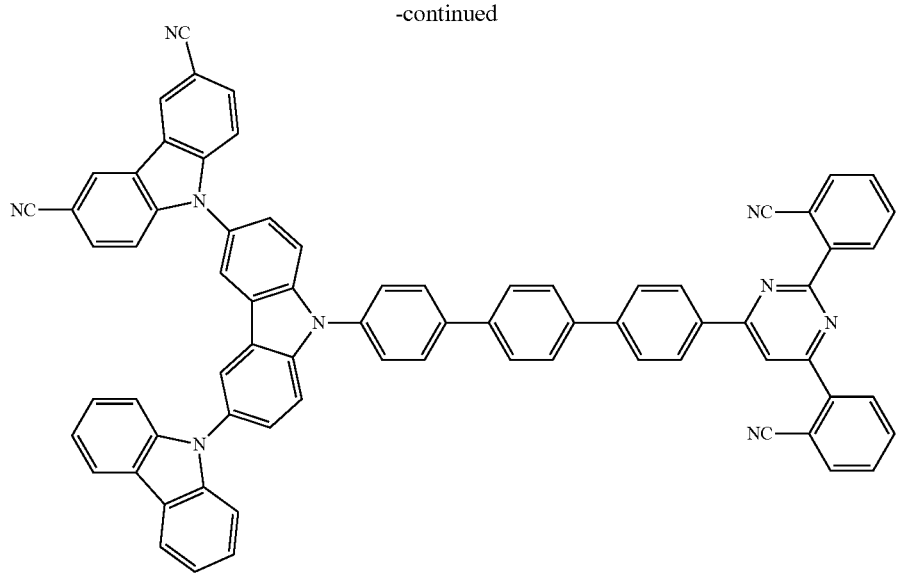
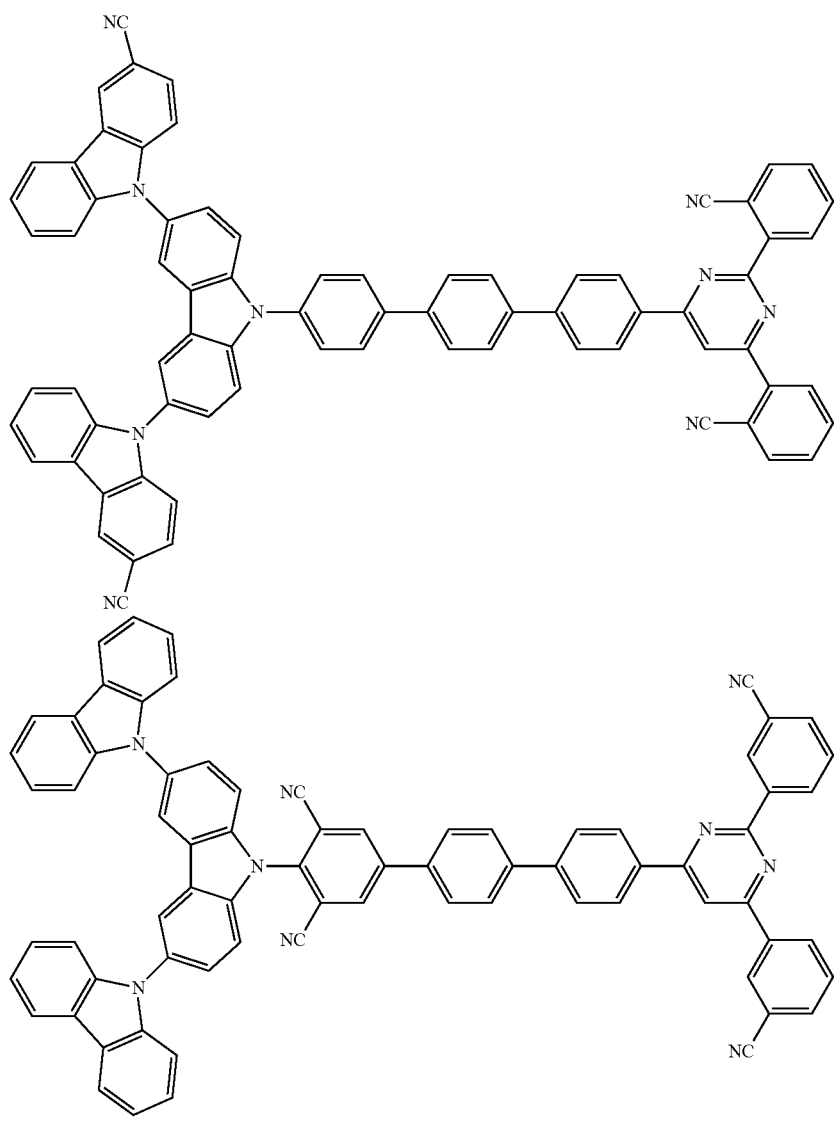

-continued
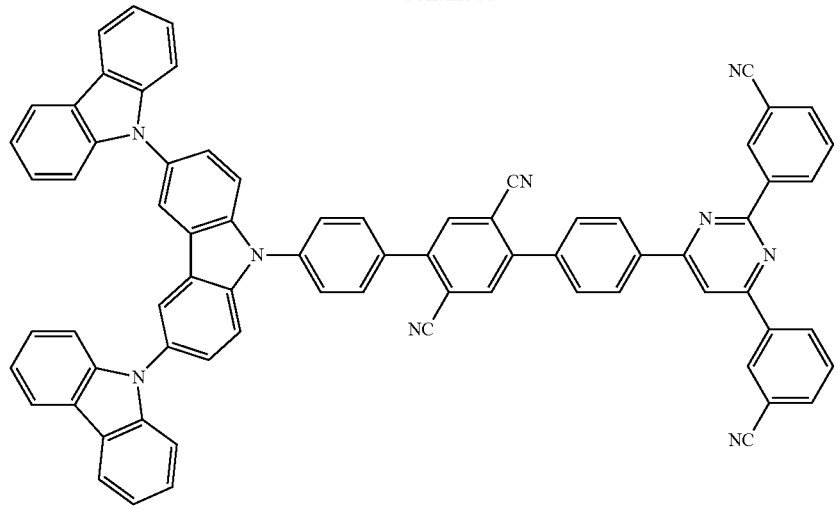
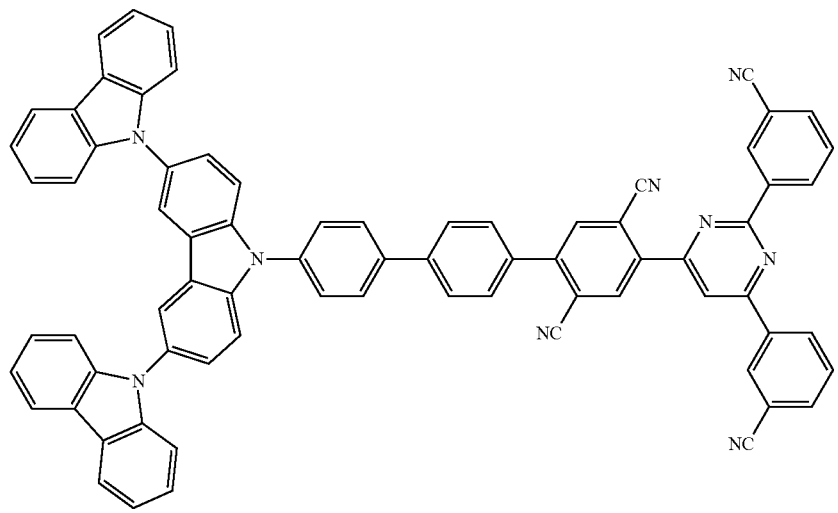
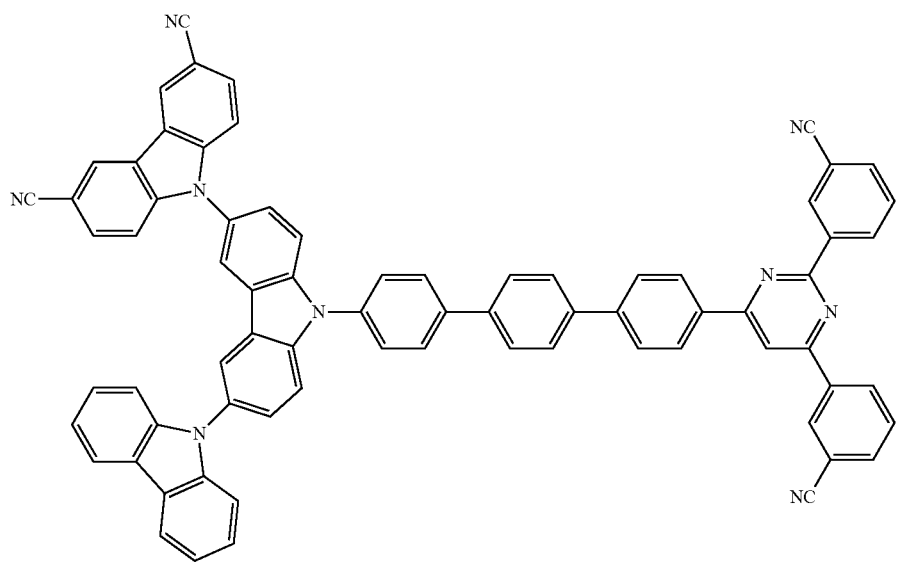

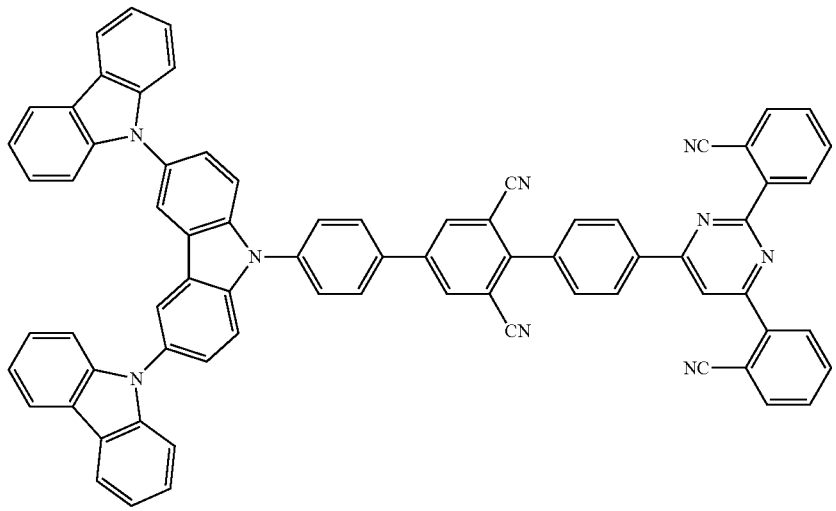

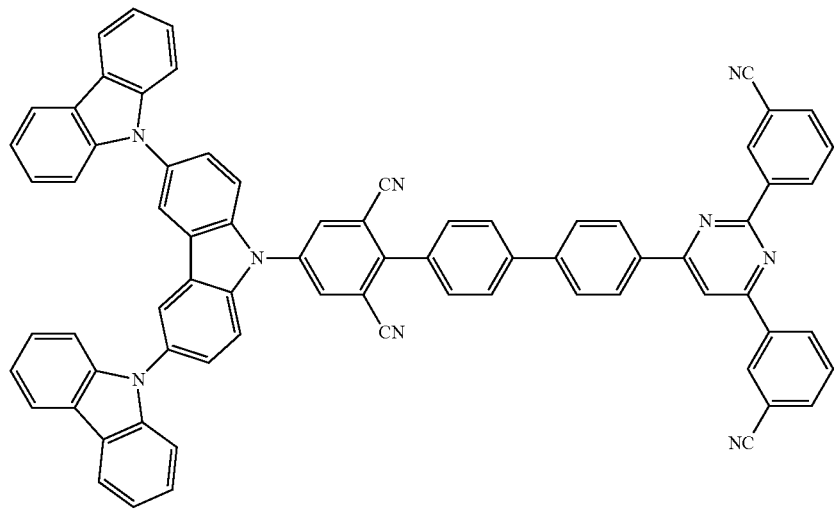
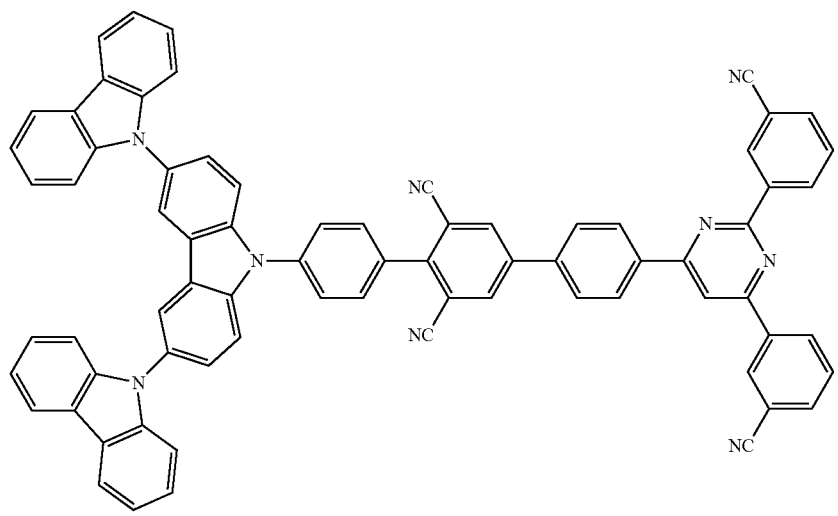
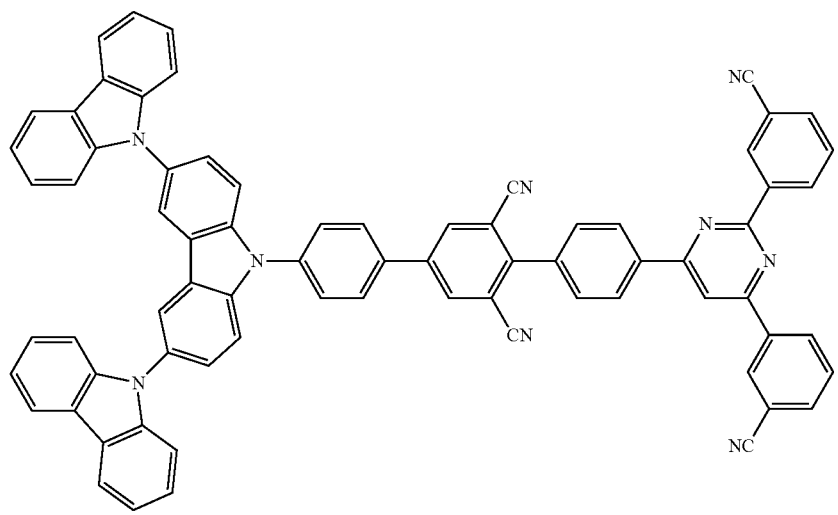

-continued
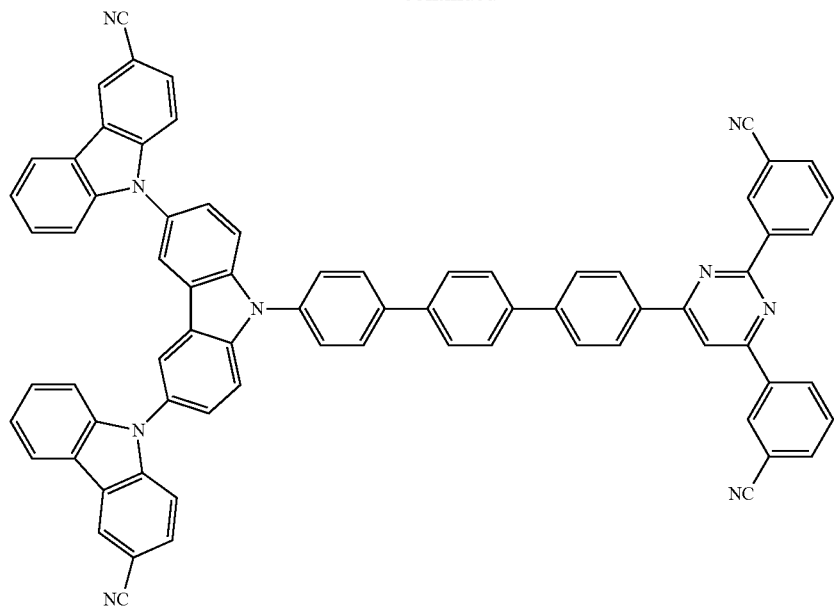
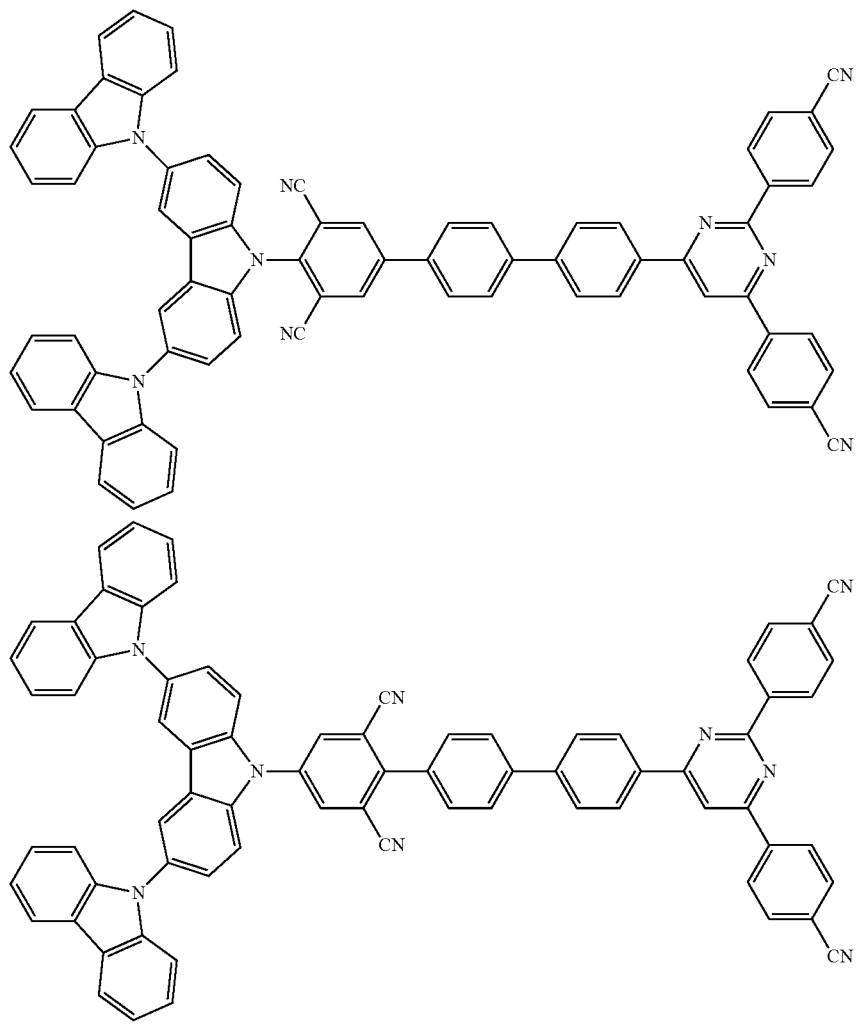

-continued
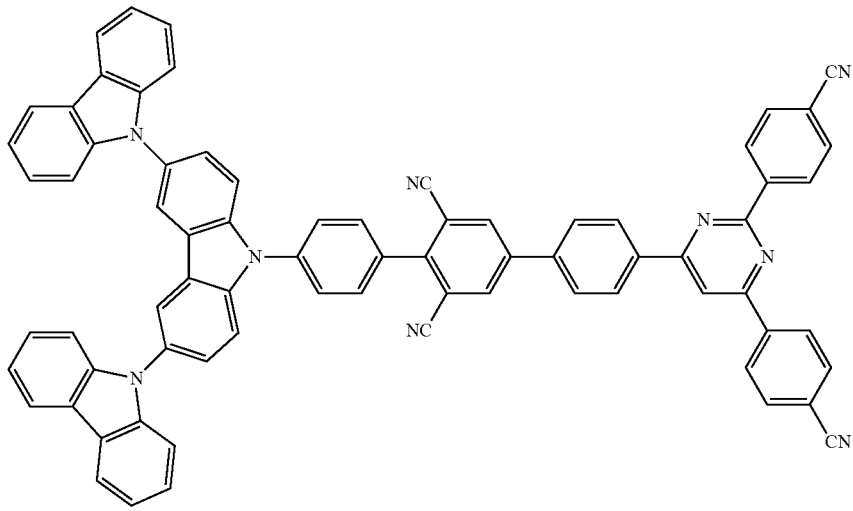
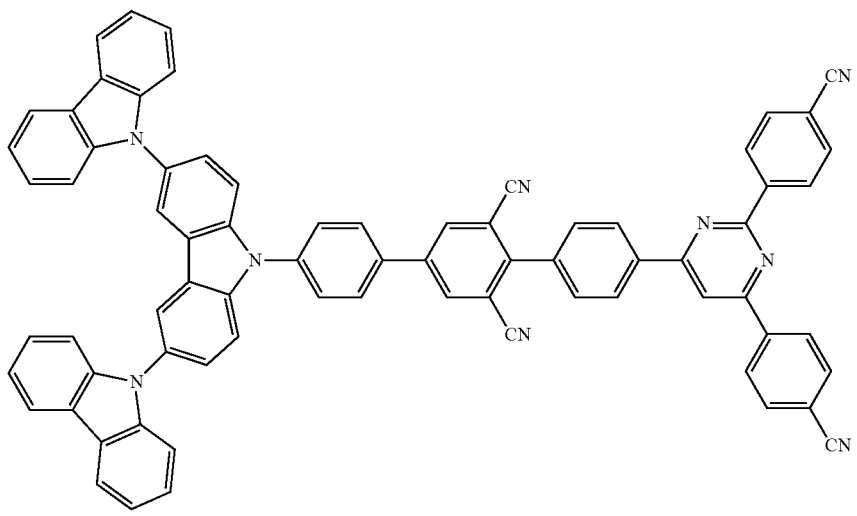

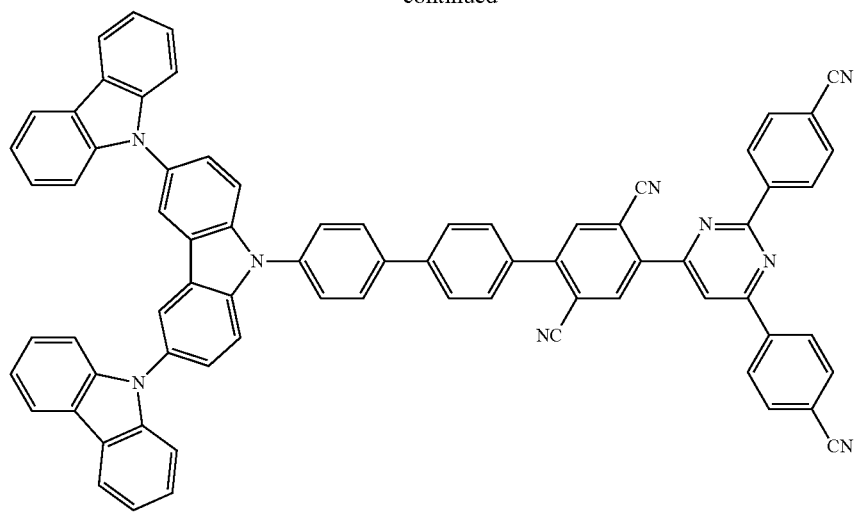
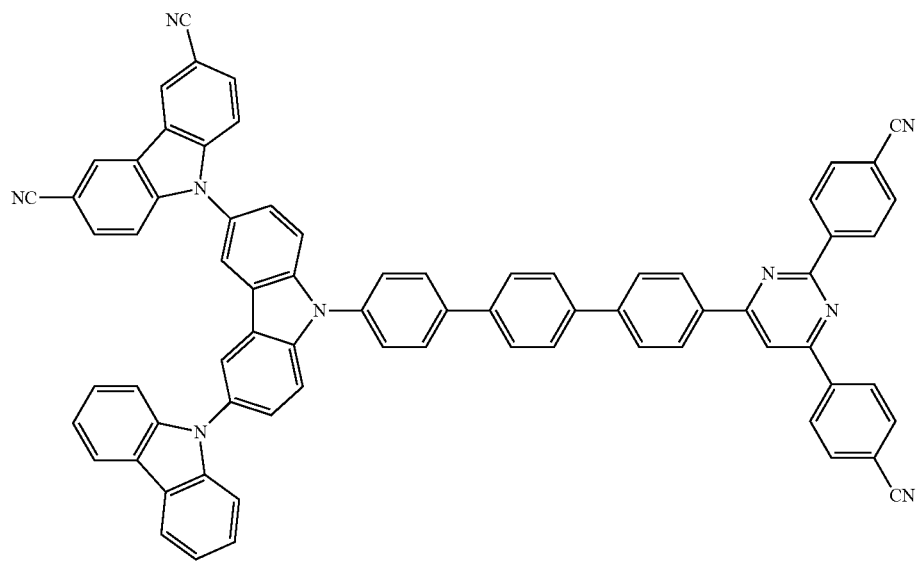
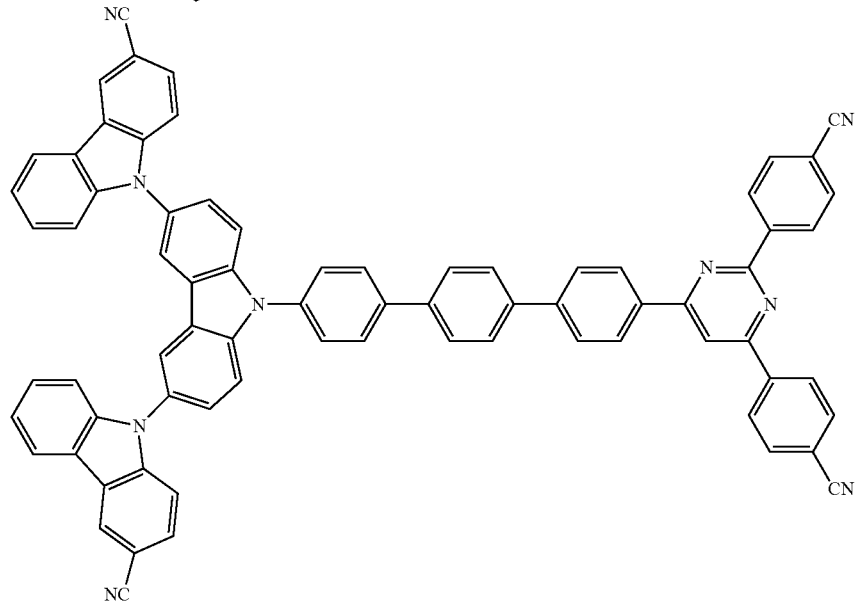

-continued
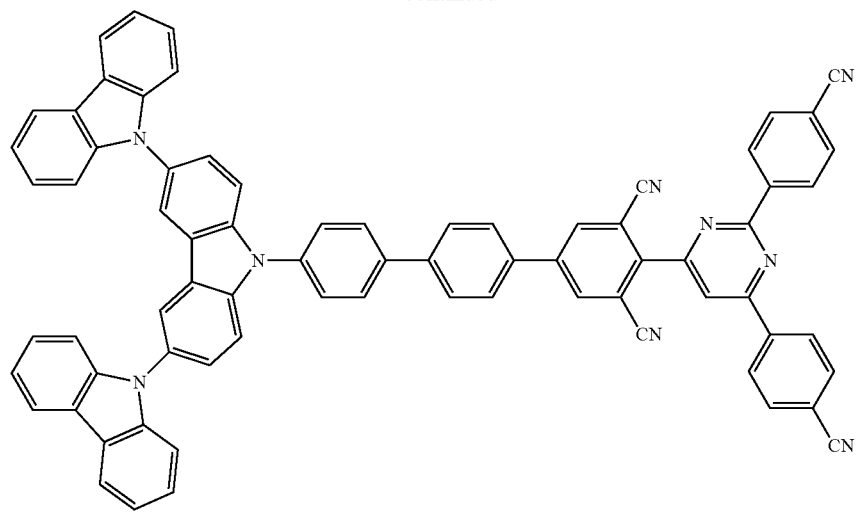
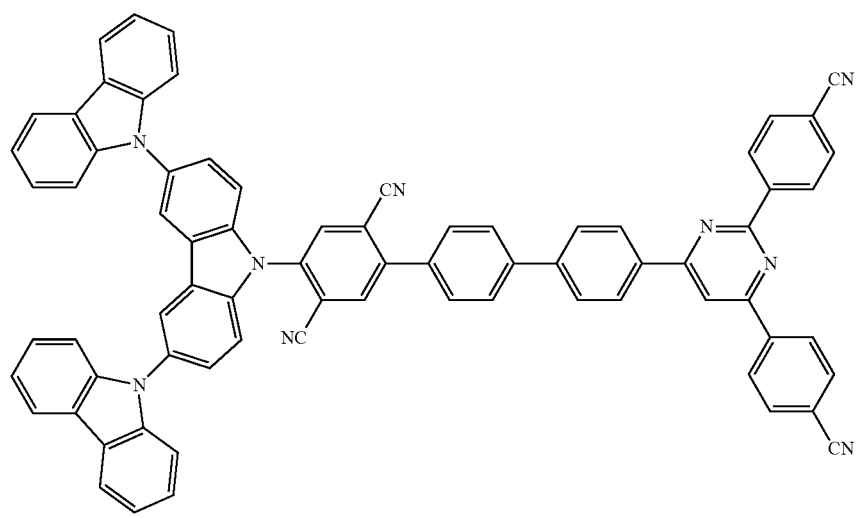
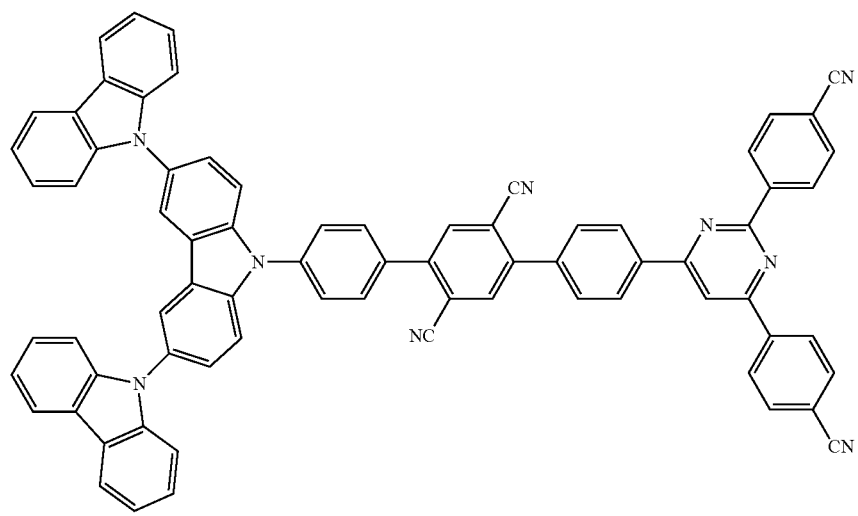

-continued
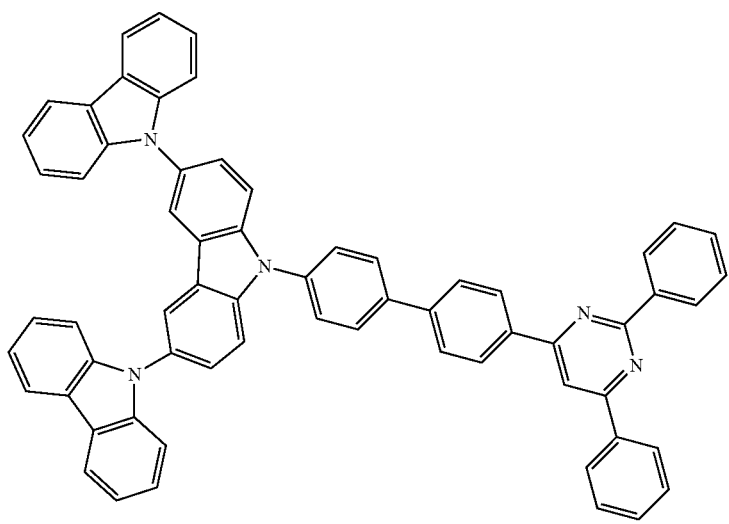
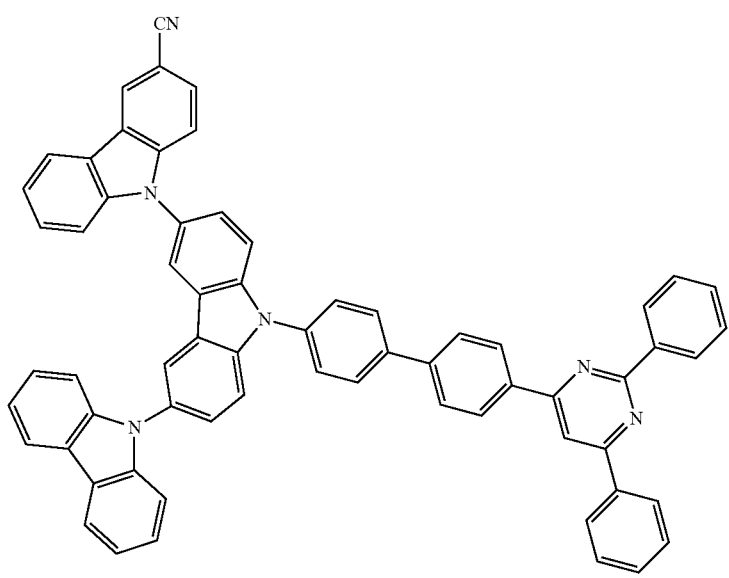
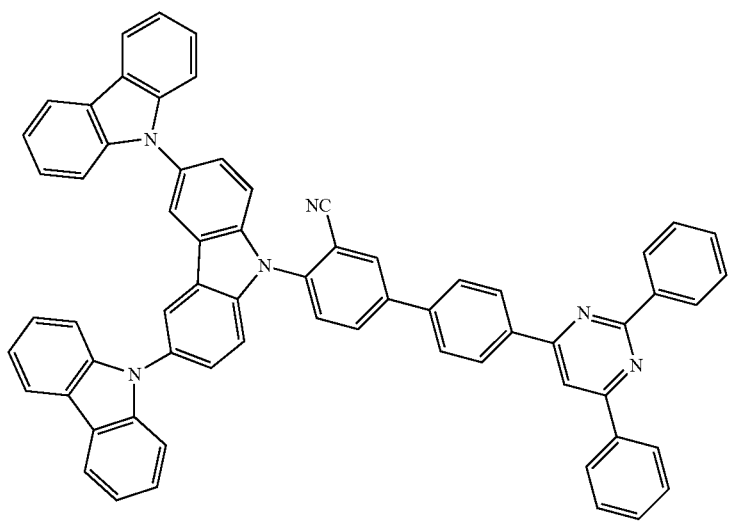

-continued
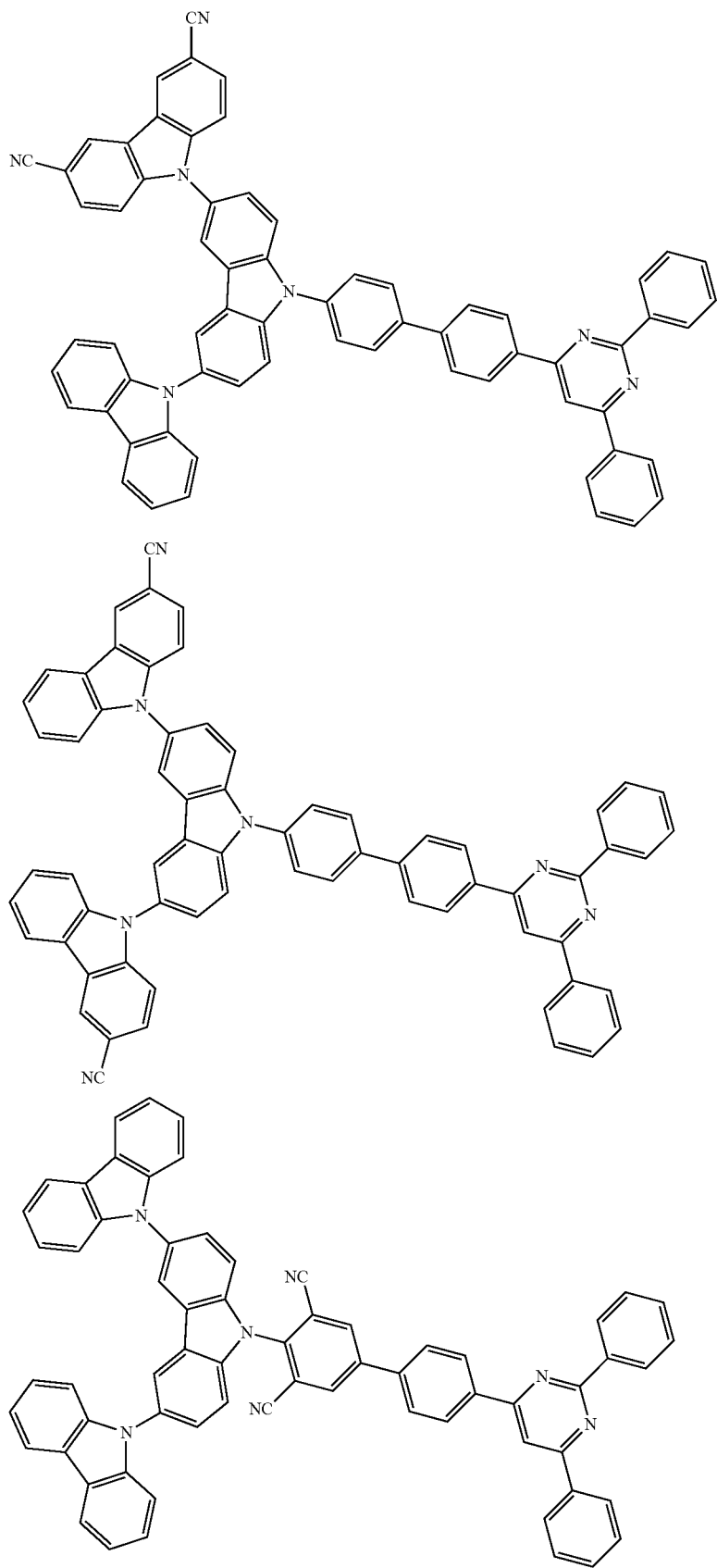

-continued
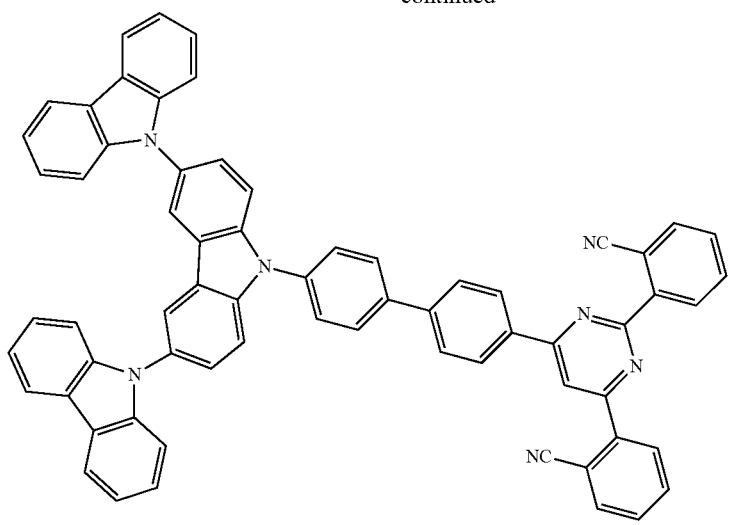
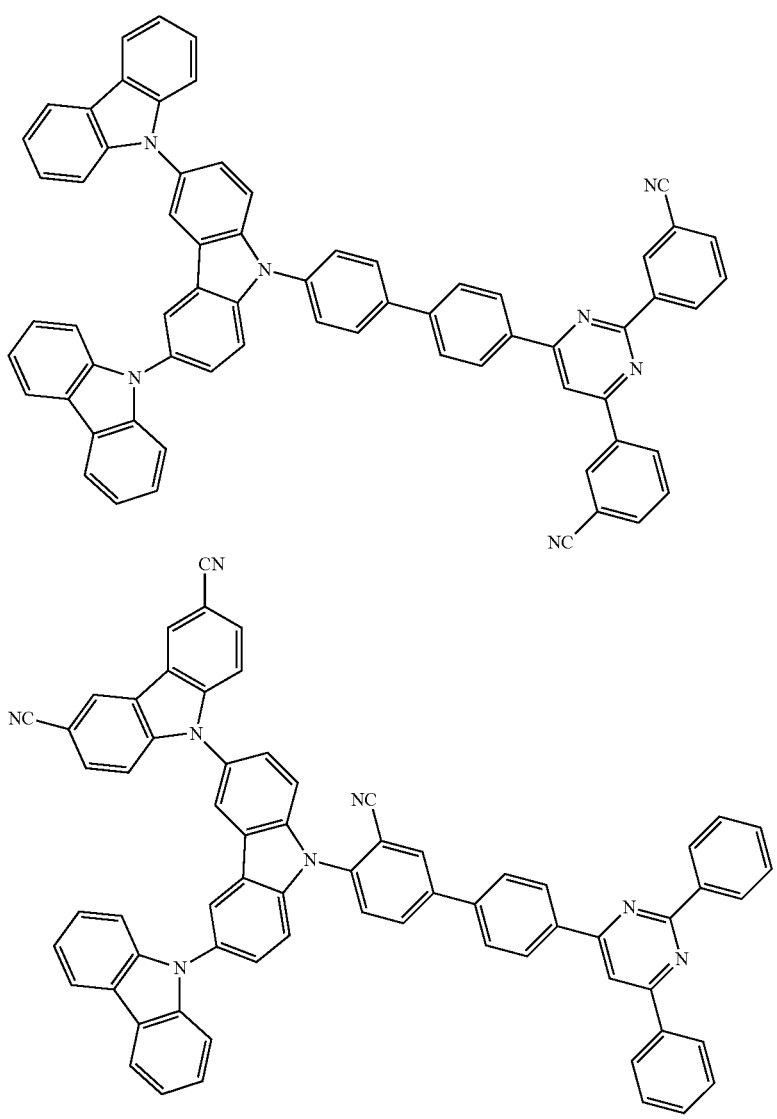

-continued
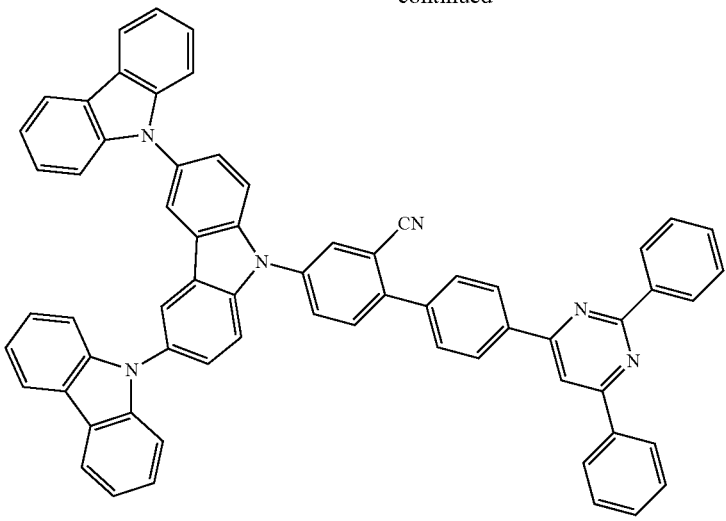
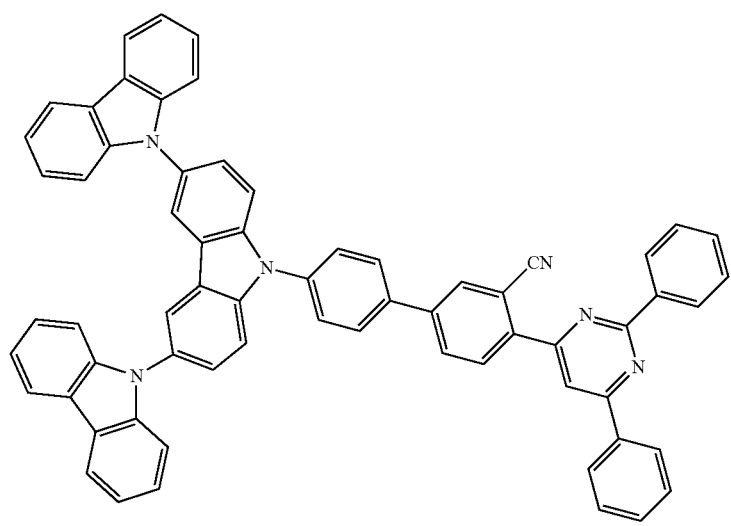
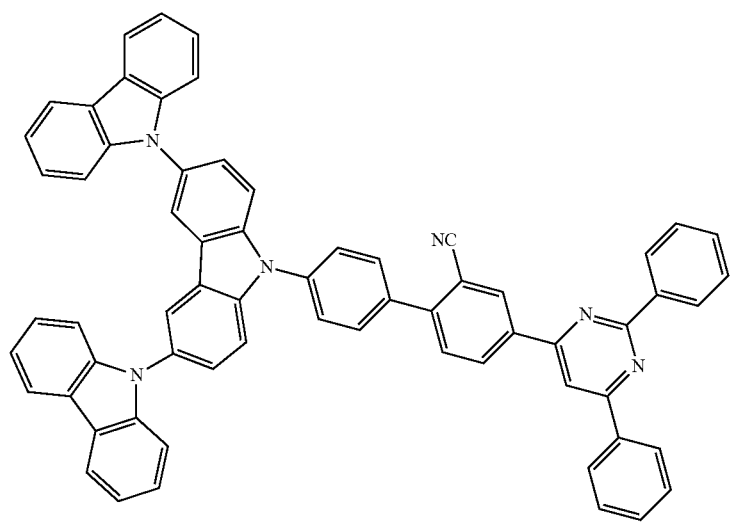

-continued
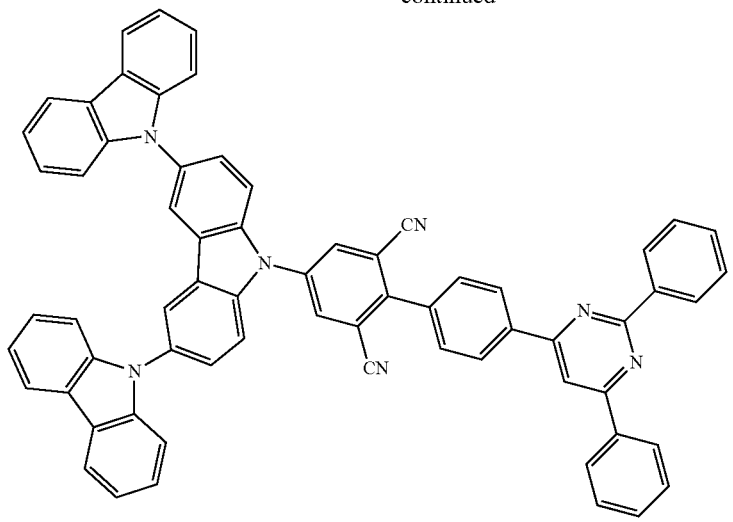
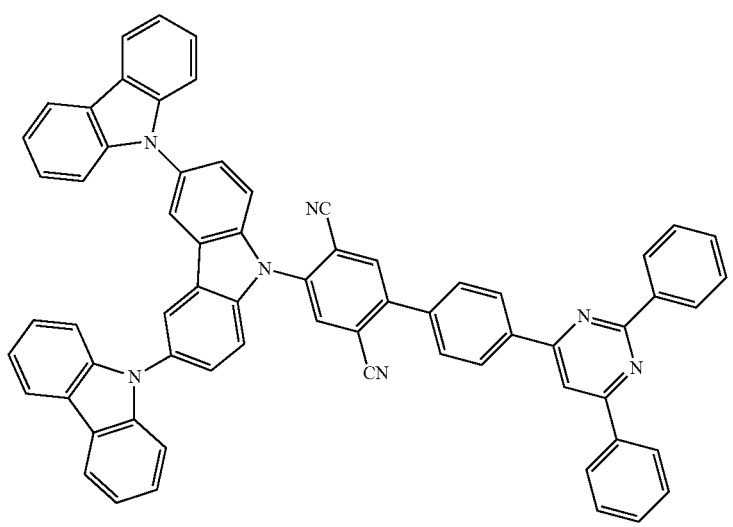
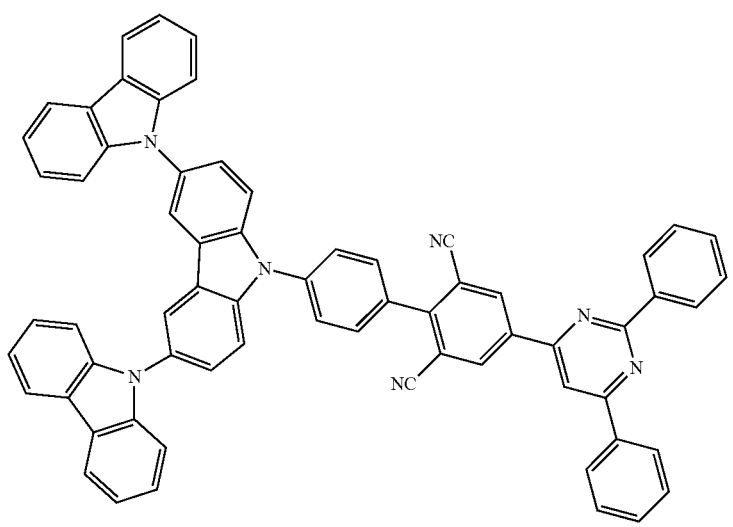

-continued
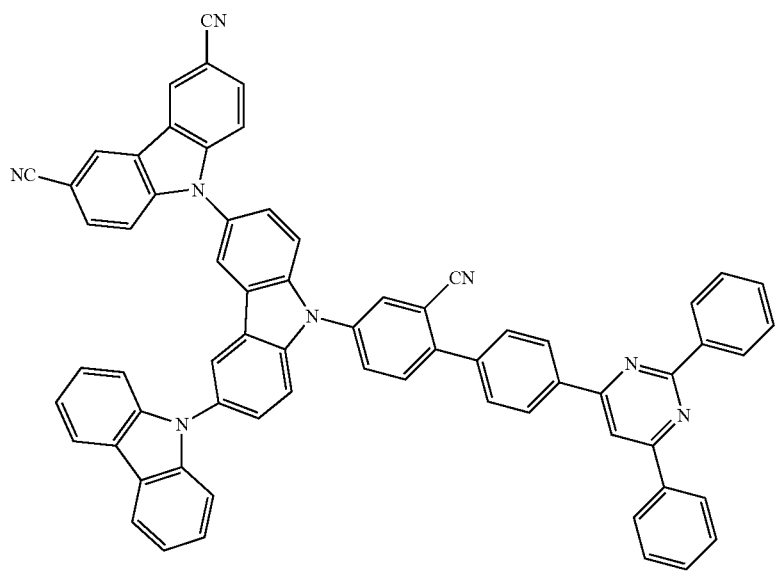
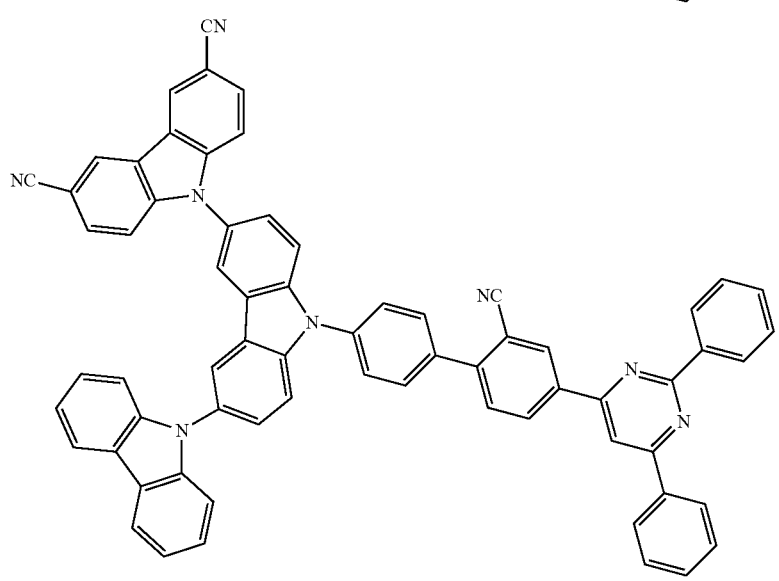
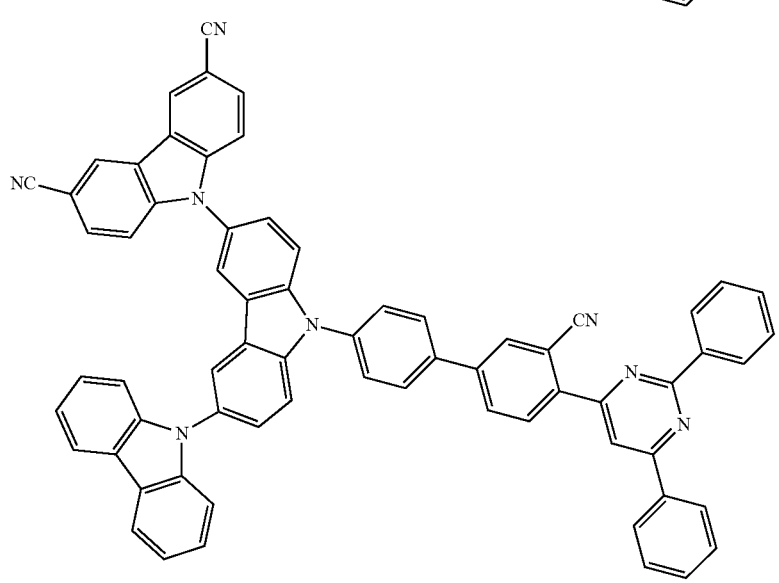

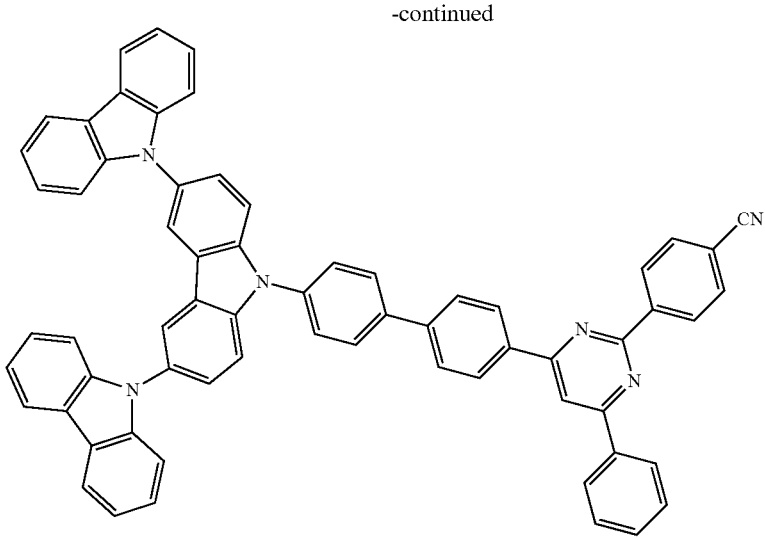

-continued
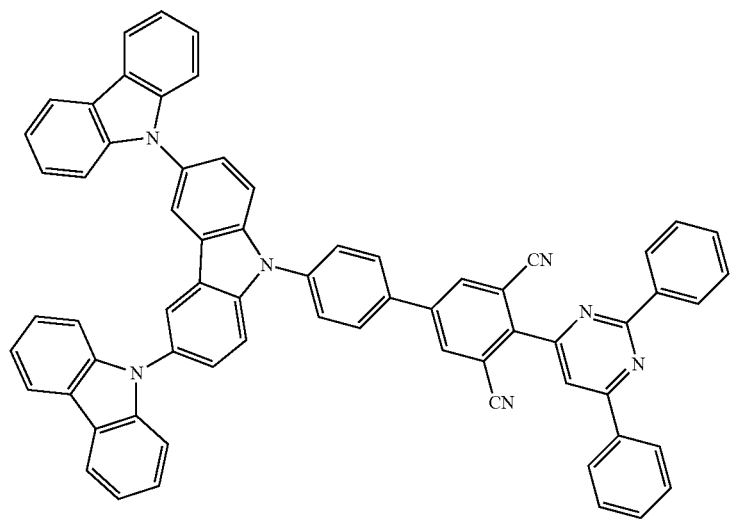
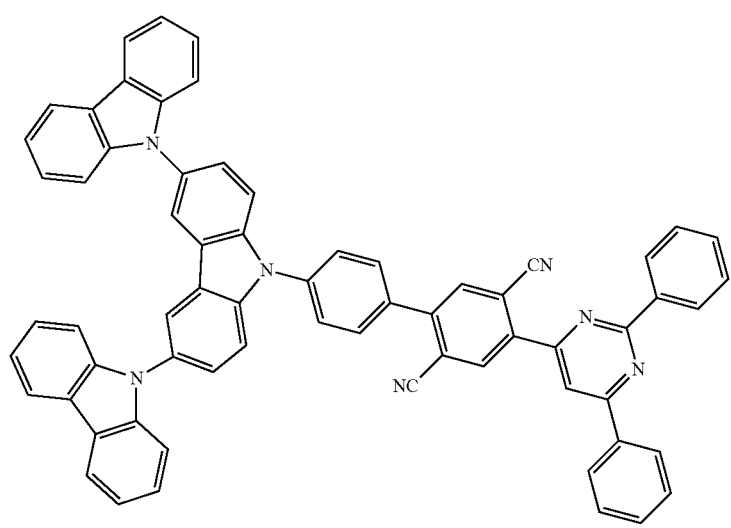
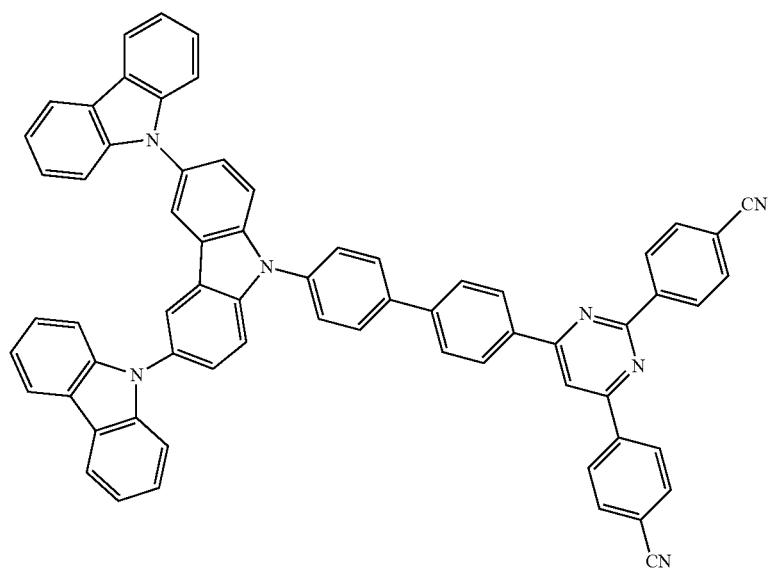

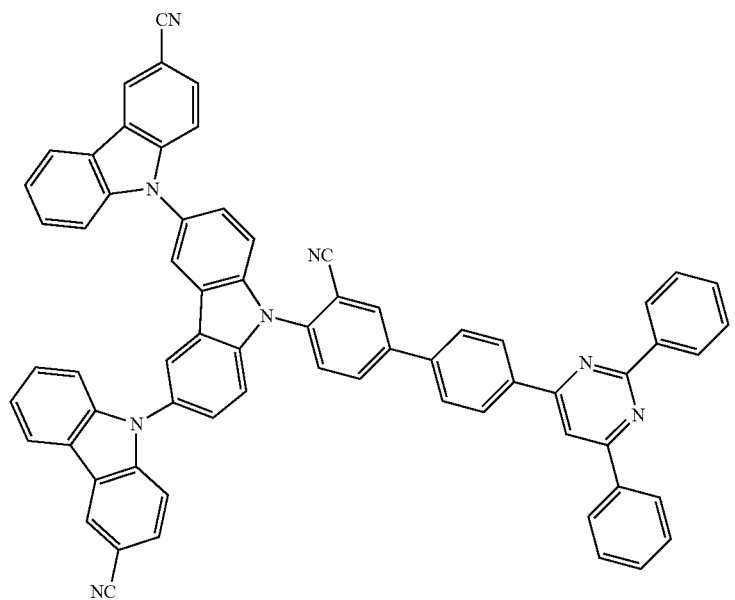
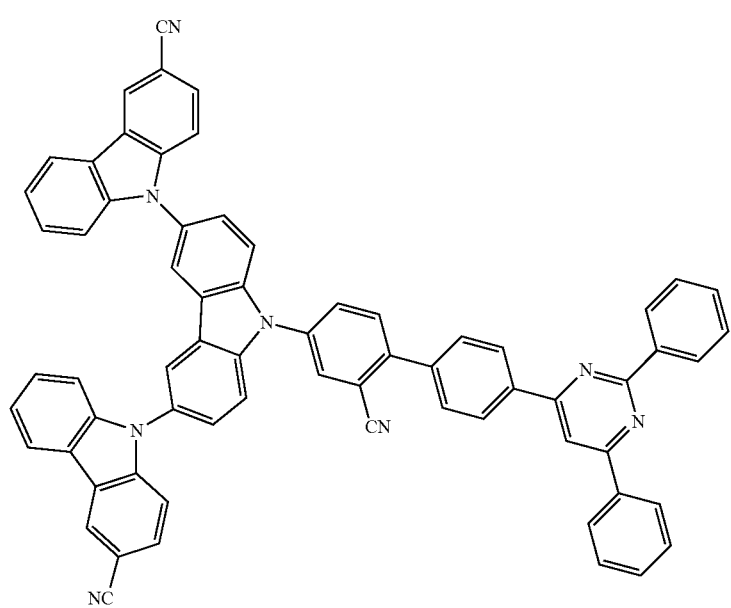

-continued
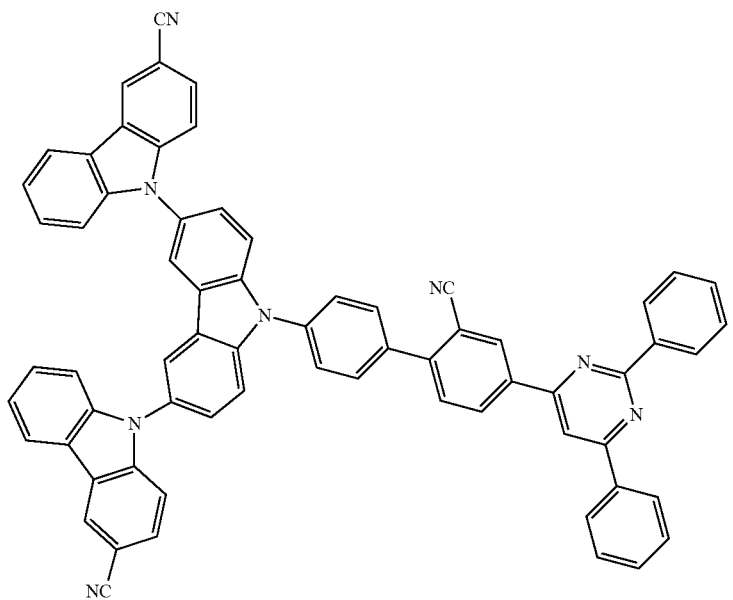
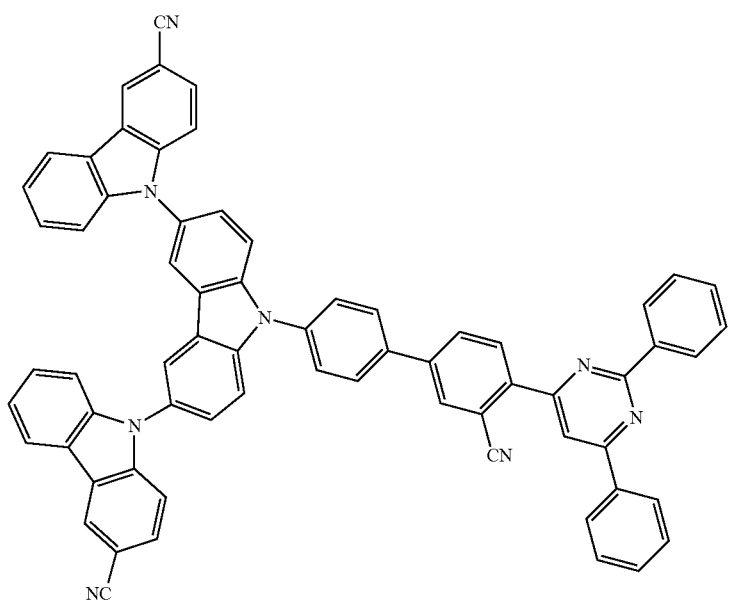

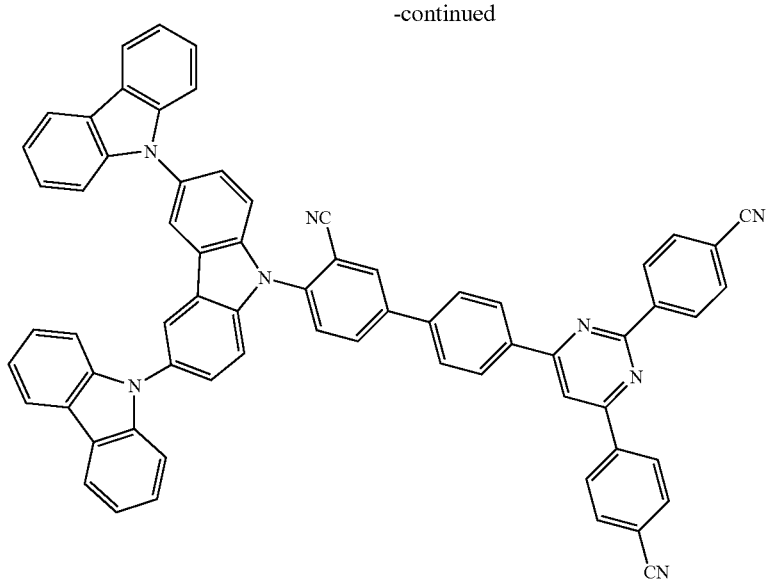
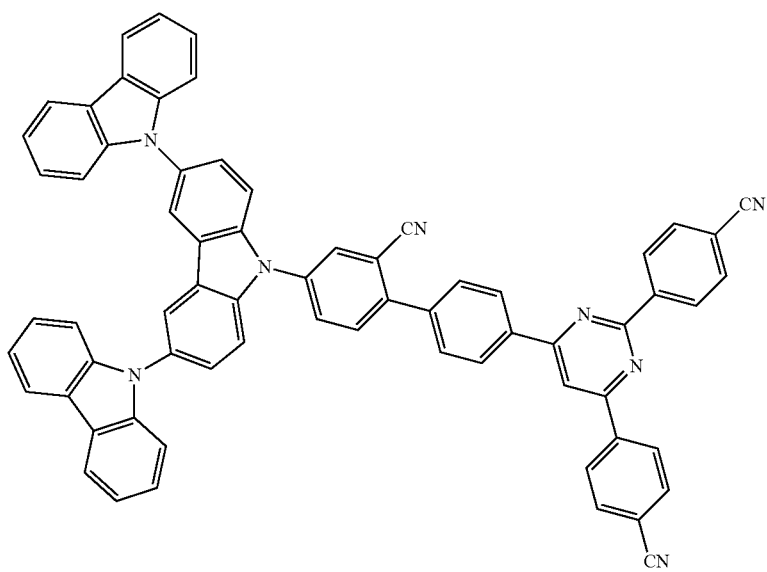
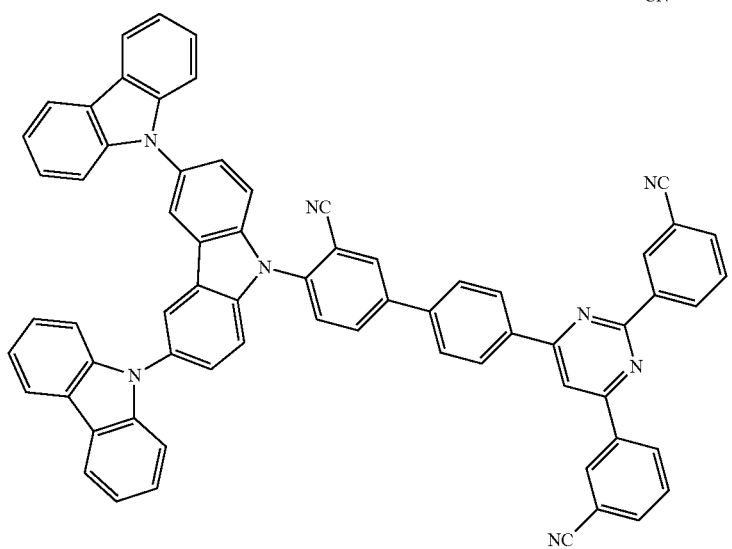

-continued
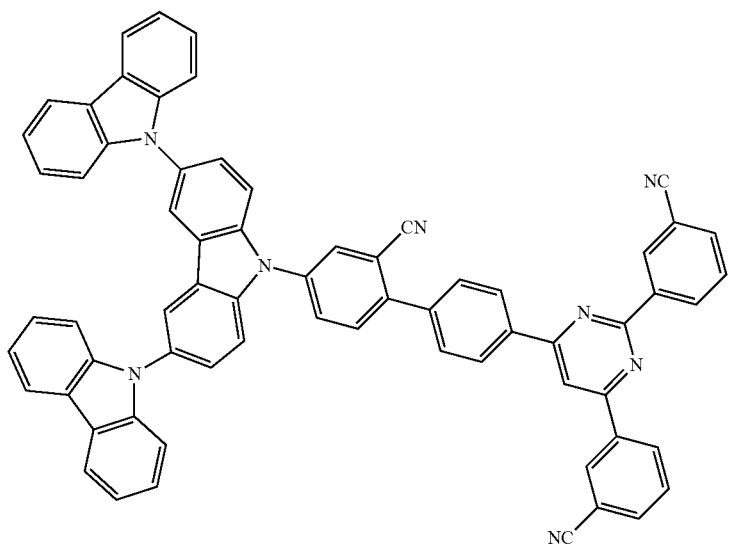
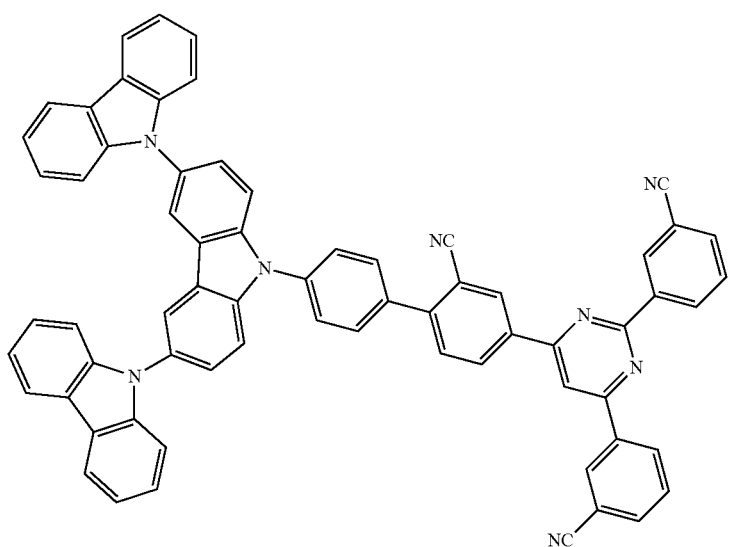
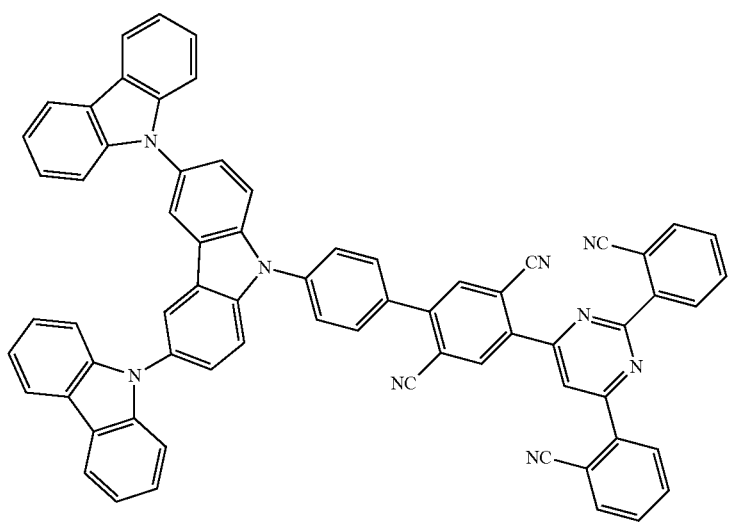

-continued
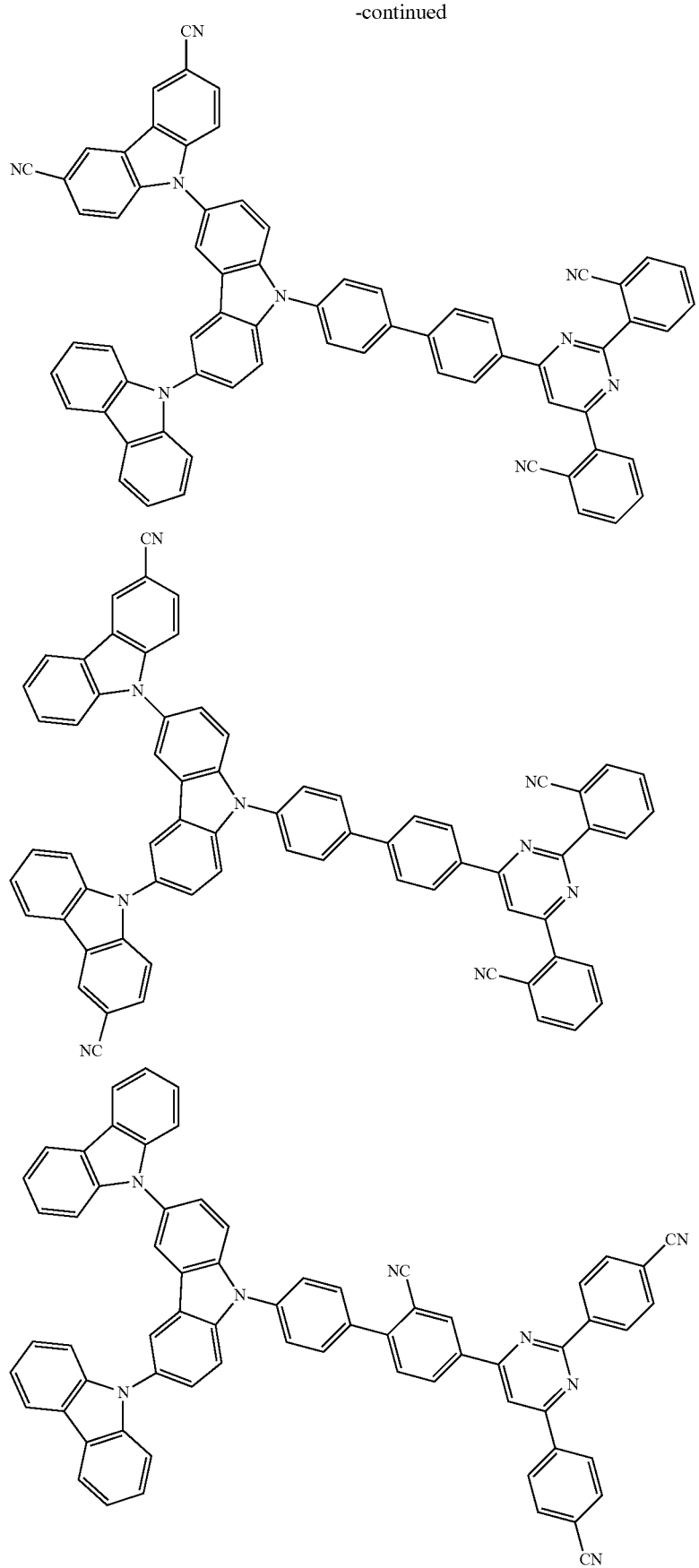

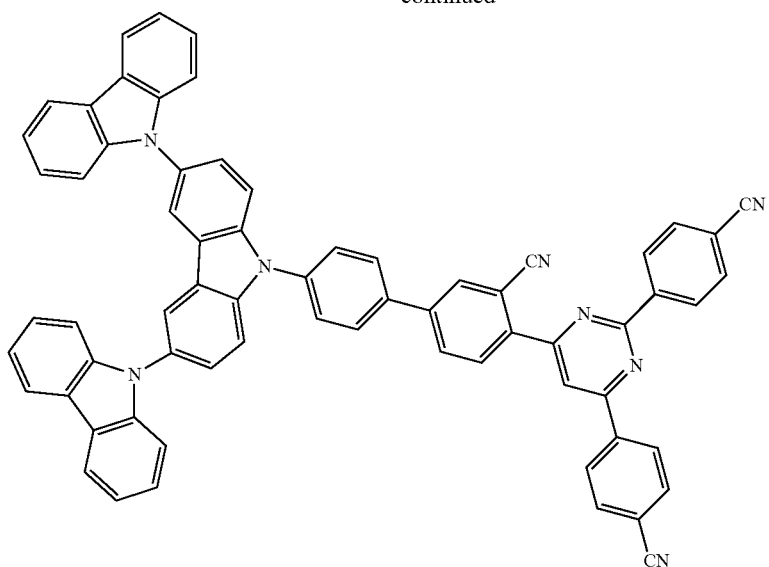
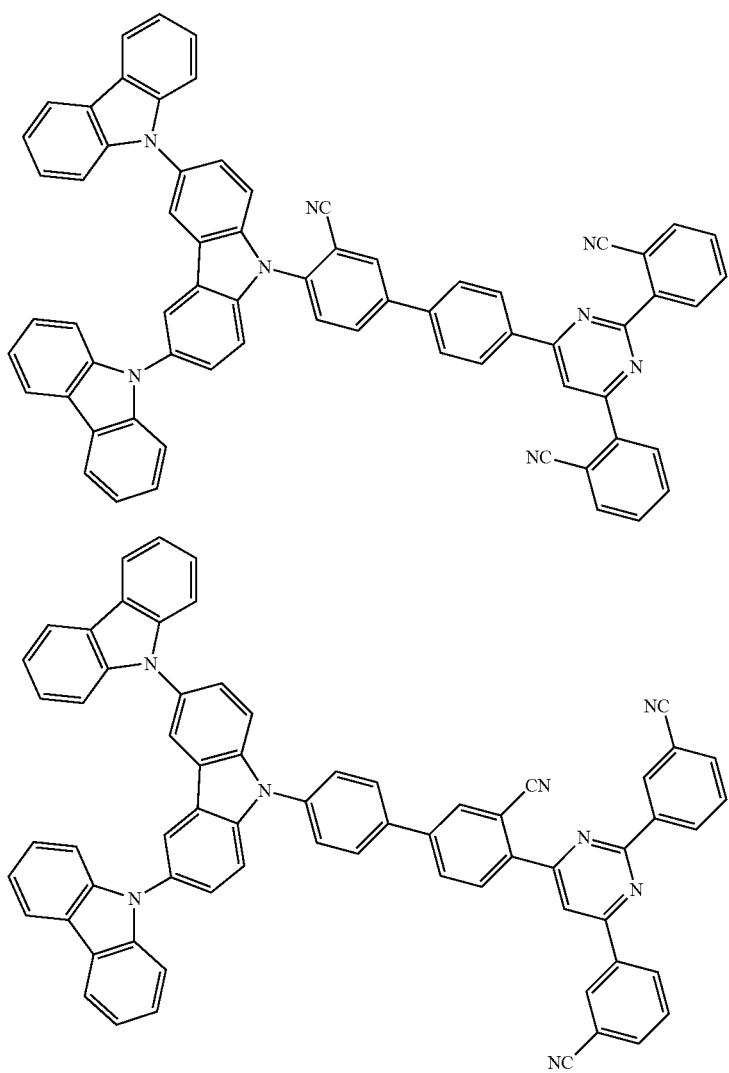

-continued
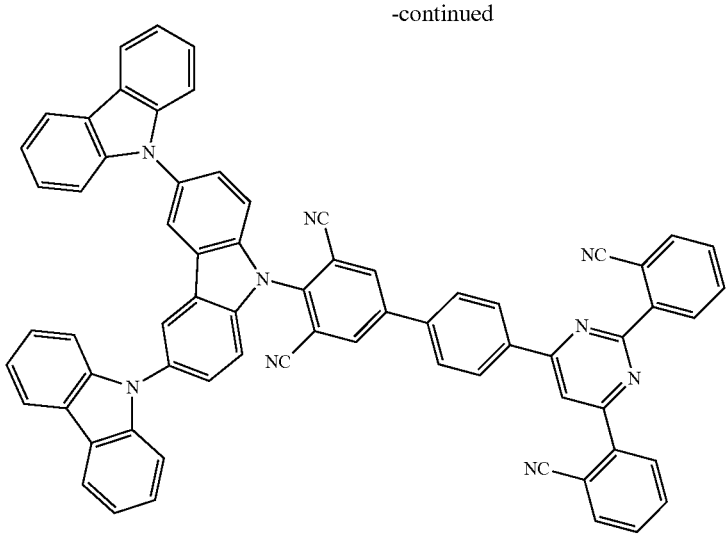
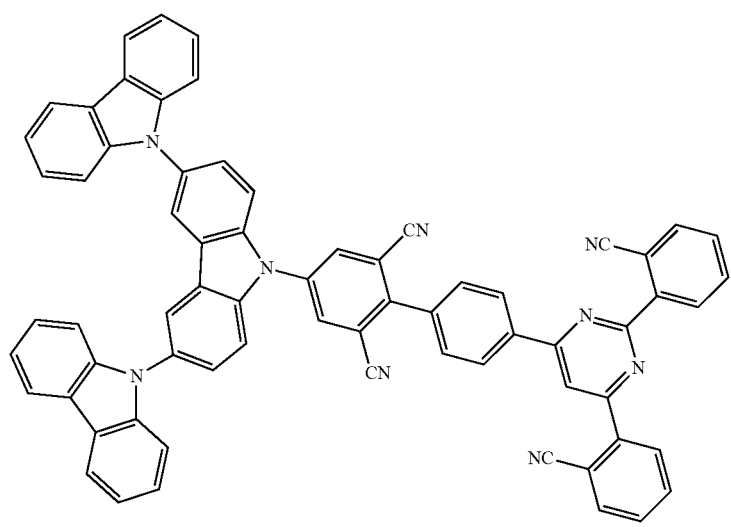
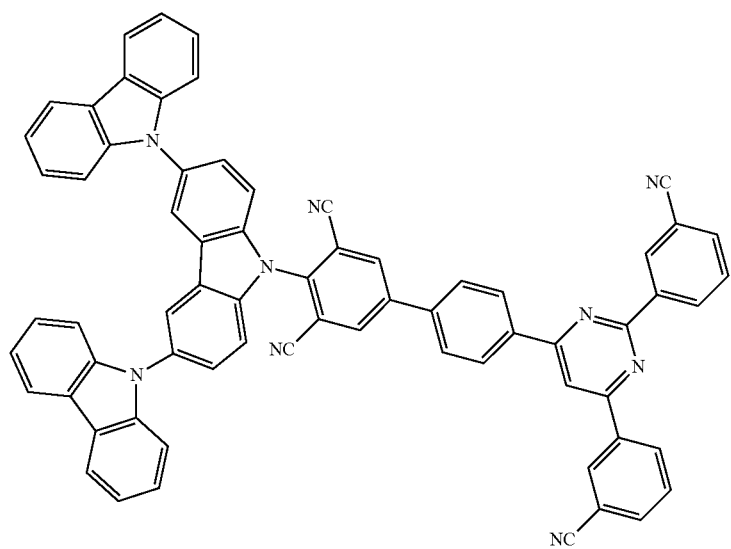

-continued
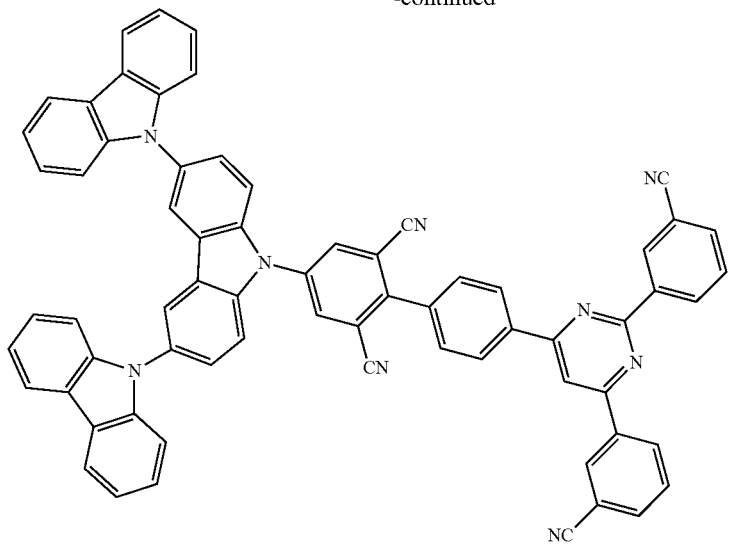
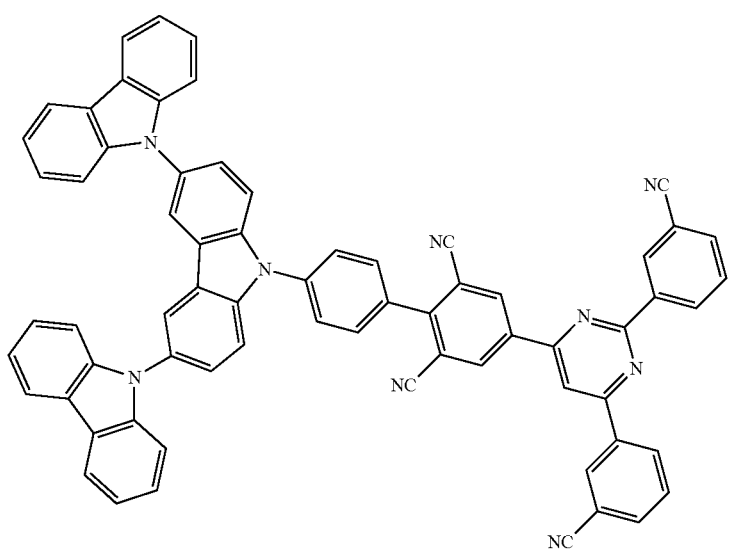
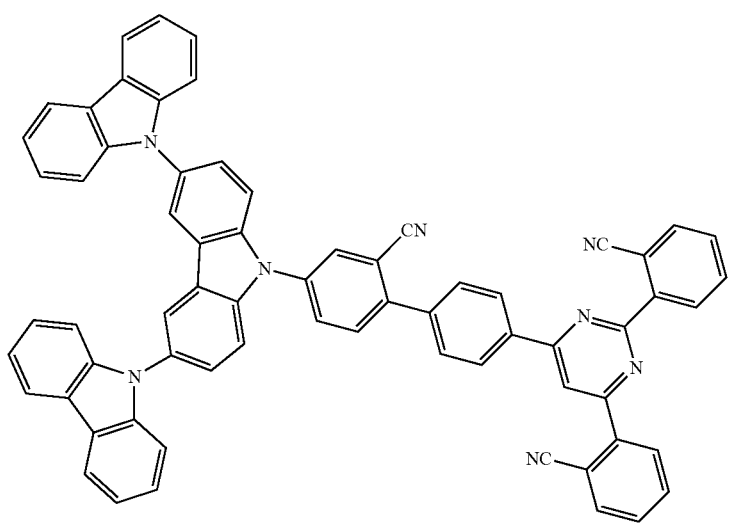

-continued
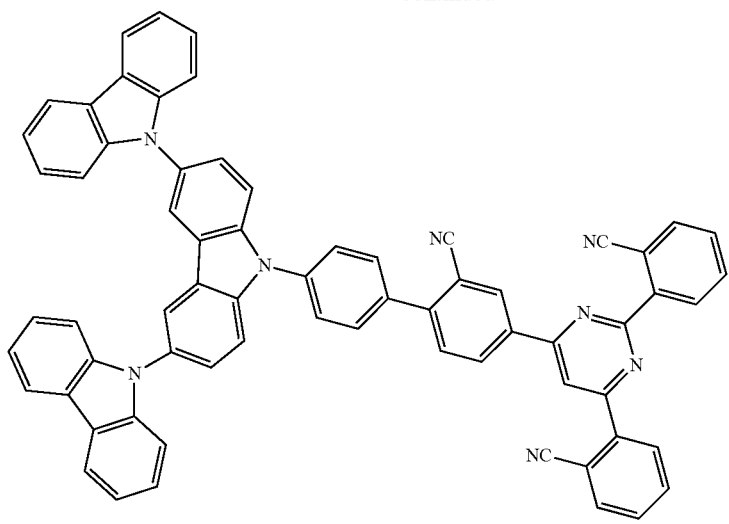
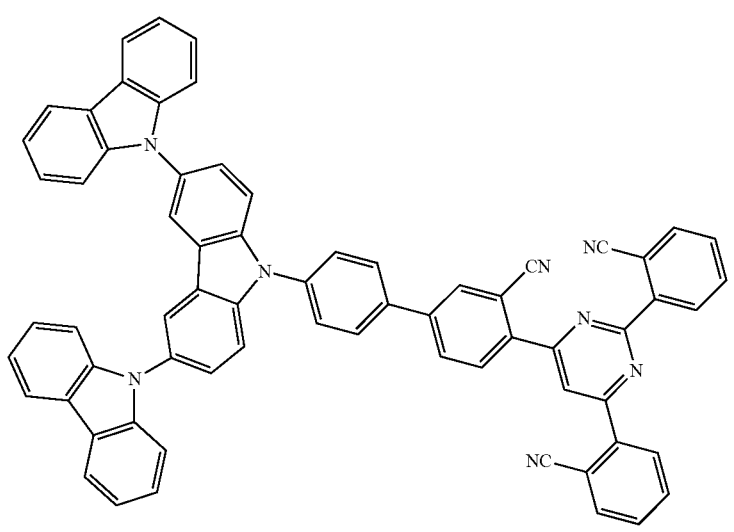
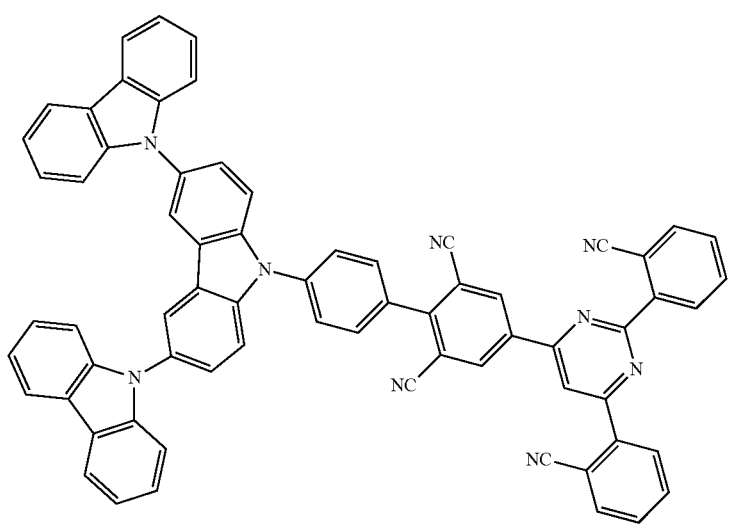

-continued
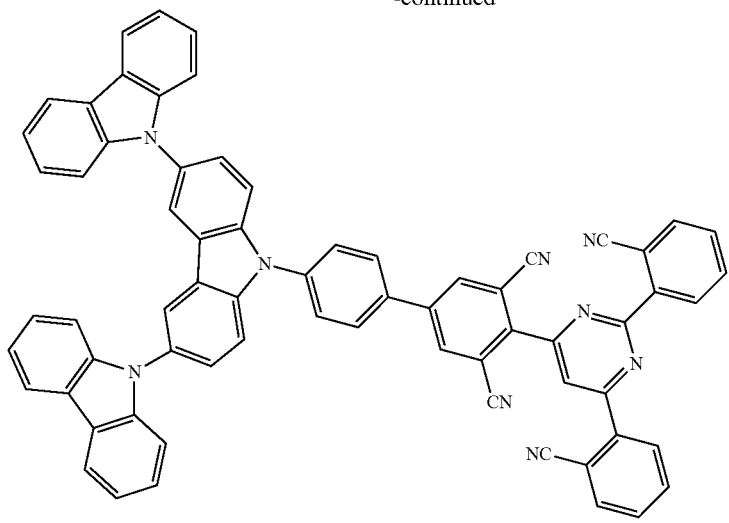
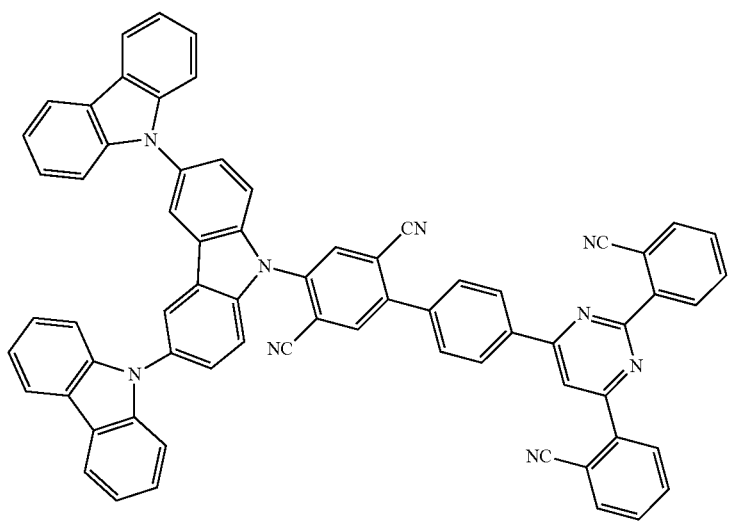
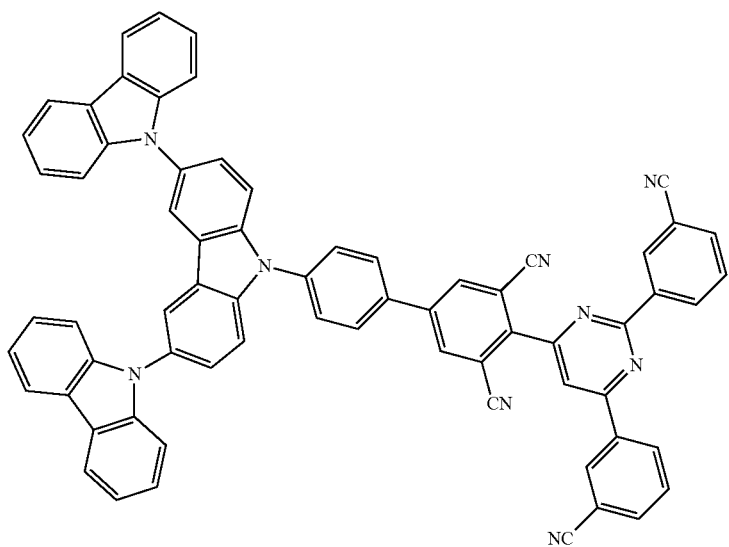

-continued
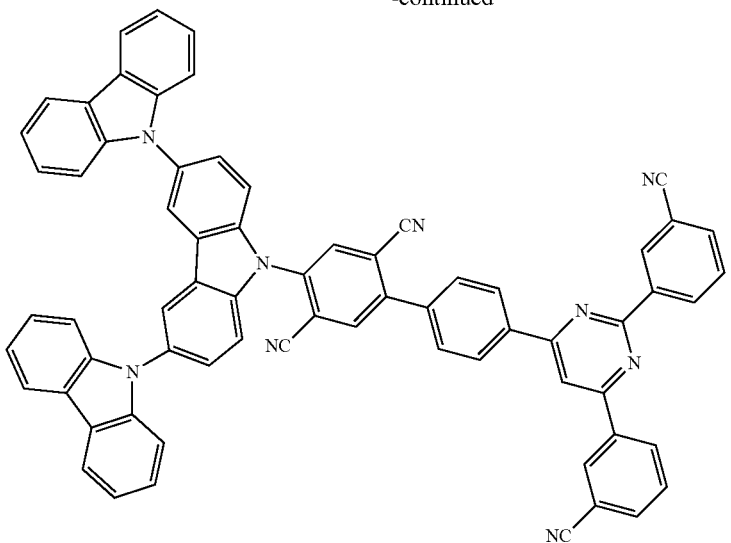
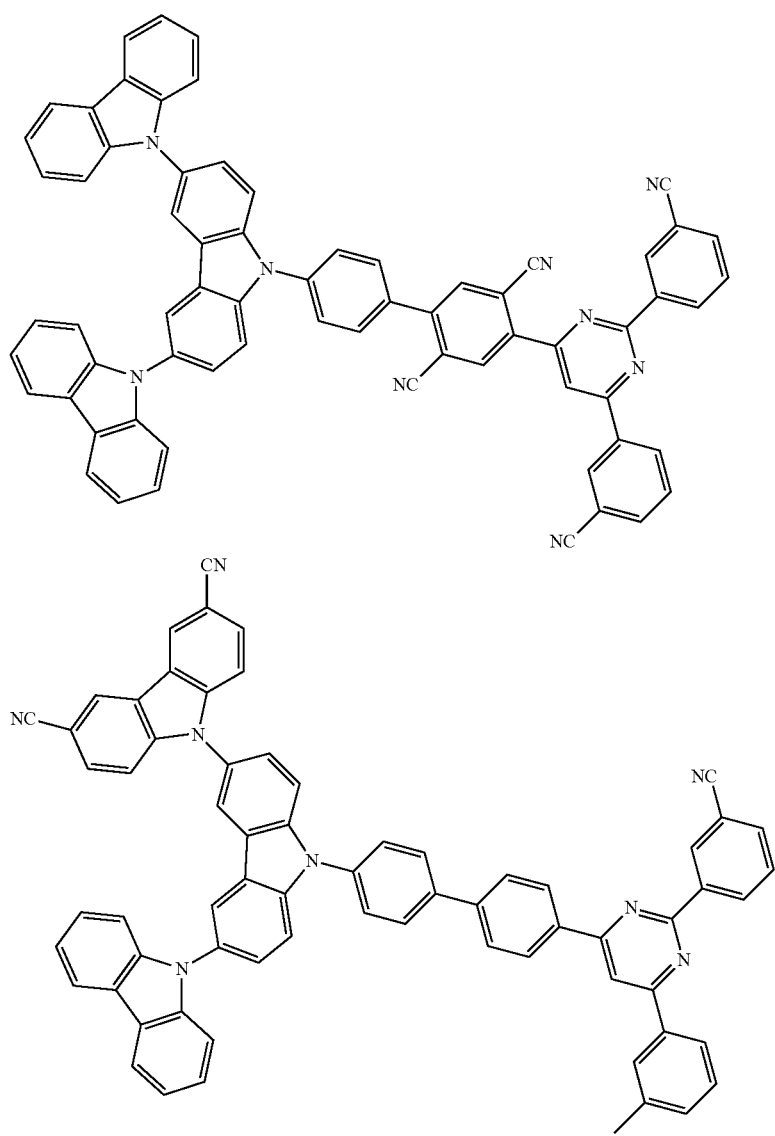

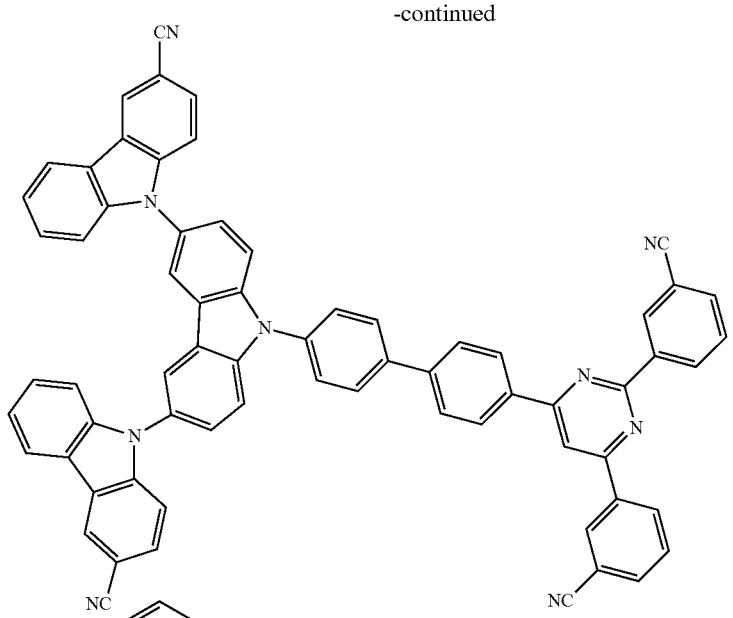
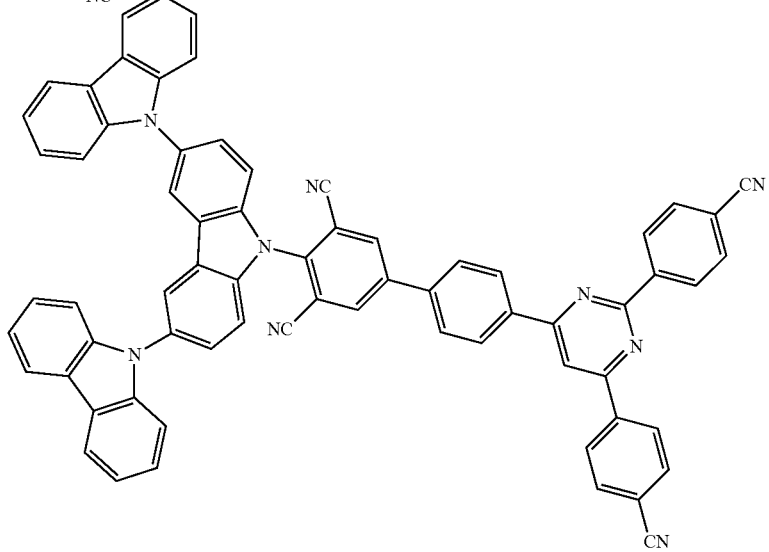
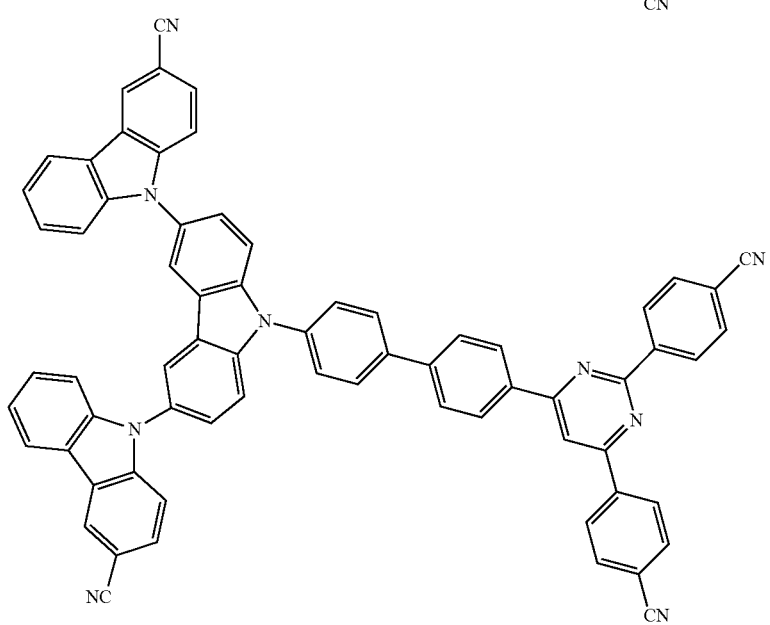

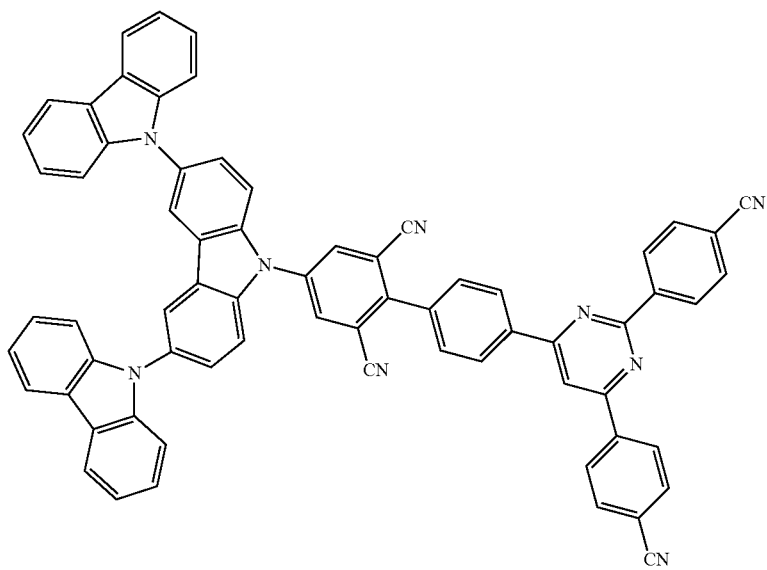
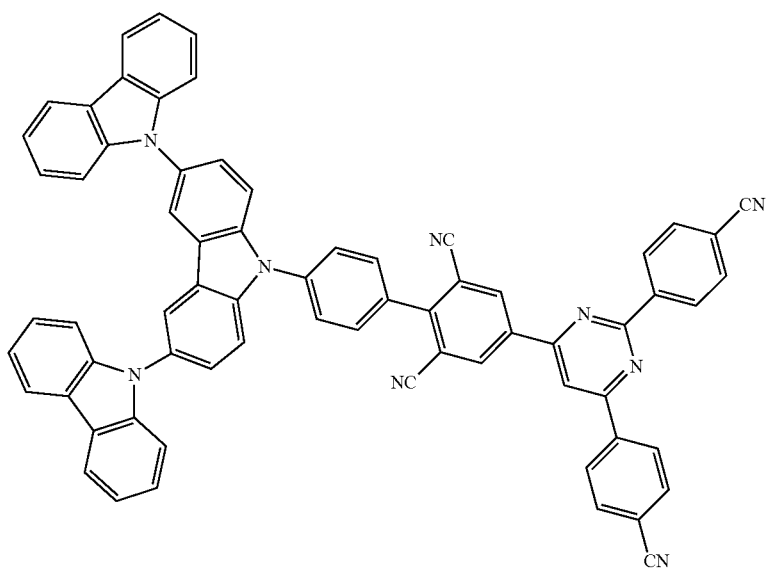
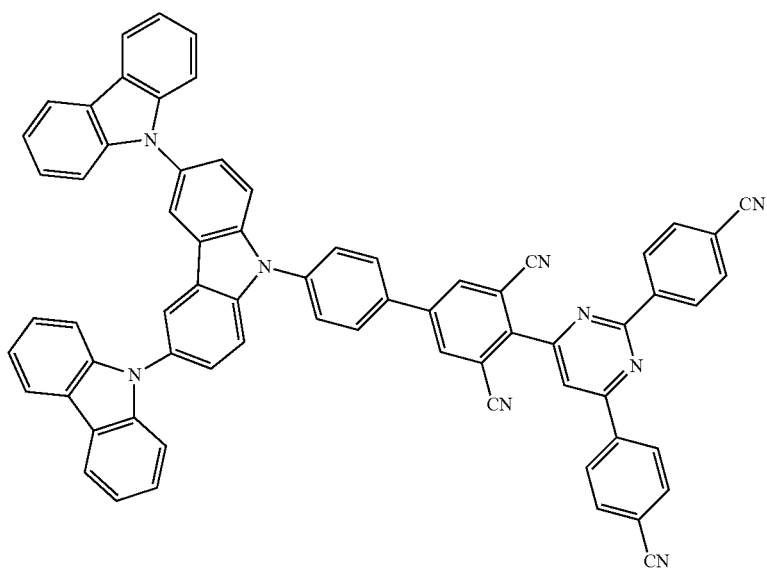

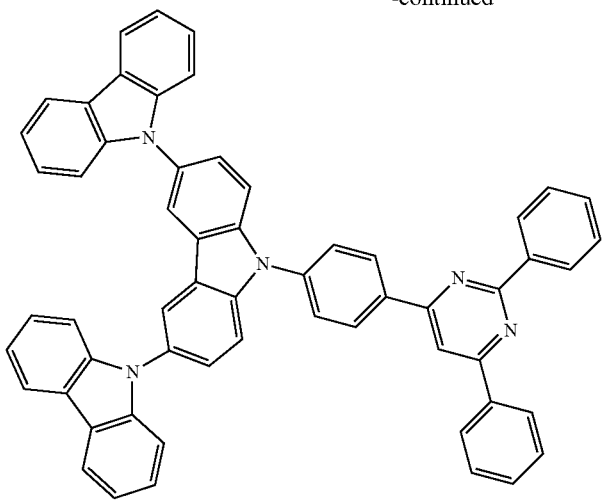
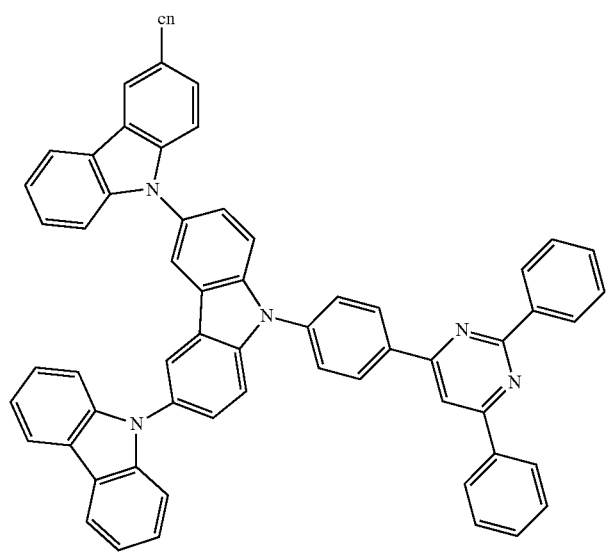
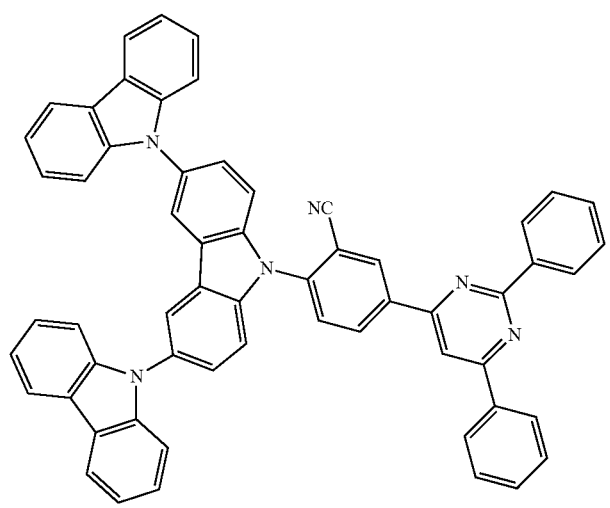

-continued
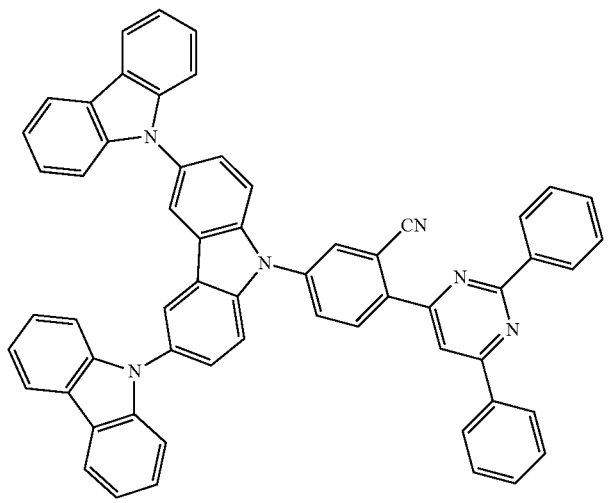
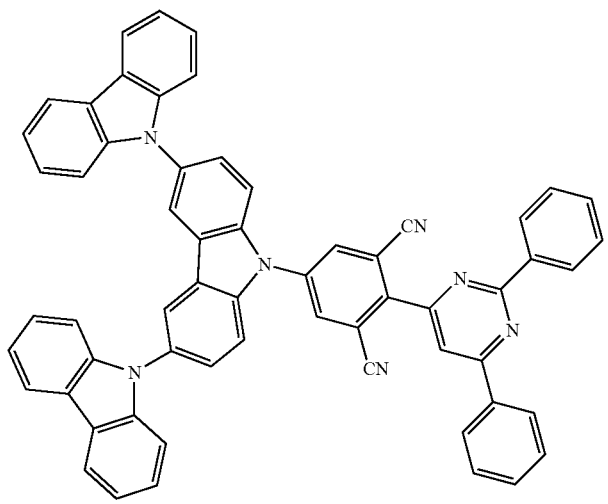
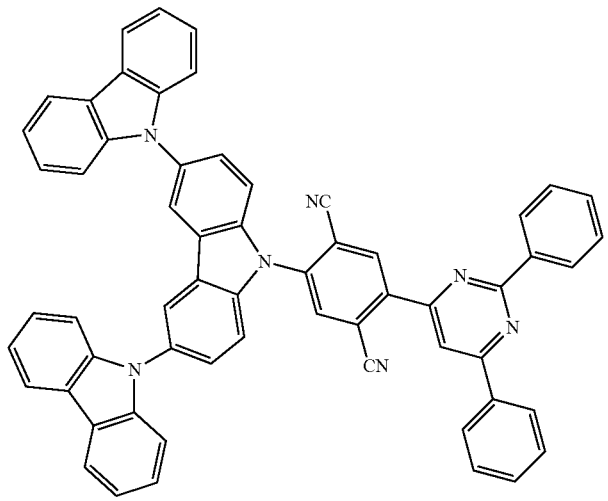

-continued
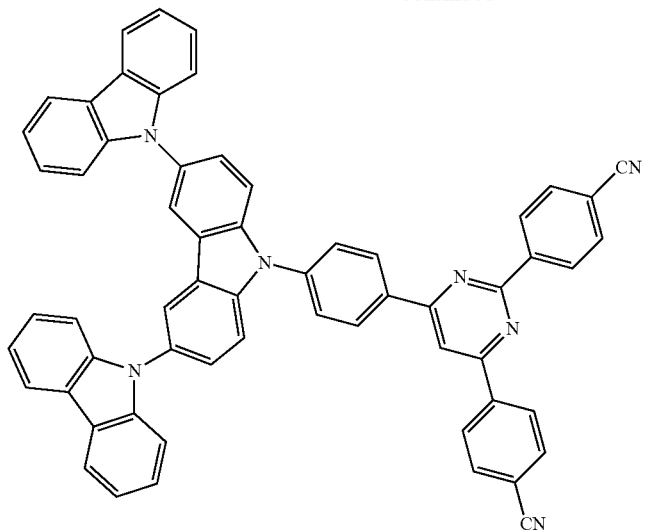
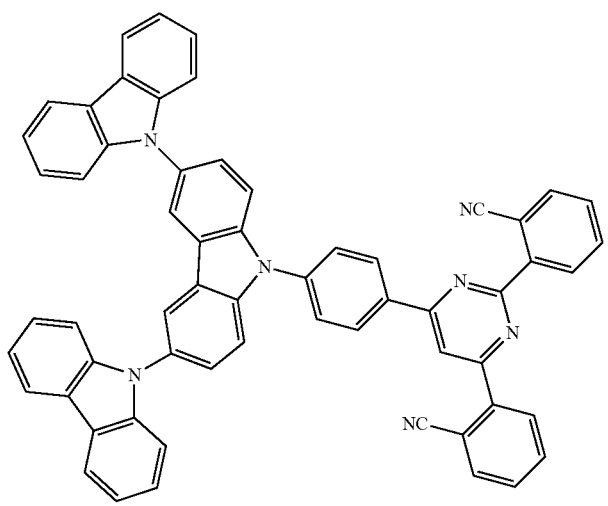
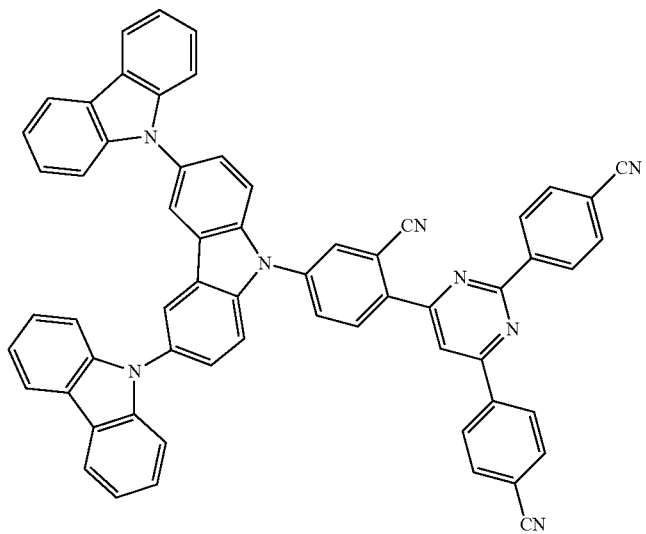

-continued
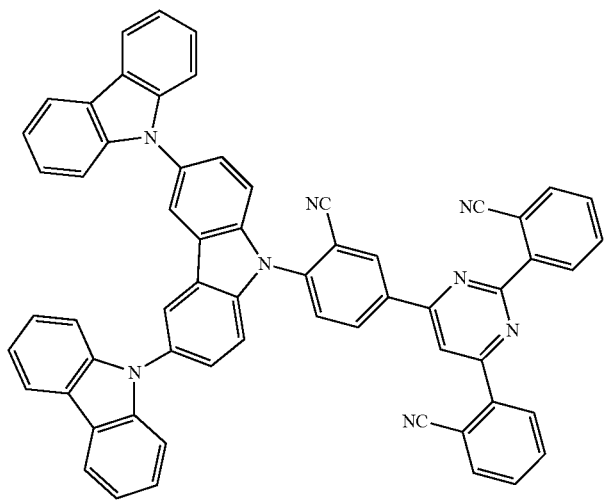
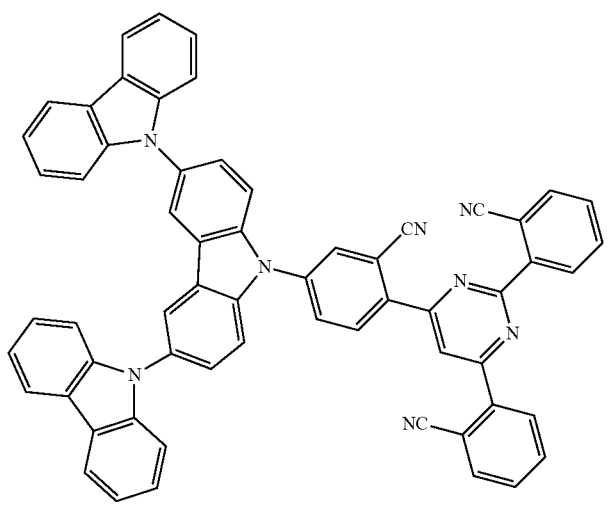
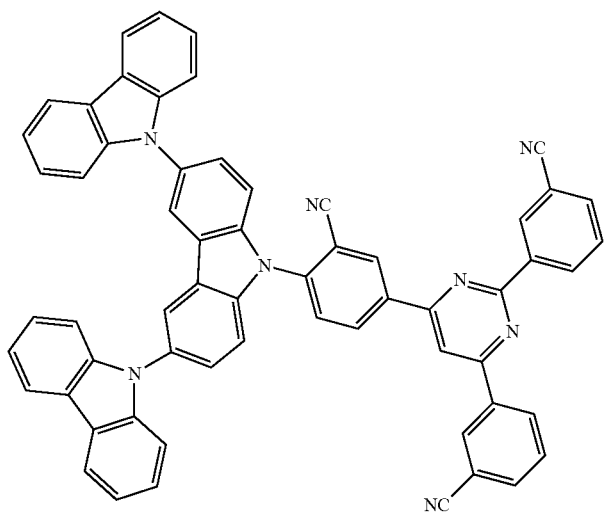

-continued
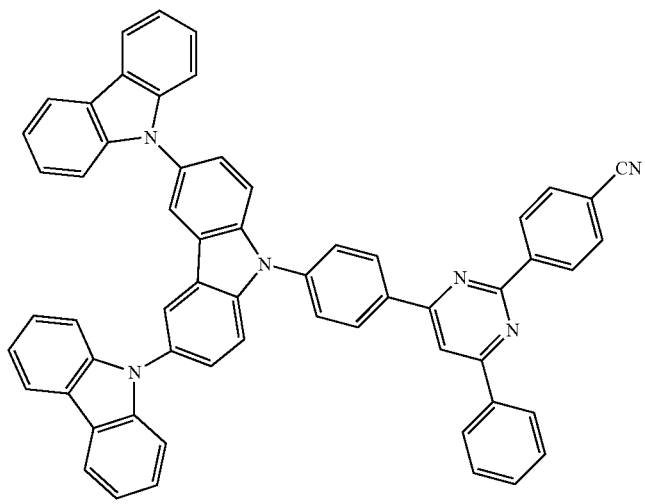
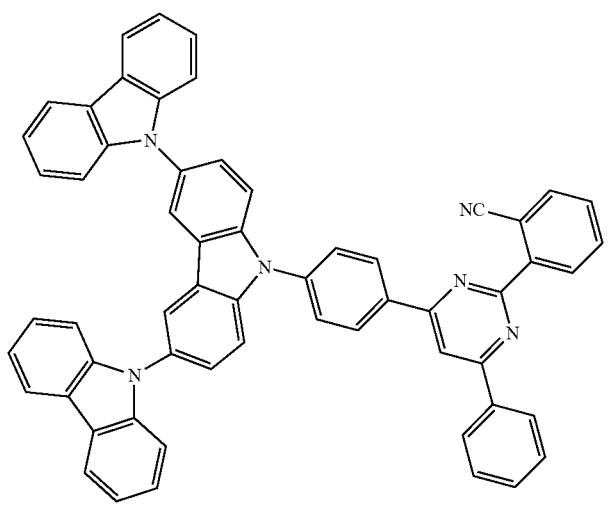
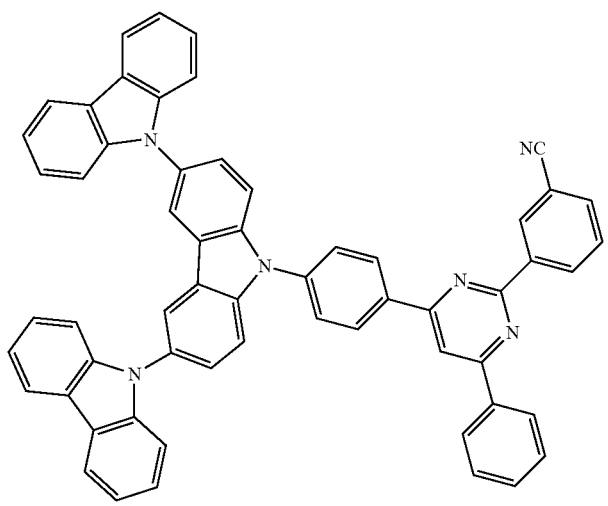

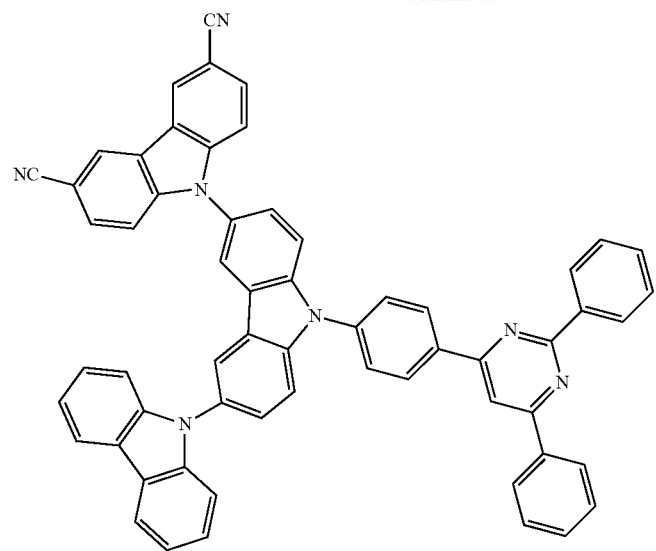
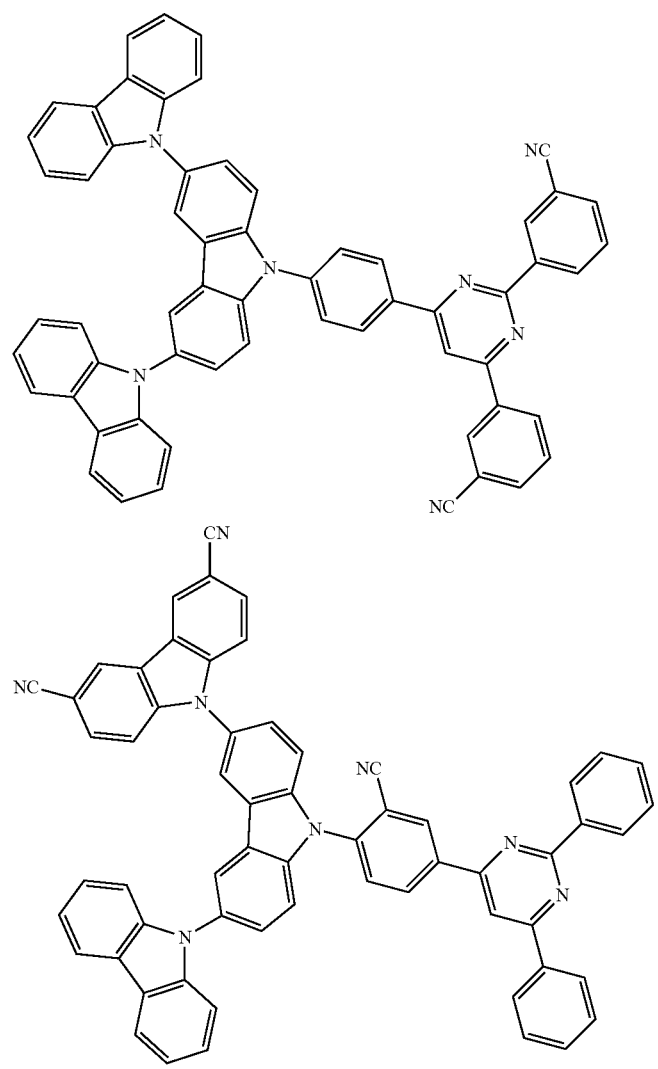

-continued
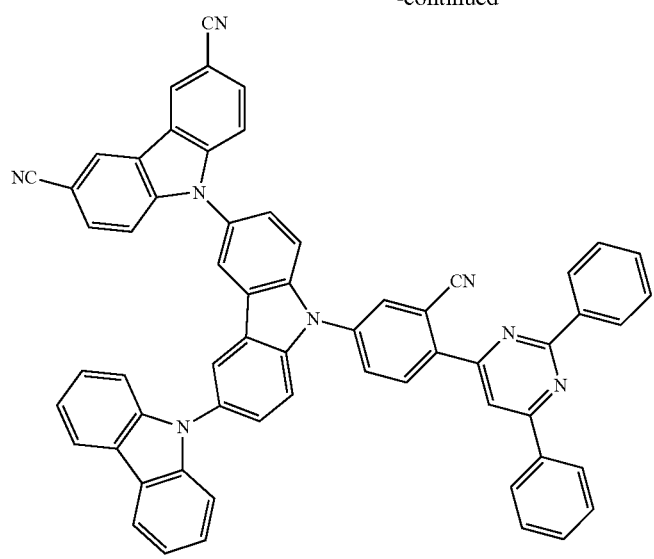
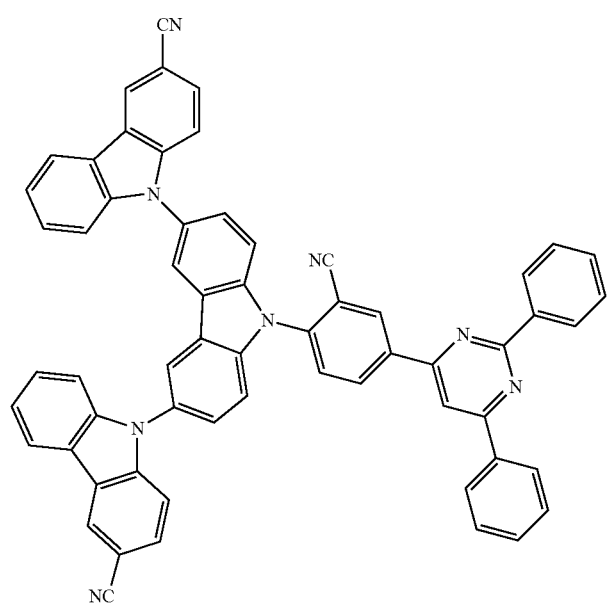
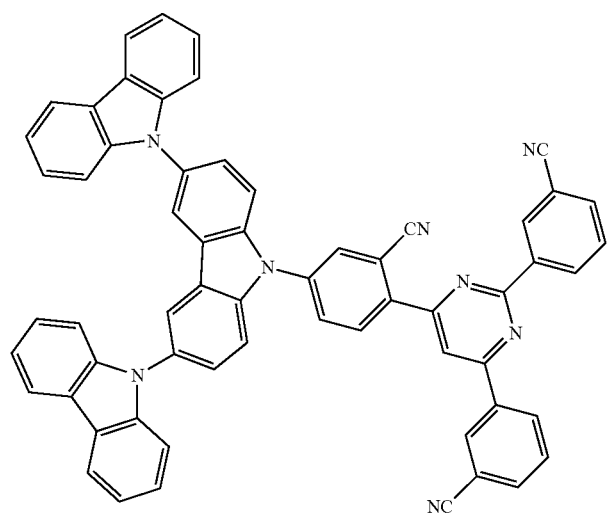

-continued
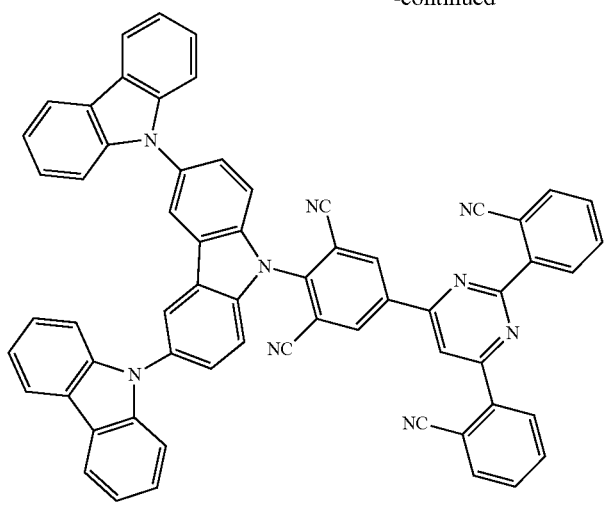
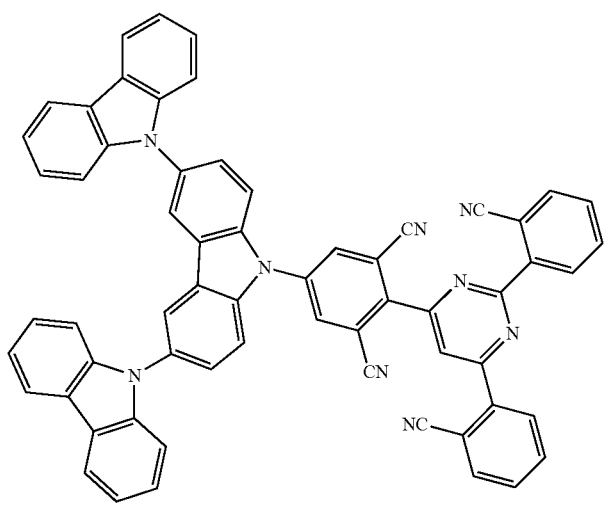
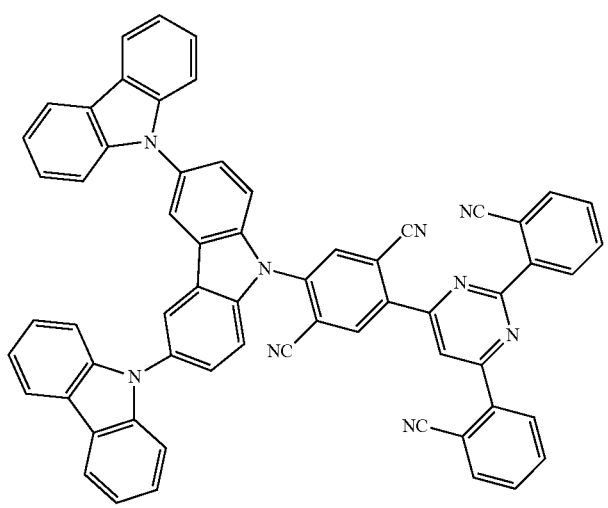

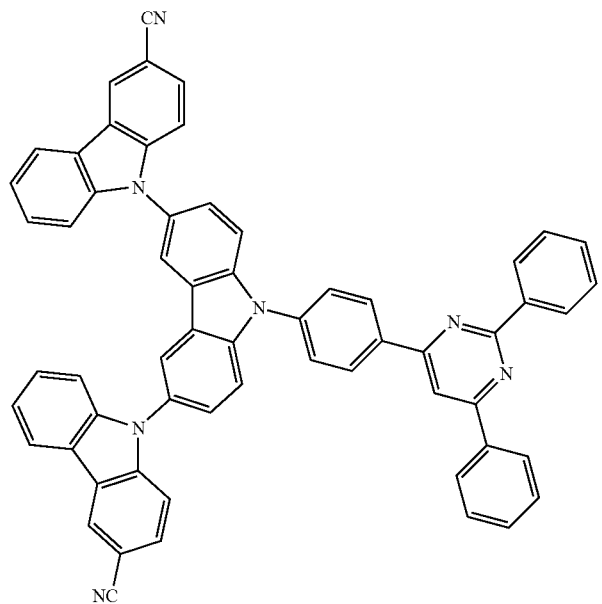

-continued
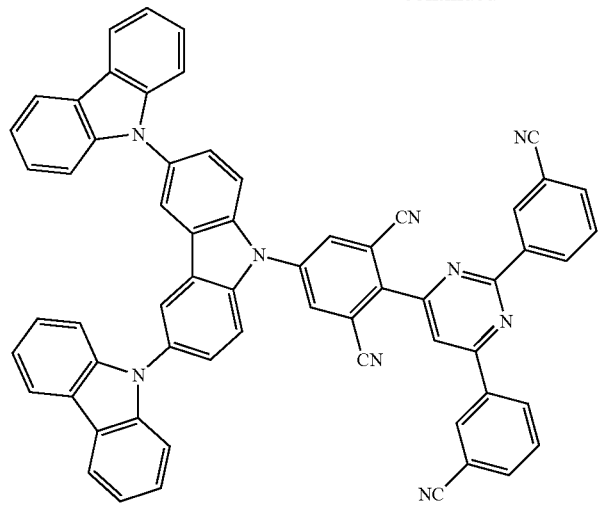
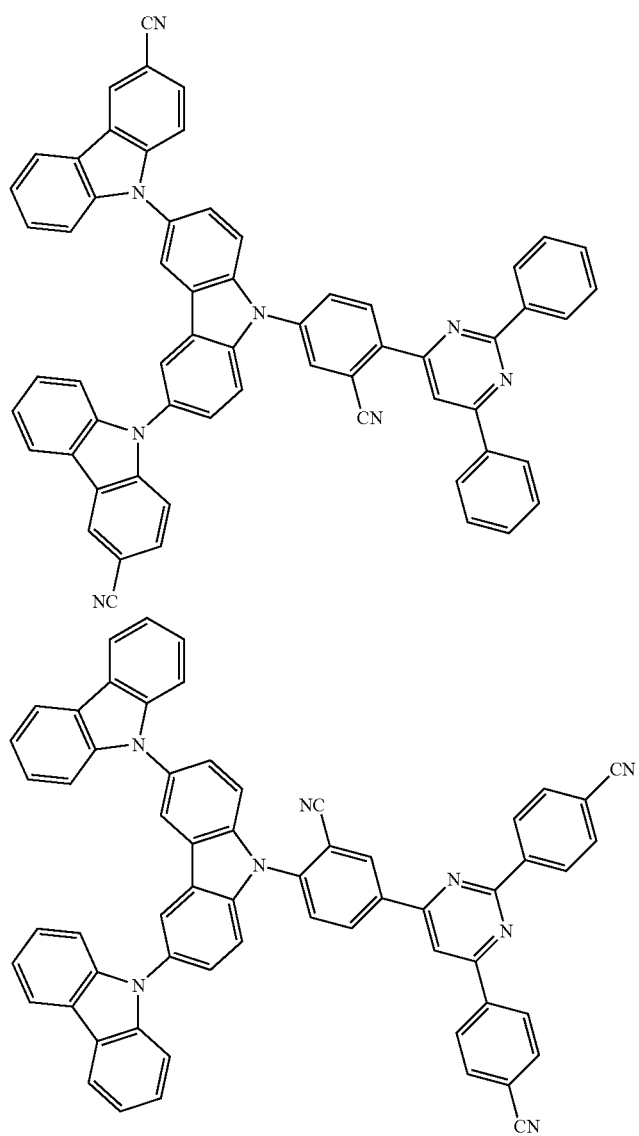

-continued
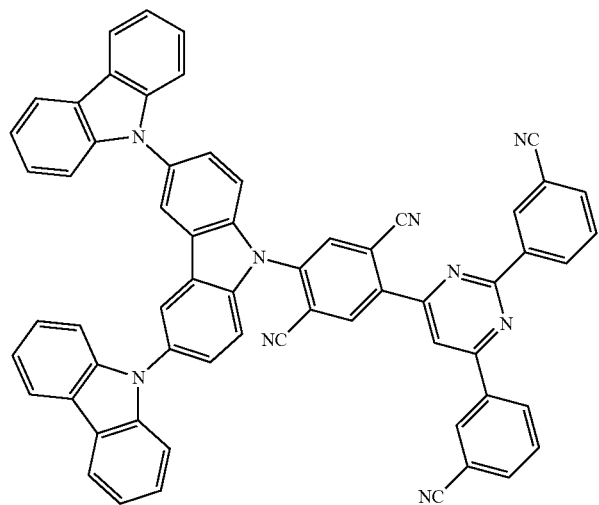
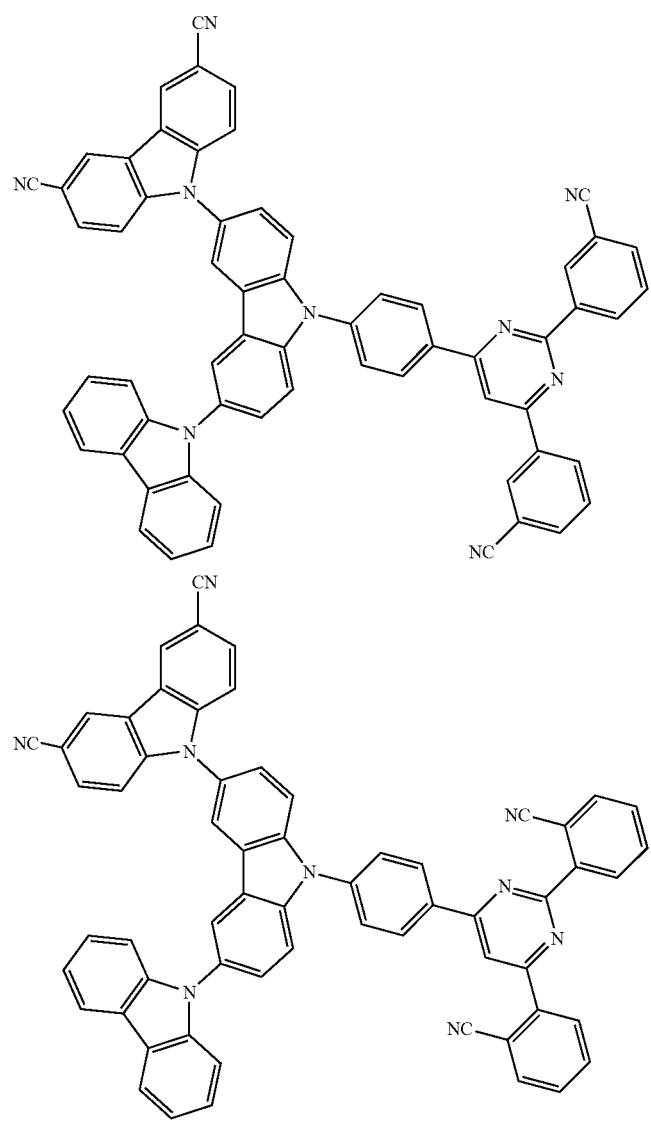

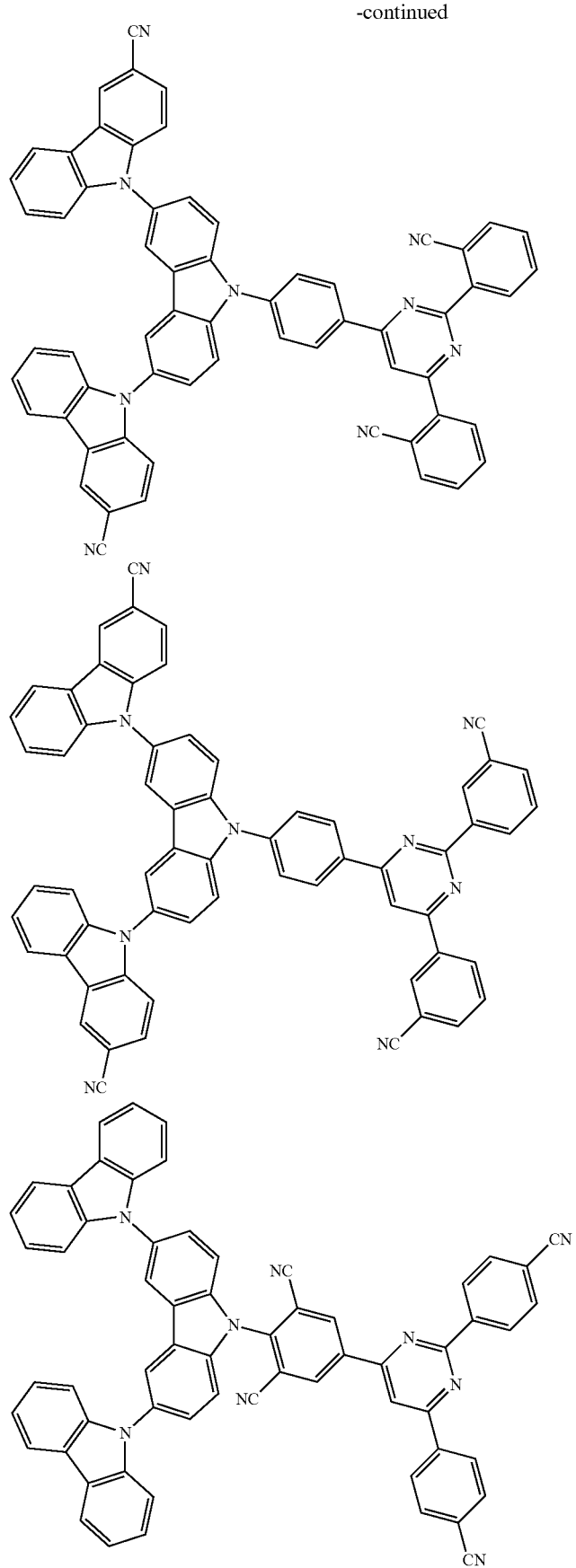

-continued
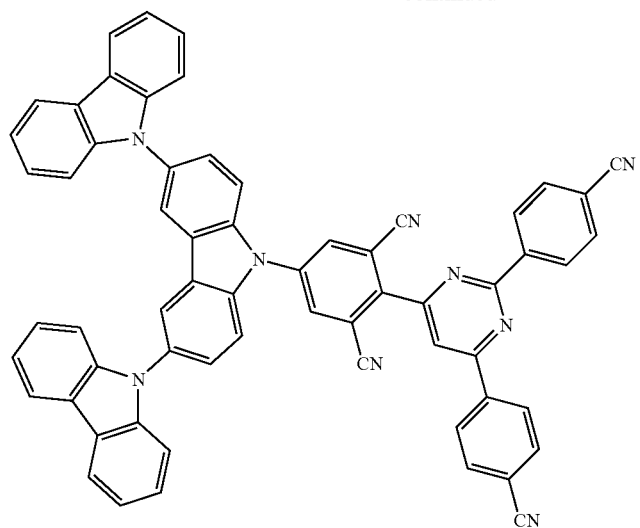
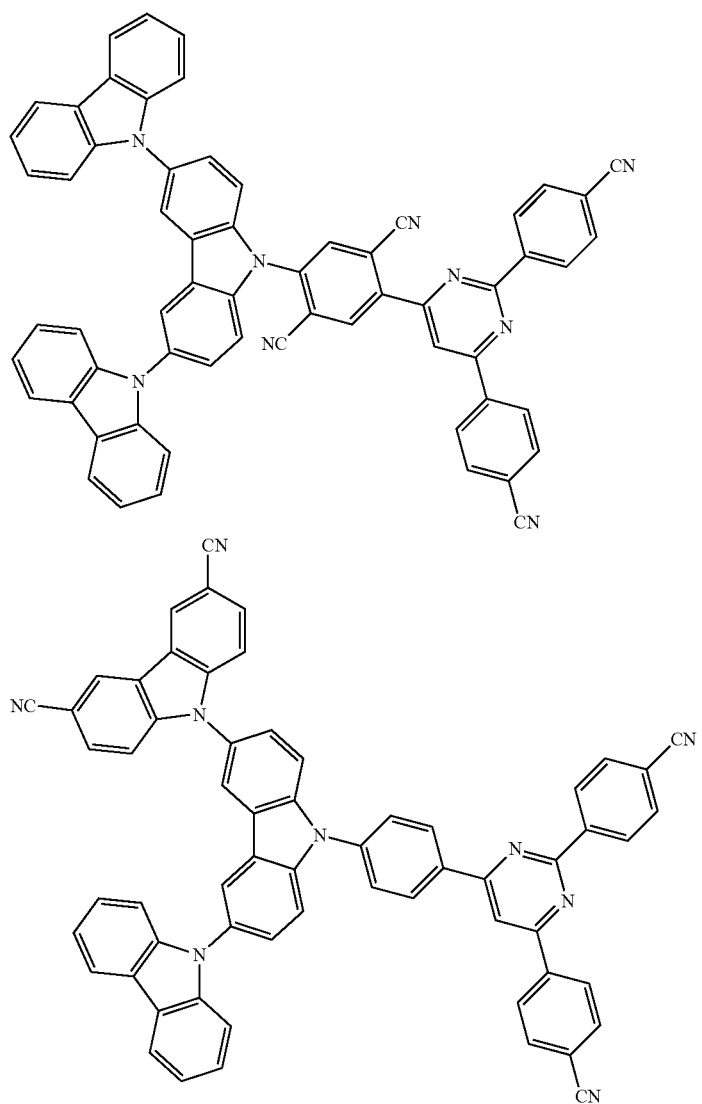

-continued
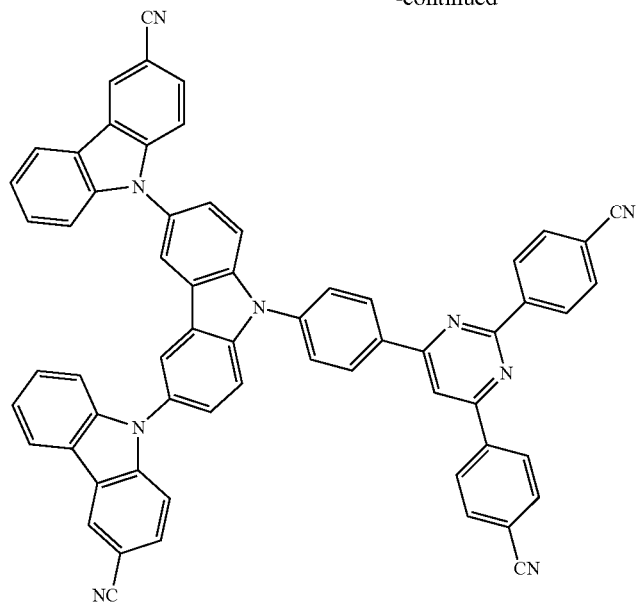
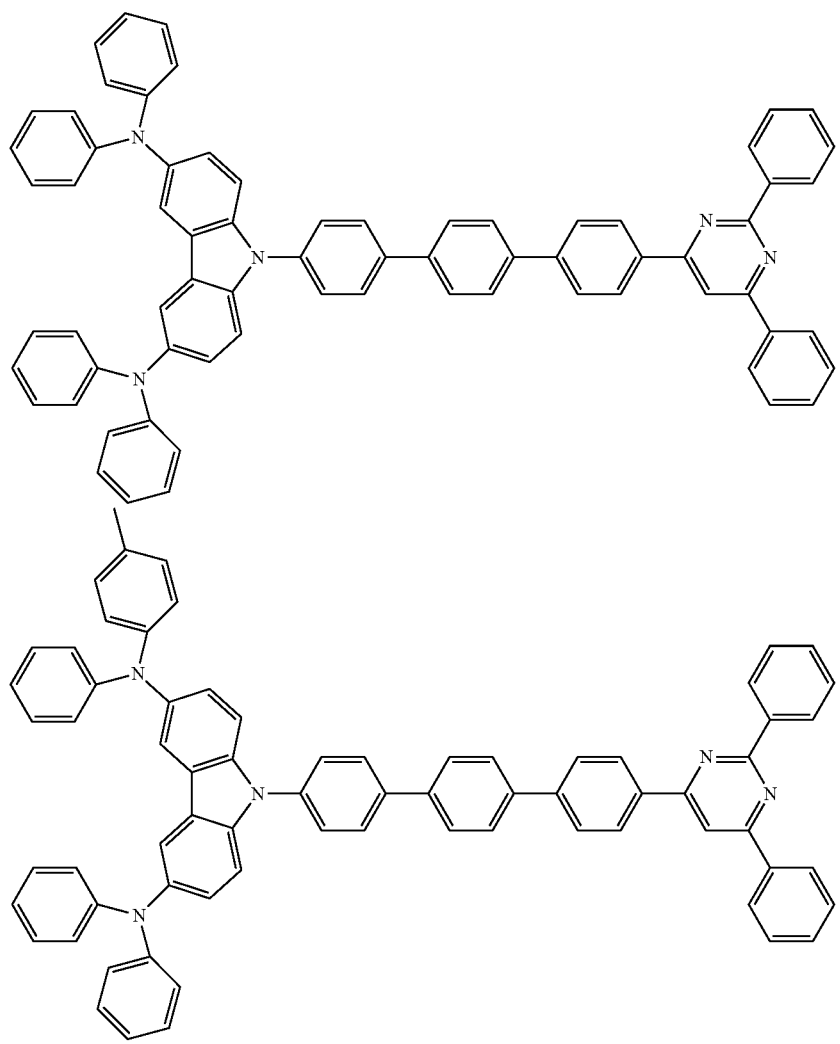

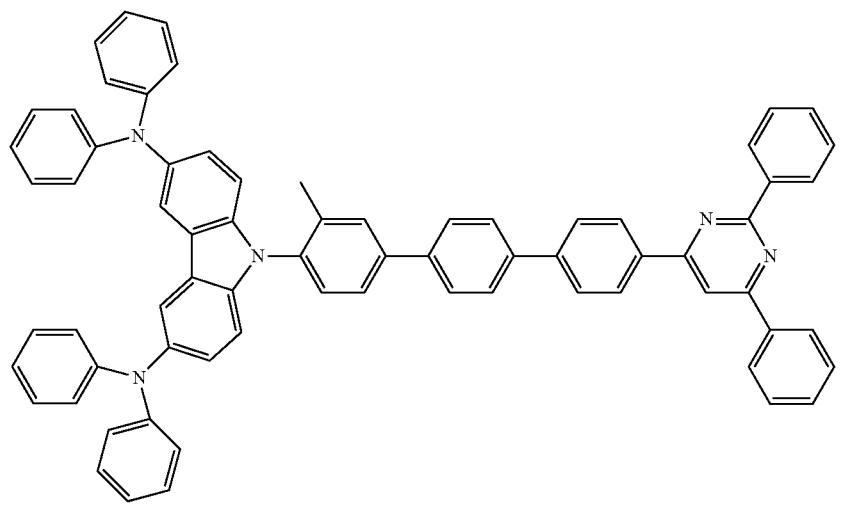
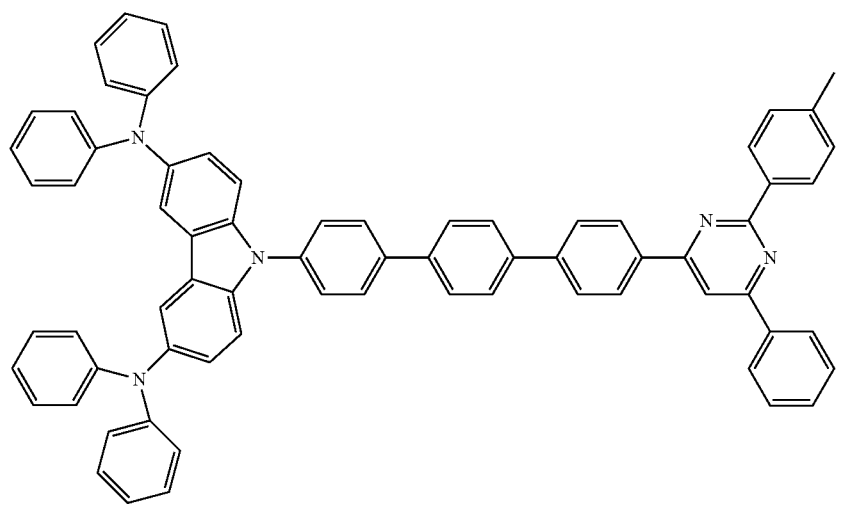

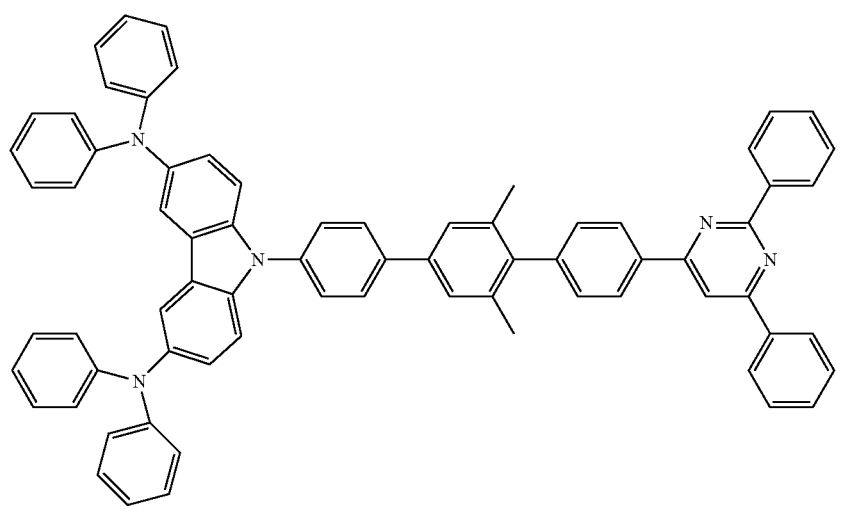

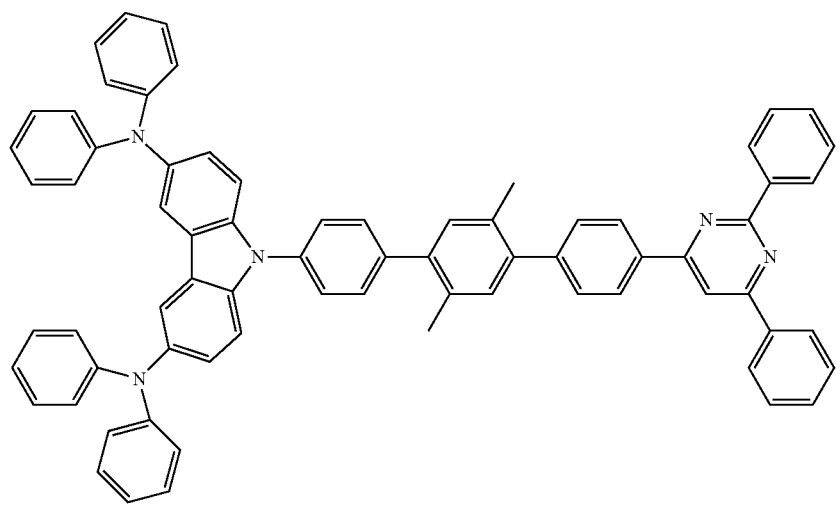
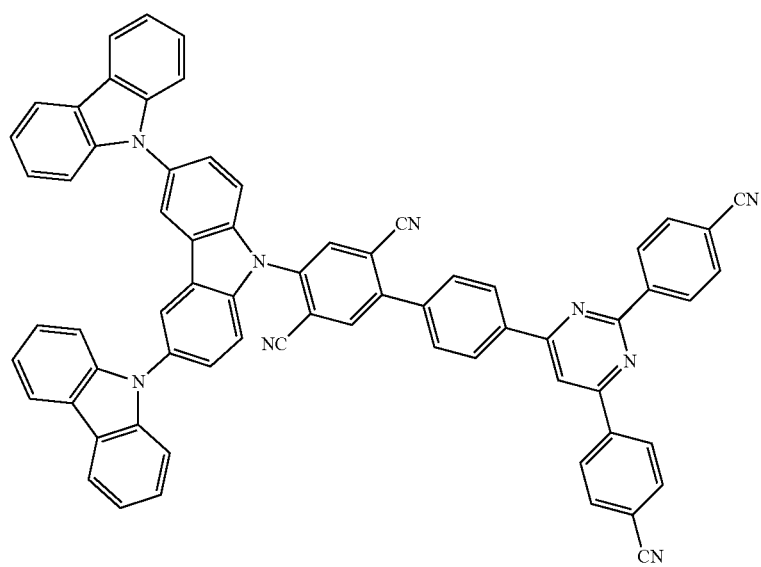
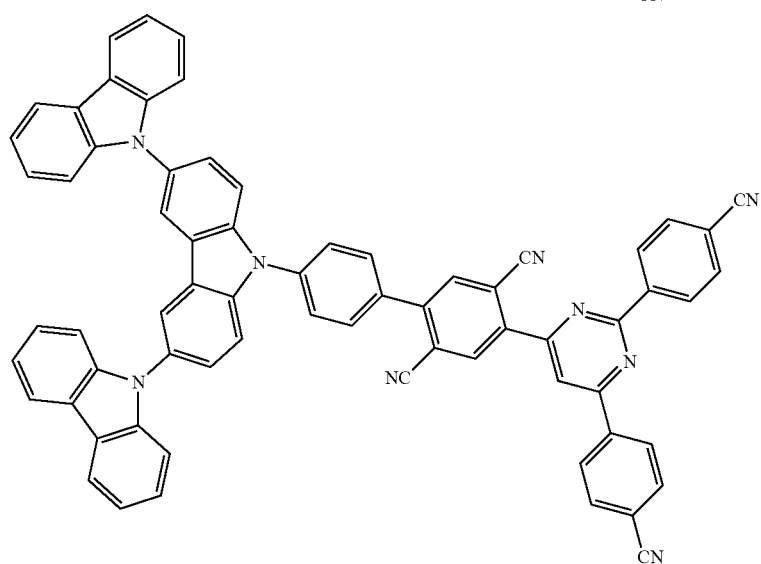

-continued
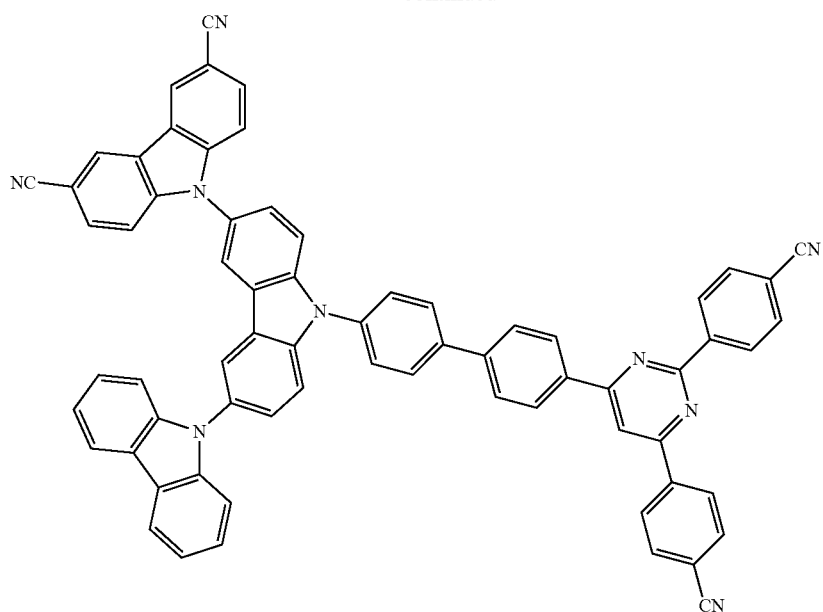
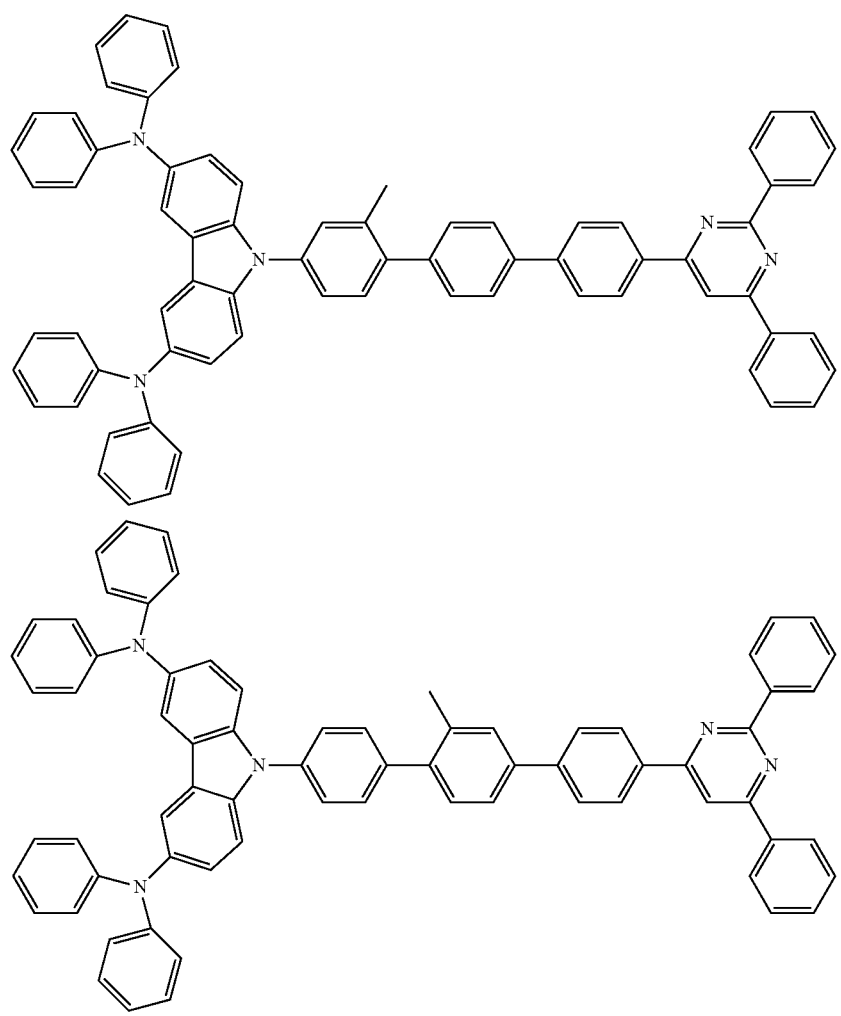

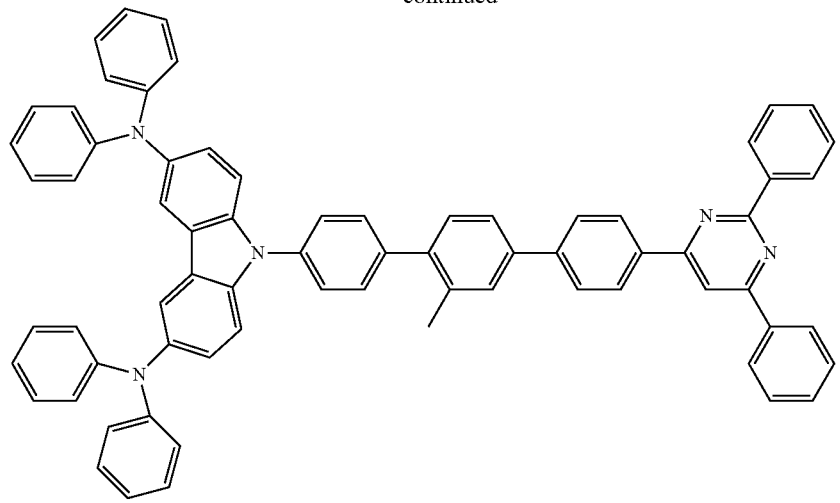
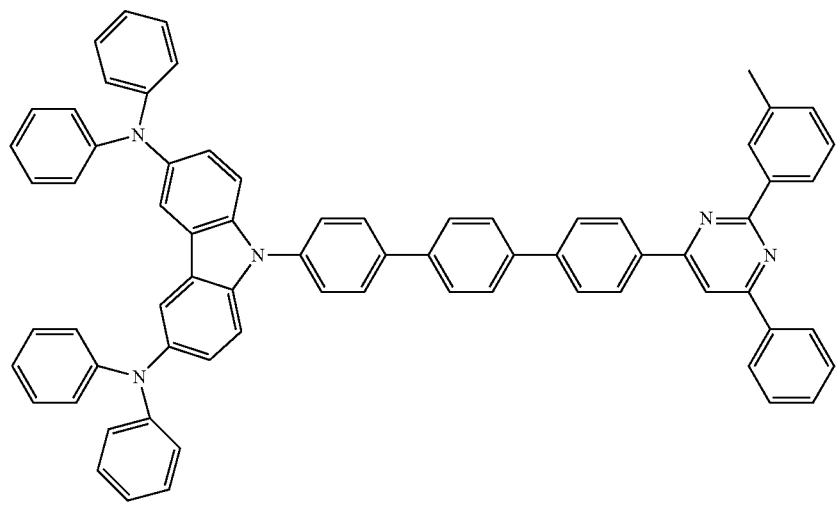
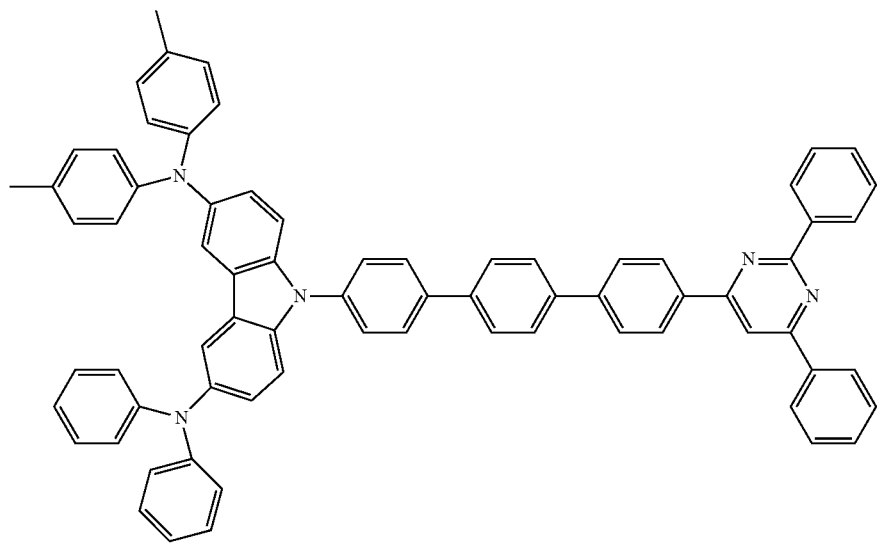

-continued
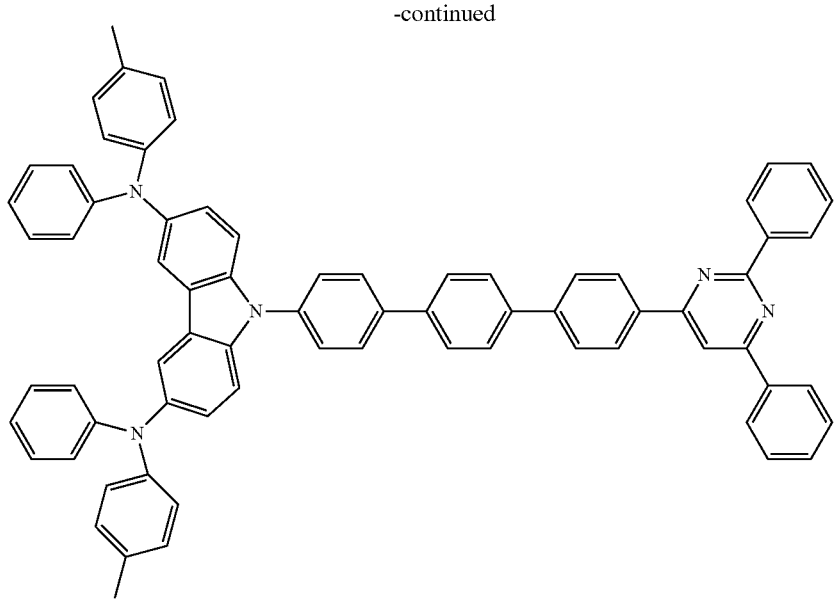
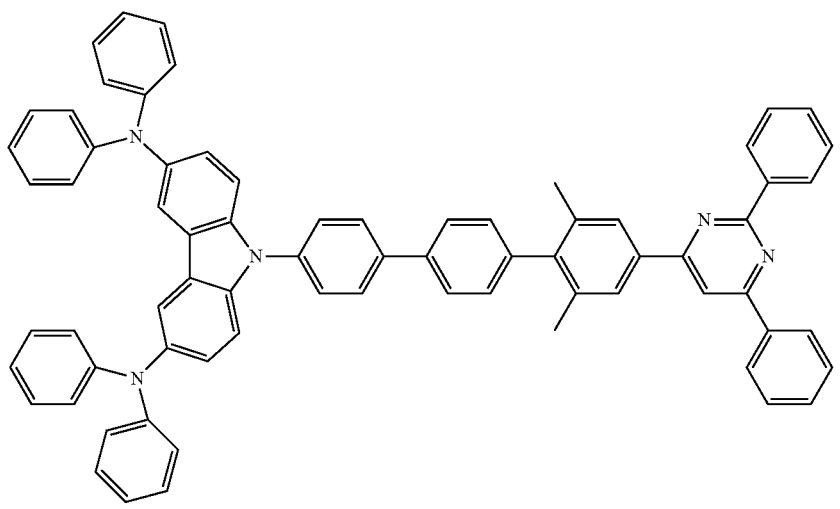
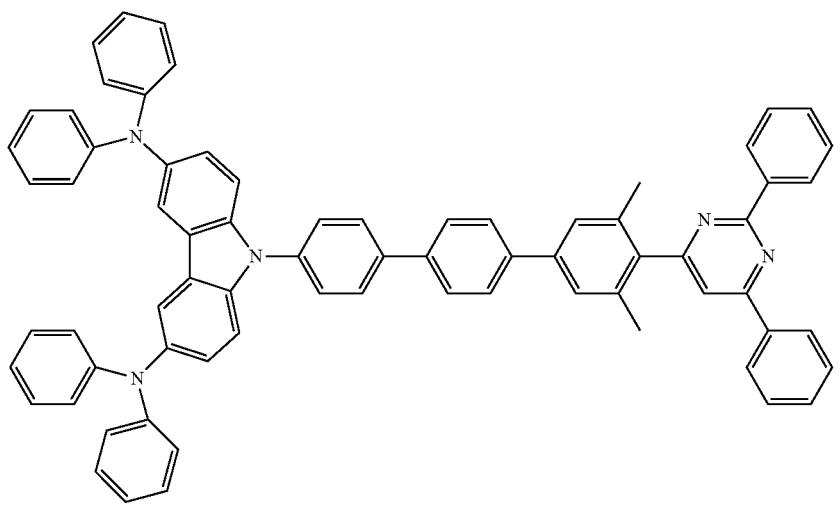

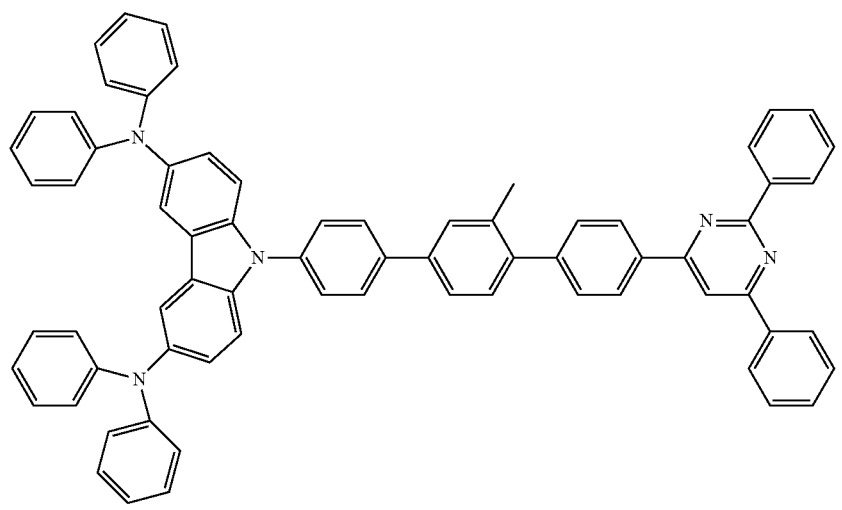
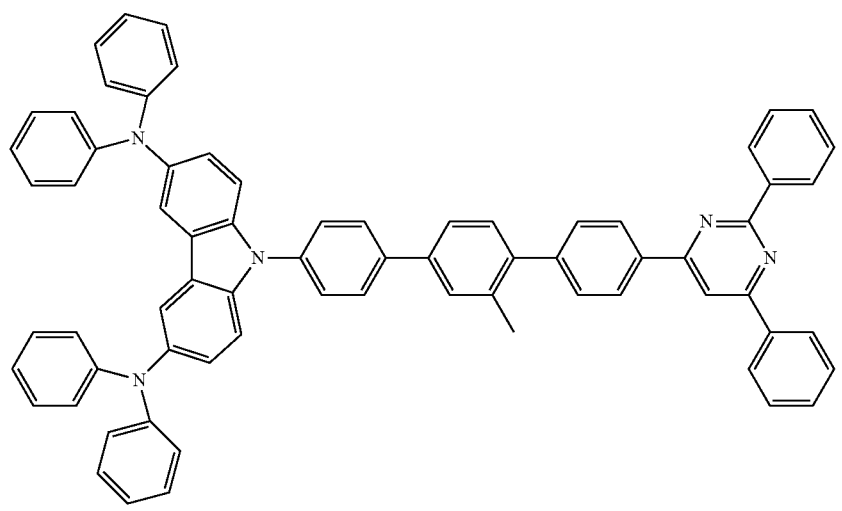

-continued
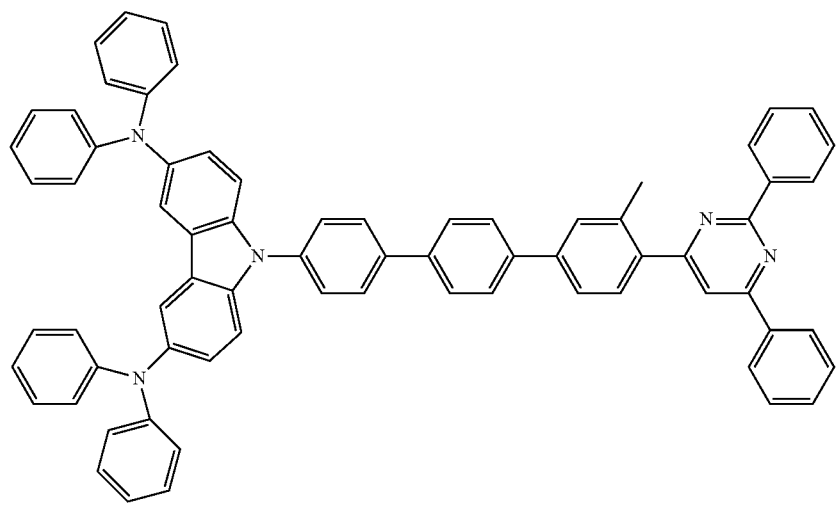
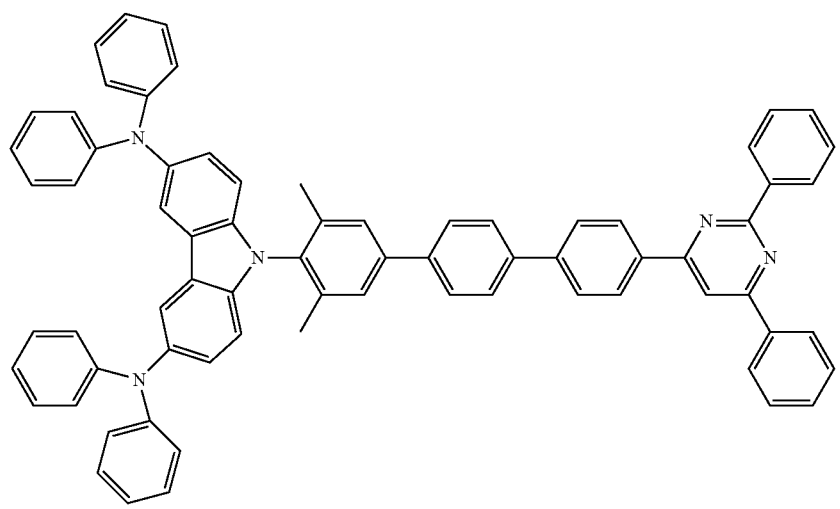
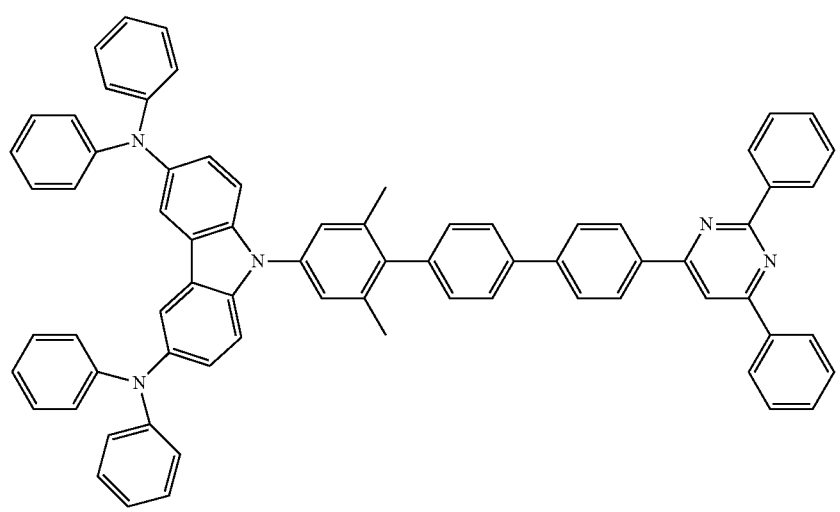

-continued
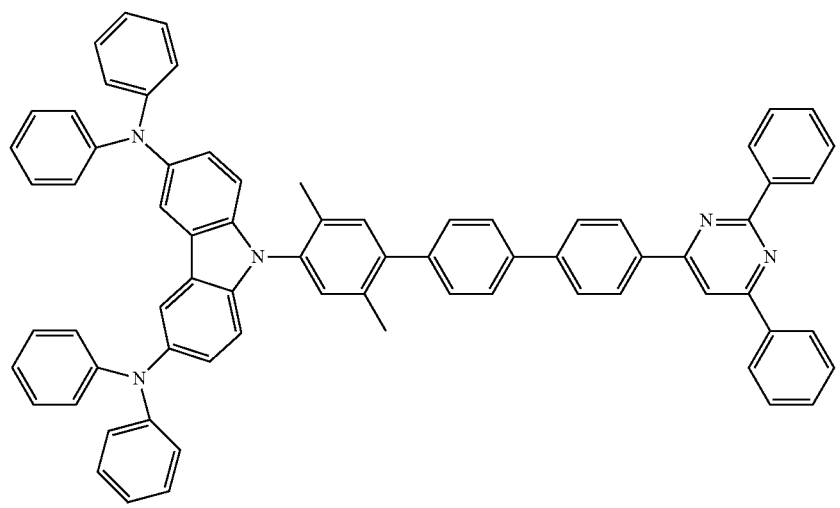
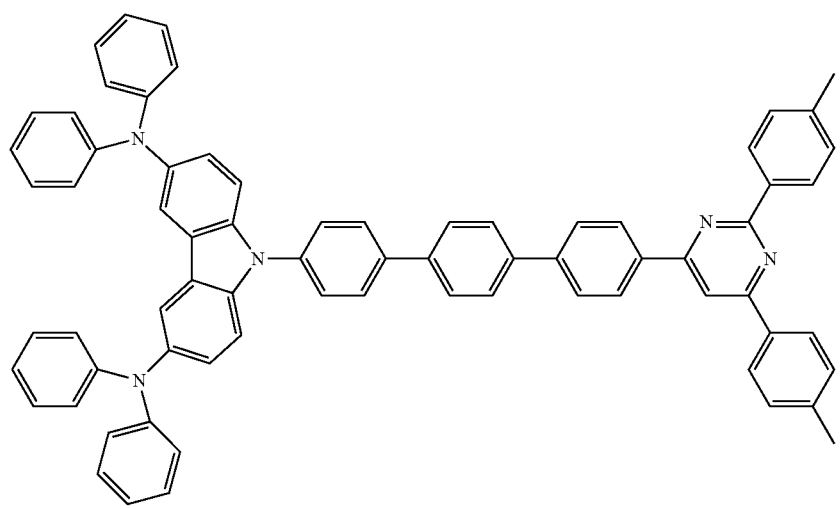
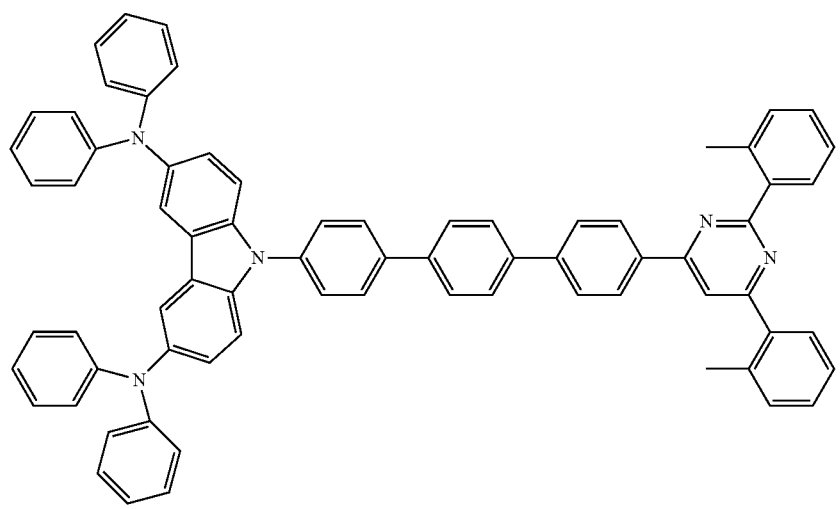

-continued
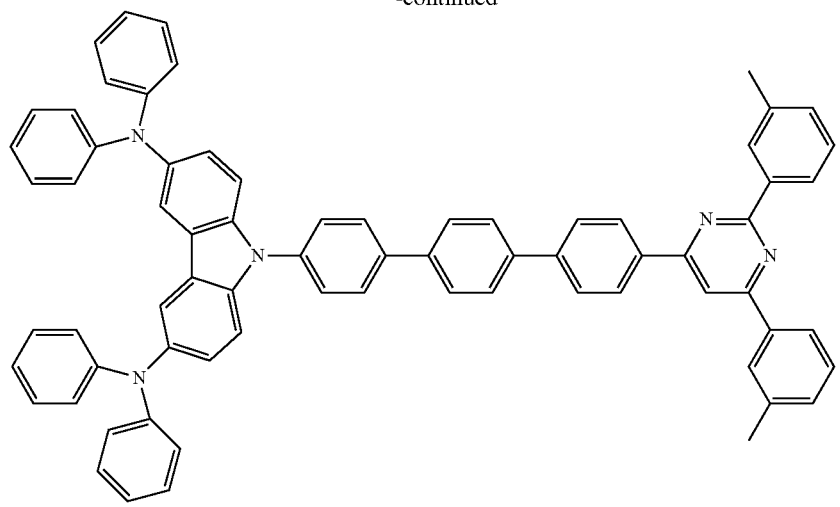
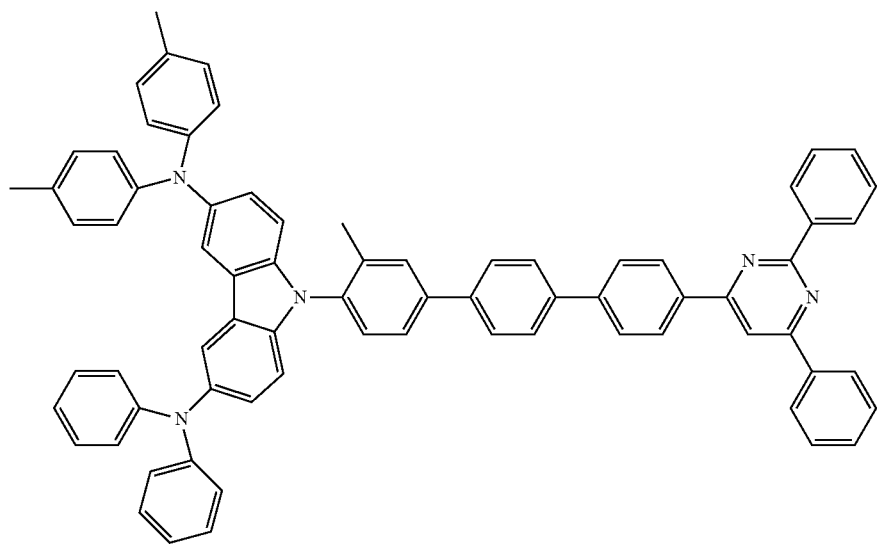
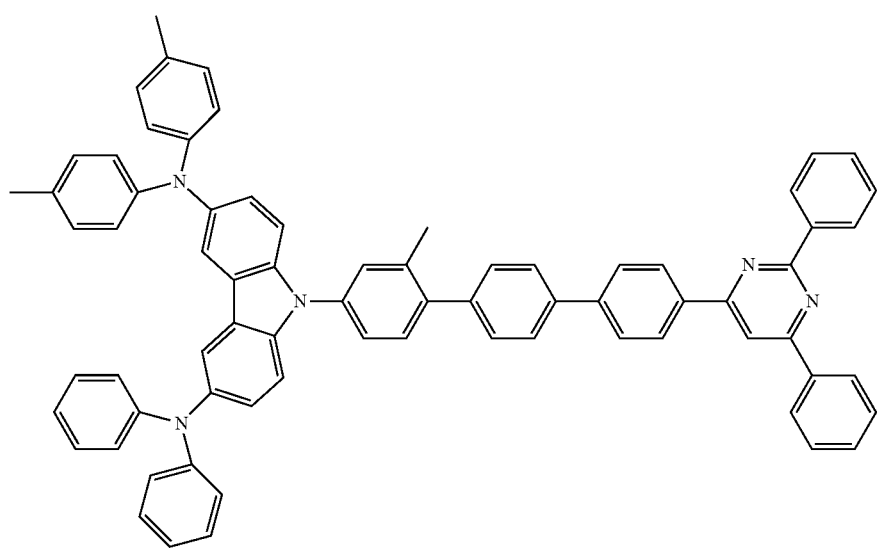

-continued
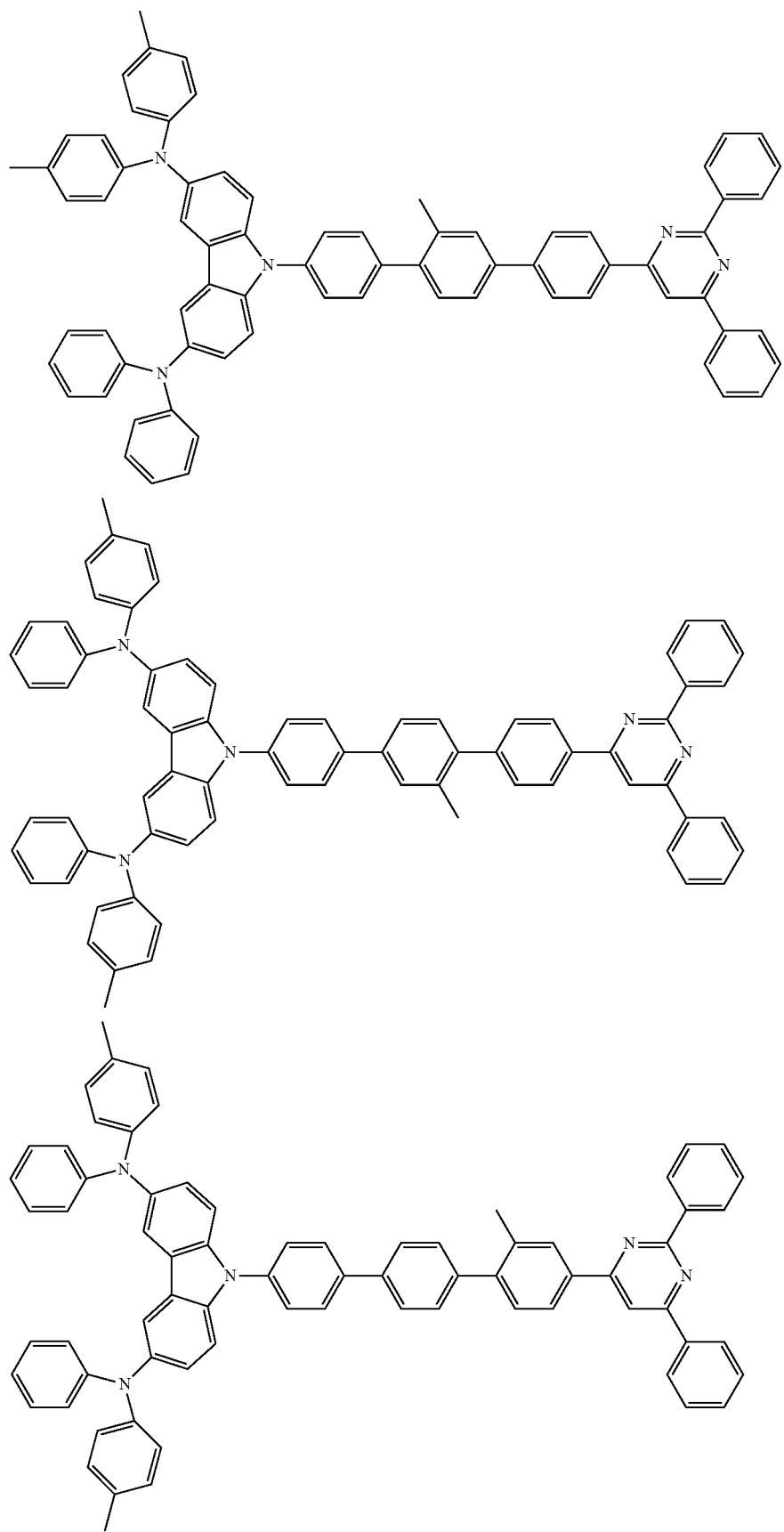

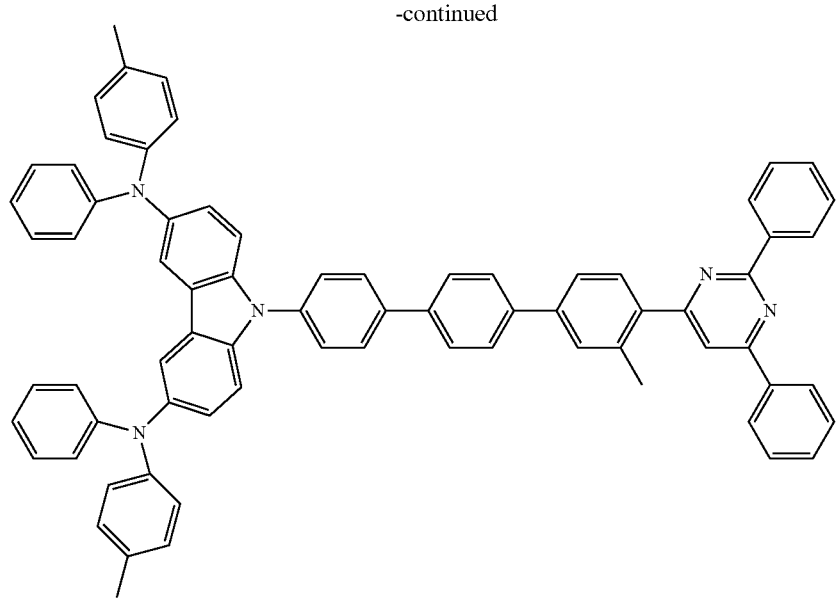
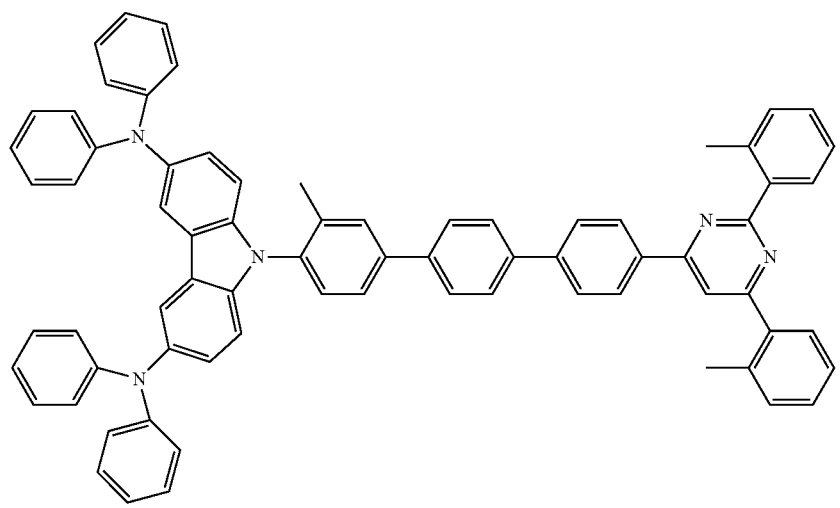
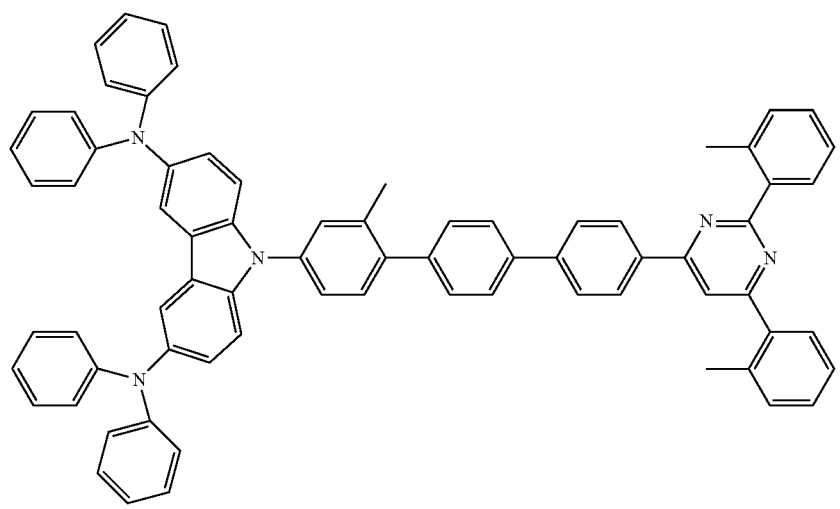

-continued
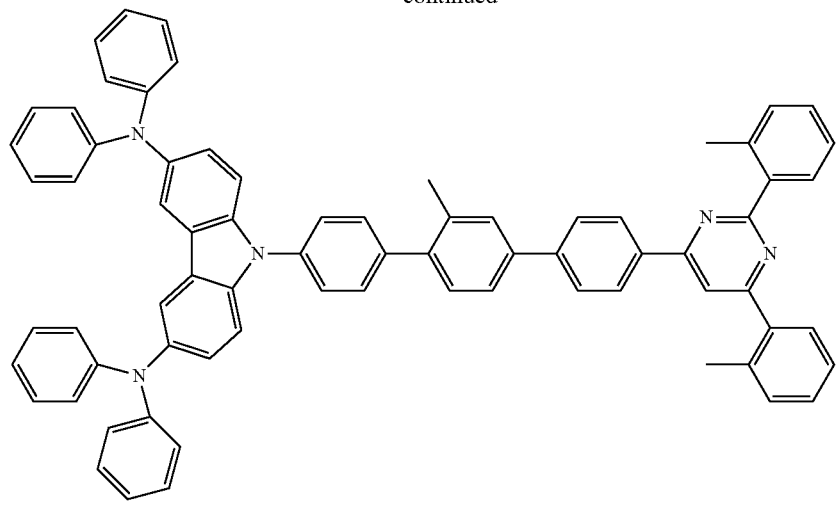
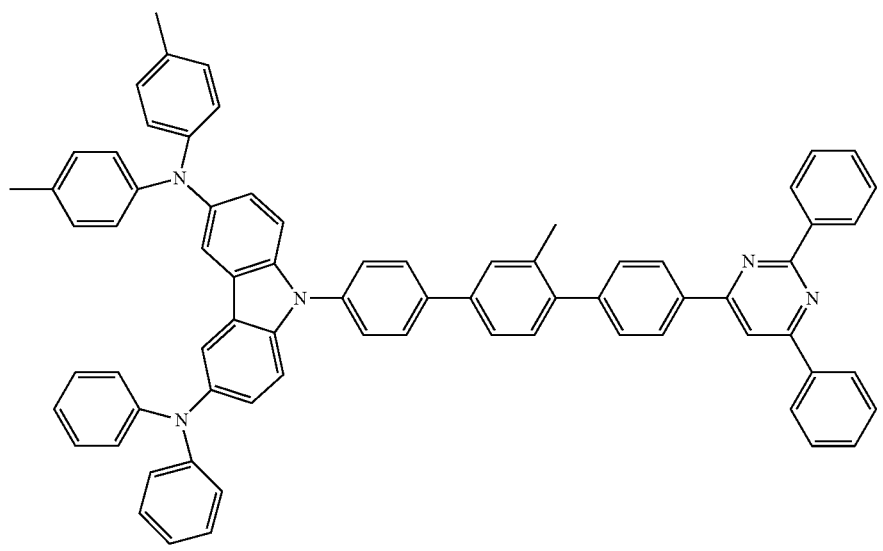
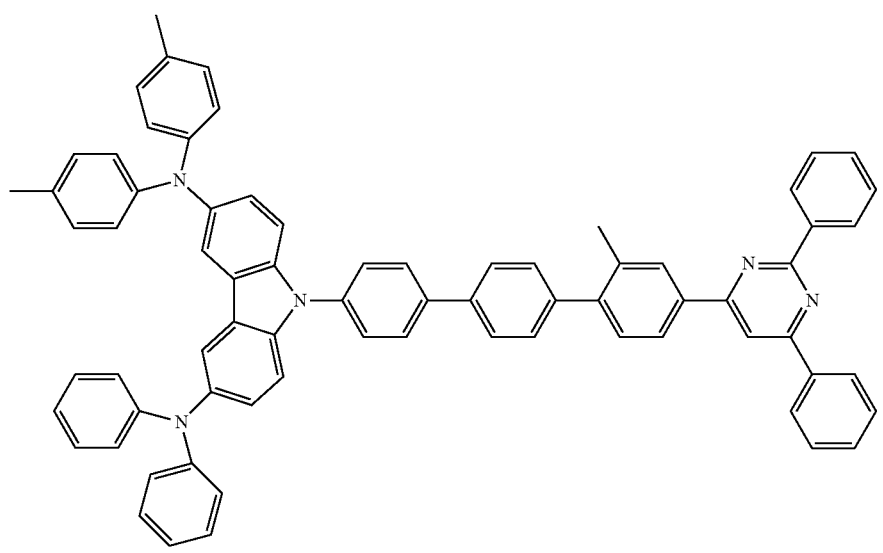

-continued
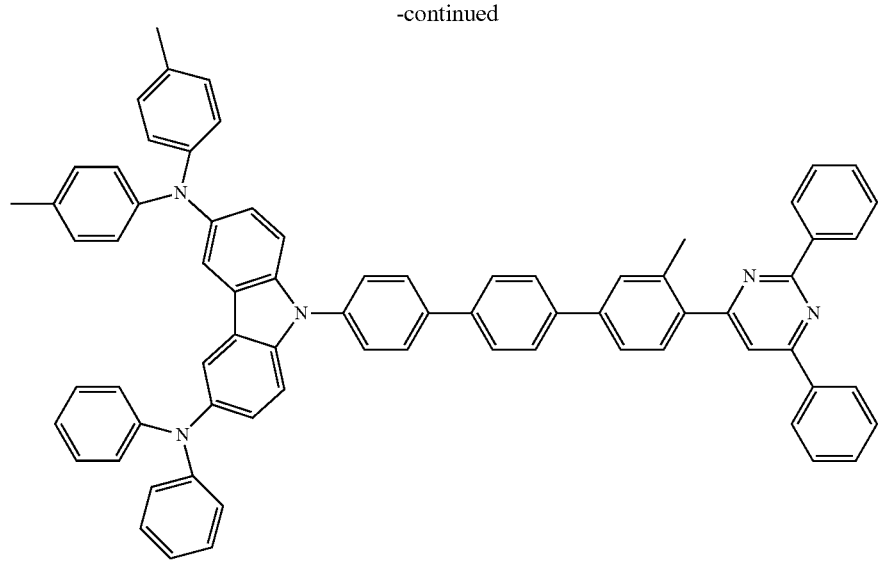
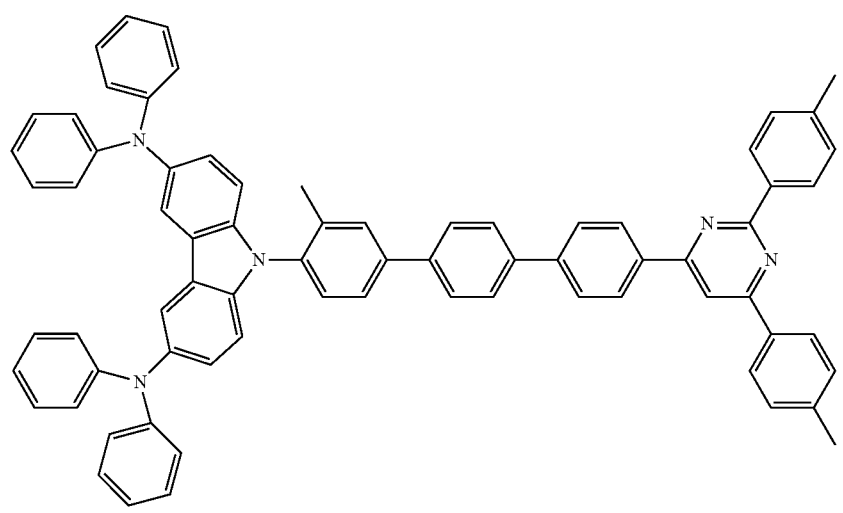
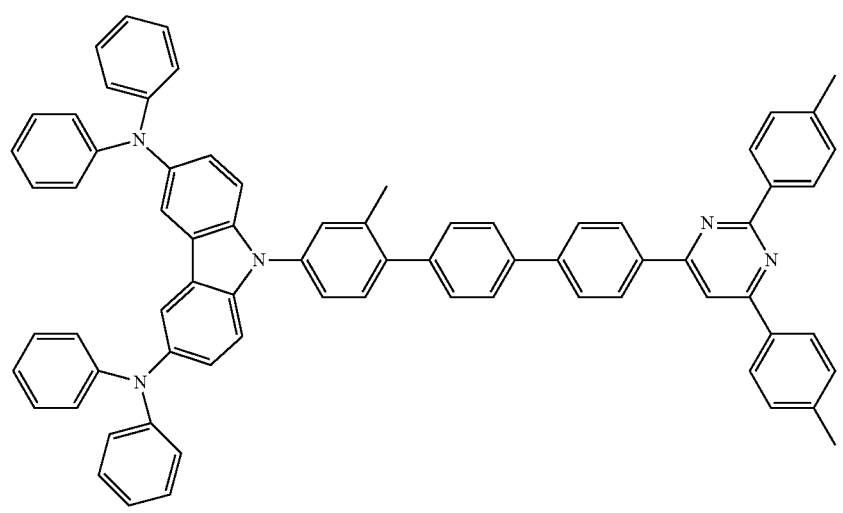

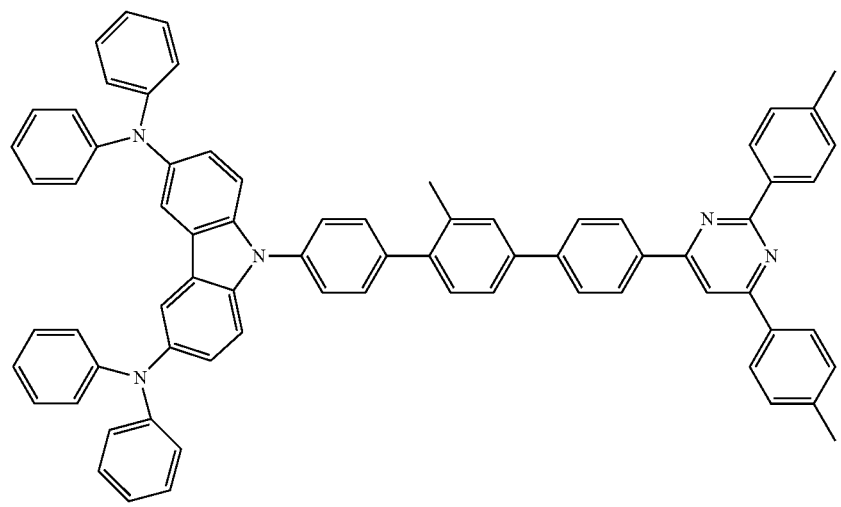
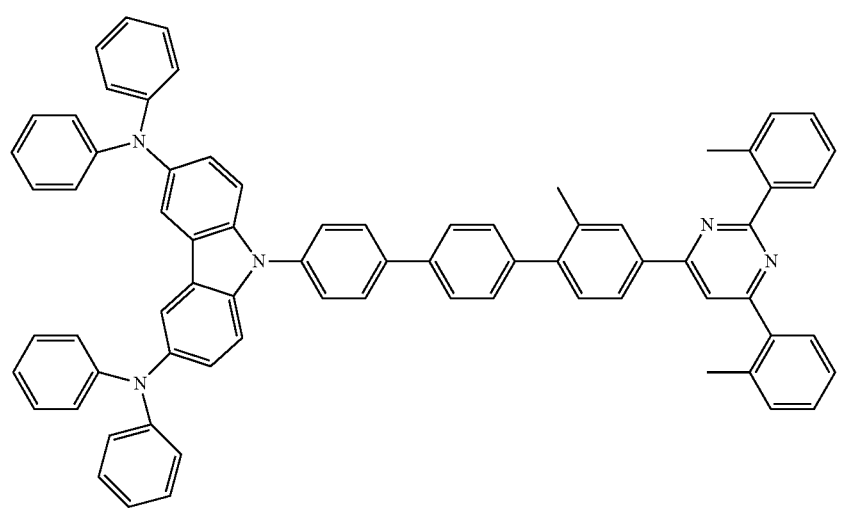

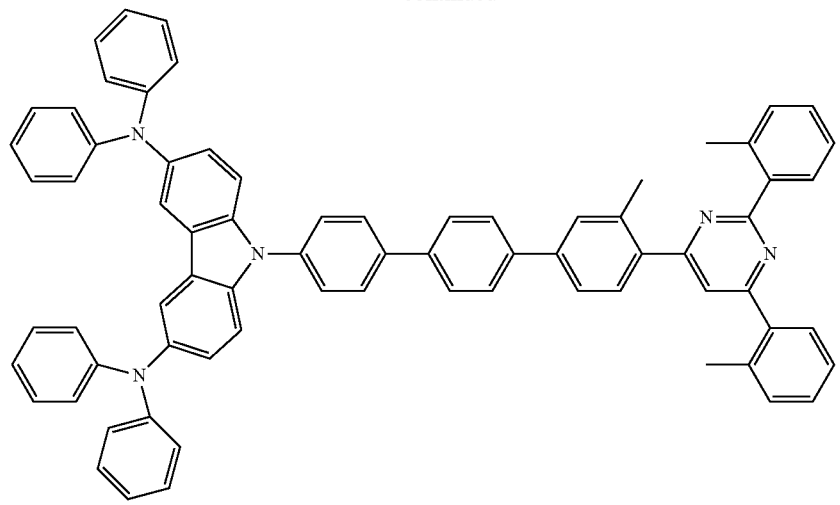
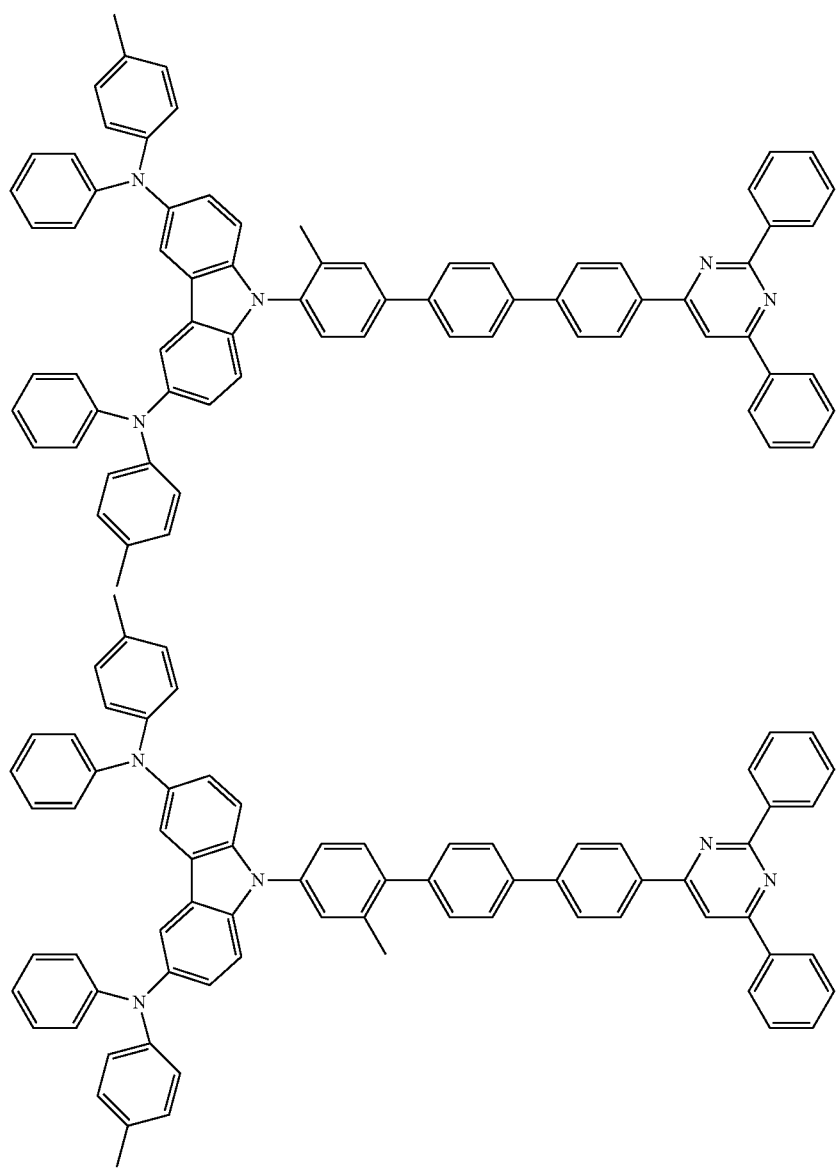

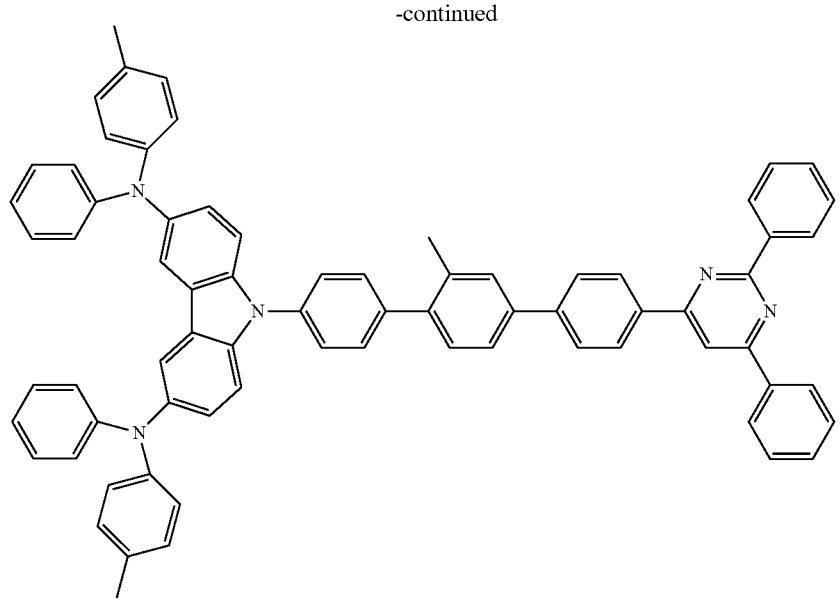
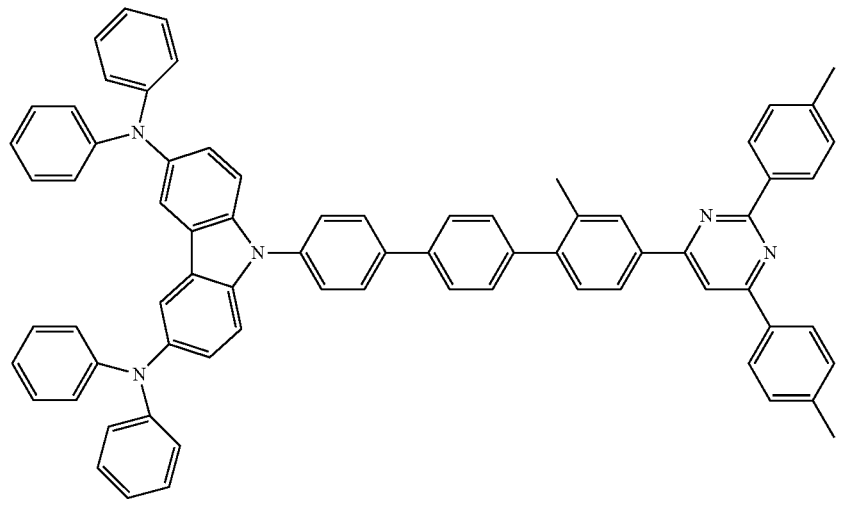

-continued
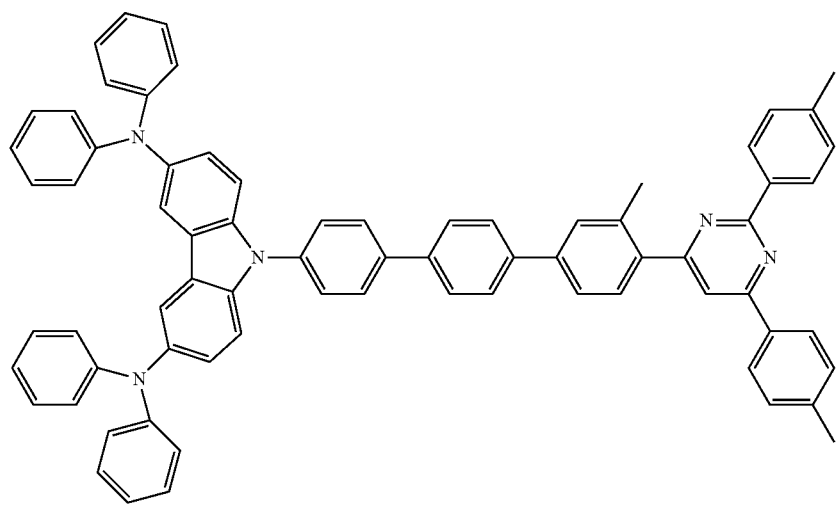
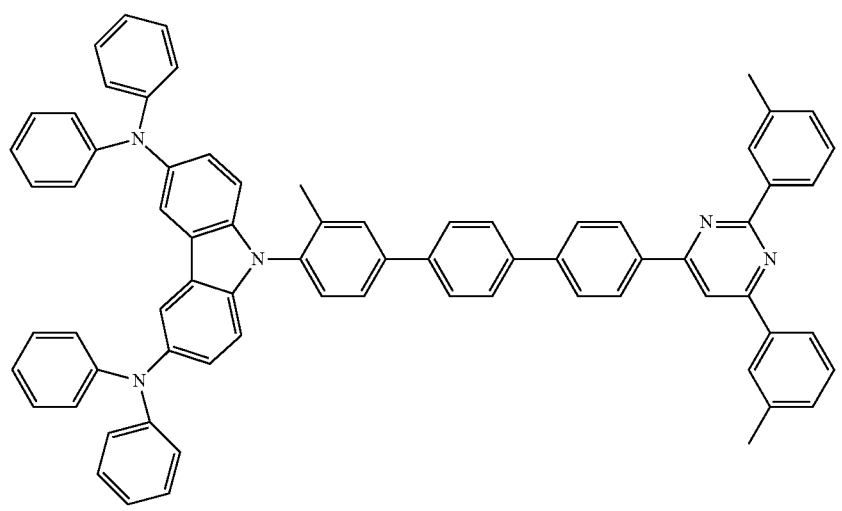
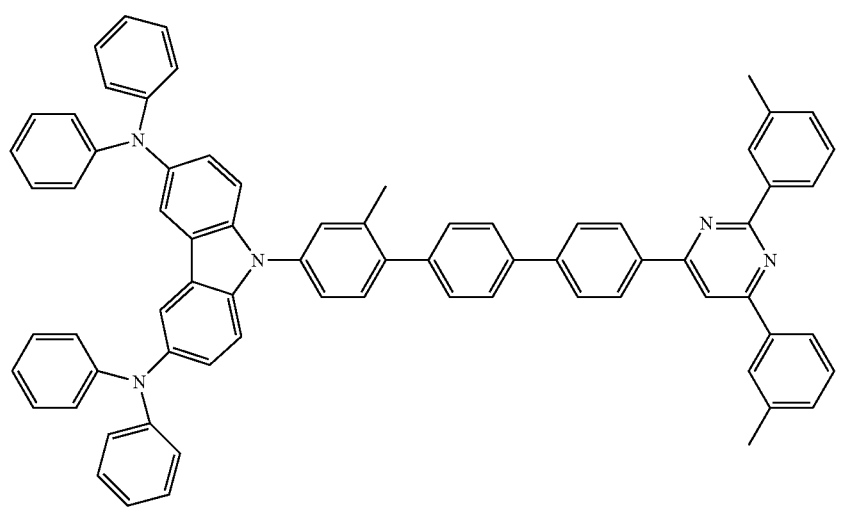

-continued
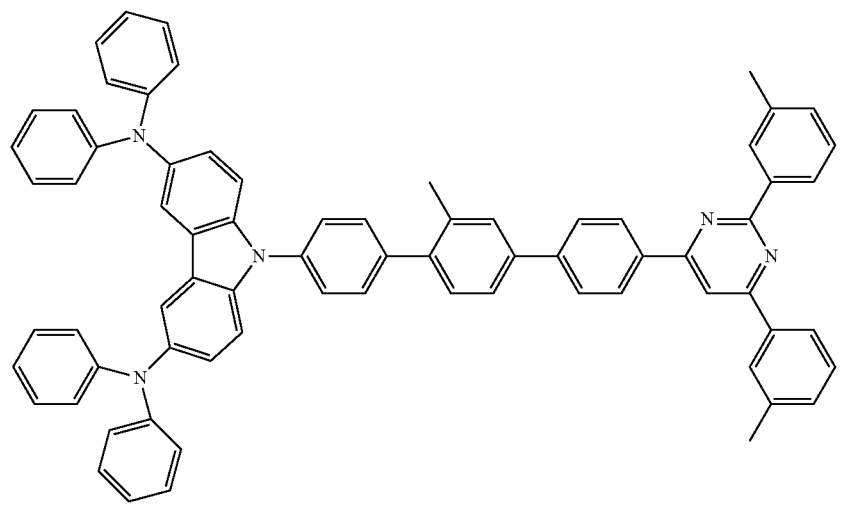
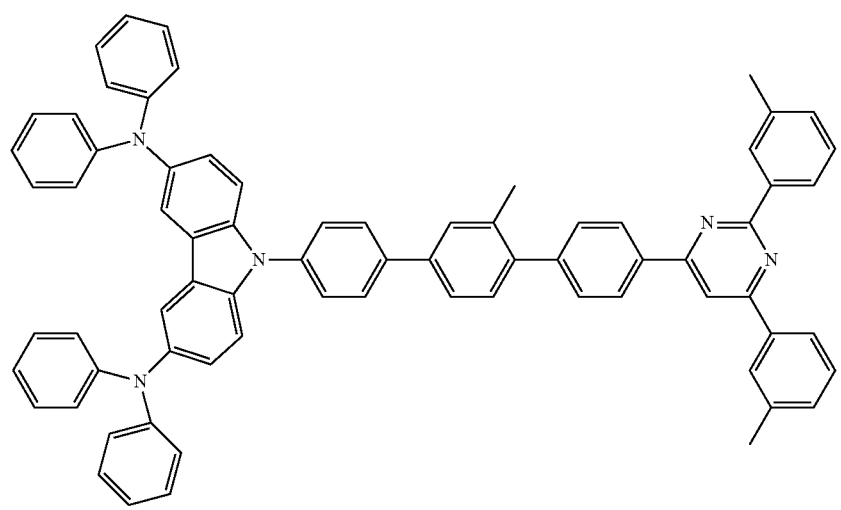
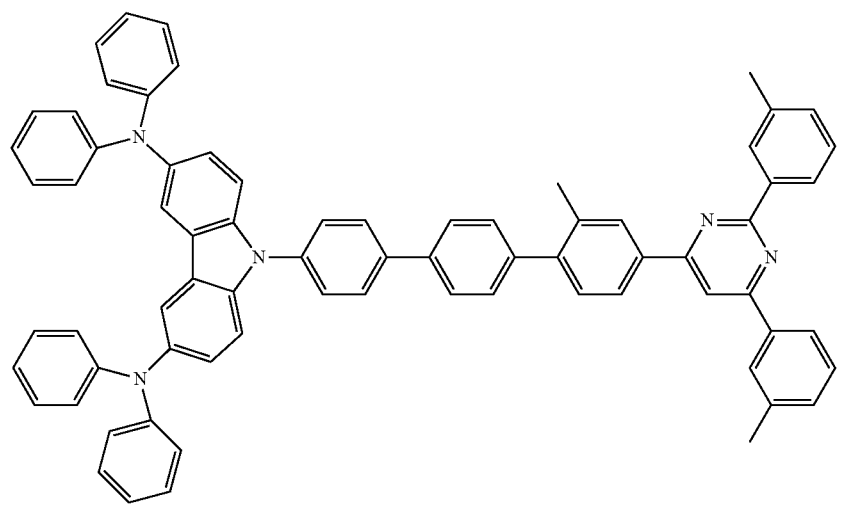

-continued
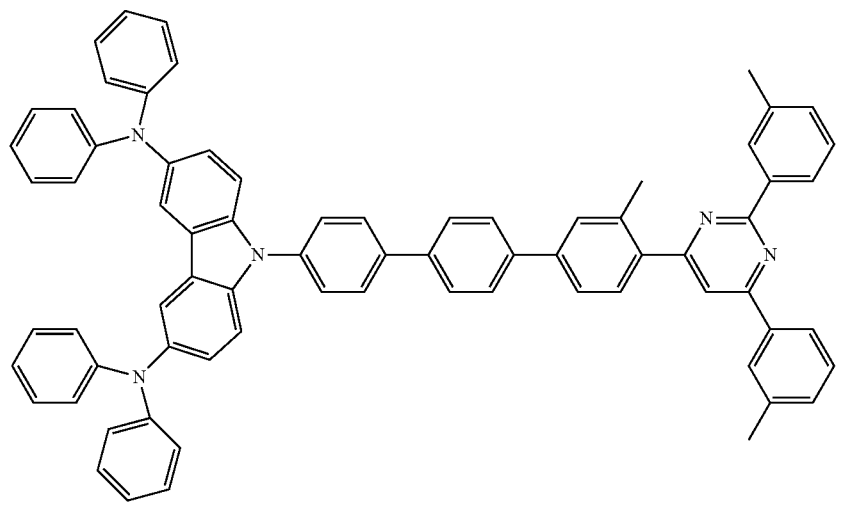
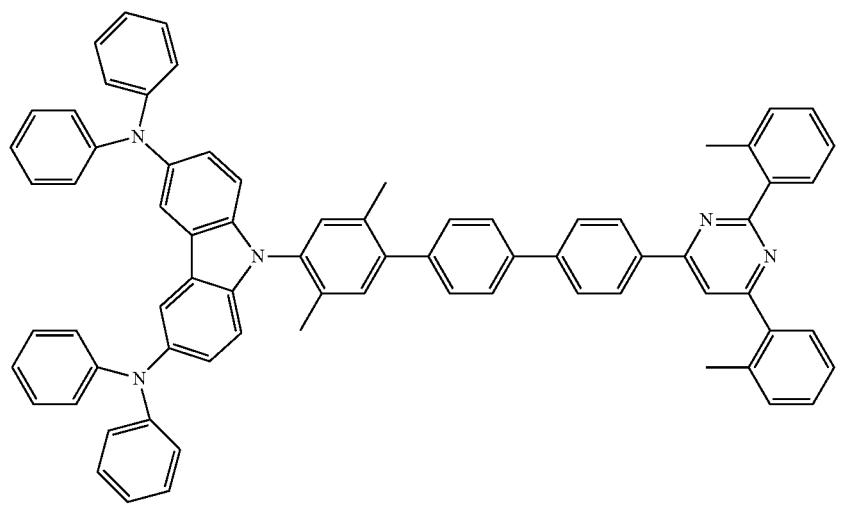
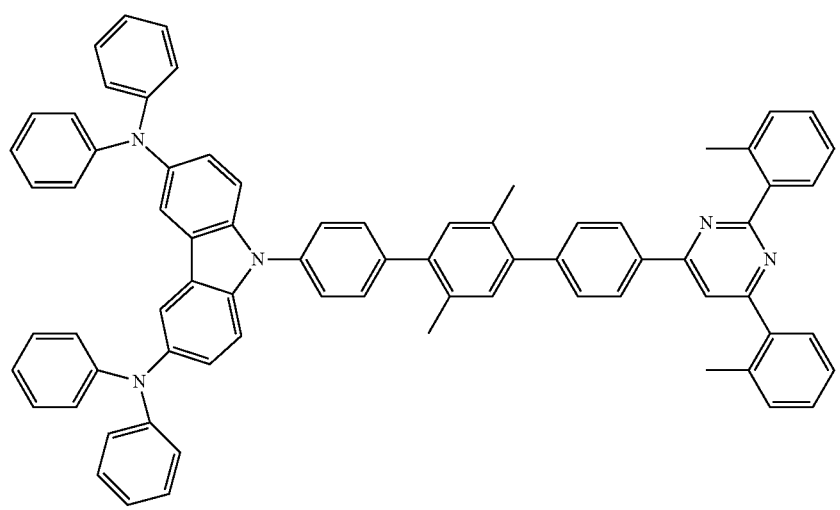

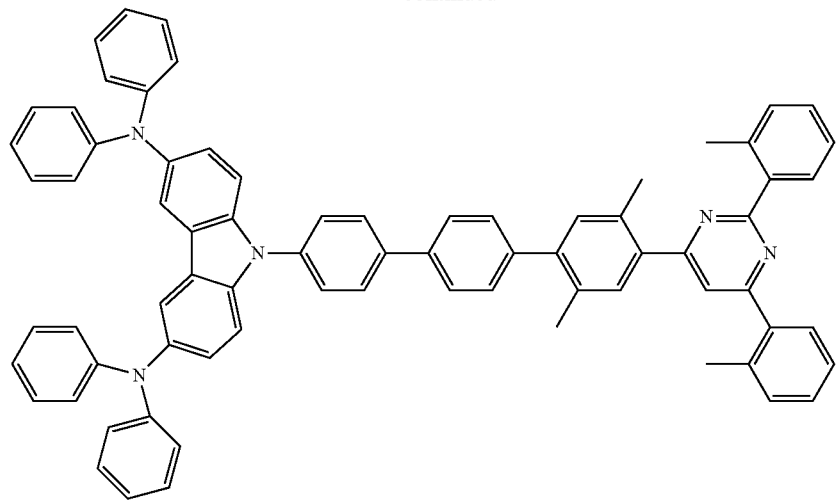
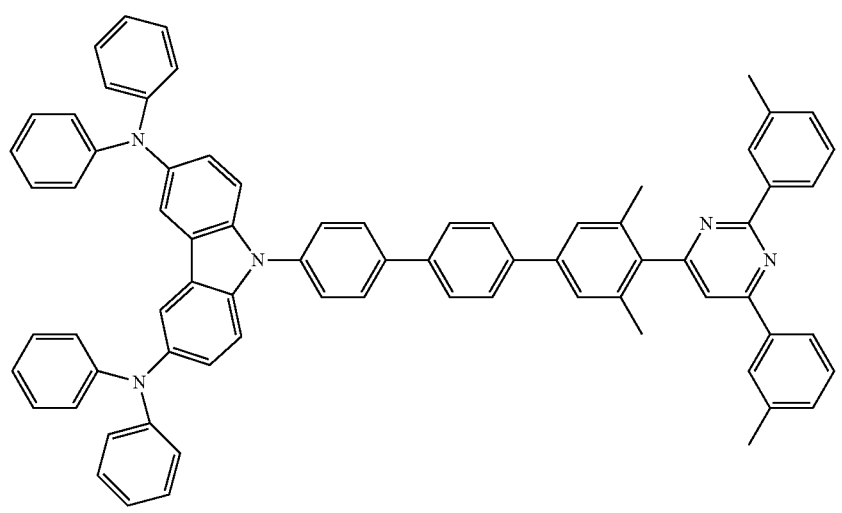

-continued
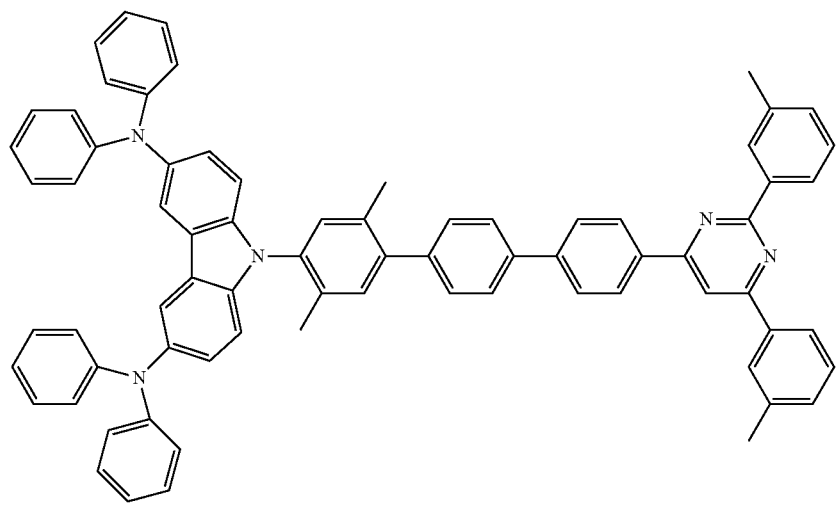
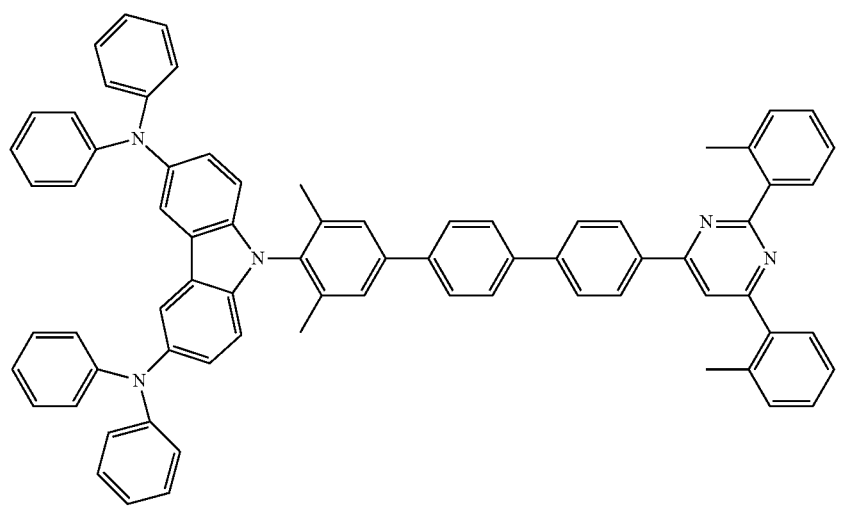

-continued
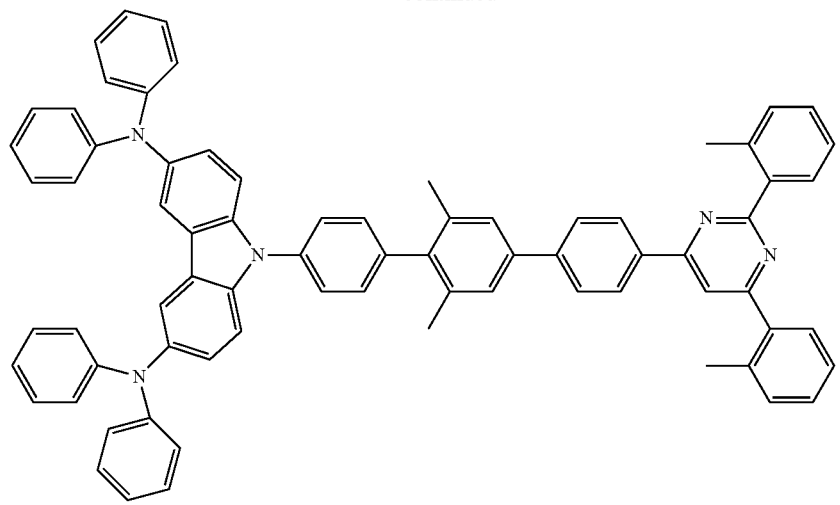
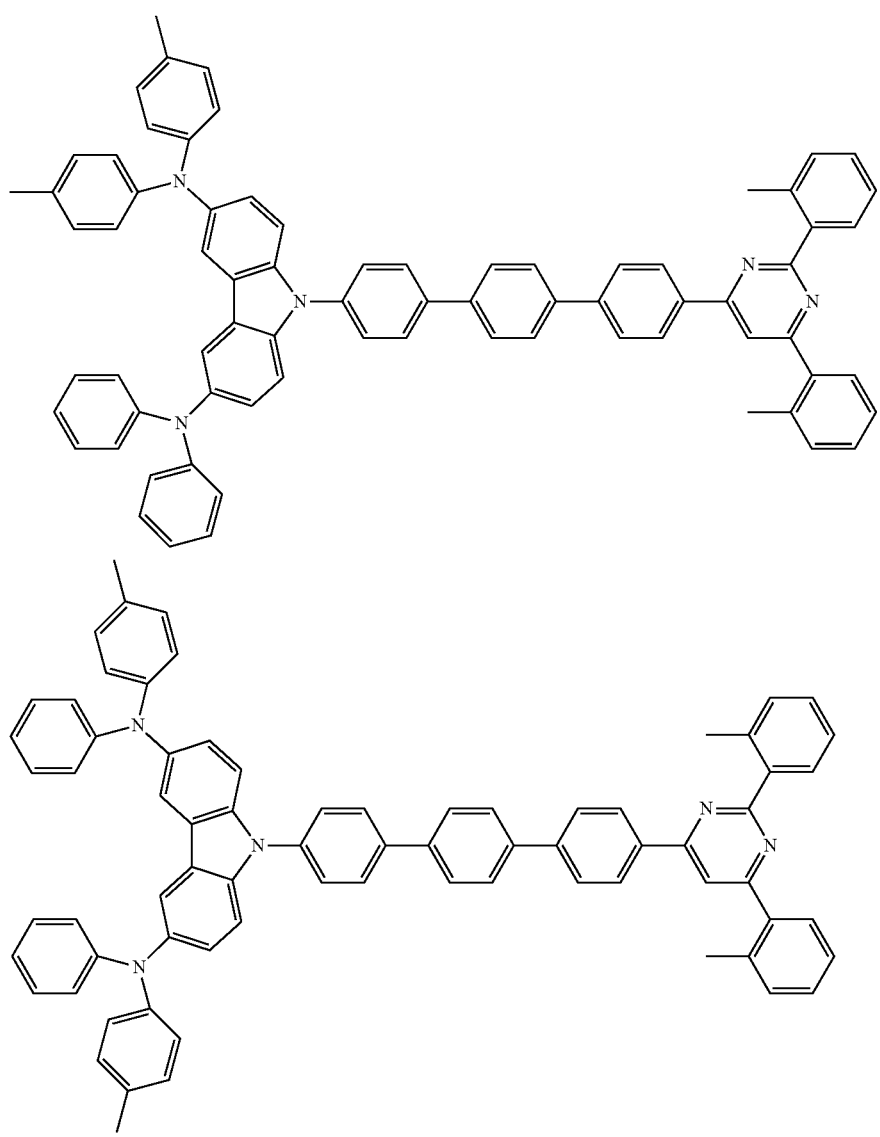

-continued
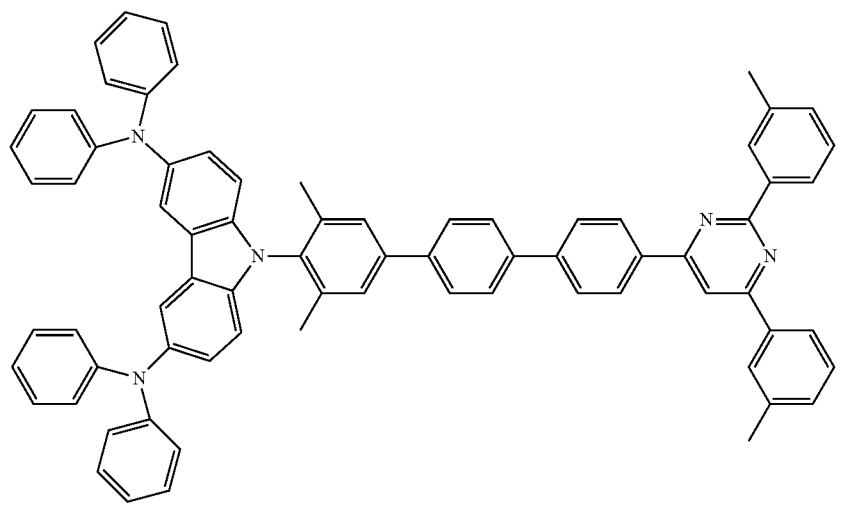
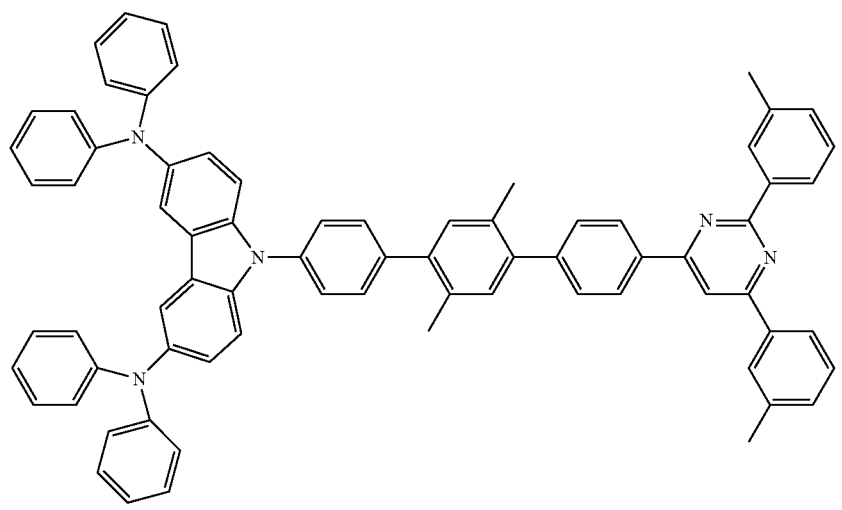
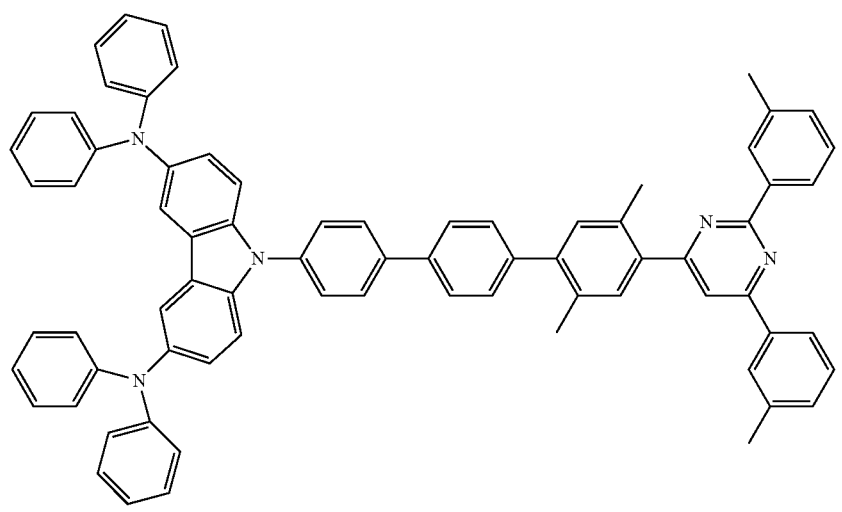

-continued
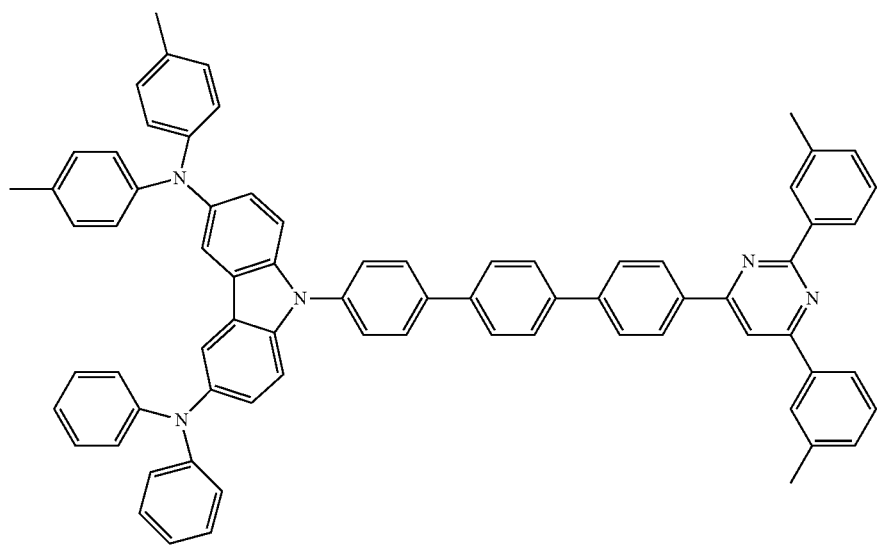
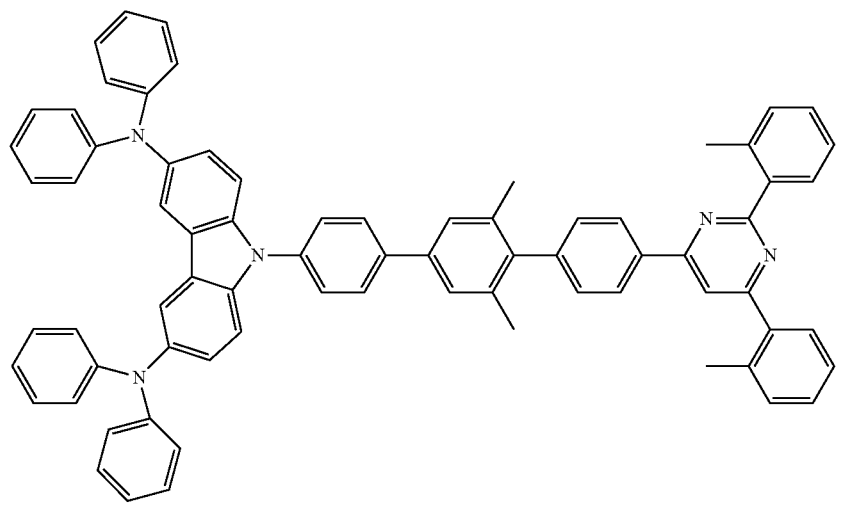
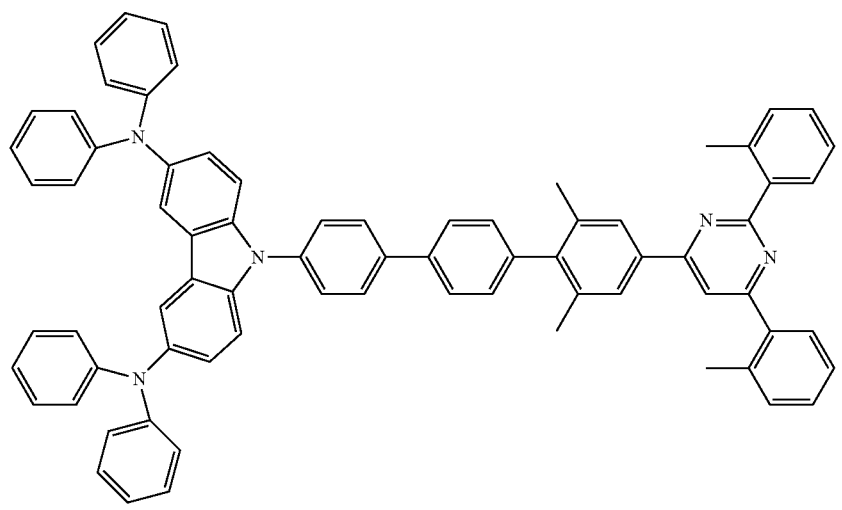

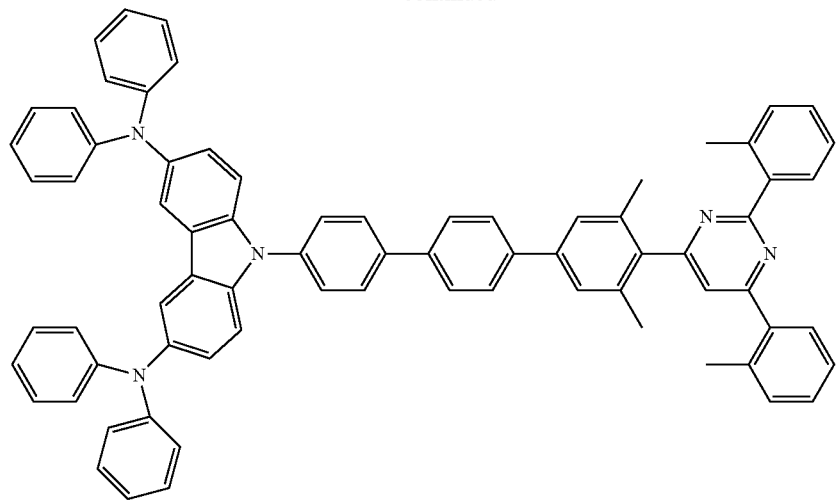
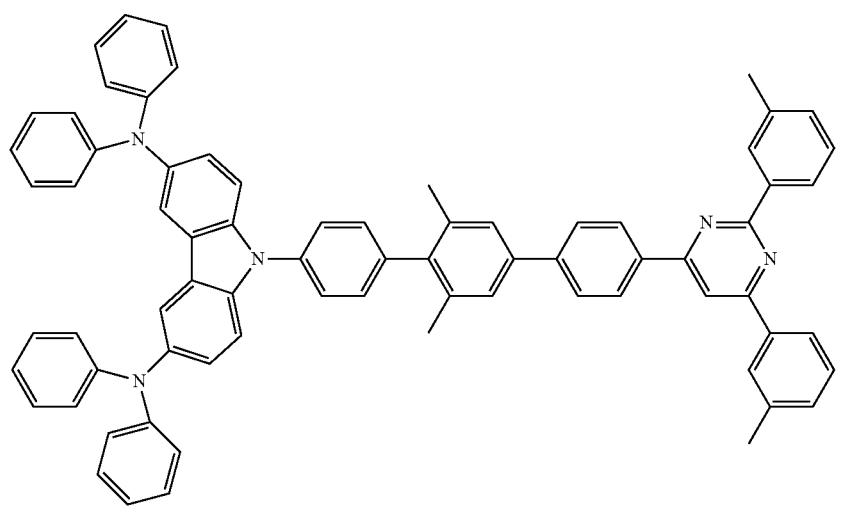

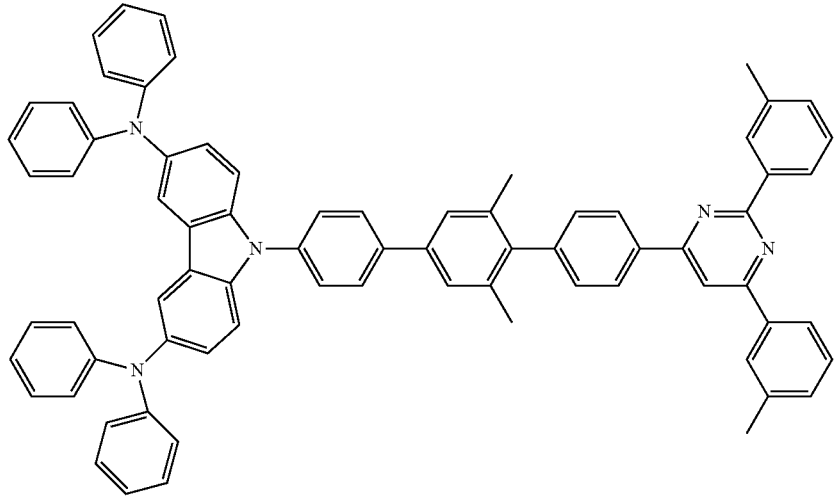
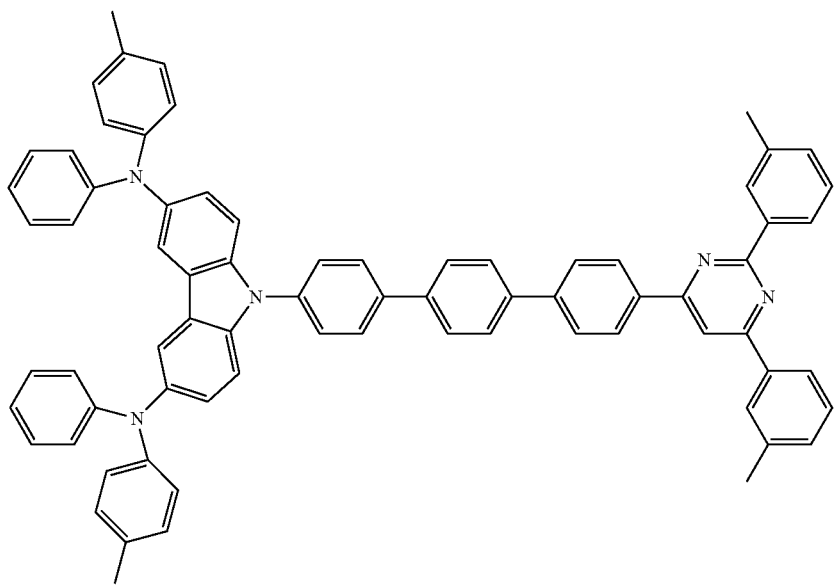
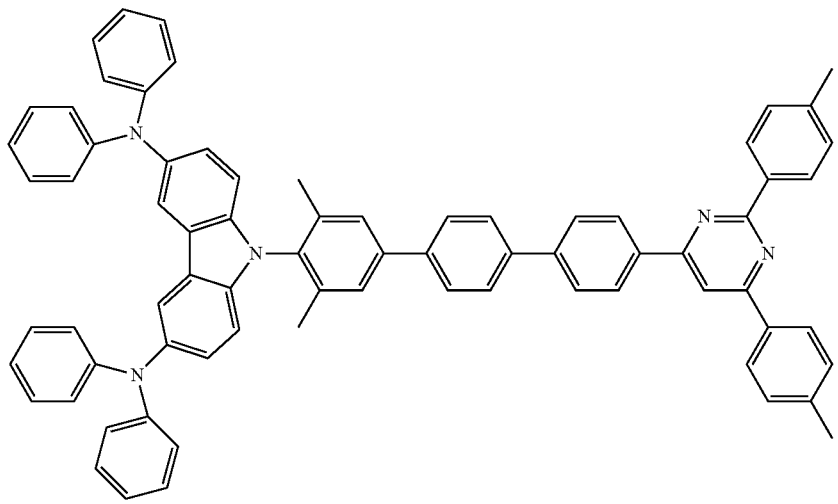


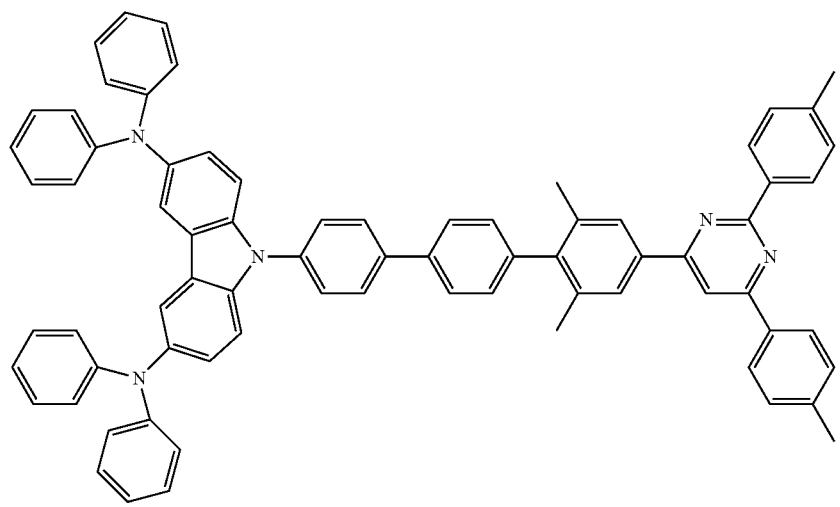
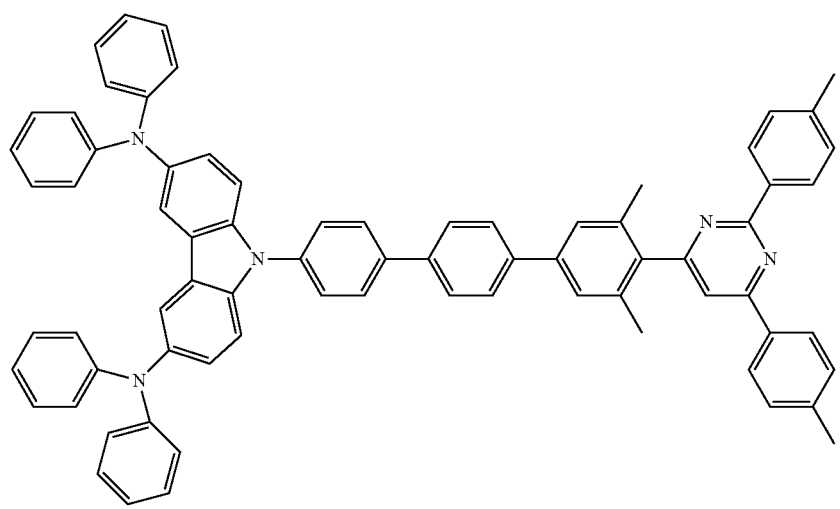
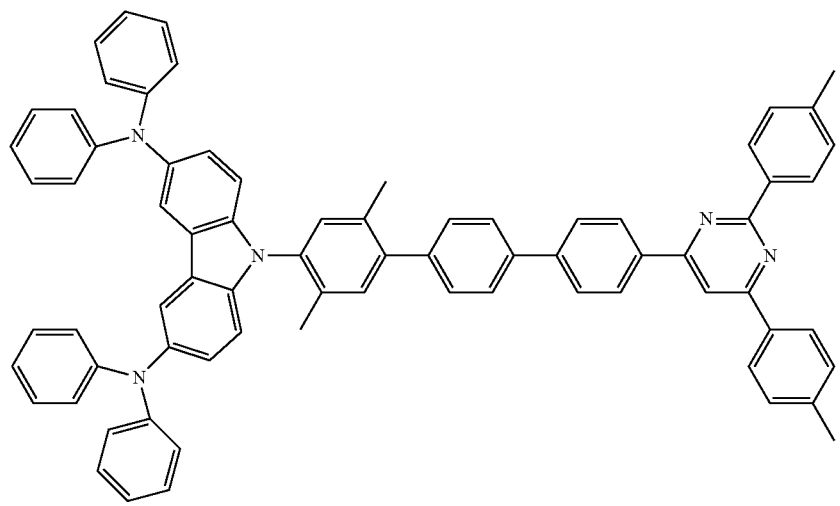

-continued
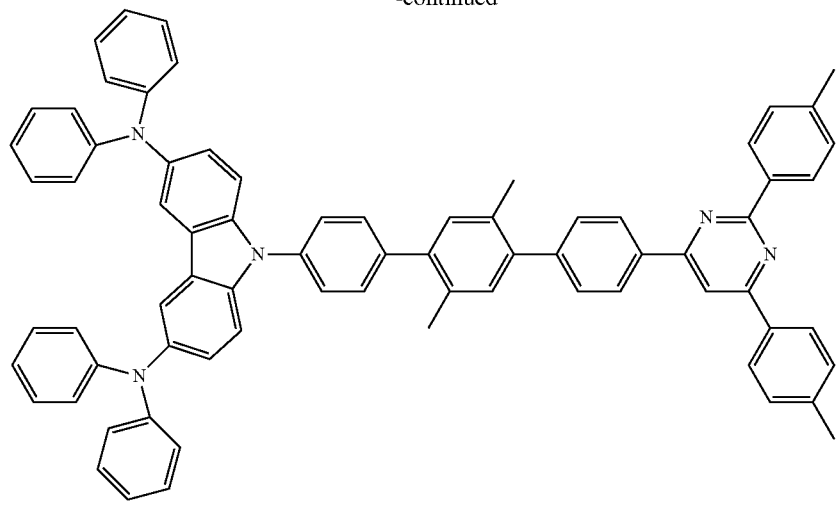
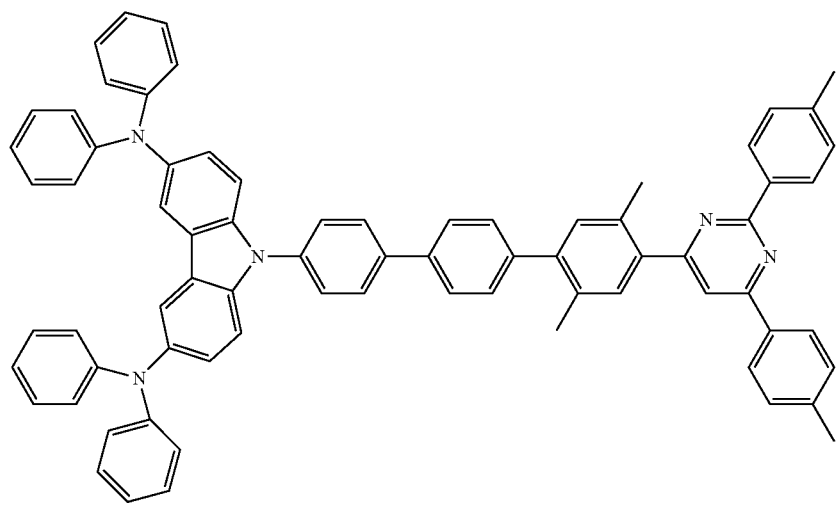
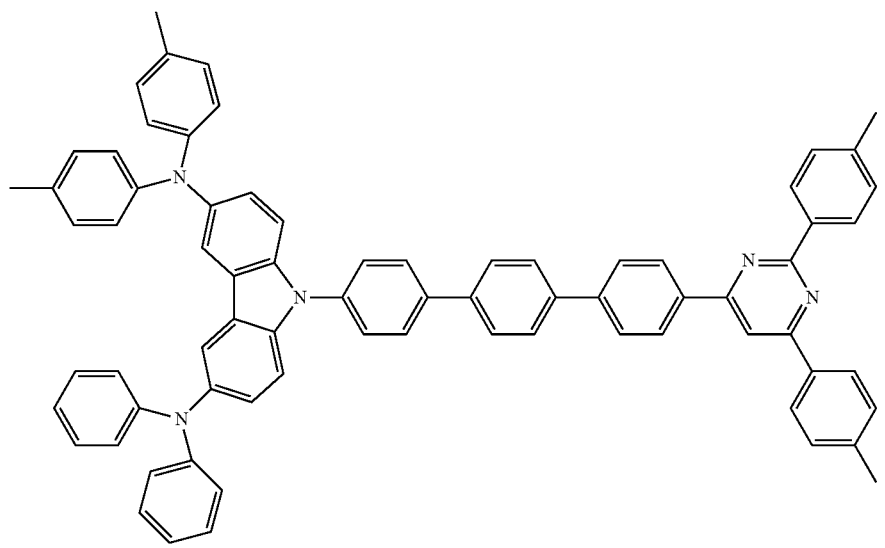

-continued
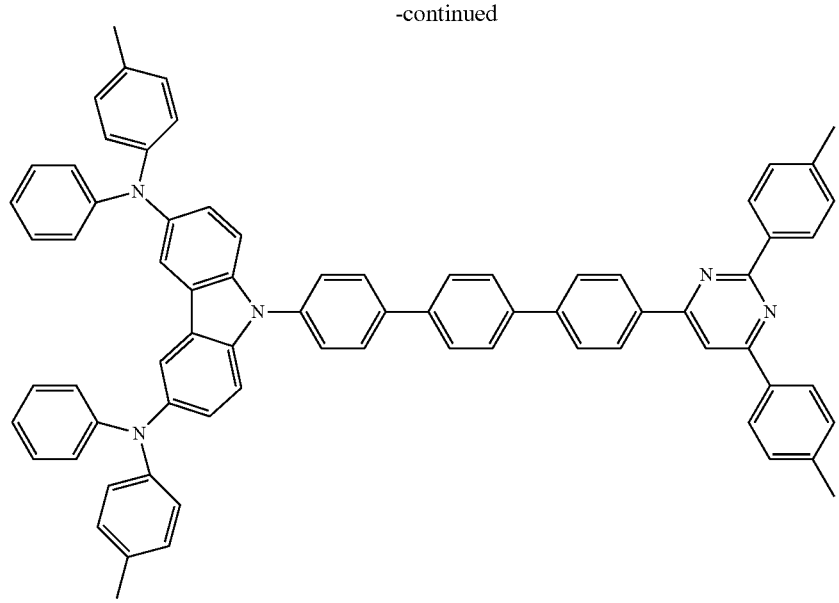
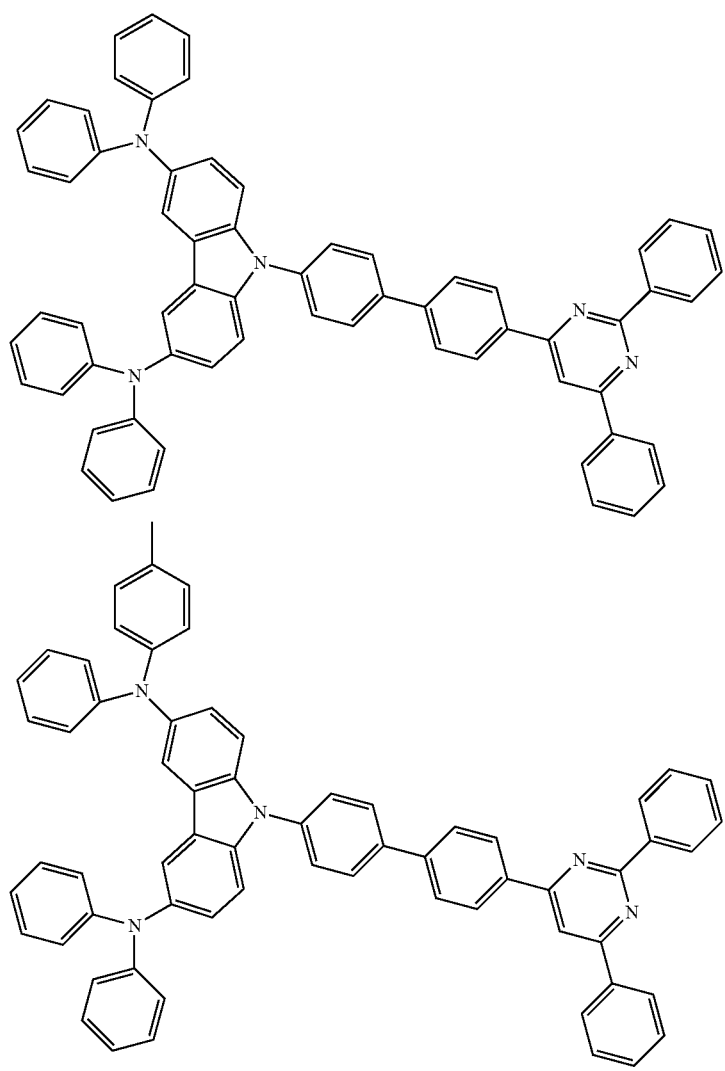

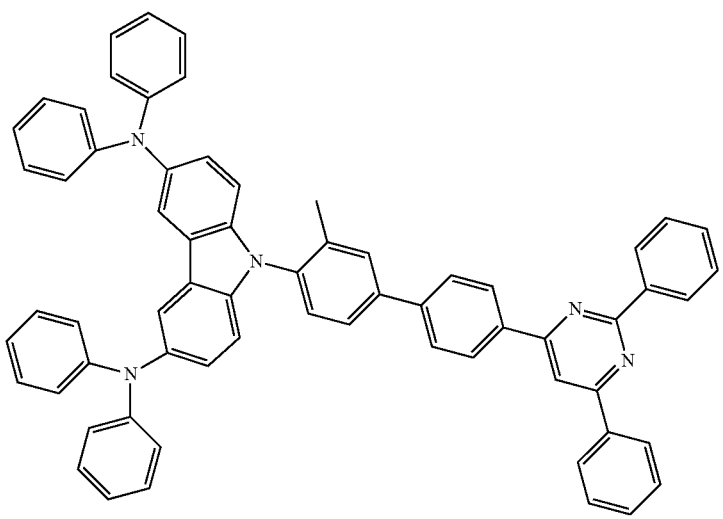
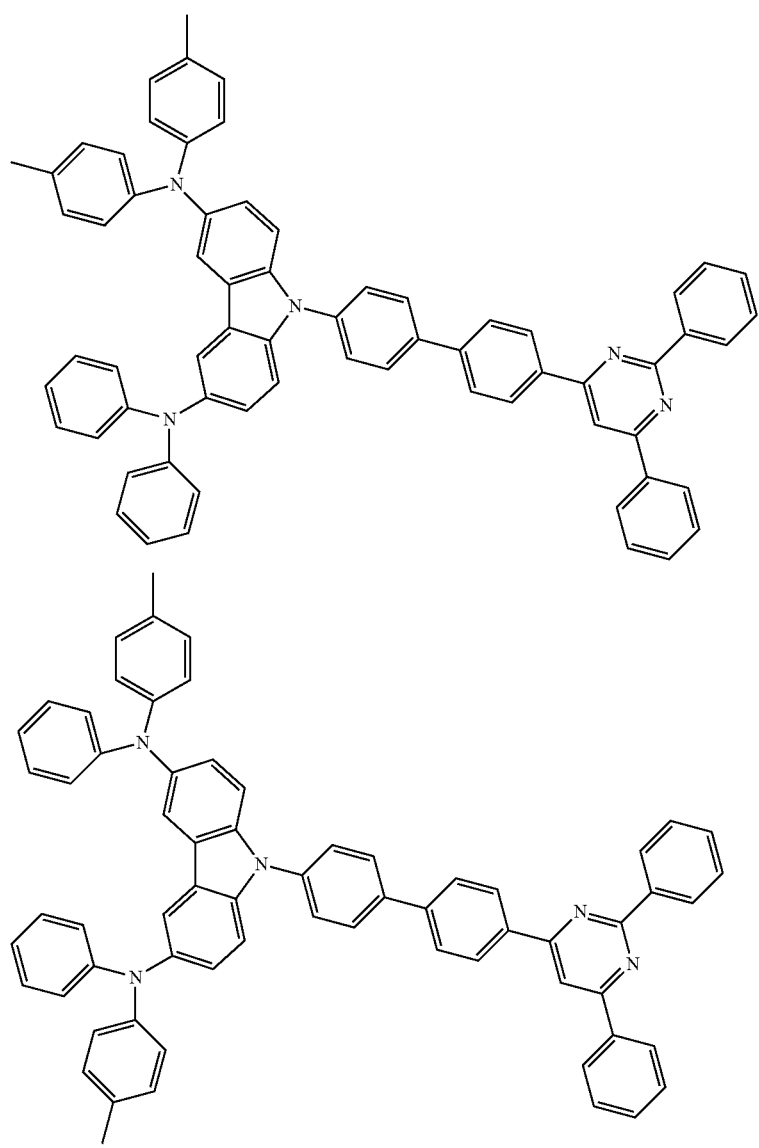

-continued
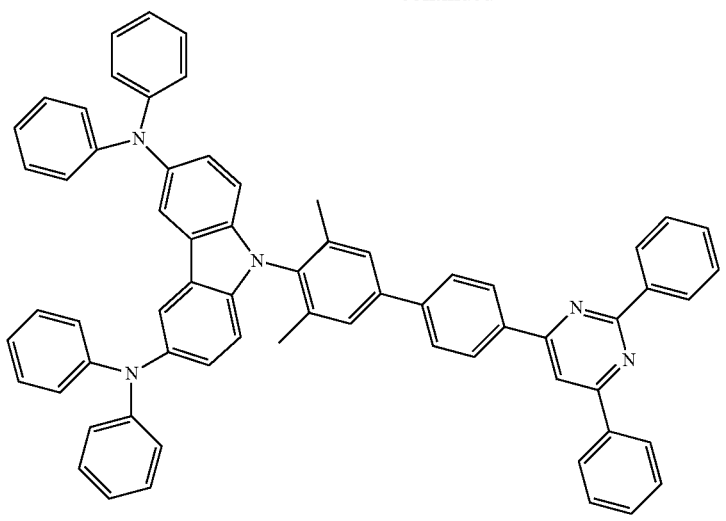
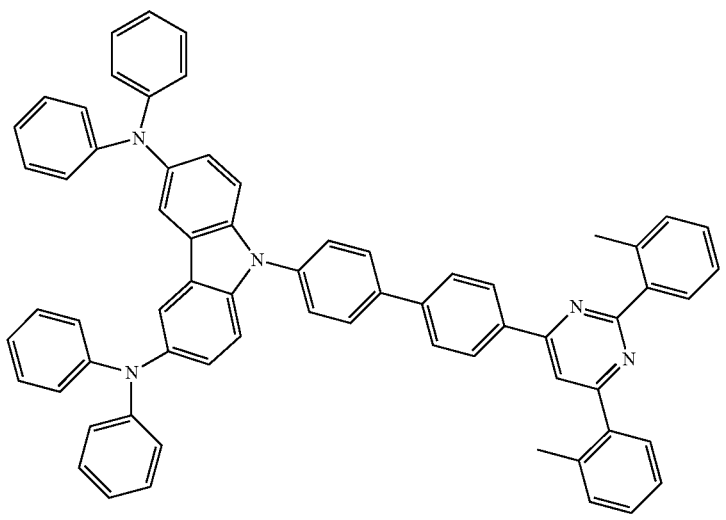
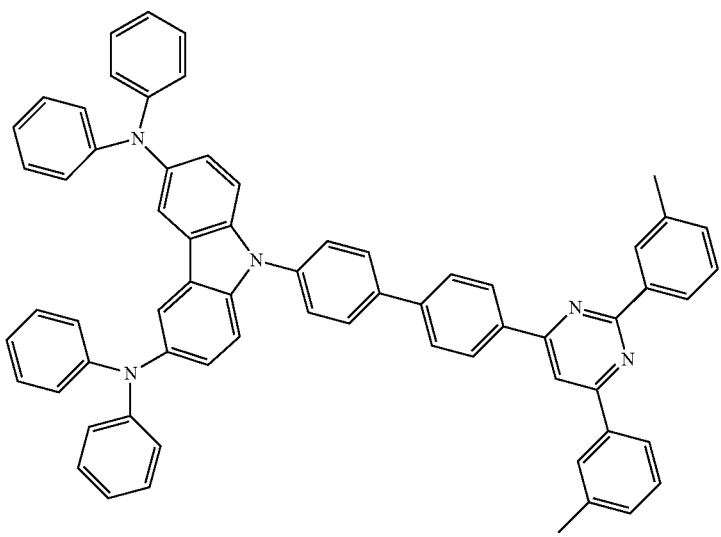

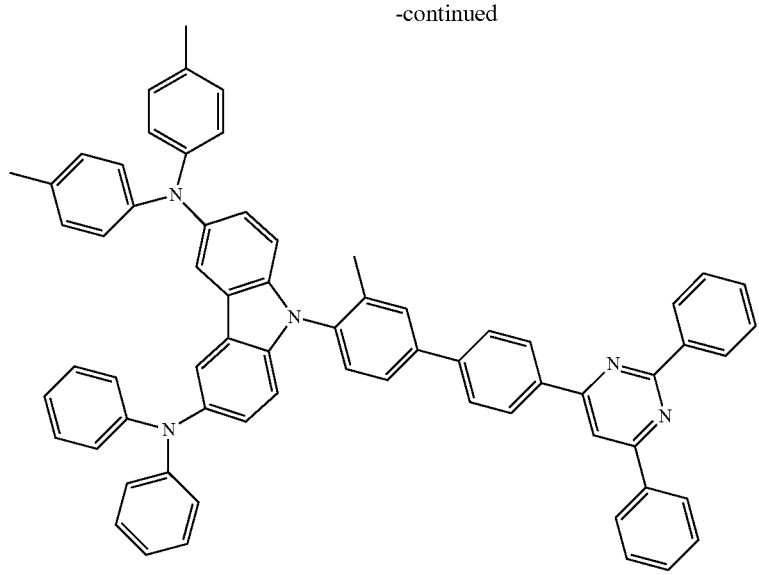
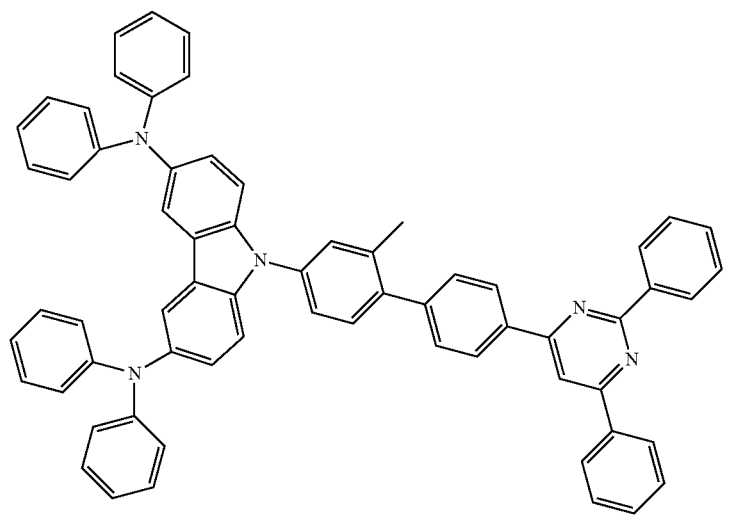
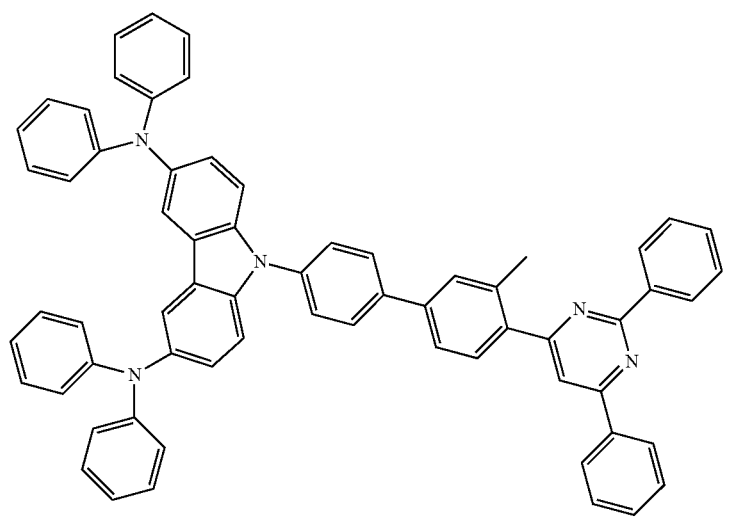

-continued
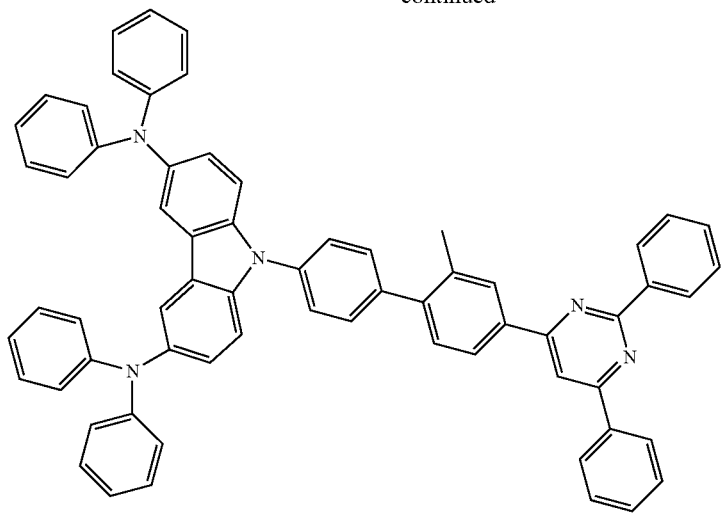
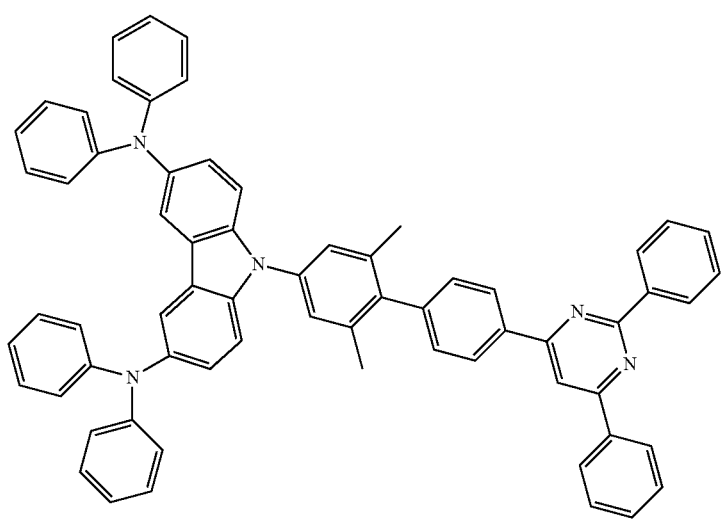
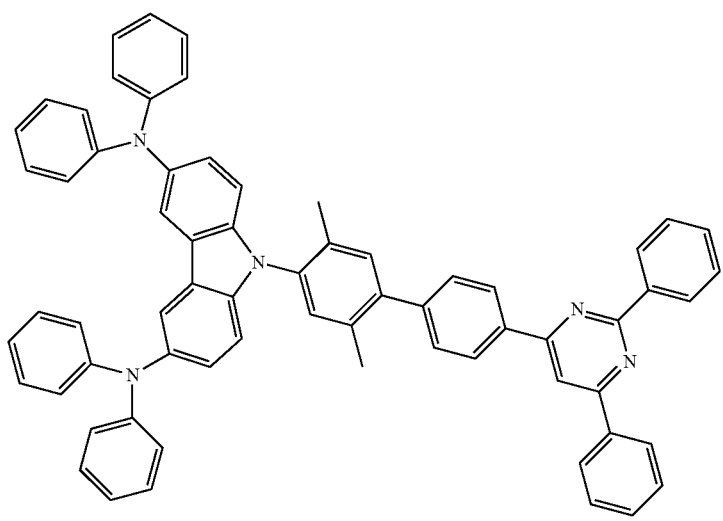

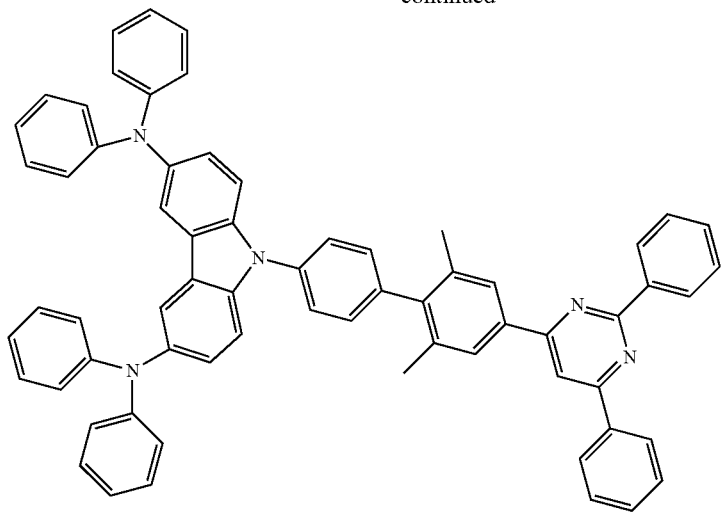
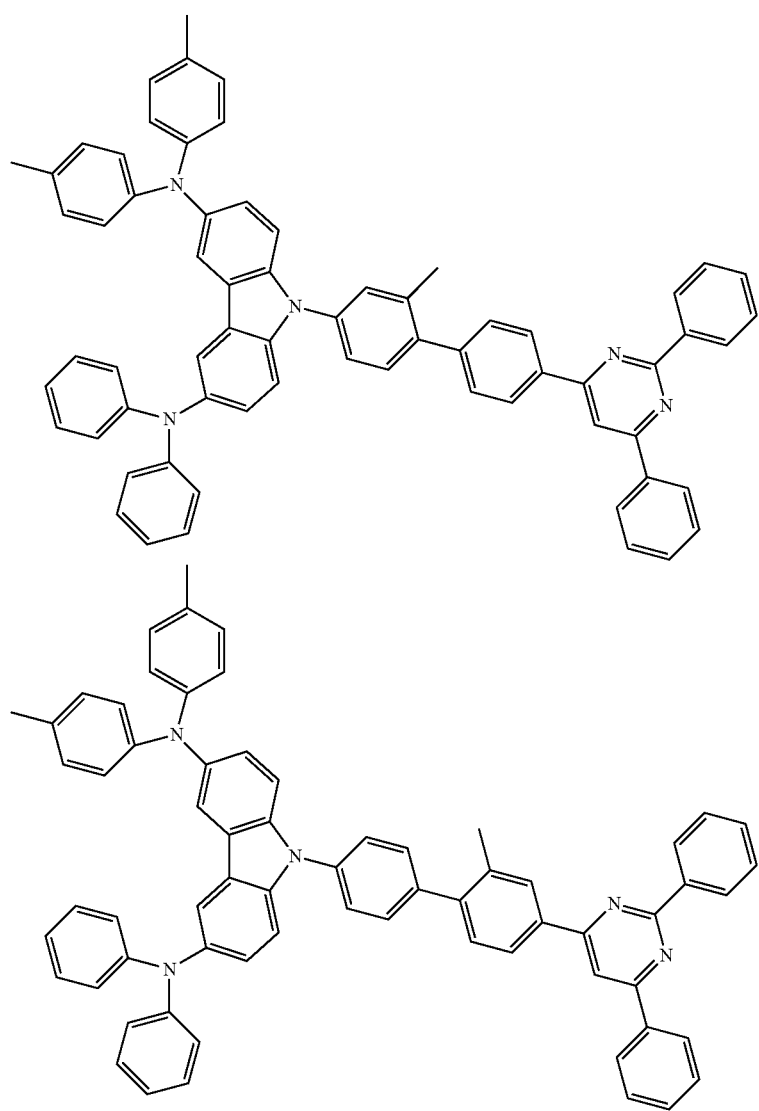

-continued
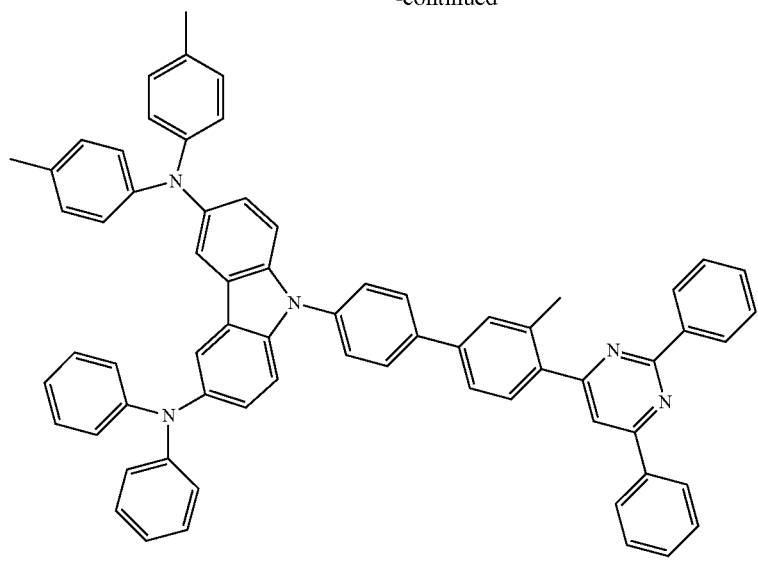
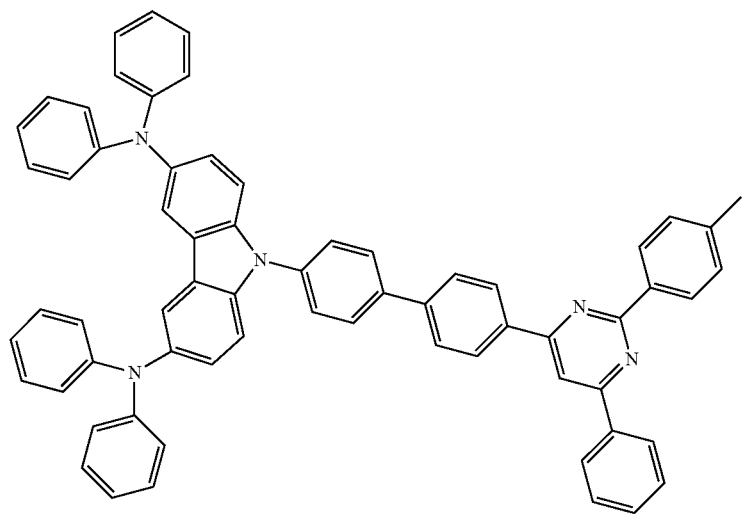
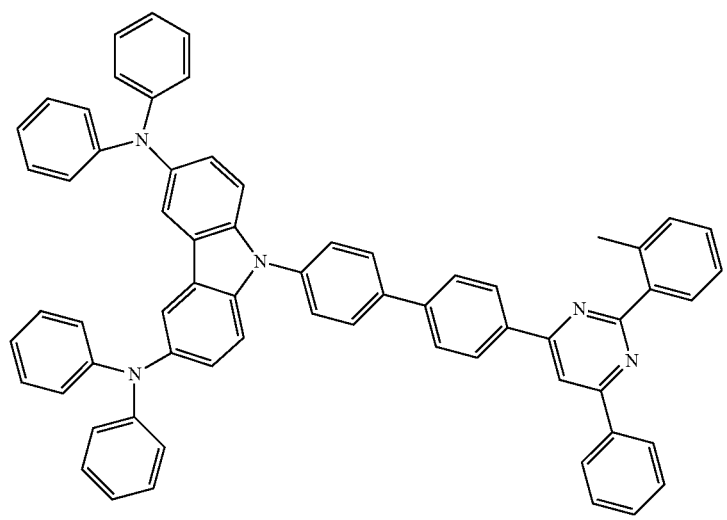

-continued
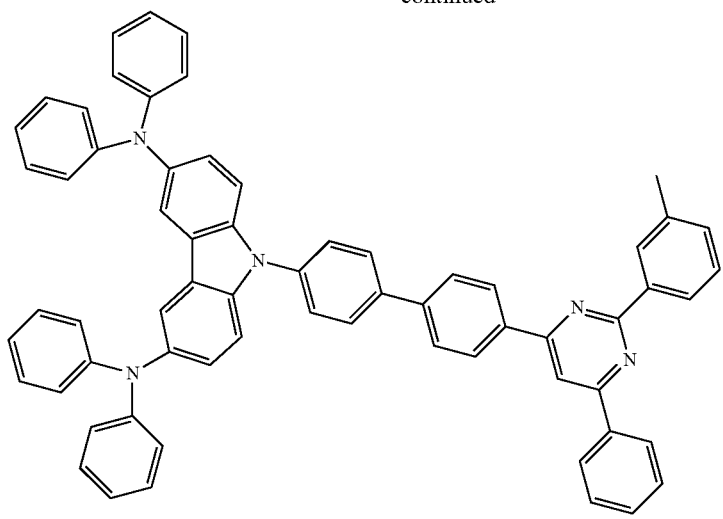
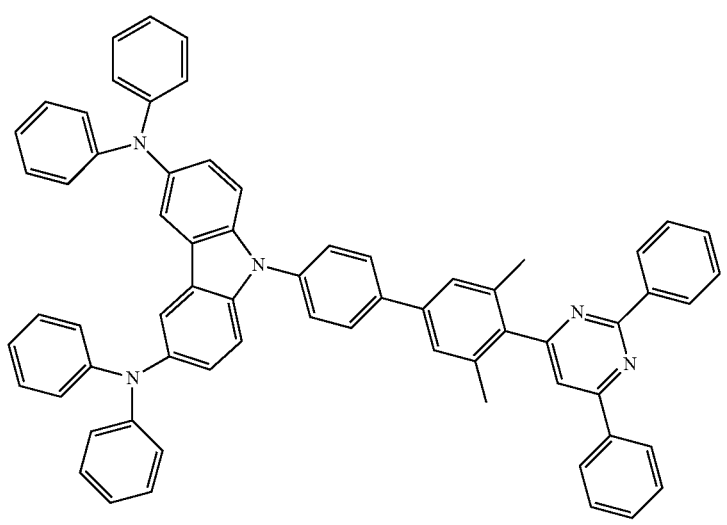
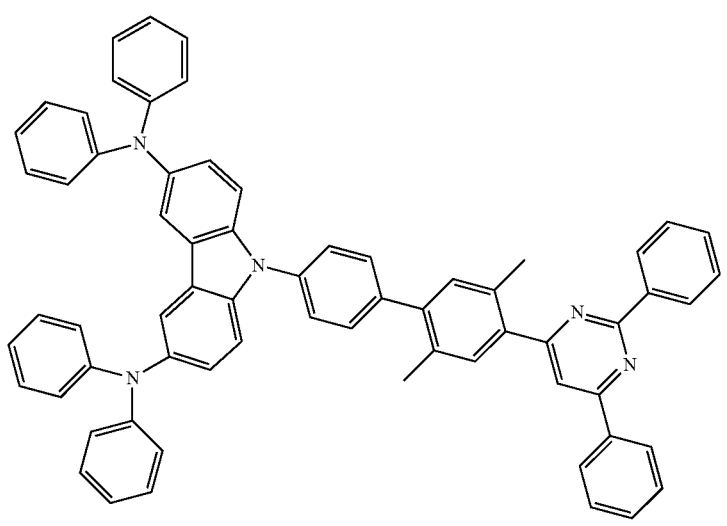

-continued
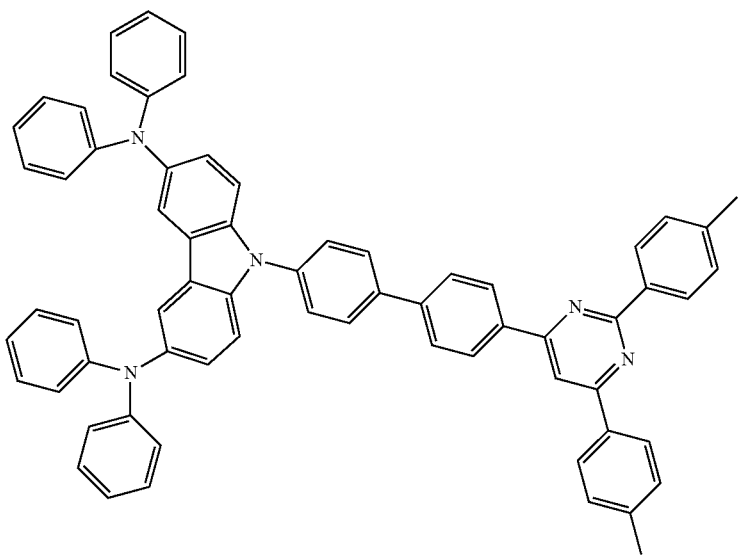

-continued
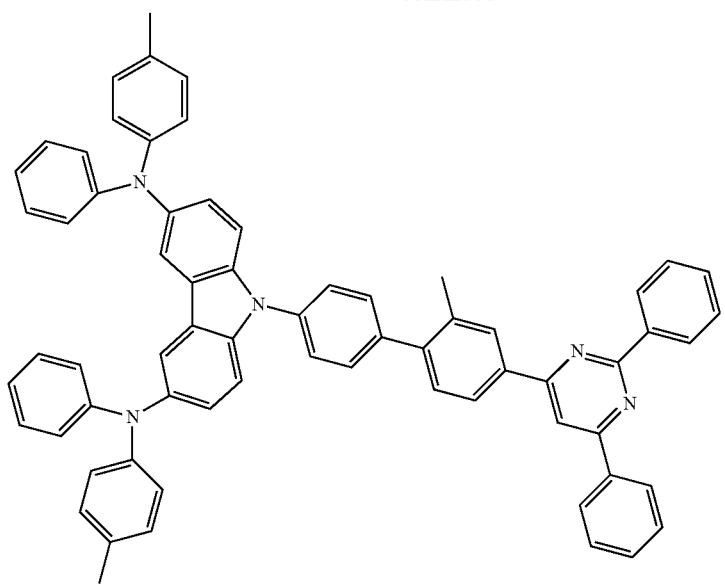
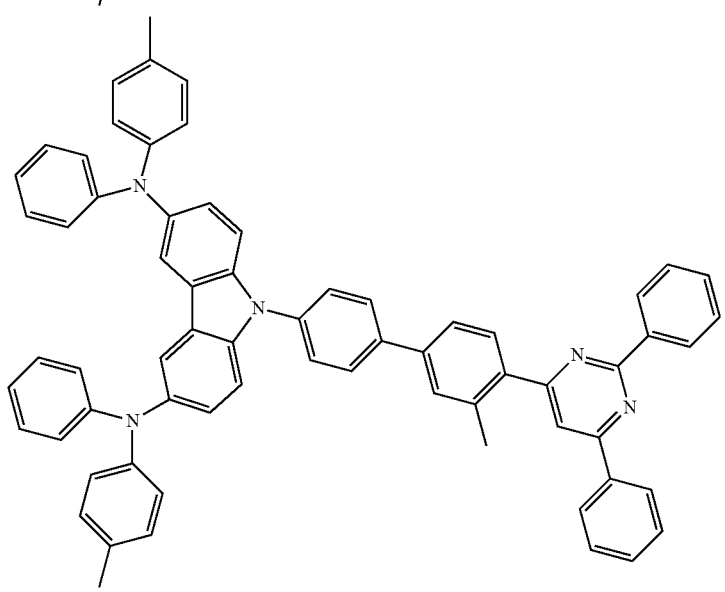
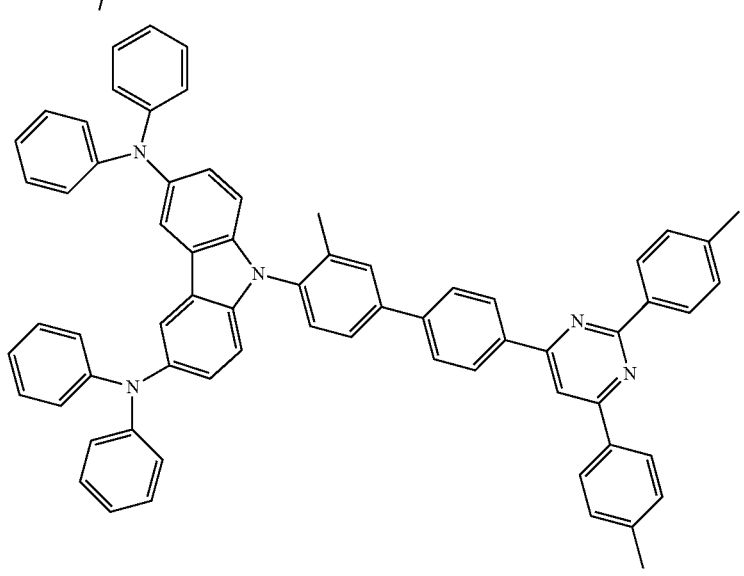

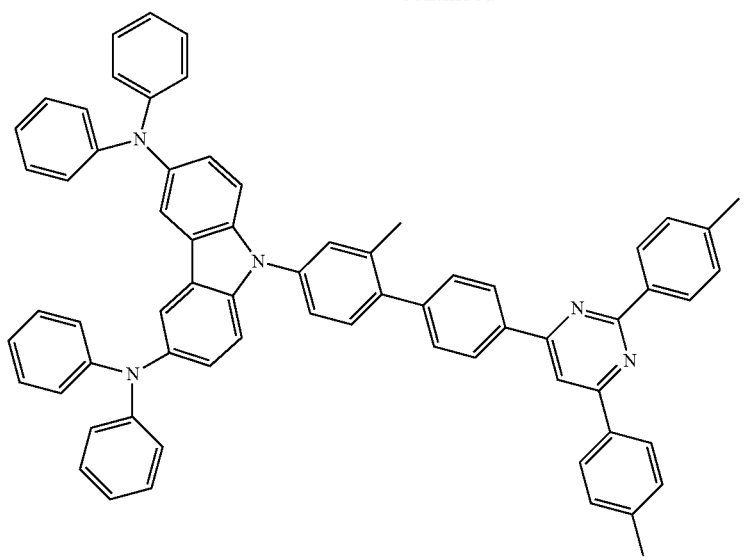
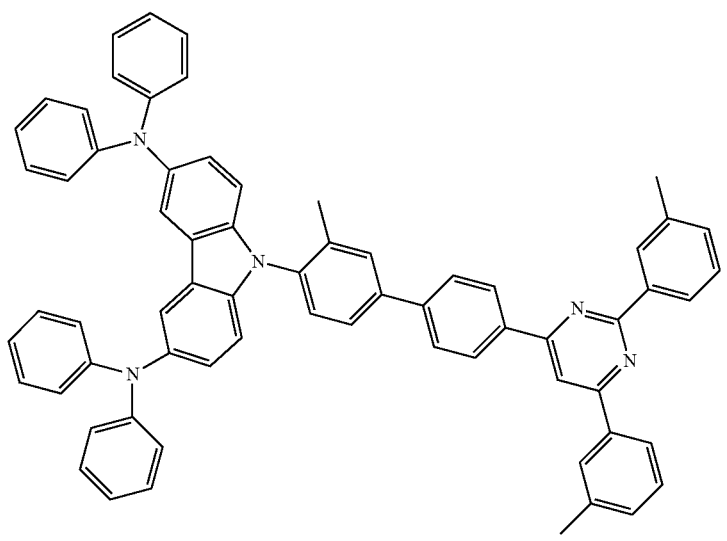
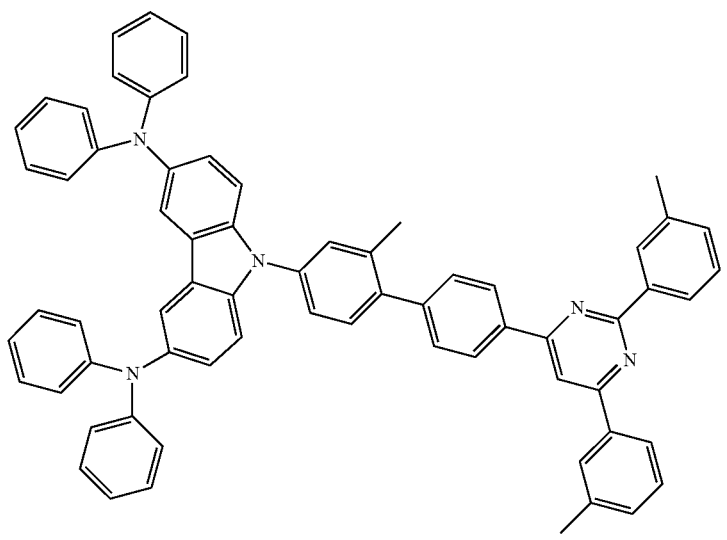

-continued
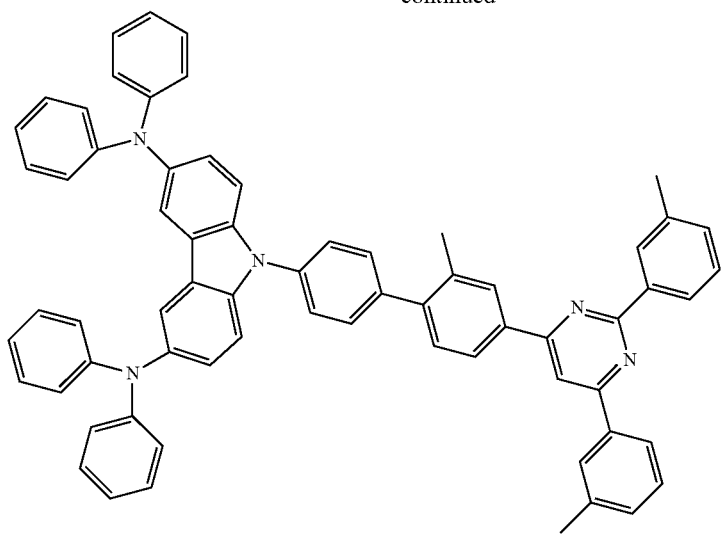
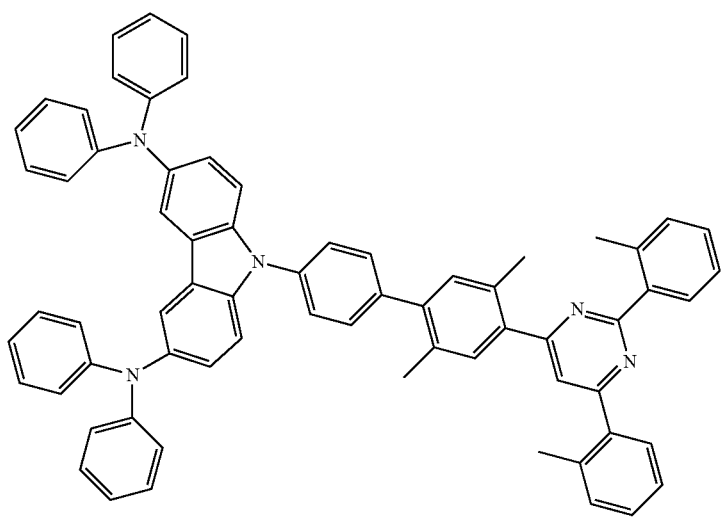
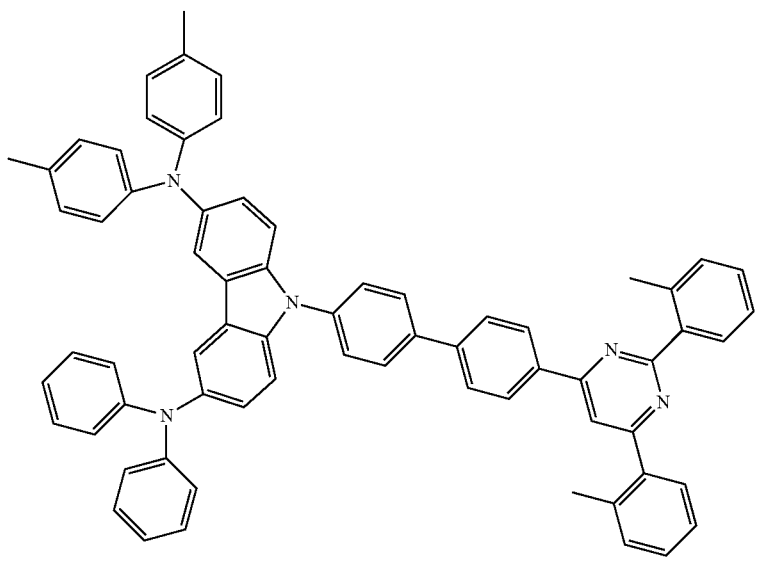

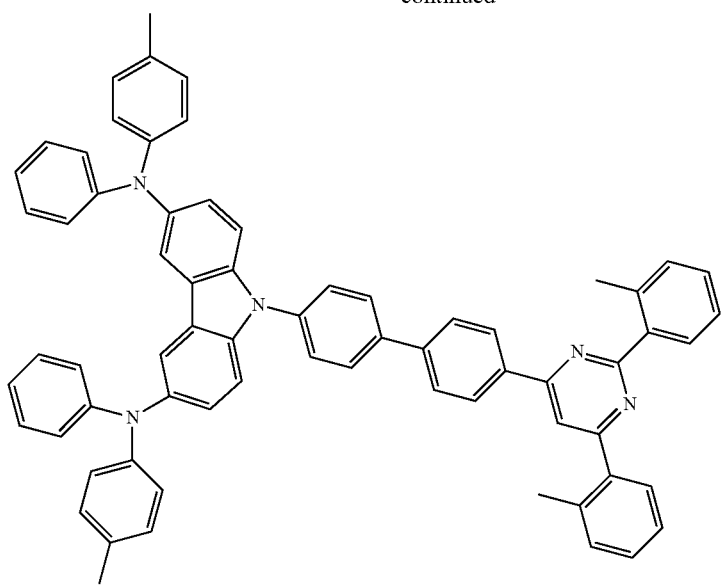
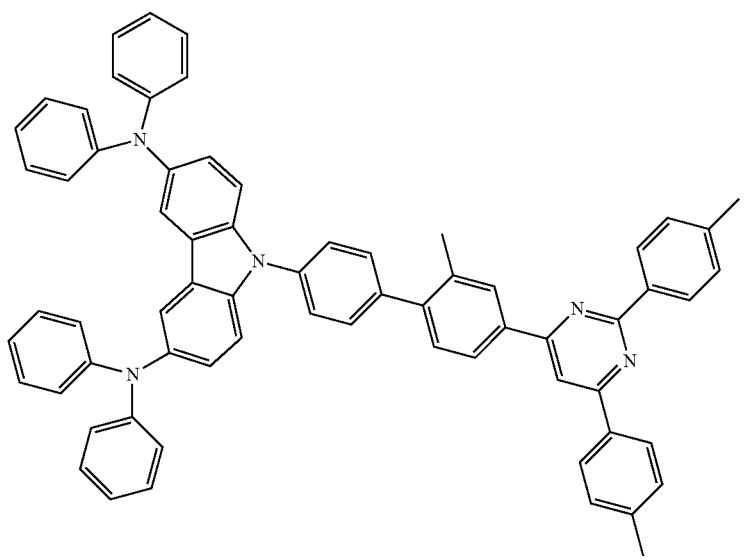
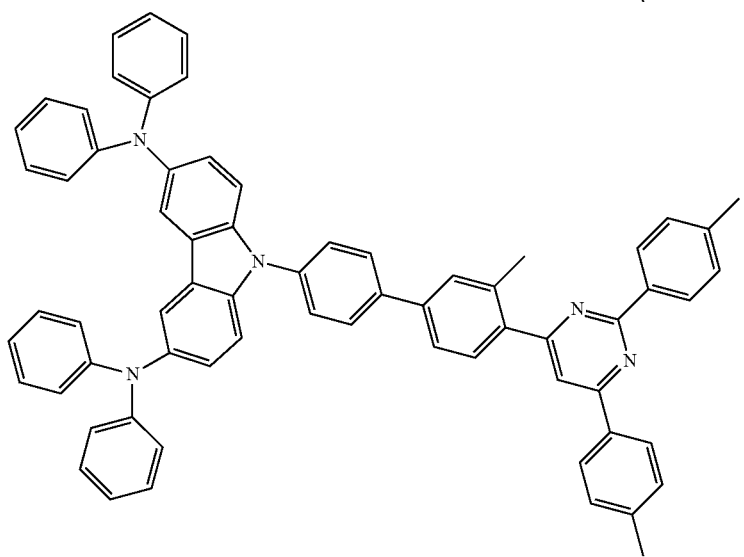

-continued
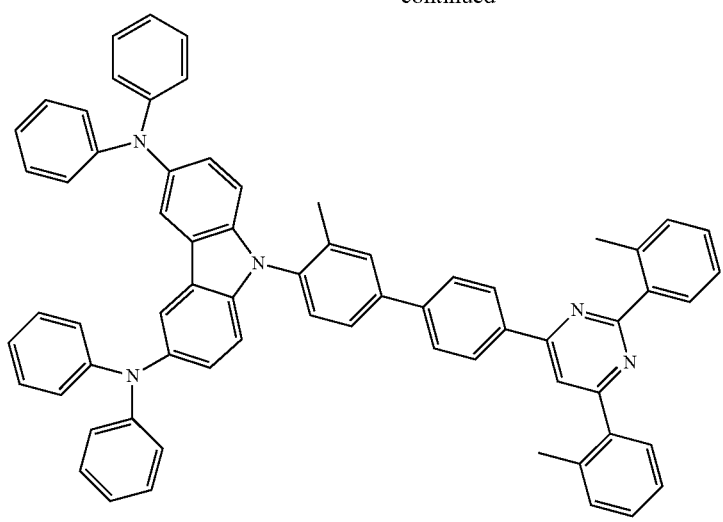
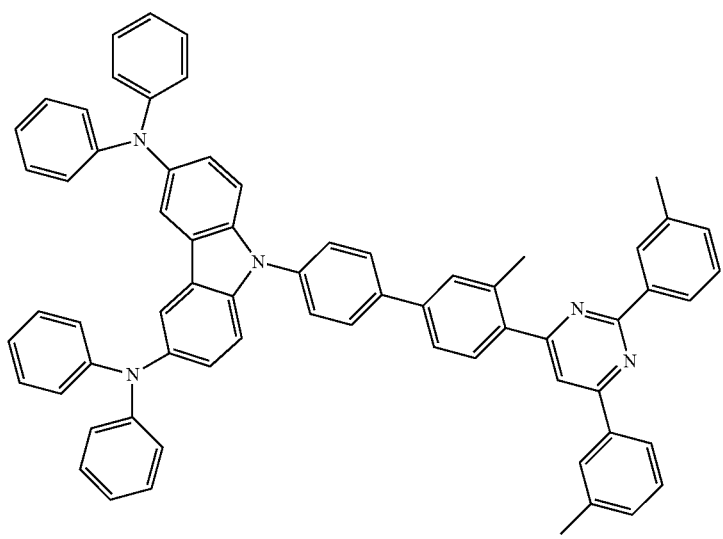
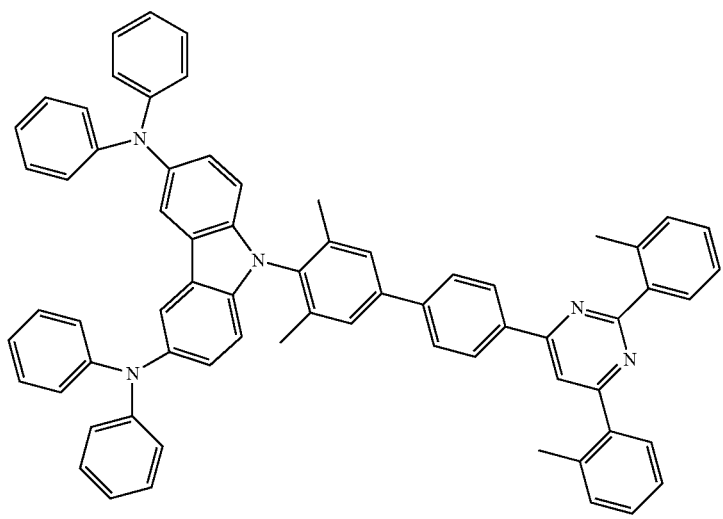

-continued
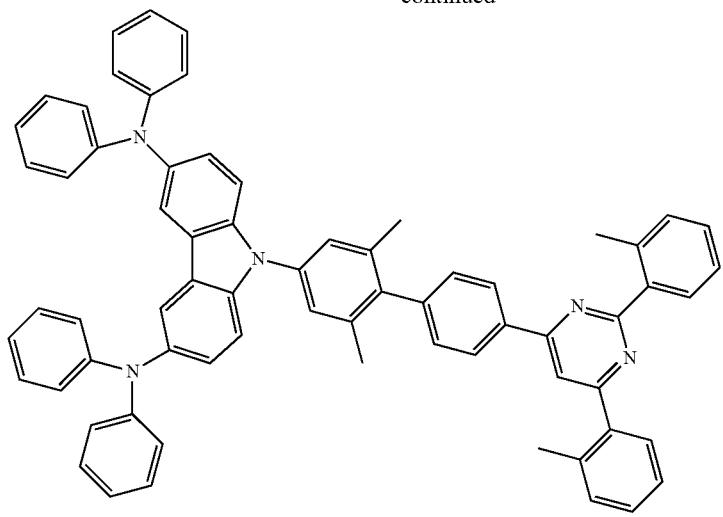
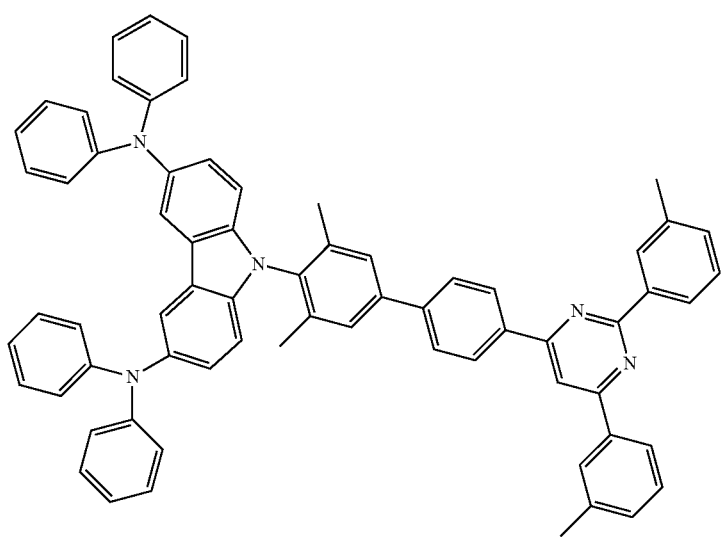
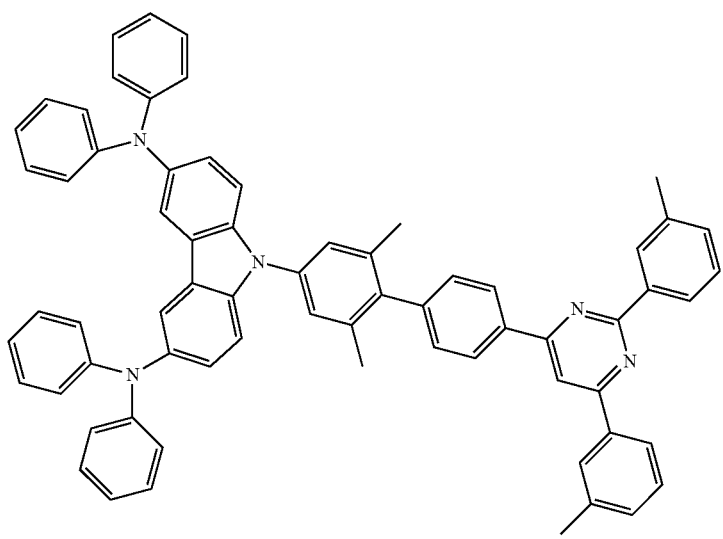

-continued
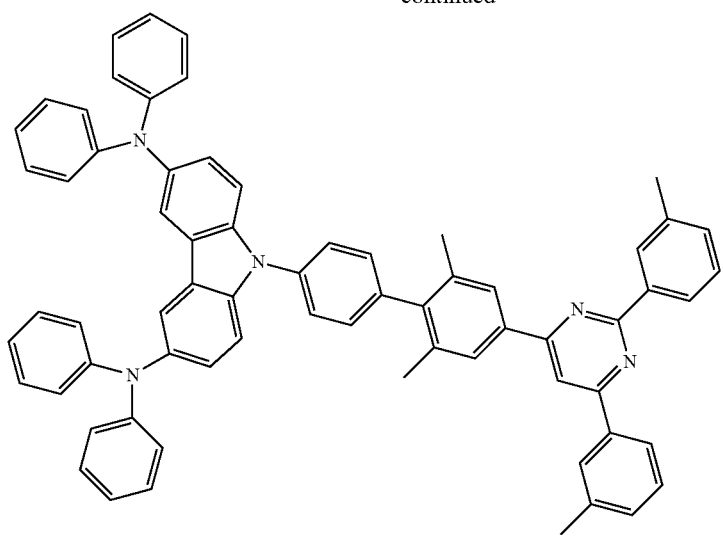
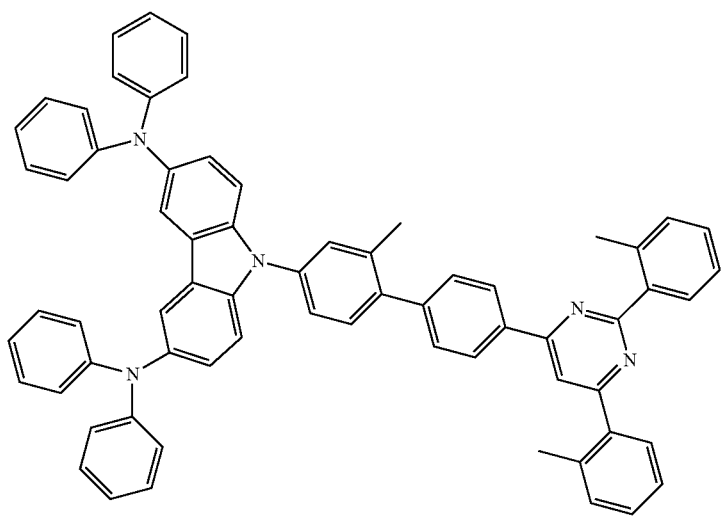
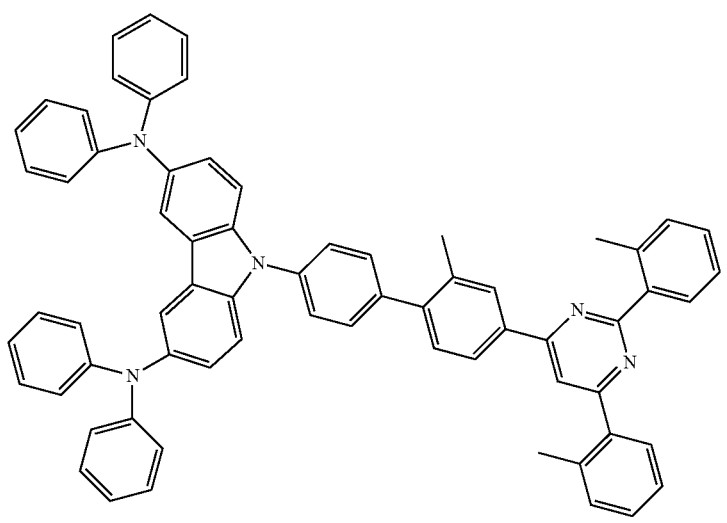

-continued
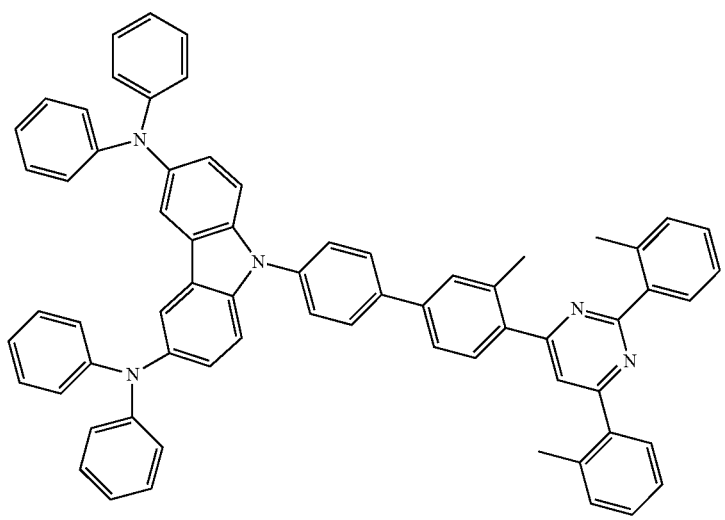
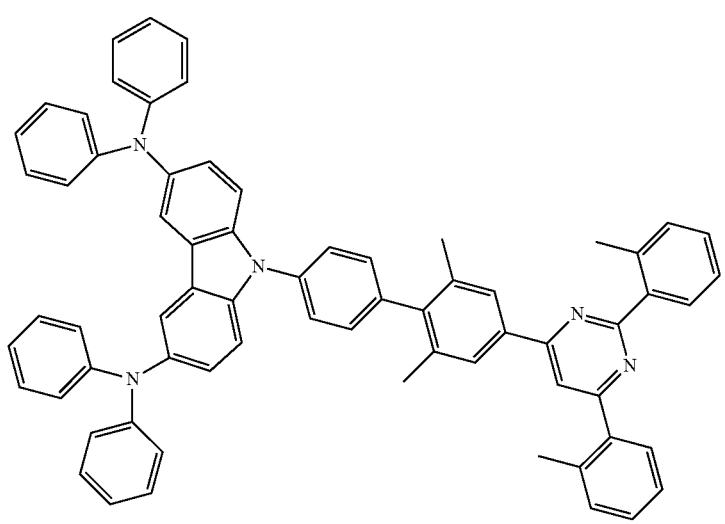
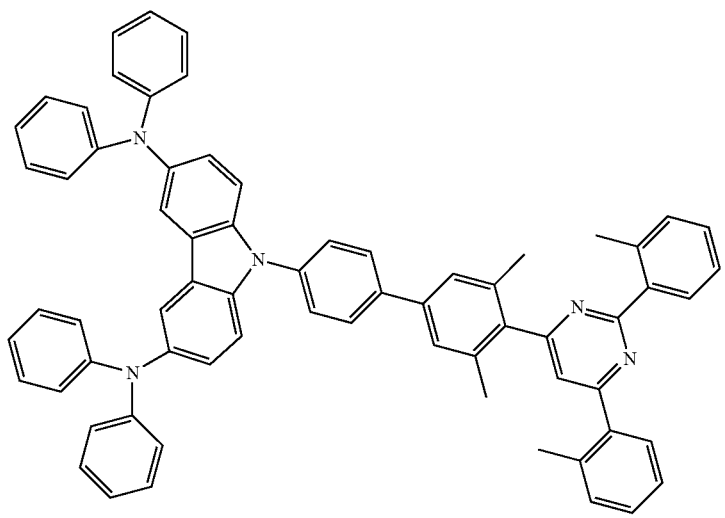

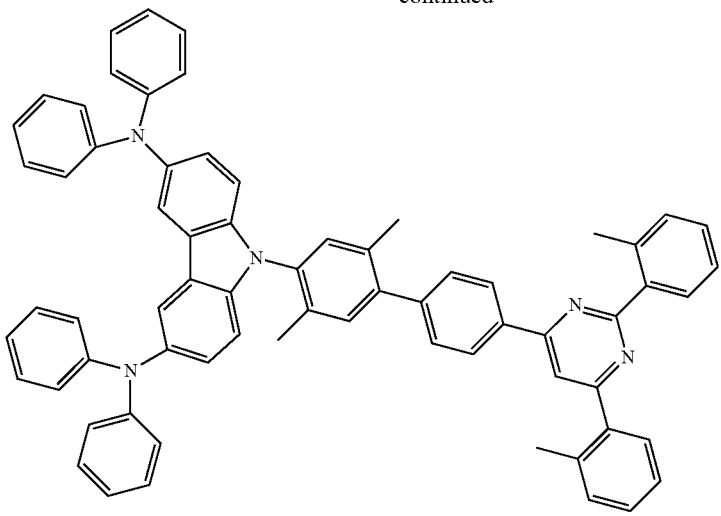
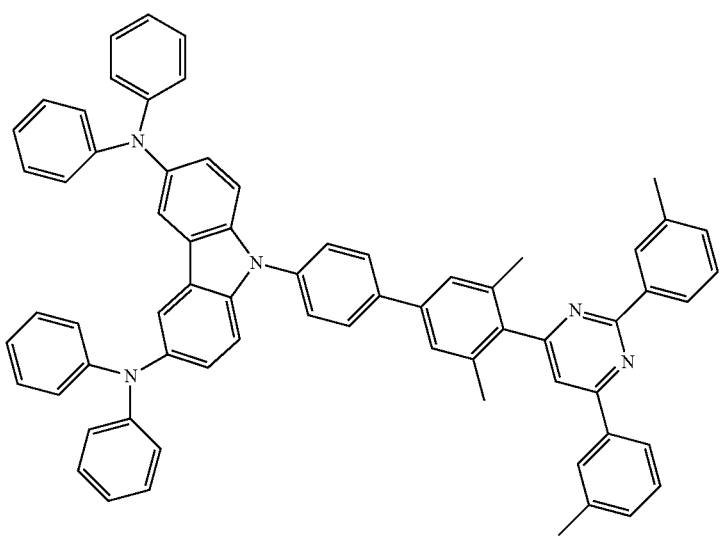
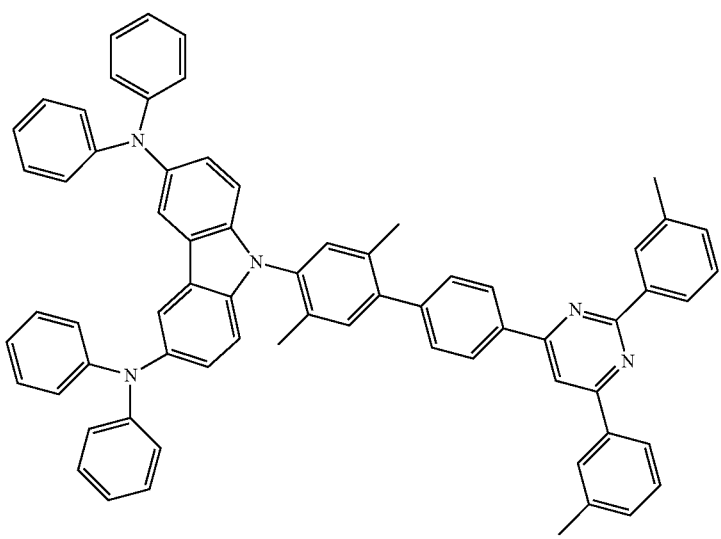

-continued
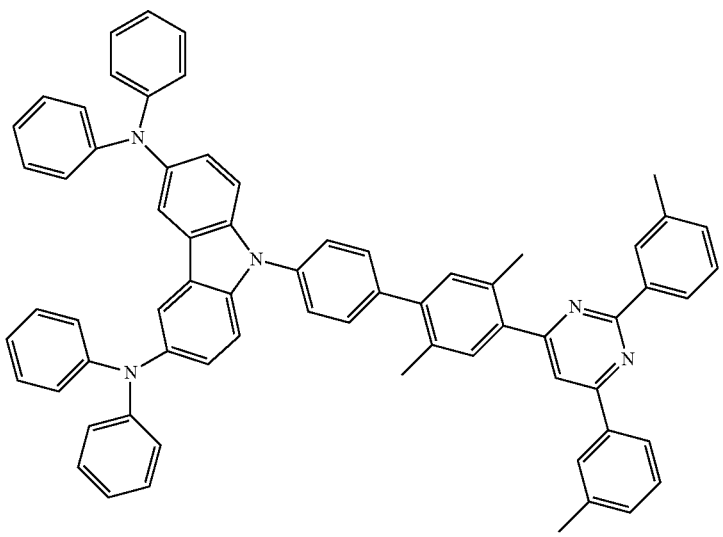
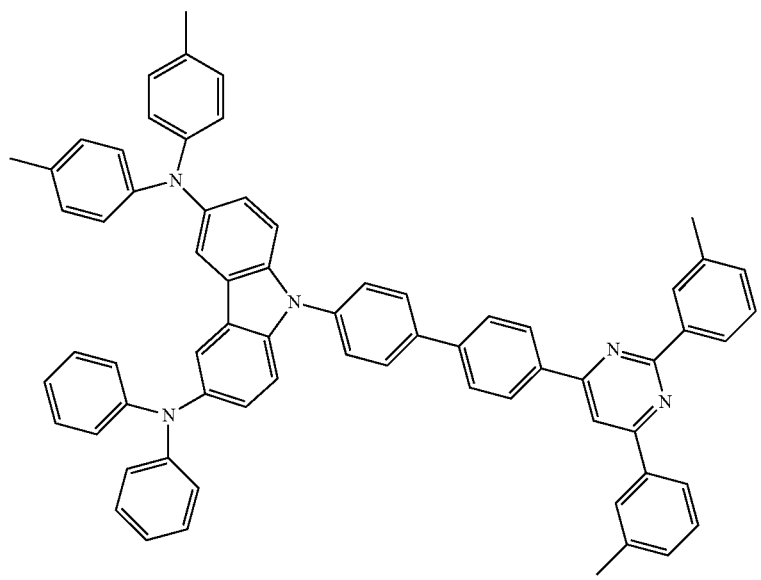
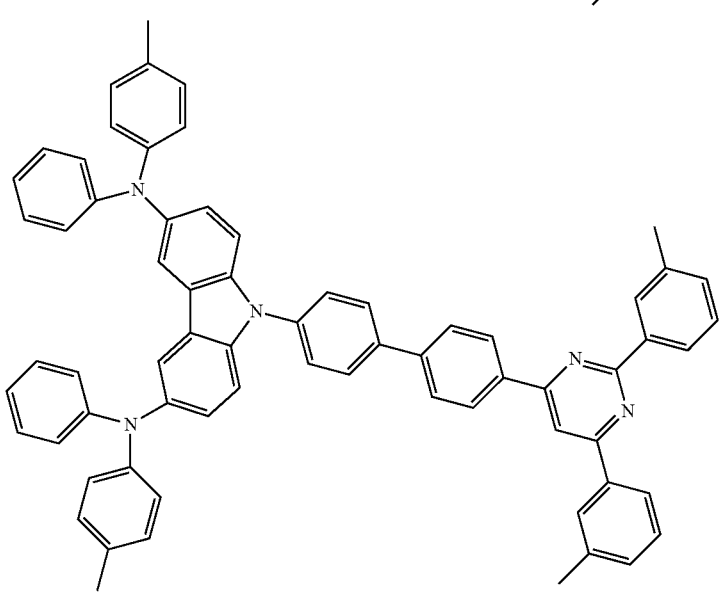

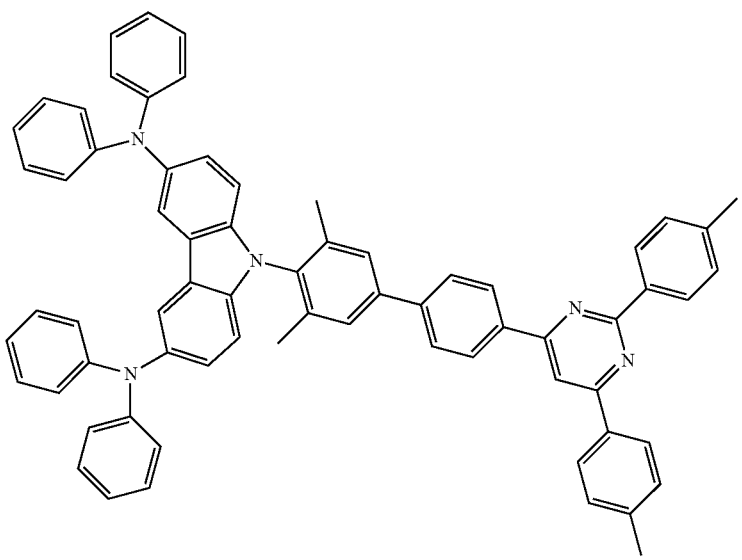
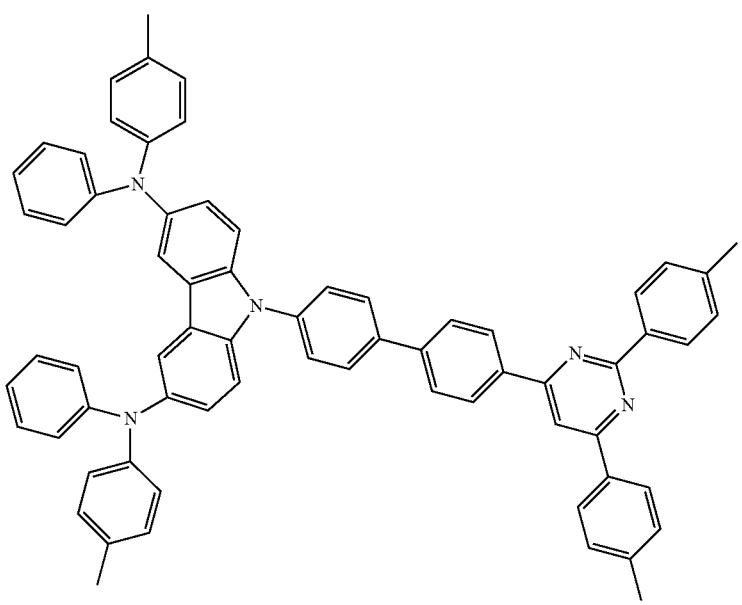
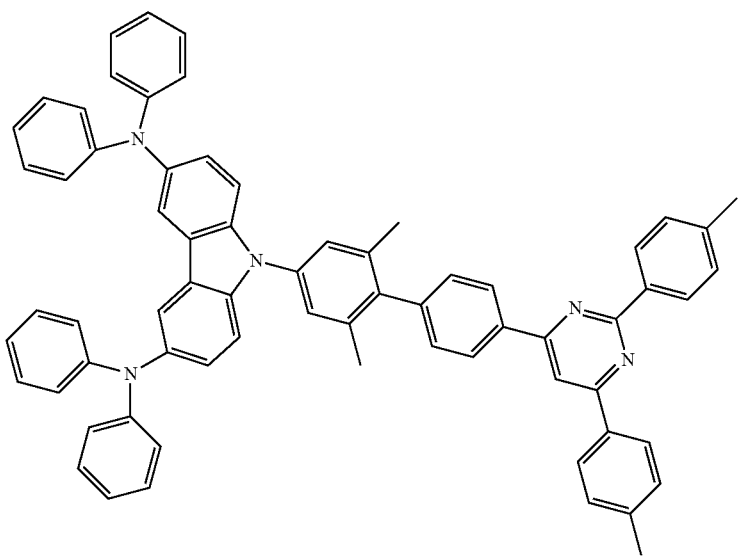

-continued
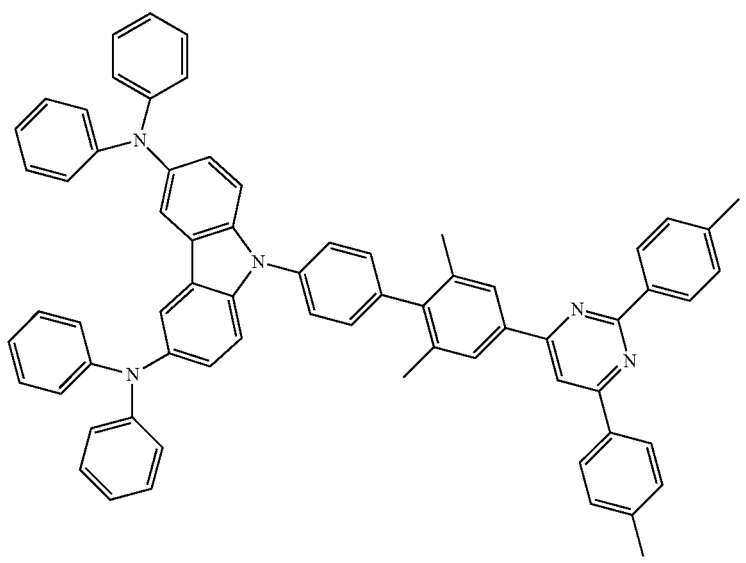
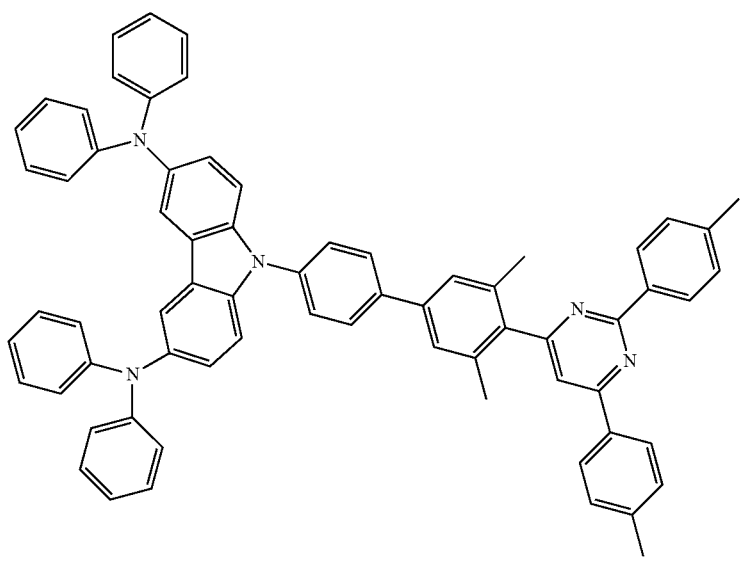
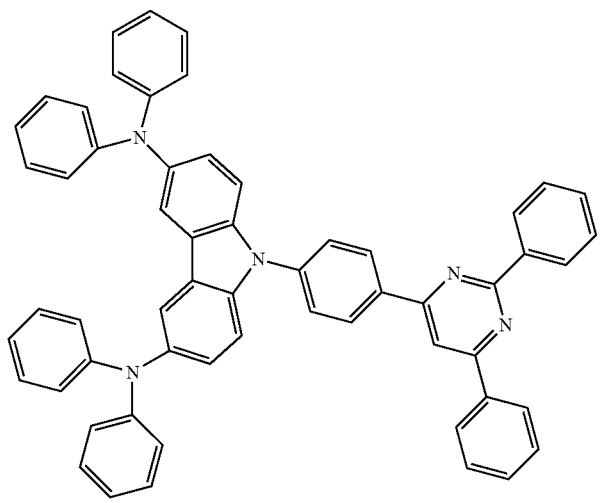

-continued
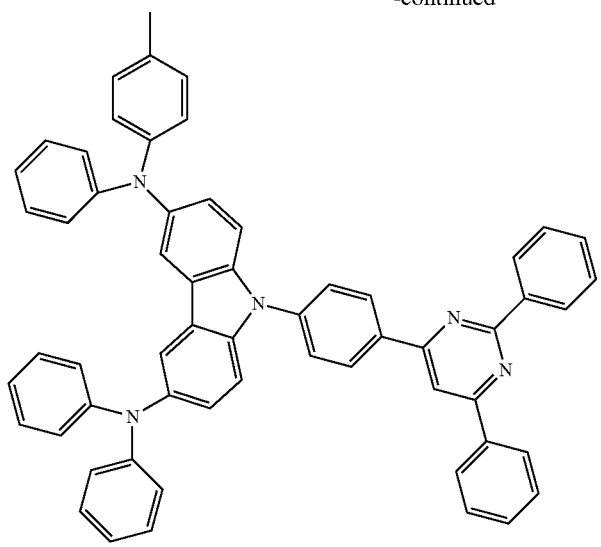
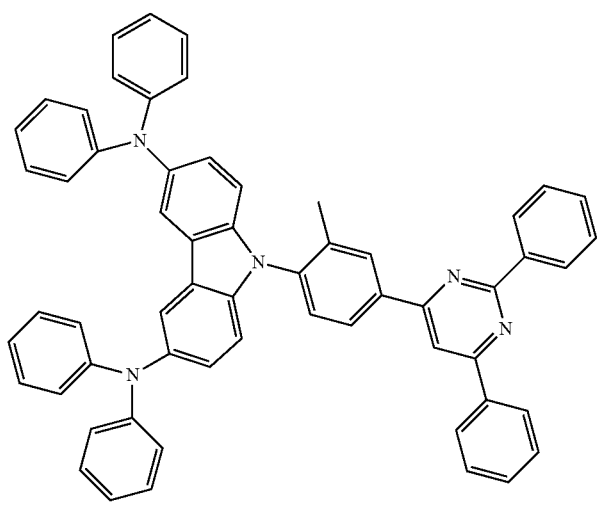
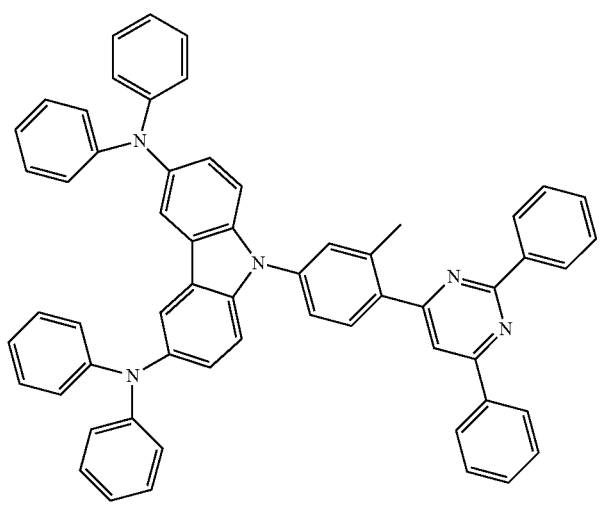

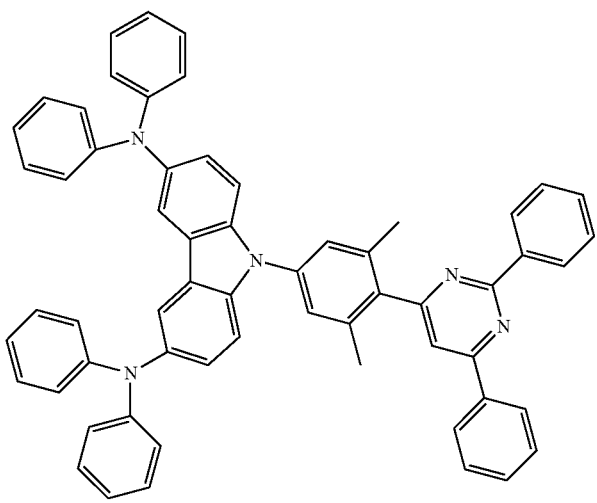
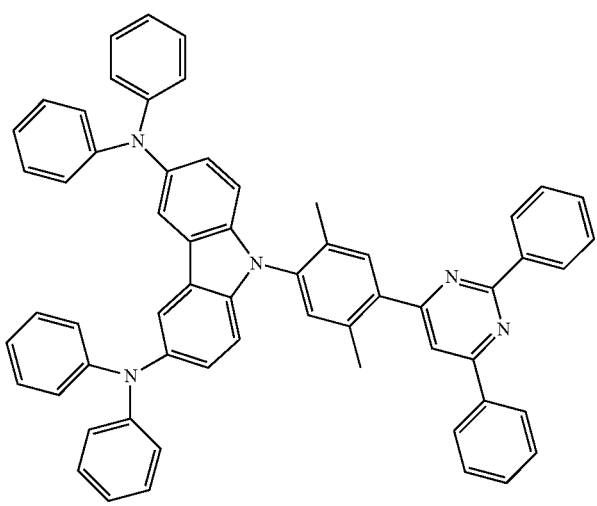
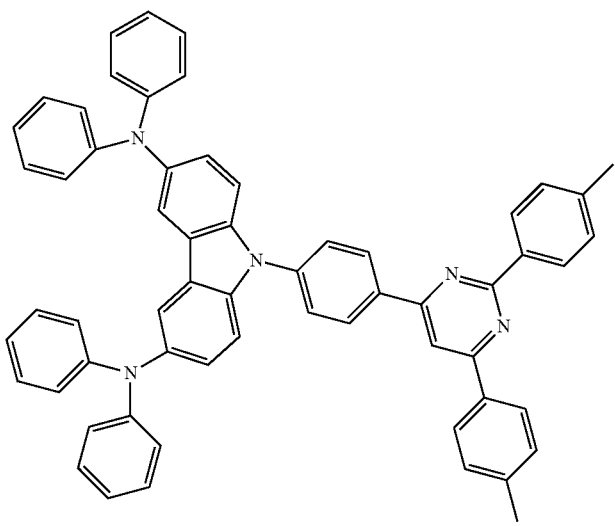

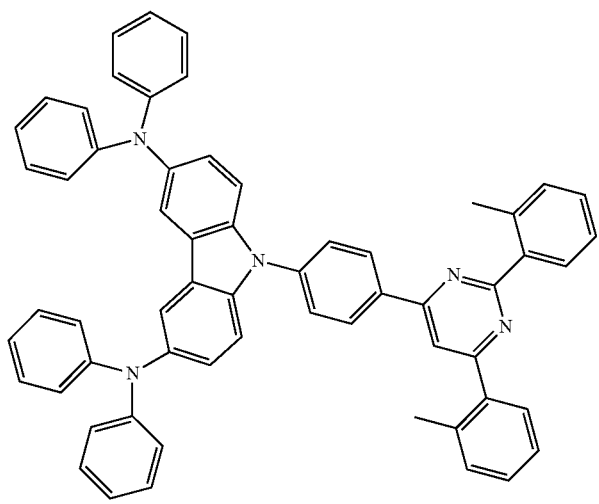
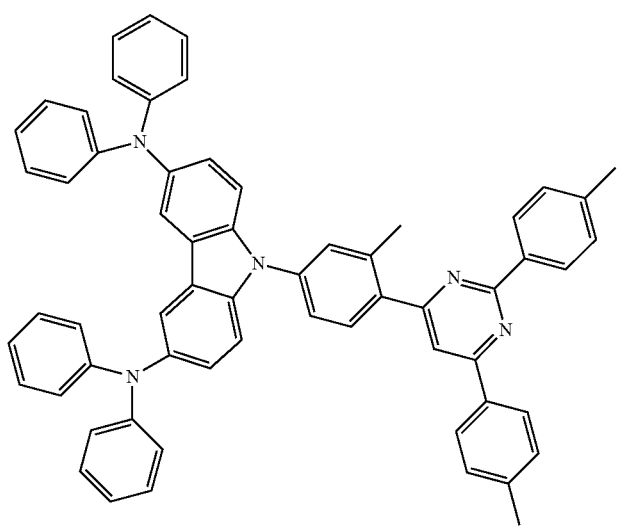
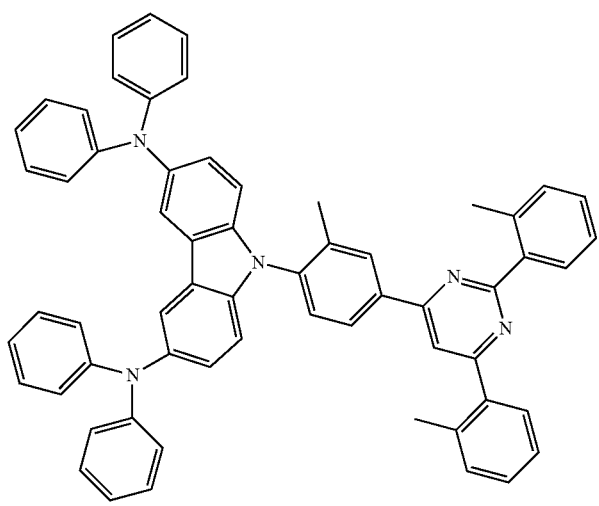

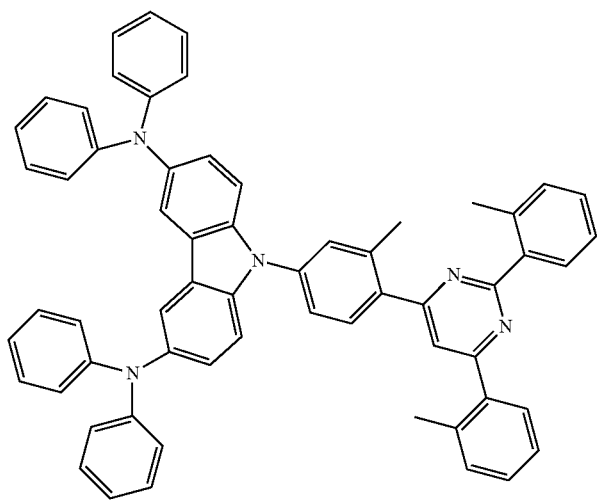
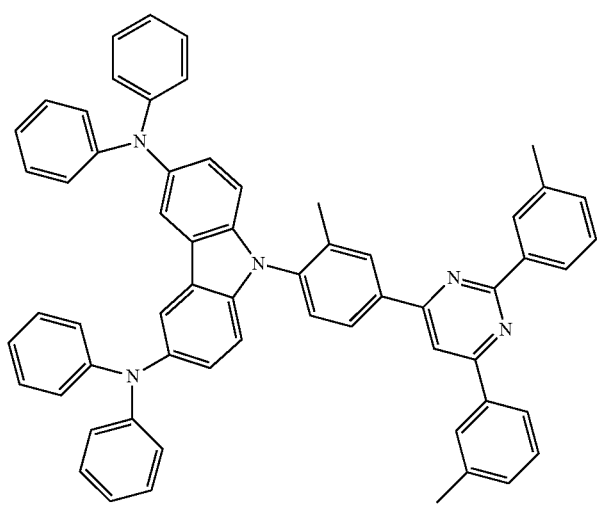
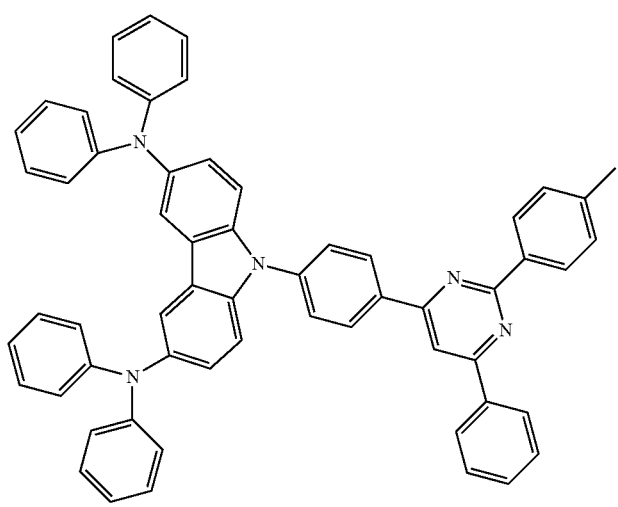

-continued
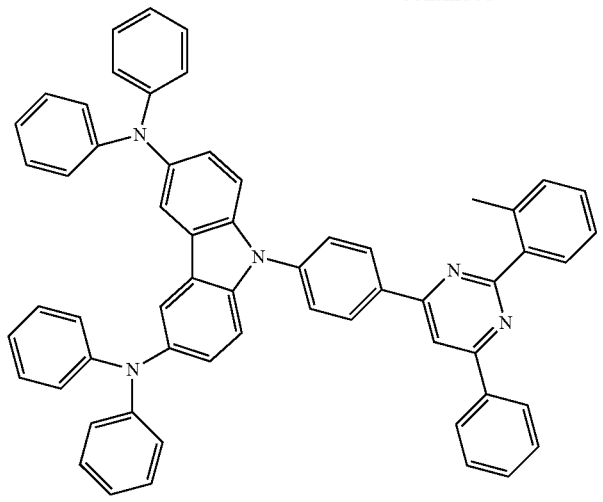
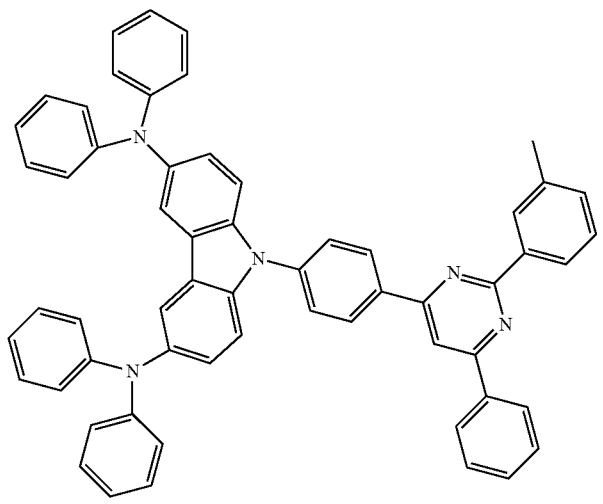
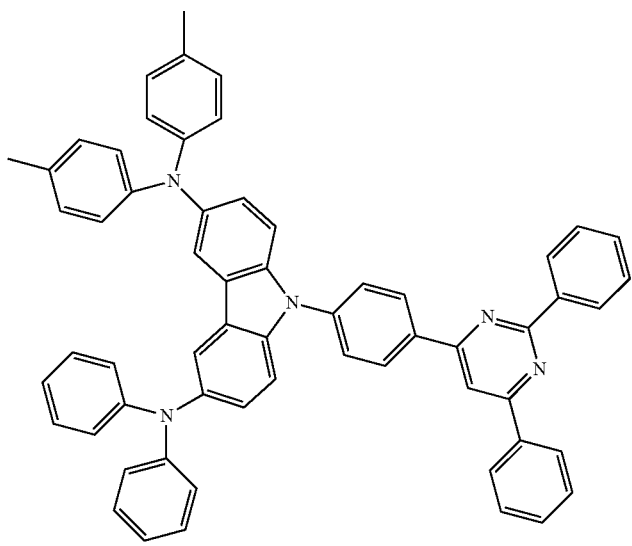

-continued
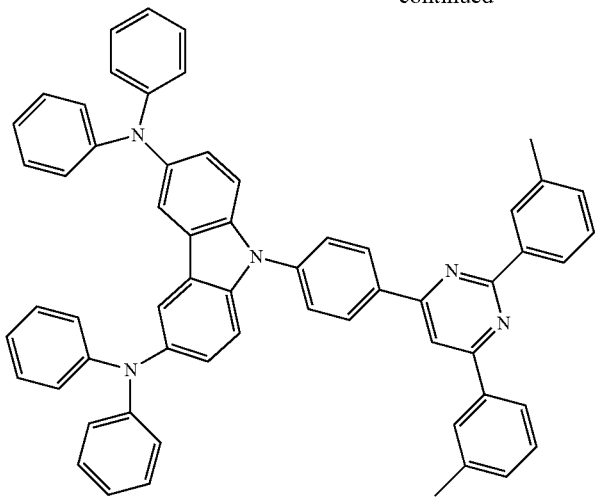
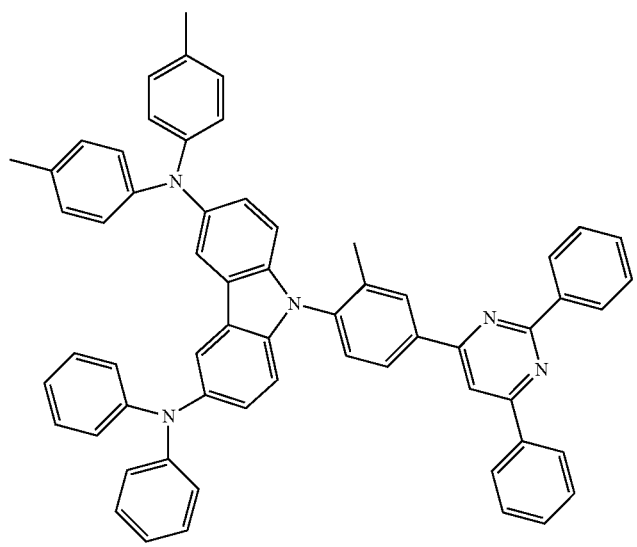
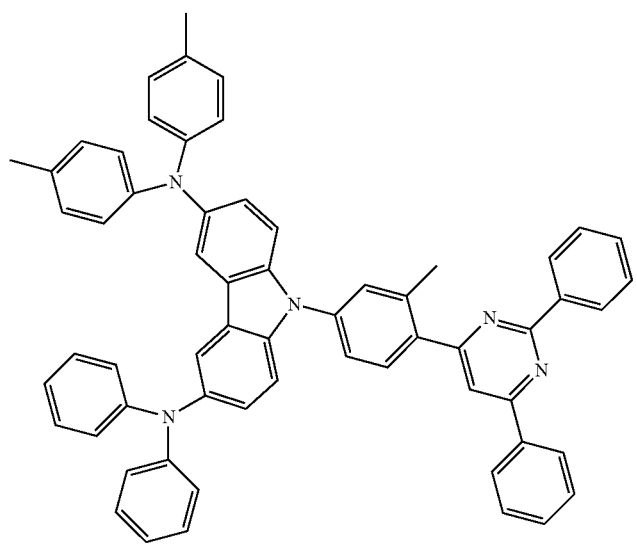

-continued
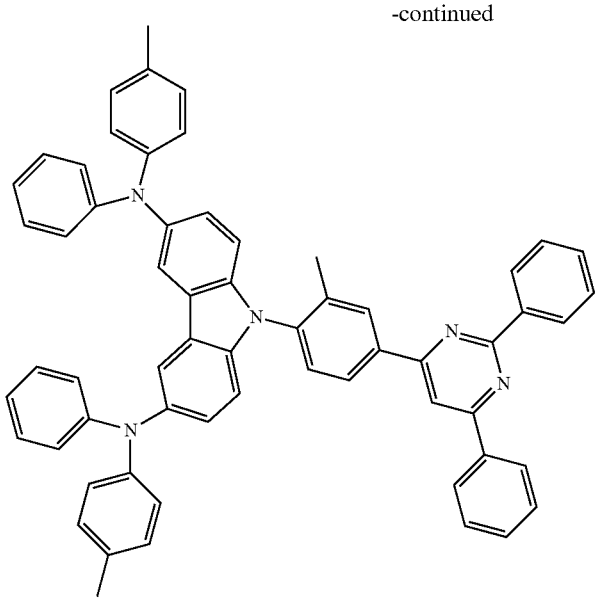
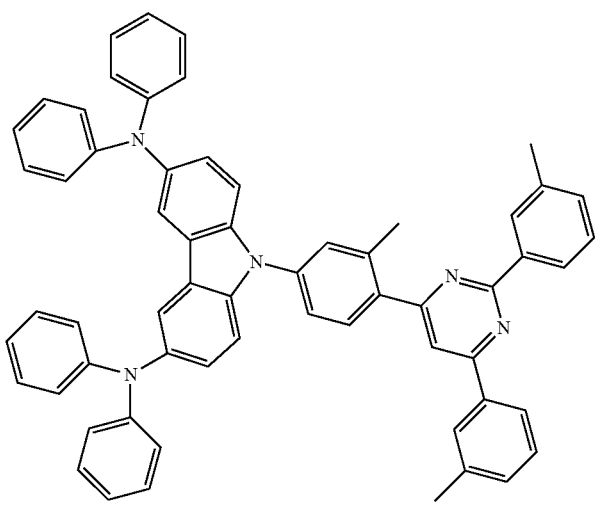
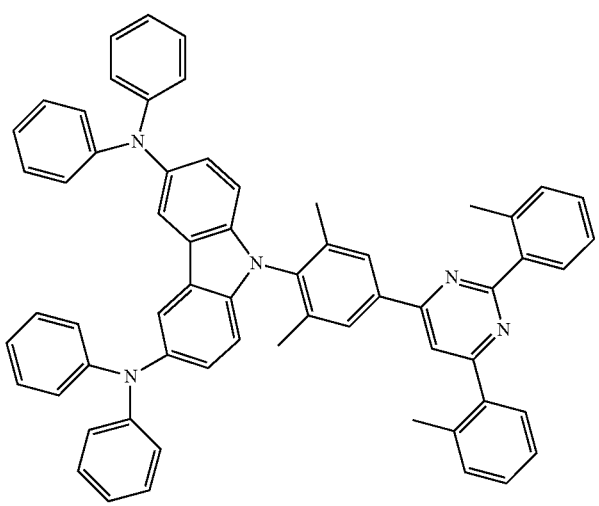

-continued
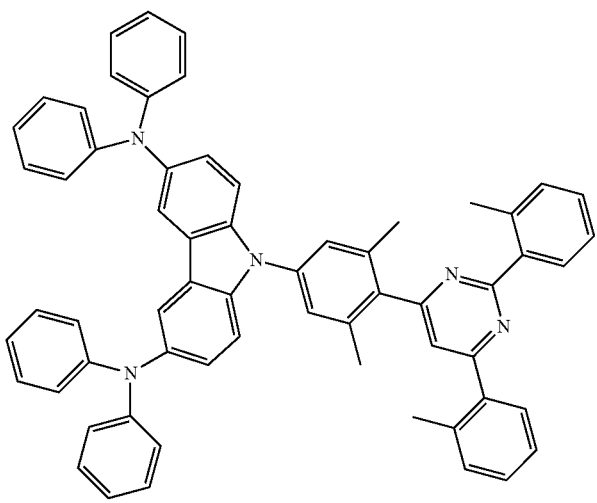
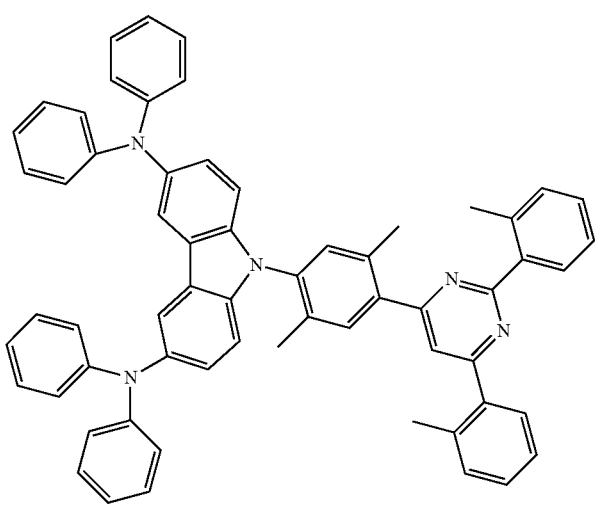
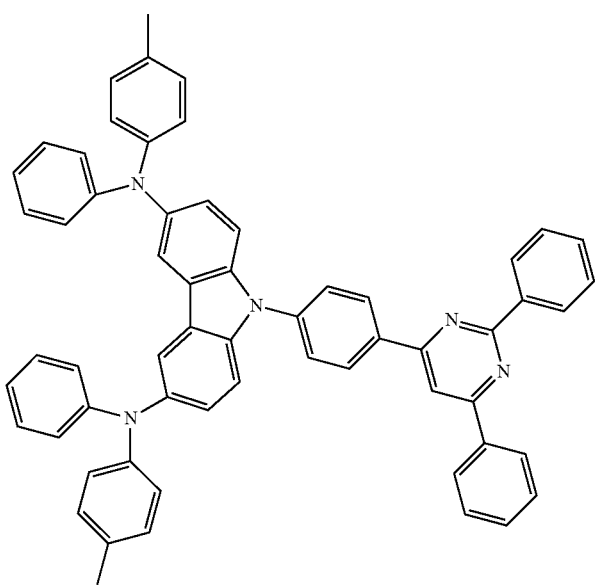

-continued
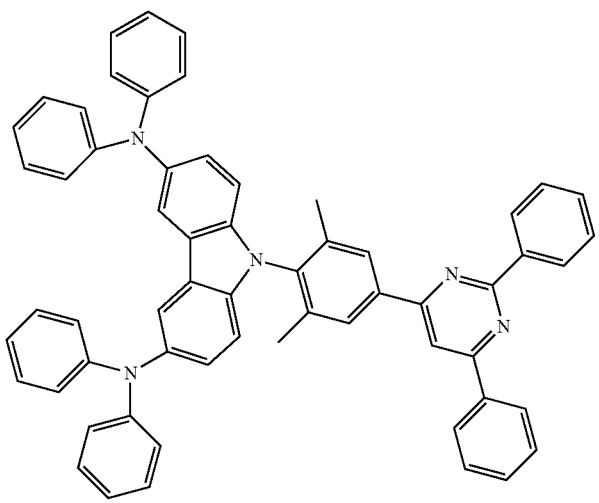
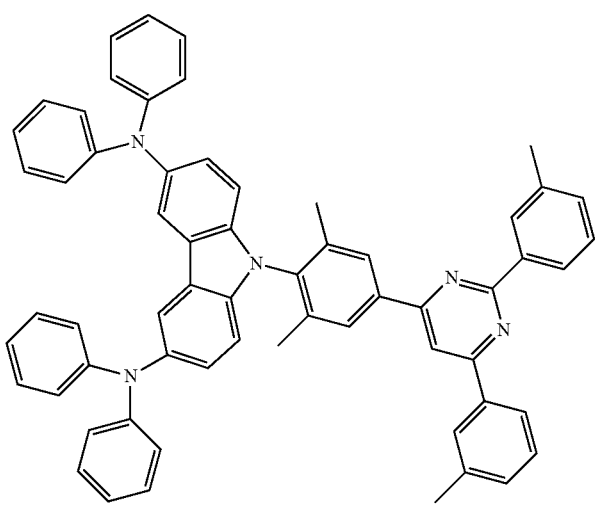
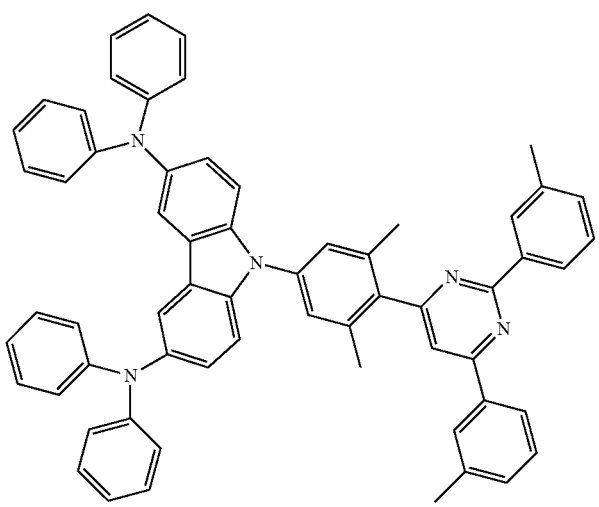

-continued
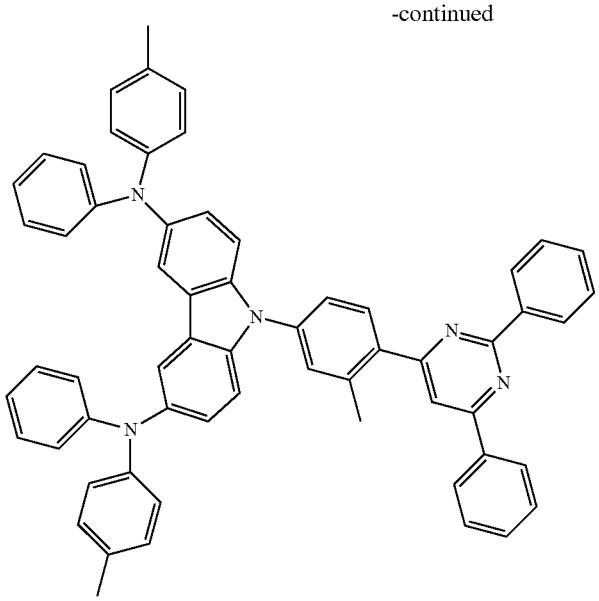
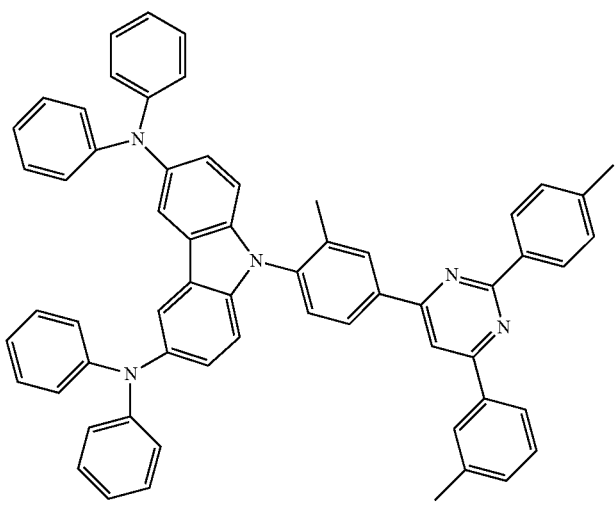
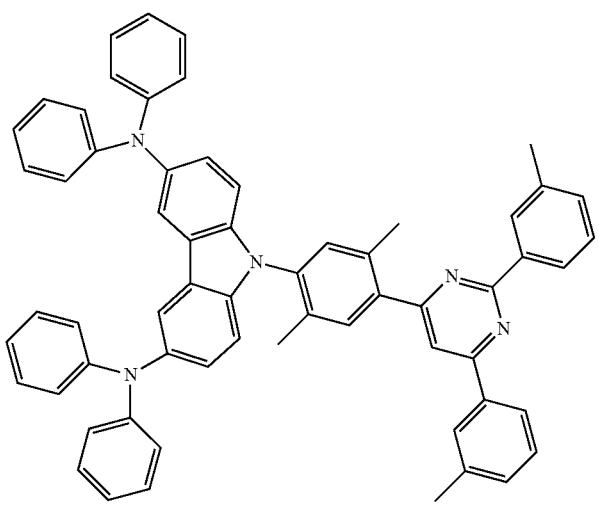

-continued
401
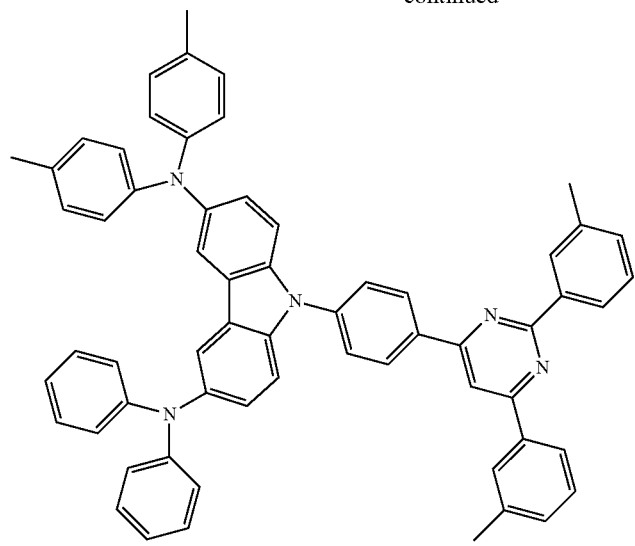
402
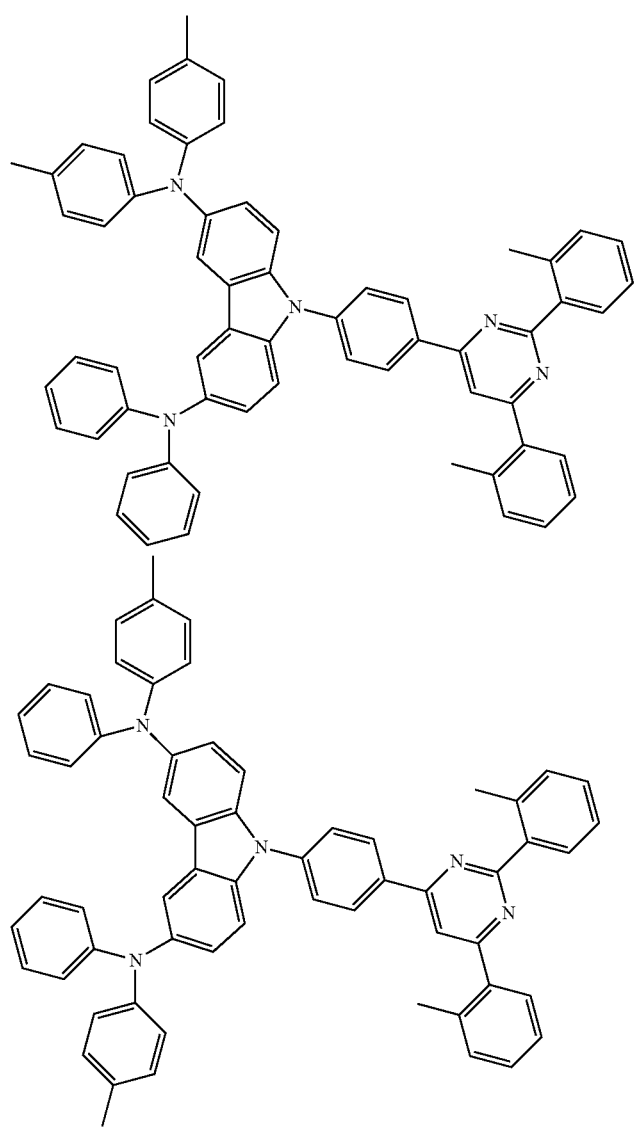

-continued
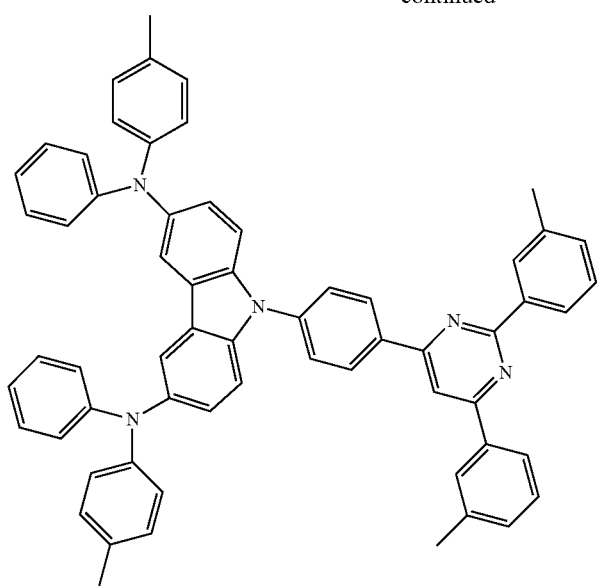
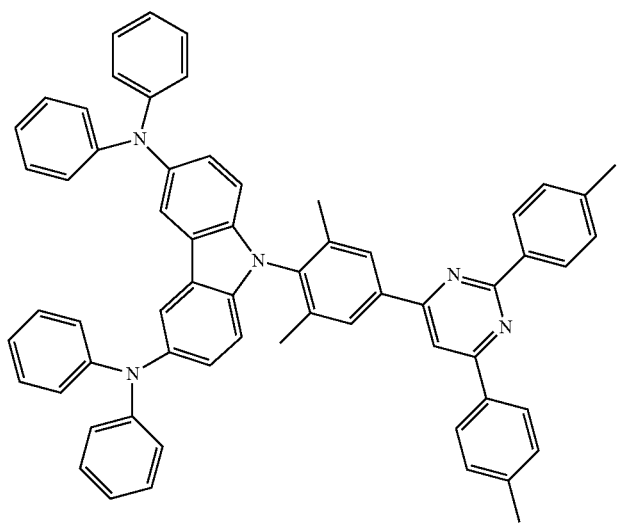
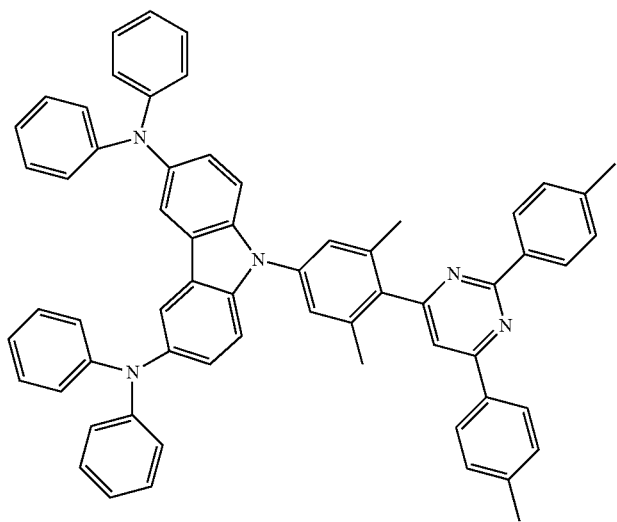

-continued
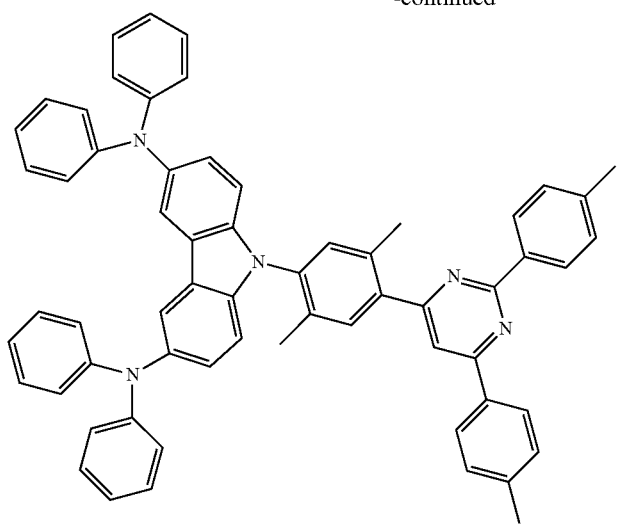
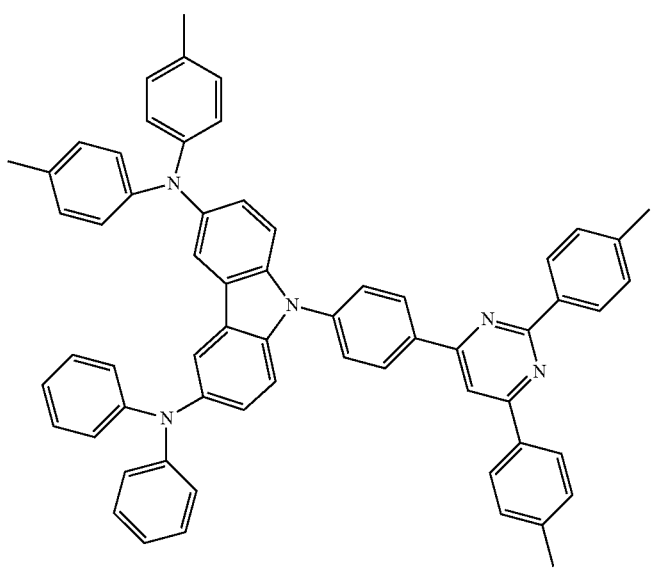
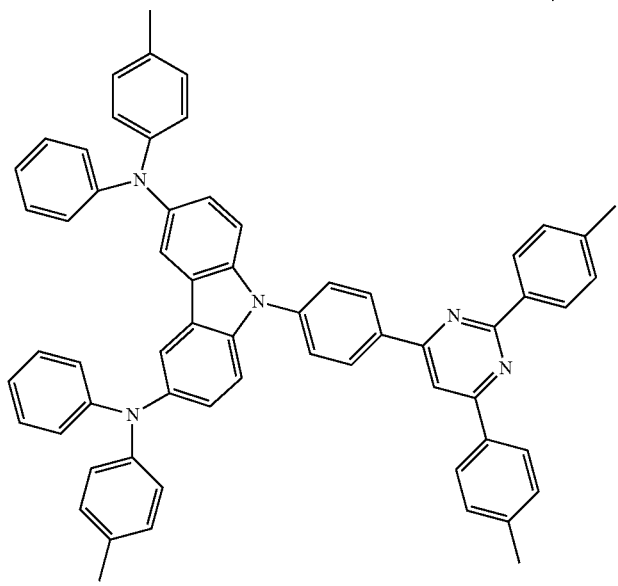

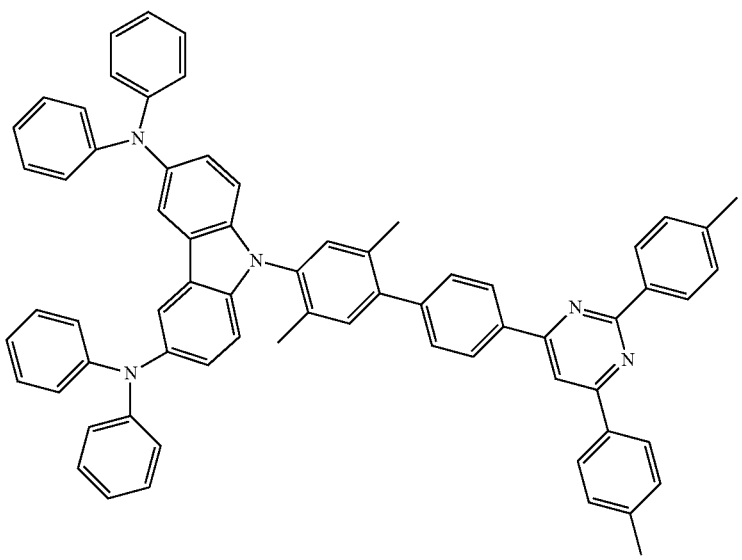
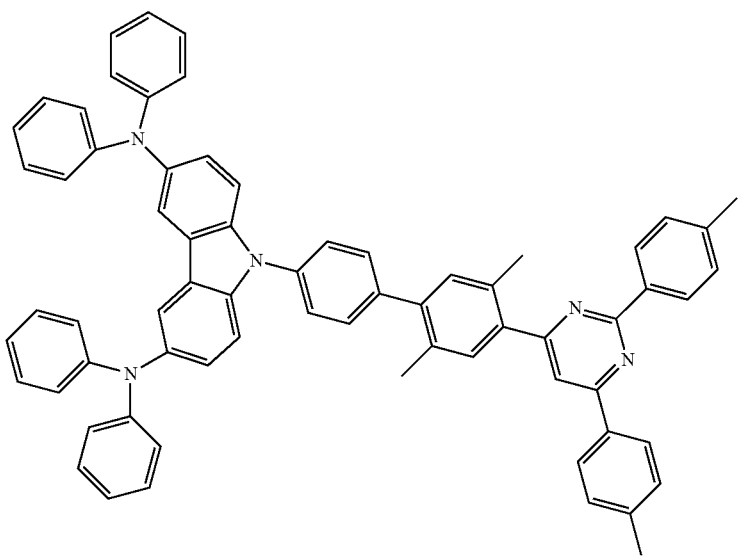
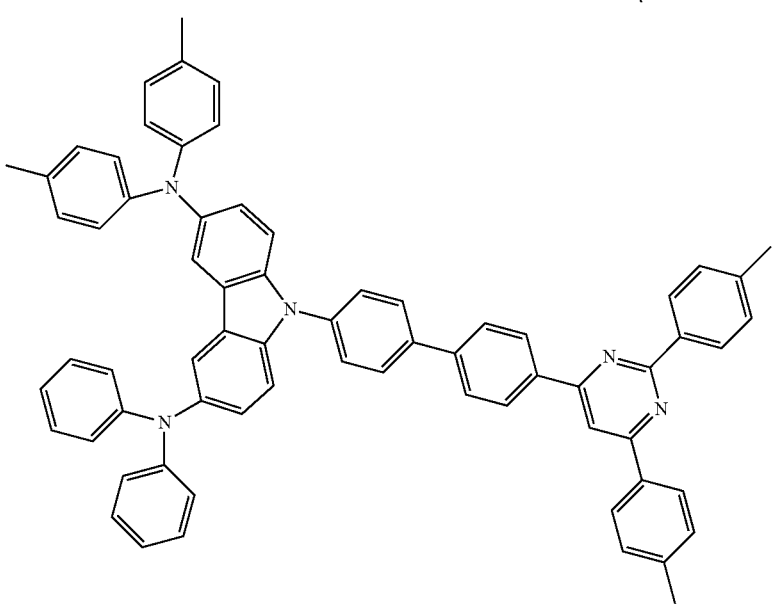

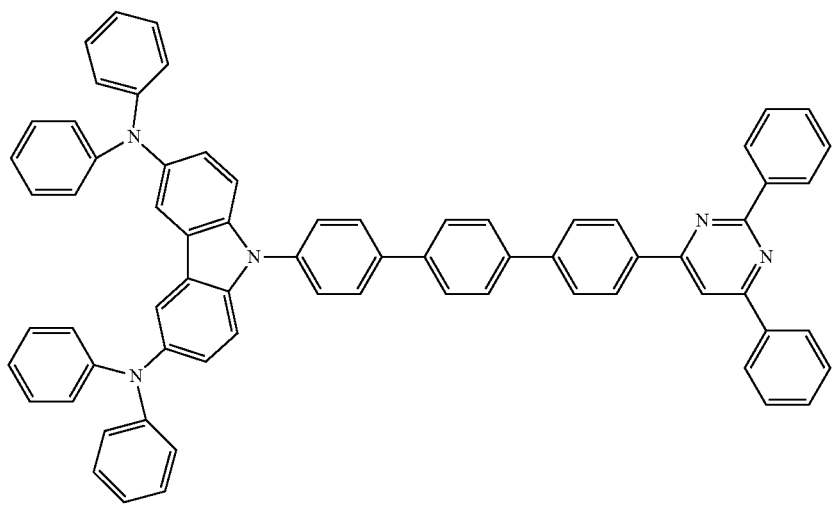
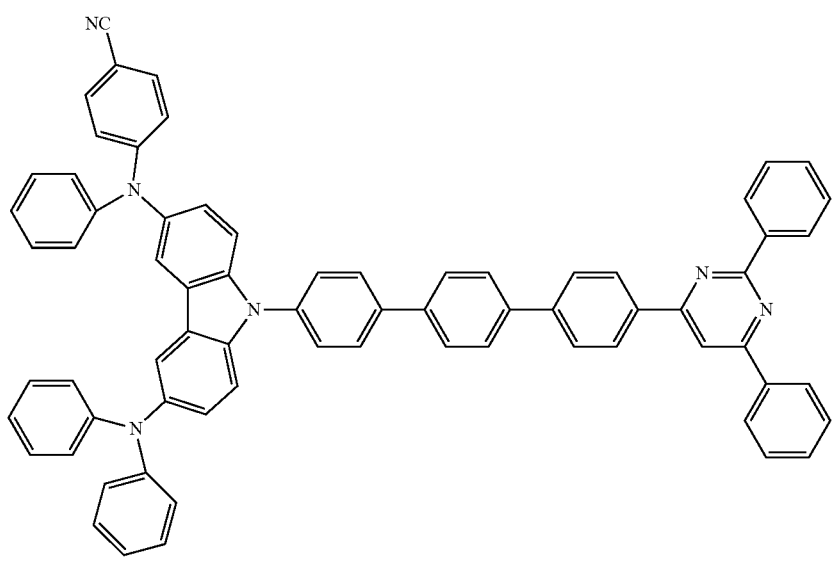
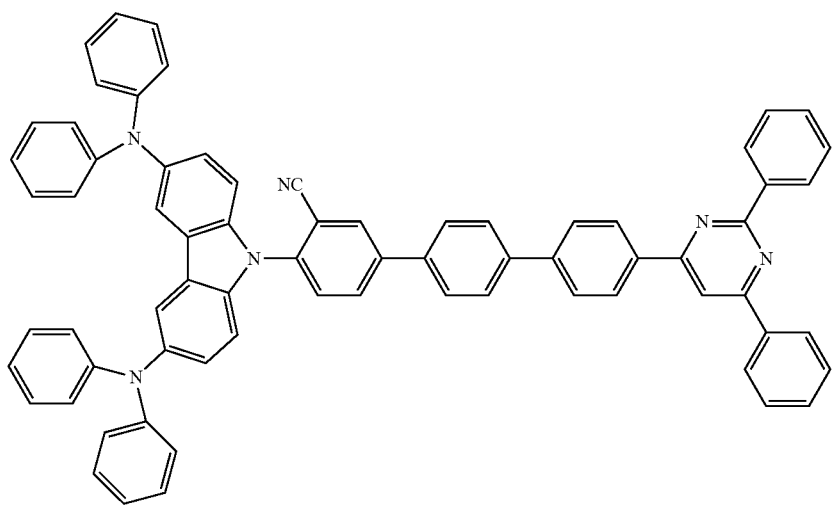

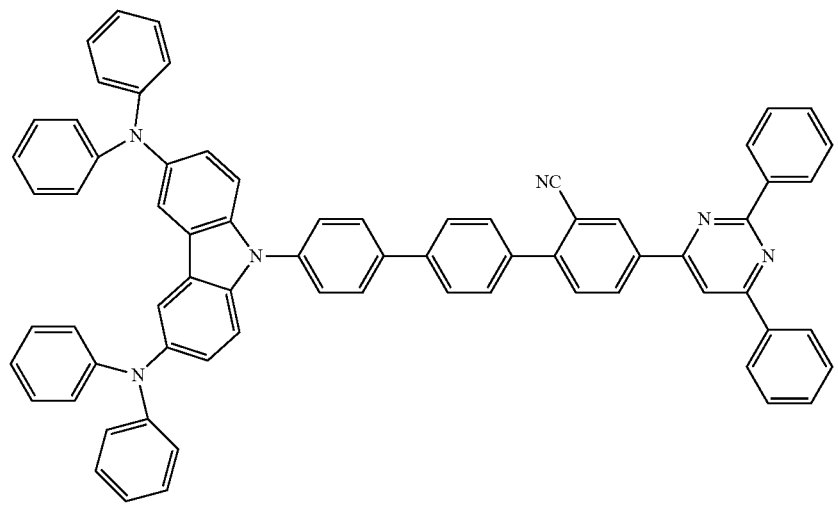
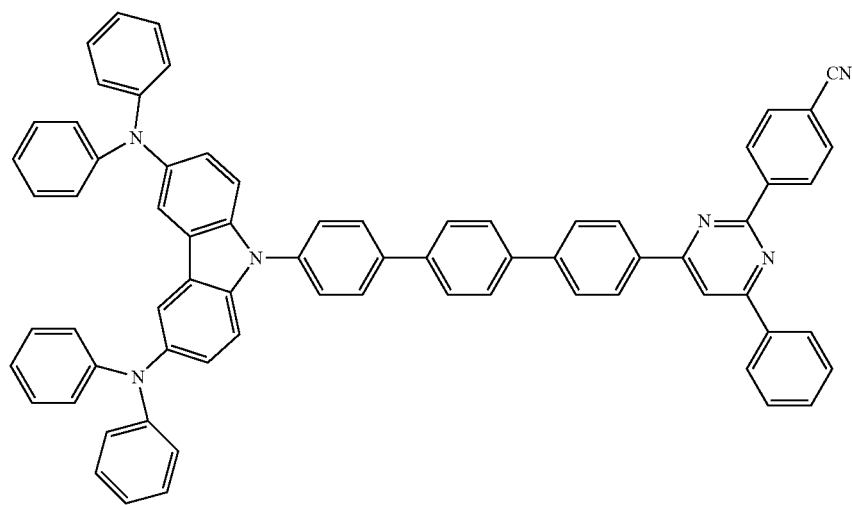
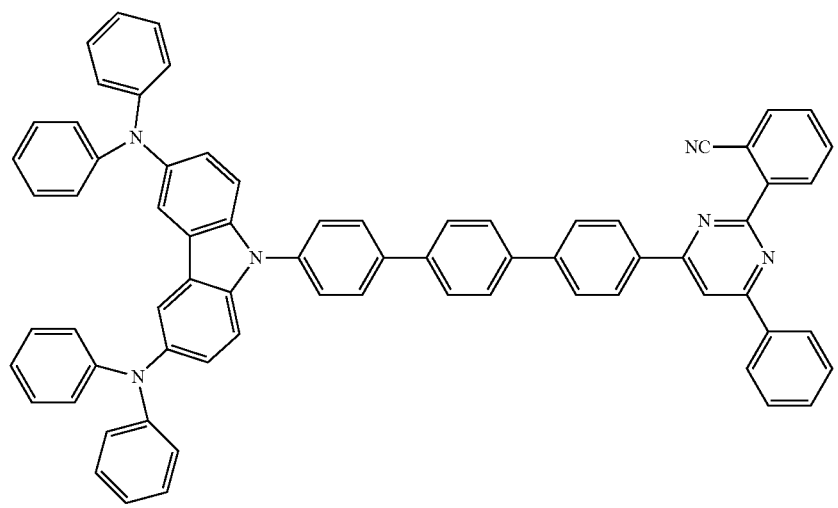

-continued
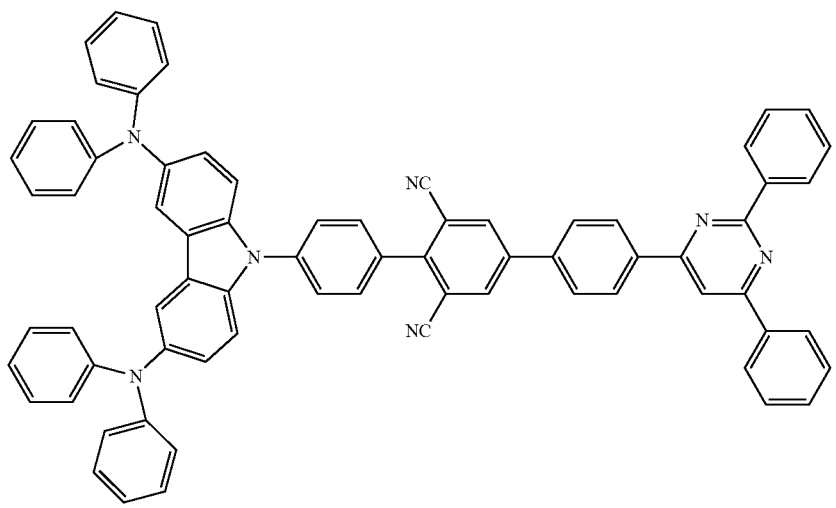
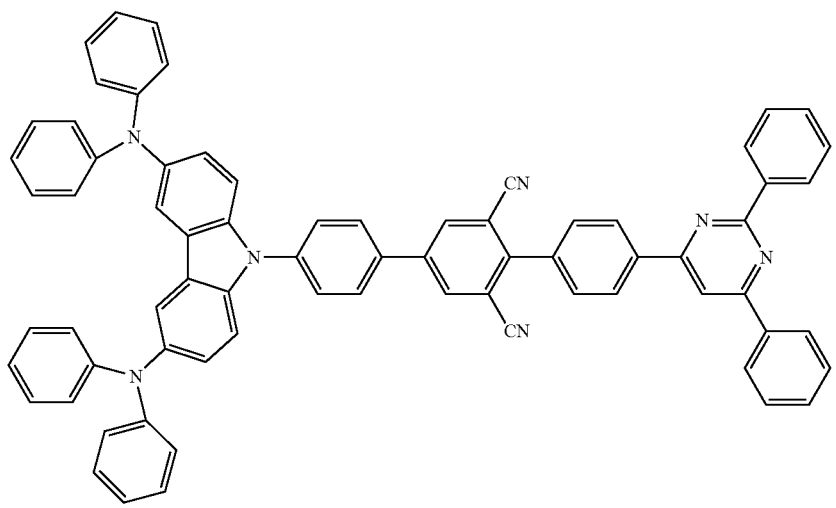
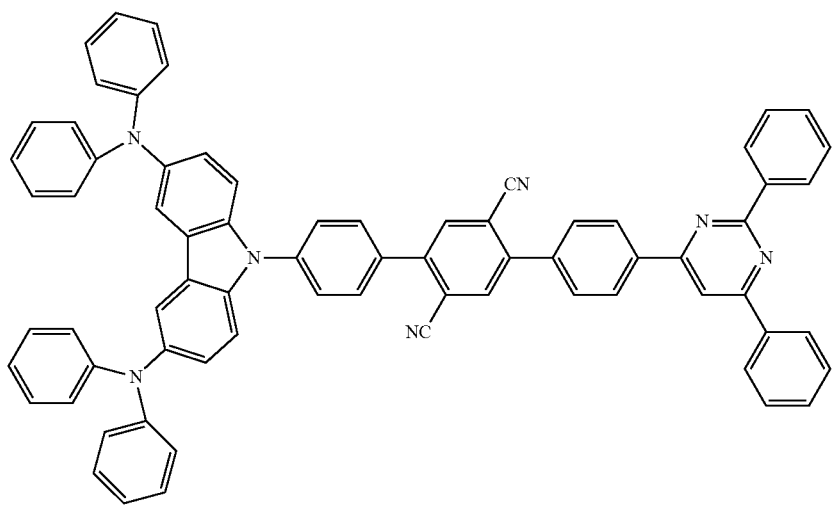

-continued
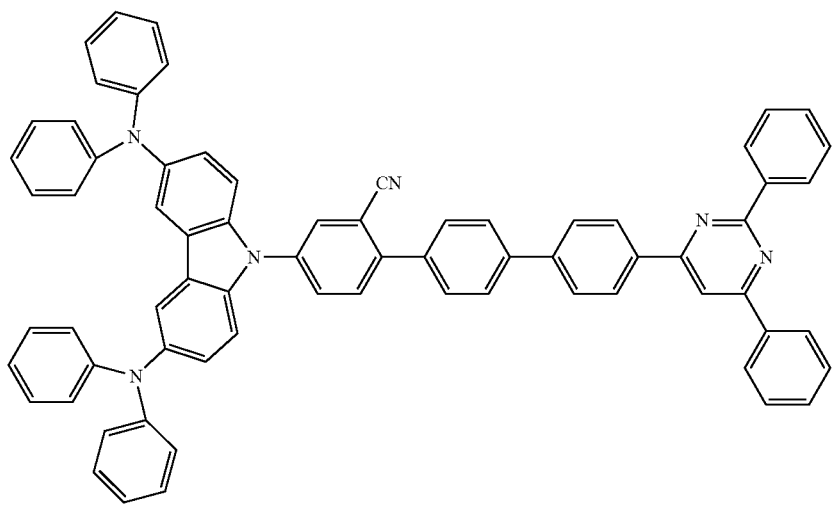
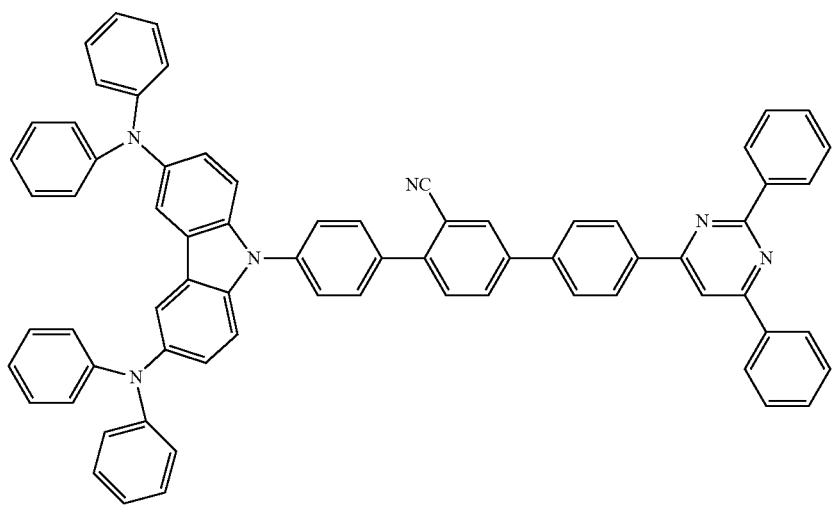
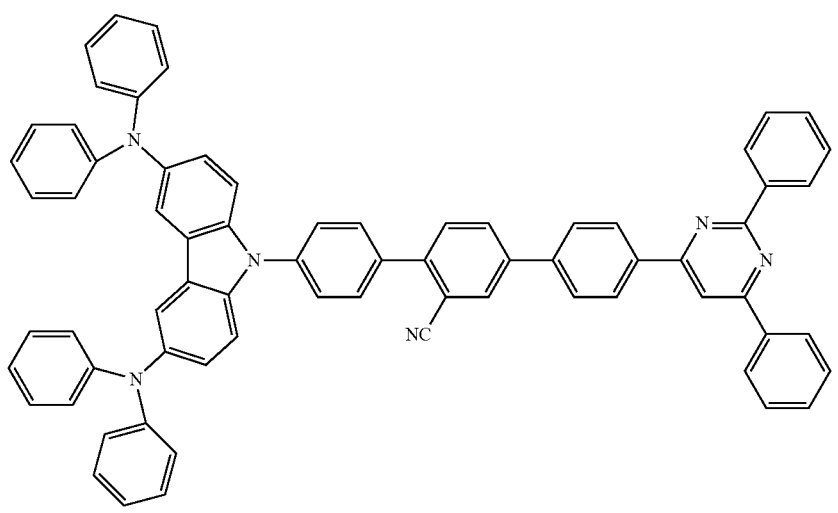

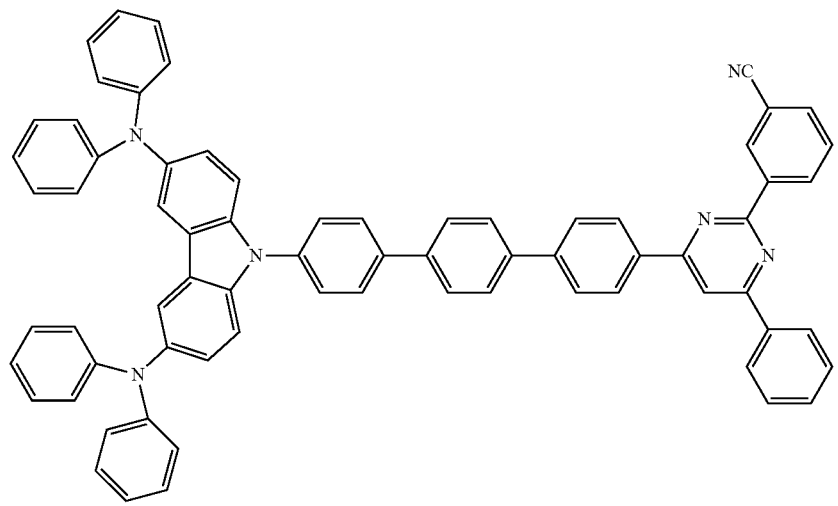
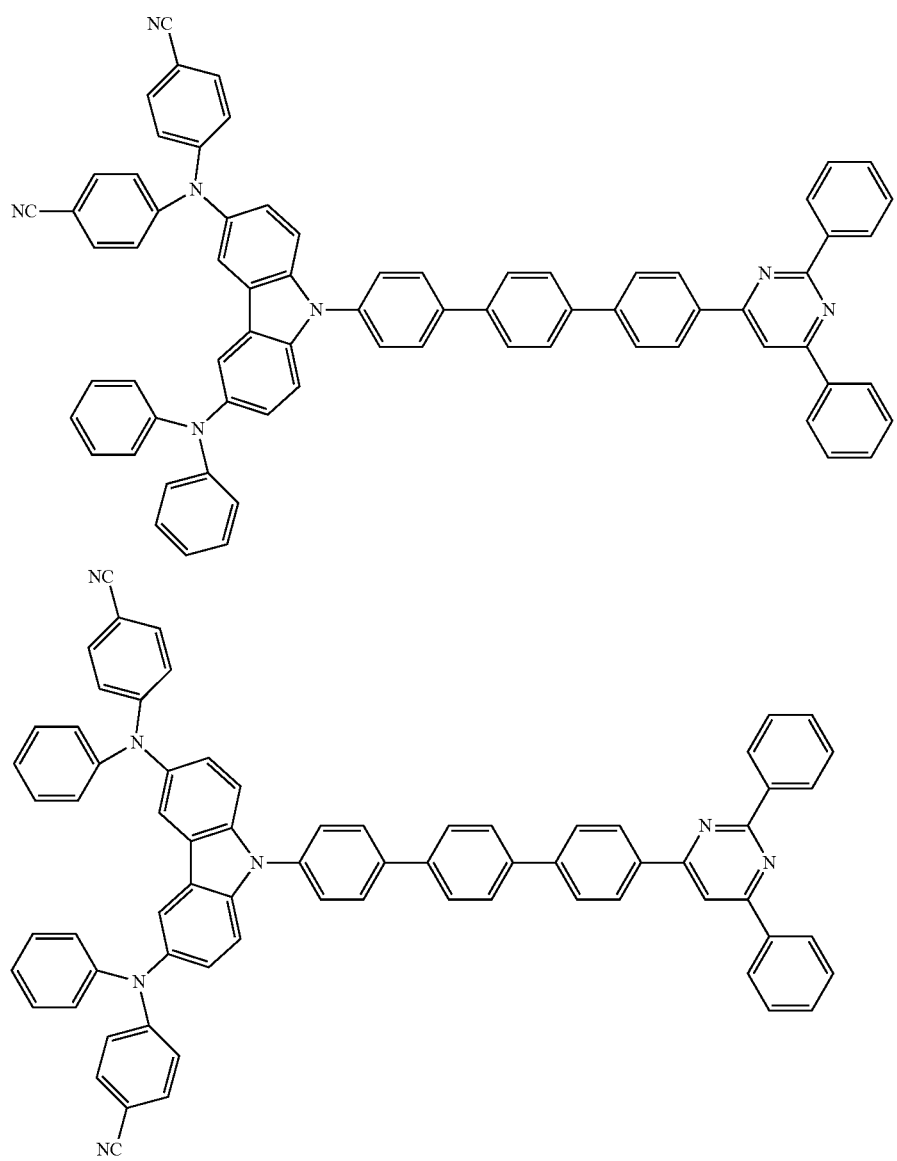

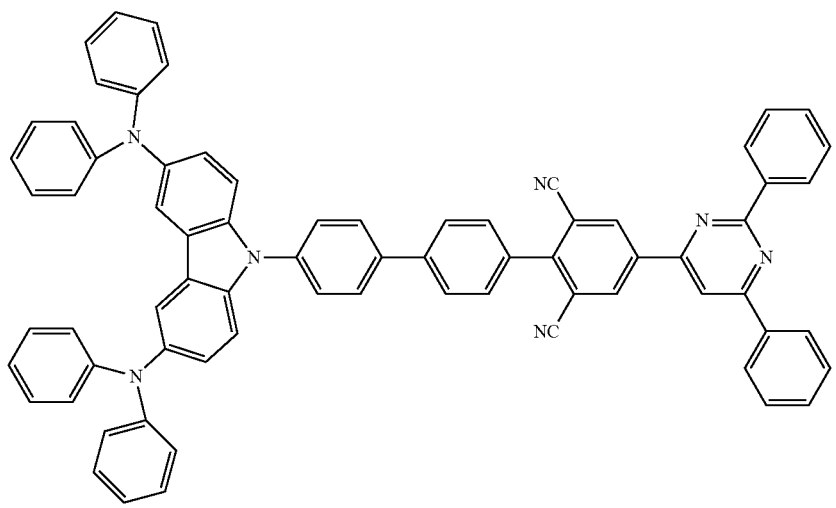
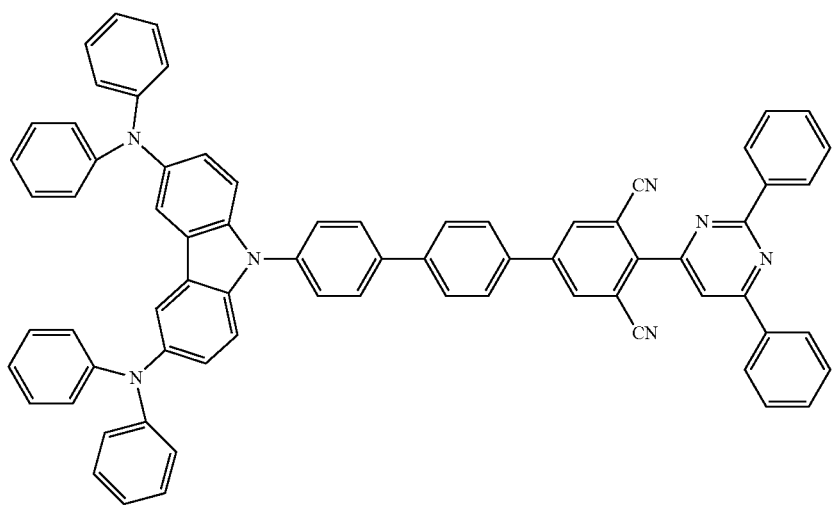
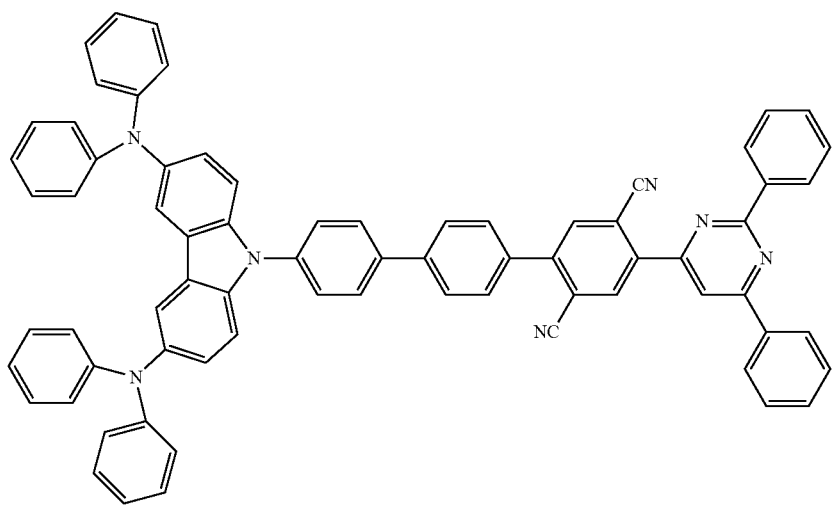

-continued
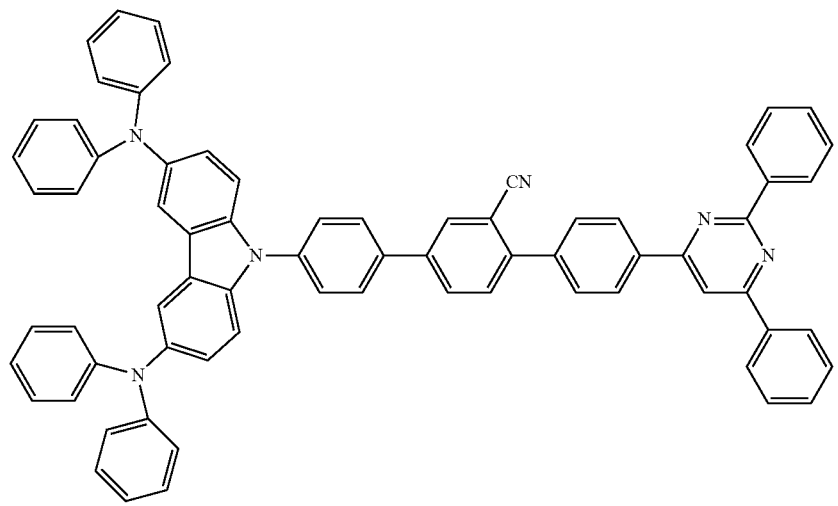
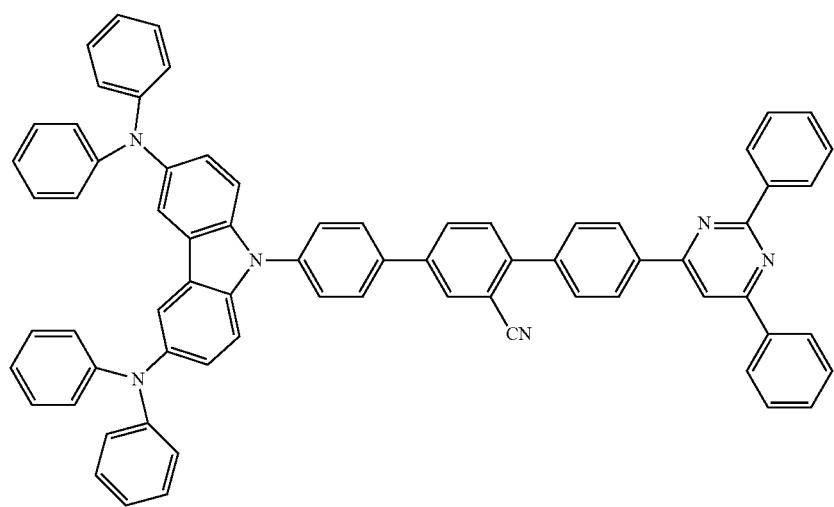
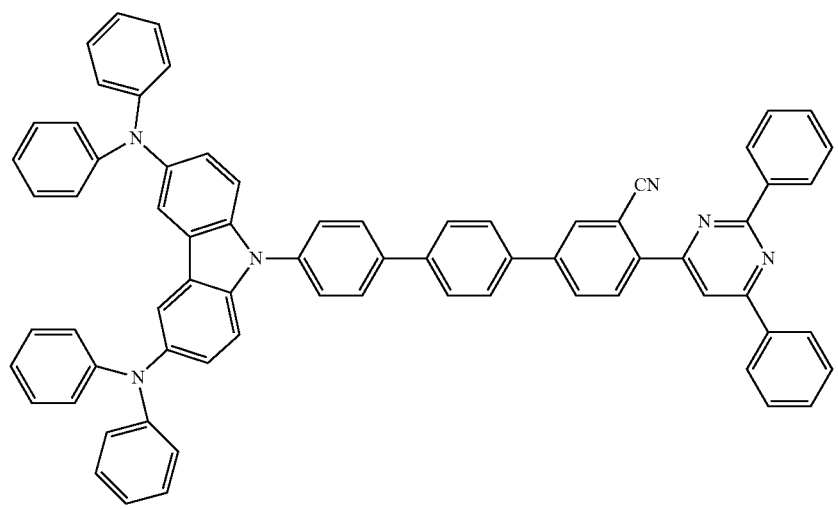

-continued
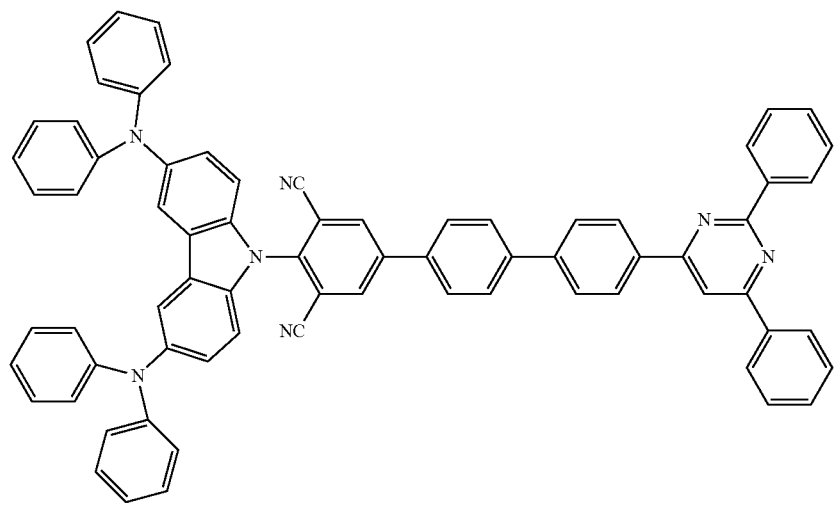
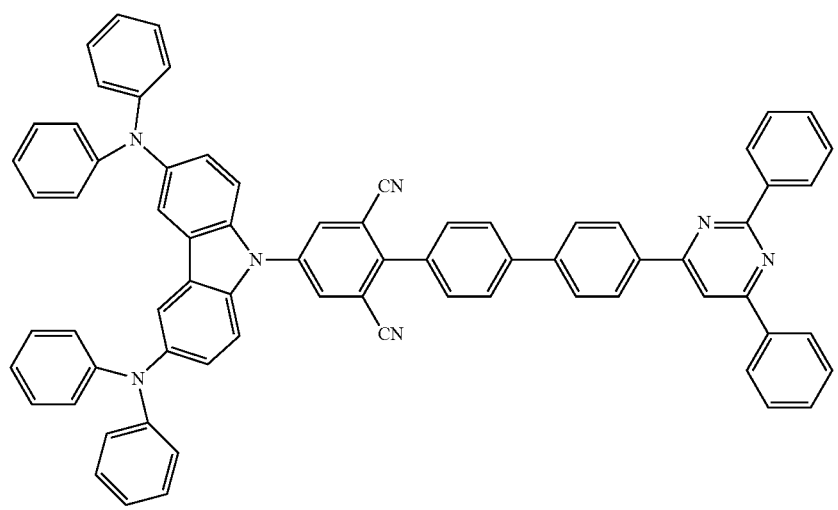
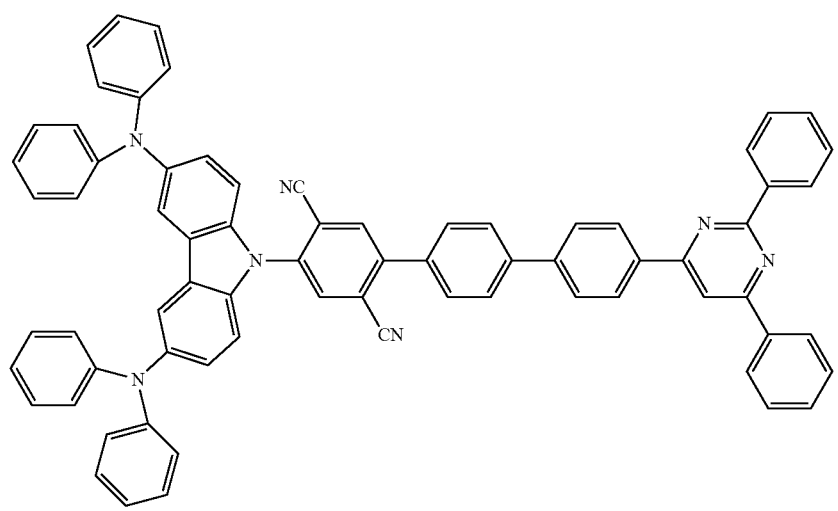

-continued
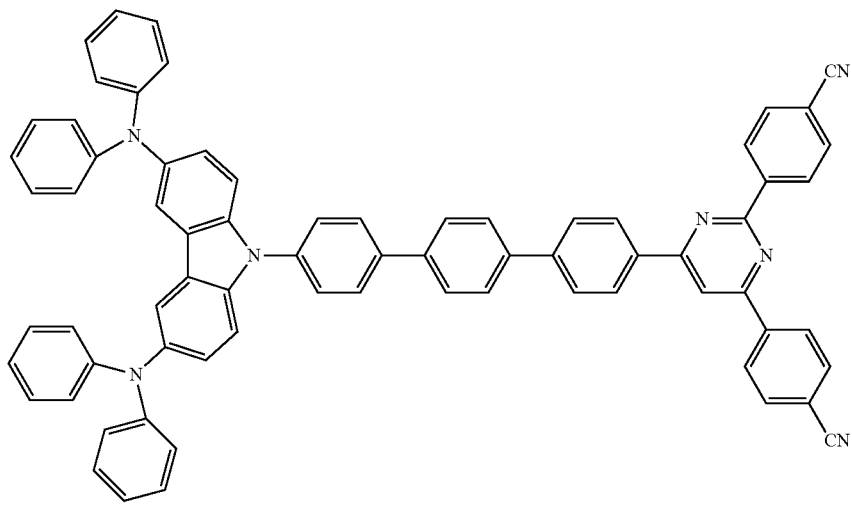
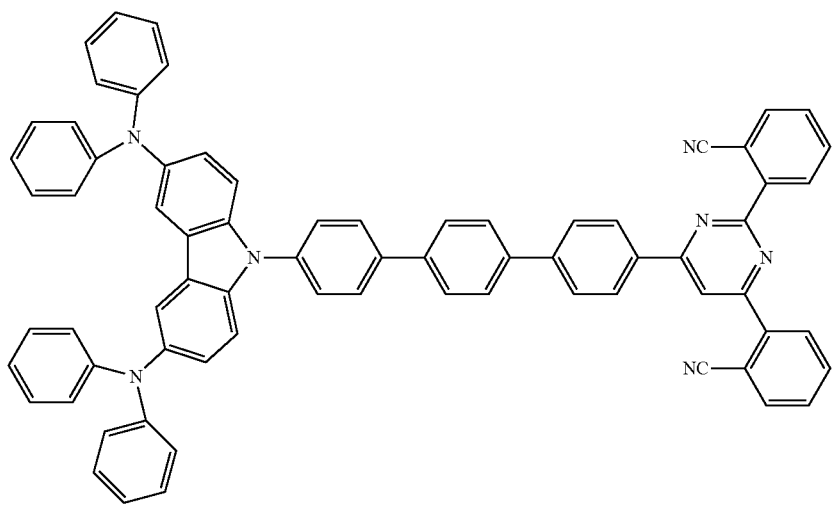
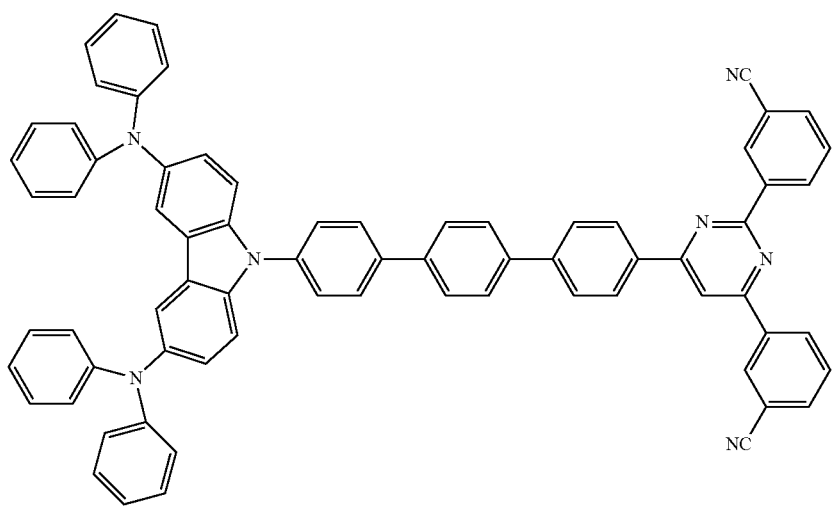

-continued
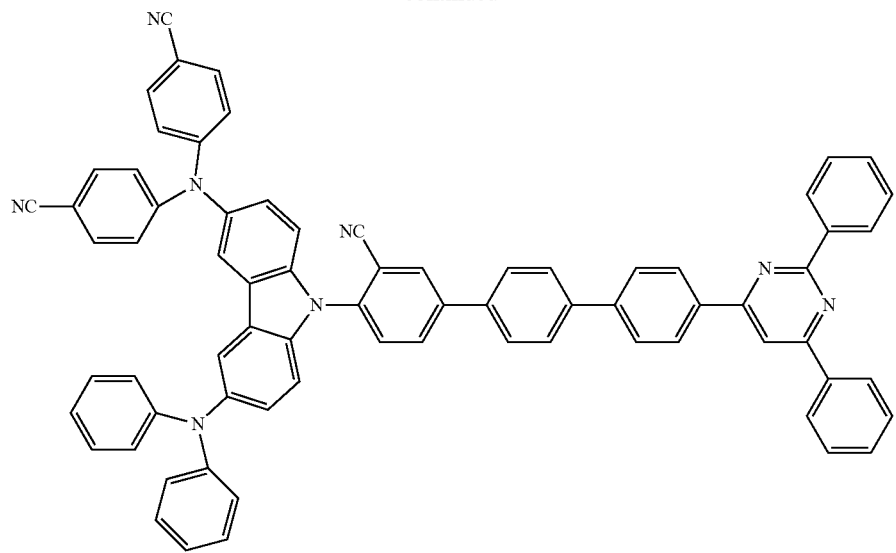
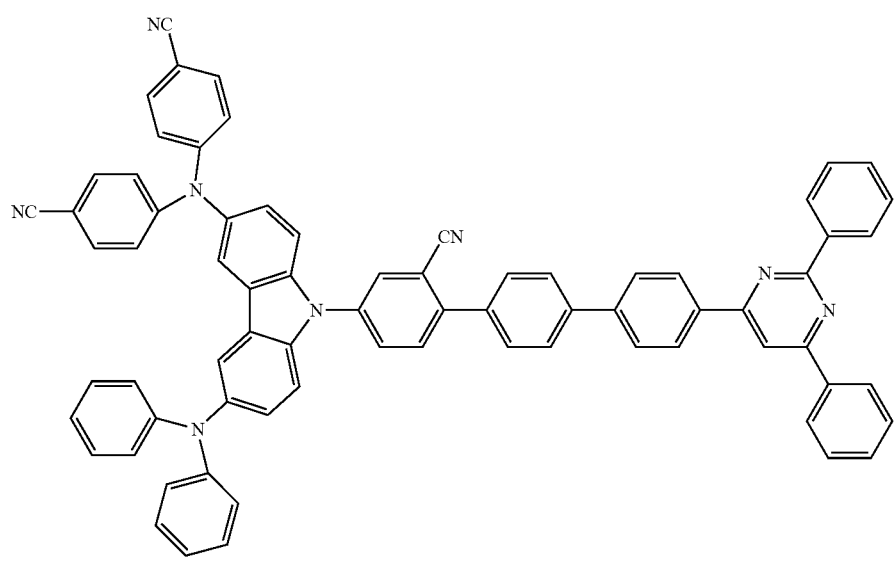
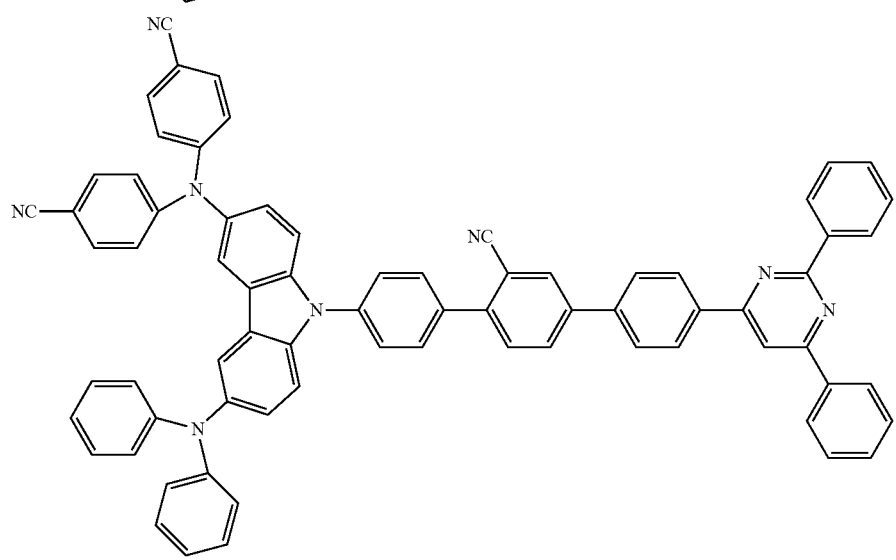

-continued
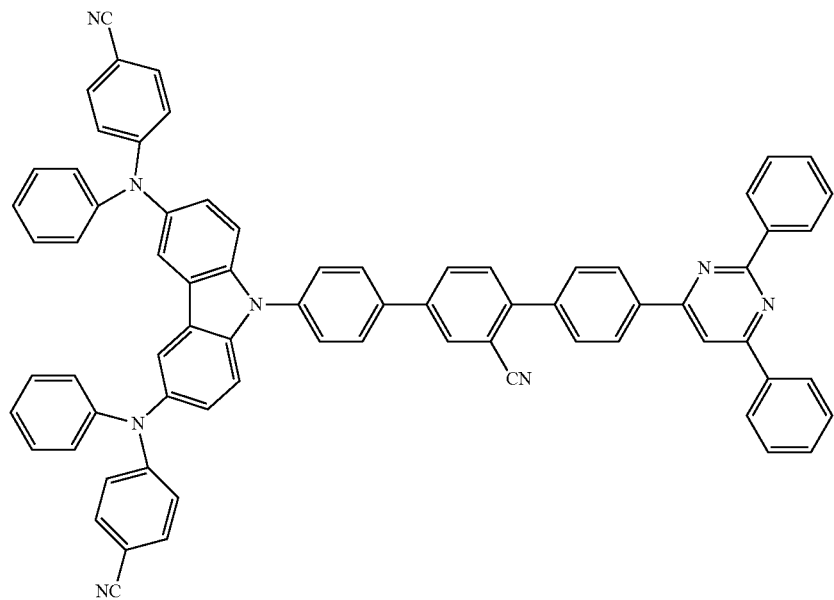
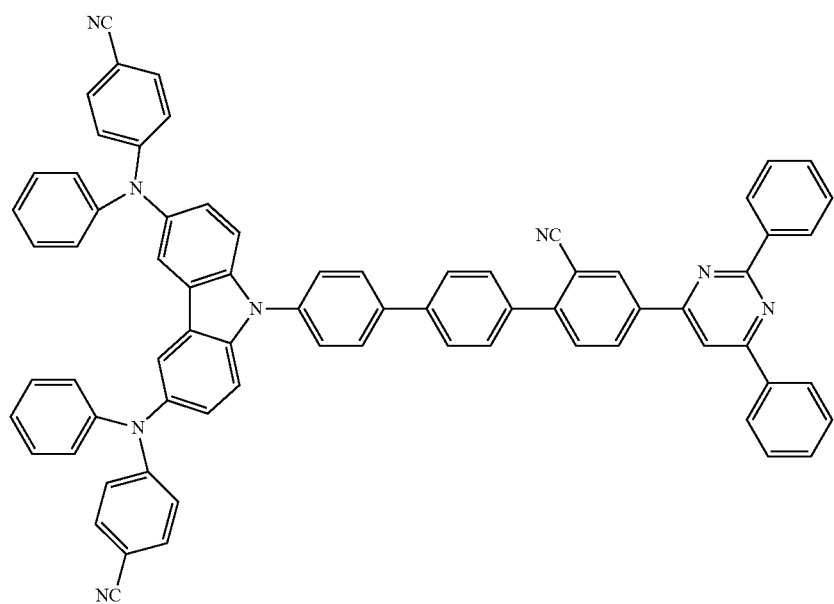

-continued
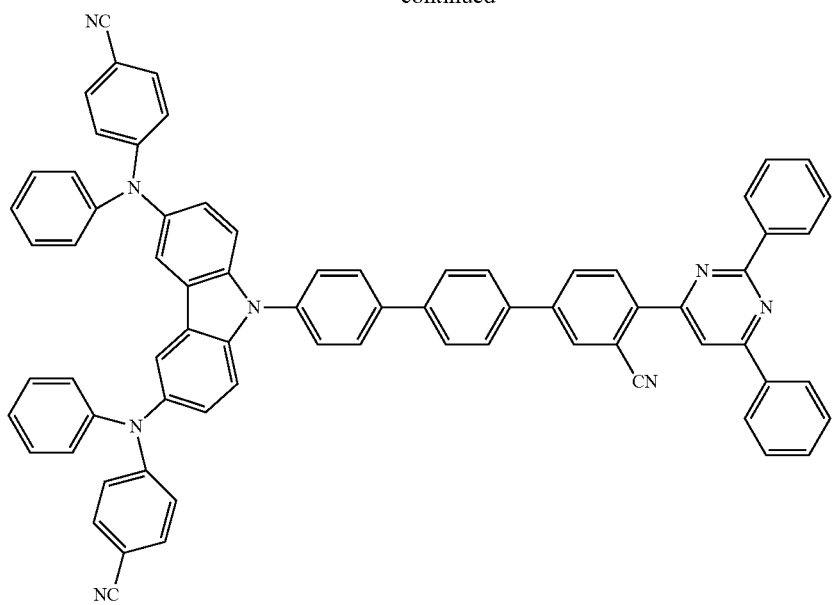
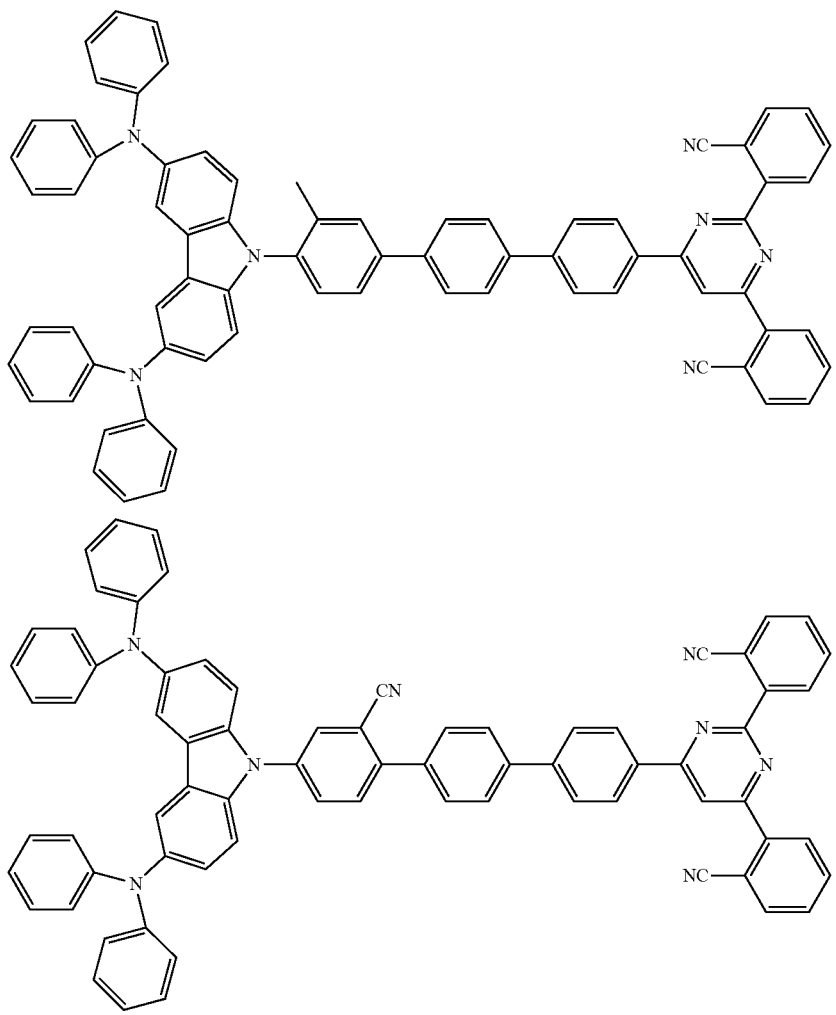

-continued
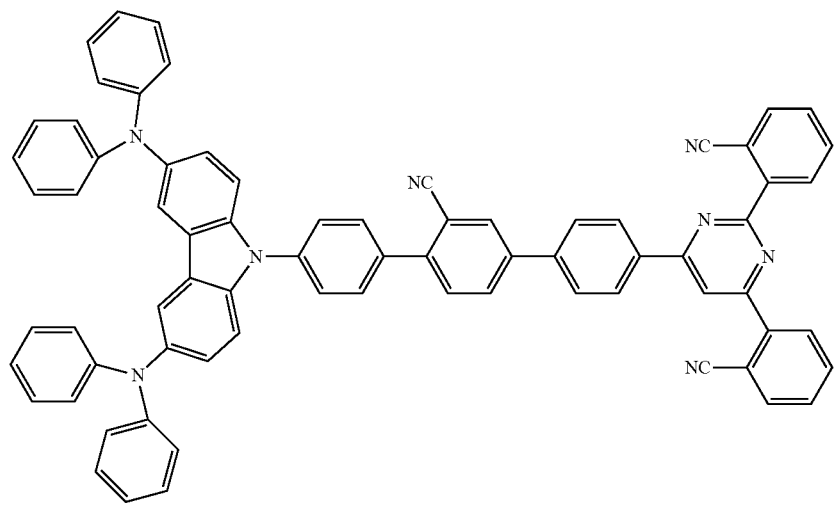
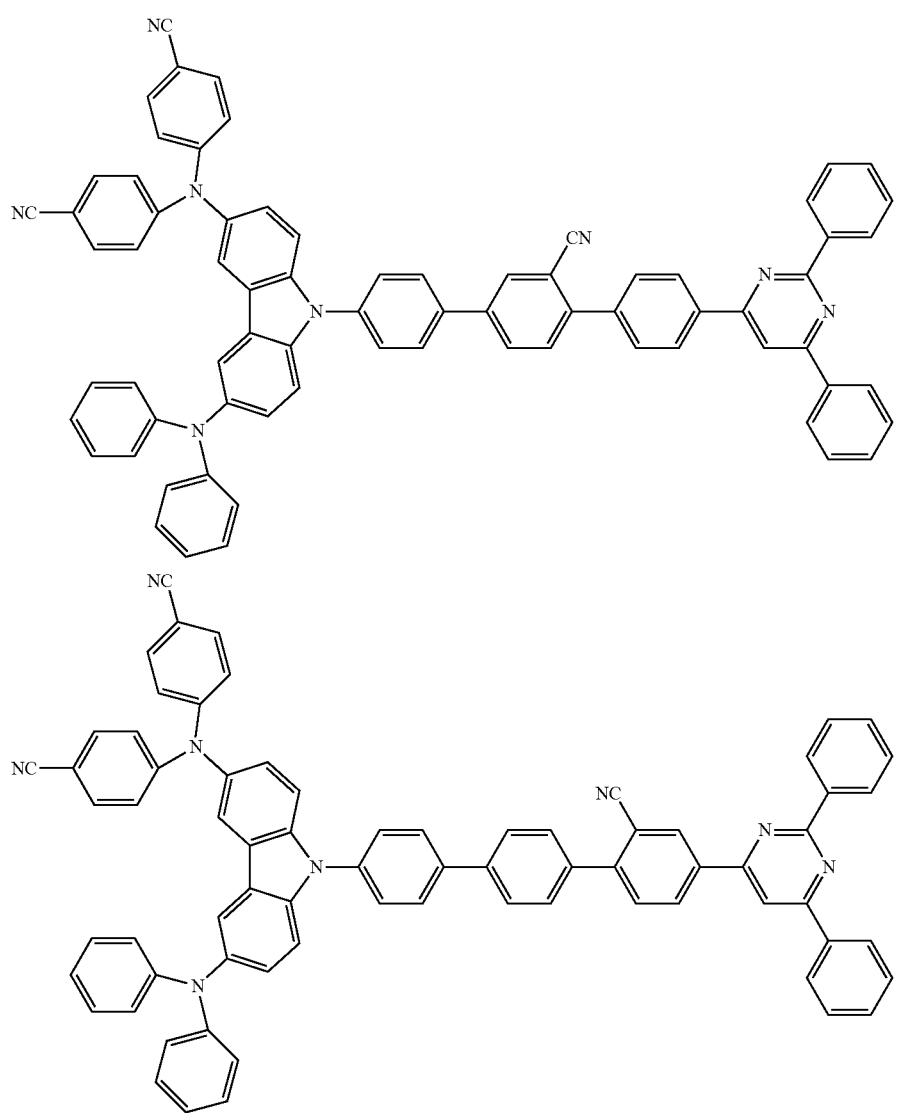

-continued
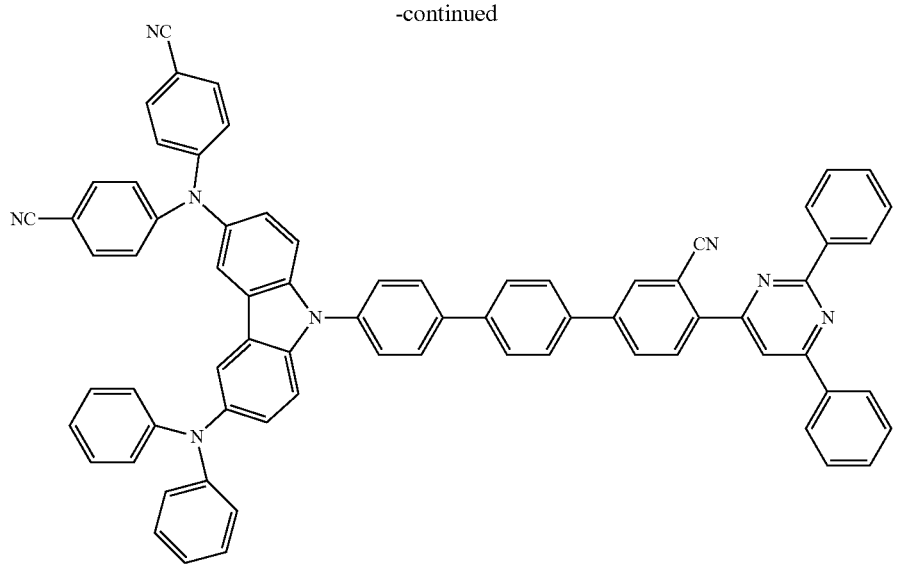
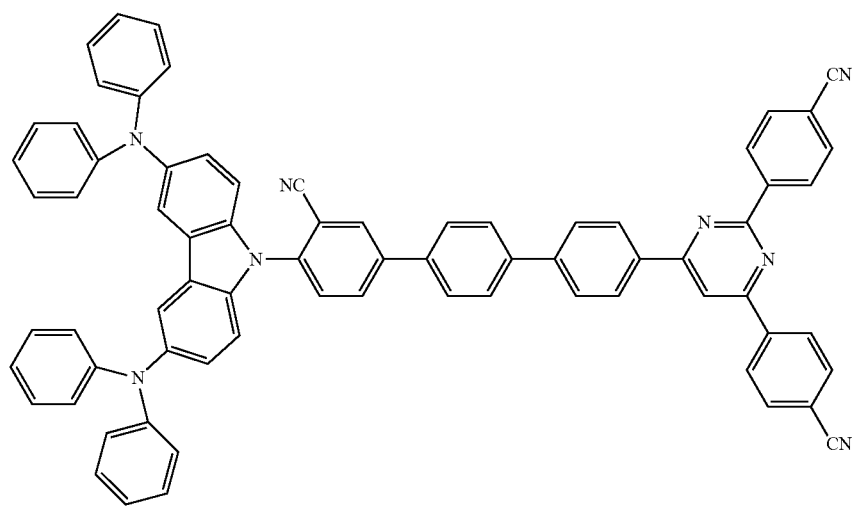
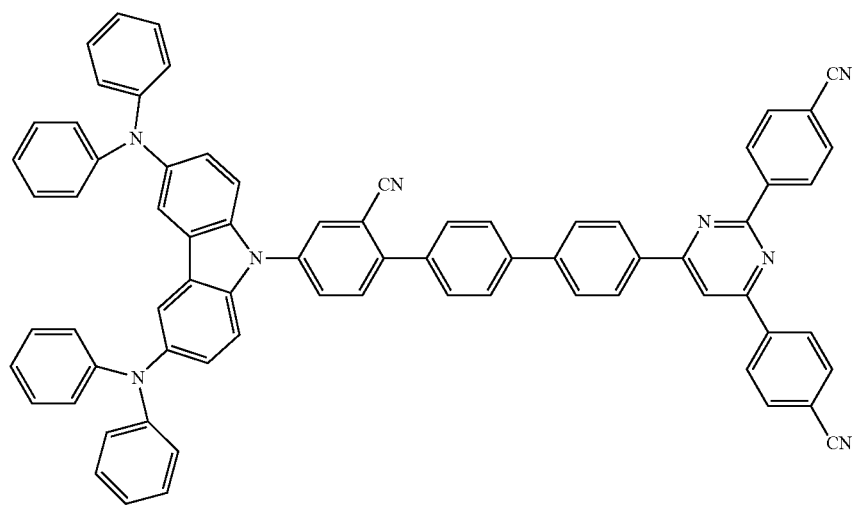

-continued
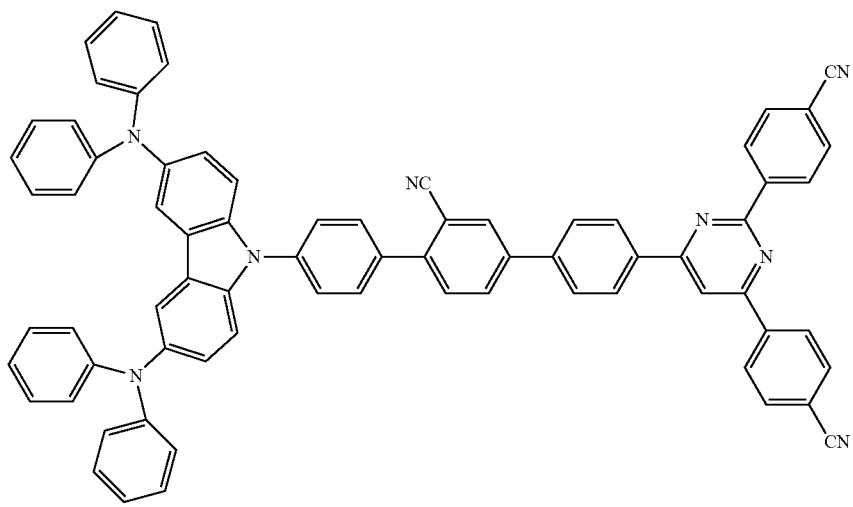
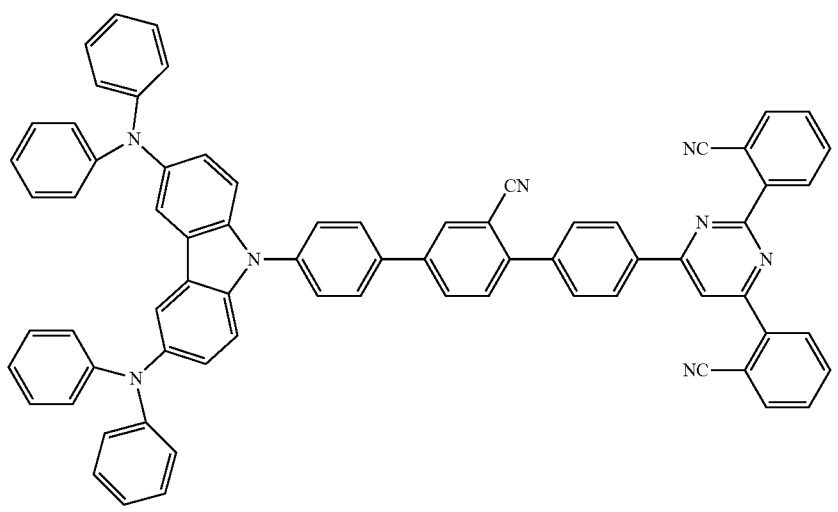
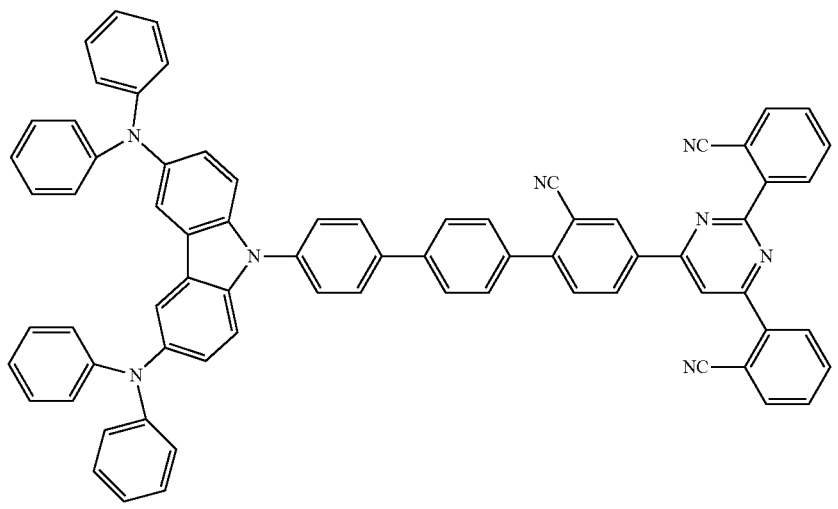

-continued
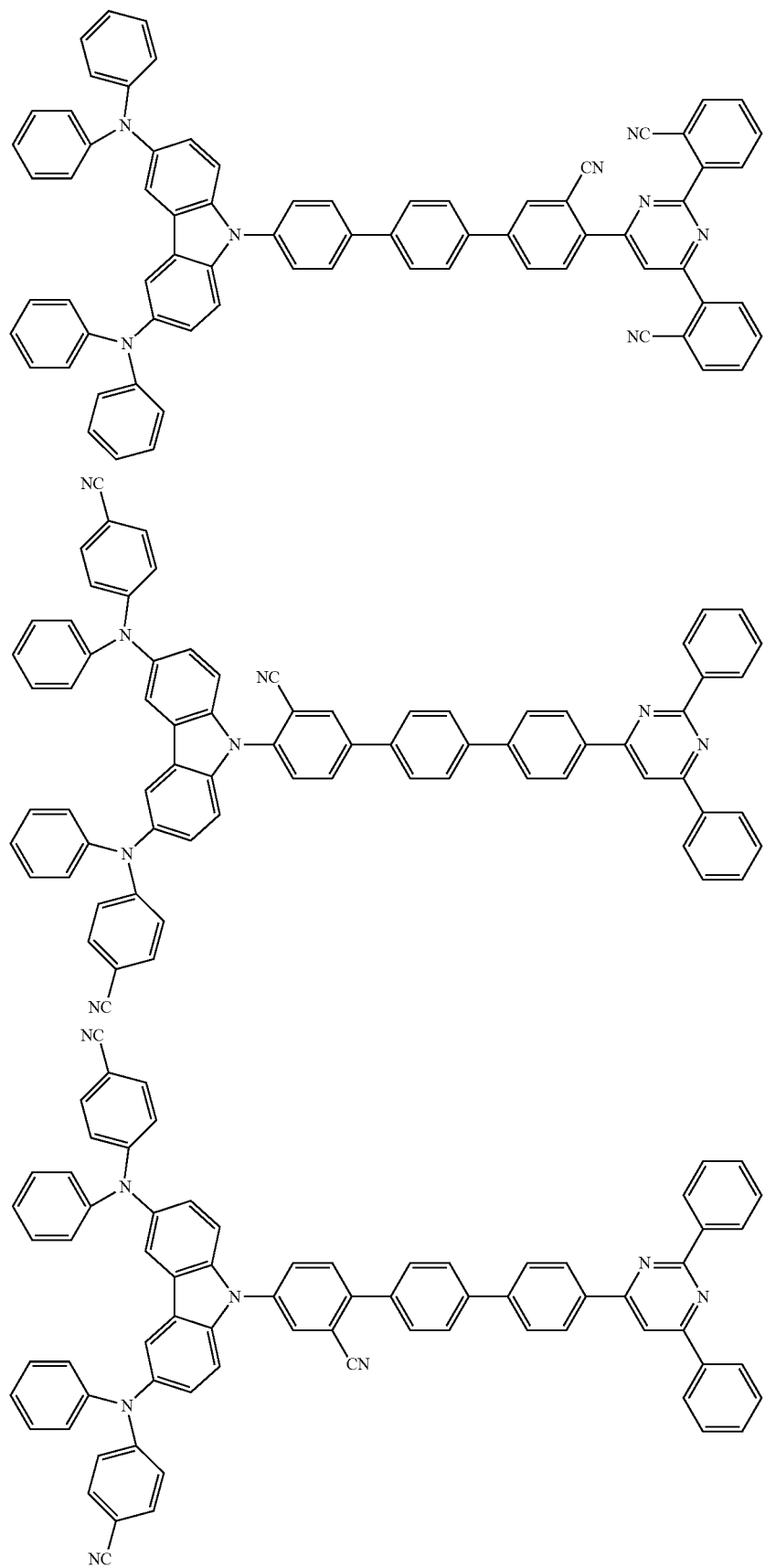

-continued
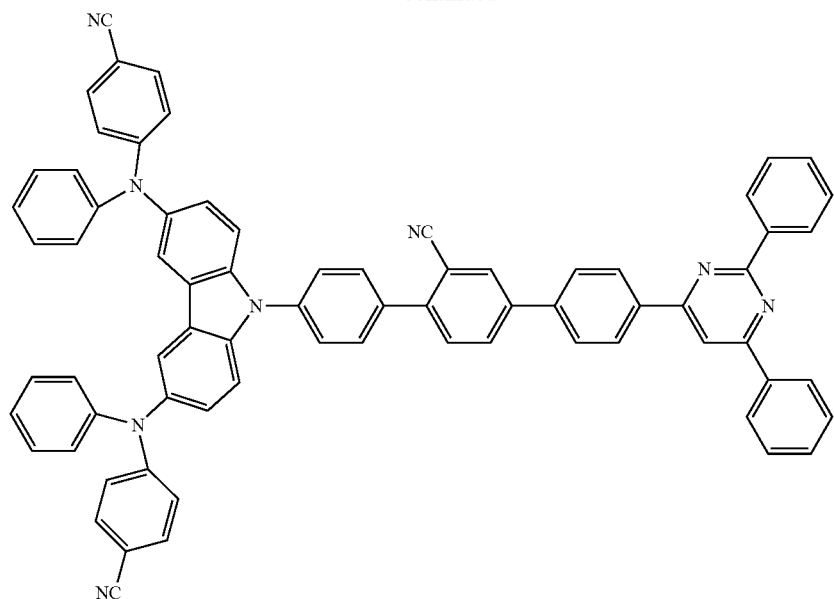
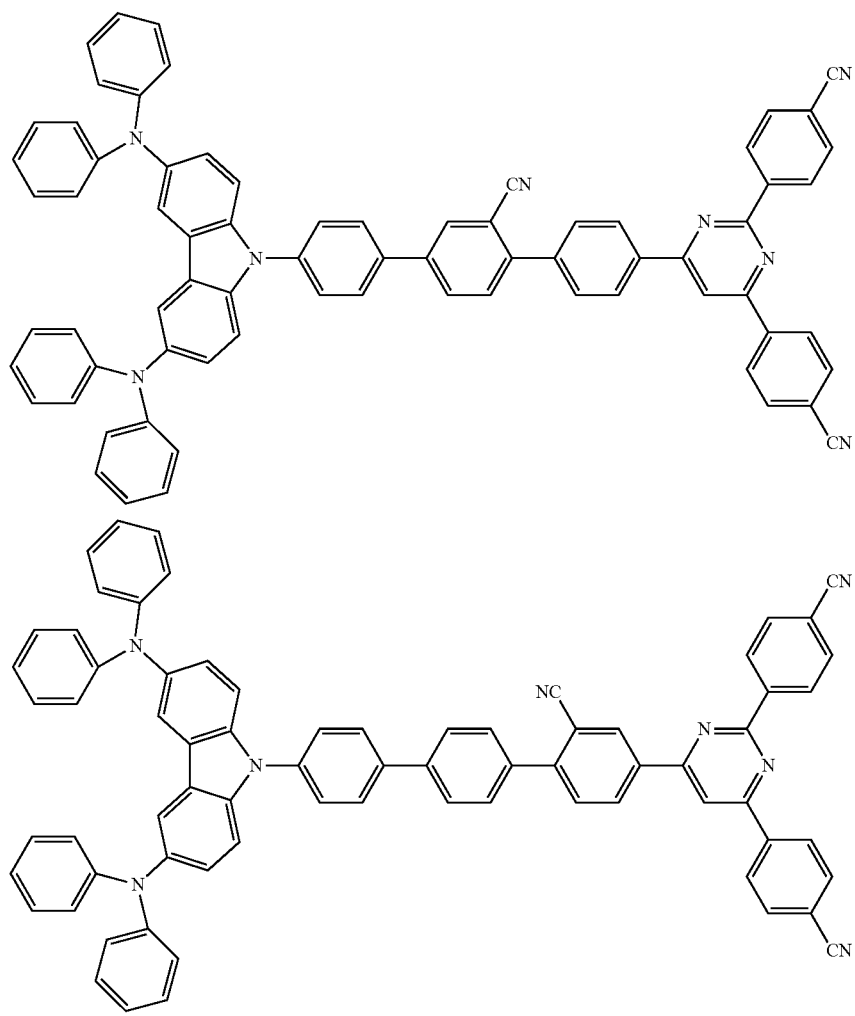

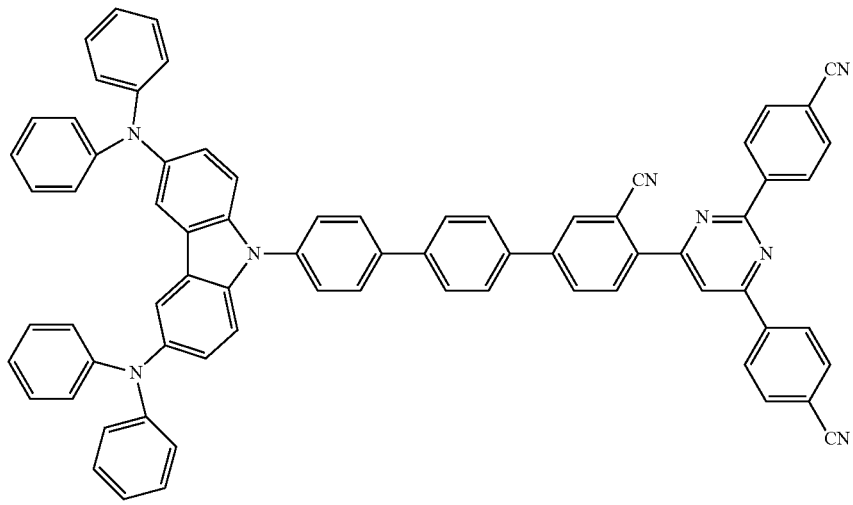
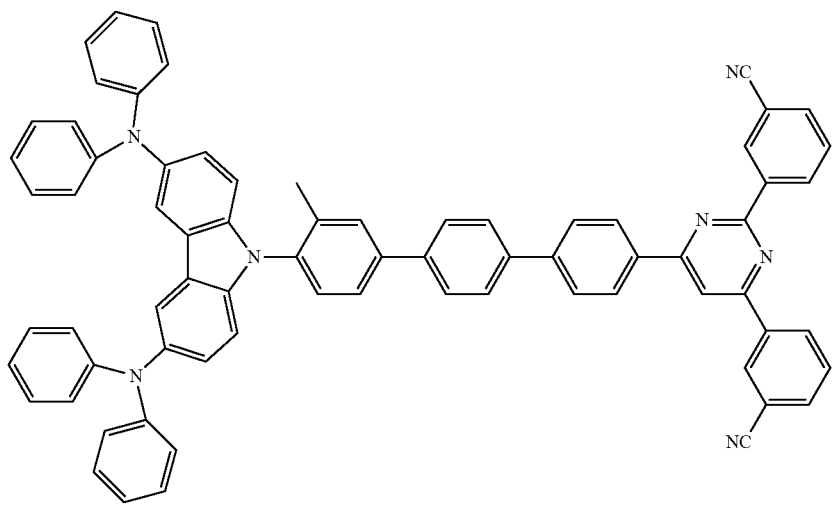
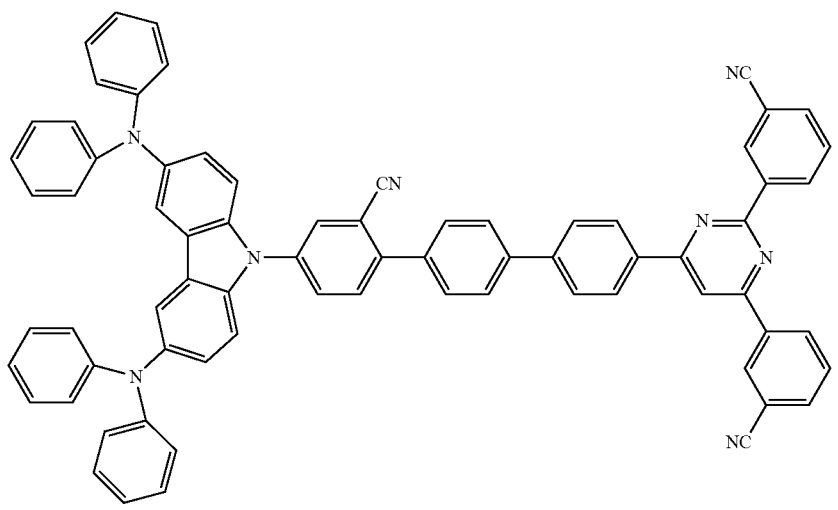

-continued
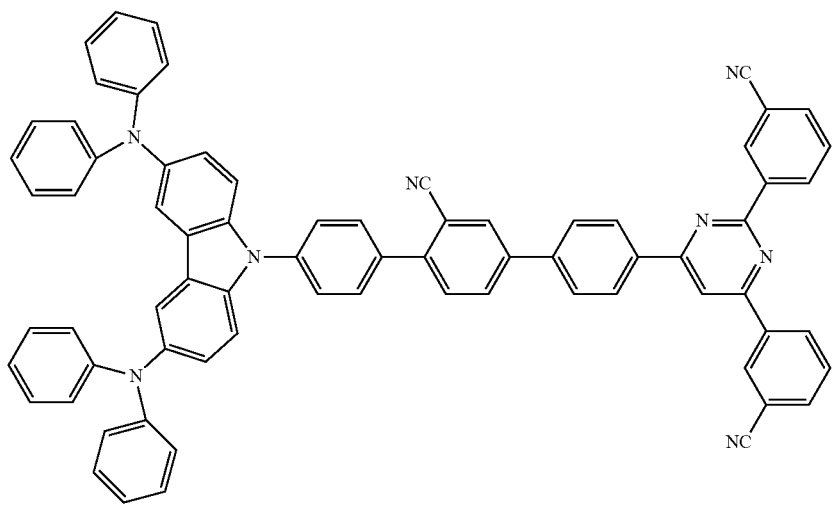
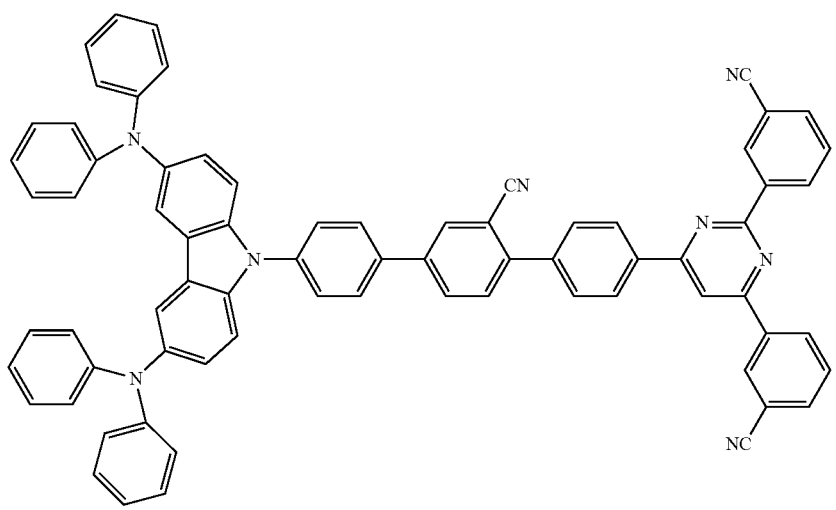
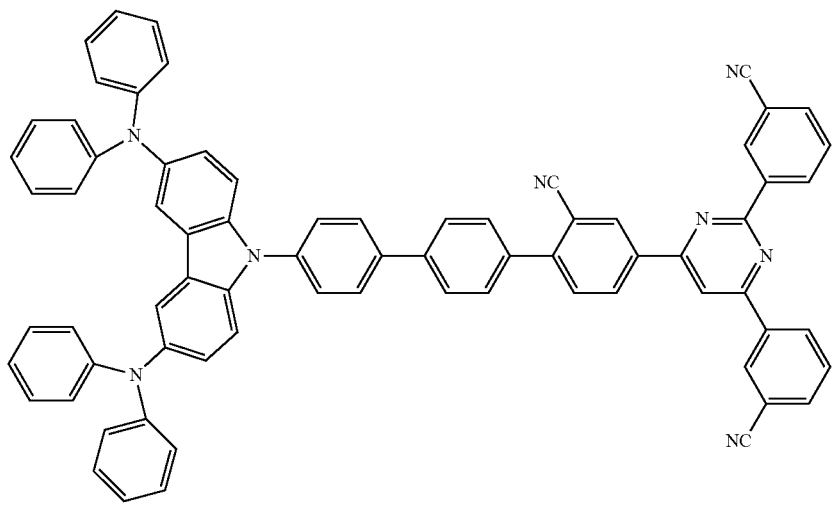

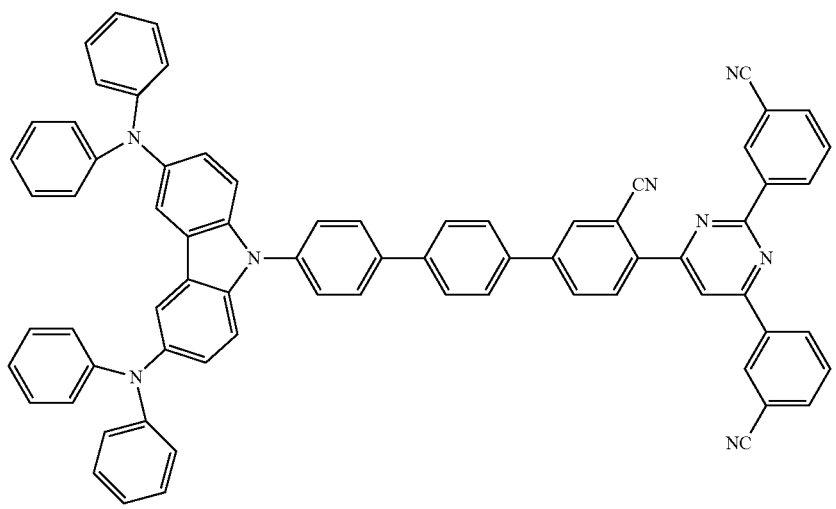
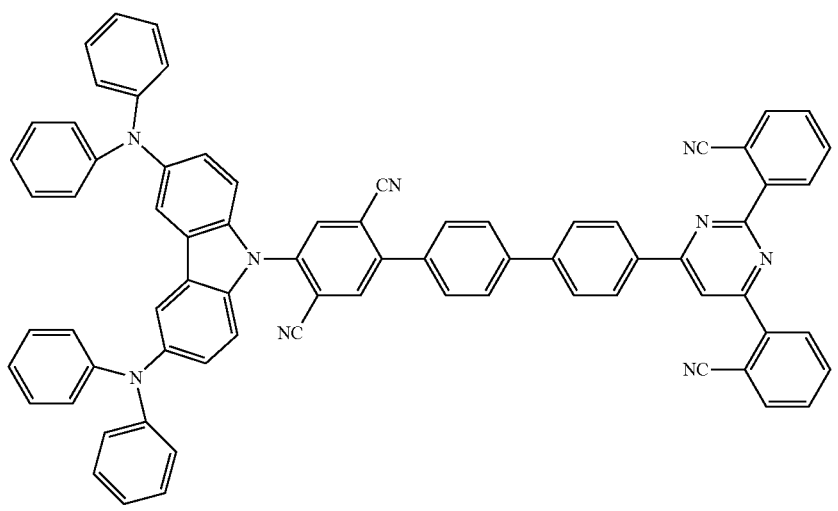
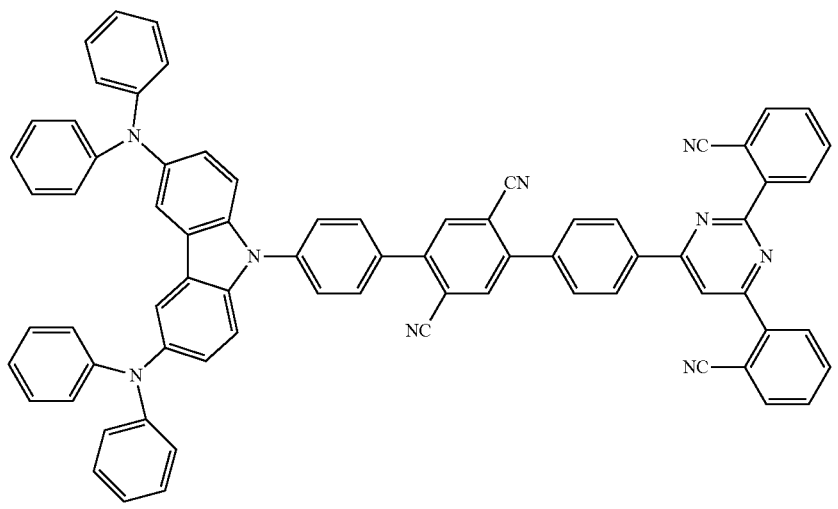

-continued
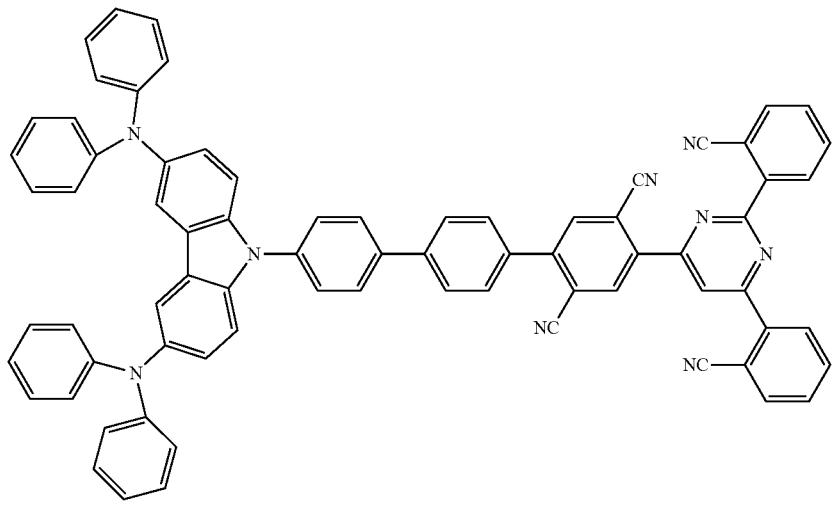
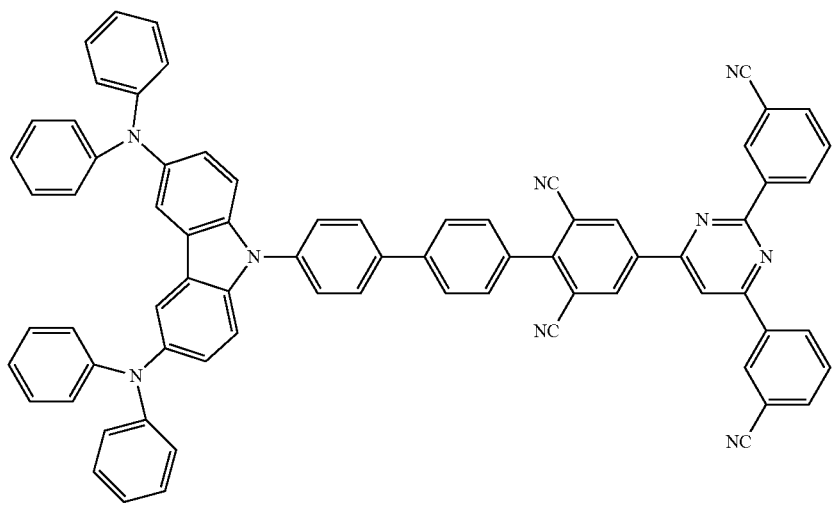
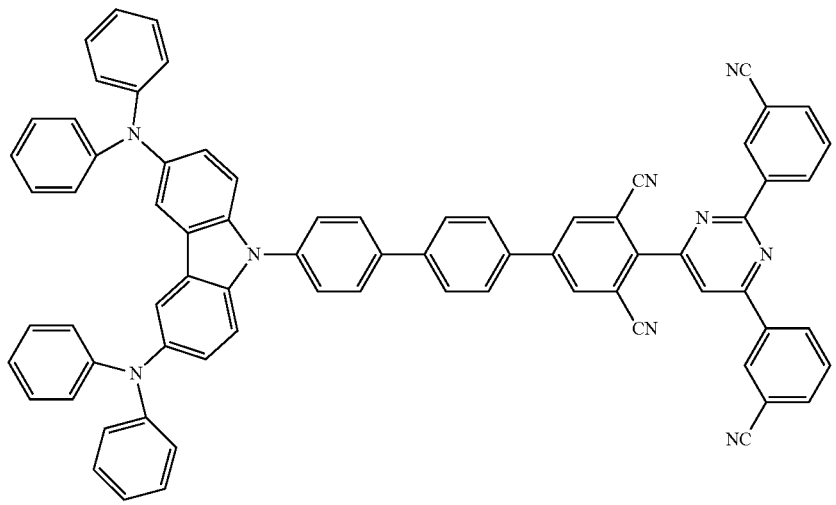

-continued
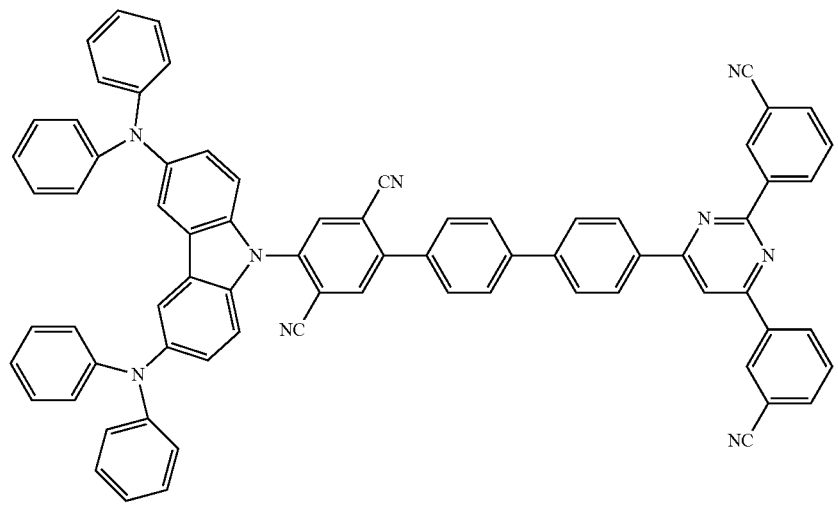
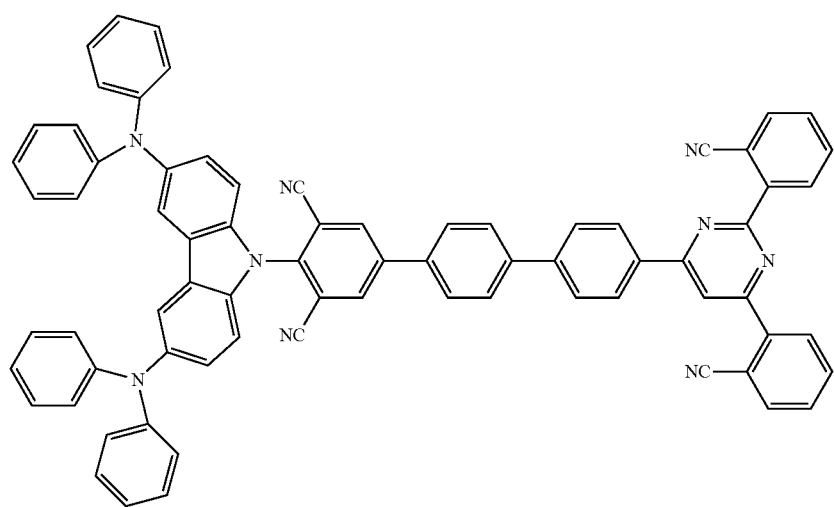
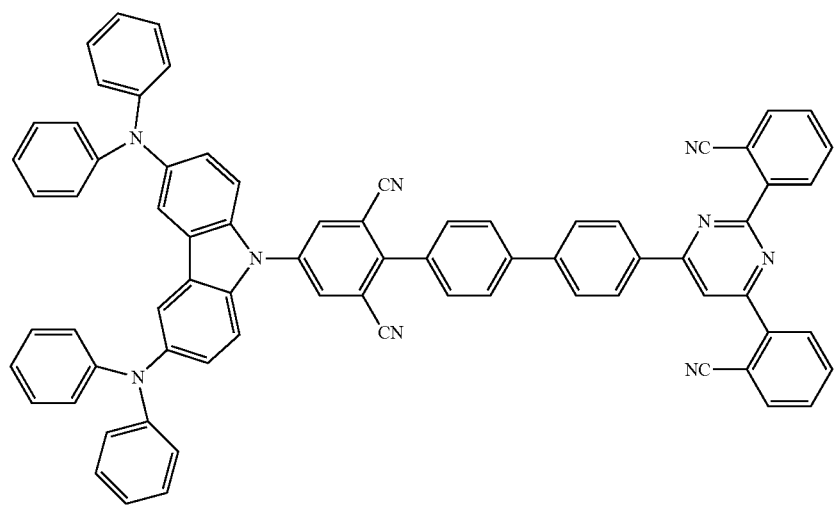

-continued
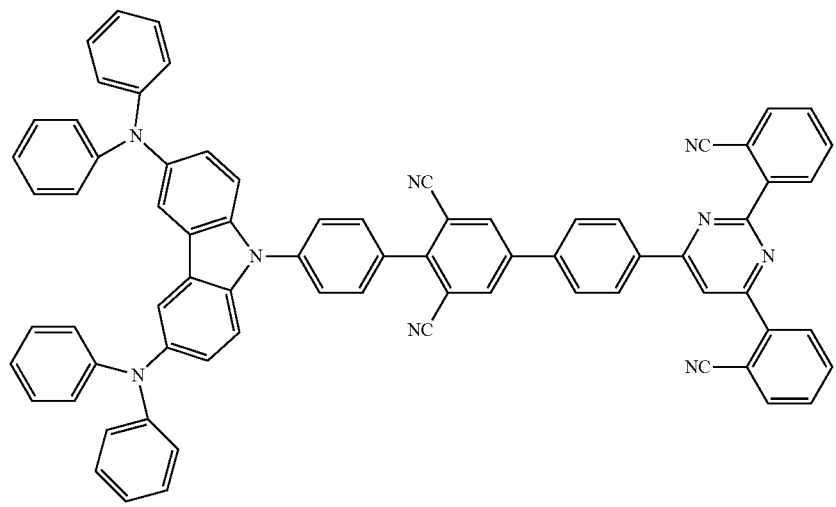
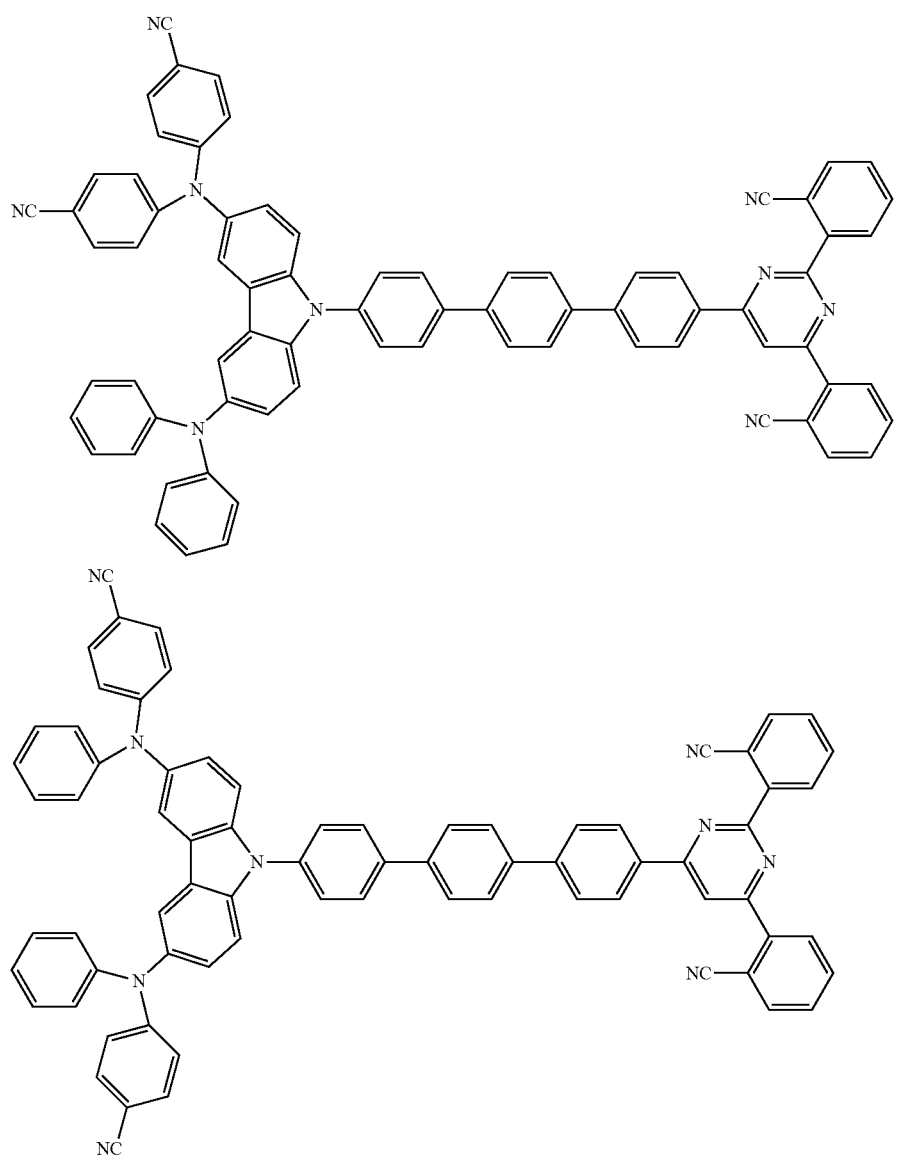

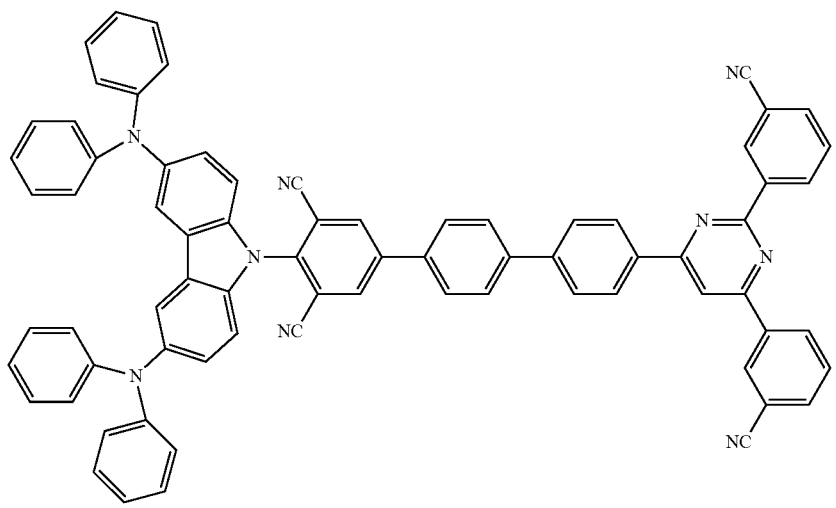
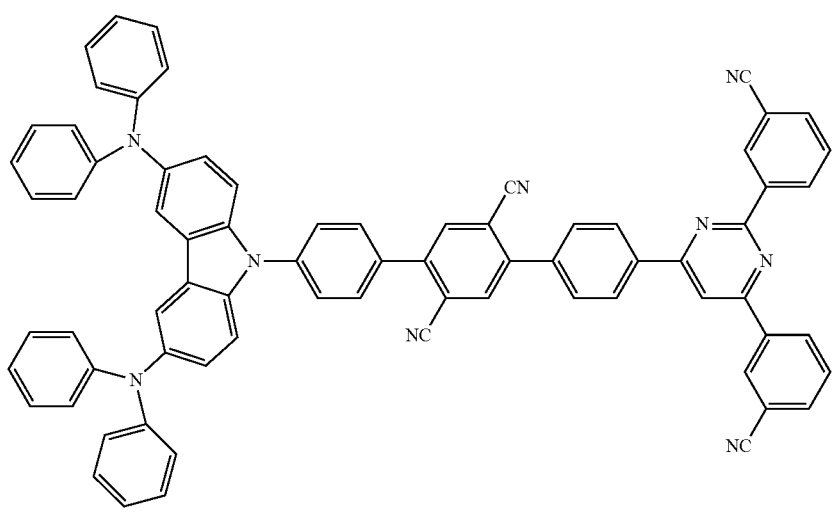
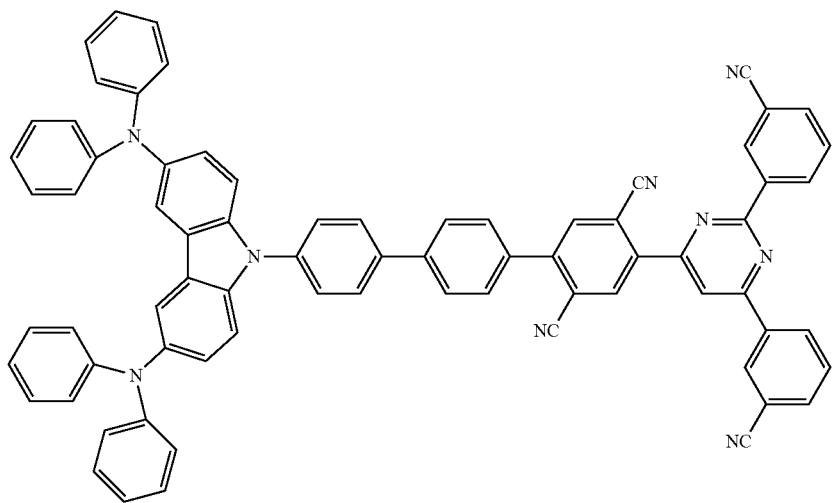

-continued
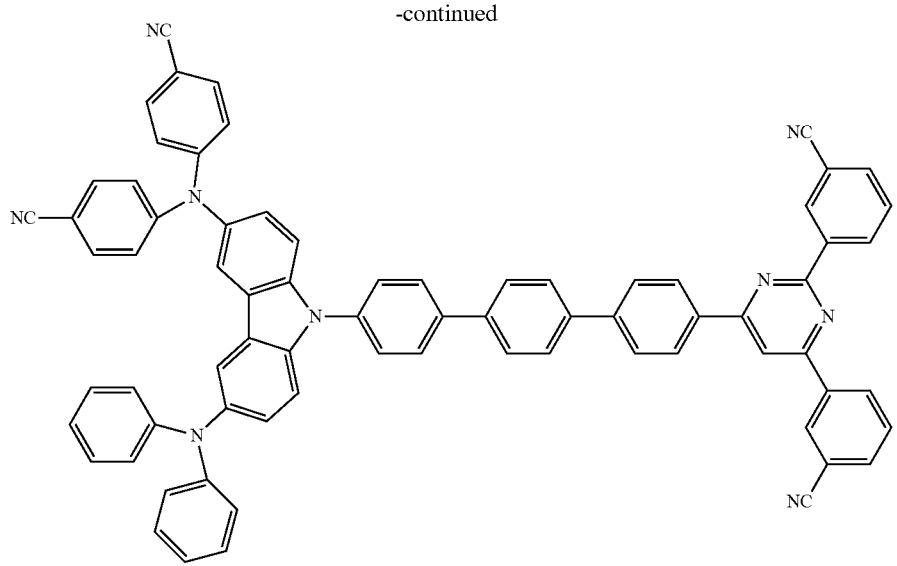
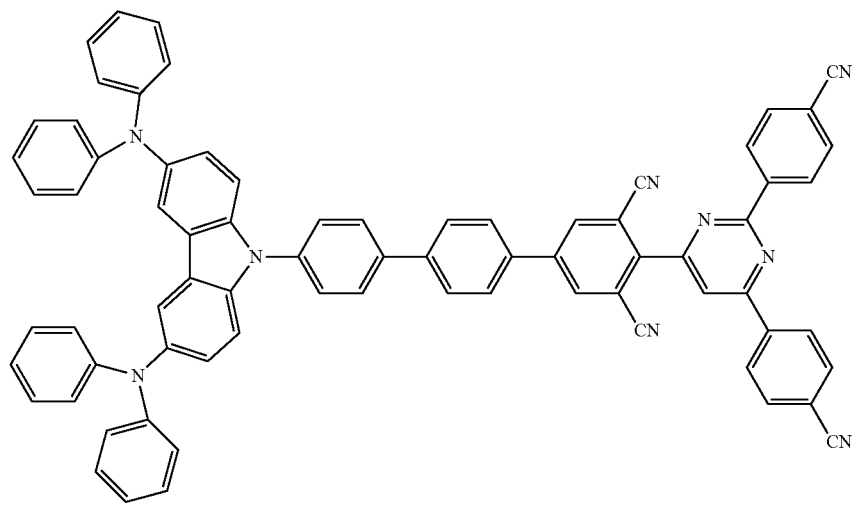
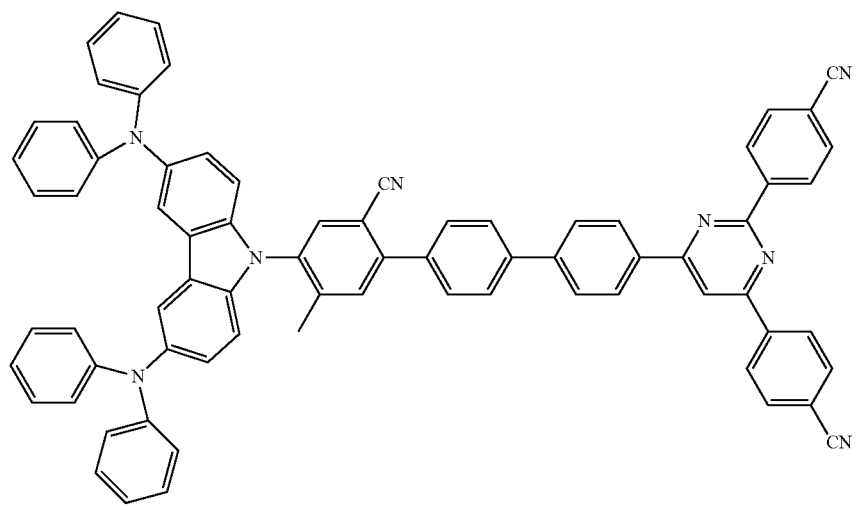

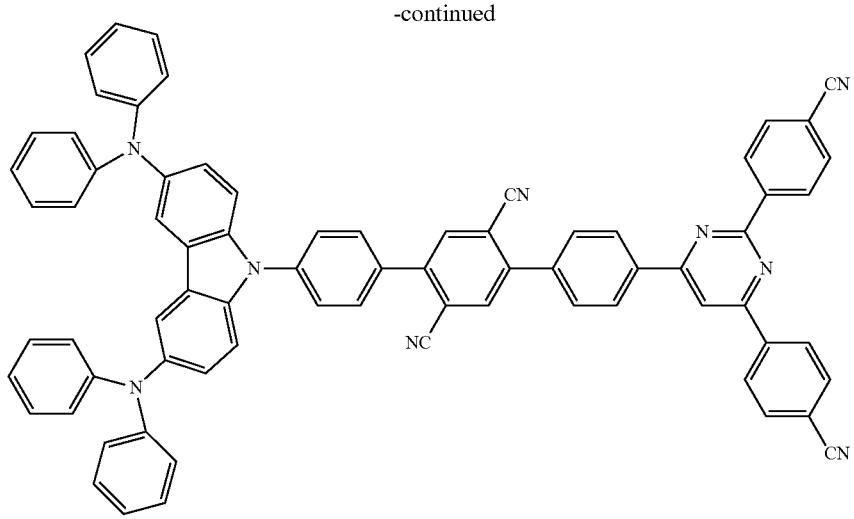
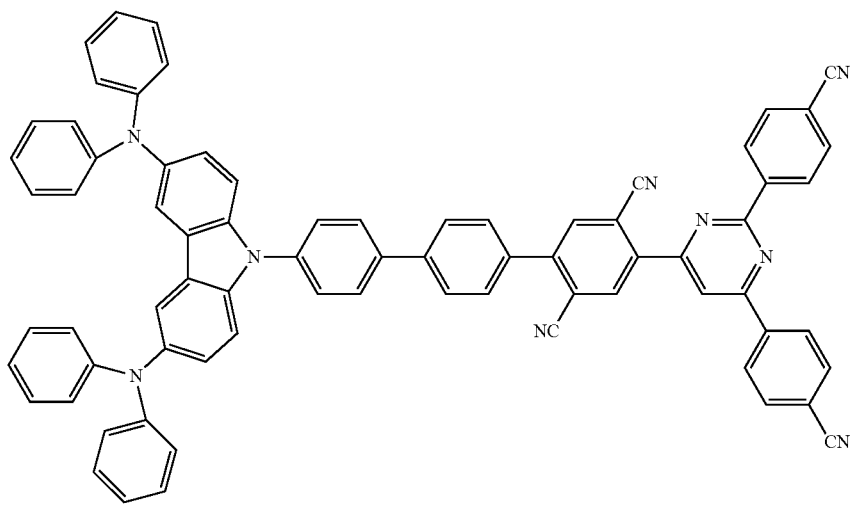
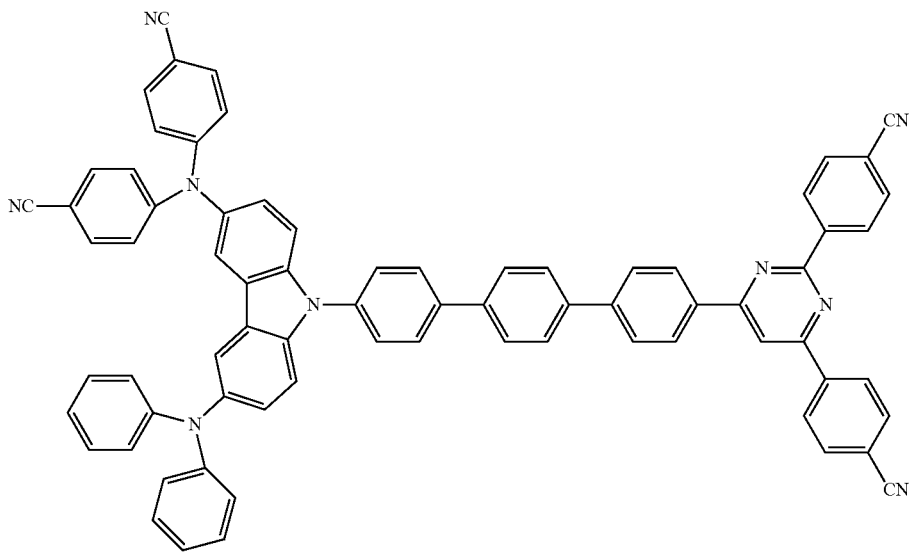

-continued
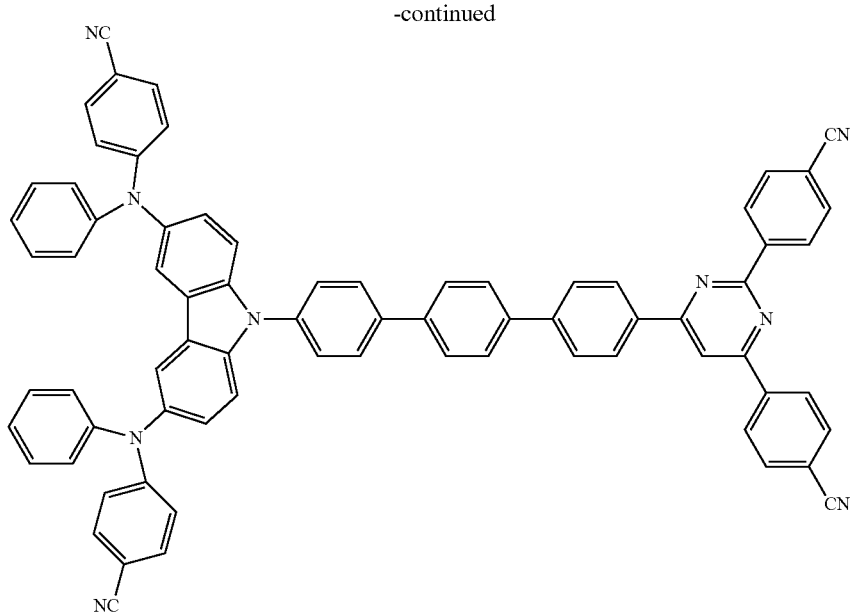
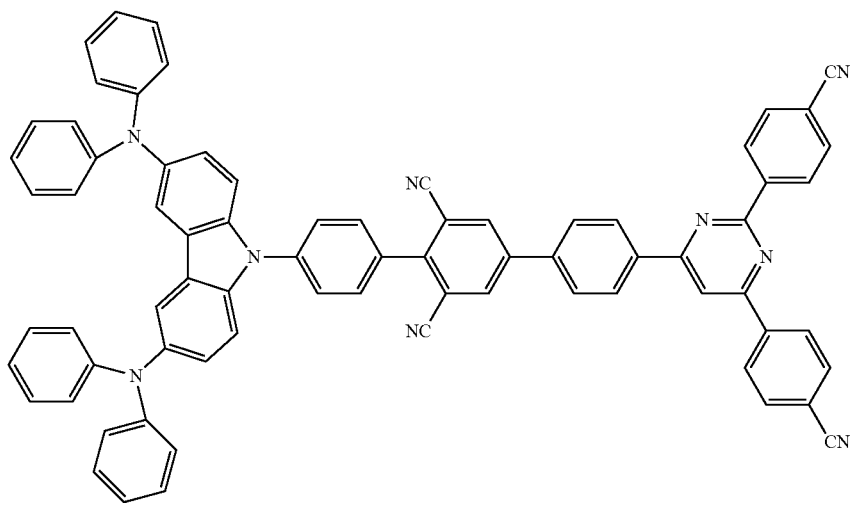

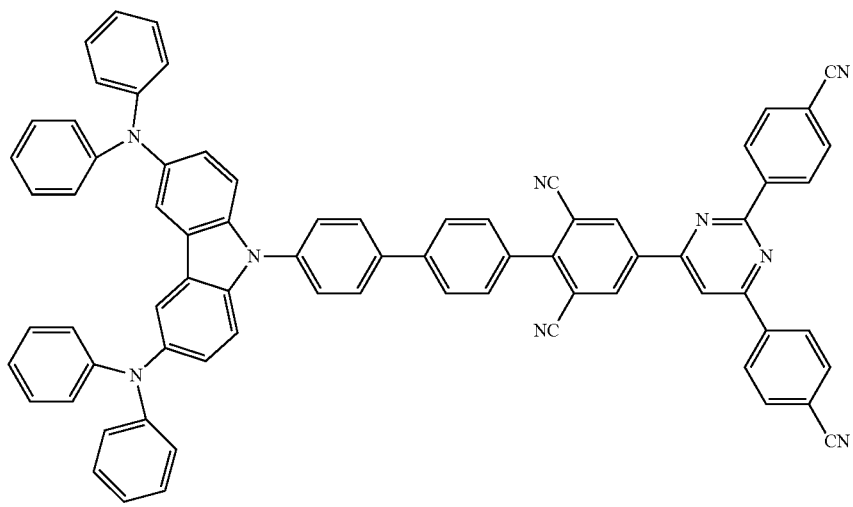
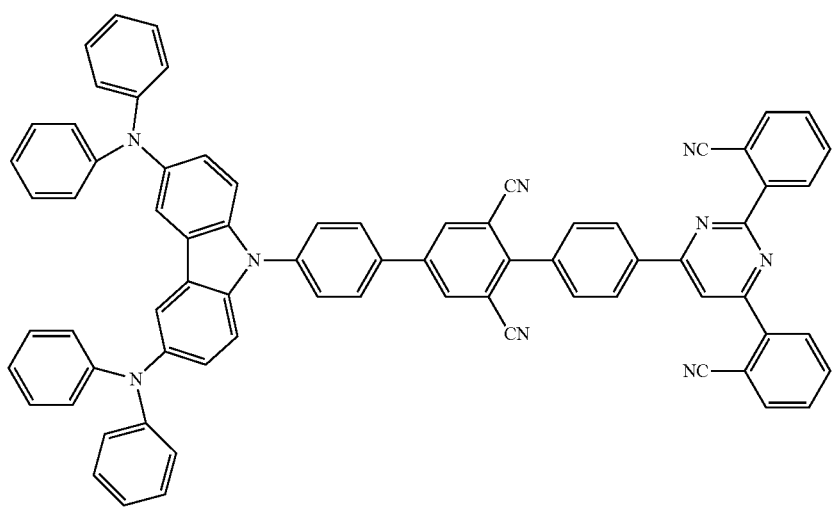
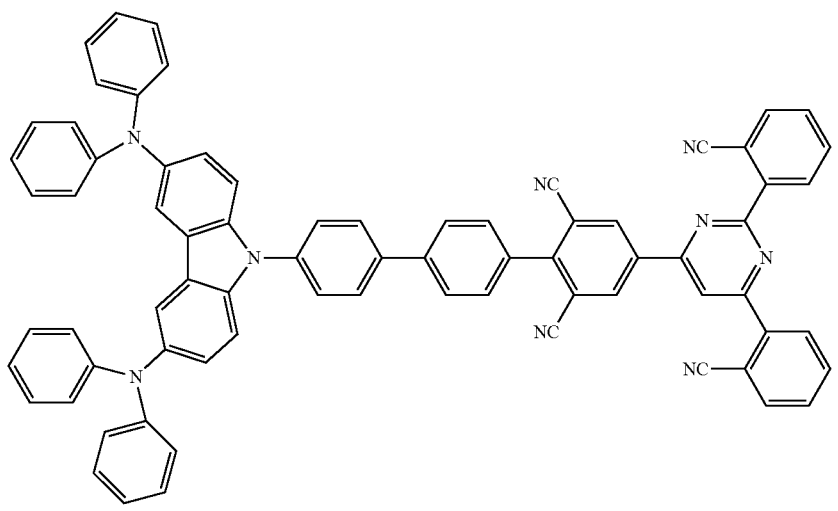

-continued
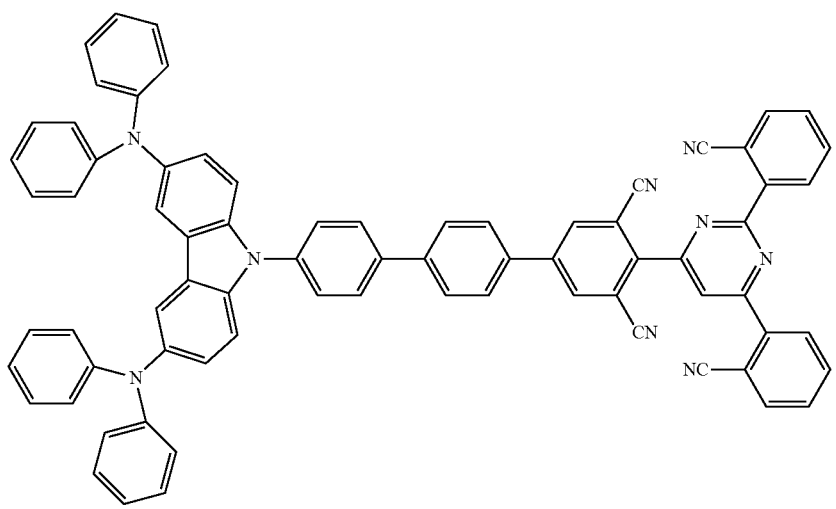
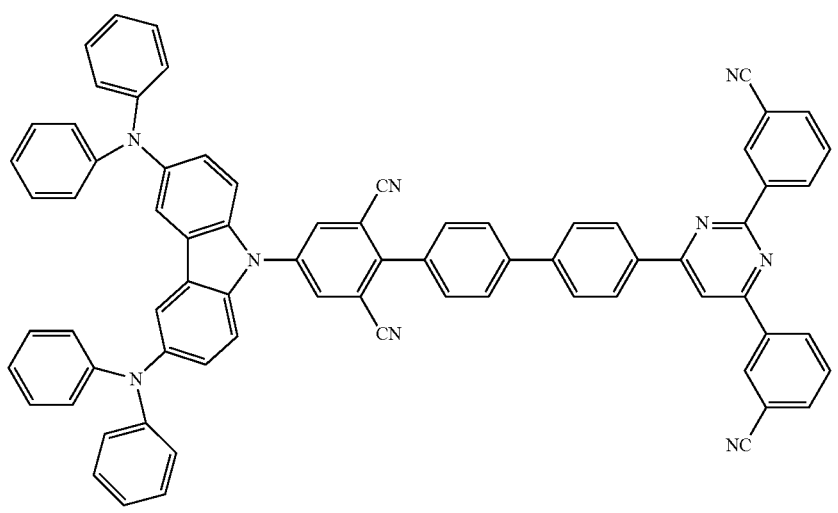
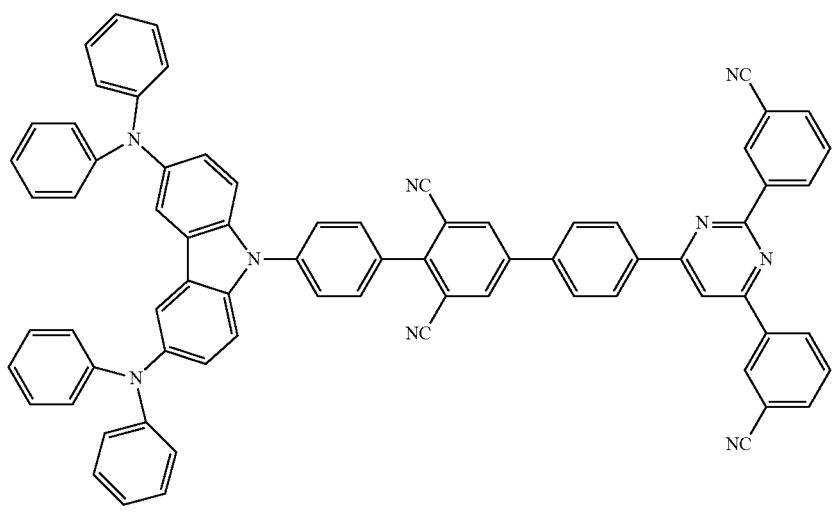

-continued
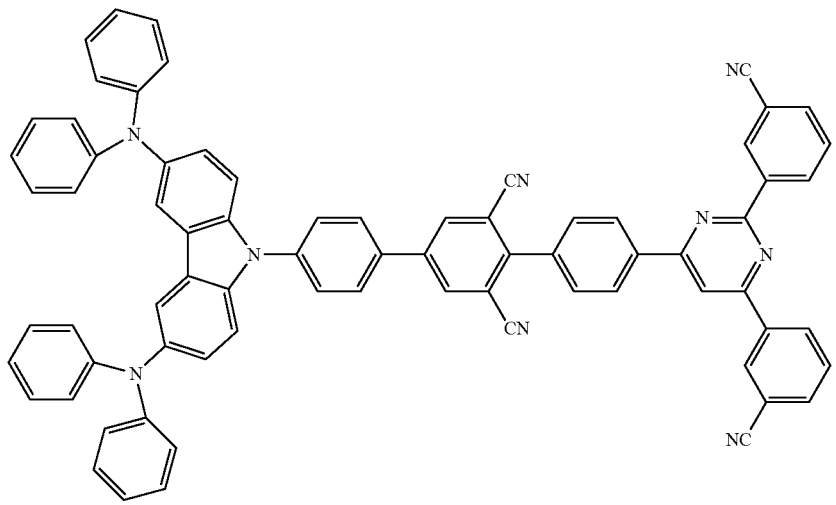
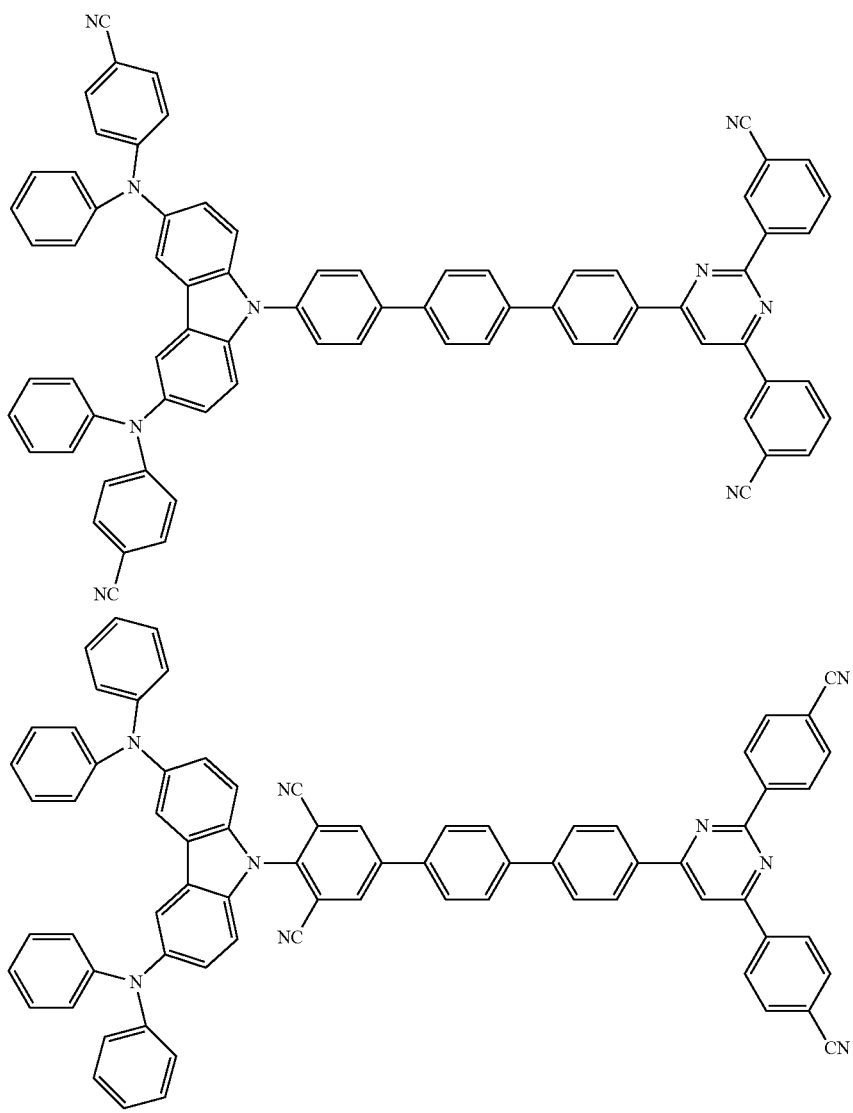

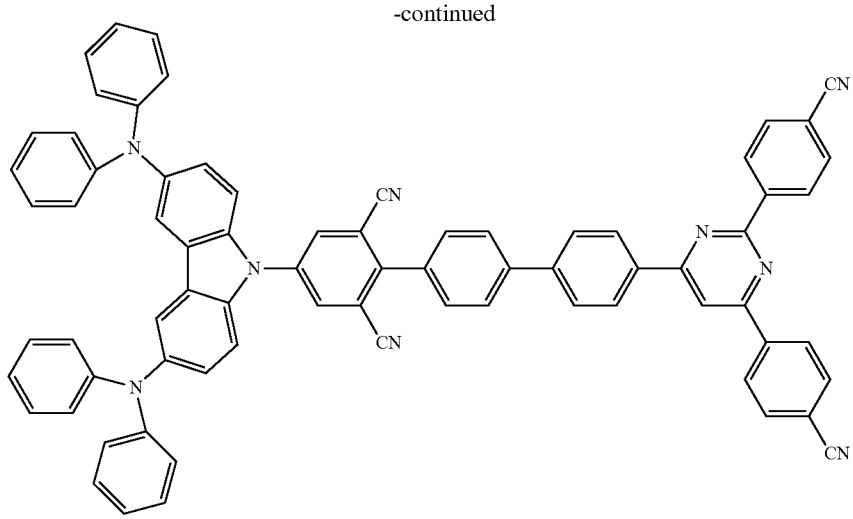
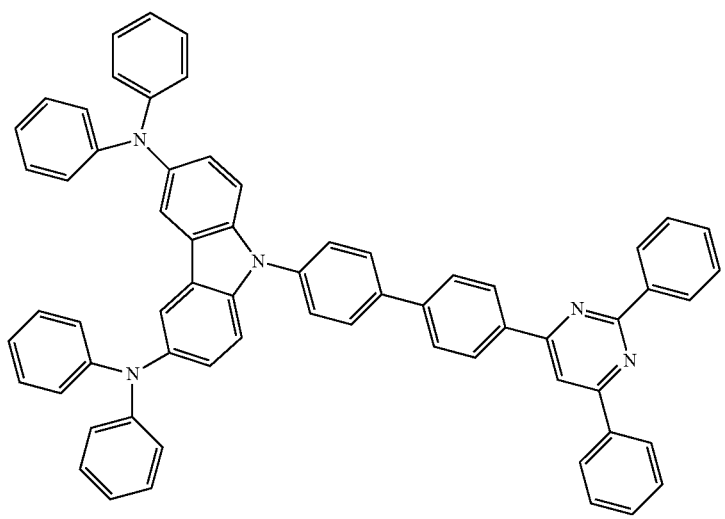
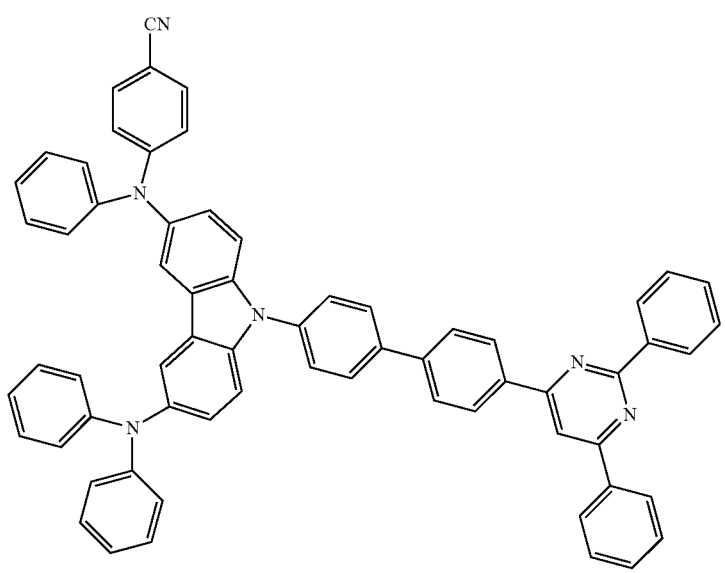

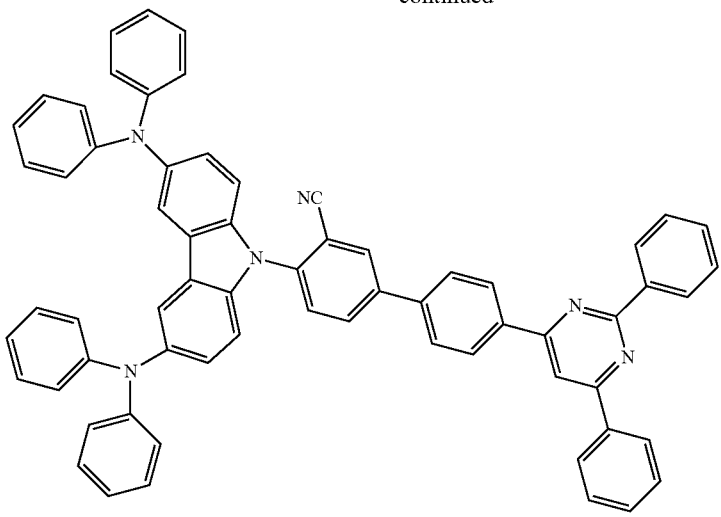
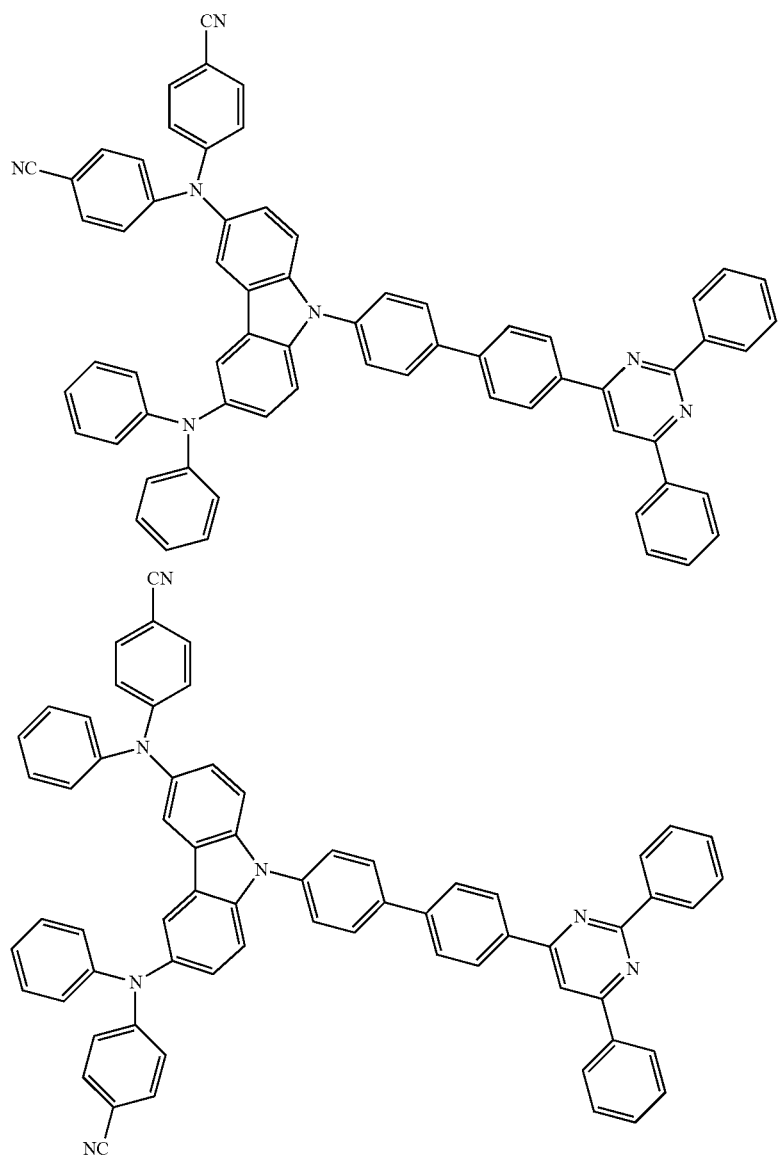

-continued
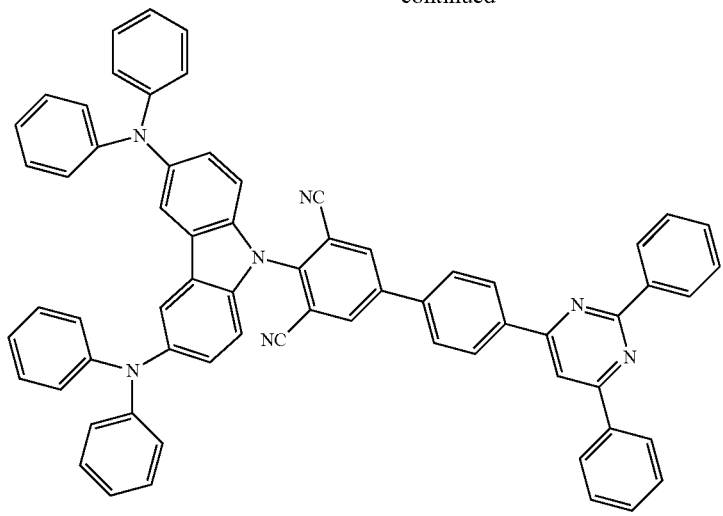
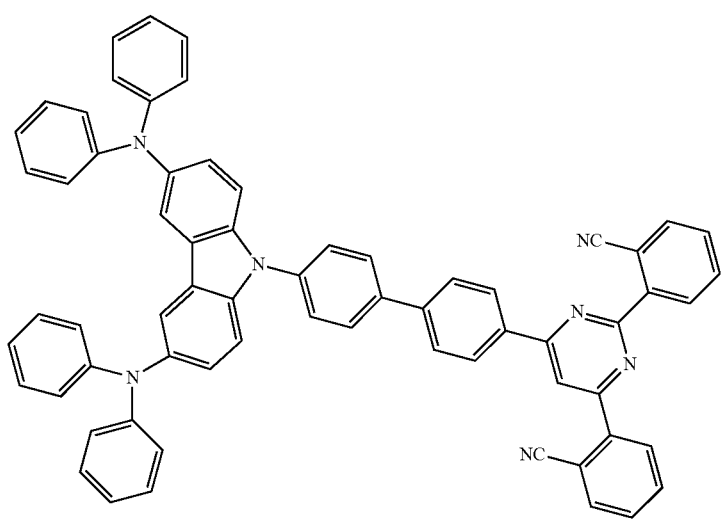
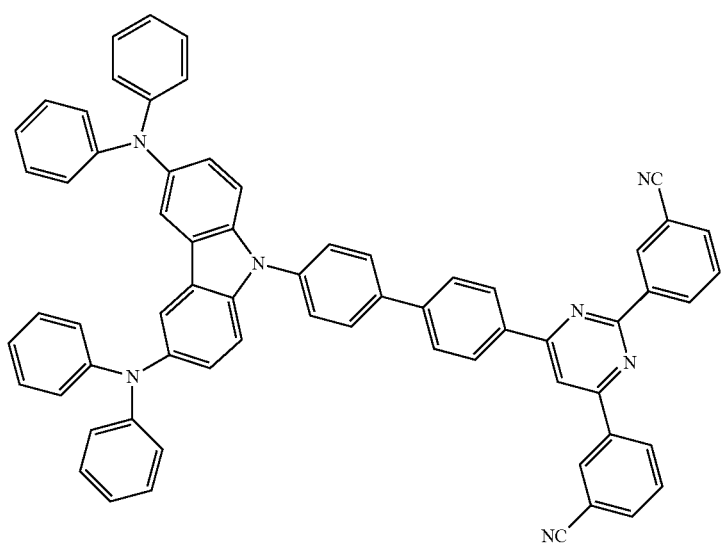

-continued
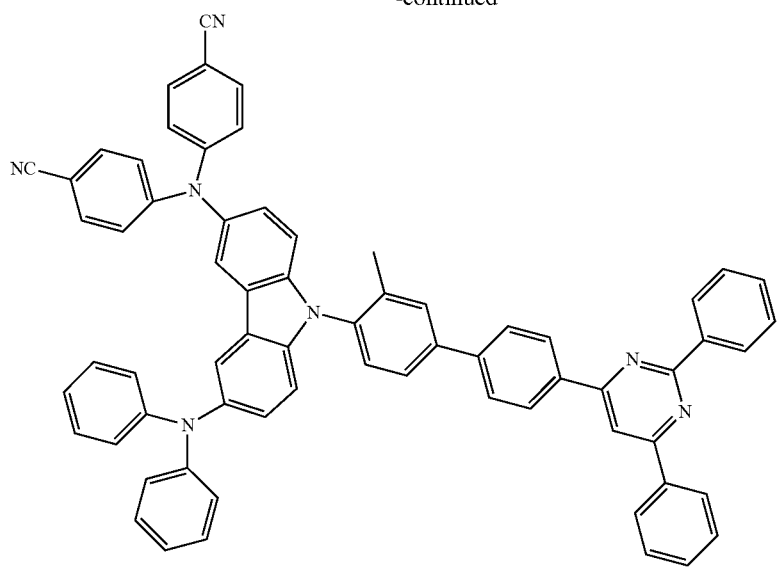
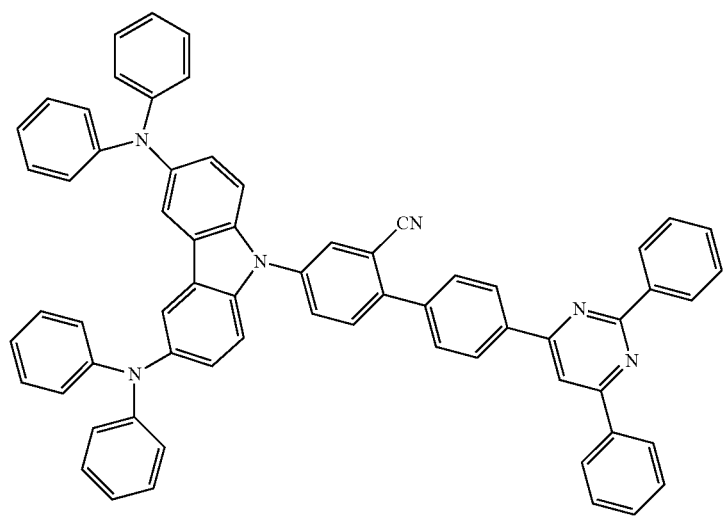
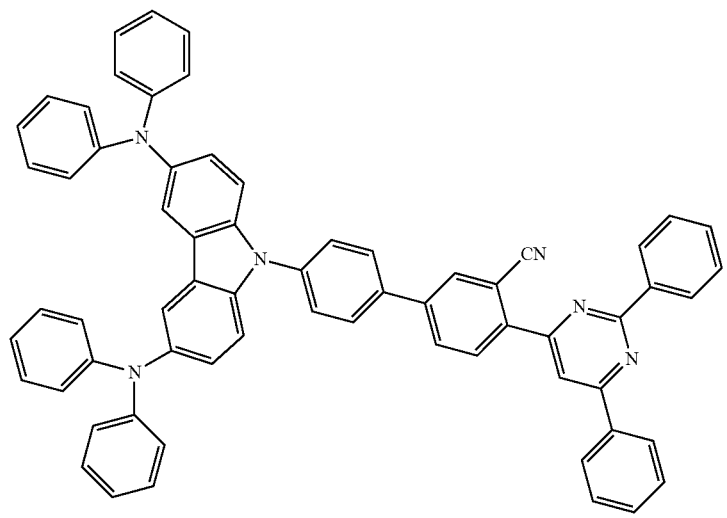

-continued
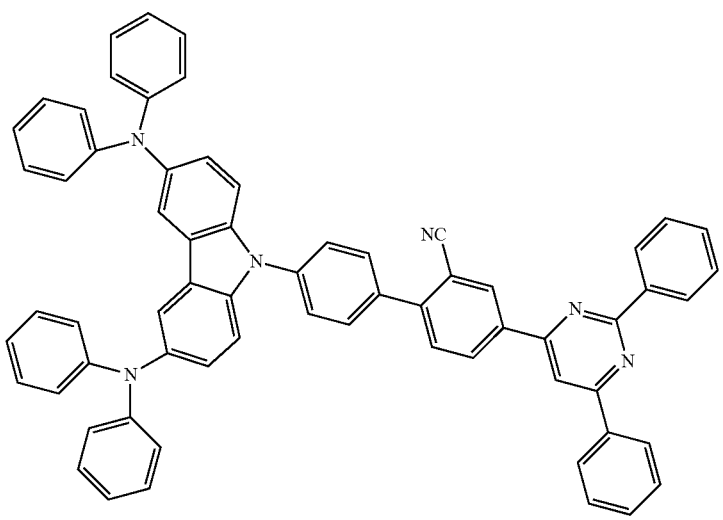
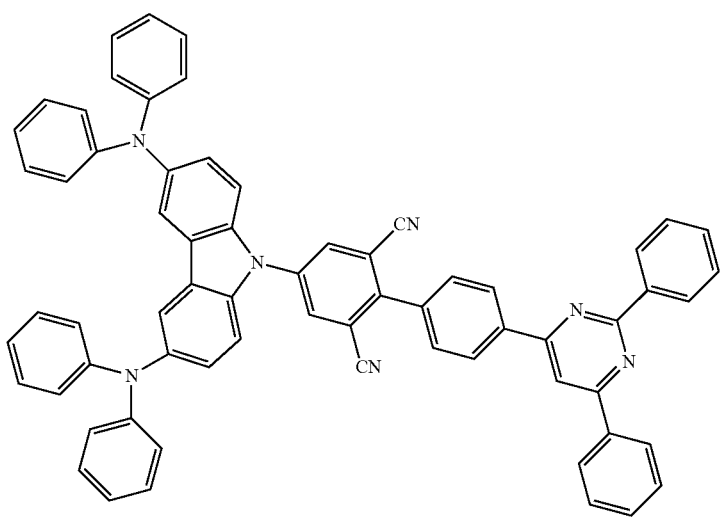
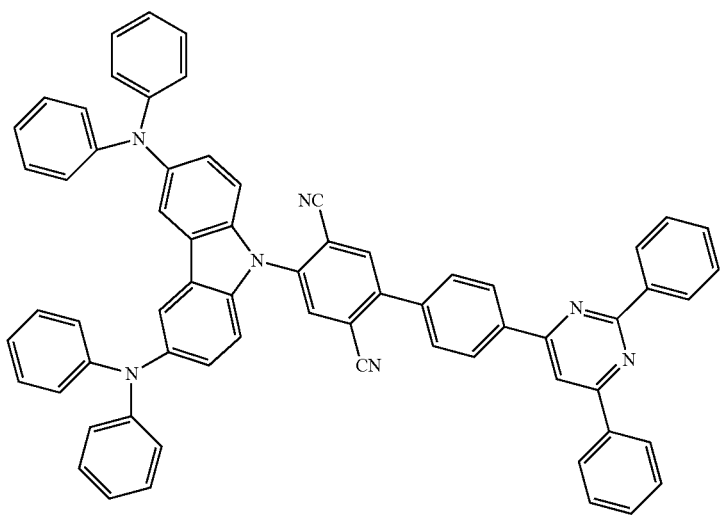

-continued
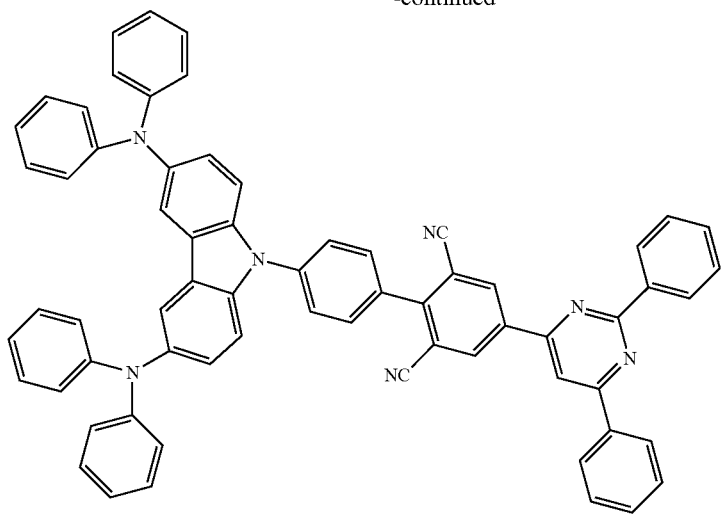
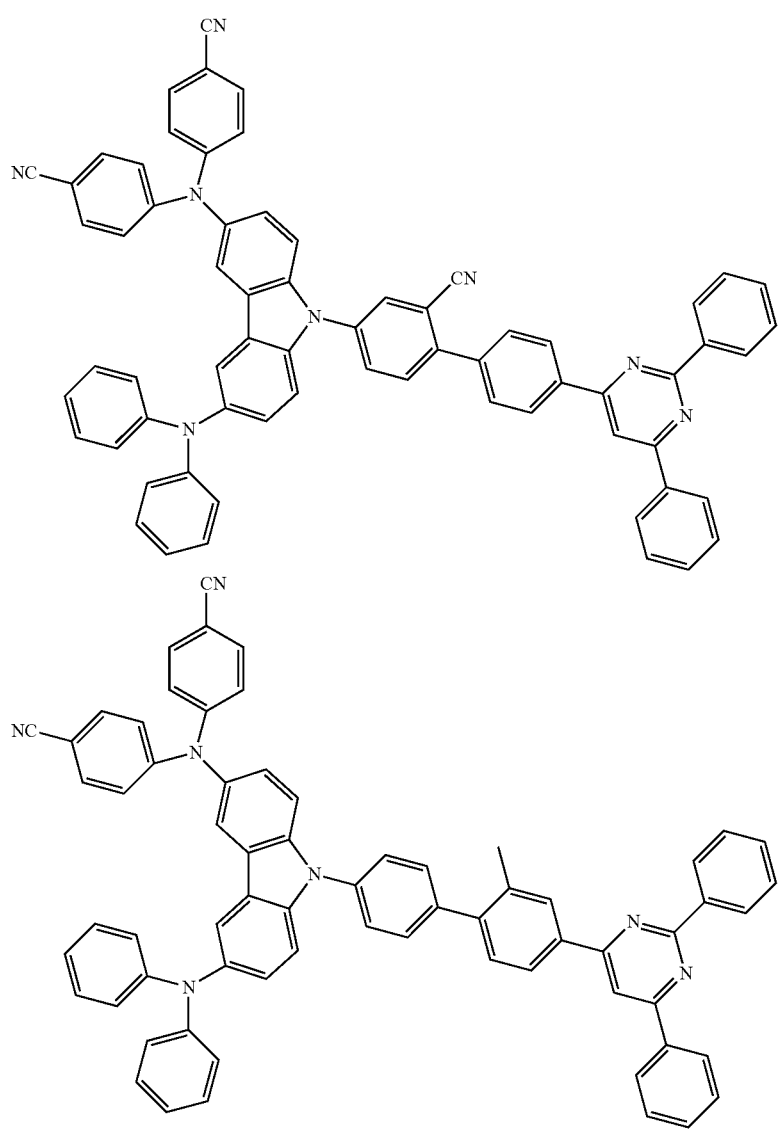

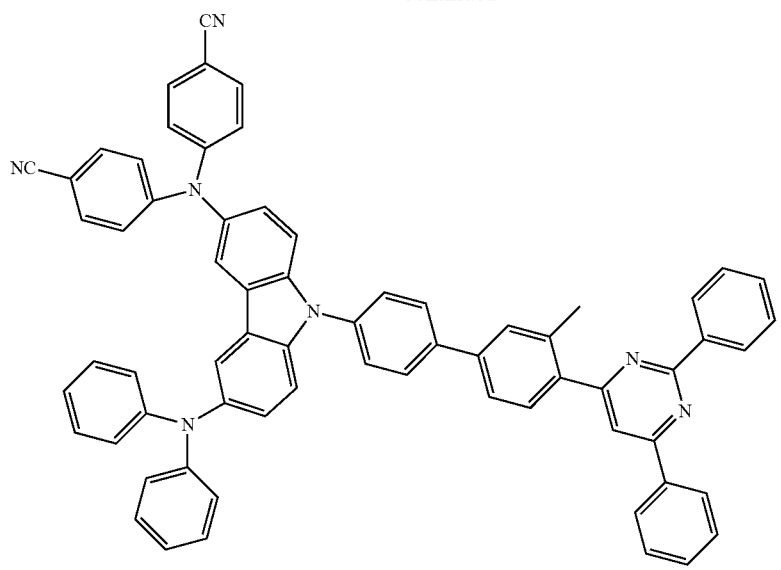
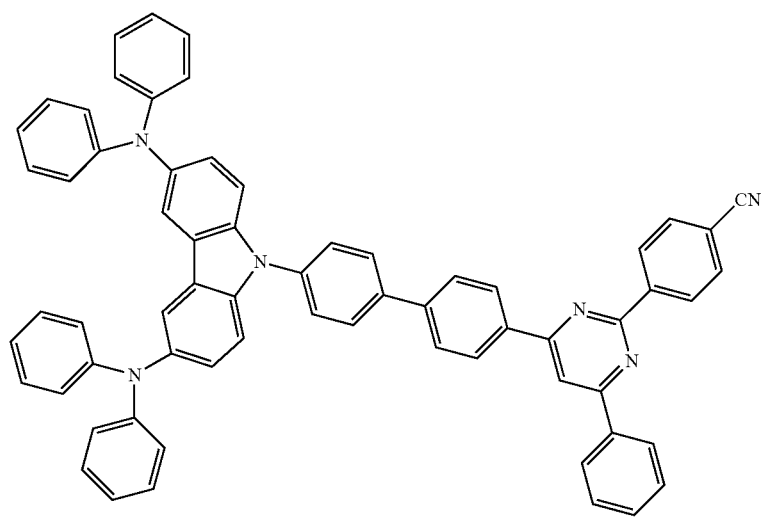
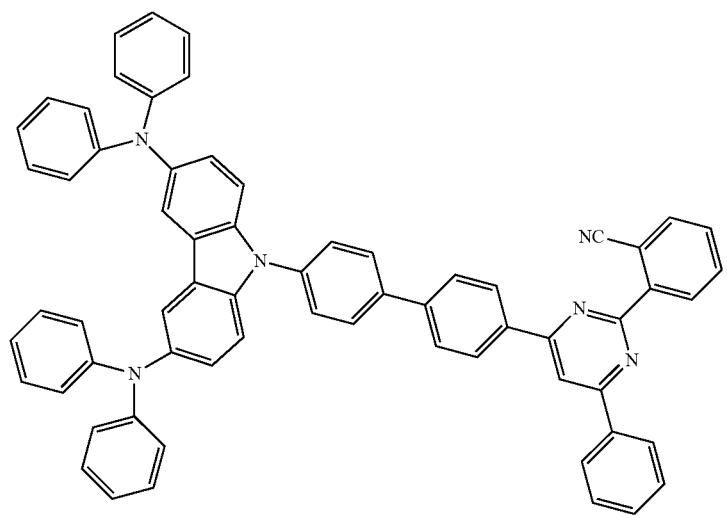

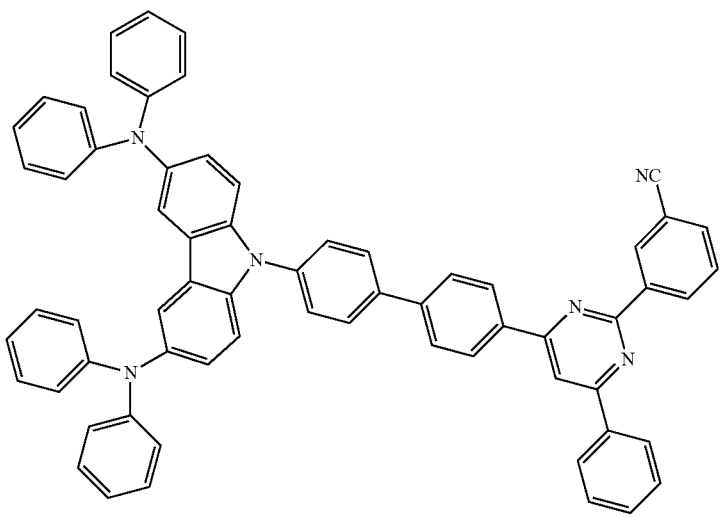
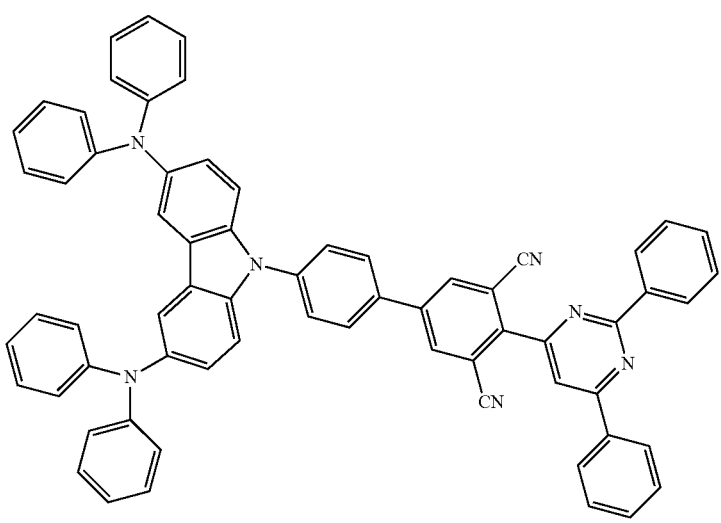
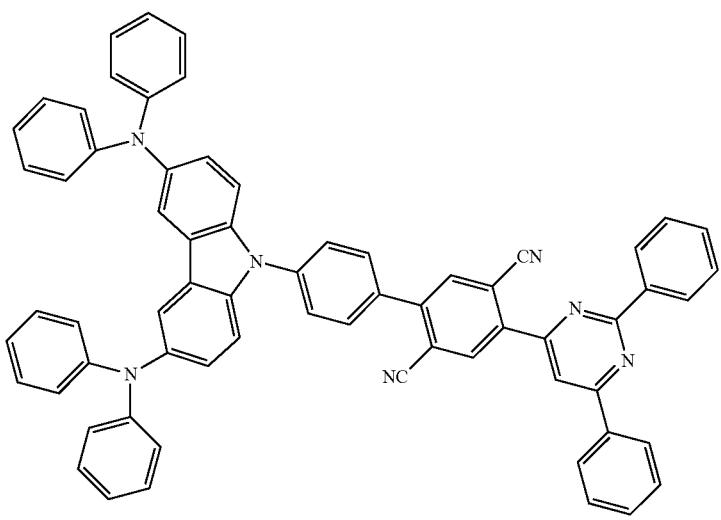

-continued
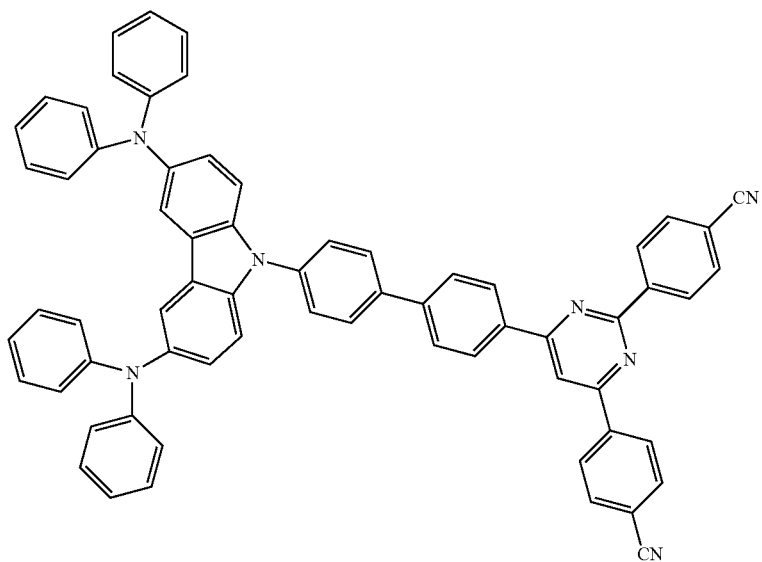
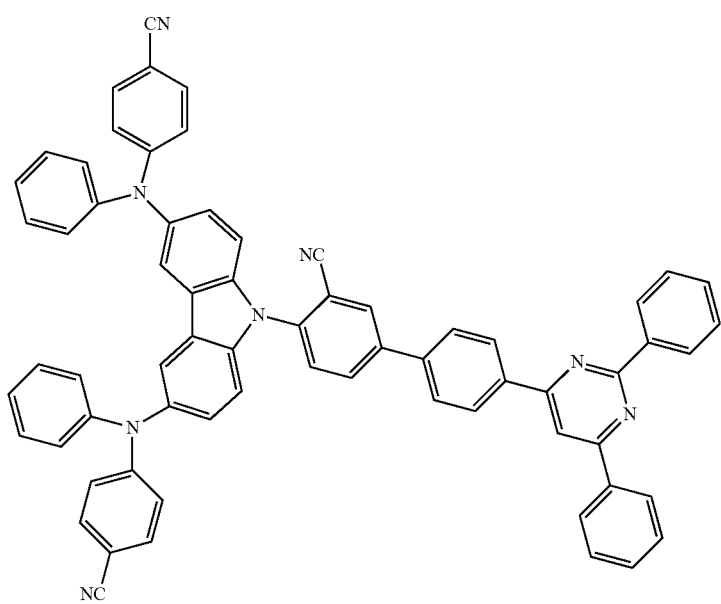

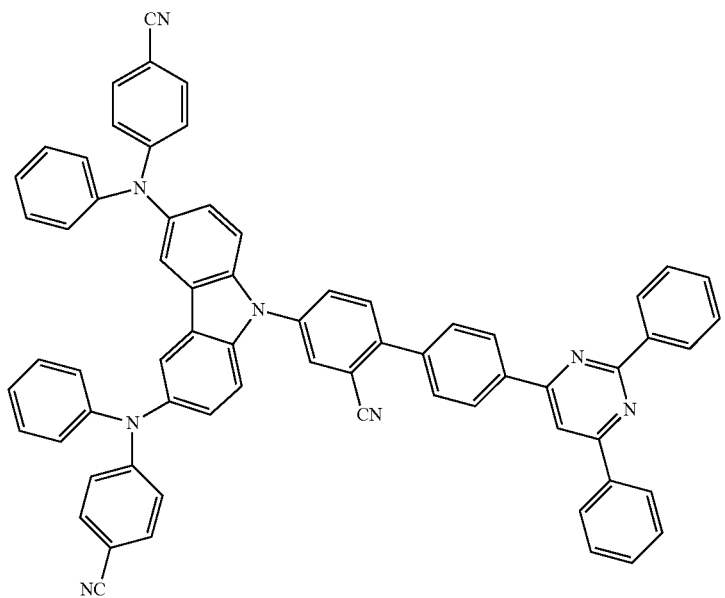
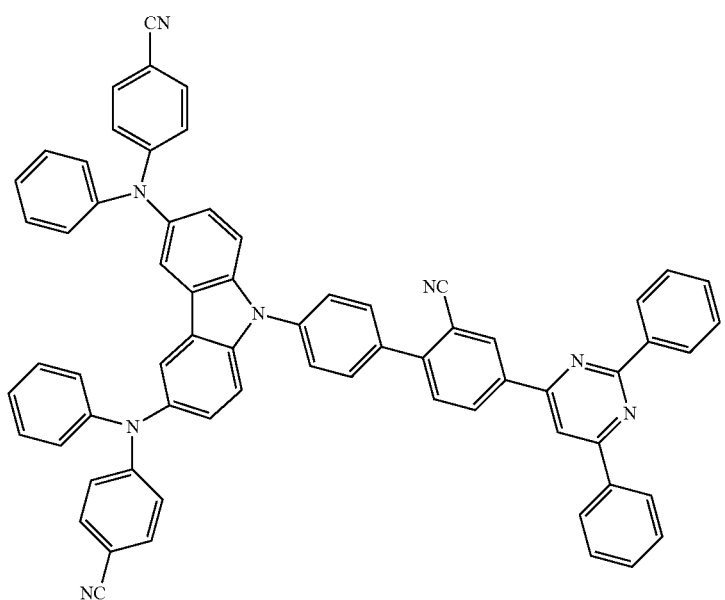

-continued
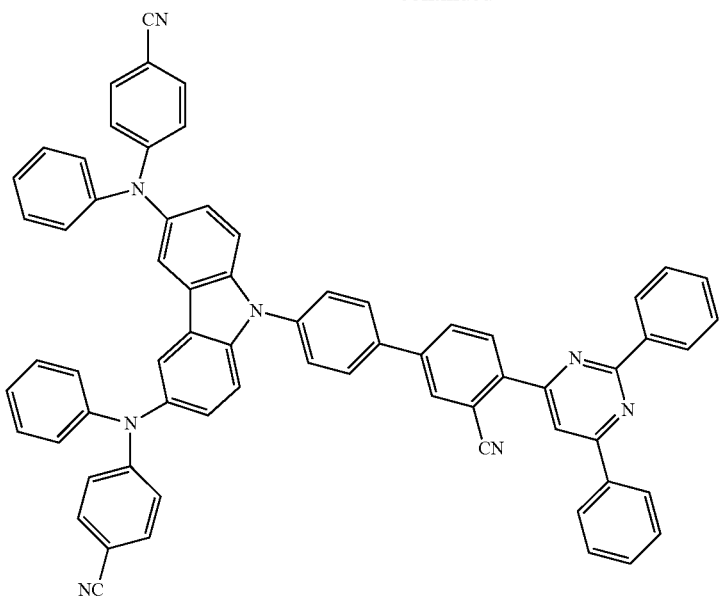
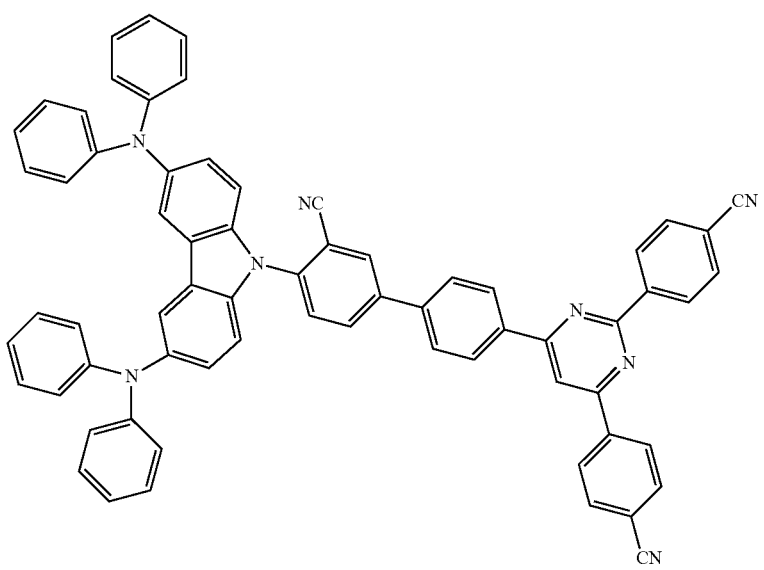

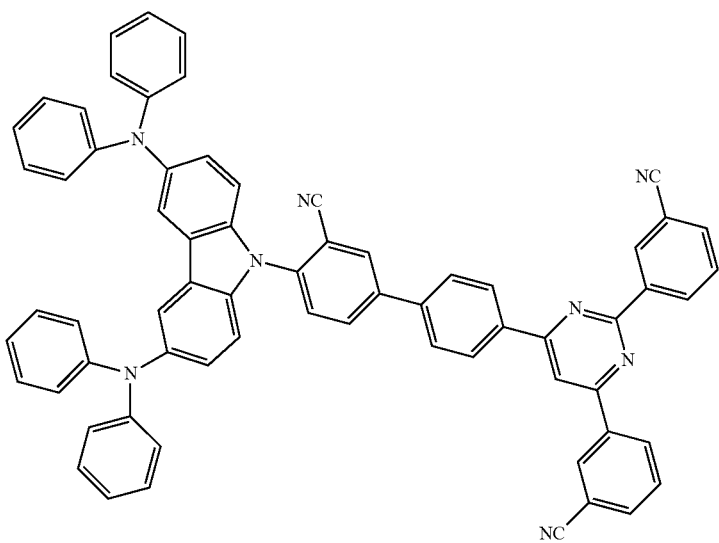
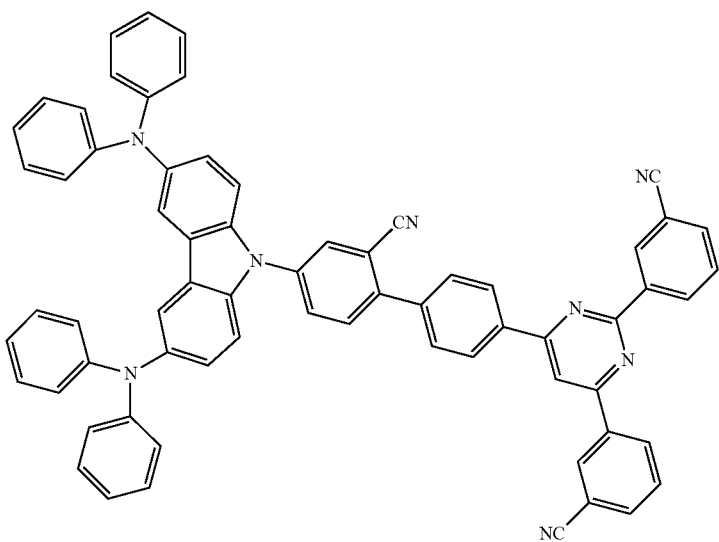
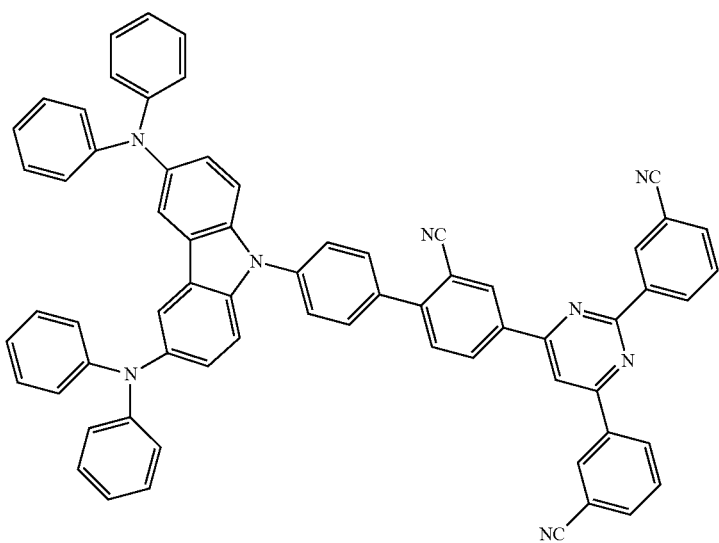

-continued
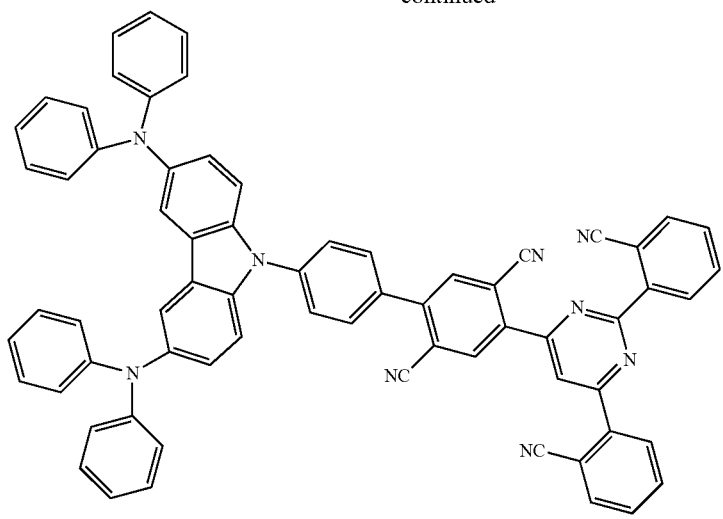
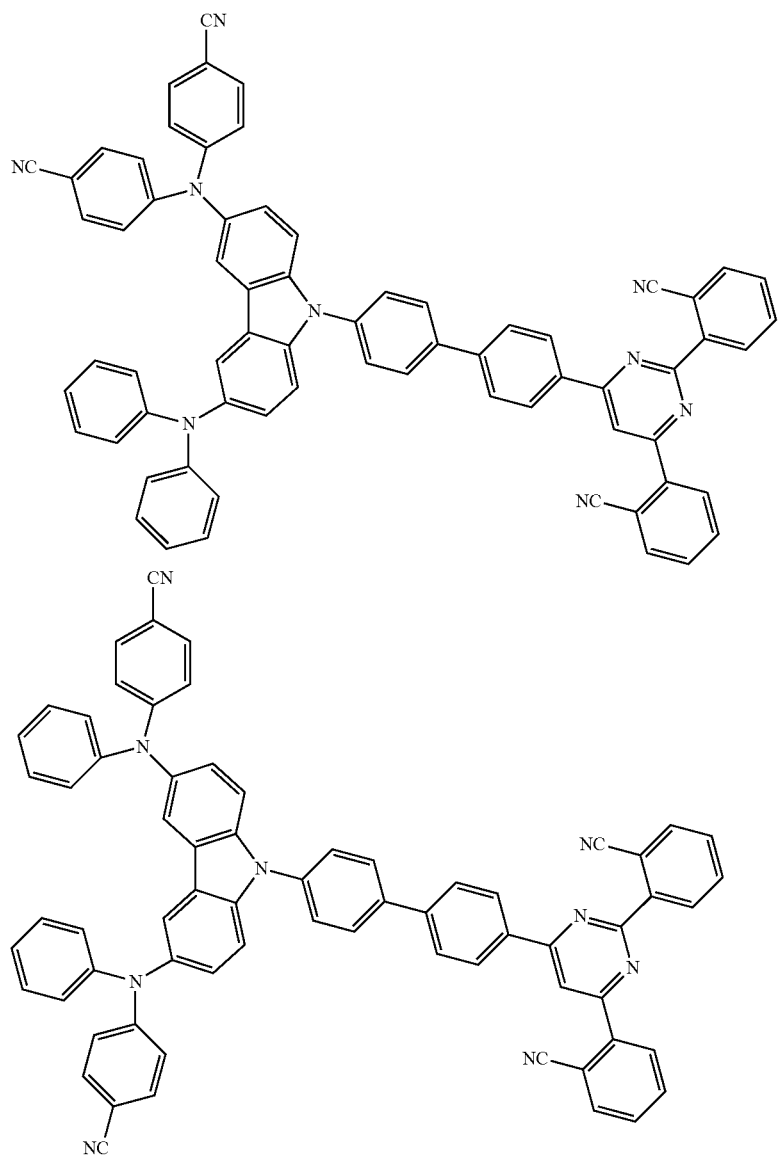

-continued
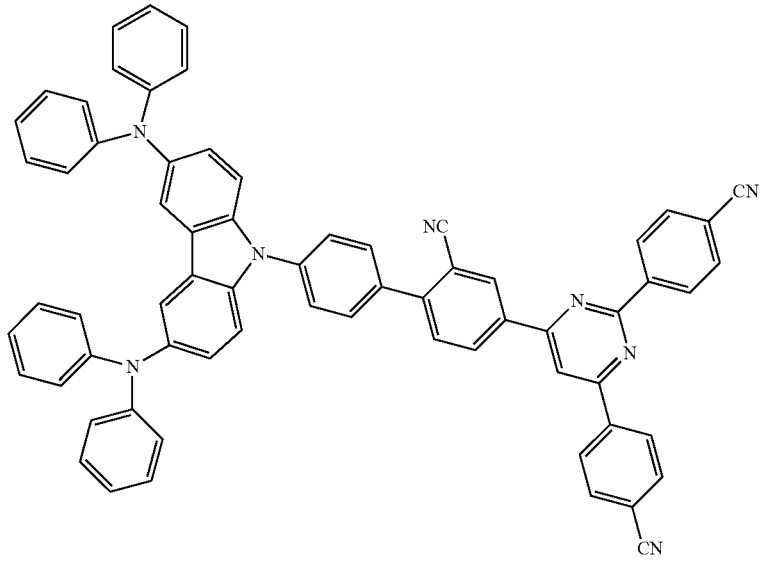
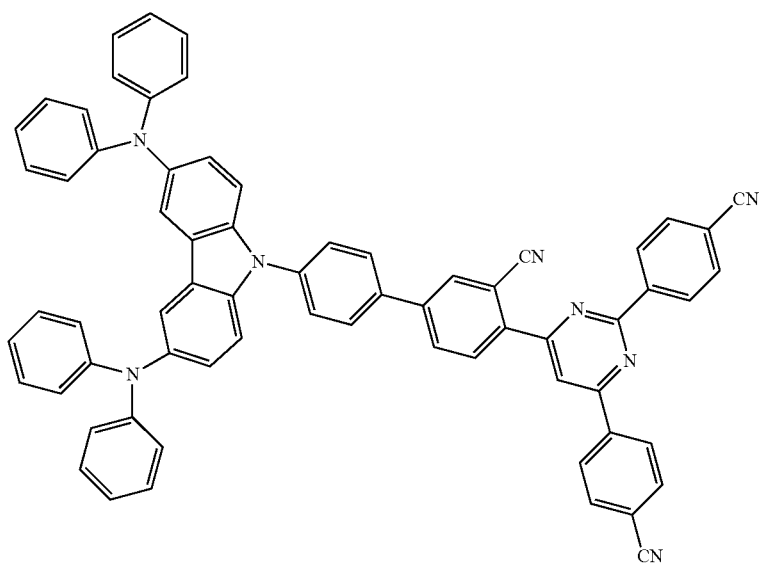
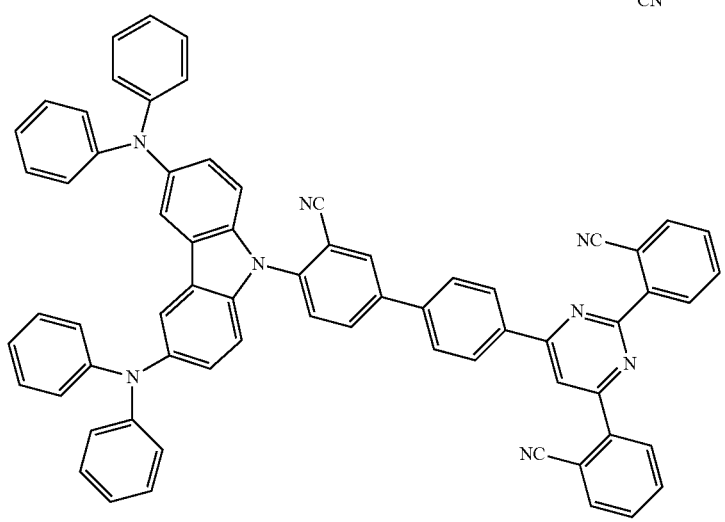

-continued
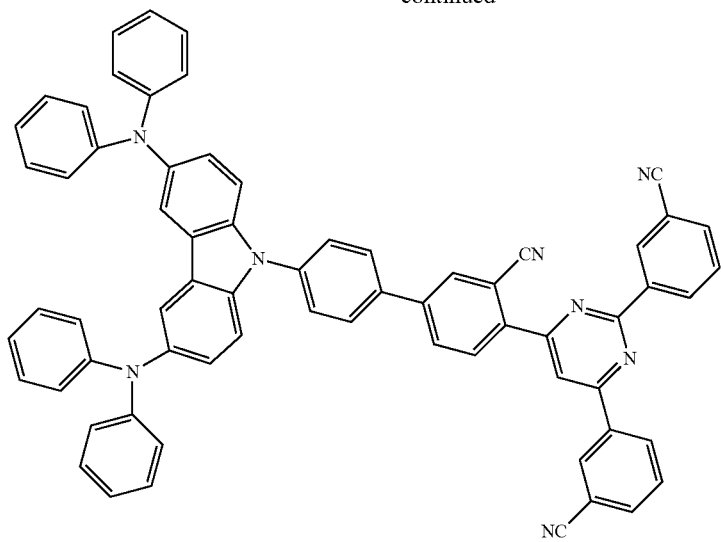
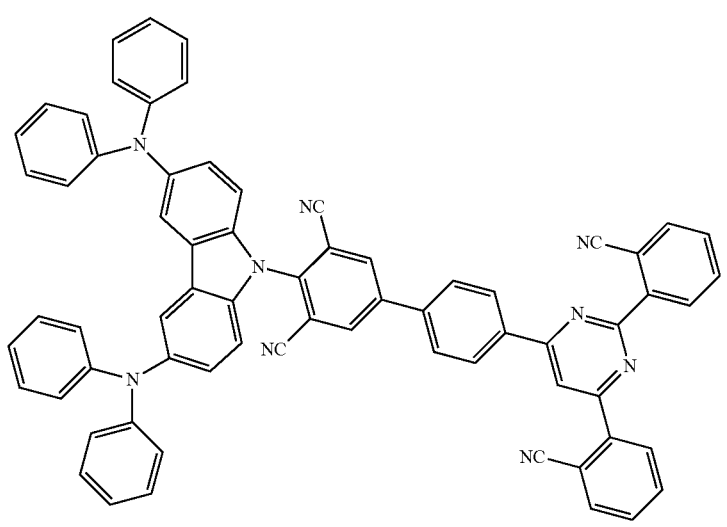
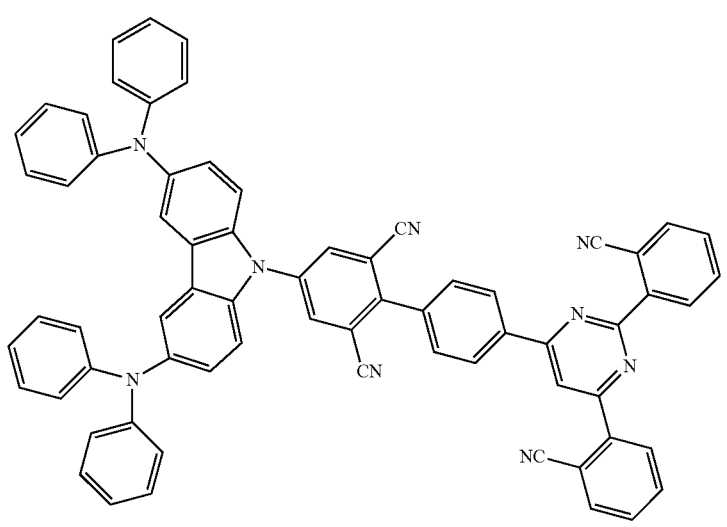

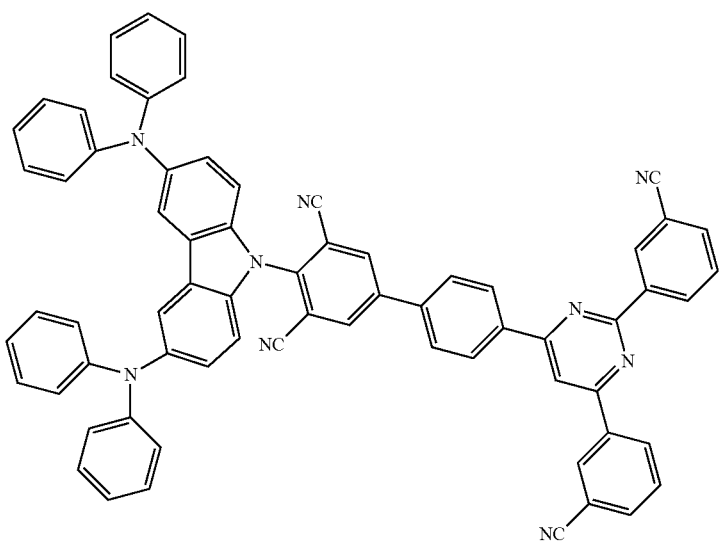
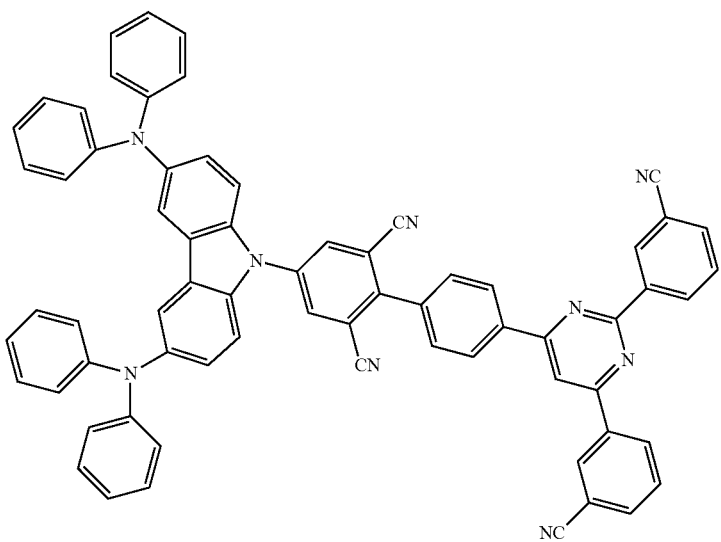
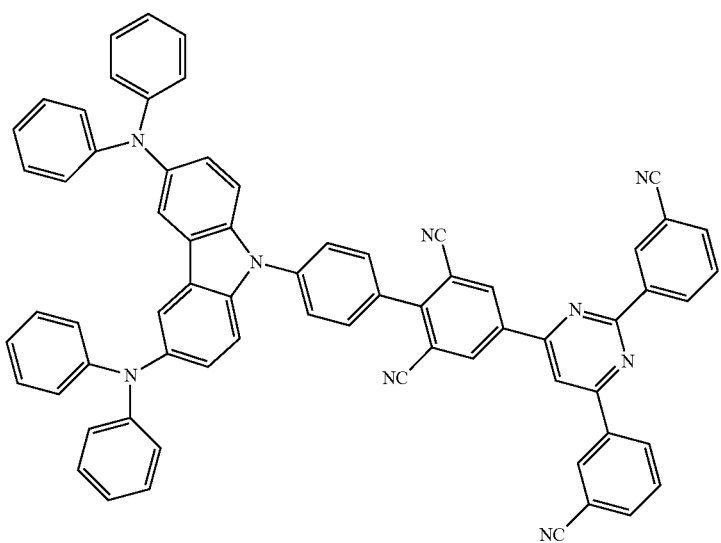

-continued
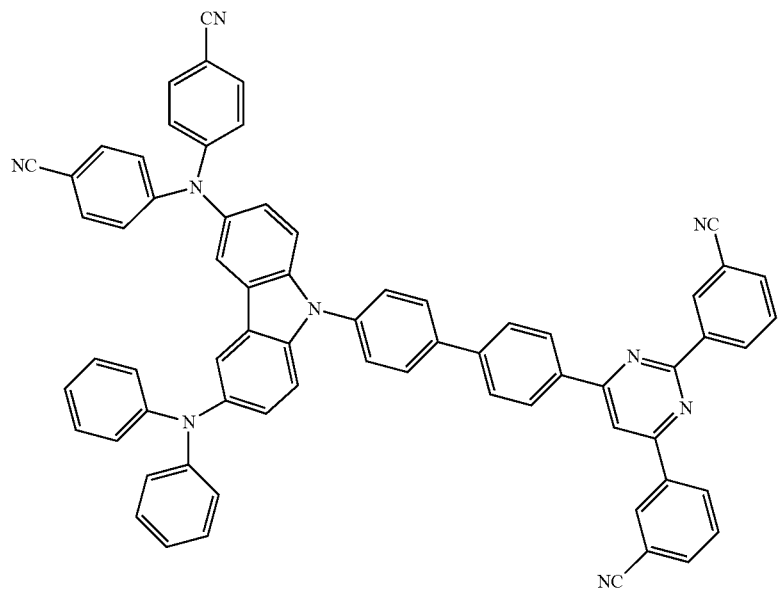
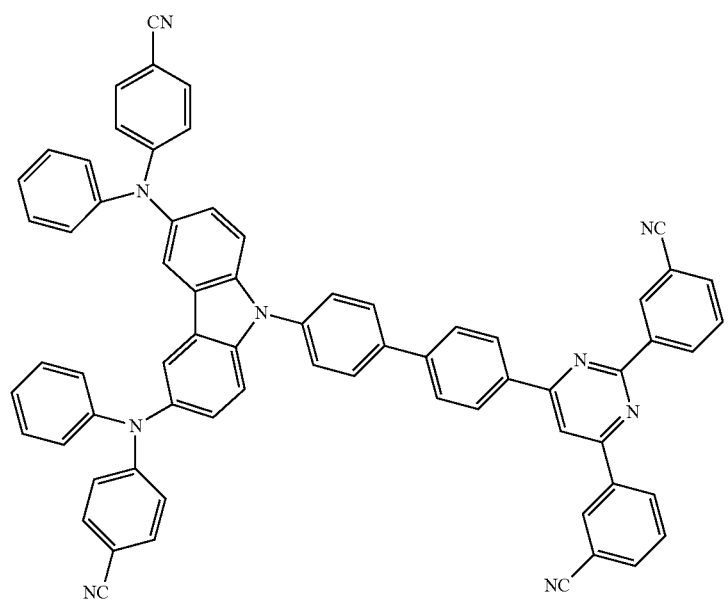

-continued
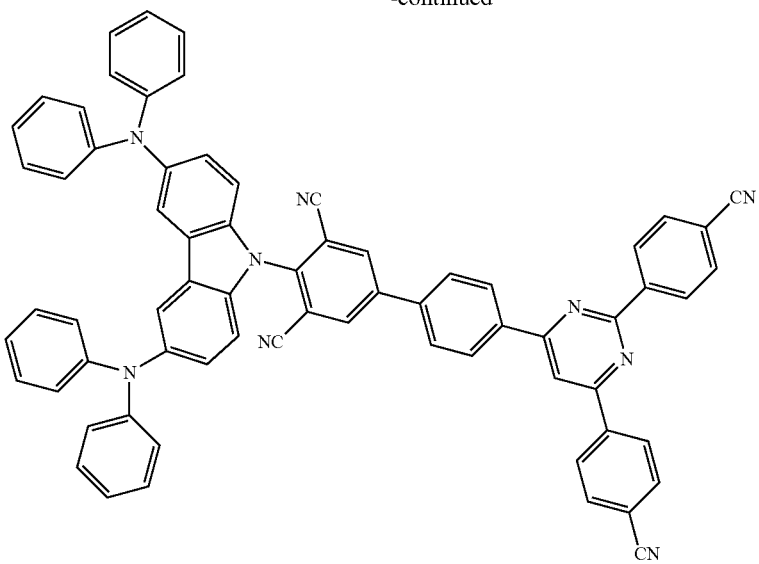
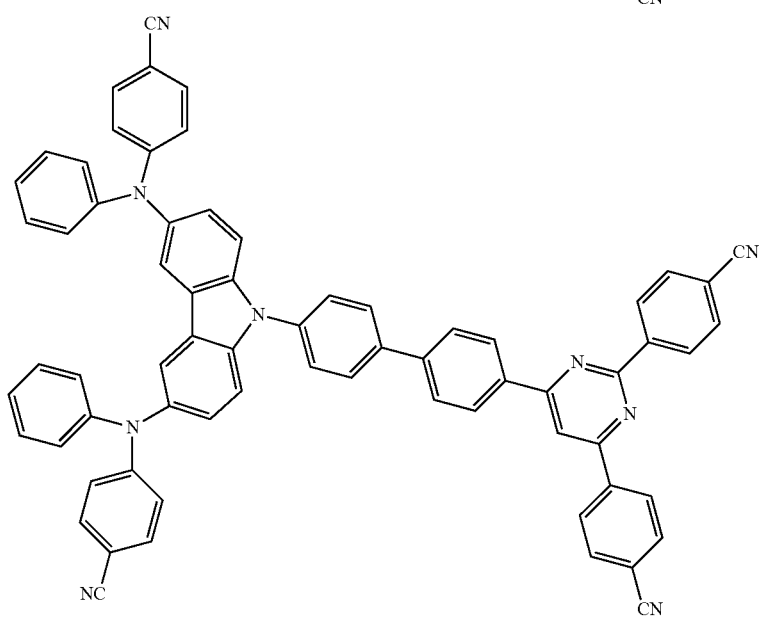
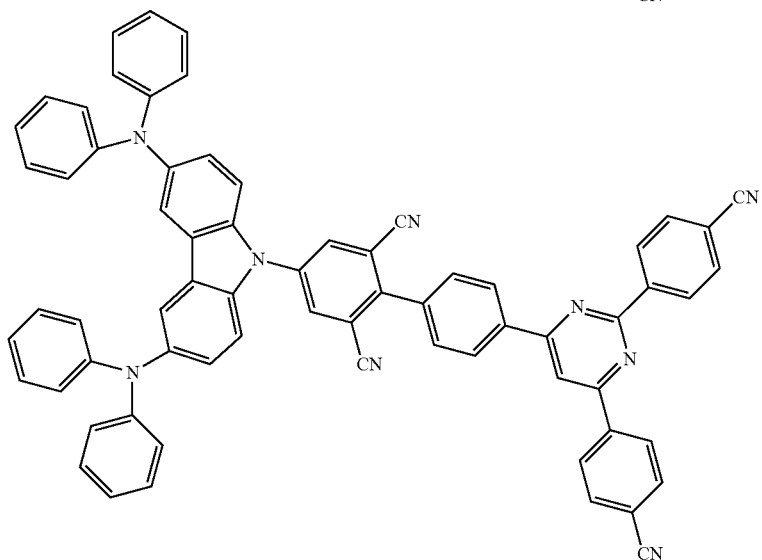

-continued
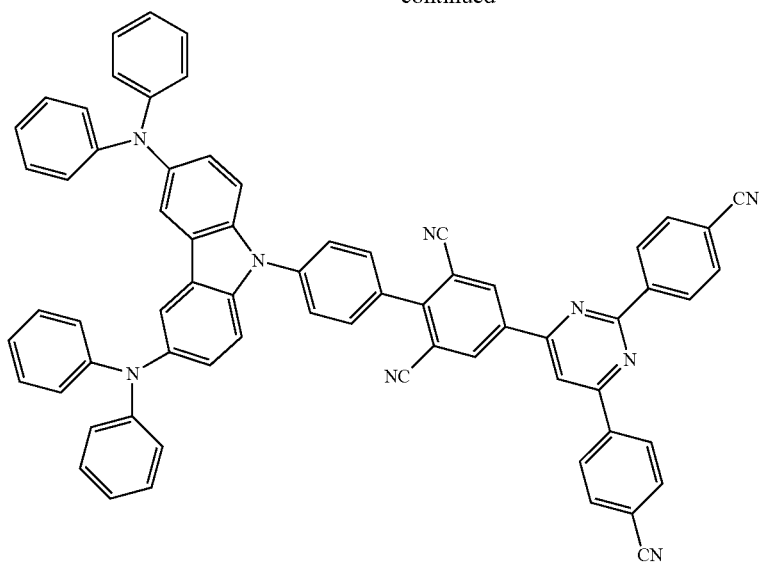
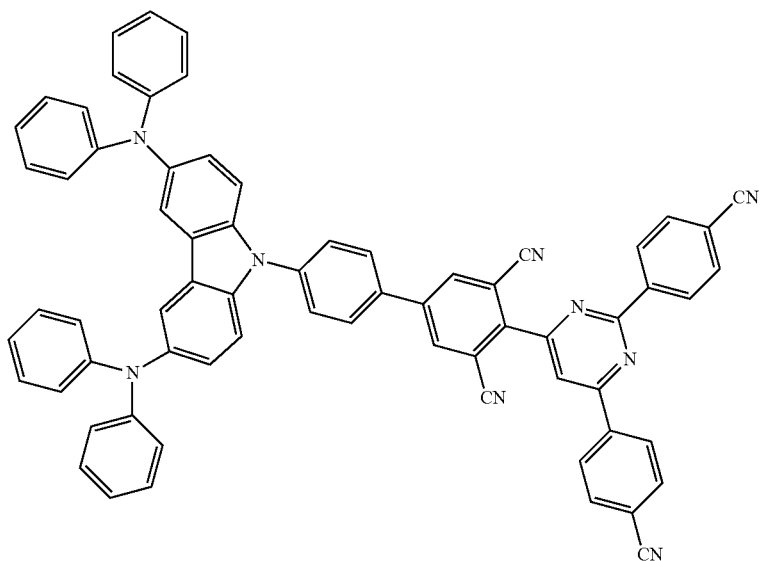 [SMILES: N#Cc1ccc(-c2cc(-c3c(C#N)cc(-c4ccc(-n5c6ccc(N(c7ccccc7)c7ccccc7)cc6c6cc(N(c7ccccc7)c7ccccc7)ccc65)cc4)cc3C#N)nc(-c3ccc(C#N)cc3)n2)cc1]
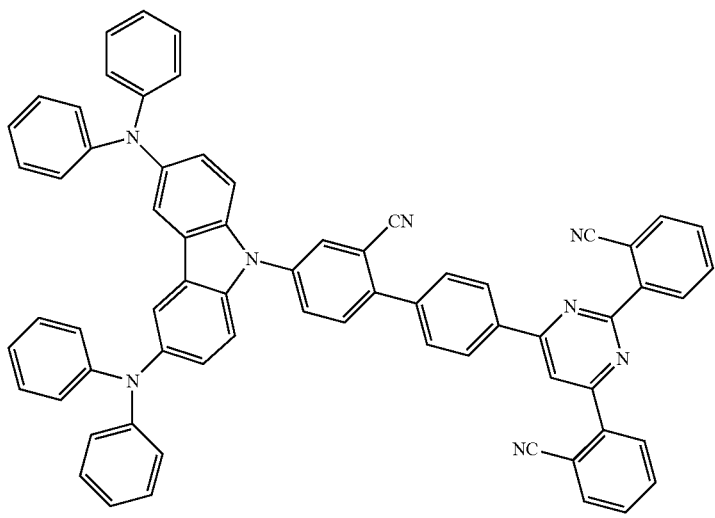

-continued
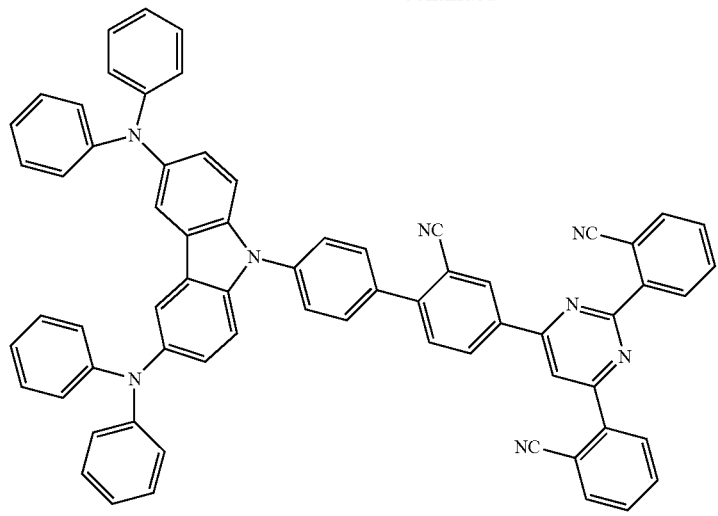
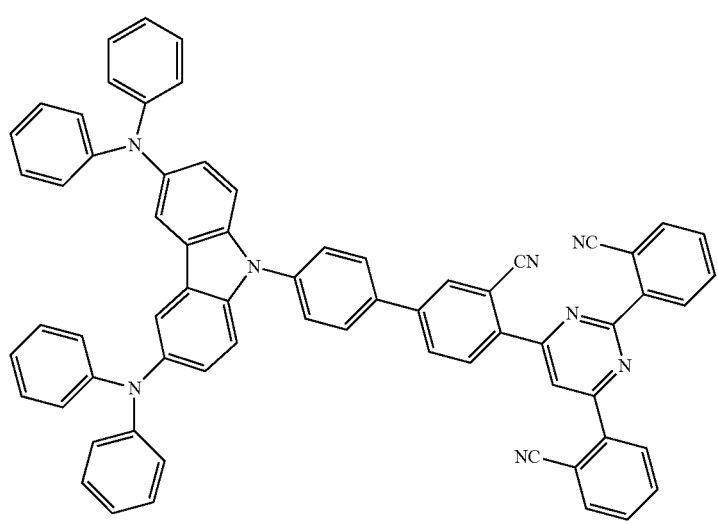
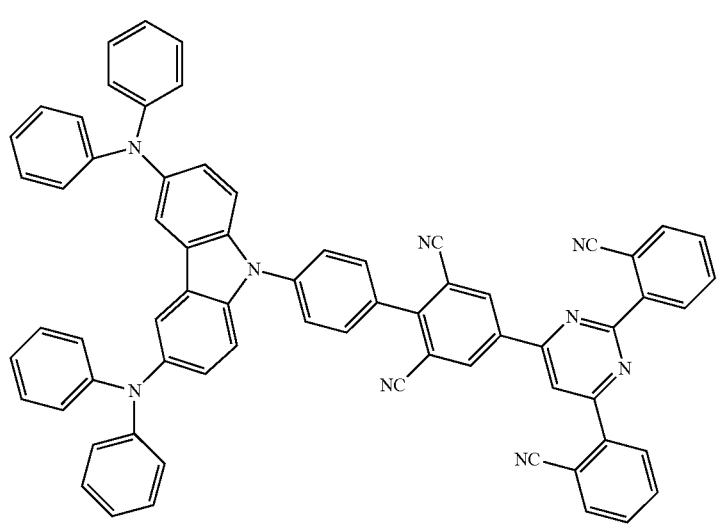

-continued
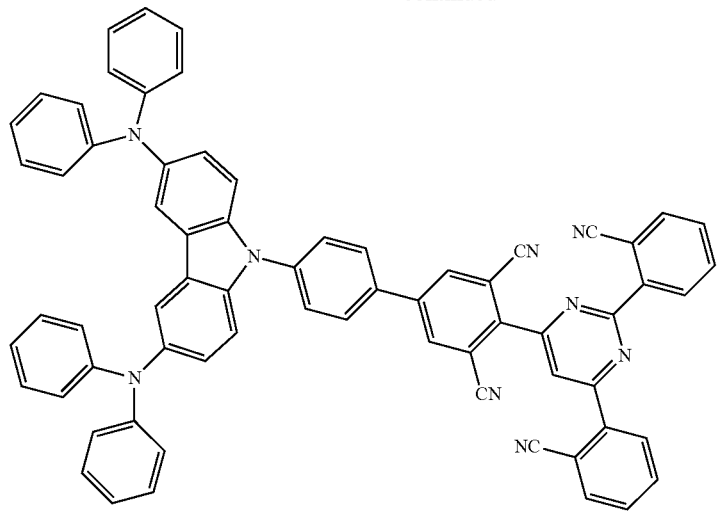
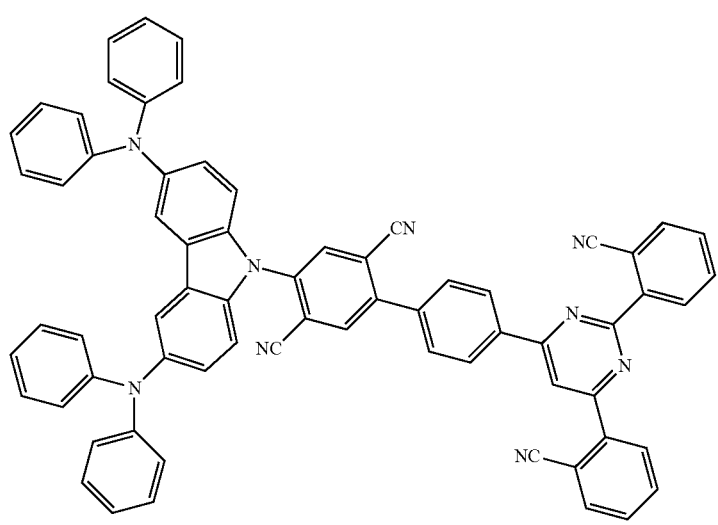
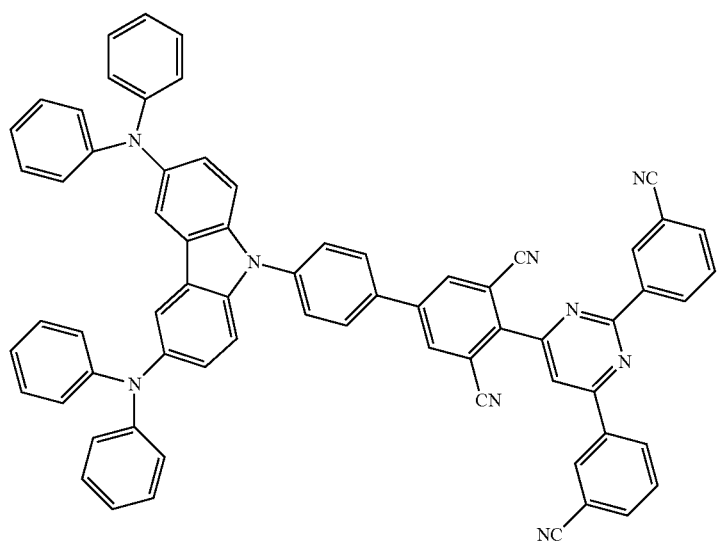

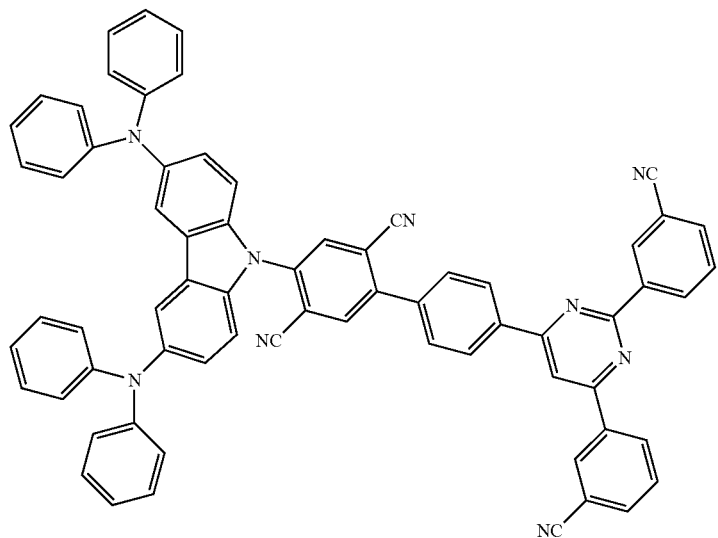
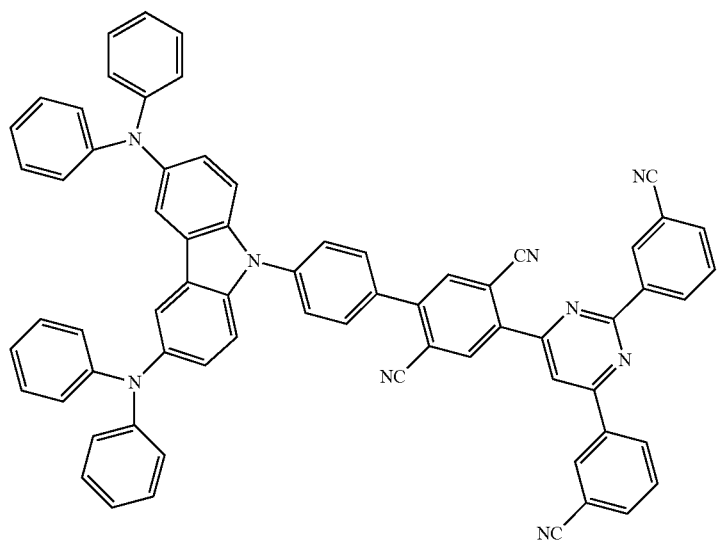
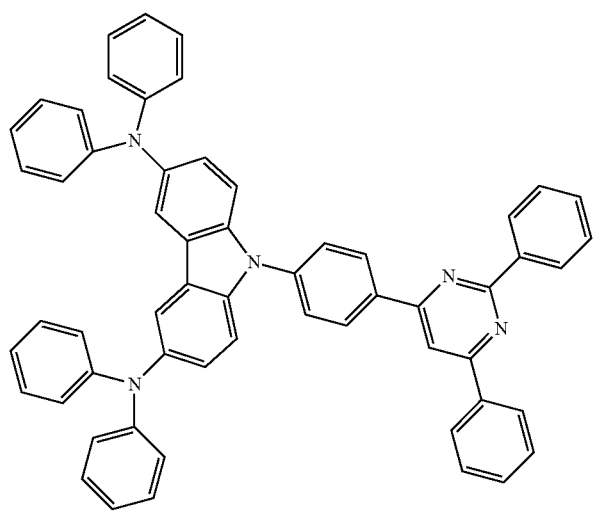

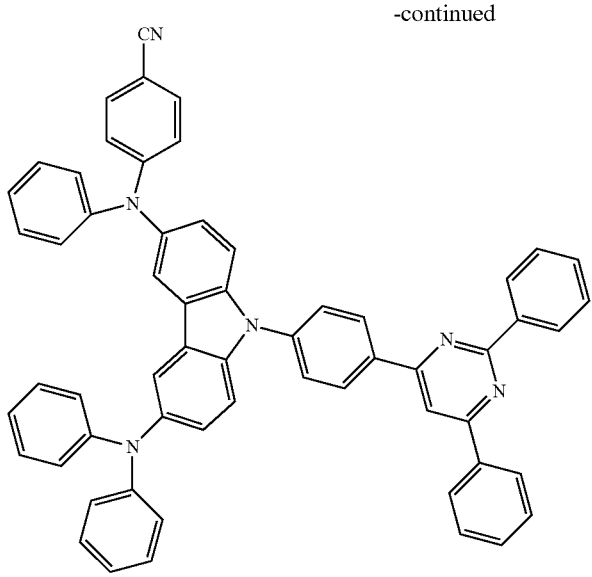
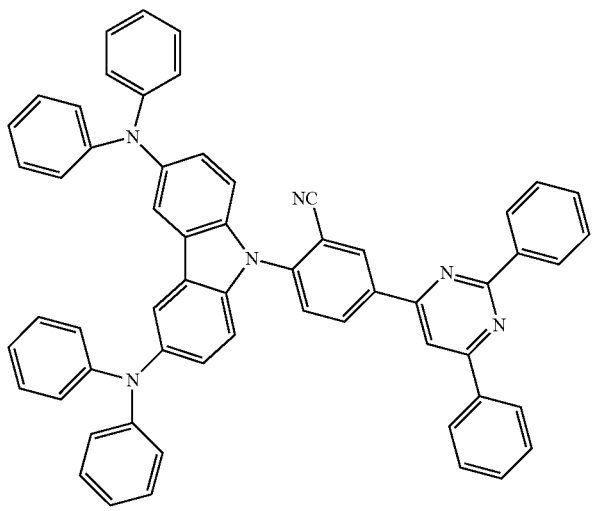
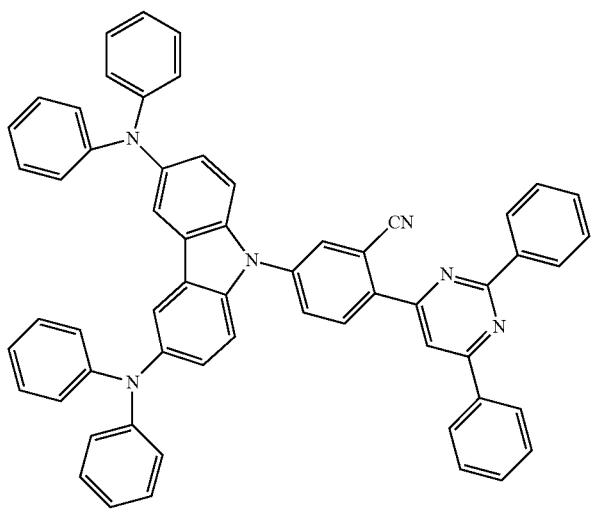

-continued
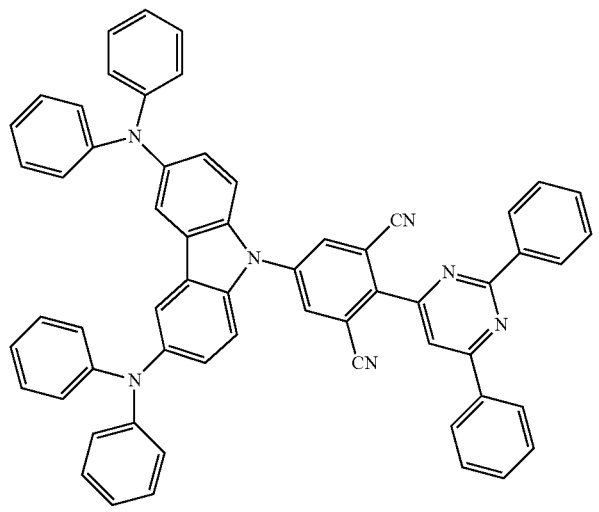
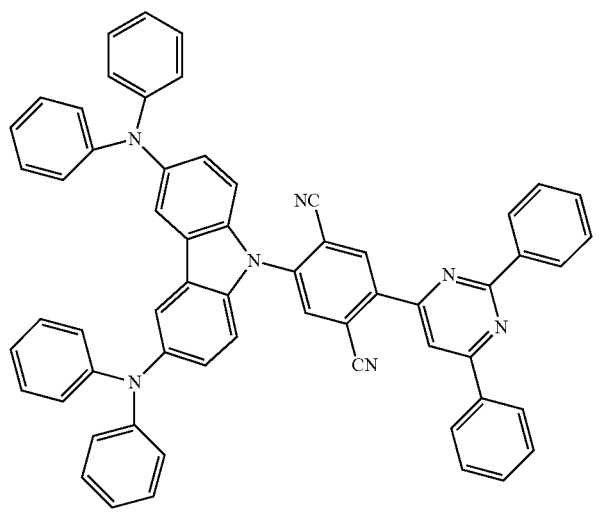
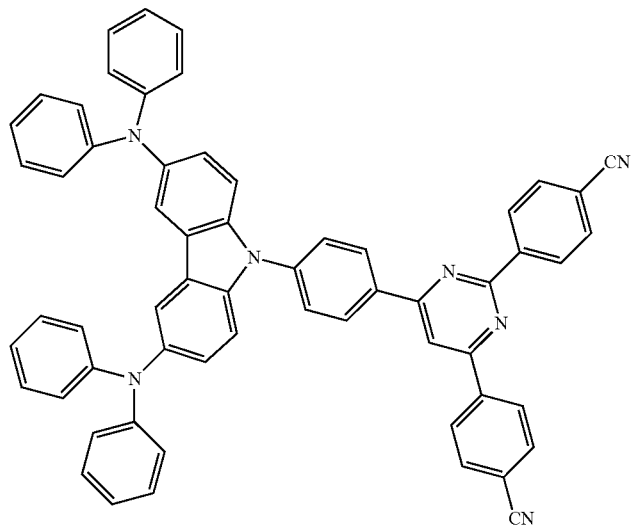

-continued
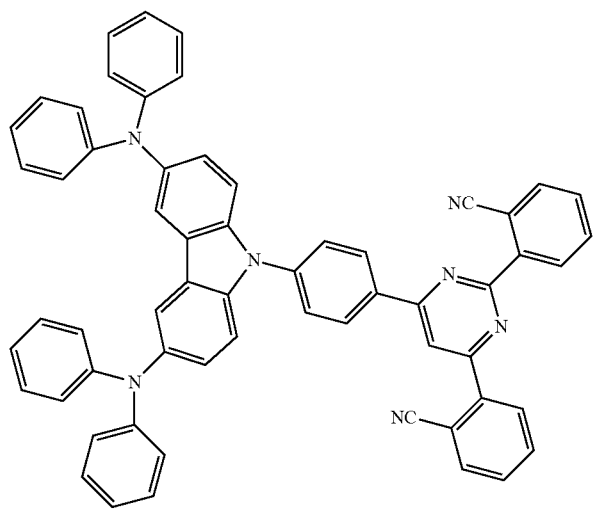
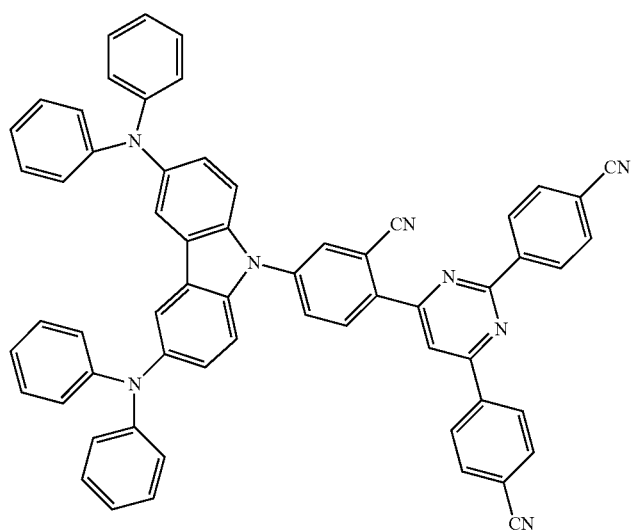
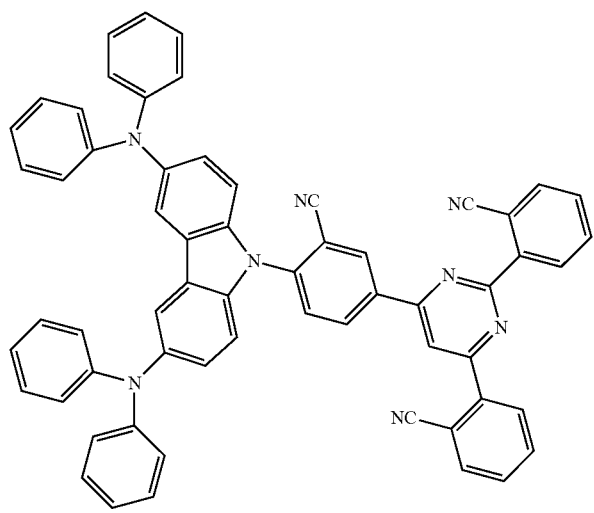

-continued
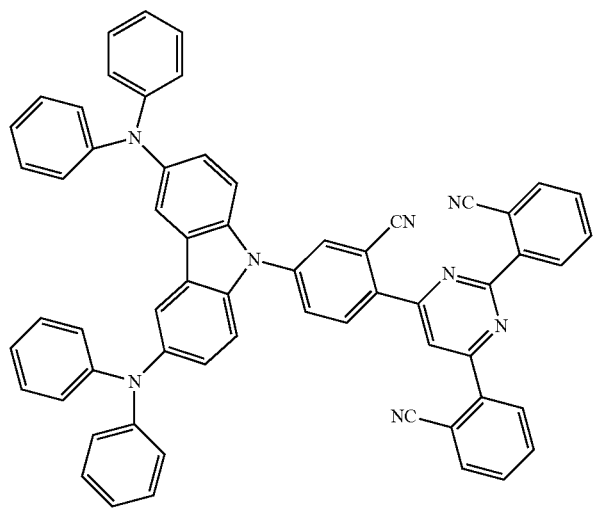
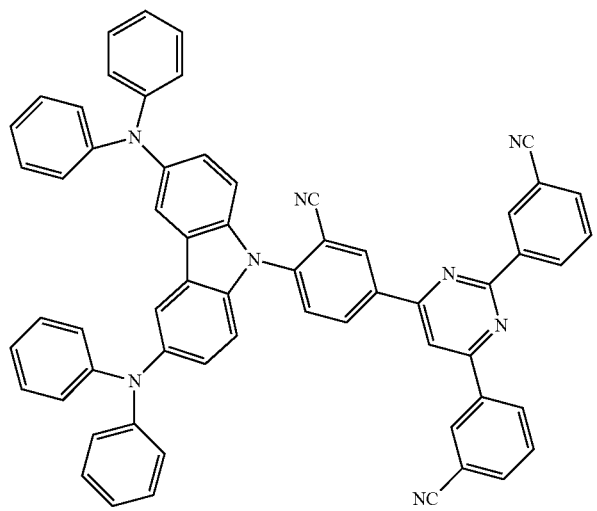
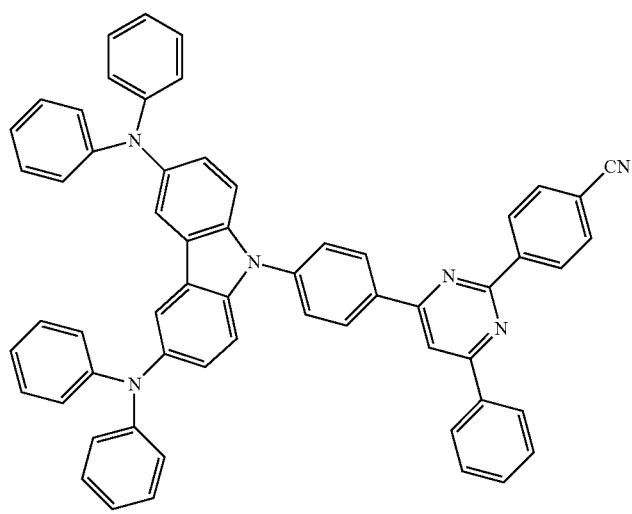

-continued
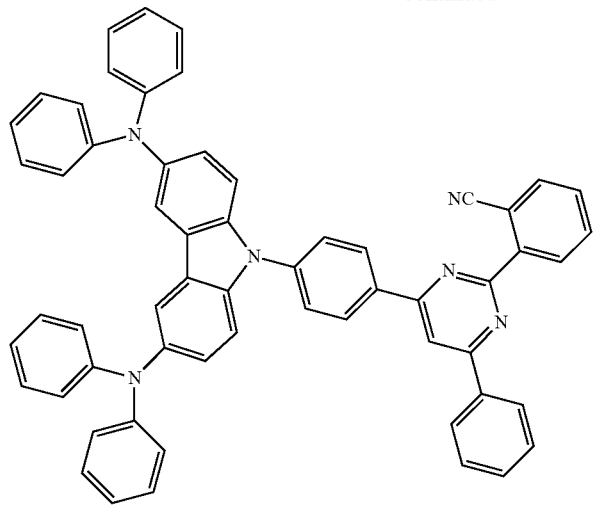
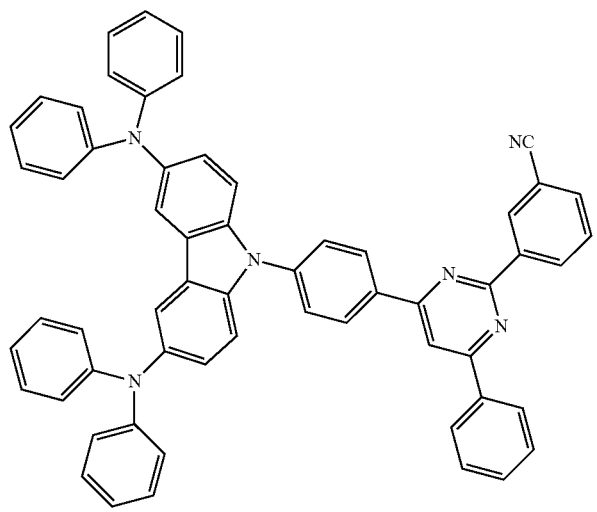
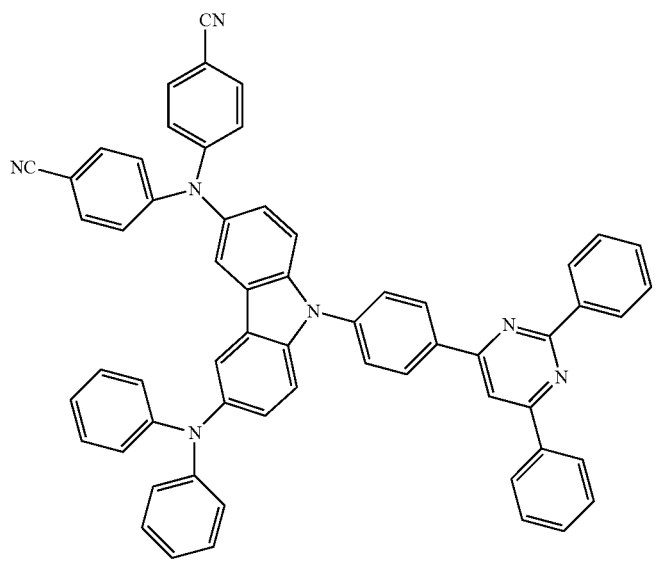

-continued
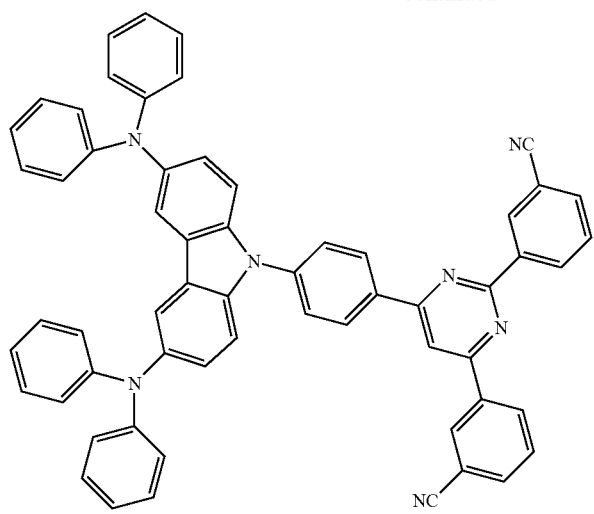
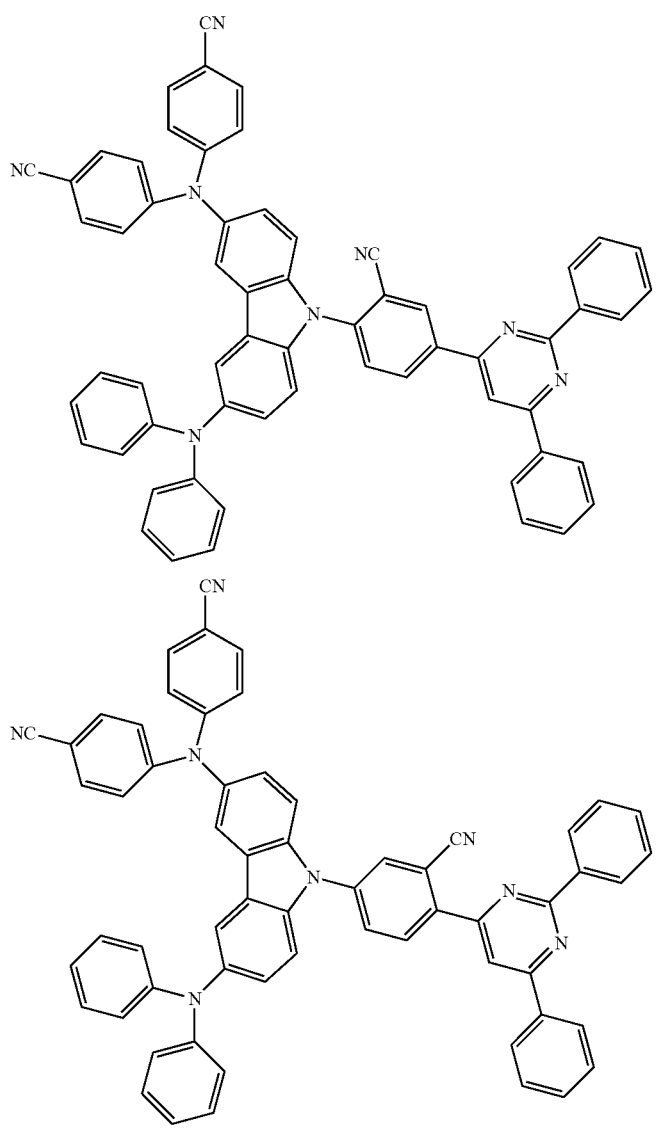

-continued
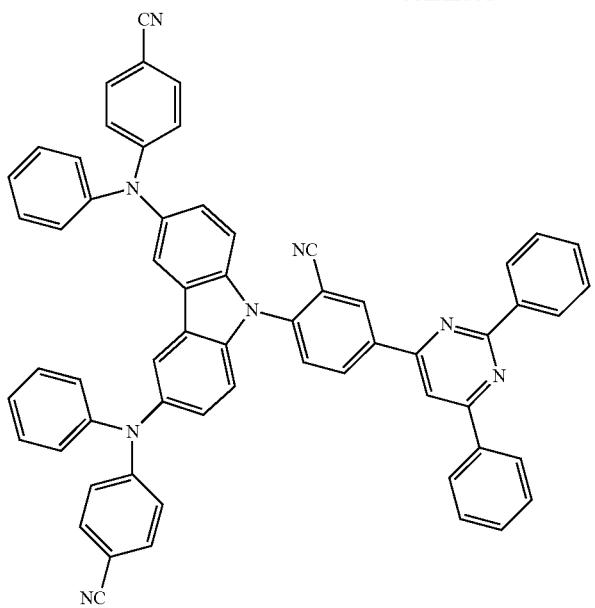
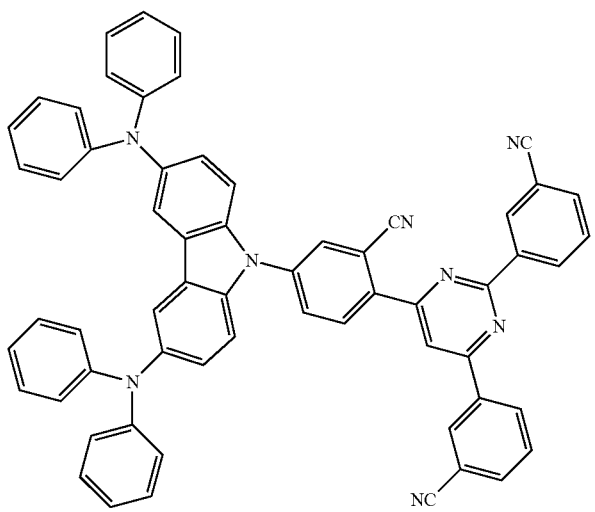
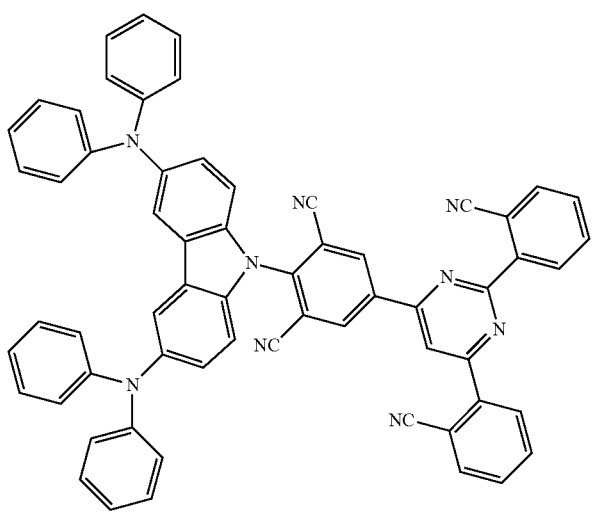

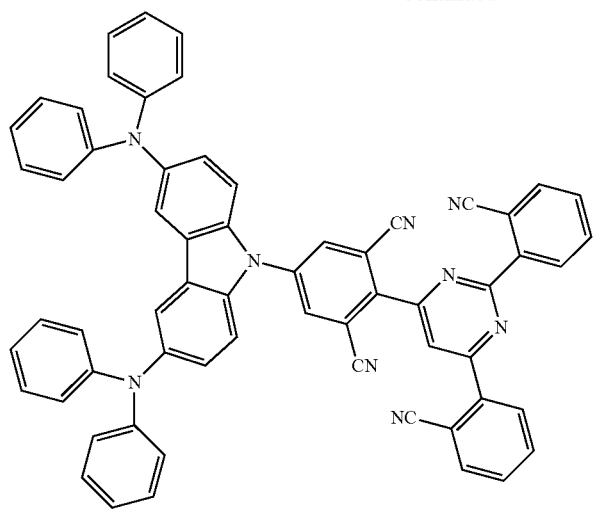
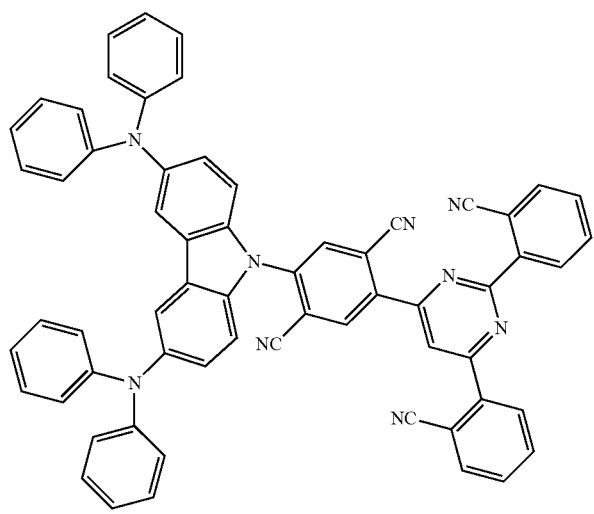
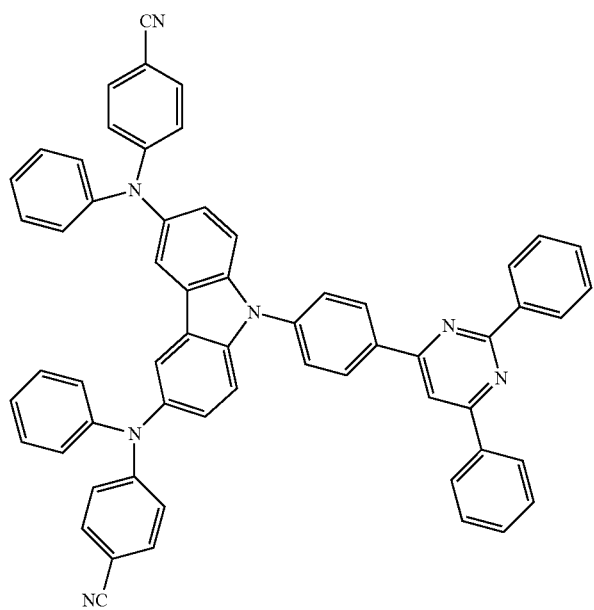

-continued
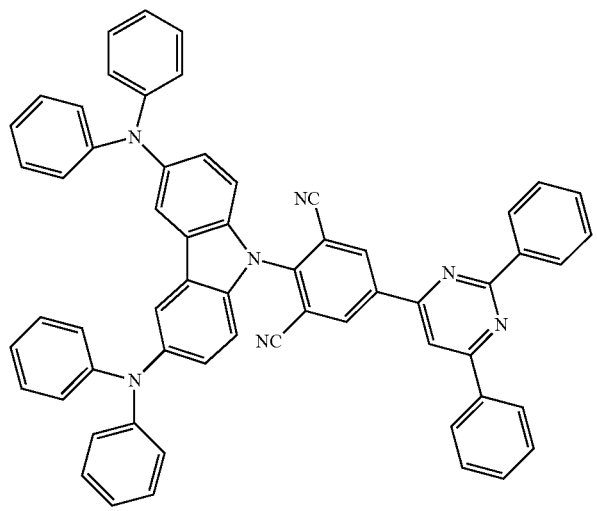
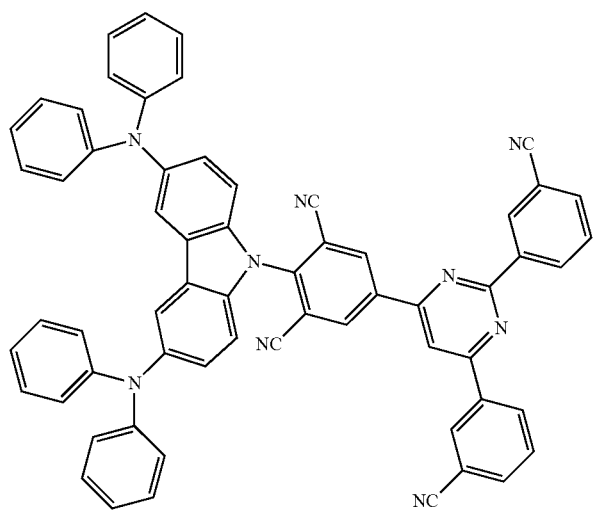
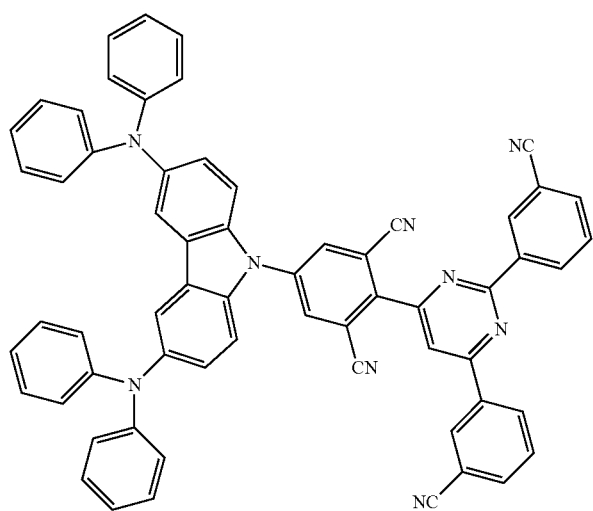

-continued
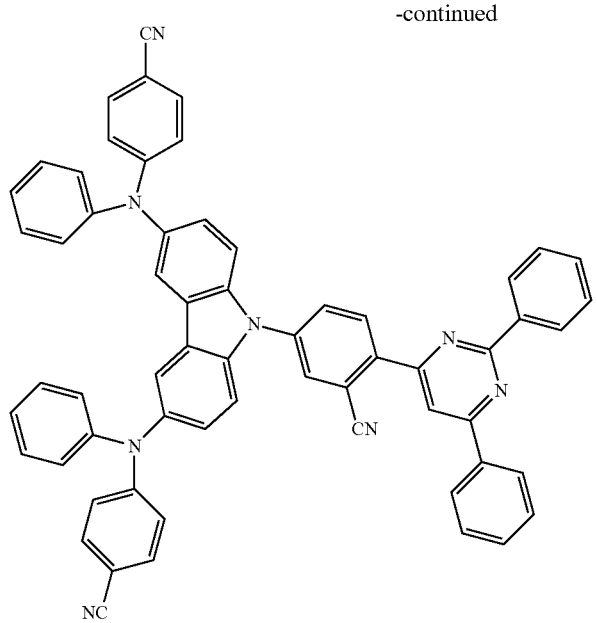
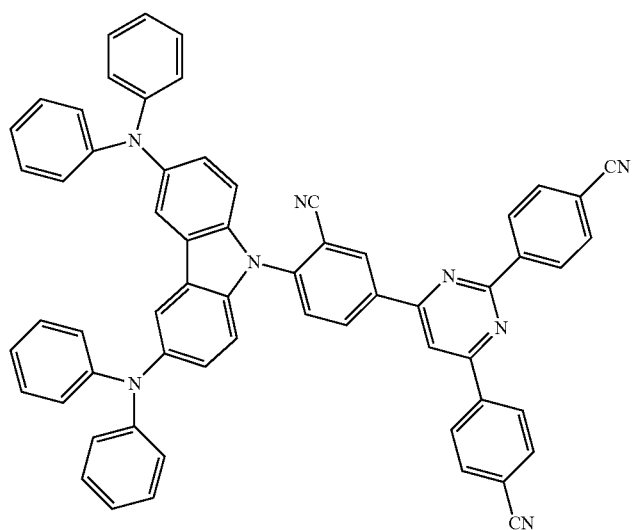
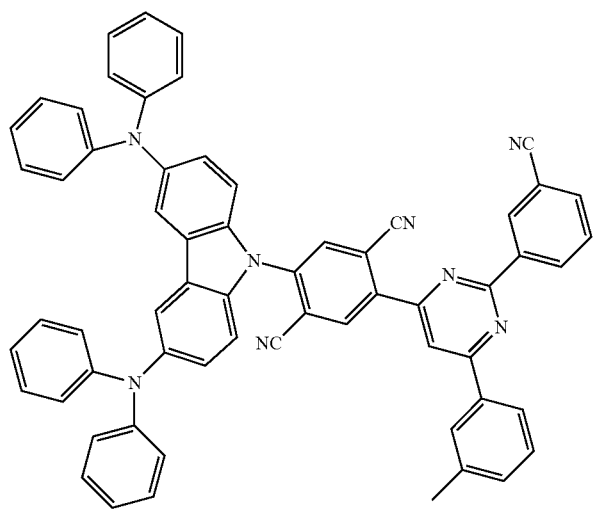

-continued
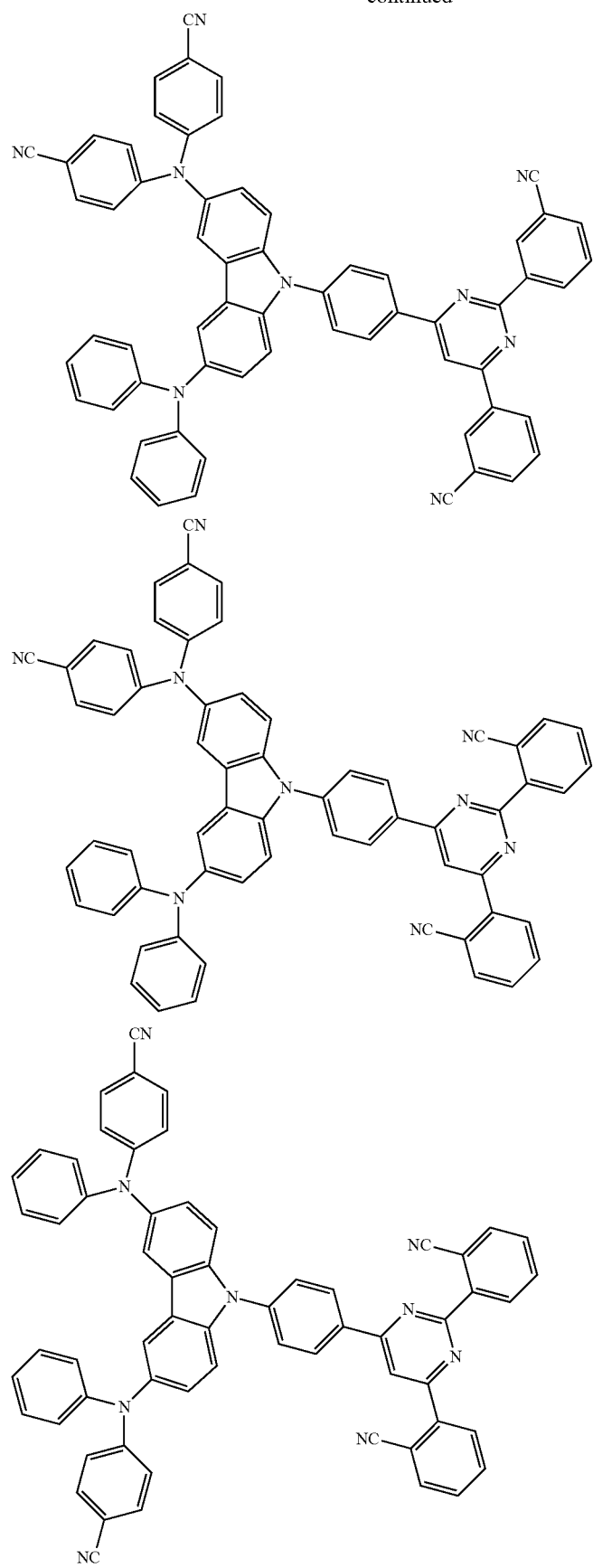

-continued
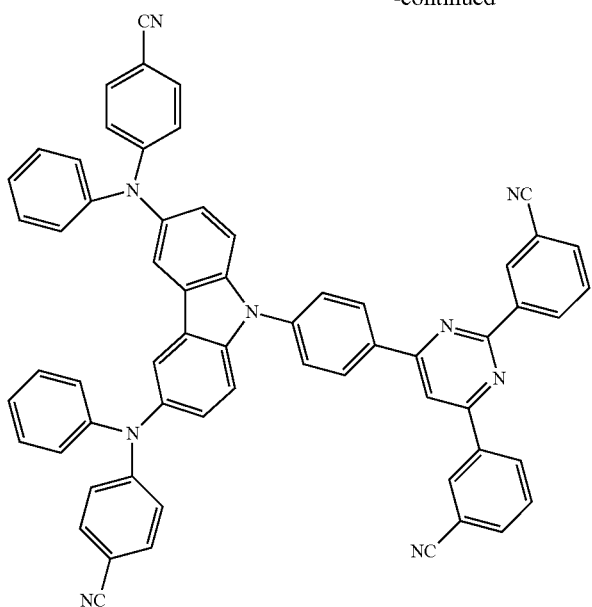
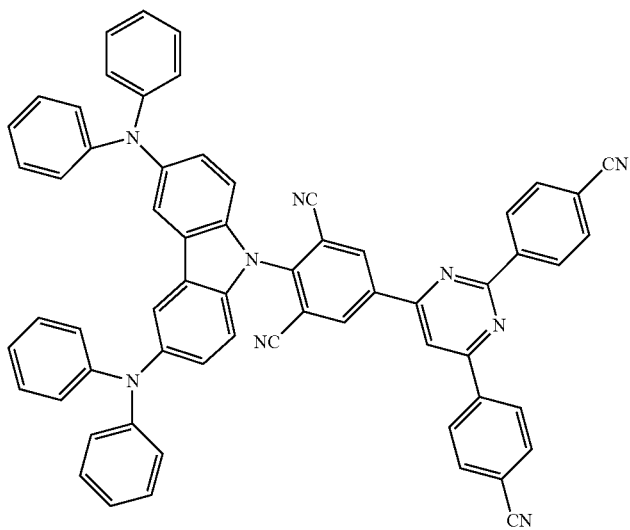
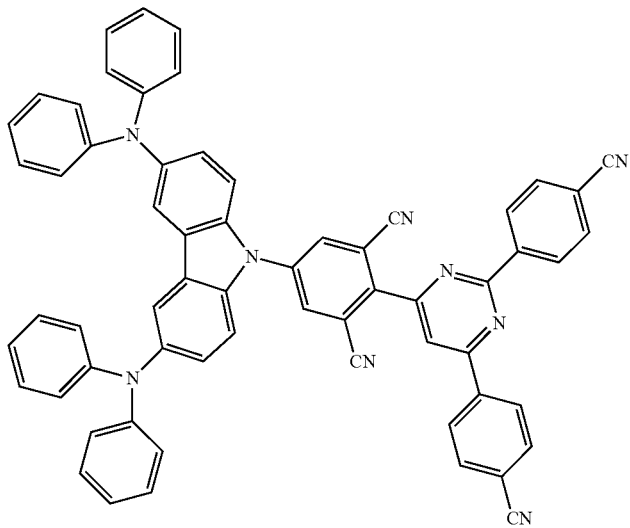

-continued
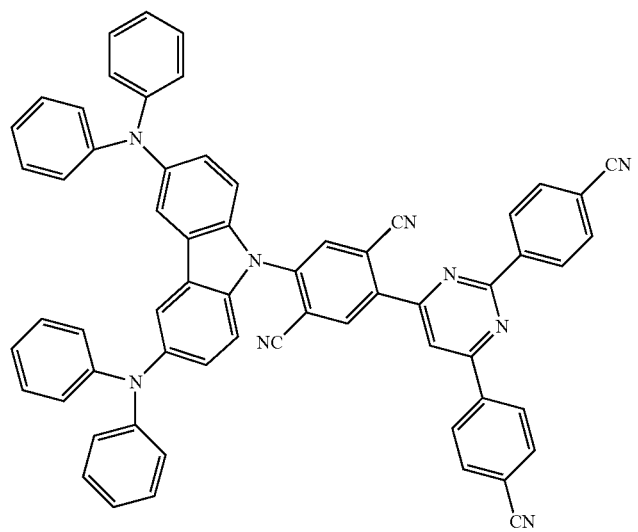
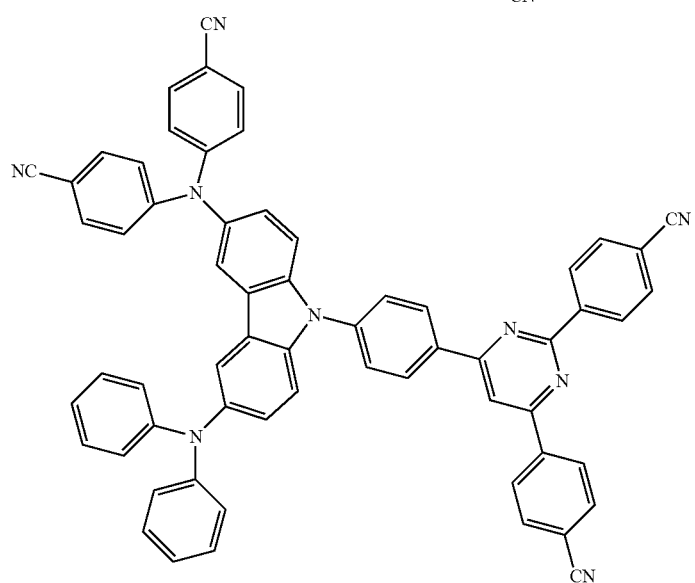
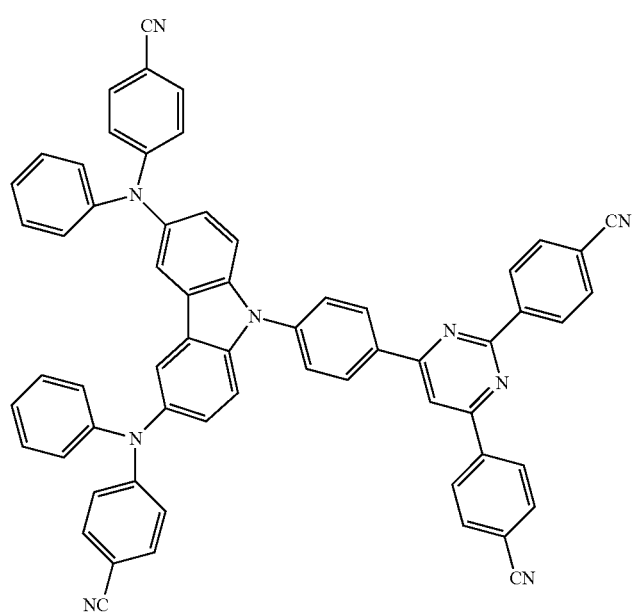

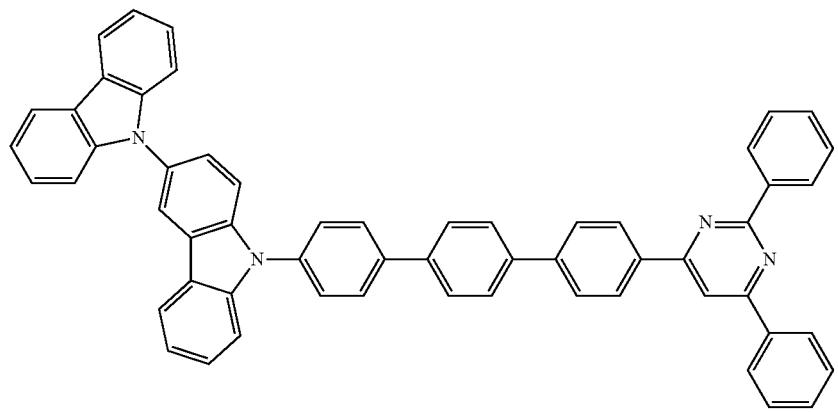
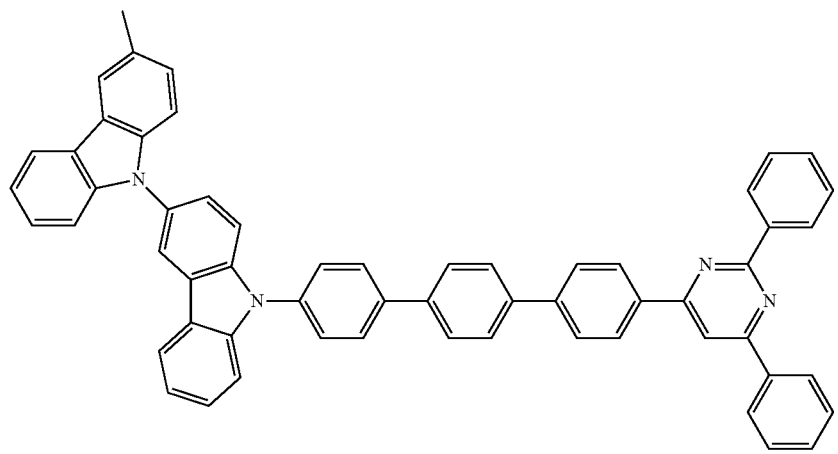
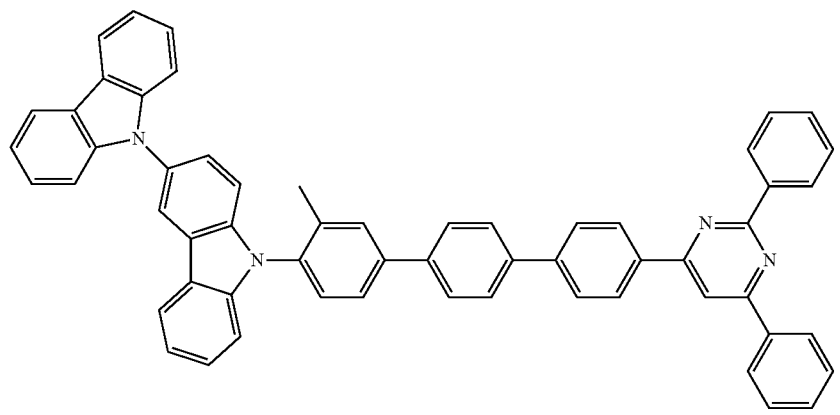
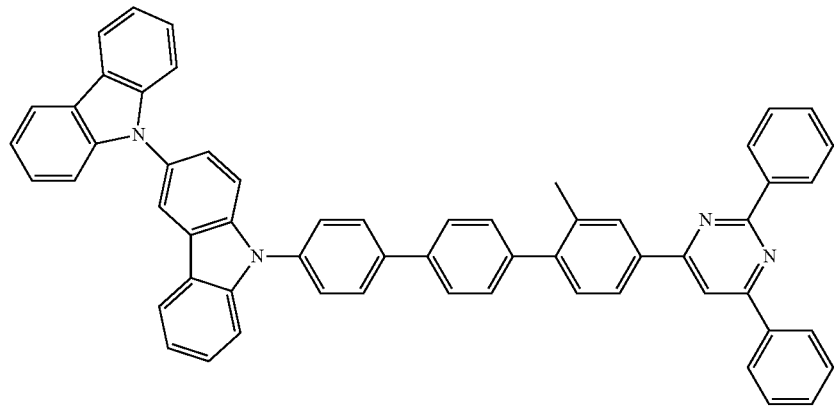

-continued
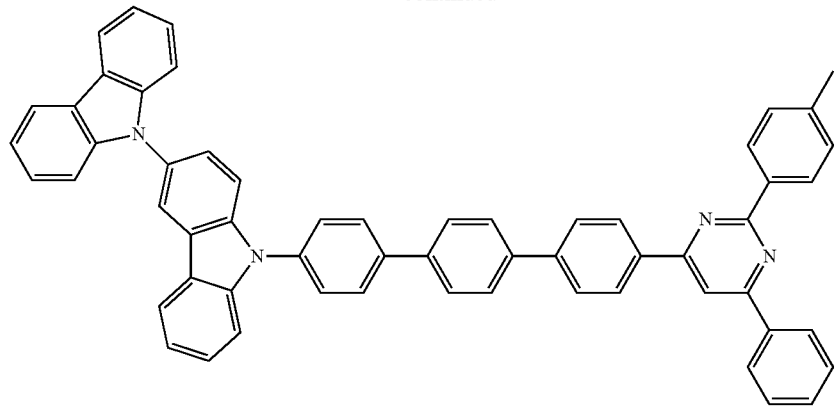
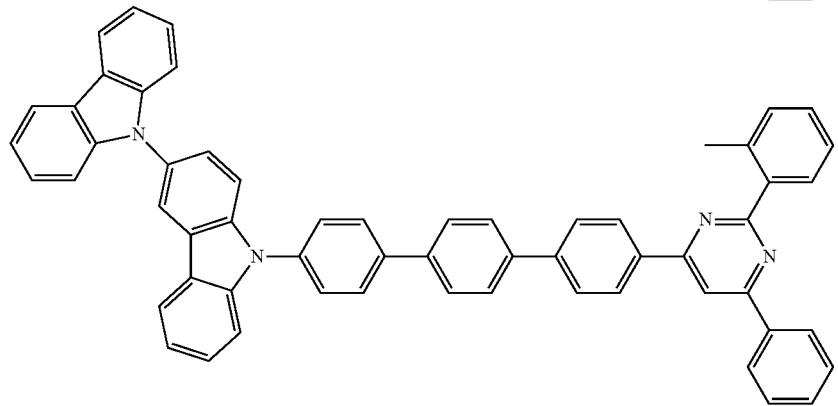
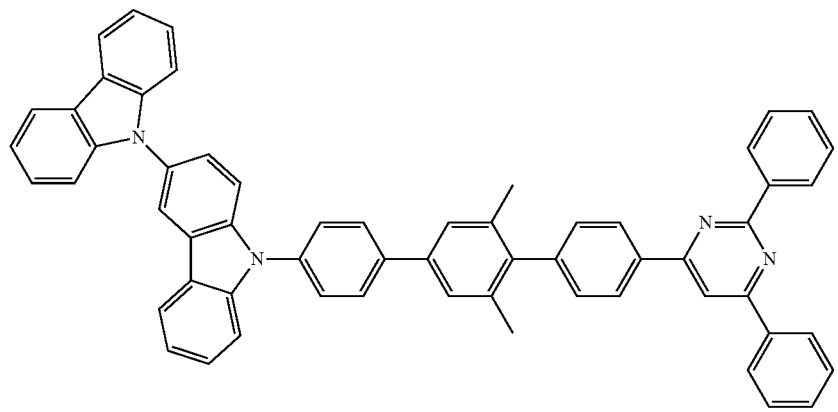
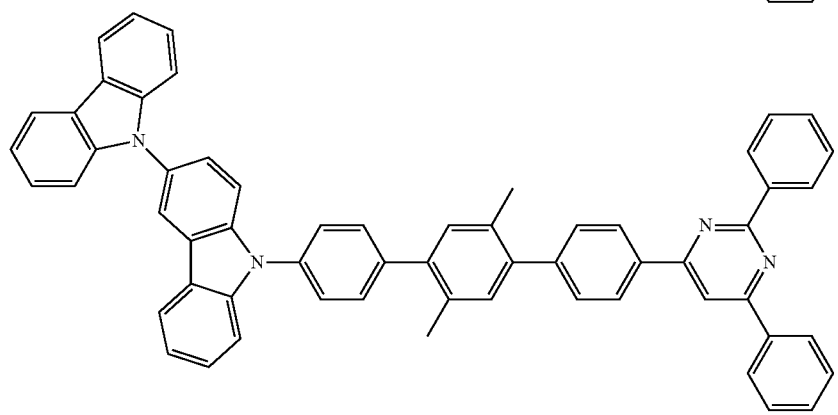

-continued
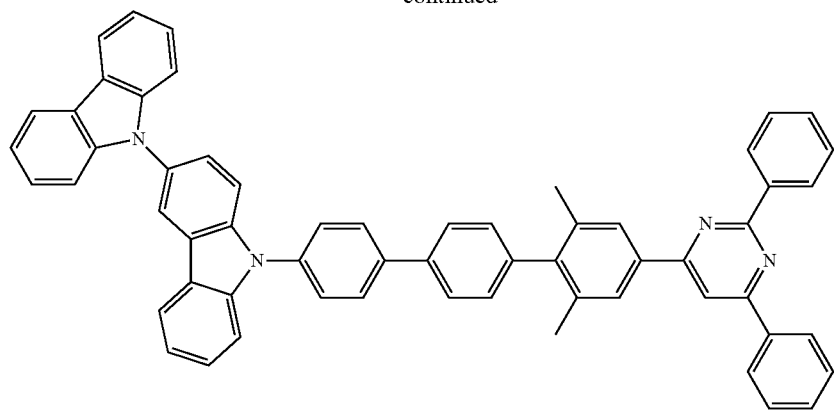
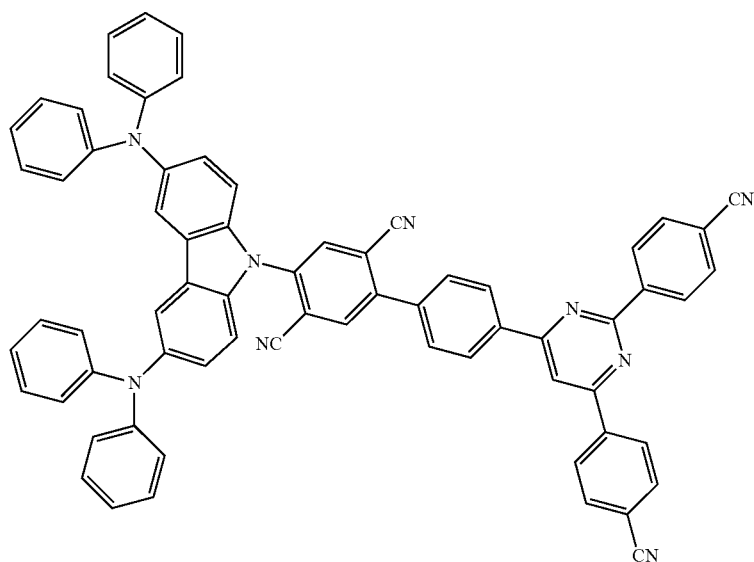
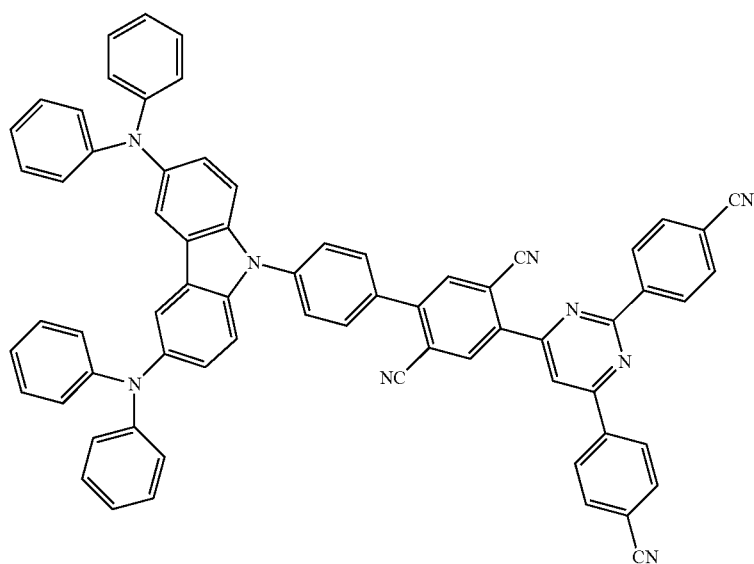

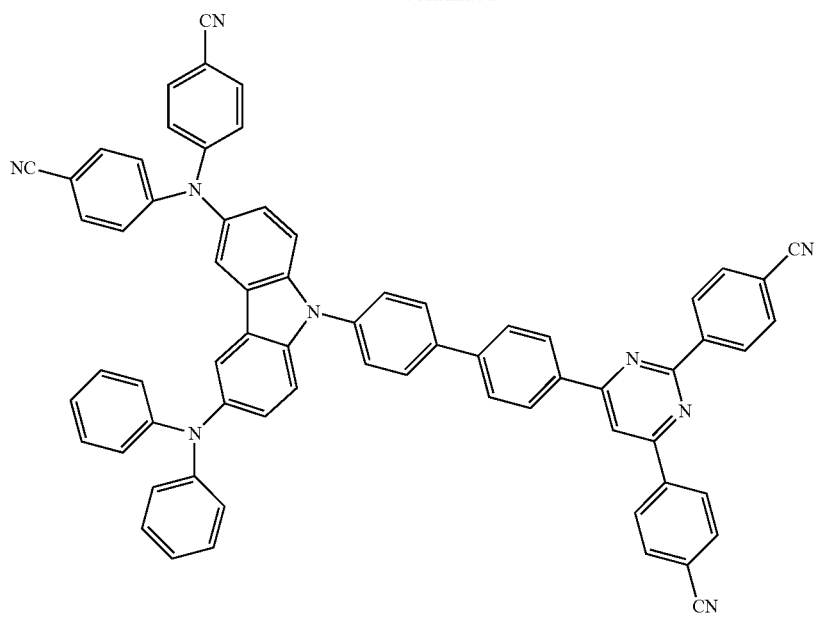
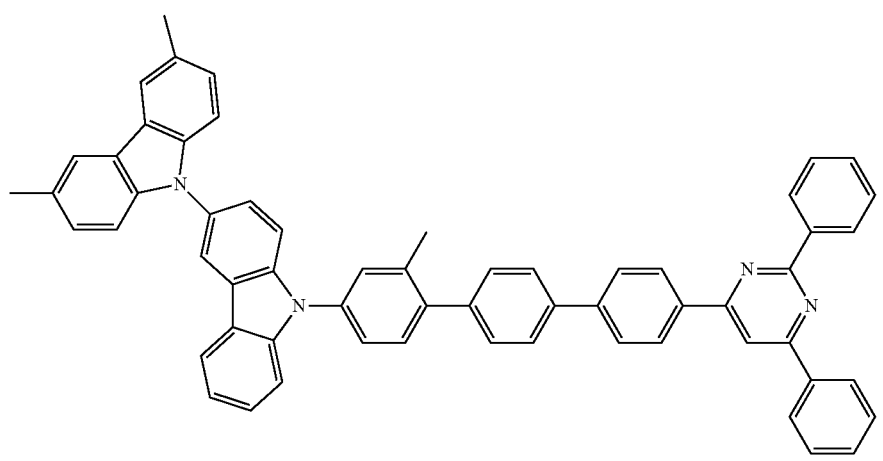

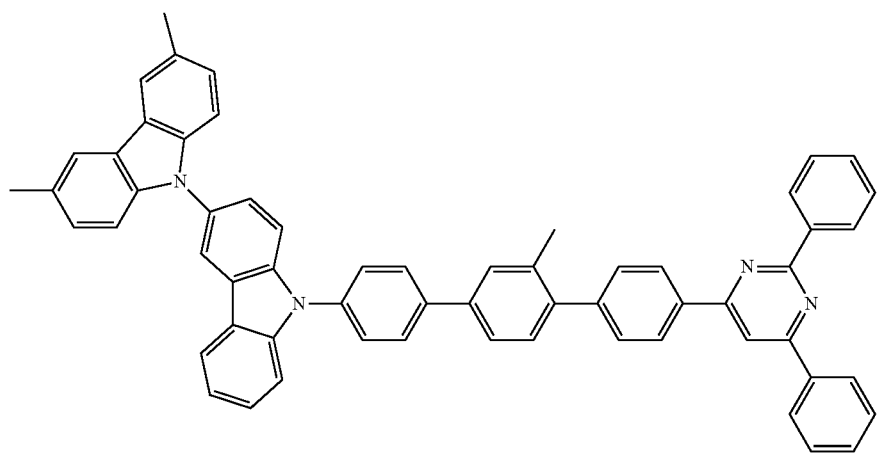

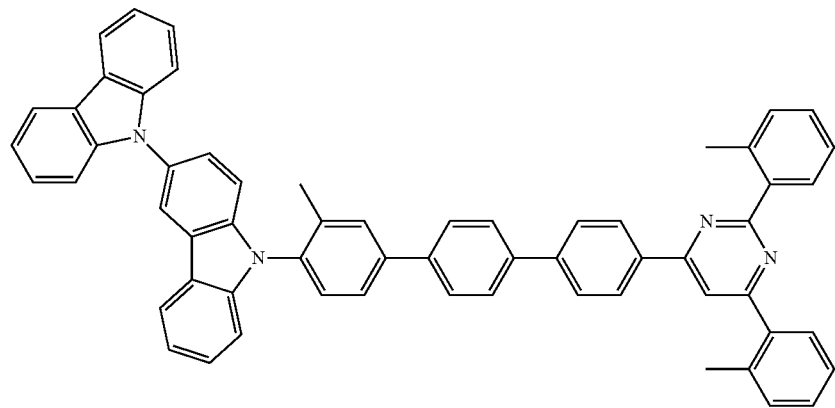
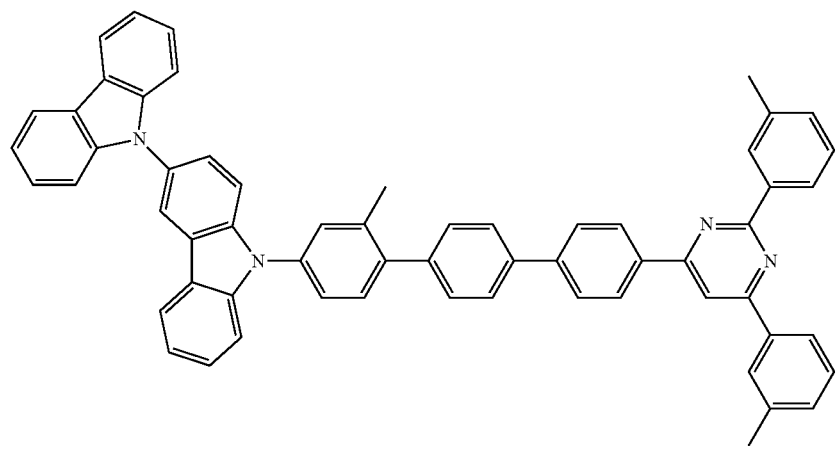
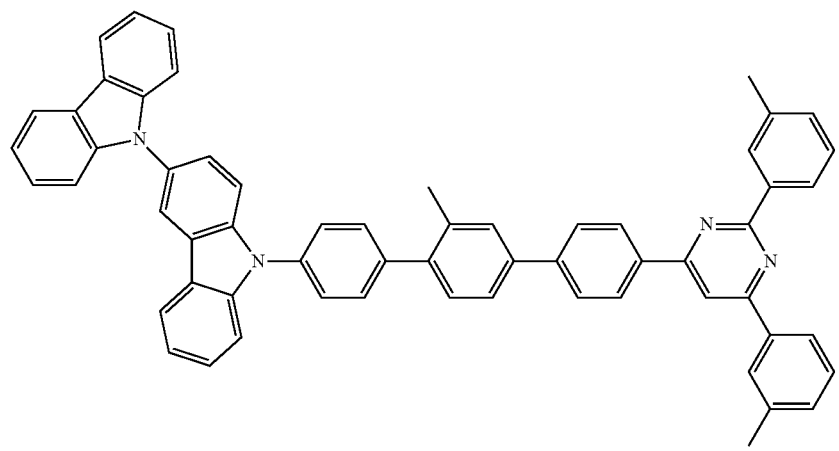

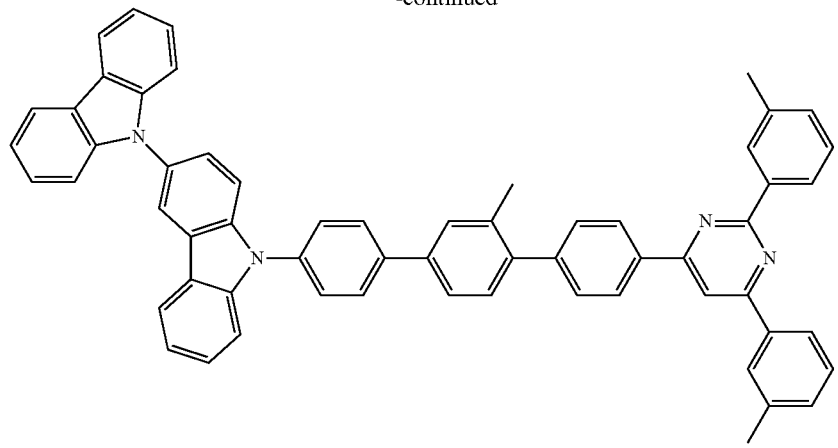
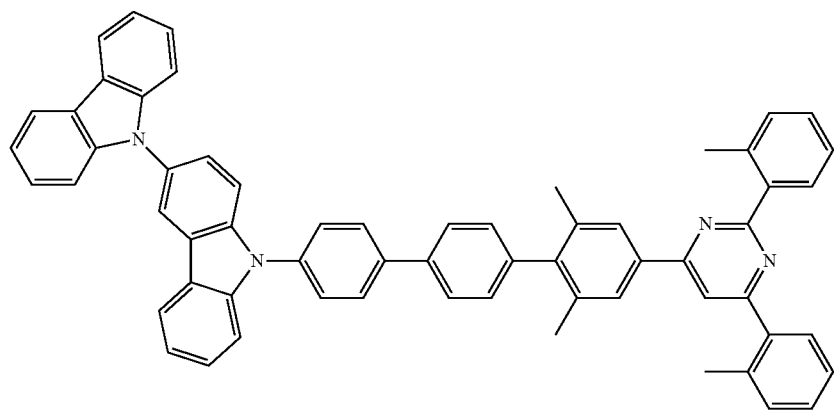
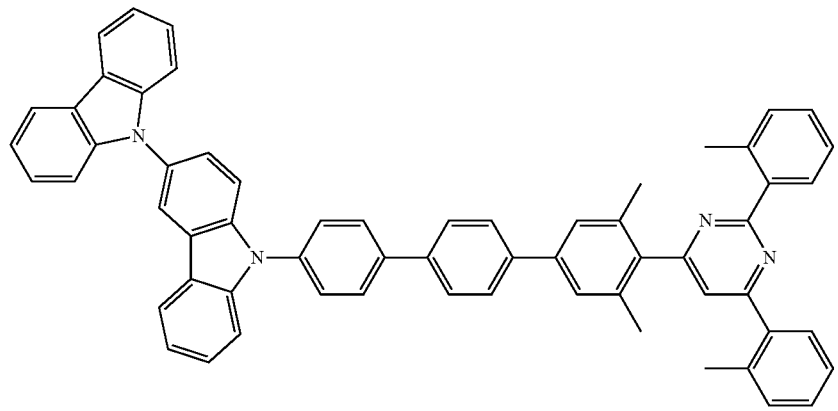
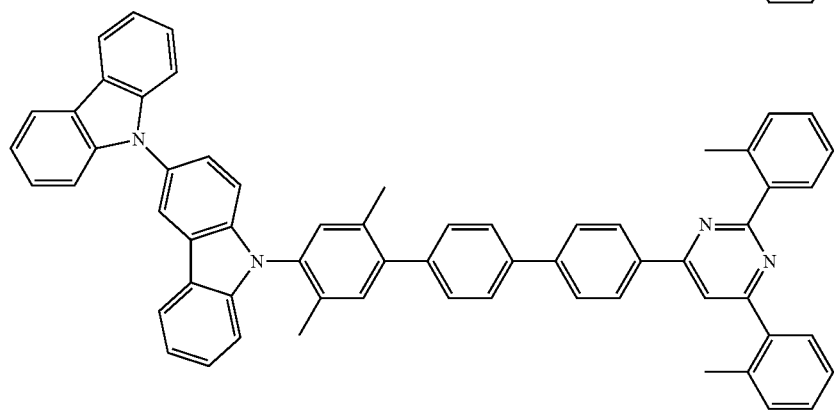

-continued
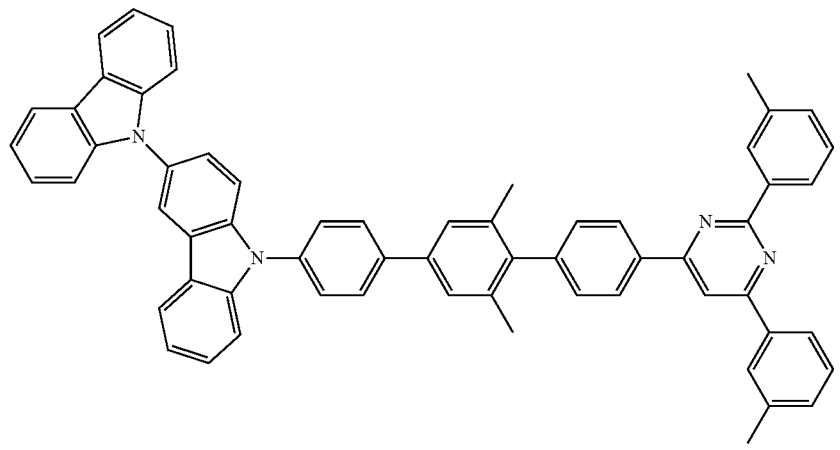
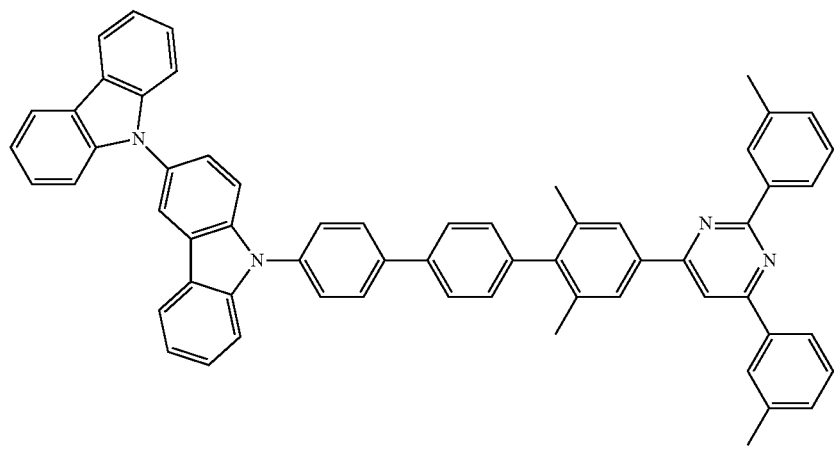
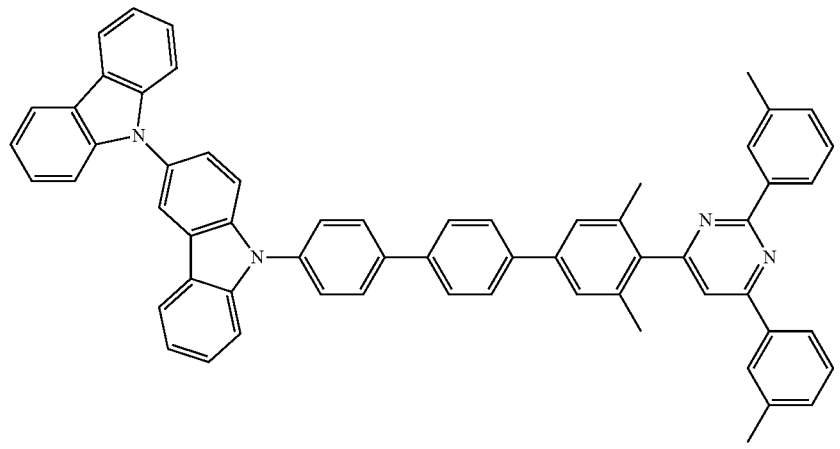

-continued
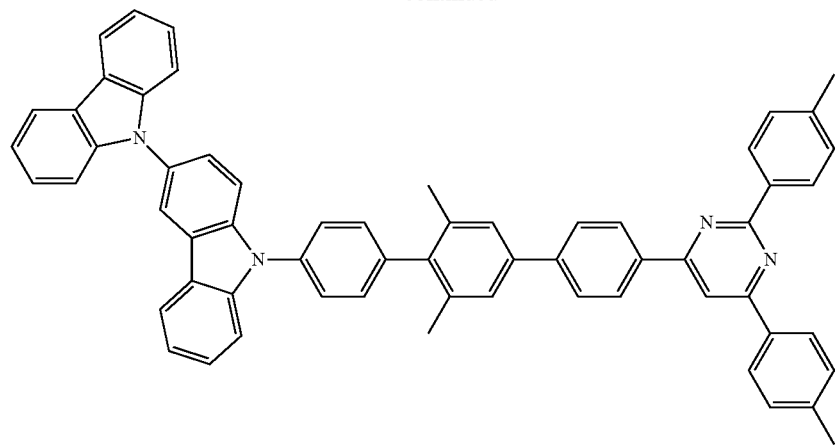
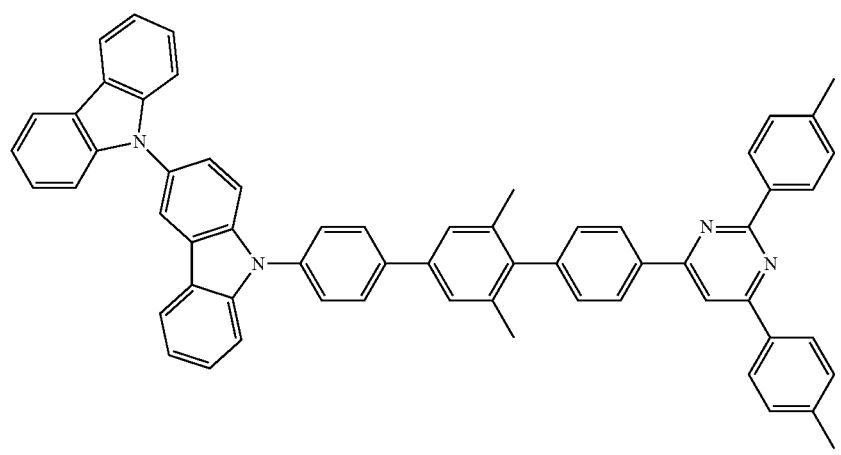
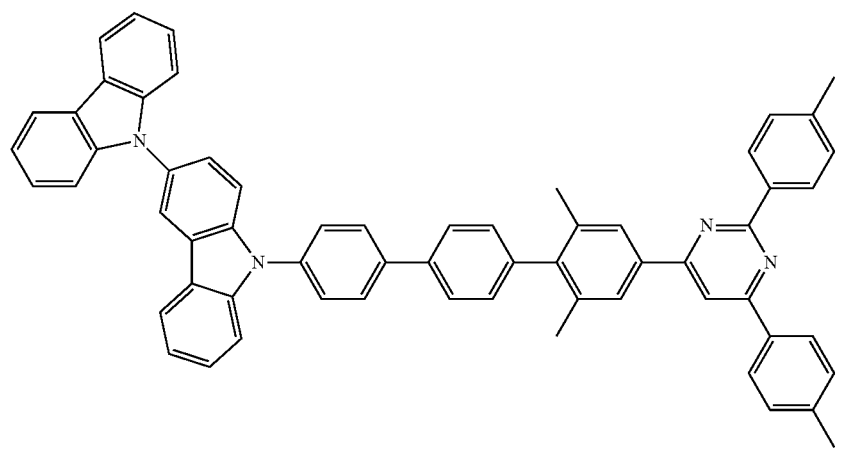

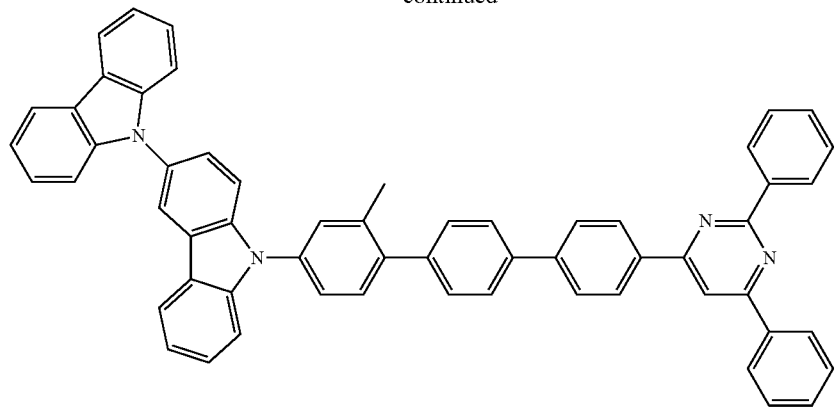
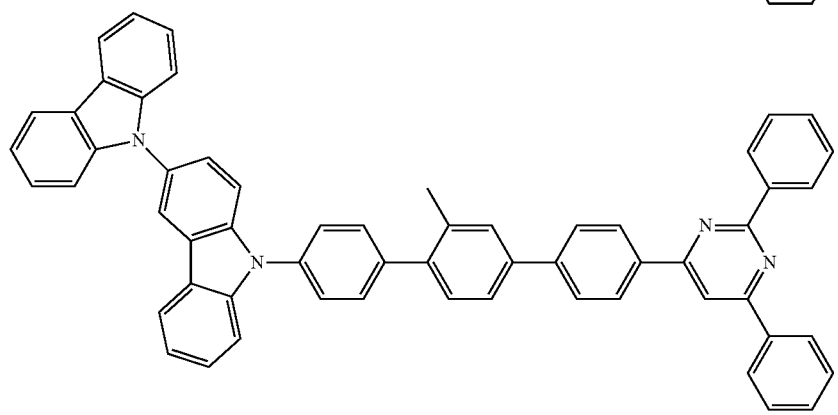
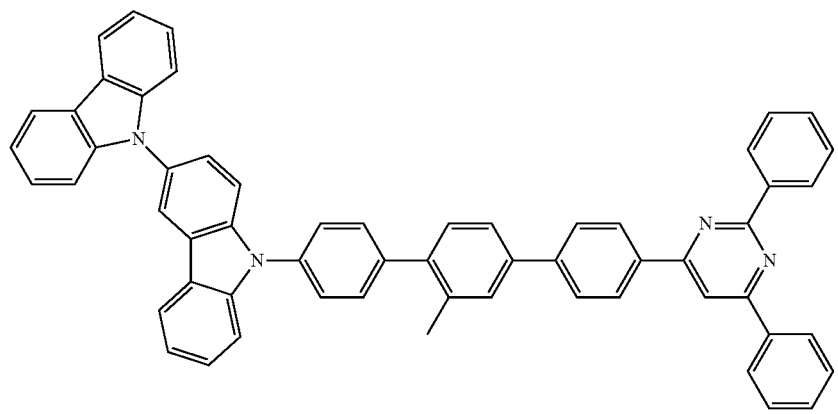
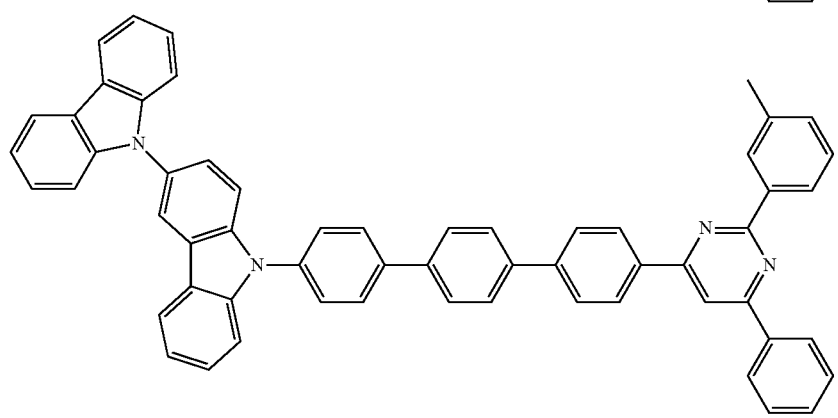

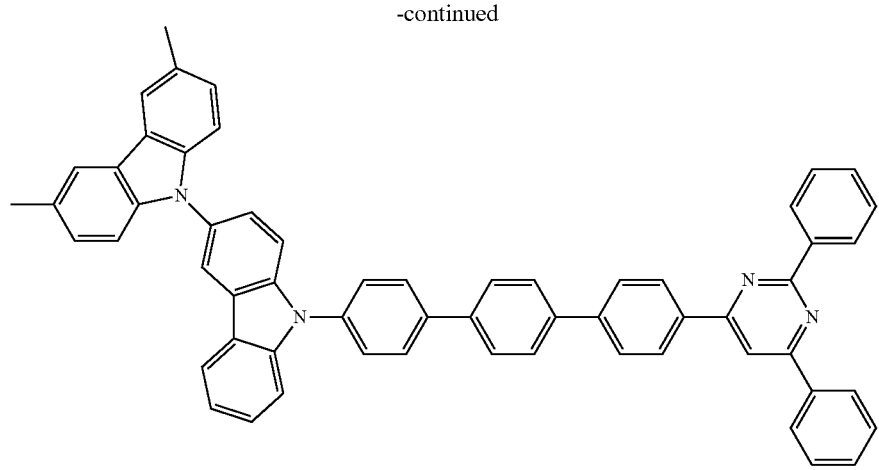
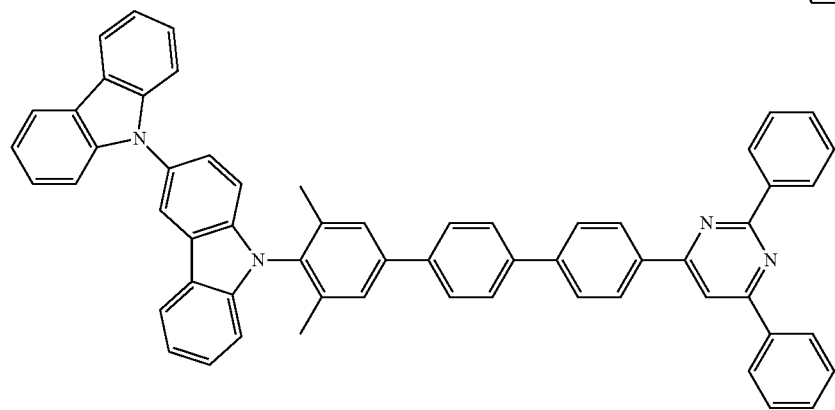
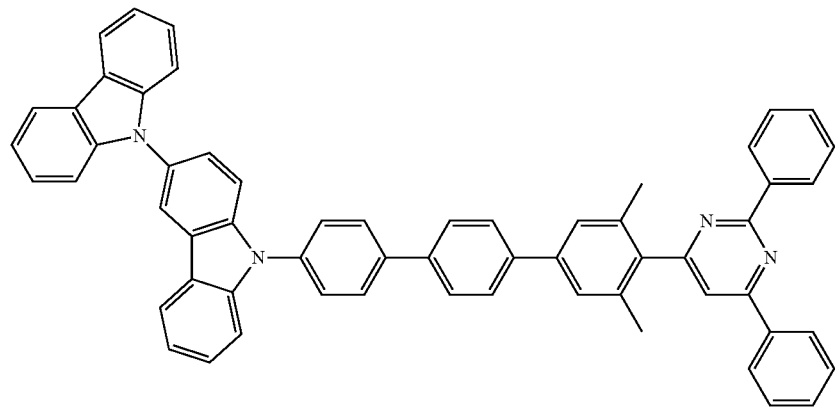
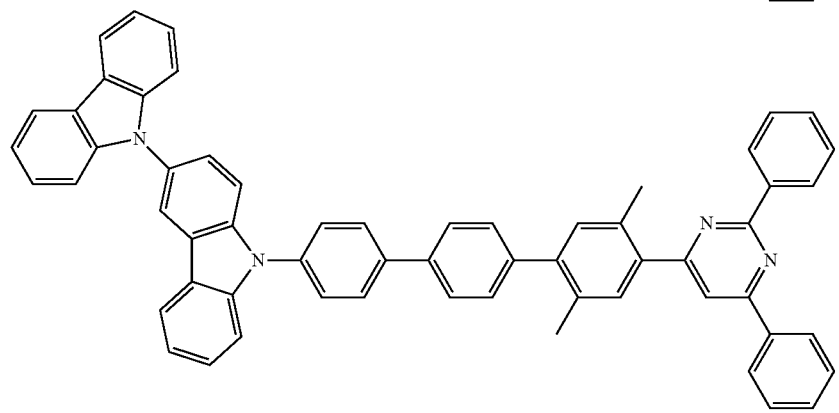

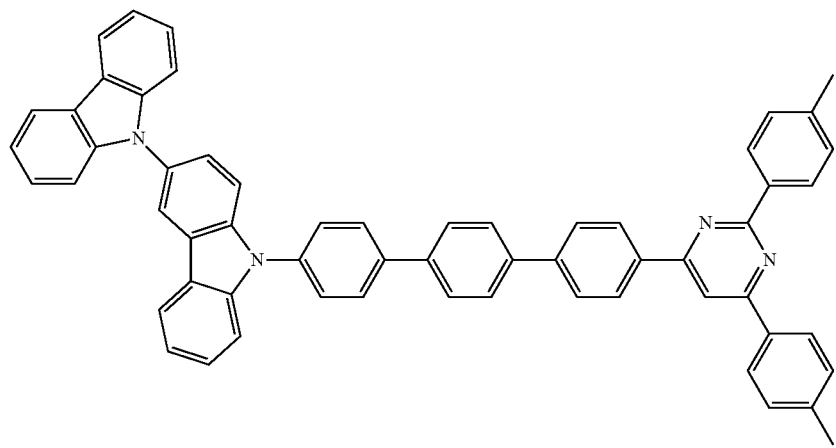
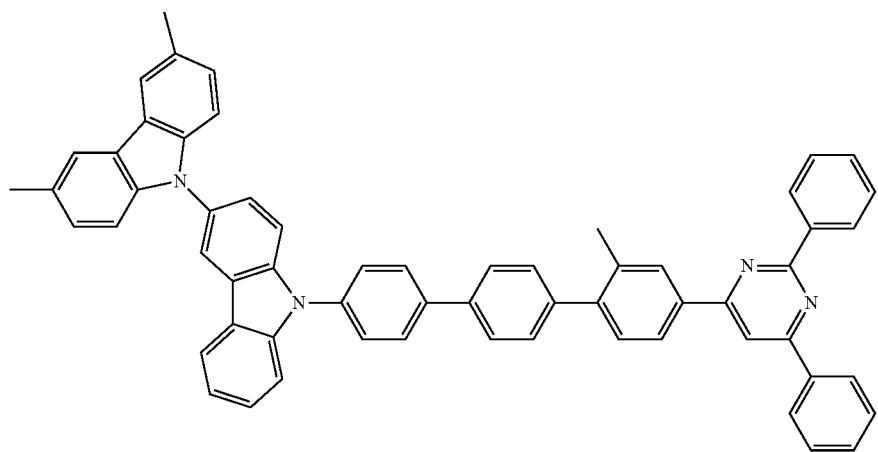
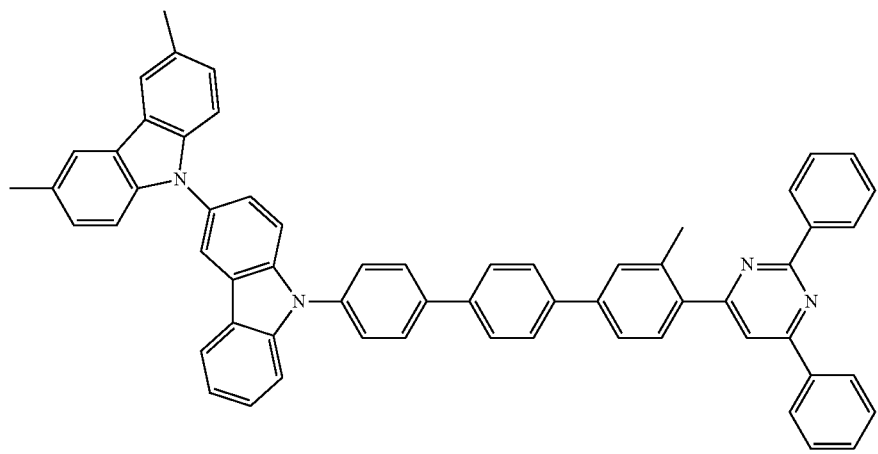

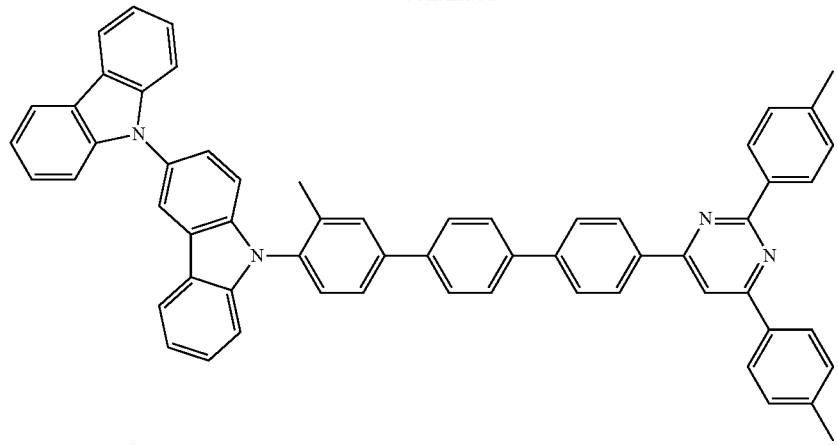
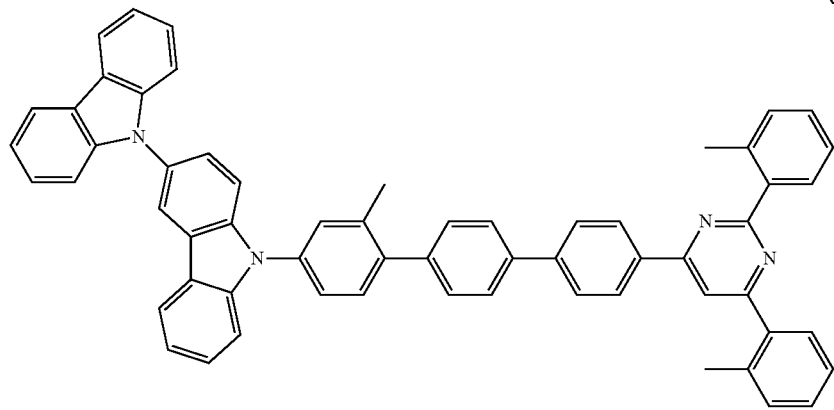
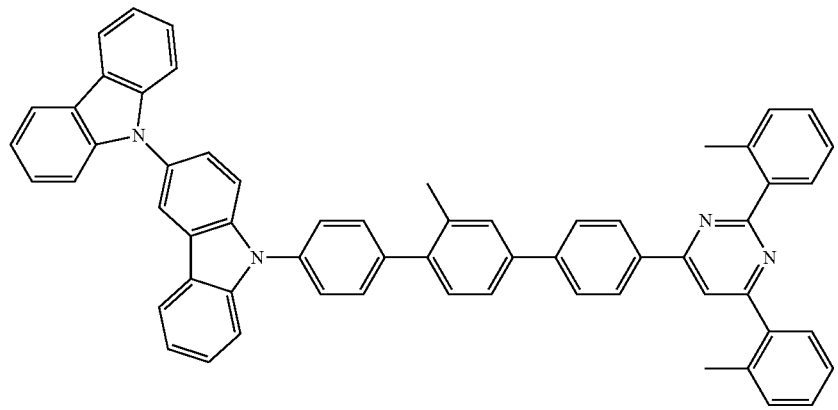
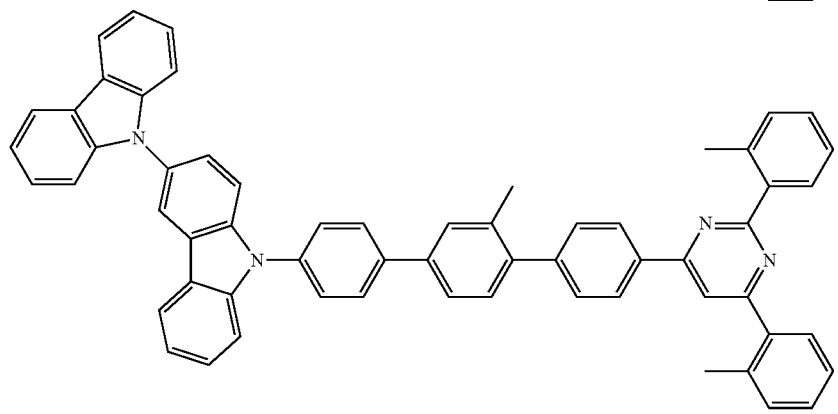

-continued
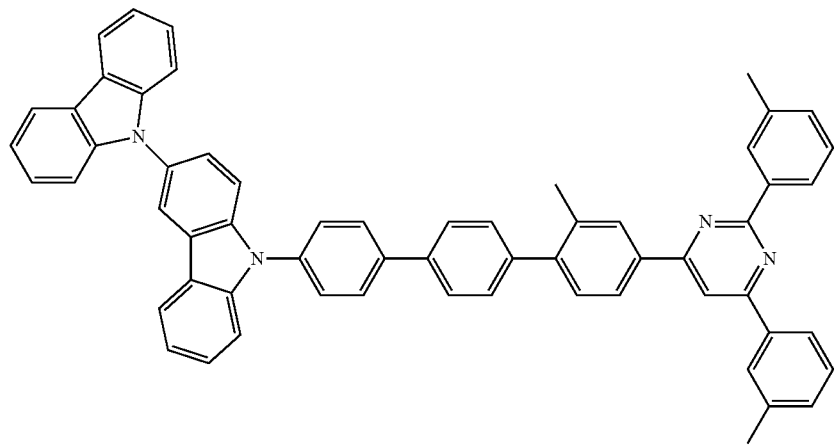
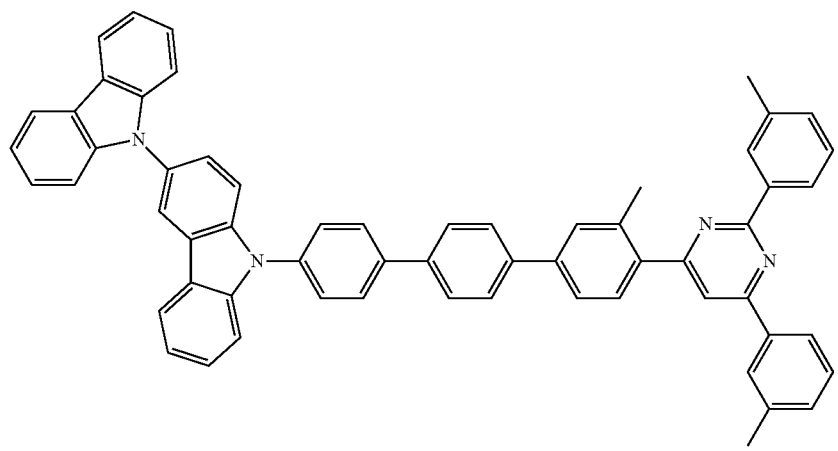
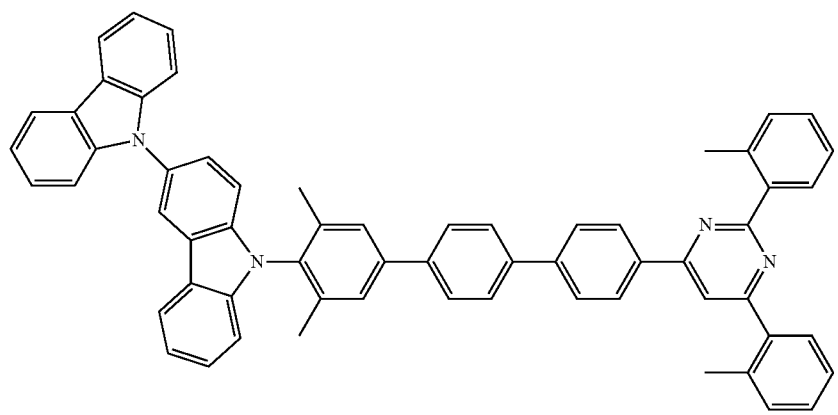
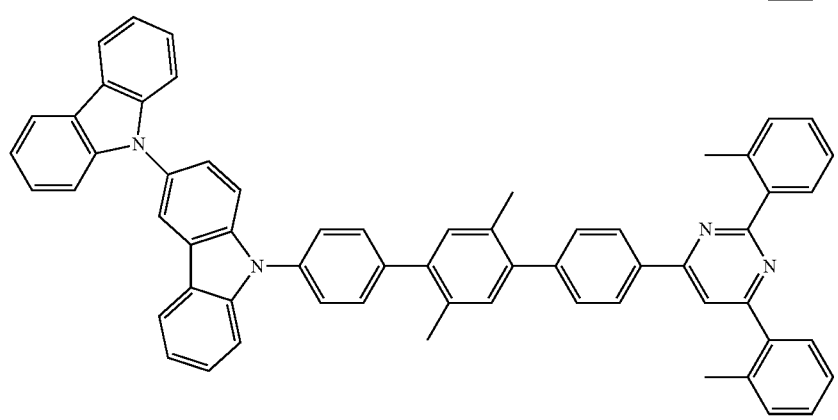

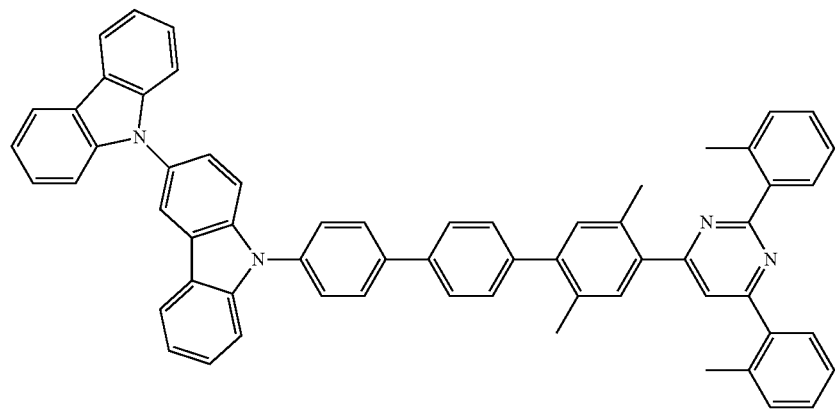
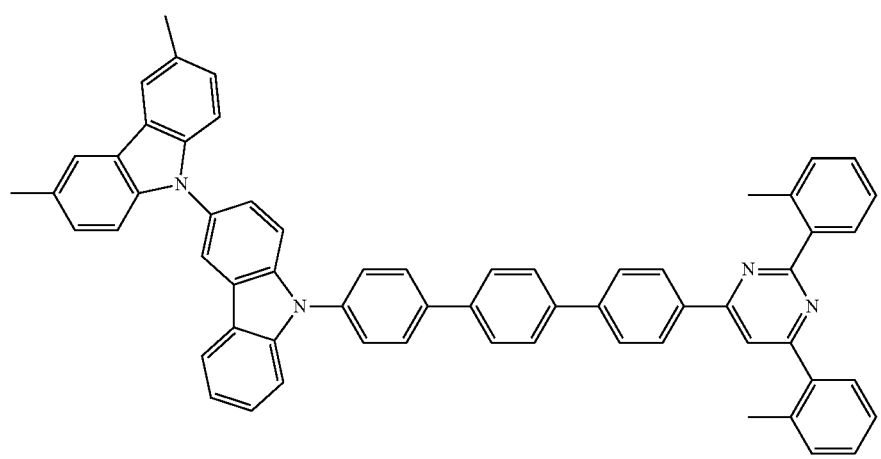
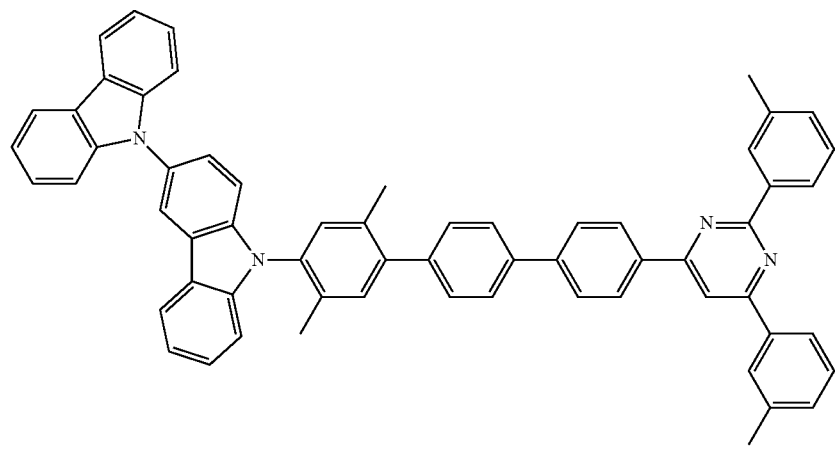

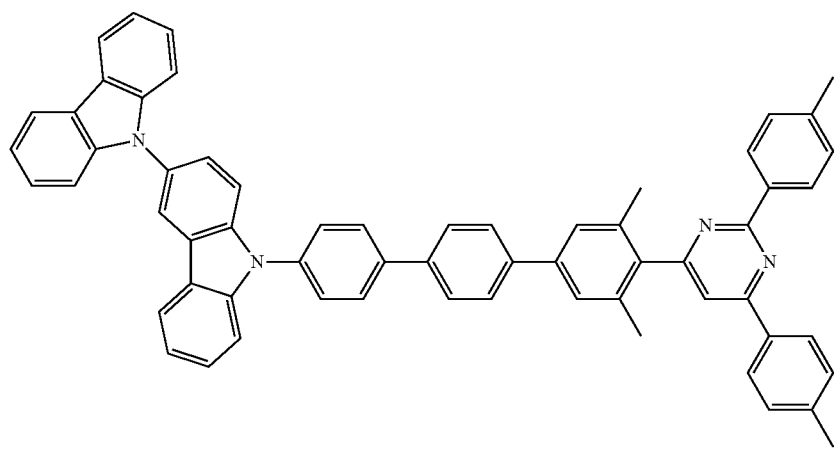

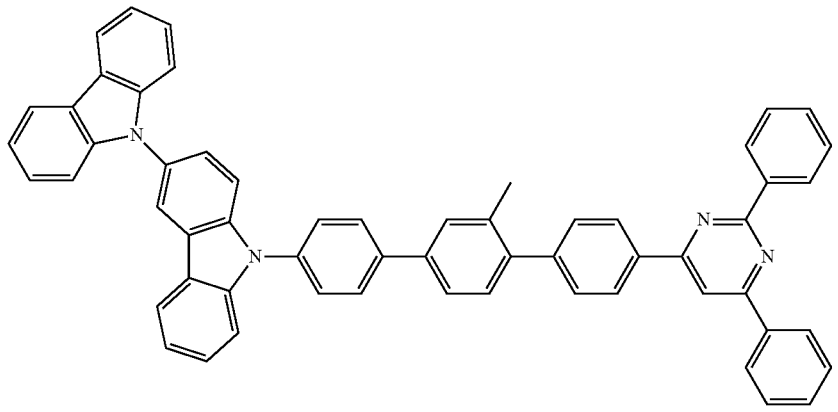

-continued
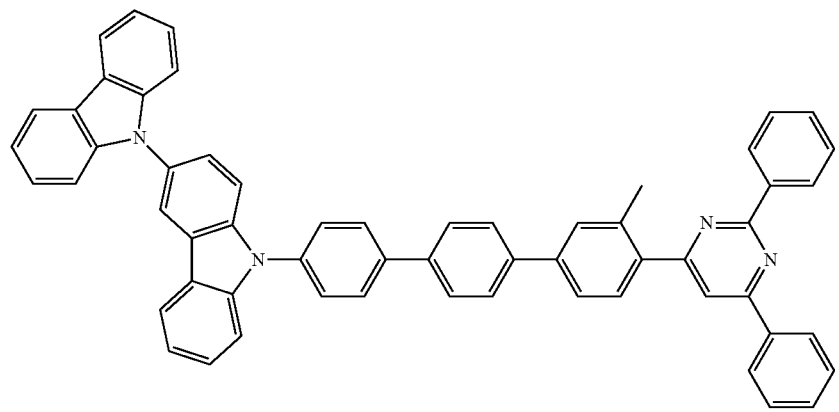
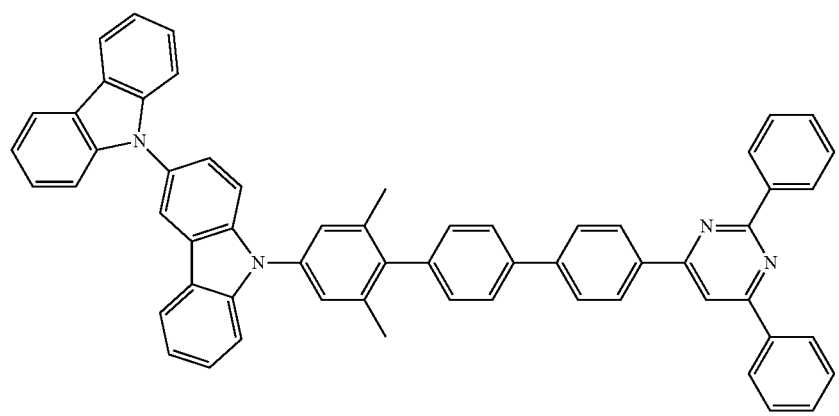
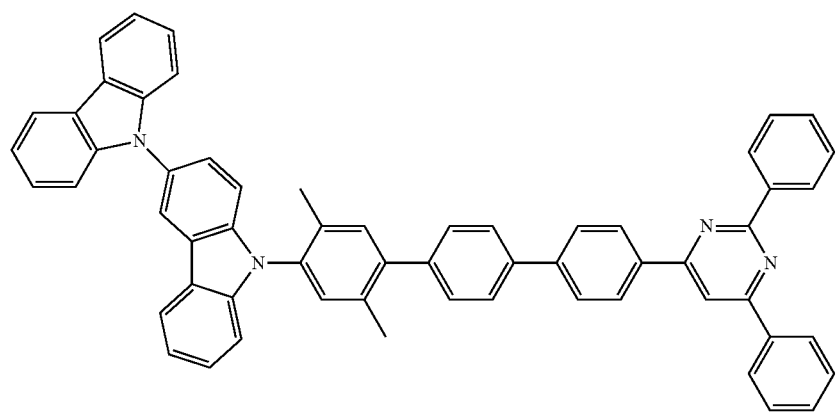
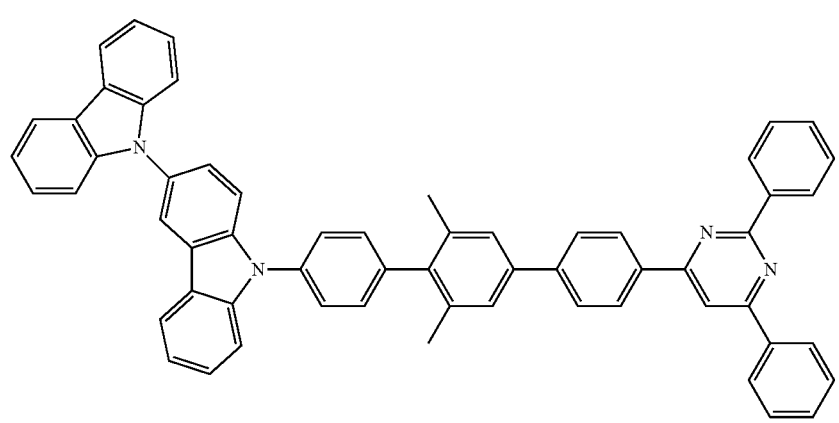

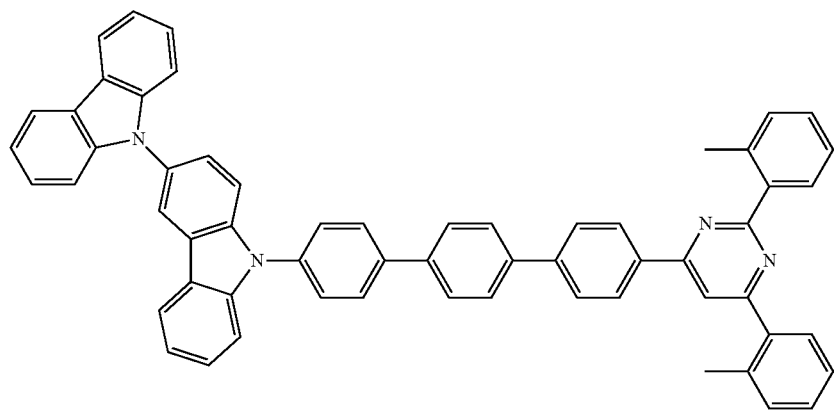
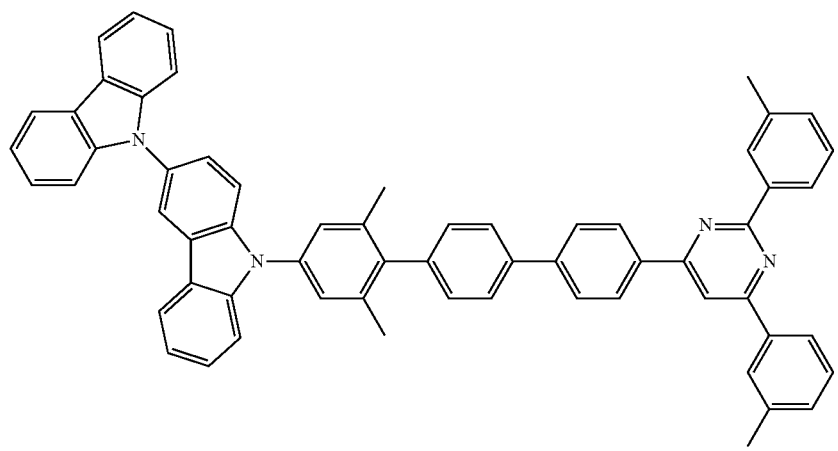
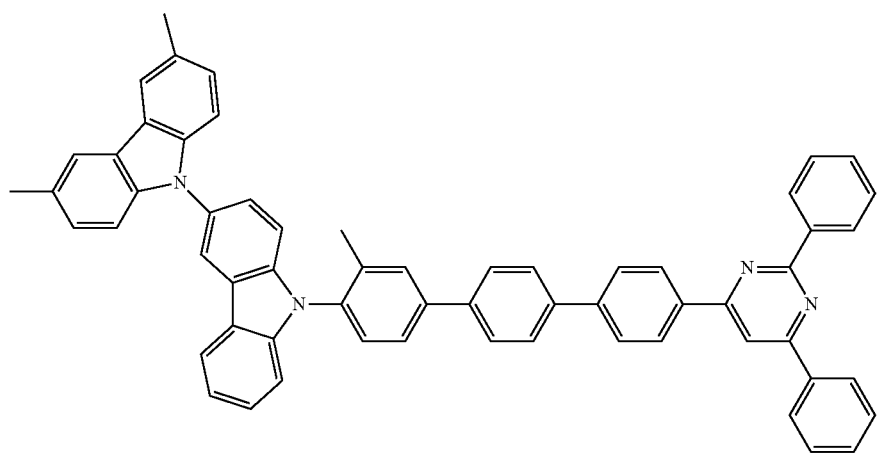

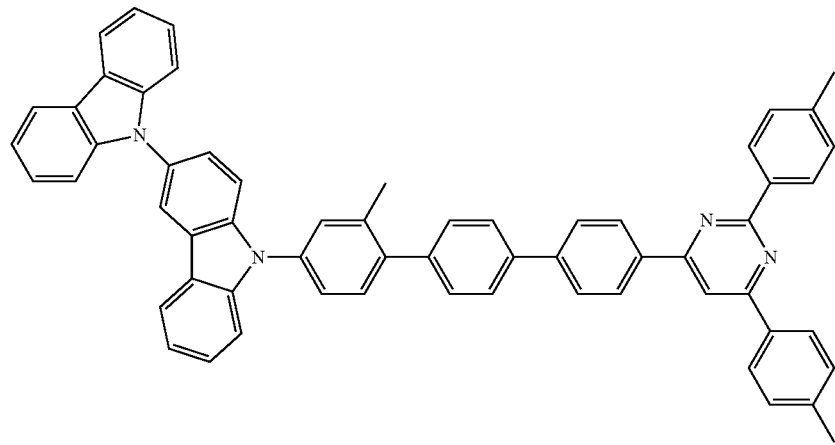

-continued
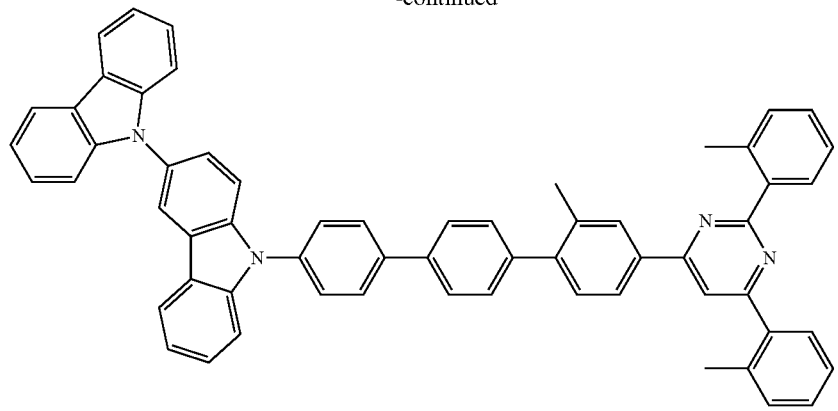
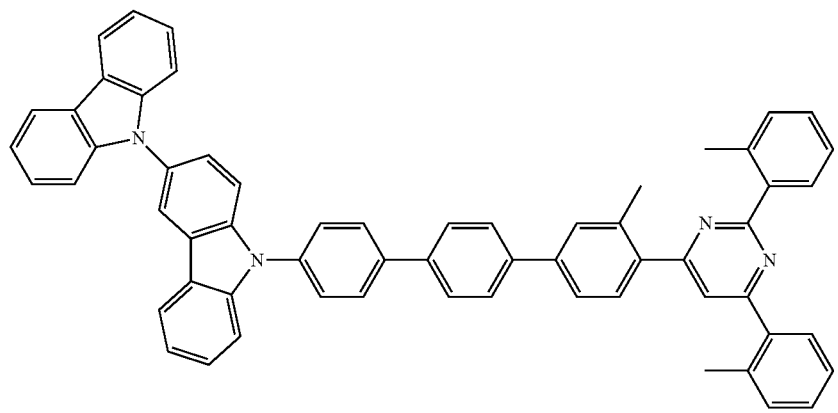
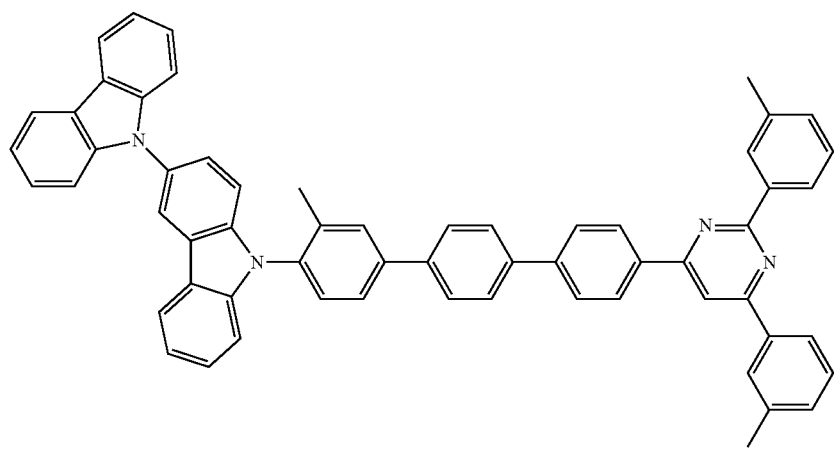
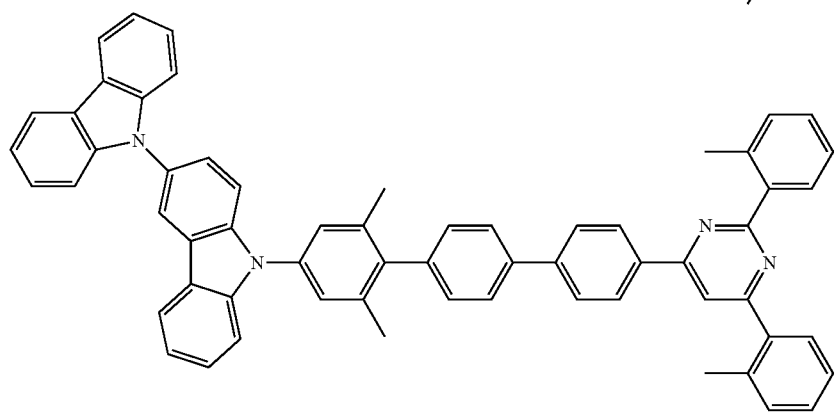

-continued
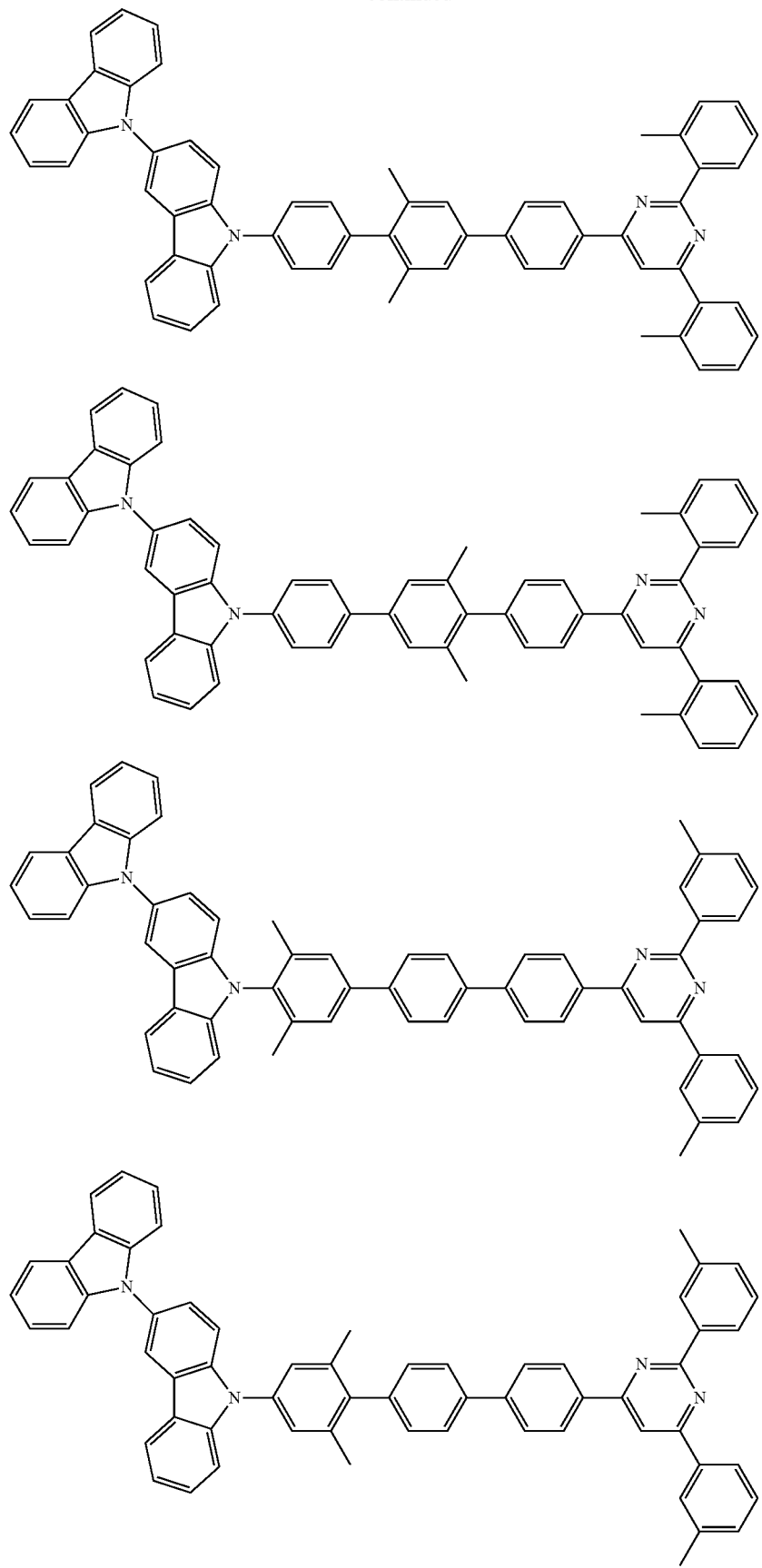

-continued
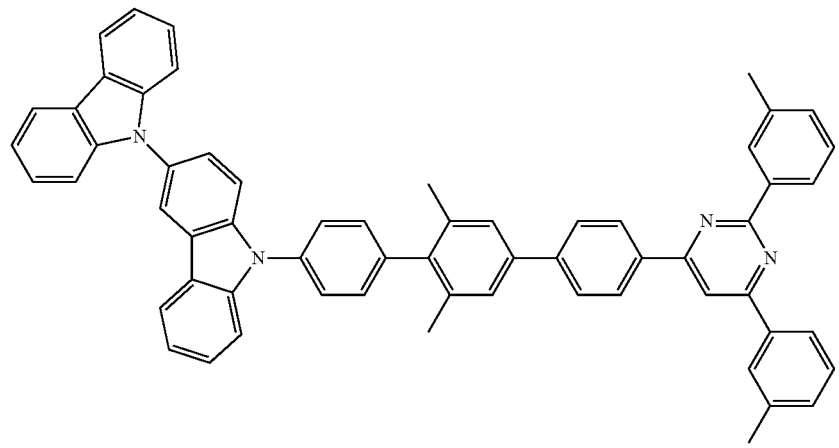
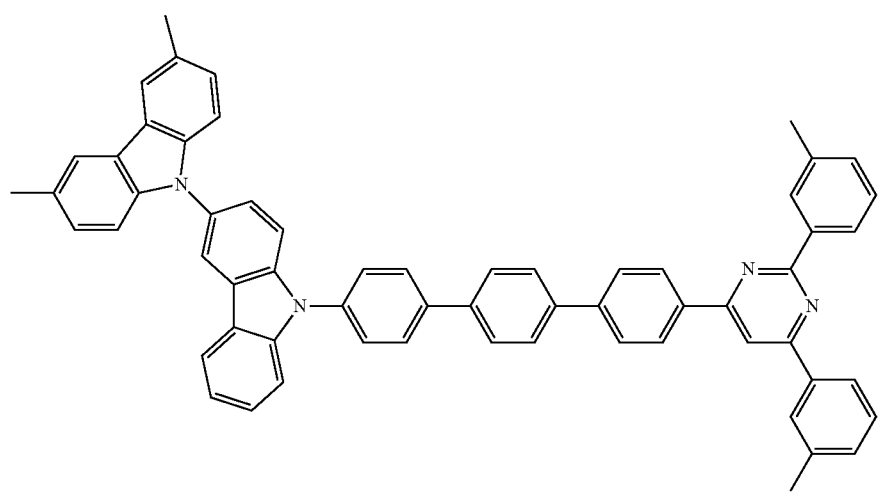
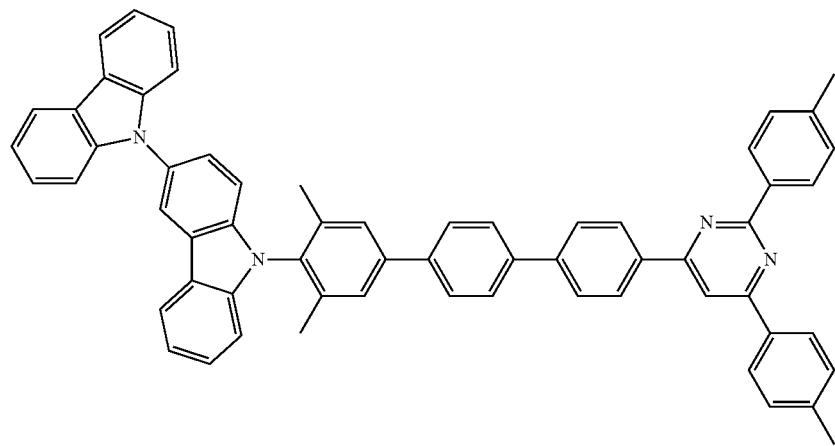

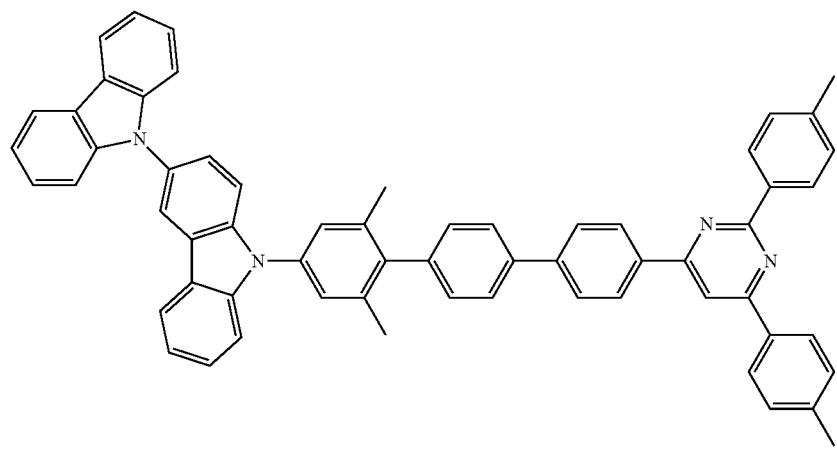
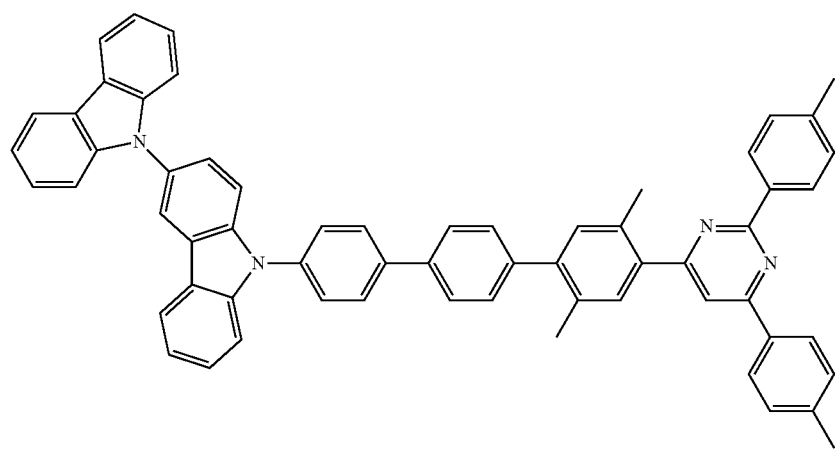
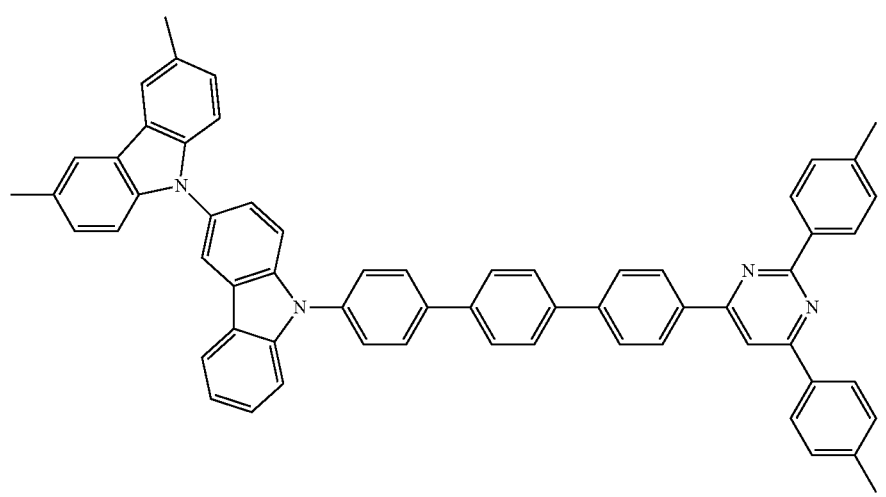

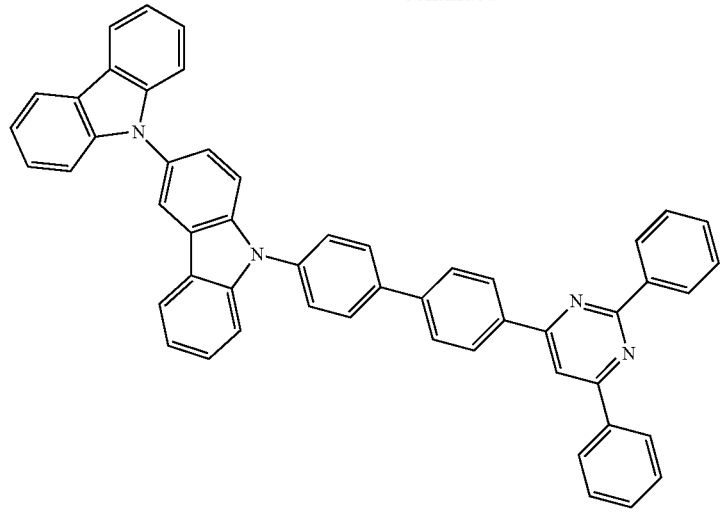
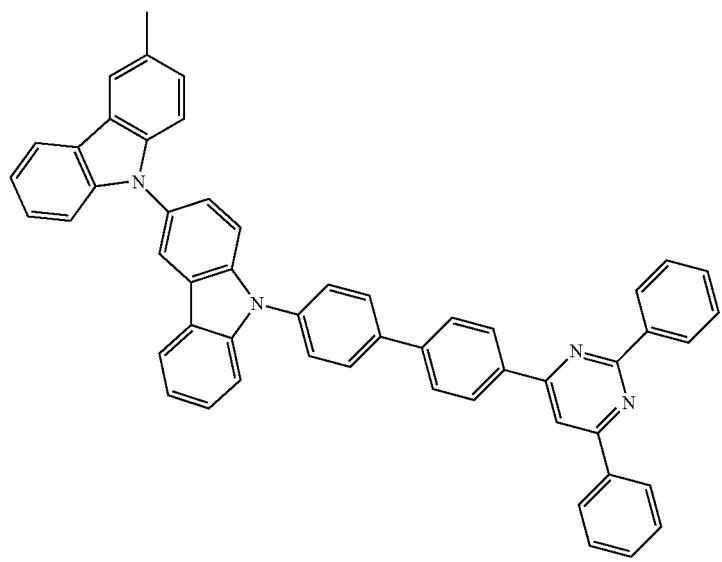
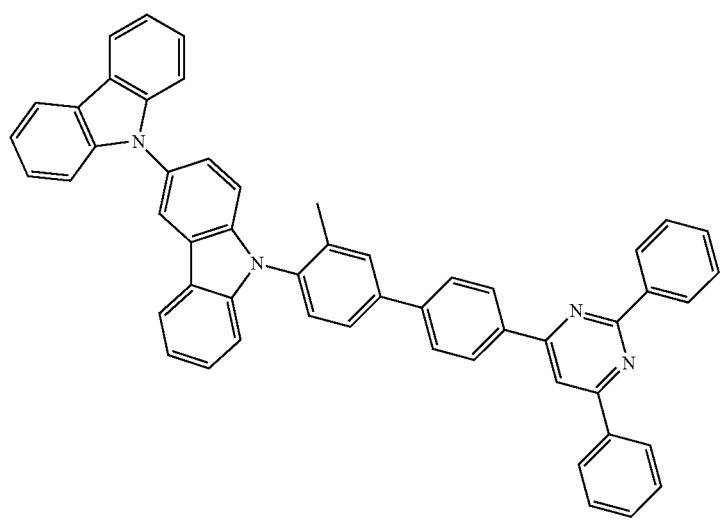

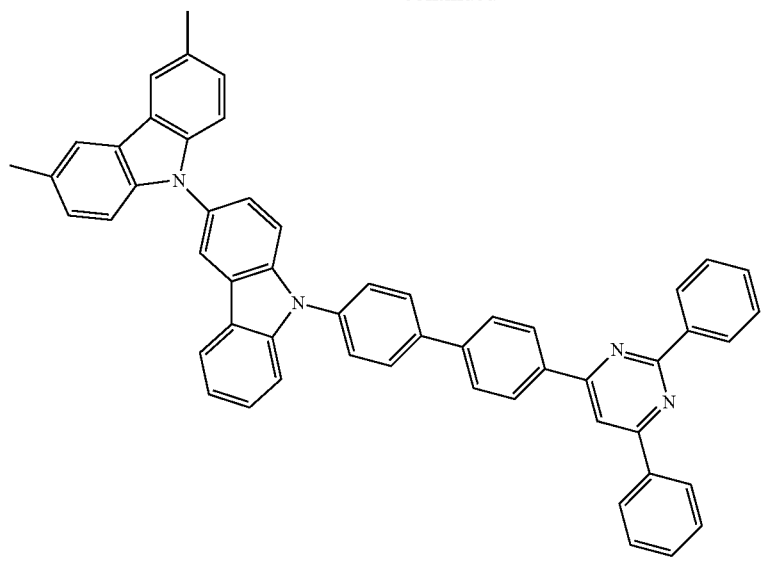
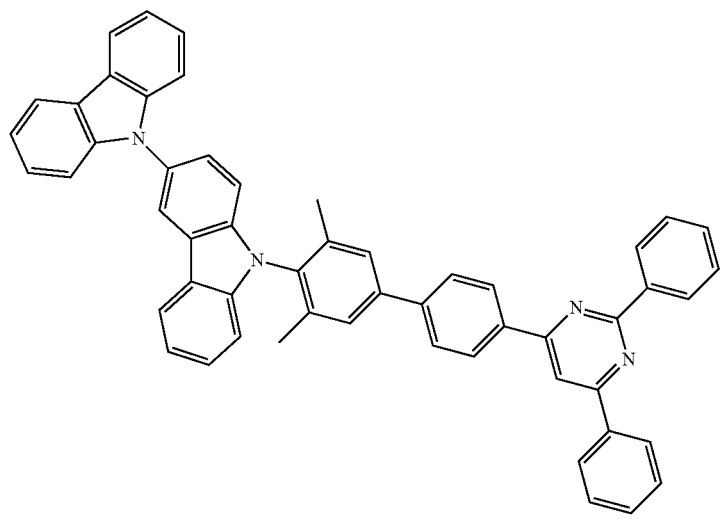
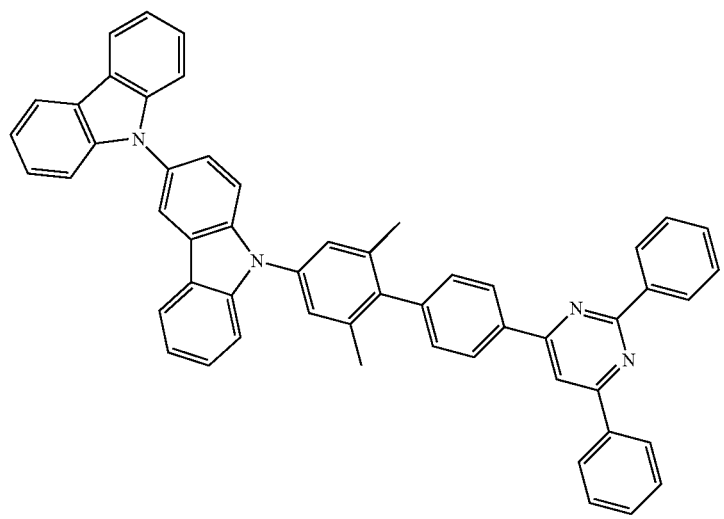

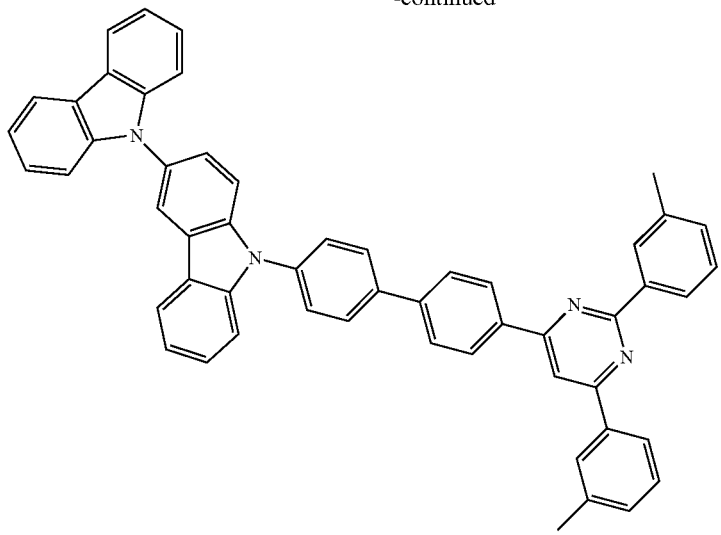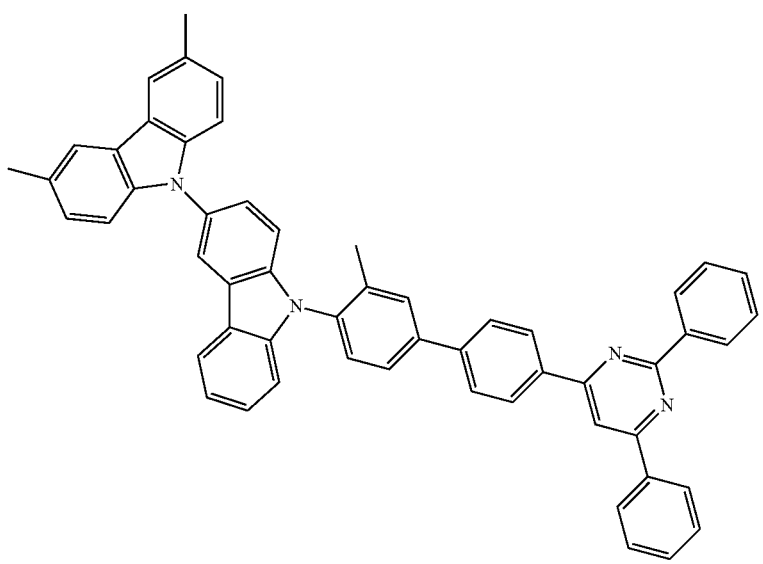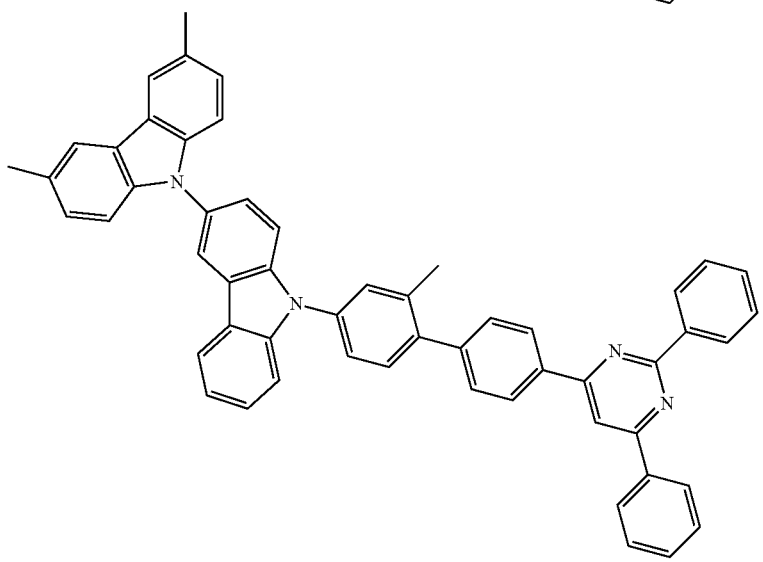

-continued
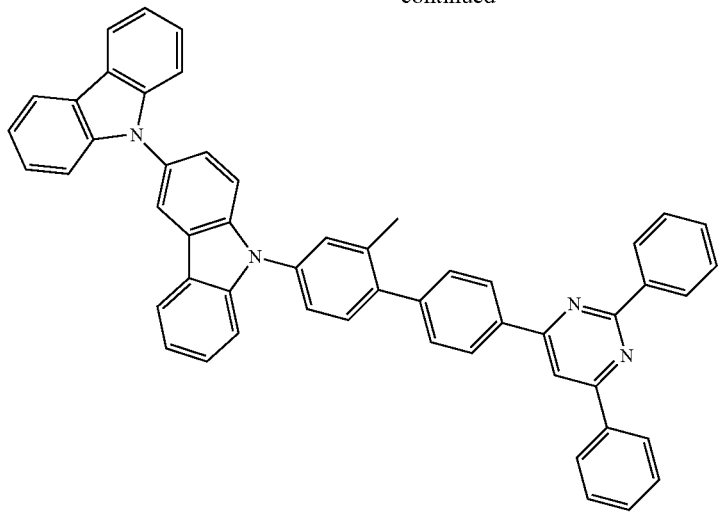
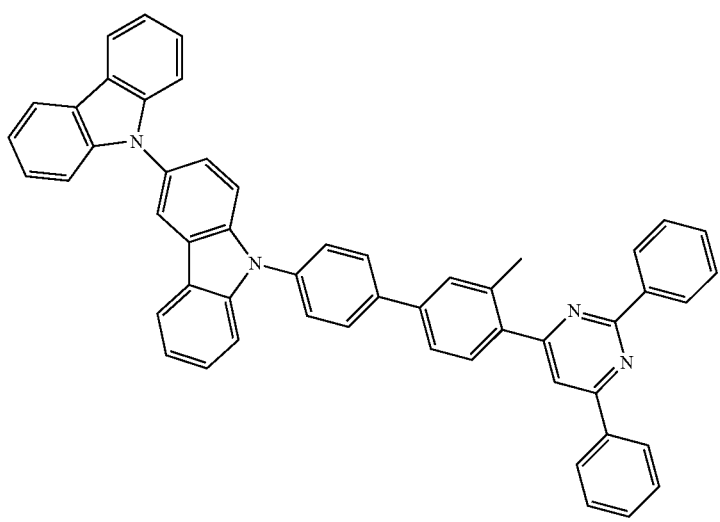
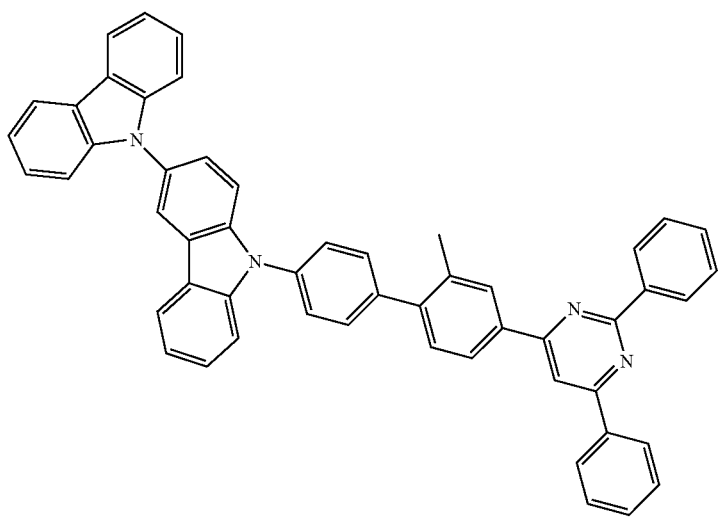

-continued
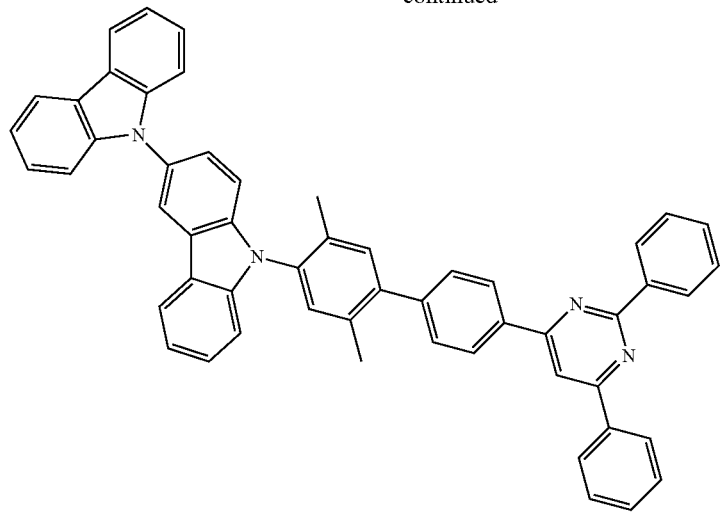
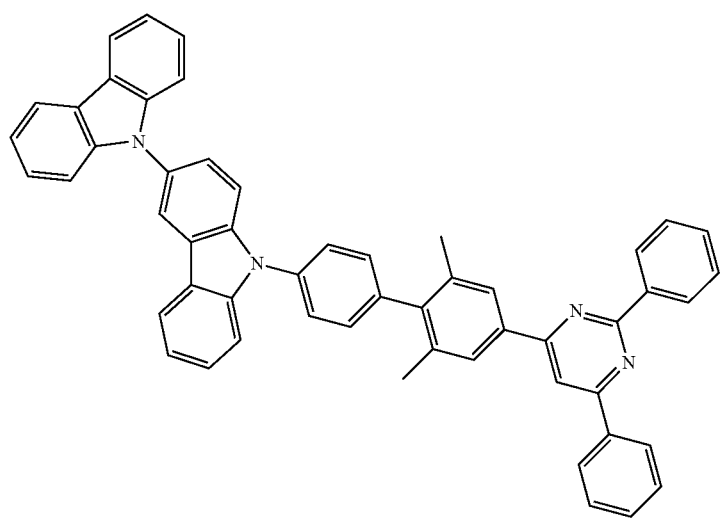
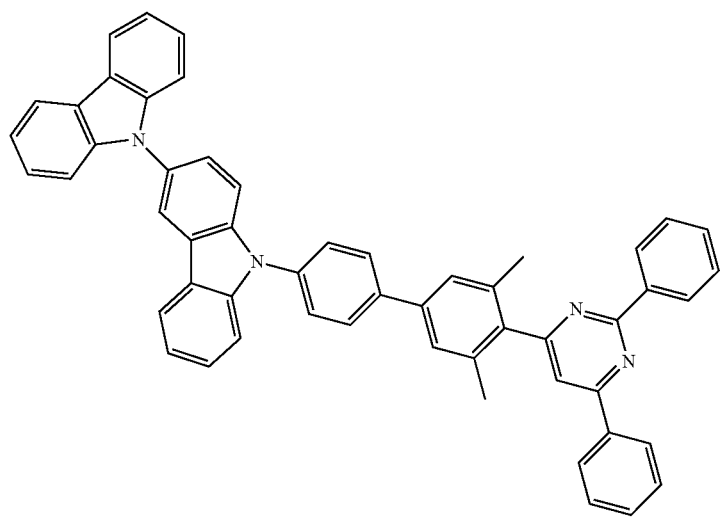

-continued
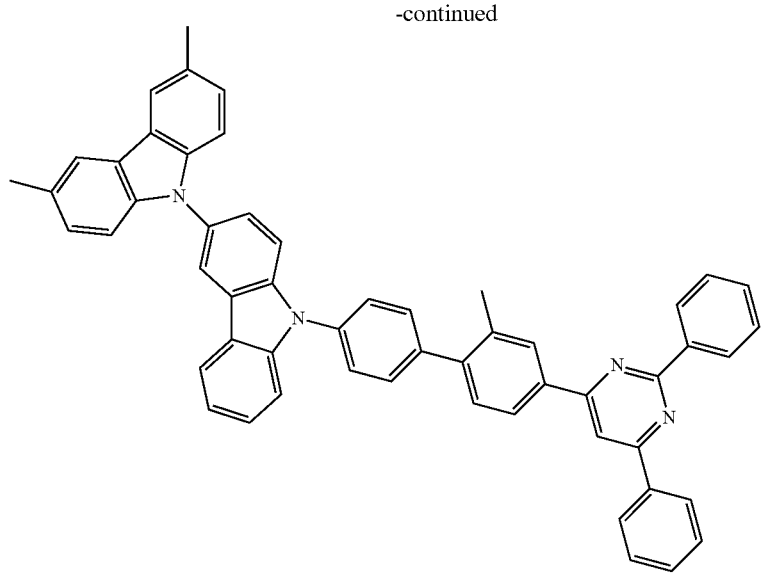
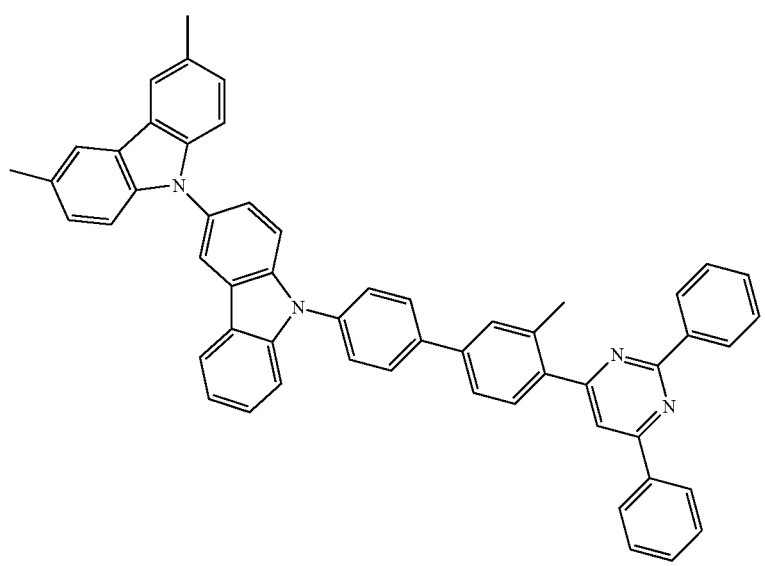
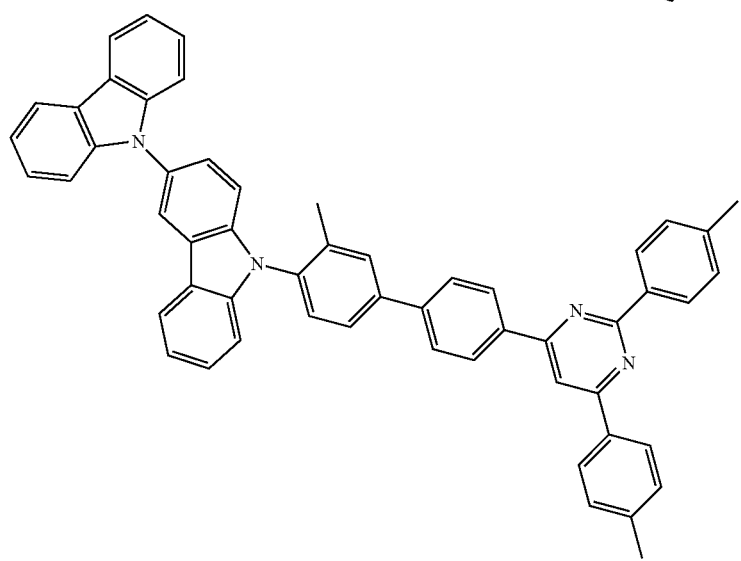

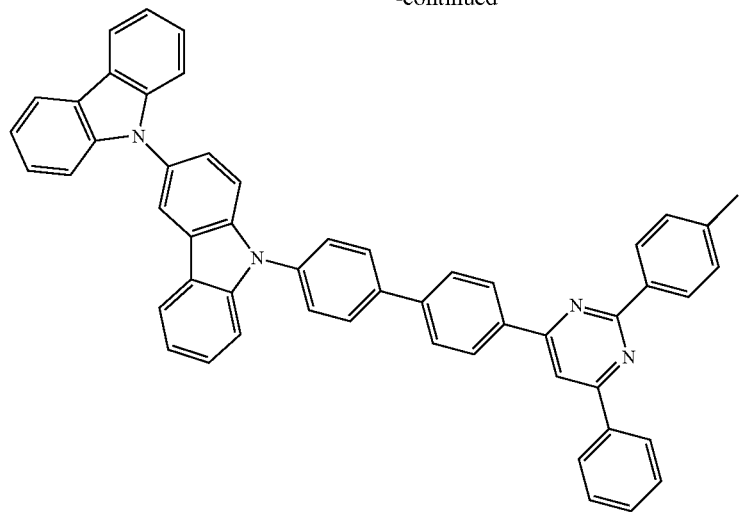
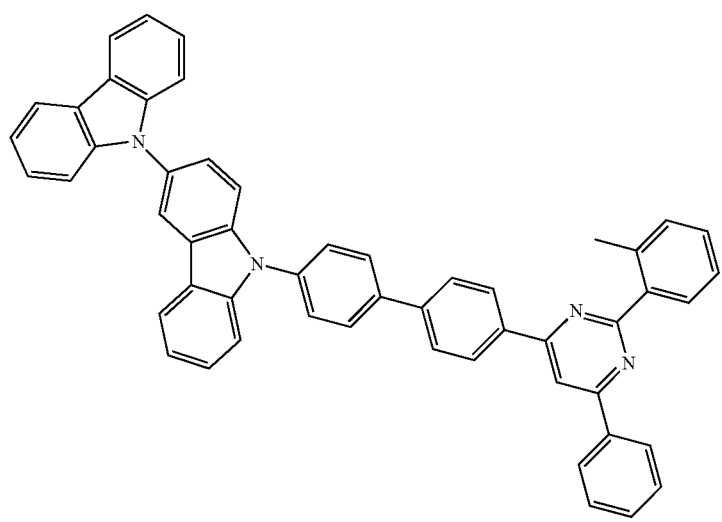
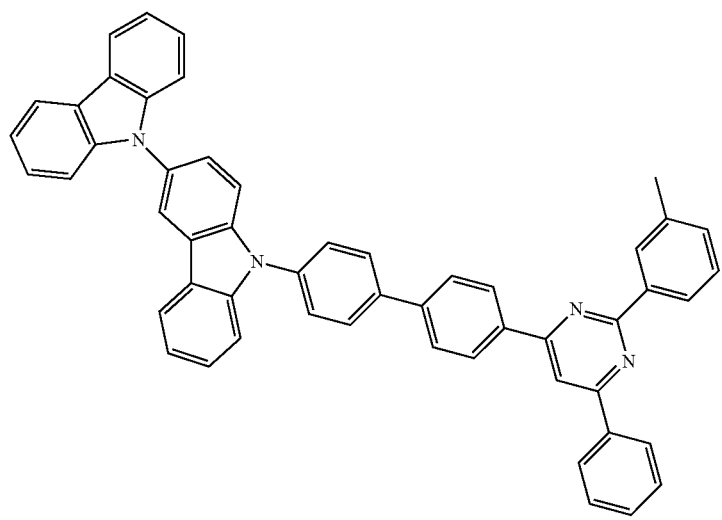

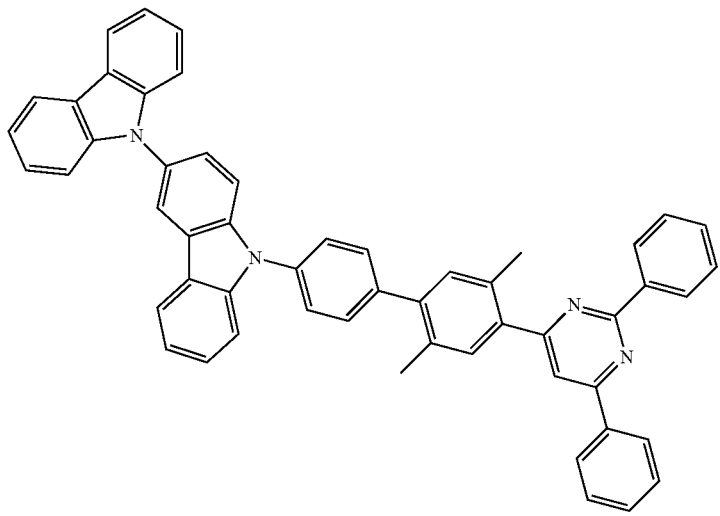
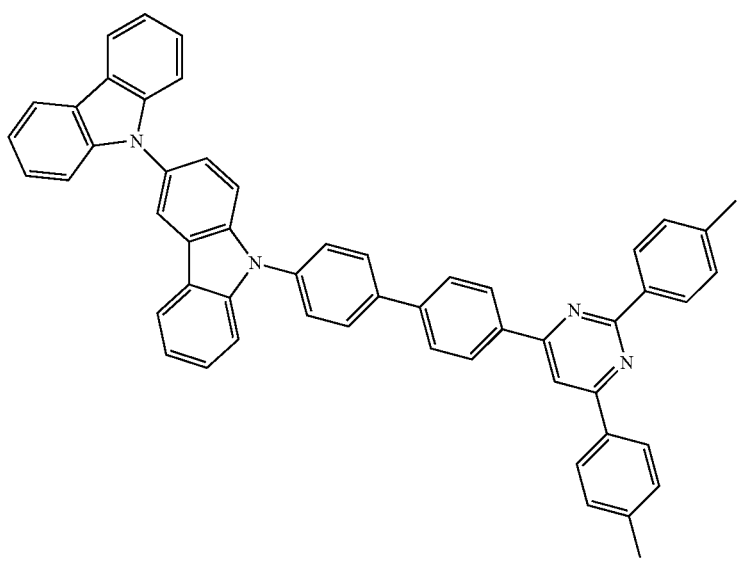
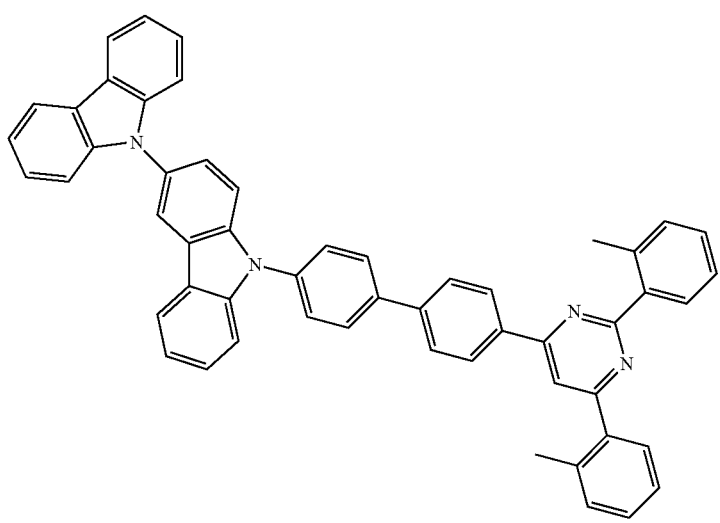

-continued
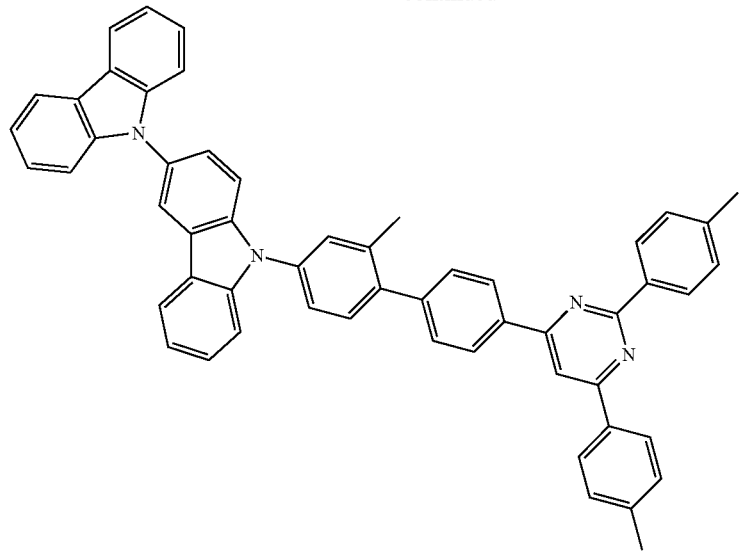
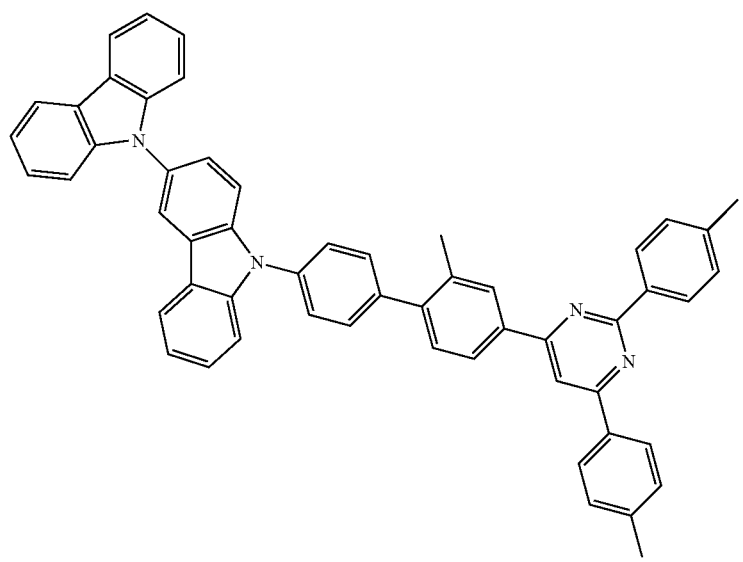
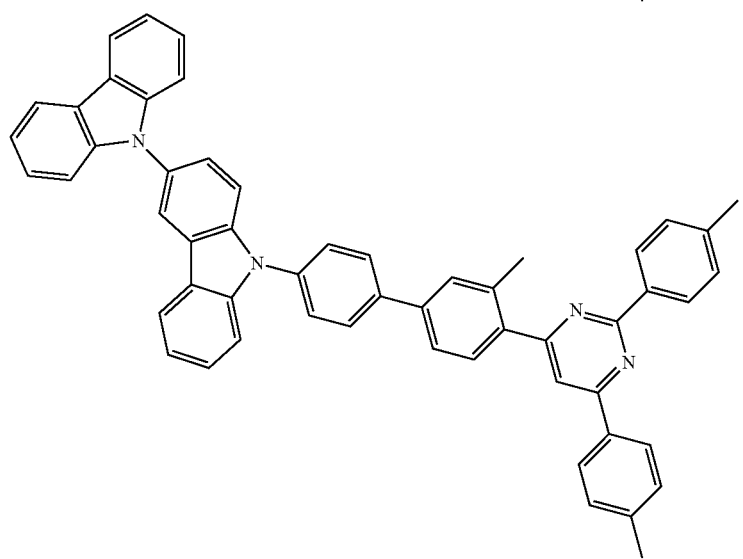

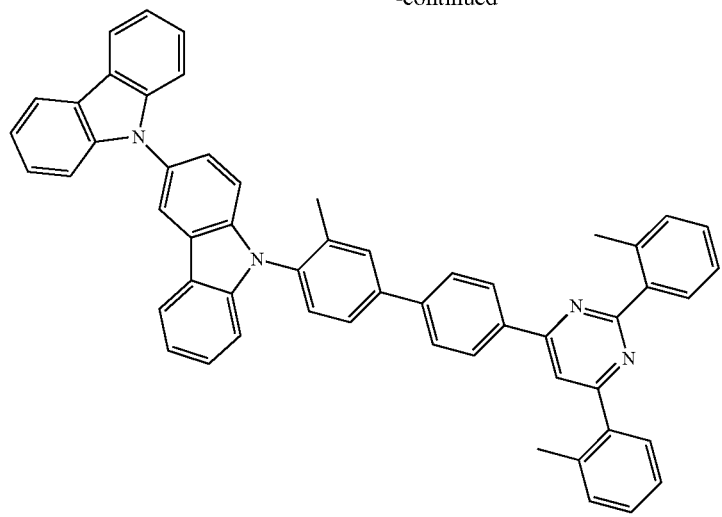
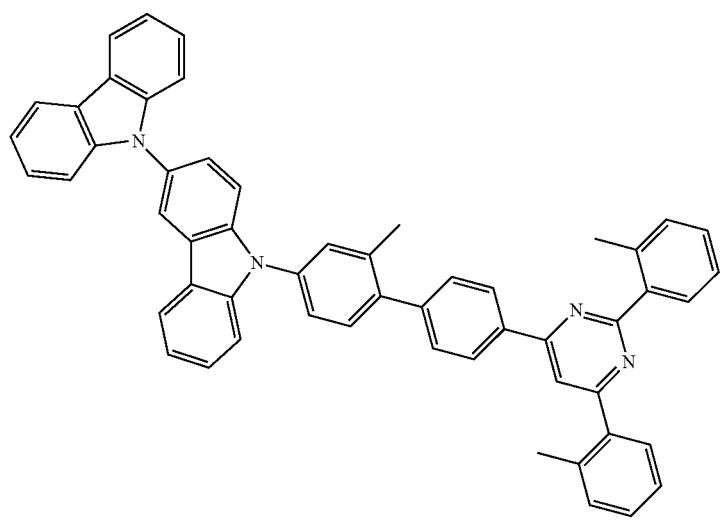
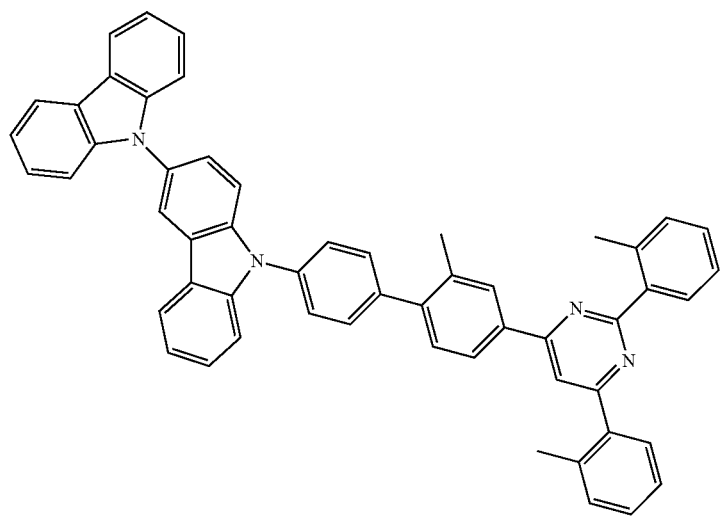

-continued
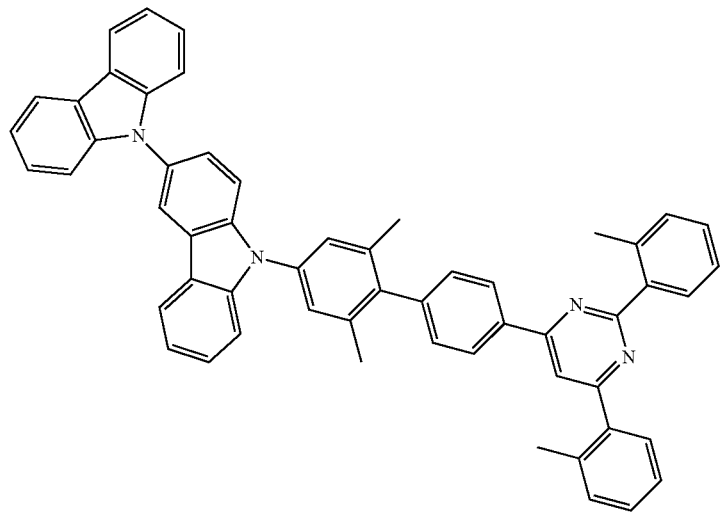
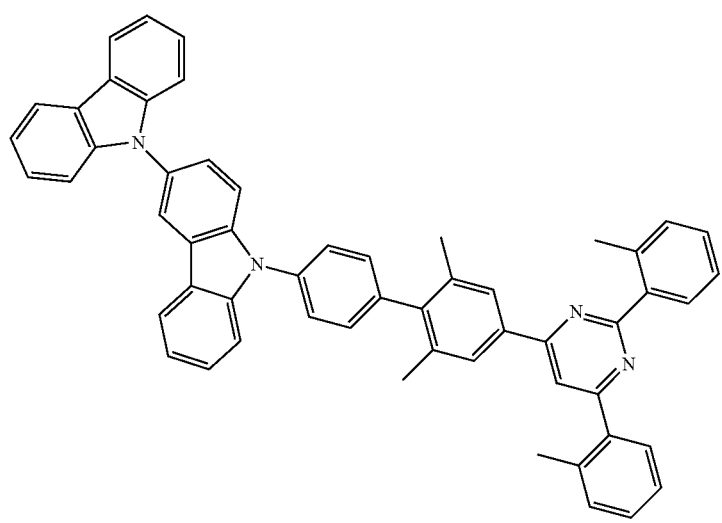
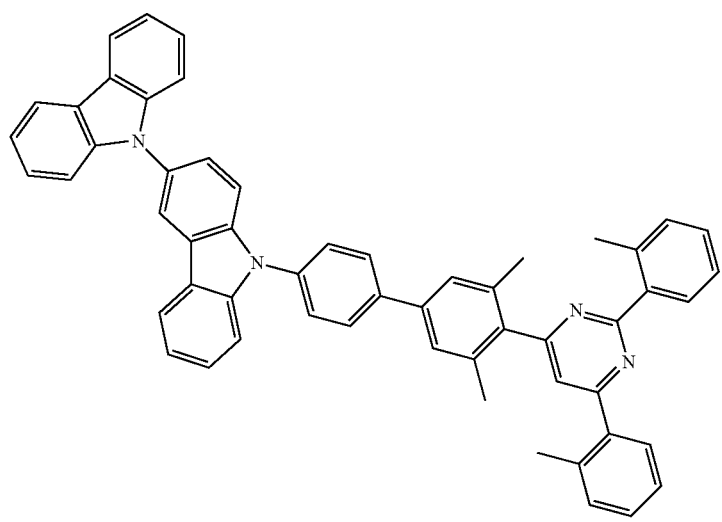

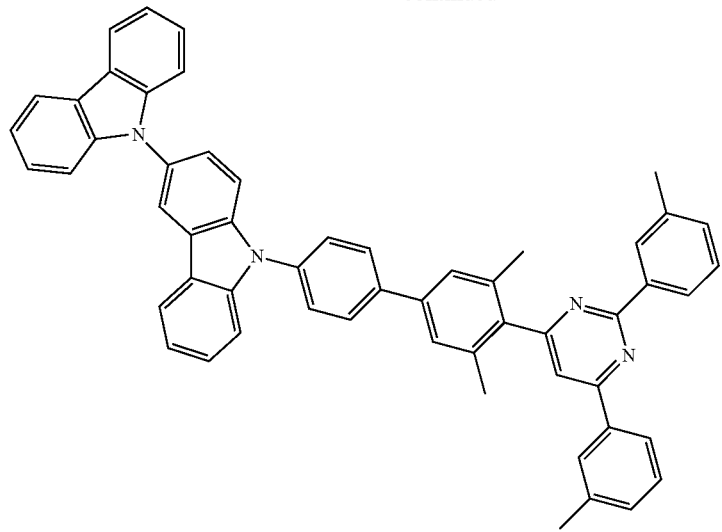

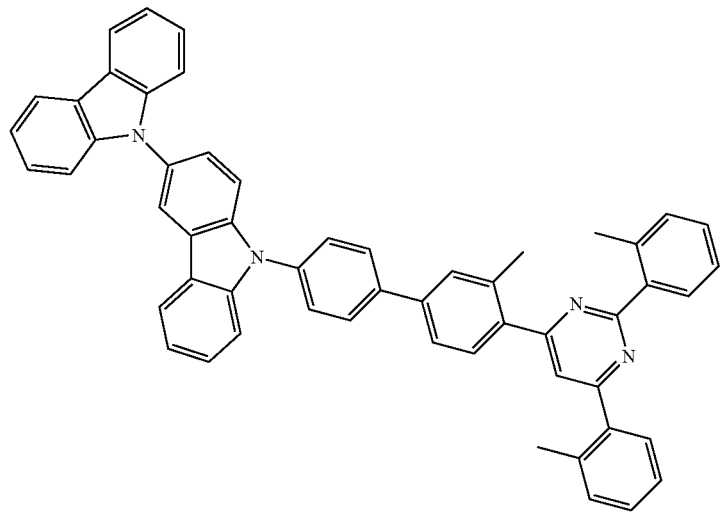
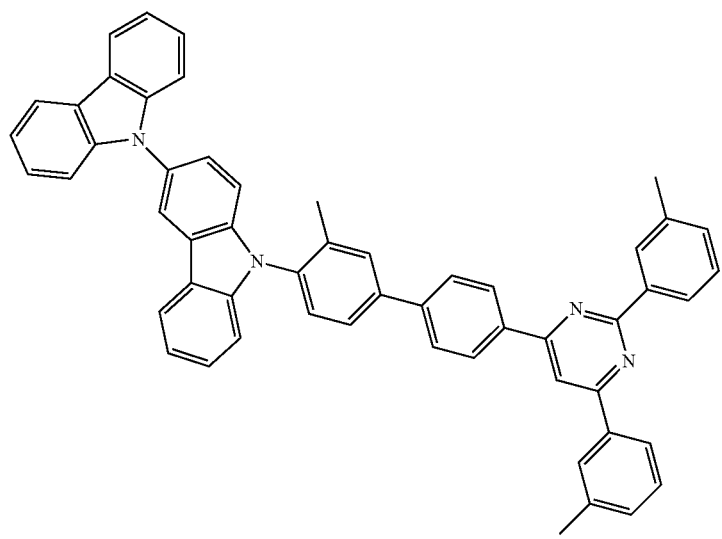
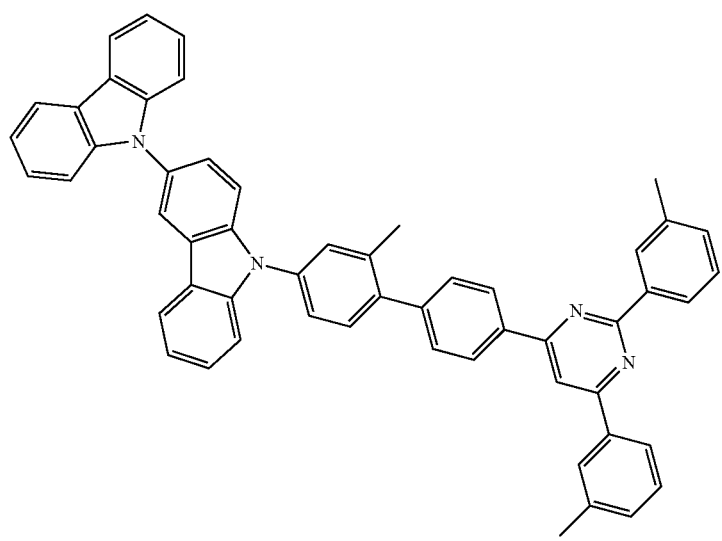

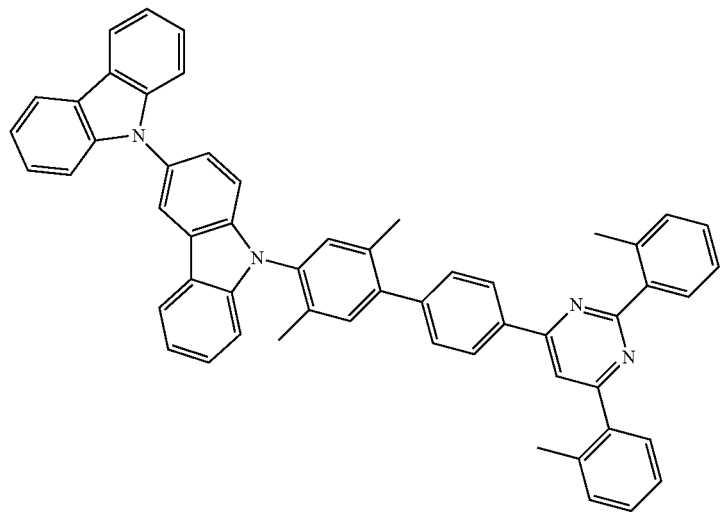
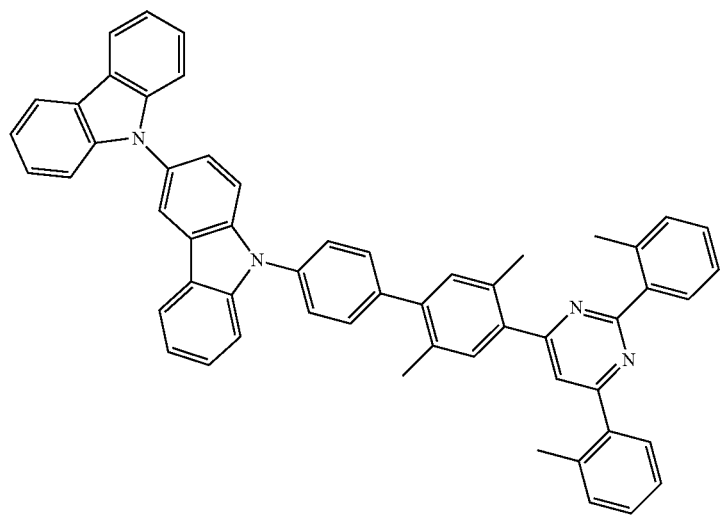
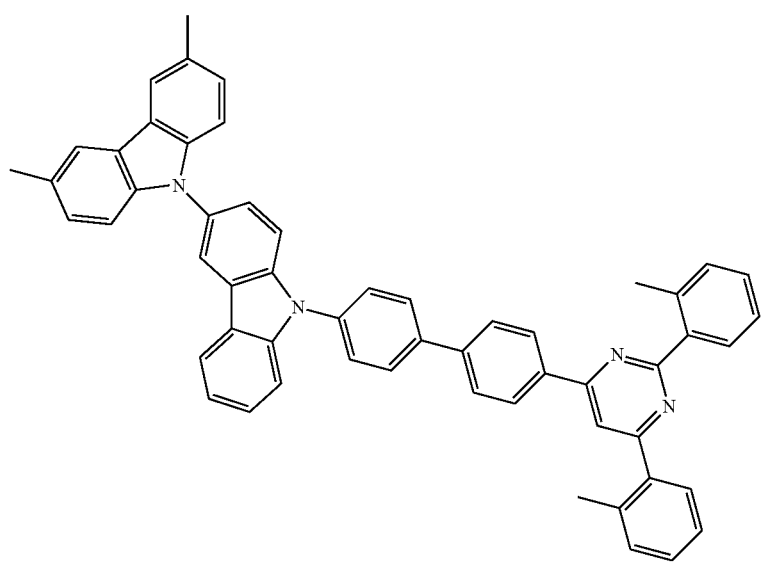

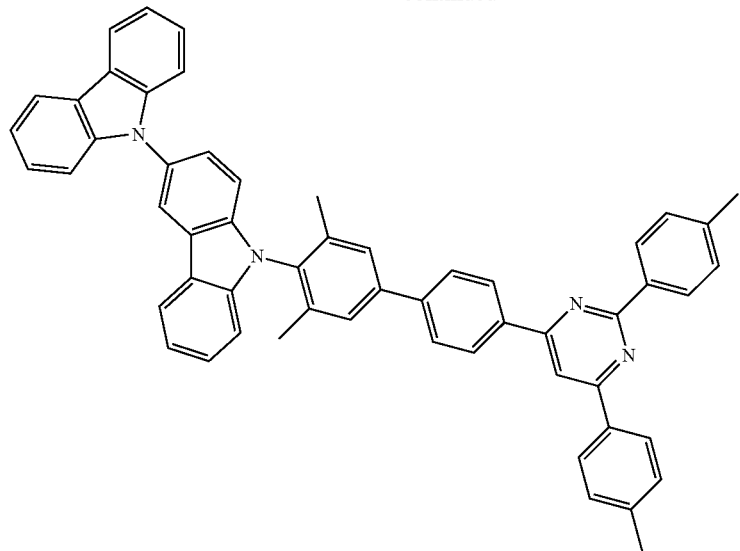
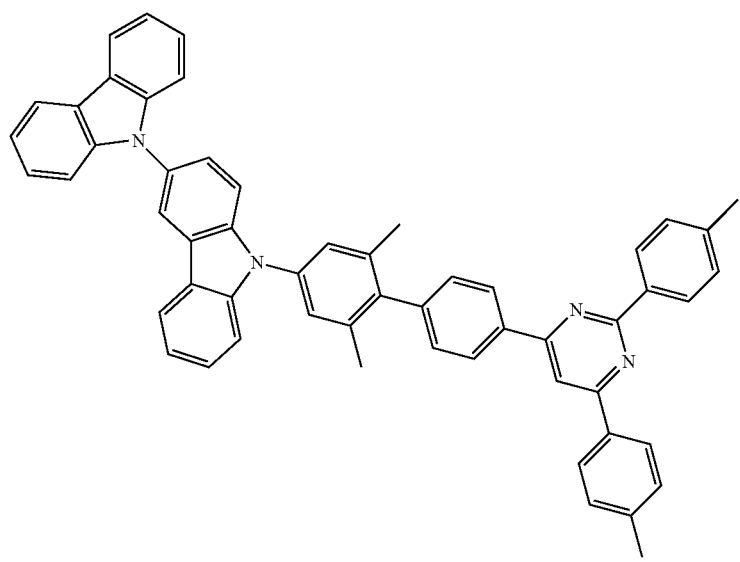
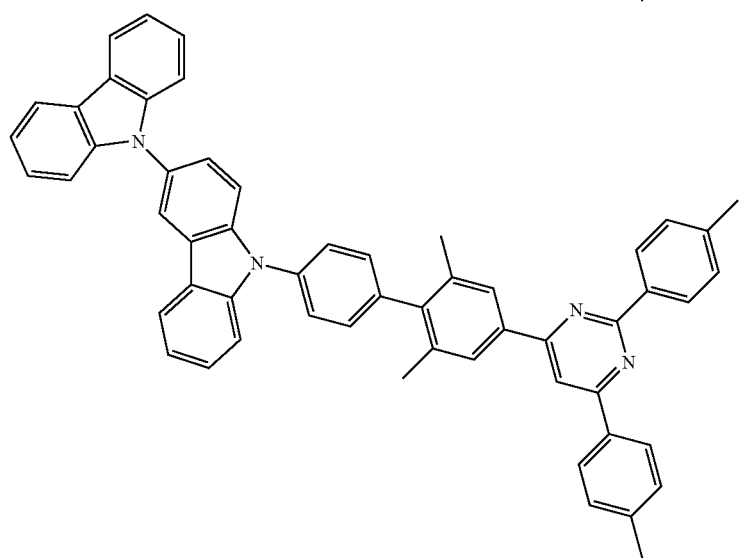

-continued
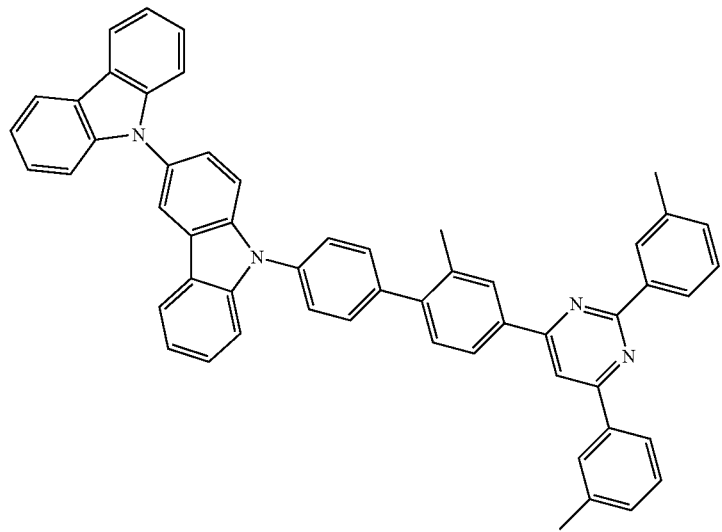
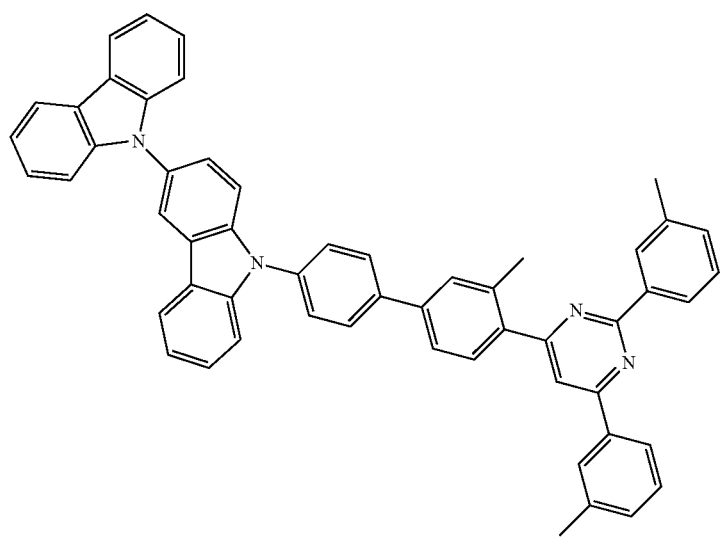
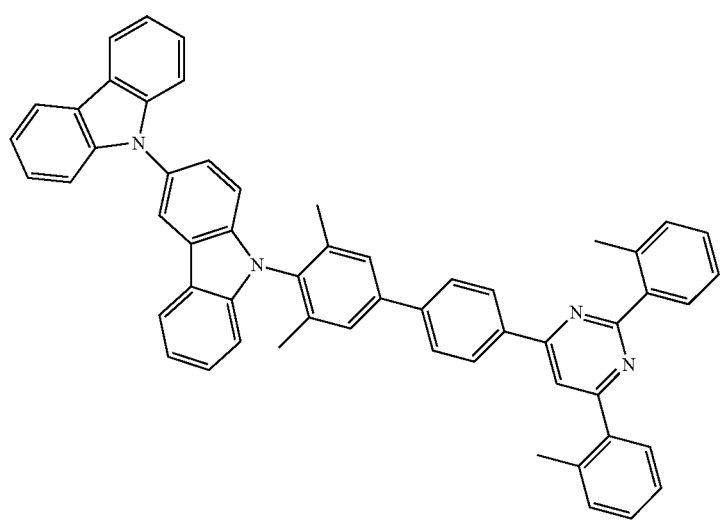

-continued
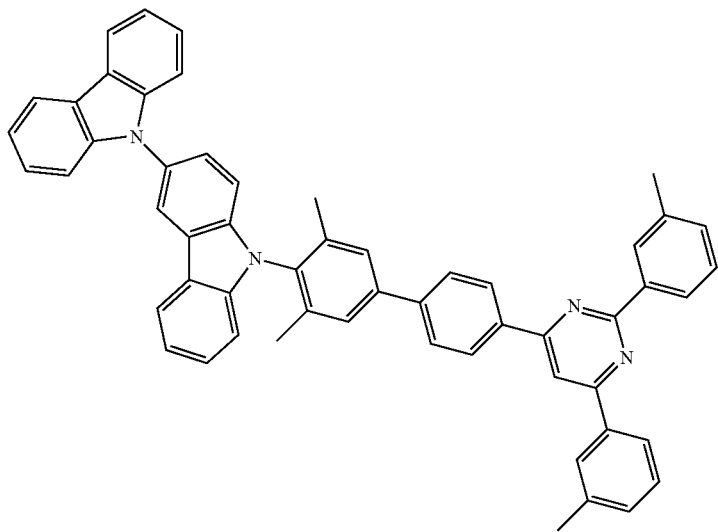
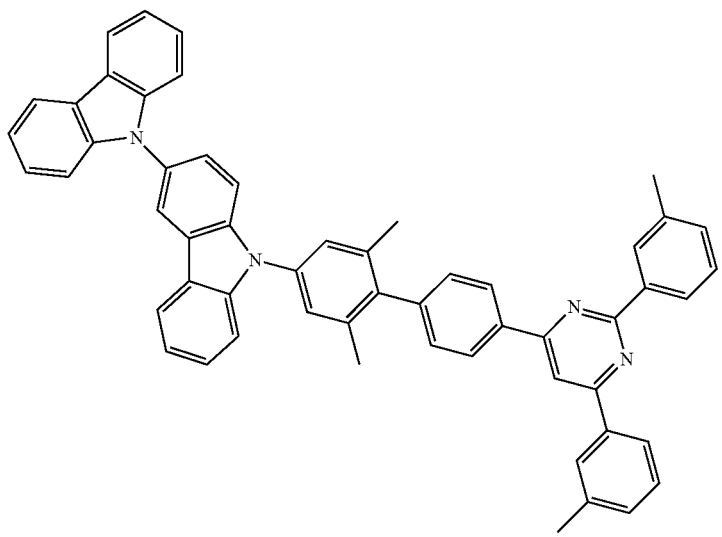
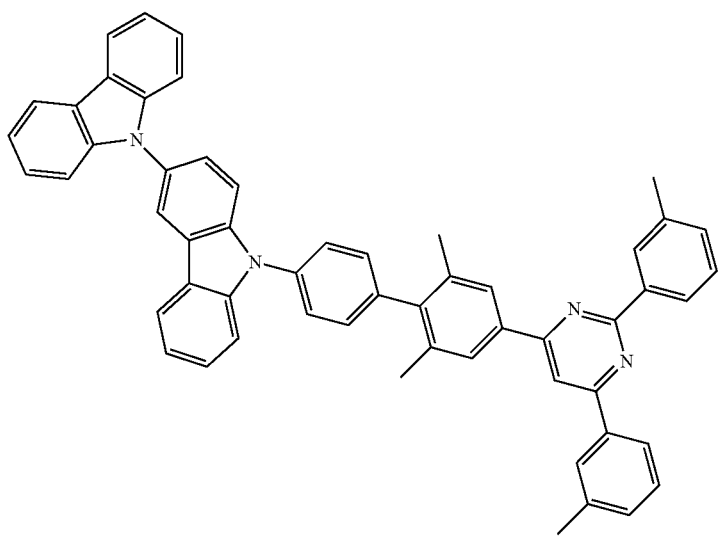

-continued
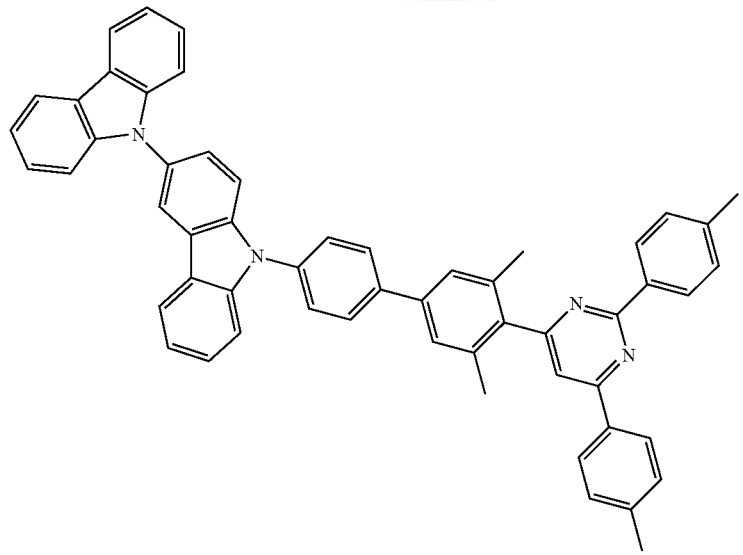
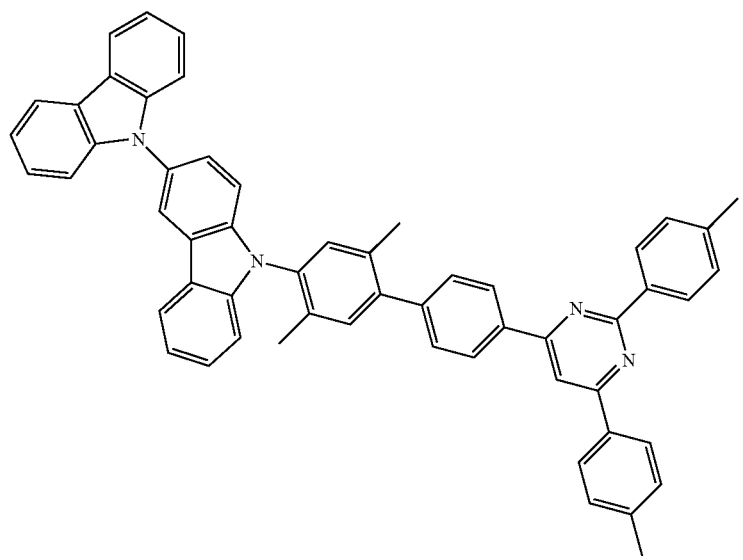
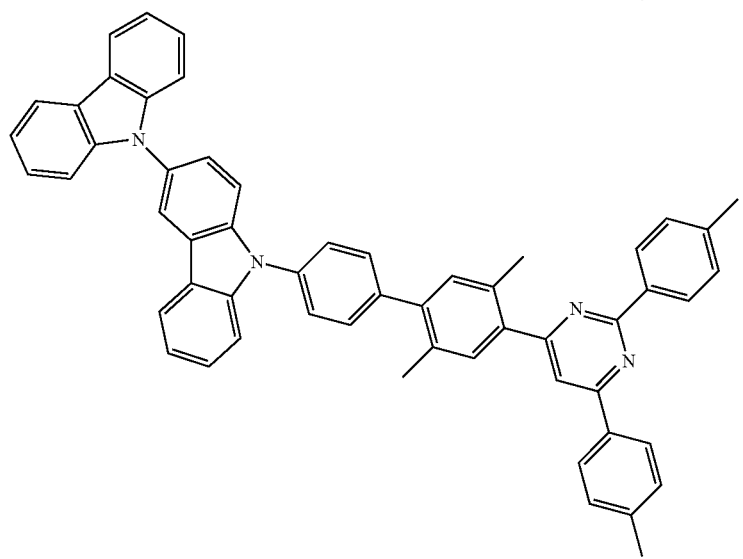

-continued
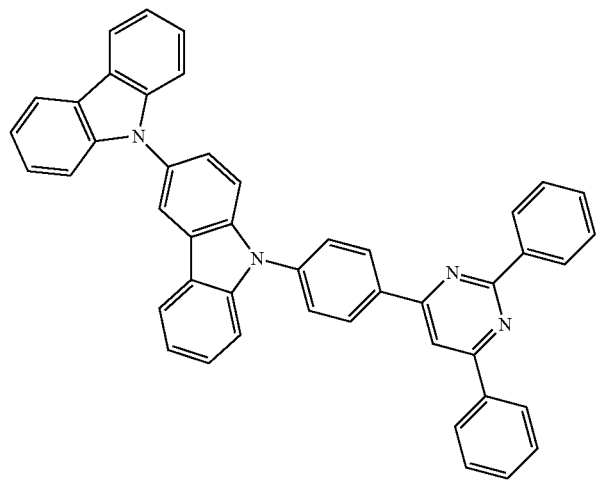
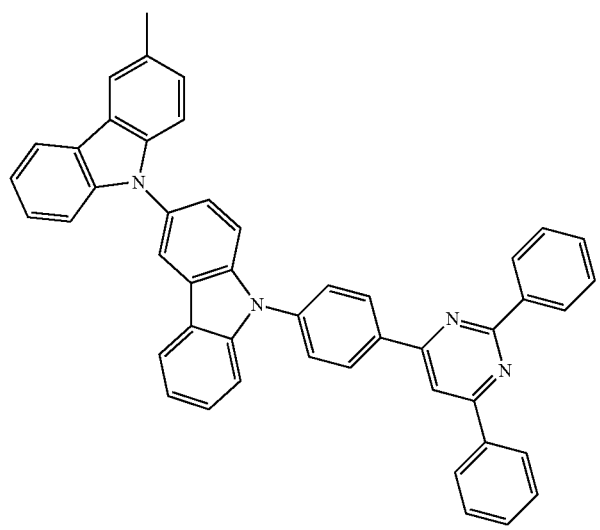
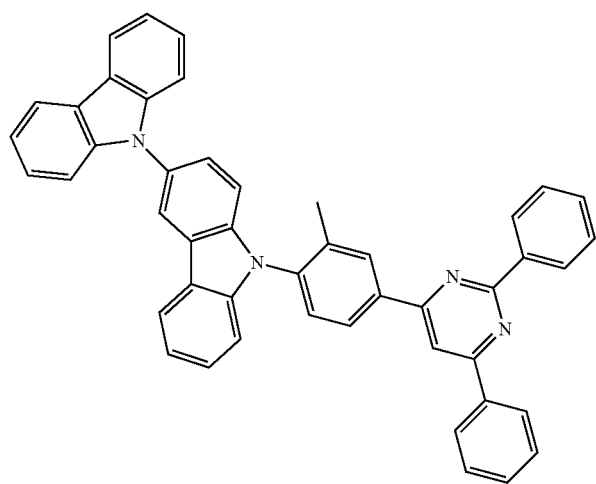

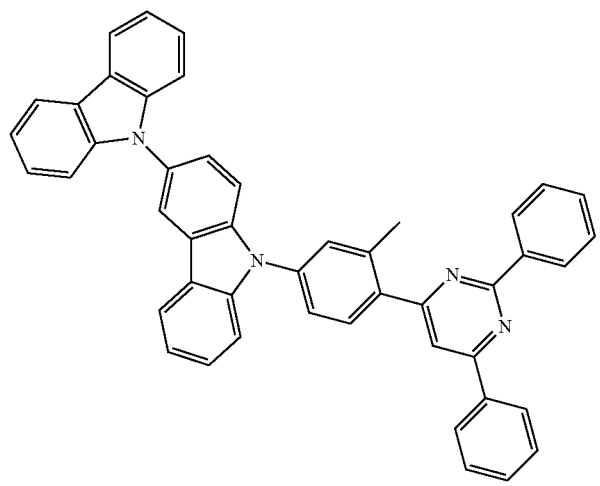
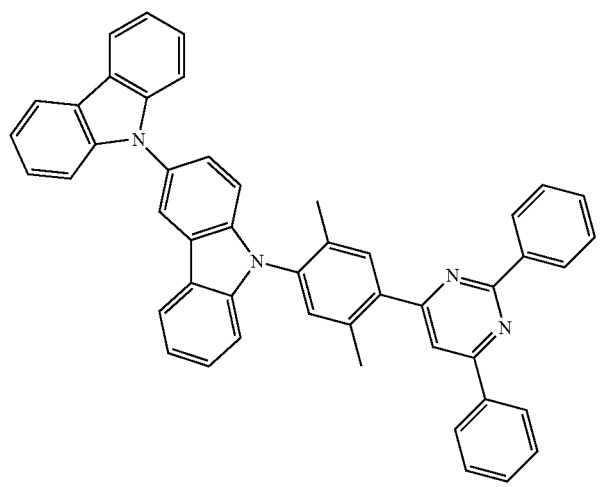
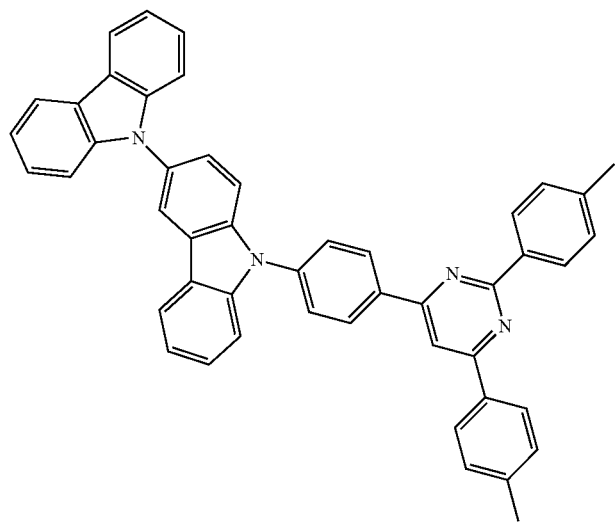

-continued
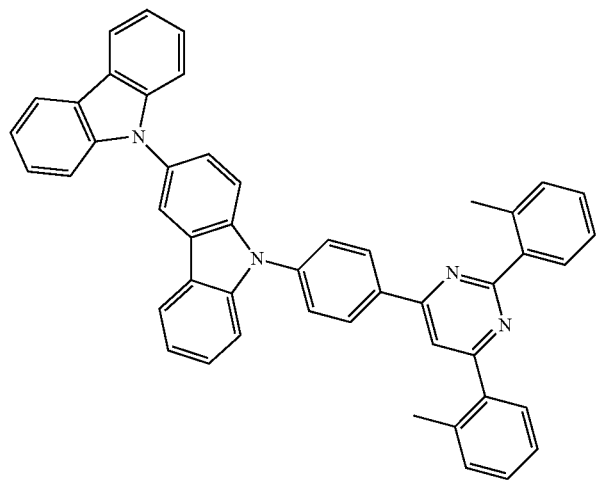
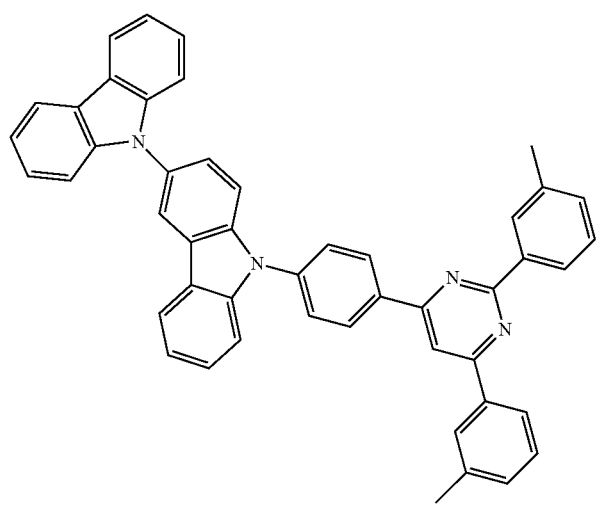
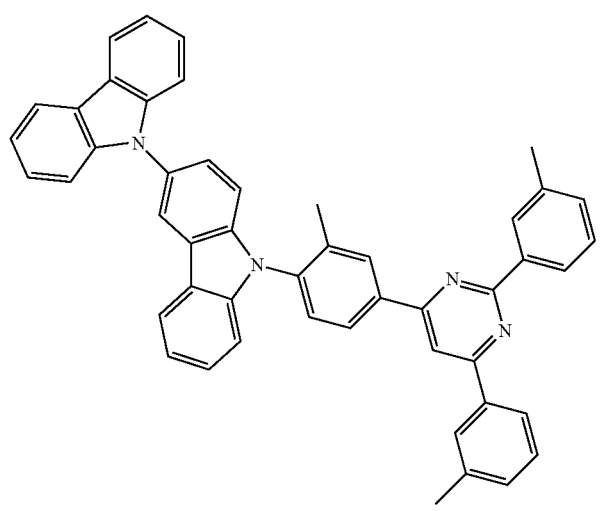

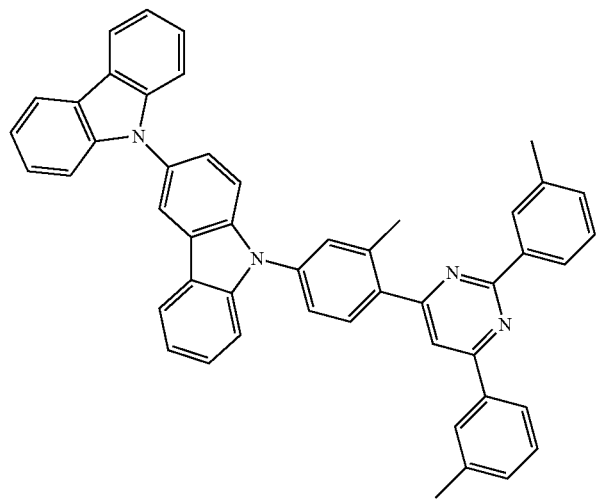
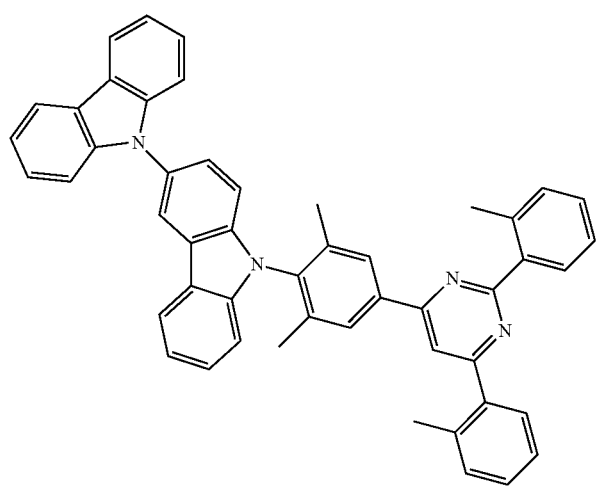
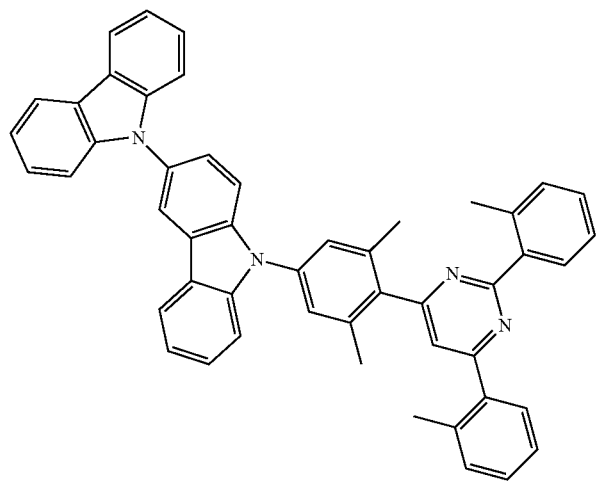

-continued
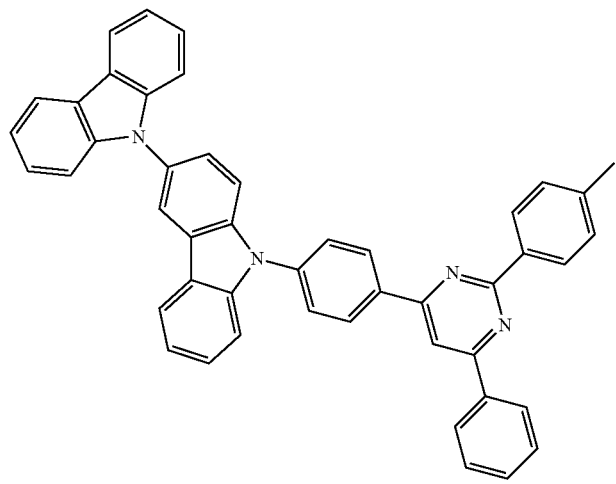
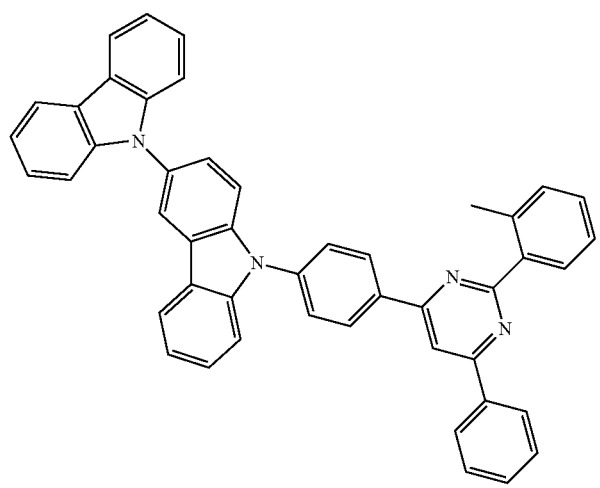
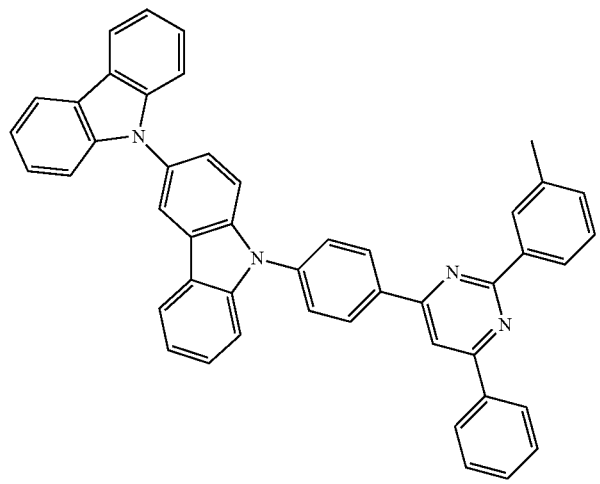

-continued
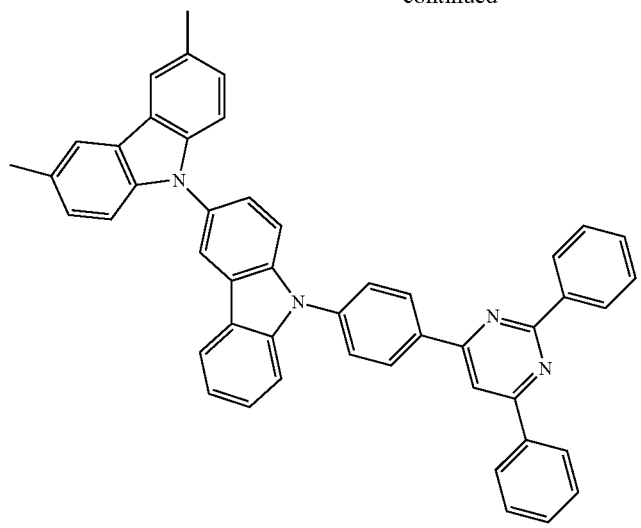
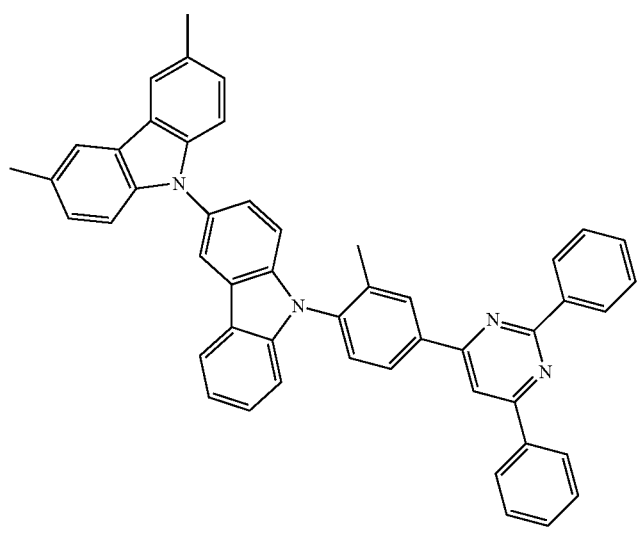
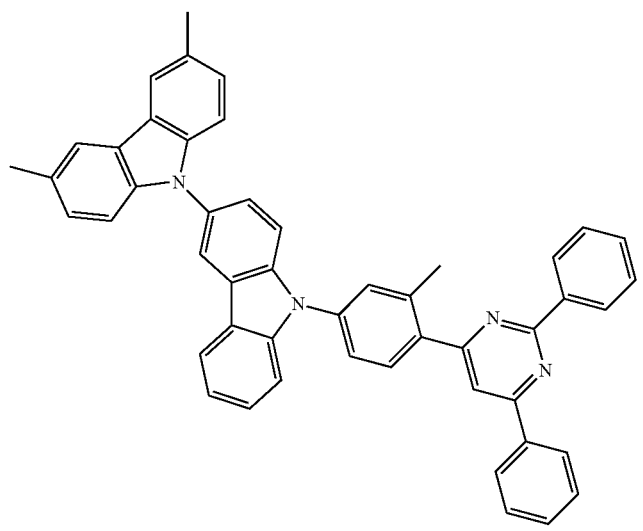

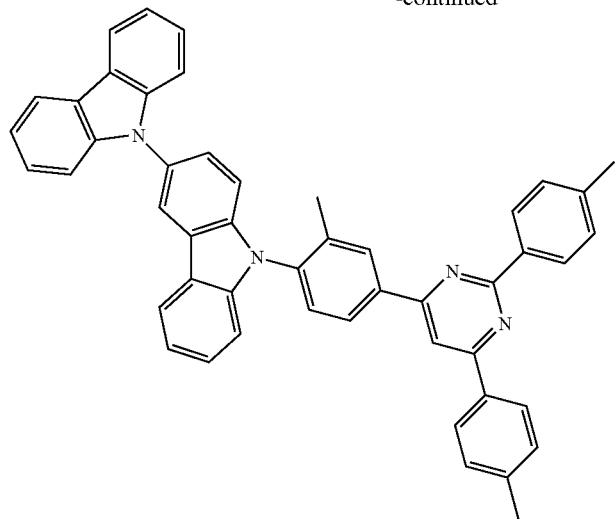
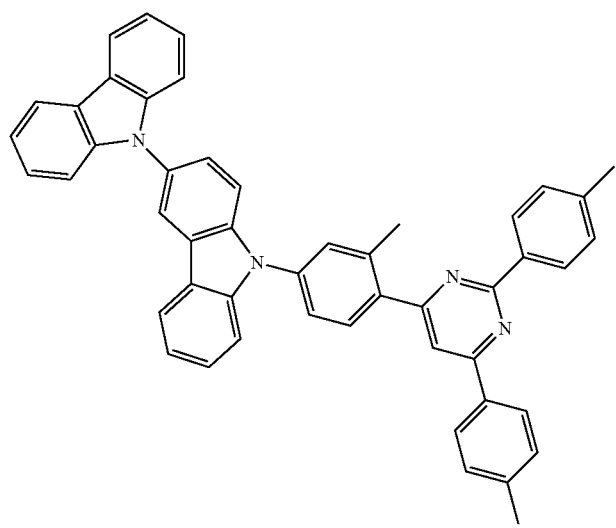
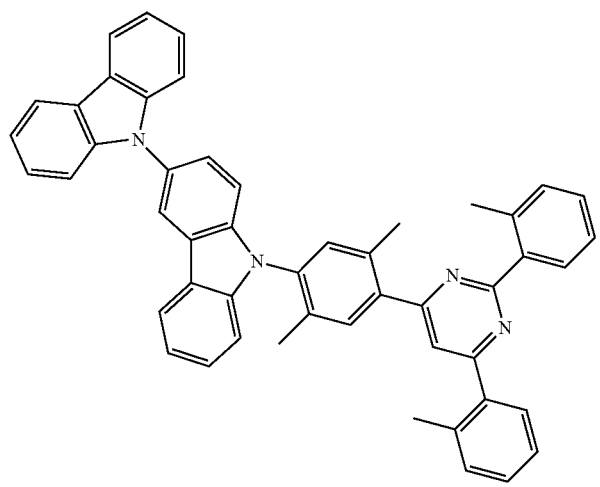

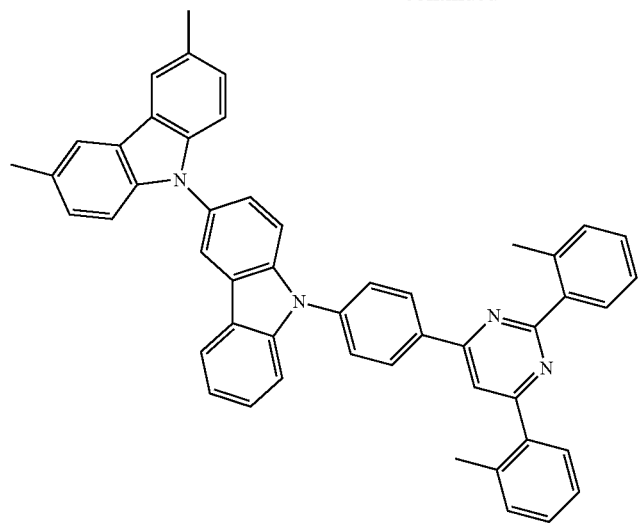
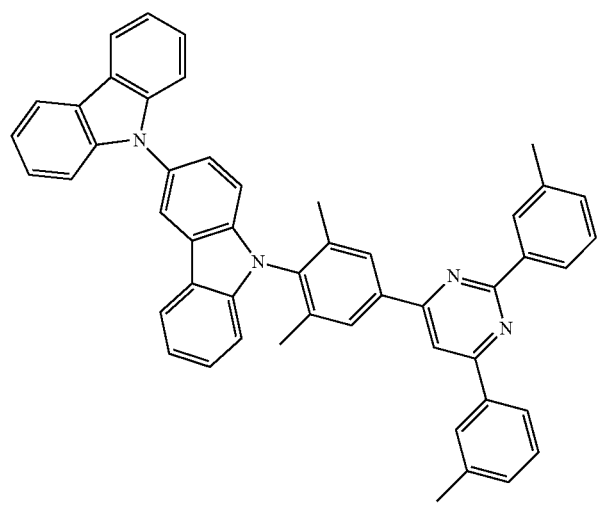
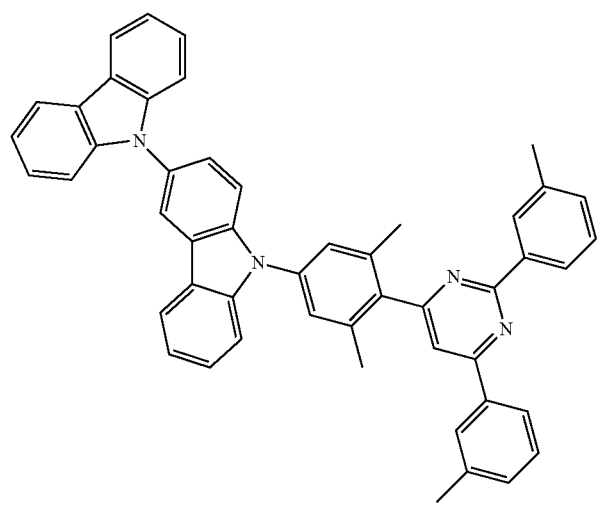

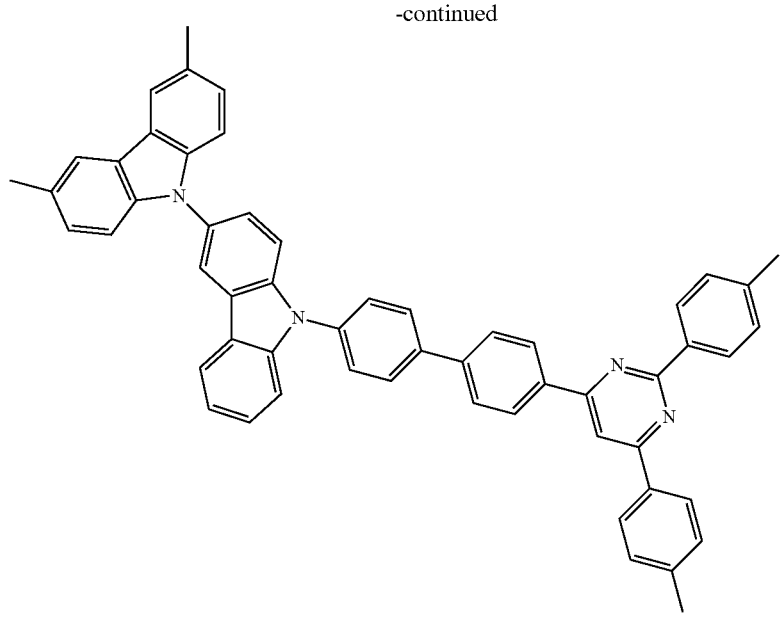
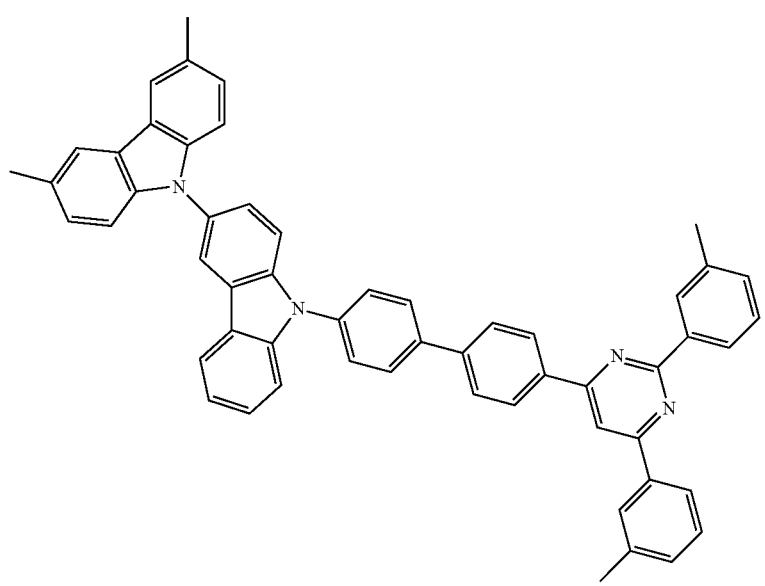
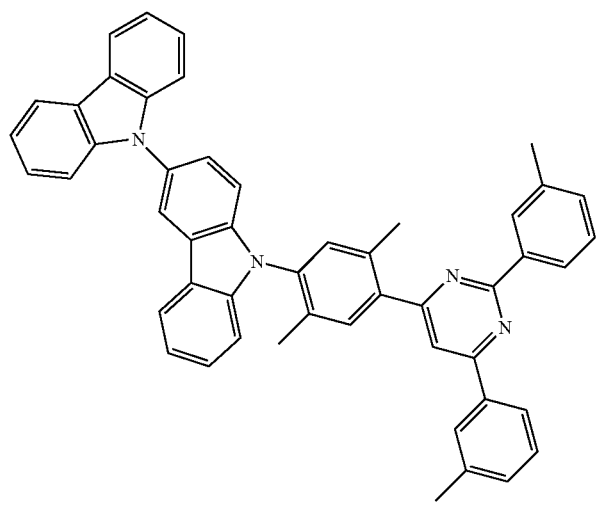

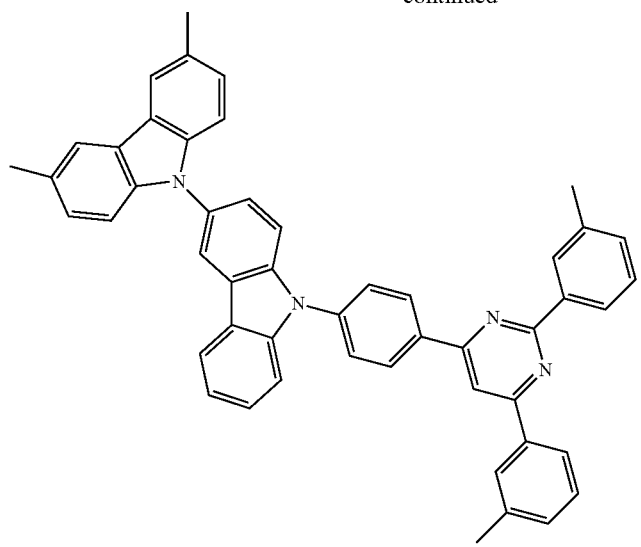
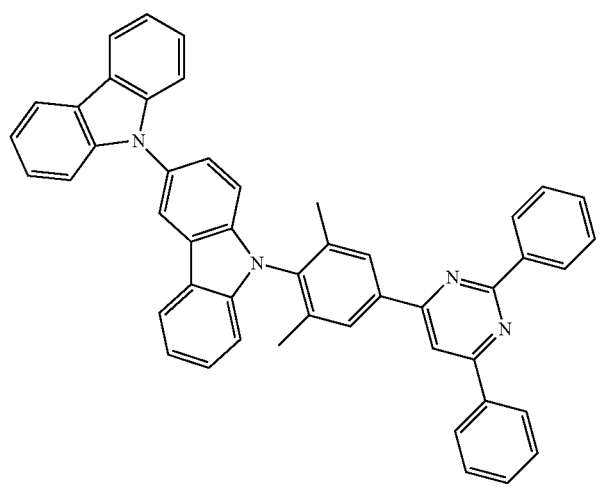
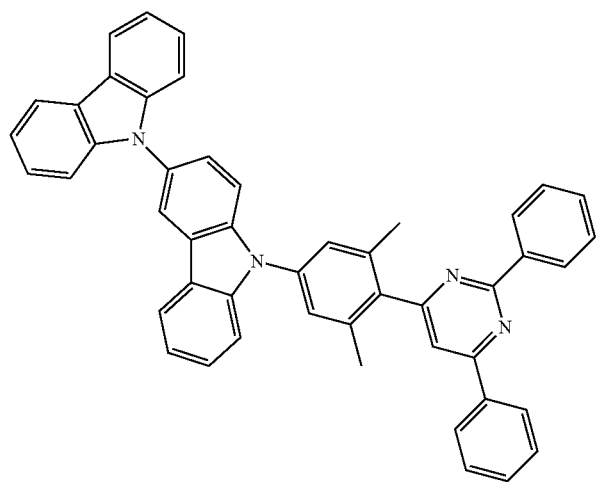

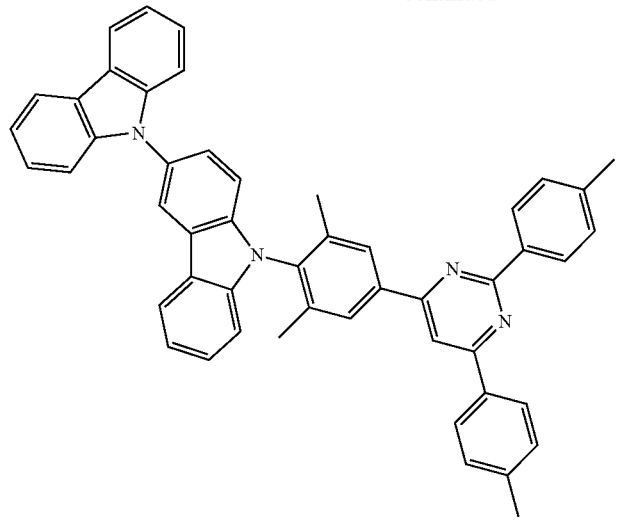
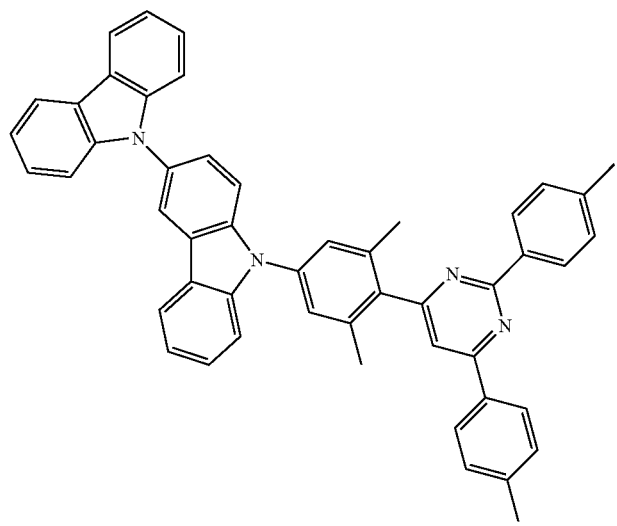
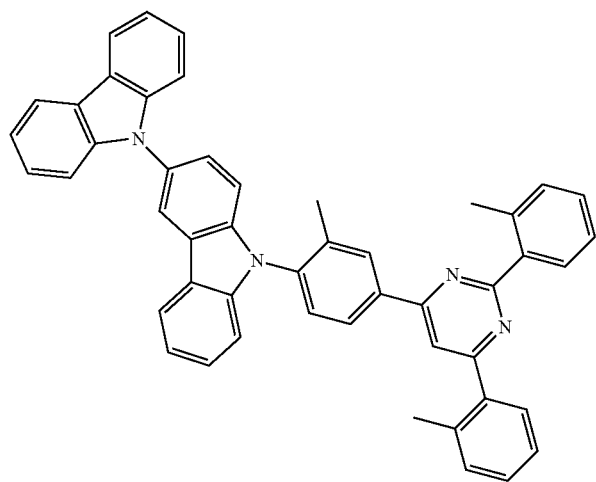

-continued
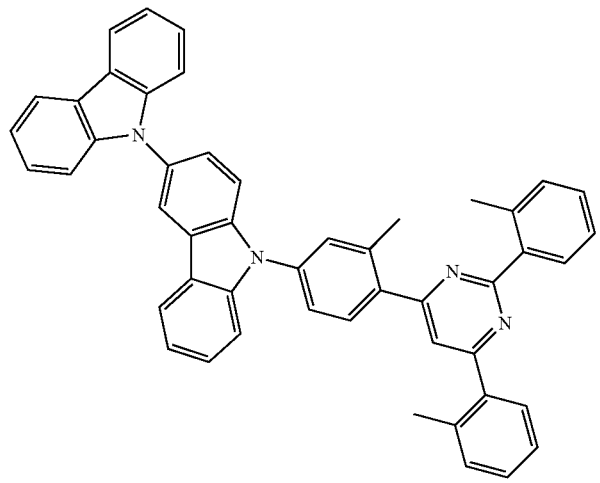
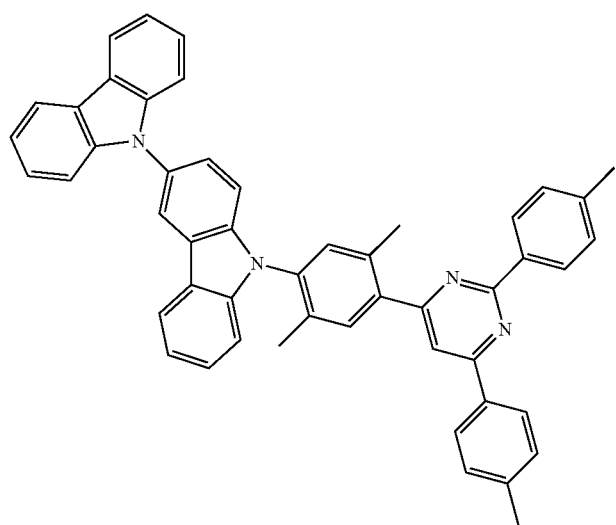
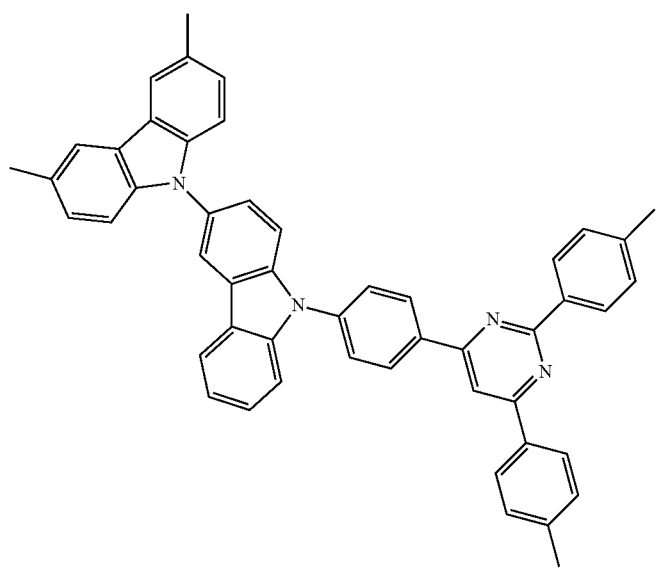

-continued
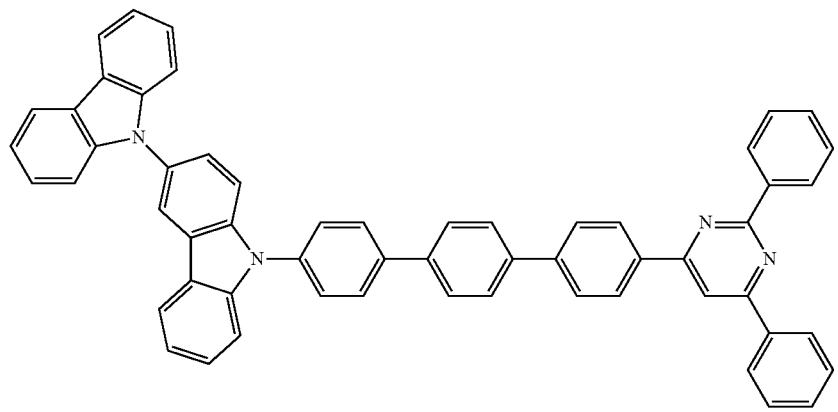
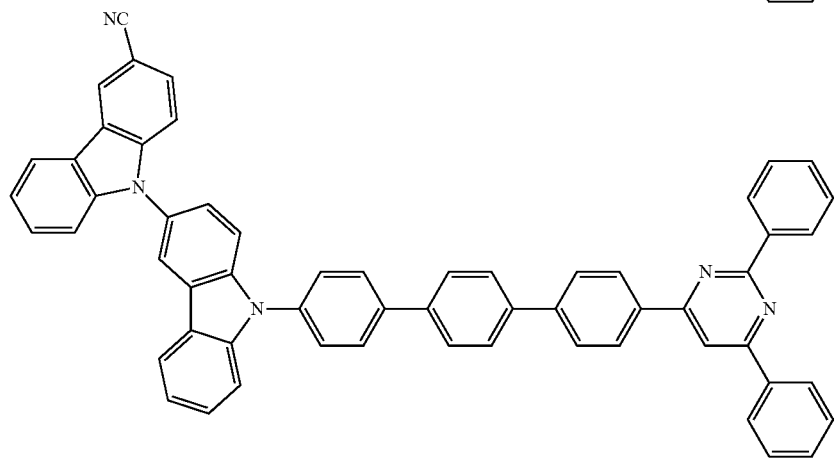
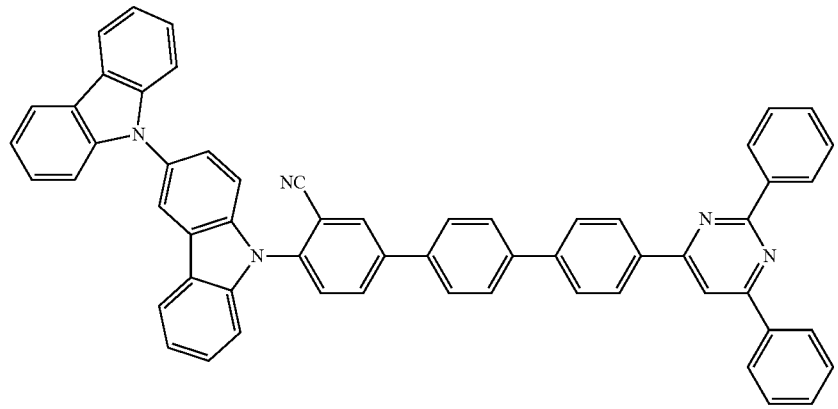
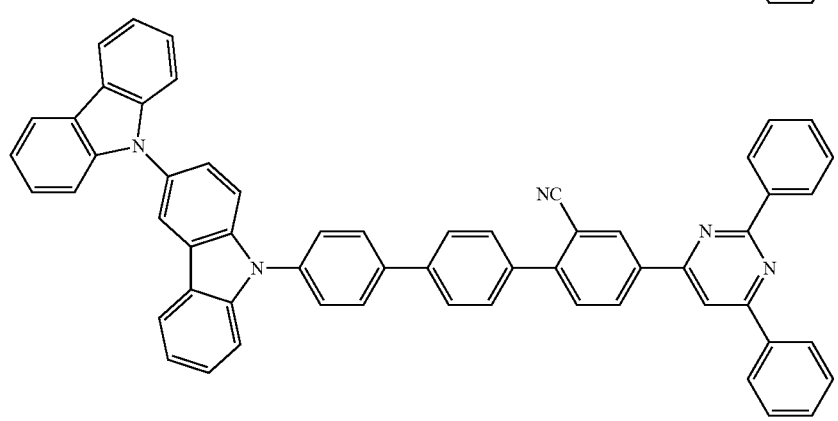

-continued
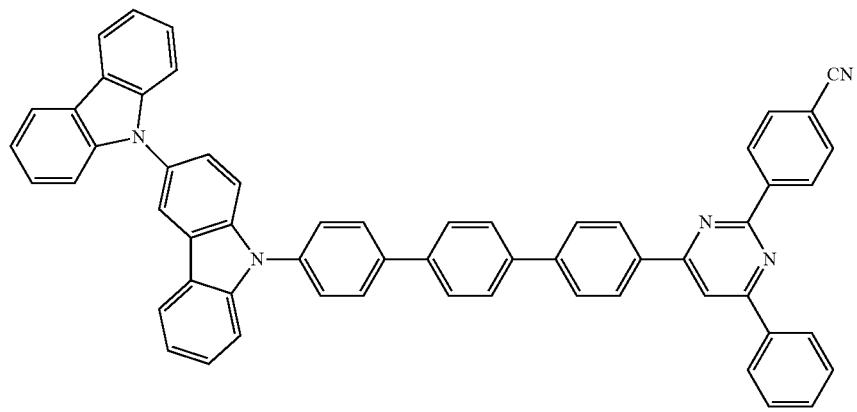
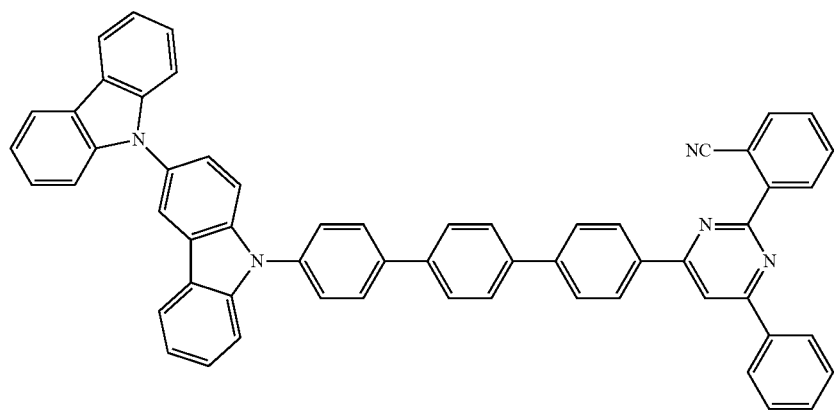
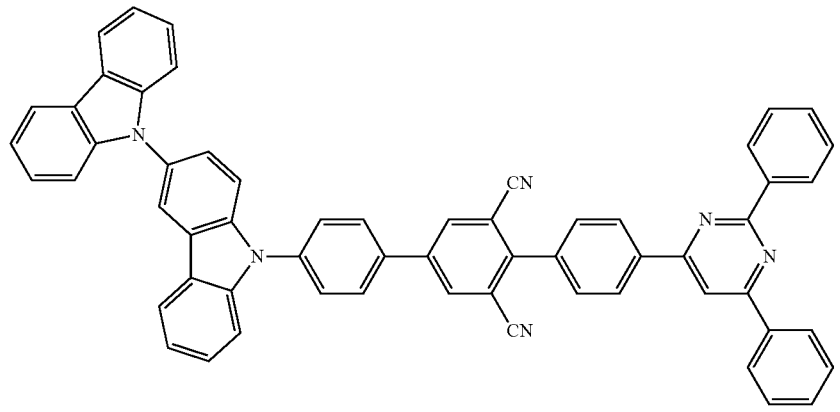
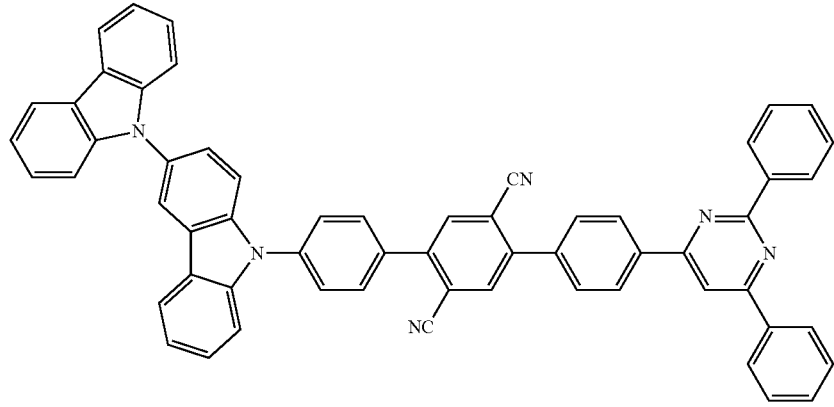

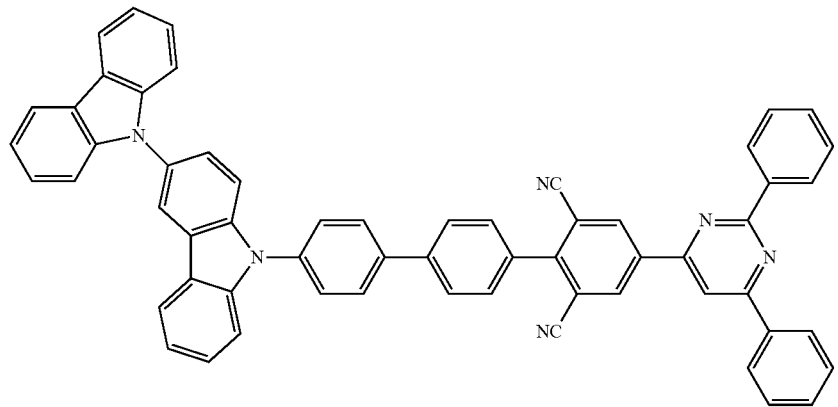
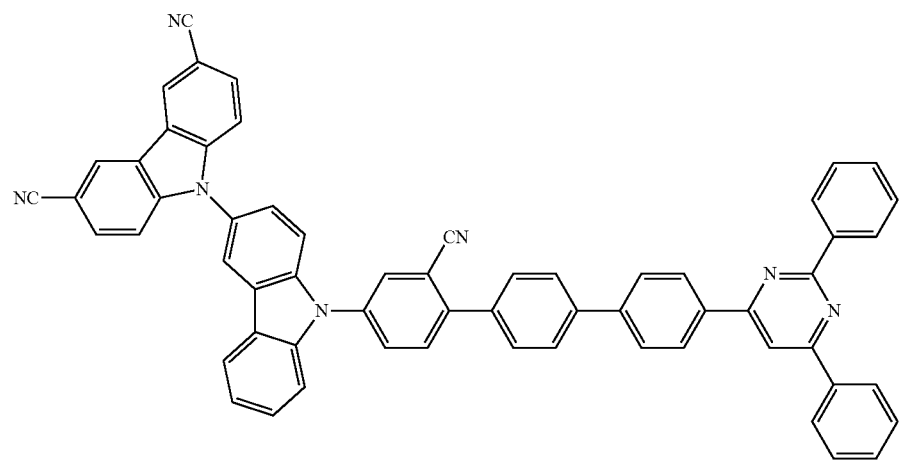
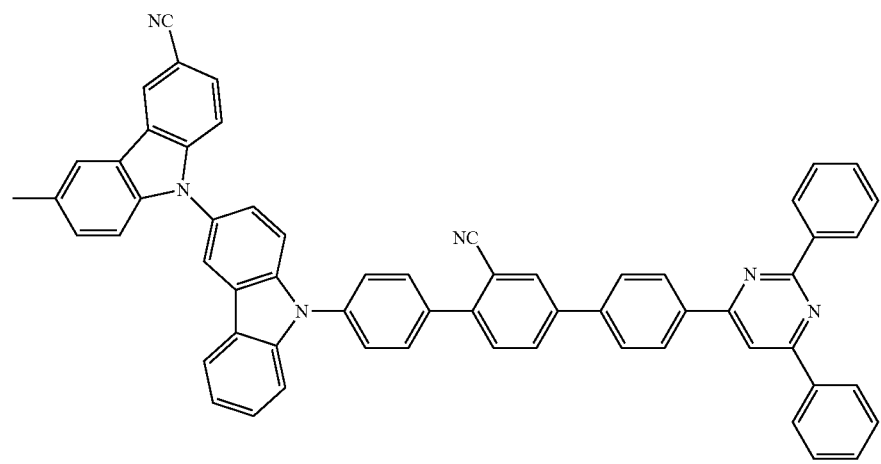

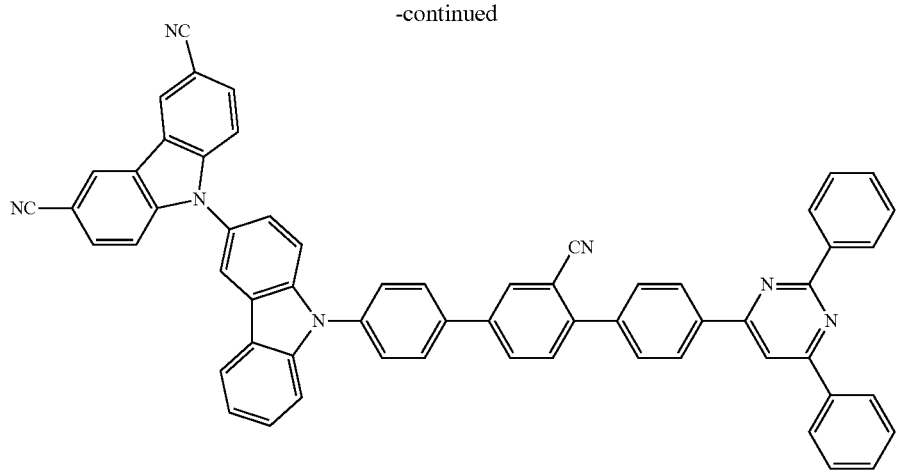
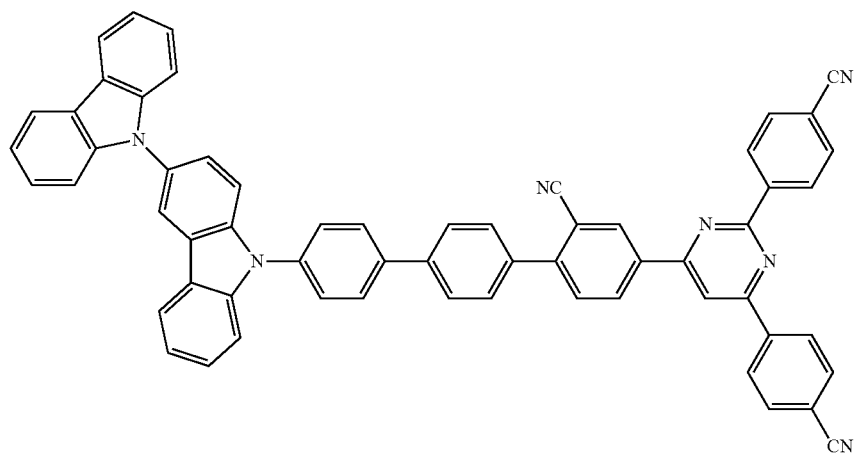

-continued
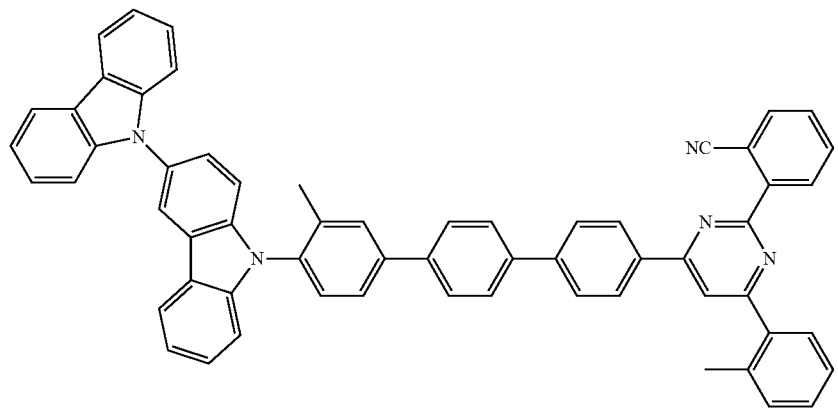
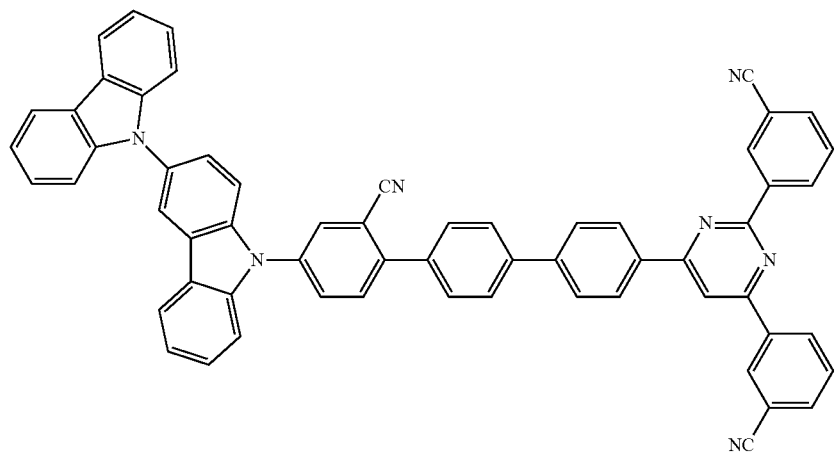
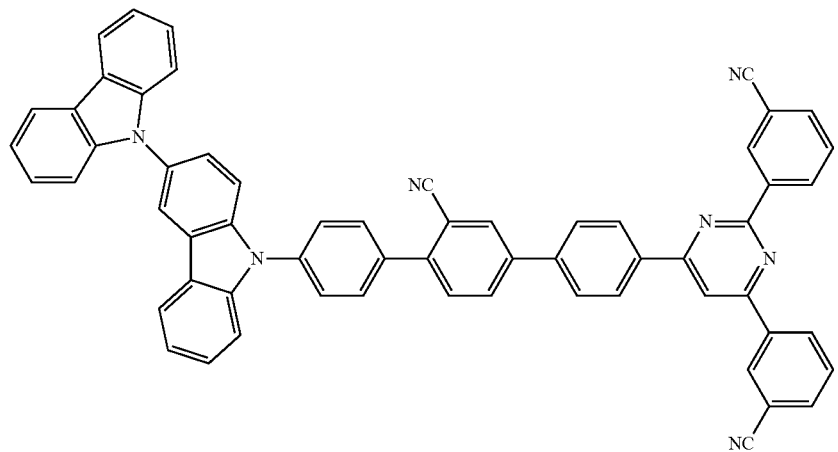

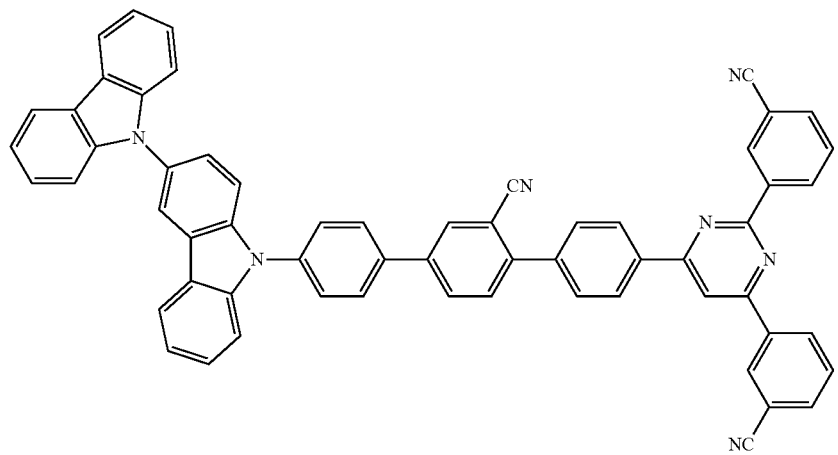
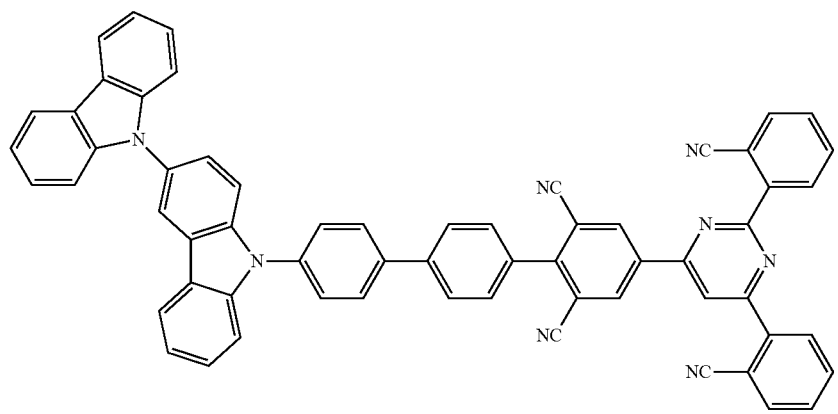
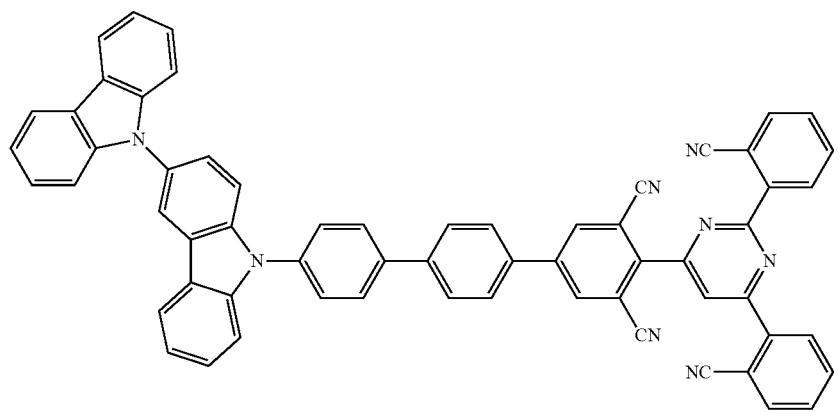
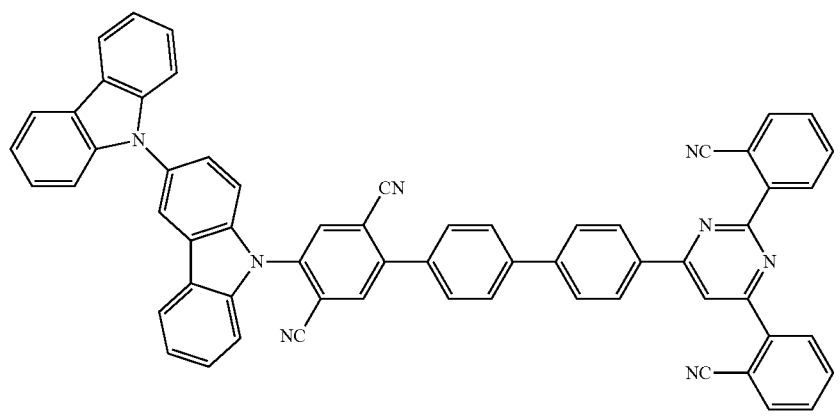

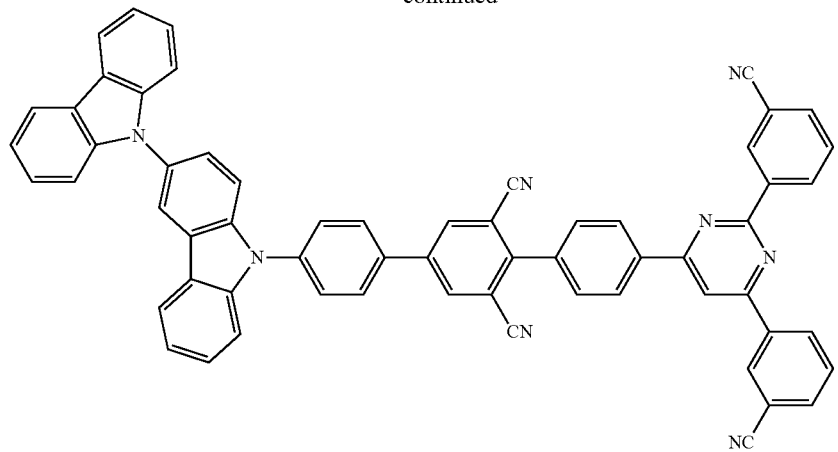
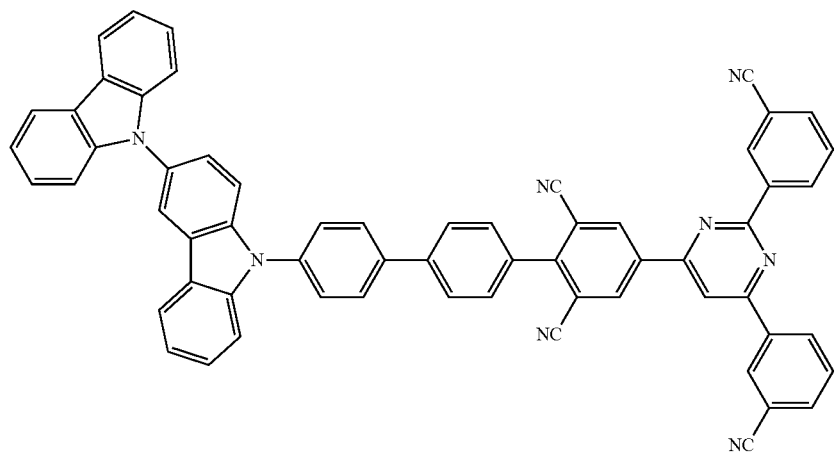
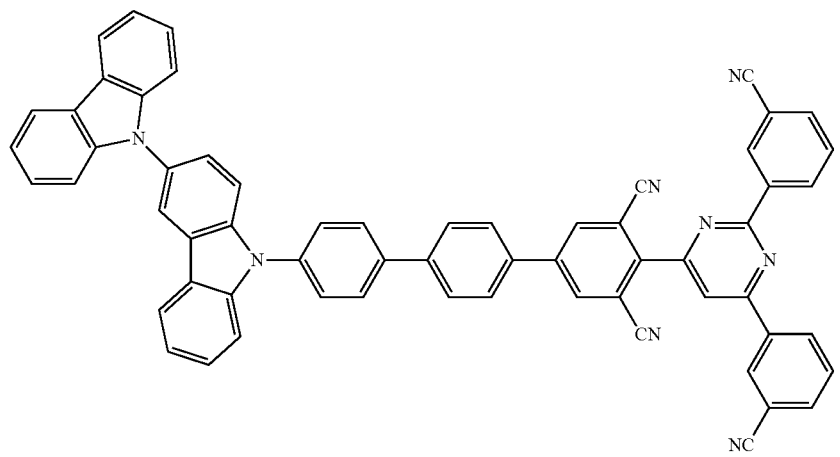

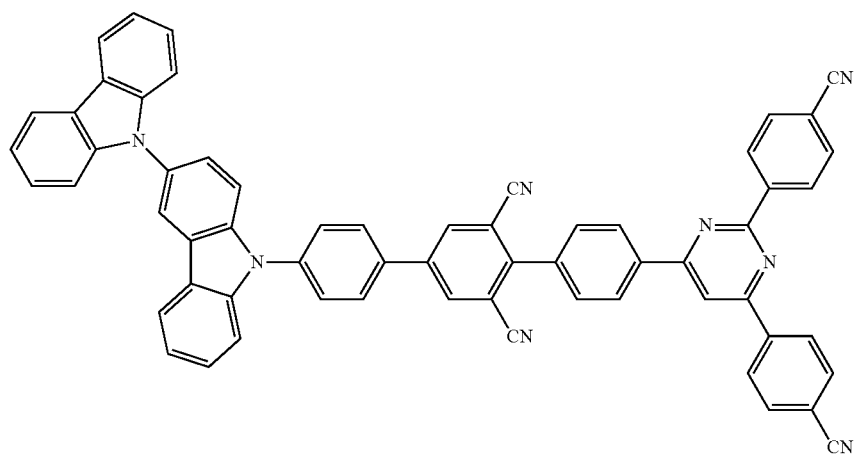
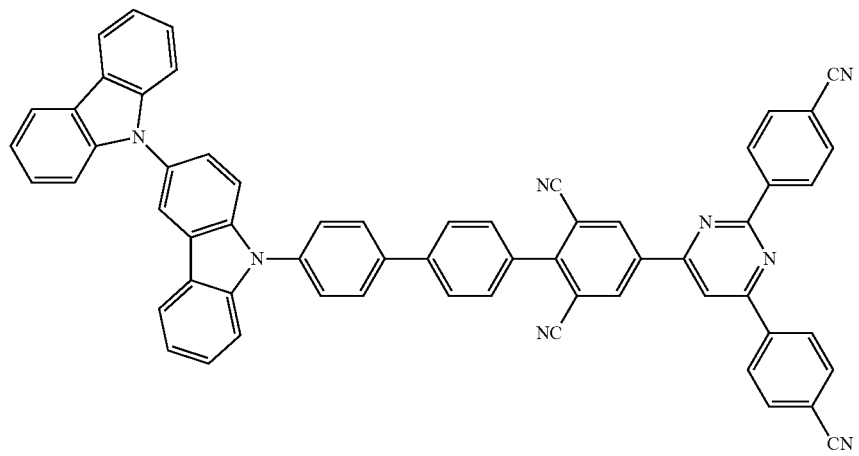

-continued
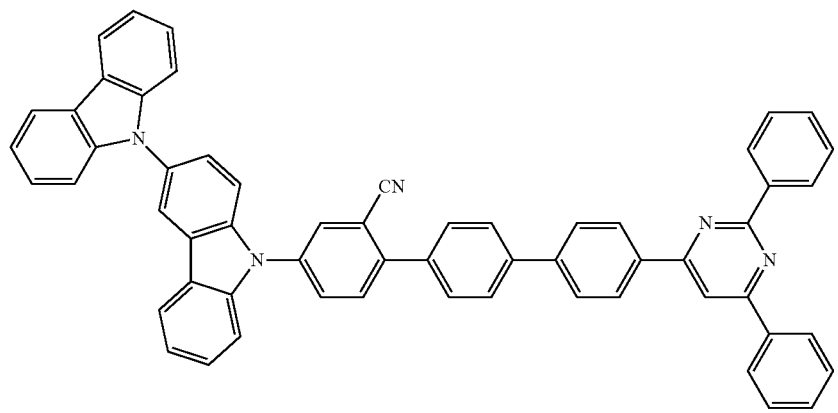
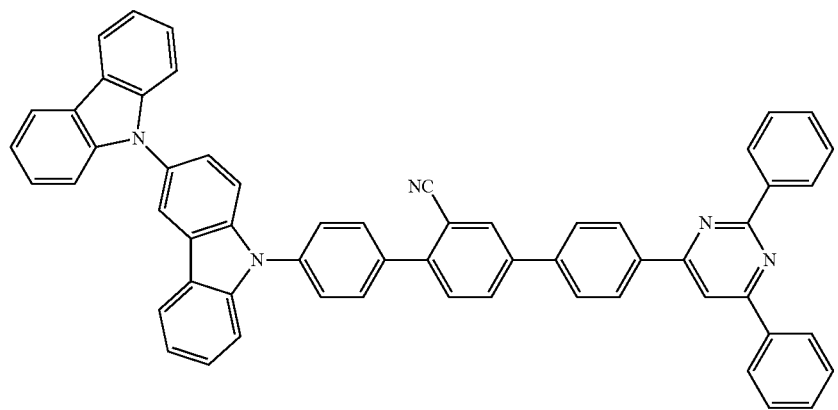
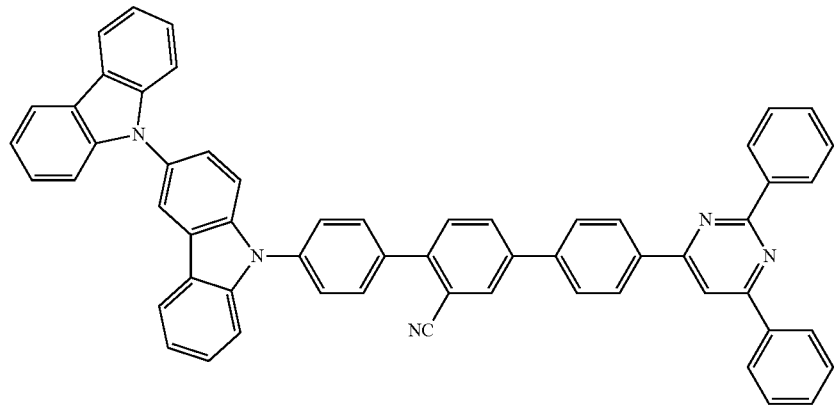
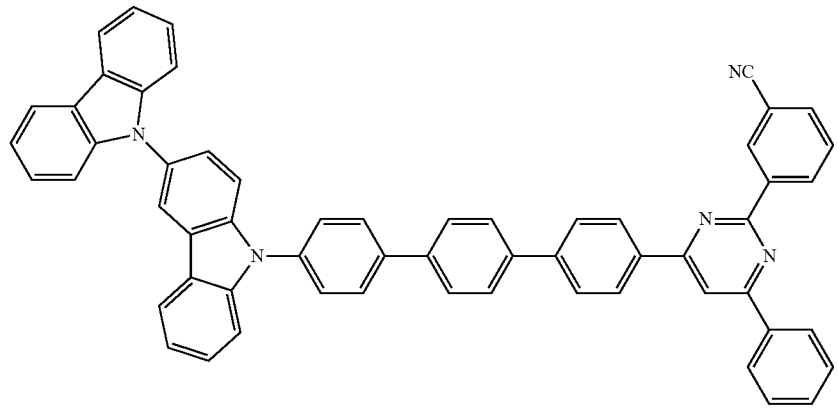

-continued
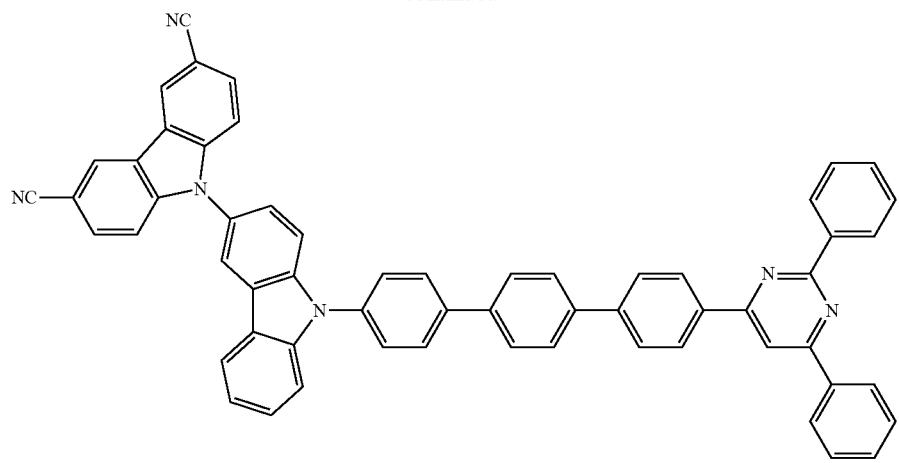
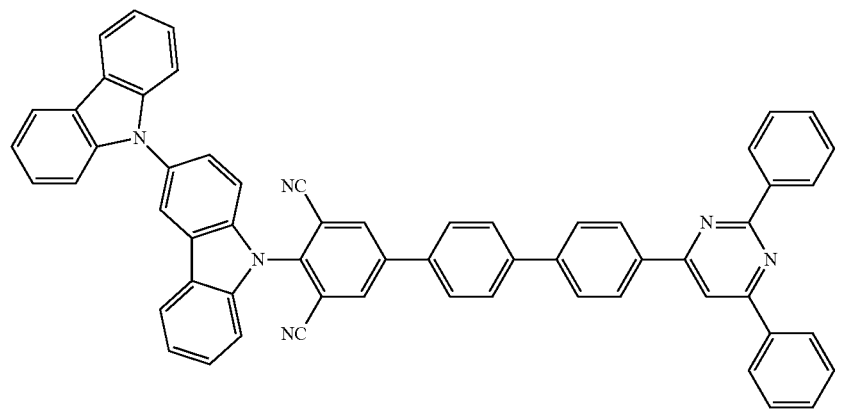
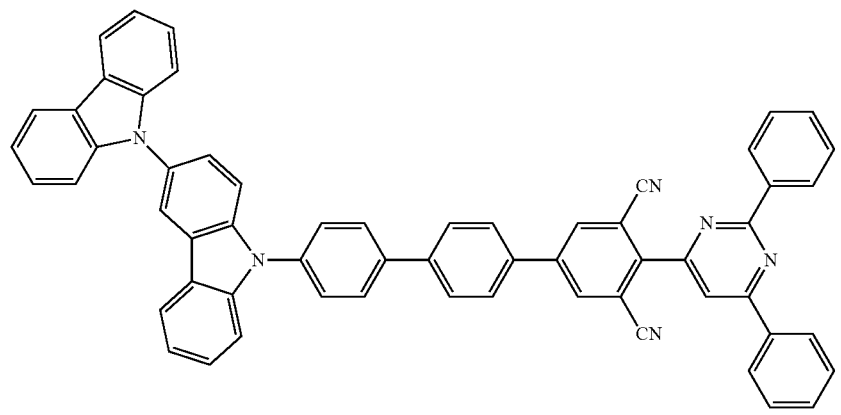
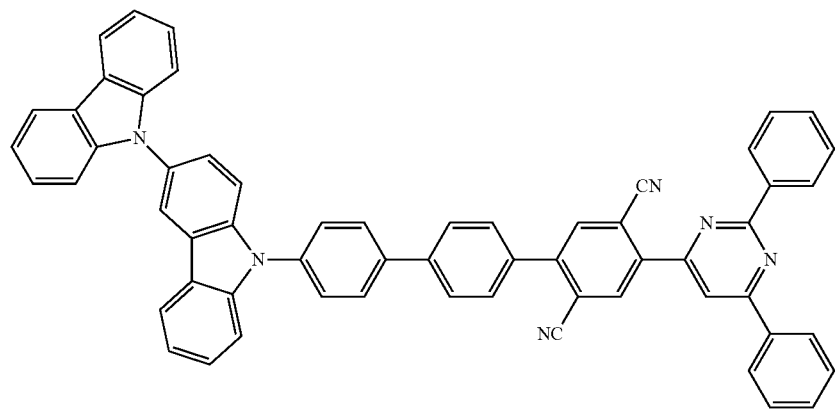

-continued
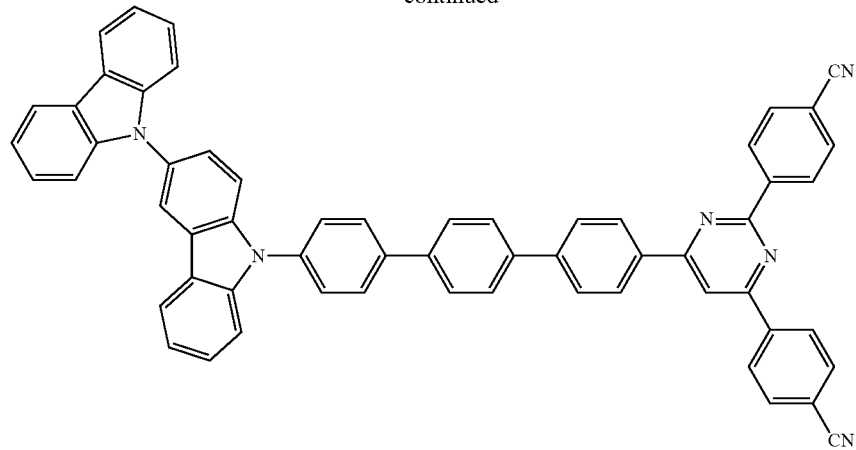
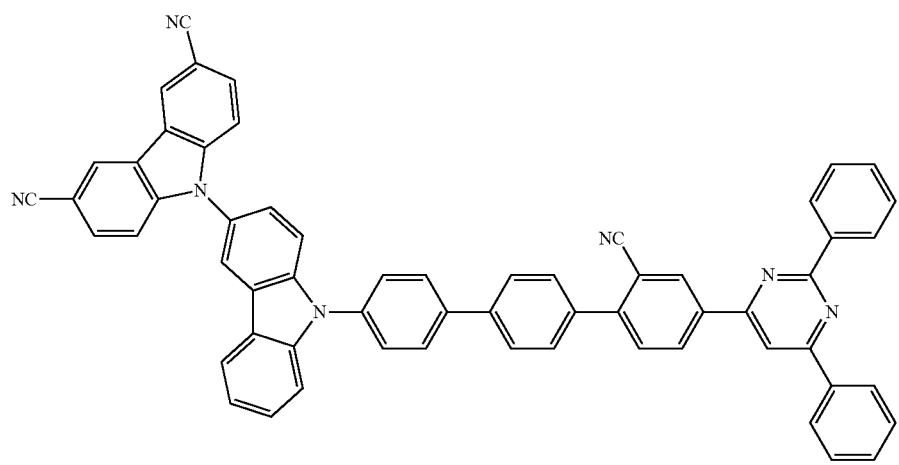
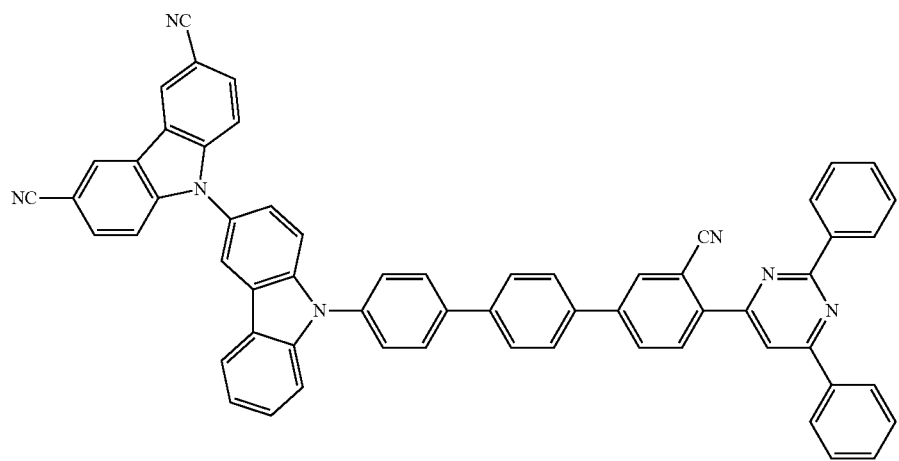

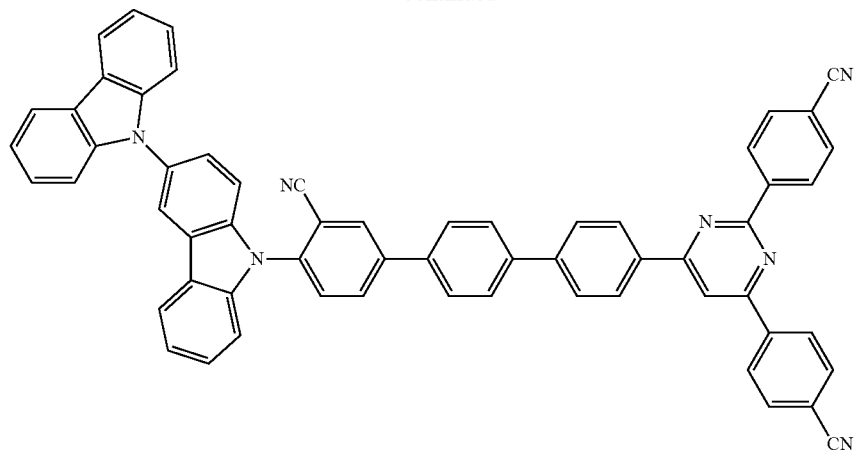
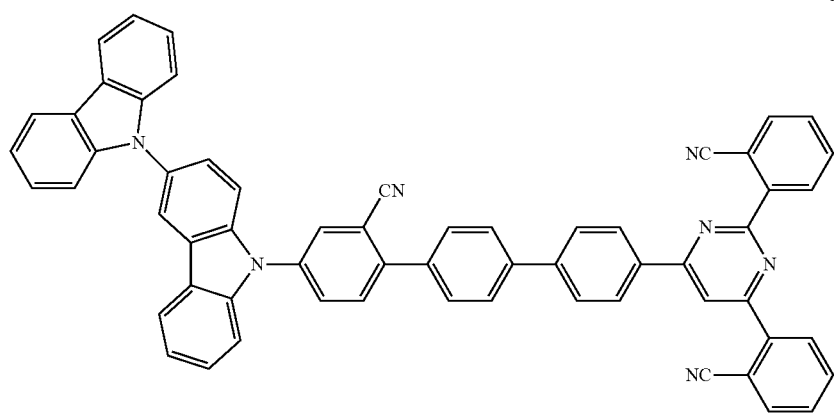
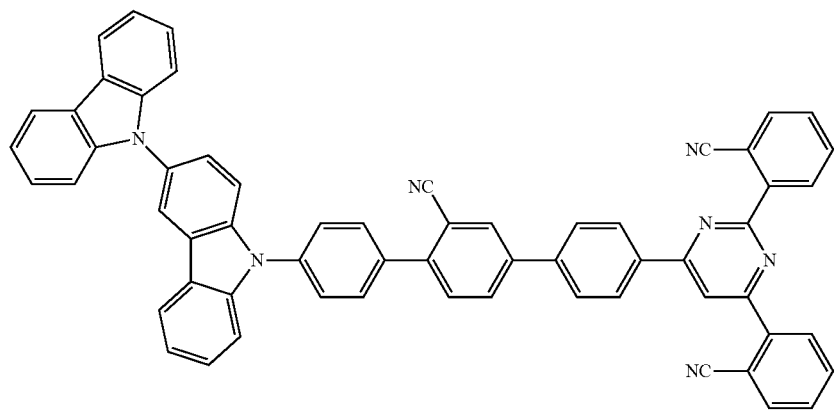
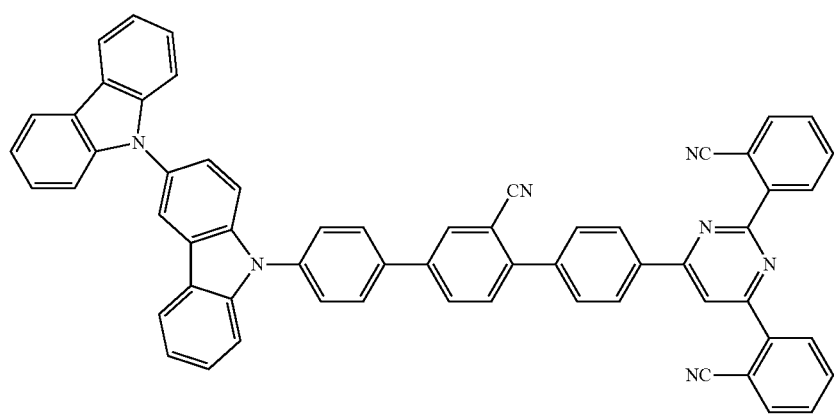

-continued
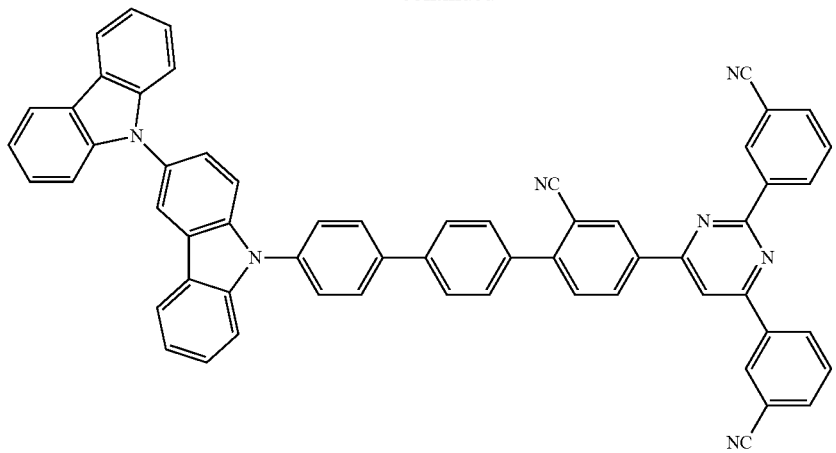
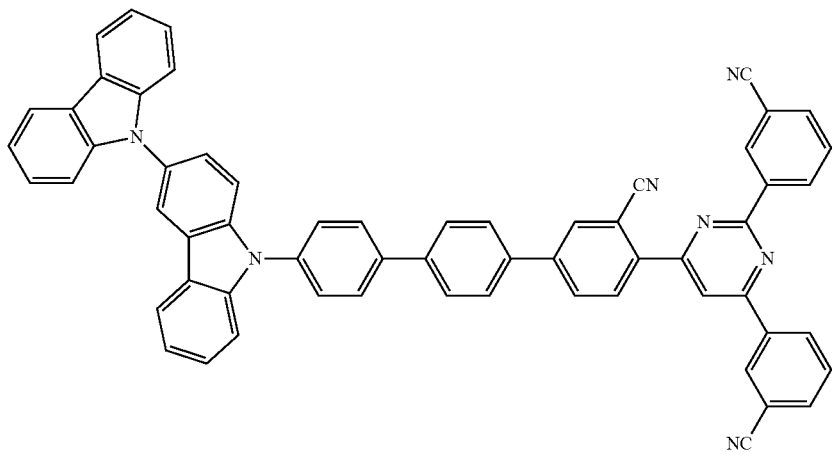
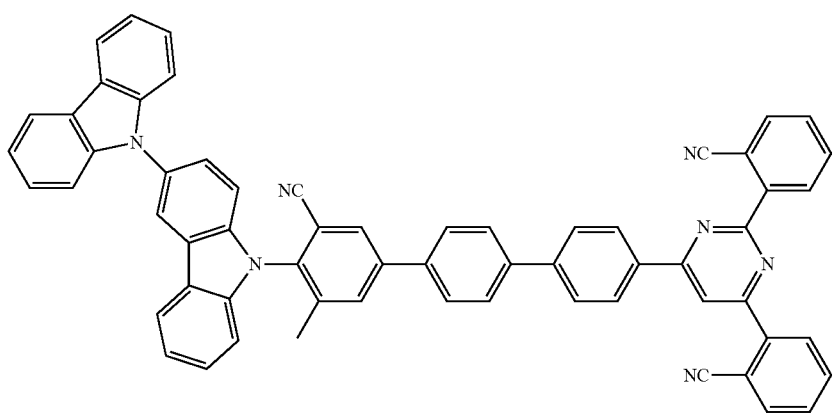
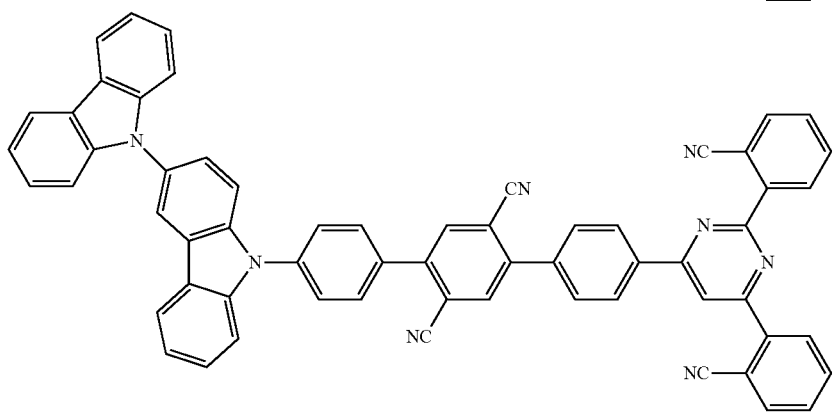

-continued
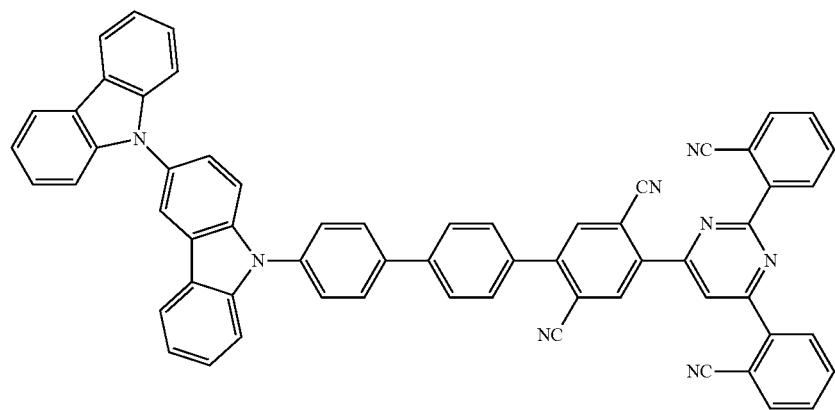
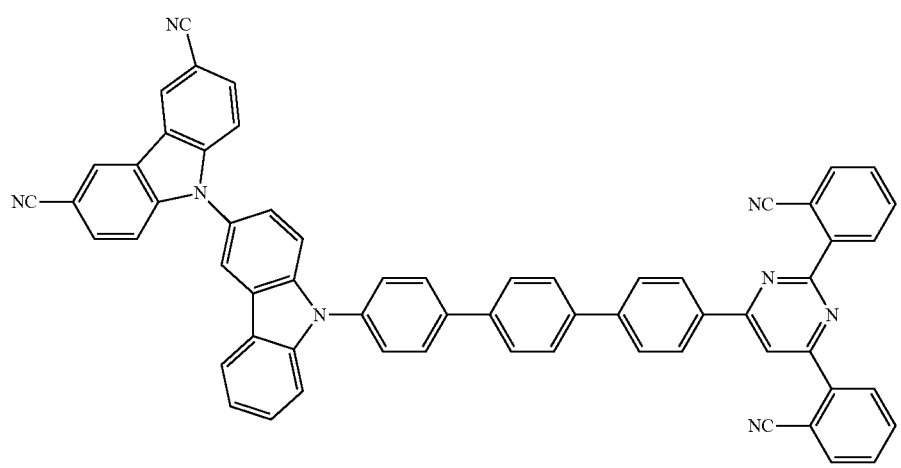
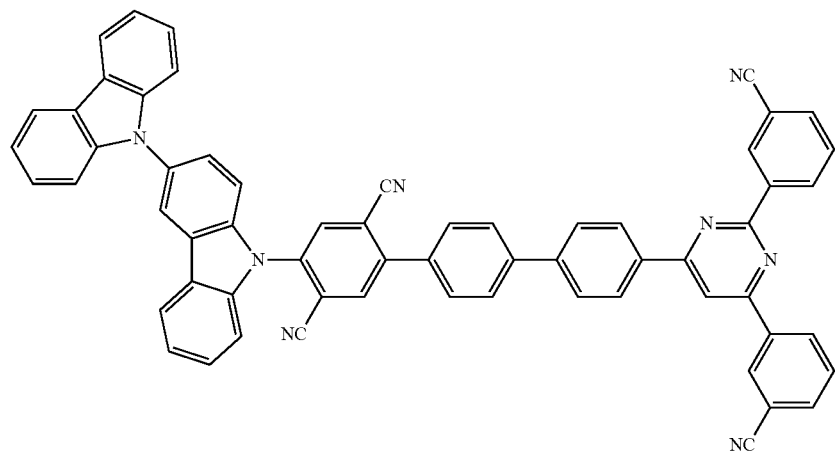

-continued
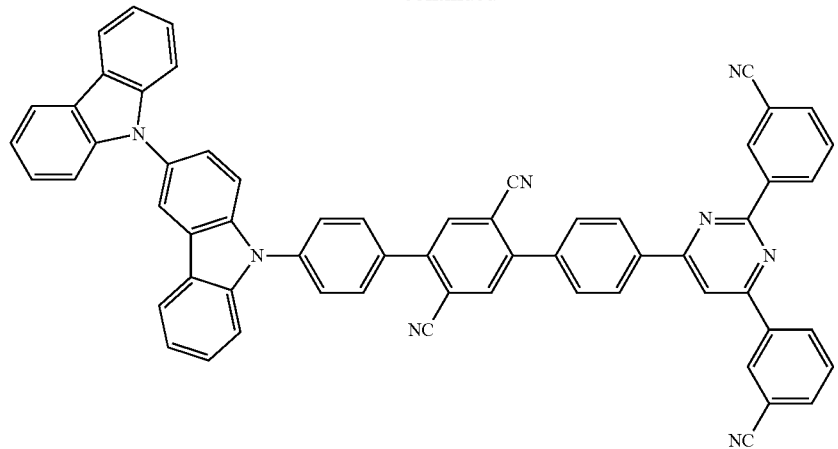
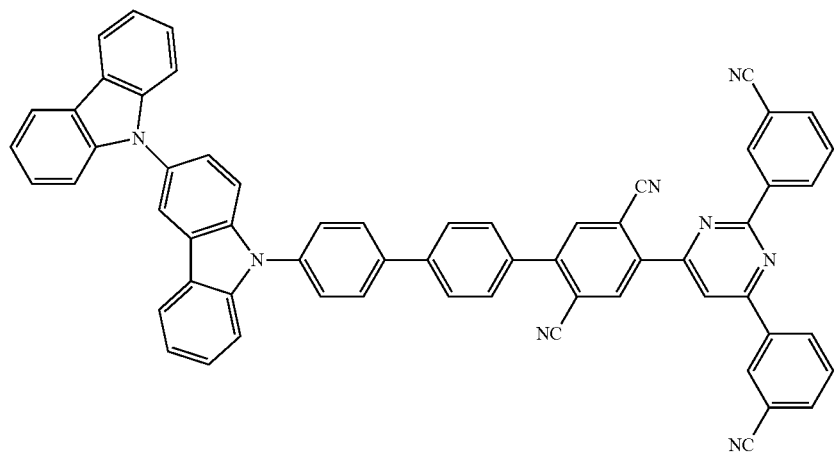
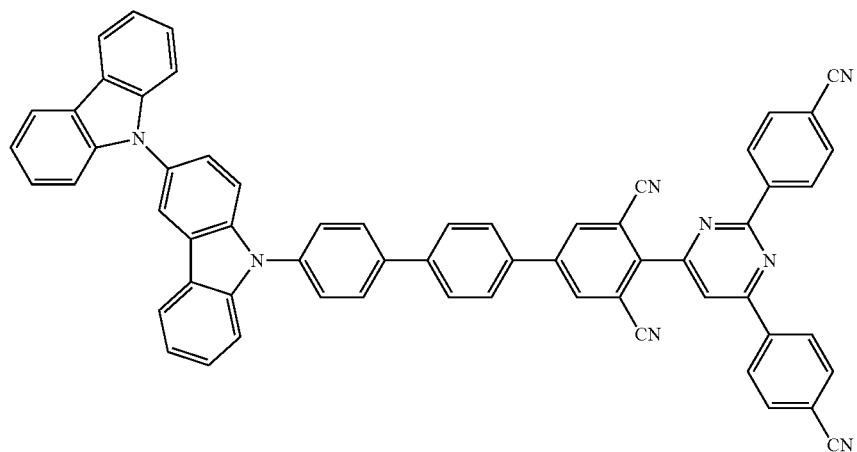

-continued
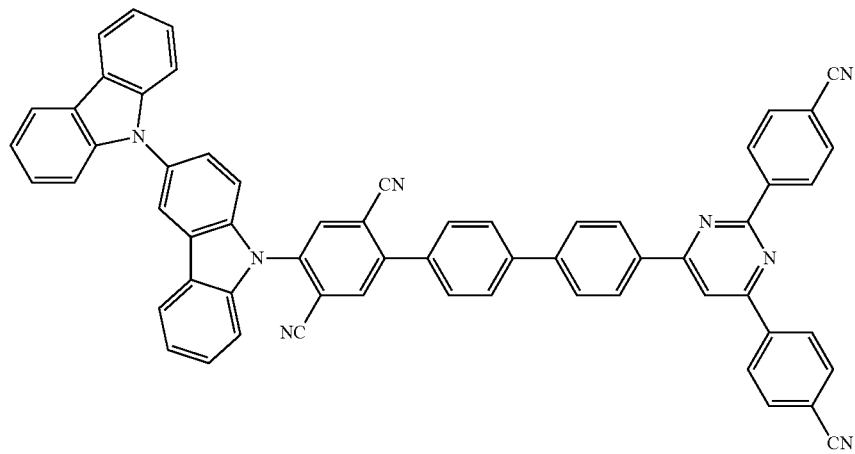
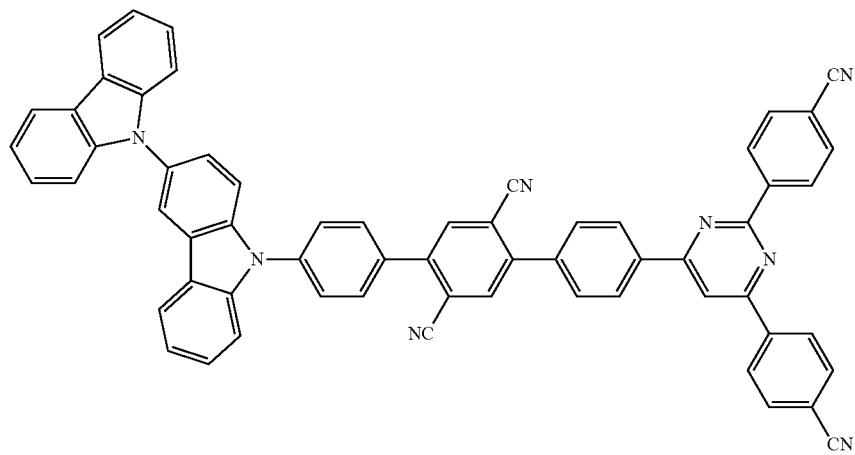
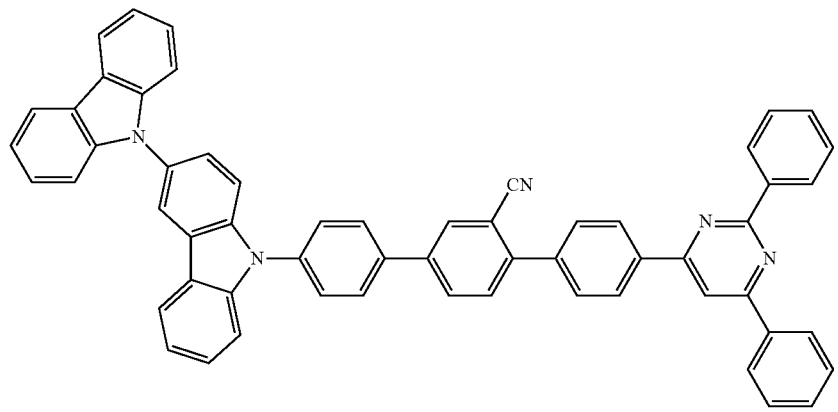
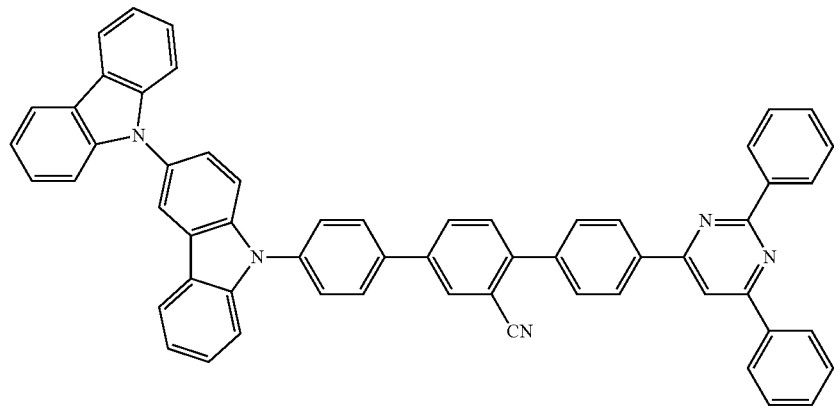

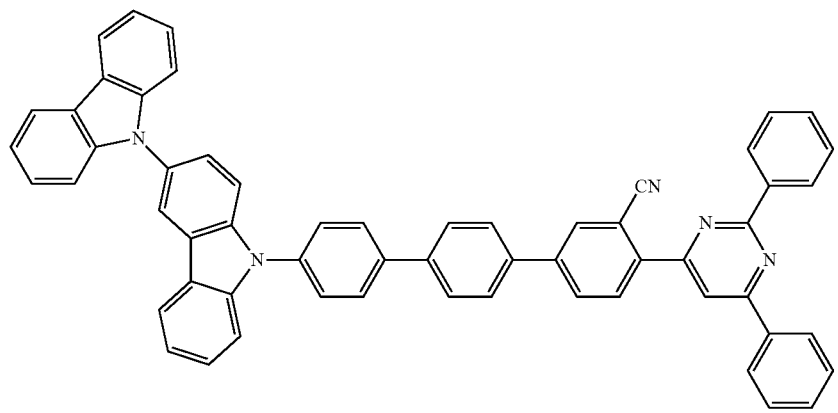
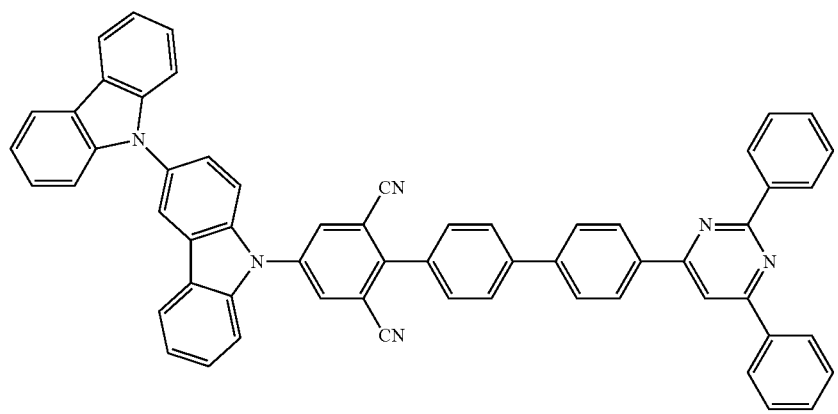
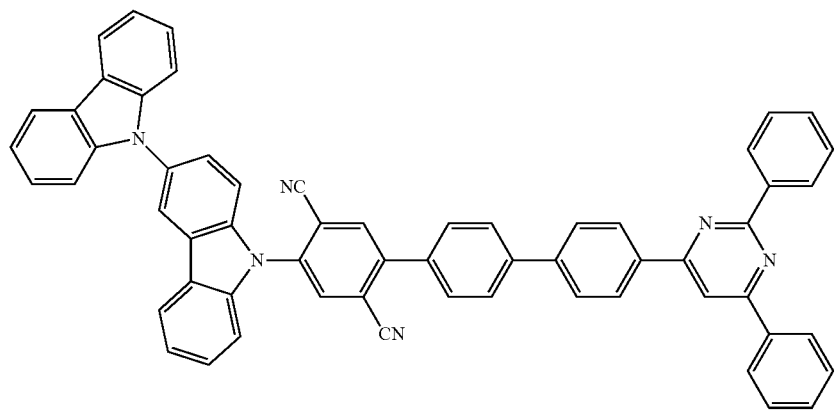
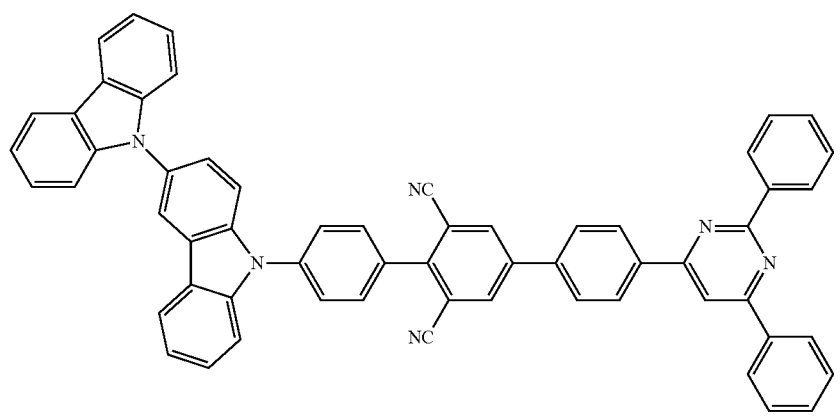

-continued
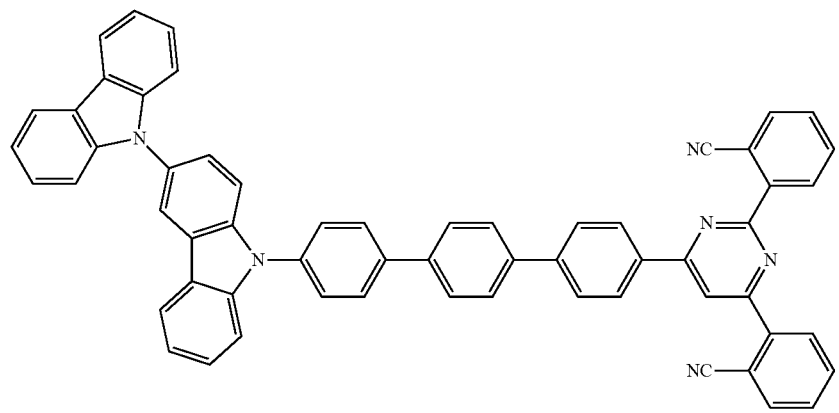
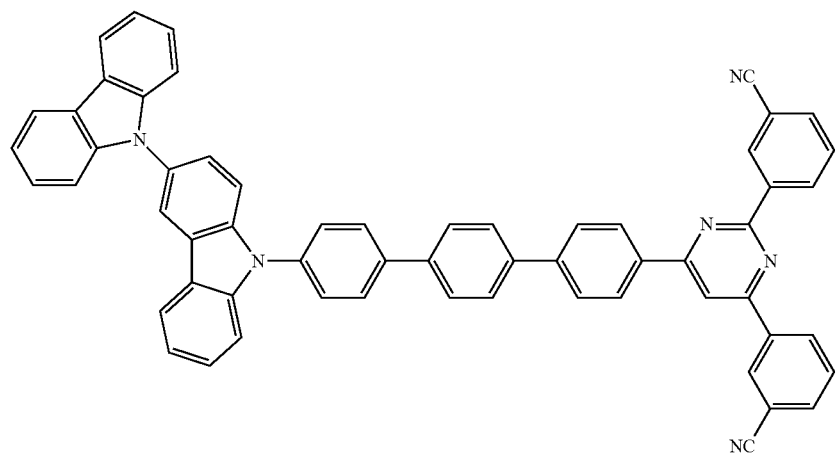
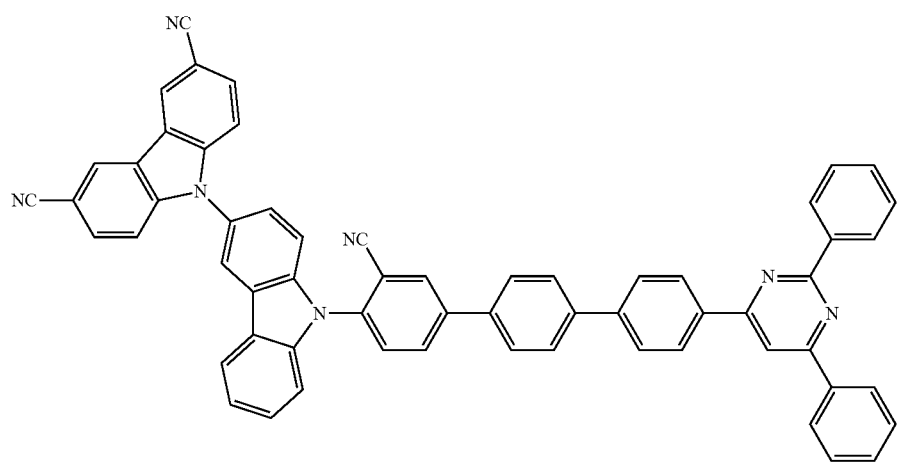

-continued
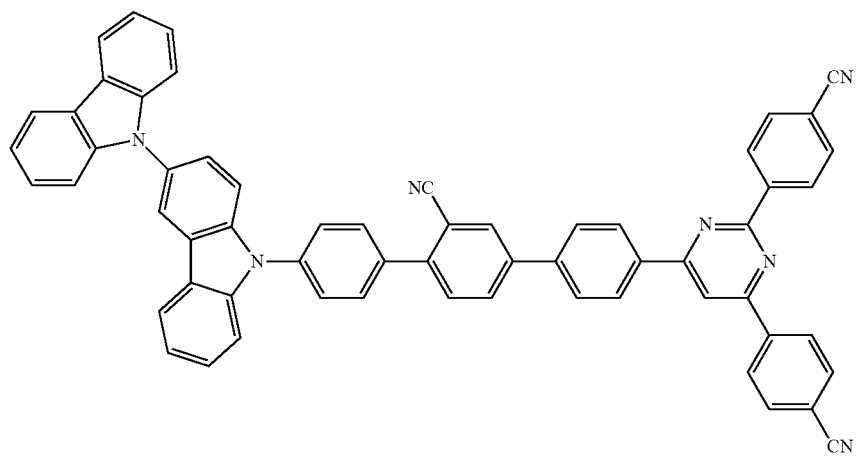
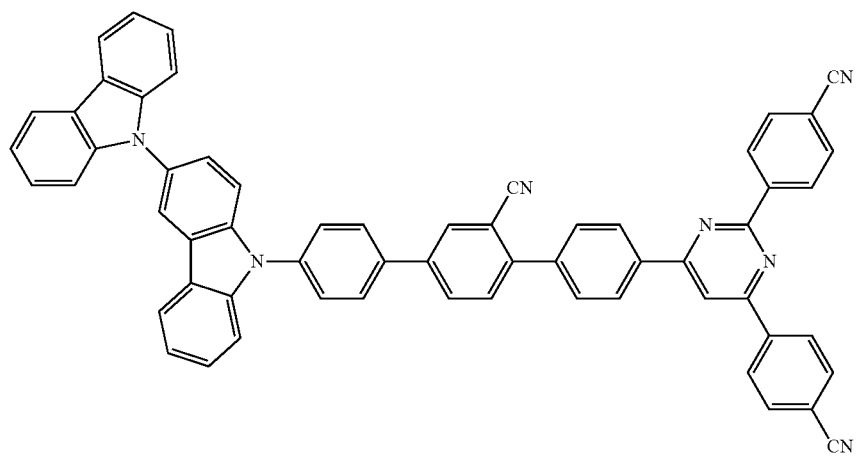

-continued
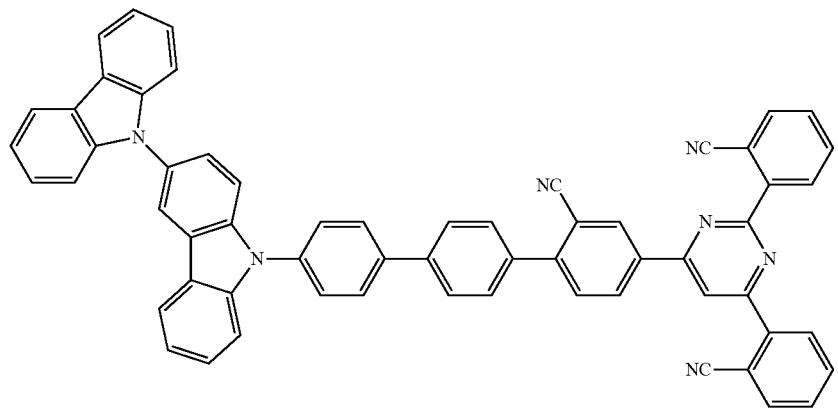
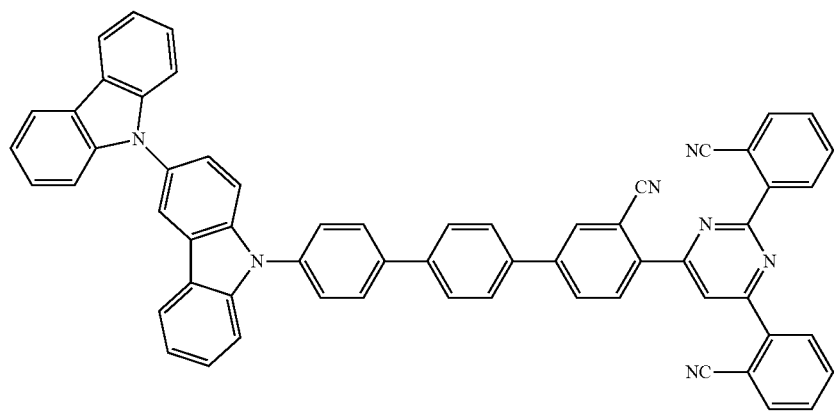
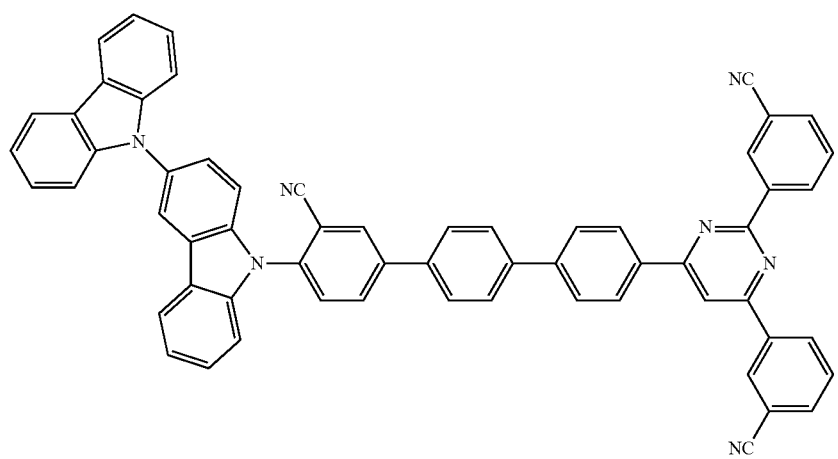
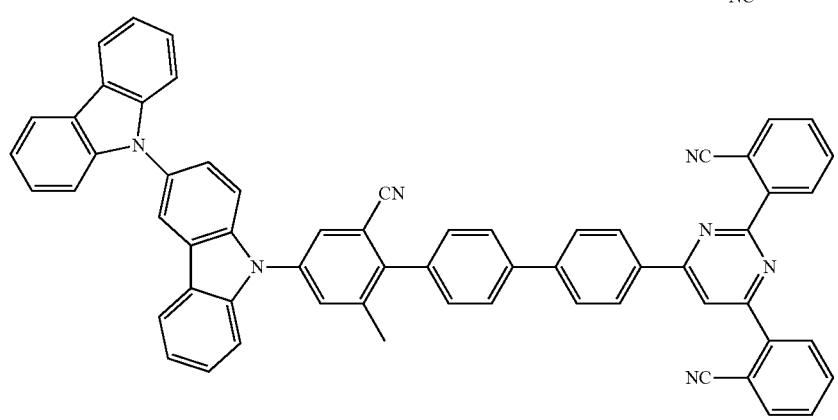

-continued
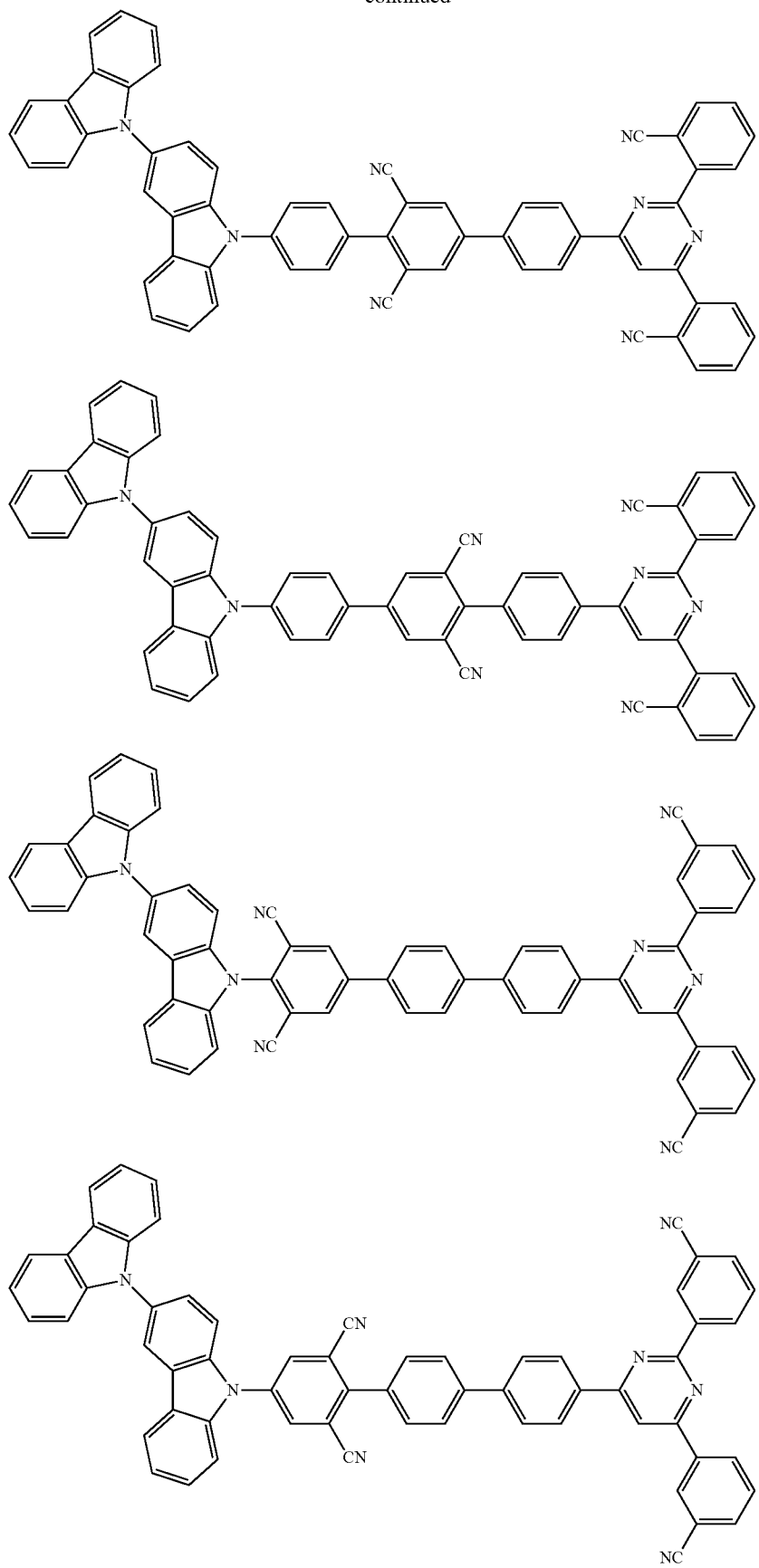

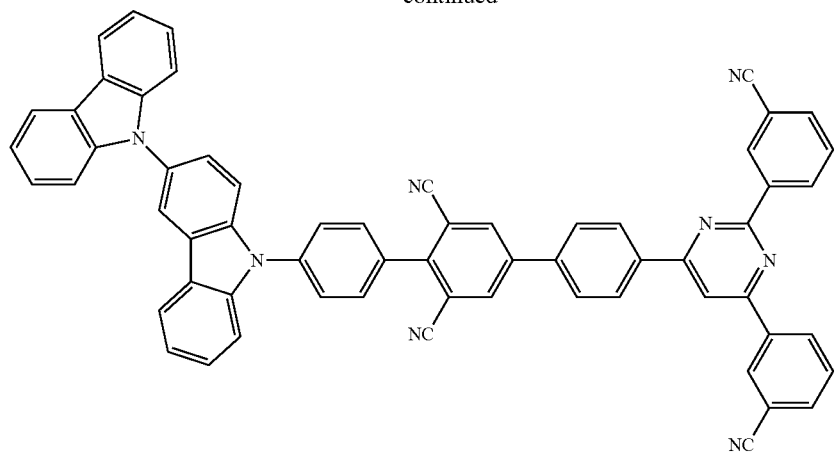
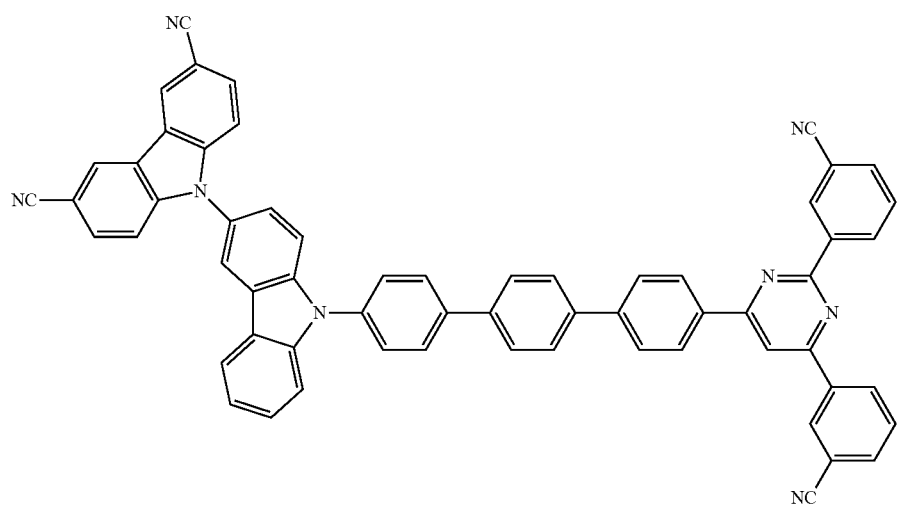
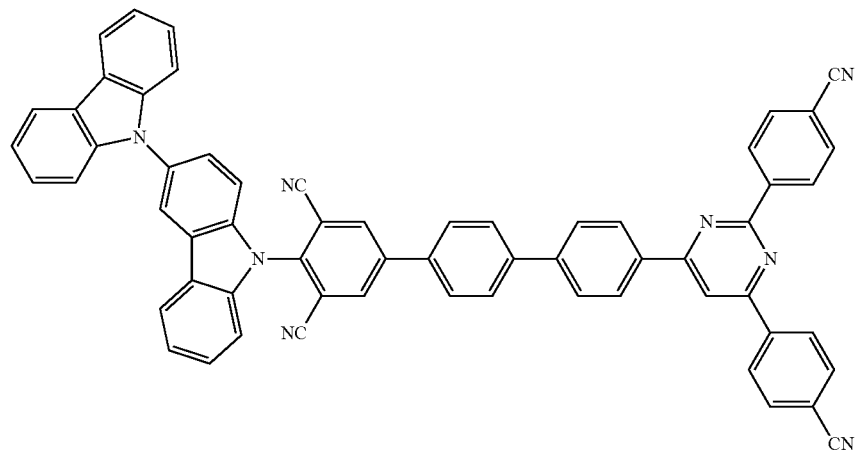

691
692
-continued
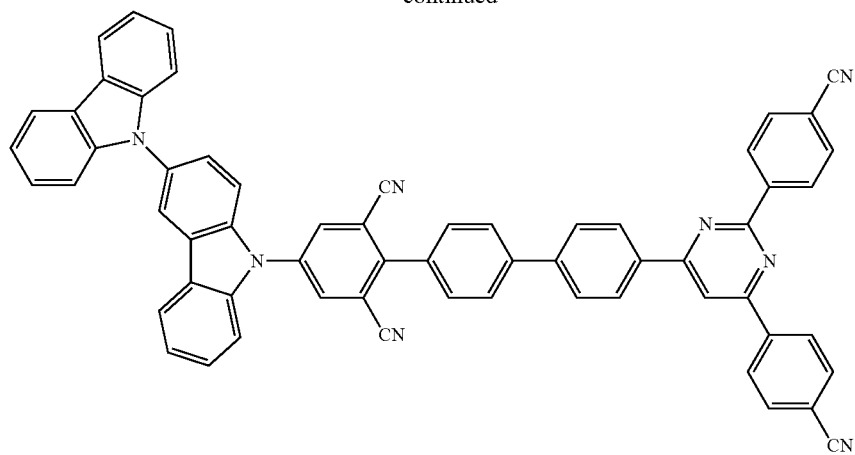
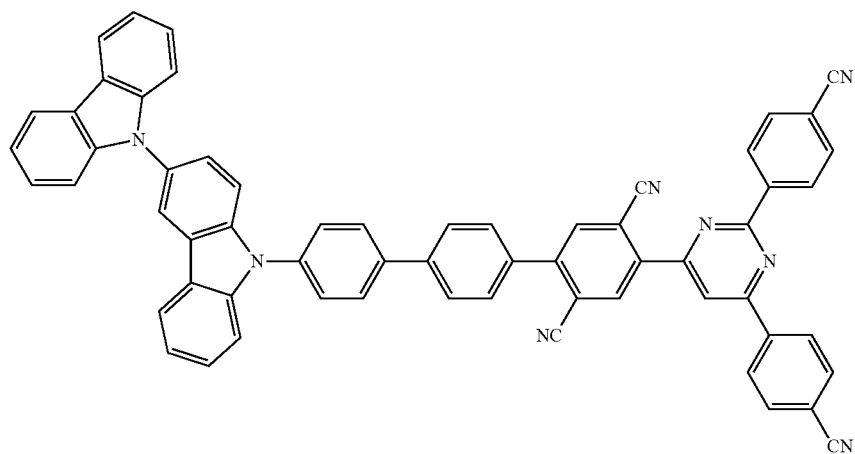
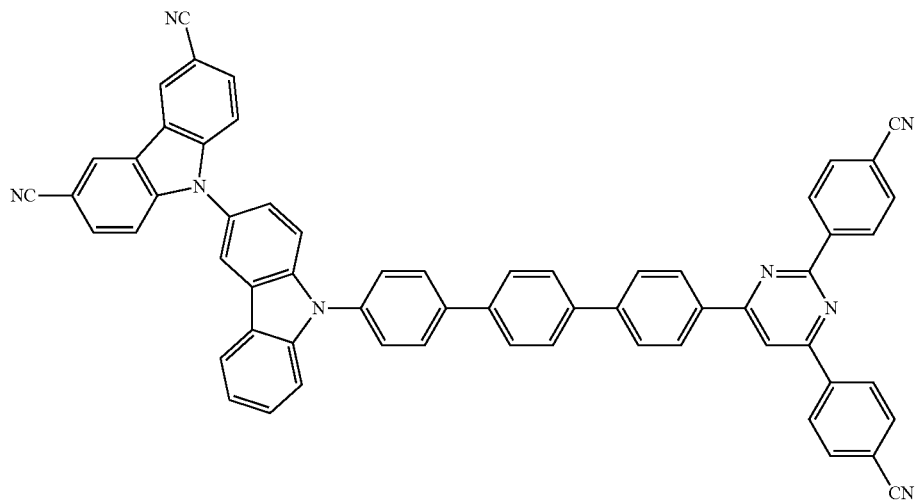

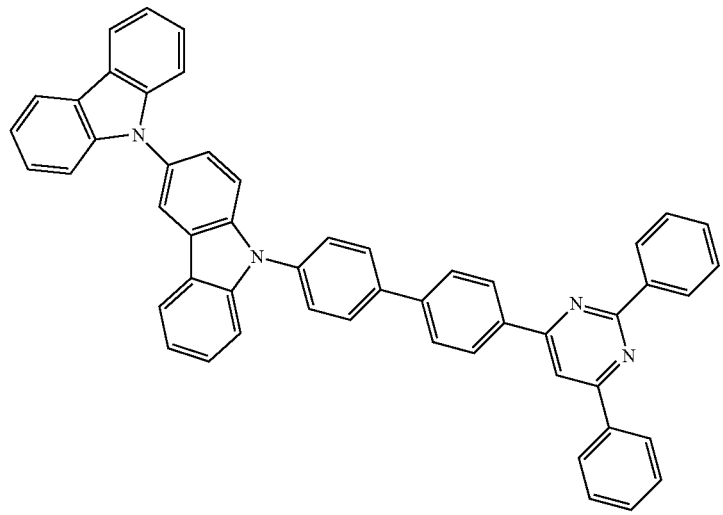
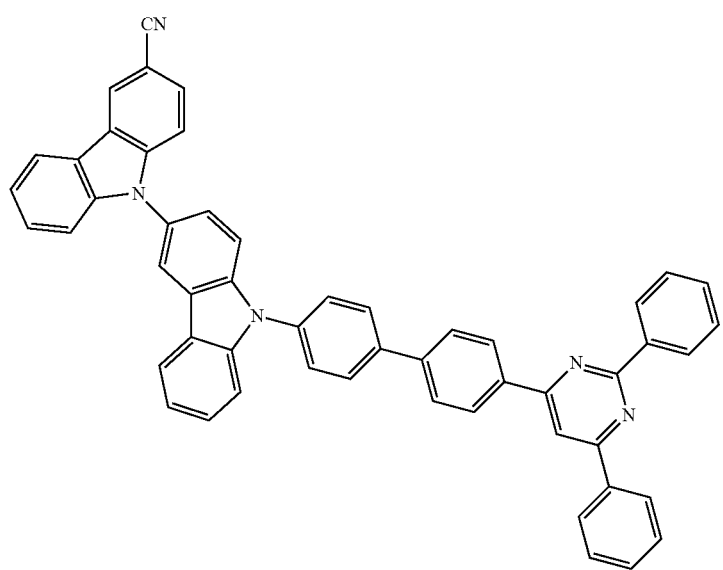
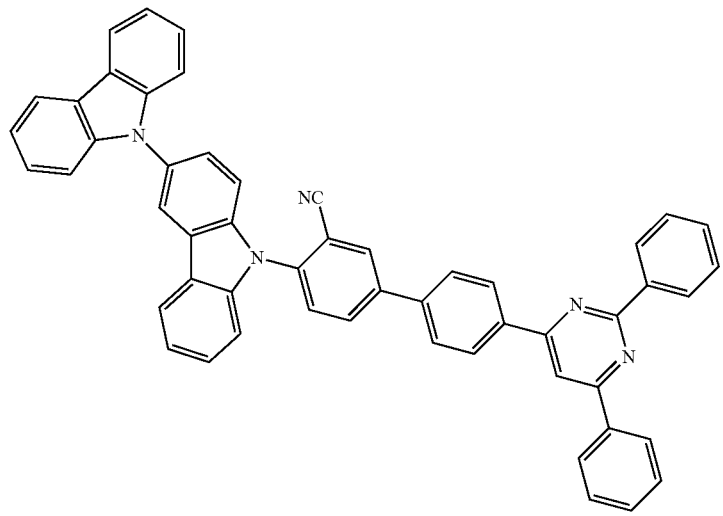

-continued
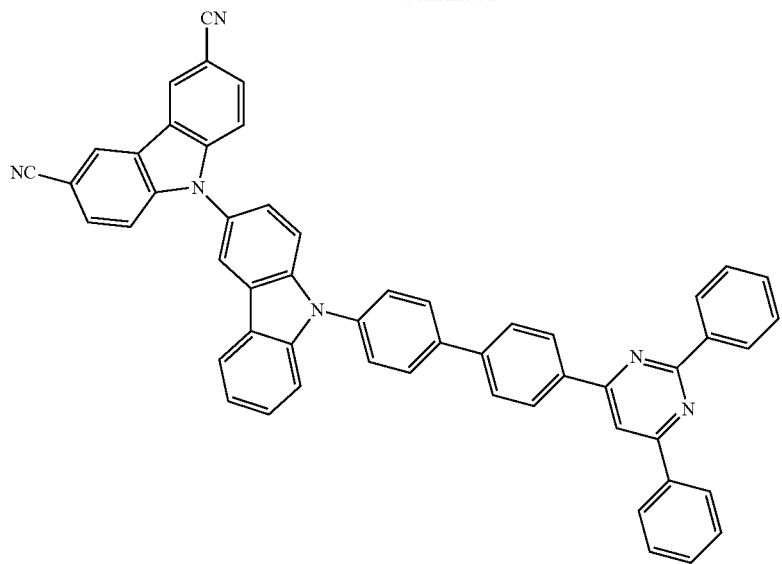
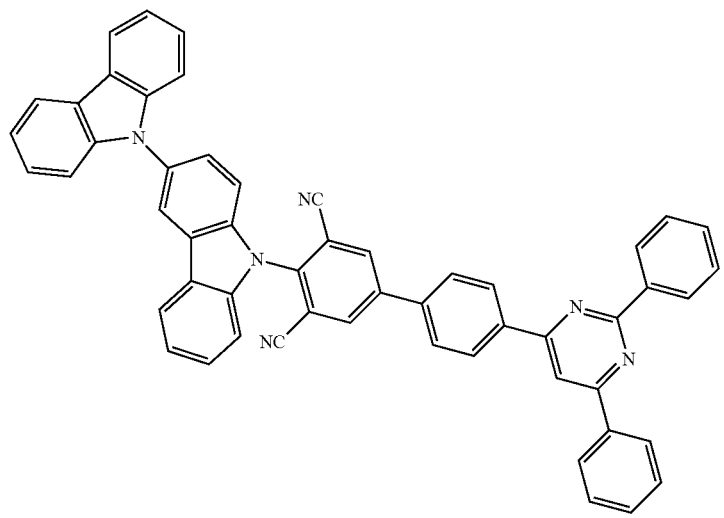
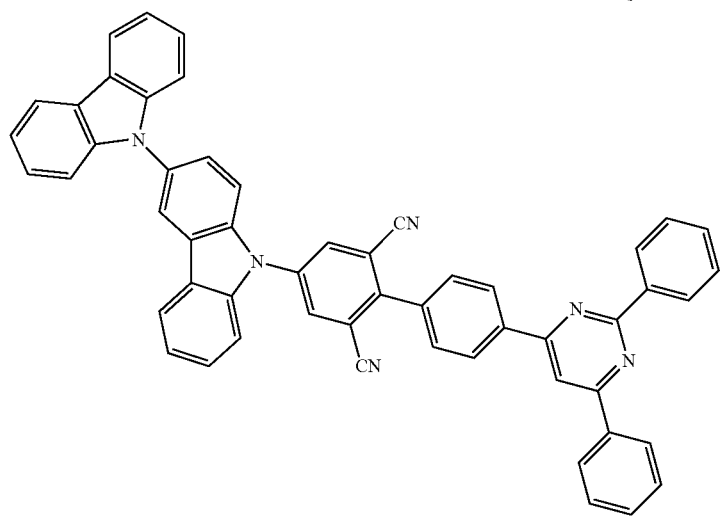

-continued
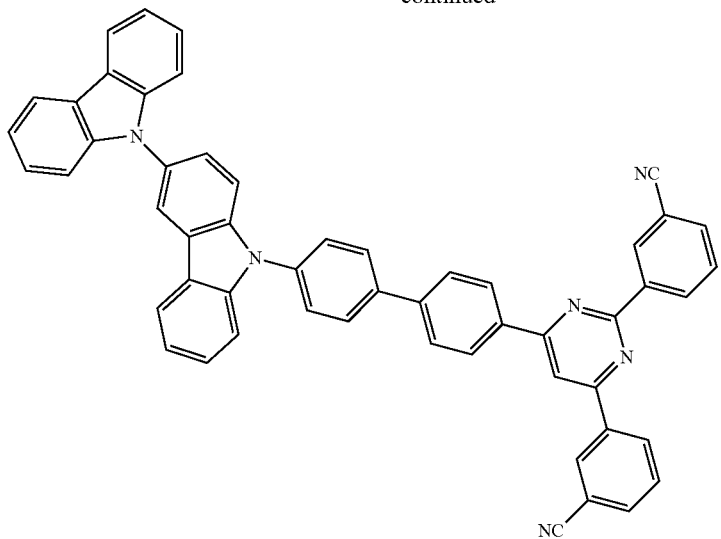
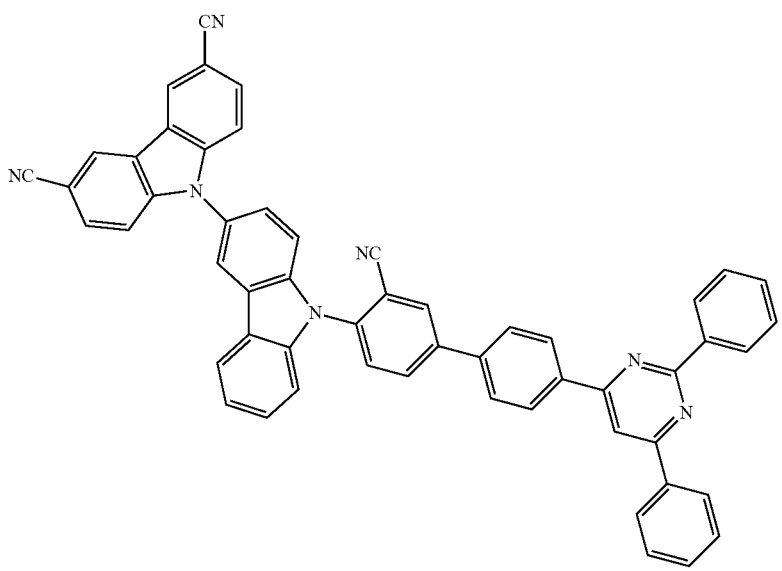
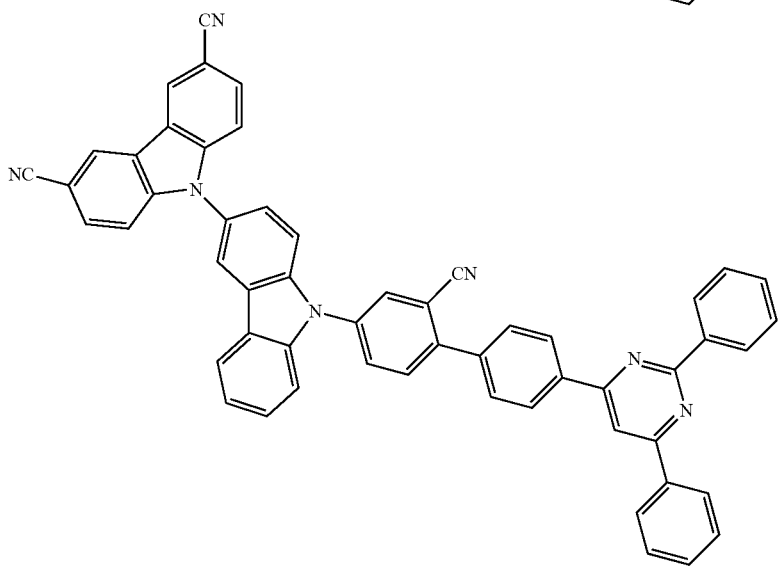

-continued
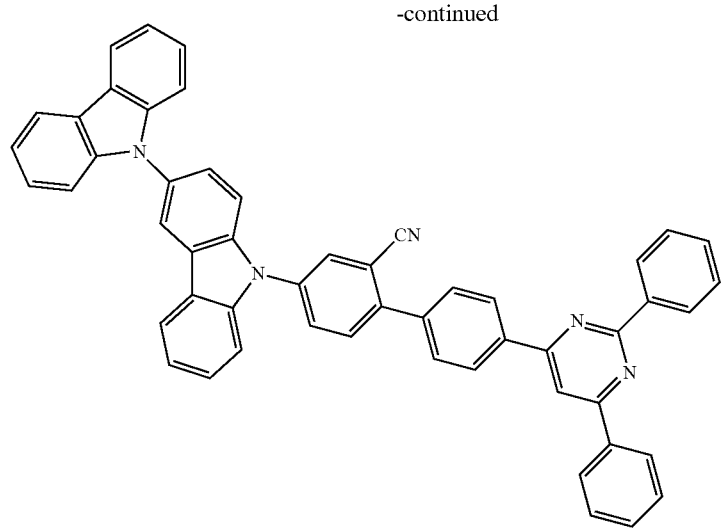
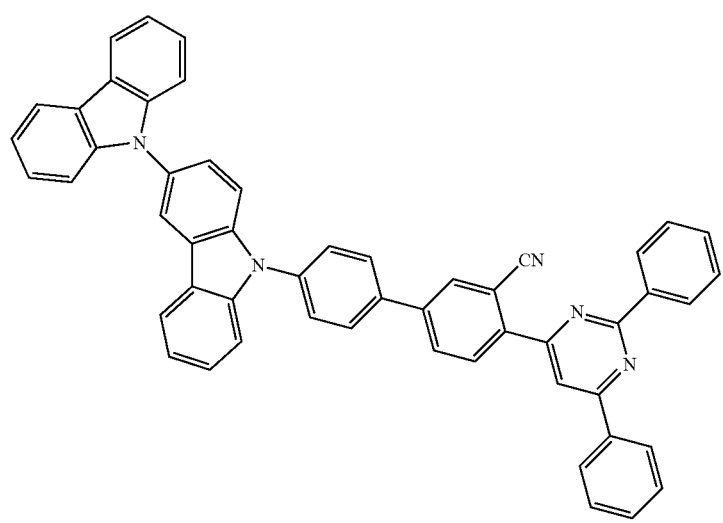
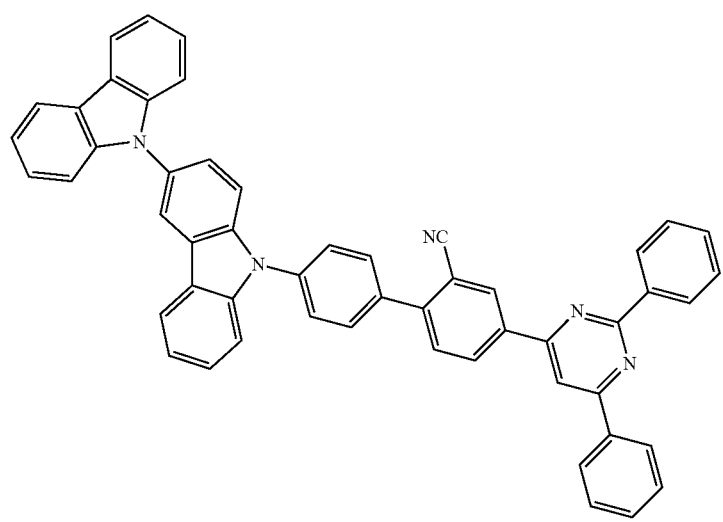

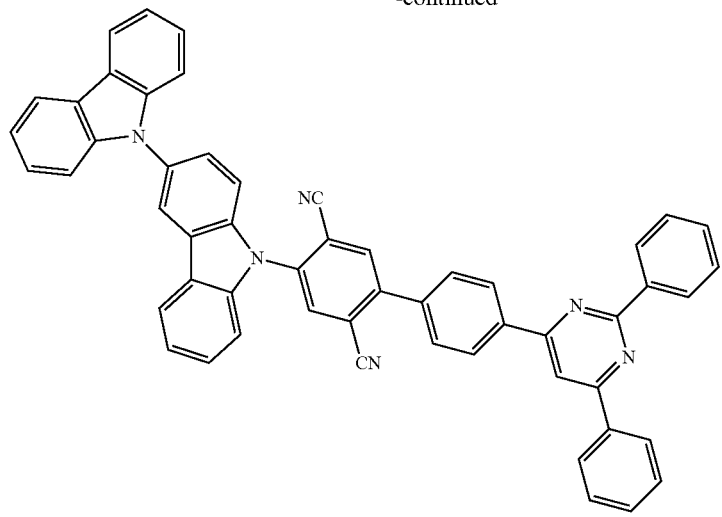
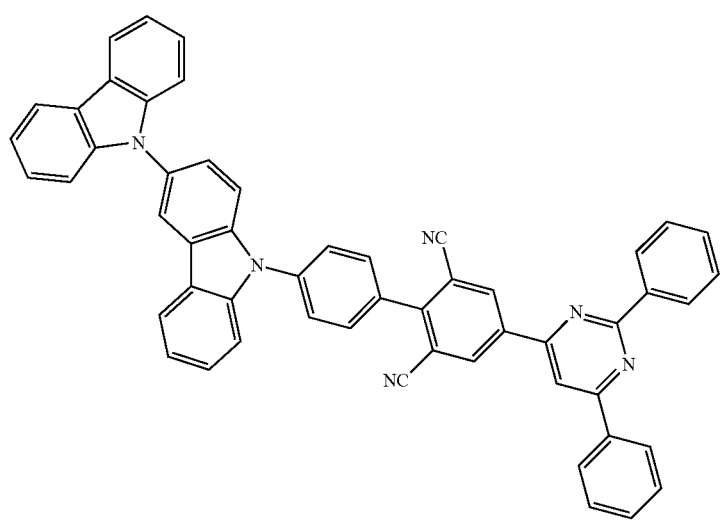
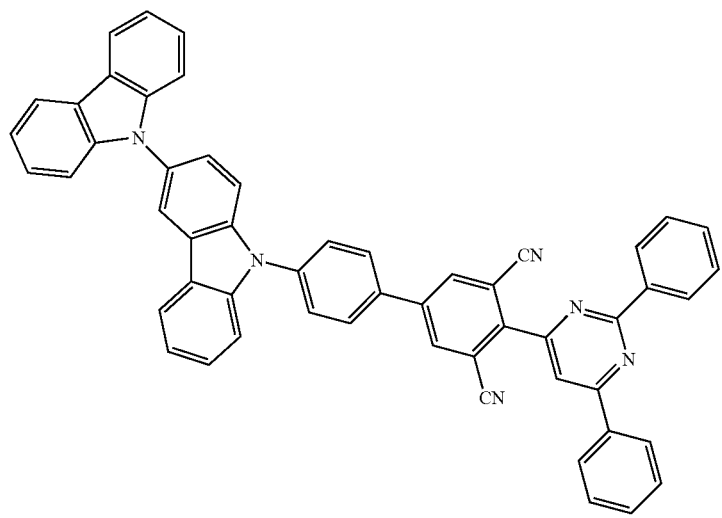

-continued
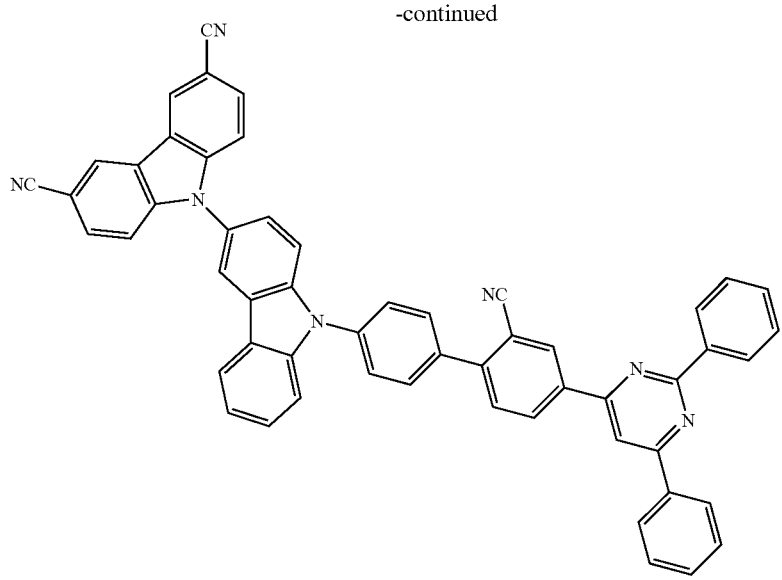
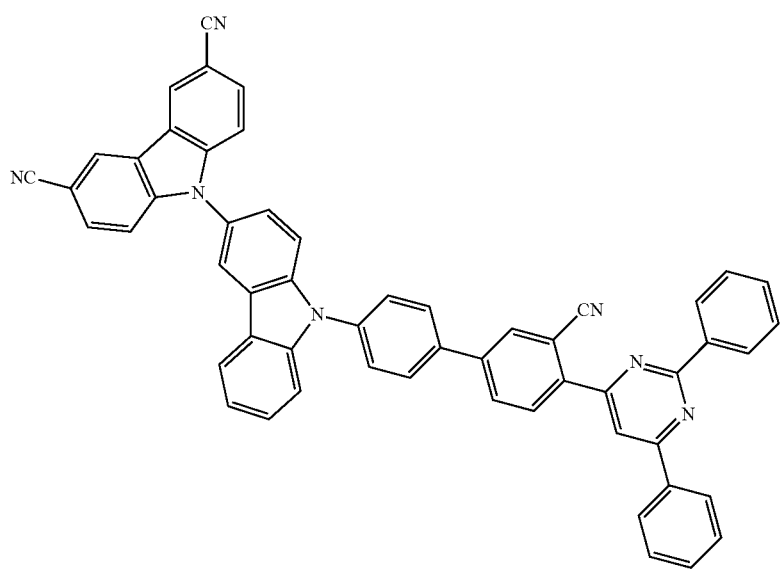
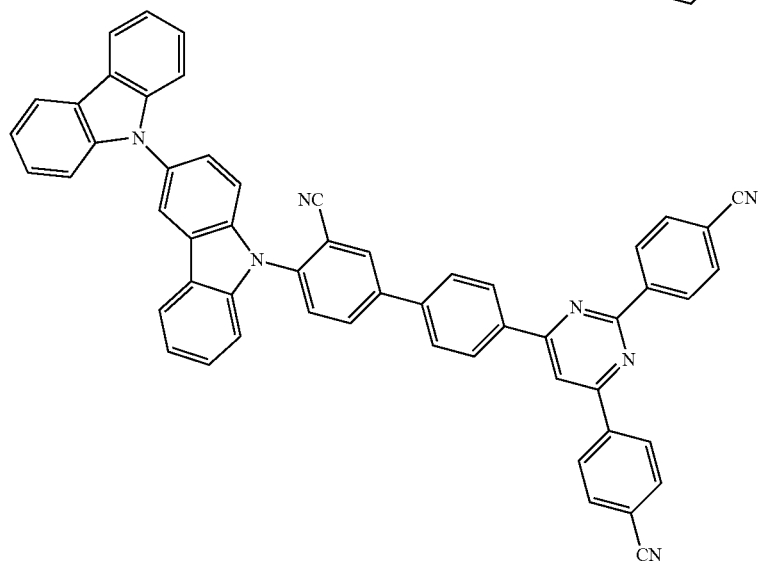

-continued
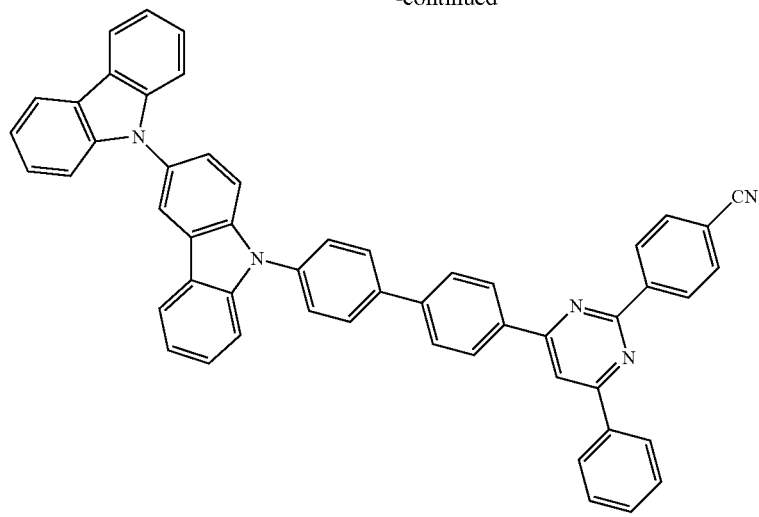
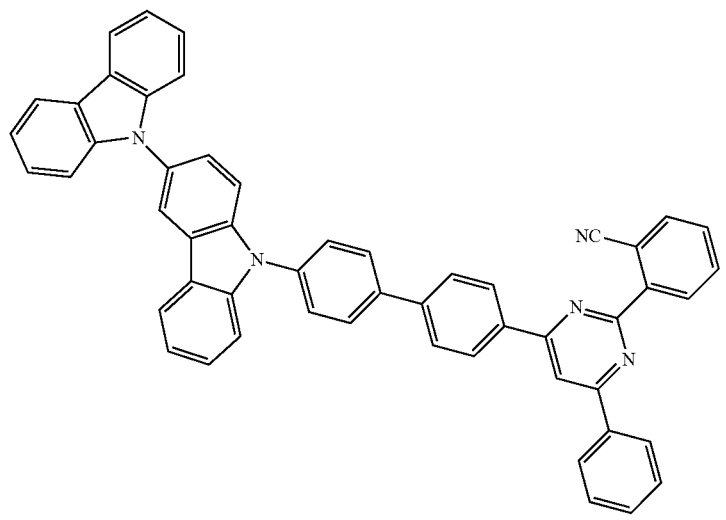
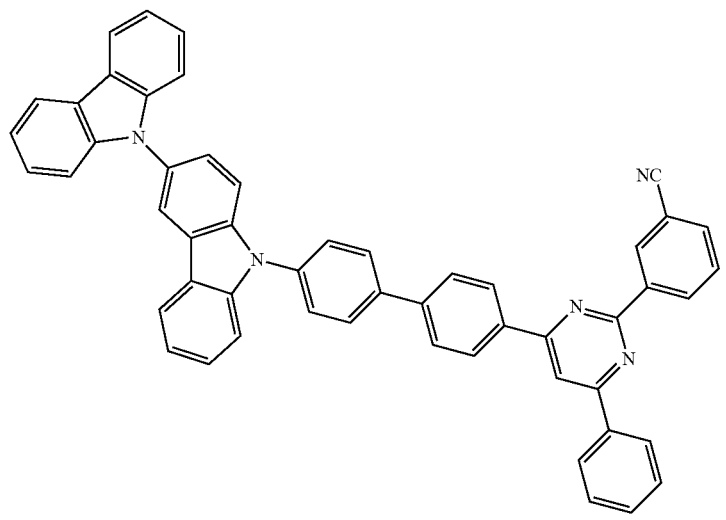

-continued
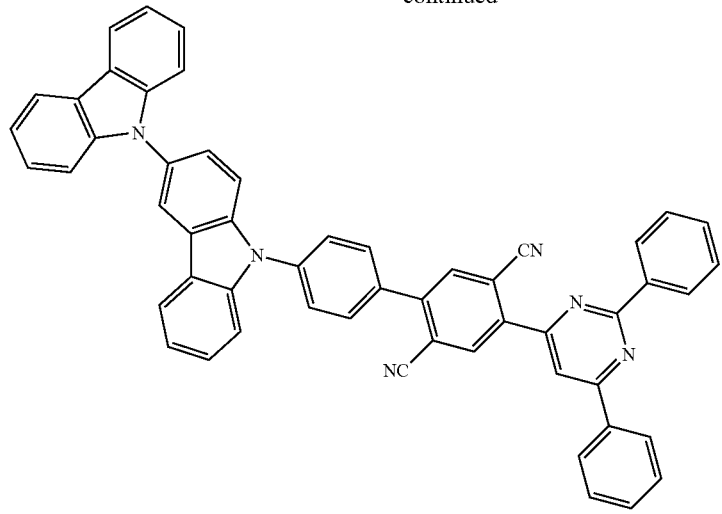
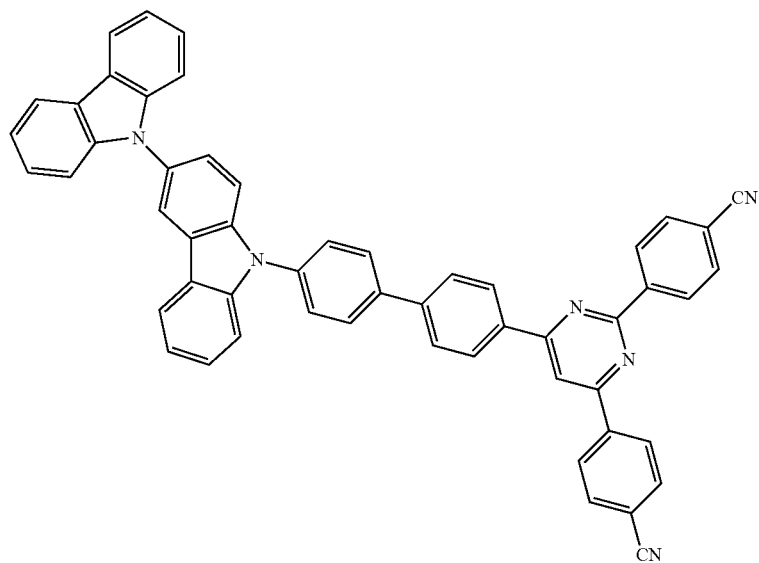
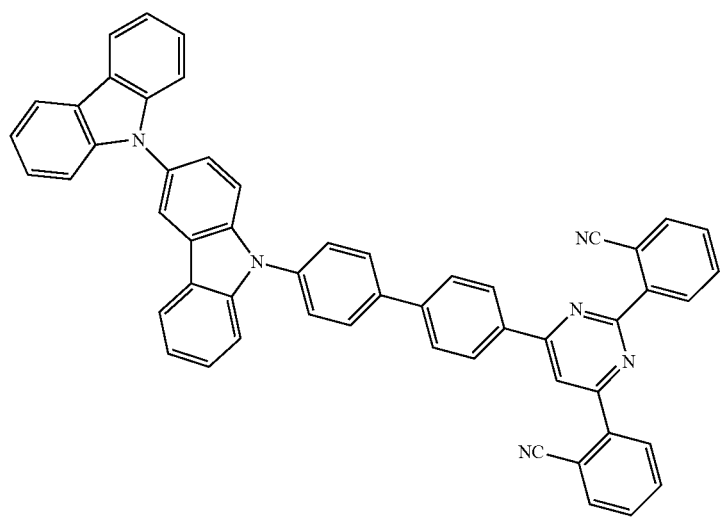

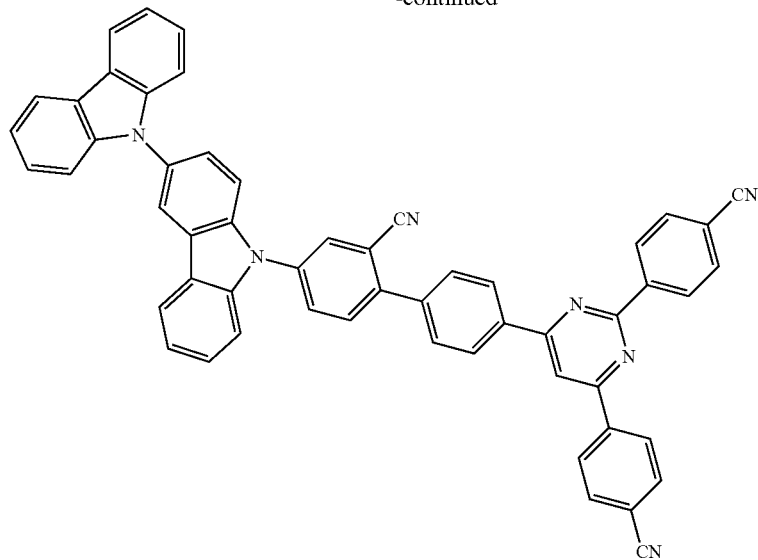
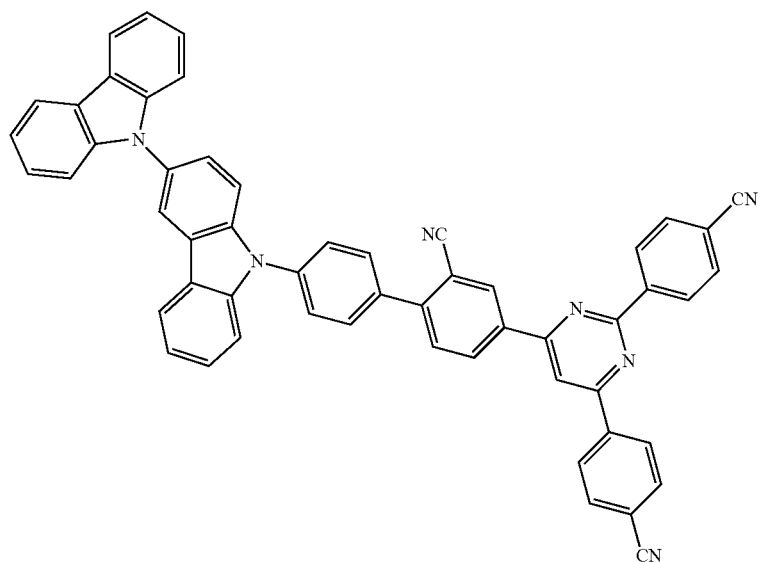
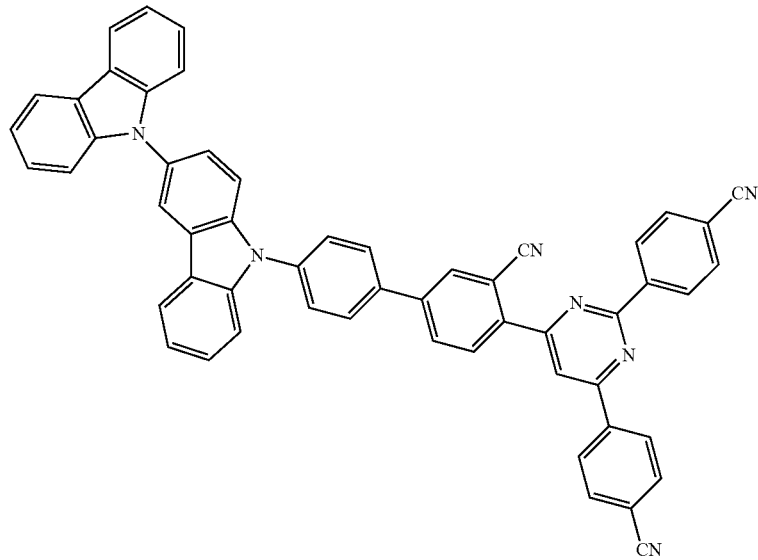

-continued
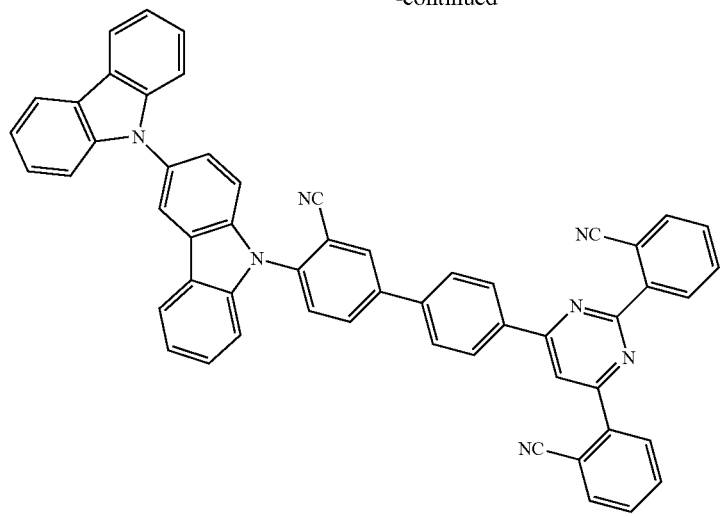
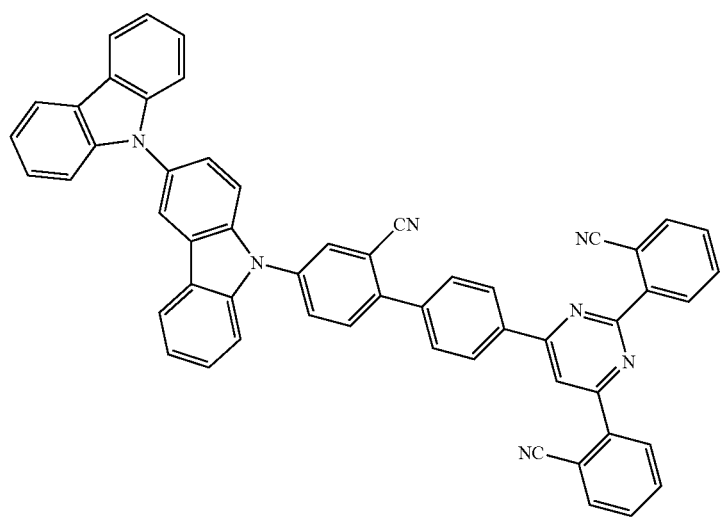
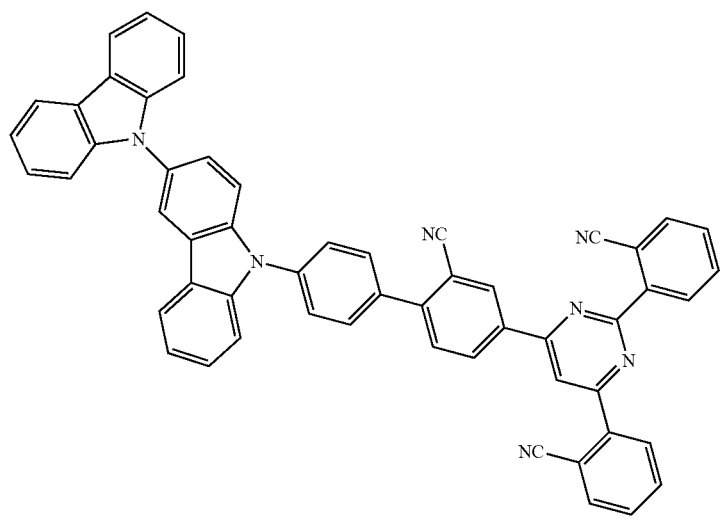

-continued
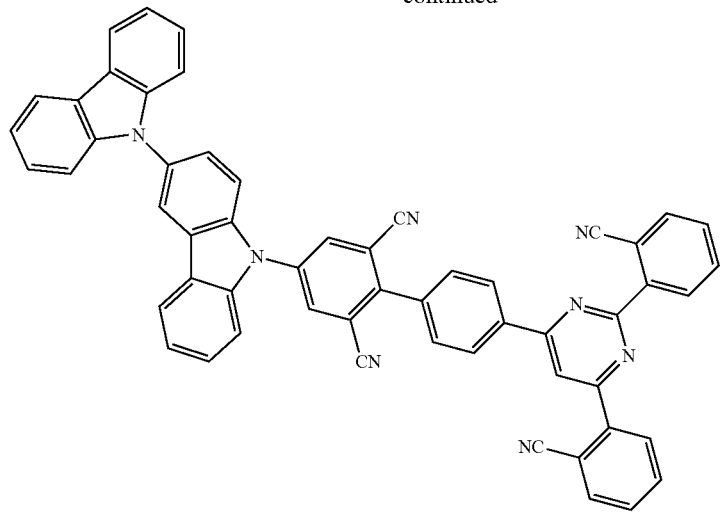
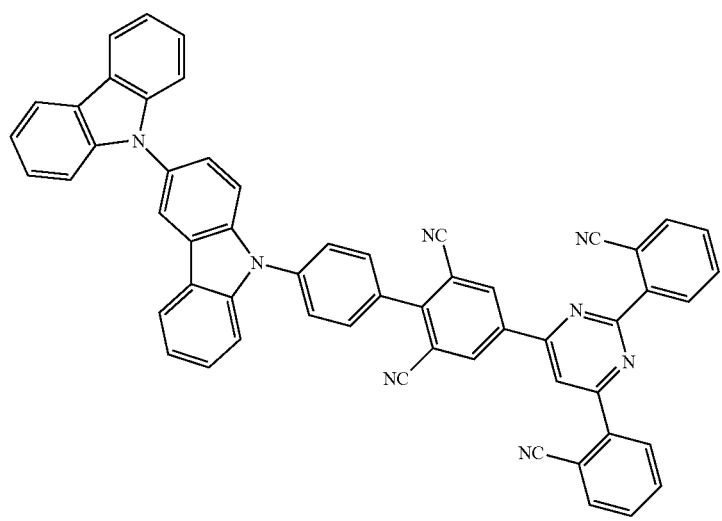
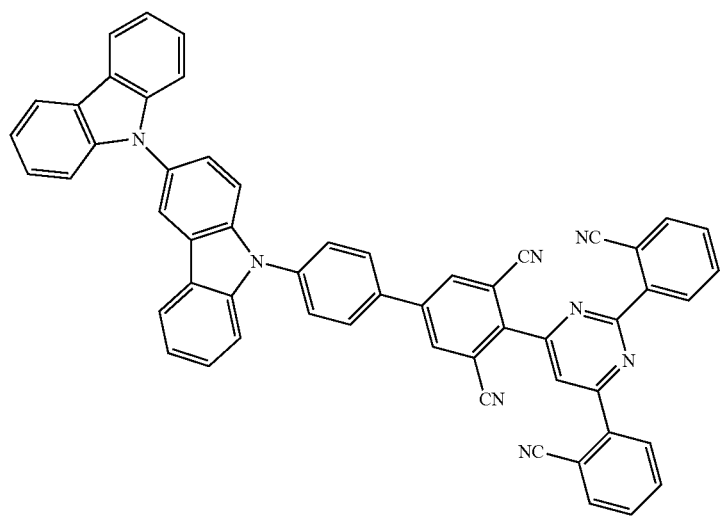

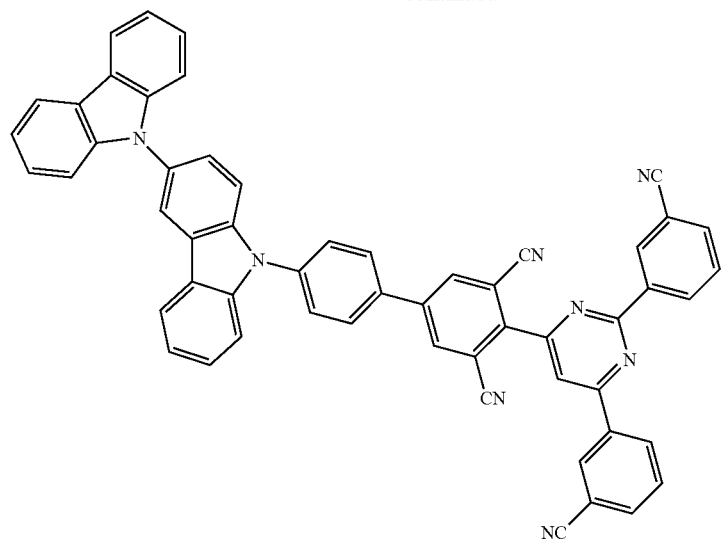
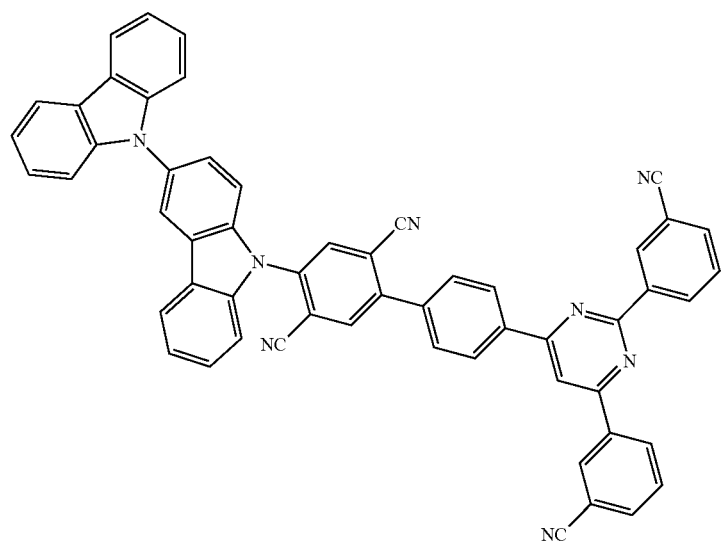
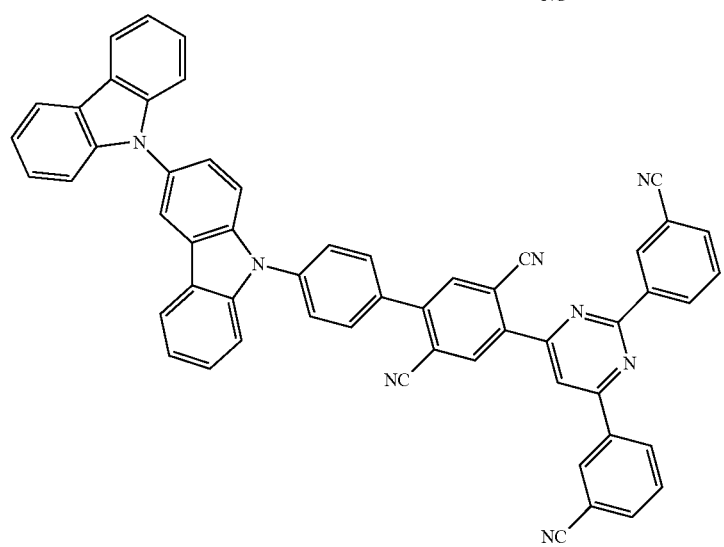

-continued
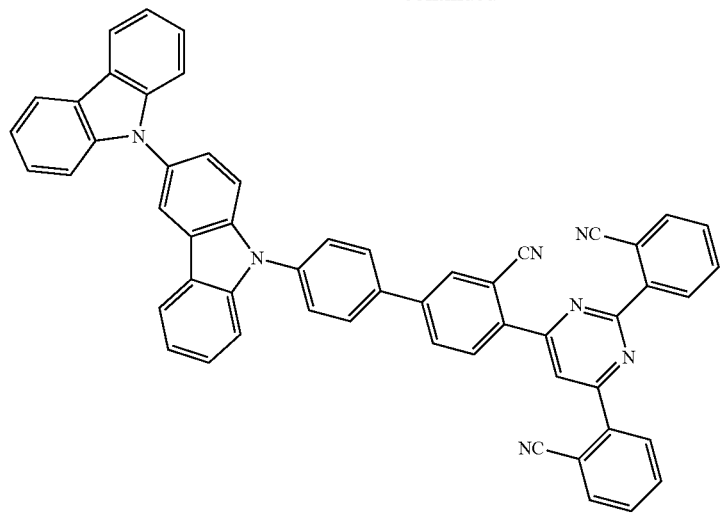
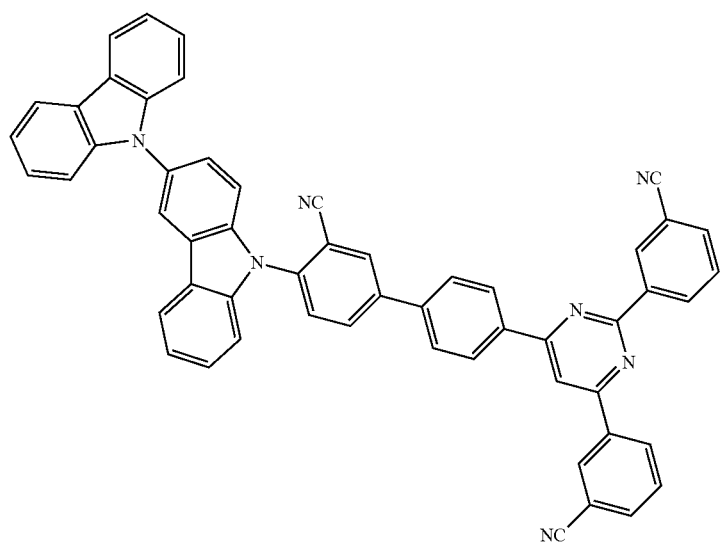
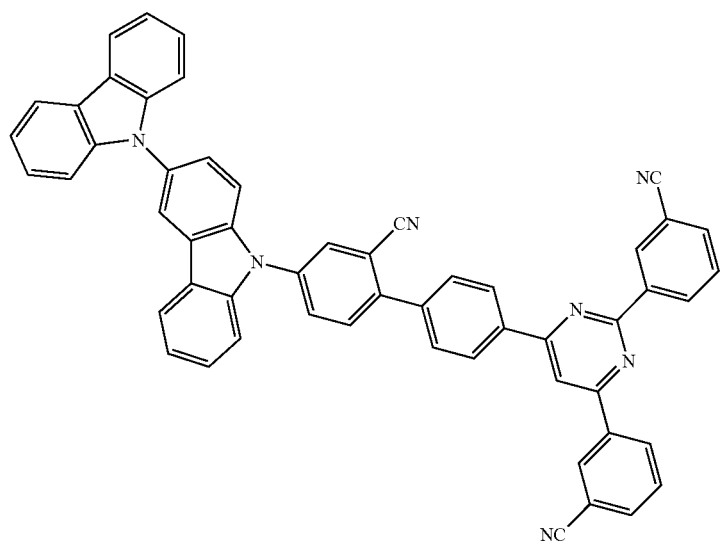

-continued
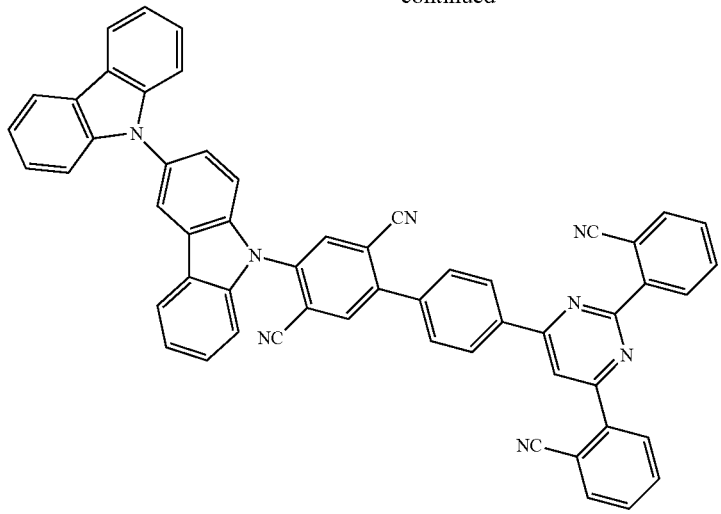
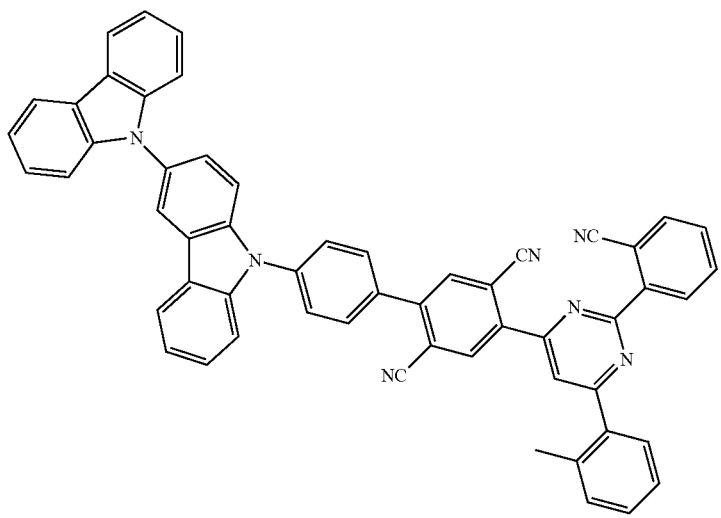
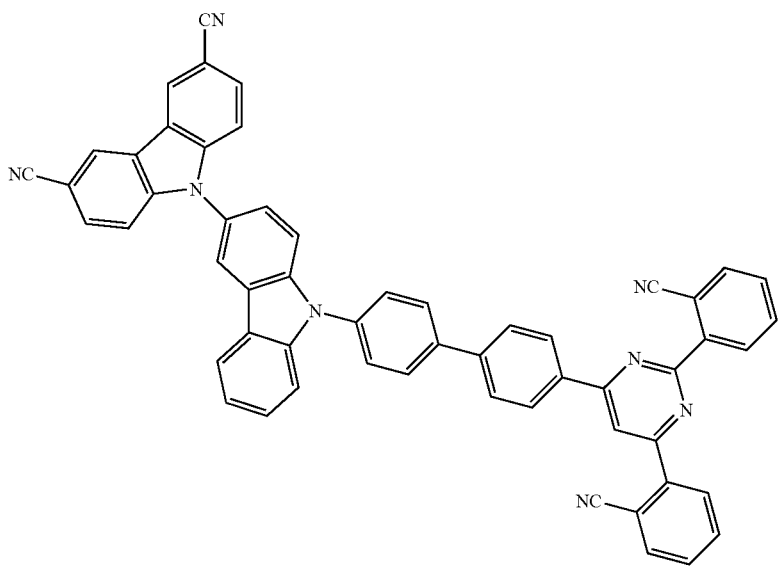

-continued
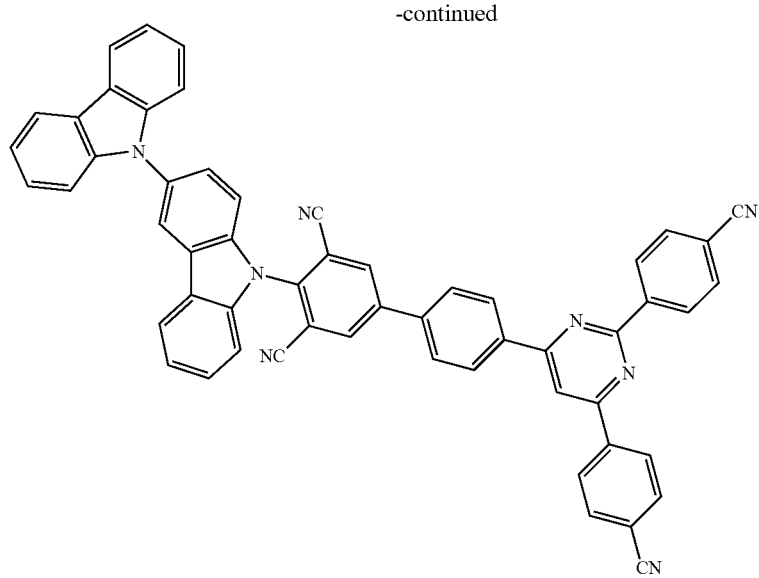
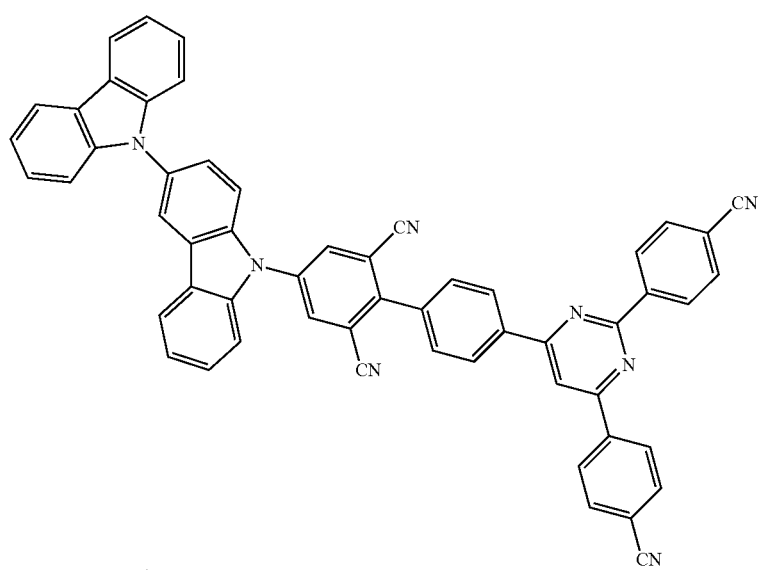
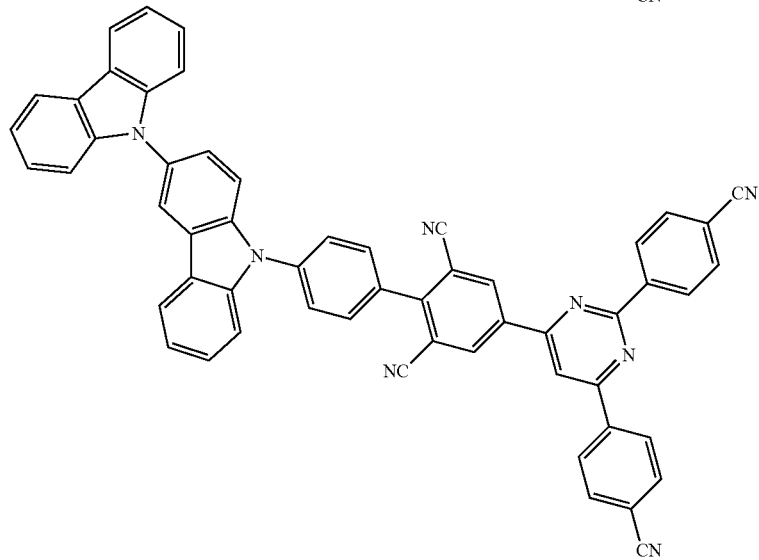

-continued
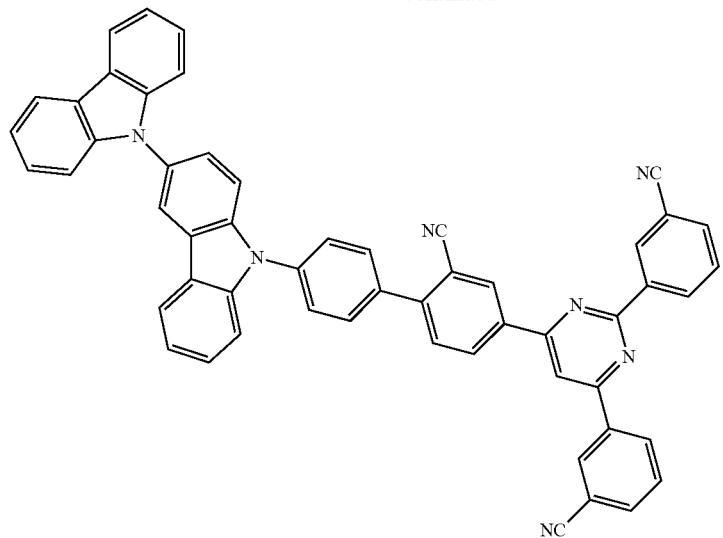
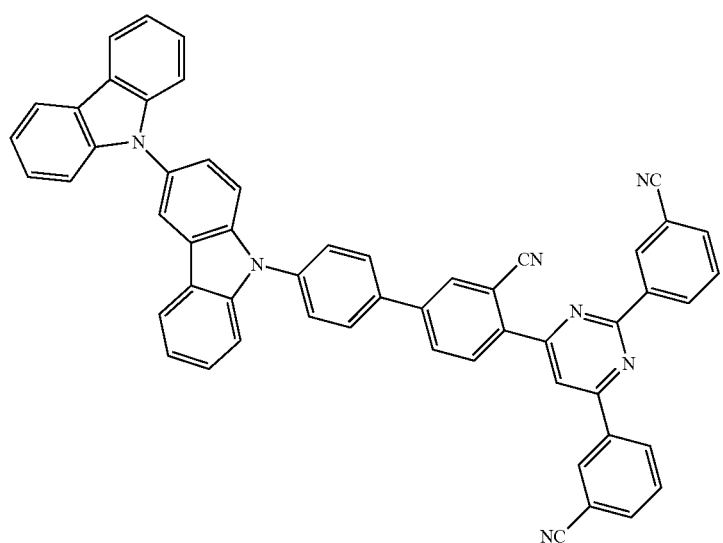
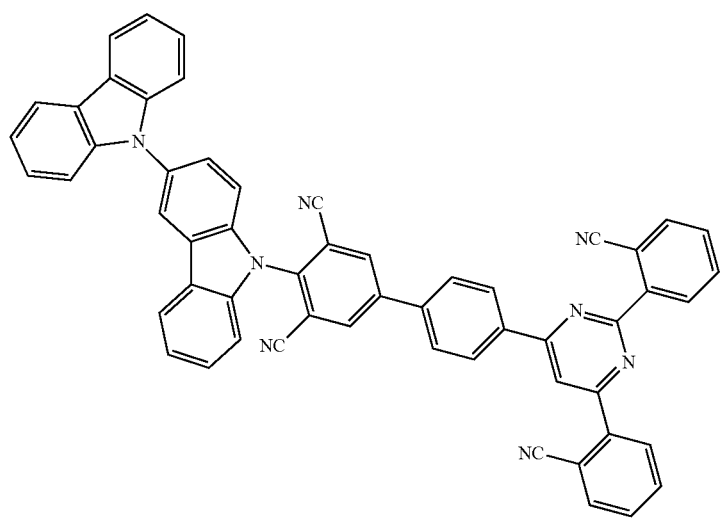

-continued
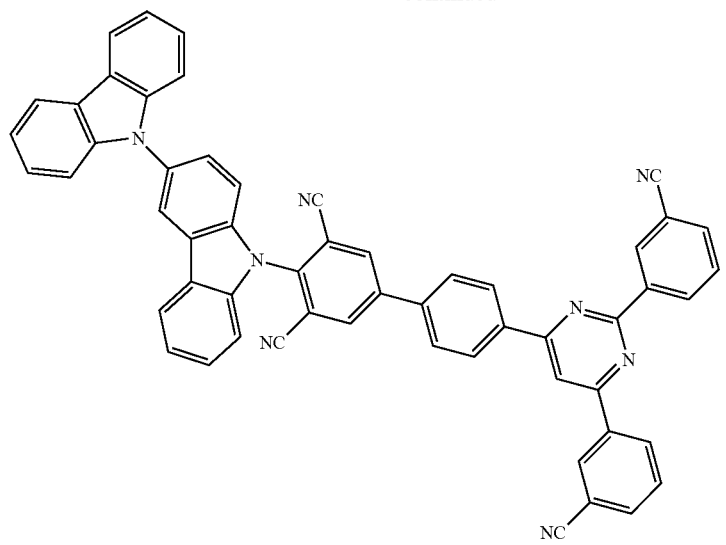
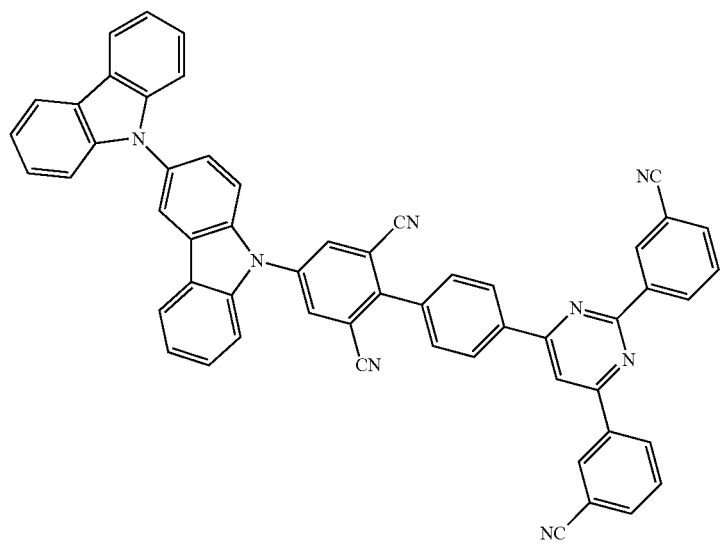
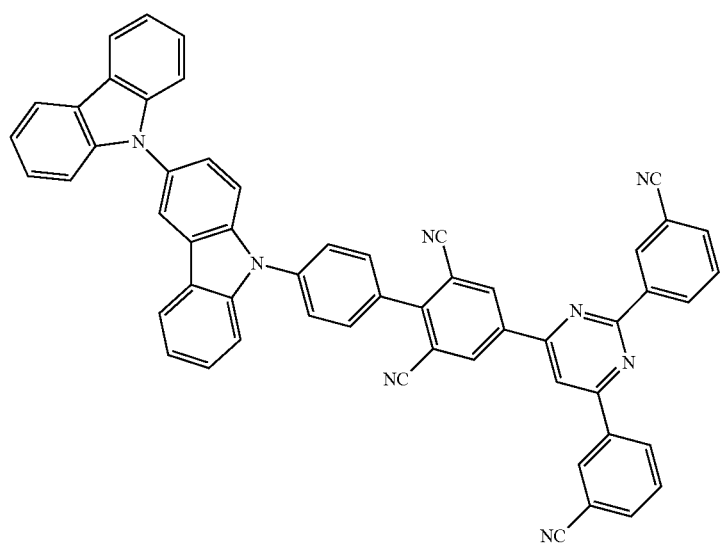

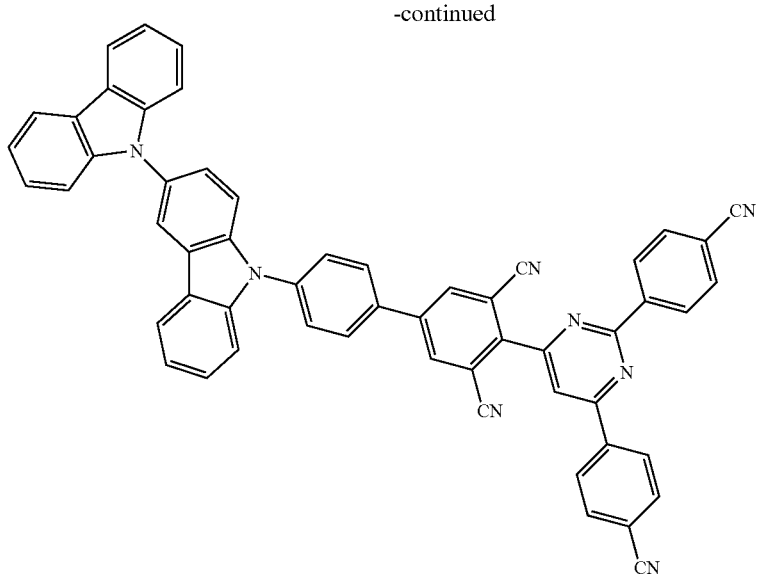
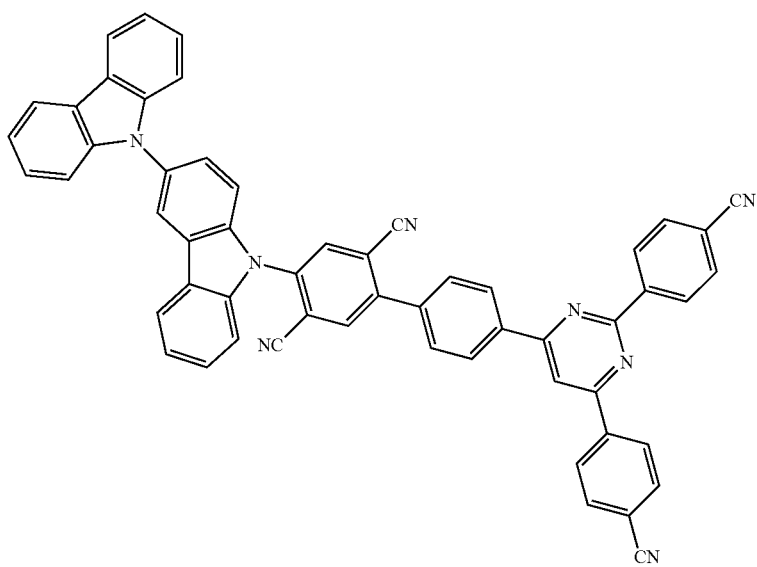
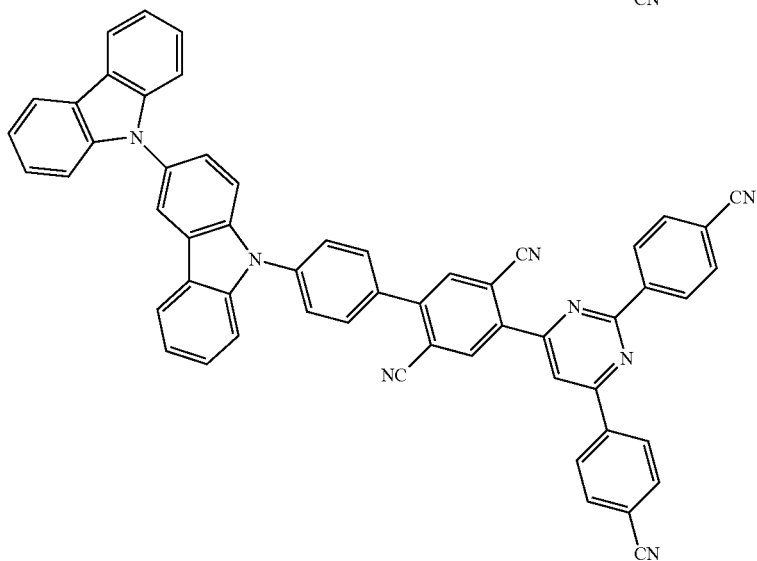

-continued
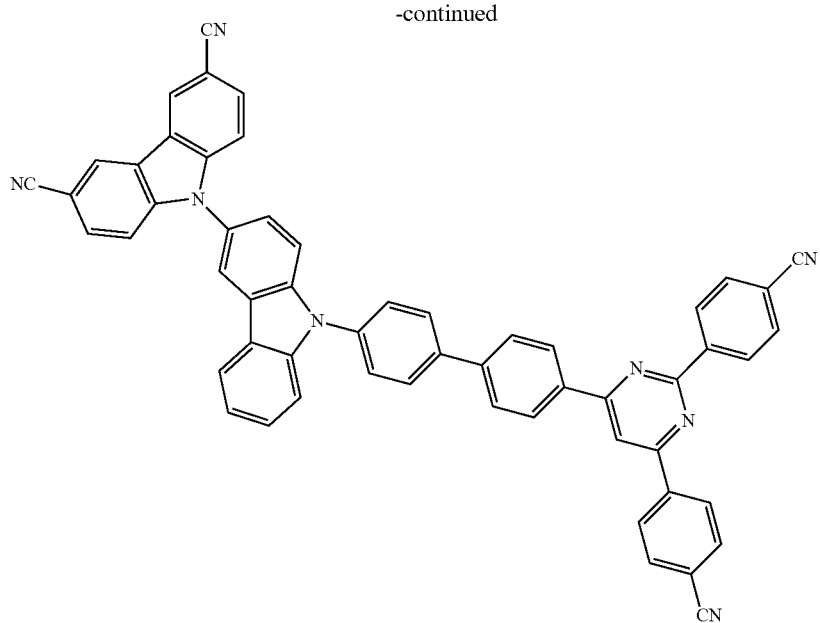
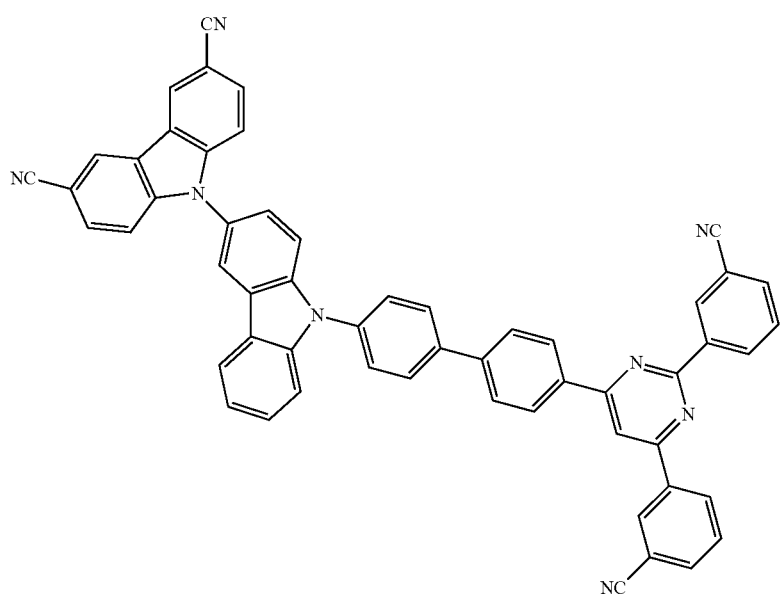
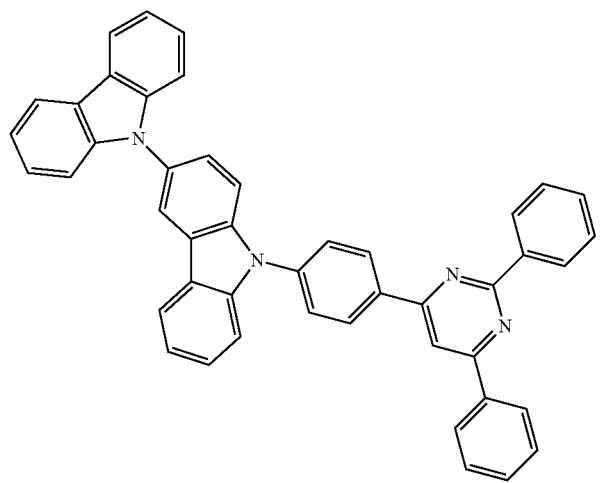

731
732
-continued
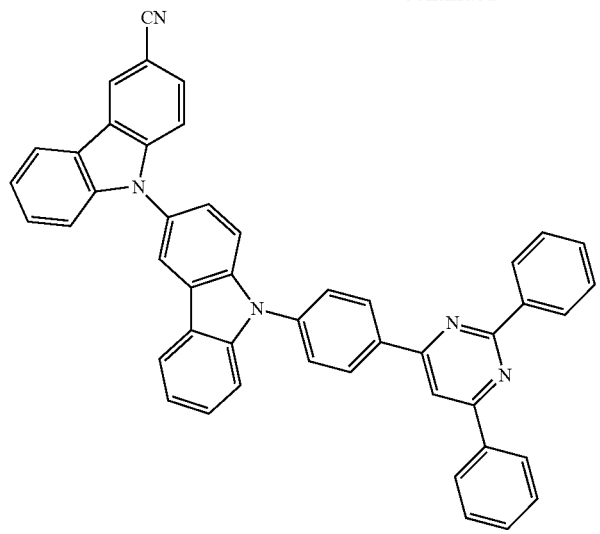
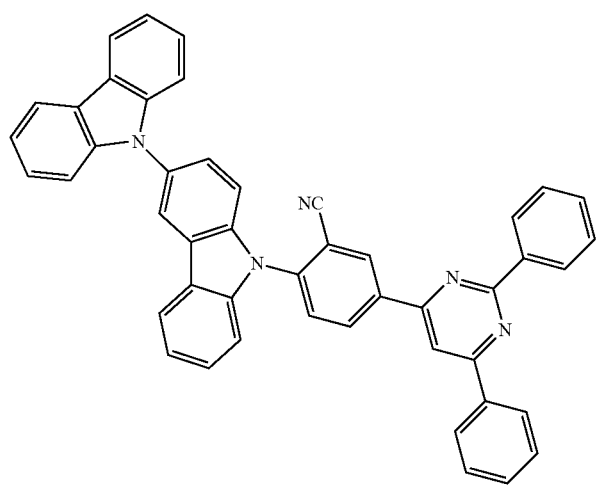
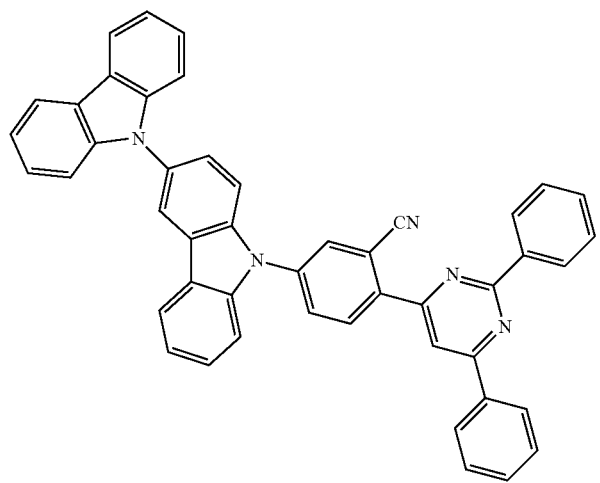

-continued
733
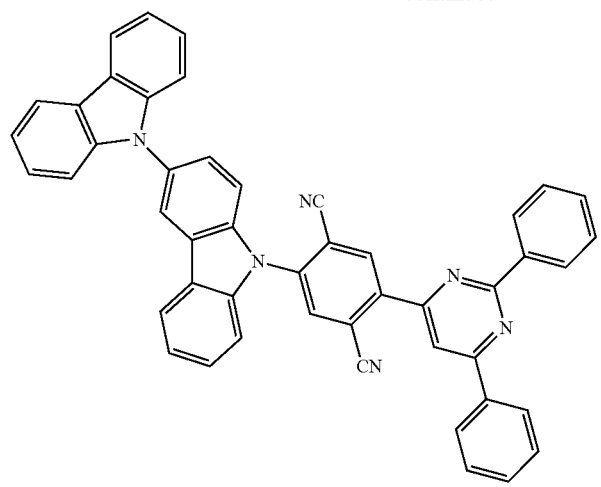
734
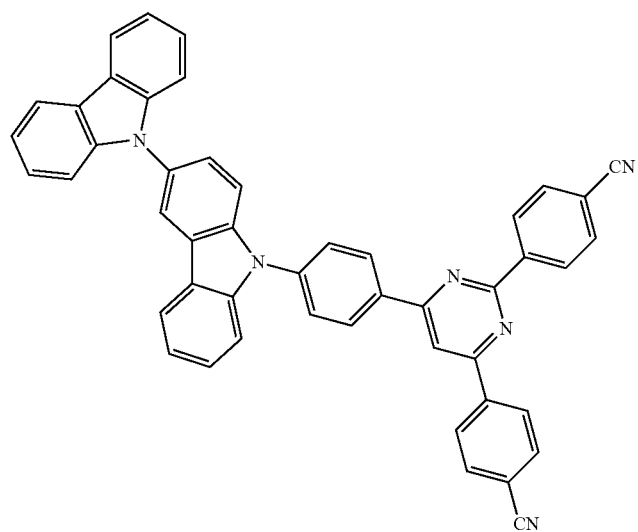
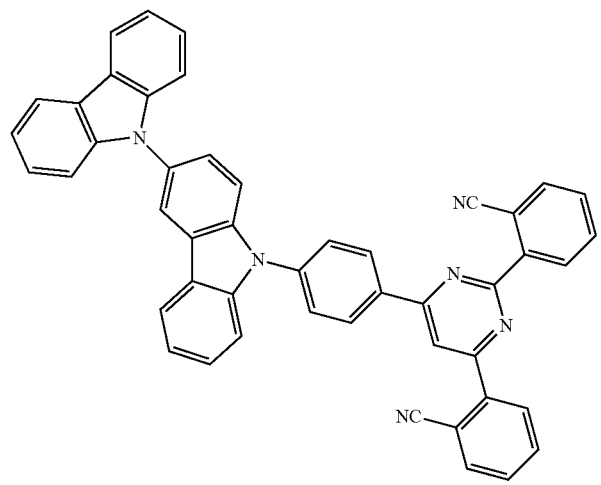

-continued
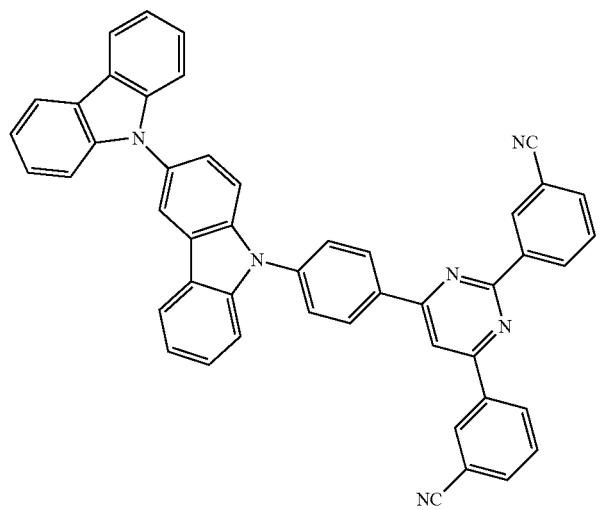
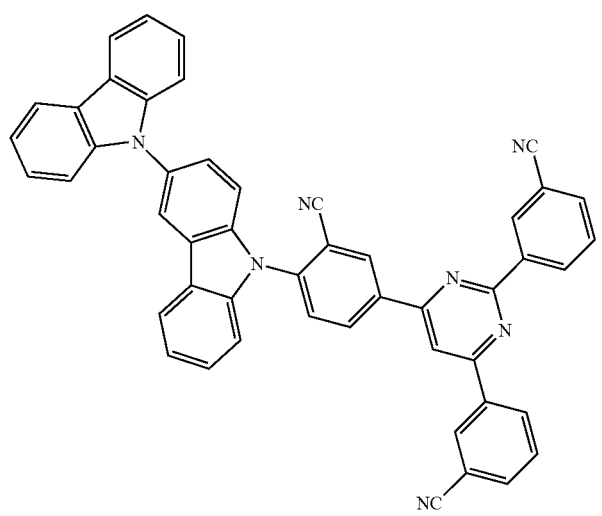
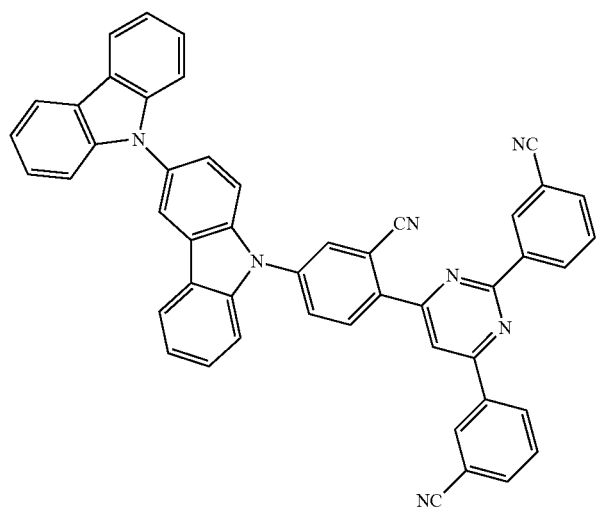

-continued
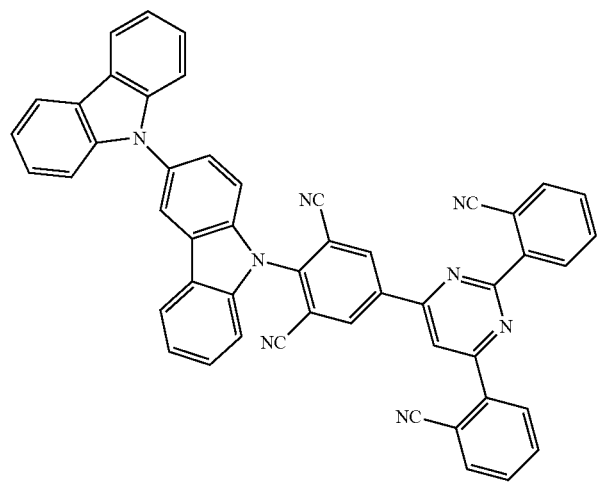
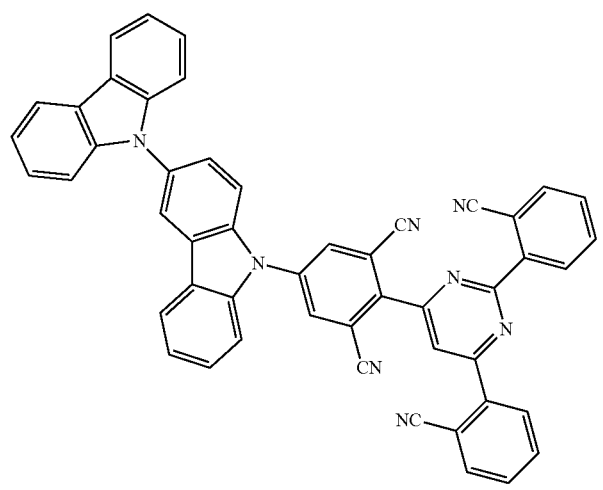
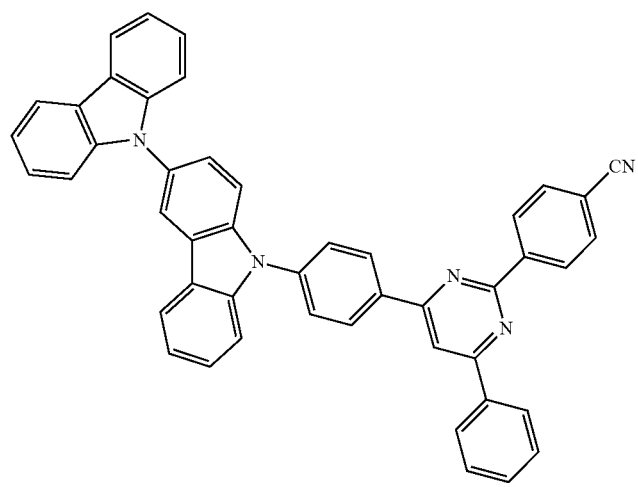

-continued
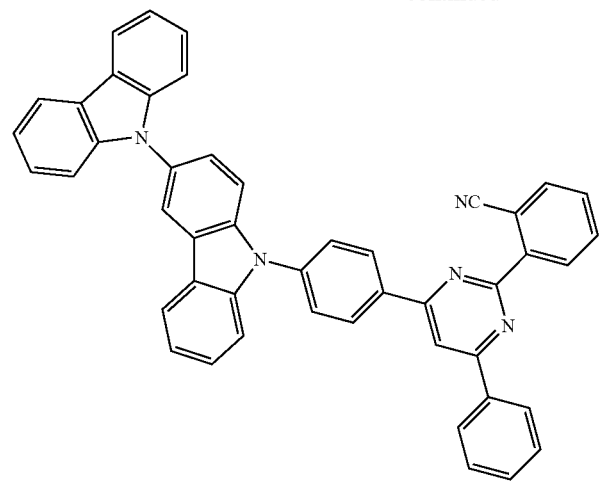
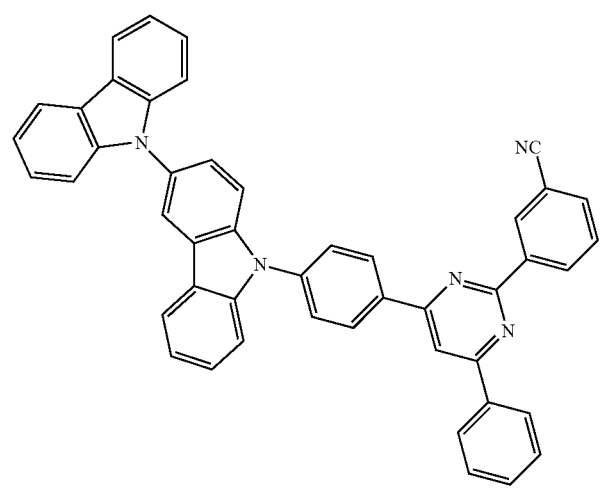
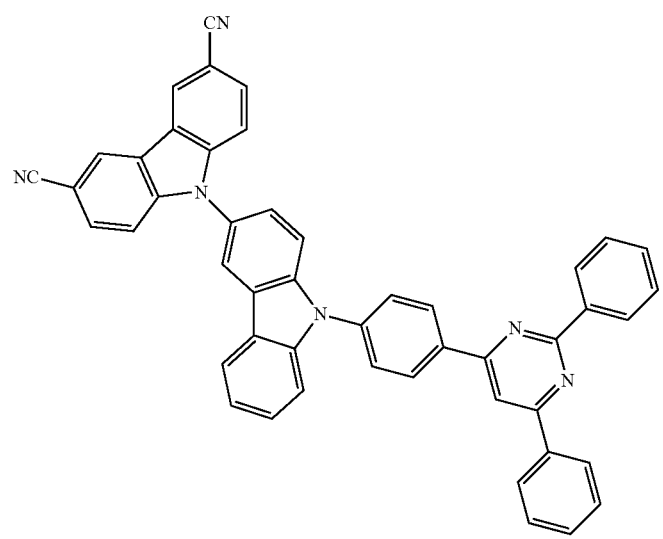

-continued
741
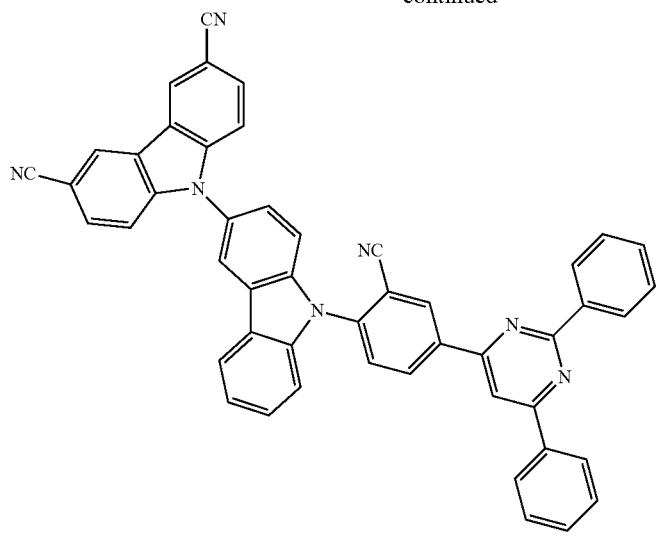
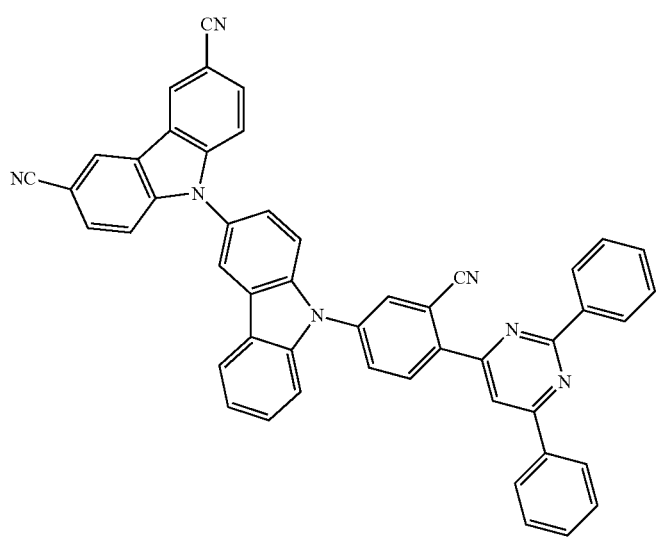
742
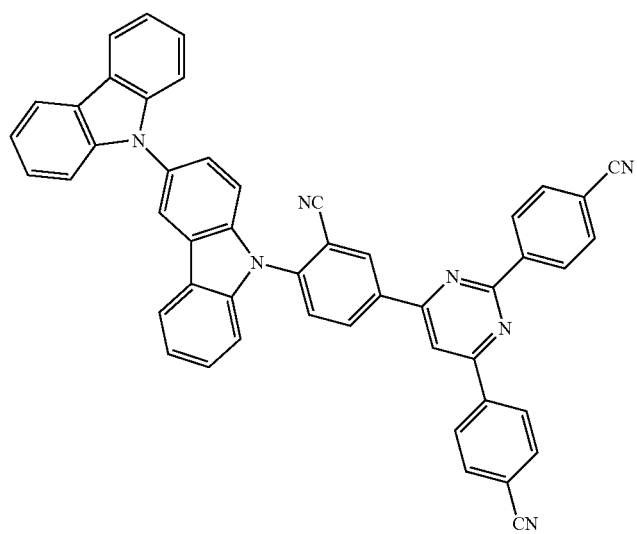

-continued
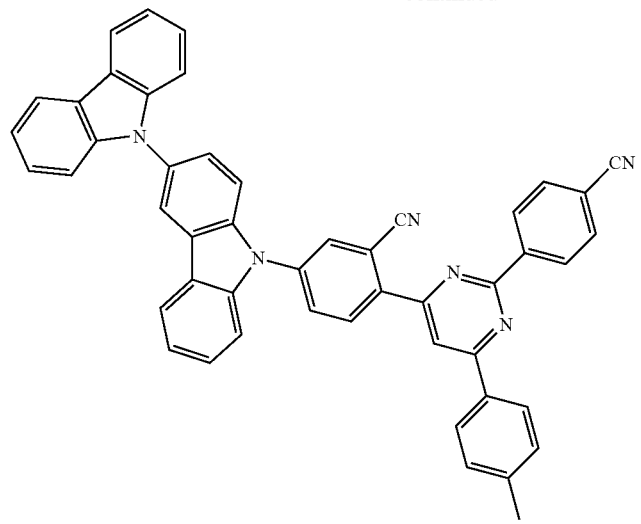
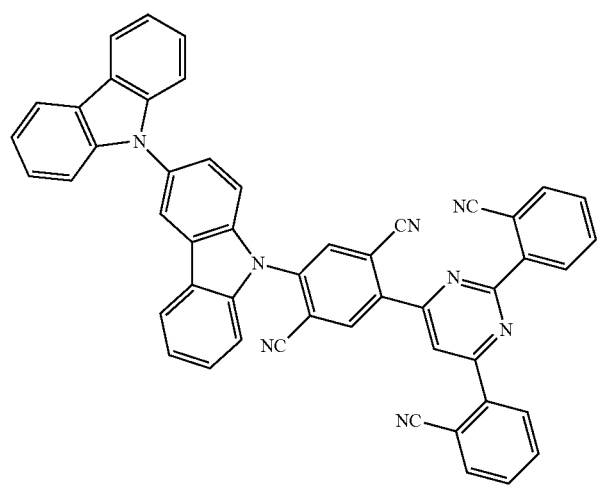
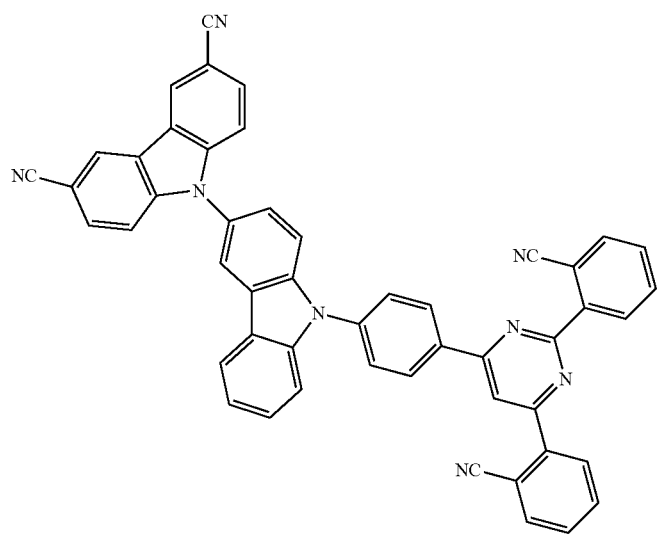

-continued
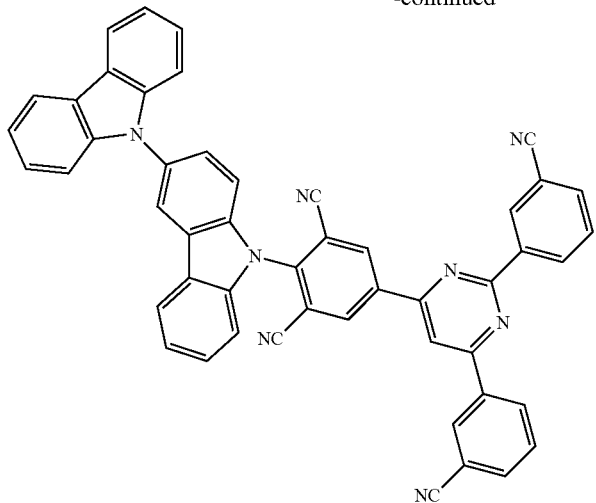
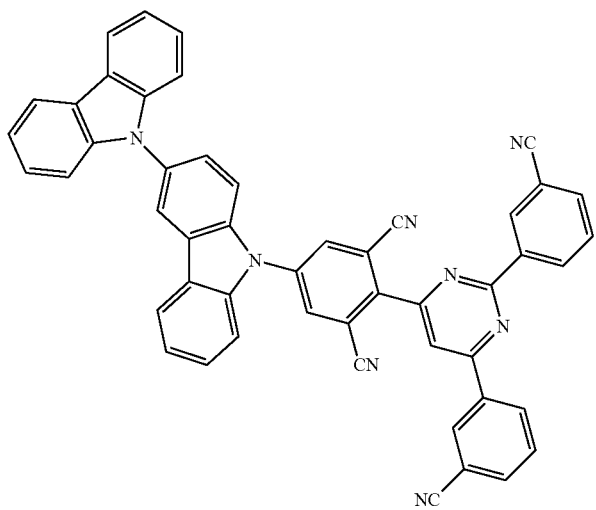 [SMILES: N#Cc1cccc(-c2cc(-c3c(C#N)cc(-n4c5ccccc5c5cc(-n6c7ccccc7c7ccccc76)ccc54)cc3C#N)nc(-c3cccc(C#N)c3)n2)c1]
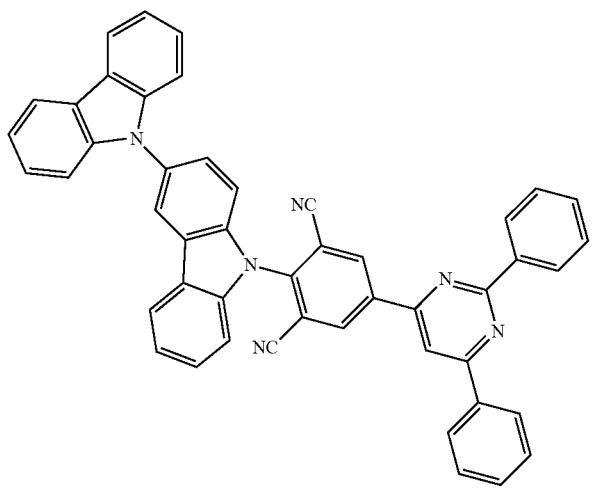

-continued
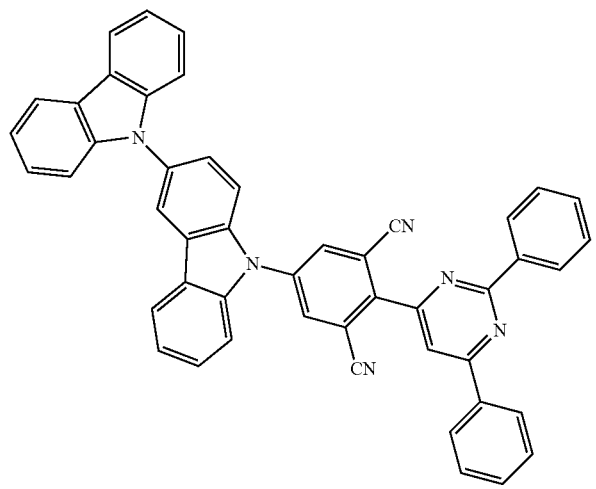
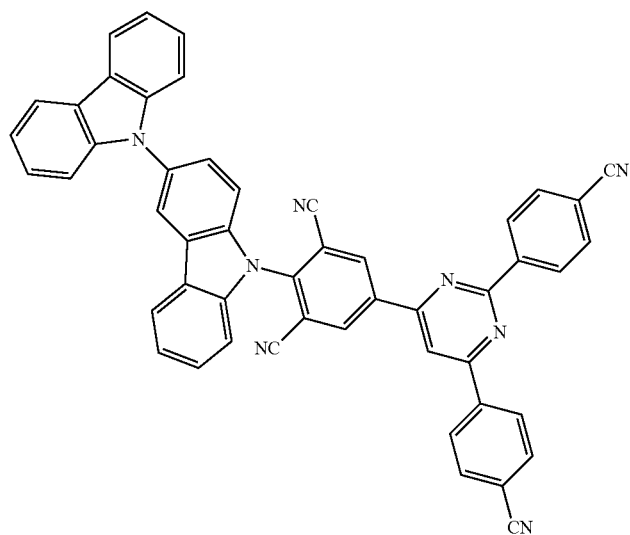
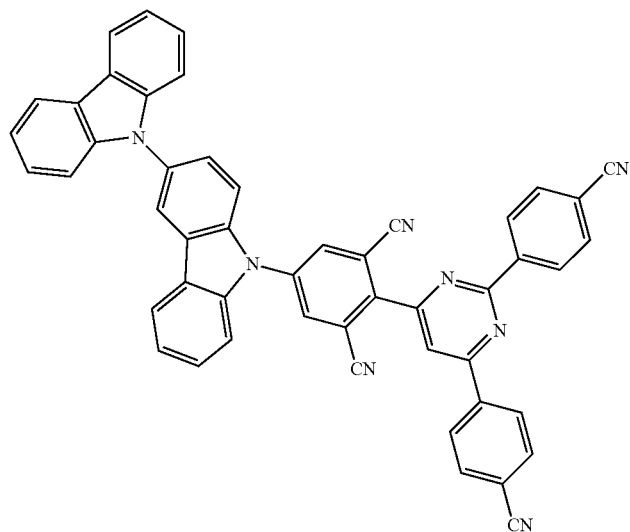

-continued
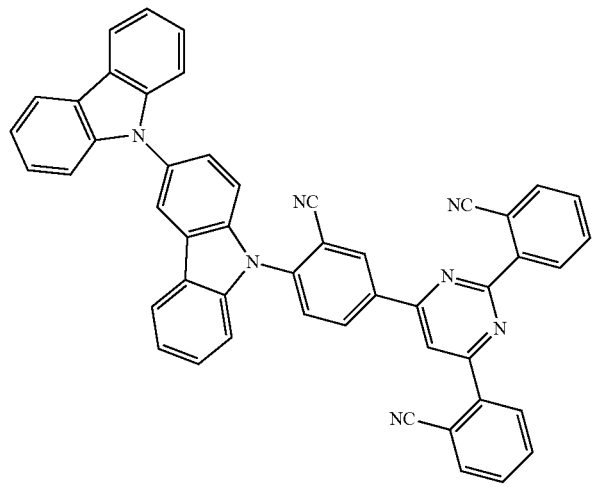
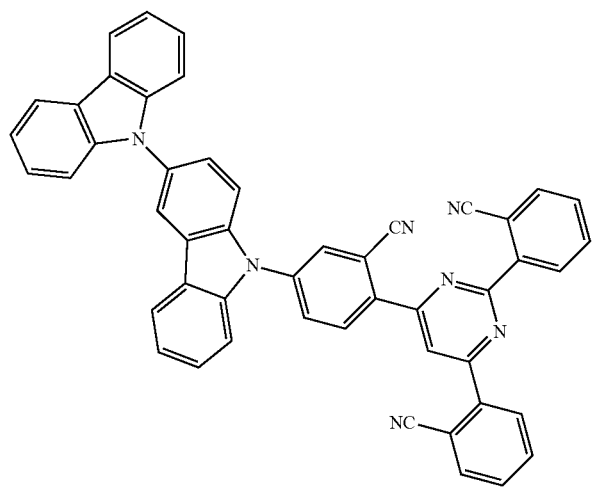
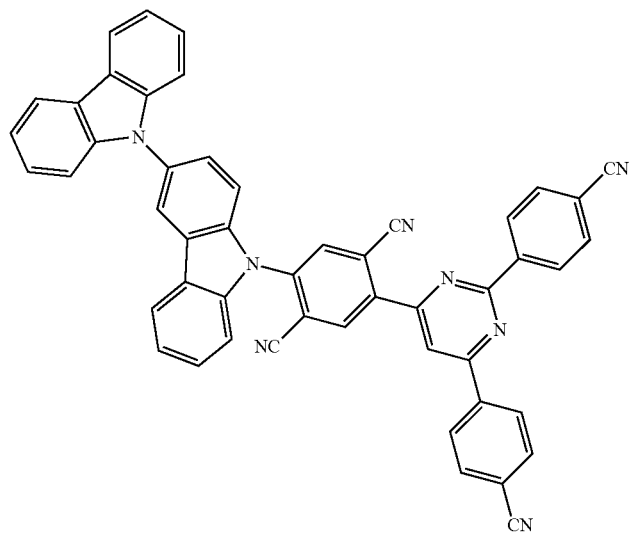

-continued
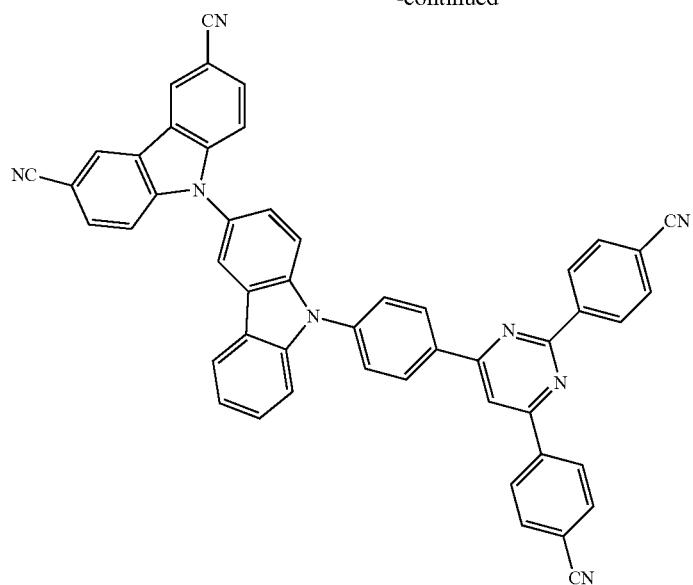
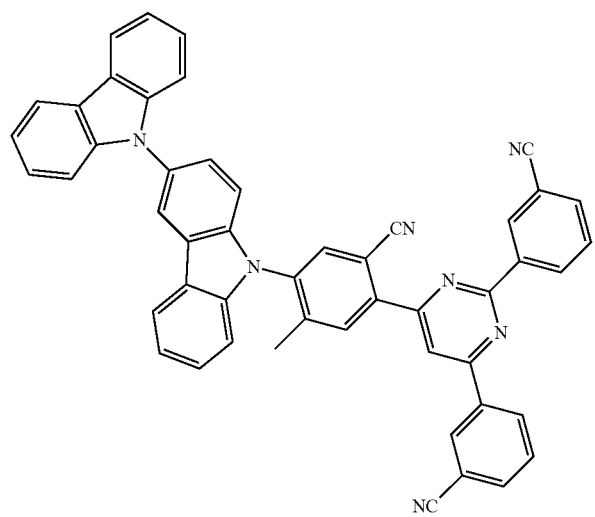
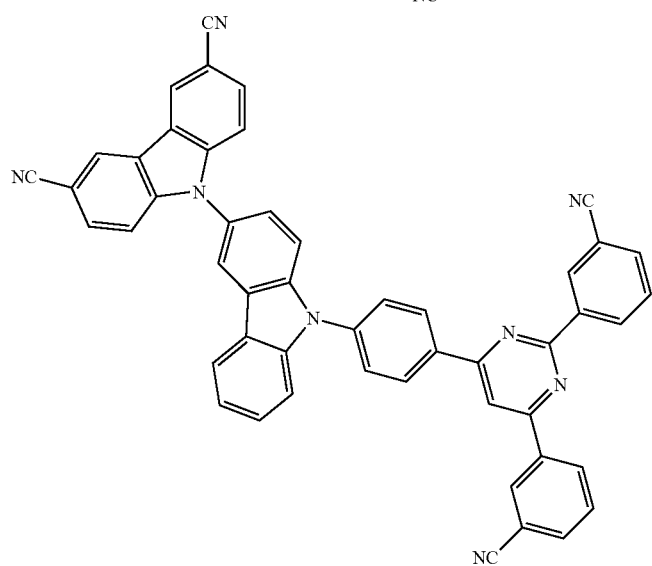

-continued
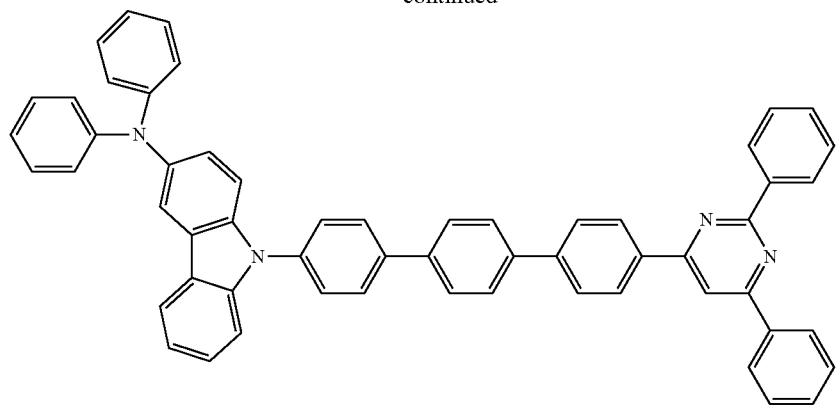
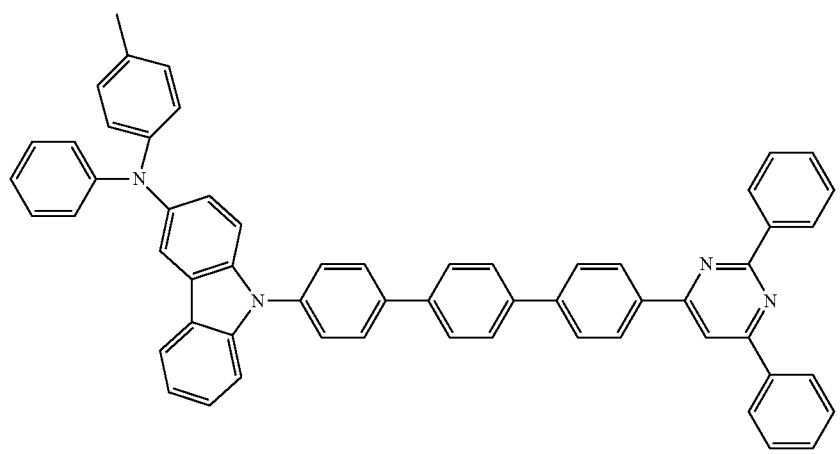
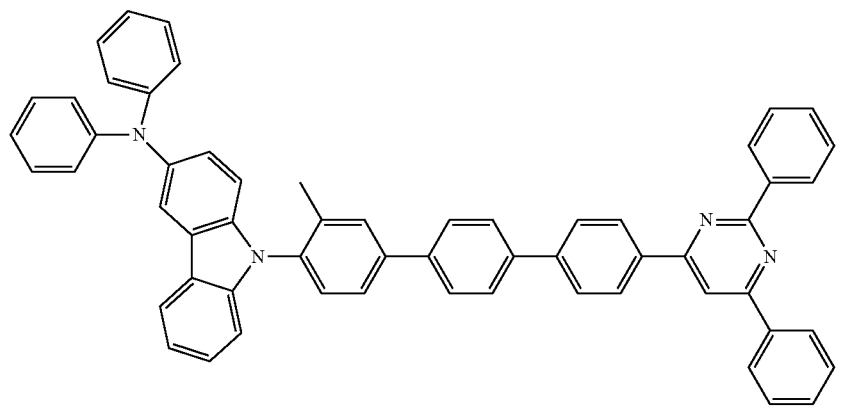
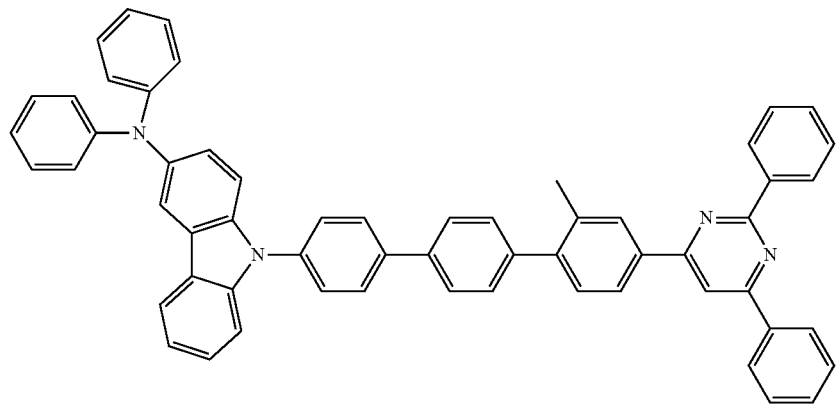

-continued
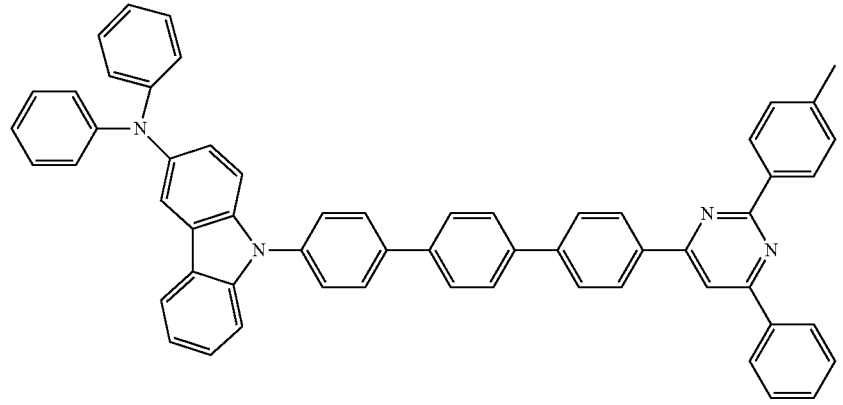
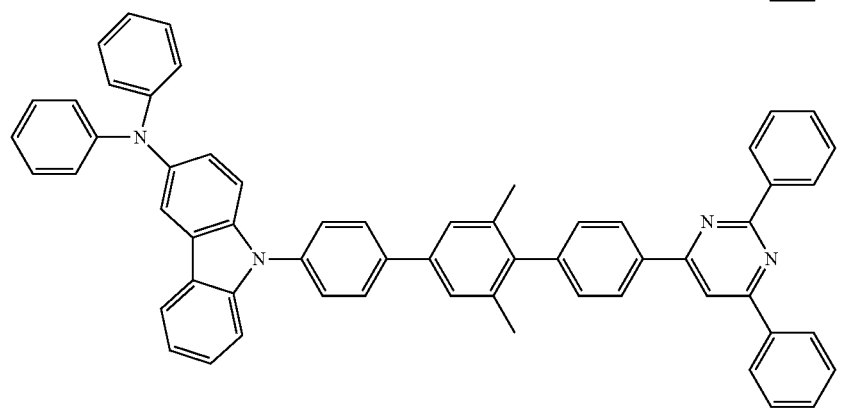
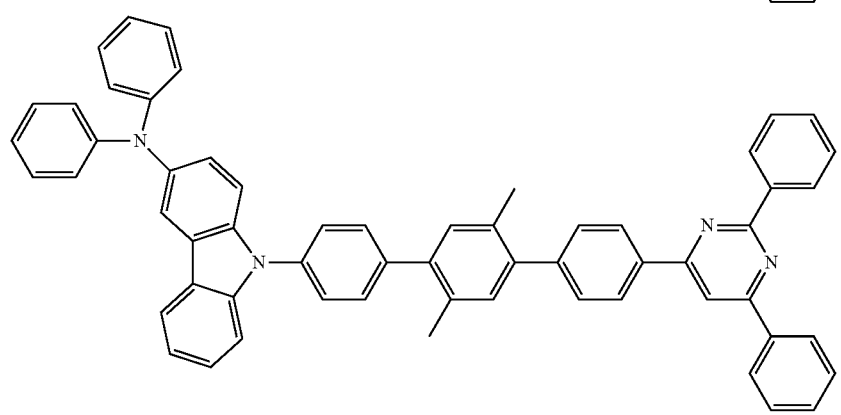

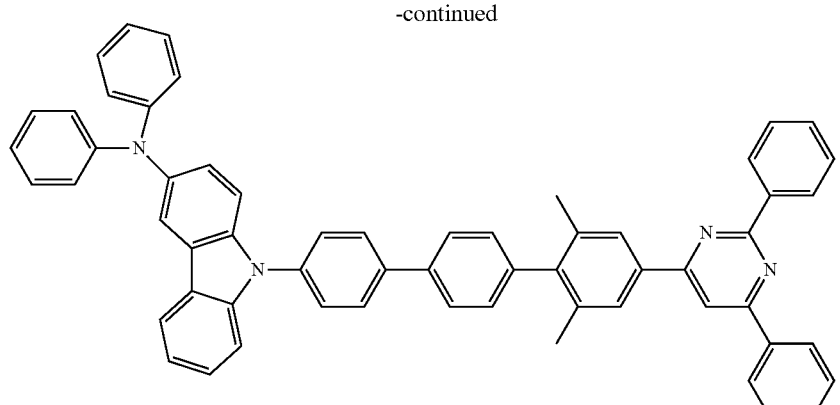
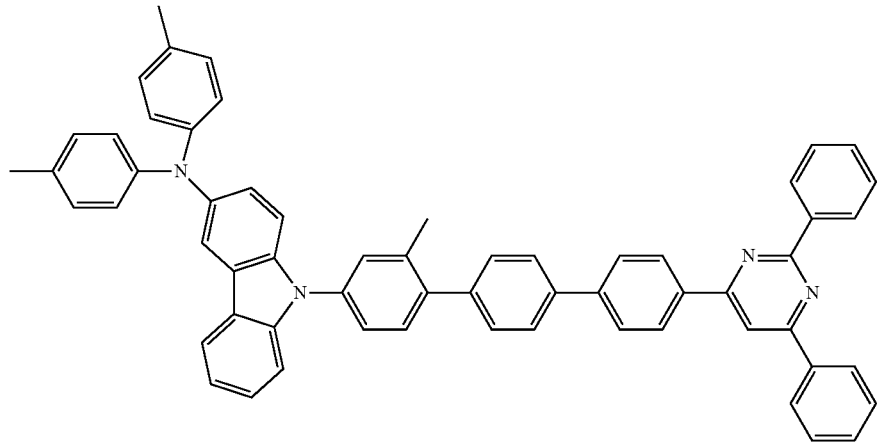
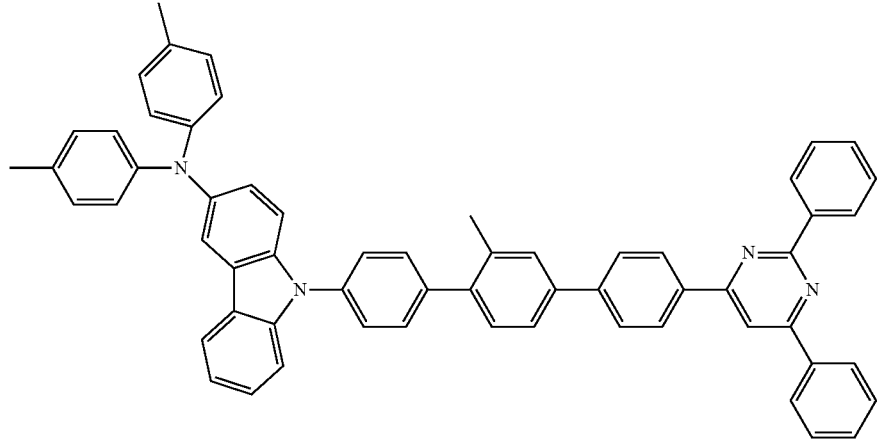
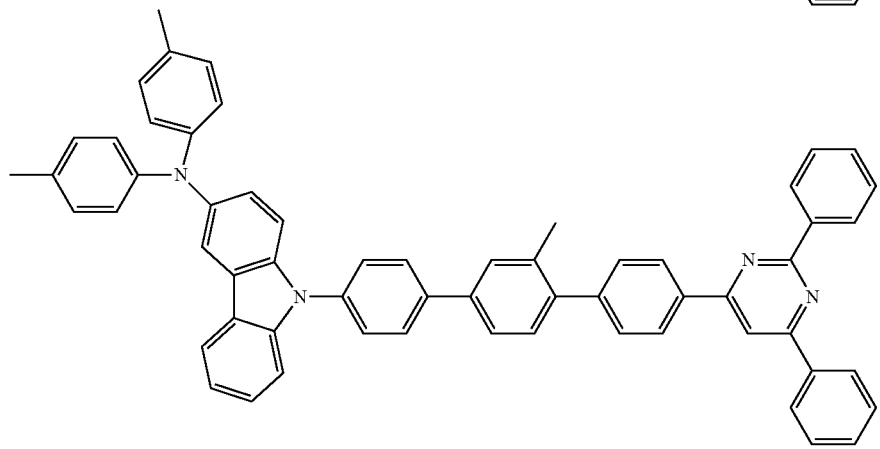

-continued
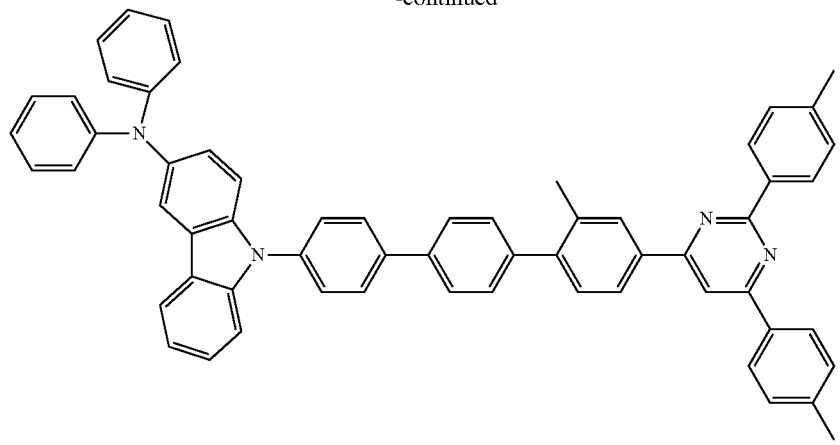
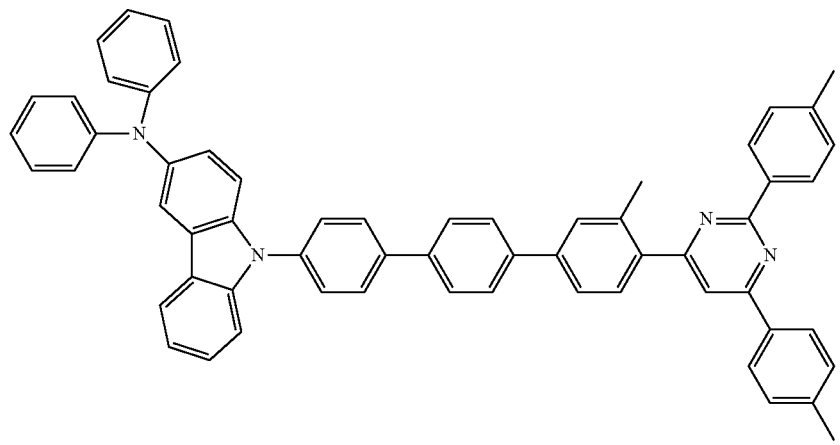
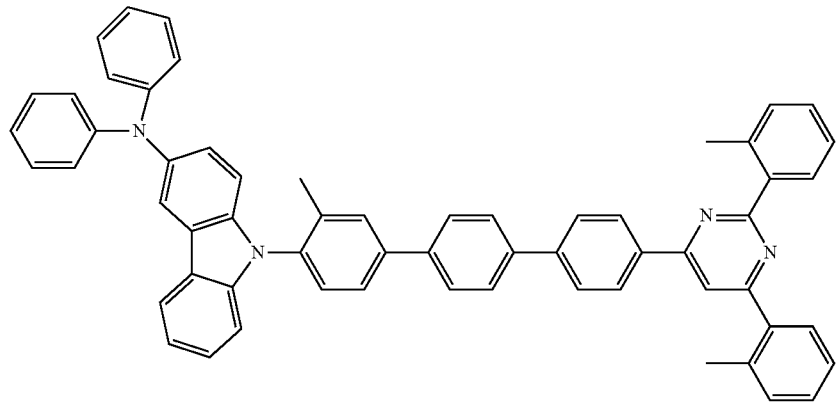
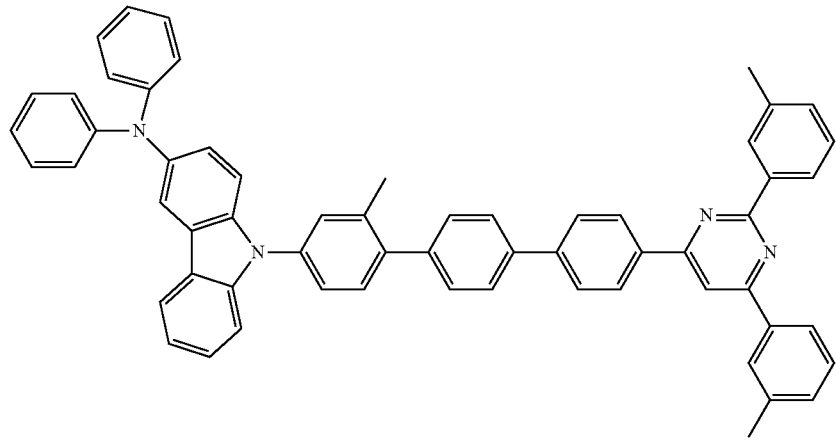

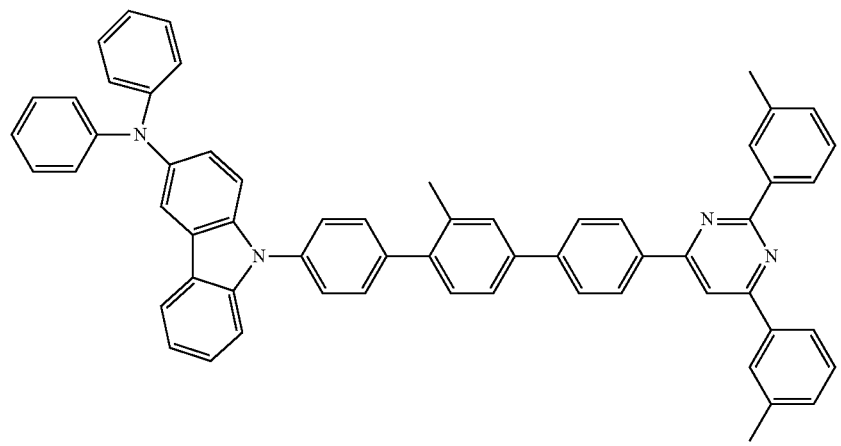
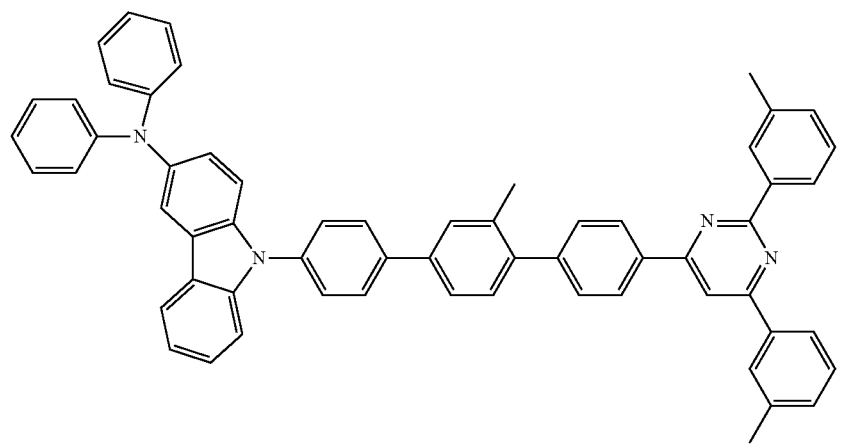
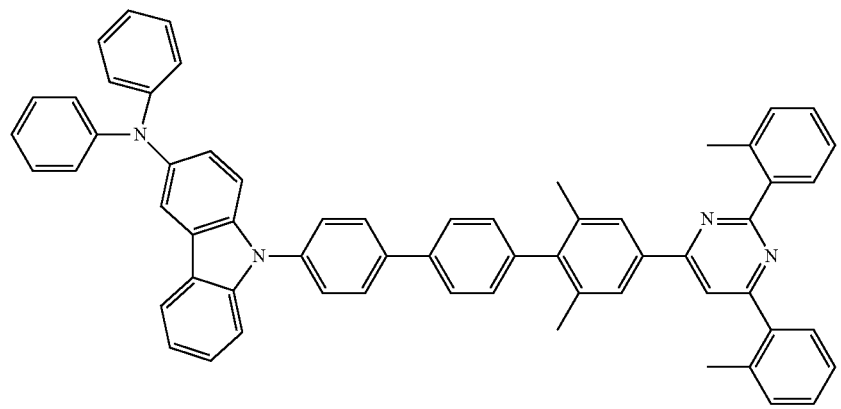
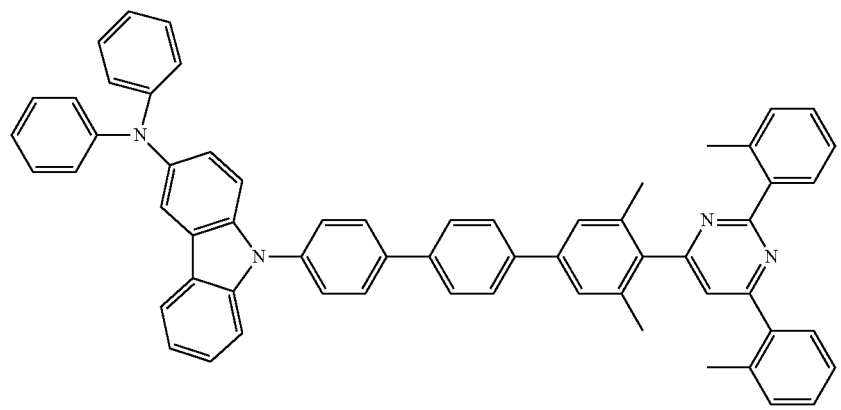

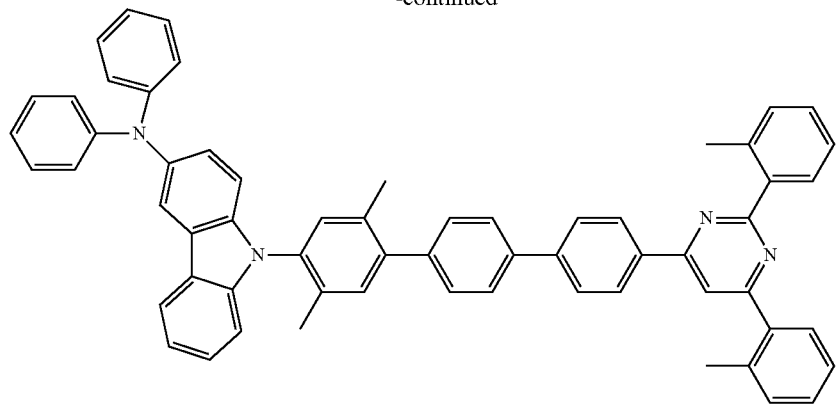
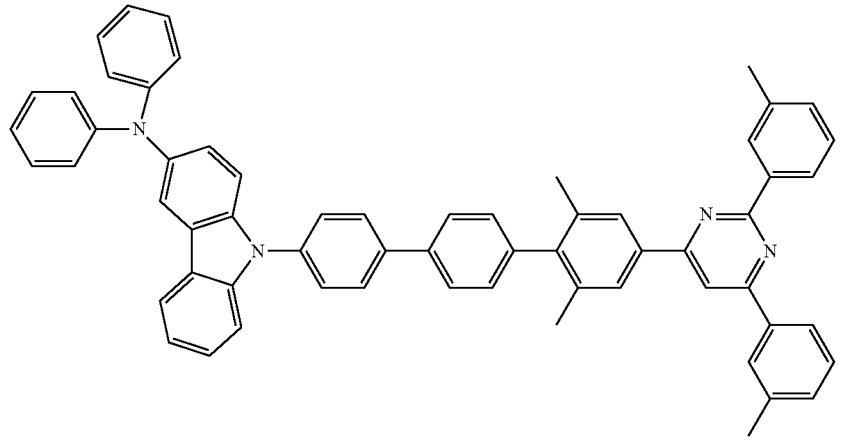
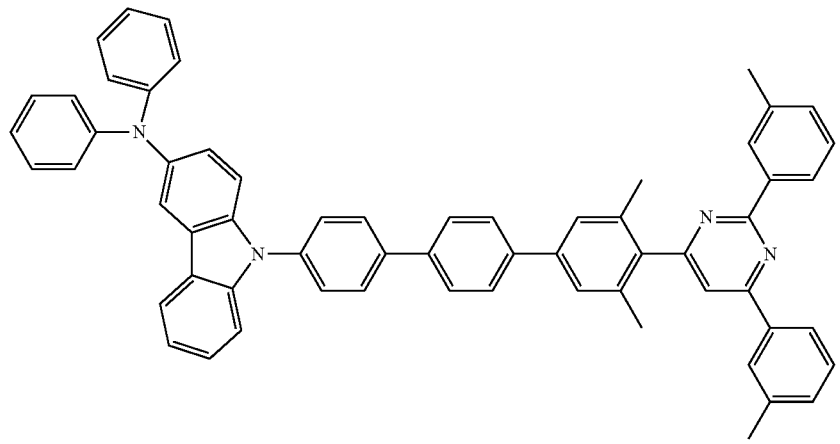

-continued
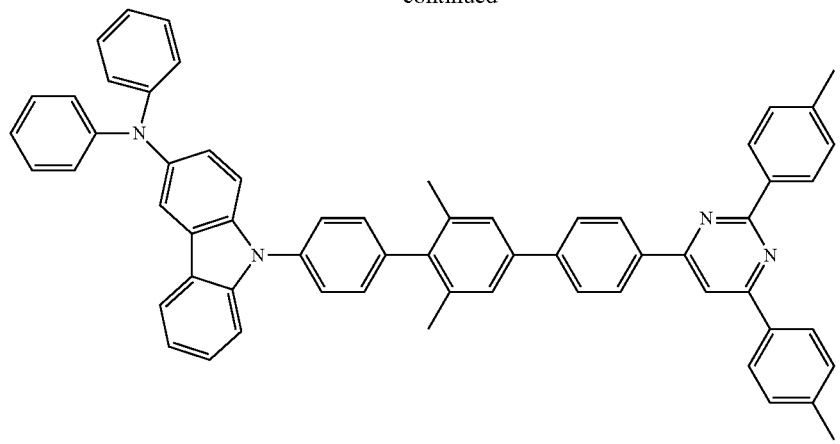
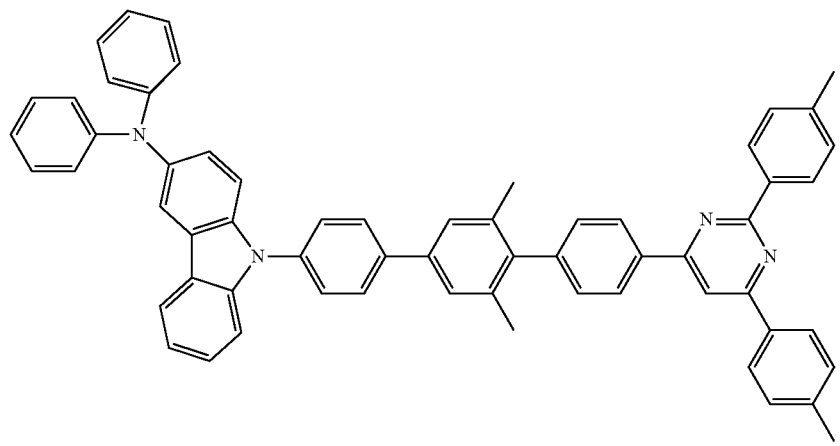
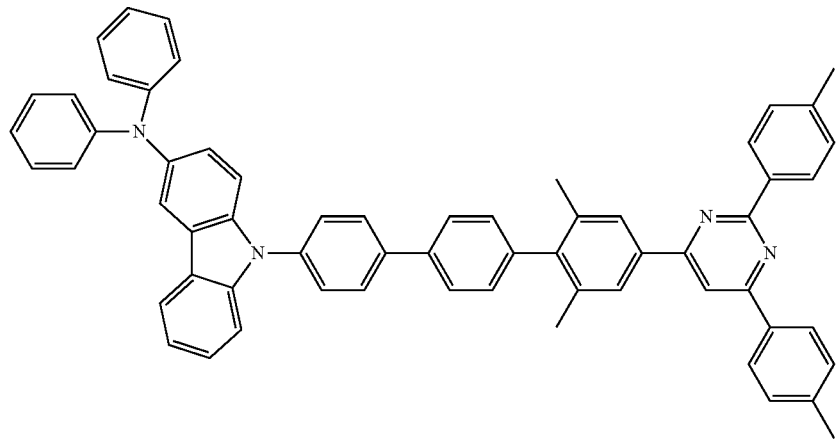
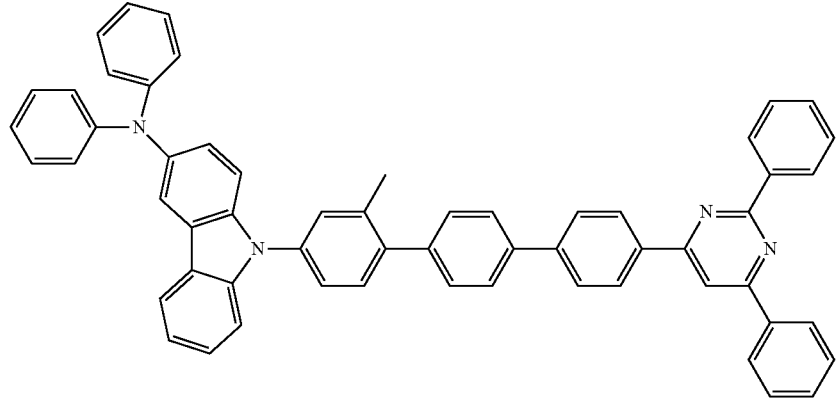

-continued
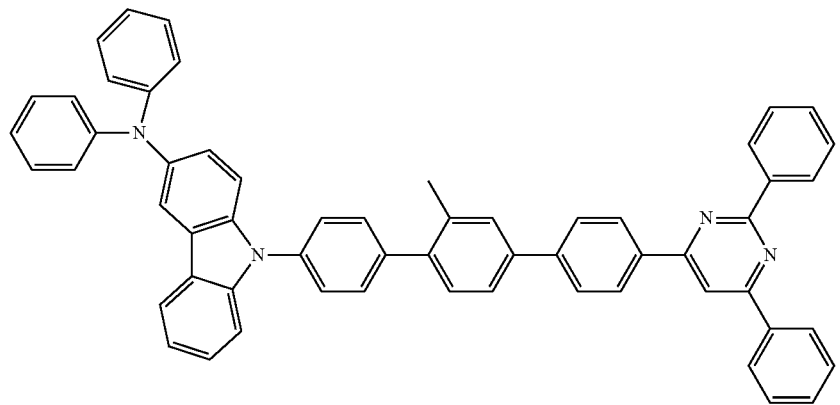
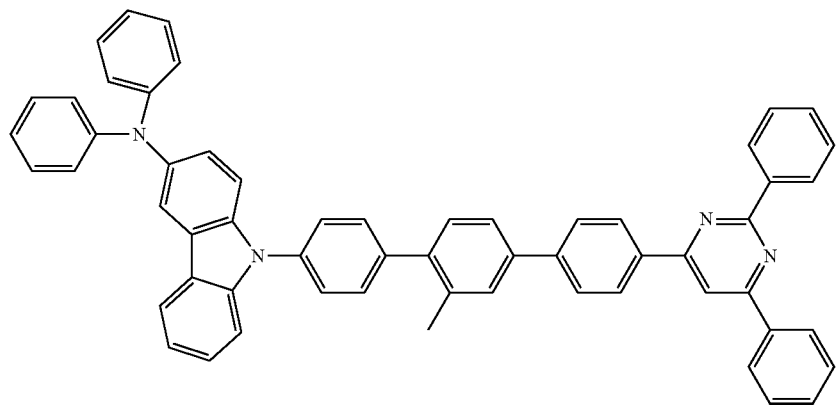
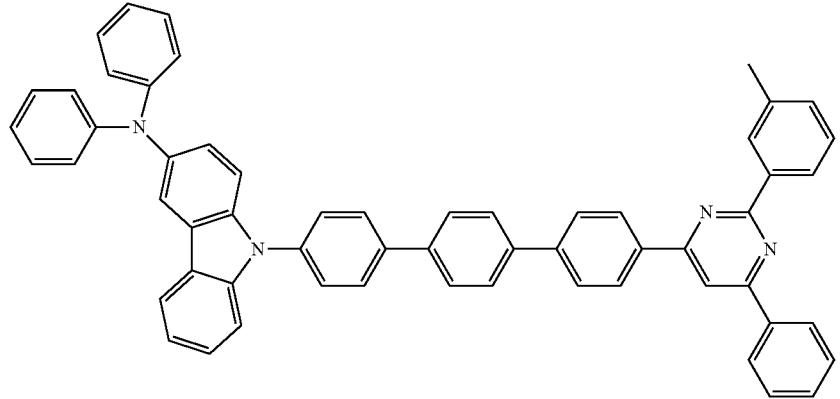
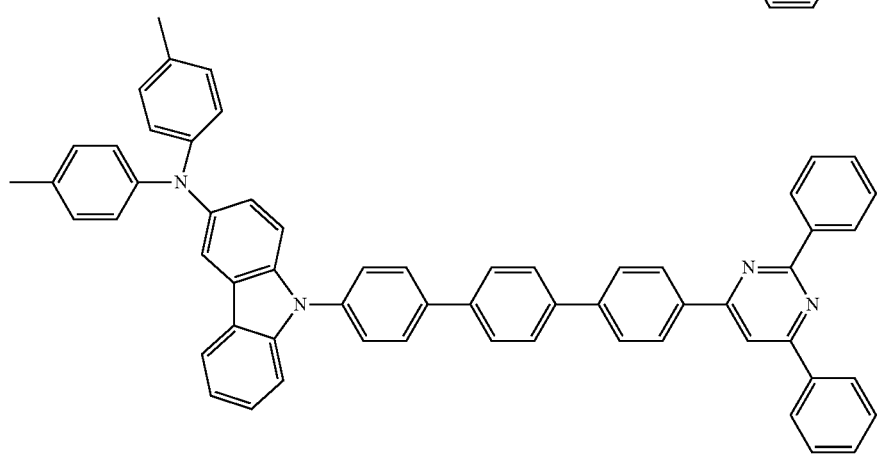

-continued
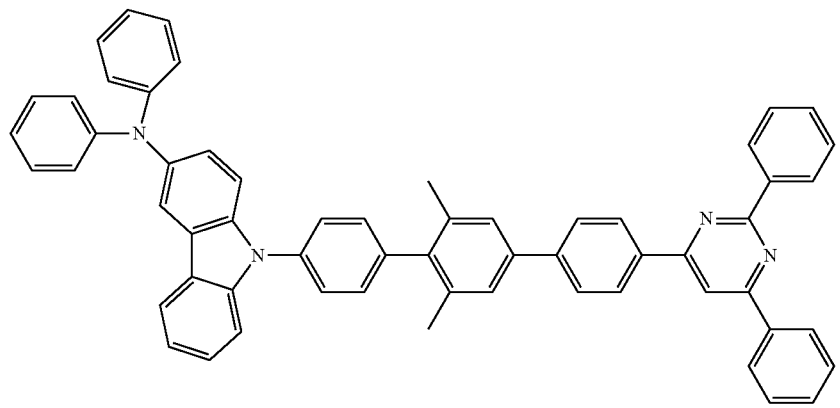
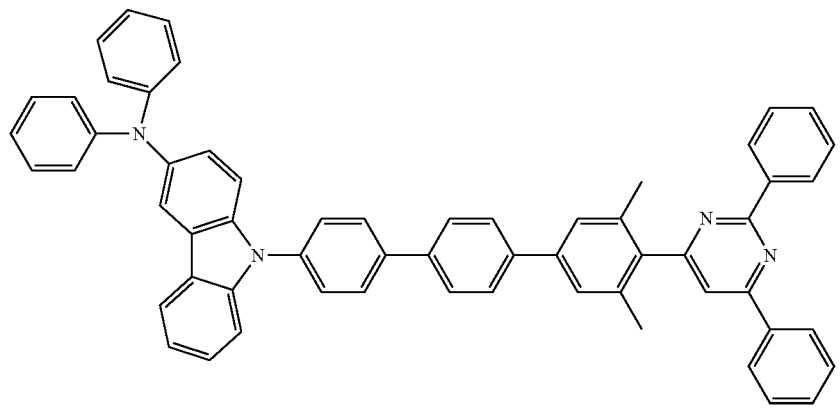
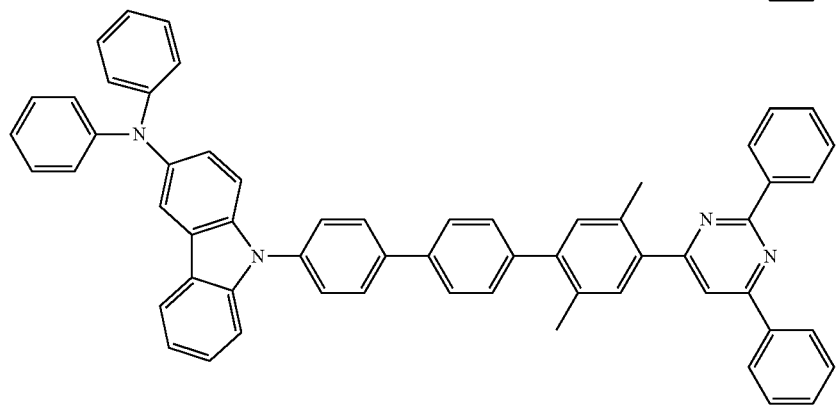
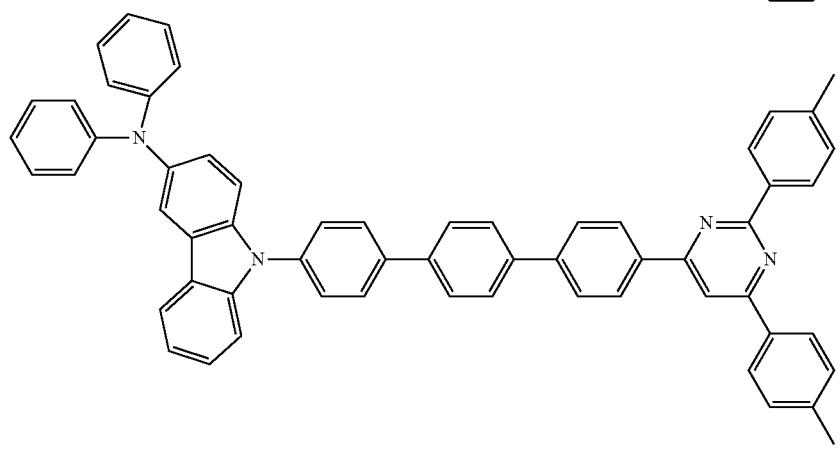

-continued
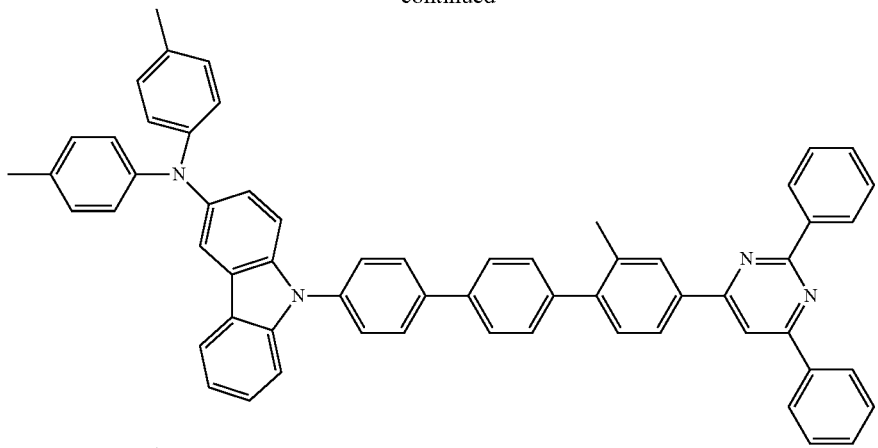
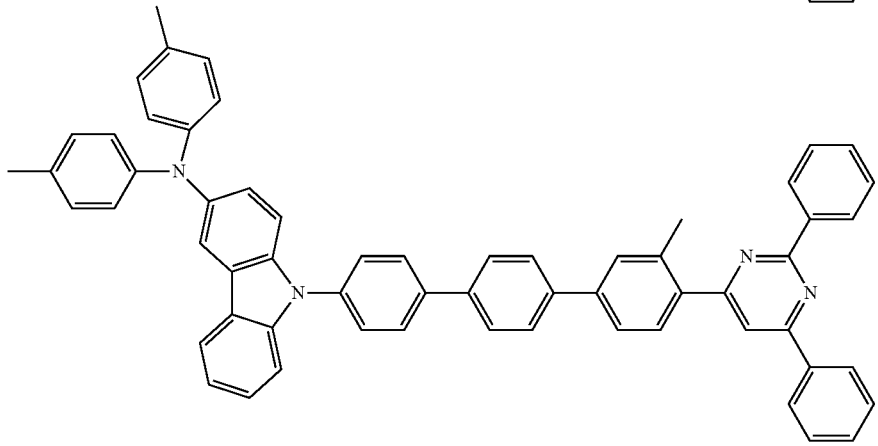
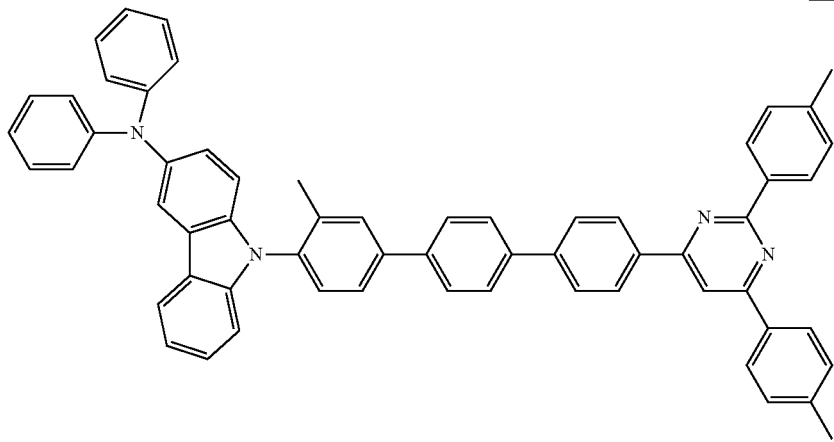
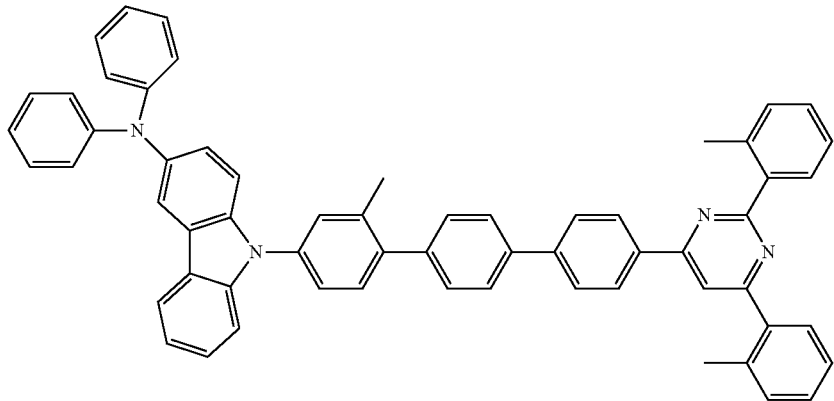

-continued
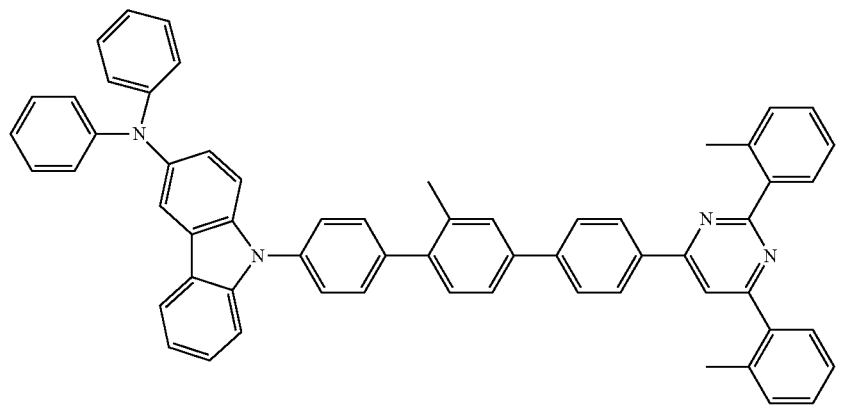
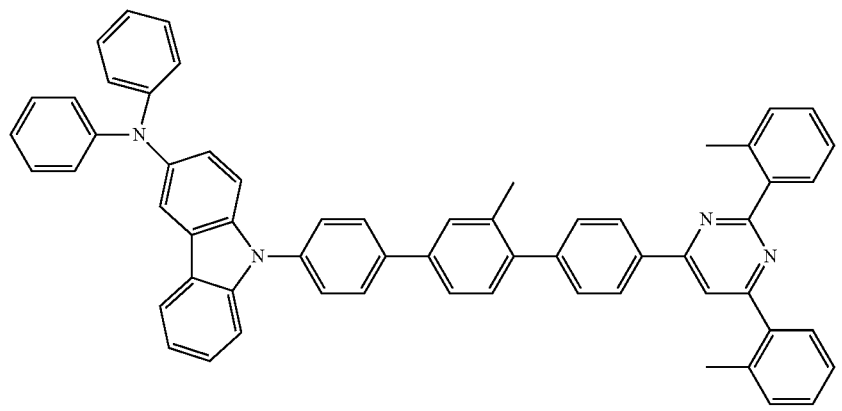
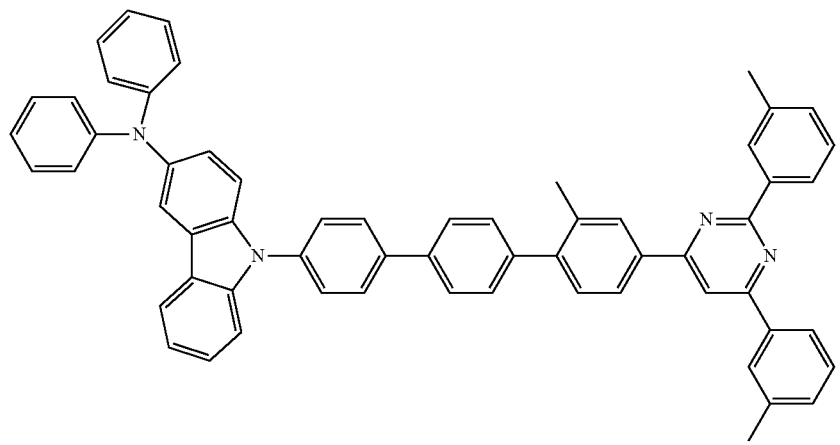
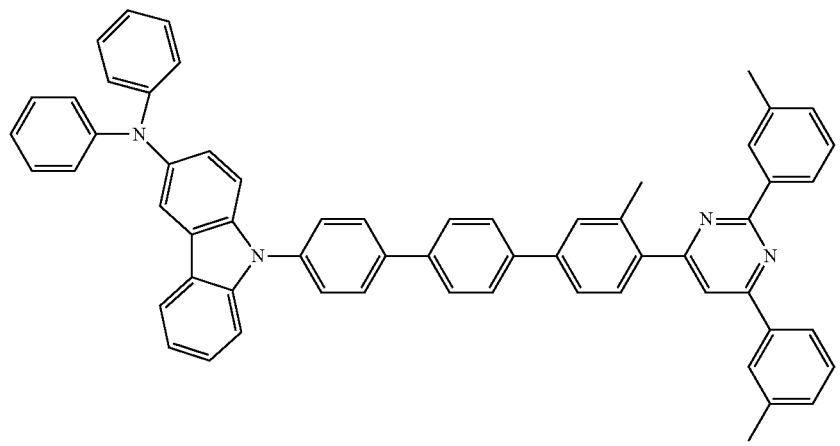

-continued
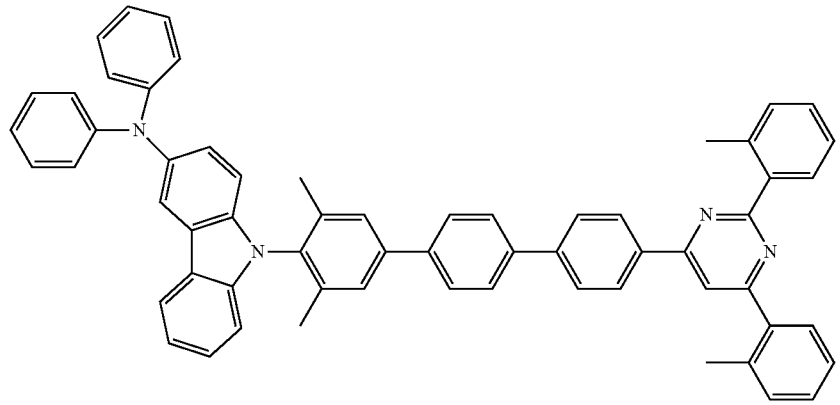
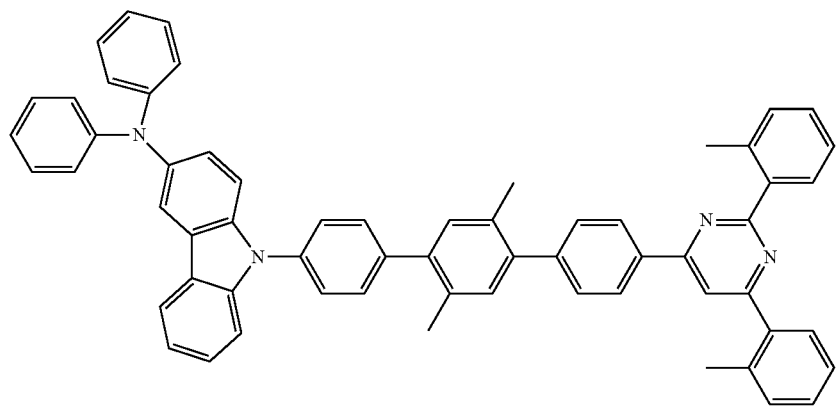
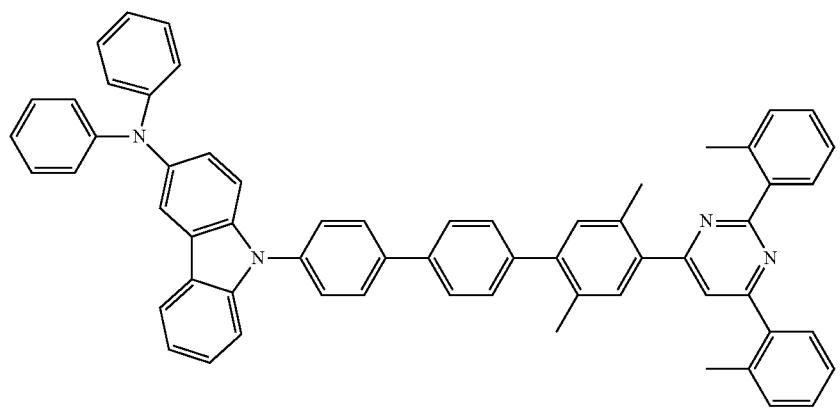
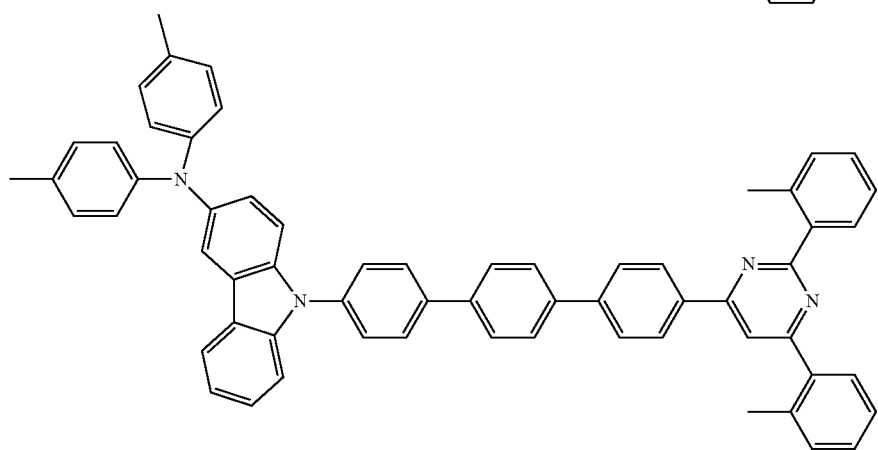

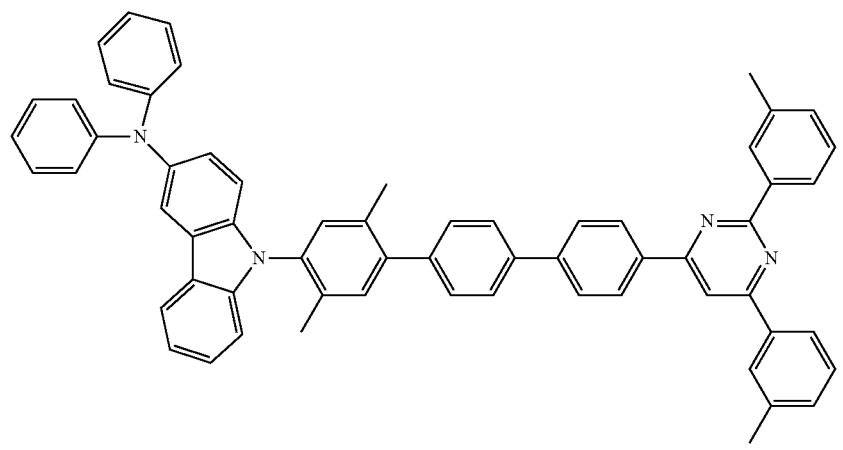
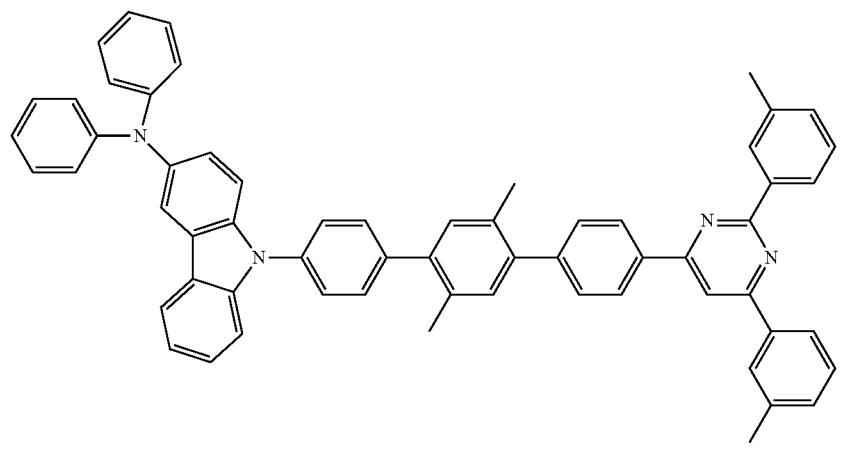
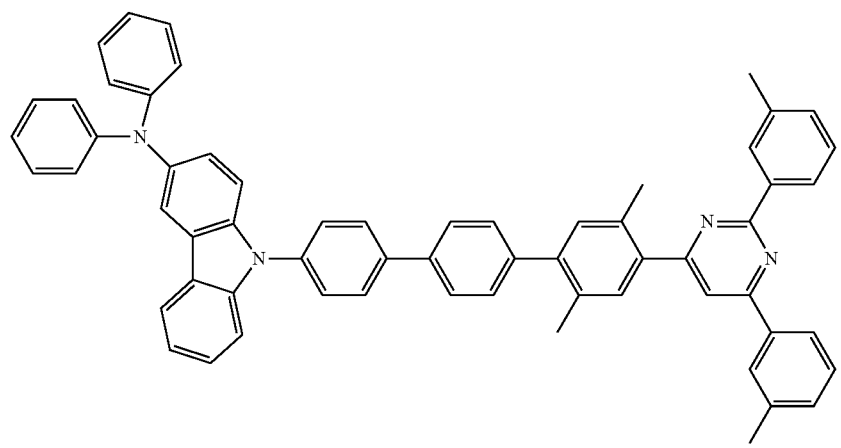

-continued
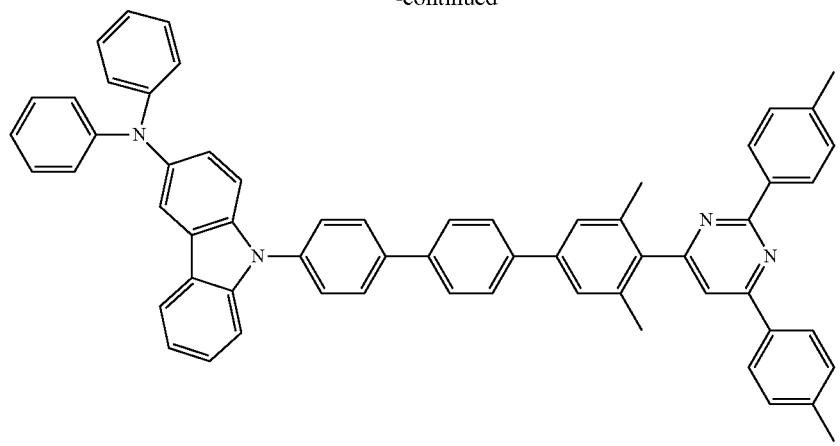
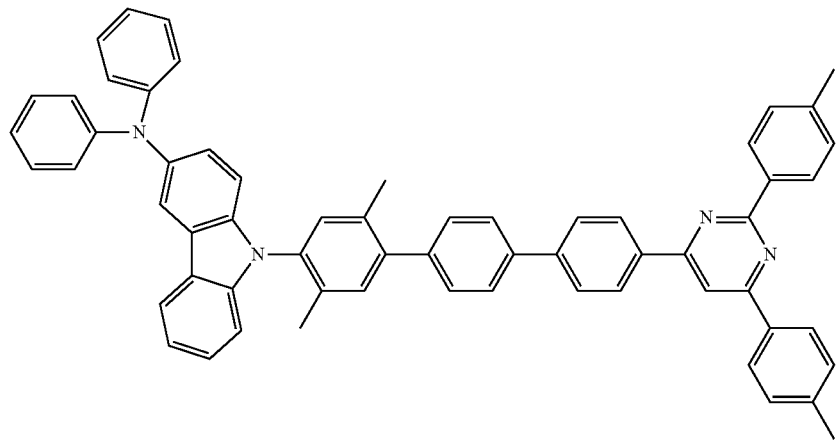
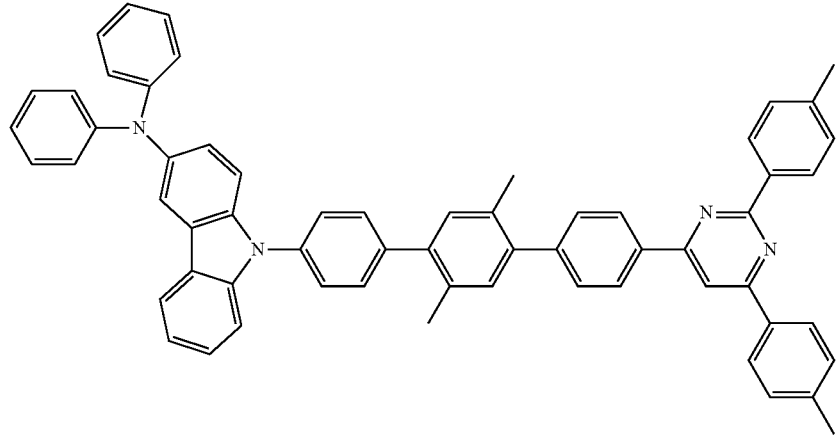
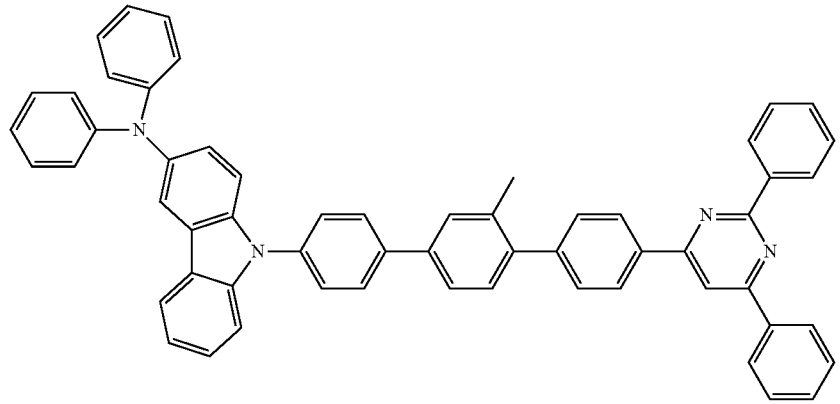

-continued
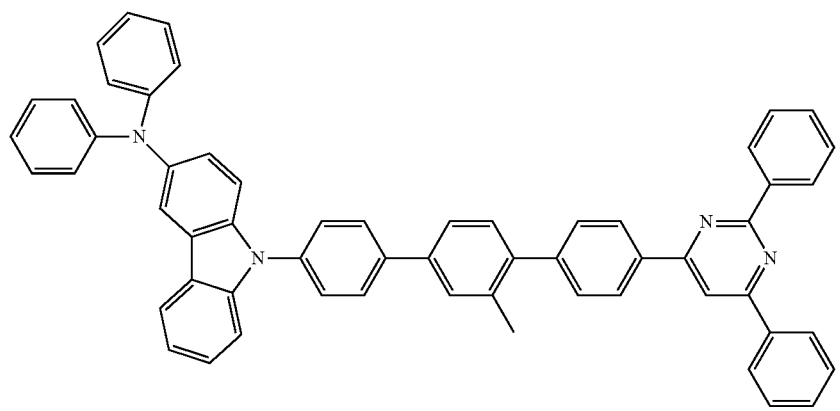
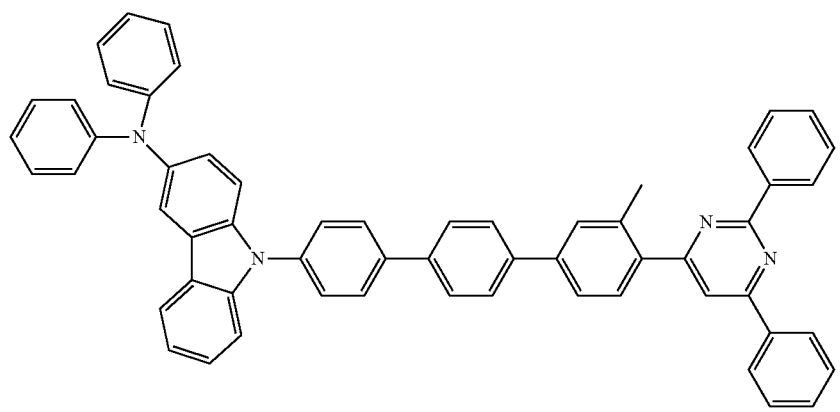
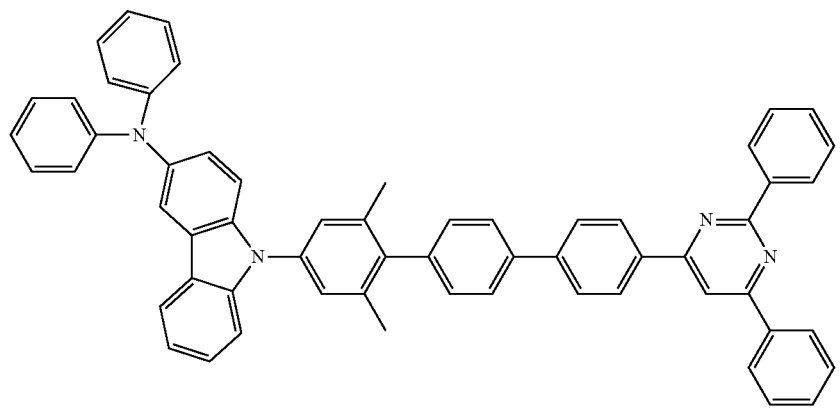
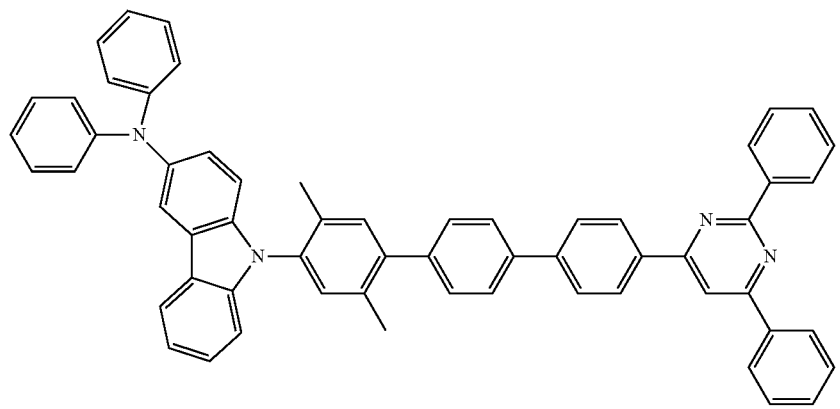

-continued
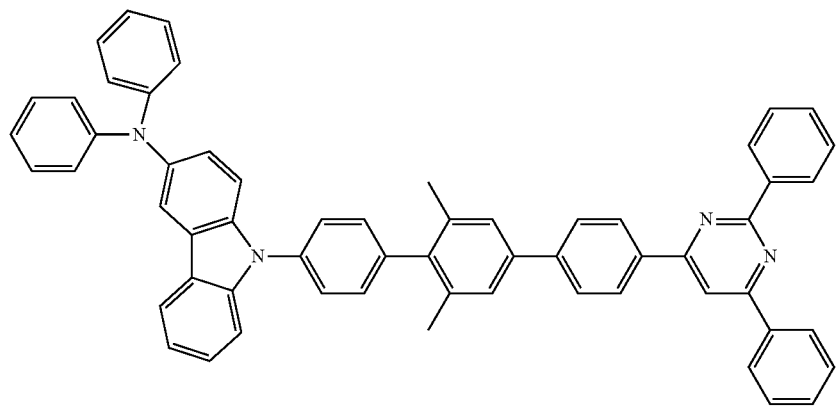
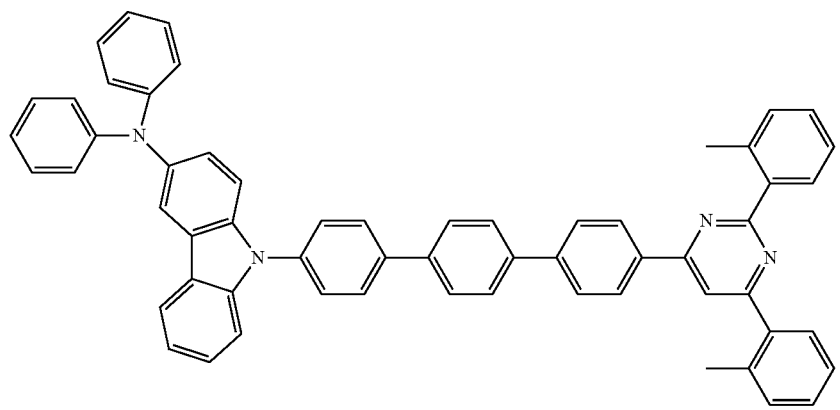
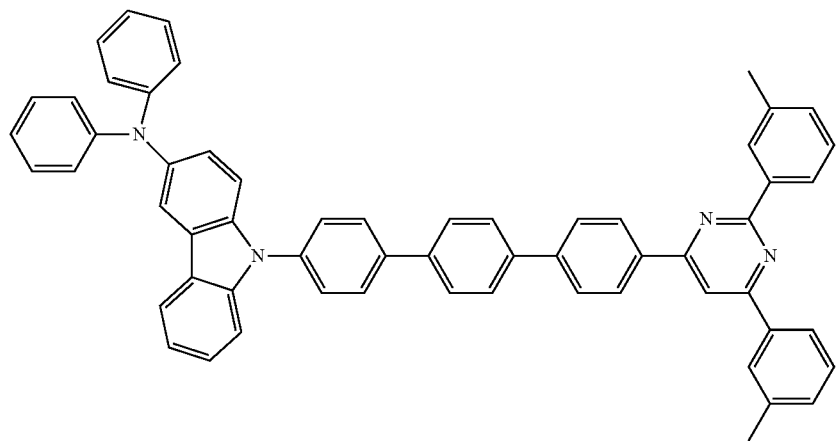
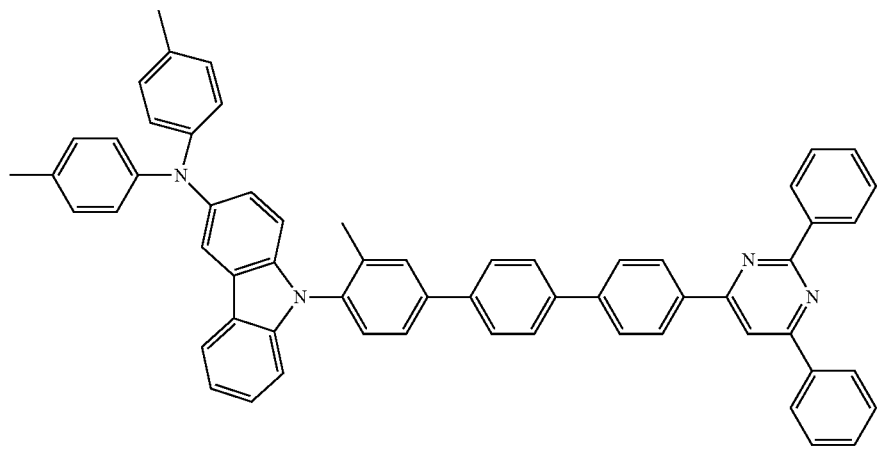

-continued
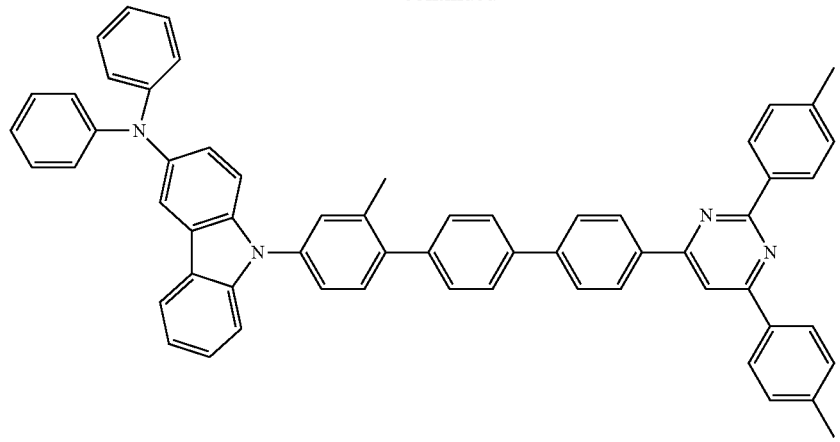
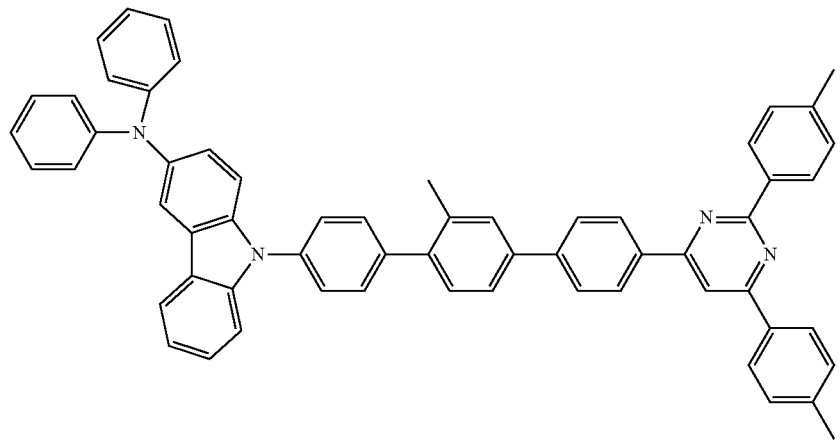
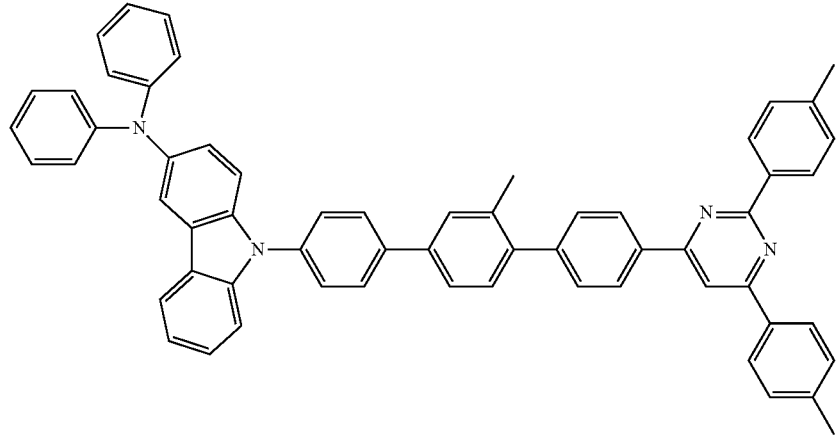
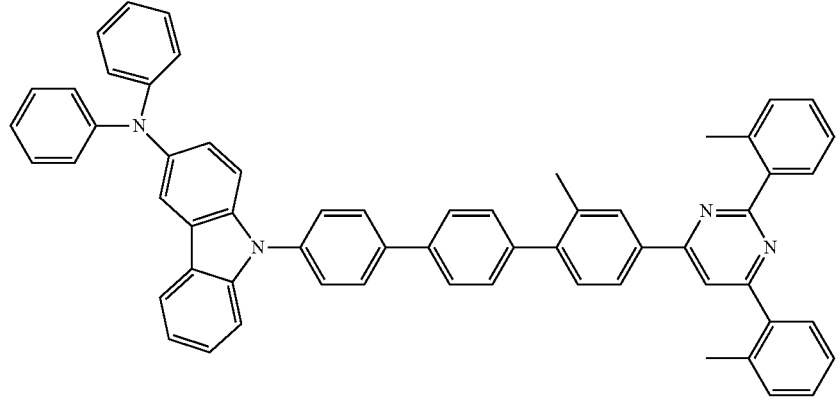

-continued
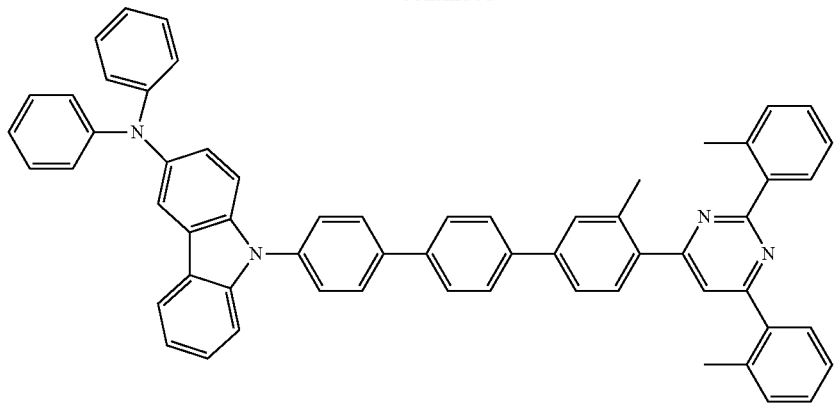
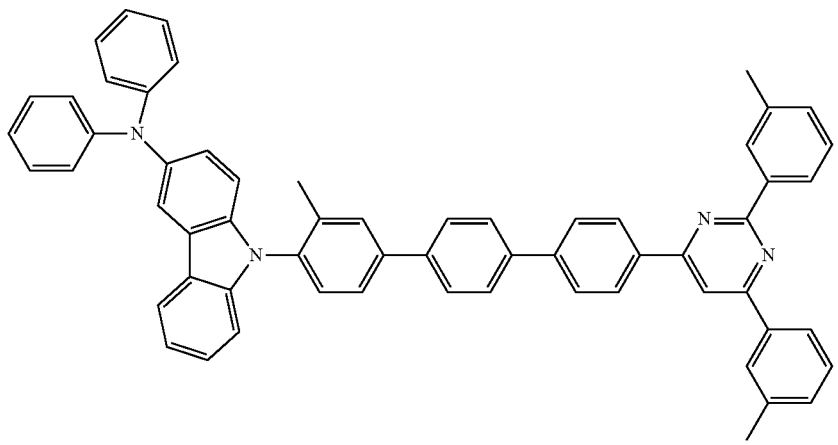
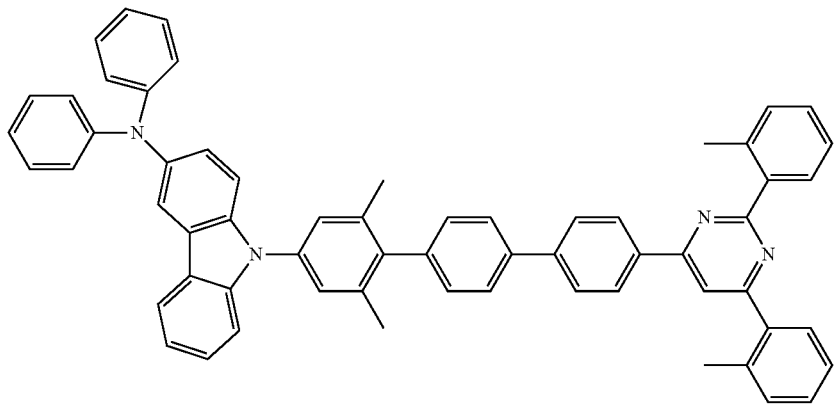
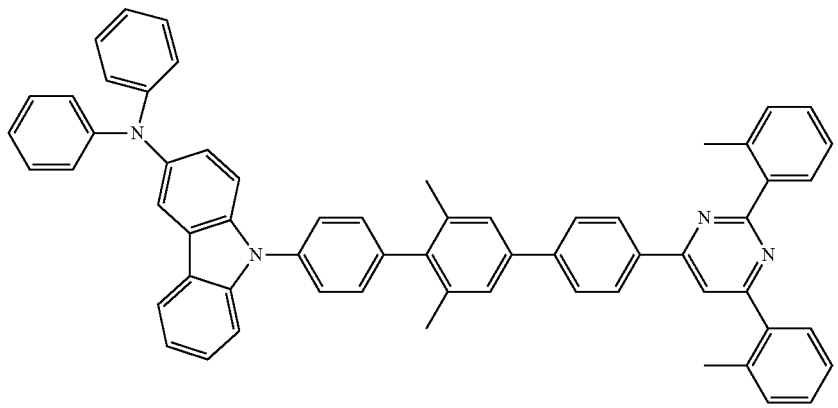

-continued
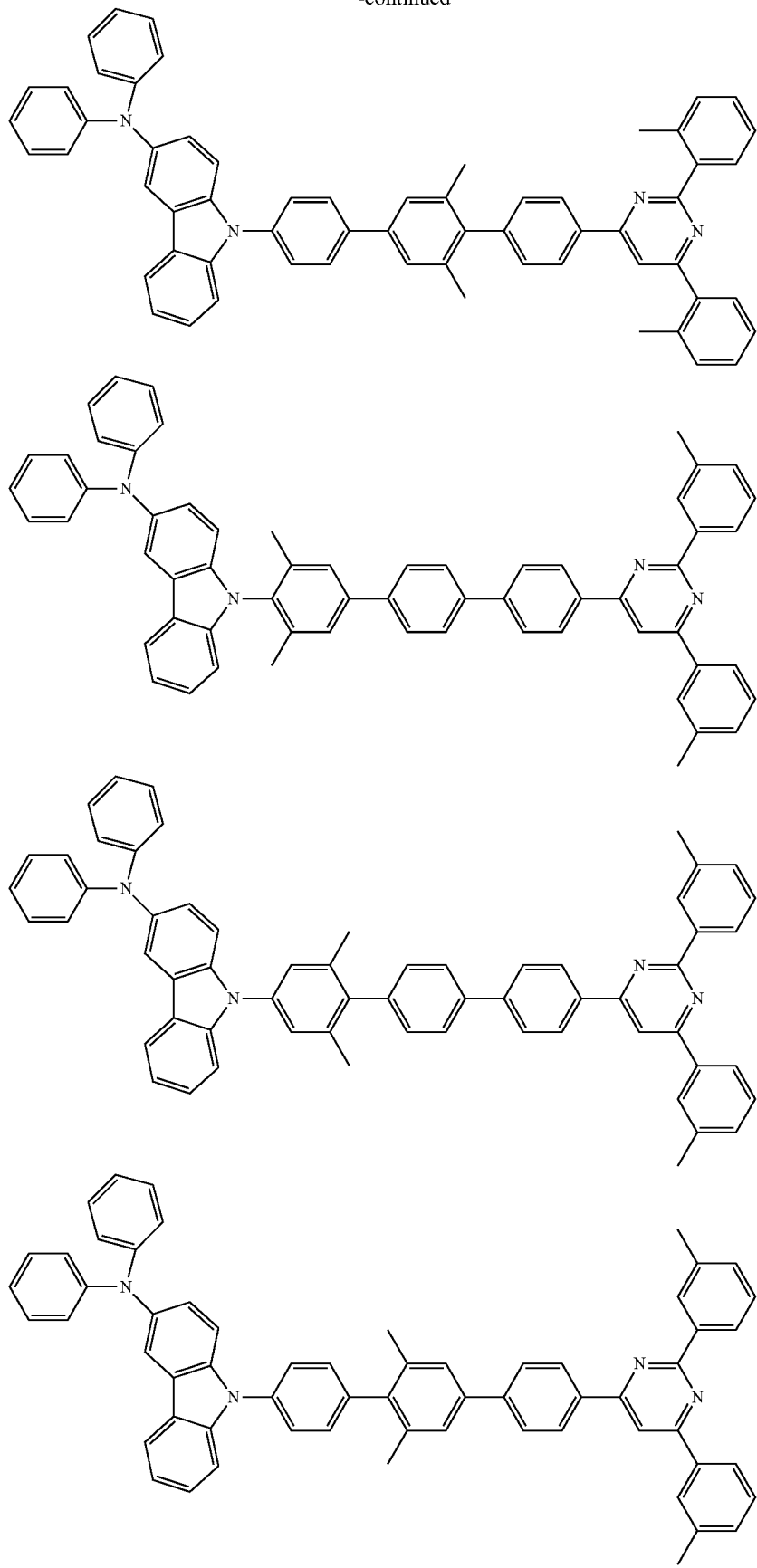

-continued
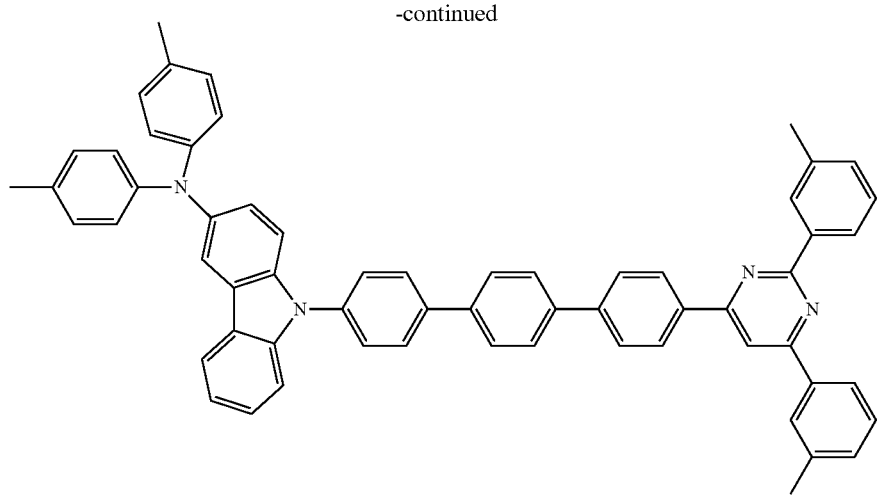
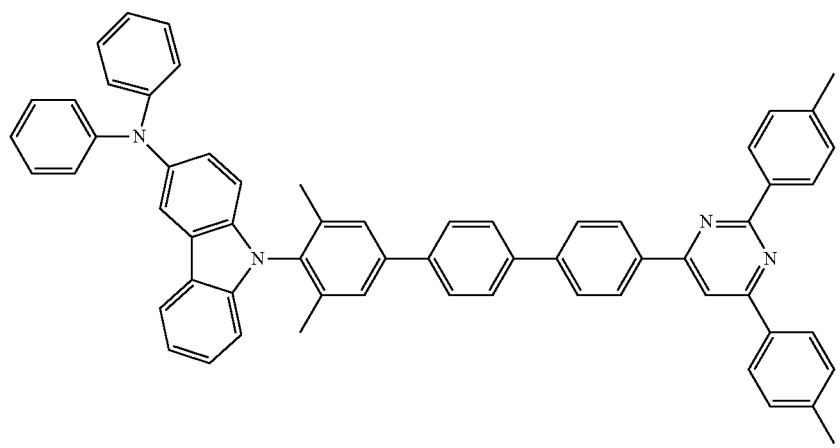
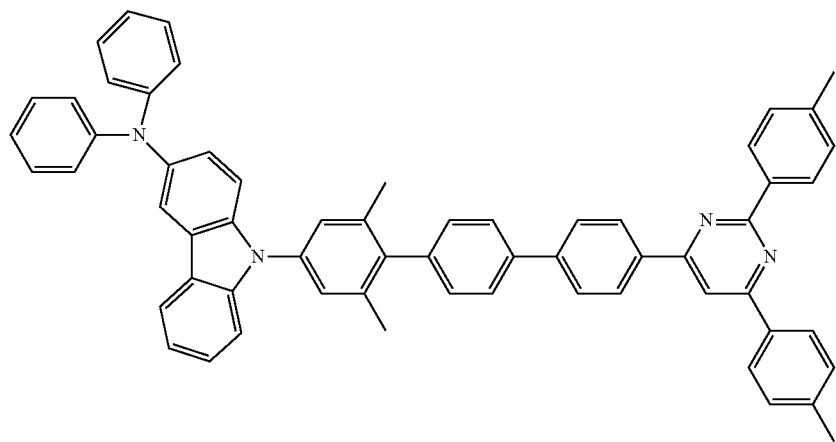

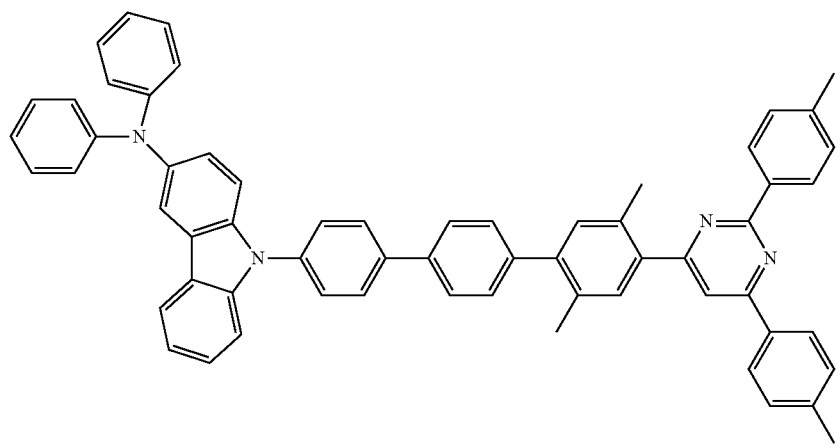
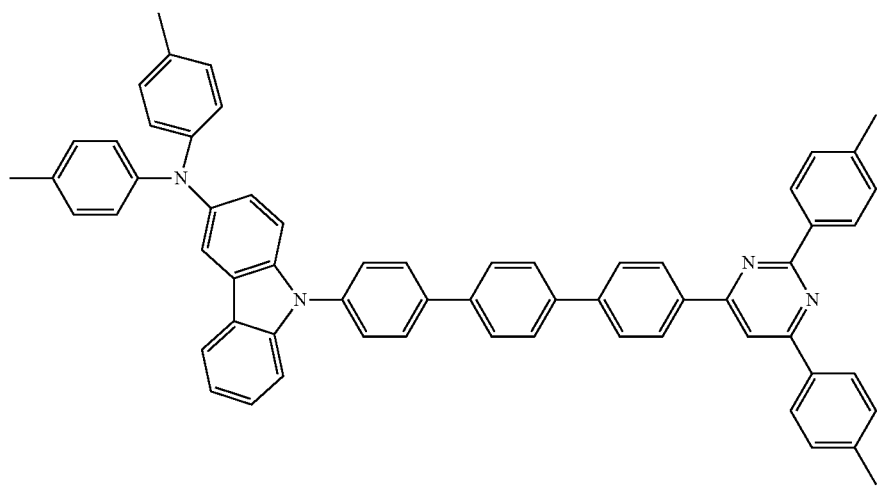
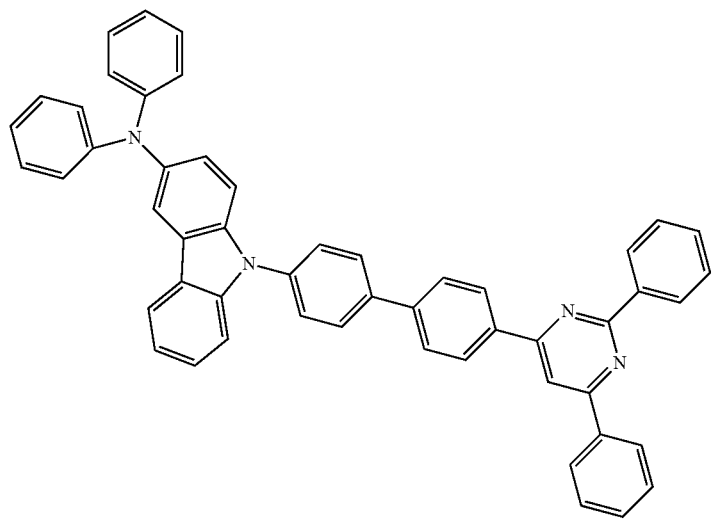

-continued
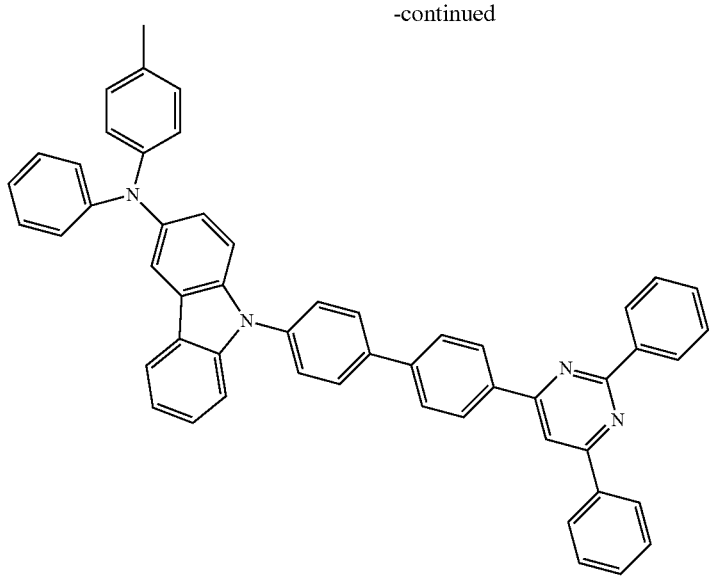
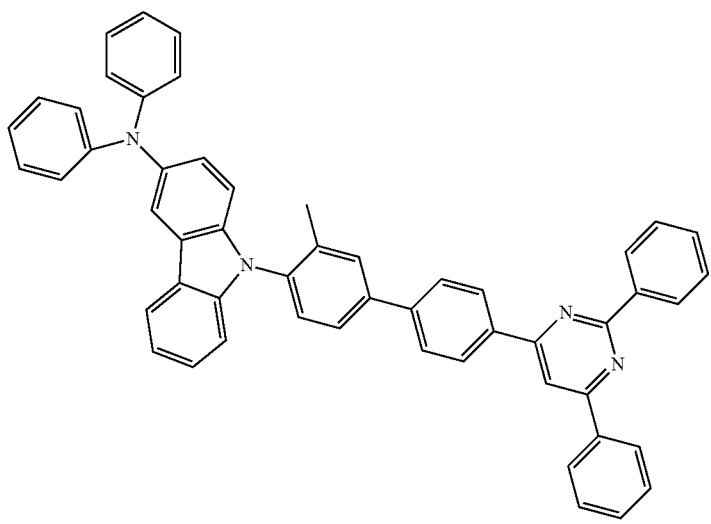
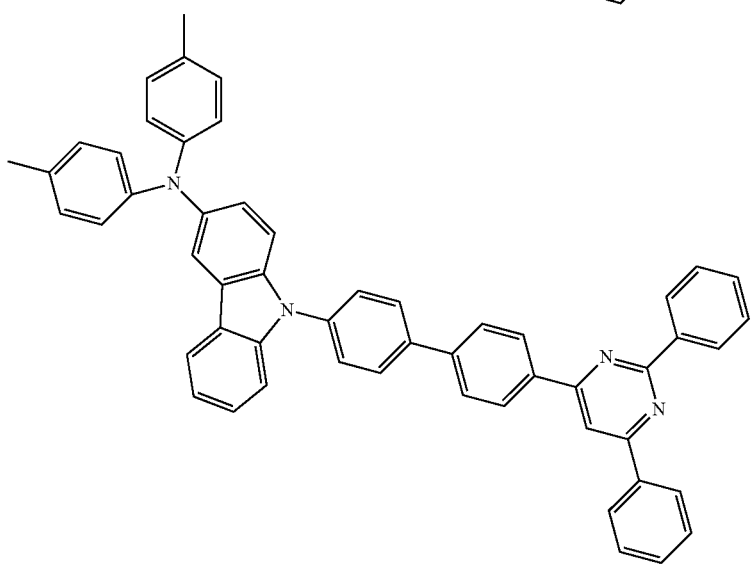

-continued
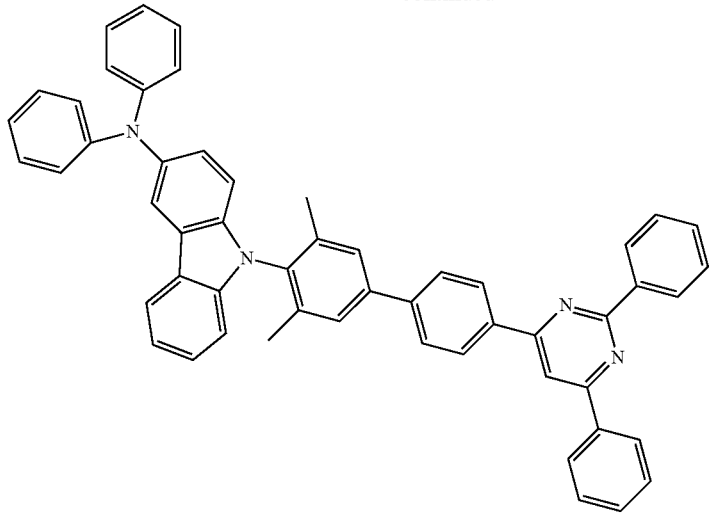
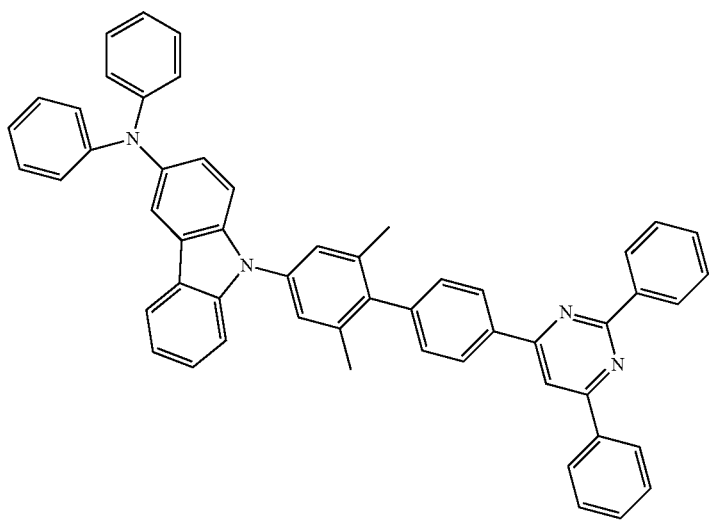
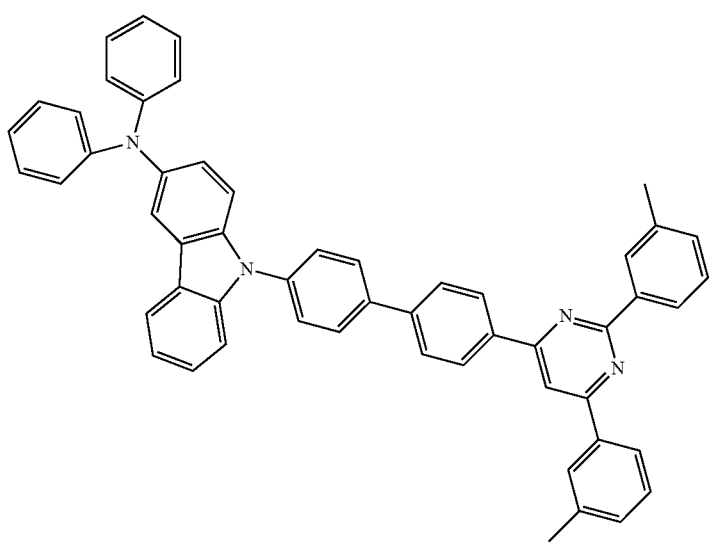

-continued
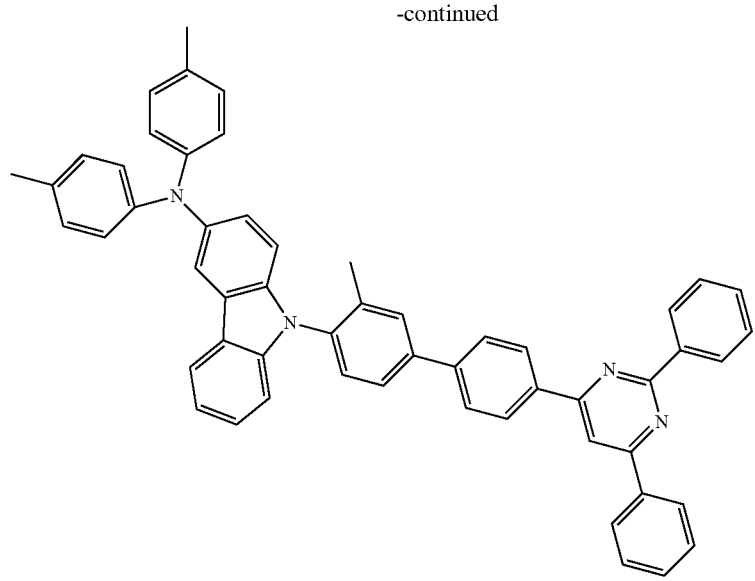
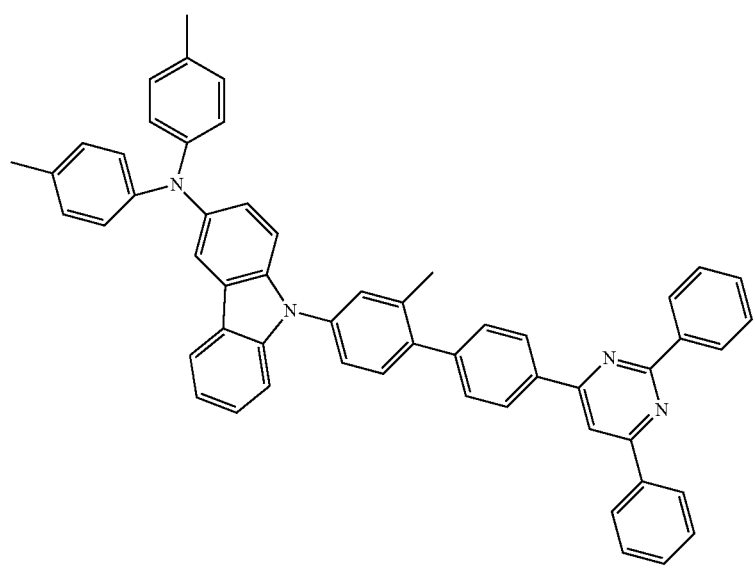
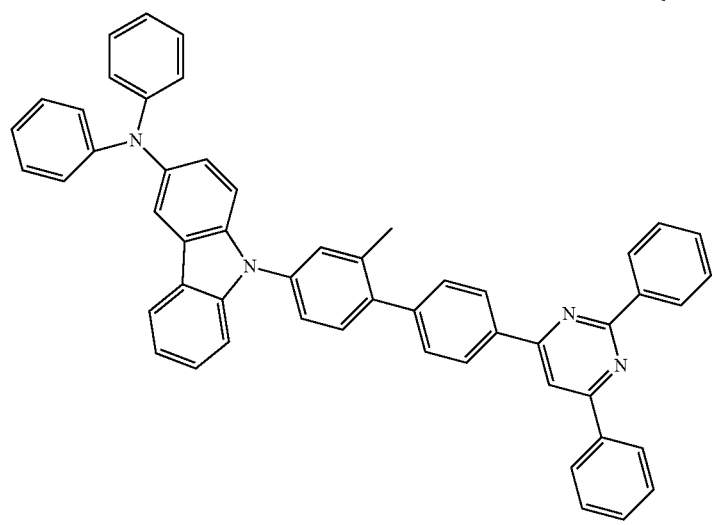

-continued
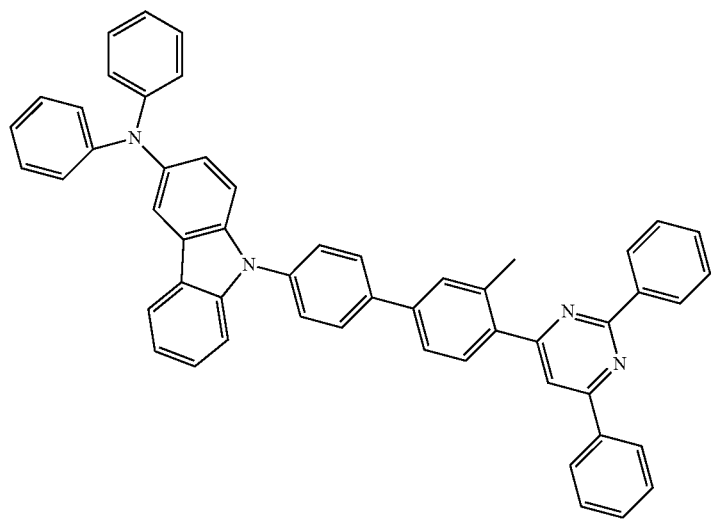
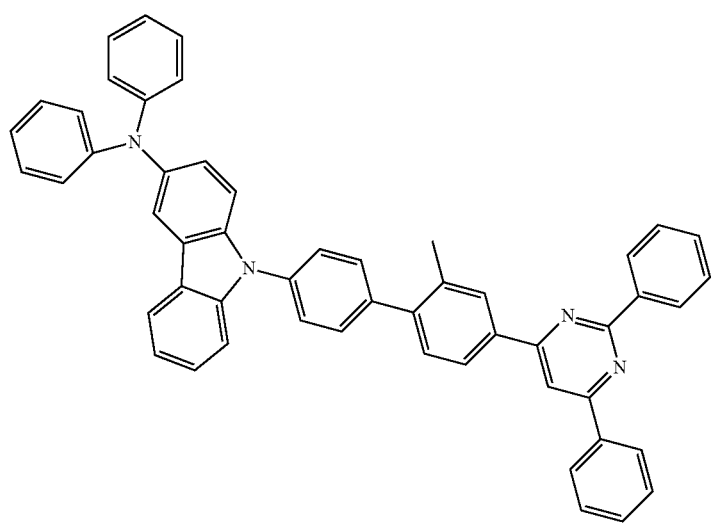
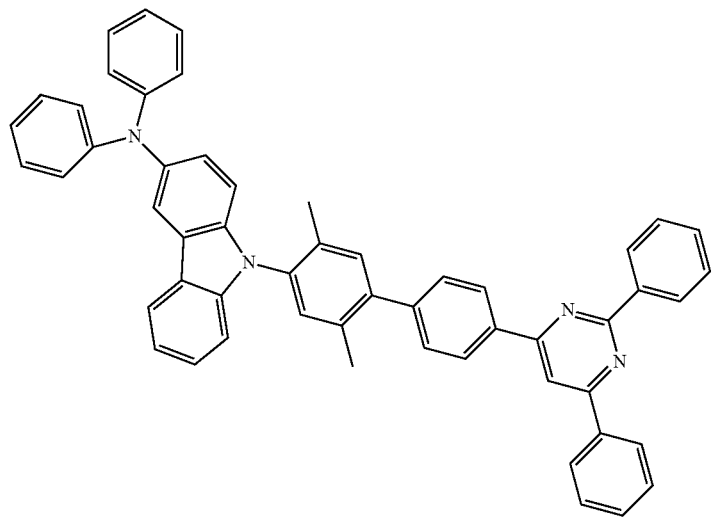

-continued
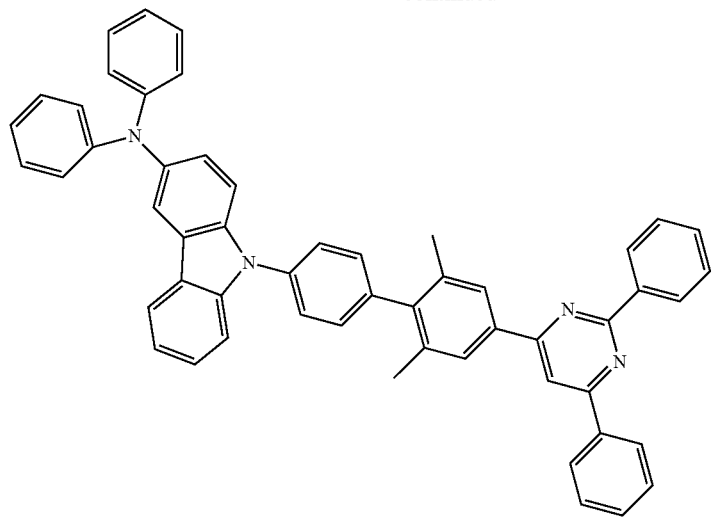
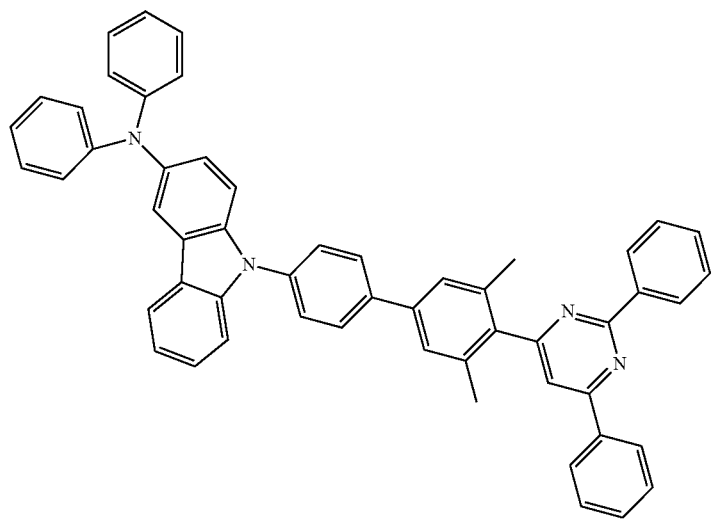
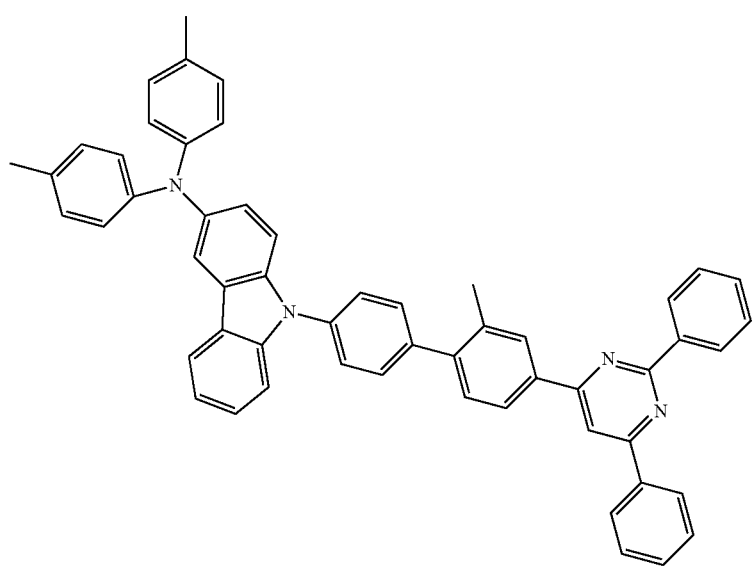

-continued
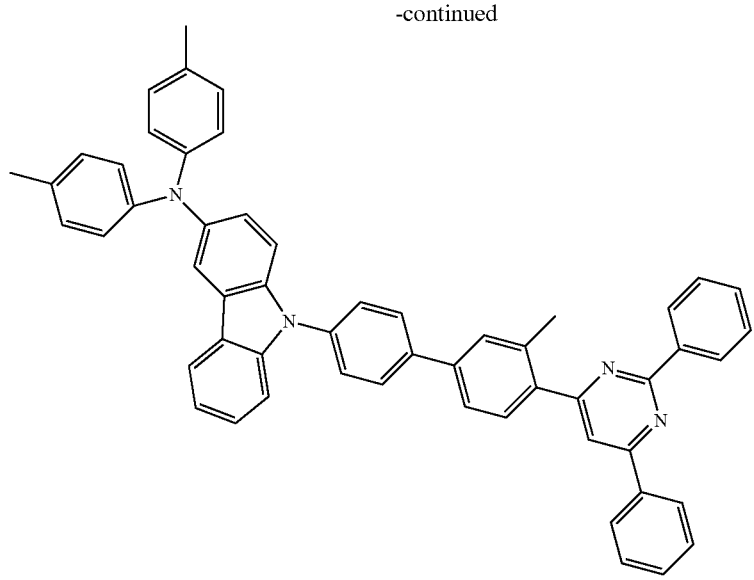
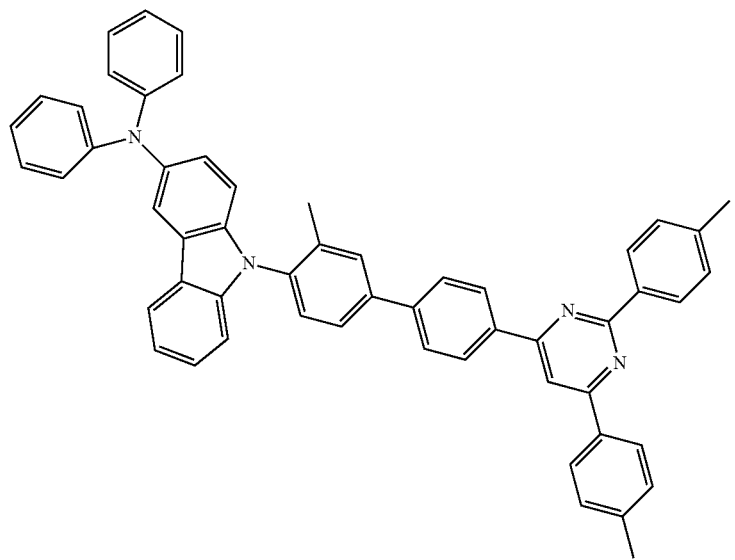
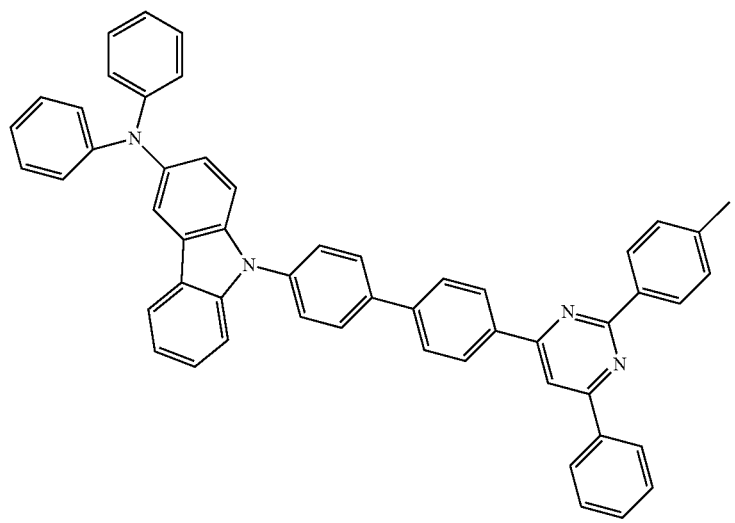

807
808
-continued
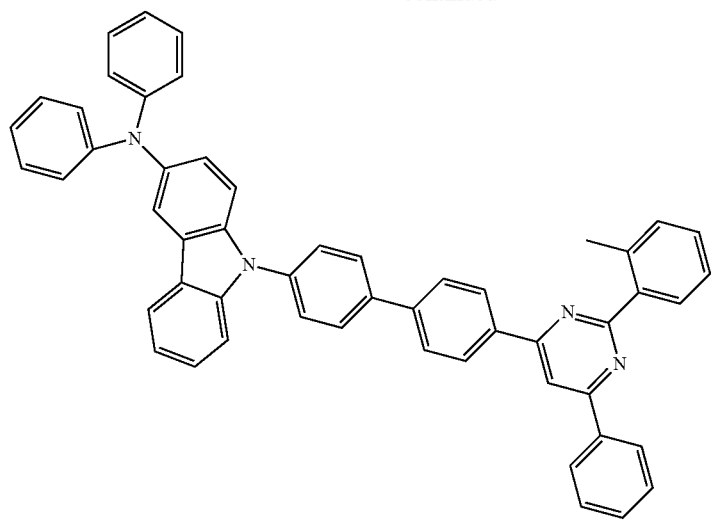
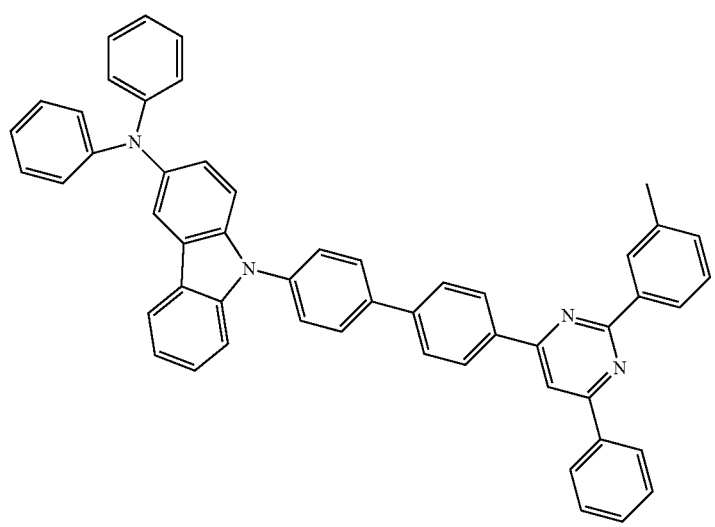
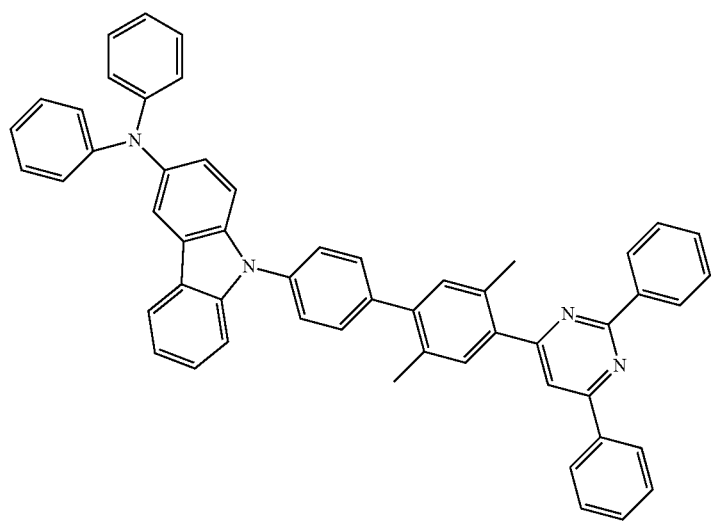

-continued
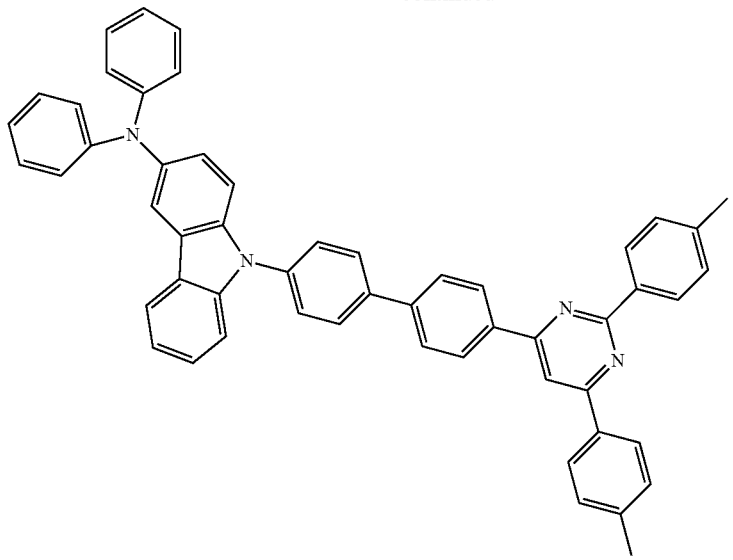
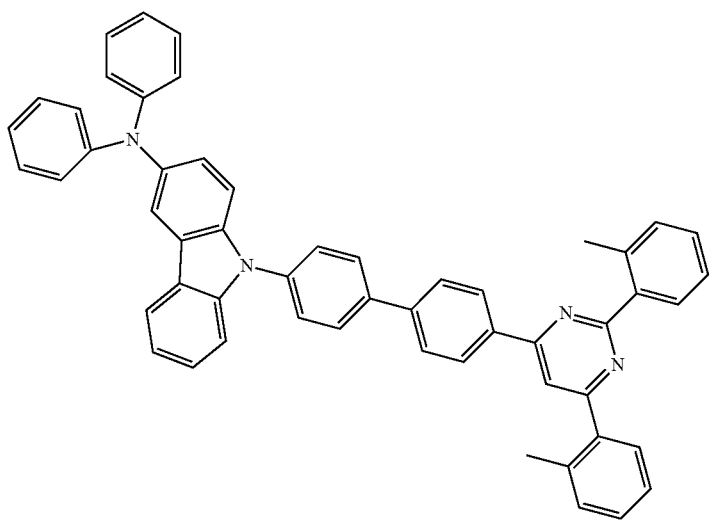
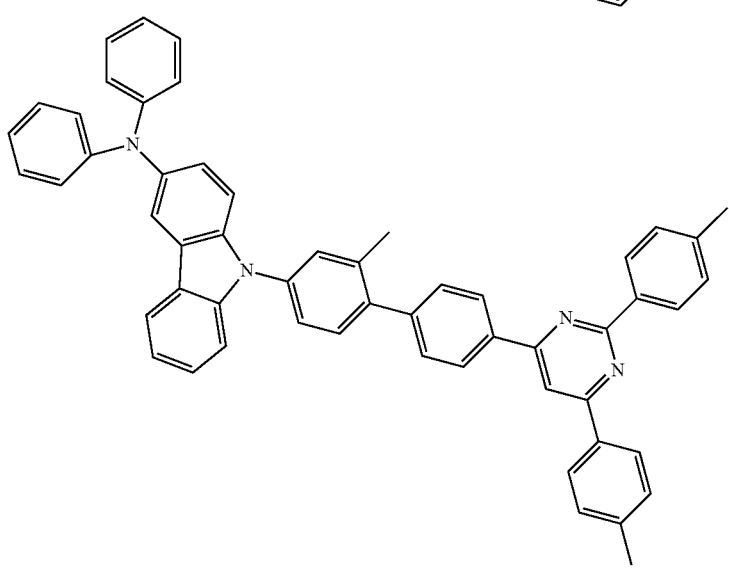

811
-continued
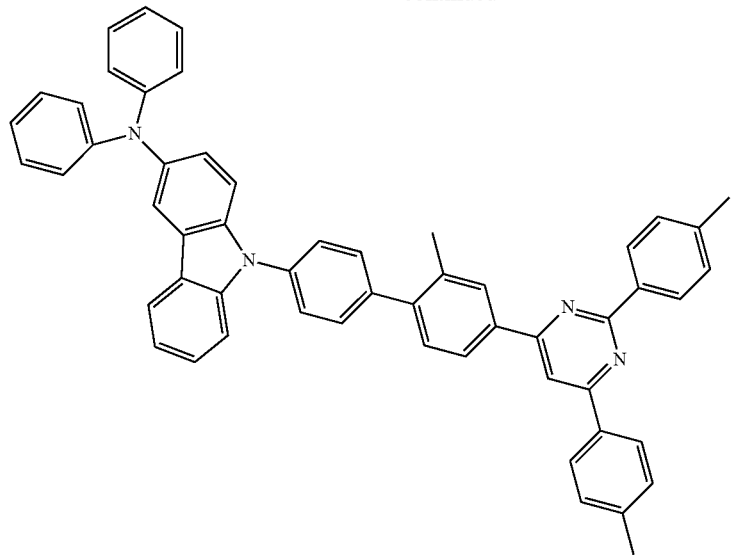
812
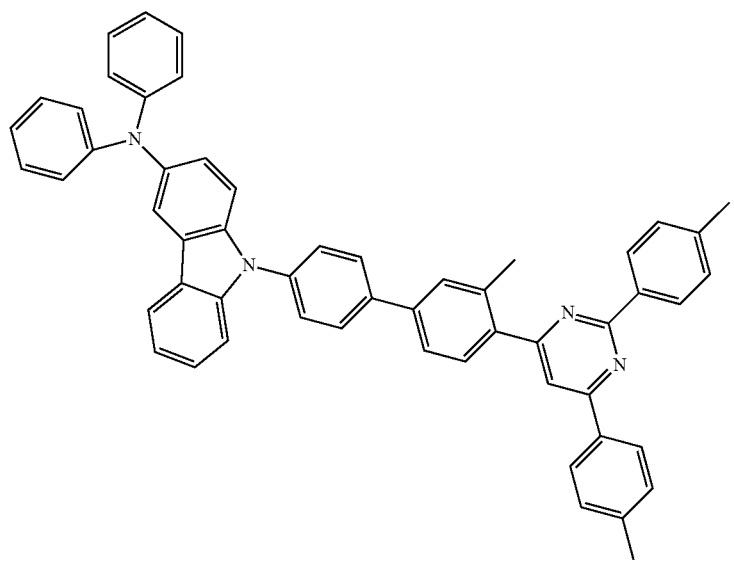
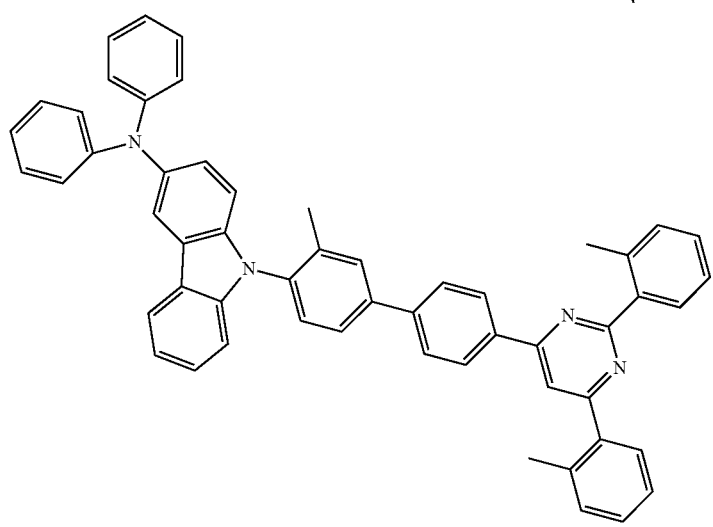

813
-continued
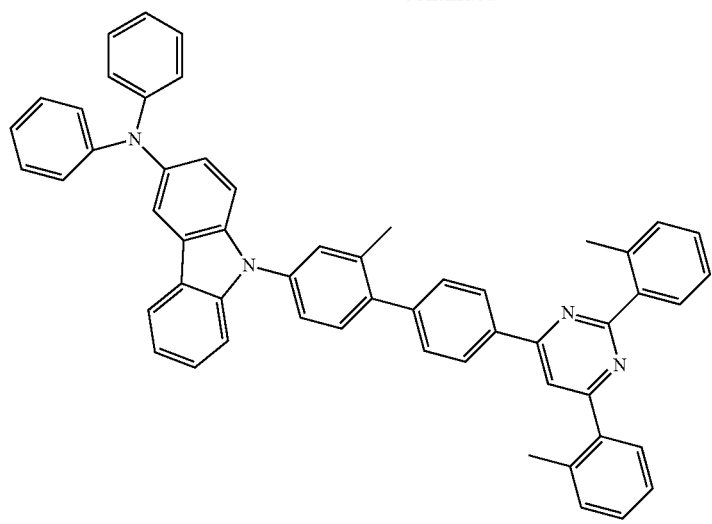
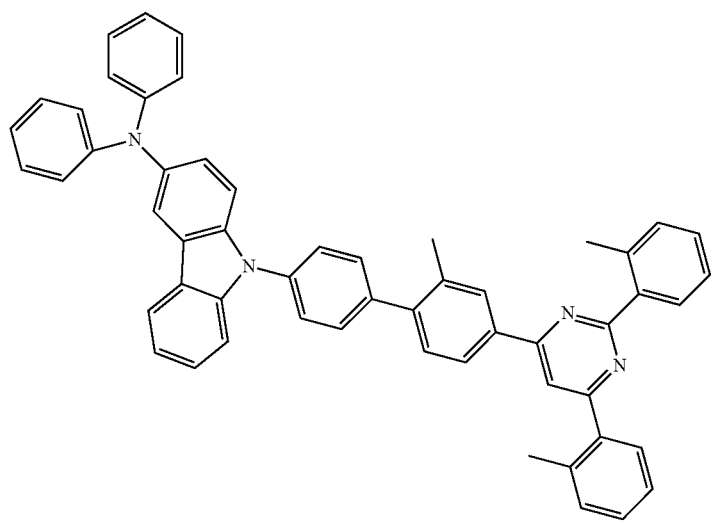
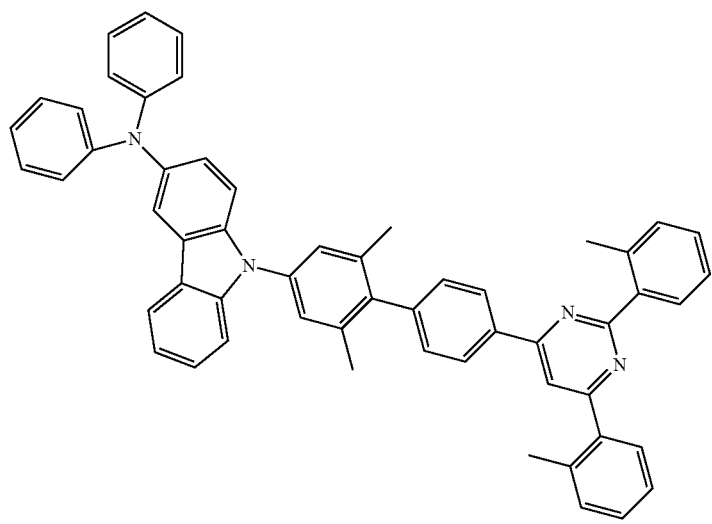
814

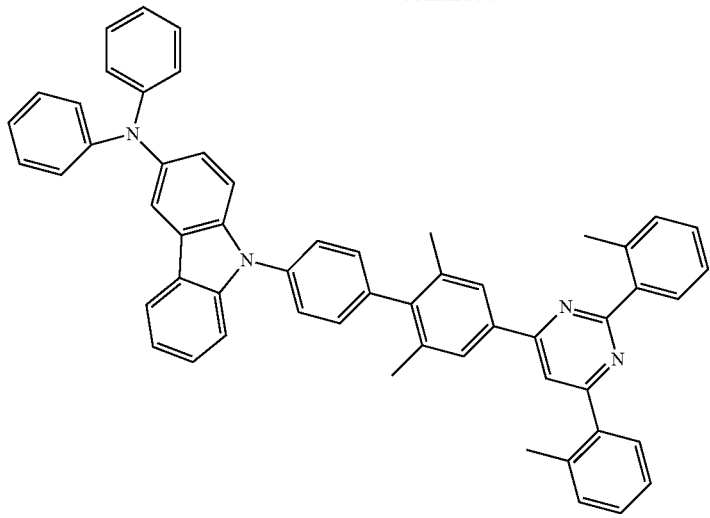
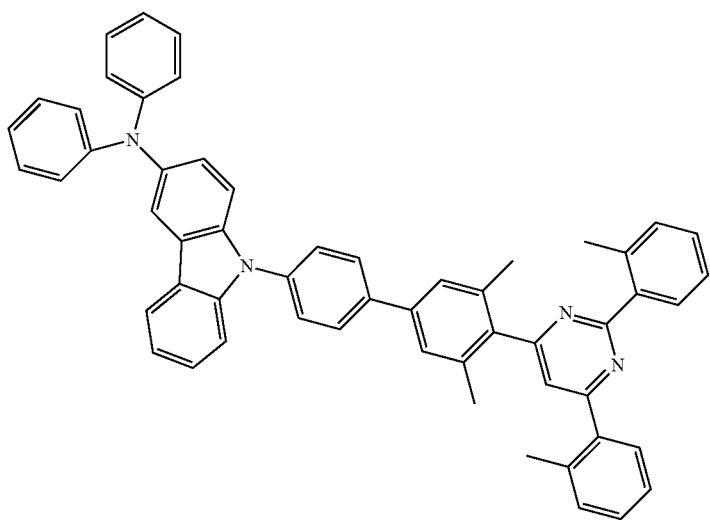
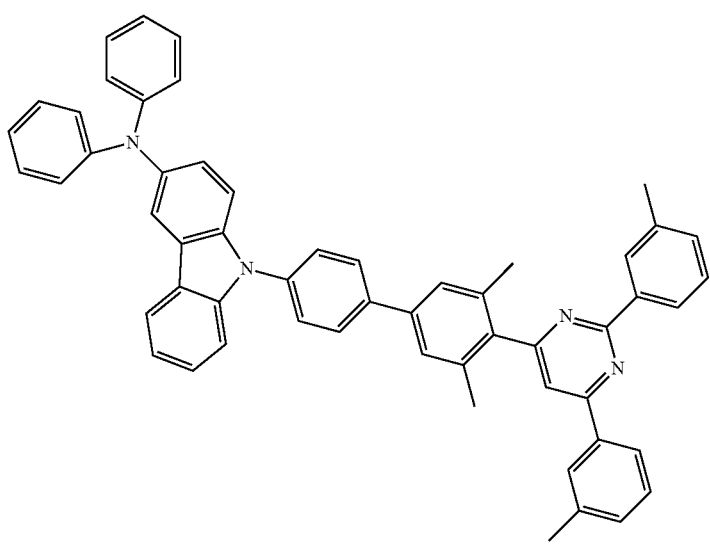

-continued
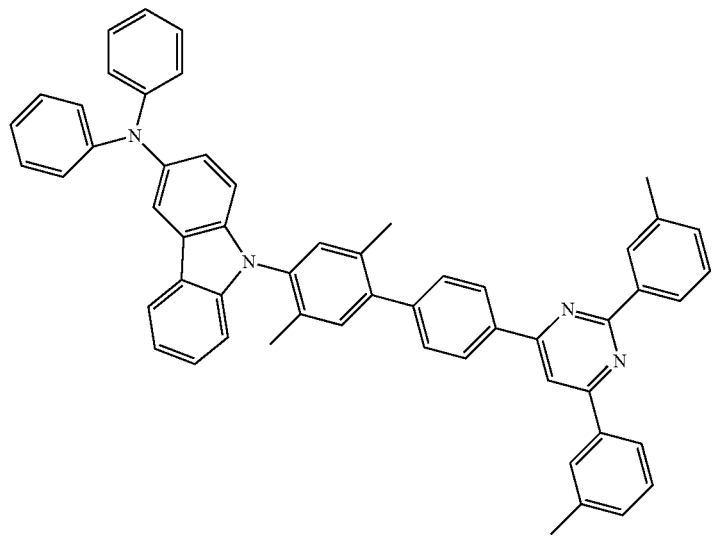
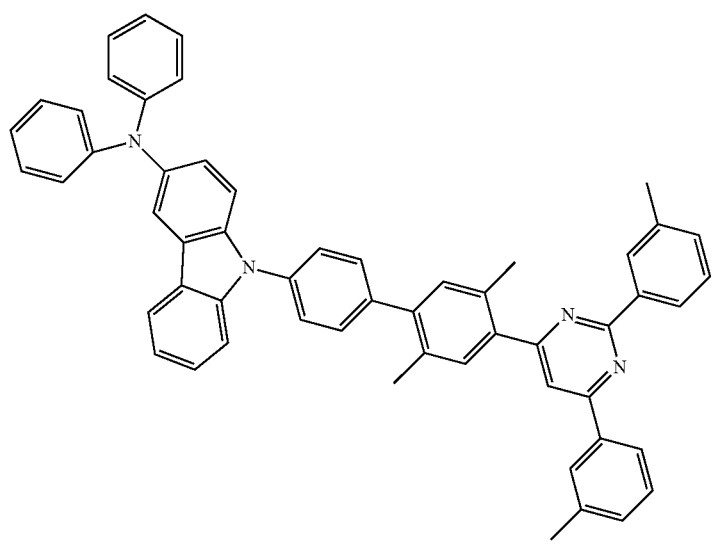
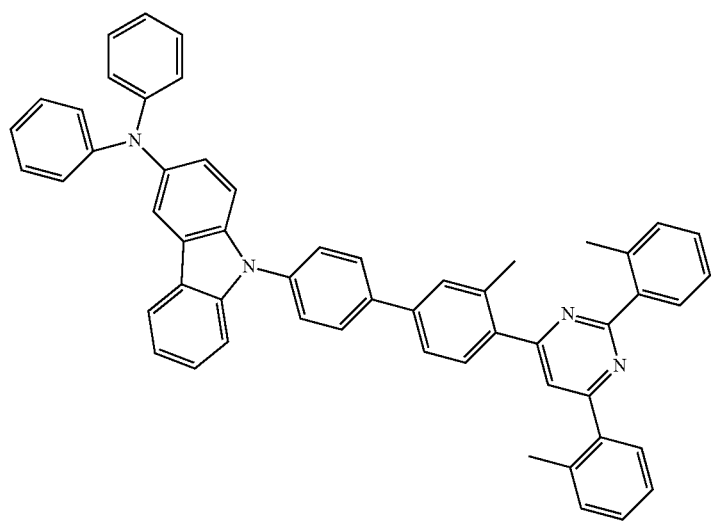

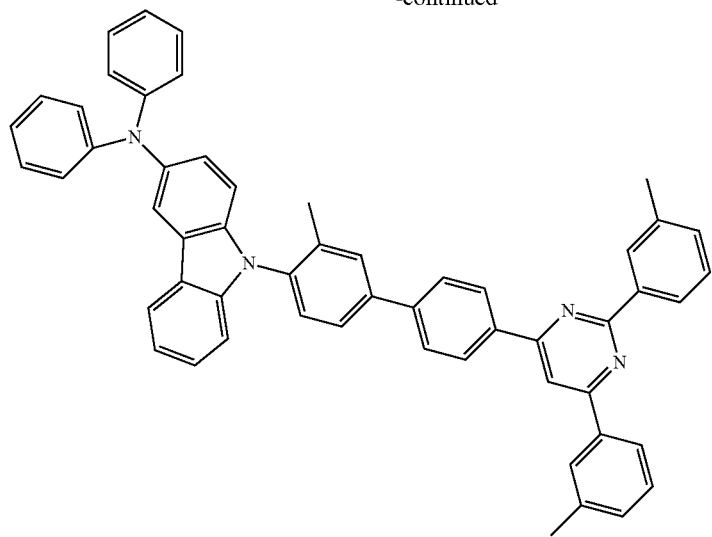
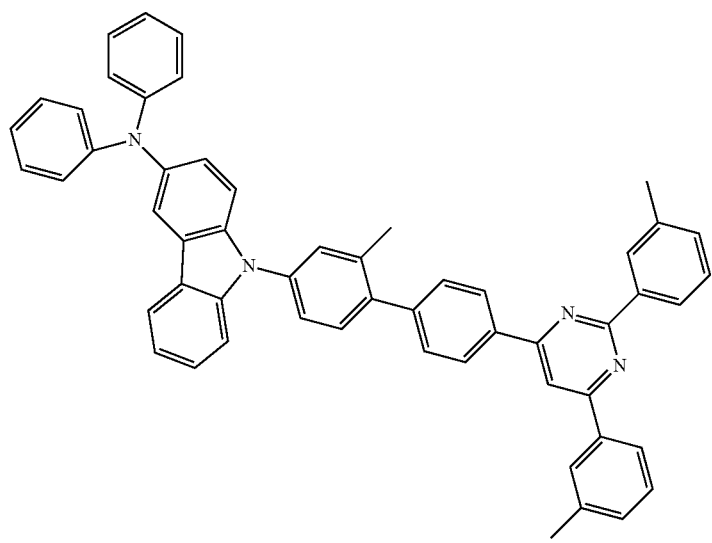
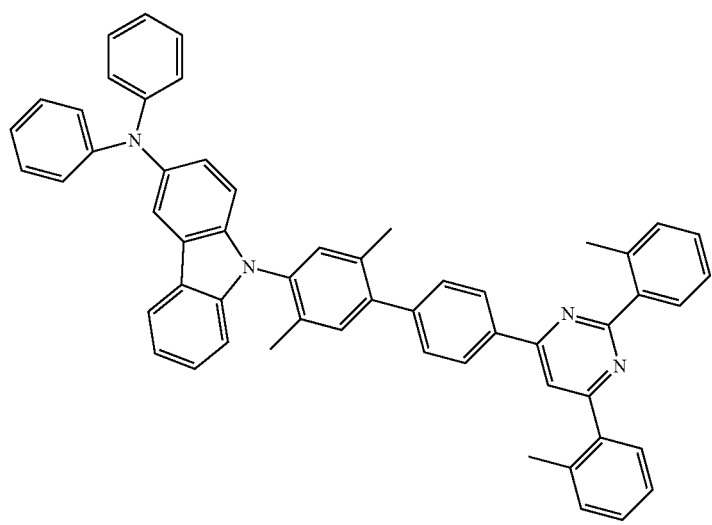

821
822
-continued
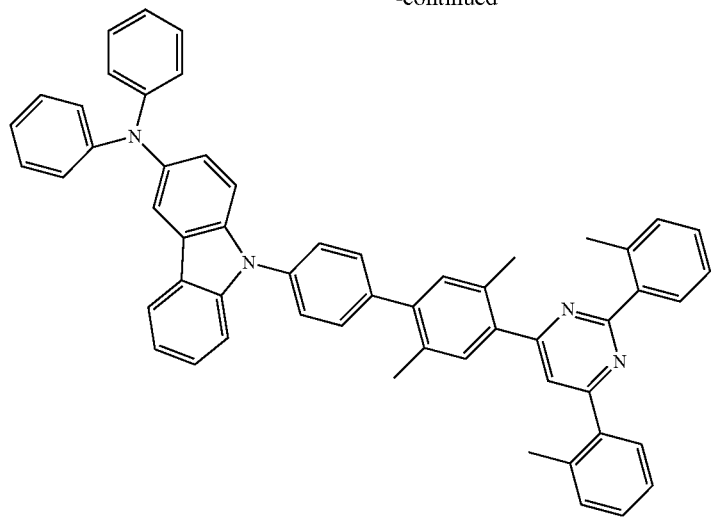
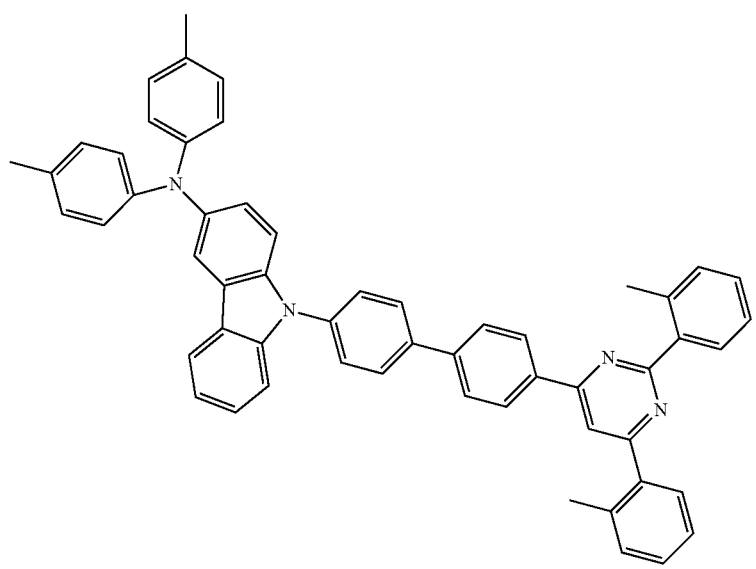
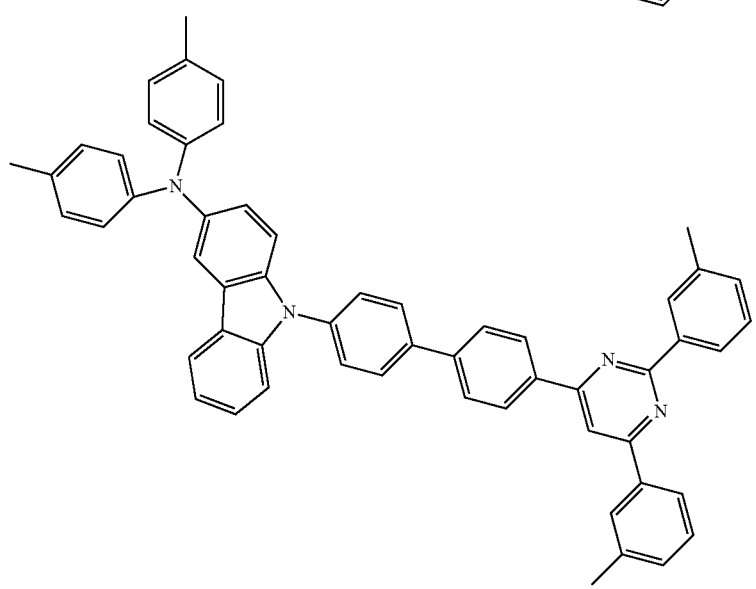

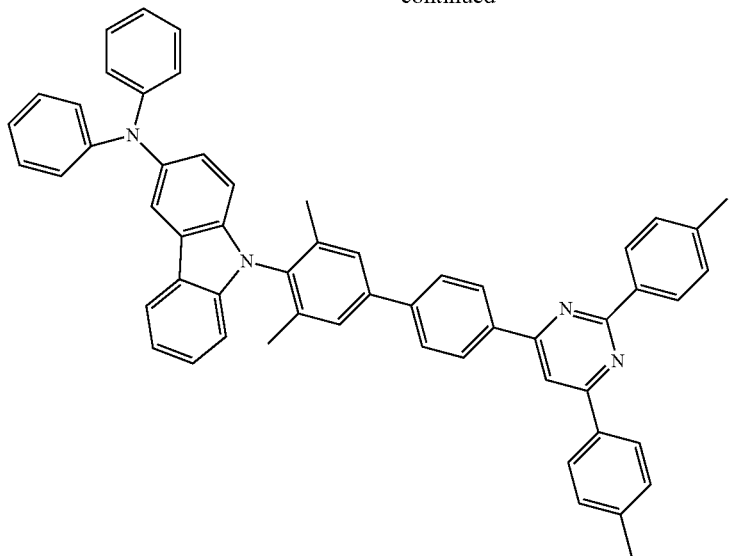
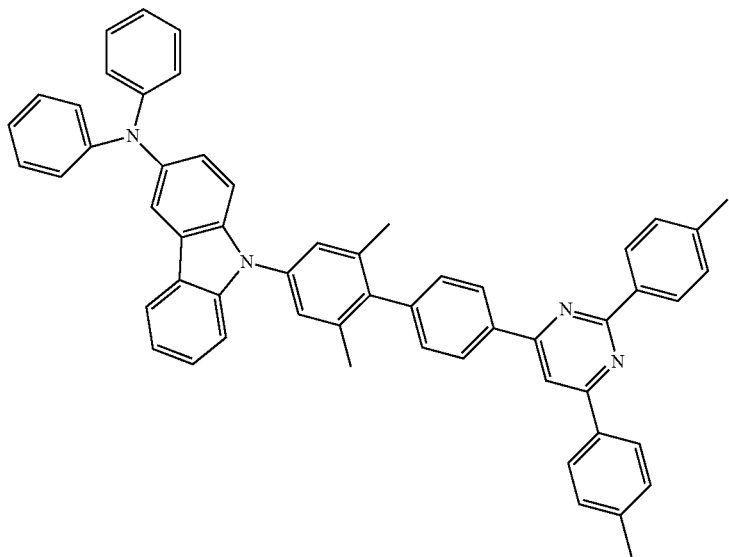
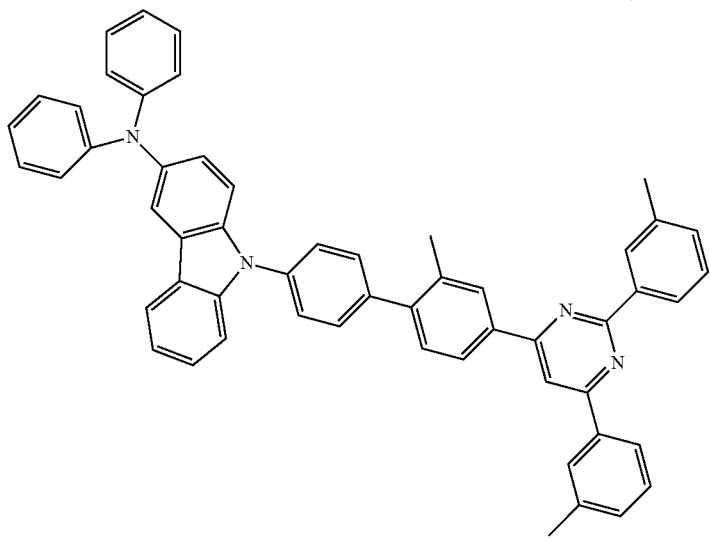

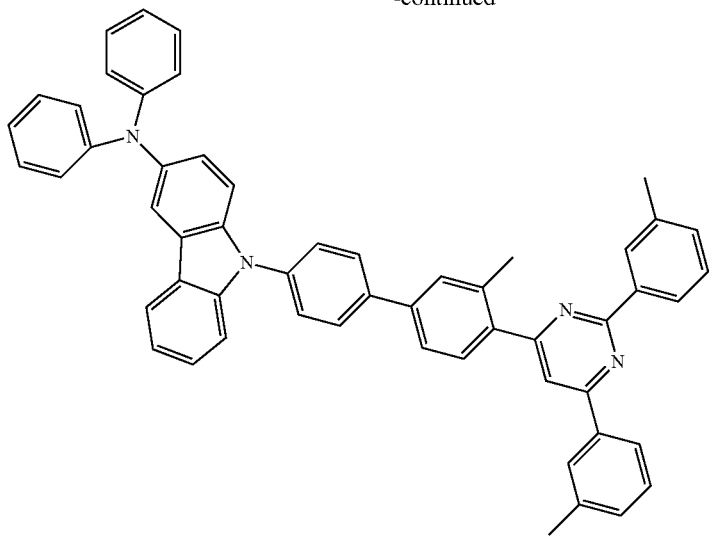
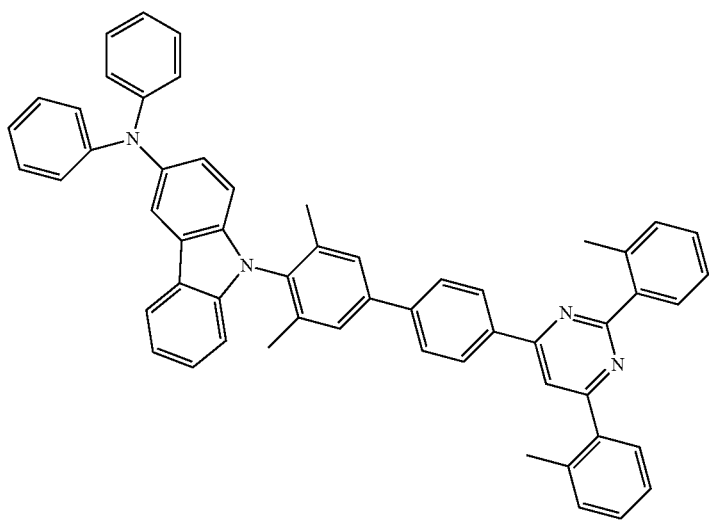
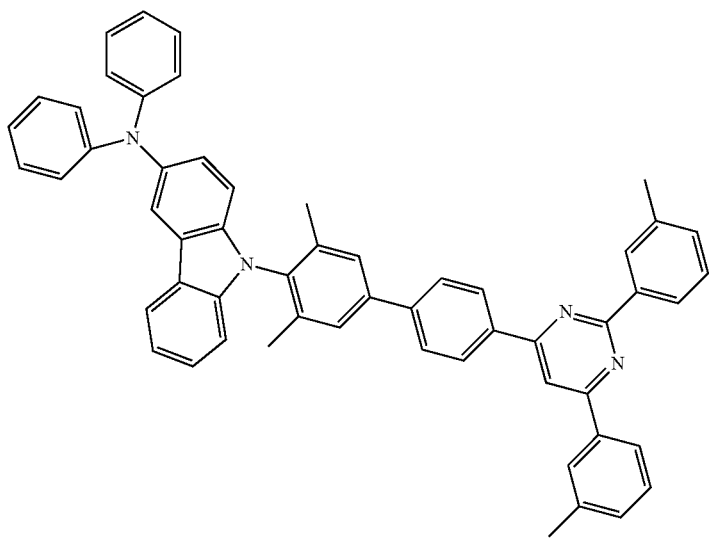

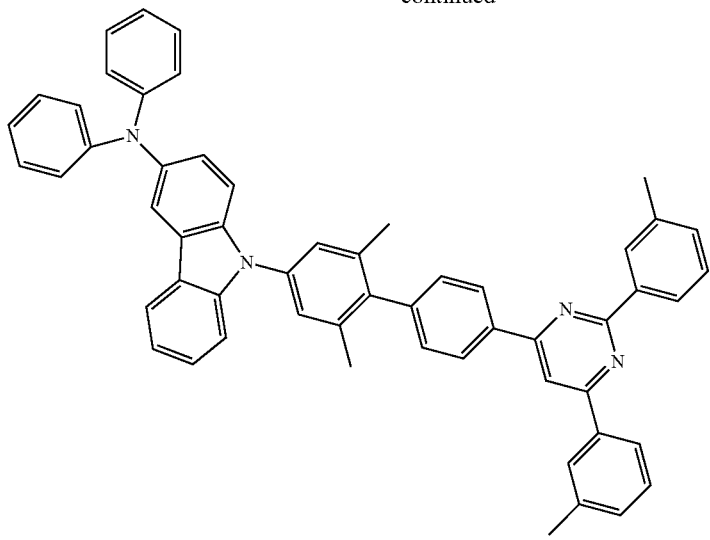
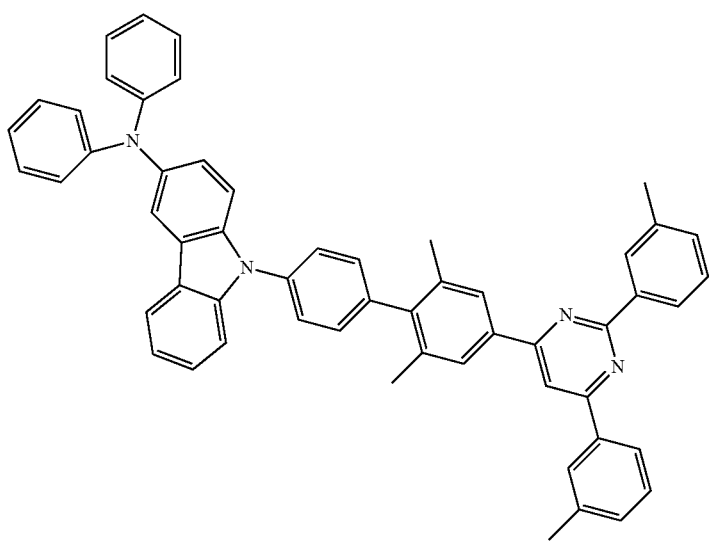
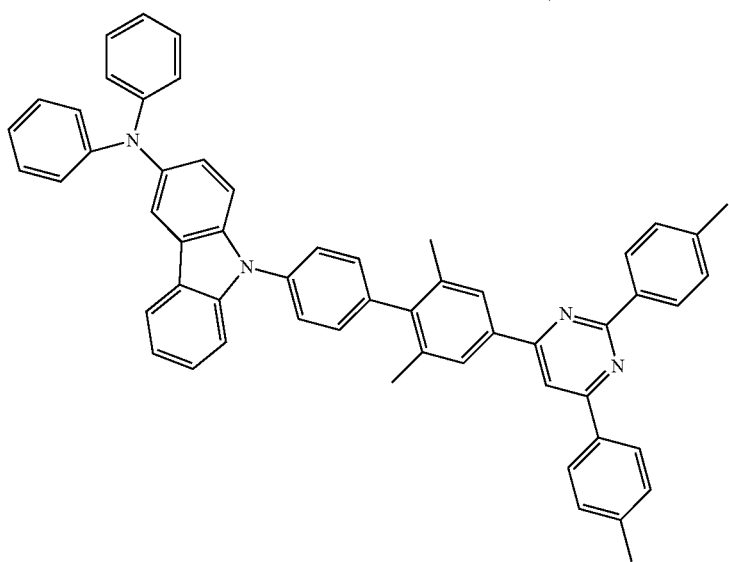

-continued
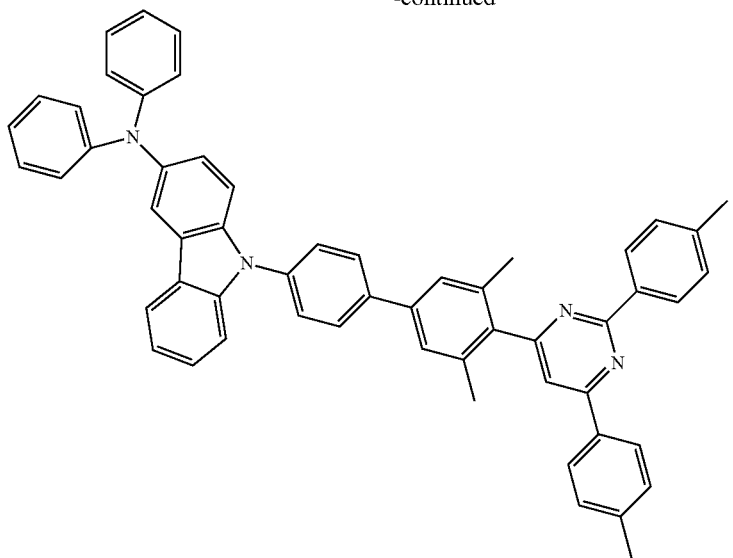
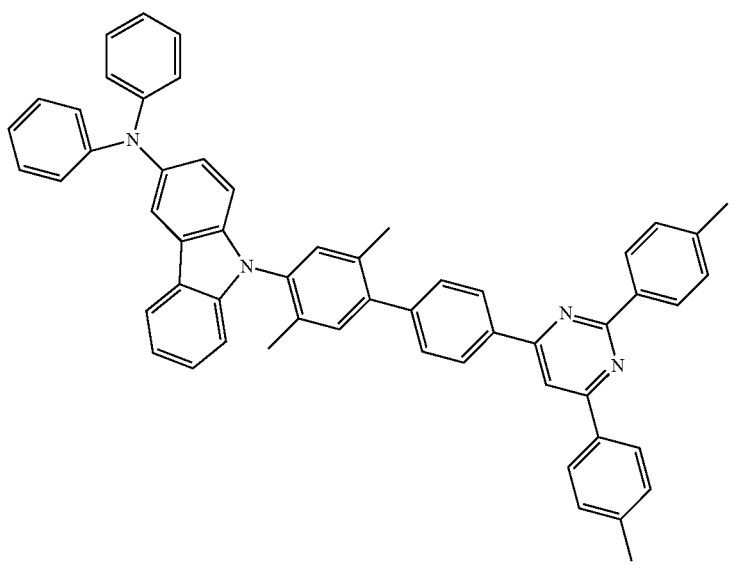
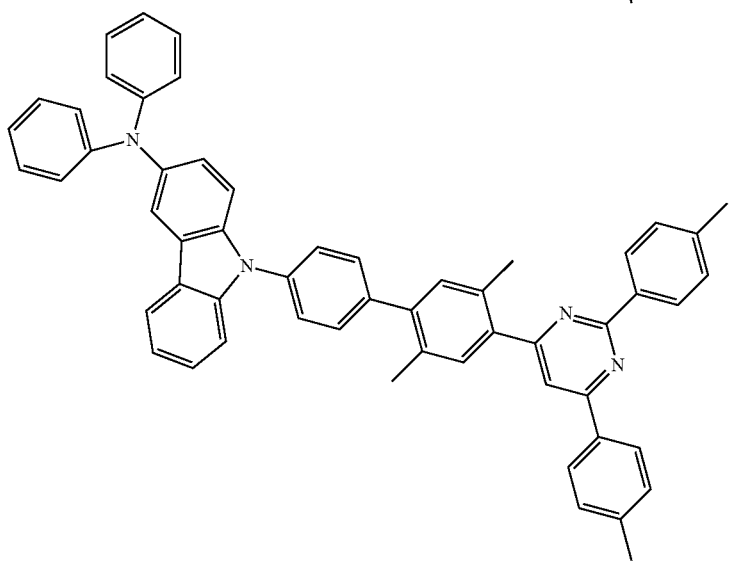

-continued
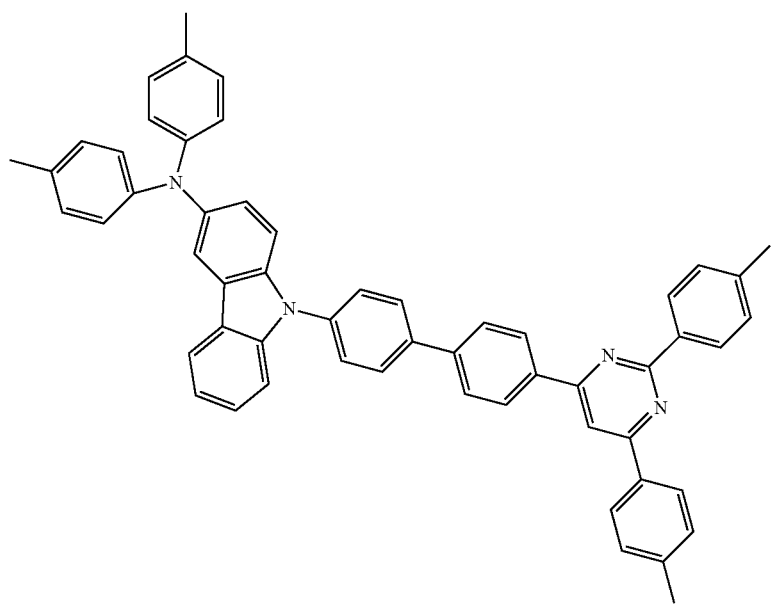
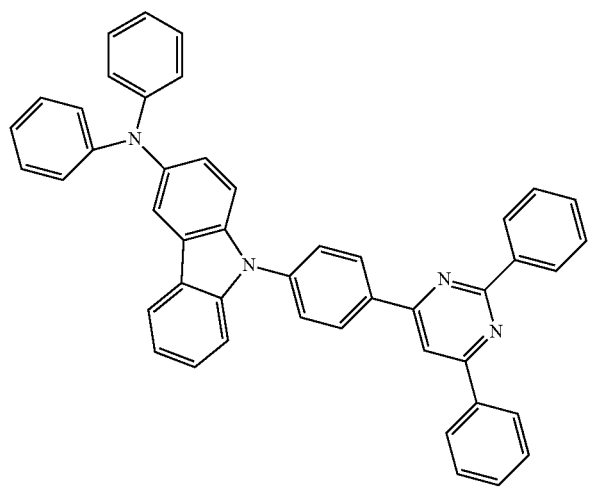
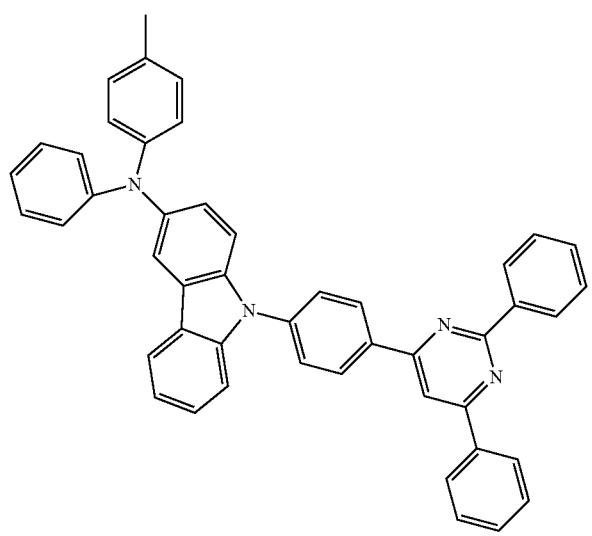

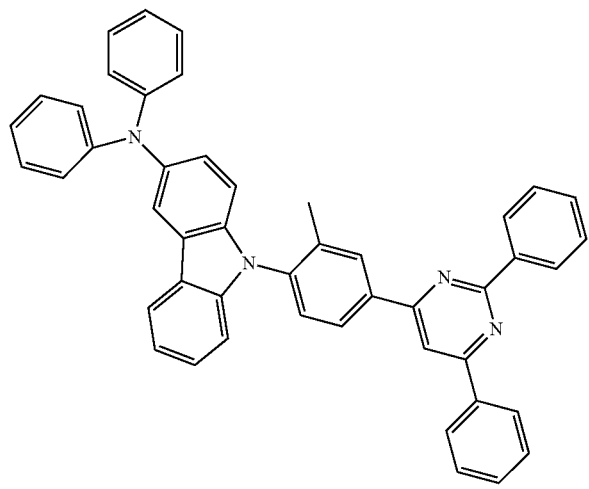
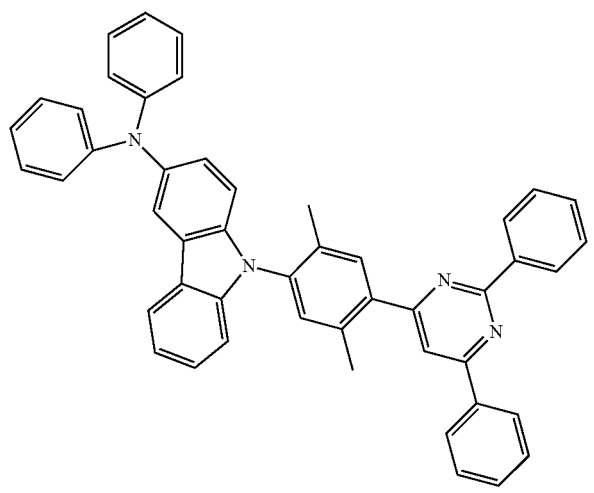

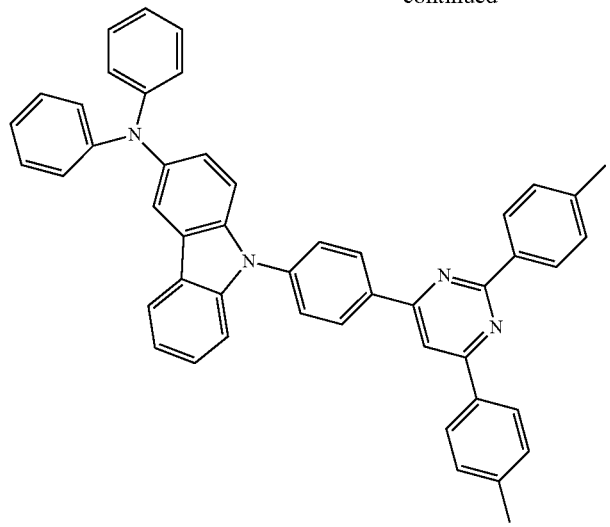
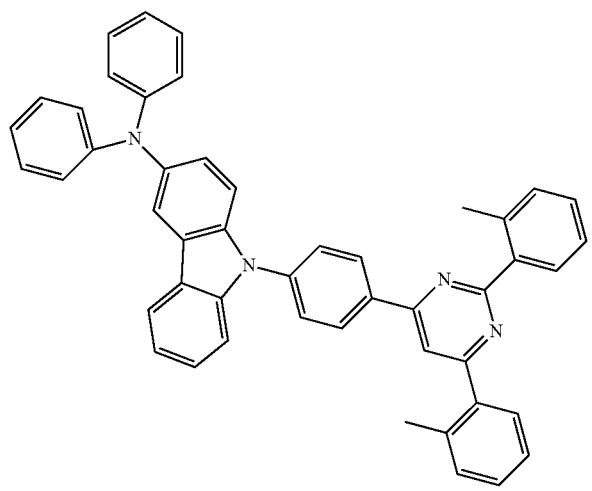
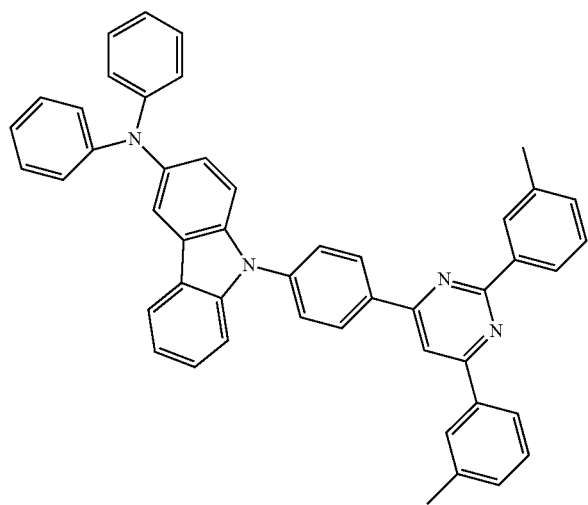

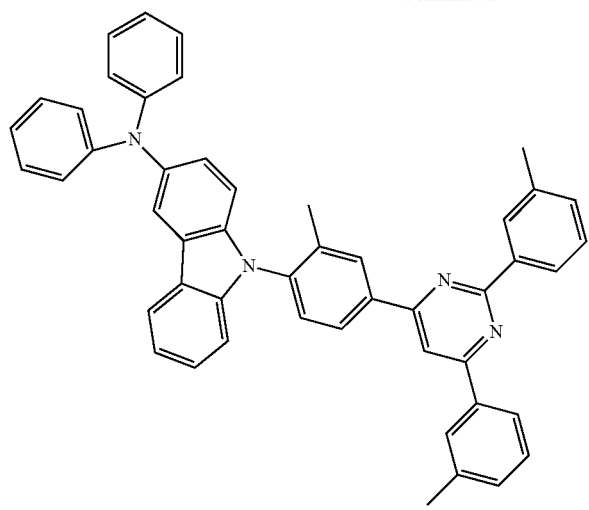
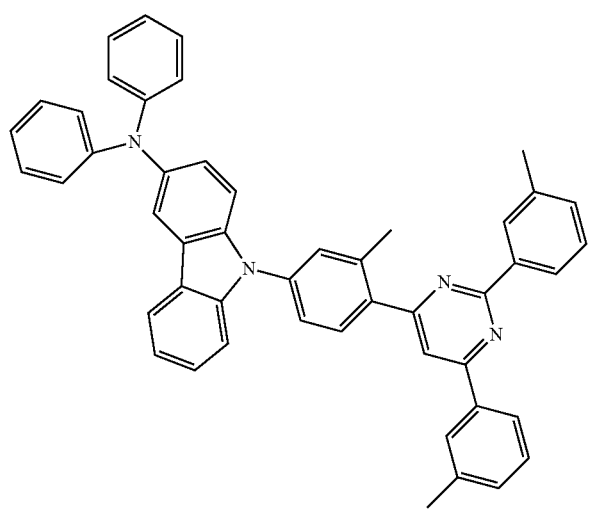
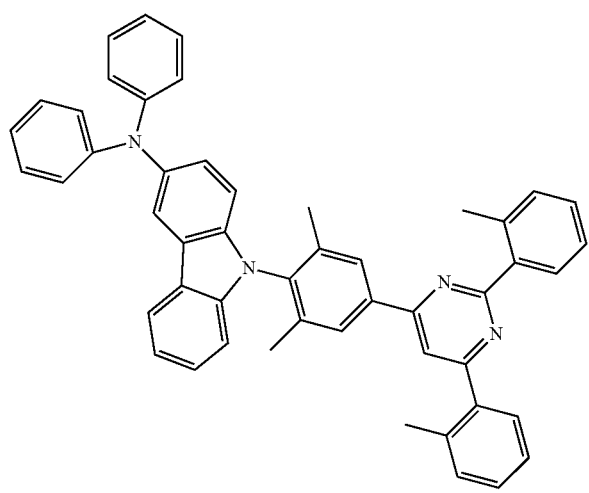

-continued
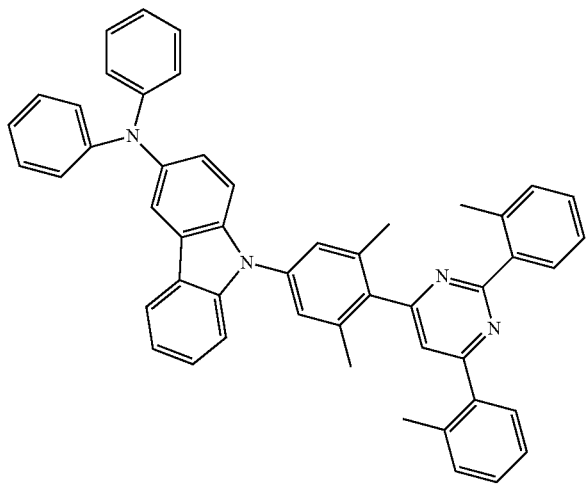
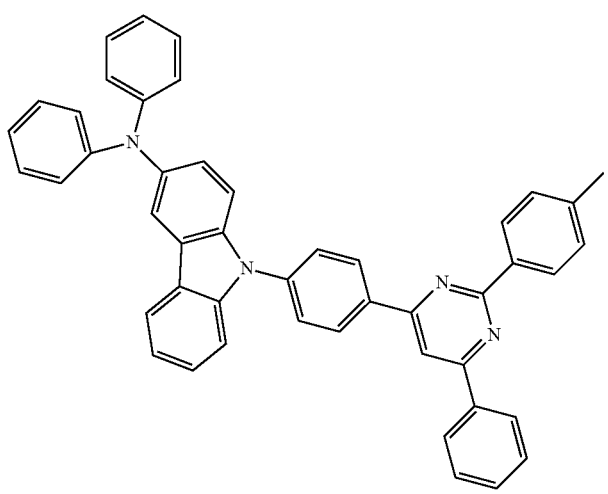
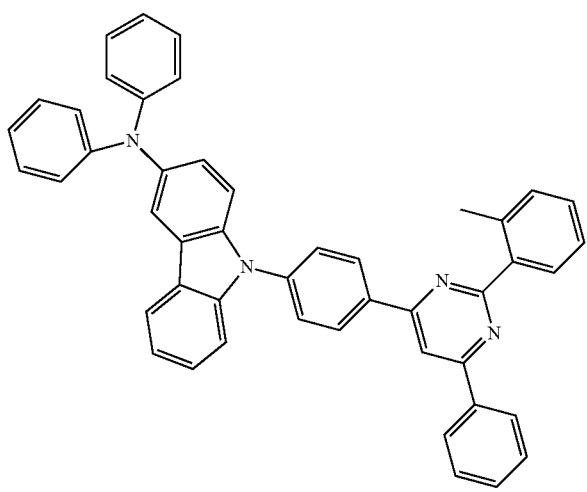

-continued
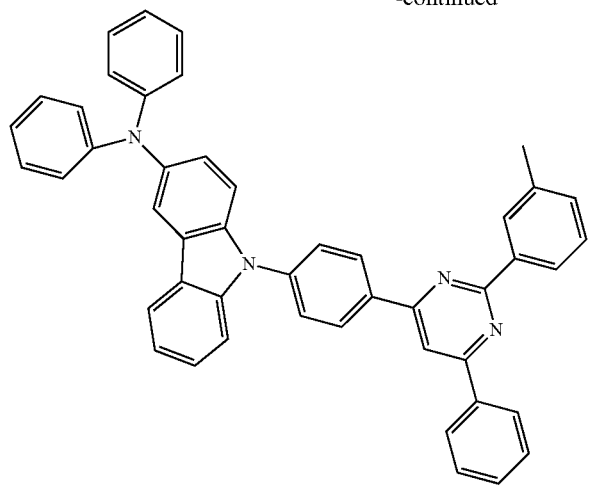
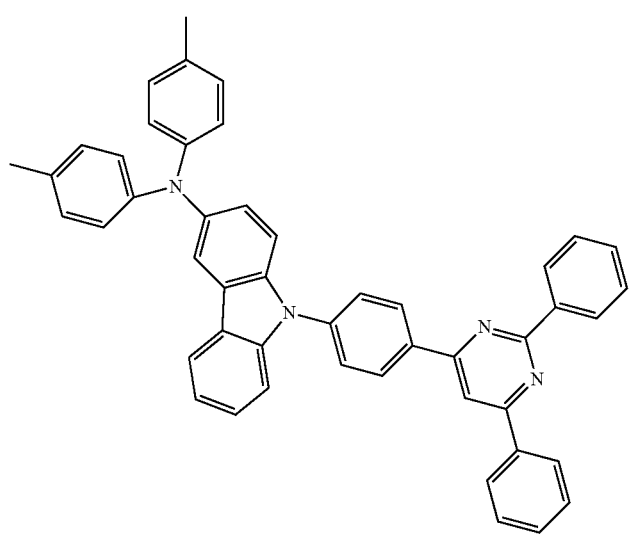
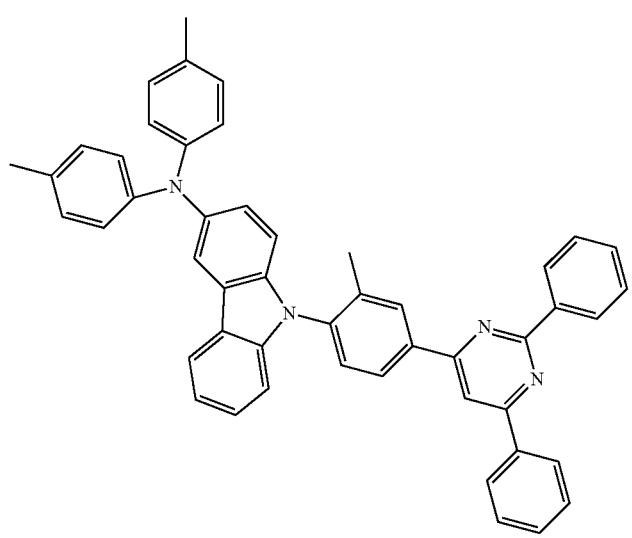

-continued
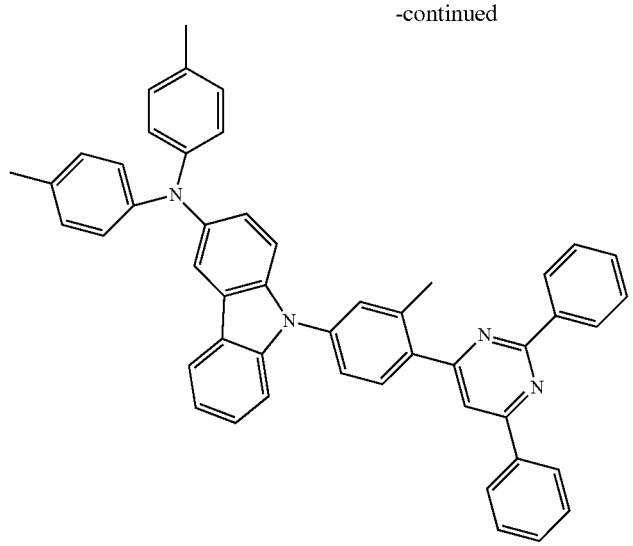
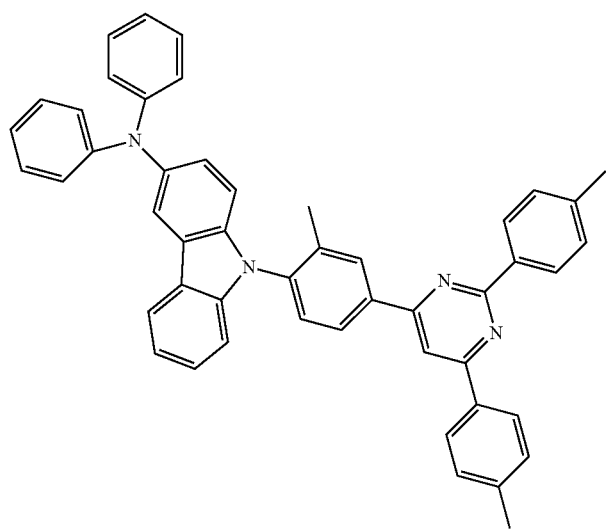
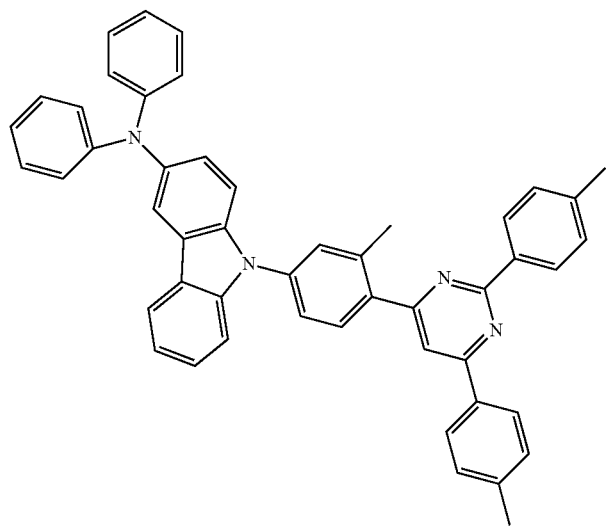

-continued
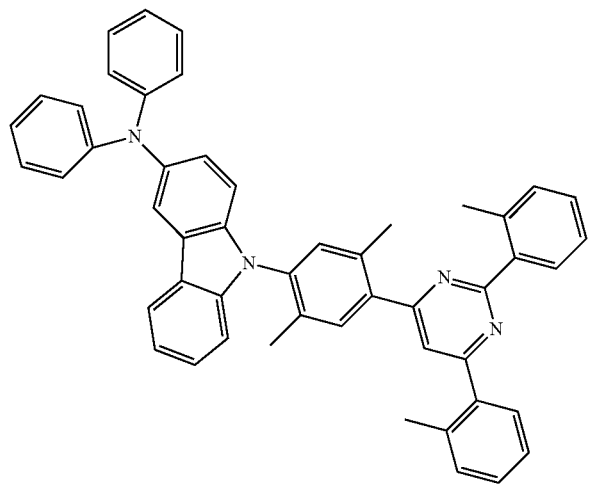
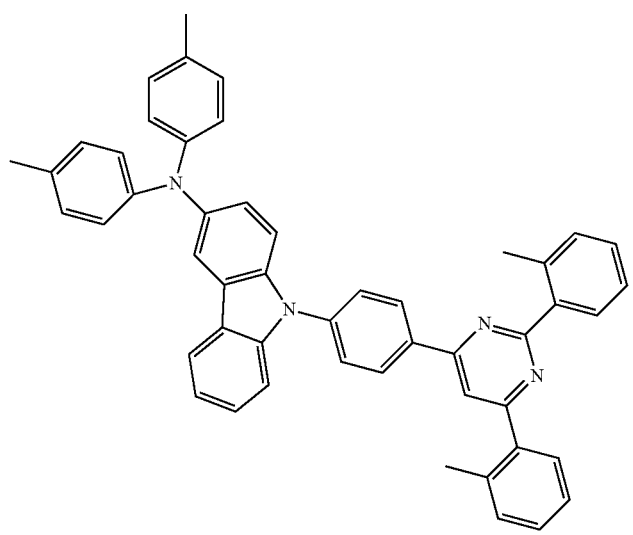
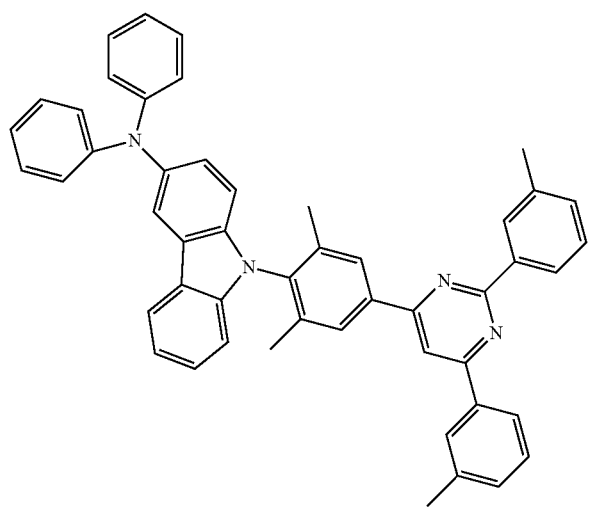

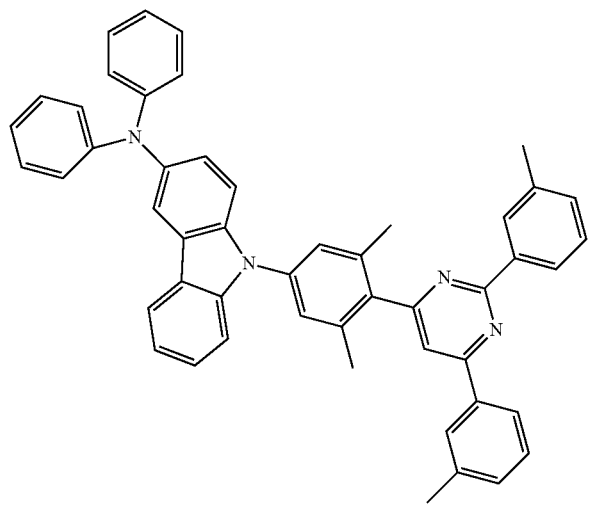
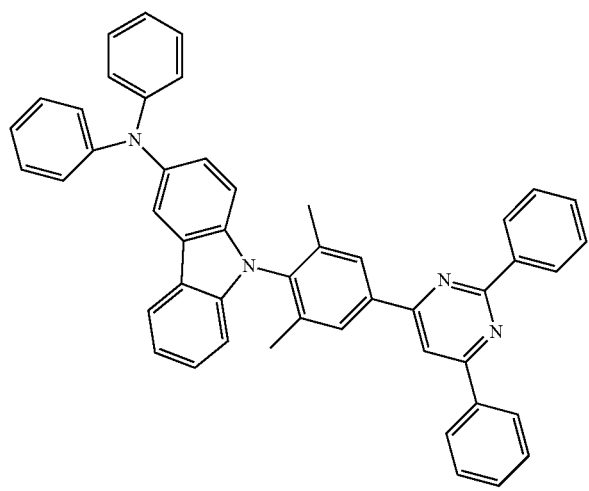
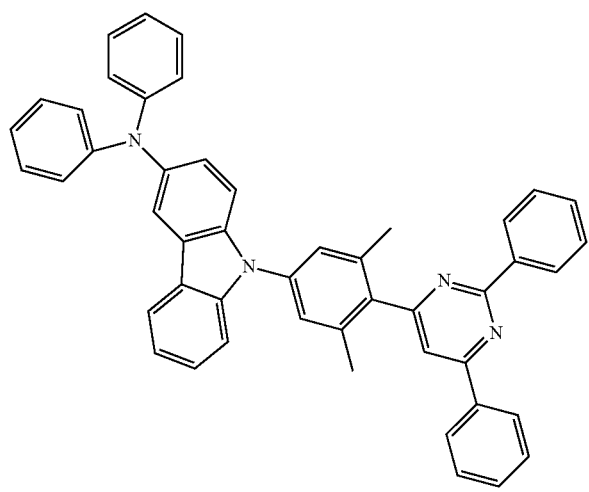

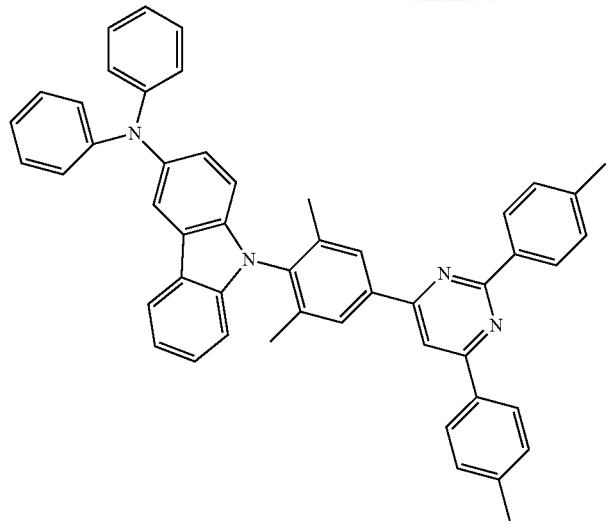
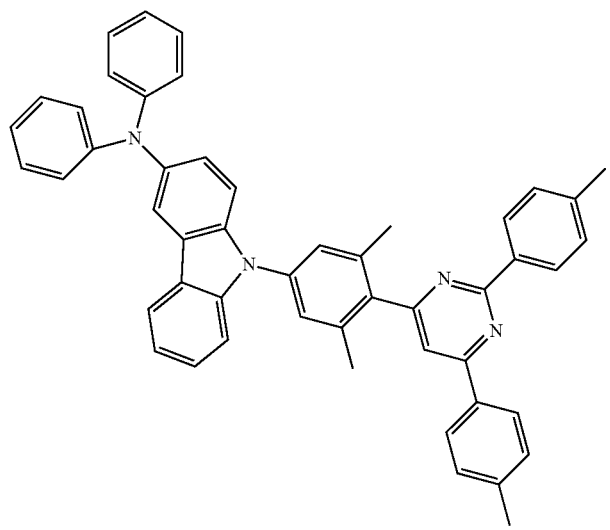
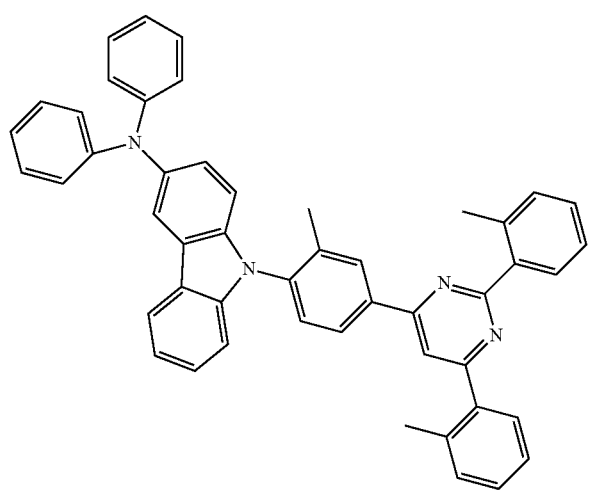

-continued
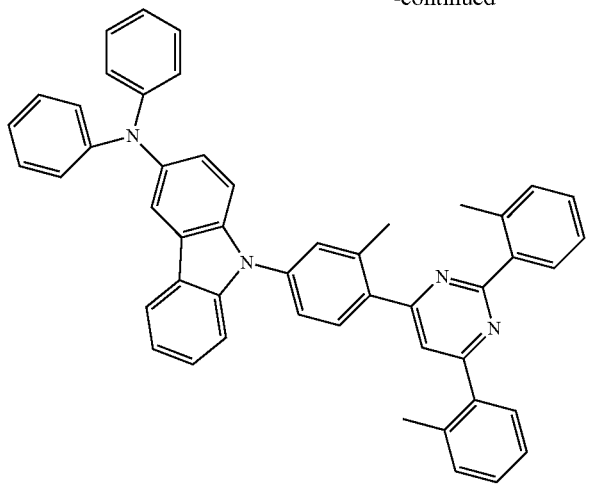
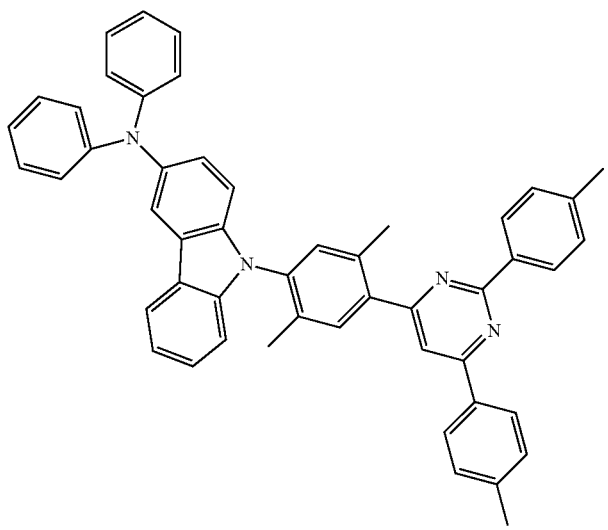
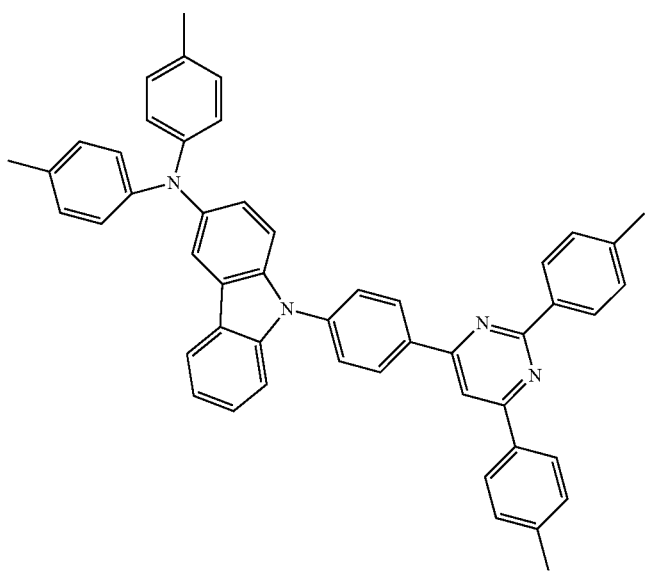

-continued
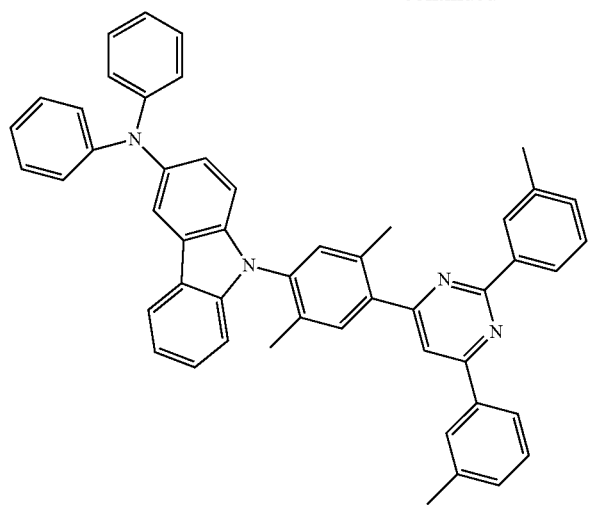
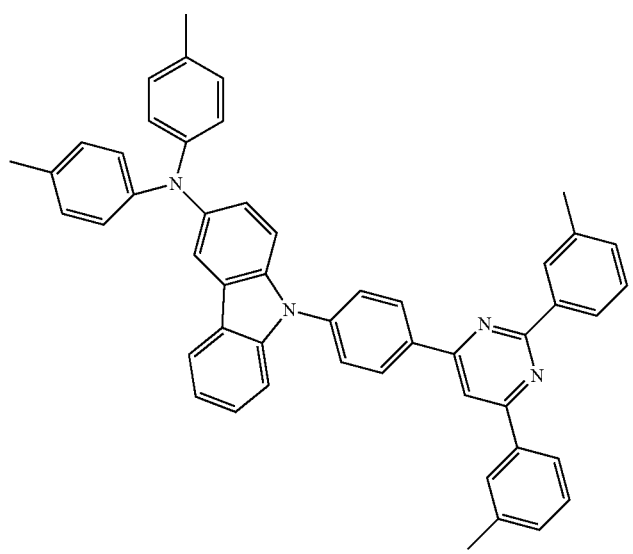
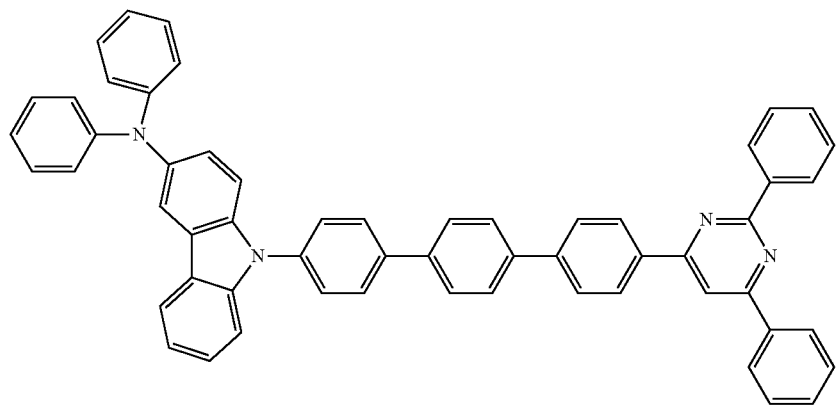

-continued
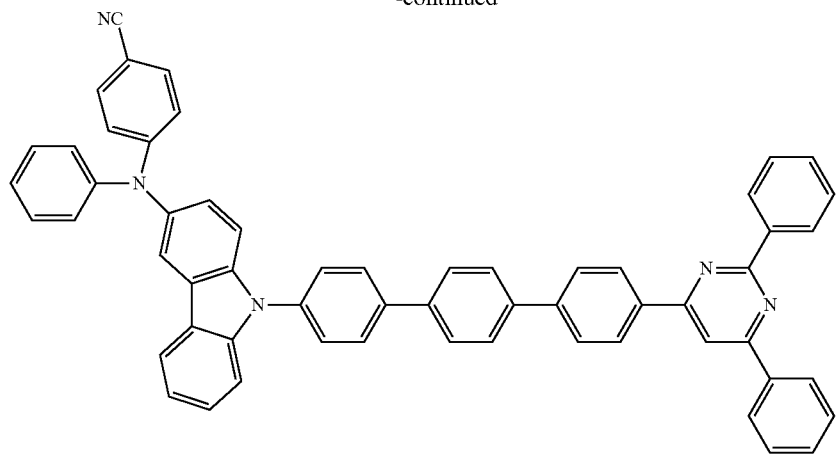
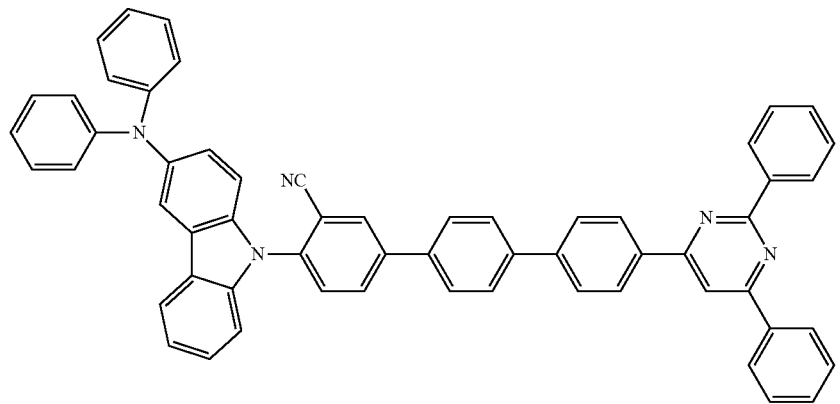
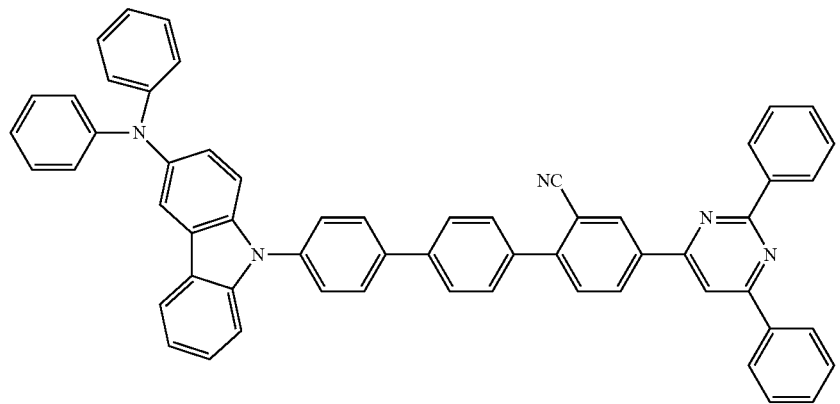
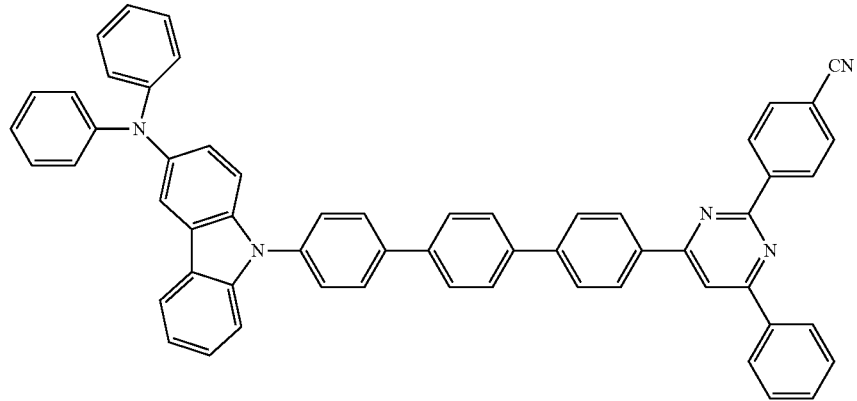

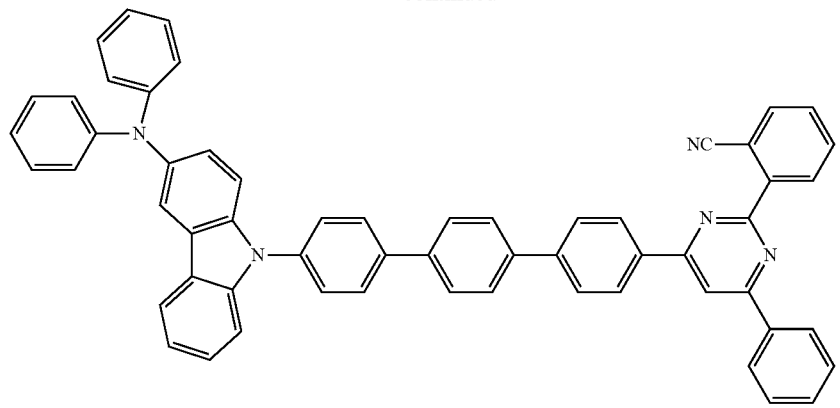
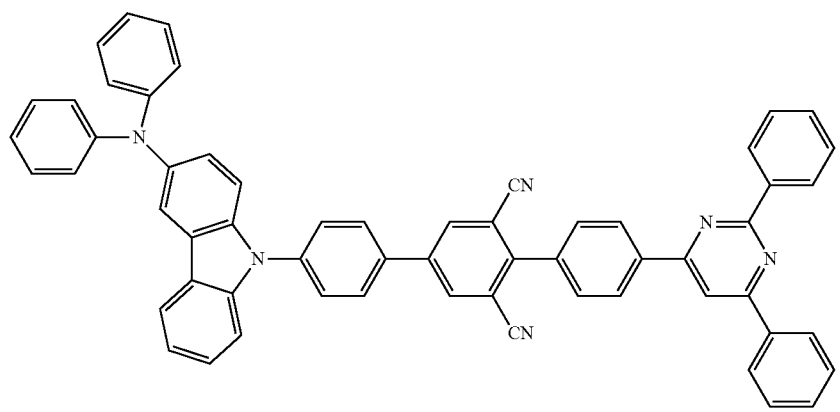
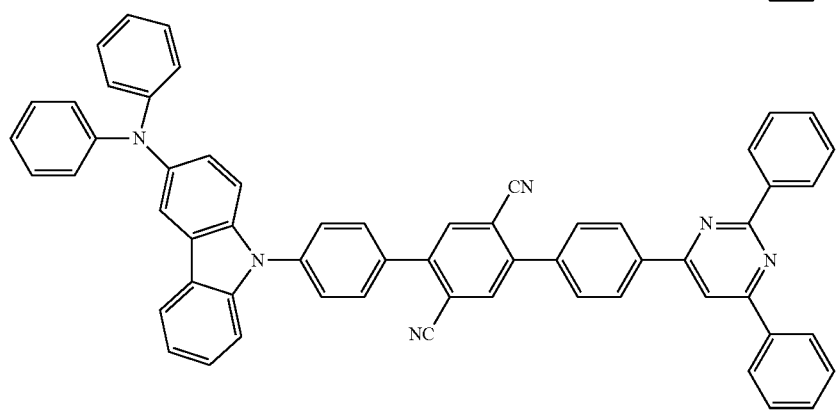
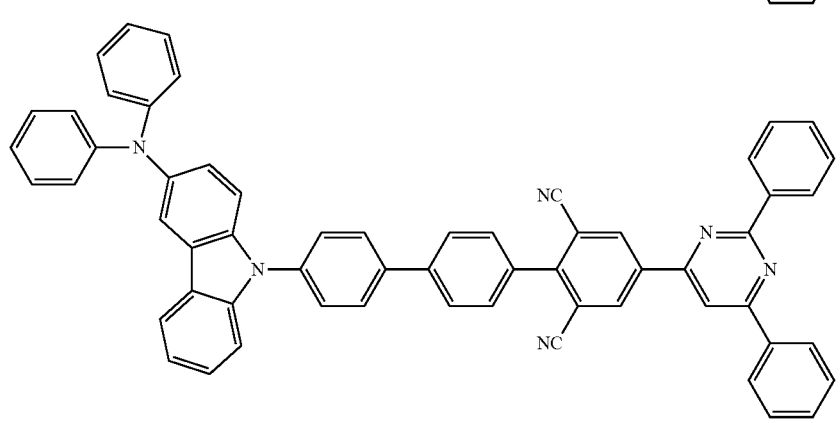

-continued
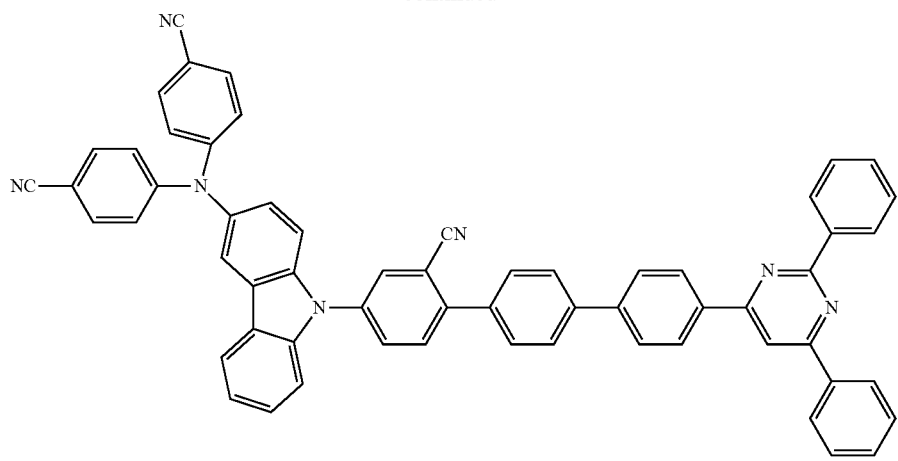
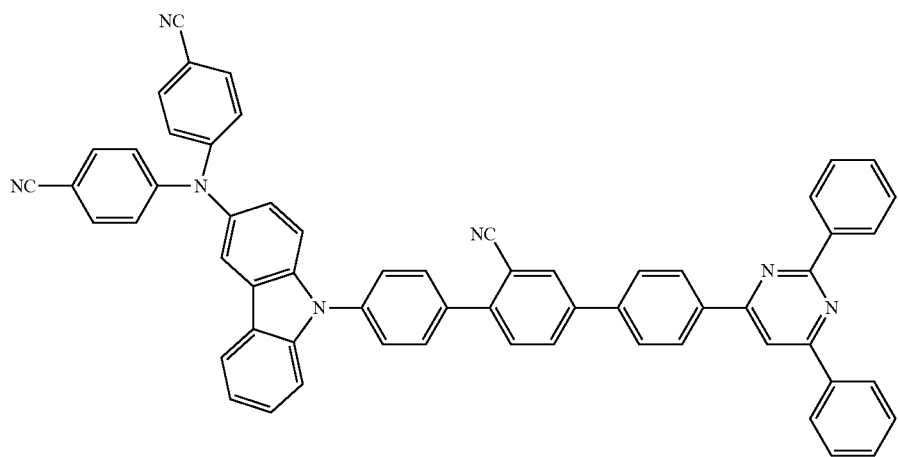
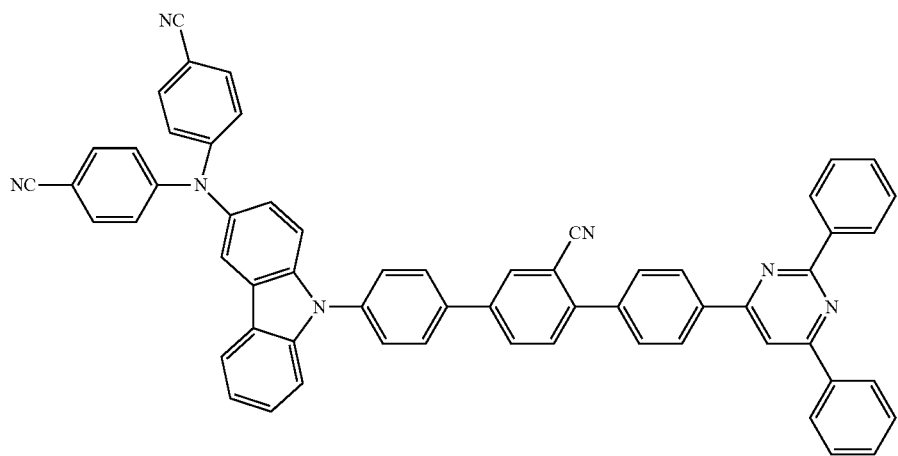

-continued
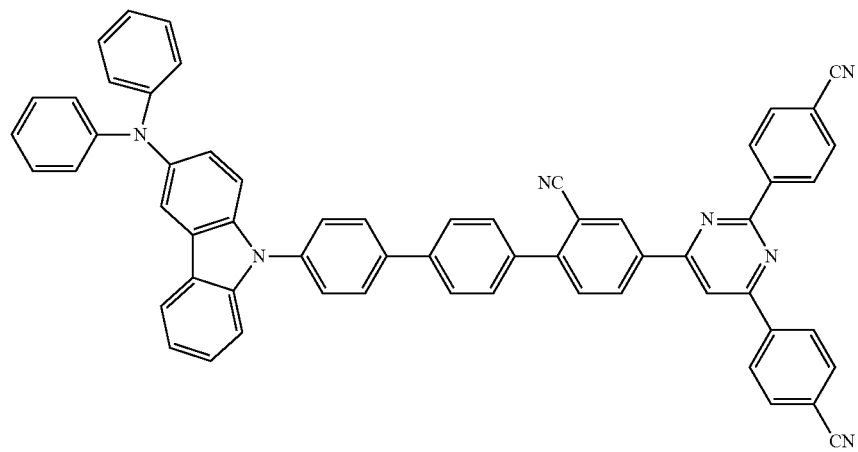
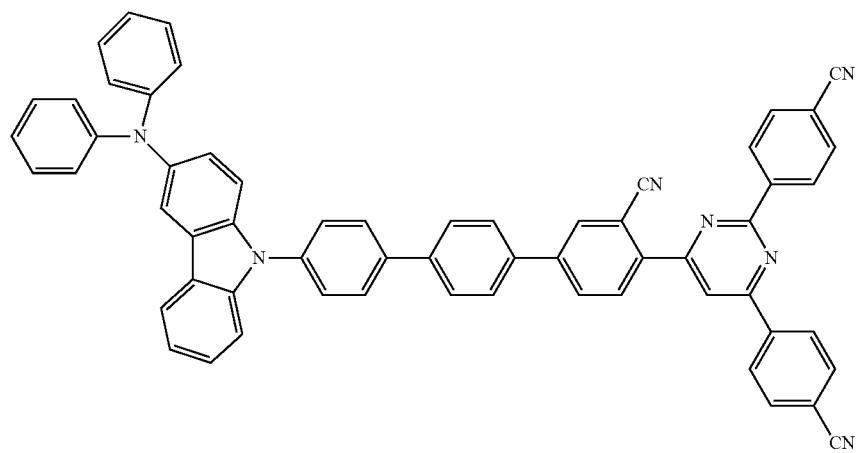
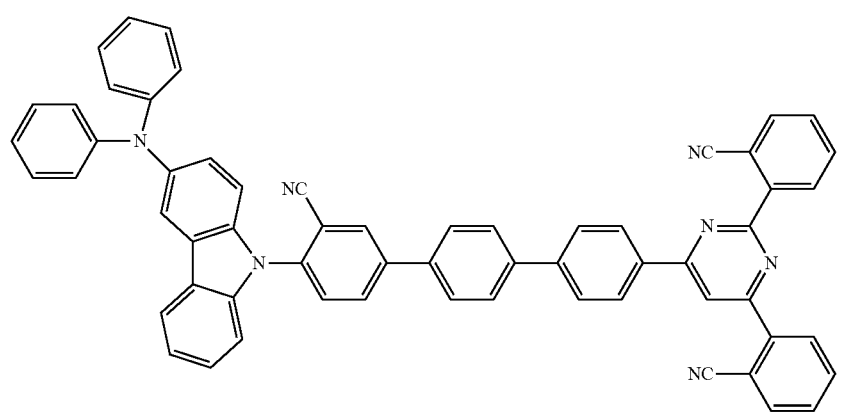

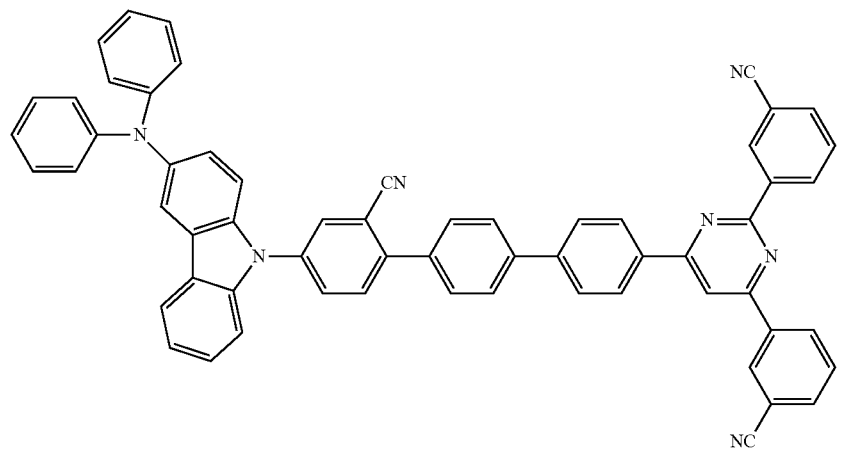
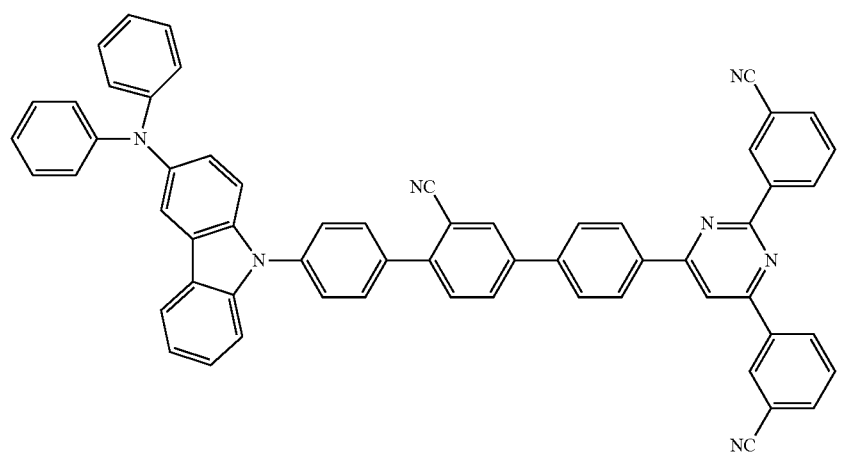
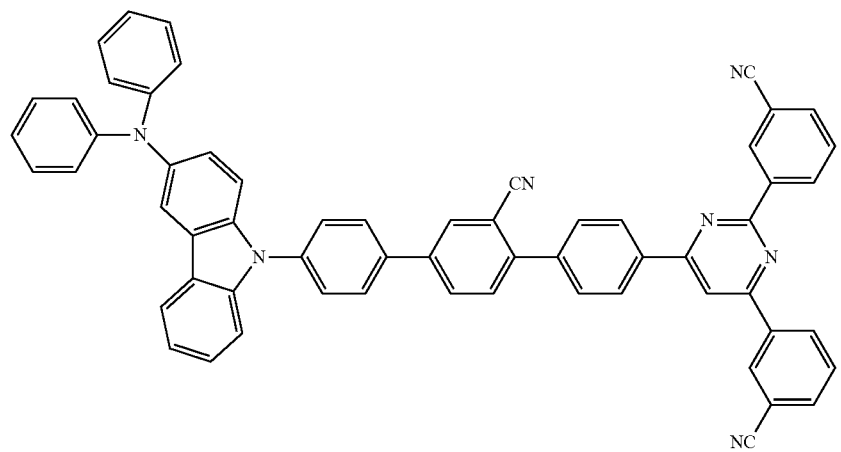

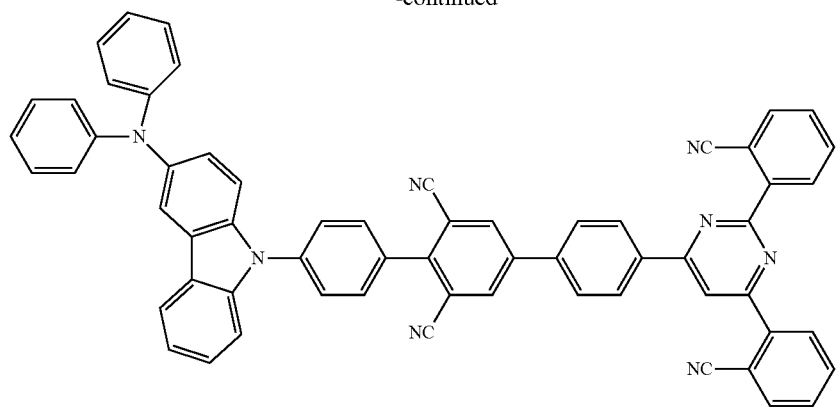
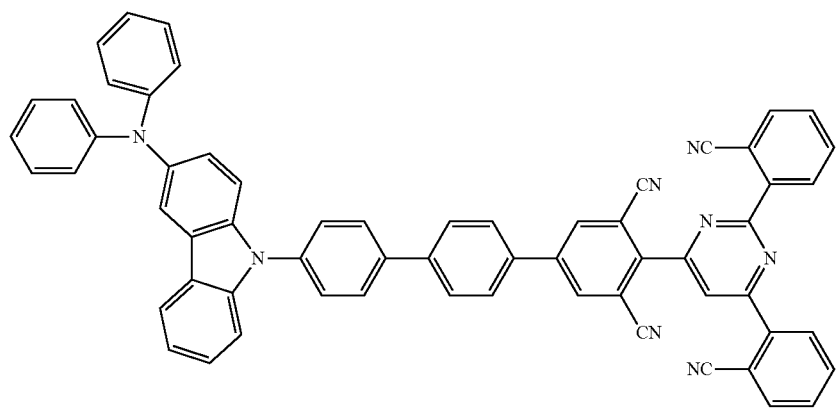
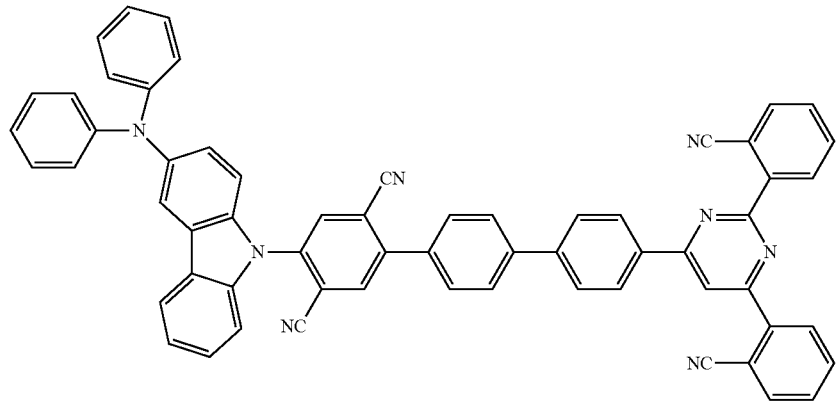
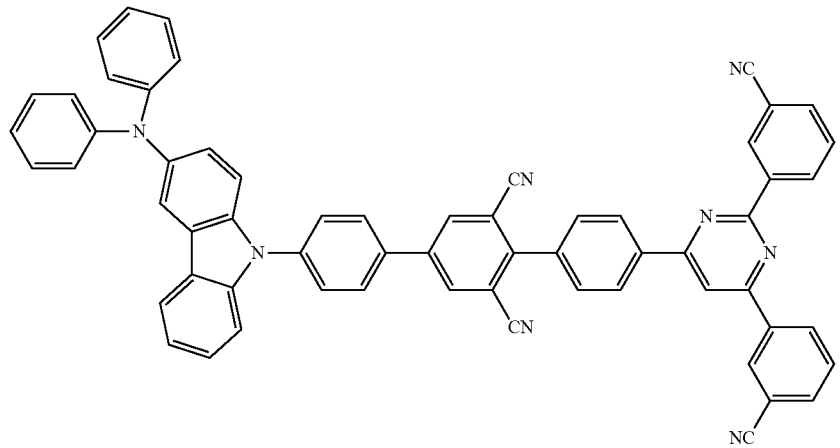

-continued
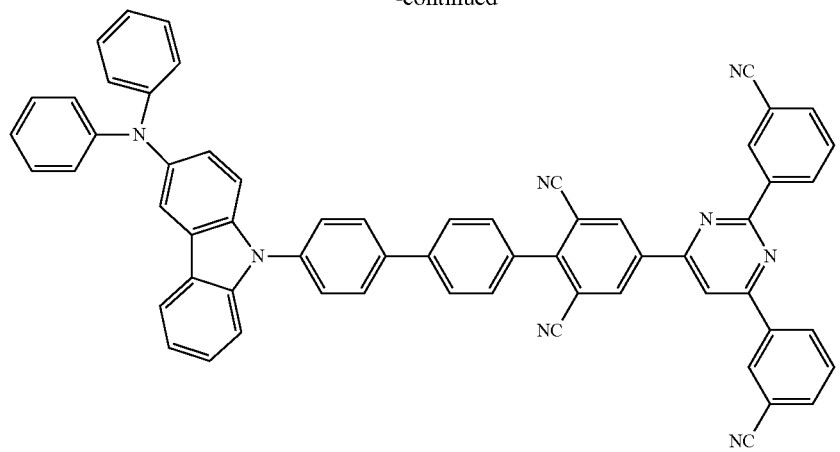
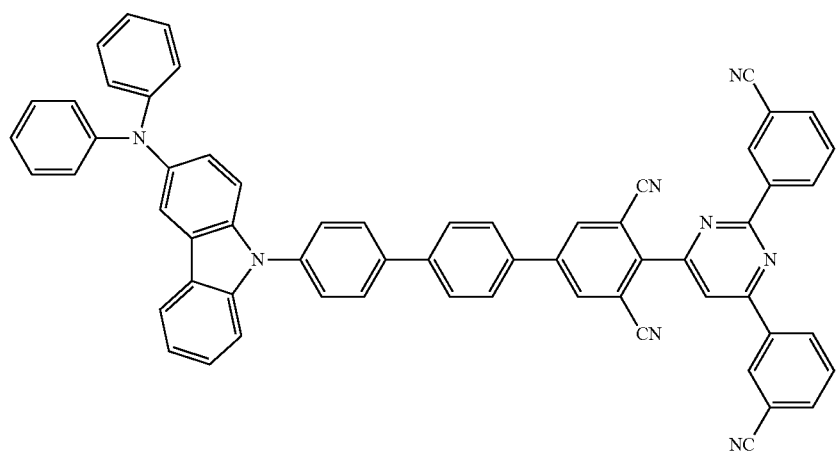
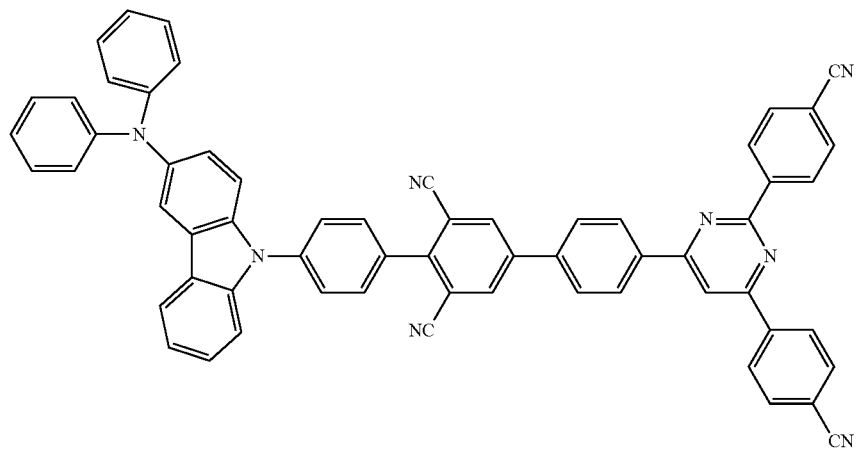

-continued
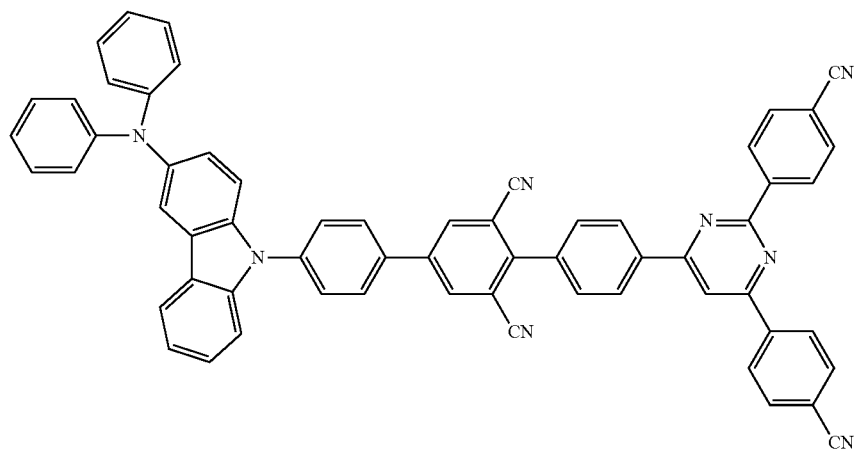
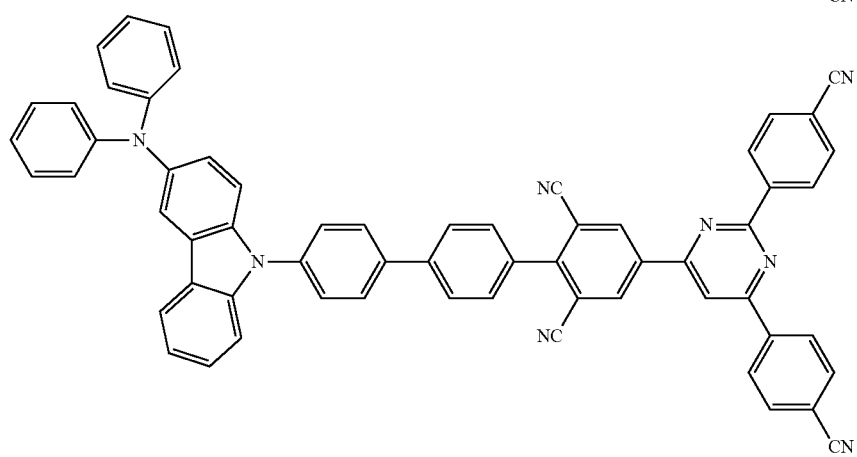
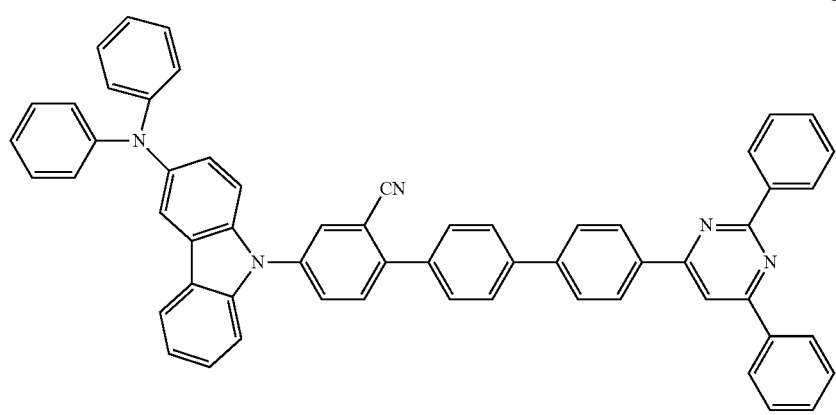
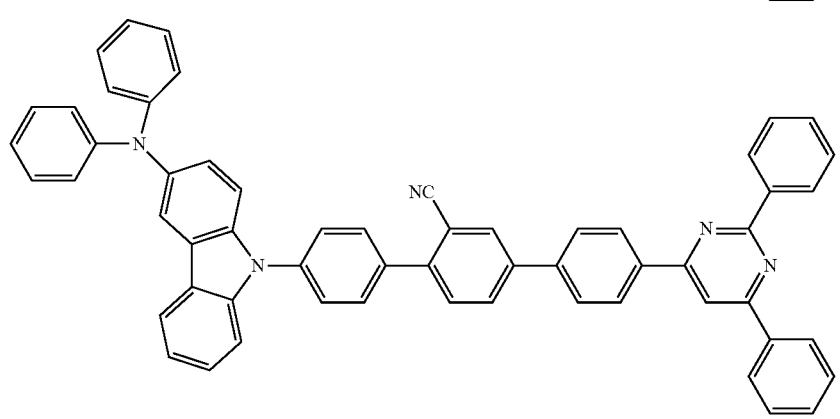

-continued
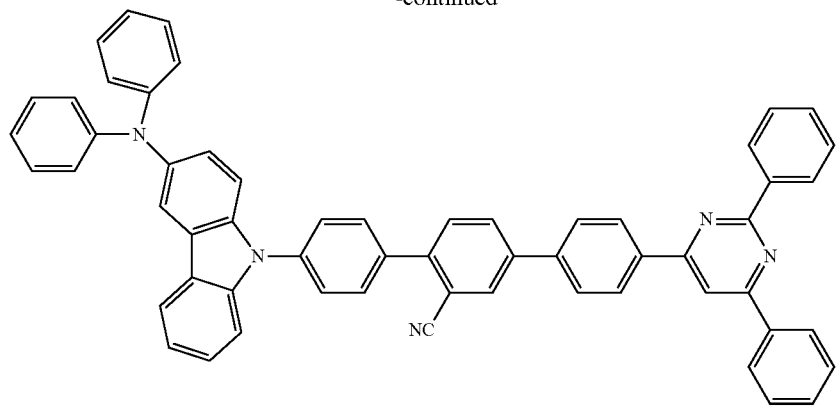
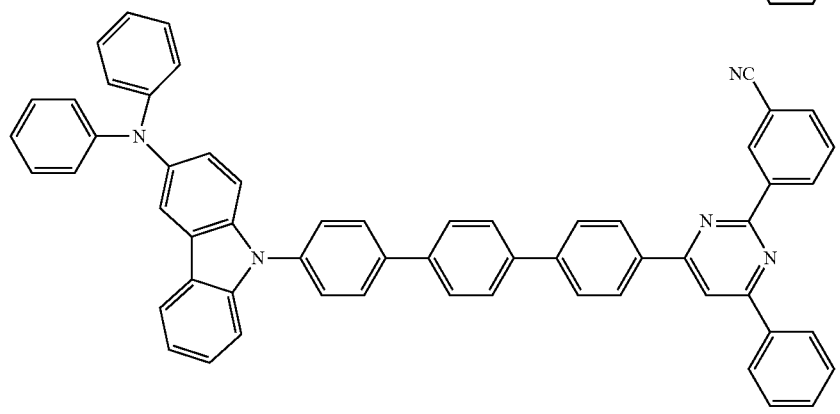
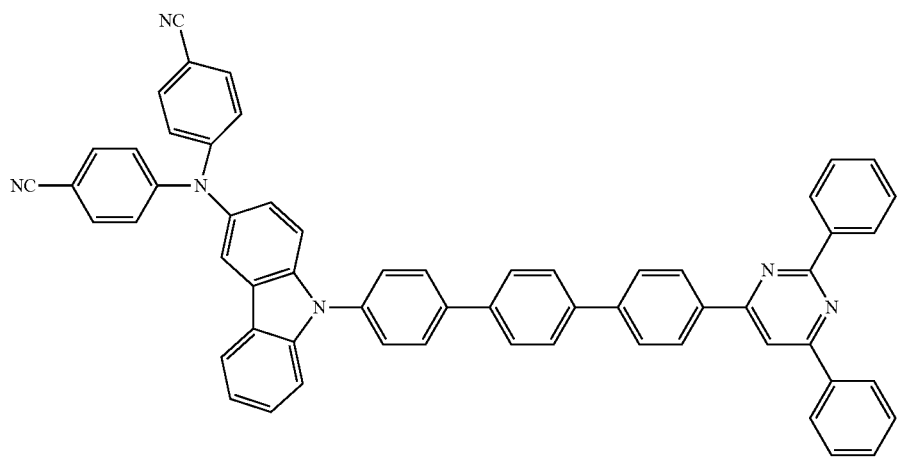
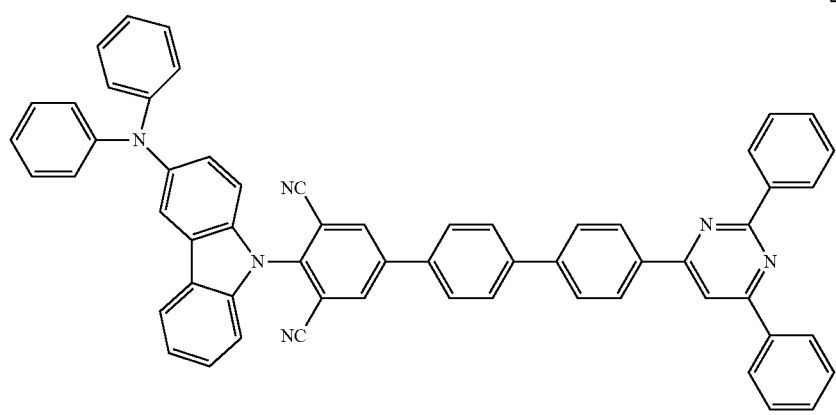

-continued
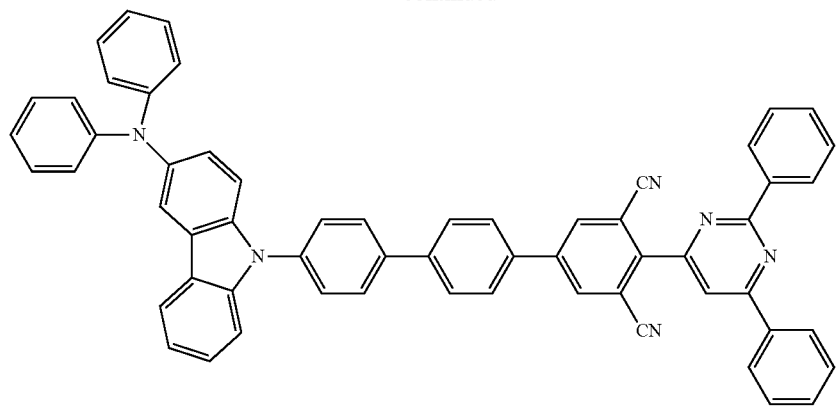
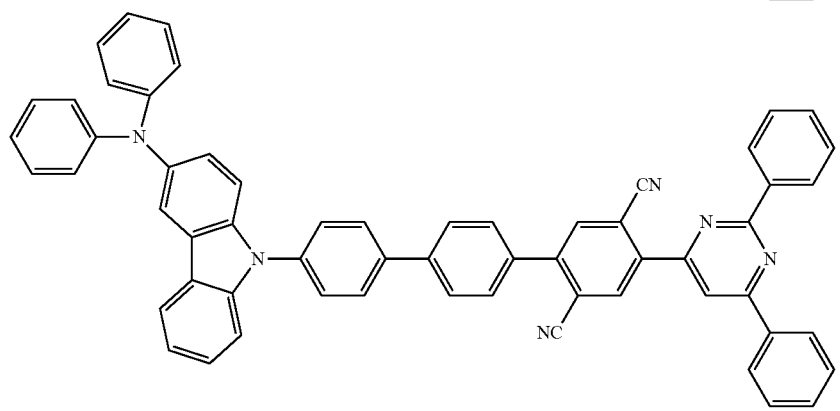
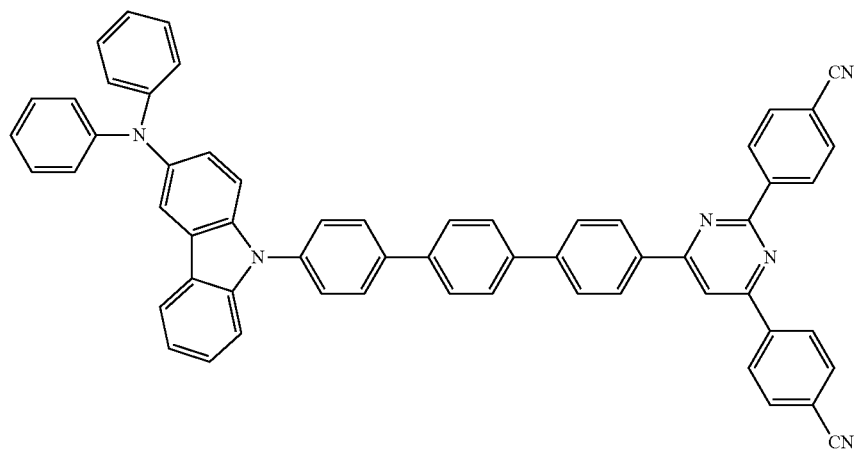
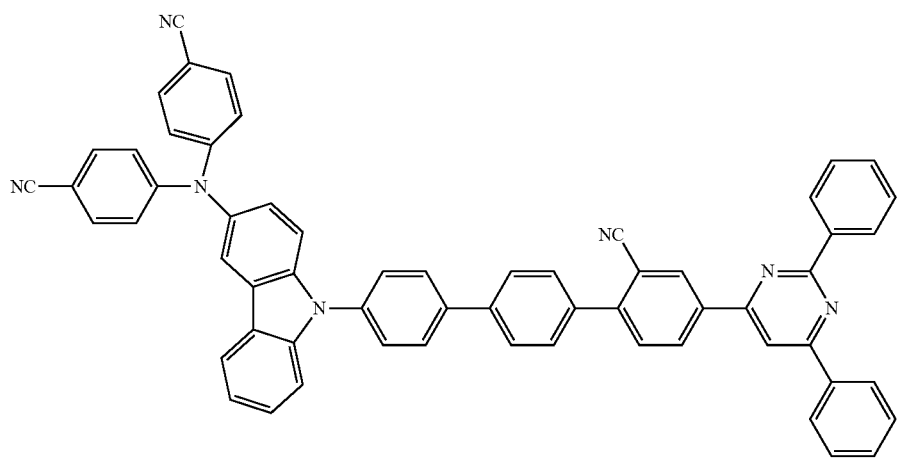

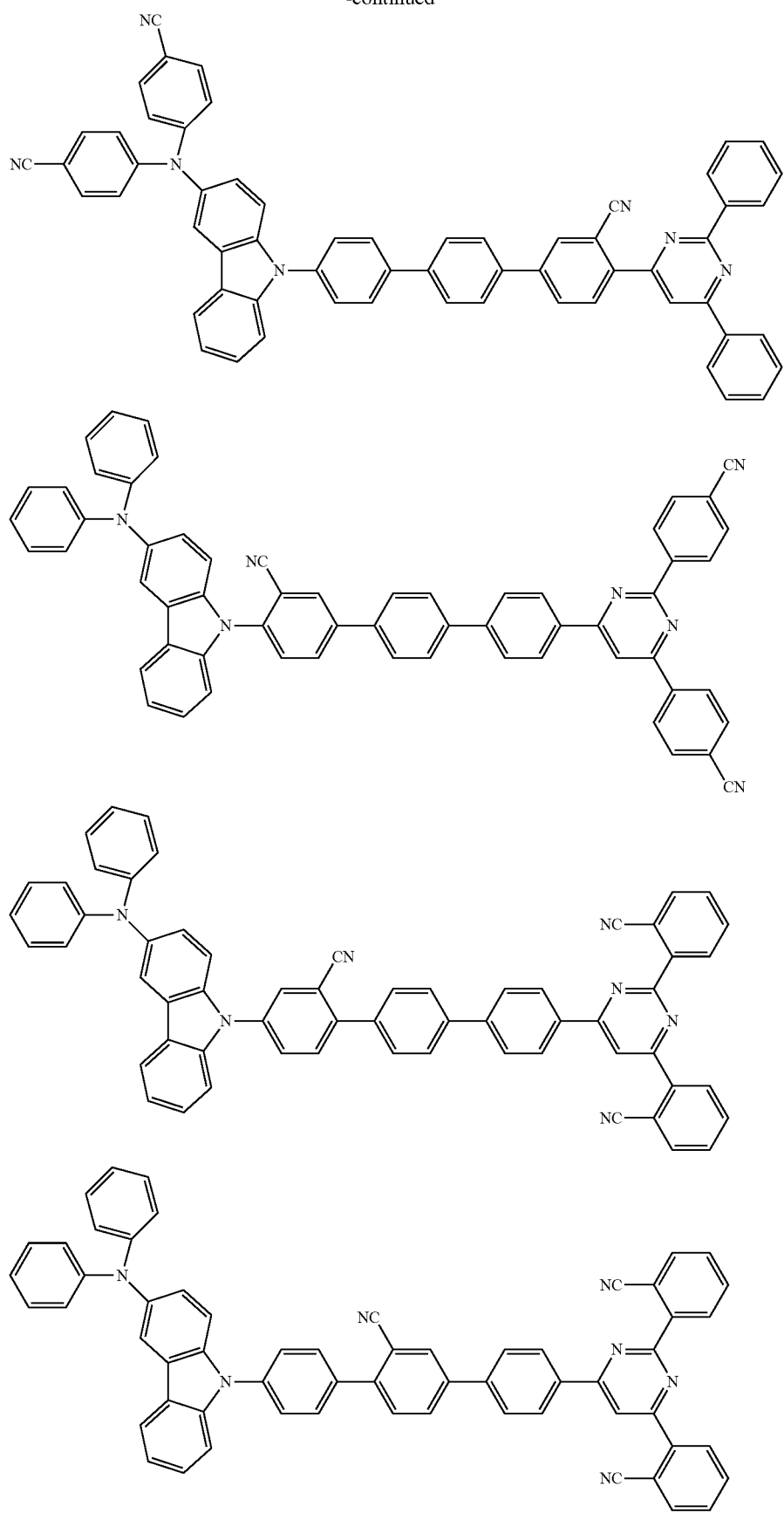

-continued
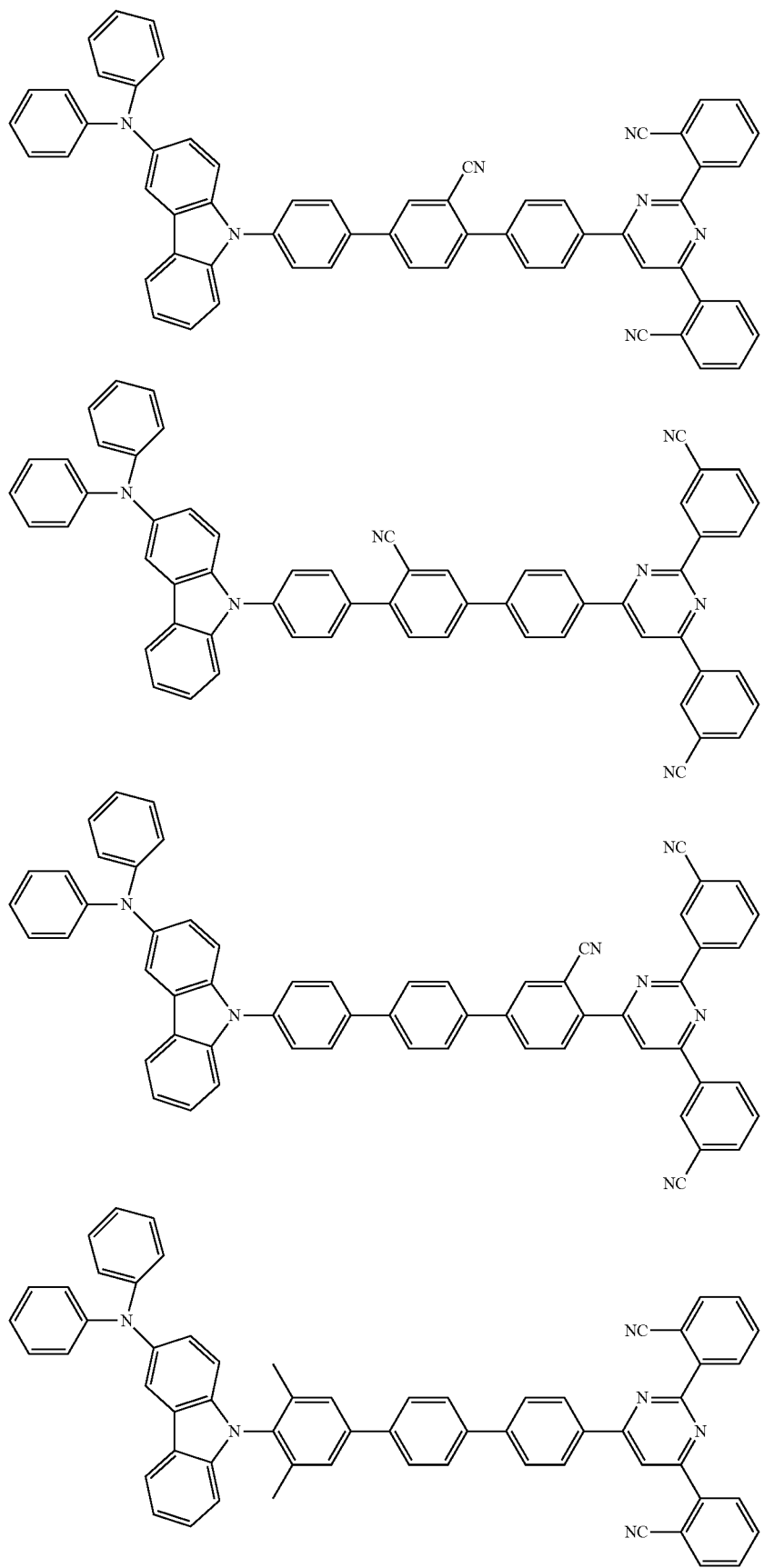

-continued
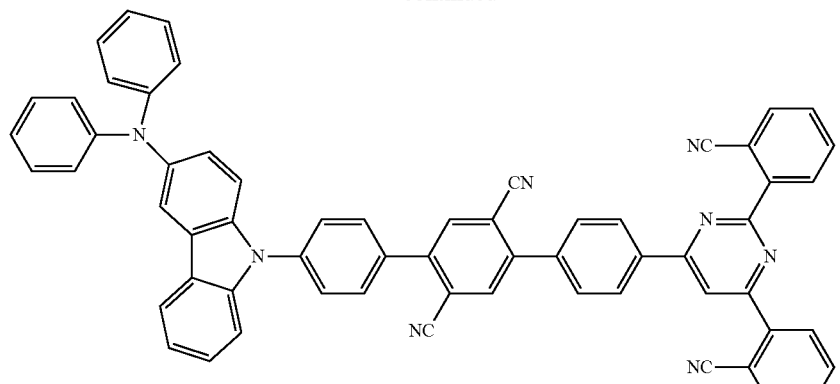
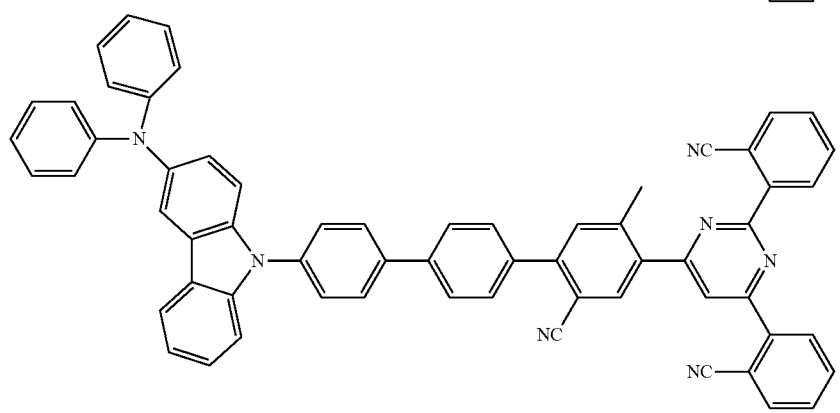
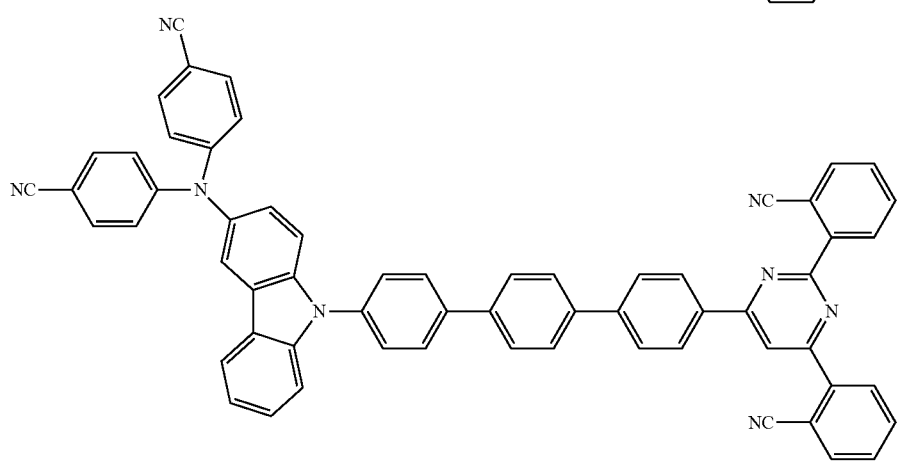
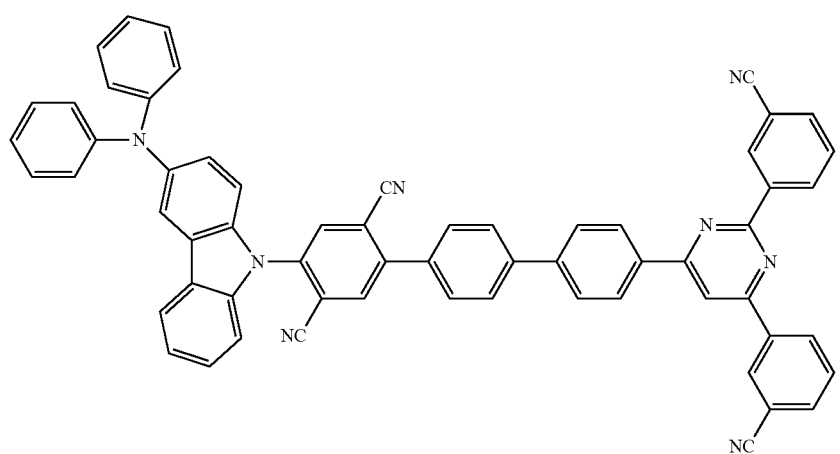

-continued
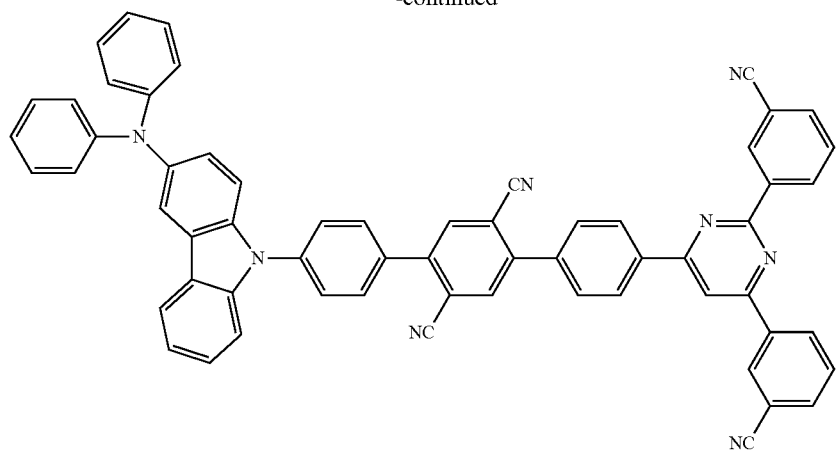
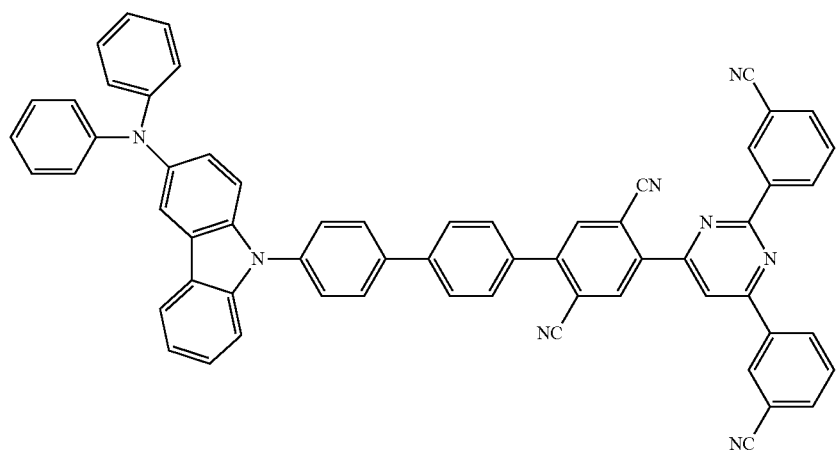
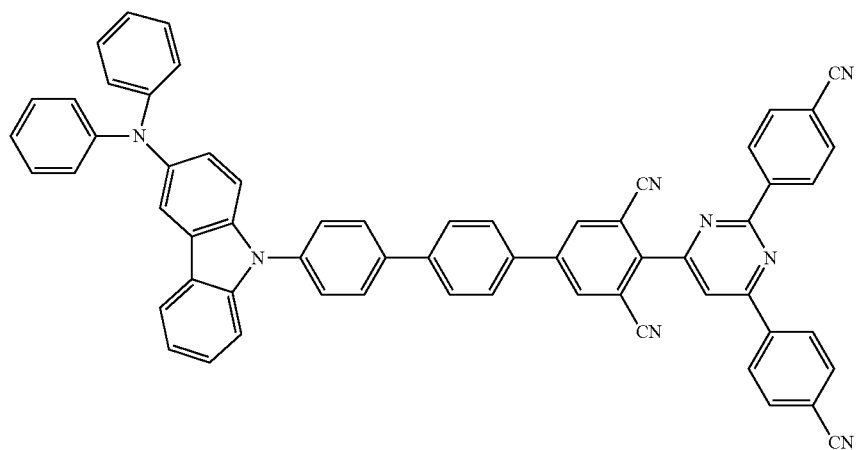

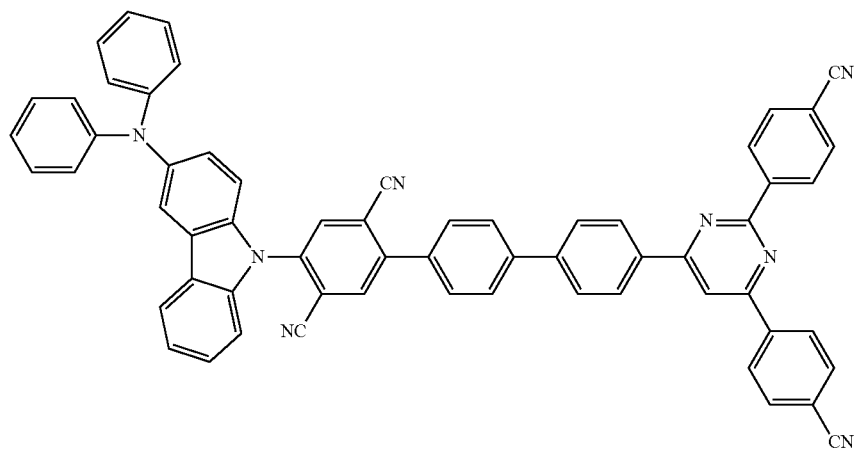
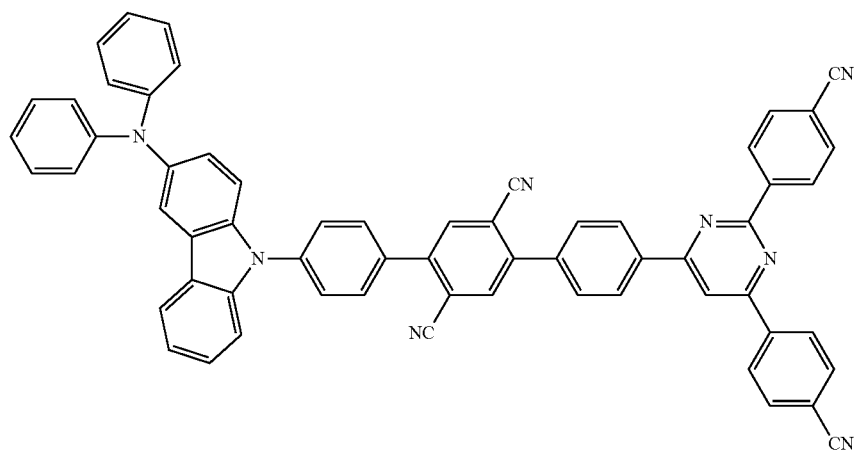
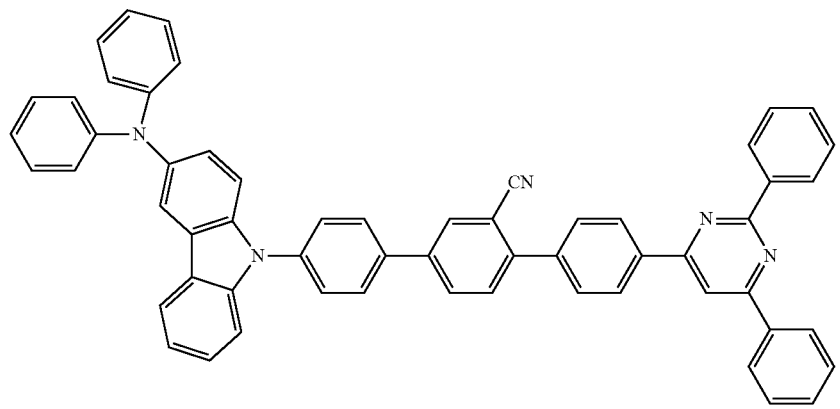
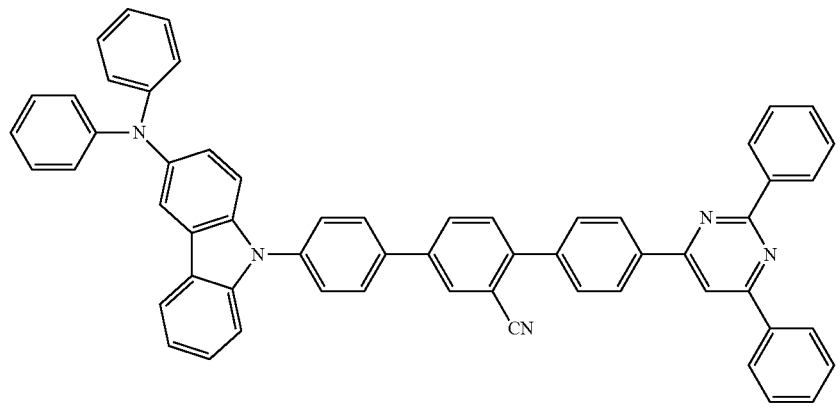

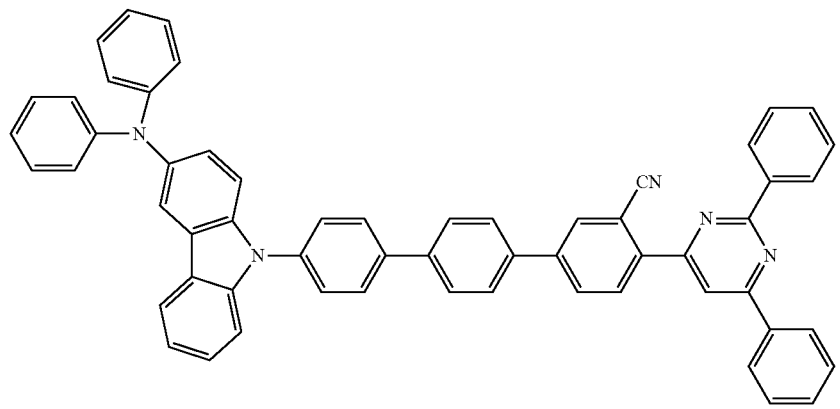
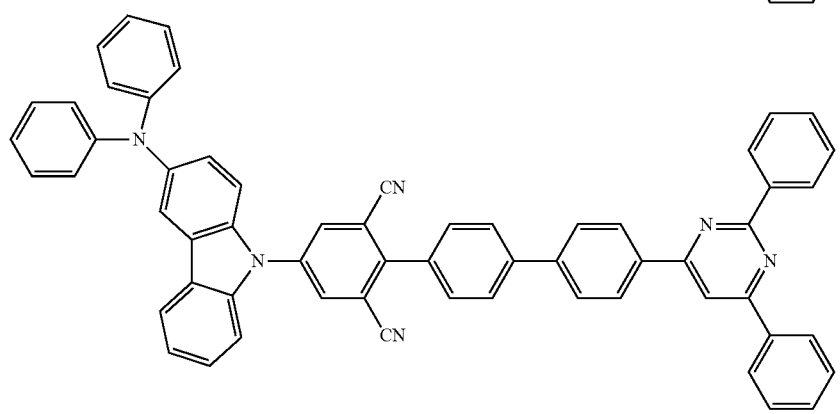
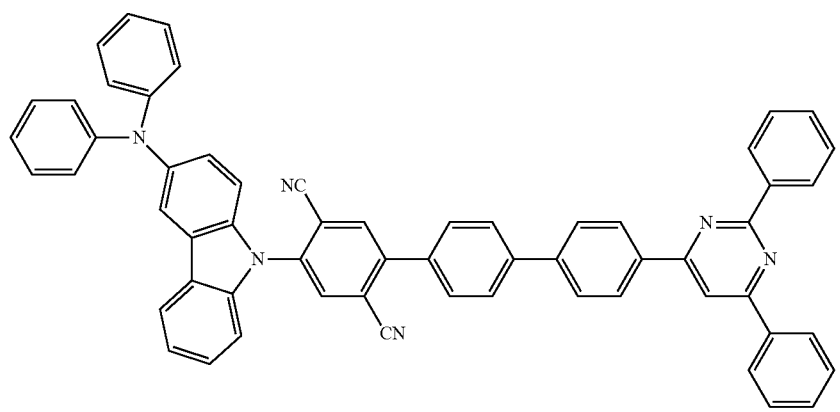
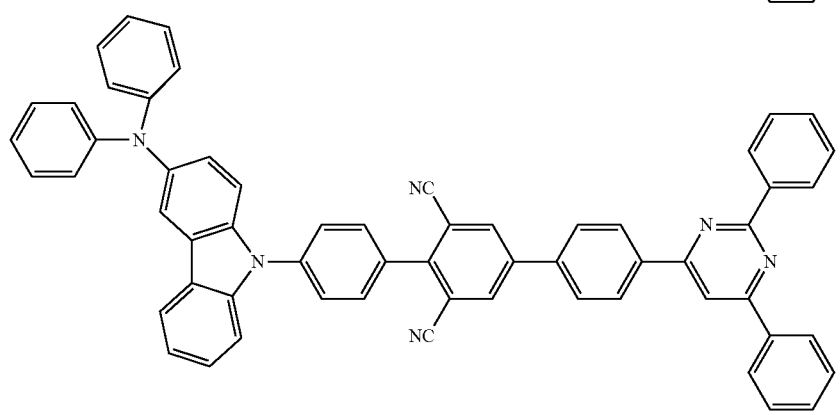

887
-continued
888
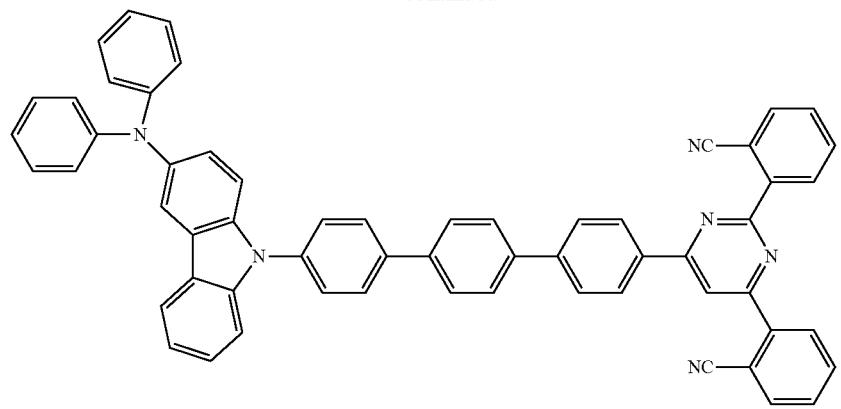
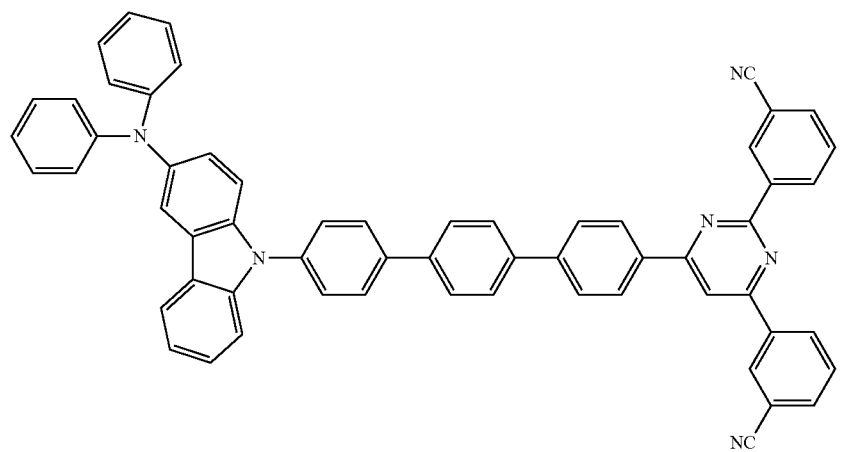
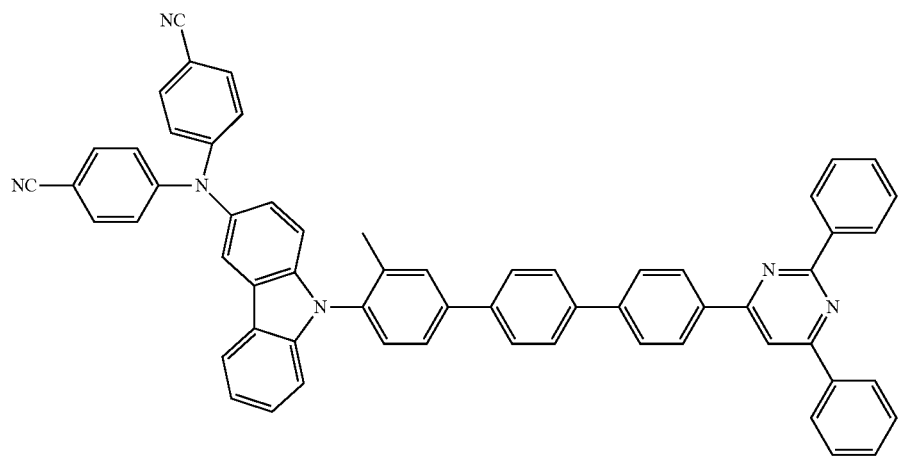

-continued
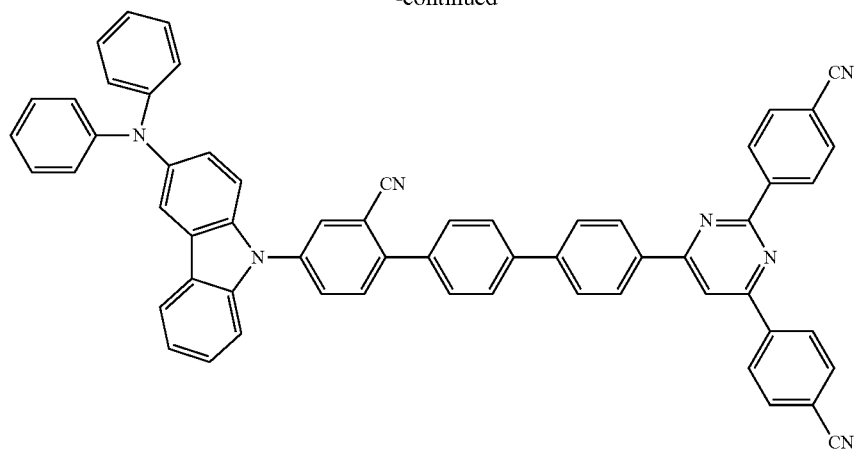
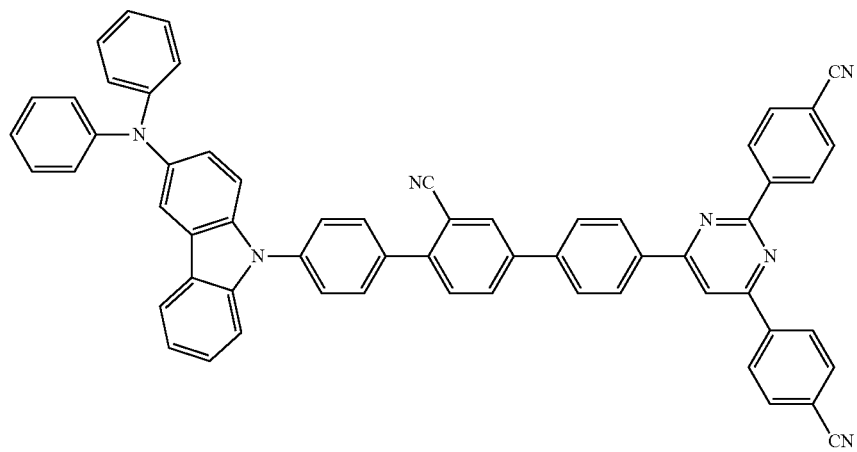
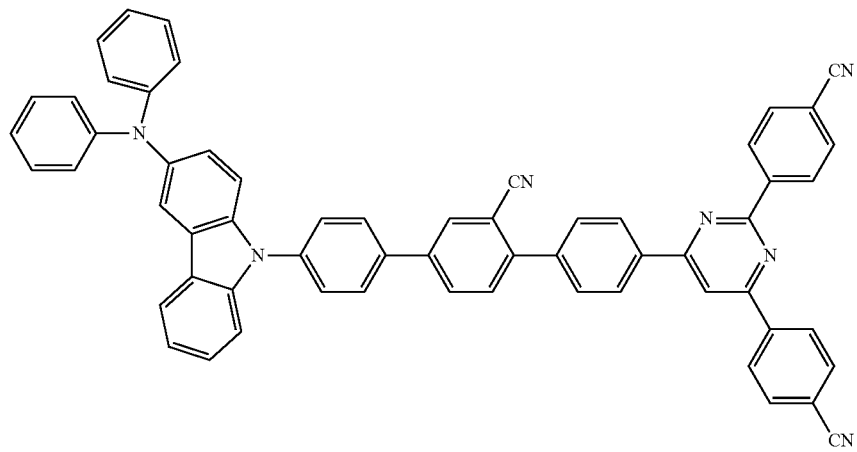

-continued
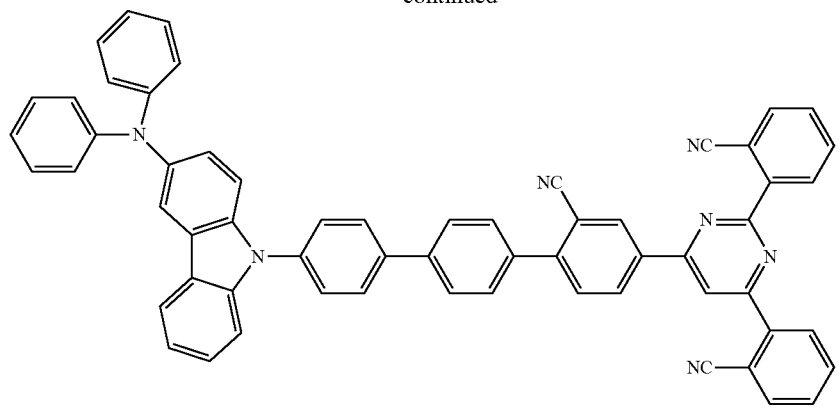
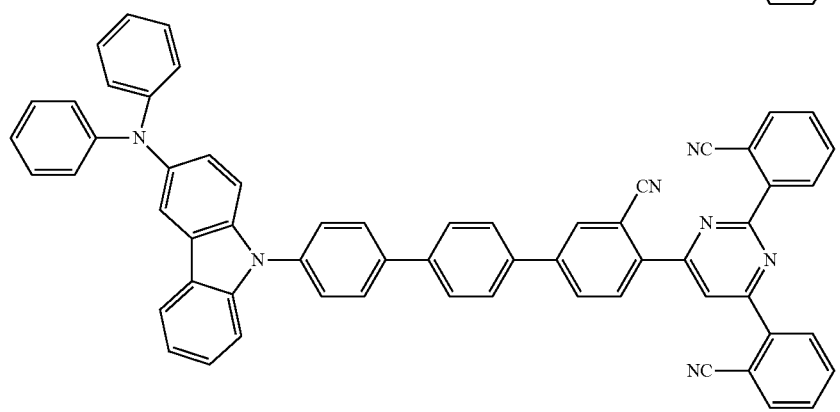
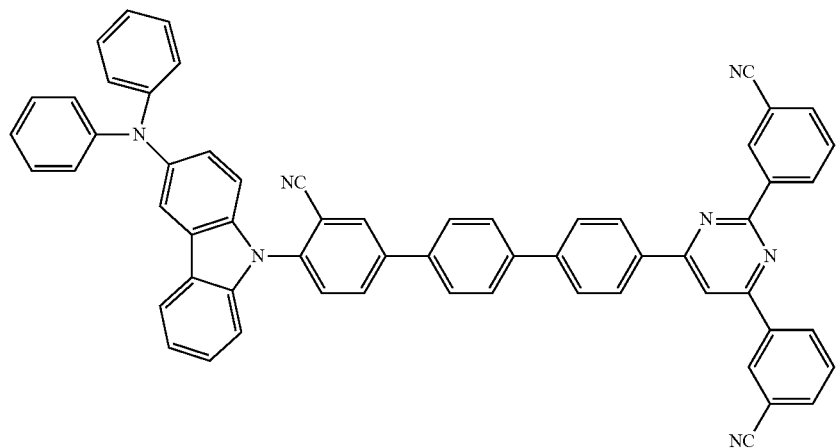
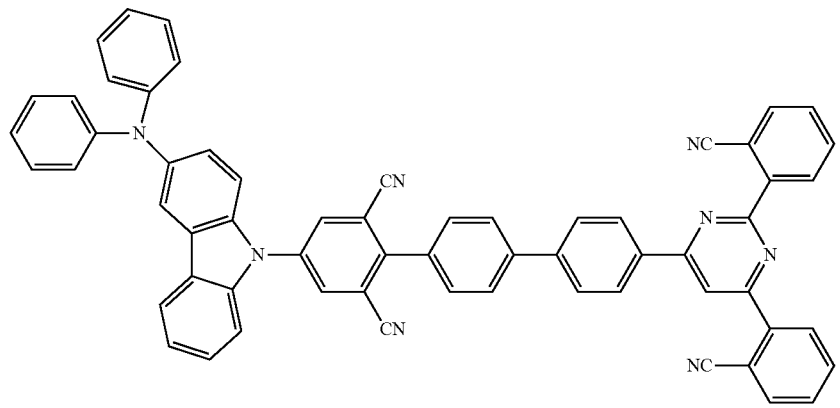

-continued
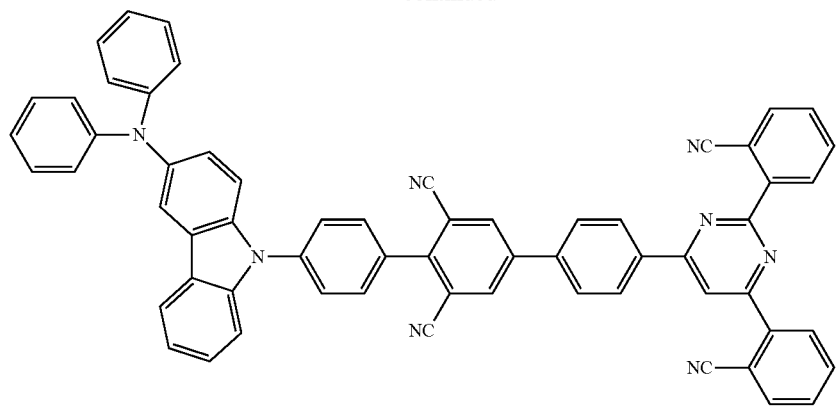
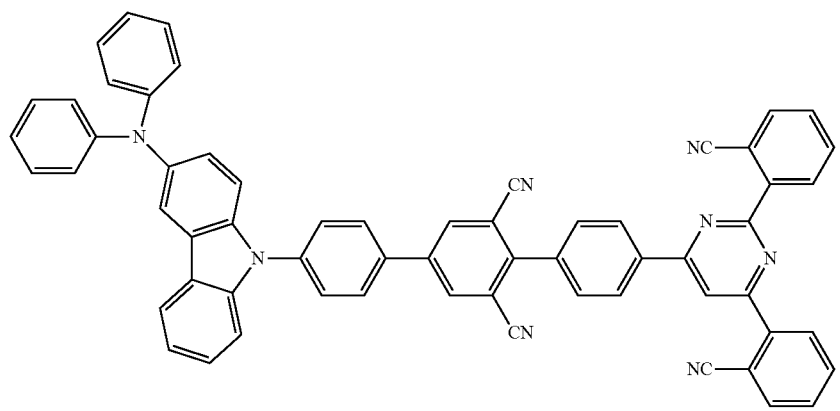
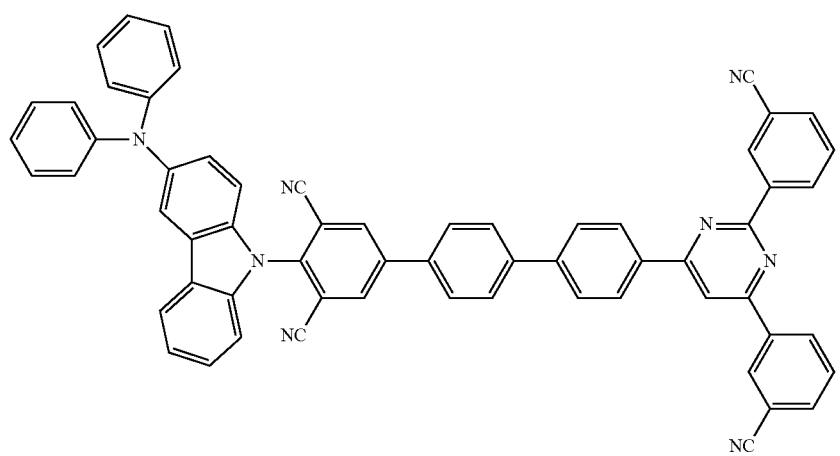
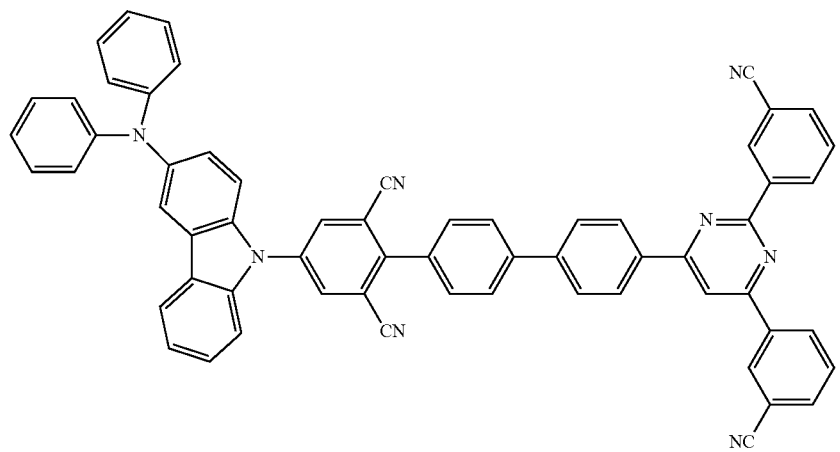

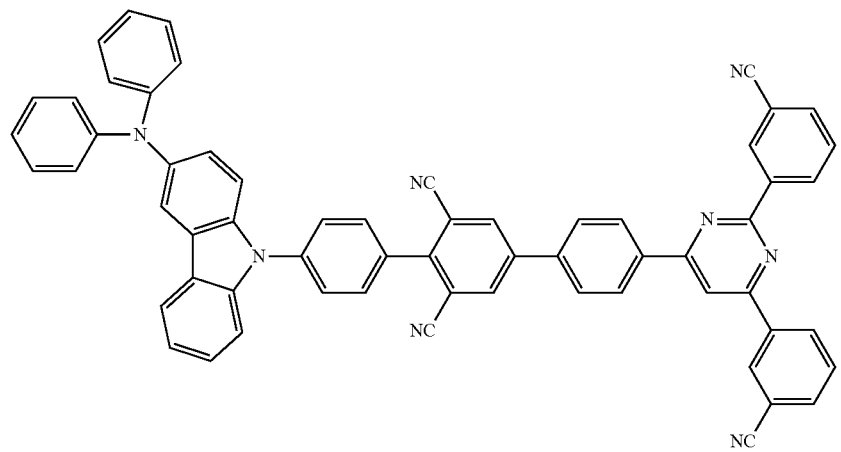
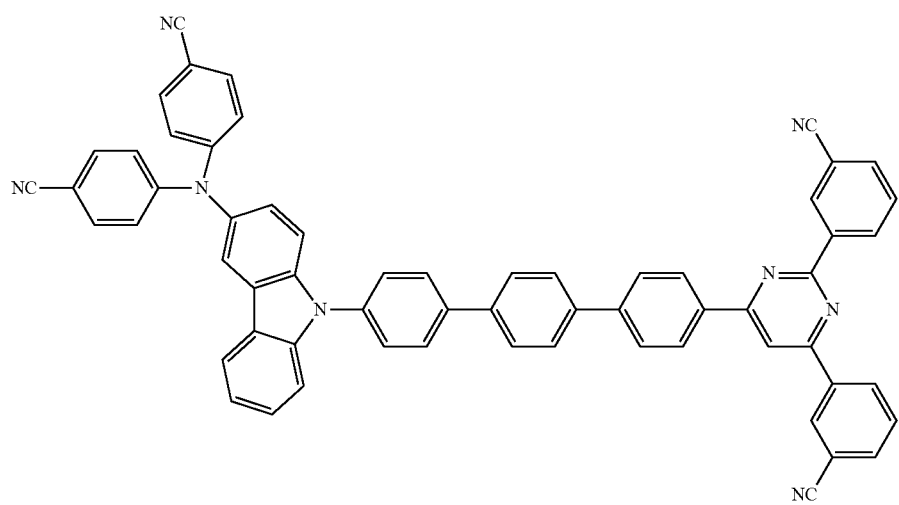
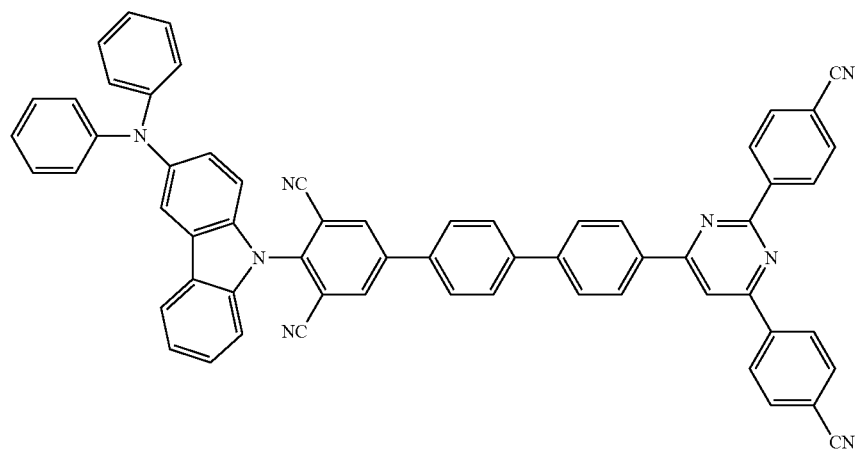

897
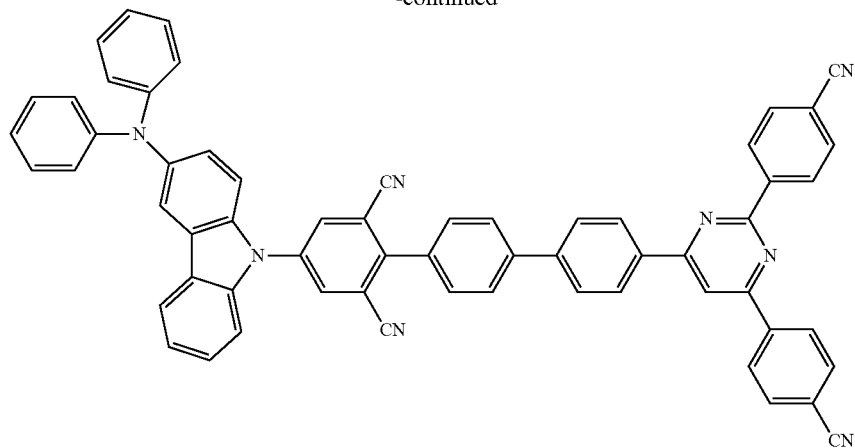
898
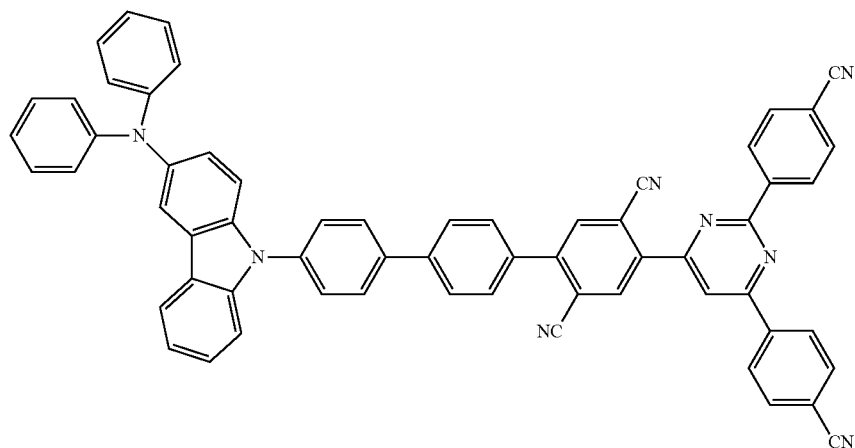
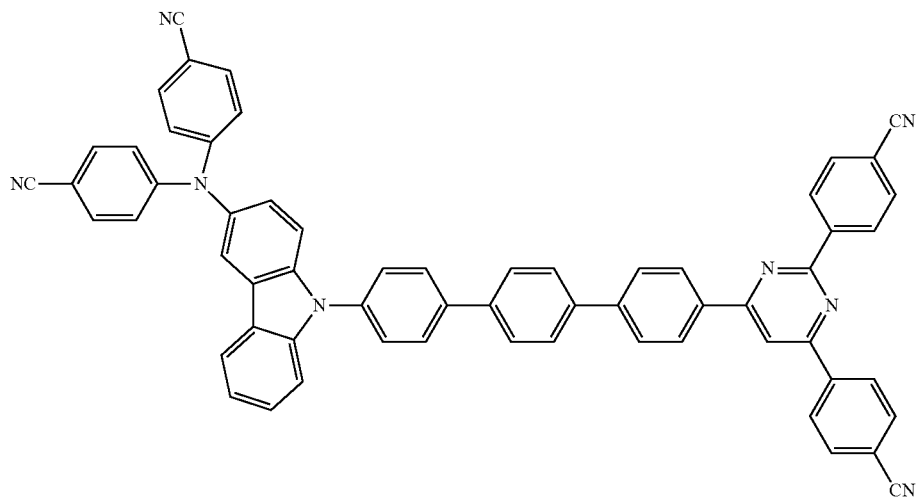

-continued
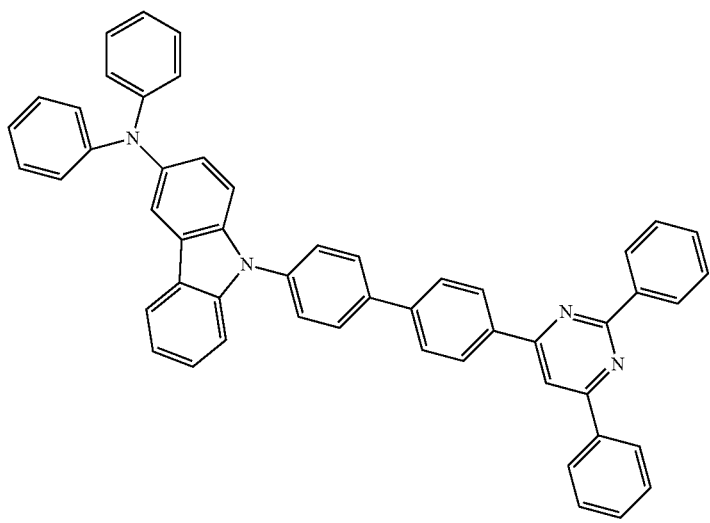
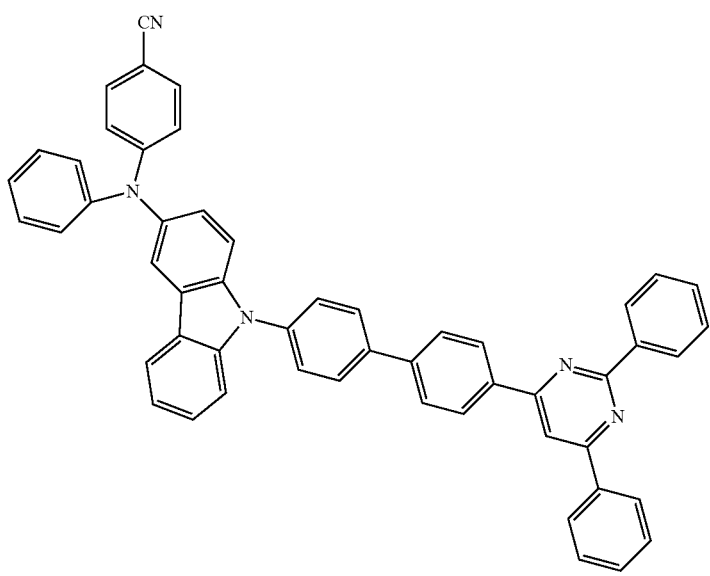
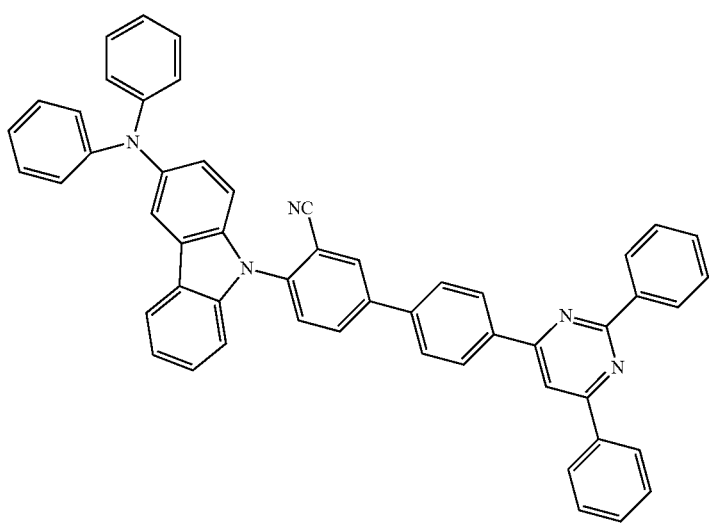

901
-continued
902
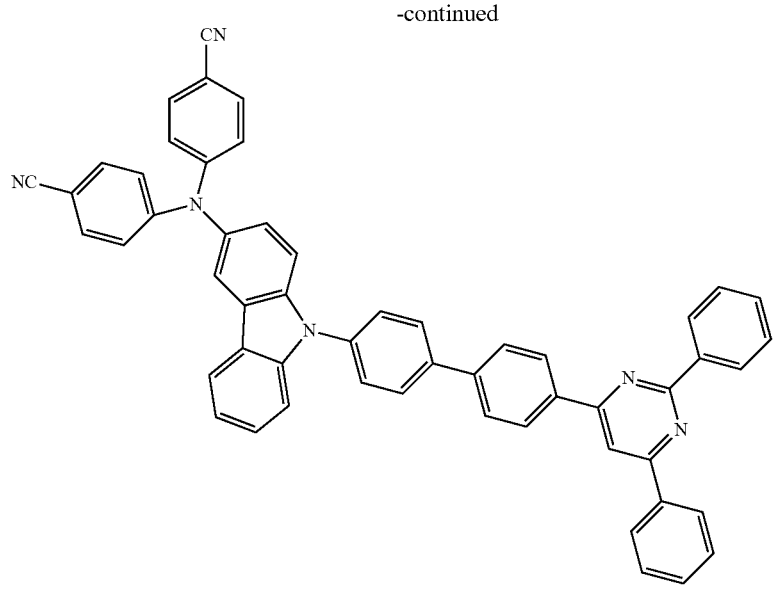
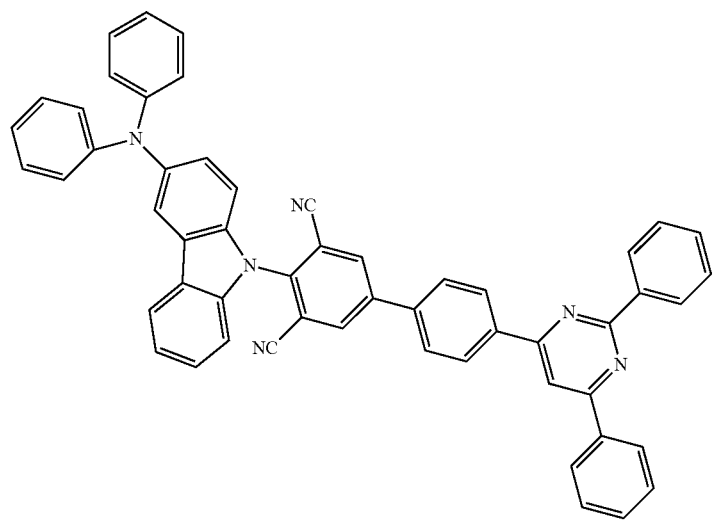
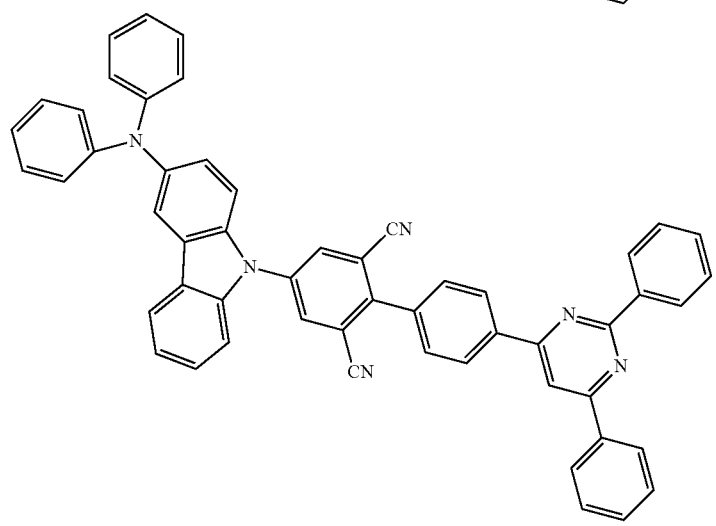

-continued
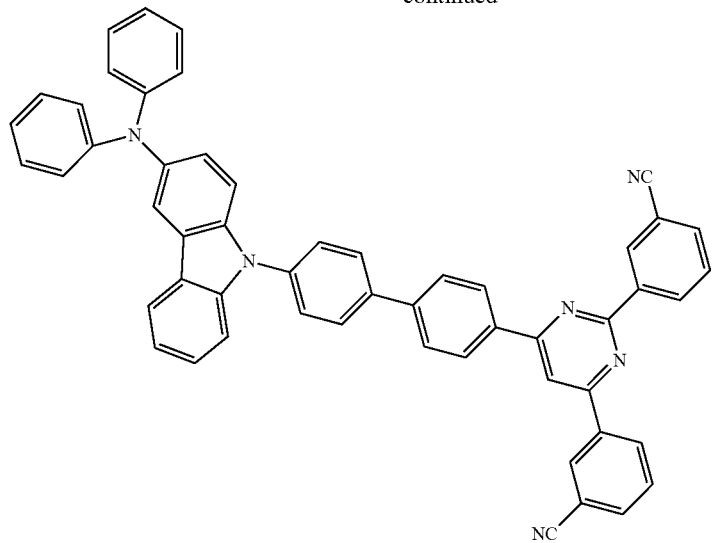
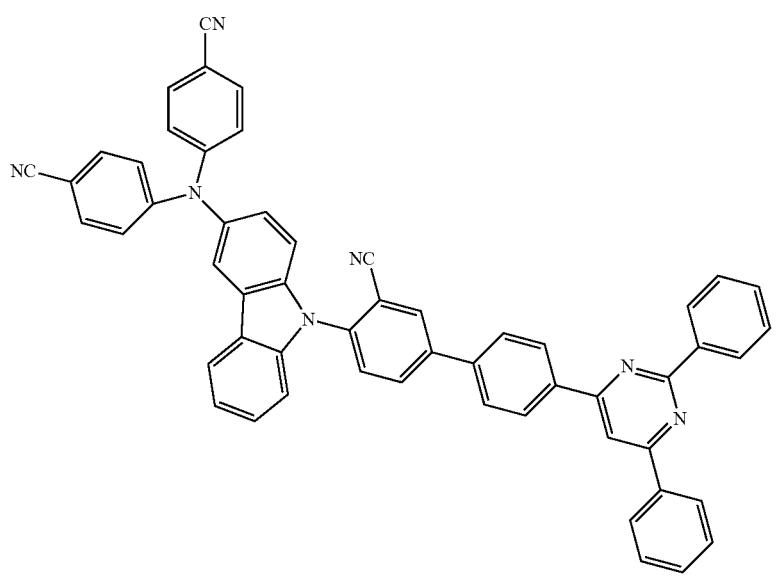
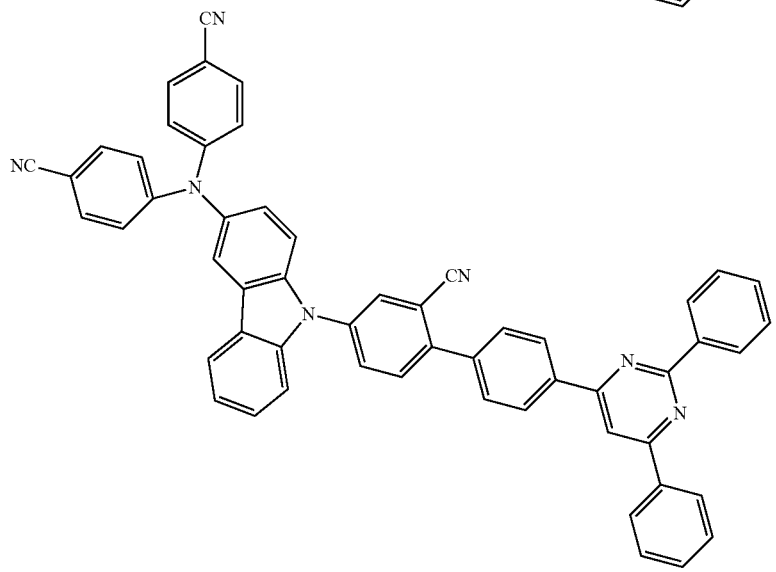

-continued
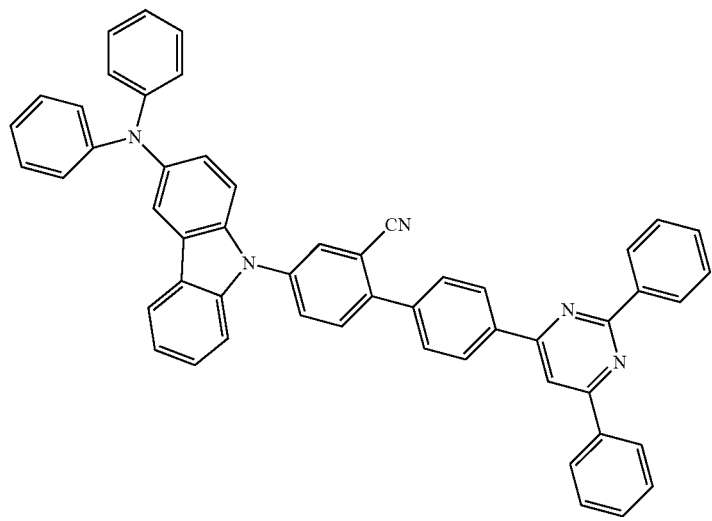
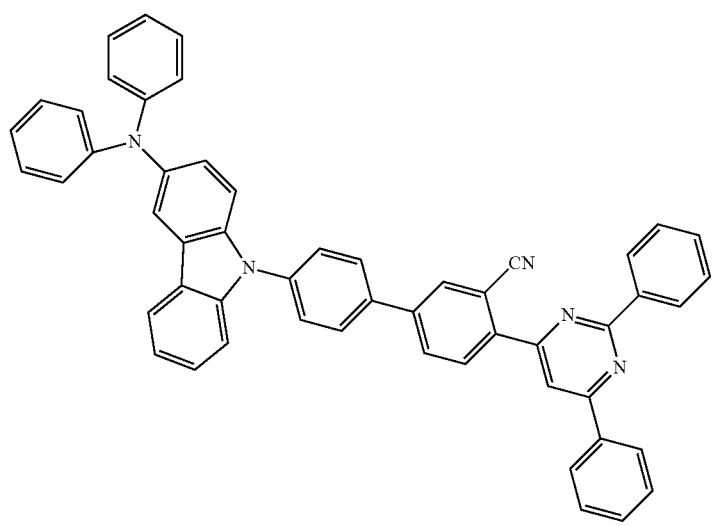
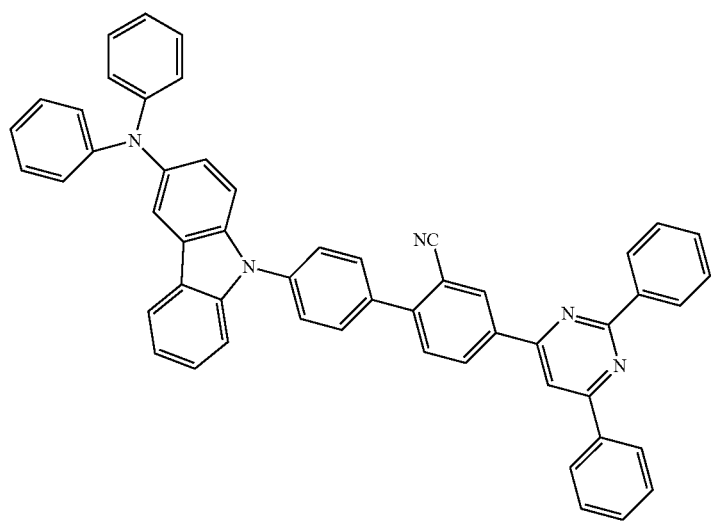

907
-continued
908
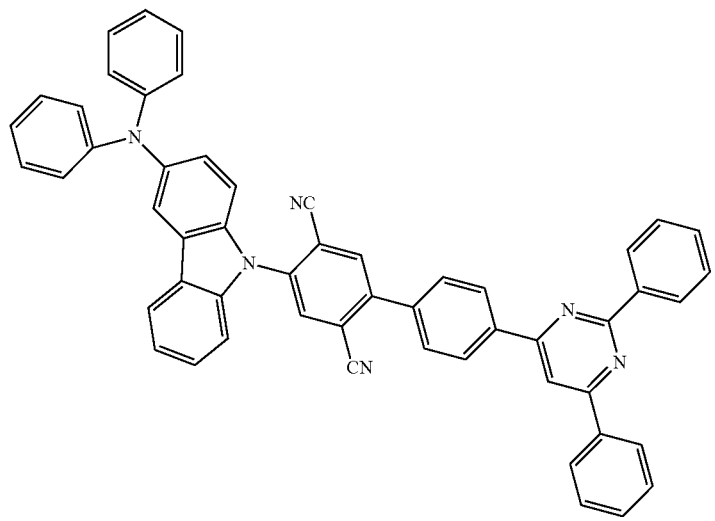
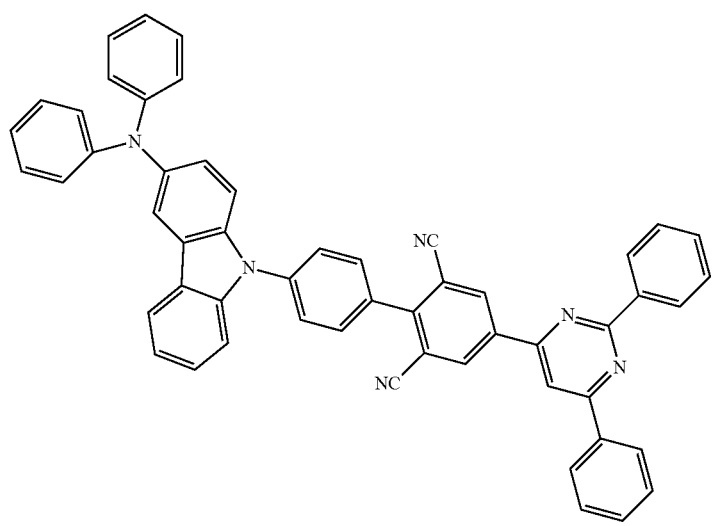
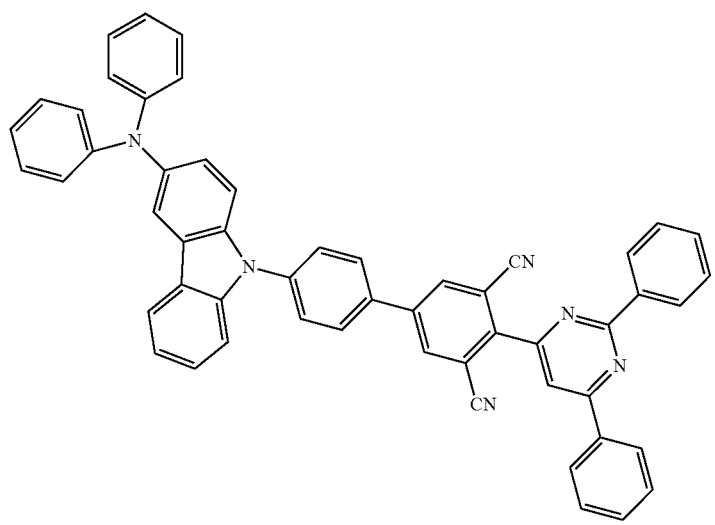

909
-continued
910
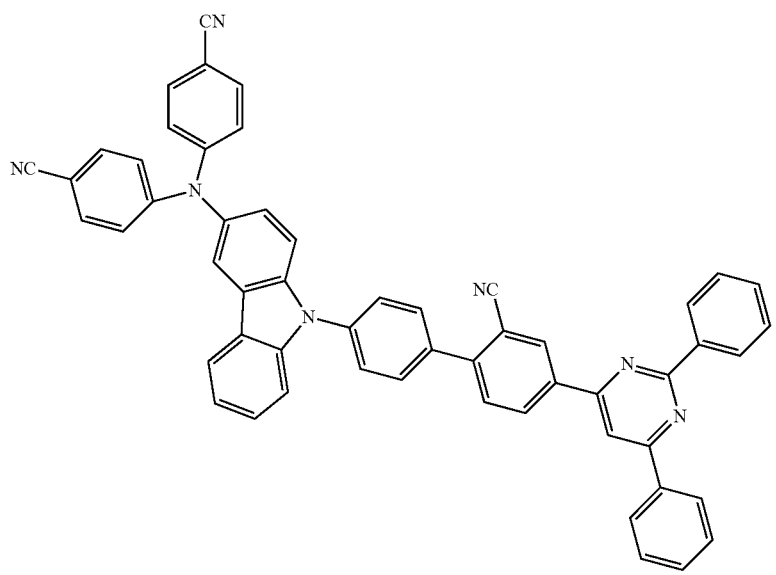
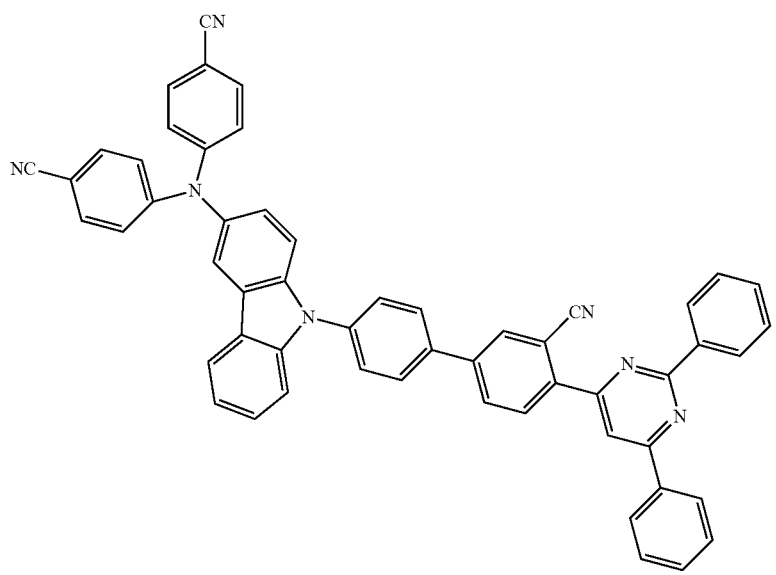
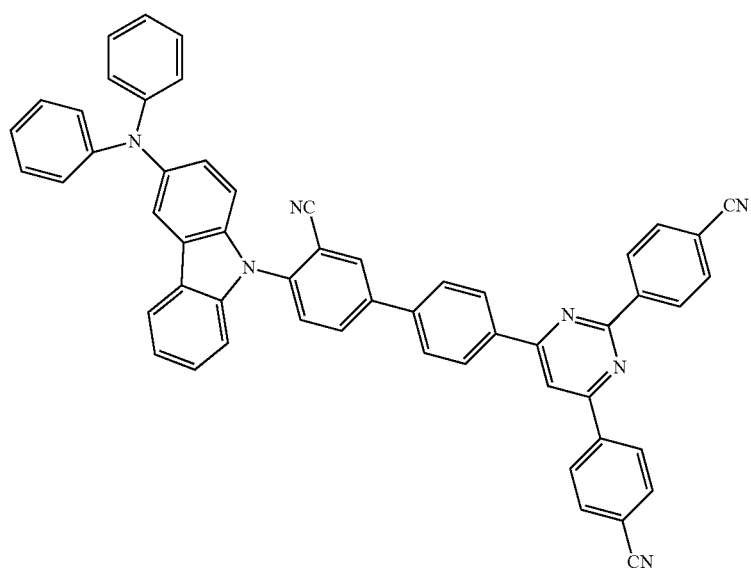

911
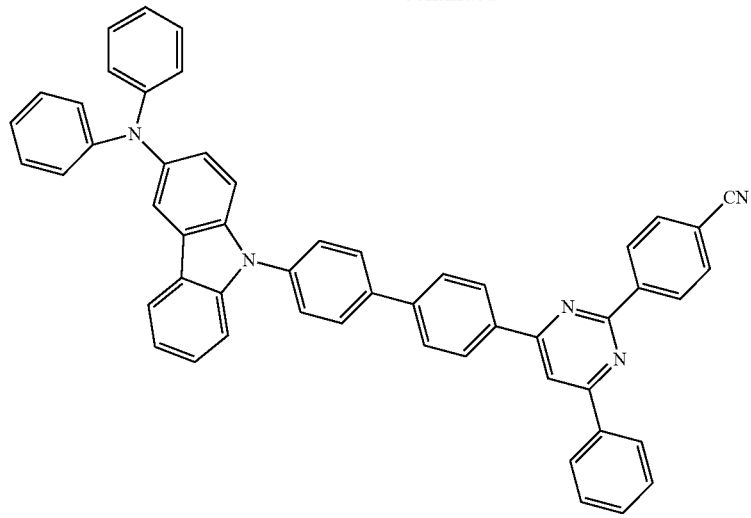
912
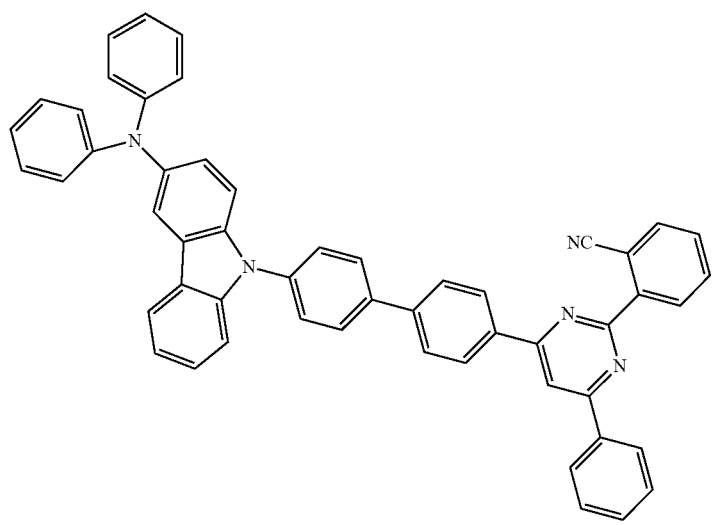
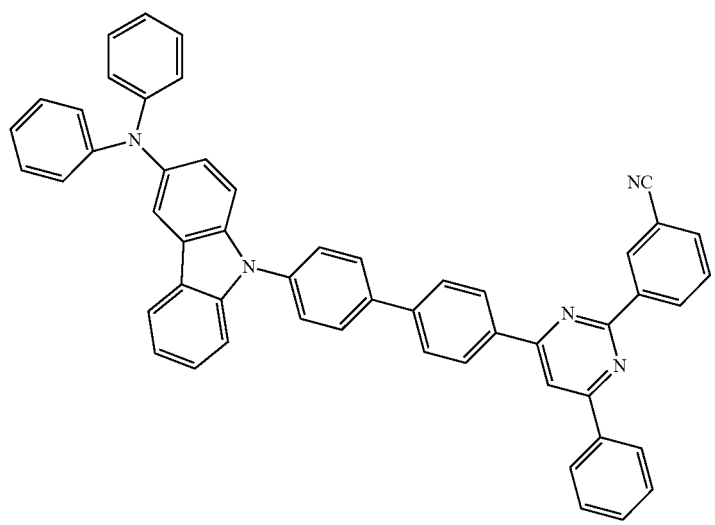

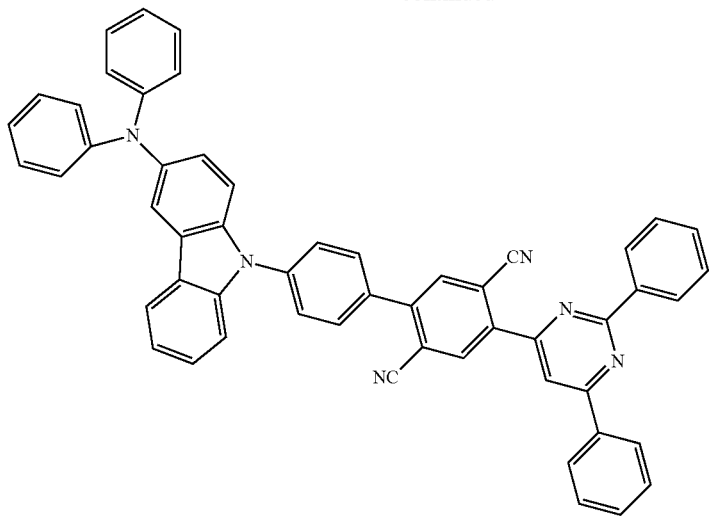
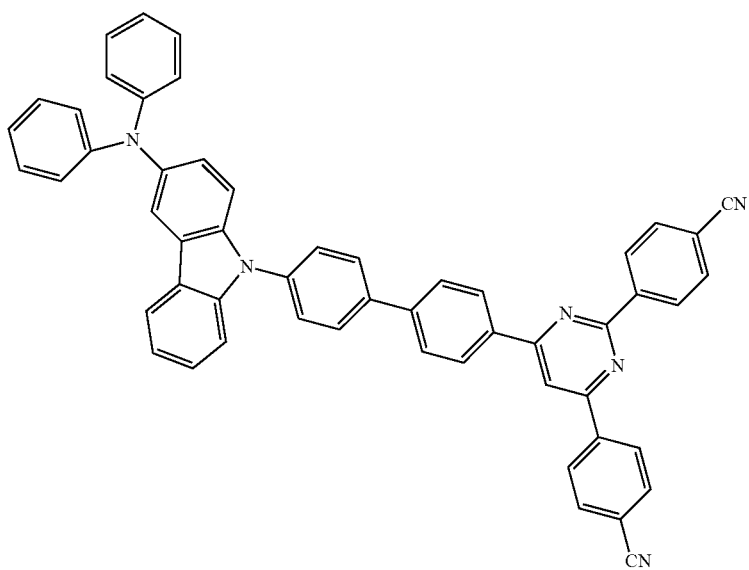
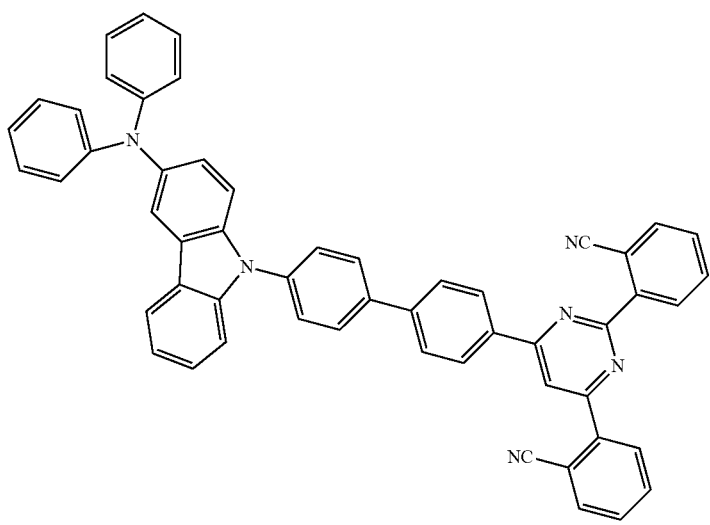

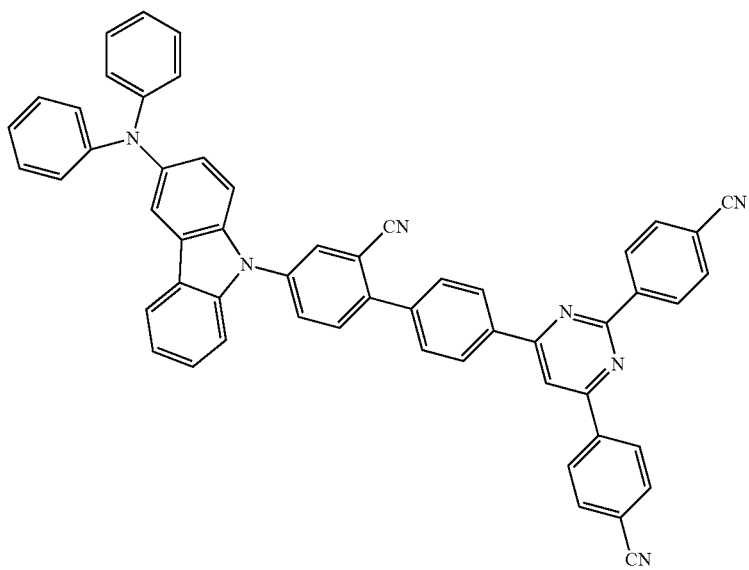
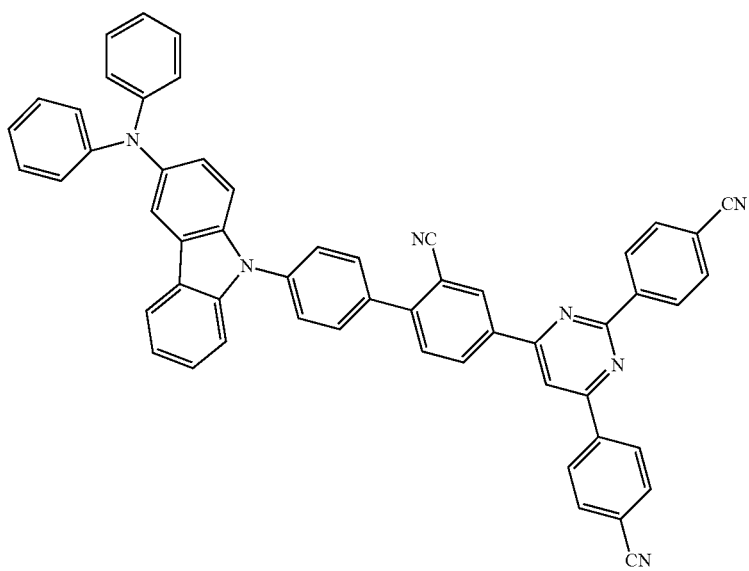
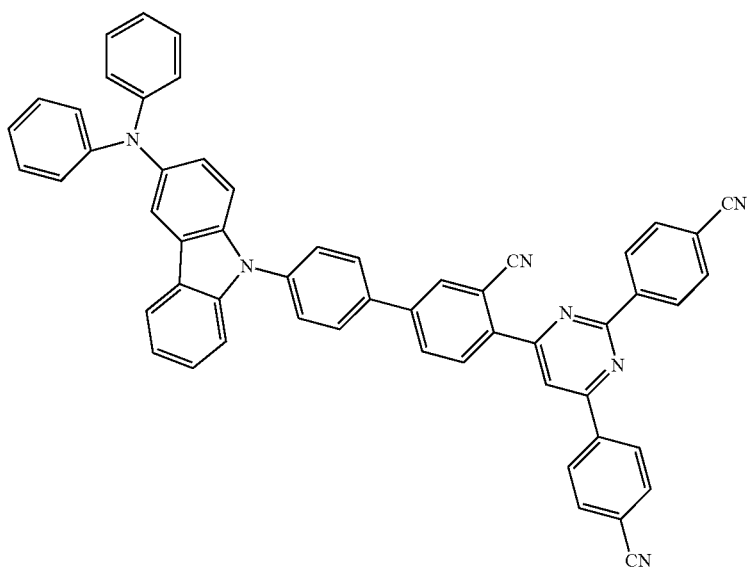

-continued
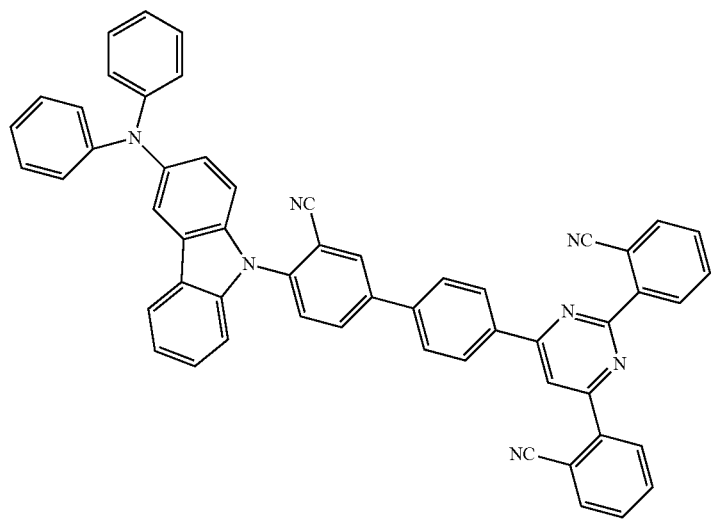
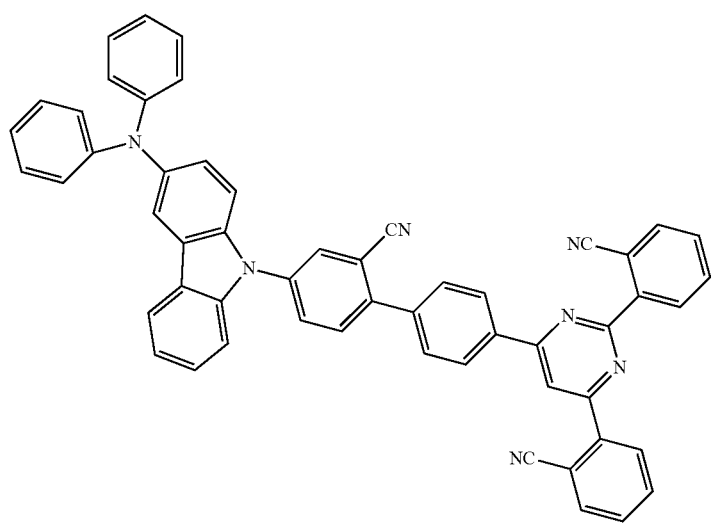
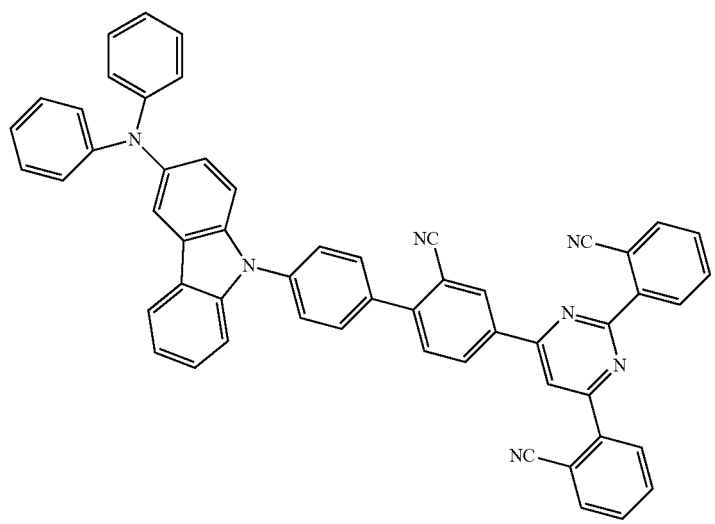

-continued
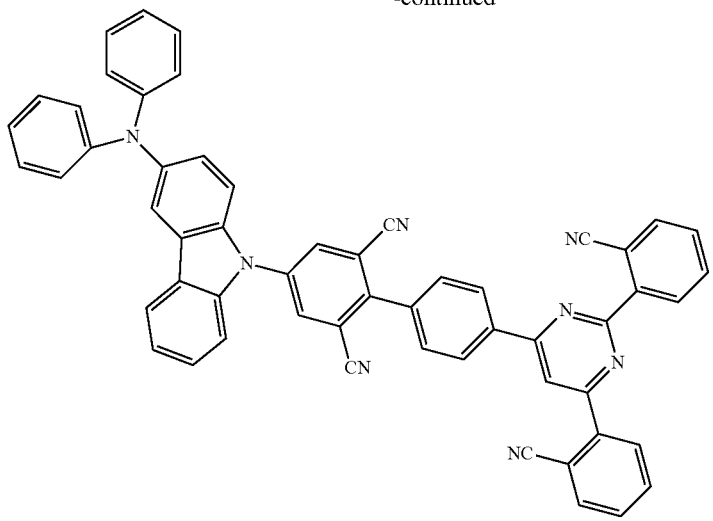
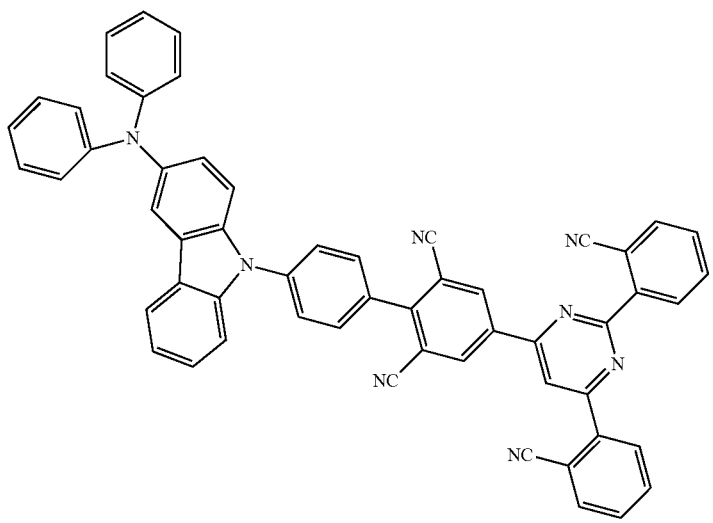
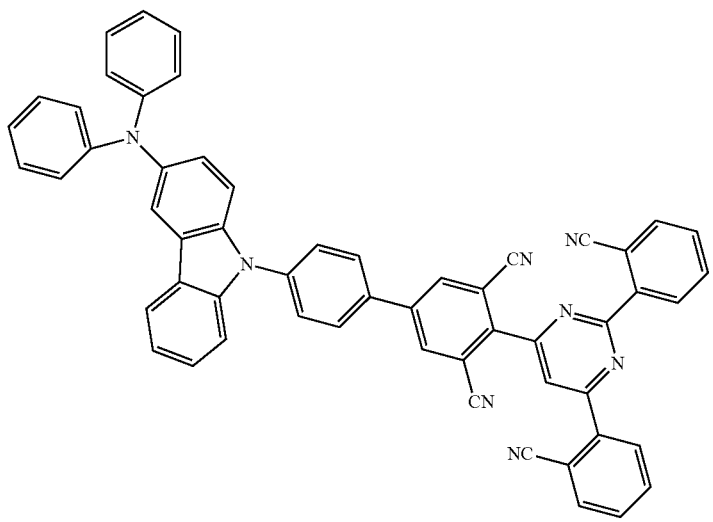

921 922
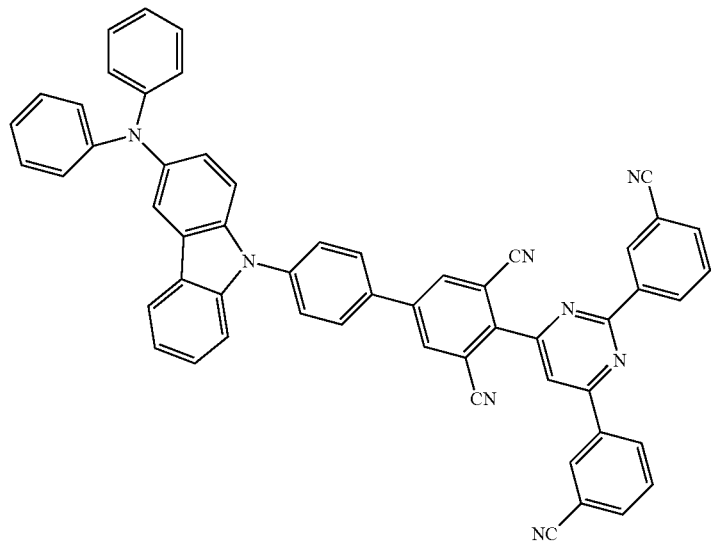
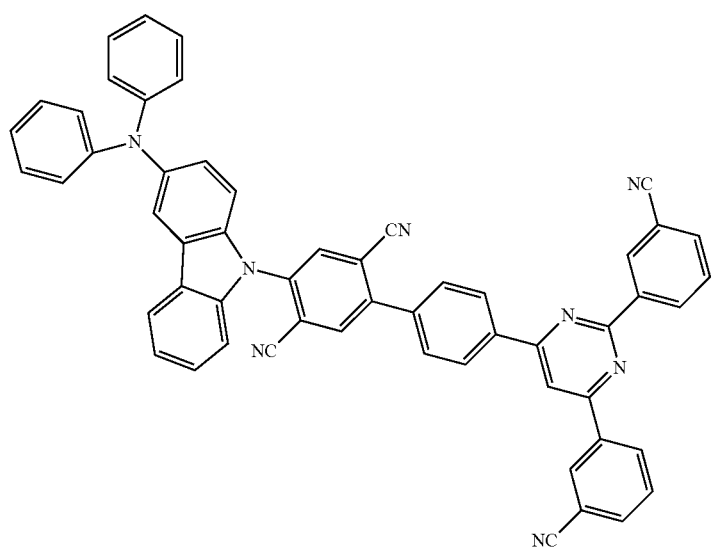
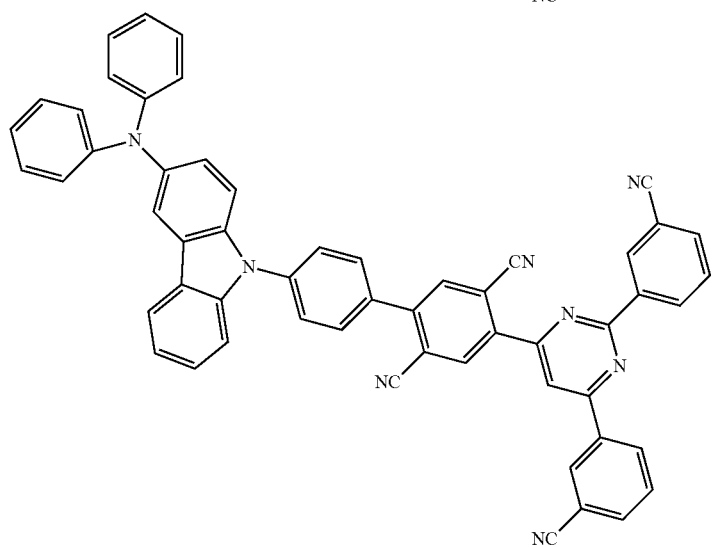

-continued
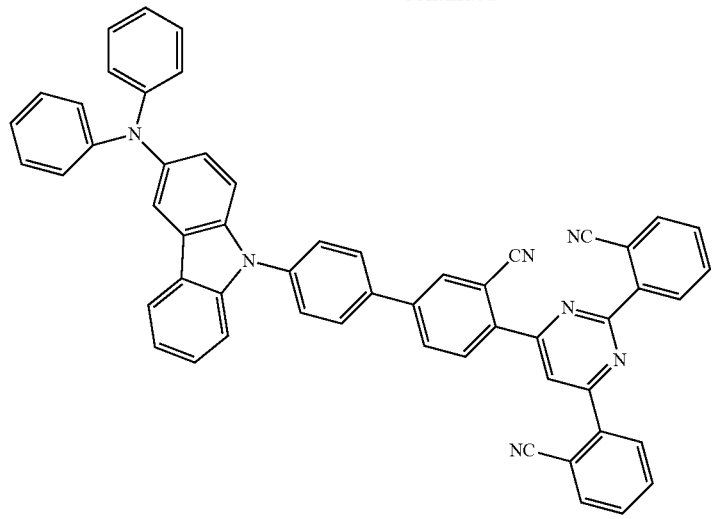
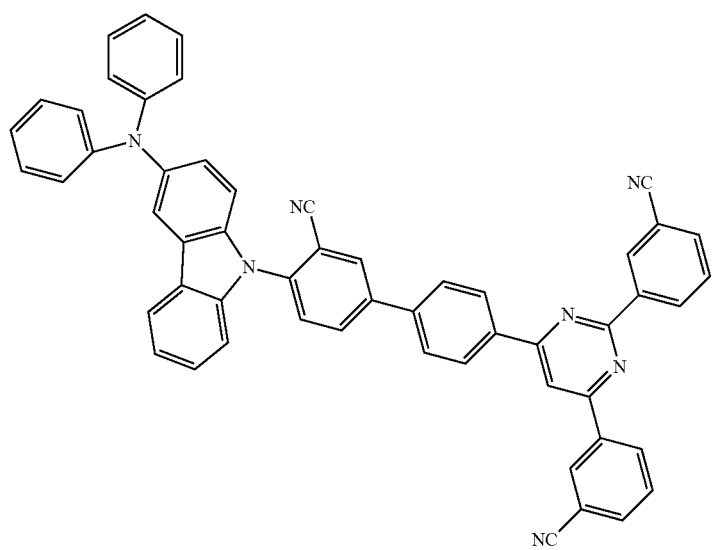
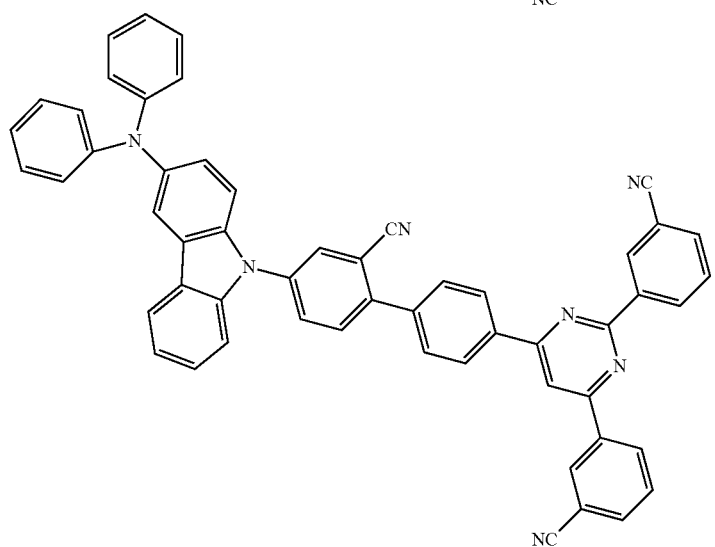

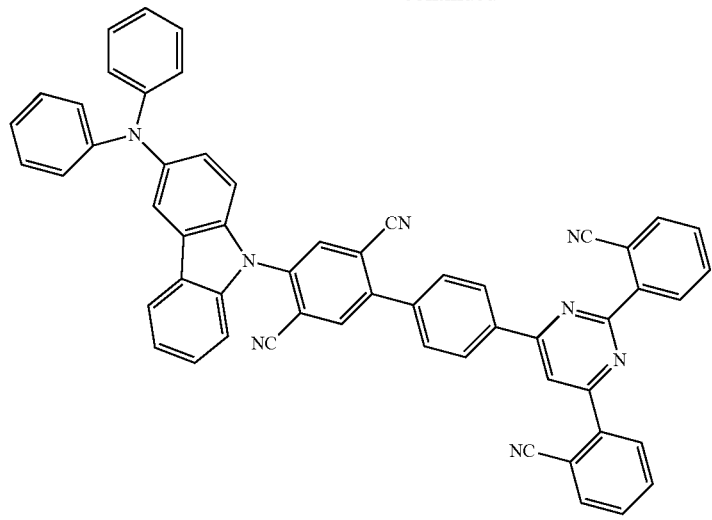
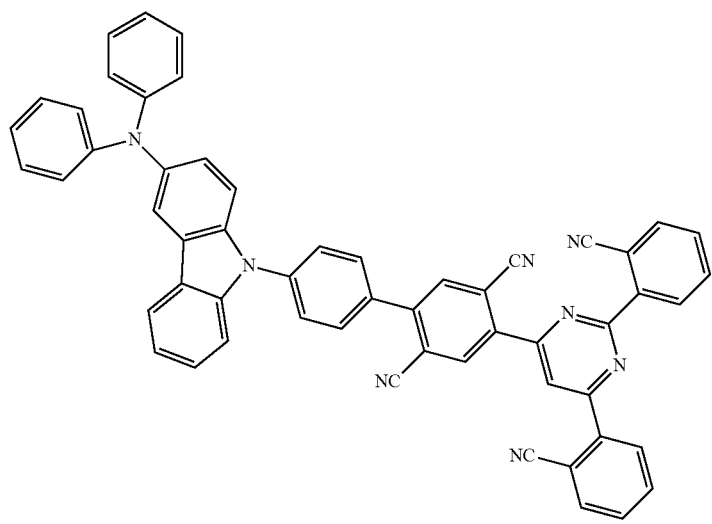
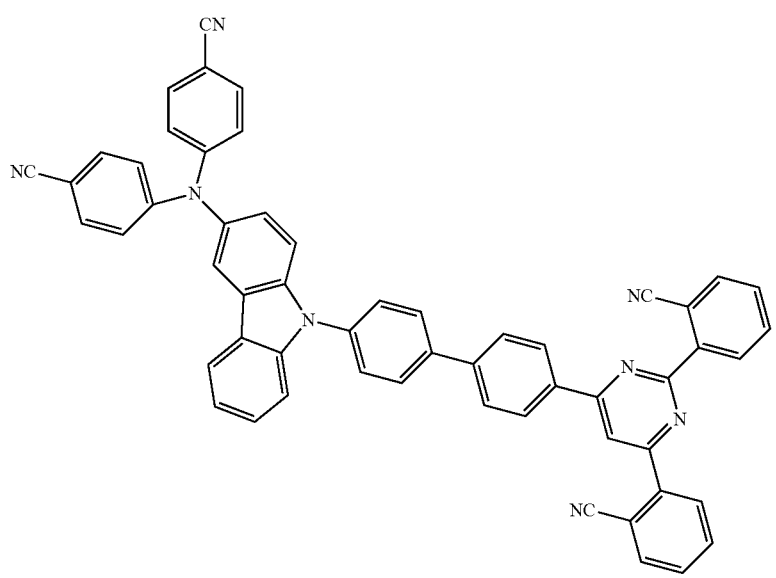

-continued
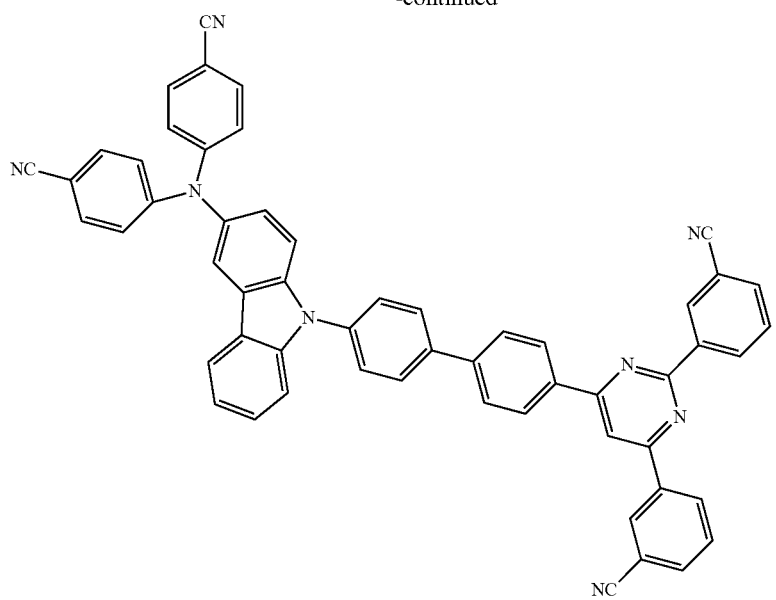
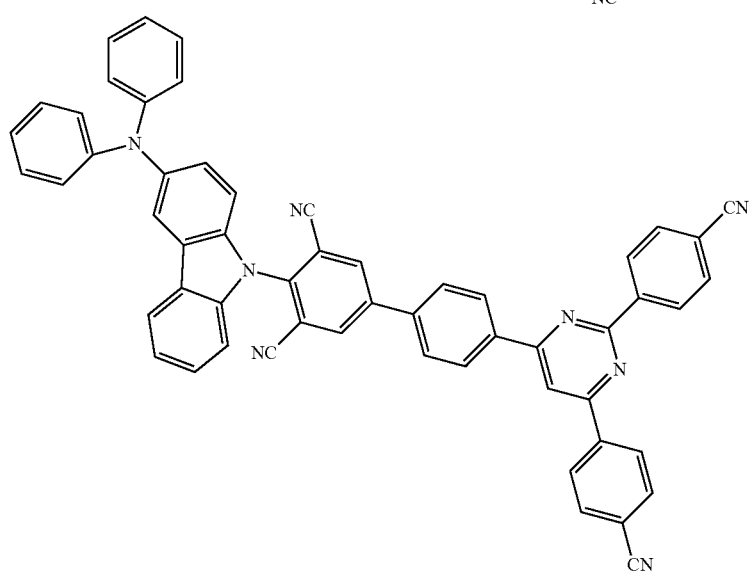
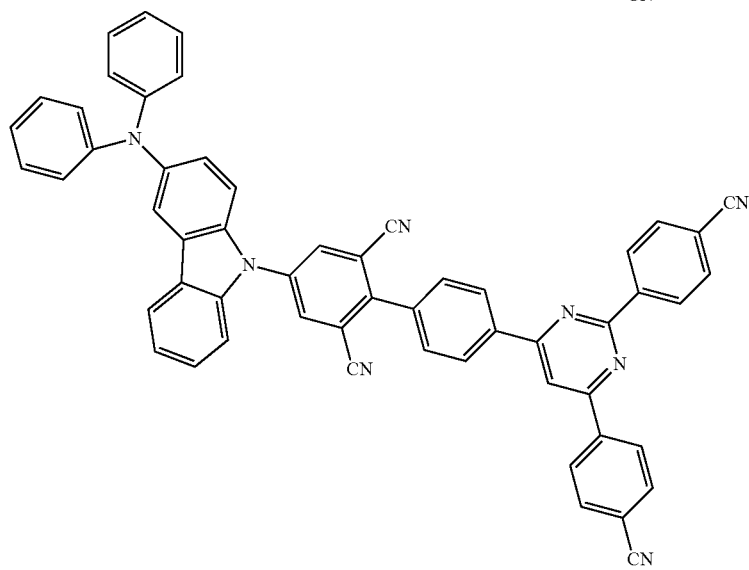

-continued
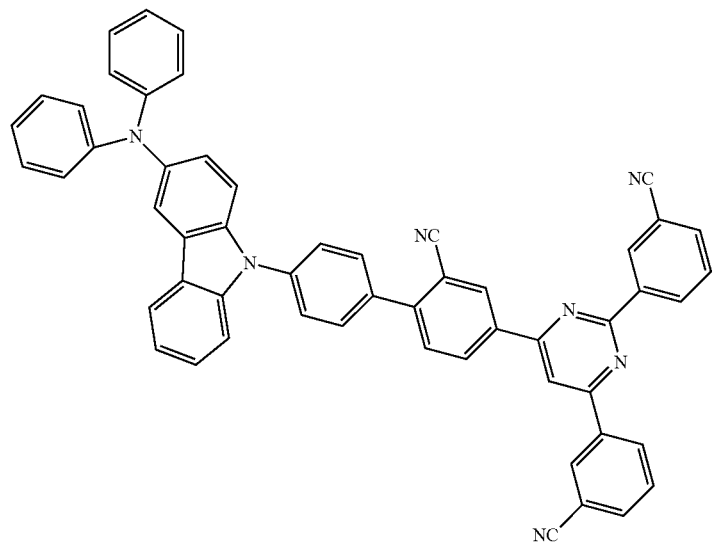
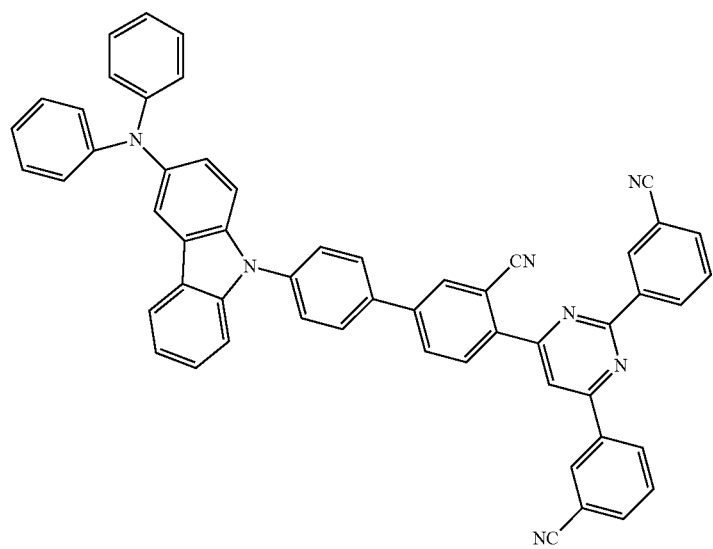
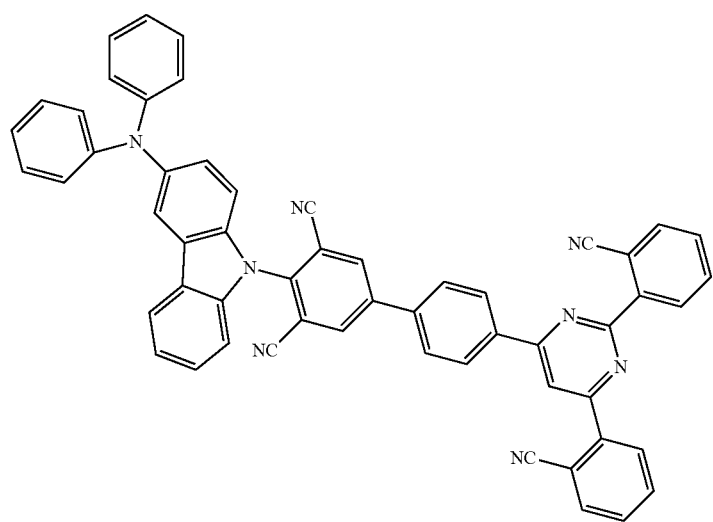

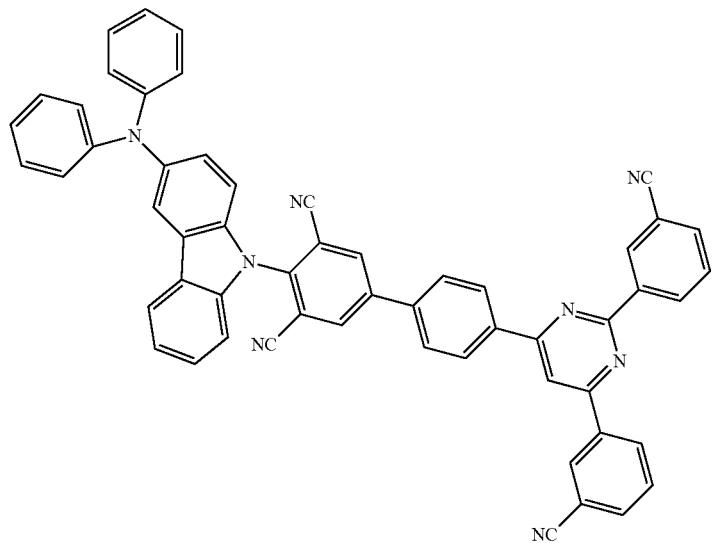
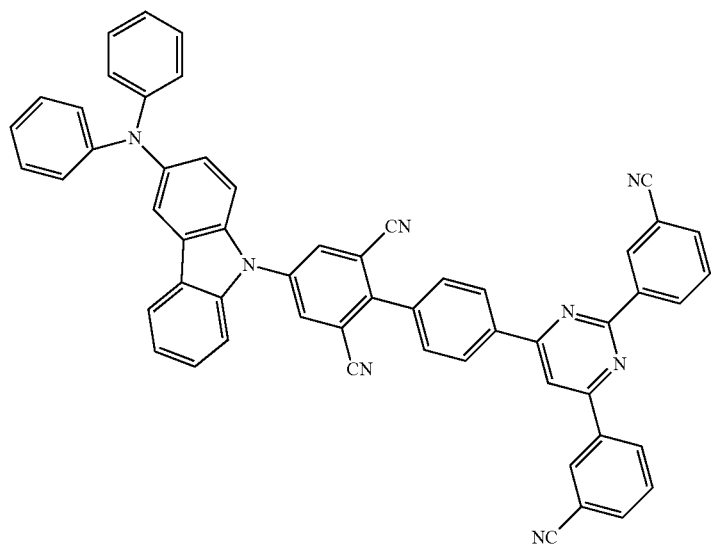
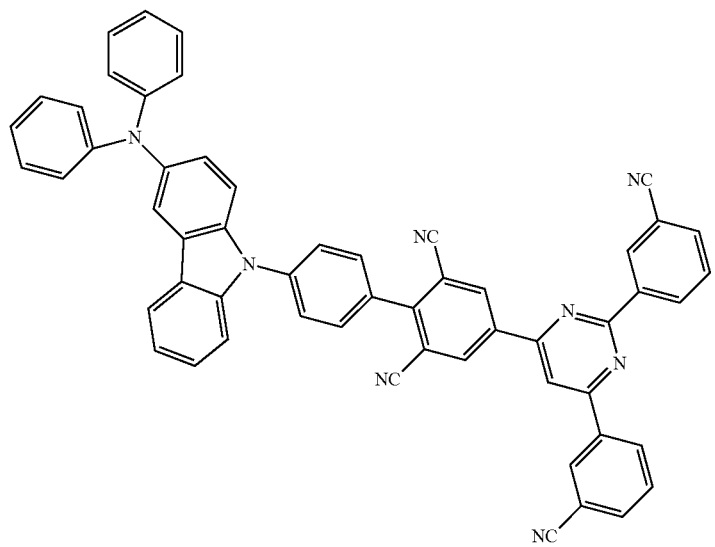

-continued
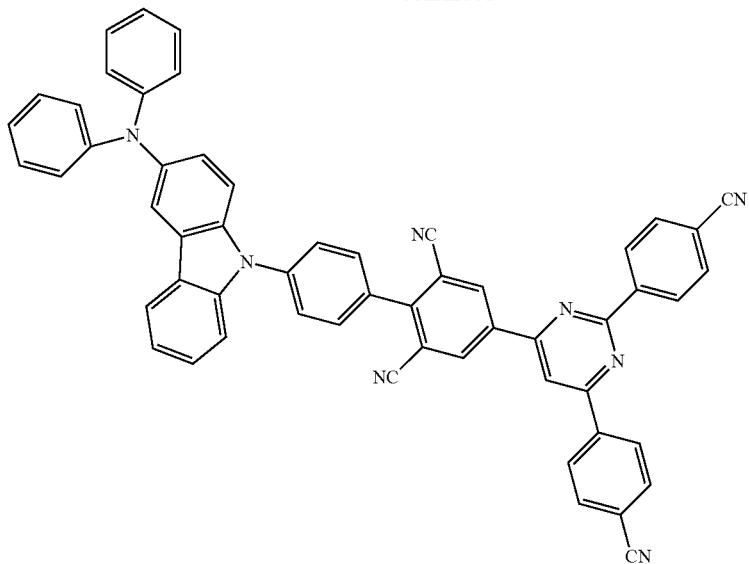
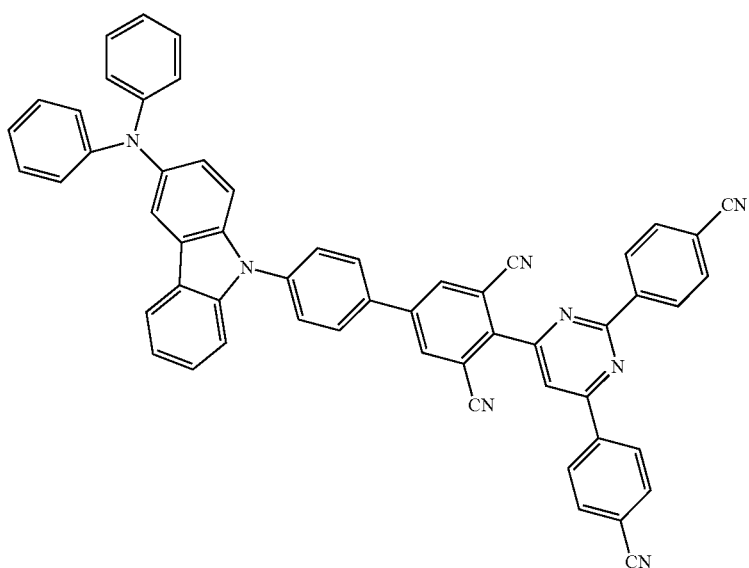
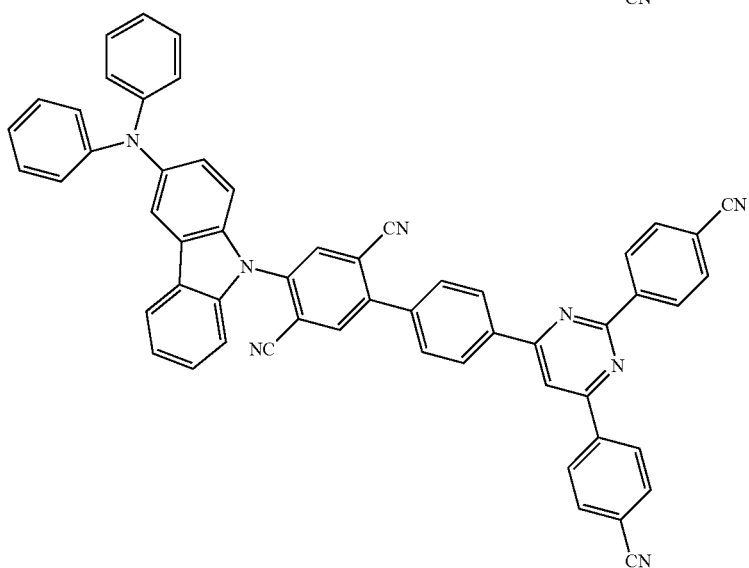

-continued
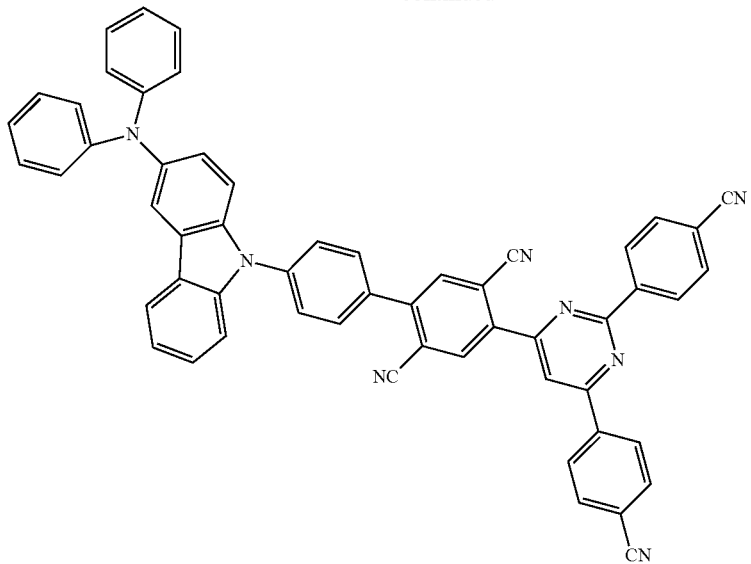
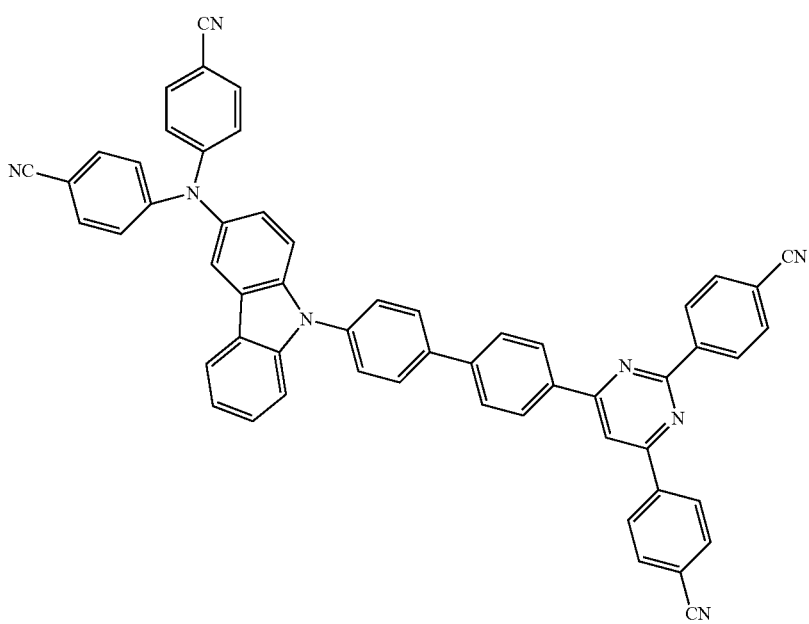
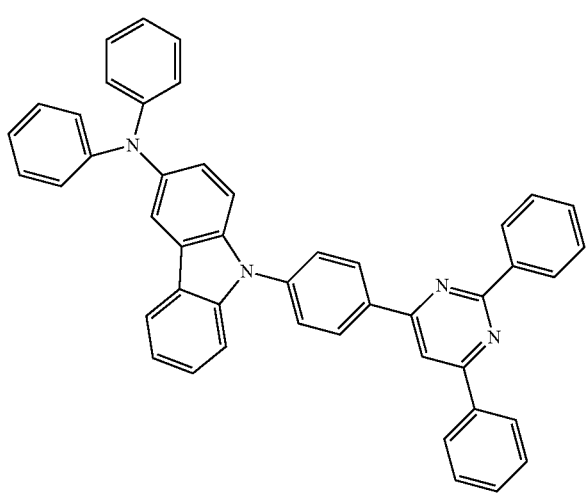

937
938
-continued
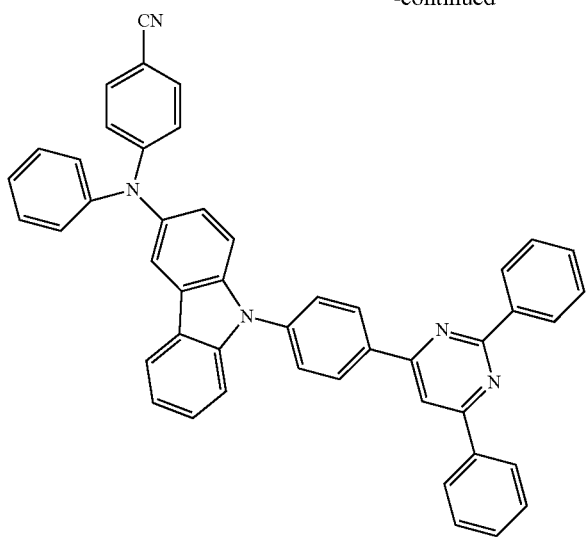
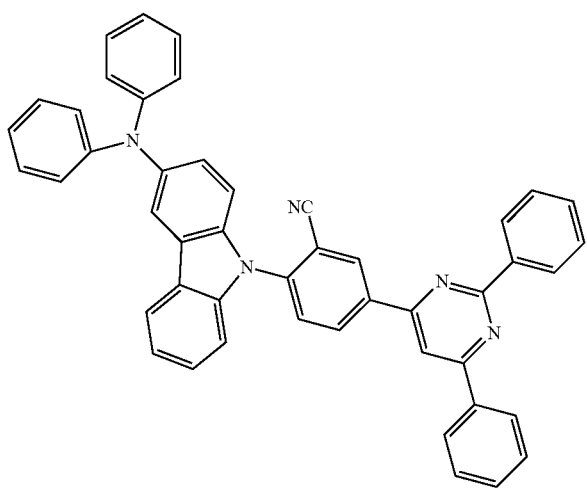
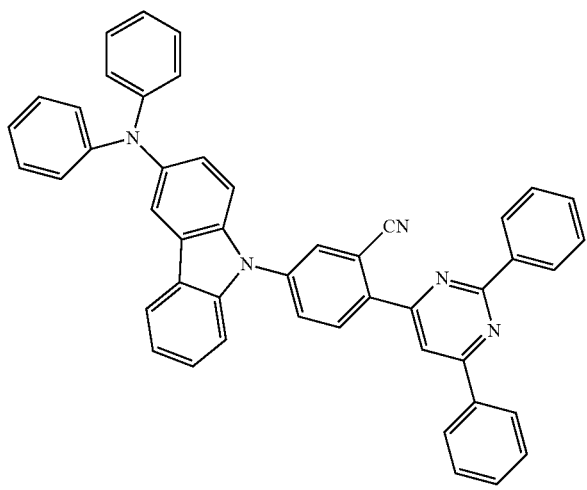

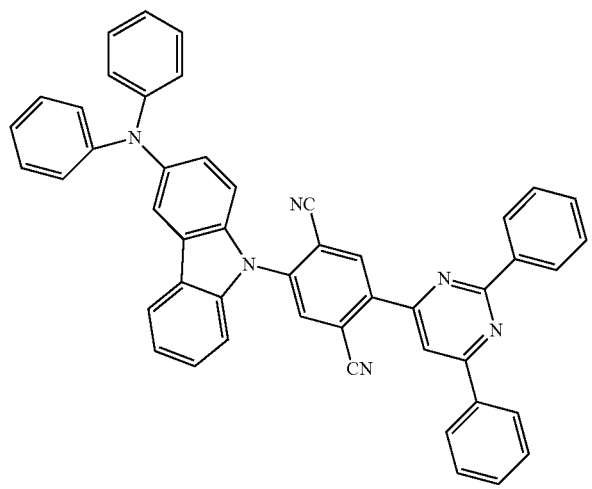
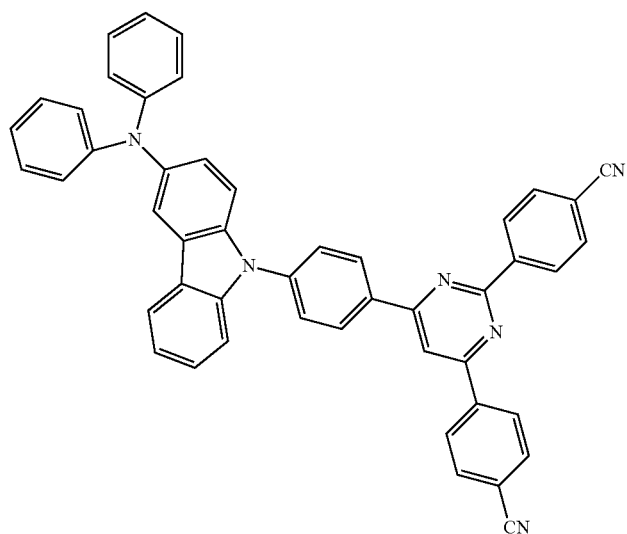
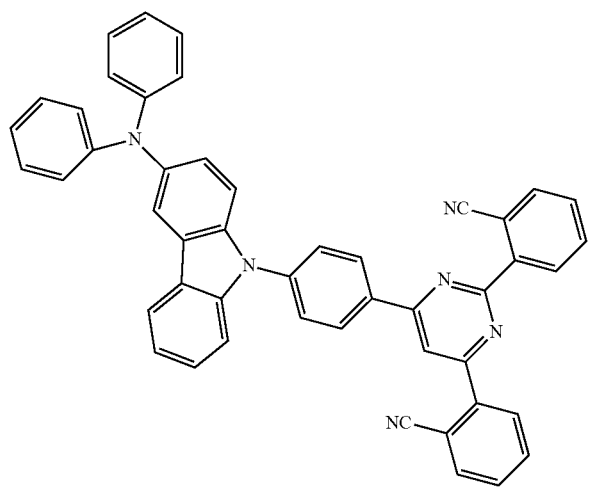

-continued
941
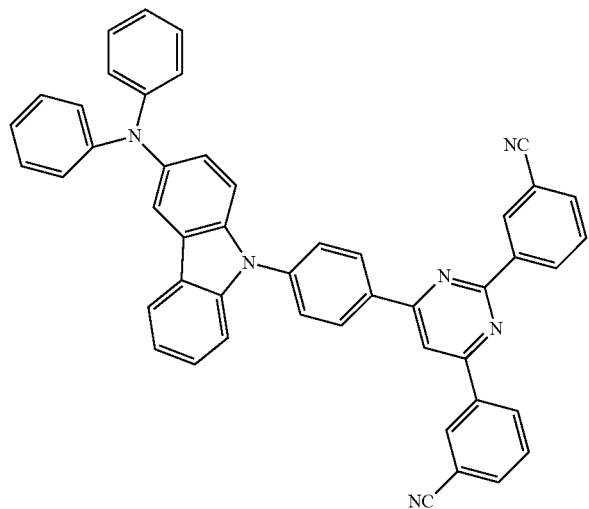
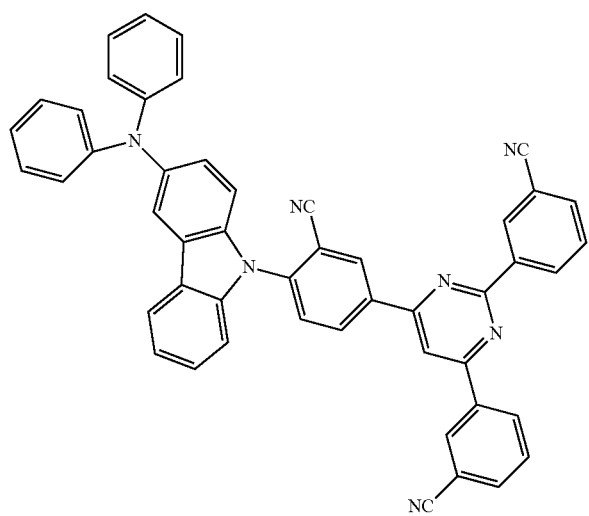
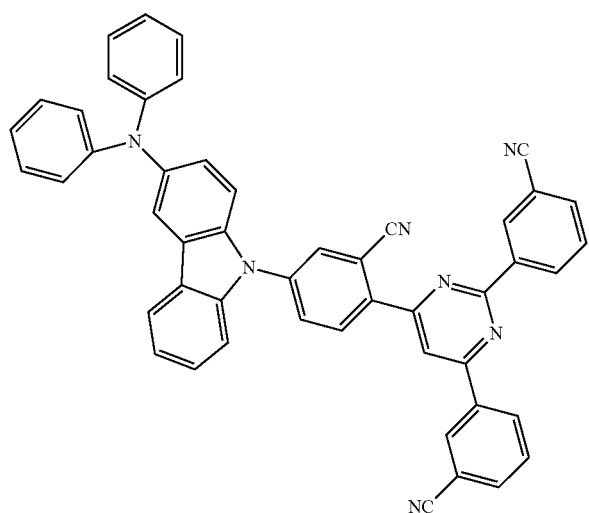
942

-continued
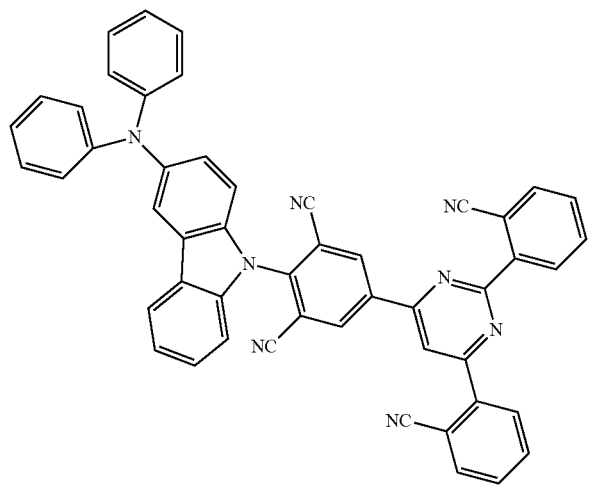
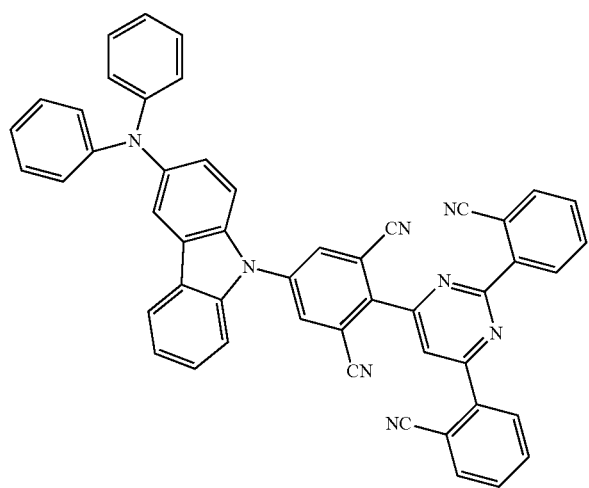
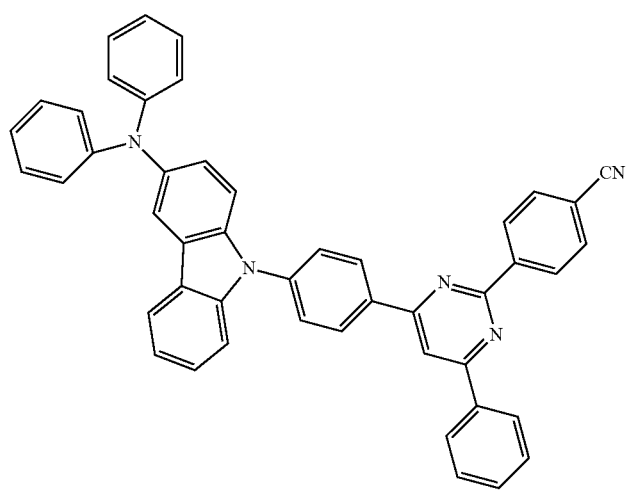

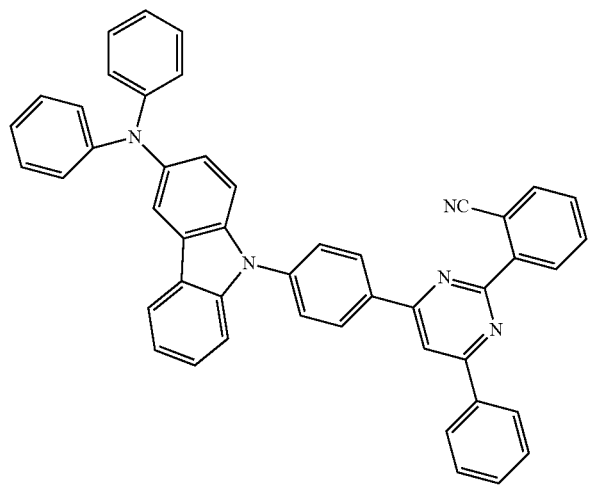
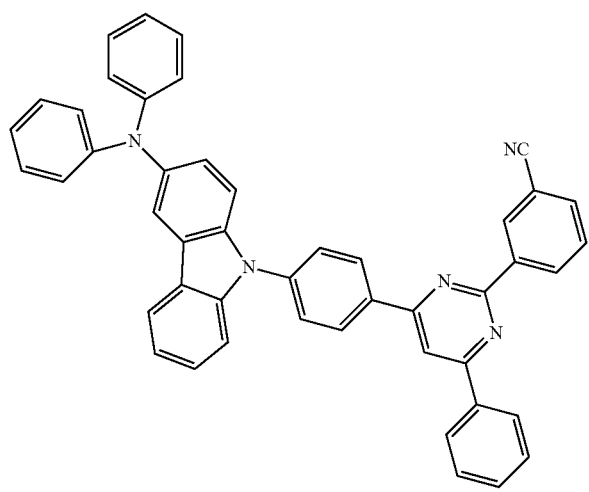
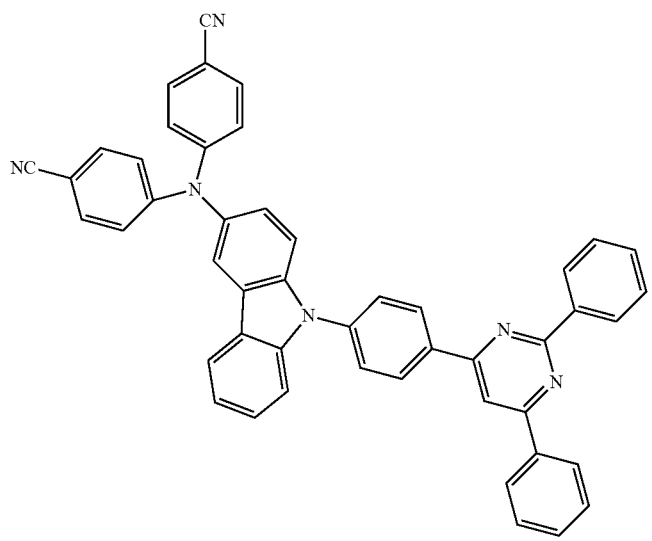

-continued
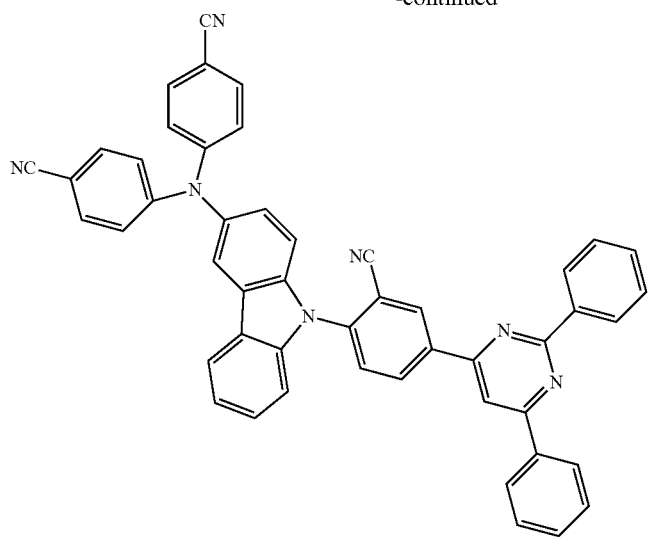
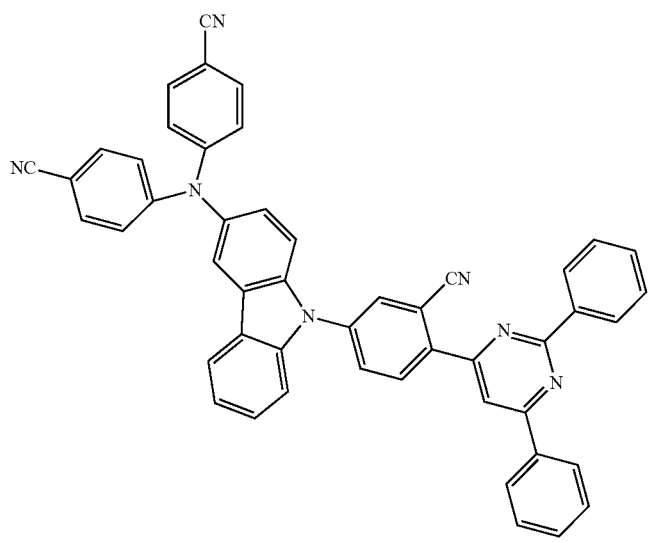
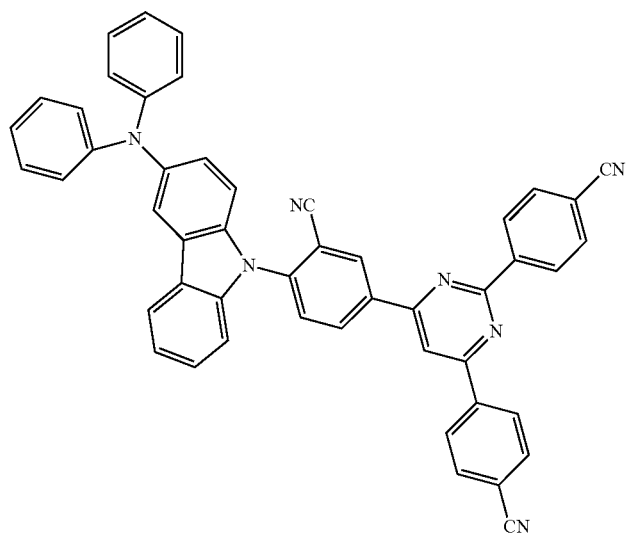

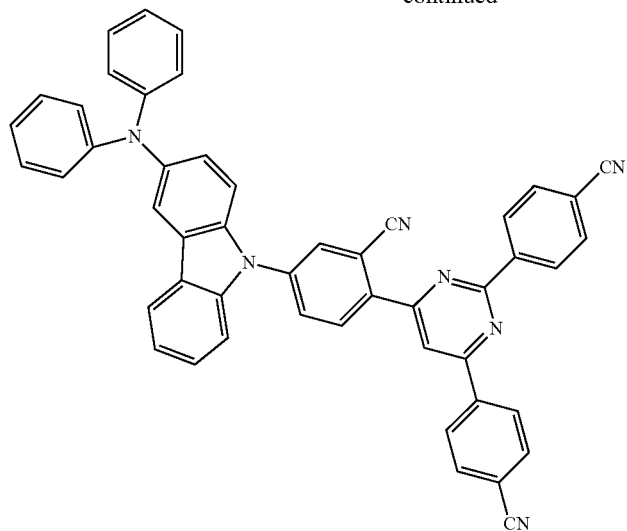
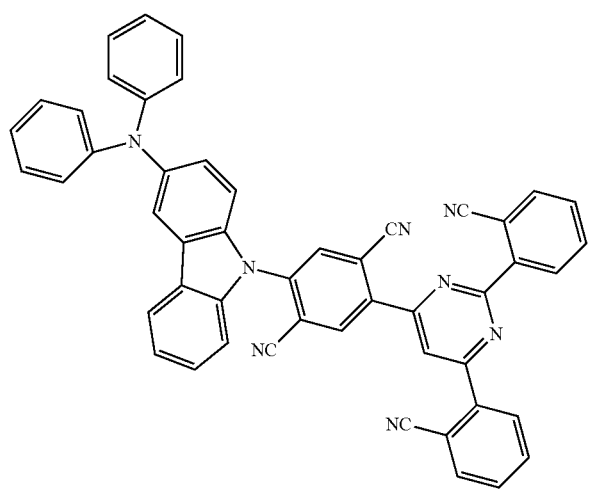
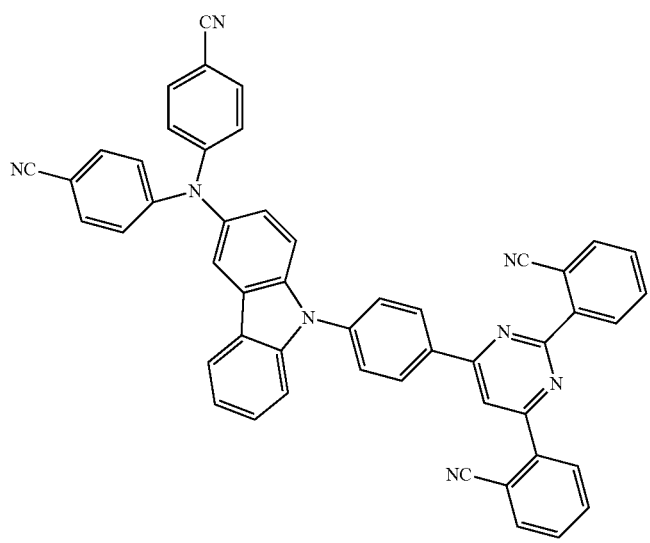

-continued
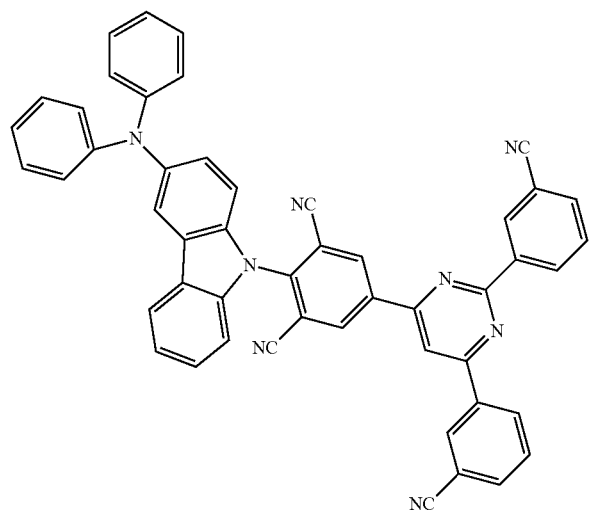
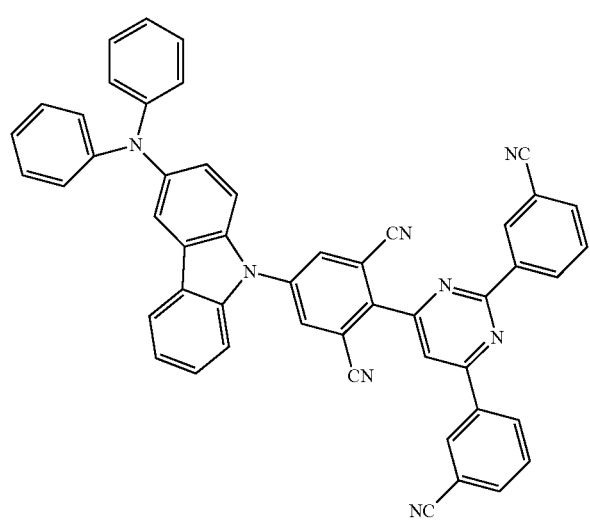
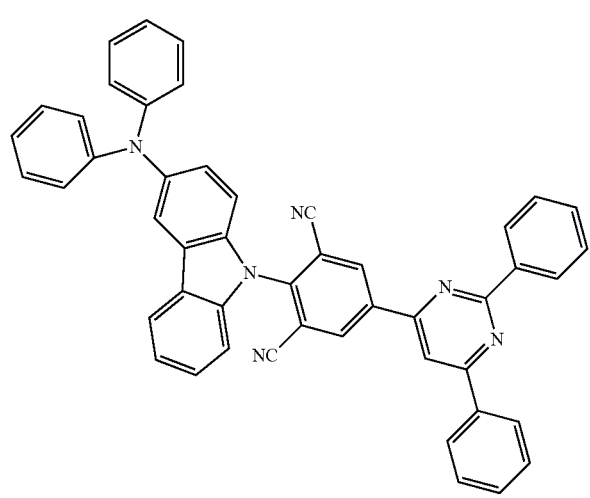

-continued
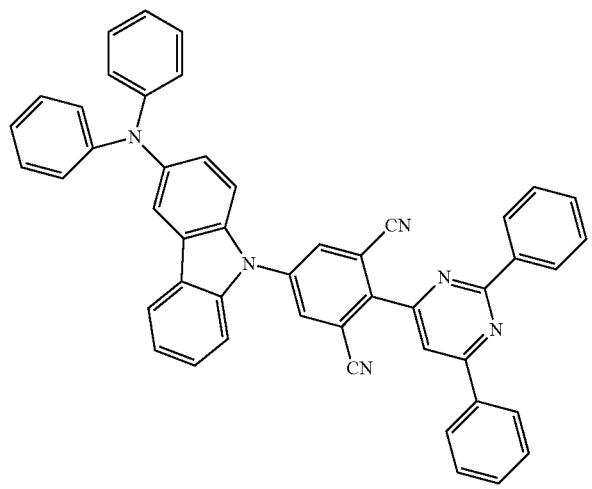
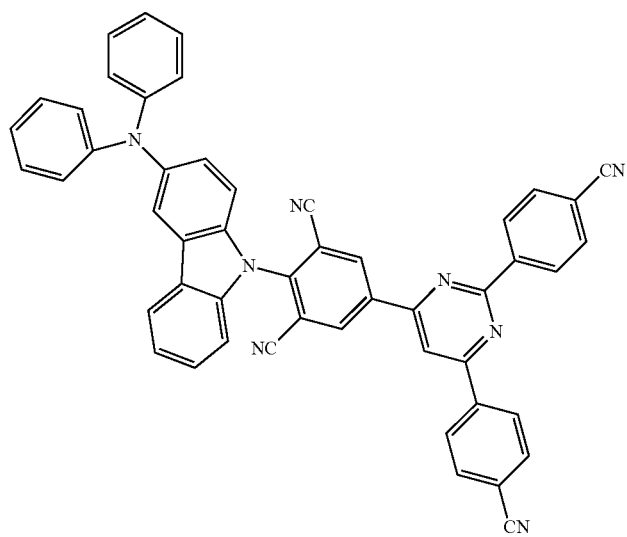
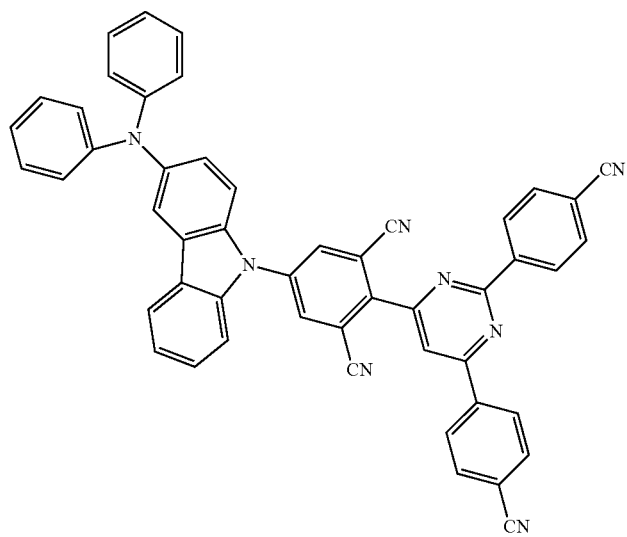

-continued
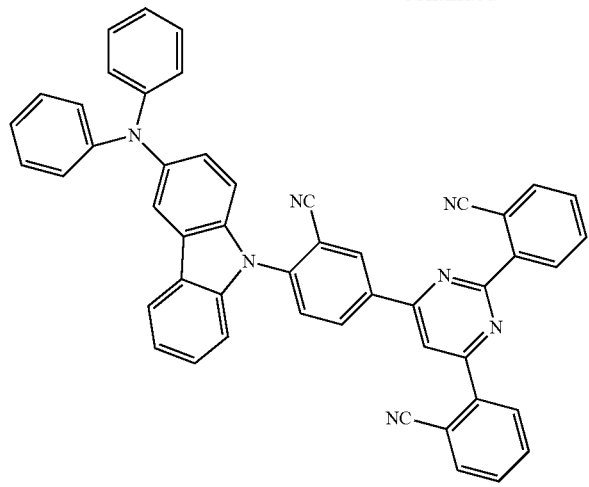
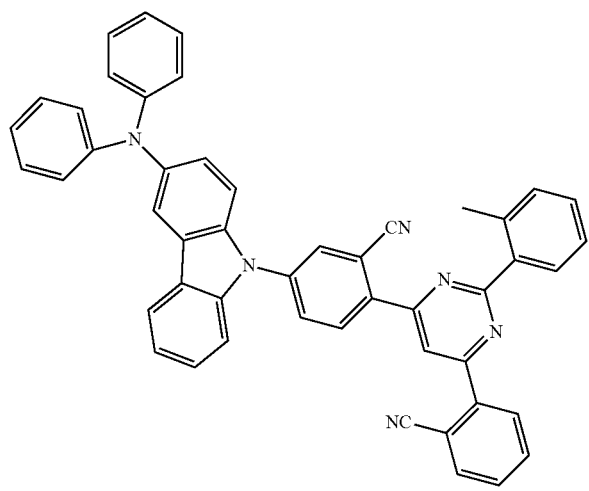
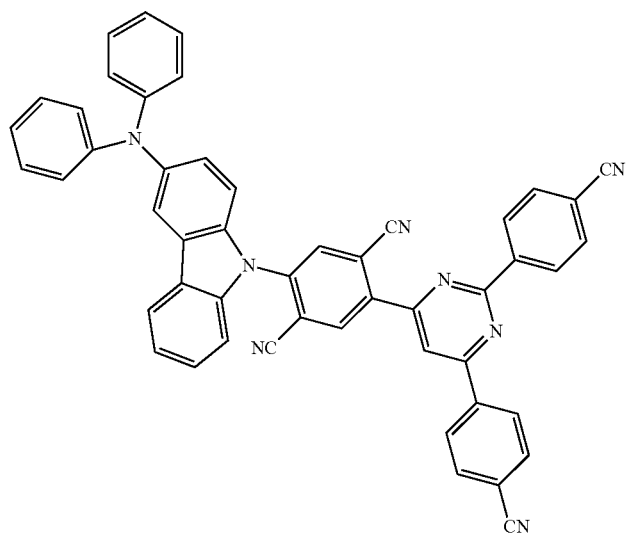

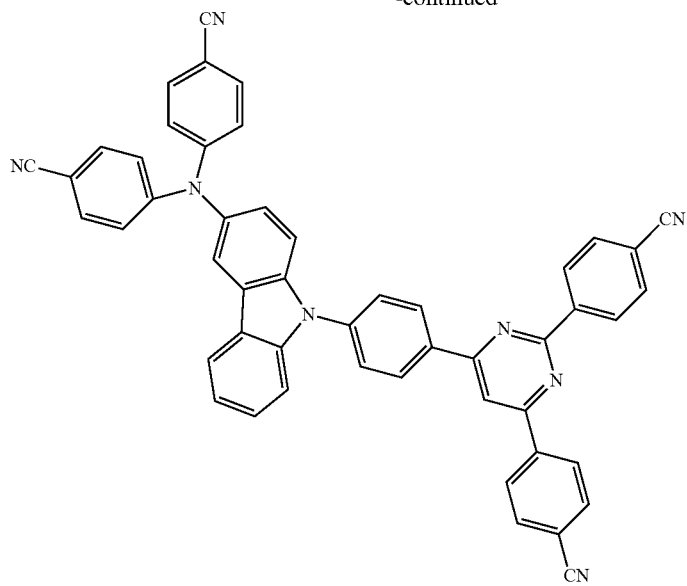
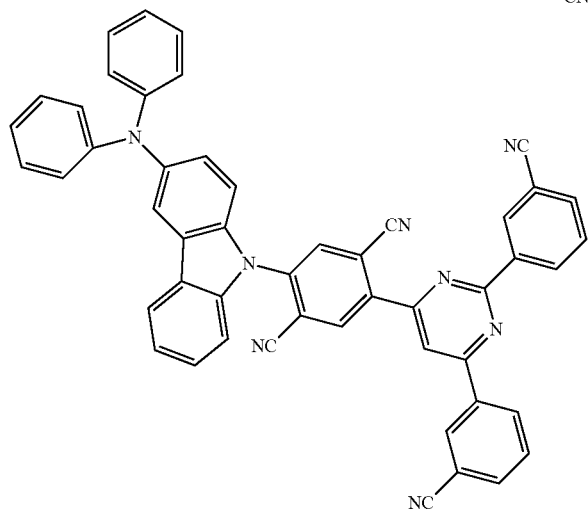
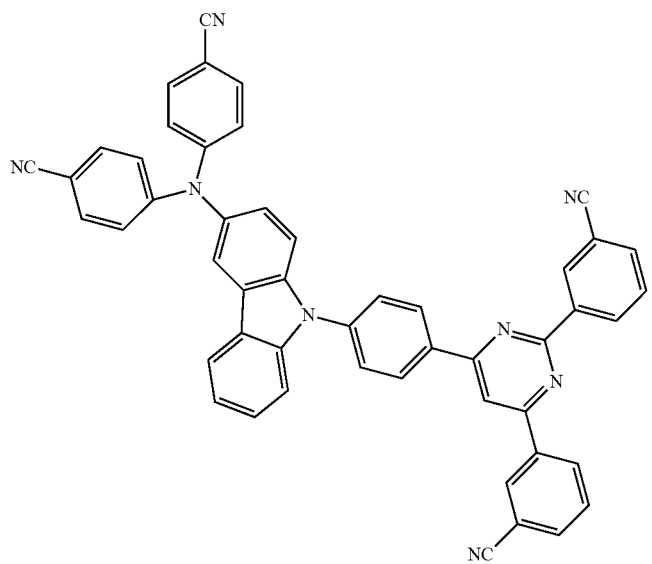

In some embodiments, the first compound may be selected from compounds below, but embodiments are not limited thereto:
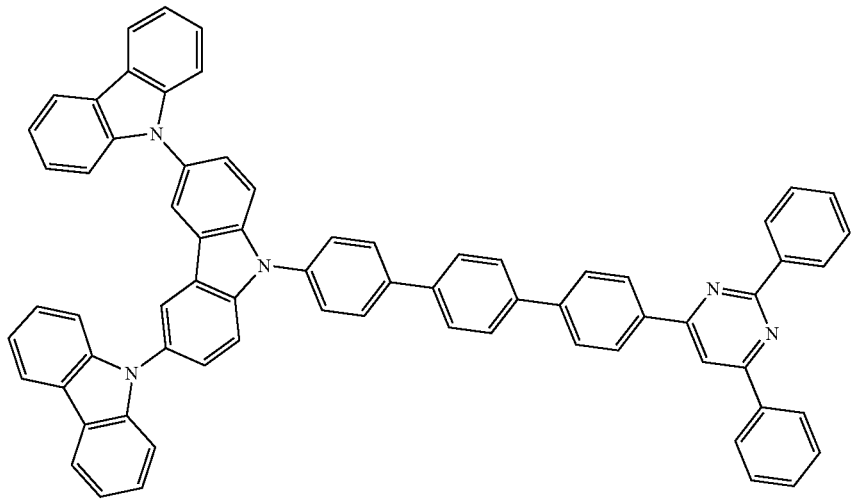
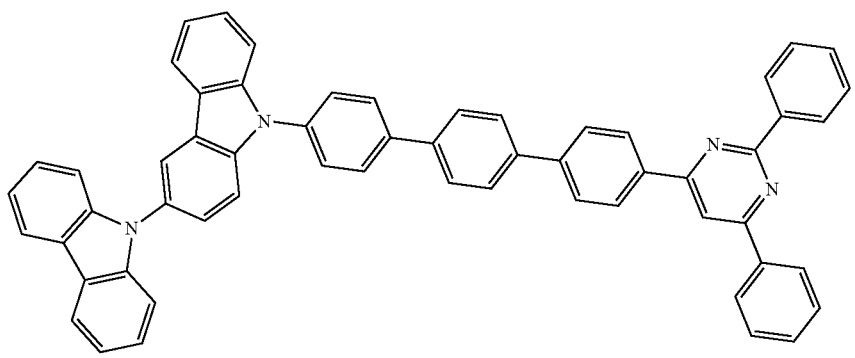
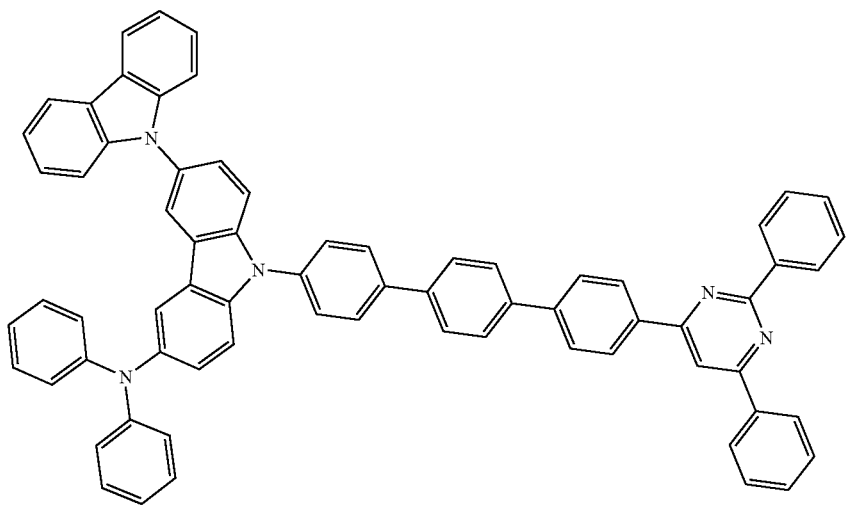

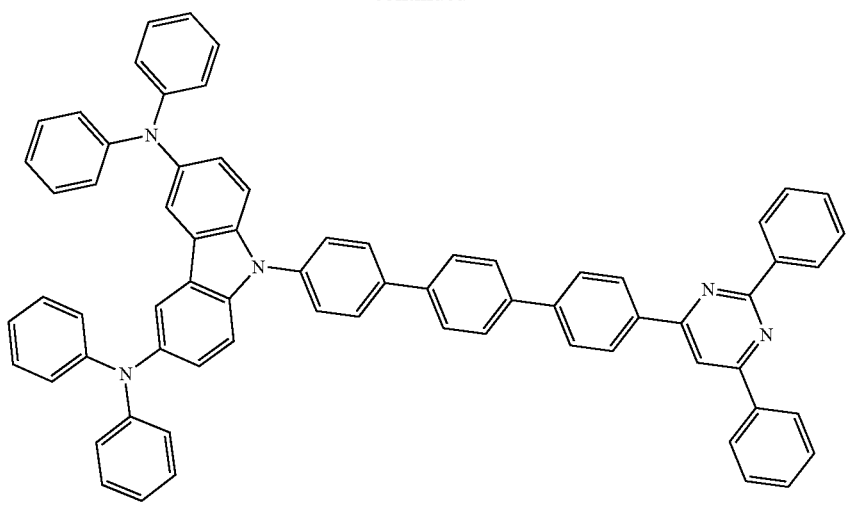
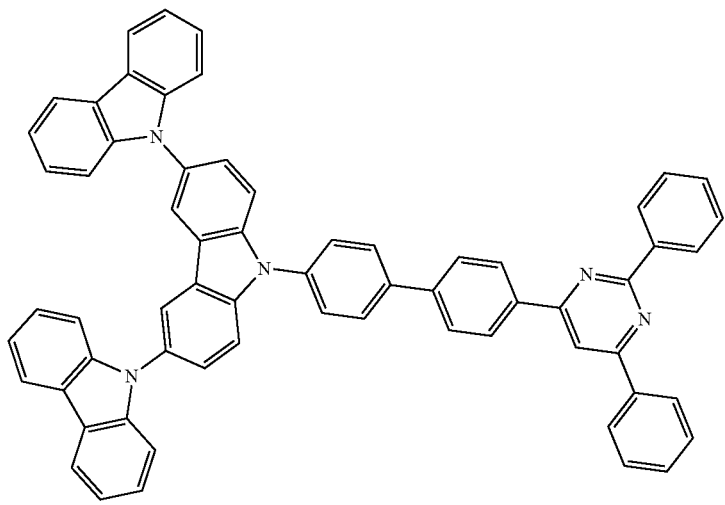
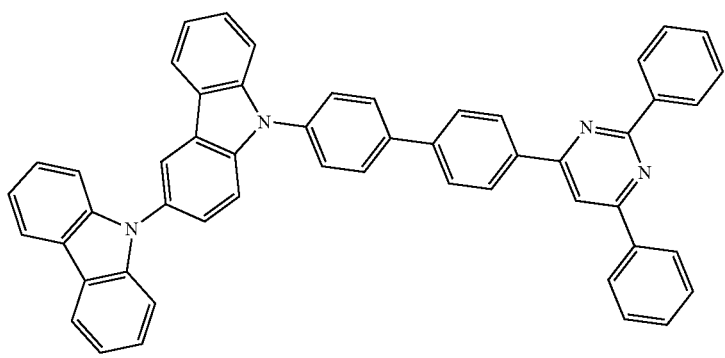

-continued
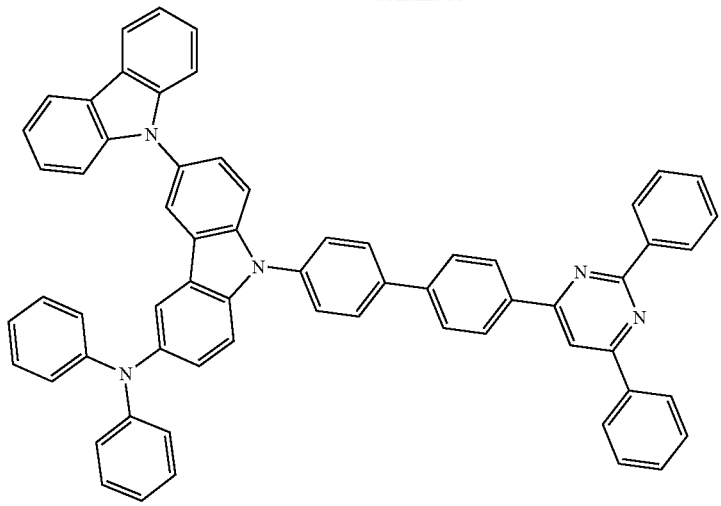
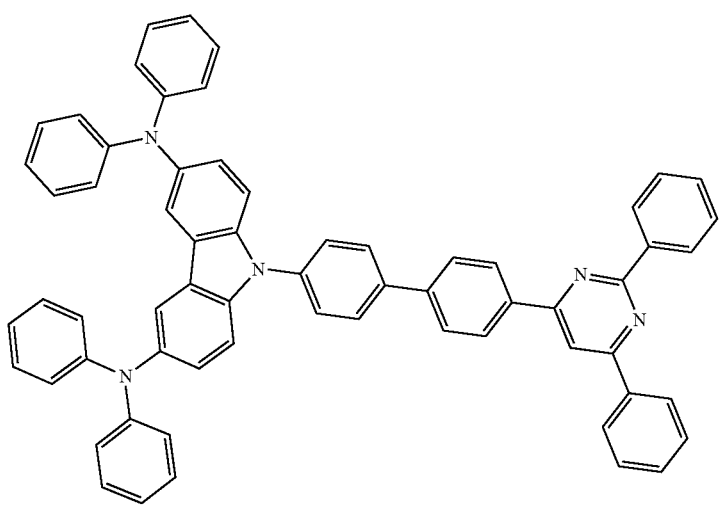
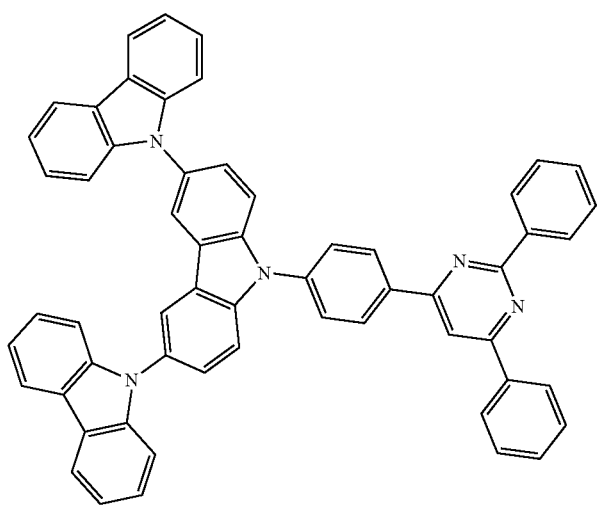

-continued
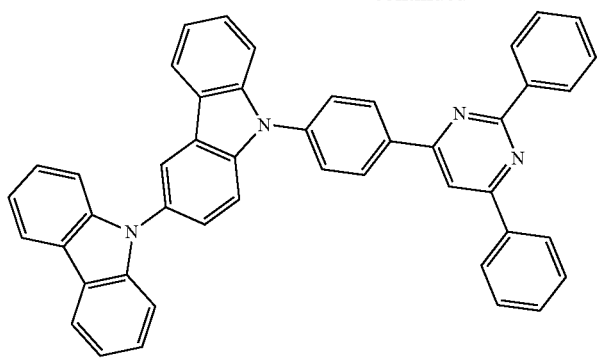
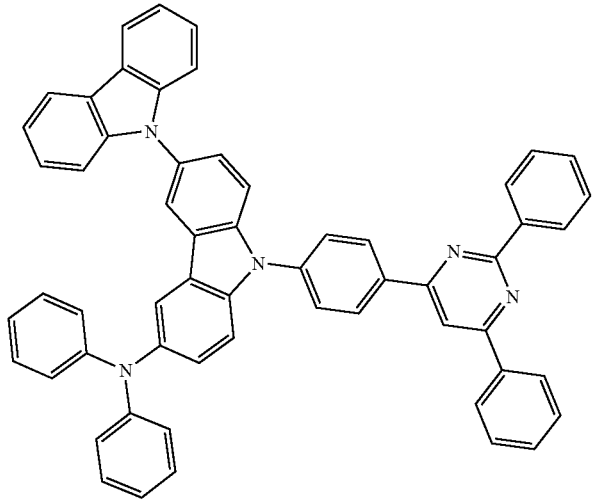
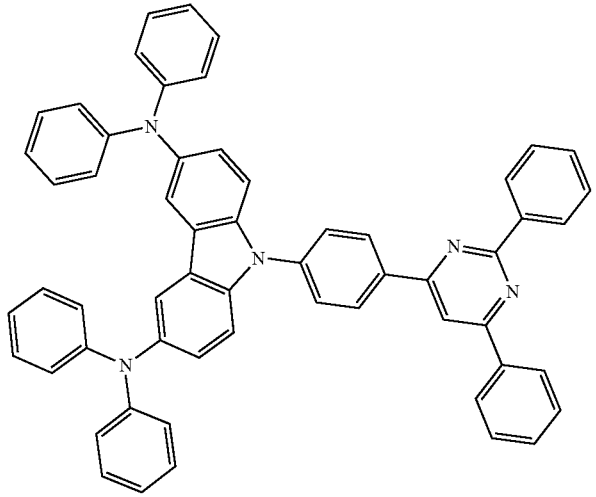
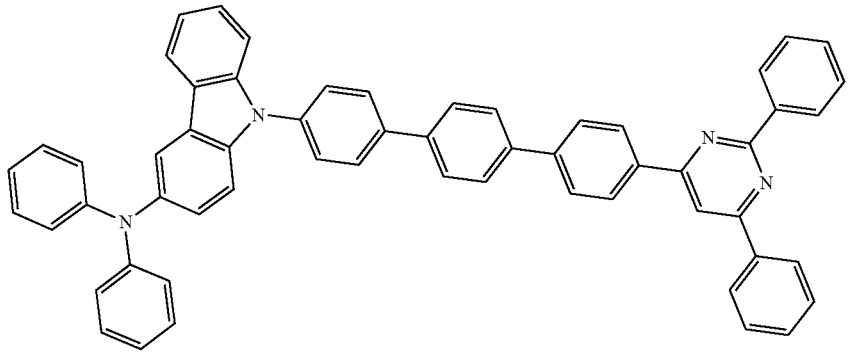

-continued

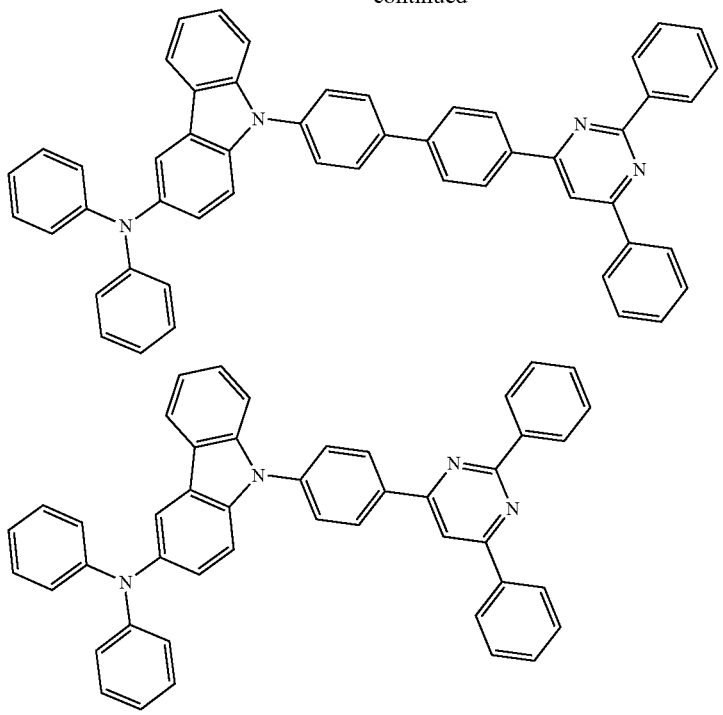

A method of synthesizing the first compound represented by Formula 1 may be understood by one of ordinary skill in the art by referring to Synthesis Examples described below.

In some embodiments, the second compound may be selected from a compound including a carbazole ring and a phosphine oxide compound, but embodiments are not limited thereto.

In some embodiments, the second compound may be represented by Formula 2, but embodiments are not limited thereto:

$$Ar_{21}—(L_{21})_{a21}—Ar_{22}$$ Formula 2

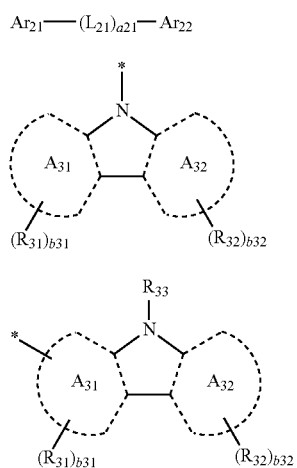

Formula 3-1

Formula 3-2 wherein, in Formulae 2, 3-1, and 3-2, $Ar_{21}$ and $Ar_{22}$ may be each independently selected from *-$(L_{22})_{a22}$-[Si($Q_1$)($Q_2$)($Q_3$)], *-$(L_{22})_{a22}$-[P(=O)($Q_1$)($Q_2$)], groups represented by Formula 3-1, and groups represented by Formula 3-2, $L_{21}$ and $L_{22}$ may be each independently selected from a single bond, *—O—', *—S—*', *—[Si($Q_1$)($Q_2$)]-*', *—[P(=O)($Q_1$)]-*', a phenylene group, a pyridinylene group, a pyrimidinylene group, a pyrazinylene group, a pyridazinylene group, a triazinylene group, a naphthylene group, a fluorenylene group, a carbazolylene group, a dibenzofuranylene group, and a dibenzothiophenylene group; and a phenylene group, a pyridinylene group, a pyrimidinylene group, a pyrazinylene group, a pyridazinylene group, a triazinylene group, a naphthylene group, a fluorenylene group, a carbazolylene group, a dibenzofuranylene group, and a dibenzothiophenylene group, each substituted with at least one selected from deuterium, —F, —Cl, —Br, —I, a hydroxyl group, a cyano group, a nitro group, an amidino group, a hydrazino group, a hydrazono group, a $C_1$-$C_{10}$ alkyl group, a $C_1$-$C_{10}$ alkoxy group, a $C_1$-$C_{10}$ alkyl group substituted with —F, a phenyl group, a phenyl group substituted with —F, a phenyl group substituted with a cyano group, a phenyl group substituted with a $C_1$-$C_{10}$ alkyl group, a biphenyl group, a terphenyl group, a naphthyl group, a pyridinyl group, a pyrimidinyl group, a pyrazinyl group, a pyridazinyl group, a triazinyl group, a fluorenyl group, a carbazolyl group, a dibenzofuranyl group, a dibenzothiophenyl group, —Si($Q_{31}$)($Q_{32}$)($Q_{33}$), and —P(=O)($Q_{31}$)($Q_{32}$), a21 and a22 may be each independently selected from 0, 1, 2, 3, 4, and 5, $A_{31}$ and $A_{32}$ may be each independently selected from a benzene group, a naphthalene group, a fluorene group, a benzofluorene group, a carbazole group, a benzocarbazole group, a dibenzofuran group, a benzonaphthofuran group, a dibenzothiophene group, and a benzonapthothiophene group, $R_{31}$ to $R_{33}$ may be each independently selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), and —P(=O)($Q_1$)($Q_2$), b31 and b32 may be each independently selected from 1, 2, 3, 4, 5, 6, 7, and 8, wherein $Q_1$ to $Q_3$ and $Q_{31}$ to $Q_{33}$ may be each independently selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group, and

* and *' each indicate a binding site to an adjacent atom.

In some embodiments, $Ar_{21}$ and $Ar_{22}$ in Formula 2 may be each independently selected from *-($L_{22}$)$_{a22}$-[Si($Q_1$)($Q_2$)($Q_3$)], *-($L_{22}$)$_{a22}$-[P(=O)($Q_1$)($Q_2$)], and groups represented by Formulae 3-11 to 3-15, but embodiments are not limited thereto:

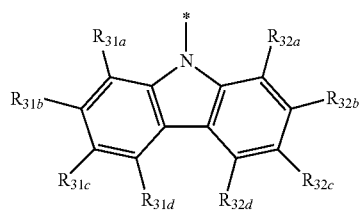

3-11

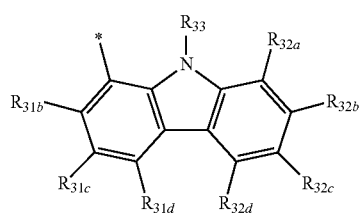

3-12

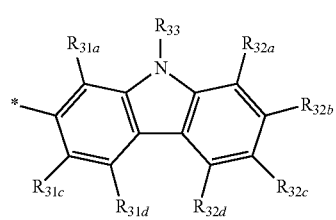

3-13

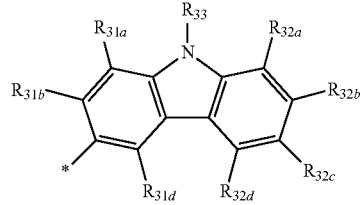

3-14

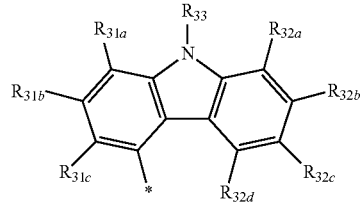

3-15 wherein, in Formulae 3-11 to 3-15, $R_{31a}$ to $R_{31d}$ may each be the same as $R_{31}$ described herein in relation to Formula 3-1, $R_{32a}$ to $R_{32d}$ may each be the same as $R_{32}$ described herein in relation to 3-1, $R_{33}$ may be the same as $R_{33}$ described herein in relation to Formula 3-2, and

* indicates a binding site to an adjacent atom.

In some embodiments, $Ar_{21}$ and $Ar_{22}$ in Formula 2 may be each independently selected from *-($L_{22}$)$_{a22}$-[Si($Q_1$)($Q_2$)($Q_3$)], *-($L_{22}$)$_{a22}$-[P(=O)($Q_1$)($Q_2$)], and groups represented by Formulae 3-11 to 3-15, wherein, in Formulae 3-11 to 3-15, $R_{31a}$ to $R_{31d}$, $R_{32a}$ to $R_{32d}$, and $R_{33}$ may be selected from hydrogen, deuterium, —F, —Cl, —Br, —I, a hydroxyl group, a cyano group, a nitro group, an amidino group, a hydrazino group, a hydrazono group, a $C_1$-$C_{10}$ alkyl group, a $C_1$-$C_{10}$ alkyl group substituted with —F, a phenyl group, a phenyl group substituted with —F, a phenyl group substituted with a cyano group, a phenyl group substituted with a $C_1$-$C_{10}$ alkyl group, a biphenyl group, a terphenyl group, a naphthyl group, a fluorenyl group, a carbazolyl group, a dibenzofuranyl group, a dibenzothiophenyl group, —Si($Q_1$)($Q_2$)($Q_3$), and —P(=O)($Q_1$)($Q_2$), wherein $Q_1$ to $Q_3$ may be each independently selected from hydrogen, a $C_1$-$C_{10}$ alkyl group, a $C_1$-$C_{10}$ alkyl group substituted with —F, a phenyl group, a phenyl group substituted with —F, a phenyl group substituted with a cyano group, a phenyl group substituted with a $C_1$-$C_{10}$ alkyl group, a biphenyl group, a terphenyl group, and a naphthyl group, and

* may indicate a binding site to an adjacent atom, but embodiments are not limited thereto.

In some embodiments, $L_{21}$ and $L_{22}$ in Formula 2 may be each independently selected from a single bond, *—O—*', *—S—*', *—[Si($Q_1$)($Q_2$)]-*', *—[P(=O)($Q_1$)]-*', and groups represented by Formulae 4-1 to 4-32, but embodiments are not limited thereto:

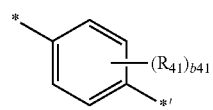

4-1

-continued
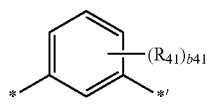
4-2
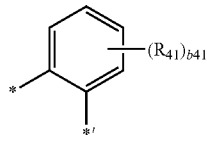
4-3
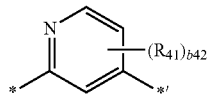
4-4
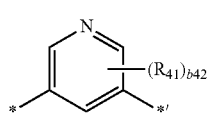
4-5
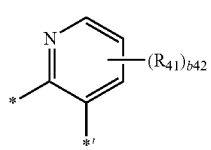
4-6
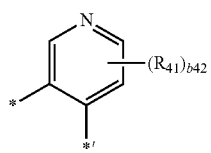
4-7
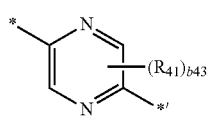
4-8
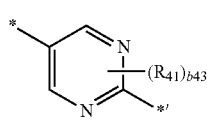
4-9
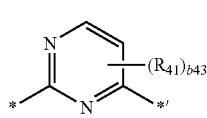
4-10
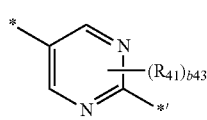
4-11
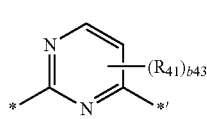
4-12
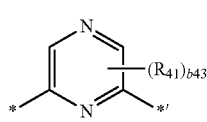
4-13
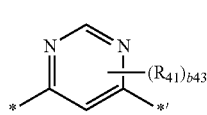
4-14
-continued
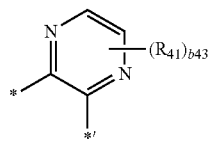
4-15
4-16
4-17
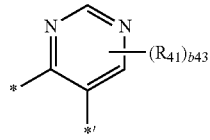
4-18
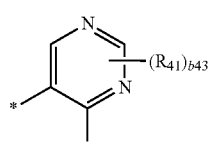
4-19
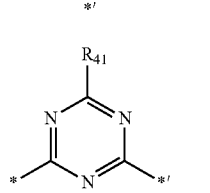
4-20
4-21
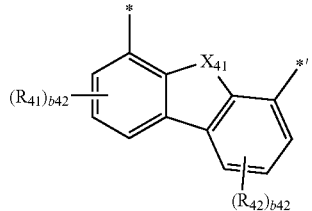
4-22

4-23 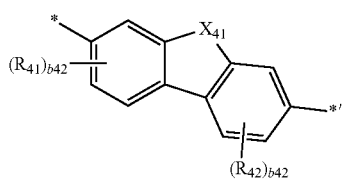

4-24 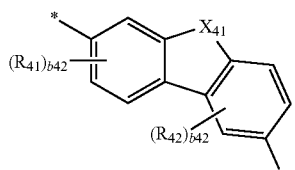

4-25 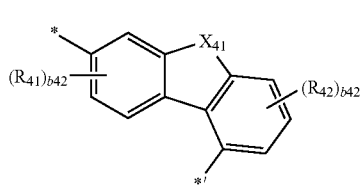

4-26 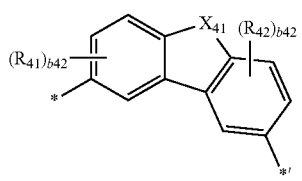

4-27 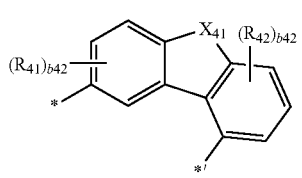

4-28 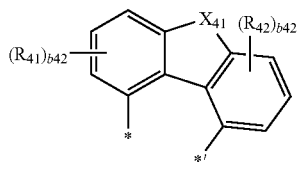

4-29 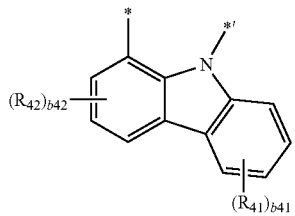

4-30 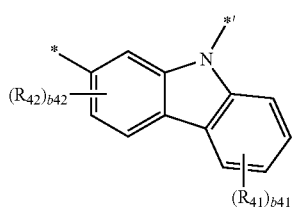

4-31 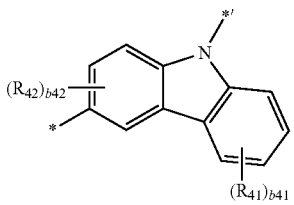

4-32 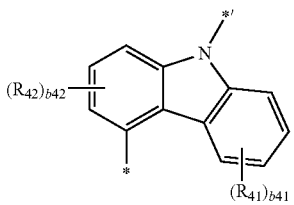

wherein, in Formulae 4-1 to 4-32, $X_{41}$ may be selected from $C(R_{43})(R_{44})$, $N(R_{43})$, O, and S, $R_{41}$ to $R_{44}$ may be each independently selected from hydrogen, deuterium, —F, —Cl, —Br, —I, a hydroxyl group, a cyano group, a nitro group, an amidino group, a hydrazino group, a hydrazono group, a $C_1$-$C_{10}$ alkyl group, a $C_1$-$C_{10}$ alkyl group substituted with —F, a phenyl group, a phenyl group substituted with —F, a phenyl group substituted with a cyano group, a phenyl group substituted with a $C_1$-$C_{10}$ alkyl group, a biphenyl group, a terphenyl group, a naphthyl group, a fluorenyl group, a carbazolyl group, a dibenzofuranyl group, a dibenzothiophenyl group, —Si$(Q_{31})(Q_{32})(Q_{33})$, and —P(=O)$(Q_{31})(Q_{32})$, wherein $Q_1$ to $Q_3$ and $Q_{31}$ to $Q_{33}$ may be each independently selected from hydrogen, a $C_1$-$C_{10}$ alkyl group, a phenyl group, a biphenyl group, a terphenyl group, and a naphthyl group, b41 may be selected from 1, 2, 3, and 4, b42 may be selected from 1, 2, and 3, b43 may be selected from 1 and 2, and

* and *' each indicate a binding site to an adjacent atom.

In some embodiments, $R_{31}$ to $R_{33}$ in Formulae 3-1 and 3-2 may be each independently selected from hydrogen, deuterium, —F, —Cl, —Br, —I, a hydroxyl group, a cyano group, a nitro group, an amidino group, a hydrazino group, a hydrazono group, a $C_1$-$C_{10}$ alkyl group, a $C_1$-$C_{10}$ alkyl group substituted with —F, a phenyl group, a phenyl group substituted with —F, a phenyl group substituted with a cyano group, a phenyl group substituted with a $C_1$-$C_{10}$ alkyl group, a biphenyl group, a terphenyl group, a naphthyl group, a fluorenyl group, a carbazolyl group, a dibenzofuranyl group, a dibenzothiophenyl group, —Si$(Q_1)(Q_2)(Q_3)$, and —P(=O)$(Q_1)(Q_2)$, wherein $Q_1$ to $Q_3$ may be each independently selected from hydrogen, a $C_1$-$C_{10}$ alkyl group, a phenyl group, a biphenyl group, a terphenyl group, and a naphthyl group, but embodiments are not limited thereto.

In some embodiments, the second compound may be selected from Compounds H1 to H17, but embodiments are not limited thereto:

975
H1
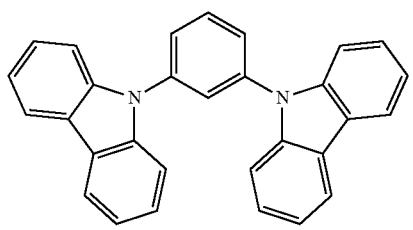
H2
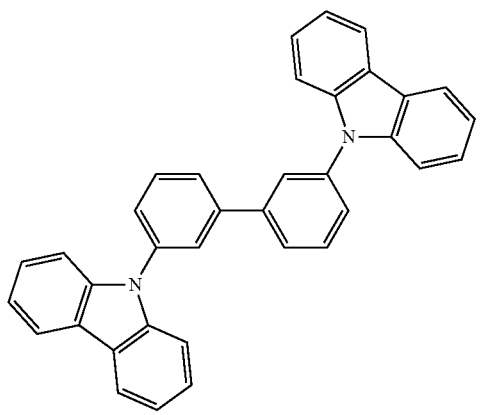
H3
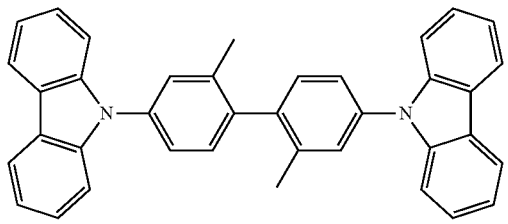
H4
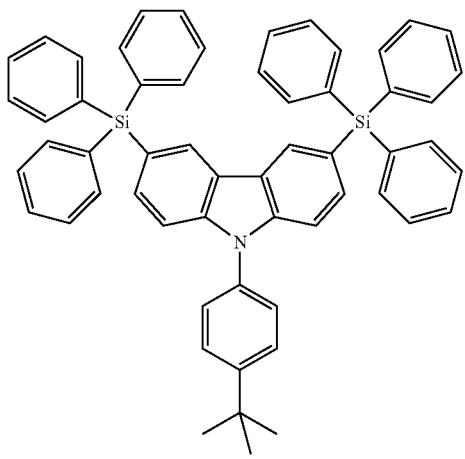
976
-continued
H5
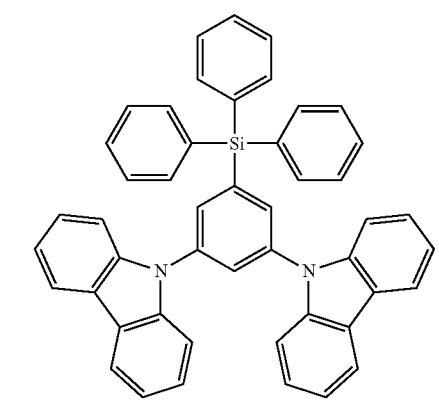
H6
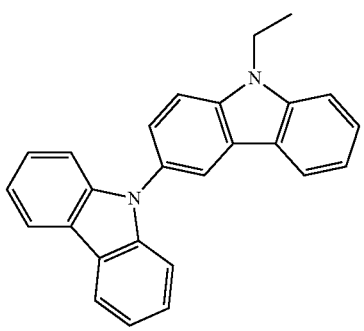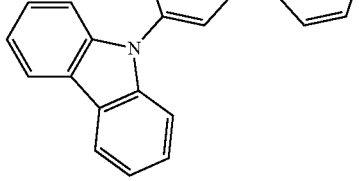
H7
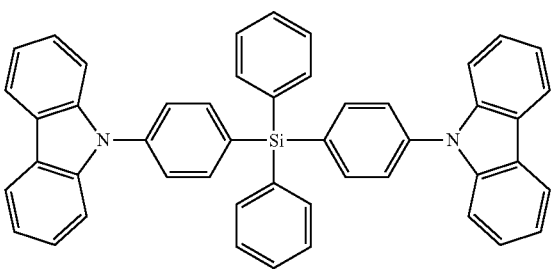
H8
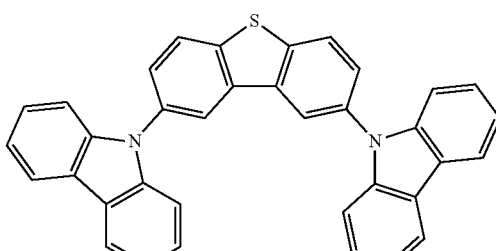
H9
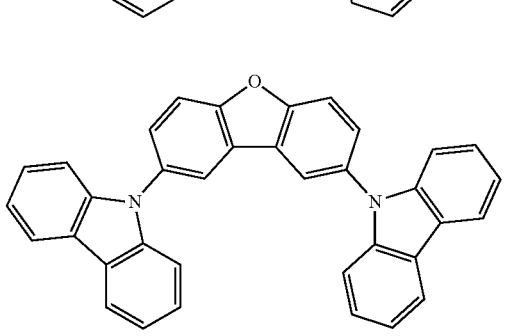

H10
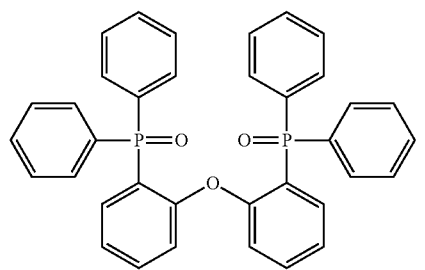
H11
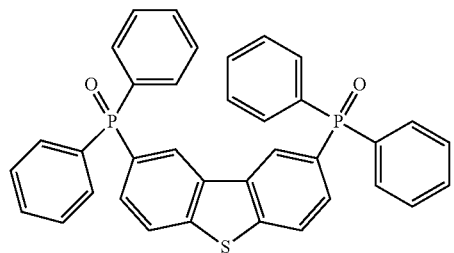
H12
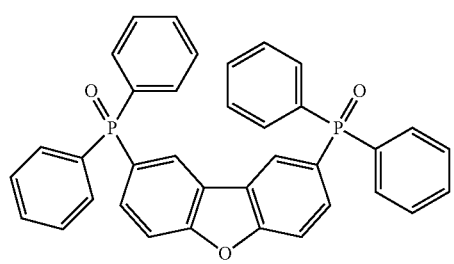
H13
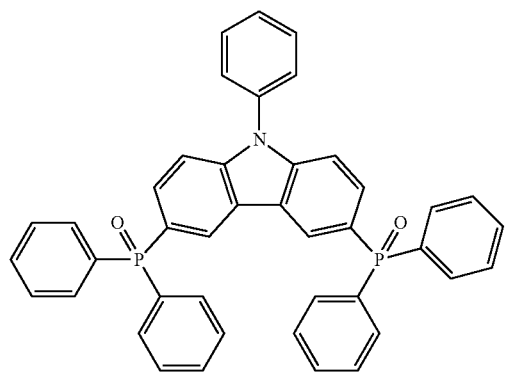
H14
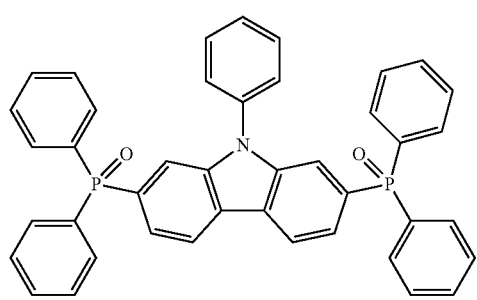
H15
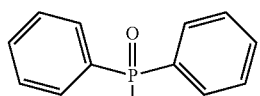
H16
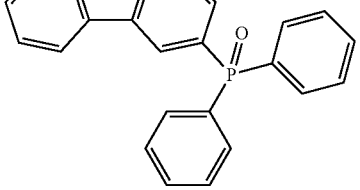
H17
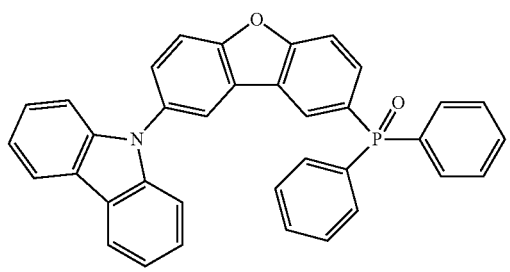
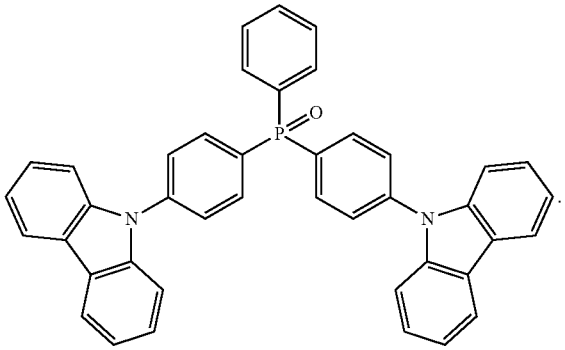
For example, the HOMO, LUMO, $T_1$ energy level, $S_1$ energy level, $\Delta E_{ST}$, and f of Compounds 1 and 2 represented by Formula 1 and Compound A were simulated by using the Gaussian. Simulation evaluation results are shown in Table 1.
TABLE 1
| Compound No. | HOMO (eV) | LUMO (eV) | $T_1$ (eV) | $S_1$ (eV) | $\Delta E_{ST}$ (eV) | f |
|---|---|---|---|---|---|---|
| 1 | −4.76 | −1.81 | 2.547 | 2.650 | 0.103 | 0.122 |
| 2 | −5.18 | −1.89 | 2.797 | 2.980 | 0.183 | 0.11 |
| A | −4.69 | −1.770 | 2.623 | 2.66 | 0.037 | 0 |

TABLE 1-continued

| Compound No. | HOMO (eV) | LUMO (eV) | $T_1$ (eV) | $S_1$ (eV) | $\Delta E_{ST}$ (eV) | f |
|---|---|---|---|---|---|---|

[Structure of Compound 1]

[Structure of Compound 2]

[Structure of Compound A]

Referring to Table 1, Compounds 1 and 2 were found to have a low LUMO energy level, as compared with Compound A. Therefore, Compounds 1 and 2 may have improved electron injectability, as compared with Compound A.

FIG. 1 is a schematic view of an organic light-emitting device 10 according to an embodiment. Hereinafter, the structure of an organic light-emitting device according to an embodiment and a method of manufacturing an organic light-emitting device, according to an embodiment, will be described in connection with FIG. 1. The organic light-emitting device 10 includes a first electrode 11, an organic layer 15, and a second electrode 19, which are sequentially stacked in this stated order.

A substrate may be additionally disposed under the first electrode 11 or above the second electrode 19. For use as the substrate, any substrate that is used in general organic light-emitting devices may be used, and the substrate may be a glass substrate or a transparent plastic substrate, each having excellent mechanical strength, thermal stability, transparency, surface smoothness, ease of handling, and water-resistance.

The first electrode 11 may be formed by vacuum depositing or sputtering a material for forming the first electrode 11 on the substrate. The first electrode 11 may be an anode. The material for forming the first electrode 11 may be selected from materials with a high work function to facilitate hole injection. The first electrode 11 may be a reflective electrode, a semi-transmissive electrode, or a transmissive electrode. The material for forming the first electrode 11 may be an indium tin oxide (ITO), indium zinc oxide (IZO), tin oxide ($SnO_2$), or zinc oxide (ZnO). In various embodiments, the material for forming the first electrode 11 may be metal, such as magnesium (Mg), aluminum (Al), aluminum-lithium (Al—Li), calcium (Ca), magnesium-indium (Mg—In), or magnesium-silver (Mg—Ag).

The first electrode 11 may have a single-layered structure or a multi-layered structure including two or more layers. For example, the first electrode 11 may have a three-layered structure of ITO/Ag/ITO, but the structure of the first electrode 11 is not limited thereto.

The organic layer 15 may be disposed on the first electrode 11.

The organic layer 15 may include a hole transport region, an emission layer, and an electron transport region.

The hole transport region may be disposed between the first electrode 11 and the emission layer.

The hole transport region may include at least one selected from a hole injection layer, a hole transport layer, an electron blocking layer, and a buffer layer.

The hole transport region may include only either a hole injection layer or a hole transport layer. In various embodiments, the hole transport region may have a structure of hole injection layer/hole transport layer or hole injection layer/hole transport layer/electron blocking layer, which are sequentially stacked in this stated order from the first electrode 11.

When the hole transport region includes a hole injection layer, the hole injection layer may be formed on the first electrode 11 by using one or more suitable methods, for example, vacuum deposition, spin coating, casting, and/or Langmuir-Blodgett (LB) deposition.

When a hole injection layer is formed by vacuum-deposition, for example, the vacuum-deposition may be performed at a deposition temperature in a range of about 100° C. to about 500° C., at a vacuum degree in a range of about $10^{-8}$ to about $10^{-3}$ torr, and at a deposition rate in a range of about 0 Angstroms per second (Å/sec) to about 100 Å/sec, though the conditions may vary depending on a compound that is used as a hole injection material and a structure and thermal properties of a desired hole injection layer, but conditions for the vacuum-deposition are not limited thereto.

When a hole injection layer is formed by spin-coating, the spin coating may be performed at a coating rate in a range of about 2,000 revolutions per minute (rpm) to about 5,000 rpm, and at a temperature in a range of about 80° C. to 200° C. for removing a solvent after the spin coating, though the conditions may vary depending on a compound that is used as a hole injection material and a structure and thermal properties of a desired hole injection layer, but the conditions are not limited thereto.

Conditions for forming a hole transport layer and an electron blocking layer may be understood by referring to conditions for forming the hole injection layer.

The hole transport region may include at least one selected from m-MTDATA, TDATA, 2-TNATA, NPB, β-NPB, TPD, Spiro-TPD, Spiro-NPB, methylated NPB, TAPC, HMTPD, 4,4',4"-tris(N-carbazolyl)triphenylamine (TCTA), polyaniline/dodecylbenzene sulfonic acid (Pani/DBSA), poly(3,4-ethylenedioxythiophene)/poly(4-styrenesulfonate) (PEDOT/PSS), polyaniline/camphor sulfonic acid (Pani/CSA), polyaniline/poly(4-styrenesulfonate) (Pani/PSS), a compound represented by Formula 201 below, and a compound represented by Formula 202 below:

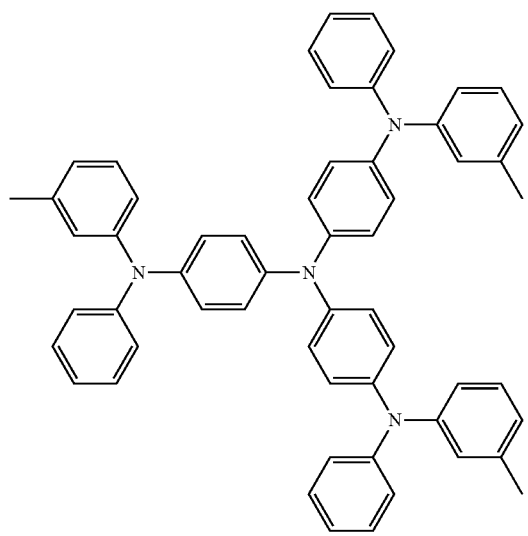

m-MTDATA

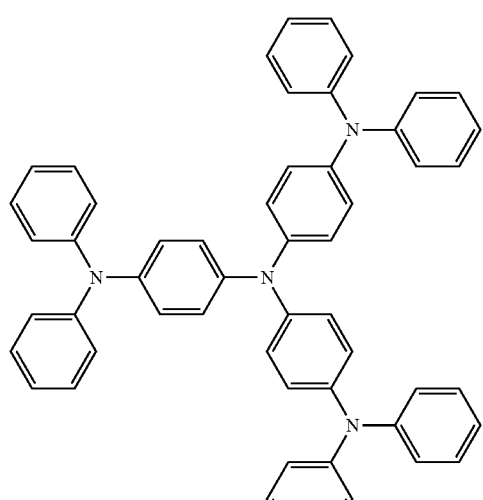

TDATA

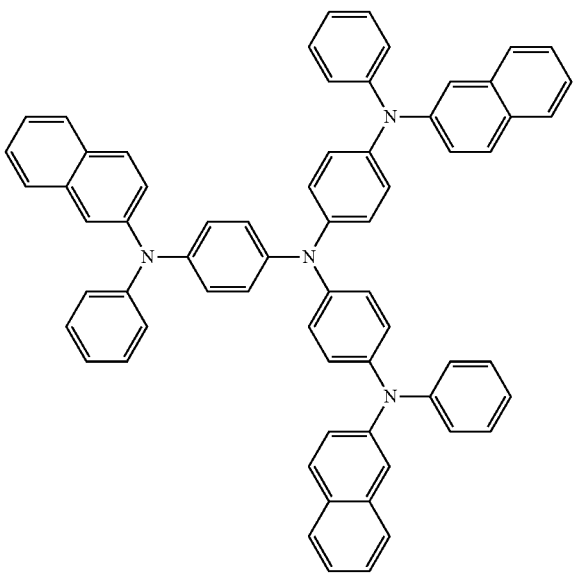

2-TNATA

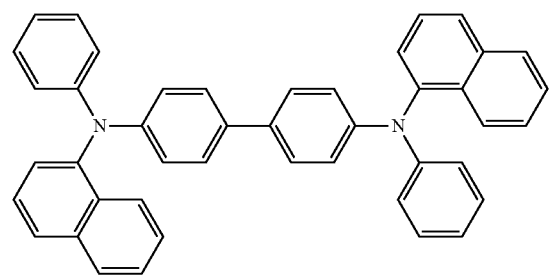

NPB

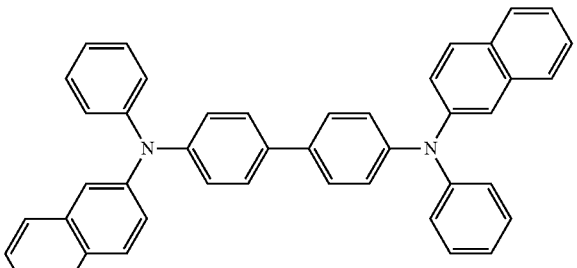

β-NPB

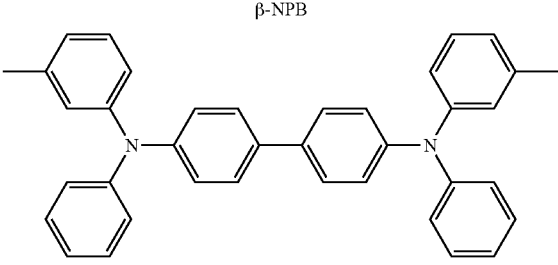

TPD

-continued

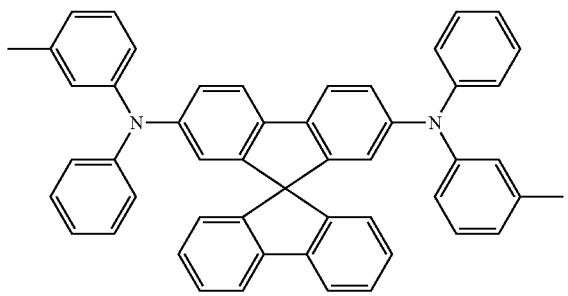

Spiro-TPD

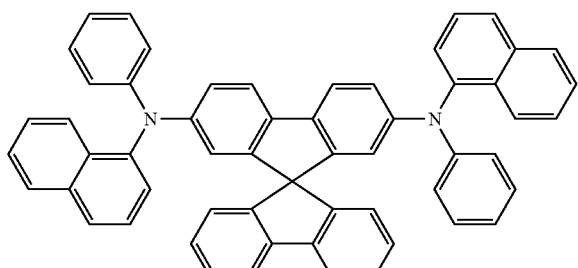

Spiro-NPB

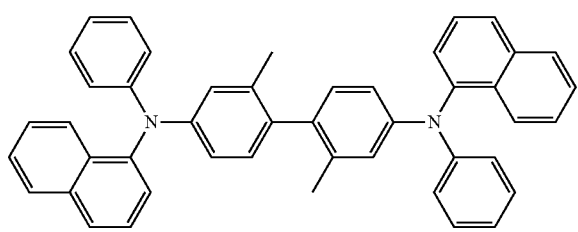

methylated NPB

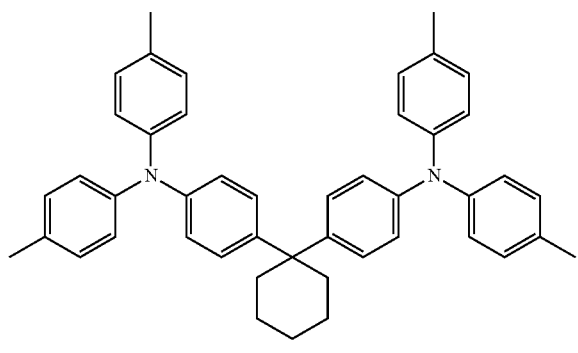

TAPC

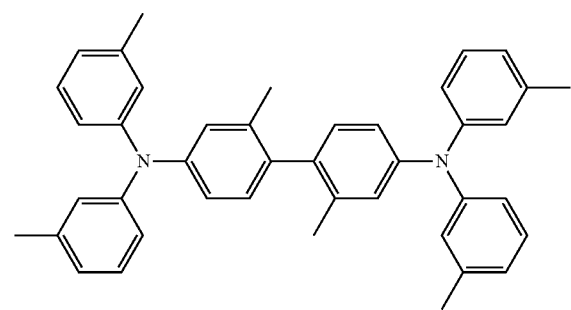

HMTPD

-continued

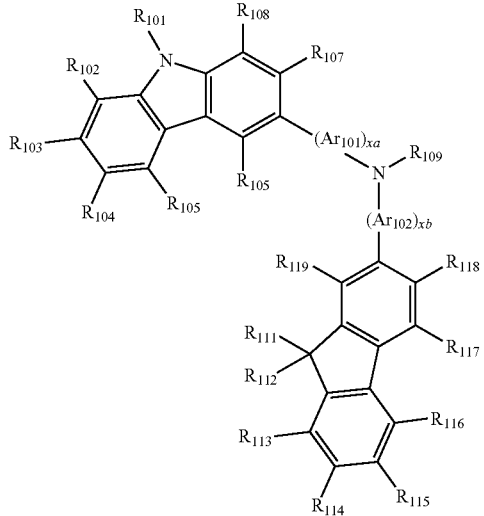

Formula 201

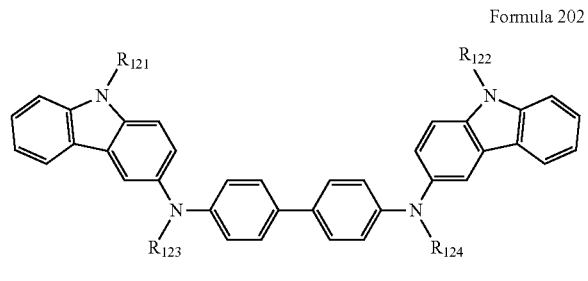

Formula 202 wherein, in Formula 201, $Ar_{101}$ and $Ar_{102}$ may be each independently selected from a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_2$-$C_{10}$ heterocycloalkyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group.

In Formula 201, xa and xb may be each independently an integer selected from 0 to 5. Alternatively, xa and xb may be each independently an integer selected from 0, 1, and 2. In some embodiments, xa may be 1 and xb may be 0, but embodiments are not limited thereto.

$R_{101}$ to $Ro_{108}$, $R_{111}$ to $R_{119}$, and $R_{121}$ to $R_{124}$ in Formulae 201 and 202 may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (e.g., a methyl group, an ethyl group, a propyl group, a butyl group, pentyl group, or a hexyl group), and a $C_1$-$C_{10}$ alkoxy group (e.g., a methoxy group, an ethoxy group, a propoxy group, a butoxy group, or a pentoxy group);

a $C_1$-$C_{10}$ alkyl group and a $C_1$-$C_{10}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, an anthracenyl group, a fluorenyl group, and a pyrenyl group; and a phenyl group, a naphthyl group, an anthracenyl group, a fluorenyl group, and a pyrenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group, but embodiments are not limited thereto.

$R_{109}$ in Formula 201 may be selected from a phenyl group, a naphthyl group, an anthracenyl group, and a pyridinyl group; and a phenyl group, a naphthyl group, an anthracenyl group, and a pyridinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, and a pyridinyl group.

In some embodiments, the compound represented by Formula 201 may be represented by Formula 201A, but embodiments are not limited thereto:

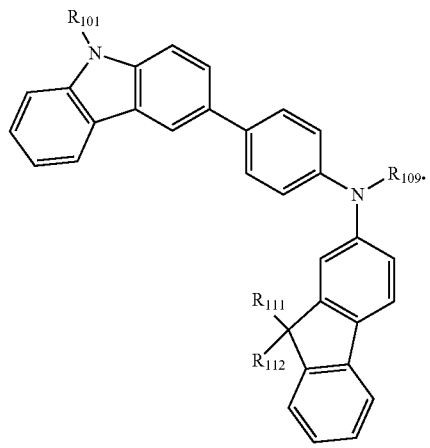

Formula 201A $R_{101}$, $R_{111}$, $R_{112}$, and $R_{109}$ in Formula 201A may be the same as those described herein.

For example, the compound represented by Formula 201 and the compound represented by Formula 202 may include Compounds HT1 to HT20, but embodiments are not limited thereto:

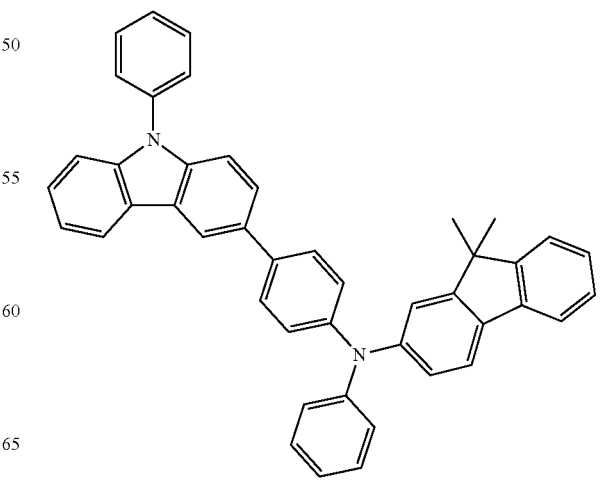

HT1

987
-continued
HT2
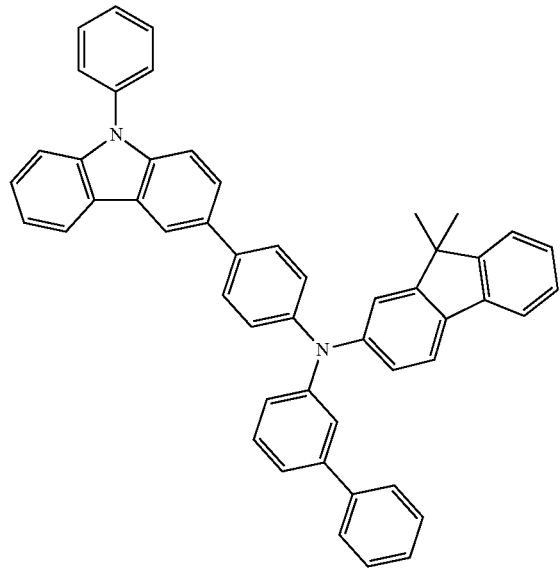
988
-continued
HT4
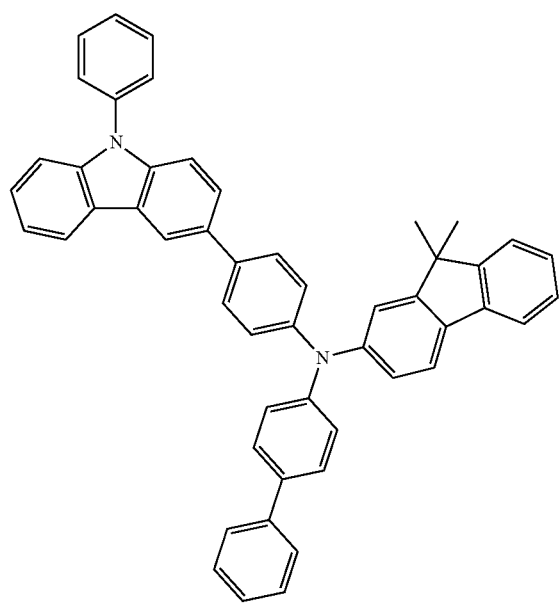
HT3
HT5
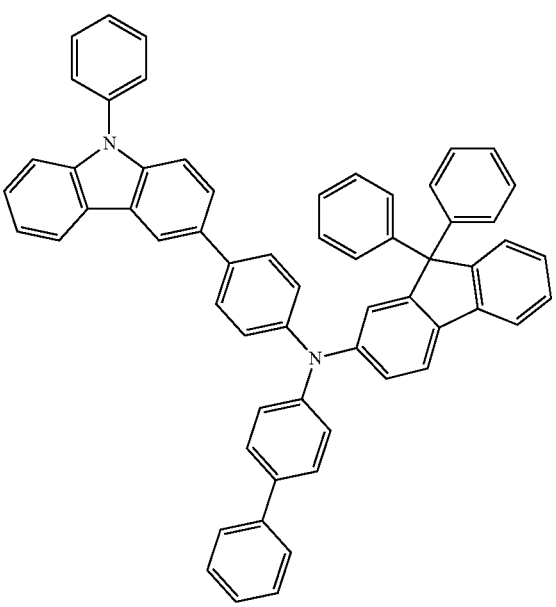

HT6
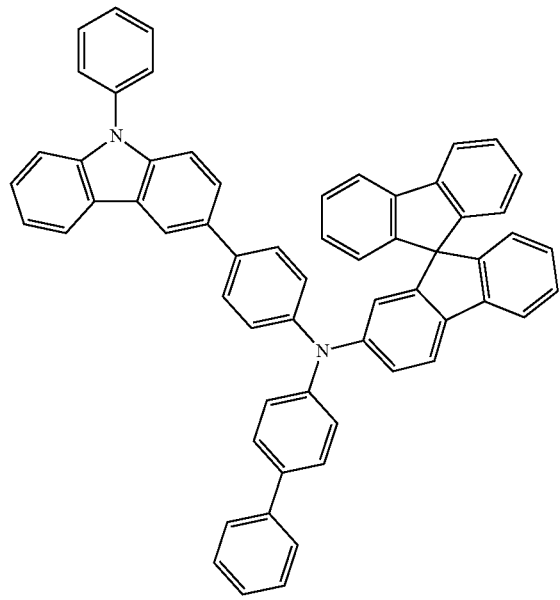
HT8
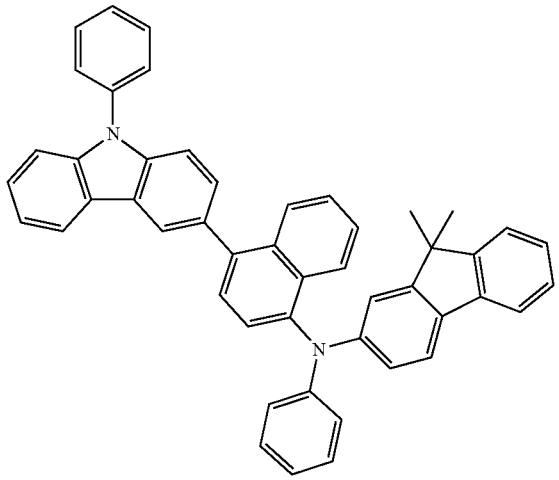
HT7
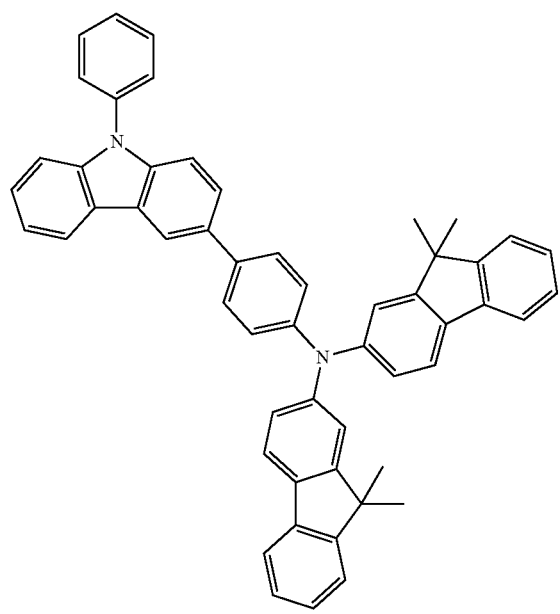
HT9
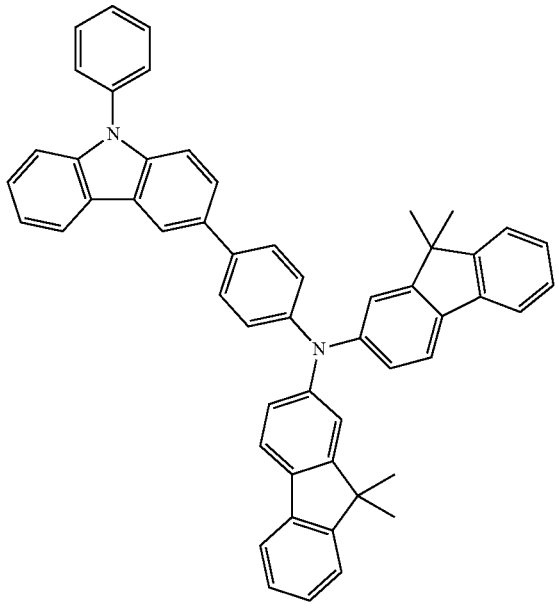

HT10
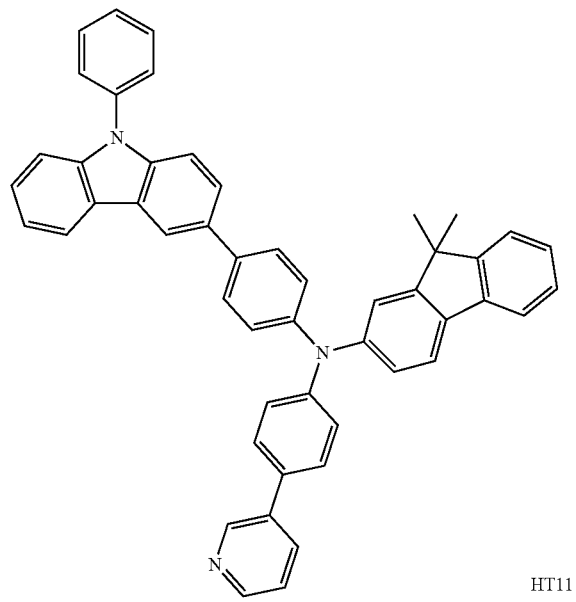
HT11
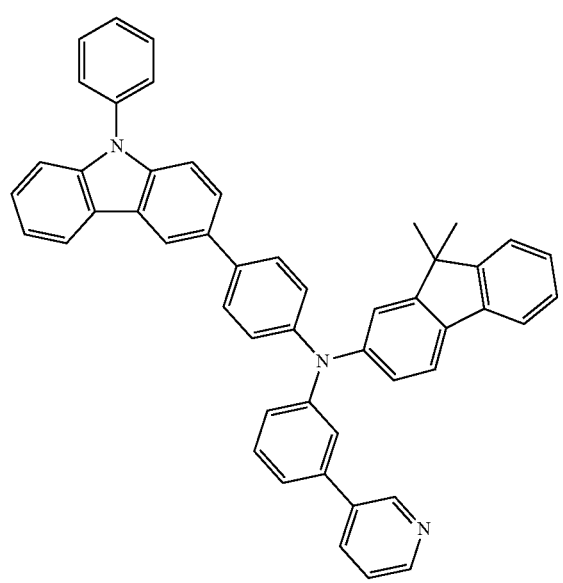
HT12
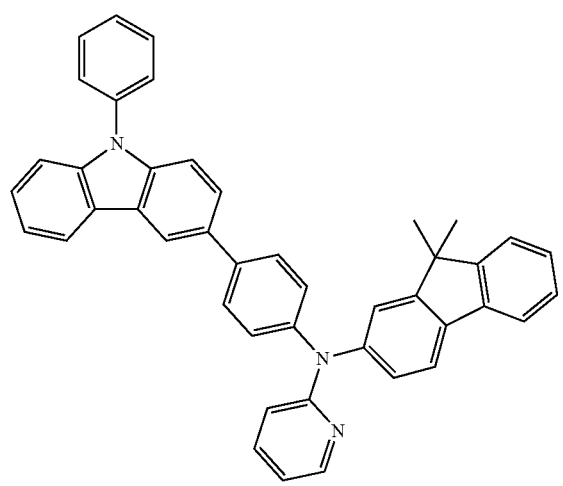
HT13
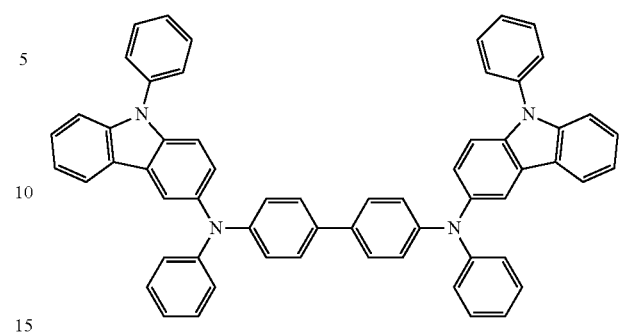
HT14
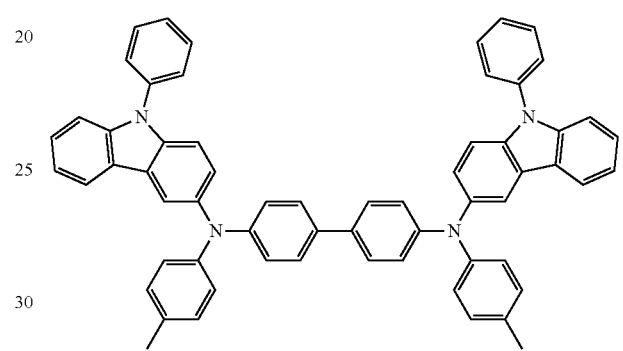
HT15
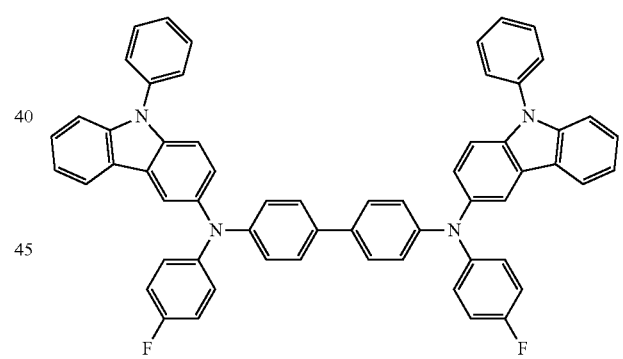
HT16
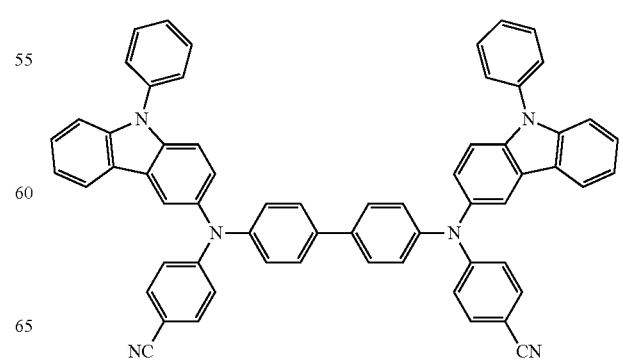

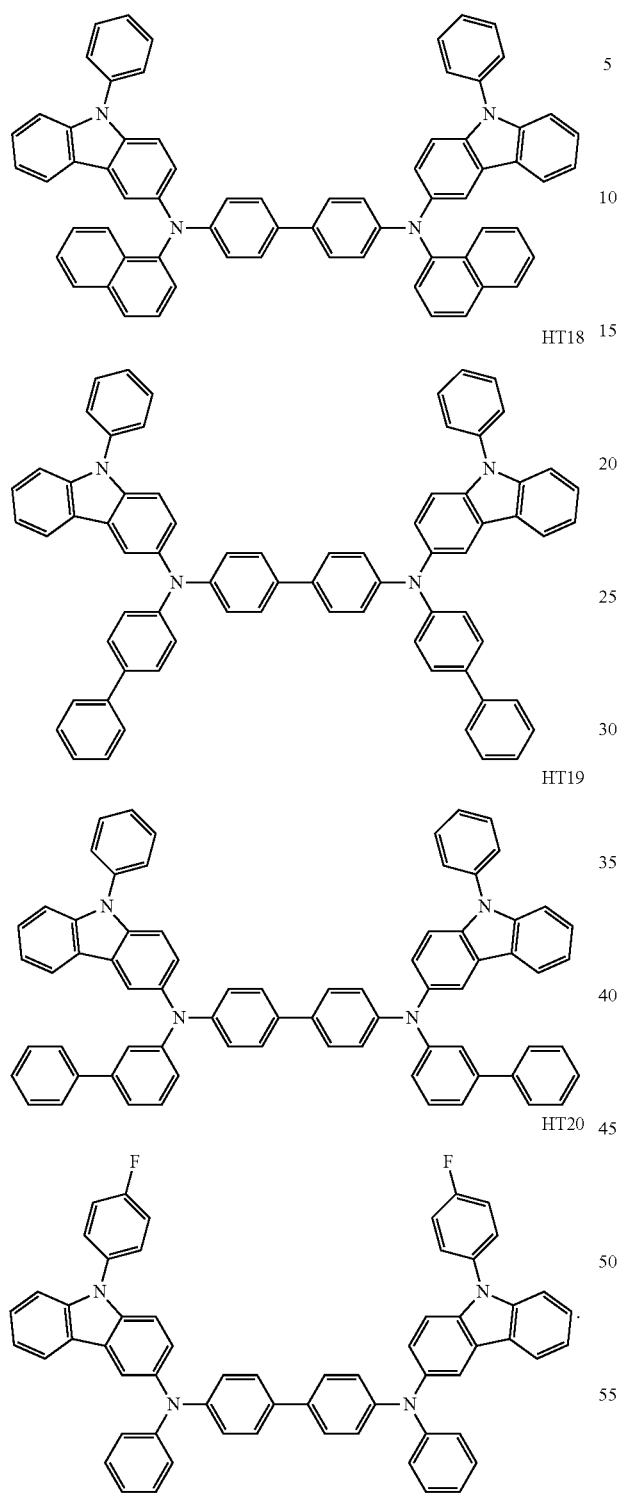

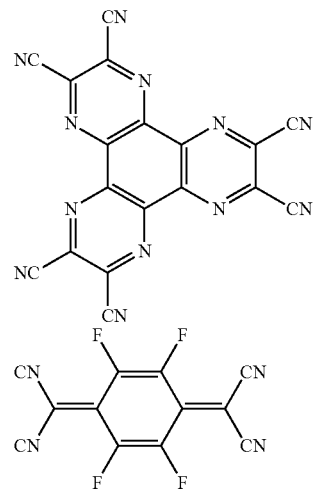

F4-TCNQ

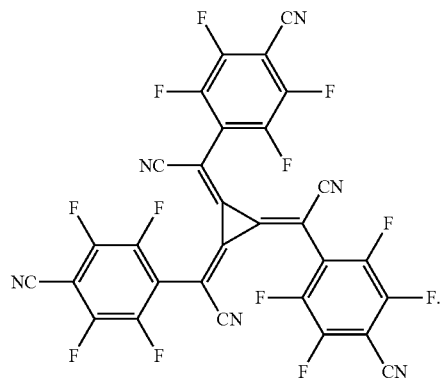

Compound HT-D1

Compound HT-D2

The thickness of the hole transport region may be in a range of about 100 Å to about 10,000 Å, and in some embodiments, about 100 Å to about 1,000 Å. When the hole transport region includes a hole injection layer and a hole transport layer, the thickness of the hole injection layer may be in a range of about 100 Å to about 10,000 Å, and for example, about 100 Å to about 1,000 Å, and the thickness of the hole transport layer may be in a range of about 50 Å to about 2,000 Å, and for example, about 100 Å to about 1,500 Å. While not wishing to be bound by theory, it is understood that when the thickness values of the hole transport region, the hole injection layer and the hole transport layer are within these ranges, satisfactory hole transporting characteristics may be obtained without a substantial increase in driving voltage.

The hole transport region may further include, in addition to these materials, a charge-generation material for the improvement of conductive properties. The charge-generation material may be homogeneously or non-homogeneously dispersed in the hole transport region.

The charge-generation material may be, e.g., a p-dopant. The p-dopant may be one selected from a quinone derivative, a metal oxide, and a cyano group-containing compound, but embodiments are not limited thereto. Non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenum oxide; and a cyano group-containing compound, such as Compound HT-D1 or Compound HT-D2 below, but are not limited thereto:

The hole transport region may include a buffer layer.

Also, the buffer layer may compensate for an optical resonance distance according to a wavelength of light emitted from the emission layer, and thus, efficiency of a formed organic light-emitting device may be improved.

The electron transport region may further include an electron blocking layer.

The electron blocking layer may include a compound having a LUMO energy level lower than that of the second compound and a triplet energy level greater than that of the second compound, but embodiments are not limited thereto.

The electron blocking layer may include, for example, mCP, but a material therefor is not limited thereto:

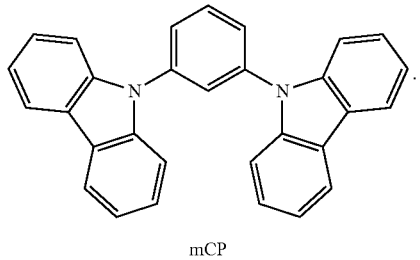 [SMILES: c1cc(-n2c3ccccc3c3ccccc32)cc(-n2c3ccccc3c3ccccc32)c1]

mCP

The thickness of the electron blocking layer may be in a range of about 50 Å to about 100 Å. While not wishing to be bound by theory, it is understood that when the thickness of the electron blocking layer is within this range, excellent electron blocking characteristics may be achieved without a substantial increase in driving voltage.

Then, an emission layer may be formed on the hole transport region by vacuum deposition, spin coating, casting, LB deposition, or the like. When the emission layer is formed by vacuum deposition or spin coating, the deposition or coating conditions may be similar to those applied to form the hole injection layer although the deposition or coating conditions may vary according to the material that is used to form the emission layer.

When the organic light-emitting device is a full color organic light-emitting device, the emission layer may be patterned into a red emission layer, a green emission layer, and a blue emission layer. In various embodiments, due to a stack structure including a red emission layer, a green emission layer, and/or a blue emission layer, the emission layer may emit white light.

The emission layer may include the first compound represented by Formula 1 and the second compound having the lowest excited triplet energy level greater than 2.73 eV.

The thickness of the emission layer may be in a range of about 100 Å to about 1,000 Å, and in some embodiments, about 200 Å to about 600 Å. While not wishing to be bound by theory, it is understood that when the thickness of the emission layer is within these ranges, excellent light-emission characteristics may be achieved without a substantial increase in driving voltage.

Then, an electron transport region may be disposed on the emission layer.

The electron transport region may include at least one selected from a hole blocking layer, an electron transport layer, and an electron injection layer.

For example, the electron transport region may have a structure of hole blocking layer/electron transport layer/electron injection layer or a structure of electron transport layer/electron injection layer, but the structure of the electron transport region is not limited thereto. The electron transport layer may have a single-layered structure or a multi-layered structure including two or more different materials.

Conditions for forming the hole blocking layer, the electron transport layer, and the electron injection layer, which constitute the electron transport region, may be understood by referring to the conditions for forming the hole injection layer.

When the electron transport region includes a hole blocking layer, the hole blocking layer, for example, may include at least one of BCP and Bphen, but embodiments are not limited thereto:

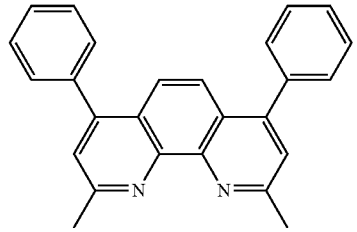

BCP

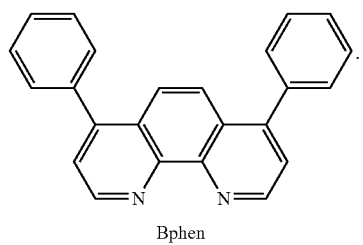

Bphen

The thickness of the hole blocking layer may be in a range of about 20 Å to about 1,000 Å, for example, about 30 Å to about 300 Å. While not wishing to be bound by theory, it is understood that when the thickness of the hole blocking layer is within these ranges, the hole blocking layer may have excellent hole blocking characteristics without a substantial increase in driving voltage.

The electron transport layer may further include at least one selected from BCP, Bphen, Alq$_3$, BAlq, TAZ, and NTAZ:

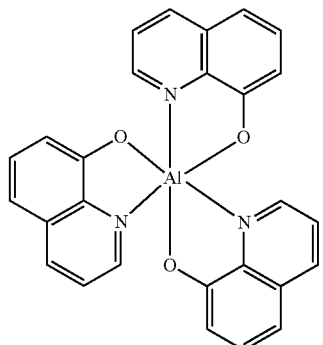

Alq$_3$

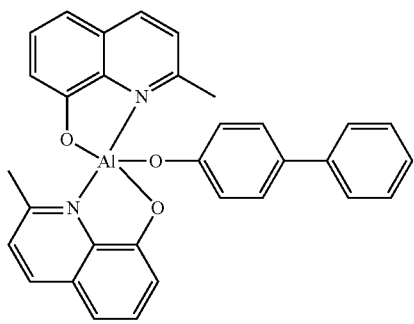
BAlq
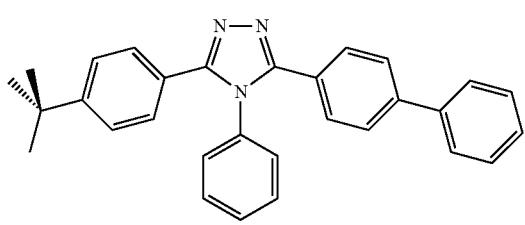
TAZ
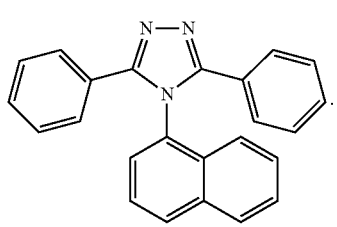
NTAZ
In various embodiments, the electron transport layer may include at least one of ET1 and ET19, but are not limited thereto:
ET1
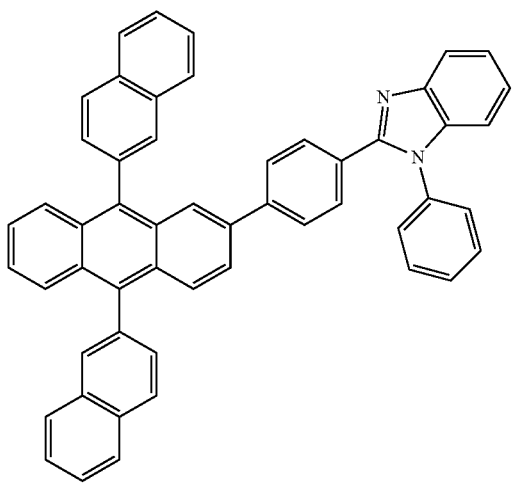
ET2
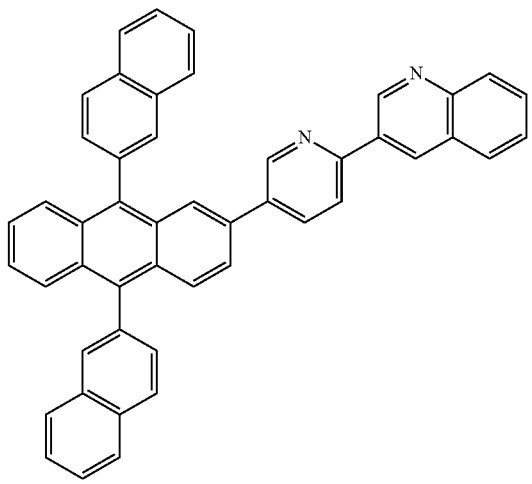
ET3
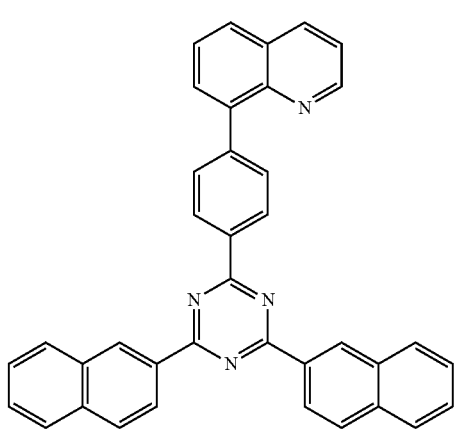
ET4
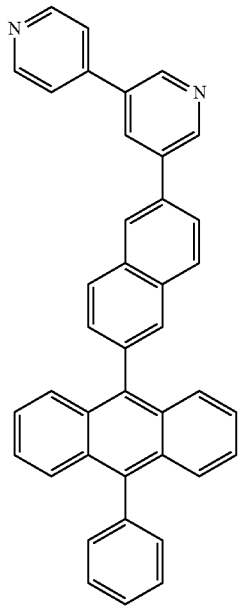

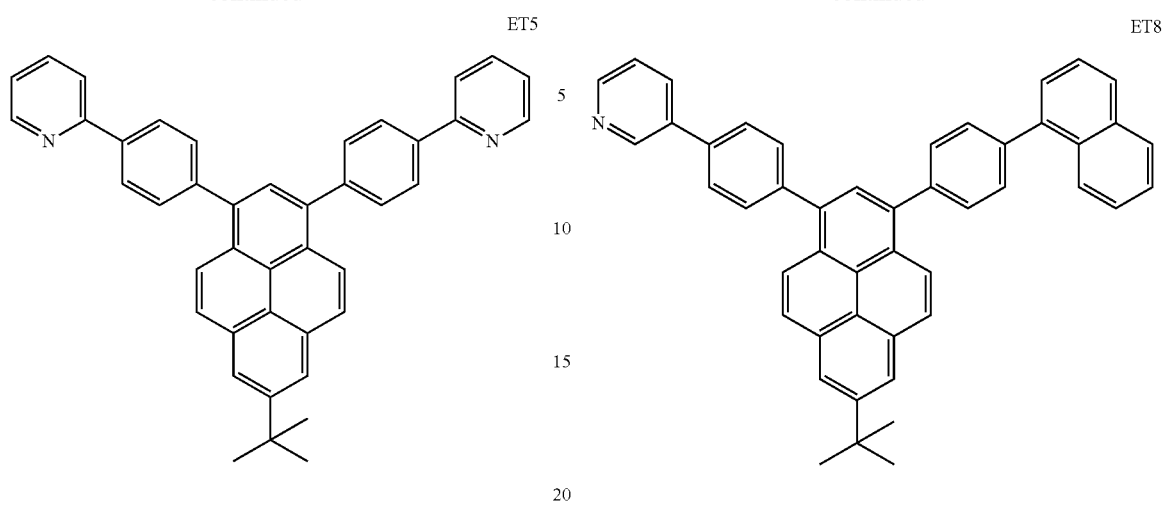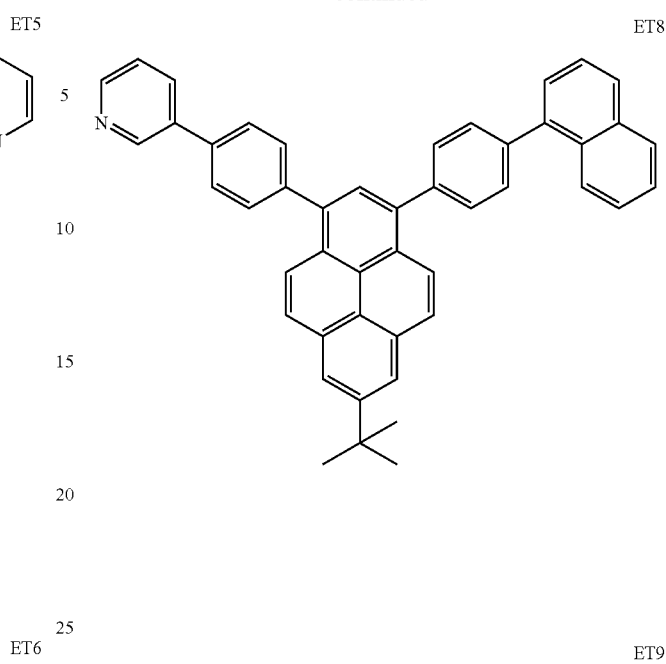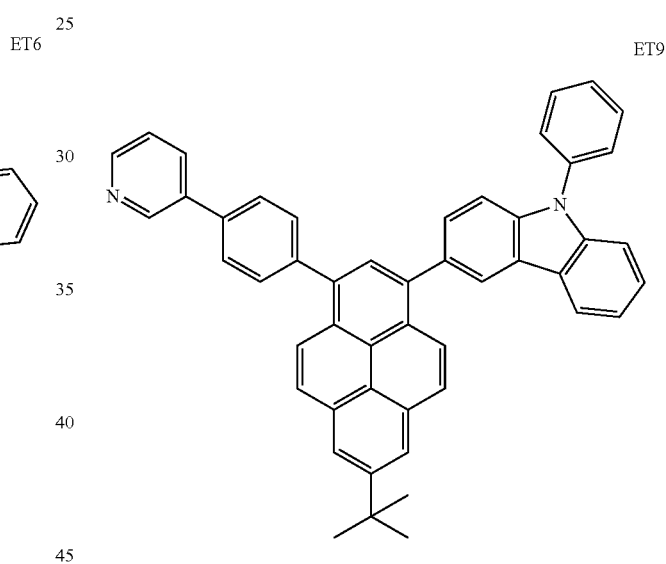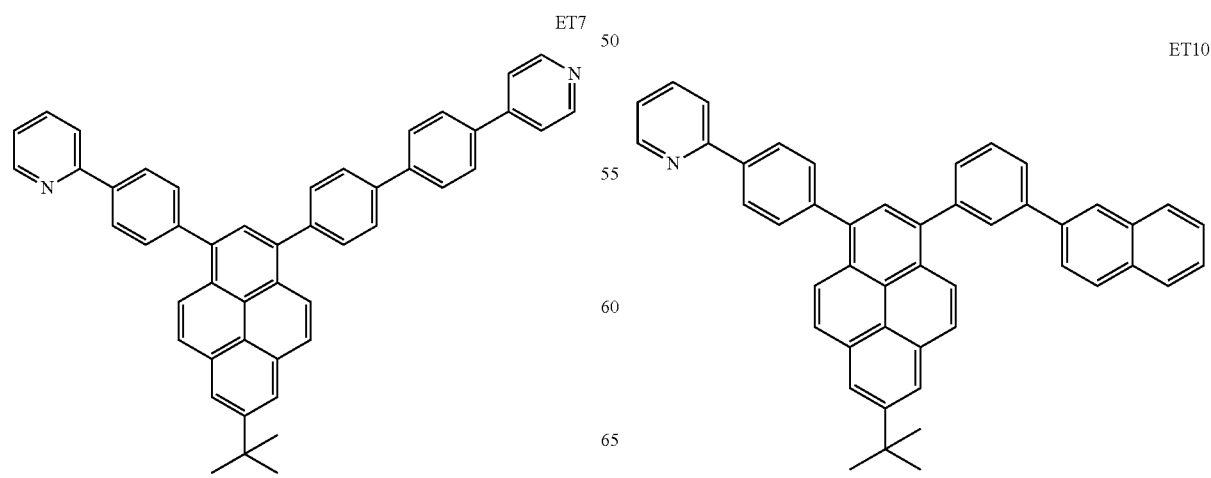

ET11
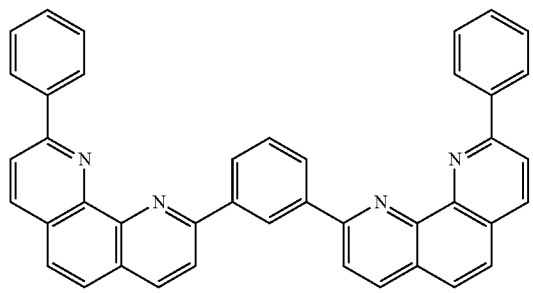
ET12
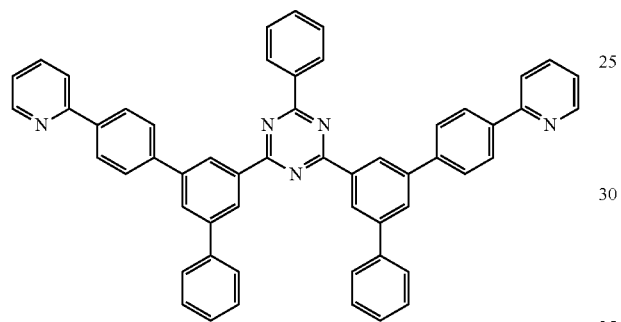
ET13
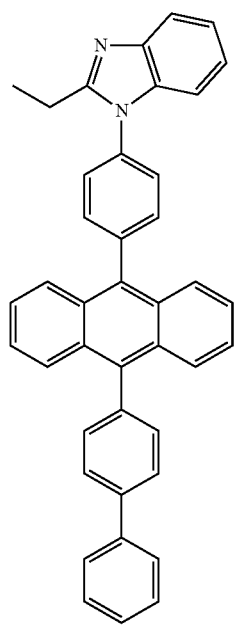
ET14
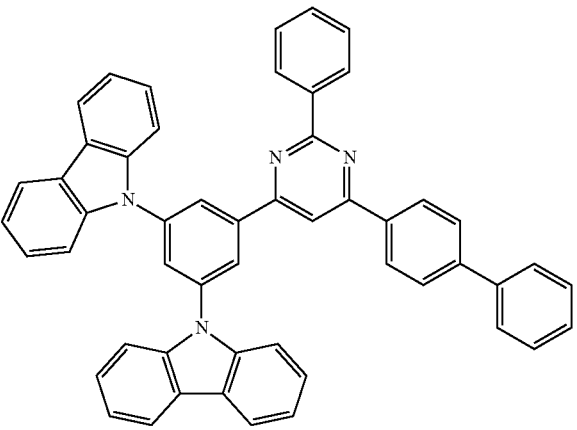
ET15
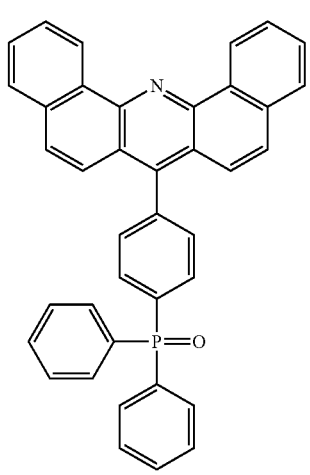
ET16
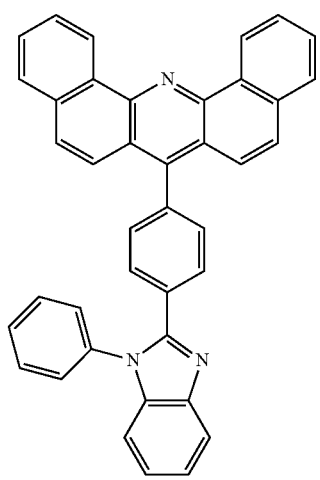

ET17

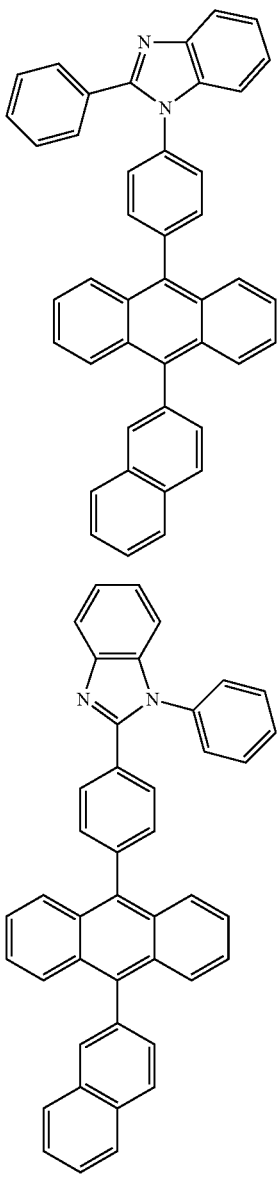

ET18

ET19

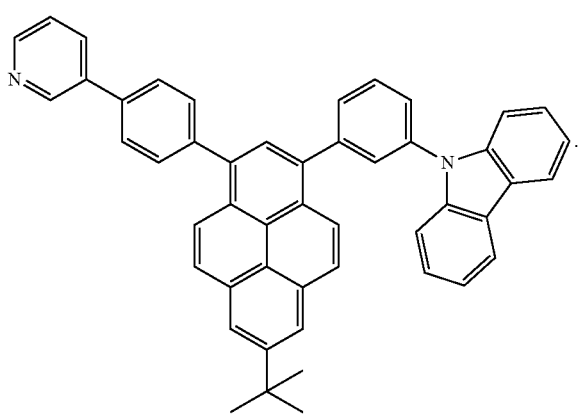

The thickness of the electron transport layer may be in a range of about 100 Å to about 1,000 Å, for example, about 150 Å to about 500 Å. While not wishing to be bound by theory, it is understood that when the thickness of the electron transport layer is within these ranges, the electron transport layer may have satisfactory electron transport characteristics without a substantial increase in driving voltage.

Also, the electron transport layer may further include, in addition to the materials described above, a metal-containing material.

The metal-containing material may include a Li complex. The Li complex may include, for example, Compound ET-D1 (lithium quinolate, LiQ) or ET-D2:

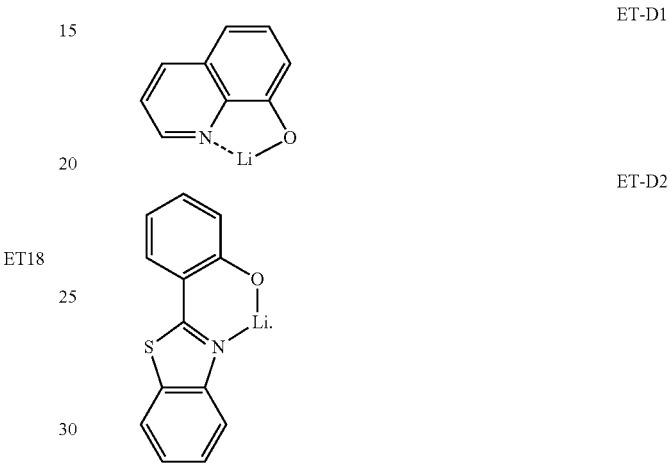

The electron transport region may include an electron injection layer that promotes flow of electrons from the second electrode 19 thereinto.

The electron injection layer may include at least one selected from LiF, NaCl, CsF, $Li_2O$, and BaO.

The thickness of the electron injection layer may be in a range of about 1 Å to about 100 Å, for example, about 3 Å to about 90 Å. While not wishing to be bound by theory, it is understood that when the thickness of the electron injection layer is within these ranges, the electron injection layer may have satisfactory electron injection characteristics without a substantial increase in driving voltage.

The second electrode 19 is disposed on the organic layer 15. The second electrode 19 may be a cathode. A material for forming the second electrode 19 may be metal, an alloy, an electrically conductive compound, and a combination thereof, which have a relatively low work function. For example, lithium (Li), magnesium (Mg), aluminum (Al), aluminum-lithium (Al—Li), calcium (Ca), magnesium-indium (Mg—In), or magnesium-silver (Mg—Ag) may be formed as the material for forming the second electrode 19. To manufacture a top emission type light-emitting device, a transmissive electrode formed using ITO or IZO may be used as the second electrode 19.

Hereinbefore, the organic light-emitting device has been described with reference to FIG. 1, but is not limited thereto.

The term "$C_1$-$C_{60}$ alkyl group" as used herein refers to a linear or branched aliphatic saturated hydrocarbon monovalent group having 1 to 60 carbon atoms. Detailed examples thereof are a methyl group, an ethyl group, a propyl group, an isobutyl group, a sec-butyl group, a tert-butyl group, a pentyl group, an iso-amyl group, and a hexyl group.

The term "$C_1$-$C_{60}$ alkoxy group" as used herein refers to a monovalent group represented by —$OA_{101}$ (wherein $A_{101}$ is the $C_1$-$C_{60}$ alkyl group). Detailed examples thereof may include a methoxy group, an ethoxy group, and an iso-propyloxy group.

The term "$C_1$-$C_{60}$ alkylthio group" as used herein refers to a monovalent group represented by —$SA_{101}$ (where $A_{101}$ is a $C_1$-$C_{60}$ alkyl group). Detailed examples thereof may include a methylthio group, an ethylthio group, and an iso-propylthio group.

The term "$C_2$-$C_{60}$ alkenyl group" as used herein refers to a group formed by placing at least one carbon double bond in the middle or at the terminus of the $C_2$-$C_{60}$ alkyl group. Detailed examples thereof may include an ethenyl group, a propenyl group, and a butenyl group.

The term "$C_2$-$C_{60}$ alkynyl group" as used herein refers to a group formed by placing at least one carbon triple bond in the middle or at the terminus of the $C_2$-$C_{30}$ alkyl group. Detailed examples thereof may include an ethenyl group and a propenyl group.

The term "$C_3$-$C_{10}$ cycloalkyl group" as used herein refers to a monovalent saturated hydrocarbon monocyclic group having 3 to 10 carbon atoms. Detailed examples thereof may include a cyclopropyl group, a cyclobutyl group, a cyclopentyl group, a cyclohexyl group, and a cycloheptyl group.

The term "$C_1$-$C_{10}$ heterocycloalkyl group" as used herein refers to a monovalent monocyclic group including at least one heteroatom selected from N, O, P, and S as a ring-forming atom and 1 to 10 carbon atoms. Detailed examples thereof may include a tetrahydrofuranyl group and a tetrahydrothiophenyl group.

The term "$C_3$-$C_{10}$ cycloalkenyl group" as used herein refers to a monovalent monocyclic group that has 3 to 10 carbon atoms and at least one carbon-carbon double bond in the ring thereof and which is not aromatic. Detailed examples thereof may include a cyclopentenyl group, a cyclohexenyl group, and a cycloheptenyl group.

The term "$C_1$-$C_{10}$ heterocycloalkenyl group" as used herein refers to a monovalent monocyclic group that has at least one heteroatom selected from N, O, P, and S as a ring-forming atom, 1 to 10 carbon atoms, and at least one carbon-carbon double bond in its ring. Detailed examples of the $C_1$-$C_{10}$ heterocycloalkenyl group may include a 2,3-dihydrofuranyl group and a 2,3-dihydrothiophenyl group.

The term "$C_6$-$C_{60}$ aryl group" as used herein refers to a monovalent group having a carbocyclic aromatic system having 6 to 60 carbon atoms. Detailed examples of the $C_6$-$C_{30}$ aryl group may include a phenyl group, a naphthyl group, an anthracenyl group, a phenanthrenyl group, a pyrenyl group, and a chrysenyl group. When the $C_6$-$C_{60}$ aryl group includes a plurality of rings, the rings may be fused.

The term "$C_6$-$C_{60}$ aryloxy group" as used herein refers to a monovalent group represented by —$OA_{101}$ (where $A_{101}$ is a $C_6$-$C_{60}$ aryl group). Detailed examples thereof may include a phenoxy group.

The term "$C_6$-$C_{60}$ arylthio group" as used herein refers to a monovalent group represented by —$SA_{101}$ (where $A_{101}$ is a $C_6$-$C_{60}$ aryl group). Detailed examples thereof may include a phenylthio group.

The term "$C_1$-$C_{60}$ heteroaryl group" as used herein refers to a monovalent group having a carbocyclic aromatic system including at least one heteroatom selected from N, O, P, and S as a ring-forming atom and 1 to 60 carbon atoms. Detailed examples of the $C_1$-$C_{60}$ heteroaryl group may include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group includes a plurality of rings, the rings may be fused.

The term "monovalent non-aromatic condensed polycyclic group" as used herein refers to a monovalent group that has two or more rings condensed to each other, only carbon atoms as ring-forming atoms, and which is non-aromatic in the entire molecular structure. Detailed examples of the monovalent non-aromatic condensed polycyclic group are a fluorenyl group.

The term "monovalent non-aromatic condensed heteropolycyclic group" as used herein refers to a monovalent group that has two or more rings condensed to each other, a heteroatom selected from N, O, P, and S, in addition to carbon atoms as ring-forming atoms, and that is non-aromatic in the entire molecular structure. Examples of the monovalent non-aromatic condensed heteropolycyclic group are a carbazolyl group.

The term "$C_6$-$C_{20}$ cyclic group" as used herein refers to an aliphatic group or an aromatic group that includes 6 to 20 carbon atoms. Detailed examples of the $C_6$-$C_{20}$ cyclic group may include a cyclohexane group, a cyclohexene group, a benzene group, and a naphthalene group. When the $C_6$-$C_{20}$ cyclic group includes a plurality of rings, the rings may be fused.

The term "$C_1$-$C_{20}$ heterocyclic group" as used herein refers to an aliphatic group or an aromatic group that includes at least one heteroatom selected from N, O, P, and S as a ring-forming atom and 1 to 20 carbon atoms. Detailed examples of the $C_1$-$C_{20}$ heterocyclic group may include a pyrrolidine, a piperidine, a tetrahydrofuran (THF), a pyrrole, a furan, and a thiophene. When the $C_1$-$C_{20}$ heterocyclic group includes a plurality of rings, the rings may be fused.

In the present specification, at least one of substituents of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, a substituted divalent non-aromatic condensed polycyclic group, a substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_1$-$C_{60}$ alkylthio group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from:

deuterium (-D), —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{11})(Q_{12})(Q_{13})$, —$N(Q_{11})(Q_{12})$, —$B(Q_{11})(Q_{12})$, —$C(=O)(Q_{11})$, —$S(=O)_2(Q_{11})$, and —$P(=O)(Q_{11})(Q_{12})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), wherein $Q_{11}$ to $Q_{13}$, $Q_{21}$ to $Q_{23}$, and $Q_{31}$ to $Q_{33}$ may be each independently selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

When a group containing a specified number of carbon atoms is substituted with any of the groups listed in the preceding paragraph, the number of carbon atoms in the resulting "substituted" group is defined as the sum of the carbon atoms contained in the original (unsubstituted) group and the carbon atoms (if any) contained in the substituent. For example, when the term "substituted $C_1$-$C_{60}$ alkyl" refers to a $C_1$-$C_{60}$ alkyl group substituted with $C_6$-$C_{60}$ aryl group, the total number of carbon atoms in the resulting aryl substituted alkyl group is $C_7$-$C_{120}$.

The term "Ph" as used herein represents a phenyl group. The term "Me" as used herein represents a methyl group. The term "Et" as used herein represents an ethyl group. The term "tert-Bu" or "Bu$^t$" as used herein represents a tert-butyl group.

The term "OMe" as used herein represents a methoxy group.

The term "biphenyl group" as used herein refers to a phenyl group substituted with a phenyl group. The "biphenyl group" may be a substituted phenyl group having a $C_6$-$C_{60}$ aryl group as a substituent.

The term "terphenyl group" as used herein refers to a phenyl group substituted with a biphenyl group. The "terphenyl group" may be a substituted phenyl group having a $C_6$-$C_{60}$ aryl group substituted with a $C_6$-$C_{60}$ aryl group as a substituent.

The symbols * and *' used herein, unless defined otherwise, refer to a binding site to a neighboring atom in a corresponding formula.

Hereinafter, an organic light-emitting device 10 according to an embodiment will be described in more detail with reference to Synthesis Examples and Examples; however, the present disclosure is not limited thereto. The wording "B was used instead of A" used in describing Synthesis Examples refers to that an identical number of molar equivalents of B was used in place of molar equivalents of A.

EXAMPLE

Synthesis Example 1: Synthesis of Compound 1

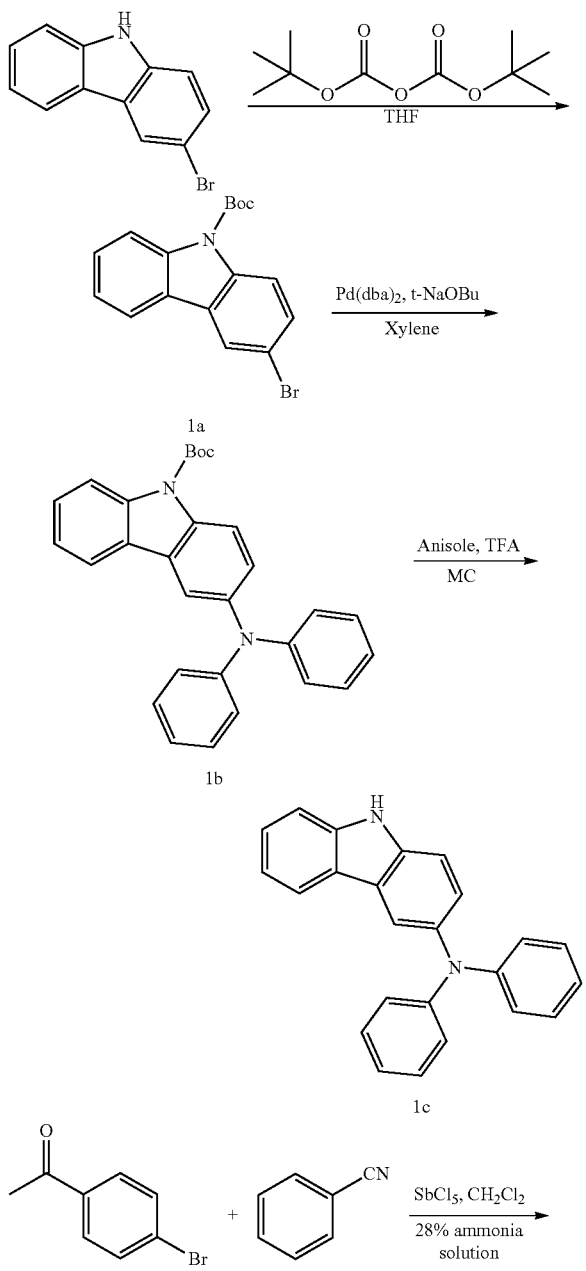

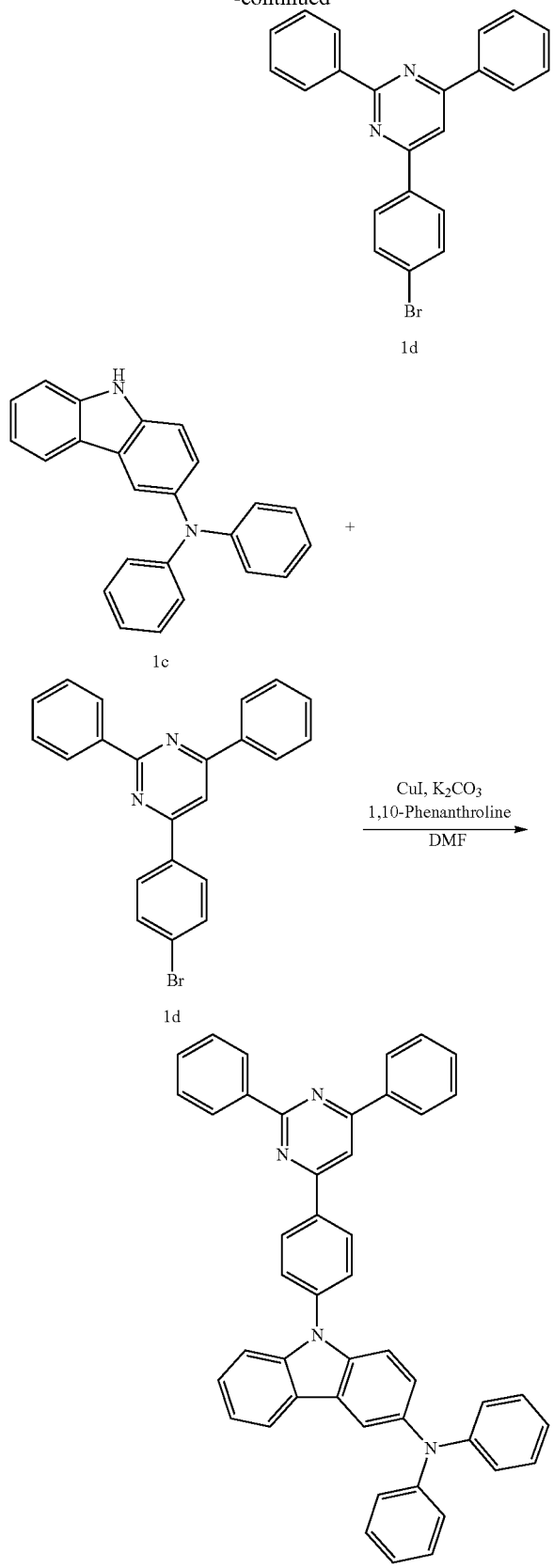

1) Synthesis of Intermediate 1a 12.3 grams (g) (49.98 millimoles, mmol) of 3-bromo-9H-carbazole, 16.4 g (74.97 mmol) of tert-butyldicarbonate, and 4-dimethylaminopyridine were mixed together with 250 milliliters (mL) of THF and then stirred at room temperature for about 3 hours. The reaction mixture was extracted with dichloromethane and water. The obtained organic layer was distilled under reduced pressure. The crude product was purified by using silica gel column chromatography using dichloromethane and n-hexane at a volume ratio of about 1:4, thus obtaining 16.1 g of Intermediate 1a as a white solid (yield: 93%).

2) Synthesis of Intermediate 1b 21.60.0 g (43.33 mmol) of Intermediate 1a, 8.80 g (51.99 mmol) of diphenylamine, and 8.32 g (86.65 mmol) of sodium-tert-butoxide were mixed together with 60 mL of xylene and then stirred at a temperature of about 165° C. under nitrogen atmosphere for about 12 hours. The reaction mixture was slowly added to a solution of 2.49 g (4.33 mmol) of Pd(dba)$_2$ and 1.75 g (8.67 mmol) of tri-tert-butylphosphine in 40 mL of xylene. The reaction mixture was cooled to room temperature, and then diluted with 200 mL of methanol and filtered. The obtained filtrate was carefully washed with 100 mL of water and 100 mL of methanol. A resulting brown solid was collected by filtration. The crude product was purified by using column chromatography using dichloromethane and n-hexane at a volume ratio of about 1:9, thus obtaining a yellow solid. The yellow solid was recrystallized from toluene and finally dried under vacuum to obtain 13.3 g of Intermediate 1b as a yellow crystal (yield: 71%).

3) Synthesis of Intermediate 1c 9 g (29.92 mmol) of Intermediate 1b and 50 mL of trifluoroacetic acid were dissolved in 80 mL of dichloromethane under nitrogen atmosphere. The reaction mixture was stirred at room temperature for about 30 minutes. After completion of the reaction, the reaction solution was neutralized with anhydrous MgSO$_4$, filtered, and concentrated. The concentrated solution was recrystallized from dichloromethane and methanol, thus obtaining 6.8 g of Intermediate 1c (yield: 68%).

4) Synthesis of Intermediate 1d 3.5 g (17.58 mmol) of 4-bromoacetophenone and 1.83 g (17.58 mmol) of benzonitrile were added to 49 mL of dichloromethane cooled at 0° C. by ice bath and stirred for 30 minutes. Then, 10.51 g (35.17 mmol) of antimony (V) chloride was added dropwise to the reaction mixture. The reaction mixture was stirred at room temperature for about 1 hour and further stirred and refluxed overnight. The reaction mixture was cooled and filtered, and a collected yellow solid was washed with dichloromethane. The solid was slowly added to 75 mL of a 28% ammonia solution cooled at 0° C. by ice bath and stirred for 30 minutes. Then the reaction mixture was stirred for 3 hours at room temperature. Subsequently, the mixture was filtered, and a white solid was collected. The white solid was then washed with water. Then the solvent was removed under vacuum, and 6.5 g (95%) of Intermediate 1d was obtained as a white solid.

5) Synthesis of Compound 1

5.18 g (15.49 mmol) of Intermediate 1c, 5.0 g (12.91 mmol) of Intermediate 1d, 1.23 g (6.46 mmol) of CuI, 2.33 g (12.91 mmol) of 1,10-phenanthroline, and 3.57 g (25.82 mmol) of potassium carbonate were mixed together with 60 mL of dimethylformamide (DMF) and stirred at a temperature of about 160° C. for about 8 hours. The reaction mixture was cooled to room temperature, and then diluted with 200 mL of methanol and filtered. The reaction mixture was carefully washed with 100 mL of water and 100 mL of methanol. A resulting brown solid was collected by filtration. The crude product was purified by using column chromatography using dichloromethane and n-hexane at a volume ratio of about 1:9, thereby obtaining a yellow solid. The yellow solid was recrystallized from toluene and finally dried under vacuum to obtain 4.5 g of Compound 1 as a yellow crystal (yield: 54%). Compound 1 was identified by using $^1$H nuclear magnetic resonance (NMR) and $^{13}$C NMR.

$^1$H NMR (500 MHz, CD$_2$Cl$_2$): δ (ppm) 8.776-8.758 (d, J=9.0 Hz, 2H), 8.598-8.581 (d, J=8.5 Hz, 2H), 8.378-8.362 (d, J=8 Hz, 2H), 8.179 (s, 1H), 8.034-8.018 (d, J=8 Hz, 1H), 7.952 (s, 1H), 7.848-7.828 (d, J=10 Hz, 2H), 7.628-7.547 (m, 7H), 7.521-7.503 (d, J=9 Hz, 1H), 7.464-7.432 (t, J=16 Hz, 1H), 7.288-7.230 (m, 6H), 7.118-7.102 (d, J=8 Hz, 4H), 6.986-6.957 (t, d=14.5 Hz, 2H);

$^{13}$C NMR (500 MHz, CD$_2$Cl$_2$): δ (ppm) 165.5, 165.1, 164.4, 149.2, 141.6, 141.5, 140.6, 138.7, 138.2, 138.0, 136.827, 131.5, 131.3, 129.7, 129.5, 129.5, 129.1, 129.0, 127.9, 127.5, 1269, 126.3, 125.3, 123.9, 123.4, 122.3, 121.1, 120.9, 119.0, 111.4, 110.9, 110.6; MALDI-TOF/MS: 641 [(M+H)$^+$].

Synthesis Example 2: Synthesis of Compound 2

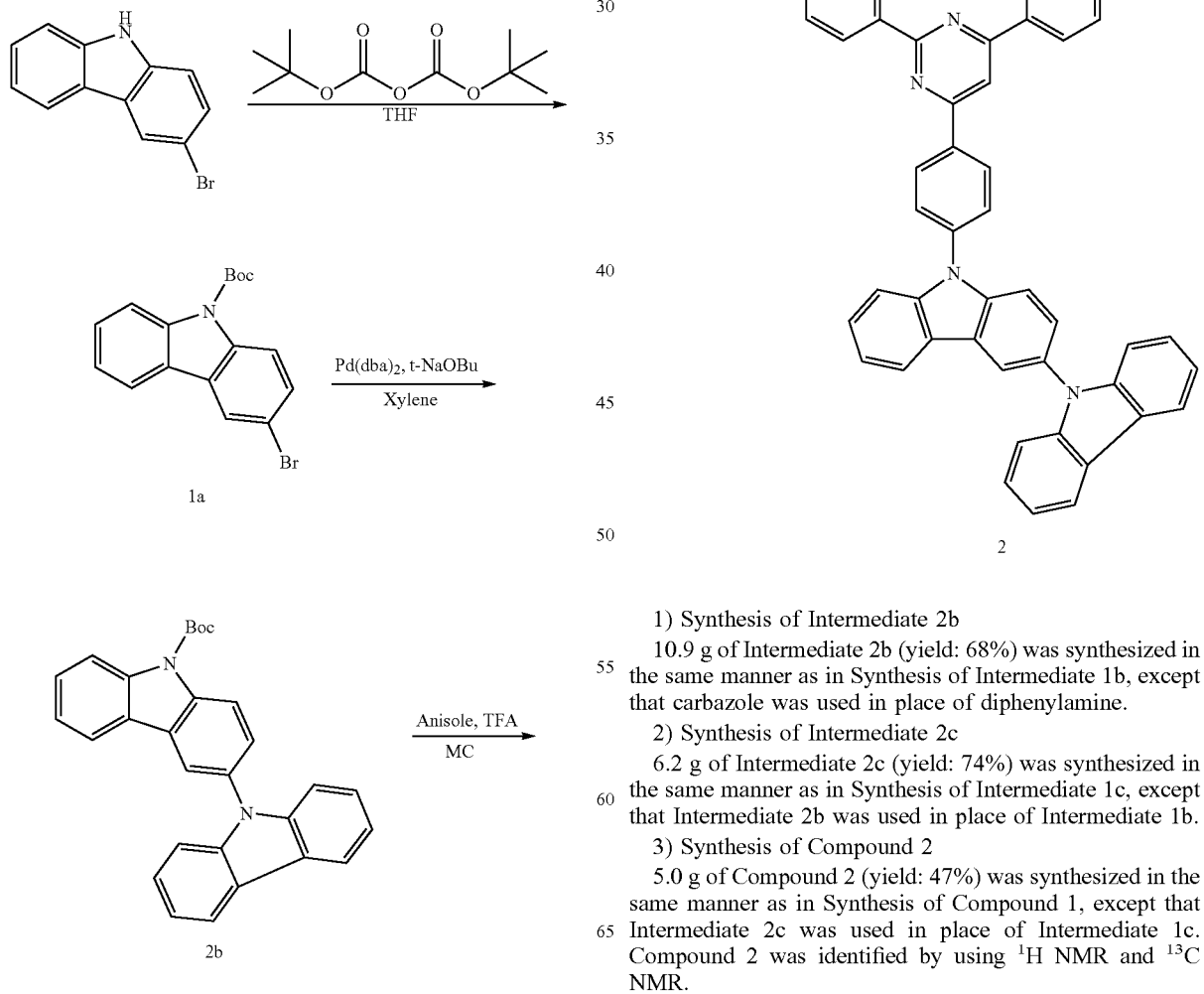

1) Synthesis of Intermediate 2b 10.9 g of Intermediate 2b (yield: 68%) was synthesized in the same manner as in Synthesis of Intermediate 1b, except that carbazole was used in place of diphenylamine.

2) Synthesis of Intermediate 2c 6.2 g of Intermediate 2c (yield: 74%) was synthesized in the same manner as in Synthesis of Intermediate 1c, except that Intermediate 2b was used in place of Intermediate 1b.

3) Synthesis of Compound 2

5.0 g of Compound 2 (yield: 47%) was synthesized in the same manner as in Synthesis of Compound 1, except that Intermediate 2c was used in place of Intermediate 1c. Compound 2 was identified by using $^1$H NMR and $^{13}$C NMR.

$^1$H NMR (500 MHz, CD$_2$Cl$_2$): δ (ppm) 8.795-8.776 (dd, J=9.5, 1.5 Hz, 2H), 8.653-8.639 (d, J=7 Hz, 2H), 8.393-8.374 (dd, J=9.5, 2.0, 1.5 Hz, 2H), 8.344-8.340 (d, J=2 Hz, 1H), 8.207-8.163 (m, 4H), 7.925-7.908 (d, J=8.5 Hz, 2H), 7.773-7.756 (d, J=8.5 Hz, 1H), 7.639-7.569 (m, 8H), 7.551-7.519 (t, J=16 Hz, 1H), 7.440-7.433 (m, 4H), 7.379-7.349 (t, J=15 Hz, 1H), 7.322-7.291 (m, 2H);

$^{13}$C NMR (500 MHz, CD$_2$Cl$_2$): δ (ppm) 165.6, 165.1, 164.3, 142.4, 141.9, 140.3, 140.3, 138.7, 138.0, 137.2, 131.6, 131.4, 130.8, 129.6, 129.5, 129.1, 129.0, 127.9, 127.7, 127.4, 126.5, 126.1, 125.3, 123.8, 123.7, 121.3, 121.2, 120.8, 120.2, 120.0, 111.6, 110.9, 110.8, 110.4; MALDI-TOF/MS: 639 [(M+H)$^+$].

Synthesis Example 3: Synthesis of Compound A

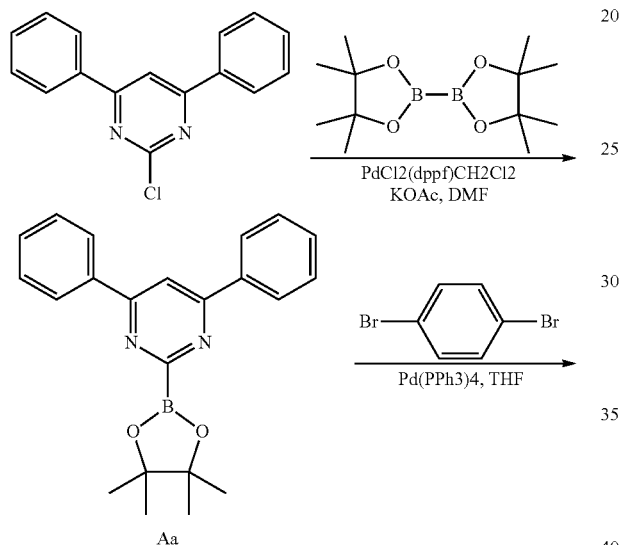

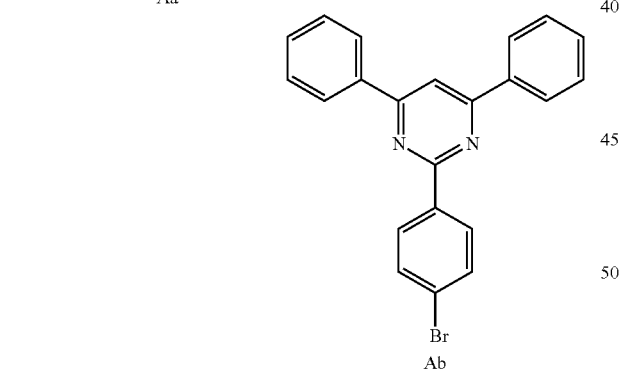

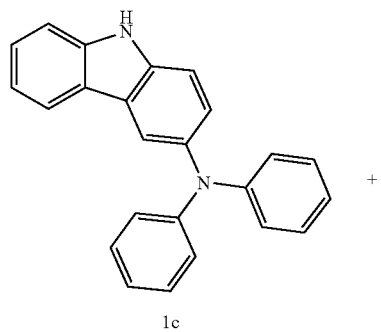

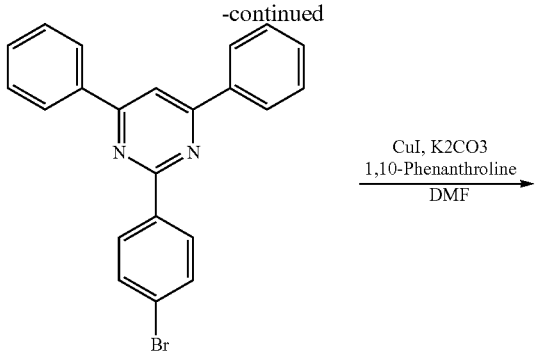

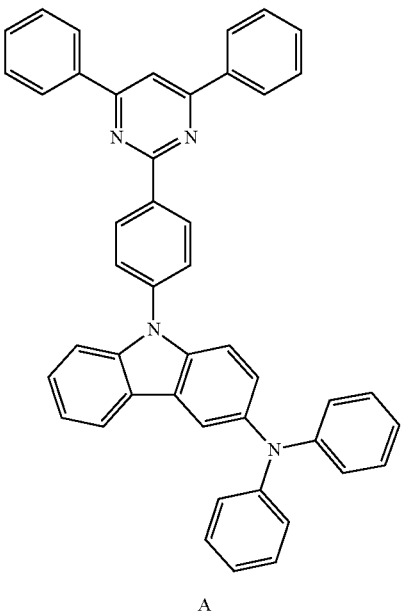

1) Synthesis of Intermediate Aa 15 g (56.24 mmol) of 2-chloro-4,6-diphenylpyrimidine, 17.13 g (67.48 mmol) of bis(pinacolato)diboron, 16.55 g (168.71 mmol) of potassium acetate, and 2.30 g (2.81 mmol) of PdCl$_2$(dppf)CH$_2$Cl$_2$ were dissolved in 180 mL of DMF under nitrogen atmosphere. The reaction mixture was stirred and refluxed for 12 hours. The reaction mixture was filtered, diluted with ethyl acetate, and washed with water. The obtained organic layer was dried using anhydrous MgSO$_4$ and distilled under reduced pressure. The crude product was purified by using silica gel column chromatography using dichloromethane and n-hexane at a volume ratio of about 1:4, and then dried under vacuum, thus obtaining 17 g of Intermediate Aa as white powder (yield: 84%).

2) Synthesis of Intermediate Ab 16.40 g (47.78 mmol) of Intermediate Aa, 9.0 g (38.15 mmol) of 1,4-dibromobenzene, and 2.21 g (5 mol %) of tetrakis(triphenylphosphine)palladium(0) were mixed together with 60 mL of anhydrous THF and refluxed under argon for 12 hours. 60 mL of an aqueous solution of 10.54 g (76.30 mmol) of potassium carbonate was slowly added to the reaction mixture. The mixture was cooled to room temperature, and then the reaction mixture was extracted with dichloromethane and water. The obtained organic layer was distilled under reduced pressure. The crude product was purified by using silica gel column chromatography using dichloromethane and n-hexane at a volume ratio of about 1:9, thus obtaining 13.5 g of Intermediate Ab as white powder (yield: 91%).

3) Synthesis of Compound A 8.3 g of Compound A (yield: 50%) was synthesized in the same manner as in Synthesis of Compound 1, except that Intermediate Ab was used in place of Intermediate 1d. Compound A was identified by using $^1$H NMR and $^{13}$C NMR.

$^1$H NMR (500 MHz, CD$_2$Cl$_2$): δ (ppm) 8.992-8.975 (d, J=8.5 Hz, 2H), 8.374-8.355 (dd, J=9.5, 2 Hz, 4H), 8.139 (s, 1H), 8.032-8.017 (d, J=7.5 Hz, 1H), 7.954 (s, 1H), 7.810-7.793 (d, J=8.5 Hz, 2H), 7.626-7.555 (m, 7H), 7.530-7.513 (d, J=8.5 Hz, 1H), 7.456-7.425 (t, J=20 Hz, 1H), 7.265-7.228 (m, 6H), 7.118-7.103 (d, J=7.5 Hz, 4H), 6.981-6.951 (t, d=15 Hz, 2H);

$^{13}$C NMR (500 MHz, CD$_2$Cl$_2$): δ (ppm) 165.5, 164.3, 149.2, 141.7, 141.4, 140.3, 138.4, 138.0, 137.7, 131.5, 130.6, 129.7, 129.5, 127.8, 127.1, 126.8, 126.3, 125.2, 123.3, 122.3, 121.0, 120.7, 119.0, 111.5, 111.1, 110.1; MALDI-TOF/MS: 641 [(M+H)$^+$].

Evaluation Example 1: UV-Vis Spectrum Evaluation on First Compound

Figure 2:
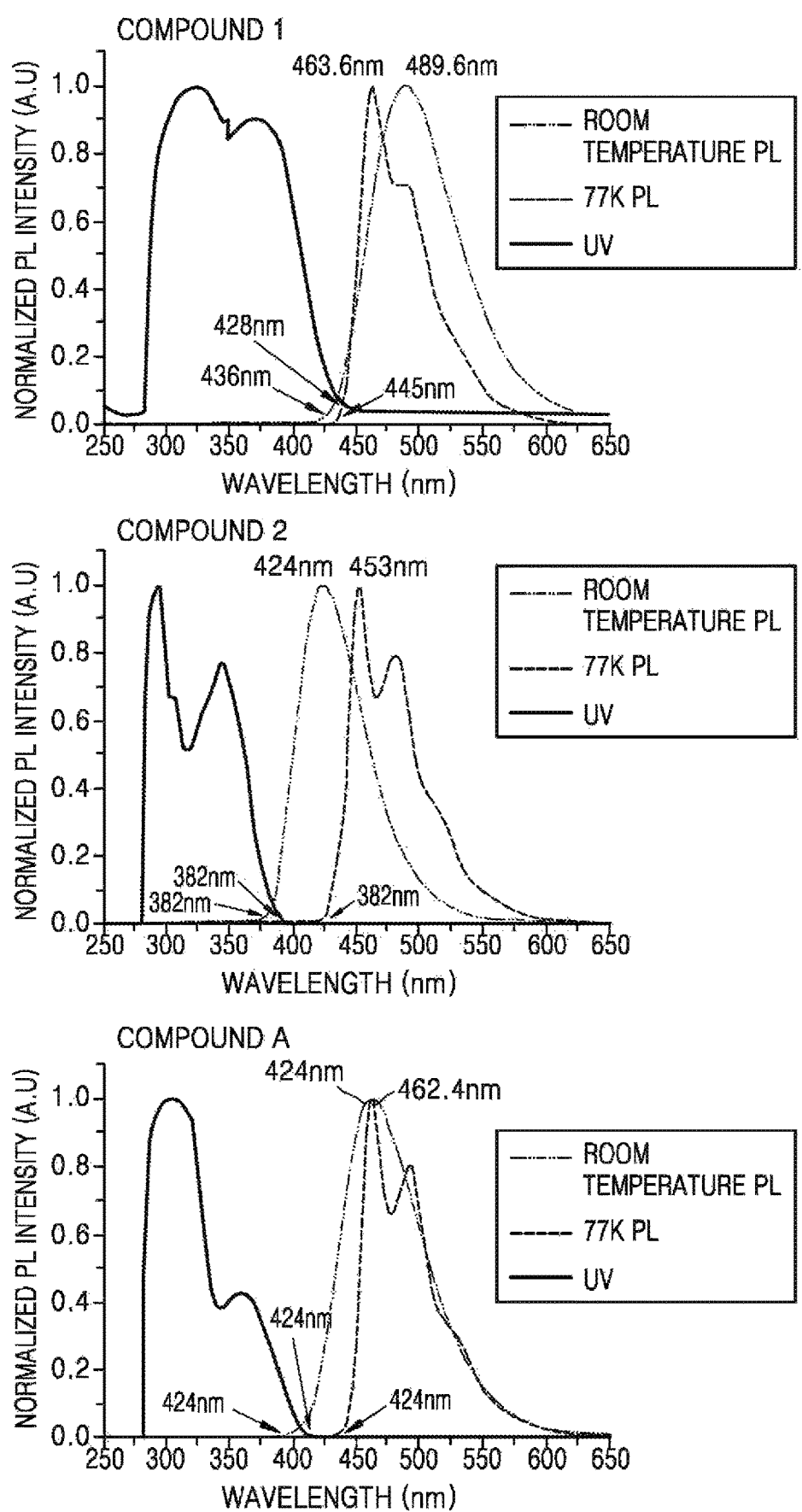
FIG. 2 is a graph of normalized photoluminescence (PL) intensity (arbitrary units, a. u.) versus wavelength (nanometers, nm) illustrating UV-Vis spectra and photoluminescence spectra of Compounds 1, 2, and A.

Compounds 1, 2, and A were diluted with toluene at a concentration of about 1×10$^{-5}$ M. Then, UV-Vis absorption spectra thereof were measured by using Shimadzu UV-350 spectrometer at room temperature. The results thereof are shown in FIG. 2.

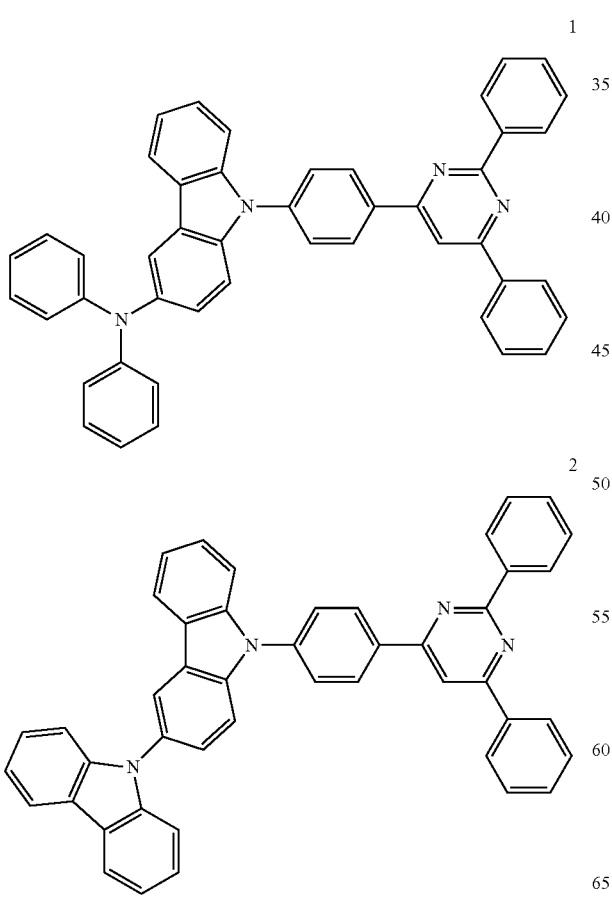

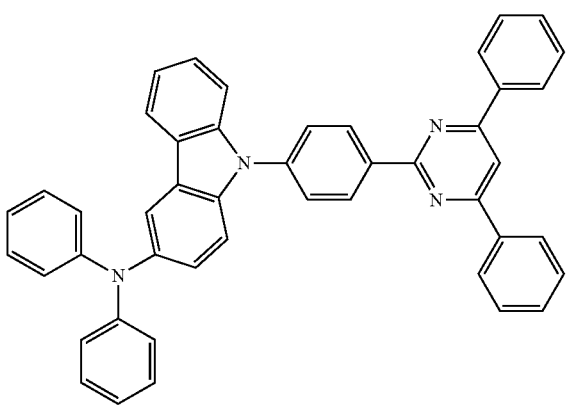

Evaluation Example 2: Photoluminescence (PL) Spectrum Evaluation on First Compound Compounds 1, 2, and A were diluted with toluene at a concentration of 0.1 millimolar (mM). Then, an ISC PC1 spectrofluorometer, in which a Xenon lamp was mounted, was used to measure PL spectra thereof at room temperature and at 77 Kelvins (K). The results thereof are shown in Table 2 and FIG. 2.

TABLE 2

| Compound No. | $\lambda_{max}$ (nm) (room temperature) | $\lambda_{max}$ (nm) (77 K) |
|---|---|---|
| 1 | 489 | 464 |
| 2 | 424 | 453 |
| A | 462 | 462 |

Evaluation Example 3: Cyclic Voltammetry Evaluation on First Compound

Figure 3:
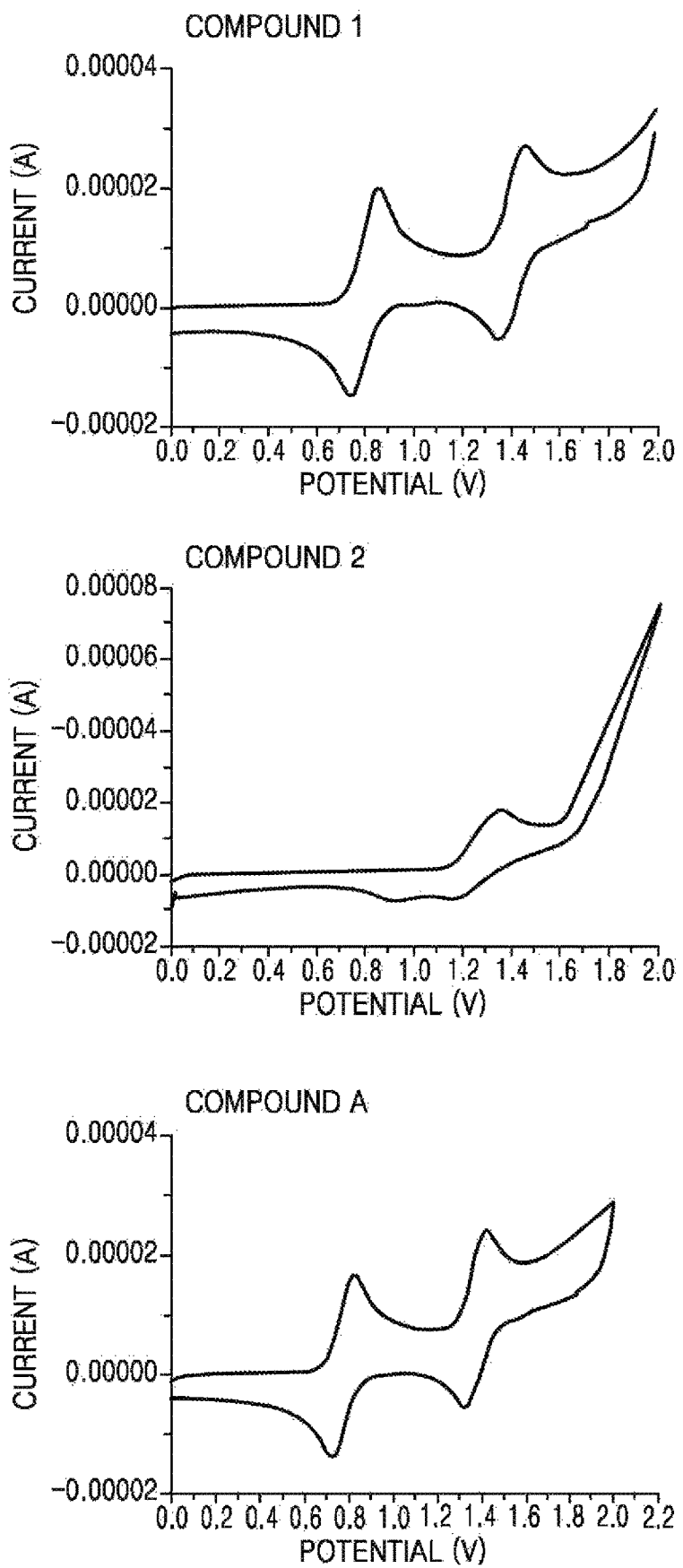
FIG. 3 is a graph of current (amperes, A) versus voltage (volts, V) illustrating CV curves of Compounds 1, 2, and A.

A potential (V)-current (A) graph of Compounds 1, 2, and A was obtained by using cyclic voltammetry (CV) (electrolyte: 0.1 M Bu$_4$NClO$_4$/solvent: CH$_2$Cl$_2$/electrode: 3-electrode system (working electrode: GC, reference electrode: Ag/AgCl, and auxiliary electrode: Pt)). The graphs thereof are shown in FIG. 3.

Evaluation Example 4: Evaluation of HOMO Energy Level, LUMO Energy Level, Singlet (S1) Energy Level, Triplet (T1) Energy Level, and $\Delta E_{ST}$ on First Compound Following the method described in Table 3, the HOMO energy level, LUMO energy level, singlet (S1) energy level, and triplet (T1) energy level of Compounds 1, 2, and A were evaluated. The results thereof are shown in Table 4.

TABLE 3

| | |
|---|---|
| HOMO energy level evaluation method | A potential (Volts, V) - current (Amperes, A) graph of each compound was obtained by using cyclic voltammetry (CV) (electrolyte: 0.1M $Bu_4NClO_4$/ solvent: $CH_2Cl_2$/electrode: 3 electrode system (working electrode: GC, reference electrode: Ag/AgCl, auxiliary electrode: Pt)). Then, from reduction onset of the graph, a HOMO energy level of a compound was calculated. |
| LUMO energy level evaluation method | Each compound was diluted with toluene at a concentration of $1 \times 10^{-4}$ M, and a UV absorption spectrum thereof was measured at room temperature by using a Shimadzu UV-350 spectrometer. Then, a LUMO energy level thereof was calculated by using an optical band gap ($E_g$) from an edge of the absorption spectrum. |
| S1 energy level evaluation method | A photoluminescence spectrum of a mixture of each compound, diluted with toluene at a concentration of about $1 \times 10^{-4}$ M, was measured by using a device for measuring photoluminescence at room temperature. The observed peaks were analyzed to calculate S1 energy levels. |
| T1 energy level evaluation method | A mixture of each compound, diluted with toluene at a concentration of about $1 \times 10^{-4}$ M, was loaded into a quartz cell. Subsequently, the resultant quartz cell was loaded into liquid nitrogen (77 K), a photoluminescence spectrum thereof was measured by using a device for measuring photoluminescence. The obtained spectrum was compared with a photoluminescence spectrum measured at room temperature, and peaks observed only at a low temperature were analyzed to calculate T1 energy levels. |
| $\Delta E_{ST}$ | Calculate the difference between the S1 energy level and the T1 energy level. |

TABLE 4

| Compound No. | HOMO (eV) | LUMO (eV) | S1 energy level (eV) | T1 energy level (eV) | $\Delta E_{ST}$ (eV) |
|---|---|---|---|---|---|
| 1 | −5.08 | −2.16 | 2.84 | 2.78 | 0.06 |
| 2 | −5.51 | −2.27 | 3.22 | 2.88 | 0.34 |
| A | −5.06 | −2.02 | 2.97 | 2.79 | 0.18 |

Referring to Table 3, it was found that the HOMO, LUMO, S1, and T1 energy levels of Compound 1 were similar with those of Compound A. However, the $\Delta E_{ST}$ of Compound 1 was smaller than that of Compound A.

Referring to Table 3, it was found that Compound 2 emits light of relatively short wavelength (blue shift), as compared with Compound A.

Evaluation Example 5: Thermal Characteristics Evaluation on First Compound

Figure 4A:
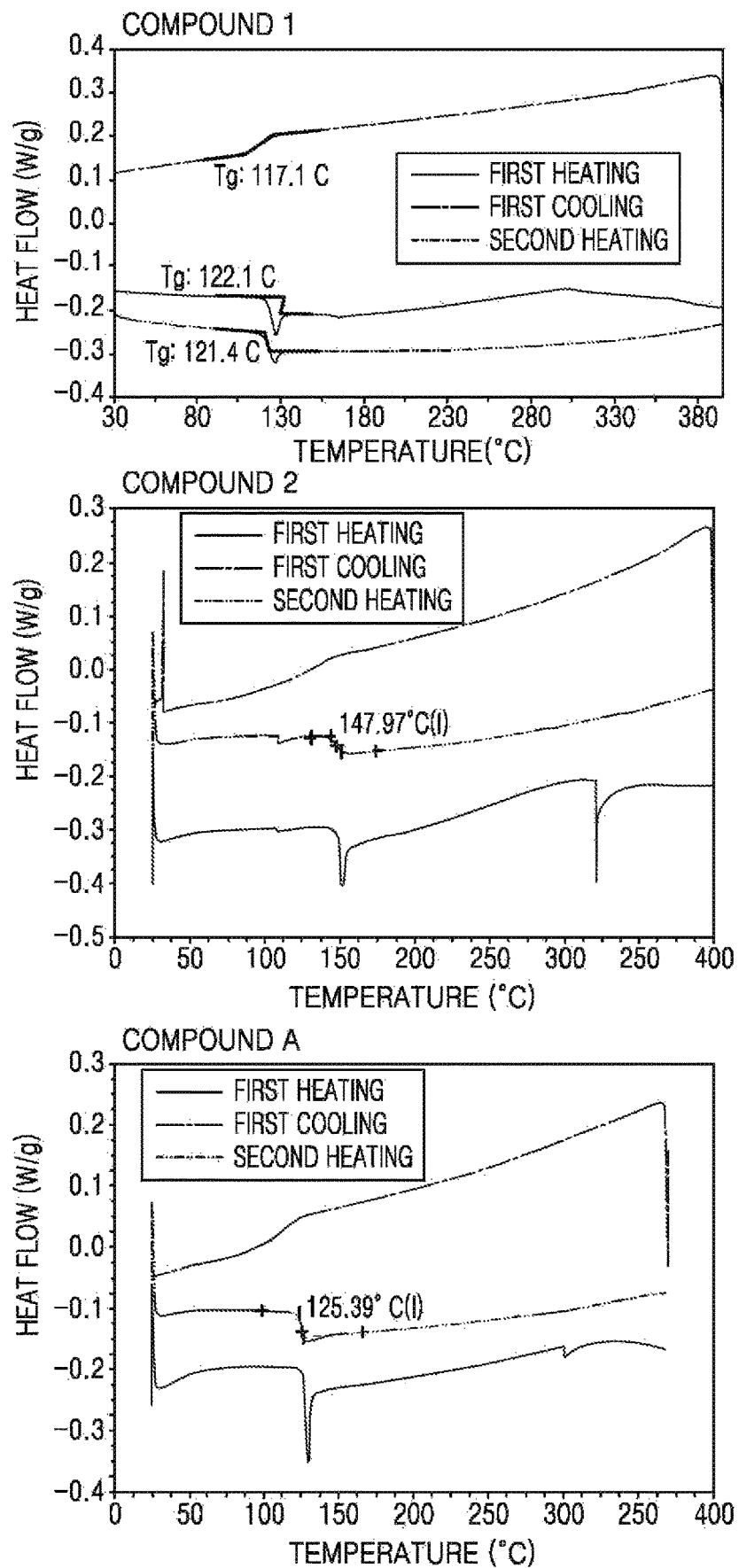
FIG. 4A is a graph of heat flow (watts per gram, W/g) versus temperature (degree Centigrade, ° C.) illustrating differential scanning calorimetry (DSC) curves of Compounds 1, 2, and A.
Figure 4B:
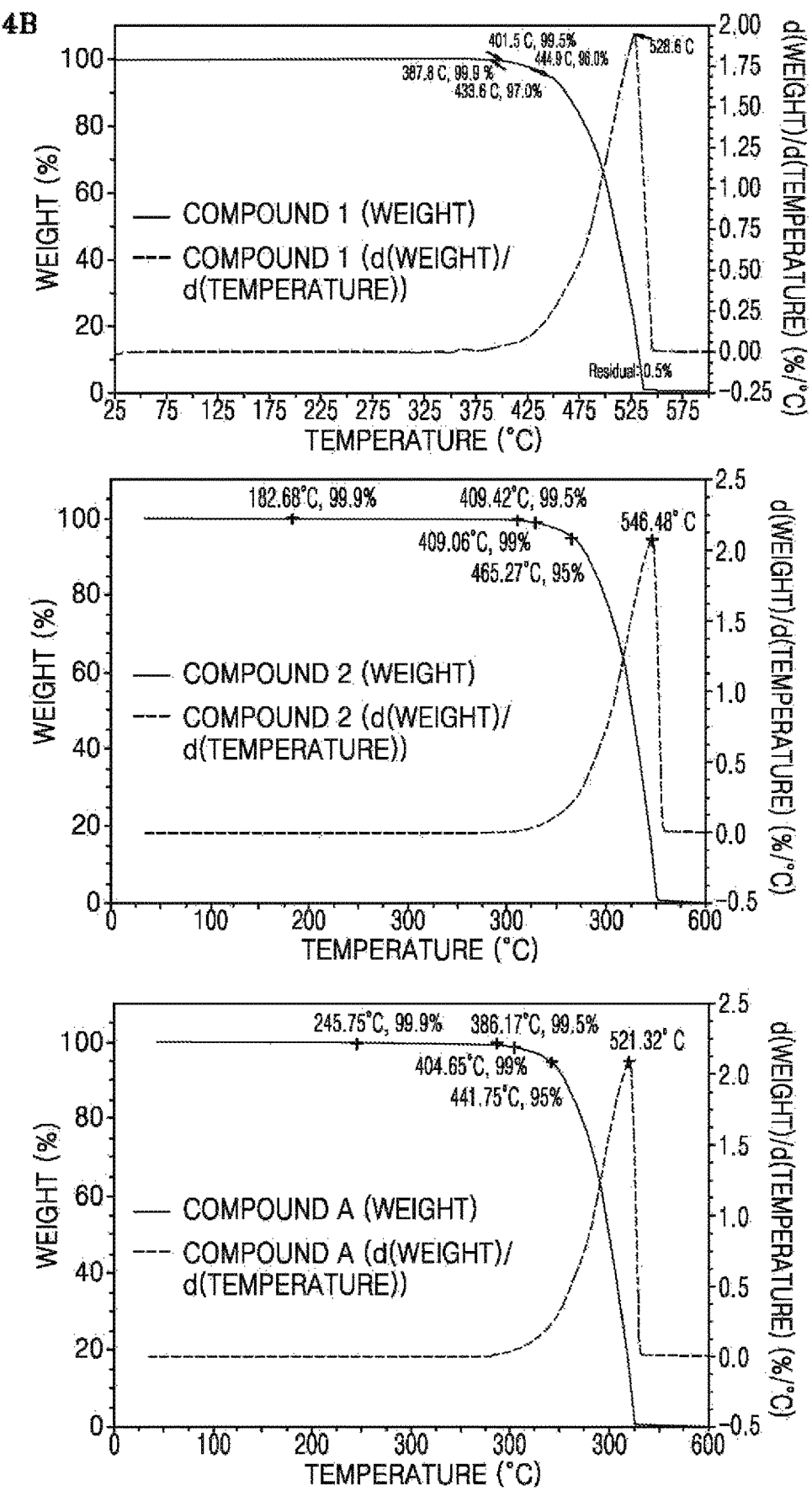
FIG. 4B is a graph of weight change (percent, %) versus temperature (degree Centigrade, ° C.) illustrating thermogravimetric analysis (TGA) curves of Compounds 1, 2, and A.

Thermal analysis ($N_2$ atmosphere, temperature range: from room temperature to 800° C. (10° C./min)-thermogravimetric analysis (TGA), from room temperature to 400° C.-differential scanning calorimetry (DSC), Pan Type: Pt Pan in disposable Al Pan (TGA) and disposable Al pan (DSC)) was performed on Compounds 2 and A by using TGA and DSC. The evaluation results are shown in Tables 5 and FIGS. 4A and 4B. Referring to Table 5, it was found that Compounds 1 and 2 had excellent thermal stability, as compared with Compound A. Referring to Table 5, Compound 1 had a slightly lower $T_g$ value than Compound A. However, if a $T_g$ value of a compound is over 100° C., the thermal stability of the compound may be sufficient. Rather, since the $T_d$ value of Compound 1 is higher than that of Compound A, the thermal stability of Compound 1 may be excellent, as compared with Compound A.

TABLE 5

| Compound No. | Tg (° C.) | Td (0.5%, ° C.) |
|---|---|---|
| 1 | 121 | 401.5 |
| 2 | 145 | 409.4 |
| A | 125 | 386.1 |

Evaluation Example 6: PL Quantum Yields Evaluation on First Compound

Figure 5:
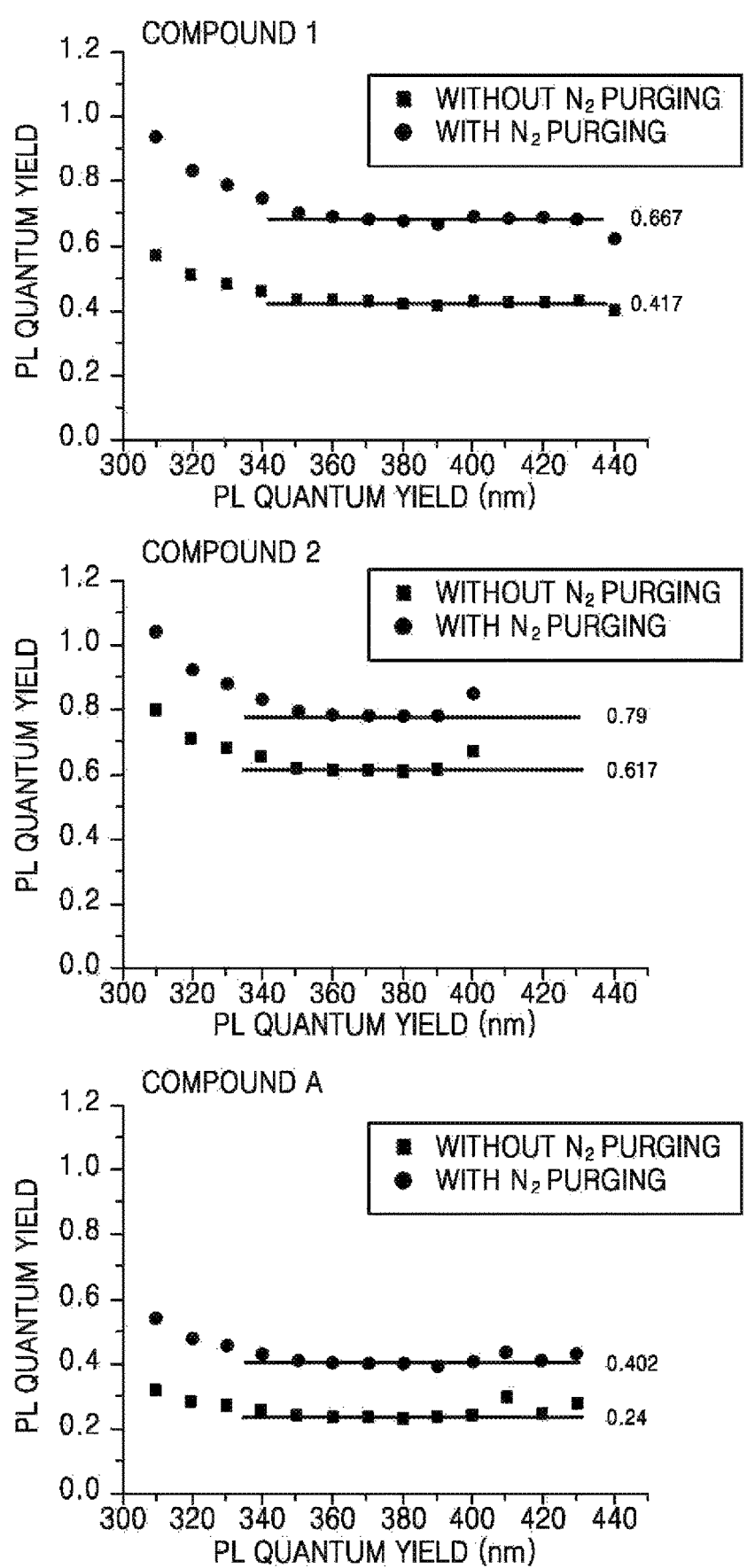
FIG. 5 is a graph of photoluminescence (PL) quantum yield versus PL quantum yield (nanometers, nm) illustrating PL quantum yields of Compounds 1, 2, and A.

Compounds 1, 2, and A were diluted with toluene at a concentration of 0.1 millimoles per liter (mM). Then, an ISC PC1 spectrofluorometer, in which a Xenon lamp was mounted, was used to measure PL spectra thereof at room temperature, with or without $N_2$ purging. The results thereof are shown in Table 6 and FIG. 5.

TABLE 6

| Compound No. | PL quantum yield (PLQY) (%, with $N_2$ purging) | PLQY (%, without $N_2$ purging) |
|---|---|---|
| 1 | 67 | 41.7 |
| 2 | 79 | 81.7 |
| A | 40.2 | 24 |

Evaluation Example 7: Triplet Energy Evaluation on Second Compound

Following the method described in Table 7, the triplet (T1) energy level of Compound H10 was evaluated. The results thereof are shown in Table 8.

TABLE 7

| | |
|---|---|
| T1 energy level evaluation method | A mixture of each compound, diluted with toluene at a concentration of about $1 \times 10^{-4}$ M, was loaded into a quartz cell. Subsequently, the resultant quartz cell was loaded into liquid nitrogen (77 K), a photoluminescence spectrum thereof was measured by using a device for measuring photoluminescence. The obtained spectrum was compared with a photoluminescence spectrum measured at room temperature, and peaks observed only at a low temperature were analyzed to calculate T1 energy levels. |

TABLE 8

| Compound No. | T1 energy level (eV) |
|---|---|
| H10 | 3.44 |

Example 1

A glass substrate having 1,600 nanometers (nm) of indium tin oxide (ITO) electrode deposited thereon was washed with distilled water in the presence of ultrasound waves. Once the washing with distilled water was complete, ultrasound wave washing was performed on the substrate by using a solvent, such as iso-propyl alcohol, acetone, or methanol. Subsequently, the substrate was dried, transferred to a plasma washer, washed for 5 minutes using oxygen plasma, and mounted in a vacuum depositor.

Compound HT3 and Compound HT-D1 were co-deposited at a weight ratio of about 95:5 on the ITO electrode of the glass substrate to form a hole injection layer having a thickness of about 100 Å. Subsequently, Compound HT3 was vacuum-deposited on the hole injection layer to form a hole transport layer having a thickness of about 1,350 Å. mCP was next vacuum-deposited on the hole transport layer to form an electron blocking layer having a thickness of about 100 Å, thereby forming a hole transport region.

Compound H10 (as a host) and Compound 1 (as a dopant) were next co-deposited at a weight ratio of about 15:100 on the hole transport region to form an emission layer having a thickness of about 300 Å.

Compound BCP was vacuum-deposited on the emission layer to form a hole blocking layer having a thickness of about 100 Å. Compound ET3 and Compound ET-D1 (Liq) were then co-deposited at a weight ratio of about 95:5 on the hole blocking layer to form an electron transport layer having a thickness of about 300 Å. Next, Compound ET-D1 (Liq) was deposited on the electron transport layer to form an electron injection layer having a thickness of about 10 Å, and then, an aluminum (Al) second electrode (a cathode) having a thickness of 1,200 Å was formed on the electron injection layer, thereby completing the manufacture of an organic light-emitting device.

Example 2

An organic light-emitting device was manufactured in the same manner as in Example 1, except that Compound 2 was used in place of Compound 1 as a dopant in the formation of the emission layer.

Comparative Example 1

An organic light-emitting device was manufactured in the same manner as in Example 1, except that Compound A was used in place of Compound 1 as a dopant in the formation of the emission layer.

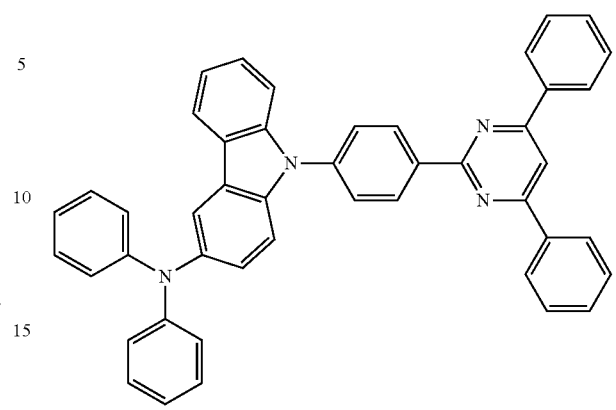

A

Evaluation Example 8: Evaluation of Characteristics of Organic Light-Emitting Device The driving voltage, current density, current efficiency, power efficiency, luminance, color-coordination, roll-off, electroluminescence wavelength, external quantum efficiency maximum value (EQE max), and external quantum efficiency (500 candelas per square meter, $cd/m^2$) of the organic light-emitting devices of Examples 1, 2, and Comparative Example 1 were measured by using a Keithley 2400 current voltmeter and a luminance meter (Minolta Cs-1000A). The results thereof are shown in Table 9 and FIGS. 6 to 8. All data except for the EQE max were measured at a luminance of about 500 $cd/m^2$.

TABLE 9

| | Host | Dopant | Theoretical external quantum efficiency (%)* | Actual external quantum efficiency (%) | Emission wavelength $\lambda_{max}$ (nm) |
|---|---|---|---|---|---|
| Example 1 | H10 | Compound 1 | 3.35 | 16.7 | 516 |
| Example 2 | H10 | Compound 2 | 3.95 | 5.8 | 435 |
| Comparative Example 1 | H10 | Compound A | 2 | 10.3 | 500 |

*Theorectical external quantum efficiency = PL quantum yield × 0.25 (branching ratio of singlet exciton formation ) × 0.2 (light outcoupling efficiency)

Figure 6:
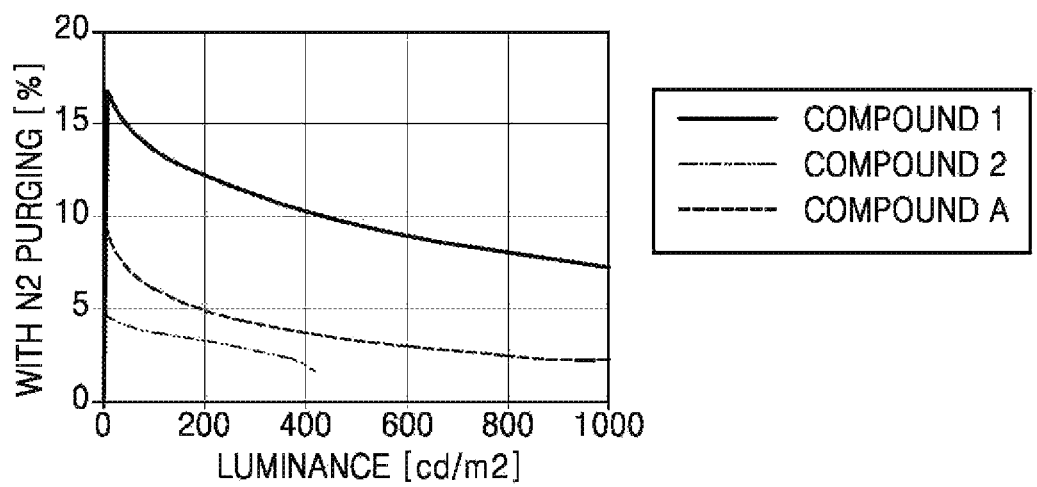
FIG. 6 is a graph of external luminance efficiency (percent, %) versus luminance (candelas per square meter, cd/m$^2$) of Examples 1 and 2 and Comparative Example 1.
Figure 7:
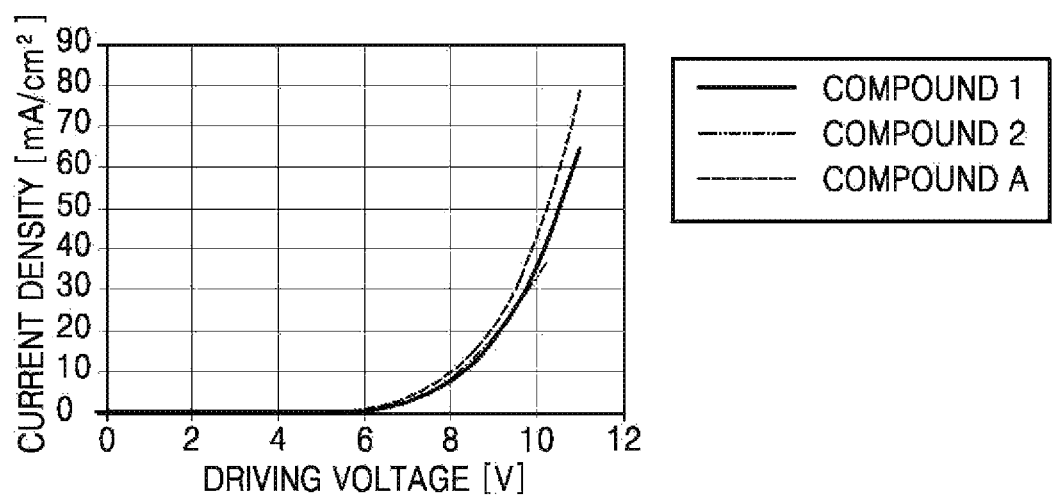
FIG. 7 is a graph of current density (milliamperes per square centimeter, mA/cm$^2$) versus driving voltage (volts, V) of Examples 1 and 2 and Comparative Example 1.
Figure 8:
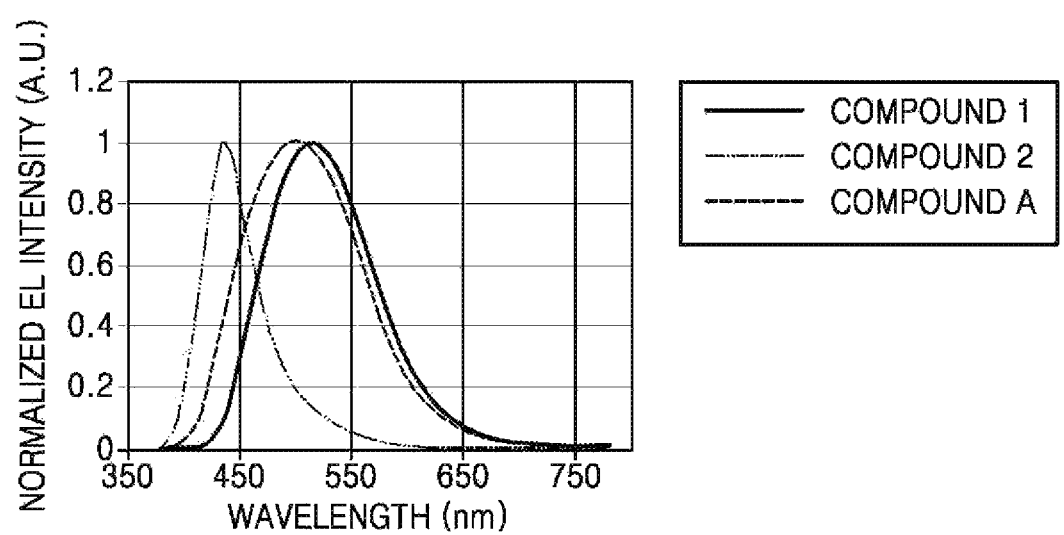
FIG. 8 is a graph of normalized electroluminescence (EL) intensity versus wavelength (nanometers, nm) illustrating electroluminescence spectra of Examples 1 and 2 and Comparative Example 1.

Referring to Table 9 and FIGS. 6 to 8, it was found that the organic light-emitting devices of Examples 1 and 2 had theoretical external quantum efficiencies about 1.5 to about 2 times higher than that of the organic light-emitting device of Comparative Example 1, as the PLQY increases. In addition, based on the actual external quantum efficiency of the organic light-emitting device of Example 1, the organic light-emitting device of Example 1 was found to have improved external quantum efficiency, as compared with that of the organic light-emitting device of Comparative Example 1.

* Theoretical external quantum efficiency=PL quantum yield×0.25 (branching ratio of singlet exciton formation)×0.2 (light outcoupling efficiency)

Furthermore, referring to Table 9 and FIGS. 6 to 8, the organic light-emitting device of Example 2 was found to have improved CIE color-coordination values, as compared with the organic light-emitting device of Comparative Example 1. From this result, it was found that high color-coordination (pure blue emission) may be achieved, which is required in a display.

As described above, according to the one or more of the above embodiments, an organic light-emitting device may have high efficiency, a low driving voltage, high color-coordination, and long lifespan characteristics.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims.

What is claimed is:
1. An organic light-emitting device comprising:
a first electrode;
a second electrode; and
an organic layer disposed between the first electrode and the second electrode,
wherein the organic layer comprises an emission layer, and
wherein the organic layer comprises a first compound represented by Formula 1 and a second compound having the lowest excited triplet energy level greater than 2.73 electron volts:

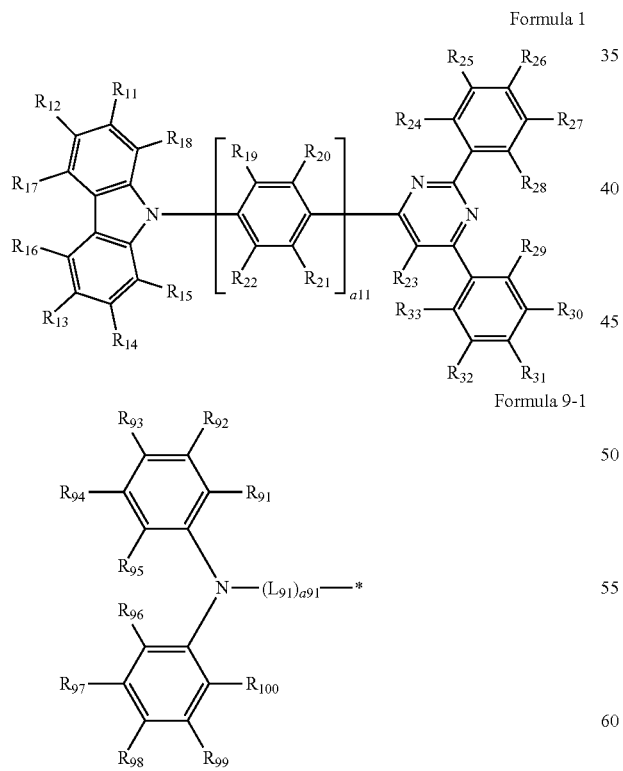

wherein, in Formulae 1 and 9-1,
$R_{11}$ to $R_{14}$ are each independently selected from hydrogen, deuterium, —F, —Cl, —Br, —I, a cyano group, a nitro group, an amidino group, a hydrazino group, a hydrazono group, a substituted or unsubstituted $C_1$-$C_{60}$ alkyl group, a substituted or unsubstituted $C_1$-$C_{60}$ alkoxy group, a substituted or unsubstituted $C_1$-$C_{60}$ alkylthio group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted $C_6$-$C_{60}$ aryloxy group, a substituted or unsubstituted $C_6$-$C_{60}$ arylthio group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)$_2$($Q_1$), —P(=O)($Q_1$)($Q_2$), groups represented by Formula 9-1,
provided that at least one selected from $R_{11}$ to $R_{14}$ is selected from groups represented by Formula 9-1,
$R_{15}$ to $R_{33}$ and $R_{91}$ to $R_{100}$ are each independently selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_1$-$C_{60}$ alkoxy group, a substituted or unsubstituted alkylthio group, a substituted or unsubstituted $C_3$-$C_{10}$ cycloalkyl group, a substituted or unsubstituted heterocycloalkyl group, a substituted or unsubstituted $C_3$-$C_{10}$ cycloalkenyl group, a substituted or unsubstituted heterocycloalkenyl group, a substituted or unsubstituted $C_6$-$C_{60}$ aryl group, a substituted or unsubstituted heteroaryl group, a substituted or unsubstituted $C_6$-$C_{60}$ aryloxy group, a substituted or unsubstituted $C_6$-$C_{60}$ arylthio group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)$_2$($Q_1$), and —P(=O)($Q_1$)($Q_2$),
a11 is selected from 2 and 3,
$L_{91}$ is selected from a substituted or unsubstituted $C_3$-$C_{10}$ cycloalkylene group, a substituted or unsubstituted heterocycloalkylene group, a substituted or unsubstituted $C_3$-$C_{10}$ cycloalkenylene group, a substituted or unsubstituted heterocycloalkenylene group, a substituted or unsubstituted $C_6$-$C_{60}$ arylene group, a substituted or unsubstituted heteroarylene group, a substituted or unsubstituted divalent non-aromatic condensed polycyclic group, and a substituted or unsubstituted divalent non-aromatic condensed heteropolycyclic group,
a91 is selected from 0, 1, and 2,
wherein $Q_1$ to $Q_3$ are each independently selected from hydrogen, deuterium, —F, —Br, a hydroxyl group, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group, and indicates a binding site to an adjacent atom.

2. The organic light-emitting device of claim 1, wherein the lowest excited triplet energy level of the second compound is greater than the lowest excited triplet energy level of the first compound.

3. The organic light-emitting device of claim 2, wherein the lowest excited triplet energy level of the first compound is about 2.7 electron volts or less.

4. The organic light-emitting device of claim 1, wherein a difference $\Delta_{EST1}$ between the lowest excited triplet energy level of the first compound and the lowest excited singlet energy level of the first compound is in a range of about 0 electron volts or greater to about 0.34 electron volts or less.

5. The organic light-emitting device of claim 1, wherein $R_{11}$ and $R_{14}$ are each independently selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_1$-$C_{60}$ alkoxy group, a substituted or unsubstituted $C_1$-$C_{60}$ alkylthio group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted $C_6$-$C_{60}$ aryloxy group, a substituted or unsubstituted $C_6$-$C_{60}$ arylthio group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)$_2$ ($Q_1$), and —P(=O)($Q_1$)($Q_2$), and $R_{12}$ and $R_{13}$ are each independently selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_1$-$C_{60}$ alkoxy group, a substituted or unsubstituted $C_1$-$C_{60}$ alkylthio group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted $C_6$-$C_{60}$ aryloxy group, a substituted or unsubstituted $C_6$-$C_{60}$ arylthio group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)$_2$($Q_1$), —P(=O)($Q_1$)($Q_2$), groups represented by Formula 9-1, provided that at least one selected from $R_{12}$ and $R_{13}$ is selected from groups represented by Formula 9-1.

6. The organic light-emitting device of claim 1, wherein $R_{11}$ to $R_{14}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a $C_1$-$C_{20}$ alkylthio group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group and —N($Q_1$)($Q_2$);

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a $C_1$-$C_{20}$ alkylthio group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, and —N($Q_{31}$)($Q_{32}$); and groups represented by Formula 9-1, provided that at least one selected from $R_{11}$ to $R_{14}$ is selected from groups represented by Formula 9-1, wherein $Q_1$, $Q_2$, $Q_{31}$, and $Q_{32}$ are each independently selected from a $C_1$-$C_{20}$ alkyl group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

7. The organic light-emitting device of claim 1, wherein $R_{11}$ to $R_{14}$ are each independently selected from hydrogen, a phenyl group, a biphenyl group, a terphenyl group, a naphthyl group, a carbazolyl group, a dibenzofuranyl group, a dibenzothiophenyl group, a benzocarbazolyl group, a dibenzocarbazolyl group, and —N($Q_1$)($Q_2$);

a phenyl group, a biphenyl group, a terphenyl group, a naphthyl group, a fluorenyl group, a spiro-bifluorenyl group, a benzofluorenyl group, a dibenzofluorenyl group, a carbazolyl group, a dibenzofuranyl group, a dibenzothiophenyl group, a benzocarbazolyl group, and a dibenzocarbazolyl group, each substituted with at least one selected from deuterium, —F, —Cl, —Br, —I, a hydroxyl group, a cyano group, a nitro group, a $C_1$-$C_{20}$ alkyl group, a phenyl group, a biphenyl group, a terphenyl group, a naphthyl group, a fluorenyl group, a spiro-bifluorenyl group, a benzofluorenyl group, a dibenzofluorenyl group, a carbazolyl group, a dibenzofuranyl group, a dibenzothiophenyl group, a benzocarbazolyl group, a dibenzocarbazolyl group, and —N($Q_{31}$)($Q_{32}$); and groups represented by Formula 9-1, provided that at least one selected from $R_{11}$ to $R_{14}$ is selected from groups represented by Formula 9-1, wherein $Q_1$, $Q_2$, $Q_{31}$, and $Q_{32}$ are each independently selected from a $C_1$-$C_{20}$ alkyl group, a phenyl group, a biphenyl group, a terphenyl group, a naphthyl group, a fluorenyl group, a spiro-bifluorenyl group, a benzofluorenyl group, a dibenzofluorenyl group, a carbazolyl group, a dibenzofuranyl group, a dibenzothiophenyl group, a benzocarbazolyl group, and a dibenzocarbazolyl group.

8. The organic light-emitting device of claim 1, wherein $R_{15}$ to $R_{33}$ and $R_{91}$ to $R_{100}$ are each independently selected from hydrogen, deuterium, —F, —Cl, —Br, —I, a cyano group, a nitro group, an amidino group, a hydrazino group, a hydrazono group, a $C_1$-$C_{20}$ alkyl group, a $C_1$-$C_{20}$ alkoxy group, a $C_1$-$C_{20}$ alkylthio group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, and —N($Q_1$)($Q_2$); and a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a $C_1$-$C_{20}$ alkylthio group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, and —N($Q_{31}$)($Q_{32}$), wherein $Q_1$, $Q_2$, $Q_{31}$, and $Q_{32}$ are each independently selected from a $C_1$-$C_{20}$ alkyl group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

9. The organic light-emitting device of claim 1, wherein $R_{15}$ to $R_{33}$ and $R_{91}$ to $R_{100}$ are each independently selected from hydrogen, a cyano group, a $C_1$-$C_{20}$ alkyl group, a phenyl group, a biphenyl group, a terphenyl group, a naphthyl group, a carbazolyl group, a dibenzofuranyl group, a dibenzothiophenyl group, a benzocarbazolyl group, a dibenzocarbazolyl group, and —N($Q_1$)($Q_2$); and a phenyl group, a biphenyl group, a terphenyl group, a naphthyl group, a fluorenyl group, a spiro-bifluorenyl group, a benzofluorenyl group, a dibenzofluorenyl group, a carbazolyl group, a dibenzofuranyl group, a dibenzothiophenyl group, a benzocarbazolyl group, and a dibenzocarbazolyl group, each substituted with at least one selected from deuterium, —F, —Cl, —Br, —I, a hydroxyl group, a cyano group, a nitro group, a $C_1$-$C_{20}$ alkyl group, a phenyl group, a biphenyl group, a terphenyl group, a naphthyl group, a fluorenyl group, a spiro-bifluorenyl group, a benzofluorenyl group, a dibenzofluorenyl group, a carbazolyl group, a dibenzofuranyl group, a dibenzothiophenyl group, a benzocarbazolyl group, a dibenzocarbazolyl group, and —N($Q_{31}$)($Q_{32}$), wherein $Q_1$, $Q_2$, $Q_{31}$, and $Q_{32}$ are each independently selected from a $C_1$-$C_{20}$ alkyl group, a phenyl group, a biphenyl group, a terphenyl group, a naphthyl group, a fluorenyl group, a spiro-bifluorenyl group, a benzofluorenyl group, a dibenzofluorenyl group, a carbazolyl group, a dibenzofuranyl group, a dibenzothiophenyl group, a benzocarbazolyl group, and a dibenzocarbazolyl group.

10. The organic light-emitting device of claim 1, wherein $R_{91}$ to $R_{100}$ are each independently selected from hydrogen, a cyano group, a $C_1$-$C_{20}$ alkyl group, a carbazolyl group, and —N($Q_1$)($Q_2$); and a carbazolyl group substituted with at least one selected from deuterium, —F, —Cl, —Br, —I, a hydroxyl group, a cyano group, a nitro group, a $C_1$-$C_{20}$ alkyl group, a phenyl group, a biphenyl group, a terphenyl group, a naphthyl group, a carbazolyl group, and —N($Q_{31}$)($Q_{32}$), wherein $Q_1$, $Q_2$, $Q_{31}$, and $Q_{32}$ are each independently selected from a phenyl group, a biphenyl group, a terphenyl group, a naphthyl group, and a carbazolyl group.

11. The organic light-emitting device of claim 1, wherein the first compound is represented by Formulae 1-1:

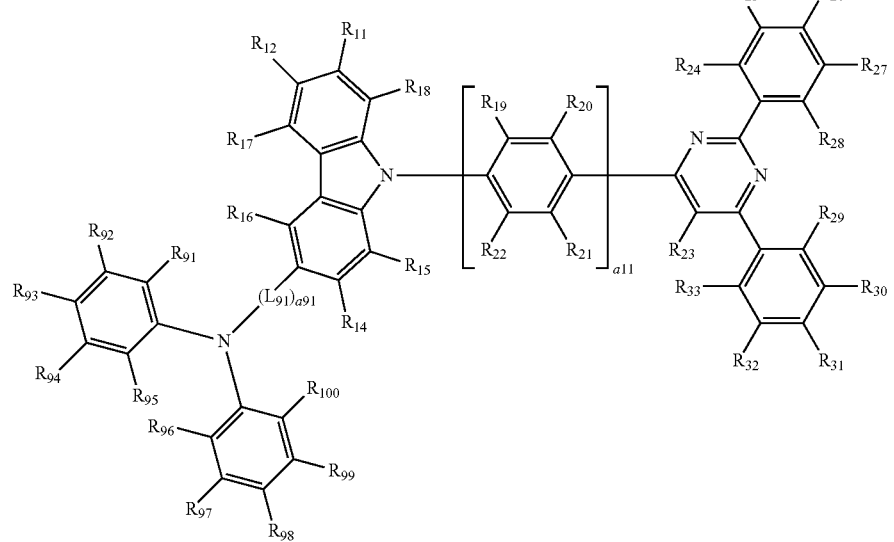

wherein, in Formula 1-1,
$R_{11}$ to $R_{33}$ and a11 are the same as in Formula 1, and
$R_{91}$ to $R_{100}$, $L_{91}$, and a91 are the same as in Formula 9-1.

12. An organic light-emitting device comprising:
a first electrode;
a second electrode; and
an organic layer disposed between the first electrode and the second electrode,
wherein the organic layer comprises an emission layer, and
wherein the emission layer of the organic layer comprises a first compound and a second compound,
wherein the first compound is selected from compounds:

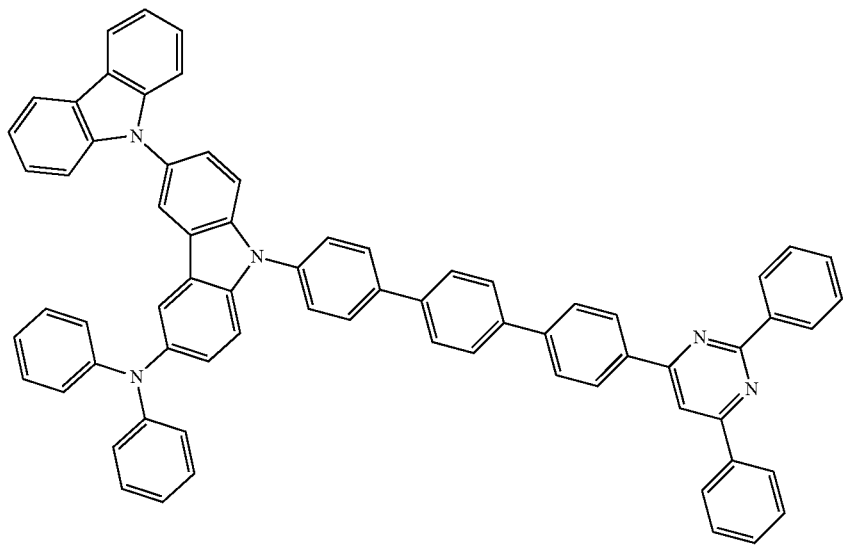

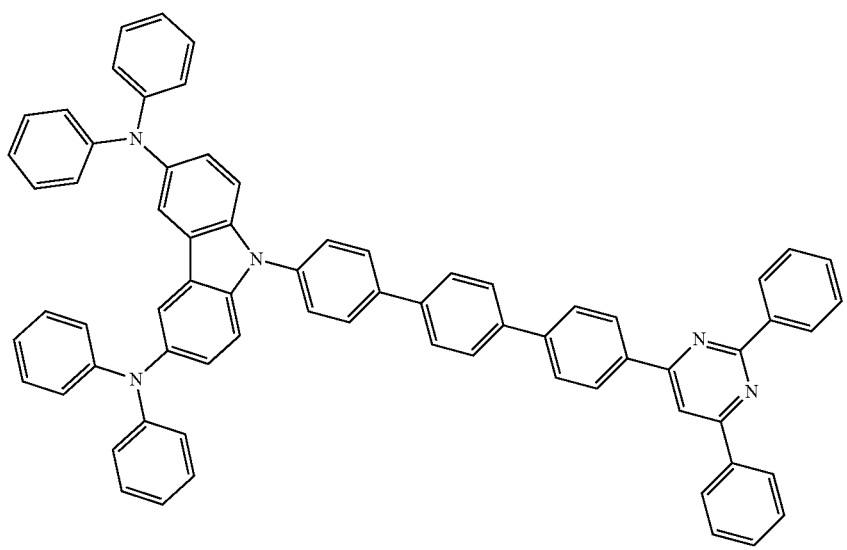

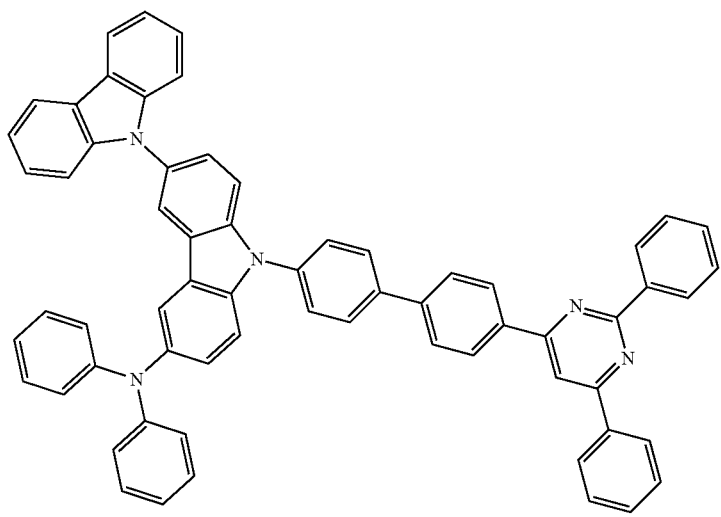
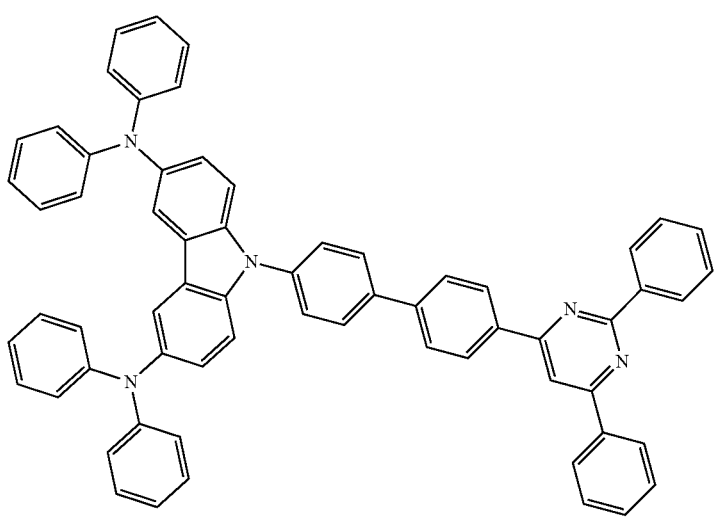
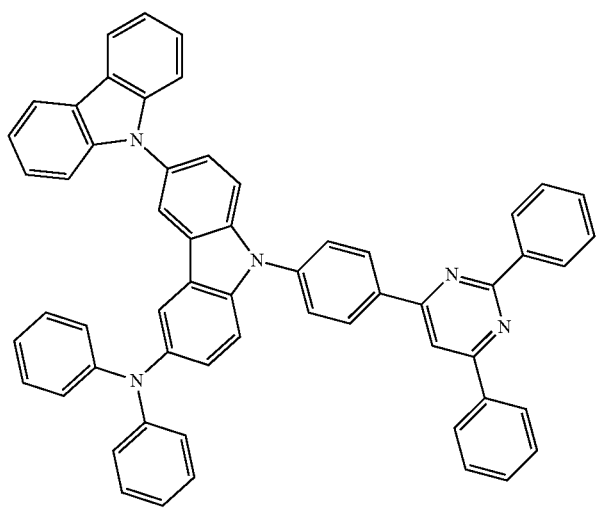

-continued
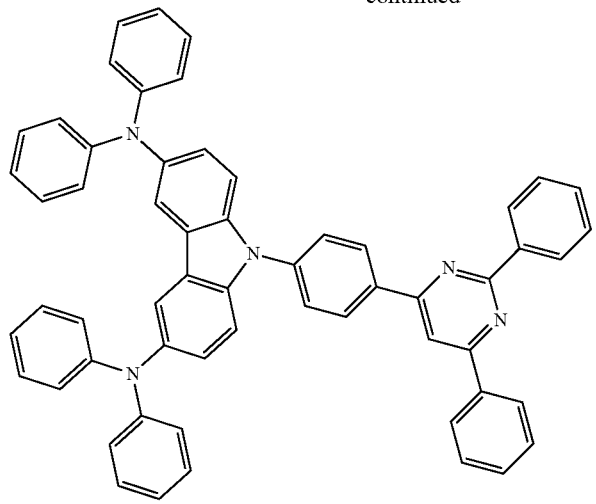
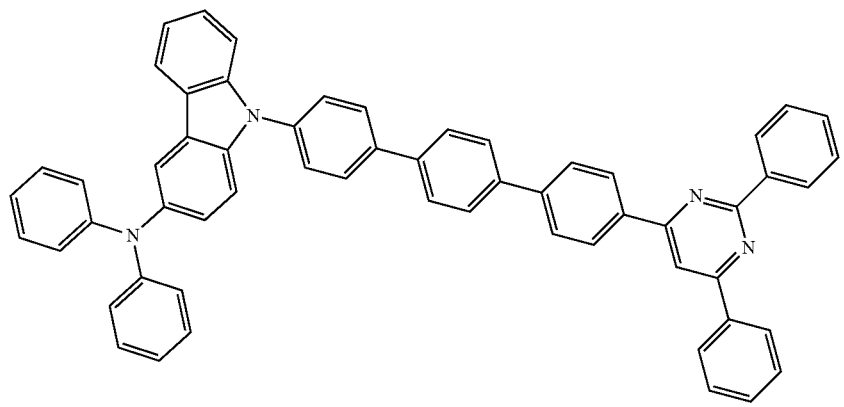
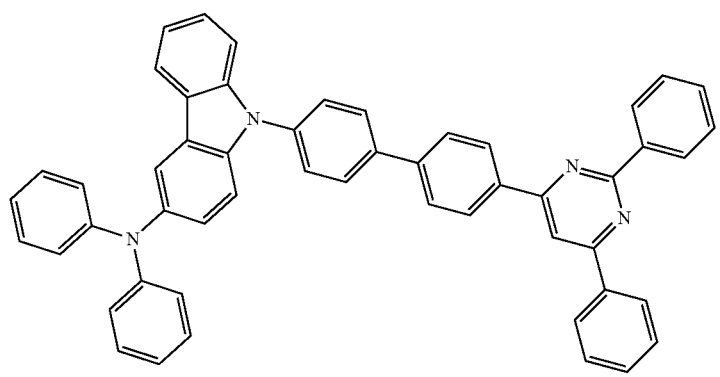
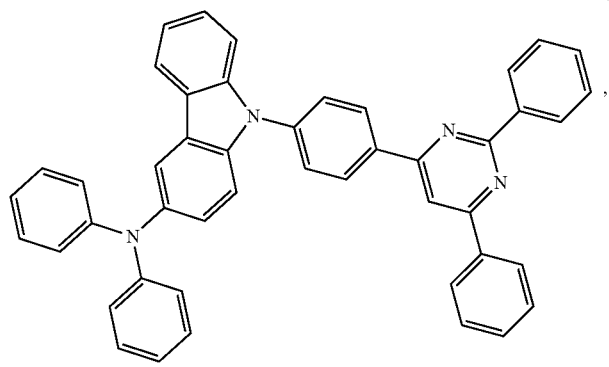

and the second compound is selected from Compounds H1 to H17:
H1
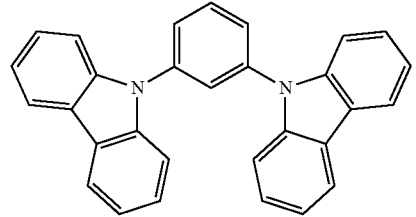
H2
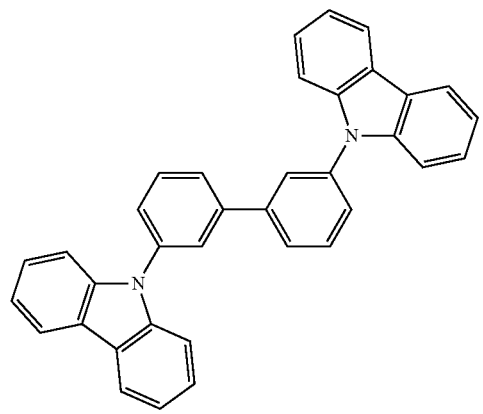
H3
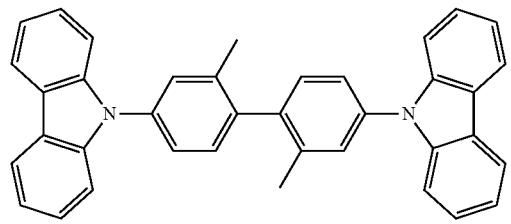
H4
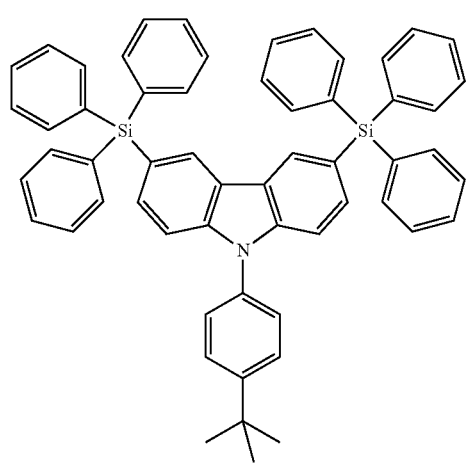
H5
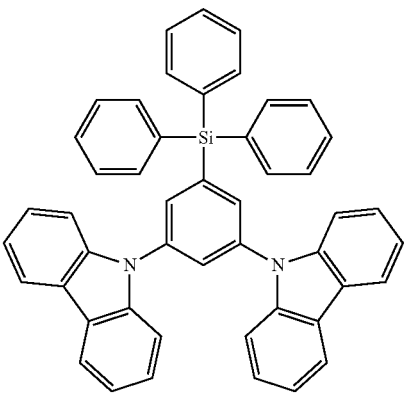
H6
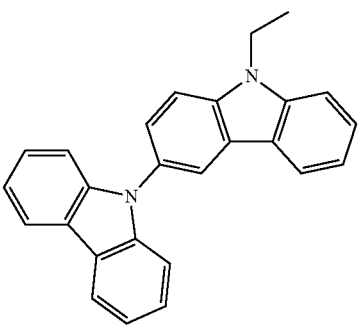
H7
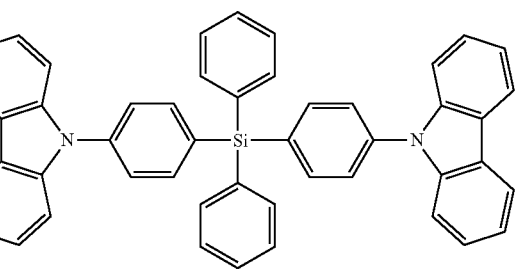
H8
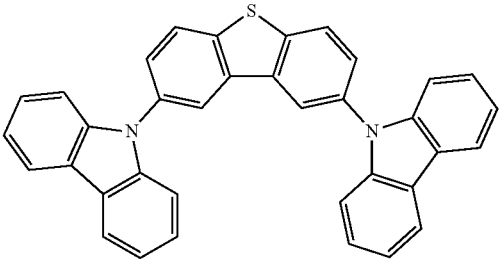
H9
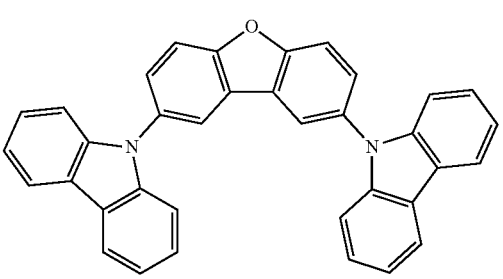

1037
-continued
H10
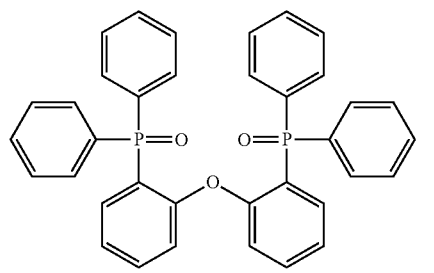
H11
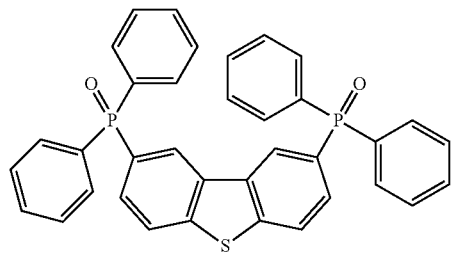
H12
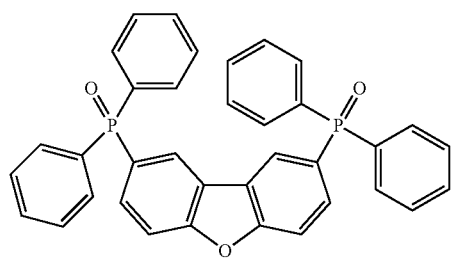
H13
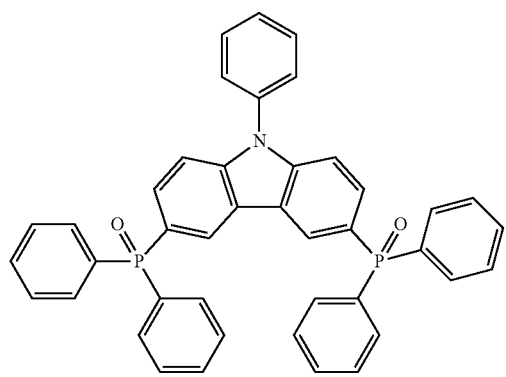
H14
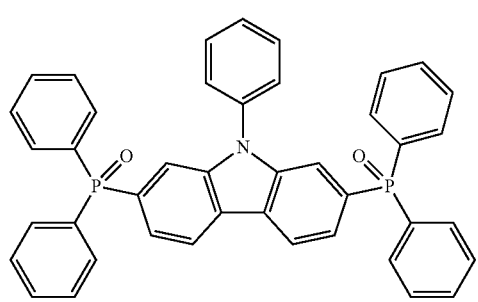
1038
-continued
H15
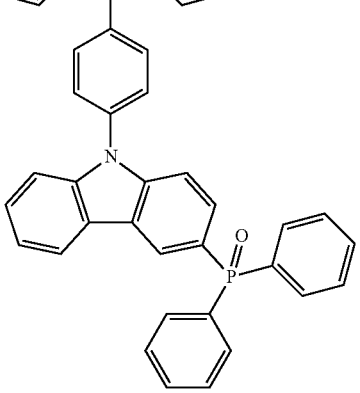
H16
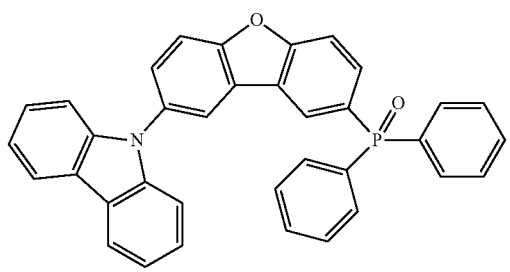
H17
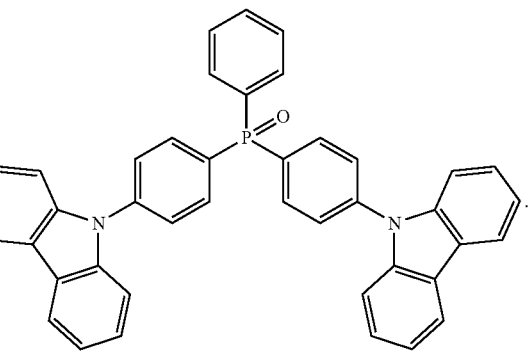
13. The organic light-emitting device of claim 1, wherein the second compound is selected from a compound comprising a carbazole ring and a phosphine oxide compound.
14. The organic light-emitting device of claim 1, wherein the second compound is represented by Formulae 2:
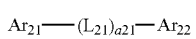
Formula 2
Formula 3-1
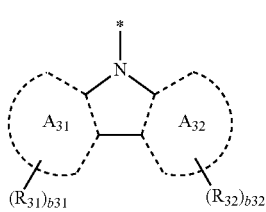

-continued

Formula 3-2

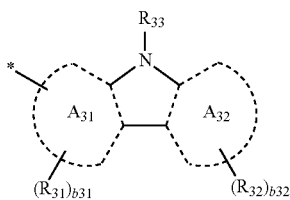

wherein, in Formulae 2, 3-1, and 3-2, $Ar_{21}$ and $Ar_{22}$ are each independently selected from *-$(L_{22})_{a22}$-[Si$(Q_1)(Q_2)(Q_3)$], *-$(L_{22})_{a22}$-[P($=$O)$(Q_1)(Q_2)$], groups represented by Formula 3-1, and groups represented by Formula 3-2, $L_{21}$ and $L_{22}$ are each independently selected from a single bond, *—O—*', *—S—*', *—[Si$(Q_1)(Q_2)$]-*', *—[P($=$O)$(Q_1)$]-*', a phenylene group, a pyridinylene group, a pyrimidinylene group, a pyrazinylene group, a pyridazinylene group, a triazinylene group, a naphthylene group, a fluorenylene group, a carbazolylene group, a dibenzofuranylene group, and a dibenzothiophenylene group; and a phenylene group, a pyridinylene group, a pyrimidinylene group, a pyrazinylene group, a pyridazinylene group, a triazinylene group, a naphthylene group, a fluorenylene group, a carbazolylene group, a dibenzofuranylene group, and a dibenzothiophenylene group, each substituted with at least one selected from deuterium, —F, —Cl, —Br, —I, a hydroxyl group, a cyano group, a nitro group, an amidino group, a hydrazino group, a hydrazono group, a $C_1$-$C_{10}$ alkyl group, a $C_1$-$C_{10}$ alkoxy group, a $C_1$-$C_{10}$ alkyl group substituted with —F, a phenyl group, a phenyl group substituted with —F, a phenyl group substituted with a cyano group, a phenyl group substituted with a $C_1$-$C_{10}$ alkyl group, a biphenyl group, a terphenyl group, a naphthyl group, a pyridinyl group, a pyrimidinyl group, a pyrazinyl group, a pyridazinyl group, a triazinyl group, a fluorenyl group, a carbazolyl group, a dibenzofuranyl group, a dibenzothiophenyl group, —Si$(Q_{31})(Q_{32})(Q_{33})$, and —P($=$O)$(Q_{31})(Q_{32})$, a21 and a22 are each independently selected from 0, 1, 2, 3, 4, and 5, $A_{31}$ and $A_{32}$ are each independently selected from a benzene group, a naphthalene group, a fluorene group, a benzofluorene group, a carbazole group, a benzocarbazole group, a dibenzofuran group, a benzonaphthofuran group, a dibenzothiophene group, and a benzonapthothiophene group, $R_{31}$ to $R_{33}$ are each independently selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{60}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si$(Q_1)(Q_2)(Q_3)$, and —P($=$O)$(Q_1)(Q_2)$, b31 and b32 are each independently selected from 1, 2, 3, 4, 5, 6, 7, and 8, wherein $Q_1$ to $Q_3$ and $Q_{31}$ to $Q_{33}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group, and

* and *' each indicate a binding site to an adjacent atom.

15. The organic light-emitting device of claim 14, wherein $Ar_{21}$ and $Ar_{22}$ are each independently selected from *-$(L_{22})_{a22}$-[Si$(Q_1)(Q_2)(Q_3)$], *-$(L_{22})_{a22}$-[P($=$O)$(Q_1)(Q_2)$], and groups represented by Formulae 3-11 to 3-15:

3-11

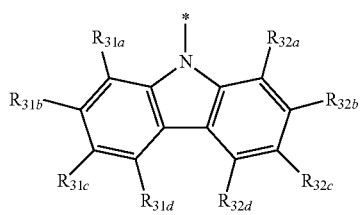

3-12

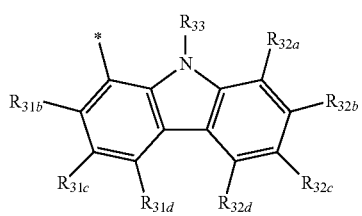

3-13

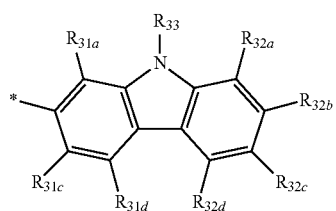

3-14

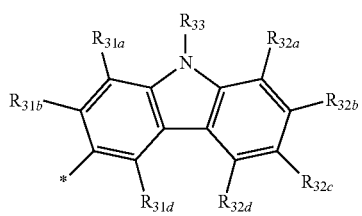

-continued 3-15

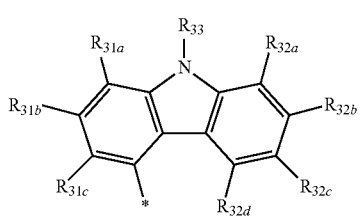

wherein, in Formulae 3-11 to 3-15,
$R_{31a}$ to $R_{31d}$ are each the same as $R_{31}$ defined herein in relation to Formula 3-1,
$R_{32a}$ to $R_{32d}$ are each the same as $R_{32}$ defined herein in relation to 3-1,
$R_{33}$ is the same as $R_{33}$ defined herein in relation to Formula 3-2, and
* indicates a binding site to an adjacent atom.

16. The organic light-emitting device of claim 14, wherein $L_{21}$ and $L_{22}$ are each independently selected from a single bond, *—O—*', *—S—*', *—[Si(Q$_1$)(Q$_2$)]-*', *—[P(=O)(Q$_1$)]-*' and groups represented by Formulae 4-1 to 4-32:

4-1
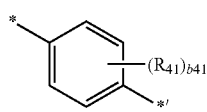

4-2
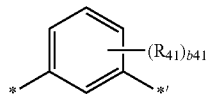

4-3
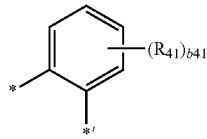

4-4
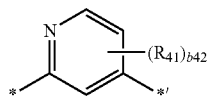

4-5
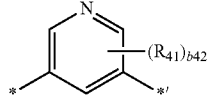

4-6
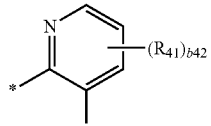

4-7
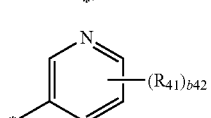

4-8
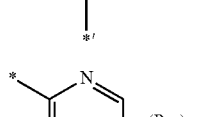

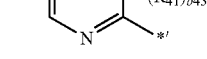

-continued 4-9
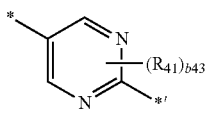

4-10
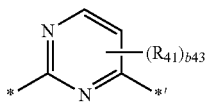

4-11
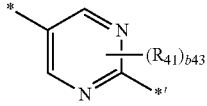

4-12
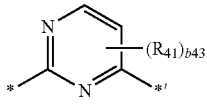

4-13
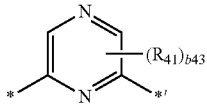

4-14
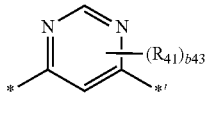

4-15
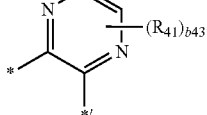

4-16
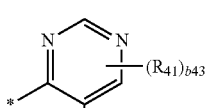

4-17
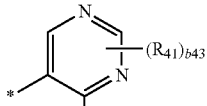

4-18
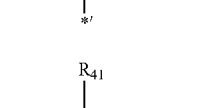

4-19
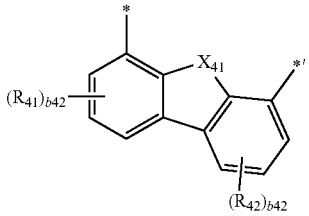

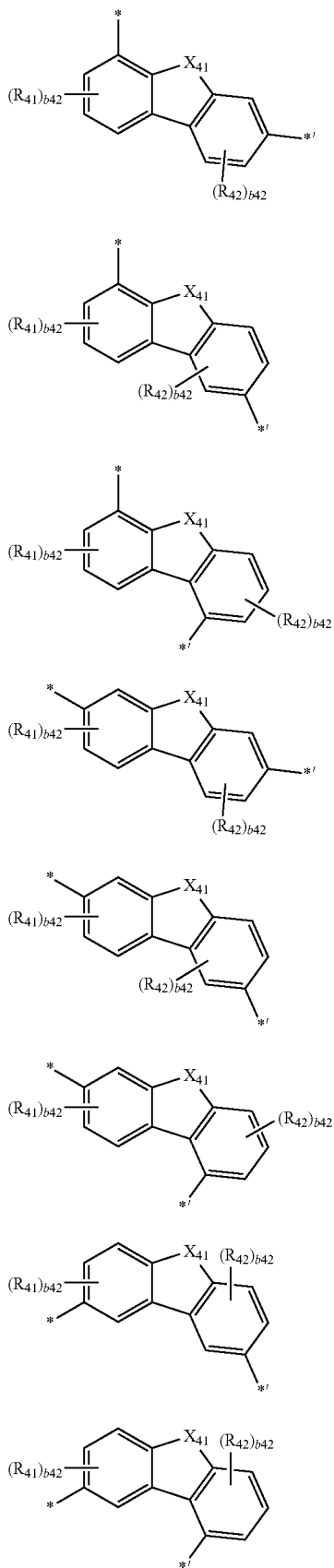

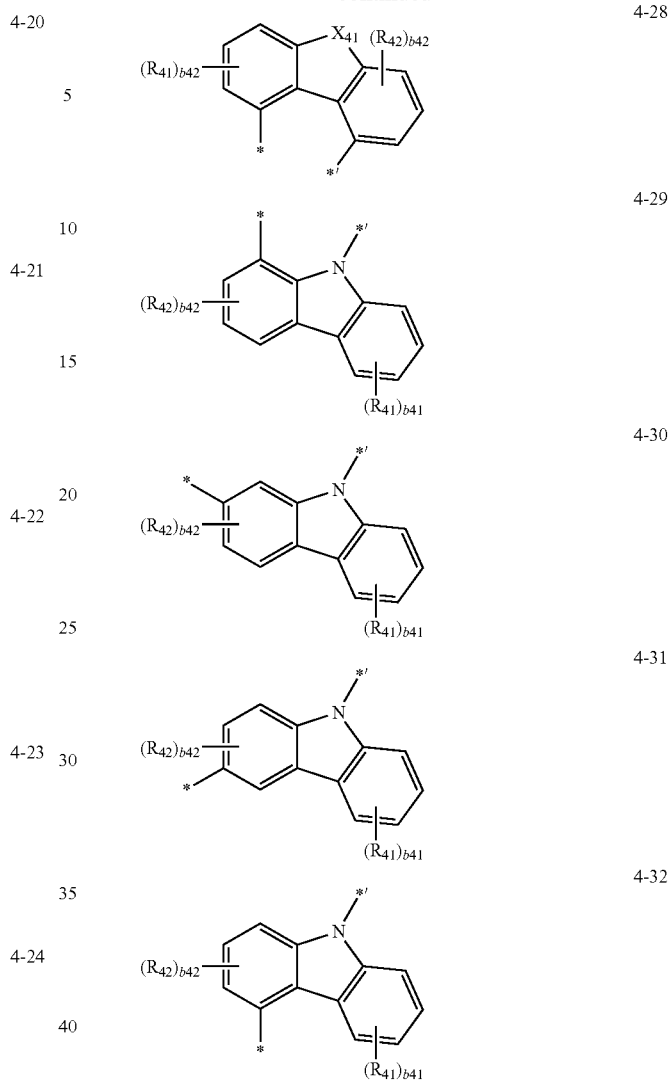

wherein, in Formulae 4-1 to 4-32,
$X_{41}$ is selected from $C(R_{43})(R_{44})$, $N(R_{43})$, O, and S,
$R_{41}$ to $R_{44}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{10}$ alkyl group, a $C_1$-$C_{10}$ alkyl group substituted with —F, a phenyl group, a phenyl group substituted with —F, a phenyl group substituted with a cyano group, a phenyl group substituted with a $C_1$-$C_{10}$ alkyl group, a biphenyl group, a terphenyl group, a naphthyl group, a fluorenyl group, a carbazolyl group, a dibenzofuranyl group, a dibenzothiophenyl group, —Si$(Q_{31})(Q_{32})(Q_{33})$, and —P(=O)(Qsl)$(Q_{32})$,
wherein $Q_1$ to $Q_3$ and $Q_{31}$ to $Q_{33}$ are each independently selected from hydrogen, a $C_1$-$C_{10}$ alkyl group, a phenyl group, a biphenyl group, a terphenyl group, and a naphthyl group,
b41 is selected from 1, 2, 3, and 4,
b42 is selected from 1, 2, and 3,
b43 is selected from 1 and 2, and
* and *' each indicate a binding site to an adjacent atom.

17. The organic light-emitting device of claim 14, wherein $R_{31}$ to $R_{33}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{10}$ alkyl group, a $C_1$-$C_{10}$ alkyl group substituted with —F, a phenyl group, a phenyl group substituted with —F, a phenyl group substituted with a cyano group, a phenyl group substituted with a $C_1$-$C_{10}$ alkyl group, a biphenyl group, a terphenyl group, a naphthyl group, a fluorenyl group, a carbazolyl group, a dibenzofuranyl group, a dibenzothiophenyl group, —Si($Q_1$)($Q_2$)($Q_3$), and —P(=O)($Q_1$)($Q_2$), wherein $Q_1$ to $Q_3$ are each independently selected from hydrogen, a $C_1$-$C_{10}$ alkyl group, a phenyl group, a biphenyl group, a terphenyl group, and a naphthyl group.

18. The organic light-emitting device of claim 1, wherein a difference between the highest occupied molecular orbital energy level of the first compound and the highest occupied molecular orbital energy level of the second compound is in a range of about 0 electron volts or greater to about 0.1 electron volts or less.

19. The organic light-emitting device of claim 1, wherein the emission layer comprises the first compound and the second compound.

\* \* \* \* \*